(12) United States Patent
Neri et al.

(10) Patent No.: US 7,432,048 B2
(45) Date of Patent: *Oct. 7, 2008

(54) REACTIONS ON A SOLID SURFACE

(75) Inventors: Bruce P. Neri, Madison, WI (US); Jeff G. Hall, Madison, WI (US); Victor Lyamichev, Madison, WI (US); Lloyd M. Smith, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/732,622

(22) Filed: Dec. 8, 2000

(65) Prior Publication Data

US 2005/0164177 A1 Jul. 28, 2005

Related U.S. Application Data

(60) Continuation-in-part of application No. 09/350,309, filed on Jul. 9, 1999, now Pat. No. 6,348,314, which is a division of application No. 08/756,386, filed on Nov. 26, 1996, now Pat. No. 5,985,557, and a continuation-in-part of application No. 09/381,212, filed as application No. PCT/US98/05809 on Mar. 24, 1998, now Pat. No. 6,872,816.

(51) Int. Cl.
*C12Q 1/68* (2006.01)

(52) U.S. Cl. .................... 435/6; 435/91.1; 435/91.2

(58) Field of Classification Search .................... None
See application file for complete search history.

(56) References Cited

U.S. PATENT DOCUMENTS

| 5,011,769 A | 4/1991 | Duck et al. ................ 435/6 |
| 5,118,605 A | 6/1992 | Urdea ...................... 435/6 |
| 5,210,015 A | 5/1993 | Gelfand et al. ............ 435/6 |
| 5,403,711 A | 4/1995 | Walder et al. ............ 435/6 |
| 5,422,253 A | 6/1995 | Dahlberg et al. ......... 435/91.53 |
| 5,424,186 A | 6/1995 | Fodor et al. .............. 435/6 |
| 5,472,881 A | 12/1995 | Beebe et al. .............. 436/94 |
| 5,516,663 A | 5/1996 | Backman et al. .......... 435/91.2 |
| 5,541,311 A * | 7/1996 | Dahlberg et al. .......... 536/23.7 |
| 5,609,907 A * | 3/1997 | Natan ..................... 427/2.12 |
| 5,614,402 A | 3/1997 | Dahlberg et al. .......... 435/199 |
| 5,691,142 A | 11/1997 | Dahlberg et al. .......... 435/6 |
| 5,719,028 A | 2/1998 | Dahlberg et al. .......... 435/6 |
| 5,744,305 A | 4/1998 | Fodor et al. .............. 435/6 |
| 5,795,763 A | 8/1998 | Dahlberg et al. .......... 435/194 |
| 5,807,682 A | 9/1998 | Grossman et al. .......... 435/6 |
| 5,830,664 A | 11/1998 | Rosemeyer et al. ......... 435/6 |
| 5,837,450 A | 11/1998 | Dahlberg et al. .......... 435/6 |
| 5,843,654 A | 12/1998 | Heisler et al. ............ 435/6 |
| 5,843,669 A | 12/1998 | Kaiser et al. ............. 435/6 |
| 5,846,717 A | 12/1998 | Brow et al. .............. 435/6 |
| 5,874,283 A * | 2/1999 | Harrington et al. ........ 435/252.3 |
| 5,882,867 A | 3/1999 | Ullman et al. ............ 435/6 |
| 5,888,780 A | 3/1999 | Dahlberg et al. ......... 435/91.53 |
| 5,985,557 A | 11/1999 | Prudent et al. ............ 435/6 |
| 5,994,069 A | 11/1999 | Hall et al. ................ 435/6 |
| 6,001,567 A | 12/1999 | Brow et al. .............. 435/6 |
| 6,060,288 A * | 5/2000 | Adams et al. ............. 435/91.2 |
| 6,090,543 A | 7/2000 | Prudent et al. ............ 435/6 |
| 6,090,606 A | 7/2000 | Kaiser et al. ............. 435/6 |
| 6,280,950 B1 * | 8/2001 | Lipshutz et al. ........... 435/6 |
| 6,348,314 B1 | 2/2002 | Prudent et al. ............ 435/6 |
| 6,372,424 B1 | 4/2002 | Brow et al. .............. 435/5 |
| 6,372,813 B1 * | 4/2002 | Johnson et al. ............ 522/114 |
| 6,375,903 B1 | 4/2002 | Cerrina et al. ............ 422/131 |
| 6,458,535 B1 | 10/2002 | Hall et al. ................ 435/6 |
| 6,500,622 B2 | 12/2002 | Bruchez, Jr. et al. ........ 435/6 |
| 6,692,917 B2 | 2/2004 | Neri et al. ................ 435/6 |
| 6,872,816 B1 | 3/2005 | Hall et al. ................ 536/24.3 |
| 6,875,572 B2 | 4/2005 | Prudent et al. ............ 435/6 |
| 2002/0187486 A1 | 12/2002 | Hall et al. ................ 435/6 |
| 2002/0197623 A1 | 12/2002 | Prudent et al. ............ 435/6 |
| 2003/0096245 A1 | 5/2003 | Prudent et al. ............ 435/6 |

FOREIGN PATENT DOCUMENTS

WO 94/29482 12/1994
WO 95/11995 5/1995

(Continued)

OTHER PUBLICATIONS

Ryan et al. Molecular Diagnosis vol. 4:135-144. 1999.*

(Continued)

*Primary Examiner*—Gary Benzion
*Assistant Examiner*—Heather G. Calamita
(74) *Attorney, Agent, or Firm*—Casimir Jones, S.C.

(57) ABSTRACT

The present invention relates to compositions and methods for the detection and characterization of nucleic acid sequences and variations in nucleic acid sequences. The present invention relates to methods for forming a nucleic acid cleavage structure on a solid support and cleaving the nucleic acid cleavage structure in a site-specific manner. For example, in some embodiments, a 5' nuclease activity from any of a variety of enzymes is used to cleave the target-dependent cleavage structure, thereby indicating the presence of specific nucleic acid sequences or specific variations thereof.

14 Claims, 127 Drawing Sheets

FOREIGN PATENT DOCUMENTS

| WO | 97/27214 | 7/1997 |
|---|---|---|
| WO | 99/42813 | 8/1999 |
| WO | 02/04597 | 1/2002 |

OTHER PUBLICATIONS

Shen et al. TIBS. 1998.*
Drmanac et al., Accurate sequencing by hybridization for DNA diagnostics and individual genomics. Nature Biotechnology, 16:54 (1998).
Chee et al., Science, 274:610 [1996].
Sosnowski et al., PNAS, 94:1119 [1997].
Pastinen et al., Genome Research, 7:606 [1997].
Shuber et al., Human Molecular Genetics, 6:337 [1997].
Kwok et al., Nuc. Acid. Res., 18:999 [1990].
Landegren et al., Science, 241:1077 [1988].
Livak et al., PCR Methods and Applications, 4:357 [1995].
Shafer et al., J. clinical Microbiology, 34:1849 [1996].
Wang et al., Science, 280:1077 [1998].
Collins et al., Science, 278:1580 [1997].
Chernukhin and Klenova, Anal. Biochem., 280:178 [2000].
Bilkova et al., J. Chromatogr. A, 852:141 [1999].
Guo et al., Nucleic Acids Res., 22:5456 [1994].
Maskos and Southern, Nucleic Acids Res., 20:1679 [1992].
Frutos et al., Nuc. Acid. Res., 25:4748 [1997].
Frey and Corn, Analytical Chem. 68-3187 (1996).
Jordan et al., Analytical Chem. 694939 [1997].
Shchepinov et al., Nucleic Acids Research 25: 1155 [1997].
Ostroff et al., Cleinical Chem., 45:1659 [1999].
Bambara et al., "Enzymes and Reactions at the Eukaryotic DNA Replication Fork," *J. Biol. Chem.* 272:4647-4650 (1997.
Harrington et al., "DNA Structural Elements Required for FEN-1 Binding," *J. Biol. Chem.* 270:4503-4508 (1995).
Harrington et al., "The characterization of a mammalian DNA structure-specific endonuclease," *EMBO Journ.* 13:1235-1246 (1994).
Harrington and Lieber, "Functional domains within FEN-1 and RAD2 define a family of structure-specific endonucleases: implications for nucleotide excision repair," *Genes and Develop.* 8:1344-1355 (1994).
Lyamichev et al."Structure-Specific Endonucleolytic Cleavage of Nucleic Acids by Eubacterial DNA Polymerases," *Science* 260:778-783 (1993).
Murante et al., "Calf 5' to 3' Exo/Endonuclease Must Slide from a 5' End of the Substrate to Perform Structure-specific Cleavage," *J. Biol. Chem.* 270:30377-30383 (1995).
Murante et al., "The Calf 5'- to 3'-Exonuclease Is Also an Endonuclease with Both Activities Dependent on Primers Annealed Upstream of the Point of Cleavage," *J. Biol. Chem.* 269:1191-1196 (1994).
Hessner et al., Genotyping of Factor V G1691A (Leiden) without the Use of PCR by Invasive Cleavage of Oligonucleotide Probes, *Clinical Chemistry* 46:1051-1056 (2000).
Lyamichev et al., Experimental and Theoretical Analysis of the Invasive Signal Amplification Reaction, *Biochemistry* 39:9523-9532 (2000).
Neri et al., Transferring Automation for Large-scale Development and Production of Invader™ SNP Assays, *Progress in Biomedical Optics* 1:117-125 (2000).
Newlin et al., The Invader Assay: An Alternative To PCR-Based Testing For The Detection Of Point Mutations Associated With Venous Thrombosis, *Clinical Hemostasis Review*, 14:10-12 (2000).
Hall et al., Sensitive detection of DNA polymorphisms by the serial invasive signal amplification reaction, PNAS 97:8272-8277 (2000).
Ledford et al., A Multi-Site Study for Detection of the Factor V (Leiden) Mutation from Genomic DNA Using Homogeneous Invader Microtiter Plate Fluorescence Resonance Energy Transfer (FRET) Assay, *J. Molecular Diagnostics* 2:97-104 (2000).
Ma et al., RNA Template-dependent 5' Nuclease Activity of *Thermus aquaticus* and *Thermus thermophilus* DNA Polymerases, *J. Biol. Chem.*, 275:24693-24700 (2000).
Fors et al., Large-scale SNP scoring from unamplified genomic DNA, *Pharmacogenomics* 1(2):219-229 (2000).
Agarwal et al., Comparison Study For Identifying Promoter Allelic Polymorphism in Interleukin 10 and Tumor Necrosis Factor á Genes, *Diagn Mol Pathol* 9(3):158-164 (2000).
Cooksey et al., Evaluation of the Invader Assay, a Linear Signal Amplification Method, for Identification of Mutation Associated with Resistance to Rifampin and Isoniazid in *Mycobacterium tuberculosis*, *Antimicrobial Agents and Chemotherapy*, 44:1296-1301 (2000).
Mein et al., Evaluation of Single Nucleotide Polymorphism Typing with Invader or PCR Amplicons and Its Automation, *Genome Research* 10:330-343 (2000).
Lieder, Excitement Builds in Molecular Biology, *Advance for Administrators of the Laboratory* 50-52 (1999).
Lieder, Invader Technology Provices Alternative to PCR, *Advance for Administrators of the Laboratory*, 70-71 (2000).
Treble et al., Invader ? technology for SNP detection, *Gene & Medicine* 4:68-72 (2000).
Kwiatkowski et al., Clinical, Genetic, and Pharmacogenetic Applications of the Invader Assay, *Molecular Diagnosis*, 4:353-364 (1999).
Check, Labs home in on mutant alleles, *College of American Pathologists Today*, 1-5 Sep. 1999.
Griffin et al., Direct genetic analysis by matrix-assisted laser desorption/ionization mass spectrometry, *PNAS* 96:6301-6306 (1999).
Ryan et al., Non-PCR-Dependent Detection of the Factor V Leiden Mutation From Genomic DNA Using a Homogeneous Invader Microtiter Plate Assay, *Molecular Diagnosis*, :135-144 (1999).
Kaiser et al., A Comparison of Eubacterial and Archaeal Structure-specific 5'-Exonucleases, *J. Biol. Chem.*, 274:21387-21394 (1999).
Lyamichev et al., Polymorphism indentification and quantitative detection of genomic DNA by invasive cleavage of oligonucleotide probes, *Nature Biotech*. 17:292-296-(1999).
Harrington, The Characterization of the Fen-1 Family of Structure-Specific Endonucleases: Implications for DNA Replication, Recombination, And Repair, Dissertation submitted to the Program in Cancer Biology and the Committee on Graduate Studies of Stanford University (1994).
DeFrancesco, The Next New Wave in Genome Analysis, *The Scientist*, 12(21):1-3 (1998).
Order and Opinion on Motion for Summary Judgment, *Third Wave Technologies, Inc. v. Eragen Biosciences, James Prudent, and David Marshall*, 02-C-507-C, United States District Court for the Western District of Wisconsin.
Order and Opinion, *Third Wave Technologies, Inc. v. Stratagene Corp.*, 04-C-680-C 02-C-507-C, United States District Court for the Western District of Wisconsin, Aug. 4, 2005.
Lieber, The FEN-1 family of structure-specific nucleases in eukaryotic DNA replication, recombination and repair, BioEssays 19:223-240 (1997).
Order and Opinion on Post-Trial Motions, *Third Wave Technologies, Inc. v. Stratagene Corp.*, 04-C-680-C 02-C-507-C, United States District Court for the Western District of Wisconsin, Dec. 16, 2005.

* cited by examiner

```
MAJORITY  ATGXXGGGGATGCTTCCCCTCTTTGAGCCCAAAGGCCGGGTCCTCTGGTGGACGGGCACCACCTGGCCT

DNAPTAQ   ....AG..G...........................G..............................  70
DNAPTFL   .......................................C..G........................  67
DNAPTTH   ...GA...................G....A......................................  70

MAJORITY  ACCGCACCTTCTTCGCCCTGAAGGGCCTCACCACCAGCCGGGGGAACGGTGCAGGCGGTCTACGGCTT

DNAPTAQ   ..........CA.........................G...G..........................  140
DNAPTFL   ...........T....C...................C...T..........................  137
DNAPTTH   .......................G............................................  140

MAJORITY  CGCCAAGAGCCTCCTCAAGGCCCTGAAGGAGGACGGGGACXXGCCGGTGXTCGTGGTCTTTGACGCCAAG

DNAPTAQ   ........................C........................A..................  207
DNAPTFL   .............A..................GT..T...............................  204
DNAPTTH   .......................................T..AA...C..CT................  280

MAJORITY  GCCCCCTCCTTCCGCCACGAGCCTACGAGCCTACAAGGCGGGCGGCCCCACCCCGGAGGACTTTC

DNAPTAQ   .................................G..GG..........................  277
DNAPTFL   .....................................G..................C......  274
DNAPTTH   ..........................................GA......G.....C......  280

MAJORITY  CCCGGCAGCTCGCCCTCATCAAGGAGCTGGTGGACCTCCTGGGGCTTGCGCGCCTCGAGGTCCCCGGCTA

DNAPTAQ   .........A...............................G................G.......  347
DNAPTFL   .........G......T...................A..C..T...G.G........T......T  344
DNAPTTH   ........................................T.A.C.....................  350
```

FIG. 1A

```
MAJORITY  CGAGGCGGACGACGTXCTGGCCACCCTGGCCAAGAAGGCGGAAAAGGAGGGGTACGAGGTGCCATCCTC

DNAPTAQ   ..........................C..........G.................C............  417
DNAPTFL   T.........................G..........CG..............................  414
DNAPTTH   ........................T.C..........................................  420

MAJORITY  ACCGCCGACCGCGACCTCTACCAGCTCCTTTCCGACCGCATCGCGCTCCTCCACCCGAGGGTACCTCA

DNAPTAQ   ......AAA......T.........................................CA........  487
DNAPTFL   ........T..............................G..G........A..........T.....  484
DNAPTTH   .........................A...G.C.......G...........CC...............  490

MAJORITY  TCACCCCGGCGTGGCTTTGGGAGAAGTACGGCCTGAGGCCGGAGCAGTGGGTGGACTACCGGGCCCTGGC

DNAPTAQ   ...........C.........A......................CC.......CC..........A..  557
DNAPTFL   ..........AC..................................CC.....C..............  554
DNAPTTH   ............A......................C.....................T......C.T...  560

MAJORITY  GGGGACCCCTCCGACAACCTCCCCGGGTCAAGGGCATCGGGGAGAAGACCGCCXGAAGCTCCTCXAG

DNAPTAQ   C......GAG..............T..............G......G..GAG....T..GG....  627
DNAPTFL   ..........G..T..A....................G...........A.G....A..CGC.A..  624
DNAPTTH   ..........................................................TC.......A..  630

MAJORITY  GAGTGGGGAGCCTGGAAAACCTCCTCAAGAACCTGGACCGGGTGAAGCCCGC..CXTCCGGGAAGA

DNAPTAQ   ..........GC.....................C........................A.....  694
DNAPTFL   .............................T.C.C.............A.......T.G......C  691
DNAPTTH   ..........A................................A......A...A.AAAA.G......  700
```

```
MAJORITY  CGGGGXCTCCTCGCCAAGGACCTGGCCGTTTTGGCCCTGAGGGAGGGCCTXGACCTTCXTGCCCGGGACG

DNAPTAQ   .....G..T.........A.......AG....C.............A....T.G.....CC......C.   1114
DNAPTFL   .....AA...G..................G........C.........G....T.C..A.A.......   1111
DNAPTTH   .....C.................C..C..........TC......G..A........G..........   1120

MAJORITY  ACCCCATGTCTCCTCTGCCTACCTCCTGGACCCCTCCAACACACCCCGAGGGGTGGCCCGGCGTACGG

DNAPTAQ   ..................................T.................................   1184
DNAPTFL   ......G...............T...................................T..........   1181
DNAPTTH   ...................................................G................   1190

MAJORITY  GGGGGAGTGGACGGAGGAXGCGGGGAGCGGGCCCTCCTXTCCGAGAGGCTCTTCCXGAACCTXXXGGAG

DNAPTAQ   C..................G...........GC....T.............GCC....GTG..G....   1254
DNAPTFL   .................T.......A..........GG.....C.C.....A..C..AAA........   1260
DNAPTTH   .......C...C..CCC.C..............C...G...........CAT.G......CCTTA...   1260

MAJORITY  CGCCTTGAGGGGGAGGAGAGGCTCCTTTGGCTTTACCAGGAGGTGGAGAAGCCCCTTTCCCGGGTCCIGG

DNAPTAQ   A.G.......A..A..A..AC.C..G...............G.........G......GCT........   1324
DNAPTFL   ..........A............A.......................C........G........GT..   1321
DNAPTTH   ....C....................................C.....A........C............   1330

MAJORITY  CCCACATGAGGCCACGGGGTXCGGCTGGACGTGGCCTACCTCCAGGCCCTXTCCCTGGAGGTGGCGGA

DNAPTAQ   ......GG......G..C................T..AG....T.G.............C.......   1394
DNAPTFL   ...............C................................C.........A.C.....   1391
DNAPTTH   ...............A...........................T...............C.T.....   1400
```

FIG. 1D

```
MAJORITY  GGAGATCCGCGCCGCCTCGAGGAGGAGGTCTTTCCGCCTGGCCGGCCACCCCTTCAACCTTCAACTCCCGGGAC         1464

DNAPTAQ   .....GC................CC..............................................         1461
DNAPTFL   ..G.G....AG..G..........................T....G..........................
DNAPTTH   .........................................................C..............         1470

MAJORITY  CAGCTGGAAAGGGTGCTCTTTGACGAGCTXGGGCTTCCCGCCATCGGCAAGACGGAGAGACXGGCAAGC              1534

DNAPTAQ   ..............C............A..............C............................         1531
DNAPTFL   ......GC................G.C.G.T............G..G.A......................
DNAPTTH   ........................TA............T.G.G......C.A....A..............         1540

MAJORITY  GCTCCACCAGCGCCGCCGCGTGCTGGAGCCCCTXCGXGAGCCCCATCGTGGAGAAGATCCTGCAGTA                1604

DNAPTAQ   ...............C..........C.C...........................................         1601
DNAPTFL   ...............T..........G.A.......CCGC................................
DNAPTTH   .................G........A..G...................C...C.................         1610

MAJORITY  CCGGGAGCTCACCAAGCTCAAGAACACTTACATXGACCCCCTGCCXGXCCTCGTCCACCCAGGACGGGC              1674

DNAPTAQ   ...............G..G.............T...........T....G.A....A..............         1671
DNAPTFL   .......................................A.....C.C....G..........C..C....
DNAPTTH   ............................................G.G......AAG......G........         1680

MAJORITY  CGCCTCCACACCCGCTTCAACCAGACGGCCACGGGCCAGGCTTAGTAGCTCCGACCCCAACCTGC                  1744

DNAPTAQ   ..................................................A.....T........C.....         1741
DNAPTFL   .G...........................C............................TCC..........
DNAPTTH   ........................................G...............................         1750
```

FIG. 1E

```
MAJORITY  AGAACATCCCCGTCCGCACCCCXCTGGGCCAGAGGATCCGCCGGGCCTTCGTGGCCGAGGAGGGXTGGGT

DNAPTAQ   ................G..T..G...................A.C...............G....C...  1814
DNAPTFL   .................T.........C.C......A.................C...........  1811
DNAPTTH   ..................CT............................C...T.....C  1820

MAJORITY  GTTGGTGGCCCTGGACTATAGCCAGATAGAGCTCCGGGTCCTGGCCCACCTCTCCGGGACGAGAACCTG

DNAPTAQ   A..................................A..G..............C..............  1884
DNAPTFL   .C.....T.T........C........T.......T.................................  1881
DNAPTTH   ...A.....................C......C......................A.............  1890

MAJORITY  ATCCGGGTCTTCCAGGAGGGGAGGACATCCACACCCAGACCGCCAGCTGGATGTTCGGCGTCCCCCGG

DNAPTAQ   ..............C...........GG.....................................G...  1954
DNAPTFL   .....T......................................................TT....C..  1951
DNAPTTH   ...A.....................A.........................................  1960

MAJORITY  AGGCCGTGGACCCCCTGATGCGCCGGCCAAGACCATCAACTTCGGGGTCCTCTACGGCATGTCGGC

DNAPTAQ   .A.GG..A.......T...................................G............G...  2024
DNAPTFL   ................................................GG.G..........C.....  2021
DNAPTTH   ......................................................................  2030

MAJORITY  CCACGCCTCTCCCAGGAGTTGCCATCCCCTACGAGGAGGGGTGGCCTTCATTGAGCGCTACTTCCAG

DNAPTAQ   ..................A......T.............CCA..................T......  2094
DNAPTFL   ...TA.G..GG..............................................T..A.......A  2091
DNAPTTH   ........................................................T..A.......A  2100
```

FIG. 1F

```
MAJORITY   AGCTTCCCCAAGGTGCGGGCCTGGATTGAGAAGACCCTGGAGGAGGGCAGGAGGCGGGGTACGTGGAGA

DNAPTAQ    ..............................................................C.CC......    2164
DNAPTFL    ......A........................GG.............................G..A......T.    2161
DNAPTTH    ...................A..A........................................A.......   2170

MAJORITY   CCCTCTTCGGCCGCCGGCCTACGTGCCCGACCTCAACGCCCGGGTGAAGAGCGTGCGGGAGGCGGCGGA

DNAPTAQ    ...................................C.....A....AG.G..........C...........     2234
DNAPTFL    ....................T...................................C................     2231
DNAPTTH    ...........AA.AA................................CA........C.............     2240

MAJORITY   GCGCATGGCCTTCAACATGCCCGTCCAGGCACCGCCGACCTCATGAAGCTGGCCATGGTGAAGCTC

DNAPTAQ    ...........................................................T.............    2304
DNAPTFL    ..................................G........................CG...T        2301
DNAPTTH    ........................................................C...............    2310

MAJORITY   TTCCCCCGGCTXCAGGAAATGGGGCCAGGATGCTCCTXCAGGTCCACGACGAGCTGGTCCTGAGGCCC

DNAPTAQ    .....A..GG.................T..............T...............................    2374
DNAPTFL    ......T...C..........G.......TT.G....G..................................    2371
DNAPTTH    ...C..C.G..G.........C.C..........CC..G.................................    2380

MAJORITY   CCAAAGAGCGGGCGGAGGXGGTGGCCGCTTTGGCCAAGGAGGTCATGGAGGGGTCTATCCCCTGGCCGT

DNAPTAQ    .A......A........CC....CGGC...............G..........................    2444
DNAPTFL    ...G..C........AG..A....................GG......CAG.................    2441
DNAPTTH    ..C..C........C......G..................AA.C........C...............    2450
```

FIG. 1G

```
MAJORITY  GCCCCTGGAGGTGGAGGTGGGGATGGGGGAGGACTGGCTCTCCGCCAAGGAGTAG

DNAPTAQ   ...........A..............................GA    2499
DNAPTFL   ..........CC.............................         2496
DNAPTTH   ...................................T.....GT...   2505
```

FIG. 1H

```
MAJORITY  MXAMLPLFEPKGRVLLVDGHHLAYRTFFALKGLTTSRGEPVQAVYGFAKSLLKALKEDG·DAVXVVFDAK

TAQ PRO   ....RG.............................H.................................I........  69
TFL PRO   ...................................................................V.V........  68
TTH PRO   ....E..........................................................YK..F..........  70

MAJORITY  APSFRHEAYEAYKAGRAPTPEDFPROLALIKELVDLLGLXRLEVPGYEADDVLATLAKKAEKEGYEVRIL

TAQ PRO   ...........GG................................A......................... 139
TFL PRO   ........................................V.....F......S.................. 138
TTH PRO   ................................................FT..................... 140

MAJORITY  TADRDLYQLLSDRIAVLHPEGYLITPAWLWEKYGLRPEQWDYRALXGDPSDNLPGVKGIGEKTAXKLLX

TAQ PRO   ......K.........H..................................D.A....T..E.......R...E  209
TFL PRO   ................E..I............Y....................A.....I......QR.IR  208
TTH PRO   ..............V..V......H....E..................F..V.................L...K  210

MAJORITY  EWGSLENLLKNLDRVKP·XXREKIXAHMEDLXLSXXLSXVRTDLPLEVDFAXRREPDREGLRAFLERLEF

TAQ PRO   ........A..........L...AI......L...D..K..WD.AK...............K.........R.....
TFL PRO   ...............FQH..Q....SL....LQ.G..A.A..RK..Q.H............GR..T.NL........  277
TTH PRO   ...............ENV....K..L...R..LE..R......................L.QG............... 280

MAJORITY  GSLLHEFGLLEXPKALEEAPWPPPEGAFVGFVLSRPEPMWAELLALAAARXGRVHRAXDPLXGLRDLKEV

TAQ PRO   ........S...............................K........D...........PE.YKA......A  348
TFL PRO   ....G..A..................L..SF...................G.WE..L...Q....R......G.  347
TTH PRO   ....A.AP......................................K....C..D..........A..A..K....  350
```

FIG. 2A

```
MAJORITY  RGLLAKDLAVLALREGLDLXPGDDPMLLAYLLDPSNTTPEGVARRYGGEWTEDAGERALLSERLFXNLXX

TAQ PRO   .........S..............G.P...........E............A...WG      418
TFL PRO   ..I......S..............F.E.........................QT.KE      417
TTH PRO   .........S..............V.........AH...............HR..LK      420

MAJORITY  RLEGEERLLWLYXEVEKPLSRVLAHMEATGVRLDVAYLQALSLEVAEEIRRLEEEVFRLAGHPFNLNSRD

TAQ PRO   ........................R................R.....A..A.................      488
TFL PRO   ..K.....................E..........................EA.V.Q...........      487
TTH PRO   ..K.....................H........................L...................      490

MAJORITY  QLERVLFDELGLPAIGKTEKTGKRSTSAAVLEALREAHPIVEKILQYRELTKLKNTYIDPLPXLVHPRTG

TAQ PRO   ...................................................S......D.I........      558
TFL PRO   ..............R..L..Q......DR......................A....K..........      557
TTH PRO   ....................................H...............V...S............      560

MAJORITY  RLHTRFNQTATATGRLSSSDPNLQNIPVRTPLGQRIRRAFVAEEGWXLVALDYSQIELRVLAHLSGDENL

TAQ PRO   ......................................................I....L........      628
TFL PRO   ...........................................................V..V.....      627
TTH PRO   ..........................................A..A......................      630

MAJORITY  IRVFQEGRDIHTQTASWMFGVPPEAVDPLMRRAAKTINFGVLYGMSAHRLSQELAIPYEEAVAFIERYFQ

TAQ PRO   ..............E..........R..........................Q................      698
TFL PRO   ..............S..........G...........................G.S.............      697
TTH PRO   ..K...........................................V......................      700
```

FIG. 2B

```
MAJORITY   SFPKVRAWIEKTLEEGRRRGYVETLFGRRRYVPDLNARVKSVREAAERMAFNMPVQGTAADLMKLAMVKL

TAQ PRO    .........E................................................................  768
TFL PRO    .Y......G.................E...............................R..............  767
TTH PRO    ...........K..............................................................  770

MAJORITY   FPRLXEMGARMLLQVHDELVLEAPKXRAEXVAALAKEVMEGVYPLAVPLEVEVGXGEDWLSAKEX

TAQ PRO    ....E..........................E..A..R.................I........  833
TFL PRO    ....Q.L........................D..R..........W..Q......L........  831
TTH PRO    ....R..................L.......QA.....E......A..KA.....M.......G  835
```

FIG. 2C

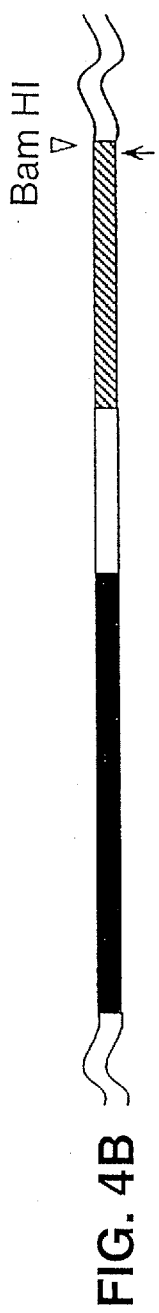
FIG. 4A
FIG. 4B

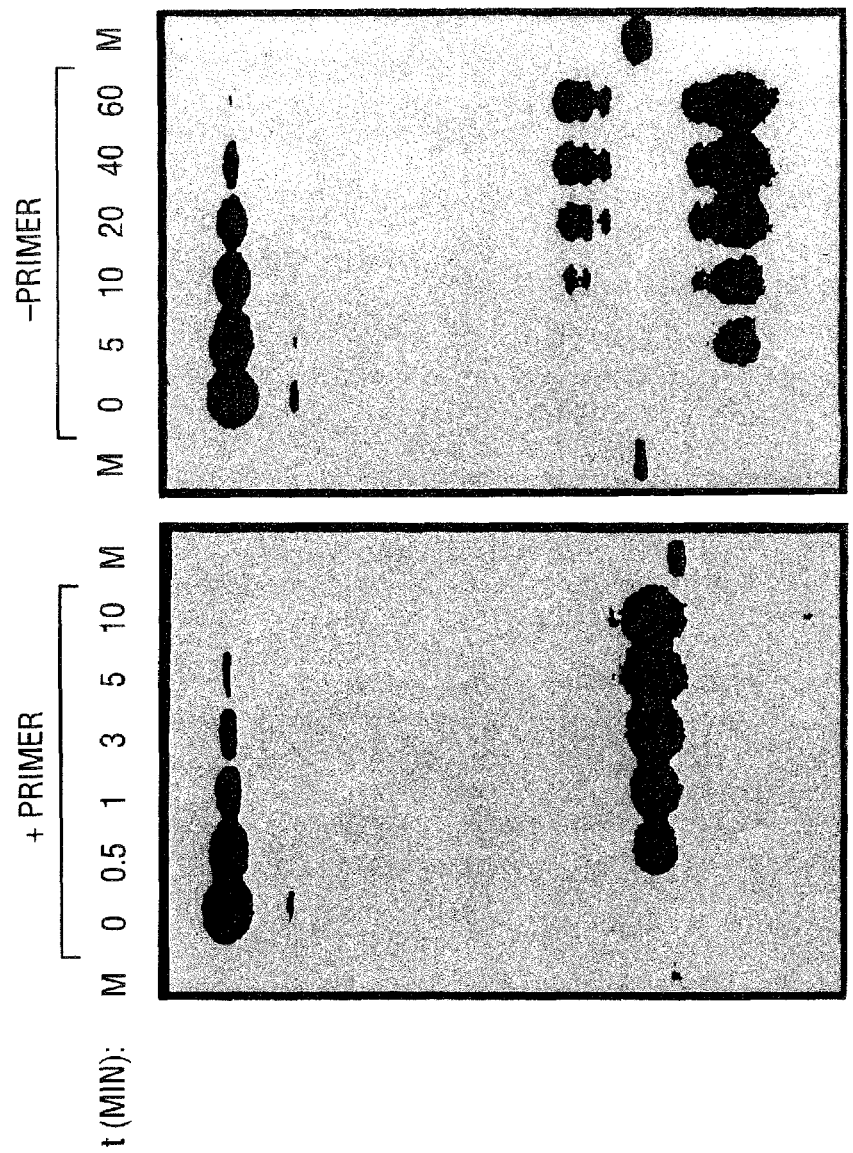

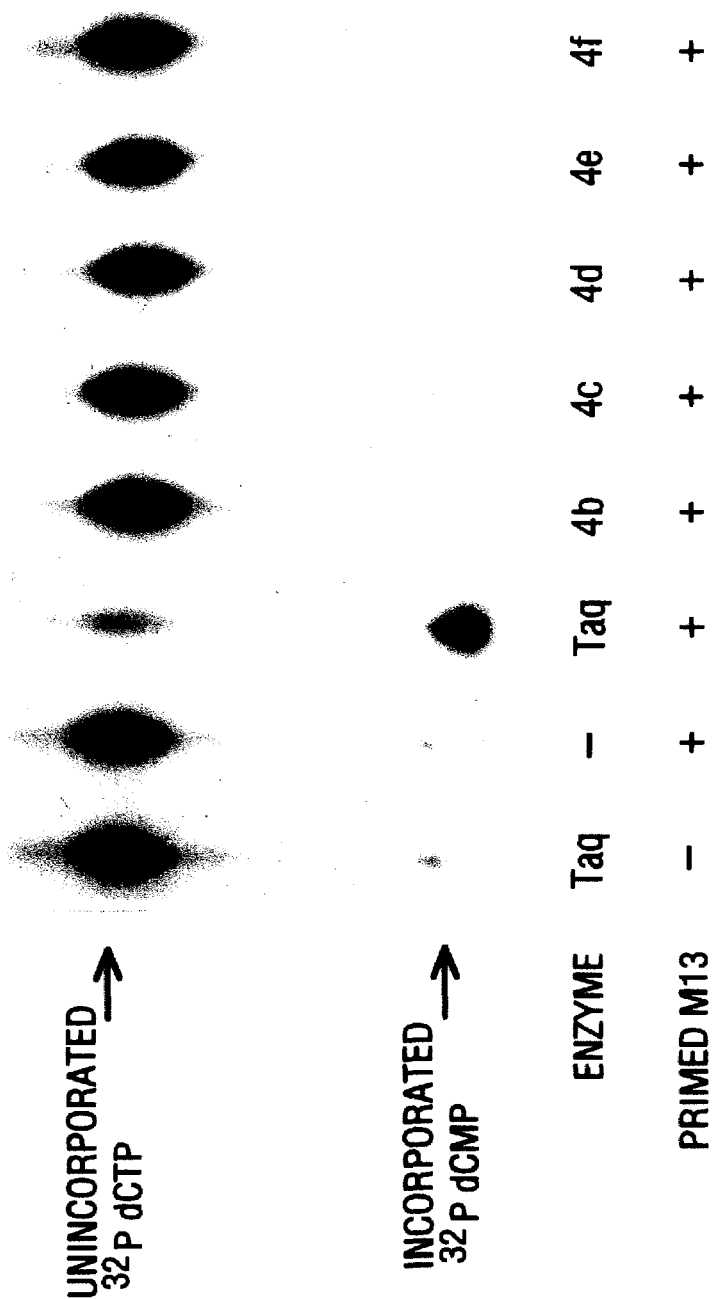

* = $^{32}P$

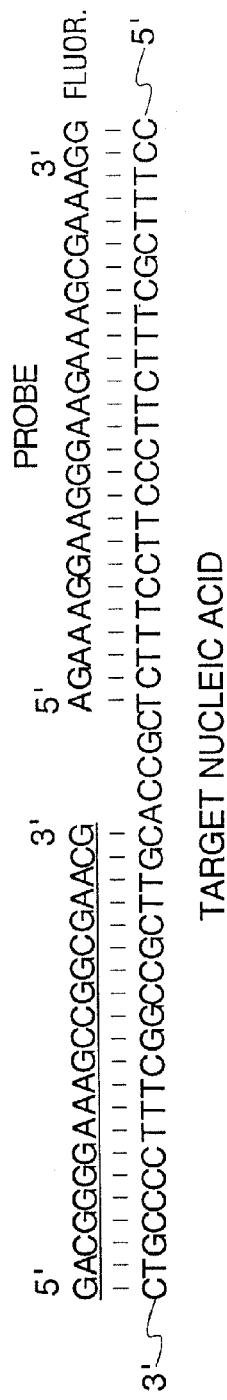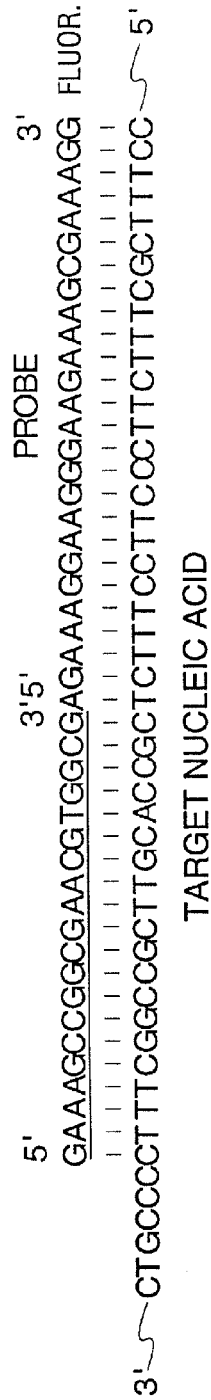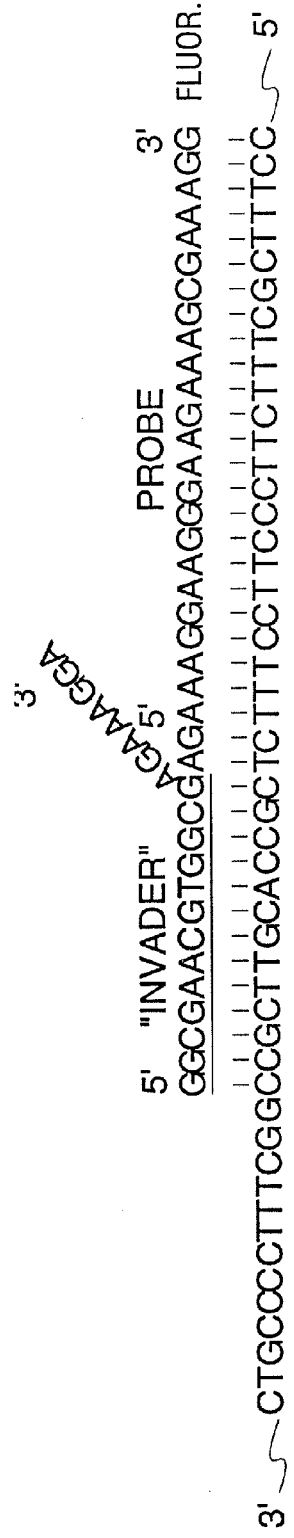
FIG. 28A
FIG. 28B
FIG. 28C

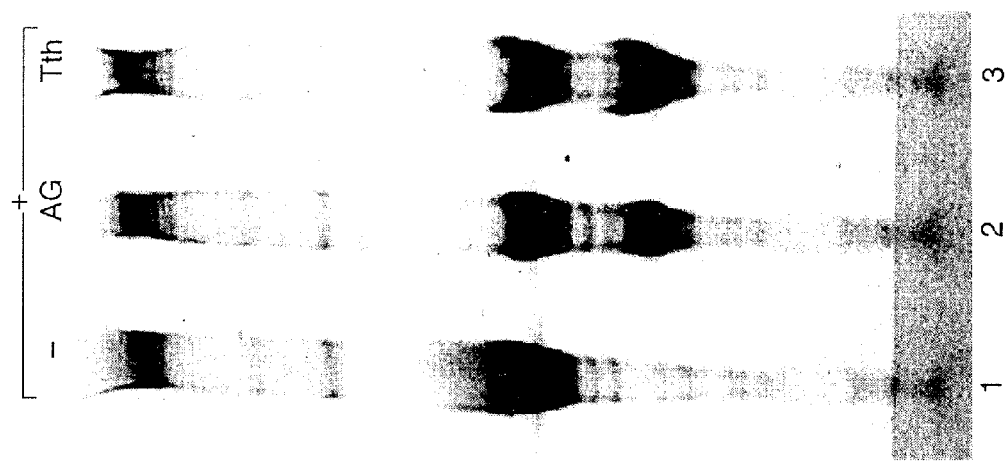
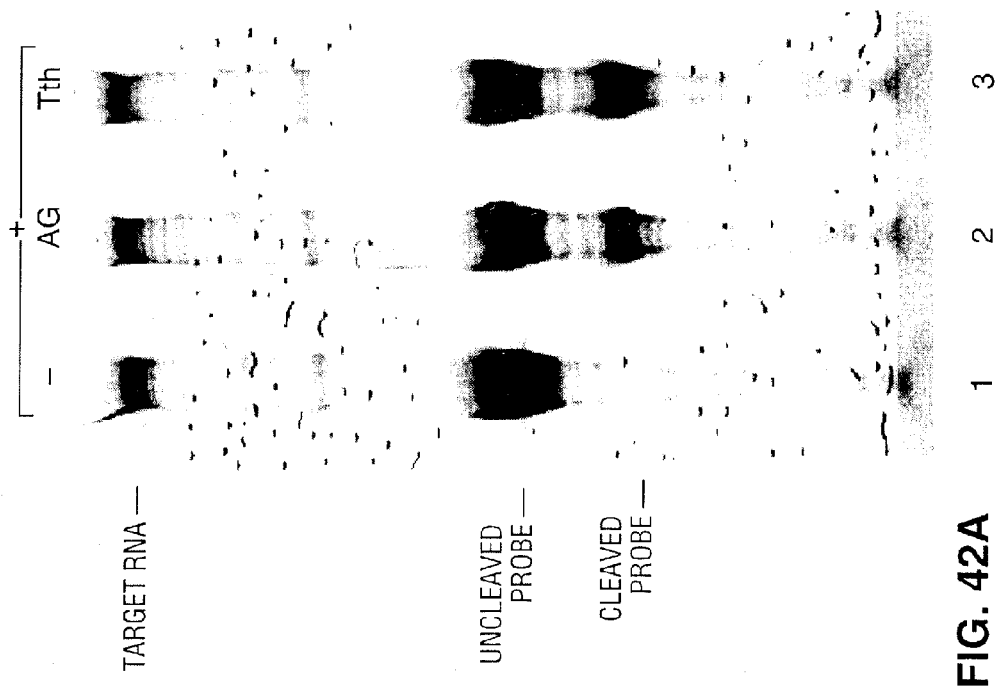
FIG. 42A
FIG. 42B

```
  1   MGVQ-----FGDFIPK--NIISFEDLKGKKVAIDGMNALYQFLTSIRLRDGSPILRNRKGEITSAYNGVFY    MJAFEN1.PRO
  1   MGVP-----IGEIIPR--KEIELENLYGKKIAIDALNAIYQFLSTIRQKDGTPLMDSKGRITSHLSGLFY    PFUFEN1.PRO
  1   MGIQGLAKLIADVAPSAIRENDIKSYFGRKVAIDASMSIYQFLIAVRQ-GGDVLQNEEGETTSHLMGMFY    HUMFEN1.PRO
  1   MGIHGLAKLIADVAPSAIRENDIKSYFGRKVAIDASMSIYQFLIAVRQ-GGDVLQNEEGETTS-LMGMFY    MUSFEN1.PRO
  1   MGIKGLNAIISEHVPSAIRKSDIKSFFGRKVAIDASMSLYQFLIAVRQQDGGQLTNEAGETTSHLMGMFY    YST510.PRO
  1   MGVHSFWDIAG-----PTARPVRLESLEDKRMAVDASIWIYQFLKAVRDQEGNAVKN-----SHITGFFR    YSTRAD2.PRO
  1   MGVSGLWNILE-----PVKRPVKLETLVNKRLAIDASIWIYQFLKAVRDKEGNQLKS-----SHVVGFFR    SPORAD13.PRO
  1   MGVQGLWKLLE-----CSGROVSPEALEGKILAVDISIWLNQALKGVRDRHGNSIEN-----PHLLTLFH    HUMXPG.PRO
  1   MGVQGLWKLLE-----CSGHRVSPEALEGKVLAVDISIWLNQALKGVRDSHGNVIEN-----AHLLTLFH    MUSXPG.PRO
  1   MGVQGLWKLLE-----CSGRPINPGTLEGKILAVDISIWLNQAVKGARDRQGNAIQN-----AHLLTLFH    XENXPG.PRO
  1   MTINGIWEWANHVV----RKVPNETMRDKTLSIDGHIWLYESLKGCEAHHQQT------PNSYLVTFFT    CELRAD2.PRO
         10        20        30        40        50        60        70

64   KTIHLLENDITPIWVFDGEPPKLKEKTRKVRREMKEKAELKMKEAIKK-----EDFEEAAKYAKRVSYLTP   MJAFEN1.PRO
 64   RTINLMEAGIKPVYVFDGEPPEFKKKELEKRREAREEAEEKWREALEK-----GEIEEARKYAQRATRVNE   PFUFEN1.PRO
 70   RTIRMMENGIKPVYVFDGKPPQLKSGELAKRSERRAEAEKQLQQAQAA-----GAEOEVEKFTKRLVKVTK   HUMFEN1.PRO
 69   RTIRM-ENGIKPVYVFDGKPPQLKSGELAKRSERRAEAEKQLQQAQEA-----GMEEEVEKFTKRLVKVTK   MUSFEN1.PRO
 71   RTLRMIDNGIKPCYVFDGKPPDLKSHELTKRSSRRVETEKKLA----EA-----TTELEKMKQERRLVKVSK   YST510.PRO
 61   RICKLLYFGIRPVFVFDGGVPVLKRETIRQKERRQGKRESAKSTARKLLALQLQNGSNDNKRDSDEVTM    YSTRAD2.PRO
 61   RICKLLFFGIKPVFVFDGGAPSLKRQTIQKRQARRLDREENATVTANKLLALQMRHQAMLLKRDADEVTQ    SPORAD13.PRO
 61   RLCKLLFFRIRPIFVFDGDAPLLKKQTLVKRQRKDLASSDSRKTTEKLLKTFLKRQAIKTERIAATVTG    HUMXPG.PRO
 61   RLCKLLFFRIRPIFVFDGDAPLLKKQTLAKRQRKDSASIDSRKTTEKLLKTFLKRQALKTDRIAASVTG    MUSXPG.PRO
 61   RLCKLLFFRIRPIFVFDGEAPLLKRQTLAKRRQRTDKASNDARKTNEKLLRTFLKRQAIKAERIAATVTG    XENXPG.PRO
 60   RIQRLLELKIIPIVVFDNINASSSAHESKDQNEFVPRKRRSFGDSPFTNLV-----------------    CELRAD2.PRO
         80        90       100       110       120       130       140
```

FIG. 59A

```
                430       440       450       460       470       480       490
314  ------------------------------------------------------------------------------                    MJAFEN1.PRO
327  ------------------------------------------------------------------------------                    PFUFEN1.PRO
348  -----------------------------------------------------------------------GSLS                       HUMFEN1.PRO
346  -----------------------------------------------------------------------GSLS                       MUSFEN1.PRO
351  ----------------------------------------------------------------------PK-T                        YST510.PRO
357  KRINEFF-----------------------------------------------------------------                          YSTRAD2.PRO
359  SNLTQFFEGGNTNVYAPRVAYHFKSKRLENALSSFKNQISNQSPMSEEIQADADAFGESKGSDELQSRIL                             SPORAD13.PRO
406  EKEFELLDKAKRKTQKRGITNTLEESSLKRKRLSDSKRKNTCGGFLGETCLSESSDGSSEHAESSSLM                               HUMXPG.PRO
406  EKEFELLDDAKGKTOKRELPYK------KETSVPKRRRPSGNGGFLGDPYCSESPQESSCEDGEGSSVM                              MUSXPG.PRO
403  ERECTNQRKGQKTNTKS---------QGTKRRKPTECSQEDQDPGGFIGIELKTLSSKAYSSD------                              XENXPG.PRO
322  MKECGWPATRTQKELALSIRRKVHLTTTVAQTRIPDFFAATKSKNFTPIVEPCESLEDYISANN-----T                             CELRAD2.PRO 500       510       520       530       540       550       560
314  ------------------------------------------------------NKTKQKTL                                   MJAFEN1.PRO
327  ------------------------------------------------------KSGKQSTL                                   PFUFEN1.PRO
352  SAKRKEPEPKGST----------------------------------------KKKAKTGAAG                                  HUMFEN1.PRO
350  SAKRKEPEPKGPA----------------------------------------KKKAKTGGAG                                  MUSFEN1.PRO
354  KEQLAAAAKRAQE----------------------------------------NKKLNKNKNK                                  YST510.PRO
364  ---------PREYISGDKKLNTSKRISTATGKL--------------------KK                                          YSTRAD2.PRO
429  RRKKMMASKNSSDSDSDSEDNFLASLTPKTNSSSISIENLPRKTKLSTSLL---KKP                                         SPORAD13.PRO
476  NVQRRTAAKEPKTSASDSONSVKEAPVKNGGATTSSSSDSDDDGGKEKMVLVTARSVFGKKRRKLRRARG                            HUMXPG.PRO
469  SARQRSAAESSKIGCSDVPDLVRDSPHGRQGCVSTSSSDSEDGEDKAKTVLVTARPVFGKKRRKLKSMK-                            MUSXPG.PRO
458  ----GSSSDAEDLPSGLIDKQSQSGIVGROKASNKVESSSSDDEDRTVMVTAKPVFQGKKTKSKTMKE                              XENXPG.PRO
387  WMRKRKRSESPQILQHHAKRQVPDRK--------------------------RSVKIRAFKPYPTDVI                              CELRAD2.PRO
```

FIG. 59D

```
     150        160        170        180        190        200        210
130  KMVENCKYLLSLMGIPYVEAPSEGEAQASYMAKKGDVWAVVSQDYDALLYGAPRVVRNLTTTKEM----    MJAFEN1.PRO
130  MLIEDAKKLLELMGIPIVQAPSEGEAQAAYMAAKGSVYASASQDYDSLLFGAPRLVRNLTITGKRKLPGK  PFUFEN1.PRO
136  QHNDECKHLLSLMGIPYLDAPSEAEASCAALVKAGKVYAAATEDMDCLTFGSPVLMRHLTASEAKKLPIQ  HUMFEN1.PRO
134  QHNDECKHLLSLMGIPYLDAPSEAEASCAALAKAGKVYAAATEDMDCLTFGSPVLMRHLTASEAKKLPIQ  MUSFEN1.PRO
134  EHNEEAQKLLGLMGIPYIIAPTEAEAQCAELLQLNLVDGIITDDSDVFLFGGTKIYKNMFHEKNY--VE   YST510.PRO
131  DMIKEVQELLSRFGIPYITAPMEAEAQCAELLQLNLVDGIITDDSDVFLFGGTKIYKNMFHEKNY--VE   YSTRAD2.PRO
131  VMIKECQELLRLFGLPYIVAPOEAEAQCSKLLELKLVDGIVTDDSDVFLFGGTRVYRNMFNQNKF---VE  SPORAD13.PRO
131  QMFLESQELIRLFGIPYIQAPMEAEAQCAILDLTDQTSGTITDDSDIWLFGARHVYRNFFNKNKF---VE  HUMXPG.PRO
131  QMFLESQELLRLFGVPYIQAPMEAEAOCAVLDLSDQTSGTITDDSDIWLFGARHVYKNFFNKNKF---VE  MUSXPG.PRO
131  QMCLESQELLQLFGIPYIVAPMEAEAQCAILDLTDQTSGTITDDSDYFLFGGKNLYRFDFTAGT-----   XENXPG.PRO
111  DHVYKTNALLTELGIKVIIAPGDGEAQCARLEQLGVTSGCITTDFDYFLFGGKNLYRFDFTAGT-----   CELRAD2.PRO 220        230        240        250        260        270        280
195  ------PELIELNEVLEDIRISLDDLIDIAIFMGTDYNPGGV-K--GIGFKRAYELVRSGVAK--DV     MJAFEN1.PRO
200  NVYVE-IKPELIILEEVLKELKLTREKLIELAILVGTDYNPGGI--K--GIGLKKALEIVRHSKDPLAKF  PFUFEN1.PRO
206  EFHLSRILQELGLNQEQFVDLCILLGSDYCESIRGIGPKRAVDLIQK--HKSIEEIVRRLDPN----KY   HUMFEN1.PRO
204  EFHLSRVIQELGLNQEQFVDLCILLGSDYCESIRGIGAKRAVDLIQK--HKSIEEIVRRLDPS----KY   MUSFEN1.PRO
204  EIDTELVLRGLDLTIEQFVDLCIMLGCDYCESIRGVGPVTALKLIKT--HGSIEKIVEFIESGESNNTKW  YST510.PRO
198  FYDAESILKLLGLDRKNMIELAQLLGSDYTNGLKGMGPVSSIEVIAEF---GNLKNFKDWYNNGOFDKRK  YSTRAD2.PRO
198  LYLMDDMKREFNVVNQMDLIKLAHLLGSDYTMGLSRVGPVLALEILHEFPGDTGLFEFKKWFQRLSTGHAS SPORAD13.PRO
119  YYQYVDFHNQLGLDRNKLINLAYLLGSDYTEGIPTVGCVTAMEILNEFPGHGLEPLLKFSEWWHEAQKNP  HUMXPG.PRO
198  YYQYVDFYSQLGLDRNKLINLAYLLGSDYTEGIPTVGCVTAMEILNEFPGRGLDPLLKFSEWWHEAQNNK  MUSXPG.PRO
198  YYQYADIHNOLGLDRSKLINLAYLLGSDYTEGIPTVGYVSAMEILNEFPGQGLEPLVKFKEWWSEAQKDK  XENXPG.PRO
175  --------SSTACLHDIMHLSLGRMFM---------------------------------------     CELRAD2.PRO
```

FIG. 59B

```
           290        300        310        320        330        340        350
251 LKKEVEYYDEIKRIFKEPKV---------------------------TD--NYSLSLKLPDKEGIIKFLVDENDFNYD  MJAFEN1.PRO
265 QKQSDVDLYAIKEFFLNPPV---------------------------TD--NYNLVWRDPDEEGILKFLCDEHDFSEE  PFUFEN1.PRO
269 PVPENWLHKEAHQLFLEPEV-----------------------LDPESVELKWSEPNEEELIKFMCGEKQFSEE     HUMFEN1.PRO
267 PVPENWLHKEAQQLFLEPEV-----------------------VDPESVELKWSEPNEEELVKFMCGEKQFSEE     MUSFEN1.PRO
272 KIPEDWPYKQARMLFLDPEV---------------------IDGNEINLKWSPPKEKELIEYLCDDKKFSEE       YST510.PRO
265 QETENKFEKDLRKKLVNNEIILDDDFPSVMVYDAYMRPEVDHDTTPFVWGVPDLDMLRSFMKTQLGWPHE          YSTRAD2.PRO
268 KNDVNTPVKKRINKLVGK--IILPSEFPNPLVDEAYLHPAVDDSKQSFQWGIPDLDELRQFLMATVGWSKQ         SPORAD13.PRO
268 KIRPNPHDTKVKKL--RTLQLTPGFPNPAVAEAYLKPVVDDSKGSFLWGKPDLDKIREFCQRYFGWNRT           HUMXPG.PRO
268 KVAENPYDTKVKKL--RKLQLTPGFPNPAVADAYLRPVVDDSRGSFLWGKPDVDKIREFCORYFGWNRM           MUSXPG.PRO
268 KMRPNPNDTKVKKL--RLLDLQQSFPNPAVASAYLKPVVDESKSAFSWGRPDLEQIREFCESRFGWYRL           XENXPG.PRO
194 ----EKKVSRPHLISTAILLGCDYFORGVQNIGIVSVFD-ILGEFGDDGNEEIDPHVILDRFASYVRE            CELRAD2.PRO 360        370        380        390        400        410        420
300 RVKKHVDKLYNLIA--------------------------------------------                     MJAFEN1.PRO
314 RVKNGLERLKKAI---------------------------------------------                     PFUFEN1.PRO
320 RIRSGVKRLSKSRQGS-TQGRLDDFFKVT-----------------------------                     HUMFEN1.PRO
318 RIRSGVKRLSKSRQGS-TQGRLDDFFKVT-----------------------------                     MUSFEN1.PRO
323 RVKSGISRLKKGLKSG-IQGRLDGFFQVV-----------------------------                     YST510.PRO
335 KSDEILIPLIRDVNKRKK--------------------------------KGKQ                        YSTRAD2.PRO
337 RTNEVLLPVIQDMHKKOF--------------------------------VGTQ                        SPORAD13.PRO
336 KTDESLFPVLKQLDAQQTQLRIDSFFRLAQQEKEDAKRIKSQRLNRAVTCMLRKEKEAAASEIEAVSVAM          HUMXPG.PRO
336 KTDESLYPVLKHLNAHQTQLRIDSFFRLAQQEKQDAKLIKSHRLSRAVTCMLRKEREEKAPELTKVTEAM          MUSXPG.PRO
336 KTDEVLLPVLKQLNAQQTQLRIDSFFRLEQHEAAG---LKSQRLRRAVTCMKRKERDVEAEEVEAAVAVM          XENXPG.PRO
257 EIPARSEDTQRKLRLRRKKYNFPVGFPNCDAVHNAITMYLRPPVSSEIPKIIPR----AANFQQVAEIM          CELRAD2.PRO
```

FIG. 59C

```
322 DAWFKZ    MJAFEN1.PRO
335 ESWFKR    PFUFEN1.PRO
375 KFKRGK    HUMFEN1.PRO
373 KFRRGK    MUSFEN1.PRO
377 VTKGRR    YST510.PRO
390 ---RKM    YSTRAD2.PRO
483 SKRRRK    SPORAD13.PRO
546 RKRKTZ    HUMXPG.PRO
538 RRKKKT    MUSXPG.PRO
523 TVKRK     XENXPG.PRO
429 ELGDSD    CELRAD2.PRO
```

FIG. 59E

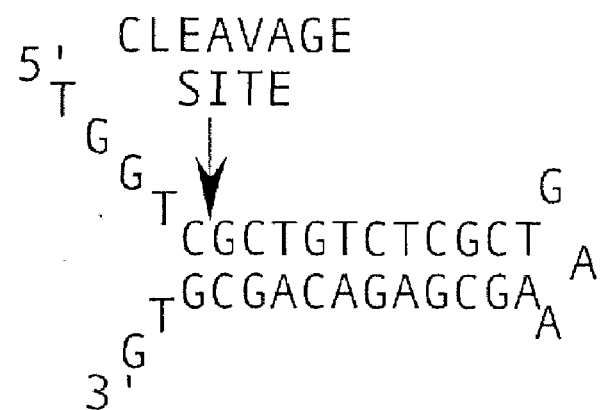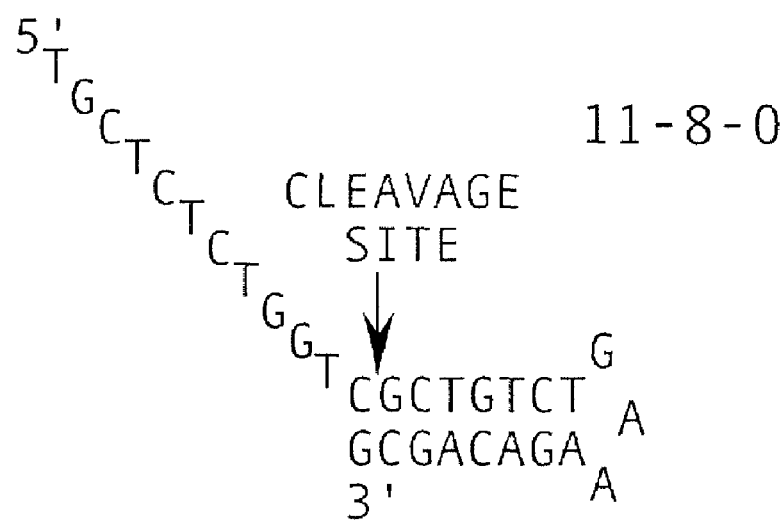
FIG. 60

5'-nAGAAAggaagggaagaaaagcgaaagG-3'

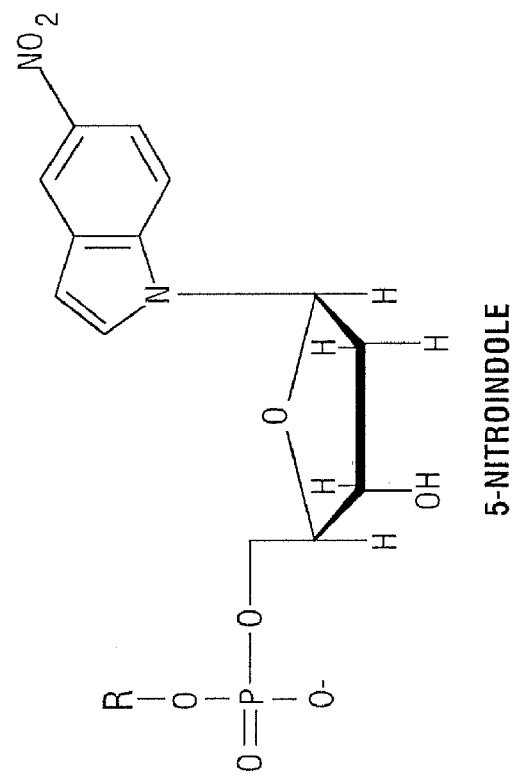
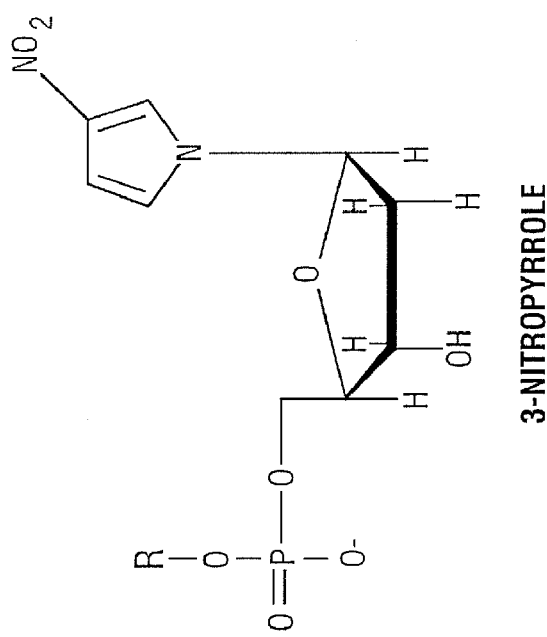
FIG. 73

F1
5' GTTCTCTGCTCTCTGGT  1819
                      ↓↓
                      CGCTGTCTCGCTTGT G A
                      GCGACAGAGCGAACA A
3' GCTCTCTGGT                        A

FIG. 78A

F1
5' GTTCTCTGCTCTCTGGTCGCT  2122
                          ↓↓
                          GTCTCGCTTGT G A
3' GCTCTCTGGTGCGACAGAGCGAACA A
5' CGAGAGACCACGCT          A
   P15          G

FIG. 78B

CONCENTRATION OF PROBE W/ AND W/O STACKER vs TEMP

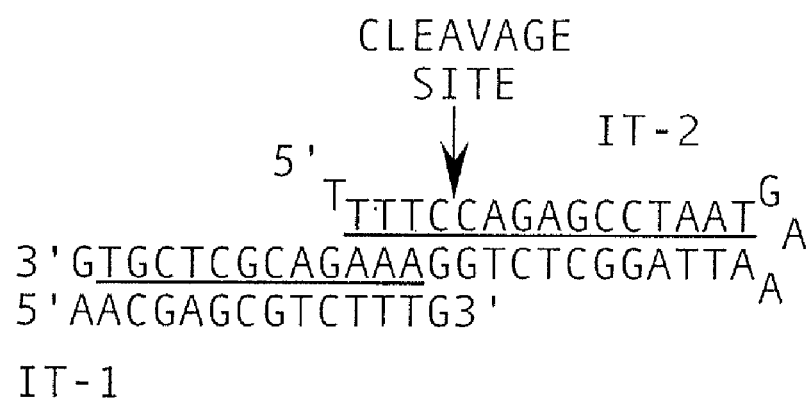
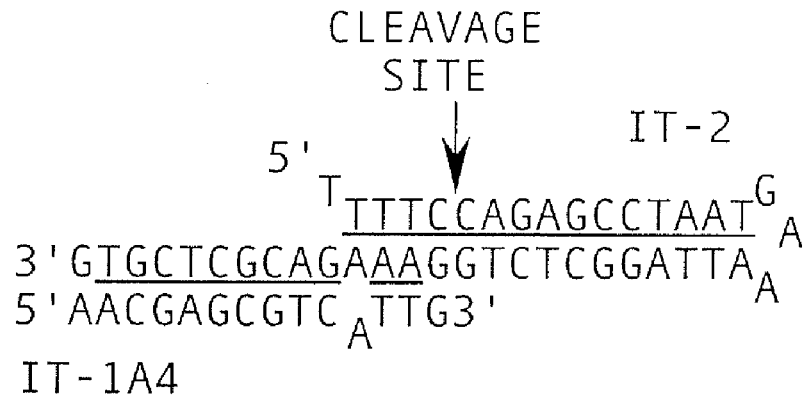
FIG. 81

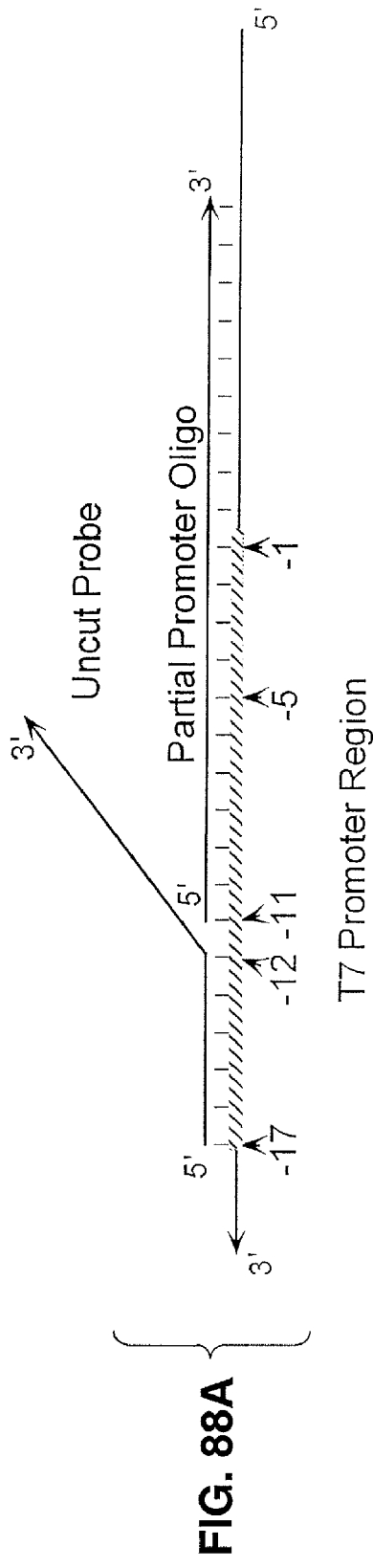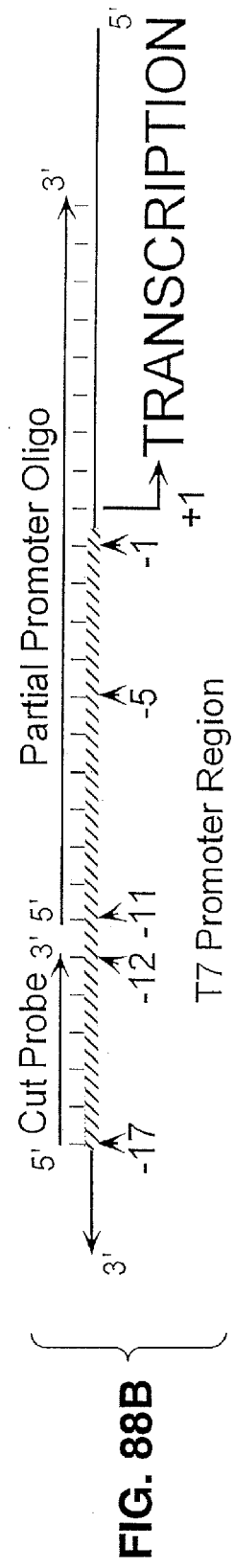
FIG. 88A
FIG. 88B

FIG. 93C 1  3'-gctttaattatgctgagtgatatcccagaagatacctccagttttgt-5'
   |——|——|——|——|——|
   -23 -20 -15 -10 -5 -1
   | T7 promoter region |

2  5'-cgaaattaatacgactcactata-3'
   3'-gctttaattatgctgagtgatatcccagaagatacctccagttttgt-5'
   |——|——|——|——|——|
   -23 -20 -15 -10 -5 -1
   | T7 promoter region |

073-065

3  5'-cgaaattaatacgactcactataccagaa-3'
   3'-gctttaattatgctgagtgatatcccagaagatacctccagttttgt-5'
   |——|——|——|——|——|
   -23 -20 -15 -10 -5 -1
   | T7 promoter region |

4  NO DNA

PR1 probe               Cleavage site
                             ▼
                5'FITTTTCCAGAGCCTAAT$^{G3'}$ IT3 Invader-Target $_A$$^A$ACGAGCGTCTTT$^{G3'}$
      GTGCTCGCAGAAGGTCTCGGATTAATTTTTTTTT5'

IT3-8 Invader-Target $_A$$^A$AGCGTCTT$^{G3'}$
      $_G$TCGCAGAAGGTCTCGGATTAATTTTTTTTT5'

IT3-6 Invader-Target $_A$$^A$CGTCTT$^{G3'}$
      $_G$GCAGAAGGTCTCGGATTAATTTTTTTTT5'

IT3-4 Invader-Target $_A$$^A$TCTT$^{G3'}$
      GAGAAGGTCTCGGATTAATTTTTTTTT5'

IT3-3 Invader-Target $_A$$^A$CTT$^{G3'}$
      GGAAGGTCTCGGATTAATTTTTTTTT5'

IT3-0 Invader-Target

3'GAAGGTCTCGGATTAATTTTTTTTT5'

FIG. 98

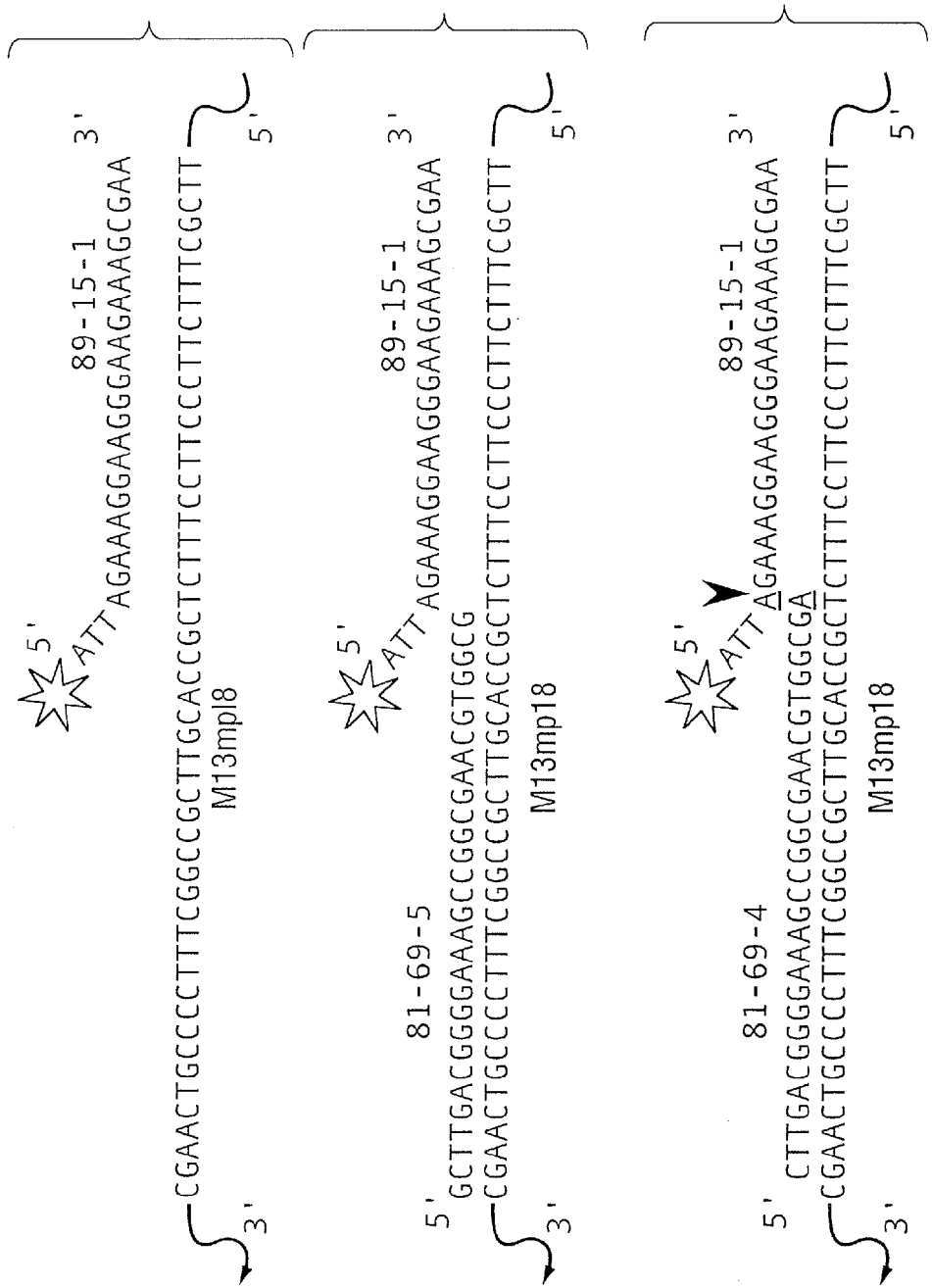

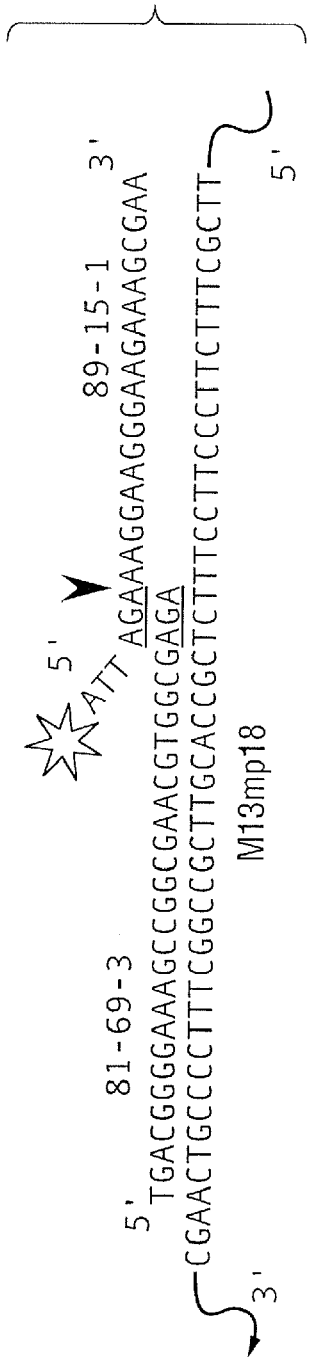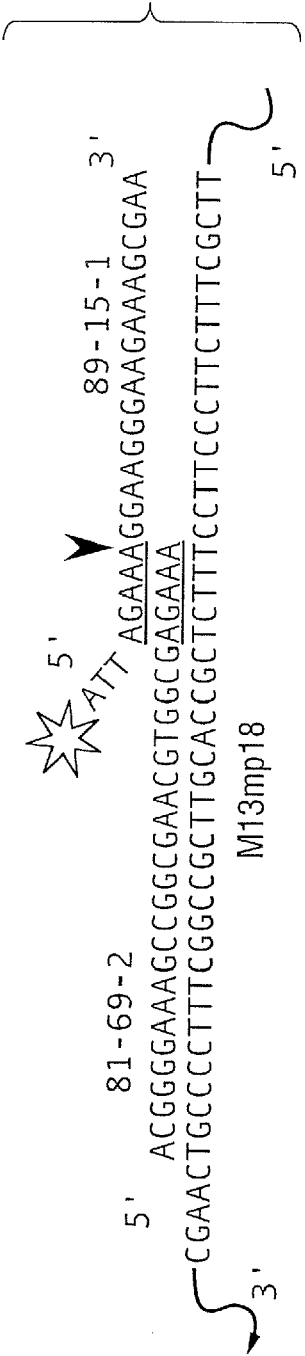

| attomoles/target | basic invader | invader sqrd |
|---|---|---|
| 1 | | 8386 |
| 10 | | 133185 |
| 100 | 8512 | 1862211 |

1 2 3 4 5 6 7 8

← 1: uncut

← 2: uncut

← 2: cut

FIG. 102

SEQUENCE LISTING

```
<160> NUMBER OF SEQ ID NOS: 410

<210> SEQ ID NO 1
<211> LENGTH: 2506
<212> TYPE: DNA
<213> ORGANISM: Thermus aquaticus

<400> SEQUENCE: 1
atgaggggga tgctgcccct ctttgagccc aagggccggg tcctcctggt ggacggccac      60
cacctggcct accgcacctt ccacgccctg aagggcctca ccaccagccg gggggagccg     120
gtgcaggcgg tctacggctt cgccaagagc ctcctcaagg ccctcaagga ggacggggac     180
gcggtgatcg tggtctttga cgccaaggcc ccctccttcc gccacgaggc ctacggcggg     240
tacaaggcgg gccgggcccc cacgccggag gactttcccc ggcaactcgc cctcatcaag     300
gagctggtgg acctcctggg gctggcgcgc ctcgaggtcc cgggctacga ggcggacgac     360
gtcctggcca gcctggccaa gaaggcggaa aaggagggct acgaggtccg catcctcacc     420
gccgacaaag acctttacca gctcctttcc gaccgcatcc acgtcctcca ccccgagggg     480
tacctcatca ccccggcctg gctttgggaa aagtacggcc tgaggcccga ccagtgggcc     540
```

```
gactaccggg ccctgaccgg ggacgagtcc gacaaccttc ccggggtcaa gggcatcggg      600
gagaagacgg cgaggaagct tctggaggag tgggggagcc tggaagccct cctcaagaac      660
ctggaccggc tgaagcccgc catccgggag aagatcctgg cccacatgga cgatctgaag      720
ctctcctggg acctggccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc ccctggccc       900 ccgccggaag gggccttcgt gggctttgtg ctttcccgca aggagcccat gtgggccgat      960
cttctggccc tggccgccgc caggggggc cgggtccacc gggcccccga gccttataaa      1020
gccctcaggg acctgaagga ggcgcggggg cttctcgcca agacctgag cgttctggcc      1080 ctgagggaag gccttggcct cccgccggc gacgacccca tgctcctcgc ctacctcctg      1140
gacccttcca acaccacccc cgagggggtg gcccggcgct acggcgggga gtggacggag      1200
gaggcggggg agcgggccgc cctttccgag aggctcttcg ccaacctgtg ggggaggctt      1260
gagggggagg agaggctcct ttggctttac cgggaggtgg agaggcccct ttccgctgtc      1320
ctggcccaca tggaggccac gggggtgcgc ctggacgtgg cctatctcag ggccttgtcc      1380
ctggaggtgg ccgaggagat cgcccgcctc gaggccgagg tcttccgcct ggccggccac      1440
cccttcaacc tcaactcccg ggaccagctg gaaagggtcc tctttgacga gctagggctt      1500
cccgccatcg gcaagacgga aagaccggc aagcgctcca ccagcgccgc cgtcctggag      1560
gccctccgcg aggcccaccc catcgtggag aagatcctgc agtaccggga gctcaccaag      1620
ctgaagagca cctacattga ccccttgccg gacctcatcc accccaggac gggccgcctc      1680
cacacccgct tcaaccagac ggccacggcc acgggcaggc taagtagctc cgatcccaac      1740
ctccagaaca tccccgtccg caccccgctt gggcagagga tccgccgggc cttcatcgcc      1800
gaggaggggt ggctattggt ggccctggac tatagccaga tagagctcag ggtgctggcc      1860
cacctctccg gcgacgagaa cctgatccgg gtcttccagg aggggcggga catccacacg      1920
gagaccgcca gctggatgtt cggcgtcccc cgggaggccg tggacccct gatgcgccgg      1980 gcggccaaga ccatcaactt cggggtcctc tacggcatgt cggcccaccg cctctcccag      2040
gagctagcca tccttacga ggaggcccag gccttcattg agcgctactt tcagagcttc      2100
cccaaggtgc gggcctggat tgagaagacc ctggaggagg caggaggcg ggggtacgtg      2160 gagaccctct tcggccgccg ccgctacgtg ccagacctag aggcccgggt gaagagcgtg      2220
cgggaggcgg ccgagcgcat ggccttcaac atgcccgtcc agggcaccgc cgccgacctc      2280
atgaagctgg ctatggtgaa gctcttcccc aggctggagg aaatgggggc caggatgctc      2340
cttcaggtcc acgacgagct ggtcctcgag gccccaaaag agagggcgga ggccgtggcc      2400
cggctggcca aggaggtcat ggaggggtg tatcccctgg ccgtgcccct ggaggtggag      2460
gtggggatag ggaggactg gctctccgcc aaggagtgat accacc                     2506
```

<210> SEQ ID NO 2
<211> LENGTH: 2496
<212> TYPE: DNA
<213> ORGANISM: Thermus flavus

<400> SEQUENCE: 2

```
atggcgatgc ttcccctctt tgagcccaaa ggccgcgtgc tcctggtgga cggccaccac       60
ctggcctacc gcaccttctt tgccctcaag ggcctcacca ccagccgcgg cgaacccgtt      120
caggcggtct acggcttcgc caaaagcctc ctcaaggccc tgaaggagga cggggacgtg      180
```

```
gtggtggtgg tctttgacgc caaggccccc tccttccgcc acgaggccta cgaggcctac    240
aaggcgggcc gggcccccac cccggaggac tttccccggc agctggccct catcaaggag    300
ttggtggacc tcctaggcct tgtgcggctg gaggttcccg gctttgaggc ggacgacgtg    360
ctggccaccc tggccaagcg ggcggaaaag gaggggtacg aggtgcgcat cctcactgcc    420
gaccgcgacc tctaccagct cctttcggag cgcatcgcca tcctccaccc tgaggggtac    480
ctgatcaccc cggcgtggct ttacgagaag tacggcctgc gcccggagca gtgggtggac    540
taccgggccc tggcggggga cccctcggat aacatccccg gggtgaaggg catcggggag    600
aagaccgccc agaggctcat ccgcgagtgg gggagcctgg aaaacctctt ccagcacctg    660
gaccaggtga agccctcctt gcgggagaag ctccaggcgg gcatggaggc cctggccctt    720
tcccggaagc tttcccaggt gcacactgac ctgcccctgg aggtggactt cgggaggcgc    780
cgcacaccca acctgagggg tctgcgggct tttttggagc ggttggagtt tggaagcctc    840
ctccacgagt tcggcctcct ggaggggccg aaggcggcag aggaggcccc ctggccccct    900
ccggaagggg cttttttggg cttttccttt tccgtcccg agcccatgtg ggccgagctt    960
ctggccctgg ctggggcgtg ggagggggcgc ctccatcggg cacaagaccc ccttagggg    1020 ctgagggacc ttaaggggt gcggggaatc ctggccaagg acctggcggt tttggccctg    1080
cgggagggcc tggacctctt cccagaggac gaccccatgc tcctggccta ccttctggac    1140
ccctccaaca ccaccccctga gggggtggcc cggcgttacg ggggggagtg gacgaggat    1200 gcggggggaga gggccctcct ggccgagcgc ctcttccaga ccctaaagga gcgccttaag    1260
ggagaagaac gcctgctttg gctttacgag gaggtggaga agccgctttc ccgggtgttg    1320
gcccggatgg aggccacggg ggtccggctg gacgtggcct acctccaggc cctctccctg    1380
gaggtggagg cggaggtgcg ccagctggag gaggaggtct tccgcctggc cggccacccc    1440
ttcaacctca actcccgcga ccagctggag cgggtgctct tgacgagct gggcctgcct    1500 gccatcggca agacggagaa gacggggaaa cgctccacca gcgctgccgt gctggaggcc    1560
ctgcgagagg cccaccccat cgtggaccgc atcctgcagt accgggagct caccaagctc    1620
aagaacacct acatagaccc cctgcccgcc ctggtccacc caagaccgg ccggctccac    1680 acccgcttca accagacggc caccgccacg ggcaggcttt ccagctccga ccccaacctg    1740
cagaacatcc ccgtgcgcac ccctctgggc cagcgcatcc gccgagcctt cgtggccgag    1800
gagggctggg tgctggtggt cttggactac agccagattg agcttcgggt cctggcccac    1860
ctctccgggg acgagaacct gatccgggtc tttcaggagg ggagggacat ccacacccag    1920
accgccagct ggatgttcgg cgtttccccc gaaggggtag accctctgat gcgccgggcg    1980
gccaagacca tcaacttcgg ggtgctctac ggcatgtccg cccaccgcct ctccggggag    2040
ctttccatcc cctacgagga ggcggtggcc ttcattgagc gctacttcca gagctacccc    2100
aaggtgcggg cctggattga ggggaccctc gaggagggcc gccggcgggg gtatgtggag    2160
accctcttcg gccgccggcg ctatgtgccc gacctcaacg cccgggtgaa gagcgtgcgc    2220
gaggcggcgg agcgcatggc cttcaacatg ccggtccagg gcaccgccgc cgacctcatg    2280
aagctggcca tggtgcggct ttttccccgg cttcaggaac tggggcgag gatgcttttg    2340 caggtgcacg acgagctggt cctcgaggcc cccaaggacc gggcggagag ggtagccgct    2400
ttggccaagg aggtcatgga gggggtctgg cccctgcagg tgcccctgga ggtggaggtg    2460
ggcctggggg aggactggct ctccgccaag gagtag                              2496
```

<210> SEQ ID NO 3
<211> LENGTH: 2504
<212> TYPE: DNA
<213> ORGANISM: Thermus thermophilus

<400> SEQUENCE: 3

| | | | | | |
|---|---|---|---|---|---|
| atggaggcga | tgcttccgct | ctttgaaccc | aaaggccggg | tcctcctggt ggacggccac | 60 |
| cacctggcct | accgcacctt | cttcgccctg | aagggcctca | ccacgagccg gggcgaaccg | 120 |
| gtgcaggcgg | tctacggctt | cgccaagagc | ctcctcaagg | ccctgaagga ggacgggtac | 180 |
| aaggccgtct | tcgtggtctt | tgacgccaag | gcccccttcct | tccgcacga ggcctacgag | 240 |
| gcctacaagg | cggggagggc | ccgacccccc | gaggacttcc | cccggcagct cgccctcatc | 300 |
| aaggagctgt | tggacctcct | ggggtttacc | cgcctcgagg | tccccggcta cgaggcggac | 360 |
| gacgttctcg | ccaccctggc | caagaaggcg | aaaaggagg | ggtacgaggt gcgcatcctc | 420 |
| accgccgacc | gcgacctcta | ccaactcgtc | tccgaccgcg | tcgccgtcct ccaccccgag | 480 |
| ggccacctca | tcaccccgga | gtggctttgg | gagaagtacg | gcctcaggcc ggagcagtgg | 540 |
| gtggacttcc | gcgccctcgt | gggggacccc | tccgacaacc | tccccggggt caagggcatc | 600 |
| ggggagaaga | ccgccctcaa | gctcctcaag | gagtggggaa | gcctggaaaa cctcctcaag | 660 |
| aacctggacc | gggtaaagcc | agaaaacgtc | cgggagaaga | tcaaggccca cctggaagac | 720 |
| ctcaggctct | ccttggagct | ctcccgggtg | cgcaccgacc | tcccccctgga ggtggacctc | 780 |
| gcccaggggc | gggagcccga | ccgggagggg | cttaggggcct | tcctggagag gctggagttc | 840 |
| ggcagcctcc | tccacgagtt | cggcctcctg | gaggcccccg | ccccccctgga ggaggccccc | 900 |
| tggcccccgc | cggaagggggc | cttcgtgggc | ttcgtcctct | cccgccccga gcccatgtgg | 960 |
| gcggagctta | agccctggcc | cgcctgcagg | gacgccgggt | gcaccgggc agcagacccc | 1020 |
| ttggcgggggc | taaaggacct | caaggaggtc | cggggcctcc | tcgccaagga cctcgccgtc | 1080 |
| ttggcctcga | gggagggggct | agacctcgtg | cccggggacg | accccatgct cctcgcctac | 1140 |
| ctcctggacc | cctccaacac | cacccccgag | ggggtggcgc | ggcgctacgg ggggagtgg | 1200 |
| acggaggacg | ccgcccaccg | ggccctcctc | tcggagaggc | tccatcggaa cctccttaag | 1260 |
| cgcctcgagg | gggaggagaa | gctcctttgg | ctctaccacg | aggtggaaaa gccctctcc | 1320 |
| cgggtcctgg | cccacatgga | ggccaccggg | gtacggctgg | acgtggccta ccttcaggcc | 1380 |
| ctttccctgg | agcttgcgga | ggagatccgc | cgcctcgagg | aggaggtctt ccgcttggcg | 1440 |
| ggccaccccct | tcaacctcaa | ctcccgggac | cagctggaaa | gggtgctctt tgacgagctt | 1500 |
| aggcttcccg | ccttggggaa | gacgcaaaag | acaggcaagc | gctccaccag cgccgcggtg | 1560 |
| ctggaggccc | tacgggaggc | ccaccccatc | gtggagaaga | tcctcagca ccgggagctc | 1620 |
| accaagctca | gaacaccta | cgtggacccc | ctcccaagcc | tcgtccaccc gaggacgggc | 1680 |
| cgcctccaca | cccgcttcaa | ccagacggcc | acggccacgg | gggaggcttag tagctccgac | 1740 |
| cccaacctgc | agaacatccc | cgtccgcacc | cccttgggcc | agaggatccg ccgggccttc | 1800 |
| gtggccgagg | cgggttgggc | gttggtggcc | ctggactata | gccagataga gctccgcgtc | 1860 |
| ctcgcccacc | tctccgggga | cgaaaacctg | atcagggtct | tccaggaggg gaaggacatc | 1920 |
| cacacccaga | ccgcaagctg | gatgttcggc | gtcccccgg | aggccgtgga ccccctgatg | 1980 |
| cgccgggcg | ccaagacggt | gaacttcggc | gtcctctacg | gcatgtccgc ccataggctc | 2040 |
| tcccaggagc | ttgccatccc | ctacgaggag | gcggtggcct | ttatagaggc tacttccaaa | 2100 |
| gcttccccaa | ggtgcgggcc | tggatagaaa | agaccctgga | ggaggggagg aagcggggct | 2160 |

-continued

```
acgtggaaac cctcttcgga agaaggcgct acgtgcccga cctcaacgcc cgggtgaaga    2220
gcgtcaggga ggccgcggag cgcatggcct tcaacatgcc cgtccagggc accgccgccg    2280
acctcatgaa gctcgccatg gtgaagctct tcccccgcct ccgggagatg ggggcccgca    2340
tgctcctcca ggtccacgac gagctcctcc tggaggcccc ccaagcgcgg gccgaggagg    2400
tggcggcttt ggccaaggag gccatggaga aggcctatcc cctcgccgtg cccctggagg    2460
tggaggtggg gatgggggag gactggcttt ccgccaaggg ttag                     2504
```

<210> SEQ ID NO 4
<211> LENGTH: 832
<212> TYPE: PRT
<213> ORGANISM: Thermus aquaticus

<400> SEQUENCE: 4

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
```

-continued

```
            305                 310                 315                 320
        Leu Leu Ala Leu Ala Ala Ala Arg Gly Gly Arg Val His Arg Ala Pro
                        325                 330                 335
        Glu Pro Tyr Lys Ala Leu Arg Asp Leu Lys Glu Ala Arg Gly Leu Leu
                        340                 345                 350
        Ala Lys Asp Leu Ser Val Leu Ala Leu Arg Glu Gly Leu Gly Leu Pro
                        355                 360                 365
        Pro Gly Asp Asp Pro Met Leu Leu Ala Tyr Leu Leu Asp Pro Ser Asn
                        370                 375                 380
        Thr Thr Pro Glu Gly Val Ala Arg Arg Tyr Gly Gly Glu Trp Thr Glu
        385                 390                 395                 400
        Glu Ala Gly Glu Arg Ala Ala Leu Ser Glu Arg Leu Phe Ala Asn Leu
                        405                 410                 415
        Trp Gly Arg Leu Glu Gly Glu Glu Arg Leu Leu Trp Leu Tyr Arg Glu
                        420                 425                 430
        Val Glu Arg Pro Leu Ser Ala Val Leu Ala His Met Glu Ala Thr Gly
                        435                 440                 445
        Val Arg Leu Asp Val Ala Tyr Leu Arg Ala Leu Ser Leu Glu Val Ala
                        450                 455                 460
        Glu Glu Ile Ala Arg Leu Glu Ala Glu Val Phe Arg Leu Ala Gly His
        465                 470                 475                 480
        Pro Phe Asn Leu Asn Ser Arg Asp Gln Leu Glu Arg Val Leu Phe Asp
                        485                 490                 495
        Glu Leu Gly Leu Pro Ala Ile Gly Lys Thr Glu Lys Thr Gly Lys Arg
                        500                 505                 510
        Ser Thr Ser Ala Ala Val Leu Glu Ala Leu Arg Glu Ala His Pro Ile
                        515                 520                 525
        Val Glu Lys Ile Leu Gln Tyr Arg Glu Leu Thr Lys Leu Lys Ser Thr
                        530                 535                 540
        Tyr Ile Asp Pro Leu Pro Asp Leu Ile His Pro Arg Thr Gly Arg Leu
        545                 550                 555                 560
        His Thr Arg Phe Asn Gln Thr Ala Thr Ala Thr Gly Arg Leu Ser Ser
                        565                 570                 575
        Ser Asp Pro Asn Leu Gln Asn Ile Pro Val Arg Thr Pro Leu Gly Gln
                        580                 585                 590
        Arg Ile Arg Arg Ala Phe Ile Ala Glu Glu Gly Trp Leu Leu Val Ala
                        595                 600                 605
        Leu Asp Tyr Ser Gln Ile Glu Leu Arg Val Leu Ala His Leu Ser Gly
                        610                 615                 620
        Asp Glu Asn Leu Ile Arg Val Phe Gln Glu Gly Arg Asp Ile His Thr
        625                 630                 635                 640
        Glu Thr Ala Ser Trp Met Phe Gly Val Pro Arg Glu Ala Val Asp Pro
                        645                 650                 655
        Leu Met Arg Arg Ala Ala Lys Thr Ile Asn Phe Gly Val Leu Tyr Gly
                        660                 665                 670
        Met Ser Ala His Arg Leu Ser Gln Glu Leu Ala Ile Pro Tyr Glu Glu
                        675                 680                 685
        Ala Gln Ala Phe Ile Glu Arg Tyr Phe Gln Ser Phe Pro Lys Val Arg
                        690                 695                 700
        Ala Trp Ile Glu Lys Thr Leu Glu Glu Gly Arg Arg Arg Gly Tyr Val
        705                 710                 715                 720
        Glu Thr Leu Phe Gly Arg Arg Arg Tyr Val Pro Asp Leu Glu Ala Arg
                        725                 730                 735
```

```
Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 5
<211> LENGTH: 831
<212> TYPE: PRT
<213> ORGANISM: Thermus flavus

<400> SEQUENCE: 5

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Asp Val Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
            100                 105                 110

Pro Gly Phe Glu Ala Asp Asp Val Leu Ala Thr Leu Ala Lys Arg Ala
            115                 120                 125

Glu Lys Glu Gly Tyr Glu Val Arg Ile Leu Thr Ala Asp Arg Asp Leu
        130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
            180                 185                 190

Pro Gly Val Lys Gly Ile Gly Glu Lys Thr Ala Gln Arg Leu Ile Arg
            195                 200                 205

Glu Trp Gly Ser Leu Glu Asn Leu Phe Gln His Leu Asp Gln Val Lys
        210                 215                 220

Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
                245                 250                 255

Phe Gly Arg Arg Arg Thr Pro Asn Leu Glu Gly Leu Arg Ala Phe Leu
            260                 265                 270

Glu Arg Leu Glu Phe Gly Ser Leu Leu His Glu Phe Gly Leu Leu Glu
```

-continued

```
            275                 280                 285
Gly Pro Lys Ala Ala Glu Glu Ala Pro Trp Pro Pro Glu Gly Ala
            290                 295                 300
Phe Leu Gly Phe Ser Phe Ser Arg Pro Glu Pro Met Trp Ala Glu Leu
305                 310                 315                 320
Leu Ala Leu Ala Gly Ala Trp Glu Gly Arg Leu His Arg Ala Gln Asp
                    325                 330                 335
Pro Leu Arg Gly Leu Arg Asp Leu Lys Gly Val Arg Gly Ile Leu Ala
                340                 345                 350
Lys Asp Leu Ala Val Leu Ala Leu Arg Glu Gly Leu Asp Leu Phe Pro
            355                 360                 365
Glu Asp Asp Pro Met Leu Leu Ala Tyr Leu Leu Asp Pro Ser Asn Thr
        370                 375                 380
Thr Pro Glu Gly Val Ala Arg Arg Tyr Gly Gly Glu Trp Thr Glu Asp
385                 390                 395                 400
Ala Gly Glu Arg Ala Leu Leu Ala Glu Arg Leu Phe Gln Thr Leu Lys
                    405                 410                 415
Glu Arg Leu Lys Gly Glu Glu Arg Leu Leu Trp Leu Tyr Glu Glu Val
                420                 425                 430
Glu Lys Pro Leu Ser Arg Val Leu Ala Arg Met Glu Ala Thr Gly Val
            435                 440                 445
Arg Leu Asp Val Ala Tyr Leu Gln Ala Leu Ser Leu Glu Val Glu Ala
        450                 455                 460
Glu Val Arg Gln Leu Glu Glu Val Phe Arg Leu Ala Gly His Pro
465                 470                 475                 480
Phe Asn Leu Asn Ser Arg Asp Gln Leu Glu Arg Val Leu Phe Asp Glu
                    485                 490                 495
Leu Gly Leu Pro Ala Ile Gly Lys Thr Glu Lys Thr Gly Lys Arg Ser
                500                 505                 510
Thr Ser Ala Ala Val Leu Glu Ala Leu Arg Glu Ala His Pro Ile Val
            515                 520                 525
Asp Arg Ile Leu Gln Tyr Arg Glu Leu Thr Lys Leu Lys Asn Thr Tyr
        530                 535                 540
Ile Asp Pro Leu Pro Ala Leu Val His Pro Lys Thr Gly Arg Leu His
545                 550                 555                 560
Thr Arg Phe Asn Gln Thr Ala Thr Ala Thr Gly Arg Leu Ser Ser Ser
                    565                 570                 575
Asp Pro Asn Leu Gln Asn Ile Pro Val Arg Thr Pro Leu Gly Gln Arg
                580                 585                 590
Ile Arg Arg Ala Phe Val Ala Glu Gly Trp Val Leu Val Val Leu
            595                 600                 605
Asp Tyr Ser Gln Ile Glu Leu Arg Val Leu Ala His Leu Ser Gly Asp
        610                 615                 620
Glu Asn Leu Ile Arg Val Phe Gln Glu Gly Arg Asp Ile His Thr Gln
625                 630                 635                 640
Thr Ala Ser Trp Met Phe Gly Val Ser Pro Glu Gly Val Asp Pro Leu
                    645                 650                 655
Met Arg Arg Ala Ala Lys Thr Ile Asn Phe Gly Val Leu Tyr Gly Met
                660                 665                 670
Ser Ala His Arg Leu Ser Gly Glu Leu Ser Ile Pro Tyr Glu Glu Ala
            675                 680                 685
Val Ala Phe Ile Glu Arg Tyr Phe Gln Ser Tyr Pro Lys Val Arg Ala
        690                 695                 700
```

```
Trp Ile Glu Gly Thr Leu Glu Gly Arg Arg Gly Tyr Val Glu
705                 710                 715                 720

Thr Leu Phe Gly Arg Arg Tyr Val Pro Asp Leu Asn Ala Arg Val
            725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Arg Leu Phe
            755                 760                 765

Pro Arg Leu Gln Glu Leu Gly Ala Arg Met Leu Leu Gln Val His Asp
            770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
            805                 810                 815

Glu Val Glu Val Gly Leu Gly Asp Trp Leu Ser Ala Lys Glu
            820                 825                 830

<210> SEQ ID NO 6
<211> LENGTH: 834
<212> TYPE: PRT
<213> ORGANISM: Thermus thermophilus

<400> SEQUENCE: 6

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
            115                 120                 125

Lys Ala Glu Lys Glu Gly Tyr Glu Val Arg Ile Leu Thr Ala Asp Arg
        130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
        210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
```

-continued

```
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
            275                 280                 285
Leu Leu Glu Ala Pro Ala Pro Leu Glu Glu Ala Pro Trp Pro Pro Pro
            290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
            325                 330                 335
Ala Ala Asp Pro Leu Ala Gly Leu Lys Asp Leu Lys Glu Val Arg Gly
            340                 345                 350
Leu Leu Ala Lys Asp Leu Ala Val Leu Ala Ser Arg Glu Gly Leu Asp
            355                 360                 365
Leu Val Pro Gly Asp Asp Pro Met Leu Leu Ala Tyr Leu Leu Asp Pro
            370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
            405                 410                 415
Asn Leu Leu Lys Arg Leu Glu Gly Glu Glu Lys Leu Leu Trp Leu Tyr
            420                 425                 430
His Glu Val Glu Lys Pro Leu Ser Arg Val Leu Ala His Met Glu Ala
            435                 440                 445
Thr Gly Val Arg Leu Asp Val Ala Tyr Leu Gln Ala Leu Ser Leu Glu
            450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
            485                 490                 495
Phe Asp Glu Leu Arg Leu Pro Ala Leu Gly Lys Thr Gln Lys Thr Gly
            500                 505                 510
Lys Arg Ser Thr Ser Ala Ala Val Leu Glu Ala Leu Arg Glu Ala His
            515                 520                 525
Pro Ile Val Glu Lys Ile Leu Gln His Arg Glu Leu Thr Lys Leu Lys
            530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
            565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
            595                 600                 605
Val Ala Leu Asp Tyr Ser Gln Ile Glu Leu Arg Val Leu Ala His Leu
            610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
            645                 650                 655
Asp Pro Leu Met Arg Arg Ala Ala Lys Thr Val Asn Phe Gly Val Leu
            660                 665                 670
```

-continued

```
Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
        820                 825                 830

Lys Gly

<210> SEQ ID NO 7
<211> LENGTH: 2502
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (181)..(182)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (738)..(738)
```

```
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1105)..(1105)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1244)..(1244)
<223> OTHER INFORMATION: n is a, c, g, or t
<220> FEATURE:
<221> NAME/KEY: misc_feature
<222> LOCATION: (1251)..(1253)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1569)..(1569)
<223> OTHER INFORMATION: n is a, c, g, or t
<220> FEATURE:
<221> NAME/KEY: misc_feature
<222> LOCATION: (1572)..(1572)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t
<220> FEATURE:
<221> NAME/KEY: misc_feature
<222> LOCATION: (1653)..(1653)
<223> OTHER INFORMATION: n is a, c, g, or t
<220> FEATURE:
<221> NAME/KEY: misc_feature
```

```
<222> LOCATION: (1655)..(1655)
<223> OTHER INFORMATION: n is a, c, g, or t
<220> FEATURE:
<221> NAME/KEY: misc_feature
<222> LOCATION: (1770)..(1770)
<223> OTHER INFORMATION: n is a, c, g, or t
<220> FEATURE:
<221> NAME/KEY: misc_feature
<222> LOCATION: (1812)..(1812)
<223> OTHER INFORMATION: n is a, c, g, or t
<220> FEATURE:
<221> NAME/KEY: misc_feature
<222> LOCATION: (2319)..(2319)
<223> OTHER INFORMATION: n is a, c, g, or t
<220> FEATURE:
<221> NAME/KEY: misc_feature
<222> LOCATION: (2346)..(2346)
<223> OTHER INFORMATION: n is a, c, g, or t
<220> FEATURE:
<221> NAME/KEY: misc_feature
<222> LOCATION: (2396)..(2396)
<223> OTHER INFORMATION: n is a, c, g, or t

<400> SEQUENCE: 7
atgnnggcga tgcttcccct ctttgagccc aaaggccggg tcctcctggt ggacggccac      60
cacctggcct accgcacctt cttcgccctg aagggcctca ccaccagccg gggcgaaccg     120
gtgcaggcgg tctacggctt cgccaagagc ctcctcaagg ccctgaagga ggacggggac     180
nnggcggtgn tcgtggtctt tgacgccaag gcccctcct tccgccacga ggcctacgag      240
gcctacaagg cgggccgggc ccccaccccg gaggactttc ccggcagct cgccctcatc      300 aaggagctgg tggacctcct ggggcttgcg cgcctcgagg tccccggcta cgaggcggac     360
gacgtnctgg ccaccctggc caagaaggcg gaaaaggagg ggtacgaggt gcgcatcctc     420
accgccgacc gcgacctcta ccagctcctt tccgaccgca tcgccgtcct ccaccccgag     480
gggtacctca tcaccccggc gtggctttgg gagaagtacg gcctgaggcc ggagcagtgg     540
gtggactacc gggccctggc gggggacccc tccgacaacc tccccggggt caagggcatc     600
ggggagaaga ccgcccngaa gctcctcnag gagtggggga gcctggaaaa cctcctcaag     660
aacctggacc gggtgaagcc cgccntccgg gagaagatcc aggcccacat ggangacctg     720
angctctcct gggagctntc ccaggtgcgc accgacctgc cctggaggt ggacttcgcc      780 aagnggcggg agcccgaccg ggaggggctt agggcctttc tggagaggct ggagtttggc     840
agcctcctcc acgagttcgg cctcctggag gccccaagg cctggagga ggcccctgg       900 cccccgccgg aagggccctt cgtgggcttt gtcctttccc gccccgagcc catgtgggcc     960
gagcttctgg ccctggccgc cgccagggag ggccgggtcc accgggcacc agaccccttt    1020
angggcctna gggacctnaa ggaggtgcgg ggnctcctcg ccaaggacct ggccgttttg    1080
gccctgaggg agggcctnga cctcntgccc ggggacgacc ccatgctcct cgcctacctc    1140
ctggacccct ccaacaccac cccgaggggg gtggcccggc gctacggggg ggagtggacg    1200
gaggangcgg gggagcgggc cctcctntcc gagaggctct tccngaacct nnngcagcgc    1260 cttgagggg aggagaggct cctttggctt taccaggagg tggagaagcc cctttcccgg    1320
gtcctggccc acatggaggc cacgggggtn cggctggacg tggcctacct ccaggccctn   1380
tccctggagg tggcggagga gatccgccgc ctcgaggagg aggtcttccg cctggccggc    1440 cacccttca acctcaactc ccgggaccag ctggaaaggg tgctctttga cgagctnggg    1500
cttcccgcca tcggcaagac ggagaagacn ggcaagcgct ccaccagcgc cgccgtgctg    1560
gaggccctnc gngaggccca ccccatcgtg gagaagatcc tgcagtaccg ggagctcacc    1620
```

```
aagctcaaga acacctacat ngaccccctg ccngnccteg tccacccccag gacgggccgc   1680 ctccacaccc gcttcaacca gacggccacg gccacgggca ggcttagtag ctccgacccc   1740
aacctgcaga acatcccegt ccgcacccen ctgggccaga ggatccgccg ggccttcgtg   1800
gccgaggagg gntgggtgtt ggtggccctg gactatagcc agatagagct ccgggtcctg   1860
gcccacctct ccggggacga gaacctgatc cgggtcttcc aggaggggag ggacatccac   1920
acccagaccg ccagctggat gttcggcgtc cccccggagg ccgtggaccc cctgatgcgc   1980
cgggcggcca agaccatcaa cttcggggtc tctacggca tgtccgccca ccgcctctcc   2040
caggagcttg ccatcccta cgaggaggcg gtggccttca ttgagcgcta cttccagagc   2100
ttccccaagg tgcgggcctg gattgagaag accctggagg agggcaggag gcgggggtac   2160
gtggagaccc tcttcggccg ccggcgctac gtgcccgacc tcaacgcccg ggtgaagagc   2220
gtgcgggagg cggcggagcg catggccttc aacatgcccg tccagggcac cgccgccgac   2280
ctcatgaagc tggccatggt gaagctcttc ccccggctnc aggaaatggg ggccaggatg   2340
ctcctncagg tccacgacga gctggtcctc gaggccccca agagcgggc ggaggnggtg   2400 gccgctttgg ccaaggaggt catggagggg gtctatcccc tggccgtgcc cctggaggtg   2460
gaggtgggga tggggagga ctggctctcc gccaaggagt ag                      2502
```

<210> SEQ ID NO 8
<211> LENGTH: 833
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (243)..(244)
<223> OTHER INFORMATION: Xaa can be any naturally occurring amino acid
<220> FEATURE:
<221> NAME/KEY: misc_feature

```
<222> LOCATION: (247)..(247)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (340)..(340)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (417)..(418)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (605)..(605)
<223> OTHER INFORMATION: Xaa can be any naturally occurring amino acid
<220> FEATURE:
<221> NAME/KEY: misc_feature
<222> LOCATION: (773)..(773)
<223> OTHER INFORMATION: Xaa can be any naturally occurring amino acid
<220> FEATURE:
<221> NAME/KEY: misc_feature
<222> LOCATION: (794)..(794)
<223> OTHER INFORMATION: Xaa can be any naturally occurring amino acid
<220> FEATURE:
<221> NAME/KEY: misc_feature
<222> LOCATION: (798)..(798)
<223> OTHER INFORMATION: Xaa can be any naturally occurring amino acid
<220> FEATURE:
<221> NAME/KEY: misc_feature
<222> LOCATION: (823)..(823)
<223> OTHER INFORMATION: Xaa can be any naturally occurring amino acid
<220> FEATURE:
<221> NAME/KEY: misc_feature
<222> LOCATION: (833)..(833)
<223> OTHER INFORMATION: Xaa can be any naturally occurring amino acid

<400> SEQUENCE: 8

Met Xaa Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Xaa Val
```

-continued

```
                50                   55                   60
Val Phe Asp Ala Lys Ala Pro Ser Phe Arg His Glu Ala Tyr Glu Ala
 65                   70                   75                   80

Tyr Lys Ala Gly Arg Ala Pro Thr Pro Glu Asp Phe Pro Arg Gln Leu
                 85                   90                   95

Ala Leu Ile Lys Glu Leu Val Asp Leu Leu Gly Leu Xaa Arg Leu Glu
                100                  105                  110

Val Pro Gly Tyr Glu Ala Asp Asp Val Leu Ala Thr Leu Ala Lys Lys
                115                  120                  125

Ala Glu Lys Glu Gly Tyr Glu Val Arg Ile Leu Thr Ala Asp Arg Asp
            130                  135                  140

Leu Tyr Gln Leu Leu Ser Asp Arg Ile Ala Val Leu His Pro Glu Gly
145                  150                  155                  160

Tyr Leu Ile Thr Pro Ala Trp Leu Trp Glu Lys Tyr Gly Leu Arg Pro
                165                  170                  175

Glu Gln Trp Val Asp Tyr Arg Ala Leu Xaa Gly Asp Pro Ser Asp Asn
                180                  185                  190

Leu Pro Gly Val Lys Gly Ile Gly Glu Lys Thr Ala Xaa Lys Leu Leu
                195                  200                  205

Xaa Glu Trp Gly Ser Leu Glu Asn Leu Leu Lys Asn Leu Asp Arg Val
210                  215                  220

Lys Pro Xaa Xaa Arg Glu Lys Ile Xaa Ala His Met Glu Asp Leu Xaa
225                  230                  235                  240

Leu Ser Xaa Xaa Leu Ser Xaa Val Arg Thr Asp Leu Pro Leu Glu Val
                245                  250                  255

Asp Phe Ala Xaa Arg Arg Glu Pro Asp Arg Glu Gly Leu Arg Ala Phe
                260                  265                  270

Leu Glu Arg Leu Glu Phe Gly Ser Leu Leu His Glu Phe Gly Leu Leu
            275                  280                  285

Glu Xaa Pro Lys Ala Leu Glu Glu Ala Pro Trp Pro Pro Glu Gly
            290                  295                  300

Ala Phe Val Gly Phe Val Leu Ser Arg Pro Glu Pro Met Trp Ala Glu
305                  310                  315                  320

Leu Leu Ala Leu Ala Ala Ala Arg Xaa Gly Arg Val His Arg Ala Xaa
                325                  330                  335

Asp Pro Leu Xaa Gly Leu Arg Asp Leu Lys Glu Val Arg Gly Leu Leu
                340                  345                  350

Ala Lys Asp Leu Ala Val Leu Ala Leu Arg Glu Gly Leu Asp Leu Xaa
                355                  360                  365

Pro Gly Asp Asp Pro Met Leu Leu Ala Tyr Leu Leu Asp Pro Ser Asn
370                  375                  380

Thr Thr Pro Glu Gly Val Ala Arg Arg Tyr Gly Gly Glu Trp Thr Glu
385                  390                  395                  400

Asp Ala Gly Glu Arg Ala Leu Leu Ser Glu Arg Leu Phe Xaa Asn Leu
                405                  410                  415

Xaa Xaa Arg Leu Glu Gly Glu Glu Arg Leu Leu Trp Leu Tyr Xaa Glu
            420                  425                  430

Val Glu Lys Pro Leu Ser Arg Val Leu Ala His Met Glu Ala Thr Gly
            435                  440                  445

Val Arg Leu Asp Val Ala Tyr Leu Gln Ala Leu Ser Leu Glu Val Ala
        450                  455                  460

Glu Glu Ile Arg Arg Leu Glu Glu Glu Val Phe Arg Leu Ala Gly His
465                  470                  475                  480
```

```
Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Asn Thr
    530                 535                 540

Tyr Ile Asp Pro Leu Pro Xaa Leu Val His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Val Ala Glu Glu Gly Trp Xaa Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Gln Thr Ala Ser Trp Met Phe Gly Val Pro Pro Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Val Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Asn Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Xaa Glu Met Gly Ala Arg Met Leu Leu Gln Val His
        770                 775                 780

Asp Glu Leu Val Leu Glu Ala Pro Lys Xaa Arg Ala Glu Xaa Val Ala
785                 790                 795                 800

Ala Leu Ala Lys Glu Val Met Glu Gly Val Tyr Pro Leu Ala Val Pro
                805                 810                 815

Leu Glu Val Glu Val Gly Xaa Gly Glu Asp Trp Leu Ser Ala Lys Glu
            820                 825                 830

Xaa

<210> SEQ ID NO 9
<211> LENGTH: 1647
<212> TYPE: DNA
<213> ORGANISM: Artificial Sequence
<220> FEATURE:
<223> OTHER INFORMATION: Synthetic

<400> SEQUENCE: 9
```

```
atgaattcgg ggatgctgcc cctctttgag cccaagggcc gggtcctcct ggtggacggc      60
caccacctgg cctaccgcac cttccacgcc ctgaagggct caccaccag ccggggggag      120
ccggtgcagg cggtctacgg cttcgccaag agcctcctca aggccctcaa ggaggacggg     180
gacgcggtga tcgtggtctt tgacgccaag gccccctcct ccgccacga ggcctacggg      240
gggtacaagg cgggccgggc ccccacgccg aggactttc cccggcaact cgccctcatc      300
aaggagctgg tggacctcct ggggctggcg cgcctcgagg tccgggcta cgaggcggac      360
gacgtcctgg ccagcctggc caagaaggcg gaaaaggagg ctacgaggt ccgcatcctc      420
accgccgaca aagacctta ccagctcctt tccgaccgca tccacgtcct ccaccccgag      480
gggtacctca tcaccccggc ctggcttttgg gaaaagtacg gcctgaggcc cgaccagtgg    540
gccgactacc gggccctgac cggggacgag tccgacaacc ttcccggggt caagggcatc    600
ggggagaaga cggcgaggaa gcttctggag gagtggggga gcctggaagc cctcctcaag   660
aacctggacc ggctgaagcc cgccatccgg gagaagatcc tggcccacat ggacgatctg    720
aagctctcct gggacctggc caaggtgcgc accgacctgc ccctggaggt ggacttcgcc    780
aaaaggcggg agcccgaccg ggagaggctt agggcctttc tggagaggct tgagtttggc    840
agcctcctcc acgagttcgg ccttctggaa agccccaagg ccctggagga ggcccctgg    900
cccccgccga agggggcctt cgtgggctt gtgctttccc gcaaggagcc catgtgggcc   960
gatcttctgg ccctggccgc cgccagggg ggccgggtcc accgggcccc cgagccttat  1020
aaagccctca gggacctgaa ggaggcgcgg ggcttctcg ccaaagacct gagcgttctg    1080
gccctgaggg aaggccttgg cctcccgccc ggcgacgacc ccatgctcct cgcctacctc   1140
ctggacccct tccaacaccac ccccgagggg gtggcccggc gctacggcgg ggagtggacg   1200
gaggaggcgg gggagcgggc cgcccttcc gagaggctct cgccaacct gtggggagg      1260
cttgagggg aggagaggct cctttggctt taccgggagg tggagaggcc cctttccgct     1320
gtcctggccc acatggaggc cacggggtg cgcctggacg tggcctatct cagggccttg    1380
tccctggagg tggccgggga gatcgcccgc ctcgaggccg aggtcttccg cctggccggc   1440
cacccttca acctcaactc ccgggaccag ctggaaaggg tcctctttga cgagctaggg   1500
cttcccgcca tcggcaagac ggagaagacc ggcaagcgct ccaccagcgc cgccgtcctg    1560
gaggccctcc gcgaggccca ccccatcgtg gagaagatcc tgcaggcatg caagcttggc   1620
actggccgtc gttttacaac gtcgtga                                       1647

<210> SEQ ID NO 10
<211> LENGTH: 2088
<212> TYPE: DNA
<213> ORGANISM: Artificial Sequence
<220> FEATURE:
<223> OTHER INFORMATION: Synthetic

<400> SEQUENCE: 10
atgaattcgg ggatgctgcc cctctttgag cccaagggcc gggtcctcct ggtggacggc      60
caccacctgg cctaccgcac cttccacgcc ctgaagggct caccaccag ccggggggag      120
ccggtgcagg cggtctacgg cttcgccaag agcctcctca aggccctcaa ggaggacggg     180
gacgcggtga tcgtggtctt tgacgccaag gccccctcct ccgccacga ggcctacggg      240
gggtacaagg cgggccgggc ccccacgccg aggactttc cccggcaact cgccctcatc      300
aaggagctgg tggacctcct ggggctggcg cgcctcgagg tccgggcta cgaggcggac      360
gacgtcctgg ccagcctggc caagaaggcg gaaaaggagg ctacgaggt ccgcatcctc      420
```

```
accgccgaca aagaccttta ccagctcctt tccgaccgca tccacgtcct ccaccccgag      480
gggtacctca tcaccccggc ctggctttgg gaaaagtacg gcctgaggcc cgaccagtgg      540
gccgactacc gggccctgac cggggacgag tccgacaacc ttcccggggt caagggcatc      600
ggggagaaga cggcgaggaa gcttctggag gagtggggga gcctggaagc cctcctcaag      660
aacctggacc ggctgaagcc cgccatccgg gagaagatcc tggcccacat ggacgatctg      720
aagctctcct gggacctggc caaggtgcgc accgacctgc cctggaggt ggacttcgcc      780 aaaaggcggg agcccgaccg ggagaggctt agggcctttc tggagaggct tgagtttggc      840
agcctcctcc acgagttcgg ccttctggaa agccccaagg ccctggagga ggcccctgg       900 cccccgccgg aagggggcctt cgtgggcttt gtgctttccc gcaaggagcc catgtgggcc      960
gatcttctgg ccctggccgc cgccagggg ggccgggtcc accgggcccc cgagccttat      1020
aaagccctca gggacctgaa ggaggcgcgg ggcttctcg ccaaagacct gagcgttctg       1080
gccctgaggg aaggccttgg cctcccgccc ggcgacgacc ccatgctcct cgcctacctc      1140
ctggaccctt ccaacaccac ccccgagggg gtggcccggc gctacggcgg ggagtggacg      1200
gaggaggcgg gggagcgggc cgcccttttcc gagaggctct tcgccaacct gtggggggagg     1260 cttgaggggg aggagaggct cctttggctt taccggagg tggagaggcc cctttccgct       1320
gtcctggccc acatggaggc cacggggtg cgcctgacg tggcctatct cagggccttg        1380
tccctggagg tggccgggga gatcgcccgc ctcgaggccg aggtcttccg cctggccggc      1440 cacccttca acctcaactc ccgggaccag ctggaaaggg tcctctttga cgagctaggg       1500
cttcccgcca tcggcaagac ggagaagacc ggcaagcgct ccaccagcgc cgccgtcctg      1560
gaggccctcc gcgaggccca ccccatcgtg agaagatcc tgcagtaccg ggagctcacc      1620
aagctgaaga gcacctacat tgacccccttg ccggacctca tccacccccag gacgggccgc      1680 ctccacaccc gcttcaacca gacgccacg gccacgggca ggctaagtag ctccgatccc      1740
aacctccaga acatccccgt ccgcacccccg cttgggcaga ggatccgccg ggccttcatc      1800
gccgaggagg ggtggctatt ggtggccctg gactatagcc agatagagct cagggtgctg      1860
gcccacctct ccggcgacga gaacctgatc cgggtcttcc aggaggggcg ggacatccac      1920
acggagaccg ccagctggat gttcggcgtc cccgggagg ccgtggaccc cctgatgcgc       1980
cgggcggcca agaccatcaa cttcgggtc ctctacggca tgtcggccca ccgcctctcc       2040
caggagctag ctagccatcc cttacgagga ggcccaggcc ttcattga                   2088
```

<210> SEQ ID NO 11
<211> LENGTH: 962
<212> TYPE: DNA
<213> ORGANISM: Artificial Sequence
<220> FEATURE:
<223> OTHER INFORMATION: Synthetic

<400> SEQUENCE: 11

```
atgaattcgg ggatgctgcc cctctttgag cccaagggcc gggtcctcct ggtggacggc       60
caccacctgg cctaccgcac cttccacgcc ctgaagggcc tcaccaccag ccggggggag      120
ccggtgcagg cggtctacgg cttcgccaag agcctcctca aggccctcaa ggaggacggg      180
gacgcggtga tcgtggtctt tgacgccaag gccccctcct ccgcacgga ggcctacggg       240 gggtacaagg cggggcgggc ccccacgccg aggactttc cccggcaact cgccctcatc       300
aaggagctgg tggacctcct ggggctggcg cgcctcgagg tccggggcta cgaggcggac      360
```

| | |
|---|---:|
| gacgtcctgg ccagcctggc caagaaggcg gaaaaggagg gctacgaggt ccgcatcctc | 420 |
| accgccgaca aagaccttta ccagcttctt tccgaccgca tccacgtcct ccaccccgag | 480 |
| gggtacctca tcaccccggc ctggctttgg gaaaagtacg gcctgaggcc cgaccagtgg | 540 |
| gccgactacc gggccctgac cggggacgag tccgacaacc ttcccggggt caagggcatc | 600 |
| ggggagaaga cggcgaggaa gcttctggag gagtggggga gcctggaagc cctcctcaag | 660 |
| aacctggacc ggctgaagcc cgccatccgg gagaagatcc tggcccacat ggacgatctg | 720 |
| aagctctcct gggacctggc caaggtgcgc accgacctgc ccctggaggt ggacttcgcc | 780 |
| aaaaggcggg agcccgaccg ggagaggctt agggcctttc tggagaggct tgagtttggc | 840 |
| agcctcctcc acgagttcgg ccttctggaa agccccaagt catggagggg gtgtatcccc | 900 |
| tggccgtgcc cctggaggtg gaggtgggga taggggagga ctggctctcc gccaaggagt | 960 |
| ga | 962 |

<210> SEQ ID NO 12
<211> LENGTH: 1600
<212> TYPE: DNA
<213> ORGANISM: Artificial Sequence
<220> FEATURE:
<223> OTHER INFORMATION: Synthetic

<400> SEQUENCE: 12

| | |
|---|---:|
| atggaattcg gggatgctgc ccctctttga gcccaagggc cgggtcctcc tggtggacgg | 60 |
| ccaccacctg gcctaccgca ccttccacgc cctgaagggc ctcaccacca gccggggggga | 120 |
| gccggtgcag gcggtctacg gcttcgccaa gagcctcctc aaggccctca aggaggacgg | 180 |
| ggacgcggtg atcgtggtct ttgacgccaa ggccccctcc ttccgccacg aggcctacgg | 240 |
| ggggtacaag gcgggccggg cccccacgcc ggaggacttt ccccggcaac tcgccctcat | 300 |
| caaggagctg gtggacctcc tggggctggc gcgcctcgag gtcccgggct acgaggcgga | 360 |
| cgacgtcctg gccagcctgg ccaagaaggc ggaaaaggag ggctacgagg tccgcatcct | 420 |
| caccgccgac aaagaccttt accagctcct ttccgaccgc atccacgtcc tcaccccga | 480 |
| ggggtacctc atcaccccgg cctggctttg ggaaaagtac ggcctgaggc ccgaccagtg | 540 |
| ggccgactac cggggcctga ccggggacga gtccgacaac cttcccgggg tcaagggcat | 600 |
| cggggagaag acggcgagga agcttctgga ggagtggggg agcctggaag ccctcctcaa | 660 |
| gaacctggac cggctgaagc ccgccatccg ggagaagatc ctggcccaca tggacgatct | 720 |
| gaagctctcc tgggacctgg ccaaggtgcg caccgacctg cccctggagg tggacttcgc | 780 |
| caaaaggcgg gagcccgacc gggagaggct tagggccttt ctggagaggc ttgagtttgg | 840 |
| cagcctcctc cacgagttcg gccttctgga aagccccaag atccgccggg ccttcatcgc | 900 |
| cgaggagggg tggctattgg tggccctgga ctatagccag atagagctca gggtgctggc | 960 |
| ccacctctcc ggcgacgaga acctgatccg ggtcttccag gaggggcggg acatccacac | 1020 |
| ggagaccgcc agctggatgt tcggcgtccc ccgggaggcc gtggaccccc tgatgcgccg | 1080 |
| ggcggccaag accatcaact tcgggtcctc tacggcatg tcggcccacc gcctctccca | 1140 |
| ggagctagcc atcccttacg aggaggccca ggccttcatt gagcgctact tcagagcttt | 1200 |
| ccccaaggtg cgggcctgga ttgagaagac cctggaggag gcaggaggc gggggtacgt | 1260 |
| ggagaccctc ttcggccgcc gccgctacgt gccagaccta gaggcccggg tgaagagcgt | 1320 |
| gcgggaggcg gccgagcgca tggccttcaa catgcccgtc cggggcaccg ccgccgacct | 1380 |
| catgaagctg gctatggtga agctcttccc caggctggag gaaatggggg ccaggatgct | 1440 |

```
ccttcaggtc cacgacgagc tggtcctcga ggccccaaaa gagagggcgg aggccgtggc    1500
ccggctggcc aaggaggtca tgagggggt gtatcccctg gccgtgcccc tggaggtgga    1560
ggtggggata gggaggact ggctctccgc caaggagtga                           1600

<210> SEQ ID NO 13
<211> LENGTH: 36
<212> TYPE: DNA
<213> ORGANISM: Artificial Sequence
<220> FEATURE:
<223> OTHER INFORMATION: Synthetic

<400> SEQUENCE: 13
cacgaattcg gggatgctgc ccctctttga gcccaa                              36

<210> SEQ ID NO 14
<211> LENGTH: 34
<212> TYPE: DNA
<213> ORGANISM: Artificial Sequence
<220> FEATURE:
<223> OTHER INFORMATION: Synthetic

<400> SEQUENCE: 14
gtgagatcta tcactccttg gcggagagcc agtc                                34

<210> SEQ ID NO 15
<211> LENGTH: 91
<212> TYPE: DNA
<213> ORGANISM: Artificial Sequence
<220> FEATURE:
<223> OTHER INFORMATION: Synthetic

<400> SEQUENCE: 15
taatacgact cactataggg agaccggaat tcgagctcgc ccgggcgagc tcgaattccg    60
tgtattctat agtgtcacct aaatcgaatt c                                   91

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
taatacgact cactataggg                                                20

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
gaattcgatt taggtgacac tatagaa                                        27

<210> SEQ ID NO 18
<211> LENGTH: 31
<212> TYPE: DNA
<213> ORGANISM: Artificial Sequence
<220> FEATURE:
<223> OTHER INFORMATION: Synthetic

<400> SEQUENCE: 18
```

```
gtaatcatgg tcatagctgg tagcttgcta c                                          31
```

<210> SEQ ID NO 19
<211> LENGTH: 42
<212> TYPE: DNA
<213> ORGANISM: Artificial Sequence
<220> FEATURE:
<223> OTHER INFORMATION: Synthetic

<400> SEQUENCE: 19

```
ggatcctcta gagtcgacct gcaggcatgc taccttggt ag                               42
```

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20

```
ggatcctcta gagtcgacct gcaggcatgc                                            30
```

<210> SEQ ID NO 21
<211> LENGTH: 2502
<212> TYPE: DNA
<213> ORGANISM: Artificial Sequence
<220> FEATURE:
<223> OTHER INFORMATION: Synthetic

<400> SEQUENCE: 21

```
atgaattcgg ggatgctgcc cctctttgag cccaagggcc gggtcctcct ggtggacggc            60
caccacctgg cctaccgcac cttccacgcc ctgaagggcc tcaccaccag ccggggggag           120
ccggtgcagg cggtctacgg cttcgccaag agcctcctca aggccctcaa ggaggacggg           180
gacgcggtga tcgtggtctt tgacgccaag gcccccctcct tccgcacgga ggcctacggg          240
gggtacaagg cgggccgggc ccccacgccg gaggactttc cccggcaact cgccctcatc           300
aaggagctgg tggaccctcct ggggctggcg cgcctcgagg tcccgggcta cgaggcggac          360
gacgtcctgg ccagcctggc caagaaggcg aaaaggagg gctacgaggt ccgcatcctc            420
accgccgaca agaccttta ccagctcctt tccgaccgca tccacgtcct ccaccccgag            480
gggtacctca tcacccccggc ctggctttgg gaaaagtacg gcctgaggcc cgaccagtgg          540
gccgactacc gggccctgac cggggacgag tccgacaacc ttcccggggt caagggcatc           600
ggggagaaga cggcgaggaa gcttctggag gagtggggga gcctggaagc cctcctcaag           660
aacctggacc ggctgaagcc cgccatccgg gagaagatcc tggcccacat ggacgatctg           720
aagctctcct gggacctggc caaggtgcgc accgacctgc cctgaggt ggacttcgcc             780
aaaaggcggg agcccgaccg ggagaggctt agggcctttc tggagaggct tgagtttggc           840
agcctcctcc acgagttcgg ccttctggaa agccccaagg ccctgaggga ggcccccctgg          900
cccccgccgg aagggcctt cgtgggcttt gtgctttccc gcaaggagcc catgtgggcc            960
gatcttctgg ccctggccgc cgccaggggg gccgggtcc accgggcccc cgagccttat          1020
aaagcccctca gggacctgaa ggaggcgcgg gggcttctcg ccaaagacct gagcgttctg        1080
gccctgaggg aaggccttgg cctccgccc ggcgacgacc ccatgctcct cgcctacctc         1140
ctggacccctt ccaacaccac ccccgagggg gtggcccggc gctacggcgg ggagtggacg       1200
gaggaggcgg gggagcgggc cgcccttttcc gagaggctct tcgccaacct gtggggagg         1260
cttgagggg aggagaggct cctttggctt taccggggagg tggagaggcc cctttccgct         1320
```

-continued

```
gtcctggccc acatggaggc cacggggtg cgcctggacg tggcctatct cagggccttg    1380
tccctggagg tggccgggga gatcgcccgc ctcgaggccg aggtcttccg cctggccggc    1440
cacccctcca acctcaactc ccgggaccag ctggaaaggg tcctctttga cgagctaggg    1500
cttcccgcca tcggcaagac ggagaagacc ggcaagcgct ccaccagcgc cgccgtcctg    1560
gaggccctcc gcgaggccca ccccatcgtg agaagatcc tgcagtaccg ggagctcacc    1620
aagctgaaga gcacctacat tgacccttg ccggacctca tccaccccag gacgggccgc    1680
ctccacaccc gcttcaacca gacggccacg gccacgggca ggctaagtag ctccgatccc    1740
aacctccaga acatccccgt ccgcaccccg cttgggcaga ggatccgccg ggccttcatc    1800
gccgaggagg ggtggctatt ggtggccctg gactatagcc agatagagct cagggtgctg    1860
gcccacctct ccggcgacga gaacctgatc cgggtcttcc aggaggggcg ggacatccac    1920
acggagaccg ccagctggat gttcggcgtc cccgggagg ccgtggaccc cctgatgcgc    1980
cgggcggcca agaccatcaa cttcggggtc ctctacggca tgtcggccca ccgcctctcc    2040
caggagctag ccatccctta cgaggaggcc caggccttca ttgagcgcta ctttcagagc    2100
ttccccaagg tgcgggcctg gattgagaag accctggagg agggcaggag gcggggtac    2160 gtggagaccc tcttcggccg ccgccgctac gtgccagacc tagaggcccg ggtgaagagc    2220
gtgcgggagg cggccgagcg catggccttc aacatgcccg tccggggcac cgccgccgac    2280
ctcatgaagc tggctatggt gaagctcttc cccaggctgg aggaaatggg ggccaggatg    2340
ctccttcagg tccacgacga gctggtcctc gaggccccaa aagagagggc ggaggccgtg    2400
gcccggctgg ccaaggaggt catggagggg gtgtatcccc tggccgtgcc cctggaggtg    2460
gaggtgggga tagggagga ctggctctcc gccaaggagt ga                       2502
```

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
gatttaggtg acactatag                                                  19

<210> SEQ ID NO 23
<211> LENGTH: 50
<212> TYPE: DNA
<213> ORGANISM: Artificial Sequence
<220> FEATURE:
<223> OTHER INFORMATION: Synthetic

<400> SEQUENCE: 23
acacaggtac cacatggtac aagaggcaag agagacgaca cagcagaaac              50

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Met Ala Ser Met Thr Gly Gly Gln Gln Met Gly Arg Ile Asn Ser
1               5                   10                  15

<210> SEQ ID NO 25
<211> LENGTH: 969
<212> TYPE: DNA
<213> ORGANISM: Artificial Sequence
<220> FEATURE:
<223> OTHER INFORMATION: Synthetic

<400> SEQUENCE: 25

```
atggctagca tgactggtgg acagcaaatg ggtcggatca attcggggat gctgcccctc      60
tttgagccca agggccgggt cctcctggtg gacggccacc acctggccta ccgcaccttc     120
cacgccctga agggcctcac caccagccgg ggggagccgg tgcaggcggt ctacggcttc     180
gccaagagcc tcctcaaggc cctcaaggag gacgggacg cggtgatcgt ggtctttgac     240
gccaaggccc cctccttccg ccacgaggcc tacggggggt acaaggcggg ccgggccccc     300
acgccggagg actttccccg gcaactcgcc ctcatcaagg agctggtgga cctcctgggg     360
ctggcgcgcc tcgaggtccc gggctacgag gcggacgacg tcctggccag cctggccaag     420
aaggcggaaa aggagggcta cgaggtccgc atcctcaccg ccgacaaaga cctttaccag     480
cttctttccg accgcatcca cgtcctccac cccgaggggt acctcatcac cccggcctgg     540
cttttgggaaa agtacggcct gaggcccgac cagtgggccg actaccgggc cctgaccggg     600
gacgagtccg acaaccttcc cggggtcaag ggcatcgggg agaagacggc gaggaagctt     660
ctggaggagt gggggagcct ggaagccctc ctcaagaacc tggaccggct gaagcccgcc     720
atccgggaga agatcctggc ccacatggac gatctgaagc tctcctggga cctggccaag     780
gtgcgcaccg acctgccccct ggaggtggac ttcgccaaaa ggcggagcc cgaccgggag     840
aggcttaggg cctttctgga gaggcttgag tttggcagcc tcctccacga gttcggcctt     900
ctggaaagcc ccaagtcatg gaggggtgt atcccctggc cgtgcccctg gaggtggagg     960
tggggatag                                                             969
```

<210> SEQ ID NO 26
<211> LENGTH: 948
<212> TYPE: DNA
<213> ORGANISM: Artificial Sequence
<220> FEATURE:
<223> OTHER INFORMATION: Synthetic

<400> SEQUENCE: 26

```
atggctagca tgactggtgg acagcaaatg ggtcggatca attcggggat gctgcccctc      60
tttgagccca agggccgggt cctcctggtg gacggccacc acctggccta ccgcaccttc     120
cacgccctga agggcctcac caccagccgg ggggagccgg tgcaggcggt ctacggcttc     180
gccaagagcc tcctcaaggc cctcaaggag gacgggacg cggtgatcgt ggtctttgac     240
gccaaggccc cctccttccg ccacgaggcc tacggggggt acaaggcggg ccgggccccc     300
acgccggagg actttccccg gcaactcgcc ctcatcaagg agctggtgga cctcctgggg     360
ctggcgcgcc tcgaggtccc gggctacgag gcggacgacg tcctggccag cctggccaag     420
aaggcggaaa aggagggcta cgaggtccgc atcctcaccg ccgacaaaga cctttaccag     480
cttctttccg accgcatcca cgtcctccac cccgaggggt acctcatcac cccggcctgg     540
cttttgggaaa agtacggcct gaggcccgac cagtgggccg actaccgggc cctgaccggg     600
gacgagtccg acaaccttcc cggggtcaag ggcatcgggg agaagacggc gaggaagctt     660
ctggaggagt gggggagcct ggaagccctc ctcaagaacc tggaccggct gaagcccgcc     720
atccgggaga agatcctggc ccacatggac gatctgaagc tctcctggga cctggccaag     780
```

```
gtgcgcaccg acctgcccct ggaggtggac ttcgccaaaa ggcgggagcc cgaccgggag      840
aggcttaggg cctttctgga gaggcttgag tttggcagcc tcctccacga gttcggcctt      900
ctggaaagcc ccaaggccgc actcgagcac caccaccacc accactga                   948
```

<210> SEQ ID NO 27
<211> LENGTH: 206
<212> TYPE: DNA
<213> ORGANISM: Artificial Sequence
<220> FEATURE:
<223> OTHER INFORMATION: Synthetic

<400> SEQUENCE: 27

```
cgccagggtt ttcccagtca cgacgttgta aaacgacggc cagtgaattg taatacgact      60
cactataggg cgaattcgag ctcggtaccc ggggatcctc tagagtcgac ctgcaggcat      120
gcaagcttga gtattctata gtgtcaccta aatagcttgg cgtaatcatg gtcatagctg      180
tttcctgtgt gaaattgtta tccgct                                          206
```

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28

```
aacagctatg accatgatta c                                                21
```

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29

```
gttctctgct ctctggtcgc tgtctcgctt gtgaaacaag cgagacagcg tggtctctcg      60
```

<210> SEQ ID NO 30
<211> LENGTH: 15
<212> TYPE: DNA
<213> ORGANISM: Artificial Sequence
<220> FEATURE:
<223> OTHER INFORMATION: Synthetic

<400> SEQUENCE: 30

```
cgagagacca cgctg                                                       15
```

<210> SEQ ID NO 31
<211> LENGTH: 52
<212> TYPE: DNA
<213> ORGANISM: Artificial Sequence
<220> FEATURE:
<223> OTHER INFORMATION: Synthetic

<400> SEQUENCE: 31

```
cctttcgctt tcttcccttc ctttctcgcc acgttcgccg gctttccccg tc              52
```

<210> SEQ ID NO 32
<211> LENGTH: 26
<212> TYPE: DNA
<213> ORGANISM: Artificial Sequence
<220> FEATURE:
<223> OTHER INFORMATION: Synthetic

<400> SEQUENCE: 32
agaaaggaag ggaagaaagc gaaagg                                      26

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
gacggggaaa gccggcgaac g                                           21

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
gaaagccggc gaacgtggcg                                             20

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
ggcgaacgtg gcgagaaagg a                                           21

<210> SEQ ID NO 36
<211> LENGTH: 42
<212> TYPE: DNA
<213> ORGANISM: Artificial Sequence
<220> FEATURE:
<223> OTHER INFORMATION: Synthetic

<400> SEQUENCE: 36
cctttcgctt tcttcccttc ctttctcgcc acgttcgccg gc                    42

<210> SEQ ID NO 37
<211> LENGTH: 42
<212> TYPE: DNA
<213> ORGANISM: Artificial Sequence
<220> FEATURE:
<223> OTHER INFORMATION: Synthetic

<400> SEQUENCE: 37
cctttcgctc tcttcccttc ctttctcgcc acgttcgccg gc                    42

<210> SEQ ID NO 38
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (8)..(8)
<223> OTHER INFORMATION: 2'-O-methyladenosine

<400> SEQUENCE: 38
agaaaggaag ggaagaaagc gaaaggt                                          27

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
gccggcgaac gtggcgagaa agga                                             24

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40 ggttttctt tgaggtttag                                                   20

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41
gcgacactcc accatagat                                                   19

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
ctgtcttcac gcagaaagc                                                   19

<210> SEQ ID NO 43
<211> LENGTH: 19
<212> TYPE: DNA
<213> ORGANISM: Artificial Sequence
<220> FEATURE:
<223> OTHER INFORMATION: Synthetic

<400> SEQUENCE: 43
gcacggtcta cgagacctc                                                   19

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
taatacgact cactataggg                                                  20

<210> SEQ ID NO 45
<211> LENGTH: 337
<212> TYPE: DNA
<213> ORGANISM: Artificial Sequence

```
<220> FEATURE:
<223> OTHER INFORMATION: Synthetic

<400> SEQUENCE: 45
gggaaagcuu gcaugccugc aggucgacuc uagaggaucu acuagucaua uggauucugu        60
cuucacgcag aaagcgucug gccauggcgu uaguaugagu gucgugcagc cuccaggacc       120
cccccucccg ggagaggcau aguggucugc ggaaccggug aguacaccgg aauugccagg       180
acgaccgggu ccuuucuugg auaaacccgc ucaaugccug gagauuuggg cgugcccccg       240
caagacugcu agccgaguag uguugggucg cgaaaggccu ugugguacug ccugauaggg       300
ugccugcgag ugccccggga ggucucguag accgugc                                337

<210> SEQ ID NO 46
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: This residue is linked to an abasic linker with
      a fluorescein dye.

<400> SEQUENCE: 46
ccggtcgtcc tggcaatcc                                                     19

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
gtttatccaa gaaaggaccc ggtc                                               24

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
cagggtgaag ggaagaagaa agcgaaaggt                                         30

<210> SEQ ID NO 49
<211> LENGTH: 30
<212> TYPE: DNA
<213> ORGANISM: Artificial Sequence
<220> FEATURE:
<223> OTHER INFORMATION: Synthetic

<400> SEQUENCE: 49 caggggaag ggaagaagaa agcgaaaggt                                          30

<210> SEQ ID NO 50
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
```

```
<222> LOCATION: (1)..(2)
<223> OTHER INFORMATION: These residues are amino modified T residues.

<400> SEQUENCE: 50
ttcttttcac cagcgagacg gg                                              22

<210> SEQ ID NO 51
<211> LENGTH: 22
<212> TYPE: DNA
<213> ORGANISM: Artificial Sequence
<220> FEATURE:
<223> OTHER INFORMATION: Synthetic

<400> SEQUENCE: 51
attgggcgcc agggtggttt tt                                              22

<210> SEQ ID NO 52
<211> LENGTH: 53
<212> TYPE: DNA
<213> ORGANISM: Artificial Sequence
<220> FEATURE:
<223> OTHER INFORMATION: Synthetic

<400> SEQUENCE: 52
cccgtctcgc tggtgaaaag aaaaaccacc ctggcgccca atacgcaaac cgc            53

<210> SEQ ID NO 53
<211> LENGTH: 31
<212> TYPE: DNA
<213> ORGANISM: Artificial Sequence
<220> FEATURE:
<223> OTHER INFORMATION: Synthetic

<400> SEQUENCE: 53
gaattcgatt taggtgacac tatagaatac a                                    31

<210> SEQ ID NO 54
<211> LENGTH: 42
<212> TYPE: DNA
<213> ORGANISM: Artificial Sequence
<220> FEATURE:
<223> OTHER INFORMATION: Synthetic

<400> SEQUENCE: 54
cctttcgctt tcttcccttc ctttctcgcc acgttcgccg gc                        42

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
gccggcgaac gtggcgagaa agga                                            24

<210> SEQ ID NO 56
<211> LENGTH: 26
<212> TYPE: DNA
<213> ORGANISM: Artificial Sequence
<220> FEATURE:
<223> OTHER INFORMATION: Synthetic

<400> SEQUENCE: 56
cagaaggaag ggaagaaagc gaaagg                                          26
```

<210> SEQ ID NO 57
<211> LENGTH: 26
<212> TYPE: DNA
<213> ORGANISM: Artificial Sequence
<220> FEATURE:
<223> OTHER INFORMATION: Synthetic

<400> SEQUENCE: 57 caggggaag ggaagaaagc gaaagg                                              26

<210> SEQ ID NO 58
<211> LENGTH: 26
<212> TYPE: DNA
<213> ORGANISM: Artificial Sequence
<220> FEATURE:
<223> OTHER INFORMATION: Synthetic

<400> SEQUENCE: 58
cagggtacag ggaagaaagc gaaagg                                              26

<210> SEQ ID NO 59
<211> LENGTH: 42
<212> TYPE: DNA
<213> ORGANISM: Artificial Sequence
<220> FEATURE:
<223> OTHER INFORMATION: Synthetic

<400> SEQUENCE: 59
gggaaagtcc tcggagccgc gcgggacgag cgtgggggcc cg                            42

<210> SEQ ID NO 60
<211> LENGTH: 963
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(960)

<400> SEQUENCE: 60

| atg | gct | agc | atg | act | ggt | gga | cag | caa | atg | ggt | cgg | atc | aat | tcg | ggg | 48 |
| Met | Ala | Ser | Met | Thr | Gly | Gly | Gln | Gln | Met | Gly | Arg | Ile | Asn | Ser | Gly | |
| 1 | | | | 5 | | | | | 10 | | | | | 15 | | |

| atg | ctg | ccc | ctc | ttt | gag | ccc | aag | ggc | cgg | gtc | ctg | ctg | gtg | gac | ggc | 96 |
| Met | Leu | Pro | Leu | Phe | Glu | Pro | Lys | Gly | Arg | Val | Leu | Leu | Val | Asp | Gly | |
| | | | 20 | | | | | 25 | | | | | 30 | | | |

| cac | cac | ctg | gcc | tac | cgc | acc | ttc | cac | gcc | ctg | aag | ggc | ctc | acc | acc | 144 |
| His | His | Leu | Ala | Tyr | Arg | Thr | Phe | His | Ala | Leu | Lys | Gly | Leu | Thr | Thr | |
| | | 35 | | | | | 40 | | | | | 45 | | | | |

| agc | cgg | ggg | gag | ccg | gtg | cag | gcg | gtc | tac | ggc | ttc | gcc | aag | agc | ctc | 192 |
| Ser | Arg | Gly | Glu | Pro | Val | Gln | Ala | Val | Tyr | Gly | Phe | Ala | Lys | Ser | Leu | |
| 50 | | | | | 55 | | | | | 60 | | | | | | |

| ctc | aag | gcc | ctc | aag | gag | gac | ggg | gac | gcg | gtg | atc | gtg | gtc | ttt | gac | 240 |
| Leu | Lys | Ala | Leu | Lys | Glu | Asp | Gly | Asp | Ala | Val | Ile | Val | Val | Phe | Asp | |
| 65 | | | | | 70 | | | | | 75 | | | | | 80 | |

| gcc | aag | gcc | ccc | tcc | ttc | cgc | cac | gag | gcc | tac | ggg | ggg | tac | aag | gcg | 288 |
| Ala | Lys | Ala | Pro | Ser | Phe | Arg | His | Glu | Ala | Tyr | Gly | Gly | Tyr | Lys | Ala | |
| | | | | 85 | | | | | 90 | | | | | 95 | | |

| ggc | cgg | gcc | ccc | acg | ctc | gtc | ccg | cgc | ggc | tcc | gag | gac | ttt | ccc | cgg | 336 |
| Gly | Arg | Ala | Pro | Thr | Leu | Val | Pro | Arg | Gly | Ser | Glu | Asp | Phe | Pro | Arg | |
| | | | 100 | | | | | 105 | | | | | 110 | | | |

| caa | ctc | gcc | ctc | atc | aag | gag | ctg | gtg | gac | ctc | ctg | ggg | ctg | gcg | cgc | 384 |
| Gln | Leu | Ala | Leu | Ile | Lys | Glu | Leu | Val | Asp | Leu | Leu | Gly | Leu | Ala | Arg | |

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  | 125 |  |  |  |  |  |
| ctc | gag | gtc | ccg | ggc | tac | gag | gcg | gac | gac | gtc | ctg | gcc | agc | ctg | gcc | 432 |
| Leu | Glu | Val | Pro | Gly | Tyr | Glu | Ala | Asp | Asp | Val | Leu | Ala | Ser | Leu | Ala |  |
| 130 |  |  |  |  | 135 |  |  |  |  | 140 |  |  |  |  |  |  |
| aag | aag | gcg | gaa | aag | gag | ggc | tac | gag | gtc | cgc | atc | ctc | acc | gcc | gac | 480 |
| Lys | Lys | Ala | Glu | Lys | Glu | Gly | Tyr | Glu | Val | Arg | Ile | Leu | Thr | Ala | Asp |  |
| 145 |  |  |  |  | 150 |  |  |  |  | 155 |  |  |  |  | 160 |  |
| aaa | gac | ctt | tac | cag | ctc | ctt | tcc | gac | cgc | atc | cac | gtc | ctc | cac | ccc | 528 |
| Lys | Asp | Leu | Tyr | Gln | Leu | Leu | Ser | Asp | Arg | Ile | His | Val | Leu | His | Pro |  |
|  |  |  |  | 165 |  |  |  |  | 170 |  |  |  |  | 175 |  |  |
| gag | ggg | tac | ctc | atc | acc | ccg | gcc | tgg | ctt | tgg | gaa | aag | tac | ggc | ctg | 576 |
| Glu | Gly | Tyr | Leu | Ile | Thr | Pro | Ala | Trp | Leu | Trp | Glu | Lys | Tyr | Gly | Leu |  |
|  |  |  | 180 |  |  |  |  | 185 |  |  |  |  | 190 |  |  |  |
| agg | ccc | gac | cag | tgg | gcc | gac | tac | cgg | gcc | ctg | acc | ggg | gac | gag | tcc | 624 |
| Arg | Pro | Asp | Gln | Trp | Ala | Asp | Tyr | Arg | Ala | Leu | Thr | Gly | Asp | Glu | Ser |  |
|  |  | 195 |  |  |  |  | 200 |  |  |  |  | 205 |  |  |  |  |
| gac | aac | ctt | ccc | ggg | gtc | aag | ggc | atc | ggg | gag | aag | acg | gcg | agg | aag | 672 |
| Asp | Asn | Leu | Pro | Gly | Val | Lys | Gly | Ile | Gly | Glu | Lys | Thr | Ala | Arg | Lys |  |
| 210 |  |  |  |  | 215 |  |  |  |  | 220 |  |  |  |  |  |  |
| ctt | ctg | gag | gag | tgg | ggg | agc | ctg | gaa | gcc | ctc | ctc | aag | aac | ctg | gac | 720 |
| Leu | Leu | Glu | Glu | Trp | Gly | Ser | Leu | Glu | Ala | Leu | Leu | Lys | Asn | Leu | Asp |  |
| 225 |  |  |  |  | 230 |  |  |  |  | 235 |  |  |  |  | 240 |  |
| cgg | ctg | aag | ccc | gcc | atc | cgg | gag | aag | atc | ctg | gcc | cac | atg | gac | gat | 768 |
| Arg | Leu | Lys | Pro | Ala | Ile | Arg | Glu | Lys | Ile | Leu | Ala | His | Met | Asp | Asp |  |
|  |  |  |  | 245 |  |  |  |  | 250 |  |  |  |  | 255 |  |  |
| ctg | aag | ctc | tcc | tgg | gac | ctg | gcc | aag | gtg | cgc | acc | gac | ctg | ccc | ctg | 816 |
| Leu | Lys | Leu | Ser | Trp | Asp | Leu | Ala | Lys | Val | Arg | Thr | Asp | Leu | Pro | Leu |  |
|  |  |  | 260 |  |  |  |  | 265 |  |  |  |  | 270 |  |  |  |
| gag | gtg | gac | ttc | gcc | aaa | agg | cgg | gag | ccc | gac | cgg | gag | agg | ctt | agg | 864 |
| Glu | Val | Asp | Phe | Ala | Lys | Arg | Arg | Glu | Pro | Asp | Arg | Glu | Arg | Leu | Arg |  |
|  |  | 275 |  |  |  |  | 280 |  |  |  |  | 285 |  |  |  |  |
| gcc | ttt | ctg | gag | agg | ctt | gag | ttt | ggc | agc | ctc | ctc | cac | gag | ttc | ggc | 912 |
| Ala | Phe | Leu | Glu | Arg | Leu | Glu | Phe | Gly | Ser | Leu | Leu | His | Glu | Phe | Gly |  |
| 290 |  |  |  |  | 295 |  |  |  |  | 300 |  |  |  |  |  |  |
| ctt | ctg | gaa | agc | ccc | aag | gcc | gca | ctc | gag | cac | cac | cac | cac | cac | cac | 960 |
| Leu | Leu | Glu | Ser | Pro | Lys | Ala | Ala | Leu | Glu | His | His | His | His | His | His |  |
| 305 |  |  |  |  | 310 |  |  |  |  | 315 |  |  |  |  | 320 |  |
| tga |  |  |  |  |  |  |  |  |  |  |  |  |  |  |  | 963 |

<210> SEQ ID NO 61
<211> LENGTH: 320
<212> TYPE: PRT
<213> ORGANISM: Artificial Sequence
<220> FEATURE:
<223> OTHER INFORMATION: Synthetic Construct

<400> SEQUENCE: 61

Met Ala Ser Met Thr Gly Gly Gln Gln Met Gly Arg Ile Asn Ser Gly
1               5                   10                  15

Met Leu Pro Leu Phe Glu Pro Lys Gly Arg Val Leu Leu Val Asp Gly
                20                  25                  30

His His Leu Ala Tyr Arg Thr Phe His Ala Leu Lys Gly Leu Thr Thr
            35                  40                  45

Ser Arg Gly Glu Pro Val Gln Ala Val Tyr Gly Phe Ala Lys Ser Leu
        50                  55                  60

Leu Lys Ala Leu Lys Glu Asp Gly Asp Ala Val Ile Val Val Phe Asp
65                  70                  75                  80

Ala Lys Ala Pro Ser Phe Arg His Glu Ala Tyr Gly Gly Tyr Lys Ala
                85                  90                  95

```
Gly Arg Ala Pro Thr Leu Val Pro Arg Gly Ser Glu Asp Phe Pro Arg
                100                 105                 110

Gln Leu Ala Leu Ile Lys Glu Leu Val Asp Leu Leu Gly Leu Ala Arg
            115                 120                 125

Leu Glu Val Pro Gly Tyr Glu Ala Asp Val Leu Ala Ser Leu Ala
        130                 135                 140

Lys Lys Ala Glu Lys Glu Gly Tyr Glu Val Arg Ile Leu Thr Ala Asp
145                 150                 155                 160

Lys Asp Leu Tyr Gln Leu Leu Ser Asp Arg Ile His Val Leu His Pro
                165                 170                 175

Glu Gly Tyr Leu Ile Thr Pro Ala Trp Leu Trp Glu Lys Tyr Gly Leu
            180                 185                 190

Arg Pro Asp Gln Trp Ala Asp Tyr Arg Ala Leu Thr Gly Asp Glu Ser
        195                 200                 205

Asp Asn Leu Pro Gly Val Lys Gly Ile Gly Glu Lys Thr Ala Arg Lys
    210                 215                 220

Leu Leu Glu Glu Trp Gly Ser Leu Glu Ala Leu Leu Lys Asn Leu Asp
225                 230                 235                 240

Arg Leu Lys Pro Ala Ile Arg Glu Lys Ile Leu Ala His Met Asp Asp
                245                 250                 255

Leu Lys Leu Ser Trp Asp Leu Ala Lys Val Arg Thr Asp Leu Pro Leu
            260                 265                 270

Glu Val Asp Phe Ala Lys Arg Arg Glu Pro Asp Arg Glu Arg Leu Arg
        275                 280                 285

Ala Phe Leu Glu Arg Leu Glu Phe Gly Ser Leu Leu His Glu Phe Gly
    290                 295                 300

Leu Leu Glu Ser Pro Lys Ala Ala Leu Glu His His His His His His
305                 310                 315                 320

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
cgatctcctc ggccacctcc                                           20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
ggcggtgccc tggacgggca                                           20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ccagctcgtt gtggacctga                                           20
```

<210> SEQ ID NO 65
<211> LENGTH: 2505
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(2499)

<400> SEQUENCE: 65

```
atg aat tcg ggg atg ctg ccc ctc ttt gag ccc aag ggc cgg gtc ctc      48
Met Asn Ser Gly Met Leu Pro Leu Phe Glu Pro Lys Gly Arg Val Leu
1               5                   10                  15 ctg gtg gac ggc cac cac ctg gcc tac cgc acc ttc cac gcc ctg aag      96
Leu Val Asp Gly His His Leu Ala Tyr Arg Thr Phe His Ala Leu Lys
            20                  25                  30 ggc ctc acc acc agc cgg ggg gag ccg gtg cag gcg gtc tac ggc ttc     144
Gly Leu Thr Thr Ser Arg Gly Glu Pro Val Gln Ala Val Tyr Gly Phe
        35                  40                  45 gcc aag agc ctc ctc aag gcc ctc aag gag gac ggg gac gcg gtg atc     192
Ala Lys Ser Leu Leu Lys Ala Leu Lys Glu Asp Gly Asp Ala Val Ile
    50                  55                  60 gtg gtc ttt gac gcc aag gcc ccc tcc ttc cgc cac gag gcc tac ggg     240
Val Val Phe Asp Ala Lys Ala Pro Ser Phe Arg His Glu Ala Tyr Gly
65                  70                  75                  80 ggg tac aag gcg ggc cgg gcc ccc acg ccg gag gac ttt ccc cgg caa     288
Gly Tyr Lys Ala Gly Arg Ala Pro Thr Pro Glu Asp Phe Pro Arg Gln
                85                  90                  95 ctc gcc ctc atc aag gag ctg gtg gac ctc ctg ggg ctg gcg cgc ctc     336
Leu Ala Leu Ile Lys Glu Leu Val Asp Leu Leu Gly Leu Ala Arg Leu
            100                 105                 110 gag gtc ccg ggc tac gag gcg gac gac gtc ctg gcc agc ctg gcc aag     384
Glu Val Pro Gly Tyr Glu Ala Asp Asp Val Leu Ala Ser Leu Ala Lys
        115                 120                 125 aag gcg gaa aag gag ggc tac gag gtc cgc atc ctc acc gcc gac aaa     432
Lys Ala Glu Lys Glu Gly Tyr Glu Val Arg Ile Leu Thr Ala Asp Lys
    130                 135                 140 gac ctt tac cag ctc ctt tcc gac cgc atc cac gtc ctc cac ccc gag     480
Asp Leu Tyr Gln Leu Leu Ser Asp Arg Ile His Val Leu His Pro Glu
145                 150                 155                 160 ggg tac ctc atc acc ccg gcc tgg ctt tgg gaa aag tac ggc ctg agg     528
Gly Tyr Leu Ile Thr Pro Ala Trp Leu Trp Glu Lys Tyr Gly Leu Arg
                165                 170                 175 ccc gac cag tgg gcc gac tac cgg gcc ctg acc ggg gac gag tcc gac     576
Pro Asp Gln Trp Ala Asp Tyr Arg Ala Leu Thr Gly Asp Glu Ser Asp
            180                 185                 190 aac ctt ccc ggg gtc aag ggc atc ggg gag aag acg gcg agg aag ctt     624
Asn Leu Pro Gly Val Lys Gly Ile Gly Glu Lys Thr Ala Arg Lys Leu
        195                 200                 205 ctg gag gag tgg ggg agc ctg gaa gcc ctc ctc aag aac ctg gac cgg     672
Leu Glu Glu Trp Gly Ser Leu Glu Ala Leu Leu Lys Asn Leu Asp Arg
    210                 215                 220 ctg aag ccc gcc atc cgg gag aag atc ctg gcc cac atg gac gat ctg     720
Leu Lys Pro Ala Ile Arg Glu Lys Ile Leu Ala His Met Asp Asp Leu
225                 230                 235                 240 aag ctc tcc tgg gac ctg gcc aag gtg cgc acc gac ctg ccc ctg gag     768
Lys Leu Ser Trp Asp Leu Ala Lys Val Arg Thr Asp Leu Pro Leu Glu
                245                 250                 255 gtg gac ttc gcc aaa agg cgg gag ccc gac cgg gag agg ctt agg gcc     816
Val Asp Phe Ala Lys Arg Arg Glu Pro Asp Arg Glu Arg Leu Arg Ala
```

-continued

```
              260                 265                 270
ttt ctg gag agg ctt gag ttt ggc agc ctc ctc cac gag ttc ggc ctt      864
Phe Leu Glu Arg Leu Glu Phe Gly Ser Leu Leu His Glu Phe Gly Leu
        275                 280                 285 ctg gaa agc ccc aag gcc ctg gag gag gcc ccc tgg ccc ccg ccg gaa      912
Leu Glu Ser Pro Lys Ala Leu Glu Glu Ala Pro Trp Pro Pro Pro Glu
    290                 295                 300 ggg gcc ttc gtg ggc ttt gtg ctt tcc cgc aag gag ccc atg tgg gcc      960
Gly Ala Phe Val Gly Phe Val Leu Ser Arg Lys Glu Pro Met Trp Ala
305                 310                 315                 320 gat ctt ctg gcc ctg gcc gcc gcc agg ggg ggc cgg gtc cac cgg gcc     1008
Asp Leu Leu Ala Leu Ala Ala Ala Arg Gly Gly Arg Val His Arg Ala
                325                 330                 335 ccc gag cct tat aaa gcc ctc agg gac ctg aag gag gcg cgg ggg ctt     1056
Pro Glu Pro Tyr Lys Ala Leu Arg Asp Leu Lys Glu Ala Arg Gly Leu
            340                 345                 350 ctc gcc aaa gac ctg agc gtt ctg gcc ctg agg gaa ggc ctt ggc ctc     1104
Leu Ala Lys Asp Leu Ser Val Leu Ala Leu Arg Glu Gly Leu Gly Leu
        355                 360                 365 ccg ccc ggc gac gac ccc atg ctc ctc gcc tac ctc ctg gac cct tcc     1152
Pro Pro Gly Asp Asp Pro Met Leu Leu Ala Tyr Leu Leu Asp Pro Ser
    370                 375                 380 aac acc acc ccc gag ggg gtg gcc cgg cgc tac ggc ggg gag tgg acg     1200
Asn Thr Thr Pro Glu Gly Val Ala Arg Arg Tyr Gly Gly Glu Trp Thr
385                 390                 395                 400 gag gag gcg ggg gag cgg gcc gcc ctt tcc gag agg ctc ttc gcc aac     1248
Glu Glu Ala Gly Glu Arg Ala Ala Leu Ser Glu Arg Leu Phe Ala Asn
                405                 410                 415 ctg tgg ggg agg ctt gag ggg gag gag agg ctc ctt tgg ctt tac cgg     1296
Leu Trp Gly Arg Leu Glu Gly Glu Glu Arg Leu Leu Trp Leu Tyr Arg
            420                 425                 430 gag gtg gag agg ccc ctt tcc gct gtc ctg gcc cac atg gag gcc acg     1344
Glu Val Glu Arg Pro Leu Ser Ala Val Leu Ala His Met Glu Ala Thr
        435                 440                 445 ggg gtg cgc ctg gac gtg gcc tat ctc agg gcc ttg tcc ctg gag gtg     1392
Gly Val Arg Leu Asp Val Ala Tyr Leu Arg Ala Leu Ser Leu Glu Val
    450                 455                 460 gcc gag gag atc gcc cgc ctc gag gcc gag gtc ttc cgc ctg gcc ggc     1440
Ala Glu Glu Ile Ala Arg Leu Glu Ala Glu Val Phe Arg Leu Ala Gly
465                 470                 475                 480 cac ccc ttc aac ctc aac tcc cgg gac cag ctg gaa agg gtc ctc ttt     1488
His Pro Phe Asn Leu Asn Ser Arg Asp Gln Leu Glu Arg Val Leu Phe
                485                 490                 495 gac gag cta ggg ctt ccc gcc atc ggc aag acg gag aag acc ggc aag     1536
Asp Glu Leu Gly Leu Pro Ala Ile Gly Lys Thr Glu Lys Thr Gly Lys
            500                 505                 510 cgc tcc acc agc gcc gcc gtc ctg gag gcc ctc cgc gag gcc cac ccc     1584
Arg Ser Thr Ser Ala Ala Val Leu Glu Ala Leu Arg Glu Ala His Pro
        515                 520                 525 atc gtg gag aag atc ctg cag tac cgg gag ctc acc aag ctg aag agc     1632
Ile Val Glu Lys Ile Leu Gln Tyr Arg Glu Leu Thr Lys Leu Lys Ser
    530                 535                 540 acc tac att gac ccc ttg ccg gac ctc atc cac ccc agg acg ggc cgc     1680
Thr Tyr Ile Asp Pro Leu Pro Asp Leu Ile His Pro Arg Thr Gly Arg
545                 550                 555                 560 ctc cac acc cgc ttc aac cag acg gcc acg gcc acg ggc agg cta agt     1728
Leu His Thr Arg Phe Asn Gln Thr Ala Thr Ala Thr Gly Arg Leu Ser
                565                 570                 575 agc tcc gat ccc aac ctc cag aac atc ccc gtc cgc acc ccg ctt ggg     1776
```

```
                Ser Ser Asp Pro Asn Leu Gln Asn Ile Pro Val Arg Thr Pro Leu Gly
                            580                 585                 590 cag agg atc cgc cgg gcc ttc atc gcc gag gag ggg tgg cta ttg gtg        1824
Gln Arg Ile Arg Arg Ala Phe Ile Ala Glu Glu Gly Trp Leu Leu Val
        595                 600                 605 gcc ctg gac tat agc cag ata gag ctc agg gtg ctg gcc cac ctc tcc        1872
Ala Leu Asp Tyr Ser Gln Ile Glu Leu Arg Val Leu Ala His Leu Ser
610                 615                 620 ggc gac gag aac ctg atc cgg gtc ttc cag gag ggg cgg gac atc cac        1920
Gly Asp Glu Asn Leu Ile Arg Val Phe Gln Glu Gly Arg Asp Ile His
625                 630                 635                 640 acg gag acc gcc agc tgg atg ttc ggc gtc ccc cgg gag gcc gtg gac        1968
Thr Glu Thr Ala Ser Trp Met Phe Gly Val Pro Arg Glu Ala Val Asp
                645                 650                 655 ccc ctg atg cgc cgg gcg gcc aag acc atc aac ttc ggg gtc ctc tac        2016
Pro Leu Met Arg Arg Ala Ala Lys Thr Ile Asn Phe Gly Val Leu Tyr
            660                 665                 670 ggc atg tcg gcc cac cgc ctc tcc cag gag cta gcc atc cct tac gag        2064
Gly Met Ser Ala His Arg Leu Ser Gln Glu Leu Ala Ile Pro Tyr Glu
        675                 680                 685 gag gcc cag gcc ttc att gag cgc tac ttt cag agc ttc ccc aag gtg        2112
Glu Ala Gln Ala Phe Ile Glu Arg Tyr Phe Gln Ser Phe Pro Lys Val
690                 695                 700 cgg gcc tgg att gag aag acc ctg gag gag ggc agg agg cgg ggg tac        2160
Arg Ala Trp Ile Glu Lys Thr Leu Glu Glu Gly Arg Arg Arg Gly Tyr
705                 710                 715                 720 gtg gag acc ctc ttc ggc cgc cgc cgc tac gtg cca gac cta gag gcc        2208
Val Glu Thr Leu Phe Gly Arg Arg Arg Tyr Val Pro Asp Leu Glu Ala
                725                 730                 735 cgg gtg aag agc gtg cgg gag gcg gcc gag cgc atg gcc ttc aac atg        2256
Arg Val Lys Ser Val Arg Glu Ala Ala Glu Arg Met Ala Phe Asn Met
            740                 745                 750 ccc gtc cag ggc acc gcc gcc gac ctc atg aag ctg gct atg gtg aag        2304
Pro Val Gln Gly Thr Ala Ala Asp Leu Met Lys Leu Ala Met Val Lys
        755                 760                 765 ctc ttc ccc agg ctg gag gaa atg ggg gcc agg atg ctc ctt cag gtc        2352
Leu Phe Pro Arg Leu Glu Glu Met Gly Ala Arg Met Leu Leu Gln Val
770                 775                 780 cac aac gag ctg gtc ctc gag gcc cca aaa gag agg gcg gag gcc gtg        2400
His Asn Glu Leu Val Leu Glu Ala Pro Lys Glu Arg Ala Glu Ala Val
785                 790                 795                 800 gcc cgg ctg gcc aag gag gtc atg gag ggg gtg tat ccc ctg gcc gtg        2448
Ala Arg Leu Ala Lys Glu Val Met Glu Gly Val Tyr Pro Leu Ala Val
                805                 810                 815 ccc ctg gag gtg gag gtg ggg ata ggg gag gac tgg ctc tcc gcc aag        2496
Pro Leu Glu Val Glu Val Gly Ile Gly Glu Asp Trp Leu Ser Ala Lys
            820                 825                 830 gag tgatag                                                             2505
Glu

<210> SEQ ID NO 66
<211> LENGTH: 833
<212> TYPE: PRT
<213> ORGANISM: Artificial Sequence
<220> FEATURE:
<223> OTHER INFORMATION: Synthetic Construct

<400> SEQUENCE: 66

Met Asn Ser Gly Met Leu Pro Leu Phe Glu Pro Lys Gly Arg Val Leu
1               5                   10                  15
```

-continued

```
Leu Val Asp Gly His His Leu Ala Tyr Arg Thr Phe His Ala Leu Lys
             20                  25                  30
Gly Leu Thr Thr Ser Arg Gly Glu Pro Val Gln Ala Val Tyr Gly Phe
         35                  40                  45
Ala Lys Ser Leu Leu Lys Ala Leu Lys Glu Asp Gly Asp Ala Val Ile
 50                  55                  60
Val Val Phe Asp Ala Lys Ala Pro Ser Phe Arg His Glu Ala Tyr Gly
 65                  70                  75                  80
Gly Tyr Lys Ala Gly Arg Ala Pro Thr Pro Glu Asp Phe Pro Arg Gln
                 85                  90                  95
Leu Ala Leu Ile Lys Glu Leu Val Asp Leu Leu Gly Leu Ala Arg Leu
             100                 105                 110
Glu Val Pro Gly Tyr Glu Ala Asp Asp Val Leu Ala Ser Leu Ala Lys
         115                 120                 125
Lys Ala Glu Lys Glu Gly Tyr Glu Val Arg Ile Leu Thr Ala Asp Lys
130                 135                 140
Asp Leu Tyr Gln Leu Leu Ser Asp Arg Ile His Val Leu His Pro Glu
145                 150                 155                 160
Gly Tyr Leu Ile Thr Pro Ala Trp Leu Trp Glu Lys Tyr Gly Leu Arg
                 165                 170                 175
Pro Asp Gln Trp Ala Asp Tyr Arg Ala Leu Thr Gly Asp Glu Ser Asp
             180                 185                 190
Asn Leu Pro Gly Val Lys Gly Ile Gly Glu Lys Thr Ala Arg Lys Leu
         195                 200                 205
Leu Glu Glu Trp Gly Ser Leu Glu Ala Leu Leu Lys Asn Leu Asp Arg
     210                 215                 220
Leu Lys Pro Ala Ile Arg Glu Lys Ile Leu Ala His Met Asp Asp Leu
225                 230                 235                 240
Lys Leu Ser Trp Asp Leu Ala Lys Val Arg Thr Asp Leu Pro Leu Glu
                 245                 250                 255
Val Asp Phe Ala Lys Arg Arg Glu Pro Asp Arg Glu Arg Leu Arg Ala
             260                 265                 270
Phe Leu Glu Arg Leu Glu Phe Gly Ser Leu Leu His Glu Phe Gly Leu
         275                 280                 285
Leu Glu Ser Pro Lys Ala Leu Glu Glu Ala Pro Trp Pro Pro Pro Glu
     290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Gly Arg Val His Arg Ala
                 325                 330                 335
Pro Glu Pro Tyr Lys Ala Leu Arg Asp Leu Lys Glu Ala Arg Gly Leu
             340                 345                 350
Leu Ala Lys Asp Leu Ser Val Leu Ala Leu Arg Glu Gly Leu Gly Leu
         355                 360                 365
Pro Pro Gly Asp Asp Pro Met Leu Leu Ala Tyr Leu Leu Asp Pro Ser
     370                 375                 380
Asn Thr Thr Pro Glu Gly Val Ala Arg Tyr Gly Gly Glu Trp Thr
385                 390                 395                 400
Glu Glu Ala Gly Glu Arg Ala Ala Leu Ser Glu Arg Leu Phe Ala Asn
                 405                 410                 415
Leu Trp Gly Arg Leu Glu Gly Glu Glu Arg Leu Leu Trp Leu Tyr Arg
             420                 425                 430
Glu Val Glu Arg Pro Leu Ser Ala Val Leu Ala His Met Glu Ala Thr
```

```
                435                 440                 445
Gly Val Arg Leu Asp Val Ala Tyr Leu Arg Ala Leu Ser Leu Glu Val
450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
                500                 505                 510
Arg Ser Thr Ser Ala Ala Val Leu Glu Ala Leu Arg Glu Ala His Pro
                515                 520                 525
Ile Val Glu Lys Ile Leu Gln Tyr Arg Glu Leu Thr Lys Leu Lys Ser
                530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
                580                 585                 590
Gln Arg Ile Arg Arg Ala Phe Ile Ala Glu Glu Gly Trp Leu Leu Val
                595                 600                 605
Ala Leu Asp Tyr Ser Gln Ile Glu Leu Arg Val Leu Ala His Leu Ser
                610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
                660                 665                 670
Gly Met Ser Ala His Arg Leu Ser Gln Glu Leu Ala Ile Pro Tyr Glu
                675                 680                 685
Glu Ala Gln Ala Phe Ile Glu Arg Tyr Phe Gln Ser Phe Pro Lys Val
                690                 695                 700
Arg Ala Trp Ile Glu Lys Thr Leu Glu Glu Gly Arg Arg Arg Gly Tyr
705                 710                 715                 720
Val Glu Thr Leu Phe Gly Arg Arg Tyr Val Pro Asp Leu Glu Ala
                725                 730                 735
Arg Val Lys Ser Val Arg Glu Ala Ala Glu Arg Met Ala Phe Asn Met
                740                 745                 750
Pro Val Gln Gly Thr Ala Ala Asp Leu Met Lys Leu Ala Met Val Lys
                755                 760                 765
Leu Phe Pro Arg Leu Glu Glu Met Gly Ala Arg Met Leu Leu Gln Val
770                 775                 780
His Asn Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
                805                 810                 815
Pro Leu Glu Val Glu Val Gly Ile Gly Glu Asp Trp Leu Ser Ala Lys
                820                 825                 830
Glu

<210> SEQ ID NO 67
<211> LENGTH: 20
```

-continued

```
<212> TYPE: DNA
<213> ORGANISM: Artificial Sequence
<220> FEATURE:
<223> OTHER INFORMATION: Synthetic

<400> SEQUENCE: 67
tggctatagr ccagggccac                                              20

<210> SEQ ID NO 68
<211> LENGTH: 2505
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(2499)

<400> SEQUENCE: 68
```

| | | | | | | | | | | | | | | | | |
|---|---|---|---|---|---|---|---|---|---|---|---|---|---|---|---|---|
| atg | aat | tcg | ggg | atg | ctg | ccc | ctc | ttt | gag | ccc | aag | ggc | cgg | gtc | ctc | 48 |
| Met | Asn | Ser | Gly | Met | Leu | Pro | Leu | Phe | Glu | Pro | Lys | Gly | Arg | Val | Leu | |
| 1 | | | | 5 | | | | | 10 | | | | | 15 | | |
| ctg | gtg | gac | ggc | cac | cac | ctg | gcc | tac | cgc | acc | ttc | cac | gcc | ctg | aag | 96 |
| Leu | Val | Asp | Gly | His | His | Leu | Ala | Tyr | Arg | Thr | Phe | His | Ala | Leu | Lys | |
| | | | 20 | | | | | 25 | | | | | 30 | | | |
| ggc | ctc | acc | acc | agc | cgg | ggg | gag | ccg | gtg | cag | gcg | gtc | tac | ggc | ttc | 144 |
| Gly | Leu | Thr | Thr | Ser | Arg | Gly | Glu | Pro | Val | Gln | Ala | Val | Tyr | Gly | Phe | |
| | | 35 | | | | | 40 | | | | | 45 | | | | |
| gcc | aag | agc | ctc | ctc | aag | gcc | ctc | aag | gag | gac | ggg | gac | gcg | gtg | atc | 192 |
| Ala | Lys | Ser | Leu | Leu | Lys | Ala | Leu | Lys | Glu | Asp | Gly | Asp | Ala | Val | Ile | |
| | 50 | | | | | 55 | | | | | 60 | | | | | |
| gtg | gtc | ttt | gac | gcc | aag | gcc | ccc | tcc | ttc | cgc | cac | gag | gcc | tac | ggg | 240 |
| Val | Val | Phe | Asp | Ala | Lys | Ala | Pro | Ser | Phe | Arg | His | Glu | Ala | Tyr | Gly | |
| 65 | | | | | 70 | | | | | 75 | | | | | 80 | |
| ggg | tac | aag | gcg | ggc | cgg | gcc | ccc | acg | ccg | gag | gac | ttt | ccc | cgg | caa | 288 |
| Gly | Tyr | Lys | Ala | Gly | Arg | Ala | Pro | Thr | Pro | Glu | Asp | Phe | Pro | Arg | Gln | |
| | | | | 85 | | | | | 90 | | | | | 95 | | |
| ctc | gcc | ctc | atc | aag | gag | ctg | gtg | gac | ctc | ctg | ggg | ctg | gcg | cgc | ctc | 336 |
| Leu | Ala | Leu | Ile | Lys | Glu | Leu | Val | Asp | Leu | Leu | Gly | Leu | Ala | Arg | Leu | |
| | | | 100 | | | | | 105 | | | | | 110 | | | |
| gag | gtc | ccg | ggc | tac | gag | gcg | gac | gac | gtc | ctg | gcc | agc | ctg | gcc | aag | 384 |
| Glu | Val | Pro | Gly | Tyr | Glu | Ala | Asp | Asp | Val | Leu | Ala | Ser | Leu | Ala | Lys | |
| | | 115 | | | | | 120 | | | | | 125 | | | | |
| aag | gcg | gaa | aag | gag | ggc | tac | gag | gtc | cgc | atc | ctc | acc | gcc | gac | aaa | 432 |
| Lys | Ala | Glu | Lys | Glu | Gly | Tyr | Glu | Val | Arg | Ile | Leu | Thr | Ala | Asp | Lys | |
| | 130 | | | | | 135 | | | | | 140 | | | | | |
| gac | ctt | tac | cag | ctc | ctt | tcc | gac | cgc | atc | cac | gtc | ctc | cac | ccc | gag | 480 |
| Asp | Leu | Tyr | Gln | Leu | Leu | Ser | Asp | Arg | Ile | His | Val | Leu | His | Pro | Glu | |
| 145 | | | | | 150 | | | | | 155 | | | | | 160 | |
| ggg | tac | ctc | atc | acc | ccg | gcc | tgg | ctt | tgg | gaa | aag | tac | ggc | ctg | agg | 528 |
| Gly | Tyr | Leu | Ile | Thr | Pro | Ala | Trp | Leu | Trp | Glu | Lys | Tyr | Gly | Leu | Arg | |
| | | | | 165 | | | | | 170 | | | | | 175 | | |
| ccc | gac | cag | tgg | gcc | gac | tac | cgg | gcc | ctg | acc | ggg | gac | gag | tcc | gac | 576 |
| Pro | Asp | Gln | Trp | Ala | Asp | Tyr | Arg | Ala | Leu | Thr | Gly | Asp | Glu | Ser | Asp | |
| | | | 180 | | | | | 185 | | | | | 190 | | | |
| aac | ctt | ccc | ggg | gtc | aag | ggc | atc | ggg | gag | aag | acg | gcg | agg | aag | ctt | 624 |
| Asn | Leu | Pro | Gly | Val | Lys | Gly | Ile | Gly | Glu | Lys | Thr | Ala | Arg | Lys | Leu | |
| | | | 195 | | | | | 200 | | | | | 205 | | | |
| ctg | gag | gag | tgg | ggg | agc | ctg | gaa | gcc | ctc | ctc | aag | aac | ctg | gac | cgg | 672 |
| Leu | Glu | Glu | Trp | Gly | Ser | Leu | Glu | Ala | Leu | Leu | Lys | Asn | Leu | Asp | Arg | |
| | 210 | | | | | 215 | | | | | 220 | | | | | |
| ctg | aag | ccc | gcc | atc | cgg | gag | aag | atc | ctg | gcc | cac | atg | gac | gat | ctg | 720 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Leu | Lys | Pro | Ala | Ile | Arg | Glu | Lys | Ile | Leu | Ala | His | Met | Asp | Asp | Leu |      |
| 225 |     |     |     |     | 230 |     |     |     |     | 235 |     |     |     |     | 240 |      |

```
aag ctc tcc tgg gac ctg gcc aag gtg cgc acc gac ctg ccc ctg gag      768
Lys Leu Ser Trp Asp Leu Ala Lys Val Arg Thr Asp Leu Pro Leu Glu
            245                 250                 255 gtg gac ttc gcc aaa agg cgg gag ccc gac cgg gag agg ctt agg gcc      816
Val Asp Phe Ala Lys Arg Arg Glu Pro Asp Arg Glu Arg Leu Arg Ala
                260                 265                 270 ttt ctg gag agg ctt gag ttt ggc agc ctc ctc cac gag ttc ggc ctt      864
Phe Leu Glu Arg Leu Glu Phe Gly Ser Leu Leu His Glu Phe Gly Leu
            275                 280                 285 ctg gaa agc ccc aag gcc ctg gag gag gcc ccc tgg ccc ccg ccg gaa      912
Leu Glu Ser Pro Lys Ala Leu Glu Glu Ala Pro Trp Pro Pro Pro Glu
        290                 295                 300 ggg gcc ttc gtg ggc ttt gtg ctt tcc cgc aag gag ccc atg tgg gcc      960
Gly Ala Phe Val Gly Phe Val Leu Ser Arg Lys Glu Pro Met Trp Ala
305             310                 315                 320 gat ctt ctg gcc ctg gcc gcc gcc agg ggg ggc cgg gtc cac cgg gcc     1008
Asp Leu Leu Ala Leu Ala Ala Ala Arg Gly Gly Arg Val His Arg Ala
                325                 330                 335 ccc gag cct tat aaa gcc ctc agg gac ctg aag gag gcg cgg ggg ctt     1056
Pro Glu Pro Tyr Lys Ala Leu Arg Asp Leu Lys Glu Ala Arg Gly Leu
            340                 345                 350 ctc gcc aaa gac ctg agc gtt ctg gcc ctg agg gaa ggc ctt ggc ctc     1104
Leu Ala Lys Asp Leu Ser Val Leu Ala Leu Arg Glu Gly Leu Gly Leu
                355                 360                 365 ccg ccc ggc gac gac ccc atg ctc ctc gcc tac ctc ctg gac cct tcc     1152
Pro Pro Gly Asp Asp Pro Met Leu Leu Ala Tyr Leu Leu Asp Pro Ser
370                 375                 380 aac acc acc ccc gag ggg gtg gcc cgg cgc tac ggc ggg gag tgg acg     1200
Asn Thr Thr Pro Glu Gly Val Ala Arg Arg Tyr Gly Gly Glu Trp Thr
385                 390                 395                 400 gag gag gcg ggg gag cgg gcc gcc ctt tcc gag agg ctc ttc gcc aac     1248
Glu Glu Ala Gly Glu Arg Ala Ala Leu Ser Glu Arg Leu Phe Ala Asn
                405                 410                 415 ctg tgg ggg agg ctt gag ggg gag gag agg ctc ctt tgg ctt tac cgg     1296
Leu Trp Gly Arg Leu Glu Gly Glu Glu Arg Leu Leu Trp Leu Tyr Arg
            420                 425                 430 gag gtg gag agg ccc ctt tcc gct gtc ctg gcc cac atg gag gcc acg     1344
Glu Val Glu Arg Pro Leu Ser Ala Val Leu Ala His Met Glu Ala Thr
                435                 440                 445 ggg gtg cgc ctg gac gtg gcc tat ctc agg gcc ttg tcc ctg gag gtg     1392
Gly Val Arg Leu Asp Val Ala Tyr Leu Arg Ala Leu Ser Leu Glu Val
450                 455                 460 gcc ggg gag atc gcc cgc ctc gag gcc gag gtc ttc cgc ctg gcc ggc     1440
Ala Gly Glu Ile Ala Arg Leu Glu Ala Glu Val Phe Arg Leu Ala Gly
465                 470                 475                 480 cac ccc ttc aac ctc aac tcc cgg gac cag ctg gaa agg gtc ctc ttt     1488
His Pro Phe Asn Leu Asn Ser Arg Asp Gln Leu Glu Arg Val Leu Phe
                485                 490                 495 gac gag cta ggg ctt ccc gcc atc ggc aag acg gag aag acc ggc aag     1536
Asp Glu Leu Gly Leu Pro Ala Ile Gly Lys Thr Glu Lys Thr Gly Lys
            500                 505                 510 cgc tcc acc agc gcc gcc gtc ctg gag gcc ctc cgc gag gcc cac ccc     1584
Arg Ser Thr Ser Ala Ala Val Leu Glu Ala Leu Arg Glu Ala His Pro
                515                 520                 525 atc gtg gag aag atc ctg cag tac cgg gag ctc acc aag ctg aag agc     1632
Ile Val Glu Lys Ile Leu Gln Tyr Arg Glu Leu Thr Lys Leu Lys Ser
530                 535                 540
```

```
acc tac att gac ccc ttg ccg gac ctc atc cac ccc agg acg ggc cgc      1680
Thr Tyr Ile Asp Pro Leu Pro Asp Leu Ile His Pro Arg Thr Gly Arg
545                 550                 555                 560 ctc cac acc cgc ttc aac cag acg gcc acg gcc acg ggc agg cta agt      1728
Leu His Thr Arg Phe Asn Gln Thr Ala Thr Ala Thr Gly Arg Leu Ser
                565                 570                 575 agc tcc gat ccc aac ctc cag aac atc ccc gtc cgc acc ccg ctt ggg      1776
Ser Ser Asp Pro Asn Leu Gln Asn Ile Pro Val Arg Thr Pro Leu Gly
            580                 585                 590 cag agg atc cgc cgg gcc ttc atc gcc gag gag ggg tgg cta ttg gtg      1824
Gln Arg Ile Arg Arg Ala Phe Ile Ala Glu Glu Gly Trp Leu Leu Val
        595                 600                 605 gcc ctg gcc tat agc cag ata gag ctc agg gtg ctg gcc cac ctc tcc      1872
Ala Leu Ala Tyr Ser Gln Ile Glu Leu Arg Val Leu Ala His Leu Ser
610                 615                 620 ggc gac gag aac ctg atc cgg gtc ttc cag gag ggg cgg gac atc cac      1920
Gly Asp Glu Asn Leu Ile Arg Val Phe Gln Glu Gly Arg Asp Ile His
625                 630                 635                 640 acg gag acc gcc agc tgg atg ttc ggc gtc ccc cgg gag gcc gtg gac      1968
Thr Glu Thr Ala Ser Trp Met Phe Gly Val Pro Arg Glu Ala Val Asp
                645                 650                 655 ccc ctg atg cgc cgg gcg gcc aag acc atc aac ttc ggg gtc ctc tac      2016
Pro Leu Met Arg Arg Ala Ala Lys Thr Ile Asn Phe Gly Val Leu Tyr
            660                 665                 670 ggc atg tcg gcc cac cgc ctc tcc cag gag cta gcc atc cct tac gag      2064
Gly Met Ser Ala His Arg Leu Ser Gln Glu Leu Ala Ile Pro Tyr Glu
        675                 680                 685 gag gcc cag gcc ttc att gag cgc tac ttt cag agc ttc ccc aag gtg      2112
Glu Ala Gln Ala Phe Ile Glu Arg Tyr Phe Gln Ser Phe Pro Lys Val
690                 695                 700 cgg gcc tgg att gag aag acc ctg gag gag ggc agg agg cgg ggg tac      2160
Arg Ala Trp Ile Glu Lys Thr Leu Glu Glu Gly Arg Arg Arg Gly Tyr
705                 710                 715                 720 gtg gag acc ctc ttc ggc cgc cgc cgc tac gtg cca gac cta gag gcc      2208
Val Glu Thr Leu Phe Gly Arg Arg Arg Tyr Val Pro Asp Leu Glu Ala
                725                 730                 735 cgg gtg aag agc gtg cgg gag gcg gcc gag cgc atg gcc ttc aac atg      2256
Arg Val Lys Ser Val Arg Glu Ala Ala Glu Arg Met Ala Phe Asn Met
            740                 745                 750 ccc gtc cag ggc acc gcc gcc gac ctc atg aag ctg gct atg gtg aag      2304
Pro Val Gln Gly Thr Ala Ala Asp Leu Met Lys Leu Ala Met Val Lys
        755                 760                 765 ctc ttc ccc agg ctg gag gaa atg ggg gcc agg atg ctc ctt cag gtc      2352
Leu Phe Pro Arg Leu Glu Glu Met Gly Ala Arg Met Leu Leu Gln Val
770                 775                 780 cac gac gag ctg gtc ctc gag gcc cca aaa gag agg gcg gag gcc gtg      2400
His Asp Glu Leu Val Leu Glu Ala Pro Lys Glu Arg Ala Glu Ala Val
785                 790                 795                 800 gcc cgg ctg gcc aag gag gtc atg gag ggg gtg tat ccc ctg gcc gtg      2448
Ala Arg Leu Ala Lys Glu Val Met Glu Gly Val Tyr Pro Leu Ala Val
                805                 810                 815 ccc ctg gag gtg gag gtg ggg ata ggg gag gac tgg ctc tcc gcc aag      2496
Pro Leu Glu Val Glu Val Gly Ile Gly Glu Asp Trp Leu Ser Ala Lys
            820                 825                 830 gag tgatag                                                            2505
Glu

<210> SEQ ID NO 69
<211> LENGTH: 833
<212> TYPE: PRT
```

<213> ORGANISM: Artificial Sequence
<220> FEATURE:
<223> OTHER INFORMATION: Synthetic Construct

<400> SEQUENCE: 69

```
Met Asn Ser Gly Met Leu Pro Leu Phe Glu Pro Lys Gly Arg Val Leu
1               5                   10                  15

Leu Val Asp Gly His His Leu Ala Tyr Arg Thr Phe His Ala Leu Lys
            20                  25                  30

Gly Leu Thr Thr Ser Arg Gly Glu Pro Val Gln Ala Val Tyr Gly Phe
        35                  40                  45

Ala Lys Ser Leu Leu Lys Ala Leu Lys Glu Asp Gly Asp Ala Val Ile
    50                  55                  60

Val Val Phe Asp Ala Lys Ala Pro Ser Phe Arg His Glu Ala Tyr Gly
65                  70                  75                  80

Gly Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Leu Ala Arg Leu
            100                 105                 110

Glu Val Pro Gly Tyr Glu Ala Asp Asp Val Leu Ala Ser Leu Ala Lys
        115                 120                 125

Lys Ala Glu Lys Glu Gly Tyr Glu Val Arg Ile Leu Thr Ala Asp Lys
    130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
        195                 200                 205

Leu Glu Glu Trp Gly Ser Leu Glu Ala Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
    275                 280                 285

Leu Glu Ser Pro Lys Ala Leu Glu Glu Ala Pro Trp Pro Pro Pro Glu
290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Thr Pro Glu Gly Val Ala Arg Arg Tyr Gly Gly Glu Trp Thr
```

-continued

```
            385                 390                 395                 400
Glu Glu Ala Gly Glu Arg Ala Leu Ser Glu Arg Leu Phe Ala Asn
                405                 410                 415
Leu Trp Gly Arg Leu Glu Gly Glu Arg Leu Leu Trp Leu Tyr Arg
                420                 425                 430
Glu Val Glu Arg Pro Leu Ser Ala Val Leu Ala His Met Glu Ala Thr
                435                 440                 445
Gly Val Arg Leu Asp Val Ala Tyr Leu Arg Ala Leu Ser Leu Glu Val
                450                 455                 460
Ala Gly Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
                500                 505                 510
Arg Ser Thr Ser Ala Ala Val Leu Glu Ala Leu Arg Glu Ala His Pro
                515                 520                 525
Ile Val Glu Lys Ile Leu Gln Tyr Arg Glu Leu Thr Lys Leu Lys Ser
530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
                580                 585                 590
Gln Arg Ile Arg Arg Ala Phe Ile Ala Glu Glu Gly Trp Leu Leu Val
                595                 600                 605
Ala Leu Ala Tyr Ser Gln Ile Glu Leu Arg Val Leu Ala His Leu Ser
610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
                660                 665                 670
Gly Met Ser Ala His Arg Leu Ser Gln Glu Leu Ala Ile Pro Tyr Glu
                675                 680                 685
Glu Ala Gln Ala Phe Ile Glu Arg Tyr Phe Gln Ser Phe Pro Lys Val
                690                 695                 700
Arg Ala Trp Ile Glu Lys Thr Leu Glu Glu Gly Arg Arg Arg Gly Tyr
705                 710                 715                 720
Val Glu Thr Leu Phe Gly Arg Arg Arg Tyr Val Pro Asp Leu Glu Ala
                725                 730                 735
Arg Val Lys Ser Val Arg Glu Ala Ala Glu Arg Met Ala Phe Asn Met
                740                 745                 750
Pro Val Gln Gly Thr Ala Ala Asp Leu Met Lys Leu Ala Met Val Lys
                755                 760                 765
Leu Phe Pro Arg Leu Glu Glu Met Gly Ala Arg Met Leu Leu Gln Val
                770                 775                 780
His Asp Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
                805                 810                 815
```

-continued

```
Pro Leu Glu Val Glu Val Gly Ile Gly Glu Asp Trp Leu Ser Ala Lys
            820                 825                 830

Glu

<210> SEQ ID NO 70
<211> LENGTH: 2505
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(2499)

<400> SEQUENCE: 70 atg aat tcg ggg atg ctg ccc ctc ttt gag ccc aag ggc cgg gtc ctc      48
Met Asn Ser Gly Met Leu Pro Leu Phe Glu Pro Lys Gly Arg Val Leu
1               5                   10                  15 ctg gtg gac ggc cac cac ctg gcc tac cgc acc ttc cac gcc ctg aag      96
Leu Val Asp Gly His His Leu Ala Tyr Arg Thr Phe His Ala Leu Lys
            20                  25                  30 ggc ctc acc acc agc cgg ggg gag ccg gtg cag gcg gtc tac ggc ttc     144
Gly Leu Thr Thr Ser Arg Gly Glu Pro Val Gln Ala Val Tyr Gly Phe
        35                  40                  45 gcc aag agc ctc ctc aag gcc ctc aag gag gac ggg gac gcg gtg atc     192
Ala Lys Ser Leu Leu Lys Ala Leu Lys Glu Asp Gly Asp Ala Val Ile
    50                  55                  60 gtg gtc ttt gac gcc aag gcc ccc tcc ttc cgc cac gag gcc tac ggg     240
Val Val Phe Asp Ala Lys Ala Pro Ser Phe Arg His Glu Ala Tyr Gly
65                  70                  75                  80 ggg tac aag gcg ggc cgg gcc ccc acg ccg gag gac ttt ccc cgg caa     288
Gly Tyr Lys Ala Gly Arg Ala Pro Thr Pro Glu Asp Phe Pro Arg Gln
                85                  90                  95 ctc gcc ctc atc aag gag ctg gtg gac ctc ctg ggg ctg gcg cgc ctc     336
Leu Ala Leu Ile Lys Glu Leu Val Asp Leu Leu Gly Leu Ala Arg Leu
            100                 105                 110 gag gtc ccg ggc tac gag gcg gac gac gtc ctg gcc agc ctg gcc aag     384
Glu Val Pro Gly Tyr Glu Ala Asp Asp Val Leu Ala Ser Leu Ala Lys
        115                 120                 125 aag gcg gaa aag gag ggc tac gag gtc cgc atc ctc acc gcc gac aaa     432
Lys Ala Glu Lys Glu Gly Tyr Glu Val Arg Ile Leu Thr Ala Asp Lys
    130                 135                 140 gac ctt tac cag ctc ctt tcc gac cgc atc cac gtc ctc cac ccc gag     480
Asp Leu Tyr Gln Leu Leu Ser Asp Arg Ile His Val Leu His Pro Glu
145                 150                 155                 160 ggg tac ctc atc acc ccg gcc tgg ctt tgg gaa aag tac ggc ctg agg     528
Gly Tyr Leu Ile Thr Pro Ala Trp Leu Trp Glu Lys Tyr Gly Leu Arg
                165                 170                 175 ccc gac cag tgg gcc gac tac cgg gcc ctg acc ggg gac gag tcc gac     576
Pro Asp Gln Trp Ala Asp Tyr Arg Ala Leu Thr Gly Asp Glu Ser Asp
            180                 185                 190 aac ctt ccc ggg gtc aag ggc atc ggg gag aag acg gcg agg aag ctt     624
Asn Leu Pro Gly Val Lys Gly Ile Gly Glu Lys Thr Ala Arg Lys Leu
        195                 200                 205 ctg gag gag tgg ggg agc ctg gaa gcc ctc ctc aag aac ctg gac cgg     672
Leu Glu Glu Trp Gly Ser Leu Glu Ala Leu Leu Lys Asn Leu Asp Arg
    210                 215                 220 ctg aag ccc gcc atc cgg gag aag atc ctg gcc cac atg gac gat ctg     720
Leu Lys Pro Ala Ile Arg Glu Lys Ile Leu Ala His Met Asp Asp Leu
225                 230                 235                 240
```

-continued

| | | |
|---|---|---|
| aag ctc tcc tgg gac ctg gcc aag gtg cgc acc gac ctg ccc ctg gag<br>Lys Leu Ser Trp Asp Leu Ala Lys Val Arg Thr Asp Leu Pro Leu Glu<br>245                        250                        255 | 768 |
| gtg gac ttc gcc aaa agg cgg gag ccc gac cgg gag agg ctt agg gcc<br>Val Asp Phe Ala Lys Arg Arg Glu Pro Asp Arg Glu Arg Leu Arg Ala<br>          260                      265                      270 | 816 |
| ttt ctg gag agg ctt gag ttt ggc agc ctc ctc cac gag ttc ggc ctt<br>Phe Leu Glu Arg Leu Glu Phe Gly Ser Leu Leu His Glu Phe Gly Leu<br>275                        280                      285 | 864 |
| ctg gaa agc ccc aag gcc ctg gag gag gcc ccc tgg ccc ccg ccg gaa<br>Leu Glu Ser Pro Lys Ala Leu Glu Glu Ala Pro Trp Pro Pro Pro Glu<br>          290                      295                      300 | 912 |
| ggg gcc ttc gtg ggc ttt gtg ctt tcc cgc aag gag ccc atg tgg gcc<br>Gly Ala Phe Val Gly Phe Val Leu Ser Arg Lys Glu Pro Met Trp Ala<br>305                        310                      315                      320 | 960 |
| gat ctt ctg gcc ctg gcc gcc gcc agg ggg ggc cgg gtc cac cgg gcc<br>Asp Leu Leu Ala Leu Ala Ala Ala Arg Gly Gly Arg Val His Arg Ala<br>                      325                      330                      335 | 1008 |
| ccc gag cct tat aaa gcc ctc agg gac ctg aag gag gcg cgg ggg ctt<br>Pro Glu Pro Tyr Lys Ala Leu Arg Asp Leu Lys Glu Ala Arg Gly Leu<br>                  340                      345                      350 | 1056 |
| ctc gcc aaa gac ctg agc gtt ctg gcc ctg agg gaa ggc ctt ggc ctc<br>Leu Ala Lys Asp Leu Ser Val Leu Ala Leu Arg Glu Gly Leu Gly Leu<br>355                        360                      365 | 1104 |
| ccg ccc ggc gac gac ccc atg ctc ctc gcc tac ctc ctg gac cct tcc<br>Pro Pro Gly Asp Asp Pro Met Leu Leu Ala Tyr Leu Leu Asp Pro Ser<br>          370                      375                      380 | 1152 |
| aac acc acc ccc gag ggg gtg gcc cgg cgc tac ggg ggg gag tgg acg<br>Asn Thr Thr Pro Glu Gly Val Ala Arg Arg Tyr Gly Gly Glu Trp Thr<br>385                        390                      395                      400 | 1200 |
| gag gag gcg ggg gag cgg gcc gcc ctt tcc gag agg ctc ttc gcc aac<br>Glu Glu Ala Gly Glu Arg Ala Ala Leu Ser Glu Arg Leu Phe Ala Asn<br>                      405                      410                      415 | 1248 |
| ctg tgg ggg agg ctt gag ggg gag gag agg ctc ctt tgg ctt tac cgg<br>Leu Trp Gly Arg Leu Glu Gly Glu Glu Arg Leu Leu Trp Leu Tyr Arg<br>                  420                      425                      430 | 1296 |
| gag gtg gag agg ccc ctt tcc gct gtc ctg gcc cac atg gag gcc acg<br>Glu Val Glu Arg Pro Leu Ser Ala Val Leu Ala His Met Glu Ala Thr<br>          435                      440                      445 | 1344 |
| ggg gtg cgc ctg gac gtg gcc tat ctc agg gcc ttg tcc ctg gag gtg<br>Gly Val Arg Leu Asp Val Ala Tyr Leu Arg Ala Leu Ser Leu Glu Val<br>450                        455                      460 | 1392 |
| gcc ggg gag atc gcc cgc ctc gag gcc gag gtc ttc cgc ctg gcc ggc<br>Ala Gly Glu Ile Ala Arg Leu Glu Ala Glu Val Phe Arg Leu Ala Gly<br>465                        470                      475                      480 | 1440 |
| cac ccc ttc aac ctc aac tcc cgg gac cag ctg gaa agg gtc ctc ttt<br>His Pro Phe Asn Leu Asn Ser Arg Asp Gln Leu Glu Arg Val Leu Phe<br>                      485                      490                      495 | 1488 |
| gac gag cta ggg ctt ccc gcc atc ggc aag acg gag aag acc ggc aag<br>Asp Glu Leu Gly Leu Pro Ala Ile Gly Lys Thr Glu Lys Thr Gly Lys<br>          500                      505                      510 | 1536 |
| cgc tcc acc agc gcc gcc gtc ctg gag gcc ctc cgc gag gcc cac ccc<br>Arg Ser Thr Ser Ala Ala Val Leu Glu Ala Leu Arg Glu Ala His Pro<br>515                        520                      525 | 1584 |
| atc gtg gag aag atc ctg cag tac cgg gag ctc acc aag ctg aag agc<br>Ile Val Glu Lys Ile Leu Gln Tyr Arg Glu Leu Thr Lys Leu Lys Ser<br>          530                      535                      540 | 1632 |
| acc tac att gac ccc ttg ccg gac ctc atc cac ccc agg acg ggc cgc<br>Thr Tyr Ile Asp Pro Leu Pro Asp Leu Ile His Pro Arg Thr Gly Arg<br>545                        550                      555                      560 | 1680 |

```
ctc cac acc cgc ttc aac cag acg gcc acg gcc acg ggc agg cta agt      1728
Leu His Thr Arg Phe Asn Gln Thr Ala Thr Ala Thr Gly Arg Leu Ser
            565                 570                 575 agc tcc gat ccc aac ctc cag aac atc ccc gtc cgc acc ccg ctt ggg      1776
Ser Ser Asp Pro Asn Leu Gln Asn Ile Pro Val Arg Thr Pro Leu Gly
        580                 585                 590 cag agg atc cgc cgg gcc ttc atc gcc gag gag ggg tgg cta ttg gtg      1824
Gln Arg Ile Arg Arg Ala Phe Ile Ala Glu Glu Gly Trp Leu Leu Val
    595                 600                 605 gcc ctg gtc tat agc cag ata gag ctc agg gtg ctg gcc cac ctc tcc      1872
Ala Leu Val Tyr Ser Gln Ile Glu Leu Arg Val Leu Ala His Leu Ser
610                 615                 620 ggc gac gag aac ctg atc cgg gtc ttc cag gag ggg cgg gac atc cac      1920
Gly Asp Glu Asn Leu Ile Arg Val Phe Gln Glu Gly Arg Asp Ile His
625                 630                 635                 640 acg gag acc gcc agc tgg atg ttc ggc gtc ccc cgg gag gcc gtg gac      1968
Thr Glu Thr Ala Ser Trp Met Phe Gly Val Pro Arg Glu Ala Val Asp
                645                 650                 655 ccc ctg atg cgc cgg gcg gcc aag acc atc aac ttc ggg gtc ctc tac      2016
Pro Leu Met Arg Arg Ala Ala Lys Thr Ile Asn Phe Gly Val Leu Tyr
            660                 665                 670 ggc atg tcg gcc cac cgc ctc tcc cag gag cta gcc atc cct tac gag      2064
Gly Met Ser Ala His Arg Leu Ser Gln Glu Leu Ala Ile Pro Tyr Glu
        675                 680                 685 gag gcc cag gcc ttc att gag cgc tac ttt cag agc ttc ccc aag gtg      2112
Glu Ala Gln Ala Phe Ile Glu Arg Tyr Phe Gln Ser Phe Pro Lys Val
    690                 695                 700 cgg gcc tgg att gag aag acc ctg gag gag ggc agg agg cgg ggg tac      2160
Arg Ala Trp Ile Glu Lys Thr Leu Glu Glu Gly Arg Arg Arg Gly Tyr
705                 710                 715                 720 gtg gag acc ctc ttc ggc cgc cgc cgc tac gtg cca gac cta gag gcc      2208
Val Glu Thr Leu Phe Gly Arg Arg Arg Tyr Val Pro Asp Leu Glu Ala
                725                 730                 735 cgg gtg aag agc gtg cgg gag gcg gcc gag cgc atg gcc ttc aac atg      2256
Arg Val Lys Ser Val Arg Glu Ala Ala Glu Arg Met Ala Phe Asn Met
            740                 745                 750 ccc gtc cag ggc acc gcc gcc gac ctc atg aag ctg gct atg gtg aag      2304
Pro Val Gln Gly Thr Ala Ala Asp Leu Met Lys Leu Ala Met Val Lys
        755                 760                 765 ctc ttc ccc agg ctg gag gaa atg ggg gcc agg atg ctc ctt cag gtc      2352
Leu Phe Pro Arg Leu Glu Glu Met Gly Ala Arg Met Leu Leu Gln Val
    770                 775                 780 cac gac gag ctg gtc ctc gag gcc cca aaa gag agg gcg gag gcc gtg      2400
His Asp Glu Leu Val Leu Glu Ala Pro Lys Glu Arg Ala Glu Ala Val
785                 790                 795                 800 gcc cgg ctg gcc aag gag gtc atg gag ggg gtg tat ccc ctg gcc gtg      2448
Ala Arg Leu Ala Lys Glu Val Met Glu Gly Val Tyr Pro Leu Ala Val
                805                 810                 815 ccc ctg gag gtg gag gtg ggg ata ggg gag gac tgg ctc tcc gcc aag      2496
Pro Leu Glu Val Glu Val Gly Ile Gly Glu Asp Trp Leu Ser Ala Lys
            820                 825                 830 gag tgatag                                                           2505
Glu

<210> SEQ ID NO 71
<211> LENGTH: 833
<212> TYPE: PRT
<213> ORGANISM: Artificial Sequence
<220> FEATURE:
<223> OTHER INFORMATION: Synthetic Construct
```

```
<400> SEQUENCE: 71

Met Asn Ser Gly Met Leu Pro Leu Phe Glu Pro Lys Gly Arg Val Leu
1               5                   10                  15

Leu Val Asp Gly His His Leu Ala Tyr Arg Thr Phe His Ala Leu Lys
            20                  25                  30

Gly Leu Thr Thr Ser Arg Gly Glu Pro Val Gln Ala Val Tyr Gly Phe
        35                  40                  45

Ala Lys Ser Leu Leu Lys Ala Leu Lys Glu Asp Gly Asp Ala Val Ile
    50                  55                  60

Val Val Phe Asp Ala Lys Ala Pro Ser Phe Arg His Glu Ala Tyr Gly
65                  70                  75                  80

Gly Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Leu Ala Arg Leu
            100                 105                 110

Glu Val Pro Gly Tyr Glu Ala Asp Asp Val Leu Ala Ser Leu Ala Lys
        115                 120                 125

Lys Ala Glu Lys Glu Gly Tyr Glu Val Arg Ile Leu Thr Ala Asp Lys
    130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
        195                 200                 205

Leu Glu Glu Trp Gly Ser Leu Glu Ala Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
```

-continued

```
            405                 410                 415
Leu Trp Gly Arg Leu Glu Gly Glu Arg Leu Leu Trp Leu Tyr Arg
            420                 425                 430
Glu Val Glu Arg Pro Leu Ser Ala Val Leu Ala His Met Glu Ala Thr
                435                 440                 445
Gly Val Arg Leu Asp Val Ala Tyr Leu Arg Ala Leu Ser Leu Glu Val
            450                 455                 460
Ala Gly Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
            500                 505                 510
Arg Ser Thr Ser Ala Ala Val Leu Glu Ala Leu Arg Glu Ala His Pro
            515                 520                 525
Ile Val Glu Lys Ile Leu Gln Tyr Arg Glu Leu Thr Lys Leu Lys Ser
            530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
            580                 585                 590
Gln Arg Ile Arg Arg Ala Phe Ile Ala Glu Gly Trp Leu Leu Val
            595                 600                 605
Ala Leu Val Tyr Ser Gln Ile Glu Leu Arg Val Leu Ala His Leu Ser
610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
            660                 665                 670
Gly Met Ser Ala His Arg Leu Ser Gln Glu Leu Ala Ile Pro Tyr Glu
            675                 680                 685
Glu Ala Gln Ala Phe Ile Glu Arg Tyr Phe Gln Ser Phe Pro Lys Val
            690                 695                 700
Arg Ala Trp Ile Glu Lys Thr Leu Glu Glu Gly Arg Arg Arg Gly Tyr
705                 710                 715                 720
Val Glu Thr Leu Phe Gly Arg Arg Arg Tyr Val Pro Asp Leu Glu Ala
                725                 730                 735
Arg Val Lys Ser Val Arg Glu Ala Ala Glu Arg Met Ala Phe Asn Met
                740                 745                 750
Pro Val Gln Gly Thr Ala Ala Asp Leu Met Lys Leu Ala Met Val Lys
                755                 760                 765
Leu Phe Pro Arg Leu Glu Glu Met Gly Ala Arg Met Leu Leu Gln Val
            770                 775                 780
His Asp Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
                805                 810                 815
Pro Leu Glu Val Glu Val Gly Ile Gly Glu Asp Trp Leu Ser Ala Lys
            820                 825                 830
```

Glu

<210> SEQ ID NO 72
<211> LENGTH: 25
<212> TYPE: DNA
<213> ORGANISM: Artificial Sequence
<220> FEATURE:
<223> OTHER INFORMATION: Synthetic

<400> SEQUENCE: 72
gggataccat gggagtgcag tttgg        25

<210> SEQ ID NO 73
<211> LENGTH: 27
<212> TYPE: DNA
<213> ORGANISM: Artificial Sequence
<220> FEATURE:
<223> OTHER INFORMATION: Synthetic

<400> SEQUENCE: 73
ggtaaatttt tctcgtcgac atcccac        27

<210> SEQ ID NO 74
<211> LENGTH: 981
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(978)

<400> SEQUENCE: 74

| atg gga gtg cag ttt ggt gat ttt att cca aaa aat att atc tcc ttt | 48 |
|---|---|
| Met Gly Val Gln Phe Gly Asp Phe Ile Pro Lys Asn Ile Ile Ser Phe | |
| 1               5                   10                  15 | |

| gaa gat tta aaa ggg aaa aaa gta gct att gat gga atg aat gca tta | 96 |
|---|---|
| Glu Asp Leu Lys Gly Lys Lys Val Ala Ile Asp Gly Met Asn Ala Leu | |
|           20                  25                  30 | |

| tat cag ttt tta aca tct ata cgt ttg aga gat ggt tct cca ttg aga | 144 |
|---|---|
| Tyr Gln Phe Leu Thr Ser Ile Arg Leu Arg Asp Gly Ser Pro Leu Arg | |
|       35                  40                  45 | |

| aat aga aaa gga gag ata acc tca gca tat aac gga gtt ttt tat aaa | 192 |
|---|---|
| Asn Arg Lys Gly Glu Ile Thr Ser Ala Tyr Asn Gly Val Phe Tyr Lys | |
|   50                  55                  60 | |

| acc ata cat ttg tta gag aat gat ata act cca atc tgg gtt ttt gat | 240 |
|---|---|
| Thr Ile His Leu Leu Glu Asn Asp Ile Thr Pro Ile Trp Val Phe Asp | |
| 65                  70                  75                  80 | |

| ggt gag cca cca aag tta aag gag aaa aca agg aaa gtt agg aga gag | 288 |
|---|---|
| Gly Glu Pro Pro Lys Leu Lys Glu Lys Thr Arg Lys Val Arg Arg Glu | |
|               85                  90                  95 | |

| atg aaa gag aaa gct gaa ctt aag atg aaa gag gca att aaa aag gag | 336 |
|---|---|
| Met Lys Glu Lys Ala Glu Leu Lys Met Lys Glu Ala Ile Lys Lys Glu | |
|           100                 105                 110 | |

| gat ttt gaa gaa gct gct aag tat gca aag agg gtt agc tat cta act | 384 |
|---|---|
| Asp Phe Glu Glu Ala Ala Lys Tyr Ala Lys Arg Val Ser Tyr Leu Thr | |
|       115                 120                 125 | |

| ccg aaa atg gtt gaa aac tgc aaa tat ttg tta agt ttg atg ggc att | 432 |
|---|---|
| Pro Lys Met Val Glu Asn Cys Lys Tyr Leu Leu Ser Leu Met Gly Ile | |
|   130                 135                 140 | |

| ccg tat gtt gaa gct ccc tct gag gga gag gca caa gca agc tat atg | 480 |
|---|---|
| Pro Tyr Val Glu Ala Pro Ser Glu Gly Glu Ala Gln Ala Ser Tyr Met | |
| 145                 150                 155                 160 | |

```
gca aag aag gga gat gtt tgg gca gtt gta agt caa gat tat gat gcc      528
Ala Lys Lys Gly Asp Val Trp Ala Val Val Ser Gln Asp Tyr Asp Ala
            165                 170                 175 ttg tta tat gga gct ccg aga gtt gtt aga aat tta aca act aca aag      576
Leu Leu Tyr Gly Ala Pro Arg Val Val Arg Asn Leu Thr Thr Thr Lys
        180                 185                 190 gag atg cca gaa ctt att gaa tta aat gag gtt tta gag gat tta aga      624
Glu Met Pro Glu Leu Ile Glu Leu Asn Glu Val Leu Glu Asp Leu Arg
    195                 200                 205 att tct ttg gat gat ttg ata gat ata gcc ata ttt atg gga act gac      672
Ile Ser Leu Asp Asp Leu Ile Asp Ile Ala Ile Phe Met Gly Thr Asp
210                 215                 220 tat aat cca gga gga gtt aaa gga ata gga ttt aaa agg gct tat gaa      720
Tyr Asn Pro Gly Gly Val Lys Gly Ile Gly Phe Lys Arg Ala Tyr Glu
225                 230                 235                 240 ttg gtt aga agt ggt gta gct aag gat gtt ttg aaa aaa gag gtt gaa      768
Leu Val Arg Ser Gly Val Ala Lys Asp Val Leu Lys Lys Glu Val Glu
                245                 250                 255 tac tac gat gag att aag agg ata ttt aaa gag cca aag gtt acc gat      816
Tyr Tyr Asp Glu Ile Lys Arg Ile Phe Lys Glu Pro Lys Val Thr Asp
            260                 265                 270 aac tat tca tta agc cta aaa ttg cca gat aaa gag gga att ata aaa      864
Asn Tyr Ser Leu Ser Leu Lys Leu Pro Asp Lys Glu Gly Ile Ile Lys
        275                 280                 285 ttc tta gtt gat gaa aat gac ttt aat tat gat agg gtt aaa aag cat      912
Phe Leu Val Asp Glu Asn Asp Phe Asn Tyr Asp Arg Val Lys Lys His
    290                 295                 300 gtt gat aaa ctc tat aac tta att gca aac aaa act aag caa aaa aca      960
Val Asp Lys Leu Tyr Asn Leu Ile Ala Asn Lys Thr Lys Gln Lys Thr
305                 310                 315                 320 tta gat gca tgg ttt aaa taa                                          981
Leu Asp Ala Trp Phe Lys
                325

<210> SEQ ID NO 75
<211> LENGTH: 326
<212> TYPE: PRT
<213> ORGANISM: Artificial Sequence
<220> FEATURE:
<223> OTHER INFORMATION: Synthetic Construct

<400> SEQUENCE: 75

Met Gly Val Gln Phe Gly Asp Phe Ile Pro Lys Asn Ile Ile Ser Phe
1               5                   10                  15

Glu Asp Leu Lys Gly Lys Lys Val Ala Ile Asp Gly Met Asn Ala Leu
            20                  25                  30

Tyr Gln Phe Leu Thr Ser Ile Arg Leu Arg Asp Gly Ser Pro Leu Arg
        35                  40                  45

Asn Arg Lys Gly Glu Ile Thr Ser Ala Tyr Asn Gly Val Phe Tyr Lys
    50                  55                  60

Thr Ile His Leu Leu Glu Asn Asp Ile Thr Pro Ile Trp Val Phe Asp
65                  70                  75                  80

Gly Glu Pro Pro Lys Leu Lys Glu Lys Thr Arg Lys Val Arg Arg Glu
                85                  90                  95

Met Lys Glu Lys Ala Glu Leu Lys Met Lys Glu Ala Ile Lys Lys Glu
            100                 105                 110

Asp Phe Glu Glu Ala Ala Lys Tyr Ala Lys Arg Val Ser Tyr Leu Thr
        115                 120                 125
```

```
Pro Lys Met Val Glu Asn Cys Lys Tyr Leu Leu Ser Leu Met Gly Ile
    130                 135                 140

Pro Tyr Val Glu Ala Pro Ser Glu Gly Glu Ala Gln Ala Ser Tyr Met
145                 150                 155                 160

Ala Lys Lys Gly Asp Val Trp Ala Val Ser Gln Asp Tyr Asp Ala
                165                 170                 175

Leu Leu Tyr Gly Ala Pro Arg Val Val Arg Asn Leu Thr Thr Thr Lys
                180                 185                 190

Glu Met Pro Glu Leu Ile Glu Leu Asn Glu Val Leu Glu Asp Leu Arg
            195                 200                 205

Ile Ser Leu Asp Asp Leu Ile Asp Ile Ala Ile Phe Met Gly Thr Asp
    210                 215                 220

Tyr Asn Pro Gly Gly Val Lys Gly Ile Gly Phe Lys Arg Ala Tyr Glu
225                 230                 235                 240

Leu Val Arg Ser Gly Val Ala Lys Asp Val Leu Lys Glu Val Glu
                245                 250                 255

Tyr Tyr Asp Glu Ile Lys Arg Ile Phe Lys Glu Pro Lys Val Thr Asp
                260                 265                 270

Asn Tyr Ser Leu Ser Leu Lys Leu Pro Asp Lys Glu Gly Ile Ile Lys
                275                 280                 285

Phe Leu Val Asp Glu Asn Asp Phe Asn Tyr Asp Arg Val Lys Lys His
    290                 295                 300

Val Asp Lys Leu Tyr Asn Leu Ile Ala Asn Lys Thr Lys Gln Lys Thr
305                 310                 315                 320

Leu Asp Ala Trp Phe Lys
                325
```

```
<210> SEQ ID NO 76
<211> LENGTH: 21
<212> TYPE: DNA
<213> ORGANISM: Artificial Sequence
<220> FEATURE:
<223> OTHER INFORMATION: Synthetic

<400> SEQUENCE: 76
gaggtgatac catgggtgtc c                                              21

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
gaaactctgc agcgcgtcag                                                20

<210> SEQ ID NO 78
<211> LENGTH: 1023
<212> TYPE: DNA
<213> ORGANISM: Pyrococcus furiosus
<220> FEATURE:
<221> NAME/KEY: CDS
<222> LOCATION: (1)..(1020)

<400> SEQUENCE: 78 atg ggt gtc cca att ggt gag att ata cca aga aaa gaa att gag tta    48
Met Gly Val Pro Ile Gly Glu Ile Ile Pro Arg Lys Glu Ile Glu Leu
1               5                   10                  15 gaa aac cta tac ggg aaa aaa atc gca atc gac gct ctt aat gca atc    96
```

```
                 Glu Asn Leu Tyr Gly Lys Lys Ile Ala Ile Asp Ala Leu Asn Ala Ile
                                  20                  25                  30 tac caa ttt ttg tcc aca ata aga cag aaa gat gga act cca ctt atg              144
Tyr Gln Phe Leu Ser Thr Ile Arg Gln Lys Asp Gly Thr Pro Leu Met
             35                  40                  45 gat tca aag ggt aga ata acc tcc cac cta agc ggg ctc ttt tac agg              192
Asp Ser Lys Gly Arg Ile Thr Ser His Leu Ser Gly Leu Phe Tyr Arg
 50                  55                  60 aca ata aac cta atg gag gct gga ata aaa cct gtg tat gtt ttt gat              240
Thr Ile Asn Leu Met Glu Ala Gly Ile Lys Pro Val Tyr Val Phe Asp
 65                  70                  75                  80 gga gaa cct cca gaa ttc aaa aag aaa gag ctc gaa aaa aga aga gaa              288
Gly Glu Pro Pro Glu Phe Lys Lys Lys Glu Leu Glu Lys Arg Arg Glu
                     85                  90                  95 gcg aga gag gaa gct gaa gaa aag tgg aga gaa gca ctt gaa aaa gga              336
Ala Arg Glu Glu Ala Glu Glu Lys Trp Arg Glu Ala Leu Glu Lys Gly
                100                 105                 110 gag ata gag gaa gca aga aaa tat gcc caa aga gca acc agg gta aat              384
Glu Ile Glu Glu Ala Arg Lys Tyr Ala Gln Arg Ala Thr Arg Val Asn
            115                 120                 125 gaa atg ctc atc gag gat gca aaa aaa ctc tta gag ctt atg gga att              432
Glu Met Leu Ile Glu Asp Ala Lys Lys Leu Leu Glu Leu Met Gly Ile
130                 135                 140 cct ata gtt caa gca cct agc gag gga gag gcc caa gct gca tat atg              480
Pro Ile Val Gln Ala Pro Ser Glu Gly Glu Ala Gln Ala Ala Tyr Met
145                 150                 155                 160 gcc gca aag ggg agc gtg tat gca tcg gct agt caa gat tac gat tcc              528
Ala Ala Lys Gly Ser Val Tyr Ala Ser Ala Ser Gln Asp Tyr Asp Ser
                    165                 170                 175 cta ctt ttt gga gct cca aga ctt gtt aga aac tta aca ata aca gga              576
Leu Leu Phe Gly Ala Pro Arg Leu Val Arg Asn Leu Thr Ile Thr Gly
                180                 185                 190 aaa aga aag ttg cct ggg aaa aat gtc tac gtc gag ata aag ccc gag              624
Lys Arg Lys Leu Pro Gly Lys Asn Val Tyr Val Glu Ile Lys Pro Glu
            195                 200                 205 ttg ata att ttg gag gaa gta ctc aag gaa tta aag cta aca aga gaa              672
Leu Ile Ile Leu Glu Glu Val Leu Lys Glu Leu Lys Leu Thr Arg Glu
210                 215                 220 aag ctc att gaa cta gca atc ctc gtt gga aca gac tac aac cca gga              720
Lys Leu Ile Glu Leu Ala Ile Leu Val Gly Thr Asp Tyr Asn Pro Gly
225                 230                 235                 240 gga ata aag ggc ata ggc ctt aaa aaa gct tta gag att gtt aga cac              768
Gly Ile Lys Gly Ile Gly Leu Lys Lys Ala Leu Glu Ile Val Arg His
                    245                 250                 255 tca aaa gat ccg cta gca aag ttc caa aag caa agc gat gtg gat tta              816
Ser Lys Asp Pro Leu Ala Lys Phe Gln Lys Gln Ser Asp Val Asp Leu
                260                 265                 270 tat gca ata aaa gag ttc ttc cta aac cca cca gtc aca gat aac tac              864
Tyr Ala Ile Lys Glu Phe Phe Leu Asn Pro Pro Val Thr Asp Asn Tyr
            275                 280                 285 aat tta gtg tgg aga gat ccc gac gaa gag gga ata cta aag ttc tta              912
Asn Leu Val Trp Arg Asp Pro Asp Glu Glu Gly Ile Leu Lys Phe Leu
290                 295                 300 tgt gac gag cat gac ttt agt gag gaa aga gta aag aat gga tta gag              960
Cys Asp Glu His Asp Phe Ser Glu Glu Arg Val Lys Asn Gly Leu Glu
305                 310                 315                 320 agg ctt aag aag gca atc aaa agt gga aaa caa tca acc ctt gaa agt             1008
Arg Leu Lys Lys Ala Ile Lys Ser Gly Lys Gln Ser Thr Leu Glu Ser
                    325                 330                 335
```

```
tgg ttc aag aga taa                                              1023
Trp Phe Lys Arg
            340

<210> SEQ ID NO 79
<211> LENGTH: 340
<212> TYPE: PRT
<213> ORGANISM: Pyrococcus furiosus

<400> SEQUENCE: 79

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Lys Asp Gly Thr Pro Leu Met
        35                  40                  45

Asp Ser Lys Gly Arg Ile Thr Ser His Leu Ser Gly Leu Phe Tyr Arg
    50                  55                  60

Thr Ile Asn Leu Met Glu Ala Gly Ile Lys Pro Val Tyr Val Phe Asp
65                  70                  75                  80

Gly Glu Pro Pro Glu Phe Lys Lys Lys Glu Leu Glu Lys Arg Arg Glu
                85                  90                  95

Ala Arg Glu Glu Ala Glu Glu Lys Trp Arg Glu Ala Leu Glu Lys Gly
            100                 105                 110

Glu Ile Glu Glu Ala Arg Lys Tyr Ala Gln Arg Ala Thr Arg Val Asn
        115                 120                 125

Glu Met Leu Ile Glu Asp Ala Lys Lys Leu Leu Glu Leu Met Gly Ile
    130                 135                 140

Pro Ile Val Gln Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                165                 170                 175

Leu Leu Phe Gly Ala Pro Arg Leu Val Arg Asn Leu Thr Ile Thr Gly
            180                 185                 190

Lys Arg Lys Leu Pro Gly Lys Asn Val Tyr Val Glu Ile Lys Pro Glu
        195                 200                 205

Leu Ile Ile Leu Glu Glu Val Leu Lys Glu Leu Lys Leu Thr Arg Glu
    210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
                245                 250                 255

Ser Lys Asp Pro Leu Ala Lys Phe Gln Lys Gln Ser Asp Val Asp Leu
            260                 265                 270

Tyr Ala Ile Lys Glu Phe Phe Leu Asn Pro Pro Val Thr Asp Asn Tyr
        275                 280                 285

Asn Leu Val Trp Arg Asp Pro Asp Glu Glu Gly Ile Leu Lys Phe Leu
    290                 295                 300

Cys Asp Glu His Asp Phe Ser Glu Glu Arg Val Lys Asn Gly Leu Glu
305                 310                 315                 320

Arg Leu Lys Lys Ala Ile Lys Ser Gly Lys Gln Ser Thr Leu Glu Ser
                325                 330                 335

Trp Phe Lys Arg
            340
```

```
<210> SEQ ID NO 80
<211> LENGTH: 25
<212> TYPE: DNA
<213> ORGANISM: Pyrococcus woesei

<400> SEQUENCE: 80
gataccatgg gtgtcccaat tggtg                                     25

<210> SEQ ID NO 81
<211> LENGTH: 37
<212> TYPE: DNA
<213> ORGANISM: Pyrococcus woesei

<400> SEQUENCE: 81
tcgacgtcga cttatctctt gaaccaactt tcaaggg                        37

<210> SEQ ID NO 82
<211> LENGTH: 20
<212> TYPE: DNA
<213> ORGANISM: Pyrococcus woesei

<400> SEQUENCE: 82
agcgagggag aggcccaagc                                           20

<210> SEQ ID NO 83
<211> LENGTH: 21
<212> TYPE: DNA
<213> ORGANISM: Pyrococcus woesei

<400> SEQUENCE: 83
gcctatgccc tttattcctc c                                         21

<210> SEQ ID NO 84
<211> LENGTH: 33
<212> TYPE: DNA
<213> ORGANISM: Artificial Sequence
<220> FEATURE:
<223> OTHER INFORMATION: Synthetic

<400> SEQUENCE: 84
tggtcgctgt ctcgctgaaa gcgagacagc gtg                            33

<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85
tgctctctgg tcgctgtctg aaagacagcg                                30

<210> SEQ ID NO 86
<211> LENGTH: 26
<212> TYPE: DNA
<213> ORGANISM: Artificial Sequence
<220> FEATURE:
<223> OTHER INFORMATION: Synthetic

<400> SEQUENCE: 86
agaaaggaag ggaagaaagc gaaagg                                    26

<210> SEQ ID NO 87
<211> LENGTH: 27
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: This residue is linked to a spacer bearing a
      Cy3 dye.
<220> FEATURE:
<221> NAME/KEY: modified_base
<222> LOCATION: (27)..(27)
<223> OTHER INFORMATION: dideoxycytidine

<400> SEQUENCE: 87
agaaaggaag ggaagaaagc gaaaggc                                        27

<210> SEQ ID NO 88
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(24)
<223> OTHER INFORMATION: dideoxycytidine

<400> SEQUENCE: 88
gccggcgaac gtggcgagaa aggc                                           24

<210> SEQ ID NO 89
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: This residue is linked to a spacer bearing a
      Cy3 dye.
<220> FEATURE:
<221> NAME/KEY: modified_base
<222> LOCATION: (27)..(27)
<223> OTHER INFORMATION: dideoxycytidine

<400> SEQUENCE: 89
agaaaggaag ggaagaaagc gaaaggc                                        27

<210> SEQ ID NO 90
<211> LENGTH: 30
<212> TYPE: DNA
<213> ORGANISM: Artificial Sequence
<220> FEATURE:
<223> OTHER INFORMATION: Synthetic

<400> SEQUENCE: 90
aaaattcctt tctctttgcc ctttgcttcc                                     30

<210> SEQ ID NO 91
<211> LENGTH: 26
<212> TYPE: DNA
<213> ORGANISM: Artificial Sequence
<220> FEATURE:
<223> OTHER INFORMATION: Synthetic

<400> SEQUENCE: 91
ggaaagccgg cgaacgtggc gagaaa                                         26
```

```
<210> SEQ ID NO 92
<211> LENGTH: 24
<212> TYPE: DNA
<213> ORGANISM: Artificial Sequence
<220> FEATURE:
<223> OTHER INFORMATION: Synthetic

<400> SEQUENCE: 92
ggaaagccgg cgaacgtggc gaga                                        24

<210> SEQ ID NO 93
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: This residue is linked to a spacer bearing a
      Cy3 dye.
<220> FEATURE:
<221> NAME/KEY: misc_difference
<222> LOCATION: (27)..(27)
<223> OTHER INFORMATION: This residue is linked to a spacer bearing a
      biotin group.

<400> SEQUENCE: 93
agaaaggaag ggaagaaagc gaaaggt                                     27

<210> SEQ ID NO 94
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: These residues have an amino group added.
<220> FEATURE:
<221> NAME/KEY: misc_feature
<222> LOCATION: (22)..(22)
<223> OTHER INFORMATION: This residue is linked to a spacer containing a
      fluorescein group.

<400> SEQUENCE: 94
ttccagagcc taatttgcca gta                                         23

<210> SEQ ID NO 95
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: This residue is linked to a spacer containing a
      fluorescein group.

<400> SEQUENCE: 95
ttccagagcc taatttgcca gta                                         23

<210> SEQ ID NO 96
<211> LENGTH: 25
<212> TYPE: DNA
<213> ORGANISM: Artificial Sequence
<220> FEATURE:
<223> OTHER INFORMATION: Synthetic
```

-continued

```
<400> SEQUENCE: 96
cttaccaacg ctaacgagcg tcttg                                          25

<210> SEQ ID NO 97
<211> LENGTH: 43
<212> TYPE: DNA
<213> ORGANISM: Artificial Sequence
<220> FEATURE:
<223> OTHER INFORMATION: Synthetic

<400> SEQUENCE: 97
cccgtctcgc tggtgaaaag aaaaaccacc ctggcgccca ata                      43

<210> SEQ ID NO 98
<211> LENGTH: 23
<212> TYPE: DNA
<213> ORGANISM: Artificial Sequence
<220> FEATURE:
<223> OTHER INFORMATION: Synthetic

<400> SEQUENCE: 98
tattgggcgc catggtggtt ttt                                            23

<210> SEQ ID NO 99
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (10)..(10)
<223> OTHER INFORMATION: 5-nitroindole
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_difference
<222> LOCATION: (16)..(16)
<223> OTHER INFORMATION: 5-nitroindole
<220> FEATURE:
<221> NAME/KEY: misc_feature
<222> LOCATION: (16)..(16)
<223> OTHER INFORMATION: n is a, c, g, or t

<400> SEQUENCE: 99
tattgggcgn cagggnggtt ttt                                            23

<210> SEQ ID NO 100
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (10)..(10)
<223> OTHER INFORMATION: 5-nitroindole
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_difference
<222> LOCATION: (16)..(16)
<223> OTHER INFORMATION: 5-nitroindole
<220> FEATURE:
<221> NAME/KEY: misc_feature
<222> LOCATION: (16)..(16)
<223> OTHER INFORMATION: n is a, c, g, or t
```

<400> SEQUENCE: 100
tattgggcgn catggnggtt ttt                                              23

<210> SEQ ID NO 101
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (16)..(16)
<223> OTHER INFORMATION: 3-nitropyrrole
<220> FEATURE:
<221> NAME/KEY: misc_feature
<222> LOCATION: (16)..(16)
<223> OTHER INFORMATION: n is a, c, g, or t

<400> SEQUENCE: 101
tattgggcgc cagggnggtt ttt                                              23

<210> SEQ ID NO 102
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (16)..(16)
<223> OTHER INFORMATION: 3-nitropyrrole
<220> FEATURE:
<221> NAME/KEY: misc_feature
<222> LOCATION: (16)..(16)
<223> OTHER INFORMATION: n is a, c, g, or t

<400> SEQUENCE: 102
tattgggcgc catggnggtt ttt                                              23

<210> SEQ ID NO 103
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(1)
<223> OTHER INFORMATION: 2' deoxycytosine 5'-O-(1-Thiomonophosphate)
<220> FEATURE:
<221> NAME/KEY: misc_difference
<222> LOCATION: (2)..(2)
<223> OTHER INFORMATION: 2' deoxythymidine 5'-O-(1-Thiomonophosphate)
<220> FEATURE:
<221> NAME/KEY: misc_difference
<222> LOCATION: (3)..(3)
<223> OTHER INFORMATION: 2' deoxyguanosine 5'-O-(1-Thiomonophosphate)
<220> FEATURE:
<221> NAME/KEY: misc_difference
<222> LOCATION: (4)..(5)
<223> OTHER INFORMATION: 2' deoxyadenosine 5'-O-(1-Thiomonophosphate)
<220> FEATURE:
<221> NAME/KEY: misc_difference
<222> LOCATION: (6)..(6)
<223> OTHER INFORMATION: 2' deoxythymidine 5'-O-(1-Thiomonophosphate)
<220> FEATURE:
<221> NAME/KEY: misc_difference
<222> LOCATION: (7)..(7)
<223> OTHER INFORMATION: 2' deoxyadenosine 5'-O-(1-Thiomonophosphate)
<220> FEATURE:
<221> NAME/KEY: misc_difference
<222> LOCATION: (8)..(8)

<223> OTHER INFORMATION: 2' deoxythymidine 5'-O-(1-Thiomonophosphate)
<220> FEATURE:
<221> NAME/KEY: misc_difference
<222> LOCATION: (9)..(10)
<223> OTHER INFORMATION: 2' deoxyadenosine 5'-O-(1-Thiomonophosphate)

<400> SEQUENCE: 103
ctgaatataa acttgtggta gttggagctg gtgccgtagg caagagtgcc ttgacg      56

<210> SEQ ID NO 104
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(1)
<223> OTHER INFORMATION: 2' deoxycytosine 5'-O-(1-Thiomonophosphate)
<220> FEATURE:
<221> NAME/KEY: misc_difference
<222> LOCATION: (2)..(2)
<223> OTHER INFORMATION: 2' deoxythymidine 5'-O-(1-Thiomonophosphate)
<220> FEATURE:
<221> NAME/KEY: misc_difference
<222> LOCATION: (3)..(3)
<223> OTHER INFORMATION: 2' deoxyguanosine 5'-O-(1-Thiomonophosphate)
<220> FEATURE:
<221> NAME/KEY: misc_difference
<222> LOCATION: (4)..(5)
<223> OTHER INFORMATION: 2' deoxyadenosine 5'-O-(1-Thiomonophosphate)
<220> FEATURE:
<221> NAME/KEY: misc_difference
<222> LOCATION: (6)..(6)
<223> OTHER INFORMATION: 2' deoxythymidine 5'-O-(1-Thiomonophosphate)
<220> FEATURE:
<221> NAME/KEY: misc_difference
<222> LOCATION: (7)..(7)
<223> OTHER INFORMATION: 2' deoxyadenosine 5'-O-(1-Thiomonophosphate)
<220> FEATURE:
<221> NAME/KEY: misc_difference
<222> LOCATION: (8)..(8)
<223> OTHER INFORMATION: 2' deoxythymidine 5'-O-(1-Thiomonophosphate)
<220> FEATURE:
<221> NAME/KEY: misc_difference
<222> LOCATION: (9)..(10)
<223> OTHER INFORMATION: 2' deoxyadenosine 5'-O-(1-Thiomonophosphate)

<400> SEQUENCE: 104
ctgaatataa acttgtggta gttggagctg gtgacgtagg caagagtgcc ttgacg      56

<210> SEQ ID NO 105
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(1)
<223> OTHER INFORMATION: 2' deoxyguanosine 5'-O-(1-Thiomonophosphate)
<220> FEATURE:
<221> NAME/KEY: misc_difference
<222> LOCATION: (2)..(2)
<223> OTHER INFORMATION: 2' deoxycytosine 5'-O-(1-Thiomonophosphate)
<220> FEATURE:
<221> NAME/KEY: misc_difference
<222> LOCATION: (3)..(3)
<223> OTHER INFORMATION: 2' deoxythymidine 5'-O-(1-Thiomonophosphate)
<220> FEATURE:
<221> NAME/KEY: misc_difference
<222> LOCATION: (4)..(4)
<223> OTHER INFORMATION: 2' deoxycytosine 5'-O-(1-Thiomonophosphate)
<220> FEATURE:
<221> NAME/KEY: misc_difference

```
<222> LOCATION: (5)..(6)
<223> OTHER INFORMATION: 2' deoxyadenosine 5'-O-(1-Thiomonophosphate)
<220> FEATURE:
<221> NAME/KEY: misc_difference
<222> LOCATION: (7)..(8)
<223> OTHER INFORMATION: 2' deoxyguanosine 5'-O-(1-Thiomonophosphate)
<220> FEATURE:
<221> NAME/KEY: misc_difference
<222> LOCATION: (9)..(9)
<223> OTHER INFORMATION: 2' deoxycytosine 5'-O-(1-Thiomonophosphate)

<400> SEQUENCE: 105
gctcaaggca ctcttgccta cga                                            23

<210> SEQ ID NO 106
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(2)
<223> OTHER INFORMATION: These residues have an amino group added.

<400> SEQUENCE: 106 ttcaccag                                                              8

<210> SEQ ID NO 107
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(1)
<223> OTHER INFORMATION: 2' deoxycytosine 5'-O-(1-Thiomonophosphate)
<220> FEATURE:
<221> NAME/KEY: misc_difference
<222> LOCATION: (2)..(2)
<223> OTHER INFORMATION: 2' deoxythymidine 5'-O-(1-Thiomonophosphate)
<220> FEATURE:
<221> NAME/KEY: misc_difference
<222> LOCATION: (3)..(4)
<223> OTHER INFORMATION: 2' deoxycytosine 5'-O-(1-Thiomonophosphate)
<220> FEATURE:
<221> NAME/KEY: misc_difference
<222> LOCATION: (5)..(6)
<223> OTHER INFORMATION: 2' deoxyadenosine 5'-O-(1-Thiomonophosphate)
<220> FEATURE:
<221> NAME/KEY: misc_difference
<222> LOCATION: (7)..(7)
<223> OTHER INFORMATION: 2' deoxycytosine 5'-O-(1-Thiomonophosphate)
<220> FEATURE:
<221> NAME/KEY: misc_difference
<222> LOCATION: (8)..(8)
<223> OTHER INFORMATION: 2' deoxythymidine 5'-O-(1-Thiomonophosphate)
<220> FEATURE:
<221> NAME/KEY: misc_difference
<222> LOCATION: (9)..(9)
<223> OTHER INFORMATION: 2' deoxyadenosine 5'-O-(1-Thiomonophosphate)

<400> SEQUENCE: 107
ctccaactac cacaagttta tattcag                                        27

<210> SEQ ID NO 108
<211> LENGTH: 14
<212> TYPE: DNA
<213> ORGANISM: Artificial Sequence
<220> FEATURE:
<223> OTHER INFORMATION: Synthetic
```

-continued

```
<400> SEQUENCE: 108
cgagagacca cgct                                                     14

<210> SEQ ID NO 109
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (14)..(14)
<223> OTHER INFORMATION: This residue contains an abasic ribose.

<400> SEQUENCE: 109
cgagagacca cgct                                                     14

<210> SEQ ID NO 110
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (14)..(14)
<223> OTHER INFORMATION: This residue contains an abasic ribose with a
      3' phosphate group.

<400> SEQUENCE: 110
cgagagacca cgct                                                     14

<210> SEQ ID NO 111
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (15)..(15)
<223> OTHER INFORMATION: This residue contains a 3' phosphate group.

<400> SEQUENCE: 111
cgagagacca cgctg                                                    15

<210> SEQ ID NO 112
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(1)
<223> OTHER INFORMATION: 2' deoxyguanosine 5'-O-(1-Thiomonophosphate)
<220> FEATURE:
<221> NAME/KEY: misc_difference
<222> LOCATION: (2)..(2)
<223> OTHER INFORMATION: 2' deoxythymidine 5'-O-(1-Thiomonophosphate)
<220> FEATURE:
<221> NAME/KEY: misc_difference
<222> LOCATION: (3)..(4)
<223> OTHER INFORMATION: 2' deoxyadenosine 5'-O-(1-Thiomonophosphate)
<220> FEATURE:
<221> NAME/KEY: misc_difference
<222> LOCATION: (5)..(5)
<223> OTHER INFORMATION: 2' deoxythymidine 5'-O-(1-Thiomonophosphate)
<220> FEATURE:
<221> NAME/KEY: misc_difference
<222> LOCATION: (6)..(6)
```

```
<223> OTHER INFORMATION: 2' deoxycytosine 5'-O-(1-Thiomonophosphate)
<220> FEATURE:
<221> NAME/KEY: misc_difference
<222> LOCATION: (7)..(8)
<223> OTHER INFORMATION: 2' deoxythymidine 5'-O-(1-Thiomonophosphate)
<220> FEATURE:
<221> NAME/KEY: misc_difference
<222> LOCATION: (9)..(9)
<223> OTHER INFORMATION: 2' deoxyadenosine 5'-O-(1-Thiomonophosphate)
<220> FEATURE:
<221> NAME/KEY: misc_difference
<222> LOCATION: (10)..(10)
<223> OTHER INFORMATION: 2' deoxycytosine 5'-O-(1-Thiomonophosphate)

<400> SEQUENCE: 112
gtaatcttac caacgctaac gagcgtcttg                                       30

<210> SEQ ID NO 113
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(2)
<223> OTHER INFORMATION: 2' deoxycytosine 5'-O-(1-Thiomonophosphate)
<220> FEATURE:
<221> NAME/KEY: misc_difference
<222> LOCATION: (3)..(3)
<223> OTHER INFORMATION: 2' deoxythymidine 5'-O-(1-Thiomonophosphate)
<220> FEATURE:
<221> NAME/KEY: misc_difference
<222> LOCATION: (4)..(5)
<223> OTHER INFORMATION: 2' deoxyadenosine 5'-O-(1-Thiomonophosphate)
<220> FEATURE:
<221> NAME/KEY: misc_difference
<222> LOCATION: (6)..(8)
<223> OTHER INFORMATION: 2' deoxythymidine 5'-O-(1-Thiomonophosphate)
<220> FEATURE:
<221> NAME/KEY: misc_difference
<222> LOCATION: (9)..(9)
<223> OTHER INFORMATION: 2' deoxyguanosine 5'-O-(1-Thiomonophosphate)
<220> FEATURE:
<221> NAME/KEY: misc_difference
<222> LOCATION: (10)..(10)
<223> OTHER INFORMATION: 2' deoxycytosine 5'-O-(1-Thiomonophosphate)

<400> SEQUENCE: 113
cctaatttgc cagttacaaa ataaacagcc c                                     31

<210> SEQ ID NO 114
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(2)
<223> OTHER INFORMATION: These residues have an amino group added.

<400> SEQUENCE: 114 ttccagag                                                                8

<210> SEQ ID NO 115
<211> LENGTH: 44
<212> TYPE: DNA
<213> ORGANISM: Artificial Sequence
<220> FEATURE:
<223> OTHER INFORMATION: Synthetic

<400> SEQUENCE: 115
```

```
ttttccagag cctaatgaaa ttaggctctg gaaagacgct cgtg                    44

<210> SEQ ID NO 116
<211> LENGTH: 14
<212> TYPE: DNA
<213> ORGANISM: Artificial Sequence
<220> FEATURE:
<223> OTHER INFORMATION: Synthetic

<400> SEQUENCE: 116
aacgagcgtc tttg                                                     14

<210> SEQ ID NO 117
<211> LENGTH: 14
<212> TYPE: DNA
<213> ORGANISM: Artificial Sequence
<220> FEATURE:
<223> OTHER INFORMATION: Synthetic

<400> SEQUENCE: 117
aacgagcgtc attg                                                     14

<210> SEQ ID NO 118
<211> LENGTH: 50
<212> TYPE: DNA
<213> ORGANISM: Artificial Sequence
<220> FEATURE:
<223> OTHER INFORMATION: Synthetic

<400> SEQUENCE: 118 tttttttta attaggctct ggaaagacgc tcgtgaaacg agcgtctttg               50

<210> SEQ ID NO 119
<211> LENGTH: 17
<212> TYPE: DNA
<213> ORGANISM: Artificial Sequence
<220> FEATURE:
<223> OTHER INFORMATION: Synthetic

<400> SEQUENCE: 119
ttttccagag cctaatg                                                  17

<210> SEQ ID NO 120
<211> LENGTH: 13
<212> TYPE: DNA
<213> ORGANISM: Artificial Sequence
<220> FEATURE:
<223> OTHER INFORMATION: Synthetic

<400> SEQUENCE: 120
ccggtcgtcc tgg                                                      13

<210> SEQ ID NO 121
<211> LENGTH: 25
<212> TYPE: DNA
<213> ORGANISM: Artificial Sequence
<220> FEATURE:
<223> OTHER INFORMATION: Synthetic

<400> SEQUENCE: 121
caattccggt gtactcaccg gttcc                                         25

<210> SEQ ID NO 122
<211> LENGTH: 16
<212> TYPE: DNA
```

```
<213> ORGANISM: Artificial Sequence
<220> FEATURE:
<223> OTHER INFORMATION: Synthetic

<400> SEQUENCE: 122
ccggtcgtcc tggcaa                                                    16

<210> SEQ ID NO 123
<211> LENGTH: 47
<212> TYPE: DNA
<213> ORGANISM: Artificial Sequence
<220> FEATURE:
<223> OTHER INFORMATION: Synthetic

<400> SEQUENCE: 123
tgttttgacc tccatagaag accctatagt gagtcgtatt aatttcg                  47

<210> SEQ ID NO 124
<211> LENGTH: 23
<212> TYPE: DNA
<213> ORGANISM: Artificial Sequence
<220> FEATURE:
<223> OTHER INFORMATION: Synthetic

<400> SEQUENCE: 124
cgaaattaat acgactcact ata                                            23

<210> SEQ ID NO 125
<211> LENGTH: 30
<212> TYPE: DNA
<213> ORGANISM: Artificial Sequence
<220> FEATURE:
<223> OTHER INFORMATION: Synthetic

<400> SEQUENCE: 125
cgaaattaat acgactcact atacccagaa                                     30

<210> SEQ ID NO 126
<211> LENGTH: 16
<212> TYPE: DNA
<213> ORGANISM: Artificial Sequence
<220> FEATURE:
<223> OTHER INFORMATION: Synthetic

<400> SEQUENCE: 126
cgaaattaat acgact                                                    16

<210> SEQ ID NO 127
<211> LENGTH: 13
<212> TYPE: DNA
<213> ORGANISM: Artificial Sequence
<220> FEATURE:
<223> OTHER INFORMATION: Synthetic

<400> SEQUENCE: 127
cgaaattaat acg                                                       13

<210> SEQ ID NO 128
<211> LENGTH: 12
<212> TYPE: DNA
<213> ORGANISM: Artificial Sequence
<220> FEATURE:
<223> OTHER INFORMATION: Synthetic

<400> SEQUENCE: 128
cgaaattaat ac                                                        12
```

<210> SEQ ID NO 129
<211> LENGTH: 25
<212> TYPE: DNA
<213> ORGANISM: Artificial Sequence
<220> FEATURE:
<223> OTHER INFORMATION: Synthetic

<400> SEQUENCE: 129
cactataggg tcttctatgg aggtc                                          25

<210> SEQ ID NO 130
<211> LENGTH: 28
<212> TYPE: DNA
<213> ORGANISM: Artificial Sequence
<220> FEATURE:
<223> OTHER INFORMATION: Synthetic

<400> SEQUENCE: 130
actcactata gggtcttcta tggaggtc                                       28

<210> SEQ ID NO 131
<211> LENGTH: 29
<212> TYPE: DNA
<213> ORGANISM: Artificial Sequence
<220> FEATURE:
<223> OTHER INFORMATION: Synthetic

<400> SEQUENCE: 131
gactcactat agggtcttct atggaggtc                                      29

<210> SEQ ID NO 132
<211> LENGTH: 30
<212> TYPE: DNA
<213> ORGANISM: Artificial Sequence
<220> FEATURE:
<223> OTHER INFORMATION: Synthetic

<400> SEQUENCE: 132
cgaaattaat acgcagtatg ttagcaaacg                                     30

<210> SEQ ID NO 133
<211> LENGTH: 30
<212> TYPE: DNA
<213> ORGANISM: Artificial Sequence
<220> FEATURE:
<223> OTHER INFORMATION: Synthetic

<400> SEQUENCE: 133
gaactggcat gattaagact ccttattacc                                     30

<210> SEQ ID NO 134
<211> LENGTH: 29
<212> TYPE: DNA
<213> ORGANISM: Artificial Sequence
<220> FEATURE:
<223> OTHER INFORMATION: Synthetic

<400> SEQUENCE: 134
gaactggcat gattaagact ccttattaa                                      29

<210> SEQ ID NO 135
<211> LENGTH: 326
<212> TYPE: PRT
<213> ORGANISM: Methanococcus jannaschii -continued

```
<400> SEQUENCE: 135

Met Gly Val Gln Phe Gly Asp Phe Ile Pro Lys Asn Ile Ile Ser Phe
1               5                   10                  15

Glu Asp Leu Lys Gly Lys Val Ala Ile Asp Gly Met Asn Ala Leu
            20                  25                  30

Tyr Gln Phe Leu Thr Ser Ile Arg Leu Arg Asp Gly Ser Pro Leu Arg
        35                  40                  45

Asn Arg Lys Gly Glu Ile Thr Ser Ala Tyr Asn Gly Val Phe Tyr Lys
    50                  55                  60

Thr Ile His Leu Leu Glu Asn Asp Ile Thr Pro Ile Trp Val Phe Asp
65                  70                  75                  80

Gly Glu Pro Pro Lys Leu Lys Glu Lys Thr Arg Lys Val Arg Arg Glu
                85                  90                  95

Met Lys Glu Lys Ala Glu Leu Lys Met Lys Glu Ala Ile Lys Lys Glu
            100                 105                 110

Asp Phe Glu Glu Ala Ala Lys Tyr Ala Lys Arg Val Ser Tyr Leu Thr
        115                 120                 125

Pro Lys Met Val Glu Asn Cys Lys Tyr Leu Leu Ser Leu Met Gly Ile
130                 135                 140

Pro Tyr Val Glu Ala Pro Ser Glu Gly Glu Ala Gln Ala Ser Tyr Met
145                 150                 155                 160

Ala Lys Lys Gly Asp Val Trp Ala Val Val Ser Gln Asp Tyr Asp Ala
                165                 170                 175

Leu Leu Tyr Gly Ala Pro Arg Val Val Arg Asn Leu Thr Thr Thr Lys
            180                 185                 190

Glu Met Pro Glu Leu Ile Glu Leu Asn Glu Val Leu Glu Asp Leu Arg
        195                 200                 205

Ile Ser Leu Asp Asp Leu Ile Asp Ile Ala Ile Phe Met Gly Thr Asp
    210                 215                 220

Tyr Asn Pro Gly Gly Val Lys Gly Ile Gly Phe Lys Arg Ala Tyr Glu
225                 230                 235                 240

Leu Val Arg Ser Gly Val Ala Lys Asp Val Leu Lys Lys Glu Val Glu
                245                 250                 255

Tyr Tyr Asp Glu Ile Lys Arg Ile Phe Lys Glu Pro Lys Val Thr Asp
            260                 265                 270

Asn Tyr Ser Leu Ser Leu Lys Leu Pro Asp Lys Glu Gly Ile Ile Lys
        275                 280                 285

Phe Leu Val Asp Glu Asn Asp Phe Asn Tyr Asp Arg Val Lys Lys His
    290                 295                 300

Val Asp Lys Leu Tyr Asn Leu Ile Ala Asn Lys Thr Lys Gln Lys Thr
305                 310                 315                 320

Leu Asp Ala Trp Phe Lys
                325

<210> SEQ ID NO 136
<211> LENGTH: 340
<212> TYPE: PRT
<213> ORGANISM: Pyrococcus furiosus

<400> SEQUENCE: 136

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
            20                  25                  30
```

```
Tyr Gln Phe Leu Ser Thr Ile Arg Gln Lys Asp Gly Thr Pro Leu Met
         35                  40                  45

Asp Ser Lys Gly Arg Ile Thr Ser His Leu Ser Gly Leu Phe Tyr Arg
     50                  55                  60

Thr Ile Asn Leu Met Glu Ala Gly Ile Lys Pro Val Tyr Val Phe Asp
 65                  70                  75                  80

Gly Glu Pro Pro Glu Phe Lys Lys Lys Glu Leu Glu Lys Arg Arg Glu
                 85                  90                  95

Ala Arg Glu Glu Ala Glu Glu Lys Trp Arg Glu Ala Leu Glu Lys Gly
             100                 105                 110

Glu Ile Glu Glu Ala Arg Lys Tyr Ala Gln Arg Ala Thr Arg Val Asn
         115                 120                 125

Glu Met Leu Ile Glu Asp Ala Lys Lys Leu Leu Glu Leu Met Gly Ile
     130                 135                 140

Pro Ile Val Gln Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                 165                 170                 175

Leu Leu Phe Gly Ala Pro Arg Leu Val Arg Asn Leu Thr Ile Thr Gly
             180                 185                 190

Lys Arg Lys Leu Pro Gly Lys Asn Val Tyr Val Glu Ile Lys Pro Glu
         195                 200                 205

Leu Ile Ile Leu Glu Glu Val Leu Lys Glu Leu Lys Leu Thr Arg Glu
     210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
                 245                 250                 255

Ser Lys Asp Pro Leu Ala Lys Phe Gln Lys Gln Ser Asp Val Asp Leu
             260                 265                 270

Tyr Ala Ile Lys Glu Phe Phe Leu Asn Pro Pro Val Thr Asp Asn Tyr
         275                 280                 285

Asn Leu Val Trp Arg Asp Pro Asp Glu Glu Gly Ile Leu Lys Phe Leu
     290                 295                 300

Cys Asp Glu His Asp Phe Ser Glu Glu Arg Val Lys Asn Gly Leu Glu
305                 310                 315                 320

Arg Leu Lys Lys Ala Ile Lys Ser Gly Lys Gln Ser Thr Leu Glu Ser
                 325                 330                 335

Trp Phe Lys Arg
         340

<210> SEQ ID NO 137
<211> LENGTH: 380
<212> TYPE: PRT
<213> ORGANISM: Homo sapiens

<400> SEQUENCE: 137

Met Gly Ile Gln Gly Leu Ala Lys Leu Ile Ala Asp Val Ala Pro Ser
 1               5                  10                  15

Ala Ile Arg Glu Asn Asp Ile Lys Ser Tyr Phe Gly Arg Lys Val Ala
             20                  25                  30

Ile Asp Ala Ser Met Ser Ile Tyr Gln Phe Leu Ile Ala Val Arg Gln
         35                  40                  45

Gly Gly Asp Val Leu Gln Asn Glu Glu Gly Glu Thr Thr Ser His Leu
     50                  55                  60
```

```
Met Gly Met Phe Tyr Arg Thr Ile Arg Met Met Glu Asn Gly Ile Lys
 65                  70                  75                  80

Pro Val Tyr Val Phe Asp Gly Lys Pro Pro Gln Leu Lys Ser Gly Glu
                 85                  90                  95

Leu Ala Lys Arg Ser Glu Arg Ala Glu Ala Lys Gln Leu Gln
            100                 105                 110

Gln Ala Gln Ala Ala Gly Ala Glu Gln Glu Val Glu Lys Phe Thr Lys
            115                 120                 125

Arg Leu Val Lys Val Thr Lys Gln His Asn Asp Glu Cys Lys His Leu
130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
                165                 170                 175

Thr Glu Asp Met Asp Cys Leu Thr Phe Gly Ser Pro Val Leu Met Arg
                180                 185                 190

His Leu Thr Ala Ser Glu Ala Lys Lys Leu Pro Ile Gln Glu Phe His
            195                 200                 205

Leu Ser Arg Ile Leu Gln Glu Leu Gly Leu Asn Gln Glu Gln Phe Val
210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
                260                 265                 270

Asn Trp Leu His Lys Glu Ala His Gln Leu Phe Leu Glu Pro Glu Val
            275                 280                 285

Leu Asp Pro Glu Ser Val Glu Leu Lys Trp Ser Glu Pro Asn Glu Glu
290                 295                 300

Glu Leu Ile Lys Phe Met Cys Gly Glu Lys Gln Phe Ser Glu Glu Arg
305                 310                 315                 320

Ile Arg Ser Gly Val Lys Arg Leu Ser Lys Ser Arg Gln Gly Ser Thr
                325                 330                 335

Gln Gly Arg Leu Asp Asp Phe Phe Lys Val Thr Gly Ser Leu Ser Ser
            340                 345                 350

Ala Lys Arg Lys Glu Pro Glu Pro Lys Gly Ser Thr Lys Lys Lys Ala
            355                 360                 365

Lys Thr Gly Ala Ala Gly Lys Phe Lys Arg Gly Lys
            370                 375                 380

<210> SEQ ID NO 138
<211> LENGTH: 378
<212> TYPE: PRT
<213> ORGANISM: Mus musculus

<400> SEQUENCE: 138

Met Gly Ile His Gly Leu Ala Lys Leu Ile Ala Asp Val Ala Pro Ser
 1               5                  10                  15

Ala Ile Arg Glu Asn Asp Ile Lys Ser Tyr Phe Gly Arg Lys Val Ala
                20                  25                  30

Ile Asp Ala Ser Met Ser Ile Tyr Gln Phe Leu Ile Ala Val Arg Gln
            35                  40                  45

Gly Gly Asp Val Leu Gln Asn Glu Glu Gly Glu Thr Thr Ser Leu Met
```

```
            50                  55                  60
Gly Met Phe Tyr Arg Thr Ile Arg Met Glu Asn Gly Ile Lys Pro Val
 65                  70                  75                  80

Tyr Val Phe Asp Gly Lys Pro Pro Gln Leu Lys Ser Gly Glu Leu Ala
                 85                  90                  95

Lys Arg Ser Glu Arg Ala Glu Ala Glu Lys Gln Leu Gln Gln Ala
            100                 105                 110

Gln Glu Ala Gly Met Glu Glu Val Glu Lys Phe Thr Lys Arg Leu
            115                 120                 125

Val Lys Val Thr Lys Gln His Asn Asp Glu Cys Lys His Leu Leu Ser
130                 135                 140

Leu Met Gly Ile Pro Tyr Leu Asp Ala Pro Ser Glu Ala Glu Ala Ser
145                 150                 155                 160

Cys Ala Ala Leu Ala Lys Ala Gly Lys Val Tyr Ala Ala Thr Glu
                165                 170                 175

Asp Met Asp Cys Leu Thr Phe Gly Ser Pro Val Leu Met Arg His Leu
            180                 185                 190

Thr Ala Ser Glu Ala Lys Lys Leu Pro Ile Gln Glu Phe His Leu Ser
            195                 200                 205

Arg Val Leu Gln Glu Leu Gly Leu Asn Gln Glu Gln Phe Val Asp Leu
210                 215                 220

Cys Ile Leu Leu Gly Ser Asp Tyr Cys Glu Ser Ile Arg Gly Ile Gly
225                 230                 235                 240

Ala Lys Arg Ala Val Asp Leu Ile Gln Lys His Lys Ser Ile Glu Glu
                245                 250                 255

Ile Val Arg Arg Leu Asp Pro Ser Lys Tyr Pro Val Pro Glu Asn Trp
            260                 265                 270

Leu His Lys Glu Ala Gln Gln Leu Phe Leu Glu Pro Glu Val Val Asp
            275                 280                 285

Pro Glu Ser Val Glu Leu Lys Trp Ser Glu Pro Asn Glu Glu Glu Leu
            290                 295                 300

Val Lys Phe Met Cys Gly Glu Lys Gln Phe Ser Glu Glu Arg Ile Arg
305                 310                 315                 320

Ser Gly Val Lys Arg Leu Ser Lys Ser Arg Gln Gly Ser Thr Gln Gly
                325                 330                 335

Arg Leu Asp Asp Phe Phe Lys Val Thr Gly Ser Leu Ser Ser Ala Lys
            340                 345                 350

Arg Lys Glu Pro Glu Pro Lys Gly Pro Ala Lys Lys Ala Lys Thr
            355                 360                 365

Gly Gly Ala Gly Lys Phe Arg Arg Gly Lys
370                 375

<210> SEQ ID NO 139
<211> LENGTH: 382
<212> TYPE: PRT
<213> ORGANISM: Saccharomyces cerevisiae

<400> SEQUENCE: 139

Met Gly Ile Lys Gly Leu Asn Ala Ile Ile Ser Glu His Val Pro Ser
 1               5                  10                  15

Ala Ile Arg Lys Ser Asp Ile Lys Ser Phe Phe Gly Arg Lys Val Ala
                 20                  25                  30

Ile Asp Ala Ser Met Ser Leu Tyr Gln Phe Leu Ile Ala Val Arg Gln
            35                  40                  45
```

-continued

Gln Asp Gly Gly Gln Leu Thr Asn Glu Ala Gly Glu Thr Thr Ser His
    50                  55                  60

Leu Met Gly Met Phe Tyr Arg Thr Leu Arg Met Ile Asp Asn Gly Ile
65                  70                  75                  80

Lys Pro Cys Tyr Val Phe Asp Gly Lys Pro Pro Asp Leu Lys Ser His
                85                  90                  95

Glu Leu Thr Lys Arg Ser Ser Arg Arg Val Glu Thr Glu Lys Lys Leu
            100                 105                 110

Ala Glu Ala Thr Thr Glu Leu Glu Lys Met Lys Gln Glu Arg Arg Leu
        115                 120                 125

Val Lys Val Ser Lys Glu His Asn Glu Glu Ala Gln Lys Leu Leu Gly
130                 135                 140

Leu Met Gly Ile Pro Tyr Ile Ile Ala Pro Thr Glu Ala Glu Ala Gln
145                 150                 155                 160

Cys Ala Glu Leu Ala Lys Lys Gly Lys Val Tyr Ala Ala Ala Ser Glu
                165                 170                 175

Asp Met Asp Thr Leu Cys Tyr Arg Thr Pro Phe Leu Leu Arg His Leu
            180                 185                 190

Thr Phe Ser Glu Ala Lys Lys Glu Pro Ile His Glu Ile Asp Thr Glu
        195                 200                 205

Leu Val Leu Arg Gly Leu Asp Leu Thr Ile Glu Gln Phe Val Asp Leu
210                 215                 220

Cys Ile Met Leu Gly Cys Asp Tyr Cys Glu Ser Ile Arg Gly Val Gly
225                 230                 235                 240

Pro Val Thr Ala Leu Lys Leu Ile Lys Thr His Gly Ser Ile Glu Lys
                245                 250                 255

Ile Val Glu Phe Ile Glu Ser Gly Glu Ser Asn Asn Thr Lys Trp Lys
            260                 265                 270

Ile Pro Glu Asp Trp Pro Tyr Lys Gln Ala Arg Met Leu Phe Leu Asp
        275                 280                 285

Pro Glu Val Ile Asp Gly Asn Glu Ile Asn Leu Lys Trp Ser Pro Pro
290                 295                 300

Lys Glu Lys Glu Leu Ile Glu Tyr Leu Cys Asp Asp Lys Lys Phe Ser
305                 310                 315                 320

Glu Glu Arg Val Lys Ser Gly Ile Ser Arg Leu Lys Lys Gly Leu Lys
                325                 330                 335

Ser Gly Ile Gln Gly Arg Leu Asp Gly Phe Phe Gln Val Val Pro Lys
            340                 345                 350

Thr Lys Glu Gln Leu Ala Ala Ala Lys Arg Ala Gln Glu Asn Lys
        355                 360                 365

Lys Leu Asn Lys Asn Lys Asn Lys Val Thr Lys Gly Arg Arg
370                 375                 380

<210> SEQ ID NO 140
<211> LENGTH: 387
<212> TYPE: PRT
<213> ORGANISM: Saccharomyces cerevisiae

<400> SEQUENCE: 140

Met Gly Val His Ser Phe Trp Asp Ile Ala Gly Pro Thr Ala Arg Pro
1               5                   10                  15

Val Arg Leu Glu Ser Leu Glu Asp Lys Arg Met Ala Val Asp Ala Ser
            20                  25                  30

Ile Trp Ile Tyr Gln Phe Leu Lys Ala Val Arg Asp Gln Glu Gly Asn
        35                  40                  45

```
Ala Val Lys Asn Ser His Ile Thr Gly Phe Phe Arg Arg Ile Cys Lys
    50                  55                  60

Leu Leu Tyr Phe Gly Ile Arg Pro Val Phe Phe Asp Gly Gly Val
65                  70                  75                  80

Pro Val Leu Lys Arg Glu Thr Ile Arg Gln Arg Lys Glu Arg Arg Gln
                85                  90                  95

Gly Lys Arg Glu Ser Ala Lys Ser Thr Ala Arg Lys Leu Leu Ala Leu
                100                 105                 110

Gln Leu Gln Asn Gly Ser Asn Asp Asn Glu Val Thr Met Asp Met Ile
                115                 120                 125

Lys Glu Val Gln Glu Leu Leu Ser Arg Phe Gly Ile Pro Tyr Ile Thr
130                 135                 140

Ala Pro Met Glu Ala Glu Ala Gln Cys Ala Glu Leu Leu Gln Leu Asn
145                 150                 155                 160

Leu Val Asp Gly Ile Ile Thr Asp Asp Ser Asp Val Phe Leu Phe Gly
                165                 170                 175

Gly Thr Lys Ile Tyr Lys Asn Met Phe His Glu Lys Asn Tyr Val Glu
                180                 185                 190

Phe Tyr Asp Ala Glu Ser Ile Leu Lys Leu Gly Leu Asp Arg Lys
                195                 200                 205

Asn Met Ile Glu Leu Ala Gln Leu Leu Gly Ser Asp Tyr Thr Asn Gly
    210                 215                 220

Leu Lys Gly Met Gly Pro Val Ser Ser Ile Glu Val Ile Ala Glu Phe
225                 230                 235                 240

Gly Asn Leu Lys Asn Phe Lys Asp Trp Tyr Asn Asn Gly Gln Phe Asp
                245                 250                 255

Lys Arg Lys Gln Glu Thr Glu Asn Lys Phe Glu Lys Asp Leu Arg Lys
                260                 265                 270

Lys Leu Val Asn Asn Glu Ile Ile Leu Asp Asp Phe Pro Ser Val
            275                 280                 285

Met Val Tyr Asp Ala Tyr Met Arg Pro Glu Val Asp His Asp Thr Thr
    290                 295                 300

Pro Phe Val Trp Gly Val Pro Asp Leu Asp Met Leu Arg Ser Phe Met
305                 310                 315                 320

Lys Thr Gln Leu Gly Trp Pro His Glu Lys Ser Asp Glu Ile Leu Ile
                325                 330                 335

Pro Leu Ile Arg Asp Val Asn Lys Arg Lys Lys Gly Lys Gln Lys
                340                 345                 350

Arg Ile Asn Glu Phe Phe Pro Arg Glu Tyr Ile Ser Gly Asp Lys Lys
                355                 360                 365

Leu Asn Thr Ser Lys Arg Ile Ser Thr Ala Thr Gly Lys Leu Lys Lys
    370                 375                 380

Arg Lys Met
385

<210> SEQ ID NO 141
<211> LENGTH: 488
<212> TYPE: PRT
<213> ORGANISM: Shizosaccharomyces pombe

<400> SEQUENCE: 141

Met Gly Val Ser Gly Leu Trp Asn Ile Leu Glu Pro Val Lys Arg Pro
1               5                   10                  15

Val Lys Leu Glu Thr Leu Val Asn Lys Arg Leu Ala Ile Asp Ala Ser
```

-continued

```
                 20                  25                  30
Ile Trp Ile Tyr Gln Phe Leu Lys Ala Val Arg Asp Lys Glu Gly Asn
             35                  40                  45

Gln Leu Lys Ser Ser His Val Gly Phe Phe Arg Arg Ile Cys Lys
         50                  55                  60

Leu Leu Phe Phe Gly Ile Lys Pro Val Phe Val Phe Asp Gly Gly Ala
 65                  70                  75                  80

Pro Ser Leu Lys Arg Gln Thr Ile Gln Lys Arg Gln Ala Arg Arg Leu
                 85                  90                  95

Asp Arg Glu Glu Asn Ala Thr Val Thr Ala Asn Lys Leu Leu Ala Leu
             100                 105                 110

Gln Met Arg His Gln Ala Met Leu Leu Lys Arg Asp Ala Asp Glu Val
         115                 120                 125

Thr Gln Val Met Ile Lys Glu Cys Gln Glu Leu Leu Arg Leu Phe Gly
         130                 135                 140

Leu Pro Tyr Ile Val Ala Pro Gln Glu Ala Glu Ala Gln Cys Ser Lys
145                 150                 155                 160

Leu Leu Glu Leu Lys Leu Val Asp Gly Ile Val Thr Asp Ser Asp
                 165                 170                 175

Val Phe Leu Phe Gly Gly Thr Arg Val Tyr Arg Asn Met Phe Asn Gln
             180                 185                 190

Asn Lys Phe Val Glu Leu Tyr Leu Met Asp Asp Met Lys Arg Glu Phe
         195                 200                 205

Asn Val Asn Gln Met Asp Leu Ile Lys Leu Ala His Leu Leu Gly Ser
         210                 215                 220

Asp Tyr Thr Met Gly Leu Ser Arg Val Gly Pro Val Leu Ala Leu Glu
225                 230                 235                 240

Ile Leu His Glu Phe Pro Gly Asp Thr Gly Leu Phe Glu Phe Lys Lys
                 245                 250                 255

Trp Phe Gln Arg Leu Ser Thr Gly His Ala Ser Lys Asn Asp Val Asn
             260                 265                 270

Thr Pro Val Lys Lys Arg Ile Asn Lys Leu Val Gly Lys Ile Ile Leu
         275                 280                 285

Pro Ser Glu Phe Pro Asn Pro Leu Val Asp Glu Ala Tyr Leu His Pro
         290                 295                 300

Ala Val Asp Asp Ser Lys Gln Ser Phe Gln Trp Gly Ile Pro Asp Leu
305                 310                 315                 320

Asp Glu Leu Arg Gln Phe Leu Met Ala Thr Val Gly Trp Ser Lys Gln
                 325                 330                 335

Arg Thr Asn Glu Val Leu Leu Pro Val Ile Gln Asp Met His Lys Lys
             340                 345                 350

Gln Phe Val Gly Thr Gln Ser Asn Leu Thr Gln Phe Phe Glu Gly Gly
         355                 360                 365

Asn Thr Asn Val Tyr Ala Pro Arg Val Ala Tyr His Phe Lys Ser Lys
         370                 375                 380

Arg Leu Glu Asn Ala Leu Ser Ser Phe Lys Asn Gln Ile Ser Asn Gln
385                 390                 395                 400

Ser Pro Met Ser Glu Glu Ile Gln Ala Asp Ala Asp Ala Phe Gly Glu
                 405                 410                 415

Ser Lys Gly Ser Asp Glu Leu Gln Ser Arg Ile Leu Arg Arg Lys Lys
             420                 425                 430

Met Met Ala Ser Lys Asn Ser Ser Asp Ser Asp Ser Glu Asp
         435                 440                 445
```

```
Asn Phe Leu Ala Ser Leu Thr Pro Lys Thr Asn Ser Ser Ile Ser
    450                 455                 460

Ile Glu Asn Leu Pro Arg Lys Thr Lys Leu Ser Thr Ser Leu Leu Lys
465                 470                 475                 480

Lys Pro Ser Lys Arg Arg Lys
                485

<210> SEQ ID NO 142
<211> LENGTH: 550
<212> TYPE: PRT
<213> ORGANISM: Homo sapiens

<400> SEQUENCE: 142

Met Gly Val Gln Gly Leu Trp Lys Leu Leu Glu Cys Ser Gly Arg Gln
1               5                   10                  15

Val Ser Pro Glu Ala Leu Glu Gly Lys Ile Leu Ala Val Asp Ile Ser
                20                  25                  30

Ile Trp Leu Asn Gln Ala Leu Lys Gly Val Arg Asp Arg His Gly Asn
            35                  40                  45

Ser Ile Glu Asn Pro His Leu Leu Thr Leu Phe His Arg Leu Cys Lys
    50                  55                  60

Leu Leu Phe Phe Arg Ile Arg Pro Ile Phe Val Phe Asp Gly Asp Ala
65                  70                  75                  80

Pro Leu Leu Lys Lys Gln Thr Leu Val Lys Arg Arg Gln Arg Lys Asp
                85                  90                  95

Leu Ala Ser Ser Asp Ser Arg Lys Thr Thr Glu Lys Leu Leu Lys Thr
                100                 105                 110

Phe Leu Lys Arg Gln Ala Ile Lys Thr Glu Arg Ile Ala Ala Thr Val
            115                 120                 125

Thr Gly Gln Met Phe Leu Glu Ser Gln Glu Leu Leu Arg Leu Phe Gly
130                 135                 140

Ile Pro Tyr Ile Gln Ala Pro Met Glu Ala Glu Ala Gln Cys Ala Ile
145                 150                 155                 160

Leu Asp Leu Thr Asp Gln Thr Ser Gly Thr Ile Thr Asp Asp Ser Asp
                165                 170                 175

Ile Trp Leu Phe Gly Ala Arg His Val Tyr Arg Asn Phe Phe Asn Lys
            180                 185                 190

Asn Lys Phe Val Glu Tyr Tyr Gln Tyr Val Asp Phe His Asn Gln Leu
            195                 200                 205

Gly Leu Asp Arg Asn Lys Leu Ile Asn Leu Ala Tyr Leu Leu Gly Ser
        210                 215                 220

Asp Tyr Thr Glu Gly Ile Pro Thr Val Gly Cys Val Thr Ala Met Glu
225                 230                 235                 240

Ile Leu Asn Glu Phe Pro Gly His Gly Leu Glu Pro Leu Leu Lys Phe
                245                 250                 255

Ser Glu Trp Trp His Glu Ala Gln Lys Asn Pro Lys Ile Arg Pro Asn
            260                 265                 270

Pro His Asp Thr Lys Val Lys Lys Lys Leu Arg Thr Leu Gln Leu Thr
            275                 280                 285

Pro Gly Phe Pro Asn Pro Ala Val Ala Glu Ala Tyr Leu Lys Pro Val
        290                 295                 300

Val Asp Asp Ser Lys Gly Ser Phe Leu Trp Gly Lys Pro Asp Leu Asp
305                 310                 315                 320

Lys Ile Arg Glu Phe Cys Gln Arg Tyr Phe Gly Trp Asn Arg Thr Lys
```

```
                325                 330                 335
Thr Asp Glu Ser Leu Phe Pro Val Leu Lys Gln Leu Asp Ala Gln Gln
                340                 345                 350

Thr Gln Leu Arg Ile Asp Ser Phe Phe Arg Leu Ala Gln Gln Glu Lys
            355                 360                 365

Glu Asp Ala Lys Arg Ile Lys Ser Gln Arg Leu Asn Arg Ala Val Thr
        370                 375                 380

Cys Met Leu Arg Lys Glu Lys Ala Ala Ala Ser Glu Ile Glu Ala
385                 390                 395                 400

Val Ser Val Ala Met Glu Lys Glu Phe Glu Leu Leu Asp Lys Ala Lys
                405                 410                 415

Arg Lys Thr Gln Lys Arg Gly Ile Thr Asn Thr Leu Glu Glu Ser Ser
            420                 425                 430

Ser Leu Lys Arg Lys Arg Leu Ser Asp Ser Lys Arg Lys Asn Thr Cys
        435                 440                 445

Gly Gly Phe Leu Gly Glu Thr Cys Leu Ser Glu Ser Ser Asp Gly Ser
    450                 455                 460

Ser Ser Glu His Ala Glu Ser Ser Leu Met Asn Val Gln Arg Arg
465                 470                 475                 480

Thr Ala Ala Lys Glu Pro Lys Thr Ser Ala Ser Asp Ser Gln Asn Ser
                485                 490                 495

Val Lys Glu Ala Pro Val Lys Asn Gly Gly Ala Thr Thr Ser Ser Ser
            500                 505                 510

Ser Asp Ser Asp Asp Gly Gly Lys Glu Lys Met Val Leu Val Thr
        515                 520                 525

Ala Arg Ser Val Phe Gly Lys Lys Arg Arg Lys Leu Arg Arg Ala Arg
    530                 535                 540

Gly Arg Lys Arg Lys Thr
545                 550

<210> SEQ ID NO 143
<211> LENGTH: 543
<212> TYPE: PRT
<213> ORGANISM: Mus musculus

<400> SEQUENCE: 143

Met Gly Val Gln Gly Leu Trp Lys Leu Leu Glu Cys Ser Gly His Arg
1               5                   10                  15

Val Ser Pro Glu Ala Leu Glu Gly Lys Val Leu Ala Val Asp Ile Ser
            20                  25                  30

Ile Trp Leu Asn Gln Ala Leu Lys Gly Val Arg Asp Ser His Gly Asn
        35                  40                  45

Val Ile Glu Asn Ala His Leu Leu Thr Leu Phe His Arg Leu Cys Lys
    50                  55                  60

Leu Leu Phe Phe Arg Ile Arg Pro Ile Phe Val Phe Asp Gly Asp Ala
65                  70                  75                  80

Pro Leu Leu Lys Lys Gln Thr Leu Ala Lys Arg Arg Gln Arg Lys Asp
                85                  90                  95

Ser Ala Ser Ile Asp Ser Arg Lys Thr Thr Glu Lys Leu Leu Lys Thr
            100                 105                 110

Phe Leu Lys Arg Gln Ala Leu Lys Thr Asp Arg Ile Ala Ala Ser Val
        115                 120                 125

Thr Gly Gln Met Phe Leu Glu Ser Gln Glu Leu Leu Arg Leu Phe Gly
    130                 135                 140
```

-continued

```
Val Pro Tyr Ile Gln Ala Pro Met Glu Ala Glu Ala Gln Cys Ala Val
145                 150                 155                 160

Leu Asp Leu Ser Asp Gln Thr Ser Gly Thr Ile Thr Asp Asp Ser Asp
            165                 170                 175

Ile Trp Leu Phe Gly Ala Arg His Val Tyr Lys Asn Phe Phe Asn Lys
        180                 185                 190

Asn Lys Phe Val Glu Tyr Tyr Gln Tyr Val Asp Phe Tyr Ser Gln Leu
    195                 200                 205

Gly Leu Asp Arg Asn Lys Leu Ile Asn Leu Ala Tyr Leu Leu Gly Ser
210                 215                 220

Asp Tyr Thr Glu Gly Ile Pro Thr Val Gly Cys Val Thr Ala Met Glu
225                 230                 235                 240

Ile Leu Asn Glu Phe Pro Gly Arg Gly Leu Asp Pro Leu Leu Lys Phe
                245                 250                 255

Ser Glu Trp Trp His Glu Ala Gln Asn Asn Lys Lys Val Ala Glu Asn
            260                 265                 270

Pro Tyr Asp Thr Lys Val Lys Lys Lys Leu Arg Lys Leu Gln Leu Thr
        275                 280                 285

Pro Gly Phe Pro Asn Pro Ala Val Ala Asp Ala Tyr Leu Arg Pro Val
    290                 295                 300

Val Asp Asp Ser Arg Gly Ser Phe Leu Trp Gly Lys Pro Asp Val Asp
305                 310                 315                 320

Lys Ile Arg Glu Phe Cys Gln Arg Tyr Phe Gly Trp Asn Arg Met Lys
                325                 330                 335

Thr Asp Glu Ser Leu Tyr Pro Val Leu Lys His Leu Asn Ala His Gln
            340                 345                 350

Thr Gln Leu Arg Ile Asp Ser Phe Phe Arg Leu Ala Gln Gln Glu Lys
        355                 360                 365

Gln Asp Ala Lys Leu Ile Lys Ser His Arg Leu Ser Arg Ala Val Thr
    370                 375                 380

Cys Met Leu Arg Lys Glu Arg Glu Lys Ala Pro Glu Leu Thr Lys
385                 390                 395                 400

Val Thr Glu Ala Met Glu Lys Glu Phe Glu Leu Leu Asp Asp Ala Lys
                405                 410                 415

Gly Lys Thr Gln Lys Arg Glu Leu Pro Tyr Lys Lys Glu Thr Ser Val
            420                 425                 430

Pro Lys Arg Arg Arg Pro Ser Gly Asn Gly Gly Phe Leu Gly Asp Pro
        435                 440                 445

Tyr Cys Ser Glu Ser Pro Gln Glu Ser Ser Cys Glu Asp Gly Glu Gly
    450                 455                 460

Ser Ser Val Met Ser Ala Arg Gln Arg Ser Ala Ala Glu Ser Ser Lys
465                 470                 475                 480

Ile Gly Cys Ser Asp Val Pro Asp Leu Val Arg Asp Ser Pro His Gly
                485                 490                 495

Arg Gln Gly Cys Val Ser Thr Ser Ser Ser Asp Ser Glu Asp Gly Glu
            500                 505                 510

Asp Lys Ala Lys Thr Val Leu Val Thr Ala Arg Pro Val Phe Gly Lys
        515                 520                 525

Lys Arg Arg Lys Leu Lys Ser Met Lys Arg Arg Lys Lys Thr
530                 535                 540
```

<210> SEQ ID NO 144
<211> LENGTH: 527
<212> TYPE: PRT

<213> ORGANISM: Xenopus laevis

<400> SEQUENCE: 144

```
Met Gly Val Gln Gly Leu Trp Lys Leu Leu Glu Cys Ser Gly Arg Pro
1               5                   10                  15
Ile Asn Pro Gly Thr Leu Glu Gly Lys Ile Leu Ala Val Asp Ile Ser
            20                  25                  30
Ile Trp Leu Asn Gln Ala Val Lys Gly Ala Arg Asp Arg Gln Gly Asn
        35                  40                  45
Ala Ile Gln Asn Ala His Leu Leu Thr Leu Phe His Arg Leu Cys Lys
    50                  55                  60
Leu Leu Phe Phe Arg Ile Arg Pro Ile Phe Val Phe Asp Gly Glu Ala
65                  70                  75                  80
Pro Leu Leu Lys Arg Gln Thr Leu Ala Lys Arg Gln Arg Thr Asp
                85                  90                  95
Lys Ala Ser Asn Asp Ala Arg Lys Thr Asn Glu Lys Leu Leu Arg Thr
            100                 105                 110
Phe Leu Lys Arg Gln Ala Ile Lys Ala Glu Arg Ile Ala Ala Thr Val
        115                 120                 125
Thr Gly Gln Met Cys Leu Glu Ser Gln Glu Leu Leu Gln Leu Phe Gly
    130                 135                 140
Ile Pro Tyr Ile Val Ala Pro Met Glu Ala Glu Ala Gln Cys Ala Ile
145                 150                 155                 160
Leu Asp Leu Thr Asp Gln Thr Ser Gly Thr Ile Thr Asp Asp Ser Asp
                165                 170                 175
Ile Trp Leu Phe Gly Ala Arg His Val Tyr Lys Asn Phe Phe Ser Gln
            180                 185                 190
Asn Lys His Val Glu Tyr Tyr Gln Tyr Ala Asp Ile His Asn Gln Leu
        195                 200                 205
Gly Leu Asp Arg Ser Lys Leu Ile Asn Leu Ala Tyr Leu Leu Gly Ser
    210                 215                 220
Asp Tyr Thr Glu Gly Ile Pro Thr Val Gly Tyr Val Ser Ala Met Glu
225                 230                 235                 240
Ile Leu Asn Glu Phe Pro Gly Gln Gly Leu Glu Pro Leu Val Lys Phe
                245                 250                 255
Lys Glu Trp Trp Ser Glu Ala Gln Lys Asp Lys Met Arg Pro Asn
            260                 265                 270
Pro Asn Asp Thr Lys Val Lys Lys Leu Arg Leu Leu Asp Leu Gln
        275                 280                 285
Gln Ser Phe Pro Asn Pro Ala Val Ala Ser Ala Tyr Leu Lys Pro Val
    290                 295                 300
Val Asp Glu Ser Lys Ser Ala Phe Ser Trp Gly Arg Pro Asp Leu Glu
305                 310                 315                 320
Gln Ile Arg Glu Phe Cys Glu Ser Arg Phe Gly Trp Tyr Arg Leu Lys
                325                 330                 335
Thr Asp Glu Val Leu Leu Pro Val Leu Lys Gln Leu Asn Ala Gln Gln
            340                 345                 350
Thr Gln Leu Arg Ile Asp Ser Phe Phe Arg Leu Glu Gln His Glu Ala
        355                 360                 365
Ala Gly Leu Lys Ser Gln Arg Leu Arg Arg Ala Val Thr Cys Met Lys
    370                 375                 380
Arg Lys Glu Arg Asp Val Glu Ala Glu Val Glu Ala Ala Val Ala
385                 390                 395                 400
```

```
Val Met Glu Arg Glu Cys Thr Asn Gln Arg Lys Gly Gln Lys Thr Asn
            405                 410                 415

Thr Lys Ser Gln Gly Thr Lys Arg Arg Lys Pro Thr Glu Cys Ser Gln
        420                 425                 430

Glu Asp Gln Asp Pro Gly Gly Gly Phe Ile Gly Ile Glu Leu Lys Thr
            435                 440                 445

Leu Ser Ser Lys Ala Tyr Ser Ser Asp Gly Ser Ser Ser Asp Ala Glu
    450                 455                 460

Asp Leu Pro Ser Gly Leu Ile Asp Lys Gln Ser Gln Ser Gly Ile Val
465                 470                 475                 480

Gly Arg Gln Lys Ala Ser Asn Lys Val Glu Ser Ser Ser Ser Ser Asp
                485                 490                 495

Asp Glu Asp Arg Thr Val Met Val Thr Ala Lys Pro Val Phe Gln Gly
            500                 505                 510

Lys Lys Thr Lys Ser Lys Thr Met Lys Glu Thr Val Lys Arg Lys
            515                 520                 525

<210> SEQ ID NO 145
<211> LENGTH: 434
<212> TYPE: PRT
<213> ORGANISM: Cunninghamella elegans

<400> SEQUENCE: 145

Met Thr Ile Asn Gly Ile Trp Glu Trp Ala Asn His Val Val Arg Lys
1               5                   10                  15

Val Pro Asn Glu Thr Met Arg Asp Lys Thr Leu Ser Ile Asp Gly His
            20                  25                  30

Ile Trp Leu Tyr Glu Ser Leu Lys Gly Cys Glu Ala His His Gln Gln
        35                  40                  45

Thr Pro Asn Ser Tyr Leu Val Thr Phe Phe Thr Arg Ile Gln Arg Leu
    50                  55                  60

Leu Glu Leu Lys Ile Ile Pro Ile Val Val Phe Asp Asn Ile Asn Ala
65                  70                  75                  80

Ser Ser Ser Ala His Glu Ser Lys Asp Gln Asn Glu Phe Val Pro Arg
                85                  90                  95

Lys Arg Arg Ser Phe Gly Asp Ser Pro Phe Thr Asn Leu Val Asp His
            100                 105                 110

Val Tyr Lys Thr Asn Ala Leu Leu Thr Glu Leu Gly Ile Lys Val Ile
        115                 120                 125

Ile Ala Pro Gly Asp Gly Glu Ala Gln Cys Ala Arg Leu Glu Asp Leu
    130                 135                 140

Gly Val Thr Ser Gly Cys Ile Thr Thr Asp Phe Asp Tyr Phe Leu Phe
145                 150                 155                 160

Gly Gly Lys Asn Leu Tyr Arg Phe Asp Phe Thr Ala Gly Thr Ser Ser
                165                 170                 175

Thr Ala Cys Leu His Asp Ile Met His Leu Ser Leu Gly Arg Met Phe
            180                 185                 190

Met Glu Lys Lys Val Ser Arg Pro His Leu Ile Ser Thr Ala Ile Leu
        195                 200                 205

Leu Gly Cys Asp Tyr Phe Gln Arg Gly Val Gln Asn Ile Gly Ile Val
    210                 215                 220

Ser Val Phe Asp Ile Leu Gly Glu Phe Gly Asp Asp Gly Asn Glu Glu
225                 230                 235                 240

Ile Asp Pro His Val Ile Leu Asp Arg Phe Ala Ser Tyr Val Arg Glu
                245                 250                 255
```

```
Glu Ile Pro Ala Arg Ser Glu Asp Thr Gln Arg Lys Leu Arg Leu Arg
            260                 265                 270

Arg Lys Lys Tyr Asn Phe Pro Val Gly Phe Pro Asn Cys Asp Ala Val
        275                 280                 285

His Asn Ala Ile Thr Met Tyr Leu Arg Pro Pro Val Ser Ser Glu Ile
    290                 295                 300

Pro Lys Ile Ile Pro Arg Ala Ala Asn Phe Gln Gln Val Ala Glu Ile
305                 310                 315                 320

Met Met Lys Glu Cys Gly Trp Pro Ala Thr Arg Thr Gln Lys Glu Leu
                325                 330                 335

Ala Leu Ser Ile Arg Arg Lys Val His Leu Thr Thr Val Ala Gln
            340                 345                 350

Thr Arg Ile Pro Asp Phe Phe Ala Thr Lys Ser Lys Asn Phe Thr
            355                 360                 365

Pro Ile Val Glu Pro Cys Glu Ser Leu Glu Asp Tyr Ile Ser Ala Asn
370                 375                 380

Asn Thr Trp Met Arg Lys Arg Lys Ser Glu Ser Pro Gln Ile Leu
385                 390                 395                 400

Gln His His Ala Lys Arg Gln Val Pro Asp Arg Lys Arg Ser Val Lys
            405                 410                 415

Ile Arg Ala Phe Lys Pro Tyr Pro Thr Asp Val Ile Glu Leu Gly Asp
            420                 425                 430

Ser Asp
```

<210> SEQ ID NO 146
<211> LENGTH: 33
<212> TYPE: DNA
<213> ORGANISM: Artificial Sequence
<220> FEATURE:
<223> OTHER INFORMATION: Synthetic

<400> SEQUENCE: 146
tactgactca ctatagggtc ttctatggag gtc                          33

<210> SEQ ID NO 147
<211> LENGTH: 42
<212> TYPE: DNA
<213> ORGANISM: Artificial Sequence
<220> FEATURE:
<223> OTHER INFORMATION: Synthetic

<400> SEQUENCE: 147 tttttttta attaggctct ggaagacgct gaaagcgtct tg                  42

<210> SEQ ID NO 148
<211> LENGTH: 38
<212> TYPE: DNA
<213> ORGANISM: Artificial Sequence
<220> FEATURE:
<223> OTHER INFORMATION: Synthetic

<400> SEQUENCE: 148 tttttttta attaggctct ggaagacgga acgtcttg                       38

<210> SEQ ID NO 149
<211> LENGTH: 34
<212> TYPE: DNA
<213> ORGANISM: Artificial Sequence
<220> FEATURE:
<223> OTHER INFORMATION: Synthetic

```
<400> SEQUENCE: 149
ttttttttta attaggctct ggaagagaat cttg                             34

<210> SEQ ID NO 150
<211> LENGTH: 32
<212> TYPE: DNA
<213> ORGANISM: Artificial Sequence
<220> FEATURE:
<223> OTHER INFORMATION: Synthetic

<400> SEQUENCE: 150
ttttttttta attaggctct ggaaggaact tg                               32

<210> SEQ ID NO 151
<211> LENGTH: 25
<212> TYPE: DNA
<213> ORGANISM: Artificial Sequence
<220> FEATURE:
<223> OTHER INFORMATION: Synthetic

<400> SEQUENCE: 151
ttttttttta attaggctct ggaag                                       25

<210> SEQ ID NO 152
<211> LENGTH: 26
<212> TYPE: DNA
<213> ORGANISM: Artificial Sequence
<220> FEATURE:
<223> OTHER INFORMATION: Synthetic

<400> SEQUENCE: 152
attagaaagg aagggaagaa agcgaa                                      26

<210> SEQ ID NO 153
<211> LENGTH: 30
<212> TYPE: DNA
<213> ORGANISM: Artificial Sequence
<220> FEATURE:
<223> OTHER INFORMATION: Synthetic

<400> SEQUENCE: 153
acggggaaag ccggcgaacg tggcgagaaa                                  30

<210> SEQ ID NO 154
<211> LENGTH: 30
<212> TYPE: DNA
<213> ORGANISM: Artificial Sequence
<220> FEATURE:
<223> OTHER INFORMATION: Synthetic

<400> SEQUENCE: 154
tgacggggaa agccggcgaa cgtggcgaga                                  30

<210> SEQ ID NO 155
<211> LENGTH: 30
<212> TYPE: DNA
<213> ORGANISM: Artificial Sequence
<220> FEATURE:
<223> OTHER INFORMATION: Synthetic

<400> SEQUENCE: 155
cttgacgggg aaagccggcg aacgtggcga                                  30

<210> SEQ ID NO 156
```

```
<211> LENGTH: 30
<212> TYPE: DNA
<213> ORGANISM: Artificial Sequence
<220> FEATURE:
<223> OTHER INFORMATION: Synthetic

<400> SEQUENCE: 156
gcttgacggg gaaagccggc gaacgtggcg                                              30

<210> SEQ ID NO 157
<211> LENGTH: 18
<212> TYPE: DNA
<213> ORGANISM: Artificial Sequence
<220> FEATURE:
<223> OTHER INFORMATION: Synthetic

<400> SEQUENCE: 157
agaaaggaag ggaagaaa                                                          18

<210> SEQ ID NO 158
<211> LENGTH: 45
<212> TYPE: DNA
<213> ORGANISM: Artificial Sequence
<220> FEATURE:
<223> OTHER INFORMATION: Synthetic

<400> SEQUENCE: 158
tggaggtcaa aacatcgata agtcgaagaa aggaagggaa gaaat                             45

<210> SEQ ID NO 159
<211> LENGTH: 14
<212> TYPE: DNA
<213> ORGANISM: Artificial Sequence
<220> FEATURE:
<223> OTHER INFORMATION: Synthetic

<400> SEQUENCE: 159
tgttttgacc tcca                                                              14

<210> SEQ ID NO 160
<211> LENGTH: 30
<212> TYPE: DNA
<213> ORGANISM: Artificial Sequence
<220> FEATURE:
<223> OTHER INFORMATION: Synthetic

<400> SEQUENCE: 160
acacagtgtc ctcccgctcc tcctgagcaa                                              30

<210> SEQ ID NO 161
<211> LENGTH: 18
<212> TYPE: DNA
<213> ORGANISM: Artificial Sequence
<220> FEATURE:
<223> OTHER INFORMATION: Synthetic

<400> SEQUENCE: 161
tttccctcct cctcttcc                                                          18

<210> SEQ ID NO 162
<211> LENGTH: 54
<212> TYPE: DNA
<213> ORGANISM: Artificial Sequence
<220> FEATURE:
<223> OTHER INFORMATION: Synthetic

<400> SEQUENCE: 162
```

```
atgaggaaga ggaggagggt gctcaggagg agcgggagga cactgtgtct gtca        54
```

<210> SEQ ID NO 163
<211> LENGTH: 53
<212> TYPE: DNA
<213> ORGANISM: Artificial Sequence
<220> FEATURE:
<223> OTHER INFORMATION: Synthetic

<400> SEQUENCE: 163

```
ttcgctttct tcccttcctt tctcgccacg ttcgccggct ttccccgtca agc         53
```

<210> SEQ ID NO 164
<211> LENGTH: 1011
<212> TYPE: DNA
<213> ORGANISM: Archaeoglobus fulgidus

<400> SEQUENCE: 164

```
atgggtgcgg atattggtga cctctttgag agggaagagg tcgagcttga gtacttctca    60
ggaaagaaaa ttgccgttga tgctttcaac acgctatacc agttcatctc gataataagg   120
cagcctgacg gtacgccgtt aaaggactca cagggcagaa tcacctctca cctttccgga   180
atcctataca gagtctccaa catggtcgag gtgggaatca ggccggtgtt tgtattcgac   240
ggagagccac cggagttcaa gaaggctgaa attgaggaga ggaaaaagag aagggctgag   300
gcagaggaga tgtggattgc ggcttttgcag gcaggagata aggacgcgaa aaagtatgct   360
caggctgcag ggagggttga cgagtacatt gttgactccg caaagacgct tttaagttac   420
atggggattc cctttgtcga tgccccgtct gaaggagagg cgcaggctgc ttacatggca   480
gcaaaaggcg atgtggagta cacaggaagc caggattacg attctctgct cttcggaagc   540
ccgagactcg ccagaaatct cgcaataacg ggaaaaagga gcttcccgg caaaaatgtc   600
tatgtggatg taaagccgga gataataatt ctggaaagca acctcaaaag ctgggtttg    660
acgagggagc agctcatcga catagcgatt ctggtcggga cggactacaa tgagggtgtg   720
aagggtgtcg gcgtcaagaa ggctttgaac tacatcaaga cctacggaga tattttcagg   780
gcactcaagg ctctgaaagt aaatattgac cacgtagagg agataaggaa tttcttcctg   840
aatcctcctg tgactgacga ctacagaata gagttcaggg agcctgactt tgagaaggcc   900
atcgagttcc tgtgcgagga gcacgacttc agcagggaga gggtcgagaa ggccttggag   960
aagctcaaag ctctgaagtc aacccaggcc acgcttgaga ggtggttctg a           1011
```

<210> SEQ ID NO 165
<211> LENGTH: 336
<212> TYPE: PRT
<213> ORGANISM: Archaeoglobus fulgidus

<400> SEQUENCE: 165

```
Met Gly Ala Asp Ile Gly Asp Leu Phe Glu Arg Glu Glu Val Glu Leu
1               5                   10                  15

Glu Tyr Phe Ser Gly Lys Lys Ile Ala Val Asp Ala Phe Asn Thr Leu
            20                  25                  30

Tyr Gln Phe Ile Ser Ile Ile Arg Gln Pro Asp Gly Thr Pro Leu Lys
        35                  40                  45

Asp Ser Gln Gly Arg Ile Thr Ser His Leu Ser Gly Ile Leu Tyr Arg
    50                  55                  60

Val Ser Asn Met Val Glu Val Gly Ile Arg Pro Val Phe Val Phe Asp
65                  70                  75                  80
```

Gly Glu Pro Pro Glu Phe Lys Lys Ala Glu Ile Glu Glu Arg Lys Lys
                85                  90                  95

Arg Arg Ala Glu Ala Glu Glu Met Trp Ile Ala Ala Leu Gln Ala Gly
            100                 105                 110

Asp Lys Asp Ala Lys Lys Tyr Ala Gln Ala Ala Gly Arg Val Asp Glu
        115                 120                 125

Tyr Ile Val Asp Ser Ala Lys Thr Leu Leu Ser Tyr Met Gly Ile Pro
    130                 135                 140

Phe Val Asp Ala Pro Ser Glu Gly Ala Gln Ala Ala Tyr Met Ala
145                 150                 155                 160

Ala Lys Gly Asp Val Glu Tyr Thr Gly Ser Gln Asp Tyr Asp Ser Leu
                165                 170                 175

Leu Phe Gly Ser Pro Arg Leu Ala Arg Asn Leu Ala Ile Thr Gly Lys
            180                 185                 190

Arg Lys Leu Pro Gly Lys Asn Val Tyr Val Asp Val Lys Pro Glu Ile
        195                 200                 205

Ile Ile Leu Glu Ser Asn Leu Lys Arg Leu Gly Leu Thr Arg Glu Gln
    210                 215                 220

Leu Ile Asp Ile Ala Ile Leu Val Gly Thr Asp Tyr Asn Glu Gly Val
225                 230                 235                 240

Lys Gly Val Gly Val Lys Lys Ala Leu Asn Tyr Ile Lys Thr Tyr Gly
                245                 250                 255

Asp Ile Phe Arg Ala Leu Lys Ala Leu Lys Val Asn Ile Asp His Val
            260                 265                 270

Glu Glu Ile Arg Asn Phe Phe Leu Asn Pro Pro Val Thr Asp Asp Tyr
        275                 280                 285

Arg Ile Glu Phe Arg Glu Pro Asp Phe Glu Lys Ala Ile Glu Phe Leu
    290                 295                 300

Cys Glu Glu His Asp Phe Ser Arg Glu Arg Val Glu Lys Ala Leu Glu
305                 310                 315                 320

Lys Leu Lys Ala Leu Lys Ser Thr Gln Ala Thr Leu Glu Arg Trp Phe
                325                 330                 335

<210> SEQ ID NO 166
<211> LENGTH: 26
<212> TYPE: DNA
<213> ORGANISM: Artificial Sequence
<220> FEATURE:
<223> OTHER INFORMATION: Synthetic

<400> SEQUENCE: 166
ccgtcaacat taccatggg tgcgga                                        26

<210> SEQ ID NO 167
<211> LENGTH: 31
<212> TYPE: DNA
<213> ORGANISM: Artificial Sequence
<220> FEATURE:
<223> OTHER INFORMATION: Synthetic

<400> SEQUENCE: 167
ccgccacctc gtagtcgaca tccttttcgt g                                 31

<210> SEQ ID NO 168
<211> LENGTH: 20
<212> TYPE: DNA
<213> ORGANISM: Artificial Sequence
<220> FEATURE:

```
<223> OTHER INFORMATION: Synthetic

<400> SEQUENCE: 168
ggcgaccaca cccgtcctgt                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
ccacgatgcg tccggcgtag                                              20

<210> SEQ ID NO 170
<211> LENGTH: 28
<212> TYPE: DNA
<213> ORGANISM: Artificial Sequence
<220> FEATURE:
<223> OTHER INFORMATION: Synthetic

<400> SEQUENCE: 170
aacgaggcgc acccacccaa ggcacagc                                     28

<210> SEQ ID NO 171
<211> LENGTH: 26
<212> TYPE: DNA
<213> ORGANISM: Artificial Sequence
<220> FEATURE:
<223> OTHER INFORMATION: Synthetic

<400> SEQUENCE: 171
acgggtcaat gtccatgccc caaaga                                       26

<210> SEQ ID NO 172
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (23)..(27)
<223> OTHER INFORMATION: 2'-O-methyls

<400> SEQUENCE: 172
gtctgagatg aaagtgcgcc tcgttaa                                      27

<210> SEQ ID NO 173
<211> LENGTH: 26
<212> TYPE: DNA
<213> ORGANISM: Artificial Sequence
<220> FEATURE:
<223> OTHER INFORMATION: Synthetic

<400> SEQUENCE: 173
tcttcgcaca tttcatctca gacgga                                       26

<210> SEQ ID NO 174
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_difference
```

```
<222> LOCATION: (1)..(21)
<223> OTHER INFORMATION: 2'-O-methyls

<400> SEQUENCE: 174
gctgtgcctt gggtgggtgc g                                              21

<210> SEQ ID NO 175
<211> LENGTH: 28
<212> TYPE: DNA
<213> ORGANISM: Artificial Sequence
<220> FEATURE:
<223> OTHER INFORMATION: Synthetic

<400> SEQUENCE: 175
aacgaggcgc acccacccaa ggcacagc                                       28

<210> SEQ ID NO 176
<211> LENGTH: 26
<212> TYPE: DNA
<213> ORGANISM: Artificial Sequence
<220> FEATURE:
<223> OTHER INFORMATION: Synthetic

<400> SEQUENCE: 176
acgggtcaat gtccatgccc caaaga                                         26

<210> SEQ ID NO 177
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (23)..(27)
<223> OTHER INFORMATION: 2'-O-methyls

<400> SEQUENCE: 177
gtctgagatg aaagtgcgcc tcgttaa                                        27

<210> SEQ ID NO 178
<211> LENGTH: 23
<212> TYPE: DNA
<213> ORGANISM: Artificial Sequence
<220> FEATURE:
<223> OTHER INFORMATION: Synthetic

<400> SEQUENCE: 178
tcttcgcaca tttcatctca gac                                            23

<210> SEQ ID NO 179
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(17)
<223> OTHER INFORMATION: 2'-O-methyls

<400> SEQUENCE: 179
gctgtgcctt gggtggg                                                   17

<210> SEQ ID NO 180
<211> LENGTH: 19
<212> TYPE: DNA
```

<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(19)
<223> OTHER INFORMATION: 2'-O-methyls

<400> SEQUENCE: 180
gctgtgcctt gggtgggtg                                                        19

<210> SEQ ID NO 181
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(21)
<223> OTHER INFORMATION: 2'-O-methyls

<400> SEQUENCE: 181
gctgtgcctt gggtgggtgc g                                                     21

<210> SEQ ID NO 182
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(22)
<223> OTHER INFORMATION: 2'O-methyls

<400> SEQUENCE: 182
gctgtgcctt gggtgggtgc gc                                                    22

<210> SEQ ID NO 183
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (22)..(22)
<223> OTHER INFORMATION: 2'-O-methyl sugar

<400> SEQUENCE: 183
gtctgagatg aaagtgctcc cgcacccacc caaggcacag c                               41

<210> SEQ ID NO 184
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(17)
<223> OTHER INFORMATION: 2'-O-methyls

<400> SEQUENCE: 184
gctgtgcctt gggtggg                                                          17

<210> SEQ ID NO 185
<211> LENGTH: 28

```
<212> TYPE: DNA
<213> ORGANISM: Artificial Sequence
<220> FEATURE:
<223> OTHER INFORMATION: Synthetic

<400> SEQUENCE: 185
aacgaggcgc acccacccaa ggcacagc                                        28

<210> SEQ ID NO 186
<211> LENGTH: 21
<212> TYPE: DNA
<213> ORGANISM: Artificial Sequence
<220> FEATURE:
<223> OTHER INFORMATION: Synthetic

<400> SEQUENCE: 186
gctgtgcctt gggtgggtgc g                                               21

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
gctgtgcctt gggtgggtgc                                                 20

<210> SEQ ID NO 188
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (15)..(20)
<223> OTHER INFORMATION: 2'-O-methyl sugars

<400> SEQUENCE: 188
gctgtgcctt gggtgggtgc                                                 20

<210> SEQ ID NO 189
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_difference
<222> LOCATION: (1)..(20)
<223> OTHER INFORMATION: 2'-O-methyl sugars

<400> SEQUENCE: 189
gctgtgcctt gggtgggtgc                                                 20

<210> SEQ ID NO 190
<211> LENGTH: 26
<212> TYPE: DNA
<213> ORGANISM: Artificial Sequence
<220> FEATURE:
<223> OTHER INFORMATION: Synthetic

<400> SEQUENCE: 190
tcttcgcaca tttcatctca gacgga                                          26

<210> SEQ ID NO 191
```

```
<211> LENGTH: 54
<212> TYPE: DNA
<213> ORGANISM: Artificial Sequence
<220> FEATURE:
<223> OTHER INFORMATION: Synthetic

<400> SEQUENCE: 191
ctgggcgcgg acatggagga cgtgcgcggc cgcctggtgc agtaccgcgg cgag          54

<210> SEQ ID NO 192
<211> LENGTH: 54
<212> TYPE: DNA
<213> ORGANISM: Artificial Sequence
<220> FEATURE:
<223> OTHER INFORMATION: Synthetic

<400> SEQUENCE: 192
ctgggcgcgg acatggagga cgtgtgcggc cgcctggtgc agtaccgcgg cgag          54

<210> SEQ ID NO 193
<211> LENGTH: 56
<212> TYPE: DNA
<213> ORGANISM: Artificial Sequence
<220> FEATURE:
<223> OTHER INFORMATION: Synthetic

<400> SEQUENCE: 193
cgcgatgccg atgacctgca gaagcgcctg gcagtgtacc aggccggggc ccgcga        56

<210> SEQ ID NO 194
<211> LENGTH: 56
<212> TYPE: DNA
<213> ORGANISM: Artificial Sequence
<220> FEATURE:
<223> OTHER INFORMATION: Synthetic

<400> SEQUENCE: 194
cgcgatgccg atgacctgca gaagtgcctg gcagtgtacc aggccggggc ccgcga        56

<210> SEQ ID NO 195
<211> LENGTH: 23
<212> TYPE: DNA
<213> ORGANISM: Artificial Sequence
<220> FEATURE:
<223> OTHER INFORMATION: Synthetic

<400> SEQUENCE: 195
cggtactgca ccaggcggcc gct                                            23

<210> SEQ ID NO 196
<211> LENGTH: 25
<212> TYPE: DNA
<213> ORGANISM: Artificial Sequence
<220> FEATURE:
<223> OTHER INFORMATION: Synthetic

<400> SEQUENCE: 196
ccccggcctg gtacactgcc aggct                                          25

<210> SEQ ID NO 197
<211> LENGTH: 27
<212> TYPE: DNA
<213> ORGANISM: Artificial Sequence
<220> FEATURE:
<223> OTHER INFORMATION: Synthetic

<400> SEQUENCE: 197
```
aacgaggcgc acgcacgtcc tccatgt                                    27

<210> SEQ ID NO 198
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: 2-amino deoxyadenosine

<400> SEQUENCE: 198
gaacgaggcg cacacacgtc ctccatgt                                   28

<210> SEQ ID NO 199
<211> LENGTH: 28
<212> TYPE: DNA
<213> ORGANISM: Artificial Sequence
<220> FEATURE:
<223> OTHER INFORMATION: Synthetic

<400> SEQUENCE: 199
aacgaggcgc acgcttctgc aggtcatc                                   28

<210> SEQ ID NO 200
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: 2-amino deoxyadenosine

<400> SEQUENCE: 200
aacgaggcgc acacttctgc aggtcatc                                   28

<210> SEQ ID NO 201
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker
      (Cy3).
<220> FEATURE:
<221> NAME/KEY: misc_feature
<222> LOCATION: (37)..(39)
<223> OTHER INFORMATION: 2'-O-methyl

<400> SEQUENCE: 201
cctcgtctcg gttttccgag acgagggtgc gcctcgttc                       39

<210> SEQ ID NO 202
<211> LENGTH: 28
<212> TYPE: DNA
<213> ORGANISM: Artificial Sequence
<220> FEATURE:
<223> OTHER INFORMATION: Synthetic

<400> SEQUENCE: 202
cccctgggga agagcagaga tatacgtc                                   28

<210> SEQ ID NO 203
<211> LENGTH: 24
<212> TYPE: DNA
<213> ORGANISM: Artificial Sequence
<220> FEATURE:
<223> OTHER INFORMATION: Synthetic

<400> SEQUENCE: 203
gggctccaca cggcgactct catt                                        24

<210> SEQ ID NO 204
<211> LENGTH: 39
<212> TYPE: DNA
<213> ORGANISM: Artificial Sequence
<220> FEATURE:
<223> OTHER INFORMATION: Synthetic

<400> SEQUENCE: 204
ggtgctccac ctggcacgta tatctctgct cttccccag                        39

<210> SEQ ID NO 205
<211> LENGTH: 39
<212> TYPE: DNA
<213> ORGANISM: Artificial Sequence
<220> FEATURE:
<223> OTHER INFORMATION: Synthetic

<400> SEQUENCE: 205
ggtgctccac ctggtacgta tatctctgct cttccccag                        39

<210> SEQ ID NO 206
<211> LENGTH: 46
<212> TYPE: DNA
<213> ORGANISM: Artificial Sequence
<220> FEATURE:
<223> OTHER INFORMATION: Synthetic

<400> SEQUENCE: 206
agctgttcgt gttctatgat catgagagtc gccgtgtgga gccccg                46

<210> SEQ ID NO 207
<211> LENGTH: 46
<212> TYPE: DNA
<213> ORGANISM: Artificial Sequence
<220> FEATURE:
<223> OTHER INFORMATION: Synthetic

<400> SEQUENCE: 207
agctgttcgt gttctatgat gatgagagtc gccgtgtgga gccccg                46

<210> SEQ ID NO 208
<211> LENGTH: 29
<212> TYPE: DNA
<213> ORGANISM: Artificial Sequence
<220> FEATURE:
<223> OTHER INFORMATION: Synthetic

<400> SEQUENCE: 208
aacgaacgcg caggccaggt ggagcattt                                   29

<210> SEQ ID NO 209
<211> LENGTH: 27
<212> TYPE: DNA
<213> ORGANISM: Artificial Sequence
<220> FEATURE:

<223> OTHER INFORMATION: Synthetic

<400> SEQUENCE: 209
aacgaacgcg cagaccaggt ggagcac                                    27

<210> SEQ ID NO 210
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker.
<220> FEATURE:
<221> NAME/KEY: misc_feature
<222> LOCATION: (38)..(40)
<223> OTHER INFORMATION: 2'-O-methyl

<400> SEQUENCE: 210
ctccgtctcg gttttccgag acggagctgc gcgttcguuu                       40

<210> SEQ ID NO 211
<211> LENGTH: 35
<212> TYPE: DNA
<213> ORGANISM: Artificial Sequence
<220> FEATURE:
<223> OTHER INFORMATION: Synthetic

<400> SEQUENCE: 211
aagcacgcag cacgatcata gaacacgaac agttt                            35

<210> SEQ ID NO 212
<211> LENGTH: 35
<212> TYPE: DNA
<213> ORGANISM: Artificial Sequence
<220> FEATURE:
<223> OTHER INFORMATION: Synthetic

<400> SEQUENCE: 212
aagcacgcag caccatcata gaacacgaac agttt                            35

<210> SEQ ID NO 213
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker.
<220> FEATURE:
<221> NAME/KEY: misc_feature
<222> LOCATION: (38)..(40)
<223> OTHER INFORMATION: 2'-O-methyl

<400> SEQUENCE: 213
acgcgtctcg gttttccgag acgcgtgtgc tgcgtgcuuu                       40

<210> SEQ ID NO 214
<211> LENGTH: 50
<212> TYPE: DNA
<213> ORGANISM: Artificial Sequence
<220> FEATURE:
<223> OTHER INFORMATION: Synthetic

<400> SEQUENCE: 214

```
gaaggtgtct gcgggagccg atttcatcat cacgcagctt ttctttgagg         50

<210> SEQ ID NO 215
<211> LENGTH: 50
<212> TYPE: DNA
<213> ORGANISM: Artificial Sequence
<220> FEATURE:
<223> OTHER INFORMATION: Synthetic

<400> SEQUENCE: 215
gaaggtgtct gcgggagtcg atttcatcat cacgcagctt ttctttgagg         50

<210> SEQ ID NO 216
<211> LENGTH: 30
<212> TYPE: DNA
<213> ORGANISM: Artificial Sequence
<220> FEATURE:
<223> OTHER INFORMATION: Synthetic

<400> SEQUENCE: 216
caaagaaaag ctgcgtgatg atgaaatcgc                               30

<210> SEQ ID NO 217
<211> LENGTH: 26
<212> TYPE: DNA
<213> ORGANISM: Artificial Sequence
<220> FEATURE:
<223> OTHER INFORMATION: Synthetic

<400> SEQUENCE: 217
aacgaggcgc acgctcccgc agacac                                   26

<210> SEQ ID NO 218
<211> LENGTH: 27
<212> TYPE: DNA
<213> ORGANISM: Artificial Sequence
<220> FEATURE:
<223> OTHER INFORMATION: Synthetic

<400> SEQUENCE: 218
aacgaggcgc acactcccgc agacacc                                  27

<210> SEQ ID NO 219
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker
      (CY3).

<400> SEQUENCE: 219
cctcgtctcg gttttccgag acgagggtgc gcctcgttt                     39

<210> SEQ ID NO 220
<211> LENGTH: 51
<212> TYPE: DNA
<213> ORGANISM: Artificial Sequence
<220> FEATURE:
<223> OTHER INFORMATION: Synthetic

<400> SEQUENCE: 220
actgggagca ttgaggctcg ctgagagtca cttttattgg gaaccatagt t        51
```

<210> SEQ ID NO 221
<211> LENGTH: 51
<212> TYPE: DNA
<213> ORGANISM: Artificial Sequence
<220> FEATURE:
<223> OTHER INFORMATION: Synthetic

<400> SEQUENCE: 221
actgggagca ttgaggcttg ctgagagtca cttttattgg gaaccatagt t            51

<210> SEQ ID NO 222
<211> LENGTH: 30
<212> TYPE: DNA
<213> ORGANISM: Artificial Sequence
<220> FEATURE:
<223> OTHER INFORMATION: Synthetic

<400> SEQUENCE: 222
tatggttccc aataaaagtg actctcagct                                    30

<210> SEQ ID NO 223
<211> LENGTH: 28
<212> TYPE: DNA
<213> ORGANISM: Artificial Sequence
<220> FEATURE:
<223> OTHER INFORMATION: Synthetic

<400> SEQUENCE: 223
aacgaggcgc acgagcctca atgctccc                                      28

<210> SEQ ID NO 224
<211> LENGTH: 28
<212> TYPE: DNA
<213> ORGANISM: Artificial Sequence
<220> FEATURE:
<223> OTHER INFORMATION: Synthetic

<400> SEQUENCE: 224
aacgaggcgc acaagcctca atgctccc                                      28

<210> SEQ ID NO 225
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker
      (CY3).

<400> SEQUENCE: 225
cctcgtctcg gttttccgag acgagggtgc gcctcgttt                          39

<210> SEQ ID NO 226
<211> LENGTH: 52
<212> TYPE: DNA
<213> ORGANISM: Artificial Sequence
<220> FEATURE:
<223> OTHER INFORMATION: Synthetic

<400> SEQUENCE: 226
tgaagtctag agaaagggtt gtacggctga ggtctggaga aatgggcatc tg           52

<210> SEQ ID NO 227
<211> LENGTH: 46
<212> TYPE: DNA
<213> ORGANISM: Artificial Sequence
<220> FEATURE:
<223> OTHER INFORMATION: Synthetic

<400> SEQUENCE: 227
tttgaaatgt cacagggttc ctaacagcca ctcttccctg gatggg        46

<210> SEQ ID NO 228
<211> LENGTH: 28
<212> TYPE: DNA
<213> ORGANISM: Artificial Sequence
<220> FEATURE:
<223> OTHER INFORMATION: Synthetic

<400> SEQUENCE: 228
agatgcccat ttctccagac ctcagccc        28

<210> SEQ ID NO 229
<211> LENGTH: 36
<212> TYPE: DNA
<213> ORGANISM: Artificial Sequence
<220> FEATURE:
<223> OTHER INFORMATION: Synthetic

<400> SEQUENCE: 229
aagcacgcag cacgtacaac cctttctcta gacaaa        36

<210> SEQ ID NO 230
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker.

<400> SEQUENCE: 230
ctccgtctcg gttttccgag acggaggtgc tgcgtgcuuu        40

<210> SEQ ID NO 231
<211> LENGTH: 25
<212> TYPE: DNA
<213> ORGANISM: Artificial Sequence
<220> FEATURE:
<223> OTHER INFORMATION: Synthetic

<400> SEQUENCE: 231
ccatccaggg aagagtggcc tgttt        25

<210> SEQ ID NO 232
<211> LENGTH: 29
<212> TYPE: DNA
<213> ORGANISM: Artificial Sequence
<220> FEATURE:
<223> OTHER INFORMATION: Synthetic

<400> SEQUENCE: 232
aagcacgcag cacaggaacc ctgtgacat        29

<210> SEQ ID NO 233
<211> LENGTH: 46
<212> TYPE: DNA

```
<213> ORGANISM: Artificial Sequence
<220> FEATURE:
<223> OTHER INFORMATION: Synthetic

<400> SEQUENCE: 233
taggttttga ggggcatggg gacggggttc agcctccagg gtccta                    46

<210> SEQ ID NO 234
<211> LENGTH: 46
<212> TYPE: DNA
<213> ORGANISM: Artificial Sequence
<220> FEATURE:
<223> OTHER INFORMATION: Synthetic

<400> SEQUENCE: 234
taggttttga ggggcatgag gacggggttc agcctccagg gtccta                    46

<210> SEQ ID NO 235
<211> LENGTH: 25
<212> TYPE: DNA
<213> ORGANISM: Artificial Sequence
<220> FEATURE:
<223> OTHER INFORMATION: Synthetic

<400> SEQUENCE: 235
gaccctggag gctgaacccc gtcca                                           25

<210> SEQ ID NO 236
<211> LENGTH: 28
<212> TYPE: DNA
<213> ORGANISM: Artificial Sequence
<220> FEATURE:
<223> OTHER INFORMATION: Synthetic

<400> SEQUENCE: 236
aacgaggcgc acccatcggg gtcaaaac                                        28

<210> SEQ ID NO 237
<211> LENGTH: 28
<212> TYPE: DNA
<213> ORGANISM: Artificial Sequence
<220> FEATURE:
<223> OTHER INFORMATION: Synthetic

<400> SEQUENCE: 237
aacgaggcgc actcatgccc ctcaaaac                                        28

<210> SEQ ID NO 238
<211> LENGTH: 56
<212> TYPE: DNA
<213> ORGANISM: Artificial Sequence
<220> FEATURE:
<223> OTHER INFORMATION: Synthetic

<400> SEQUENCE: 238
aaggacaaaa tacctgtatt cctcgcctgt ccagggatct gctcttacag attaga         56

<210> SEQ ID NO 239
<211> LENGTH: 56
<212> TYPE: DNA
<213> ORGANISM: Artificial Sequence
<220> FEATURE:
<223> OTHER INFORMATION: Synthetic

<400> SEQUENCE: 239
aaggacaaaa tacctgtatt ccttgcctgt ccagggatct gctcttacag attaga         56
```

```
<210> SEQ ID NO 240
<211> LENGTH: 31
<212> TYPE: DNA
<213> ORGANISM: Artificial Sequence
<220> FEATURE:
<223> OTHER INFORMATION: Synthetic

<400> SEQUENCE: 240
taatctgtaa gagcagatcc ctggacagrc c                                31

<210> SEQ ID NO 241
<211> LENGTH: 33
<212> TYPE: DNA
<213> ORGANISM: Artificial Sequence
<220> FEATURE:
<223> OTHER INFORMATION: Synthetic

<400> SEQUENCE: 241
aacgaggcgc acgaggaata caggtatttt gtc                              33

<210> SEQ ID NO 242
<211> LENGTH: 33
<212> TYPE: DNA
<213> ORGANISM: Artificial Sequence
<220> FEATURE:
<223> OTHER INFORMATION: Synthetic

<400> SEQUENCE: 242
aacgaggcgc acaaggaata caggtatttt gtc                              33

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggtaaaggtt ggcaaaaaga taac                                        24

<210> SEQ ID NO 244
<211> LENGTH: 27
<212> TYPE: DNA
<213> ORGANISM: Artificial Sequence
<220> FEATURE:
<223> OTHER INFORMATION: Synthetic

<400> SEQUENCE: 244
gcgccgaggt cttggggtgg ttacaag                                     27

<210> SEQ ID NO 245
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: This residue is linked to an abasic linker
      (CY3).

<400> SEQUENCE: 245
tctcgtctcg gttttccgag actgagacct cggcgcg                          37
```

<210> SEQ ID NO 246
<211> LENGTH: 29
<212> TYPE: DNA
<213> ORGANISM: Artificial Sequence
<220> FEATURE:
<223> OTHER INFORMATION: Synthetic

<400> SEQUENCE: 246
cacttgcttc aggaccatat ttctctctc                                    29

<210> SEQ ID NO 247
<211> LENGTH: 33
<212> TYPE: DNA
<213> ORGANISM: Artificial Sequence
<220> FEATURE:
<223> OTHER INFORMATION: Synthetic

<400> SEQUENCE: 247
cgcgccgagg acaccttttt tagggtgctt tgt                               33

<210> SEQ ID NO 248
<211> LENGTH: 22
<212> TYPE: DNA
<213> ORGANISM: Artificial Sequence
<220> FEATURE:
<223> OTHER INFORMATION: Synthetic

<400> SEQUENCE: 248
aaaatcgatg gtaaaggttg gc                                           22

<210> SEQ ID NO 249
<211> LENGTH: 22
<212> TYPE: DNA
<213> ORGANISM: Artificial Sequence
<220> FEATURE:
<223> OTHER INFORMATION: Synthetic

<400> SEQUENCE: 249
agttctgcag taccggattt gc                                           22

<210> SEQ ID NO 250
<211> LENGTH: 20
<212> TYPE: DNA
<213> ORGANISM: Artificial Sequence
<220> FEATURE:
<223> OTHER INFORMATION: Synthetic

<400> SEQUENCE: 250
tcgctactag ttgcttagtg                                              20

<210> SEQ ID NO 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
gtaaacataa gcaactttag                                              20

<210> SEQ ID NO 252
<211> LENGTH: 41
<212> TYPE: DNA
<213> ORGANISM: Artificial Sequence
<220> FEATURE:
<223> OTHER INFORMATION: Synthetic -continued

<400> SEQUENCE: 252
cttgtaacca ccccaagatt atcttttgc caacctttac c　　　　　　　　　41

<210> SEQ ID NO 253
<211> LENGTH: 51
<212> TYPE: DNA
<213> ORGANISM: Artificial Sequence
<220> FEATURE:
<223> OTHER INFORMATION: Synthetic

<400> SEQUENCE: 253
acaaagcacc ctaaaaaagg tgtagagaga aatatggtcc tgaagcaagt g　　　　51

<210> SEQ ID NO 254
<211> LENGTH: 28
<212> TYPE: DNA
<213> ORGANISM: Artificial Sequence
<220> FEATURE:
<223> OTHER INFORMATION: Synthetic

<400> SEQUENCE: 254
cacgaattcc gaggcgatgc ttccgctc　　　　　　　　　　　　　　　　28

<210> SEQ ID NO 255
<211> LENGTH: 30
<212> TYPE: DNA
<213> ORGANISM: Artificial Sequence
<220> FEATURE:
<223> OTHER INFORMATION: Synthetic

<400> SEQUENCE: 255
tcgacgtcga ctaacccttg gcggaaagcc　　　　　　　　　　　　　　　30

<210> SEQ ID NO 256
<211> LENGTH: 23
<212> TYPE: DNA
<213> ORGANISM: Artificial Sequence
<220> FEATURE:
<223> OTHER INFORMATION: Synthetic

<400> SEQUENCE: 256
gcatcgcctc ggaattcatg gtc　　　　　　　　　　　　　　　　　　23

<210> SEQ ID NO 257
<211> LENGTH: 26
<212> TYPE: DNA
<213> ORGANISM: Artificial Sequence
<220> FEATURE:
<223> OTHER INFORMATION: Synthetic

<400> SEQUENCE: 257
caggaggagc tcgttgtgga cctgga　　　　　　　　　　　　　　　　26

<210> SEQ ID NO 258
<211> LENGTH: 2511
<212> TYPE: DNA
<213> ORGANISM: Artificial Sequence
<220> FEATURE:
<223> OTHER INFORMATION: Synthetic

<400> SEQUENCE: 258
atgaattccg aggcgatgct tccgctcttt gaacccaaag gccgggtcct cctggtggac　　60 ggccaccacc tggcctaccg caccttcttc gccctgaagg gcctcaccac gagccggggc　　120 gaaccggtgc aggcggtcta cggcttcgcc aagagcctcc tcaaggccct gaaggaggac　　180

-continued

```
gggtacaagg ccgtcttcgt ggtctttgac gccaaggccc cctccttccg ccacgaggcc    240
tacgaggcct acaaggcggg gagggcccg accccgagg acttccccg gcagctcgcc        300 ctcatcaagg agctggtgga cctcctgggg tttacccgcc tcgaggtccc cggctacgag    360
gcggacgacg ttctcgccac cctggccaag aaggcggaaa aggaggggta cgaggtgcgc    420
atcctcaccg ccgaccgcga cctctaccaa ctcgtctccg accgcgtcgc cgtcctccac    480
cccgagggcc acctcatcac cccggagtgg ctttgggaga agtacggcct caggccggag    540
cagtgggtgg acttccgcgc cctcgtgggg gaccccgccg acaacctccc cggggtcaag    600
ggcatcgggg agaagaccgc cctcaagctc ctcaaggagt ggggaagcct ggaaaacctc    660
ctcaagaacc tggaccgggt aaagccagaa aacgtccggg agaagatcaa ggcccacctg    720
gaagacctca ggctctcctt ggagctctcc cgggtgcgca ccgacctccc cctggaggtg    780
gacctcgccc aggggcggga gcccgaccgg gaggggctta ggccttcct ggagaggctg     840 gagttcggca gcctcctcca cgagttcggc ctcctggagg ccccgccc cctggaggag      900 gcccctggc cccgccgga agggccttc gtgggcttcg tcctctcccg ccccgagccc       960
atgtgggcgg agcttaaagc cctggccgcc tgcagggacg gccgggtgca ccgggcagca    1020 gacccccttgg cggggctaaa ggacctcaag gaggtccggg gcctcctcgc caaggacctc   1080
gccgtcttgg cctcgaggga ggggctagac ctcgtgcccg ggacgaccc catgctcctc    1140 gcctacctcc tggaccccct caacaccacc cccgaggggg tggcgcggcg ctacgggggg   1200
gagtggacgg aggacgccgc ccaccgggcc ctcctctcgg agaggctcca tcggaacctc   1260
cttaagcgcc tcgaggggga ggagaagctc ctttggctct accacgaggt ggaaaagccc    1320
ctctcccggg tcctggccca catggaggcc accggggtac ggcgggacgt ggcctacctt   1380
caggcccttt ccctggagct tgcggaggag atccgccgcc tcgaggagga ggtcttccgc   1440
ttggcgggca ccccttcaa cctcaactcc cgggaccagc tggaaagggt gctctttgac    1500
gagcttaggc ttcccgcctt ggggaagacg caaaagacag gcaagcgctc caccagcgcc   1560
gcggtgctgg aggccctacg ggaggccac cccatcgtgg agaagatcct ccagcaccgg    1620
gagctcacca agctcaagaa cacctacgtg gacccctcc caagcctcgt ccacccgagg    1680
acgggccgcc tccacacccg cttcaaccag acggccacgg ccacggggag gcttagtagc   1740 tccgaccca acctgcagaa catccccgtc cgcacccct gggccagag atccgccgg       1800 gccttcgtgg ccgaggcggg ttgggcgttg gtgccctgg actatagcca gatagagctc    1860
cgcgtcctcg cccacctctc cggggacgaa aacctgatca gggtcttcca ggaggggaag   1920
gacatccaca cccagaccgc aagctggatg ttcggcgtcc cccggaggc cgtgaccccc     1980 ctgatgcgcc gggcggccaa gacggtgaac ttcggcgtcc tctacggcat gtccgcccat   2040
aggctctccc aggagcttgc catccctac gaggaggcgg tggcctttat agagcgctac    2100
ttccaaagct cccccaaggt gcgggcctgg atagaaaaga cctggagga ggggaggaag    2160 cggggctacg tggaaaccct cttcggaaga aggcgctacg tgcccgacct caacgcccgg   2220
gtgaagagcg tcagggaggc cgcggagcgc atggcttca acatgcccgt ccagggcacc    2280
gccgccgacc tcatgaagct cgccatggtg aagctcttcc ccgcctccg ggagatgggg    2340 gcccgcatgc tcctccaggt ccacaacgag ctcctcctgg agcccccca agcgcgggcc    2400 gaggaggtgg cggctttggc caaggaggcc atggagaagg cctatcccct cgccgtgccc   2460
ctggaggtgg aggtggggat gggggaggac tggctttccg ccaagggtta g            2511
```

-continued

<210> SEQ ID NO 259
<211> LENGTH: 836
<212> TYPE: PRT
<213> ORGANISM: Artificial Sequence
<220> FEATURE:
<223> OTHER INFORMATION: Synthetic

<400> SEQUENCE: 259

Met Asn Ser Glu Ala Met Leu Pro Leu Phe Glu Pro Lys Gly Arg Val
1               5                   10                  15

Leu Leu Val Asp Gly His His Leu Ala Tyr Arg Thr Phe Phe Ala Leu
            20                  25                  30

Lys Gly Leu Thr Thr Ser Arg Gly Glu Pro Val Gln Ala Val Tyr Gly
        35                  40                  45

Phe Ala Lys Ser Leu Leu Lys Ala Leu Lys Glu Asp Gly Tyr Lys Ala
    50                  55                  60

Val Phe Val Val Phe Asp Ala Lys Ala Pro Ser Phe Arg His Glu Ala
65                  70                  75                  80

Tyr Glu Ala Tyr Lys Ala Gly Arg Ala Pro Thr Pro Glu Asp Phe Pro
                85                  90                  95

Arg Gln Leu Ala Leu Ile Lys Glu Leu Val Asp Leu Leu Gly Phe Thr
            100                 105                 110

Arg Leu Glu Val Pro Gly Tyr Glu Ala Asp Asp Val Leu Ala Thr Leu
        115                 120                 125

Ala Lys Lys Ala Glu Lys Glu Gly Tyr Glu Val Arg Ile Leu Thr Ala
    130                 135                 140

Asp Arg Asp Leu Tyr Gln Leu Val Ser Asp Arg Val Ala Val Leu His
145                 150                 155                 160

Pro Glu Gly His Leu Ile Thr Pro Glu Trp Leu Trp Glu Lys Tyr Gly
                165                 170                 175

Leu Arg Pro Glu Gln Trp Val Asp Phe Arg Ala Leu Val Gly Asp Pro
            180                 185                 190

Ser Asp Asn Leu Pro Gly Val Lys Gly Ile Gly Glu Lys Thr Ala Leu
        195                 200                 205

Lys Leu Leu Lys Glu Trp Gly Ser Leu Glu Asn Leu Leu Lys Asn Leu
    210                 215                 220

Asp Arg Val Lys Pro Glu Asn Val Arg Glu Lys Ile Lys Ala His Leu
225                 230                 235                 240

Glu Asp Leu Arg Leu Ser Leu Glu Leu Ser Arg Val Arg Thr Asp Leu
                245                 250                 255

Pro Leu Glu Val Asp Leu Ala Gln Gly Arg Glu Pro Asp Arg Glu Gly
            260                 265                 270

Leu Arg Ala Phe Leu Glu Arg Leu Glu Phe Gly Ser Leu Leu His Glu
        275                 280                 285

Phe Gly Leu Leu Glu Ala Pro Ala Pro Leu Glu Glu Ala Pro Trp Pro
    290                 295                 300

Pro Pro Glu Gly Ala Phe Val Gly Phe Val Leu Ser Arg Pro Glu Pro
305                 310                 315                 320

Met Trp Ala Glu Leu Lys Ala Leu Ala Ala Cys Arg Asp Gly Arg Val
                325                 330                 335

His Arg Ala Ala Asp Pro Leu Ala Gly Leu Lys Asp Leu Lys Glu Val
            340                 345                 350

Arg Gly Leu Leu Ala Lys Asp Leu Ala Val Leu Ala Ser Arg Glu Gly
        355                 360                 365

-continued

```
Leu Asp Leu Val Pro Gly Asp Pro Met Leu Leu Ala Tyr Leu Leu
    370                 375                 380

Asp Pro Ser Asn Thr Thr Pro Glu Gly Val Ala Arg Arg Tyr Gly Gly
385                 390                 395                 400

Glu Trp Thr Glu Asp Ala Ala His Arg Ala Leu Leu Ser Glu Arg Leu
                405                 410                 415

His Arg Asn Leu Leu Lys Arg Leu Glu Gly Glu Glu Lys Leu Leu Trp
            420                 425                 430

Leu Tyr His Glu Val Glu Lys Pro Leu Ser Arg Val Leu Ala His Met
        435                 440                 445

Glu Ala Thr Gly Val Arg Arg Asp Val Ala Tyr Leu Gln Ala Leu Ser
    450                 455                 460

Leu Glu Leu Ala Glu Glu Ile Arg Arg Leu Glu Glu Val Phe Arg
465                 470                 475                 480

Leu Ala Gly His Pro Phe Asn Leu Asn Ser Arg Asp Gln Leu Glu Arg
                485                 490                 495

Val Leu Phe Asp Glu Leu Arg Leu Pro Ala Leu Gly Lys Thr Gln Lys
            500                 505                 510

Thr Gly Lys Arg Ser Thr Ser Ala Ala Val Leu Glu Ala Leu Arg Glu
        515                 520                 525

Ala His Pro Ile Val Glu Lys Ile Leu Gln His Arg Glu Leu Thr Lys
    530                 535                 540

Leu Lys Asn Thr Tyr Val Asp Pro Leu Pro Ser Leu Val His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Val Ala Glu Ala Gly Trp
        595                 600                 605

Ala Leu Val Ala Leu Asp Tyr Ser Gln Ile Glu Leu Arg Val Leu Ala
    610                 615                 620

His Leu Ser Gly Asp Glu Asn Leu Ile Arg Val Phe Gln Glu Gly Lys
625                 630                 635                 640

Asp Ile His Thr Gln Thr Ala Ser Trp Met Phe Gly Val Pro Pro Glu
                645                 650                 655

Ala Val Asp Pro Leu Met Arg Arg Ala Ala Lys Thr Val Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Val Ala Phe Ile Glu Arg Tyr Phe Gln Ser Phe
    690                 695                 700

Pro Lys Val Arg Ala Trp Ile Glu Lys Thr Leu Glu Glu Gly Arg Lys
705                 710                 715                 720

Arg Gly Tyr Val Glu Thr Leu Phe Gly Arg Arg Tyr Val Pro Asp
                725                 730                 735

Leu Asn Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765

Met Val Lys Leu Phe Pro Arg Leu Arg Glu Met Gly Ala Arg Met Leu
    770                 775                 780

Leu Gln Val His Asn Glu Leu Leu Leu Glu Ala Pro Gln Ala Arg Ala
```

Glu Glu Val Ala Ala Leu Ala Lys Glu Ala Met Glu Lys Ala Tyr Pro
         785                 790                 795                 800

Leu Ala Val Pro Leu Glu Val Glu Val Gly Met Gly Glu Asp Trp Leu
         805                 810                 815

Ser Ala Lys Gly
         820                 825                 830

<210> SEQ ID NO 260
<211> LENGTH: 777
<212> TYPE: DNA
<213> ORGANISM: Methanobacterium thermoautotrophicum

<400> SEQUENCE: 260
atgggagtta aactcaggga tgttgtatca ccccgcagga tacgccttga ggaccttagg      60
ggaagaacgg tcgcagtcga tgcagccaac acactctacc agttcctatc aagcataagg    120
cagagggatg gaacacccct catggattcc aggggtagag taacatcaca cctcagcggc    180
atactctaca ggacggccgc ggtcatggag agggagataa gggtcatata tgtcttcgat    240
ggaaggtccc accacctcaa gggcgagacc gtgagcagga gggctgatat ccggaagaaa    300
tctgaggttg agtggaagag ggcccttgag gaggggaca ttgacagggc gaaaaaatat     360
gctgtaaggt cctcaaggat gtcctcagaa atactgaga gttcaaagag ctcctggaa      420
cttctgggaa taccctatgt acaggcaccc ggtgaggggg aggctcaggc atcatacatg    480
gttaagatgg gcgatgcatg ggccgtggca tcccaggact atgactgtct cctctttggc    540
gccccaaggg ttgtaaggaa cctcacccctc agcggaaaac ttgaggaccc cgagatcatt   600
gaactggagt ccaccctcag ggaactctca atcagccaca cacagctcgt ggatatggca   660
ctactcgtcg ggactgactt caatgagggt gtaaggggga taggcgcaag gaggggactc   720
aaactcatca gggagaaggg cgacattttc aaagtcatca gggaccttga agcttga      777

<210> SEQ ID NO 261
<211> LENGTH: 258
<212> TYPE: PRT
<213> ORGANISM: Methanobacterium thermoautotrophicum

<400> SEQUENCE: 261

Met Gly Val Lys Leu Arg Asp Val Val Ser Pro Arg Arg Ile Arg Leu
1               5                   10                  15

Glu Asp Leu Arg Gly Arg Thr Val Ala Val Asp Ala Ala Asn Thr Leu
            20                  25                  30

Tyr Gln Phe Leu Ser Ser Ile Arg Gln Arg Asp Gly Thr Pro Leu Met
        35                  40                  45

Asp Ser Arg Gly Arg Val Thr Ser His Leu Ser Gly Ile Leu Tyr Arg
    50                  55                  60

Thr Ala Ala Val Met Glu Arg Glu Ile Arg Val Ile Tyr Val Phe Asp
65                  70                  75                  80

Gly Arg Ser His His Leu Lys Gly Glu Thr Val Ser Arg Arg Ala Asp
            85                  90                  95

Ile Arg Lys Lys Ser Glu Val Glu Trp Lys Arg Ala Leu Glu Glu Gly
            100                 105                 110

Asp Ile Asp Arg Ala Lys Lys Tyr Ala Val Arg Ser Ser Arg Met Ser
        115                 120                 125

Ser Glu Ile Leu Glu Ser Ser Lys Arg Leu Leu Glu Leu Leu Gly Ile
    130                 135                 140

```
Pro Tyr Val Gln Ala Pro Gly Glu Gly Glu Ala Gln Ala Ser Tyr Met
145                 150                 155                 160

Val Lys Met Gly Asp Ala Trp Ala Val Ala Ser Gln Asp Tyr Asp Cys
                165                 170                 175

Leu Leu Phe Gly Ala Pro Arg Val Val Arg Asn Leu Thr Leu Ser Gly
            180                 185                 190

Lys Leu Glu Asp Pro Glu Ile Ile Glu Leu Ser Thr Leu Arg Glu
        195                 200                 205

Leu Ser Ile Ser His Thr Gln Leu Val Asp Met Ala Leu Leu Val Gly
    210                 215                 220

Thr Asp Phe Asn Glu Gly Val Lys Gly Ile Gly Ala Arg Arg Gly Leu
225                 230                 235                 240

Lys Leu Ile Arg Glu Lys Gly Asp Ile Phe Lys Val Ile Arg Asp Leu
                245                 250                 255

Glu Ala

<210> SEQ ID NO 262
<211> LENGTH: 28
<212> TYPE: DNA
<213> ORGANISM: Artificial Sequence
<220> FEATURE:
<223> OTHER INFORMATION: Synthetic

<400> SEQUENCE: 262
gggtgttccc atgggagtta aactcagg                                           28

<210> SEQ ID NO 263
<211> LENGTH: 22
<212> TYPE: DNA
<213> ORGANISM: Artificial Sequence
<220> FEATURE:
<223> OTHER INFORMATION: Synthetic

<400> SEQUENCE: 263
ctgaattctg cagaaaaagg gg                                                 22

<210> SEQ ID NO 264
<211> LENGTH: 987
<212> TYPE: DNA
<213> ORGANISM: Methanobacterium thermoautotrophicum

<400> SEQUENCE: 264
atgggagtta aactcaggga tgttgtatca ccccgcagga tacgccttga ggaccttagg        60
ggaagaacgg tcgcagtcga tgcagccaac acactctacc agttcctatc aagcataagg      120
cagagggatg aacacccct catggattcc aggggtagag taacatcaca cctcagcggc       180
atactctaca ggacggccgc ggtcatggag agggagataa gggtcatata tgtcttcgat      240
ggaaggtccc accactcaa gggcgagacc gtgagcagga ggctgatat ccggaagaaa        300 tctgaggttg agtggaagag ggcccttgag gaggggaca ttgacagggc gagaaaatat       360
gctgtaaggt cctcaaggat gtcctcagaa atactgagag gttcaaagag gctcctggaa      420
cttctgggaa taccctatgt acaggcaccc ggtgagggg aggctcaggc atcatacatg       480
gttaagatgg gcgatgcatg ggccgtggca tcccaggact atgactgtct cctctttggc      540
gccccaaggg ttgtaaggaa ggtcaccctc agcggaaaac ttgaggaccc ccacatcatt      600
gaactggagt ccaccctcag ggccctctca atcagccaca cacagctcgt ggatatggca      660
ctactcgtcg ggactgactt caatgagggt gtaaaggggt atggcgcaag gaggggactc      720
```

```
aaactcatca gggagaaggg cgacattttc aaagtcatca gggaccttga agctgacata      780
ggtggcgacc cccaggtcct caggaggatc tttctggagc cagaggtttc agaggactat      840
gagatcaggt ggagaaaacc tgacgtggaa ggtgttatcg agttcctgtg cactgaacac      900
ggcttttcag aggaccgtgt gagggatgca cttaaaaaat tgagggtgc atcctccacc      960 cagaagagcc tggaggactg gttctga                                         987

<210> SEQ ID NO 265
<211> LENGTH: 328
<212> TYPE: PRT
<213> ORGANISM: Methanobacterium thermoautotrophicum

<400> SEQUENCE: 265
```

| Met | Gly | Val | Lys | Leu | Arg | Asp | Val | Val | Ser | Pro | Arg | Arg | Ile | Arg | Leu |
|---|---|---|---|---|---|---|---|---|---|---|---|---|---|---|---|
| 1 | | | | 5 | | | | | 10 | | | | | 15 | |

| Glu | Asp | Leu | Arg | Gly | Arg | Thr | Val | Ala | Val | Asp | Ala | Ala | Asn | Thr | Leu |
| | | | 20 | | | | | 25 | | | | | 30 | | |

| Tyr | Gln | Phe | Leu | Ser | Ser | Ile | Arg | Gln | Arg | Asp | Gly | Thr | Pro | Leu | Met |
| | | | 35 | | | | | 40 | | | | | 45 | | |

| Asp | Ser | Arg | Gly | Arg | Val | Thr | Ser | His | Leu | Ser | Gly | Ile | Leu | Tyr | Arg |
| | 50 | | | | | 55 | | | | | 60 | | | | |

| Thr | Ala | Ala | Val | Met | Glu | Arg | Glu | Ile | Arg | Val | Ile | Tyr | Val | Phe | Asp |
| 65 | | | | | 70 | | | | | 75 | | | | | 80 |

| Gly | Arg | Ser | His | His | Leu | Lys | Gly | Glu | Thr | Val | Ser | Arg | Arg | Ala | Asp |
| | | | | 85 | | | | | 90 | | | | | 95 | |

| Ile | Arg | Lys | Lys | Ser | Glu | Val | Glu | Trp | Lys | Arg | Ala | Leu | Glu | Glu | Gly |
| | | | 100 | | | | | 105 | | | | | 110 | | |

| Asp | Ile | Asp | Arg | Ala | Arg | Lys | Tyr | Ala | Val | Arg | Ser | Ser | Arg | Met | Ser |
| | | | 115 | | | | | 120 | | | | | 125 | | |

| Ser | Glu | Ile | Leu | Glu | Ser | Ser | Lys | Arg | Leu | Leu | Glu | Leu | Leu | Gly | Ile |
| | 130 | | | | | 135 | | | | | 140 | | | | |

| Pro | Tyr | Val | Gln | Ala | Pro | Gly | Glu | Gly | Glu | Ala | Gln | Ala | Ser | Tyr | Met |
| 145 | | | | | 150 | | | | | 155 | | | | | 160 |

| Val | Lys | Met | Gly | Asp | Ala | Trp | Ala | Val | Ala | Ser | Gln | Asp | Tyr | Asp | Cys |
| | | | | 165 | | | | | 170 | | | | | 175 | |

| Leu | Leu | Phe | Gly | Ala | Pro | Arg | Val | Val | Arg | Lys | Val | Thr | Leu | Ser | Gly |
| | | | 180 | | | | | 185 | | | | | 190 | | |

| Lys | Leu | Glu | Asp | Pro | His | Ile | Ile | Glu | Leu | Glu | Ser | Thr | Leu | Arg | Ala |
| | | | 195 | | | | | 200 | | | | | 205 | | |

| Leu | Ser | Ile | Ser | His | Thr | Gln | Leu | Val | Asp | Met | Ala | Leu | Leu | Val | Gly |
| | 210 | | | | | 215 | | | | | 220 | | | | |

| Thr | Asp | Phe | Asn | Glu | Gly | Val | Lys | Gly | Tyr | Gly | Ala | Arg | Arg | Gly | Leu |
| 225 | | | | | 230 | | | | | 235 | | | | | 240 |

| Lys | Leu | Ile | Arg | Glu | Lys | Gly | Asp | Ile | Phe | Lys | Val | Ile | Arg | Asp | Leu |
| | | | | 245 | | | | | 250 | | | | | 255 | |

| Glu | Ala | Asp | Ile | Gly | Gly | Asp | Pro | Gln | Val | Leu | Arg | Arg | Ile | Phe | Leu |
| | | | 260 | | | | | 265 | | | | | 270 | | |

| Glu | Pro | Glu | Val | Ser | Glu | Asp | Tyr | Glu | Ile | Arg | Trp | Arg | Lys | Pro | Asp |
| | | | 275 | | | | | 280 | | | | | 285 | | |

| Val | Glu | Gly | Val | Ile | Glu | Phe | Leu | Cys | Thr | Glu | His | Gly | Phe | Ser | Glu |
| | 290 | | | | | 295 | | | | | 300 | | | | |

| Asp | Arg | Val | Arg | Asp | Ala | Leu | Lys | Lys | Phe | Glu | Gly | Ala | Ser | Ser | Thr |
| 305 | | | | | 310 | | | | | 315 | | | | | 320 |

```
Gln Lys Ser Leu Glu Asp Trp Phe
            325
```

<210> SEQ ID NO 266
<211> LENGTH: 17
<212> TYPE: DNA
<213> ORGANISM: Artificial Sequence
<220> FEATURE:
<223> OTHER INFORMATION: Synthetic

<400> SEQUENCE: 266
tgtggaattg tgagcgg                                                17

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
tggaggctct ccatcaaaaa c                                           21

<210> SEQ ID NO 268
<211> LENGTH: 296
<212> TYPE: DNA
<213> ORGANISM: Artificial Sequence
<220> FEATURE:
<223> OTHER INFORMATION: Synthetic

<400> SEQUENCE: 268
tgtggaattg tgagcggata acaatttcac acaggaaaca gaccatggga gtgcagtttg      60
gtgattttat tccaaaaaat attatctcct tgaagattt aaaagggaaa aaagtagcta     120
ttgatggaat gaatgcatta tatcagtttt taacatctat acgtttgaga gatggttctc    180
cattgagaaa tagaaaagga gagataacct cagcatataa cggagttttt tataaaacca    240
tacatttgtt agagaatgat ataactccaa tctgggtttt tgatggagag cctcca        296

<210> SEQ ID NO 269
<211> LENGTH: 17
<212> TYPE: DNA
<213> ORGANISM: Artificial Sequence
<220> FEATURE:
<223> OTHER INFORMATION: Synthetic

<400> SEQUENCE: 269
taatctgtat caggctg                                                17

<210> SEQ ID NO 270
<211> LENGTH: 21
<212> TYPE: DNA
<213> ORGANISM: Artificial Sequence
<220> FEATURE:
<223> OTHER INFORMATION: Synthetic

<400> SEQUENCE: 270
gtttttgatg gagagcctcc a                                           21

<210> SEQ ID NO 271
<211> LENGTH: 889
<212> TYPE: DNA
<213> ORGANISM: Artificial Sequence
<220> FEATURE:
<223> OTHER INFORMATION: Synthetic

<400> SEQUENCE: 271

```
gtttttgatg agagcctcc agaattcaaa agaaagagc tcgaaaaaag aagagaagcg      60
agagaggaag ctgaagaaaa gtggagagaa gcacttgaaa aaggagagat agaggaagca    120
agaaaatatg cccaaagagc aaccagggta atgaaatgc tcatcgagga tgcaaaaaaa    180
ctcttagagc ttatgggaat tcctatagtt caagcaccta gcgagggaga ggcccaagct    240
gcatatatgg ccgcaaaggg gagcgtgtat gcatcggcta gtcaagatta cgattcccta    300
cttttggag ctccaagact tgttagaaac ttaacaataa caggaaaaag aaagttgcct    360
gggaaaaatg tctacgtcga gataaagccc gagttgataa ttttggagga agtactcaag    420
gaattaaagc taacaagaga aaagctcatt gaactagcaa tcctcgttgg aacagactac    480
aacccaggag aataaaggg cataggcctt aaaaagctt tagagattgt tagacactca    540
aaagatccgc tagcaaagtt ccaaaagcaa agcgatgtgg atttatatgc aataaaagag    600
ttcttcctaa acccaccagt cacagataac tacaatttag tgtggagaga tcccgacgaa    660
gagggaatac taaagttctt atgtgacgag catgacttta gtgaggaaag agtaaagaat    720
ggattagaga ggcttaagaa ggcaatcaaa agtggaaaac aatcaaccct gaaagttgg    780
ttcaagagat aaccttaaag tctattgcaa tgttatactg acgcgctgca ggcatgcaag    840
cttggctgtt ttggcggatg agaagatt ttcagcctga tacagatta                    889
```

<210> SEQ ID NO 272
<211> LENGTH: 1164
<212> TYPE: DNA
<213> ORGANISM: Artificial Sequence
<220> FEATURE:
<223> OTHER INFORMATION: Synthetic

<400> SEQUENCE: 272

```
tgtggaattg tgagcggata acaatttcac acaggaaaca gaccatggga gtgcagtttg     60
gtgattttat tccaaaaat attatctcct ttgaagattt aaaagggaaa aaagtagcta    120
ttgatggaat gaatgcatta tatcagtttt taacatctat acgtttgaga gatggttctc    180
cattgagaaa tagaaaagga gagataacct cagcatataa cggagttttt tataaaacca    240
tacatttgtt agagaatgat ataactccaa tctgggtttt tgatggagag cctccagaat    300
tcaaaagaa agagctcgaa aaaagaagag aagcgagaga ggaagctgaa gaaagtgga    360
gagaagcact tgaaaagga gagatagagg aagcaagaaa atatgcccaa agagcaacca    420
gggtaaatga aatgctcatc gaggatgcaa aaaactctt agagcttatg ggaattccta    480
tagttcaagc acctagcgag ggagaggccc aagctgcata tatggccgca aaggggagcg    540
tgtatgcatc ggctagtcaa gattacgatt ccctactttt tggagctcca agacttgtta    600
gaaacttaac aataacagga aaagaaagt tgcctgggaa aaatgtctac gtcgagataa    660
agcccgagtt gataattttg gaggaagtac tcaaggaatt aaagctaaca agagaaaagc    720
tcattgaact agcaatcctc gttggaacag actacaaccc aggaggaata aagggcatag    780
gccttaaaaa agcttagag attgttagac actcaaaaga tccgctagca aagttccaaa    840
agcaaagcga tgtggattta tatgcaataa aagagttctt cctaaaccca ccagtcacag    900
ataactacaa tttagtgtgg agagatcccg acgaagaggg aatactaaag ttcttatgtg    960
acgagcatga ctttagtgag gaaagagtaa agaatggatt agagaggctt aagaaggcaa   1020
tcaaaagtgg aaaacaatca acccttgaaa gttggttcaa gagataacct taagtctat   1080
tgcaatgtta tactgacgcg ctgcaggcat gcaagcttgg ctgttttggc ggatgagaga   1140
```
agattttcag cctgatacag atta 1164

<210> SEQ ID NO 273
<211> LENGTH: 296
<212> TYPE: DNA
<213> ORGANISM: Artificial Sequence
<220> FEATURE:
<223> OTHER INFORMATION: Synthetic

<400> SEQUENCE: 273
tgtggaattg tgagcggata acaatttcac acaggaaaca gaccatgggt gtcccaattg 60
gtgagattat accaagaaaa gaattgagt tagaaaacct atacgggaaa aaaatcgcaa 120
tcgacgctct taatgcaatc taccaatttt tgtccacaat aagacagaaa gatgaactc 180 cacttatgga ttcaaagggt agaataacct cccacctaag cgggctcttt tacaggacaa 240
taaacctaat ggaggctgga ataaaacctg tgtatgtttt tgatggagag cctcca 296

<210> SEQ ID NO 274
<211> LENGTH: 840
<212> TYPE: DNA
<213> ORGANISM: Artificial Sequence
<220> FEATURE:
<223> OTHER INFORMATION: Synthetic

<400> SEQUENCE: 274
gtttttgatg gagagcctcc aaagttaaag gagaaaacaa ggaaagttag gagagagatg 60
aaagagaaag ctgaacttaa gatgaaagag gcaattaaaa aggaggattt tgaagaagct 120
gctaagtatg caaagagggt tagctatcta actccgaaaa tggttgaaaa ctgcaaatat 180
ttgttaagtt tgatgggcat tccgtatgtt gaagctccct ctgagggaga ggcacaagca 240
agctatatgg caaagaaggg agatgtttgg gcagttgtaa gtcaagatta tgatgccttg 300
ttatatggag ctccgagagt tgttagaaat ttaacaacta caaggagat gccagaactt 360 attgaattaa atgaggtttt agaggattta agaatttctt tggatgattt gatagatata 420
gccatattta tgggaactga ctataatcca ggaggagtta aaggaatagg atttaaaagg 480
gcttatgaat tggttagaag tggtgtagct aaggatgttt tgaaaaaga ggttgaatac 540 tacgatgaga ttaagaggat atttaaagag ccaaaggtta ccgataacta ttcattaagc 600
ctaaaattgc cagataaaga gggaattata aaattcttag ttgatgaaaa tgactttaat 660
tatgataggg ttaaaaagca tgttgataaa ctctataact taattgcaaa caaaactaag 720
caaaaaacat tagatgcatg gtttaaataa tttatataat tttgtgggat gtcgacctgc 780
aggcatgcaa gcttggctgt tttggcggat gagagaagat tttcagcctg atacagatta 840

<210> SEQ ID NO 275
<211> LENGTH: 1115
<212> TYPE: DNA
<213> ORGANISM: Artificial Sequence
<220> FEATURE:
<223> OTHER INFORMATION: Synthetic

<400> SEQUENCE: 275
tgtggaattg tgagcggata acaatttcac acaggaaaca gaccatgggt gtcccaattg 60
gtgagattat accaagaaaa gaattgagt tagaaaacct atacgggaaa aaaatcgcaa 120
tcgacgctct taatgcaatc taccaatttt tgtccacaat aagacagaaa gatgaactc 180 cacttatgga ttcaaagggt agaataacct cccacctaag cgggctcttt tacaggacaa 240

```
taaacctaat ggaggctgga ataaaacctg tgtatgtttt tgatggagag cctccaaagt      300
taaaggagaa aacaaggaaa gttaggagag agatgaaaga gaaagctgaa cttaagatga      360
aagaggcaat taaaaggag gattttgaag aagctgctaa gtatgcaaag agggttagct      420
atctaactcc gaaaatggtt gaaaactgca aatatttgtt aagtttgatg ggcattccgt      480
atgttgaagc tccctctgag ggagaggcac aagcaagcta tatggcaaag aagggagatg      540
tttgggcagt tgtaagtcaa gattatgatg ccttgttata tggagctccg agagttgtta      600
gaaatttaac aactacaaag gagatgccag aacttattga attaaatgag gttttagagg      660
atttaagaat ttctttggat gatttgatag atatagccat atttatggga actgactata      720
atccaggagg agttaaagga ataggattta aagggctta tgaattggtt agaagtggtg      780
tagctaagga tgttttgaaa aaagaggttg aatactacga tgagattaag aggatattta      840
aagagccaaa ggttaccgat aactattcat taagcctaaa attgccagat aaagagggaa      900
ttataaaatt cttagttgat gaaaatgact ttaattatga tagggttaaa aagcatgttg      960
ataaactcta taacttaatt gcaaacaaaa ctaagcaaaa aacattagat gcatggttta      1020
aataatttat ataattttgt gggatgtcga cctgcaggca tgcaagcttg gctgttttgg      1080
cggatgagag aagattttca gcctgataca gatta                                 1115

<210> SEQ ID NO 276
<211> LENGTH: 386
<212> TYPE: DNA
<213> ORGANISM: Artificial Sequence
<220> FEATURE:
<223> OTHER INFORMATION: Synthetic

<400> SEQUENCE: 276
tgtggaattg tgagcggata caatttcac acaggaaaca gaccatgggt gtcccaattg       60
gtgagattat accaagaaaa gaaattgagt tagaaaacct atacgggaaa aaaatcgcaa      120
tcgacgctct taatgcaatc taccaatttt tgtccacaat aagacagaaa gatggaactc      180
cacttatgga ttcaaagggt agaataacct cccacctaag cgggctcttt tacaggacaa      240
taaacctaat ggaggctgga ataaaacctg tgtatgtttt tgatggagaa cctccagaat      300
tcaaaaagaa agagctcgaa aaaagaagag aagcgagaga ggaagctgaa gaaaagtgga      360
gagaagcact tgaaaaagga gagata                                           386

<210> SEQ ID NO 277
<211> LENGTH: 33
<212> TYPE: DNA
<213> ORGANISM: Artificial Sequence
<220> FEATURE:
<223> OTHER INFORMATION: Synthetic

<400> SEQUENCE: 277
tacttagcag cttcttctat ctctccttt tca                                    33

<210> SEQ ID NO 278
<211> LENGTH: 668
<212> TYPE: DNA
<213> ORGANISM: Artificial Sequence
<220> FEATURE:
<223> OTHER INFORMATION: Synthetic

<400> SEQUENCE: 278
gaagaagctg ctaagtatgc aaagagggtt agctatctaa ctccgaaaat ggttgaaaac       60
tgcaaatatt tgttaagttt gatgggcatt ccgtatgttg aagctccctc tgagggagag      120
```

```
gcacaagcaa gctatatggc aaagaaggga gatgtttggg cagttgtaag tcaagattat      180
gatgccttgt tatatggagc tccgagagtt gttagaaatt taacaactac aaaggagatg      240
ccagaactta ttgaattaaa tgaggtttta gaggatttaa gaatttcttt ggatgatttg      300
atagatatag ccatatttat gggaactgac tataatccag gaggagttaa aggaatagga      360
tttaaaaggg cttatgaatt ggttagaagt ggtgtagcta aggatgtttt gaaaaaagag      420
gttgaatact acgatgagat taagaggata tttaagagc caaaggttac cgataactat       480
tcattaagcc taaaattgcc agataaagag ggaattataa aattcttagt tgatgaaaat      540
gactttaatt atgatagggt taaaaagcat gttgataaac tctataactt aattgcaaac      600
aaaactaagc aaaaaacatt agatgcatgg tttaaacacc accaccacca ccactaactg      660
cagcggta                                                              668

<210> SEQ ID NO 279
<211> LENGTH: 53
<212> TYPE: DNA
<213> ORGANISM: Artificial Sequence
<220> FEATURE:
<223> OTHER INFORMATION: Synthetic

<400> SEQUENCE: 279
taccgctgca gttagtggtg gtggtggtgg tgtttaaacc atgcatctaa tgt             53

<210> SEQ ID NO 280
<211> LENGTH: 17
<212> TYPE: DNA
<213> ORGANISM: Artificial Sequence
<220> FEATURE:
<223> OTHER INFORMATION: Synthetic

<400> SEQUENCE: 280
gaagaagctg ctaagta                                                    17

<210> SEQ ID NO 281
<211> LENGTH: 1054
<212> TYPE: DNA
<213> ORGANISM: Artificial Sequence
<220> FEATURE:
<223> OTHER INFORMATION: Synthetic

<400> SEQUENCE: 281
tgtggaattg tgagcggata acaatttcac acaggaaaca gaccatgggt gtcccaattg      60
gtgagattat accaagaaaa gaattgagt tagaaaacct atacgggaaa aaaatcgcaa       120
tcgacgctct taatgcaatc taccaatttt tgtccacaat aagacagaaa gatgaactc       180 cacttatgga ttcaaagggt agaataacct cccacctaag cgggctcttt tacaggacaa      240
taaacctaat ggaggctgga ataaaacctg tgtatgtttt tgatggagaa cctccagaat      300
tcaaaaagaa agagctcgaa aaaagaagag aagcgagaga ggaagctgaa gaaaagtgga      360
gagaagcact tgaaaaagga gagatagaag aagctgctaa gtatgcaaag agggttagct      420
atctaactcc gaaaatggtt gaaaactgca atatttgtt aagtttgatg ggcattccgt       480
atgttgaagc tccctctgag ggagaggcac aagcaagcta tatggcaaag aagggagatg      540
tttgggcagt tgtaagtcaa gattatgatg ccttgttata tggagctccg agagttgtta      600
gaaatttaac aactacaaag gagatgccag aacttattga attaaatgag gtttagagg       660 atttaagaat ttctttggat gatttgatag atatagccat atttatggga actgactata      720
```

| | |
|---|---|
| atccaggagg agttaaagga ataggattta aaagggctta tgaattggtt agaagtggtg | 780 |
| tagctaagga tgttttgaaa aaagaggttg aatactacga tgagattaag aggatattta | 840 |
| aagagccaaa ggttaccgat aactattcat taagcctaaa attgccagat aaagagggaa | 900 |
| ttataaaatt cttagttgat gaaaatgact ttaattatga tagggttaaa aagcatgttg | 960 |
| ataaactcta taacttaatt gcaaacaaaa ctaagcaaaa acattagat gcatggttta | 1020 |
| aacaccacca ccaccaccac taactgcagc ggta | 1054 |

<210> SEQ ID NO 282
<211> LENGTH: 514
<212> TYPE: DNA
<213> ORGANISM: Artificial Sequence
<220> FEATURE:
<223> OTHER INFORMATION: Synthetic

<400> SEQUENCE: 282

| | |
|---|---|
| tgtggaattg tgagcggata acaatttcac acaggaaaca gaccatggga gtgcagtttg | 60 |
| gtgattttat tccaaaaaat attatctcct ttgaagattt aaaagggaaa aaagtagcta | 120 |
| ttgatggaat gaatgcatta tatcagtttt taacatctat acgtttgaga gatggttctc | 180 |
| cattgagaaa tagaaaagga gagataacct cagcatataa cggagttttt tataaaacca | 240 |
| tacatttgtt agagaatgat ataactccaa tctgggtttt tgatggtgag ccaccaaagt | 300 |
| taaaggagaa acaaggaaa gttaggagag agatgaaaga gaaagctgaa cttaagatga | 360 |
| aagaggcaat taaaaggag gattttgaag aagctgctaa gtatgcaaag agggttagct | 420 |
| atctaactcc gaaatggtt gaaaactgca atatttgtt aagtttgatg ggcattccgt | 480 |
| atgttgaagc tccctctgag ggagaggccc aagc | 514 |

<210> SEQ ID NO 283
<211> LENGTH: 17
<212> TYPE: DNA
<213> ORGANISM: Artificial Sequence
<220> FEATURE:
<223> OTHER INFORMATION: Synthetic

<400> SEQUENCE: 283

| | |
|---|---|
| gcttgggcct ctccctc | 17 |

<210> SEQ ID NO 284
<211> LENGTH: 667
<212> TYPE: DNA
<213> ORGANISM: Artificial Sequence
<220> FEATURE:
<223> OTHER INFORMATION: Synthetic

<400> SEQUENCE: 284

| | |
|---|---|
| gagggagagg cccaagctgc atatatggcc gcaaggggga gcgtgtatgc atcggctagt | 60 |
| caagattacg attccctact ttttggagct ccaagacttg ttagaaactt aacaataaca | 120 |
| ggaaaaagaa agttgcctgg gaaaaatgtc tacgtcgaga taaagcccga gttgataatt | 180 |
| ttggaggaag tactcaagga attaaagcta acaagagaaa agctcattga actagcaatc | 240 |
| ctcgttggaa cagactacaa cccaggagga ataaagggca taggccttaa aaaagcttta | 300 |
| gagattgtta gacactcaaa agatccgcta gcaaagttcc aaaagcaaag cgatgtggat | 360 |
| ttatatgcaa taaagagtt cttcctaaac ccaccagtca cagataacta caatttagtg | 420 |
| tggagagatc ccgacgaaga gggaatacta aagttcttat gtgacgagca tgactttagt | 480 |
| gaggaaagag taaagaatgg attagagagg cttaagaagg caatcaaaag tggaaaacaa | 540 |

```
tcaaccctTg aaagttggtt caagagataa ccttaaagtc tattgcaatg ttatactgac      600
gcgctgcagg catgcaagct tggctgtttt ggcggatgag agaagatttt cagcctgata      660
cagatta                                                                667

<210> SEQ ID NO 285
<211> LENGTH: 17
<212> TYPE: DNA
<213> ORGANISM: Artificial Sequence
<220> FEATURE:
<223> OTHER INFORMATION: Synthetic

<400> SEQUENCE: 285
gagggagagg cccaagc                                                     17

<210> SEQ ID NO 286
<211> LENGTH: 1164
<212> TYPE: DNA
<213> ORGANISM: Artificial Sequence
<220> FEATURE:
<223> OTHER INFORMATION: Synthetic

<400> SEQUENCE: 286
tgtggaattg tgagcggata acaatttcac acaggaaaca gaccatggga gtgcagtttg       60
gtgattttat tccaaaaaat attatctcct ttgaagattt aaaagggaaa aaagtagcta      120
ttgatggaat gaatgcatta tatcagtttt taacatctat acgtttgaga gatggttctc      180
cattgagaaa tagaaaagga gagataaacct cagcatataa cggagttttt tataaaacca      240
tacatttgtt agagaatgat ataactccaa tctgggtttt tgatggtgag ccaccaaagt      300
taaaggagaa aacaaggaaa gttaggagag agatgaaaga gaaagctgaa cttaagatga      360
aagaggcaat taaaaggag gattttgaag aagctgctaa gtatgcaaag agggttagct      420
atctaactcc gaaaatggtt gaaaactgca atatttgtt aagtttgatg ggcattccgt      480
atgttgaagc tccctctgag ggagaggccc aagctgcata tggccgcca aaggggagcg      540 tgtatgcatc ggctagtcaa gattacgatt ccctactttt tggagctcca agacttgtta      600
gaaacttaac aataacagga aaaagaaagt tgcctgggaa aaatgtctac gtcgagataa      660
agcccgagtt gataatttg gaggaagtac tcaaggaatt aaagctaaca agagaaaagc      720
tcattgaact agcaatcctc gttggaacag actacaaccc aggaggaata aagggcatag      780
gccttaaaaa agctttagag attgttagac actcaaaaga tccgctagca agttccaaa      840 agcaaagcga tgtggattta tatgcaataa aagagttctt cctaaaccca ccagtcacag      900
ataactacaa tttagtgtgg agagatcccg acgaagaggg aatactaaag ttcttatgtg      960
acgagcatga cttagtgag gaaagagtaa agaatggatt agagaggctt aagaaggcaa     1020 tcaaagtgg aaaacaatca acccttgaaa gttggttcaa gagataacct taaagtctat     1080
tgcaatgtta tactgacgcg ctgcaggcat gcaagcttgg ctgttttggc ggatgagaga     1140
agattttcag cctgatacag atta                                            1164

<210> SEQ ID NO 287
<211> LENGTH: 514
<212> TYPE: DNA
<213> ORGANISM: Artificial Sequence
<220> FEATURE:
<223> OTHER INFORMATION: Synthetic

<400> SEQUENCE: 287
```

```
tgtggaattg tgagcggata acaatttcac acaggaaaca gaccatgggt gtcccaattg     60
gtgagattat accaagaaaa gaaattgagt tagaaaacct atacgggaaa aaaatcgcaa    120
tcgacgctct taatgcaatc taccaatttt tgtccacaat aagacagaaa gatggaactc    180
cacttatgga ttcaaagggt agaataacct cccacctaag cgggctcttt tacaggacaa    240
taaacctaat ggaggctgga ataaaacctg tgtatgtttt tgatggagaa cctccagaat    300
tcaaaaagaa agagctcgaa aaagaagag aagcgagaga ggaagctgaa gaaaagtgga    360
gagaagcact tgaaaagga gagatagagg aagcaagaaa atatgcccaa agagcaacca    420
gggtaaatga aatgctcatc gaggatgcaa aaaaactctt agagcttatg ggaattccta    480
tagttcaagc acctagcgag ggagaggccc aagc                               514
```

```
<210> SEQ ID NO 288
<211> LENGTH: 618
<212> TYPE: DNA
<213> ORGANISM: Artificial Sequence
<220> FEATURE:
<223> OTHER INFORMATION: Synthetic

<400> SEQUENCE: 288
```

```
gagggagagg cccaagcaag ctatatggca agaagggag atgtttgggc agttgtaagt     60
caagattatg atgccttgtt atatggagct ccgagagttg ttagaaattt aacaactaca    120
aaggagatgc cagaacttat tgaattaaat gaggttttag aggatttaag aatttctttg    180
gatgatttga tagatatagc catatttatg ggaactgact ataatccagg aggagttaaa    240
ggaataggat ttaaaagggc ttatgaattg gttagaagtg gtgtagctaa ggatgttttg    300 aaaaagagg ttgaatacta cgatgagatt aagaggatat ttaaagagcc aaaggttacc    360
gataactatt cattaagcct aaaattgcca gataaagagg gaattataaa attcttagtt    420
gatgaaaatg actttaatta tgatagggtt aaaaagcatg ttgataaact ctataactta    480
attgcaaaca aaactaagca aaaaacatta gatgcatggt ttaaataatt tatataatttt   540 tgtgggatgt cgacctgcag gcatgcaagc ttggctgttt tggcggatga gagaagatttt   600 tcagcctgat acagatta                                                 618
```

```
<210> SEQ ID NO 289
<211> LENGTH: 1115
<212> TYPE: DNA
<213> ORGANISM: Artificial Sequence
<220> FEATURE:
<223> OTHER INFORMATION: Synthetic

<400> SEQUENCE: 289
```

```
tgtggaattg tgagcggata acaatttcac acaggaaaca gaccatgggt gtcccaattg     60
gtgagattat accaagaaaa gaaattgagt tagaaaacct atacgggaaa aaaatcgcaa    120
tcgacgctct taatgcaatc taccaatttt tgtccacaat aagacagaaa gatggaactc    180
cacttatgga ttcaaagggt agaataacct cccacctaag cgggctcttt tacaggacaa    240
taaacctaat ggaggctgga ataaaacctg tgtatgtttt tgatggagaa cctccagaat    300
tcaaaaagaa agagctcgaa aaagaagag aagcgagaga ggaagctgaa gaaaagtgga    360
gagaagcact tgaaaagga gagatagagg aagcaagaaa atatgcccaa agagcaacca    420
gggtaaatga aatgctcatc gaggatgcaa aaaaactctt agagcttatg ggaattccta    480
tagttcaagc acctagcgag ggagaggccc aagcaagcta tatggcaaag aagggagatg    540
tttgggcagt tgtaagtcaa gattatgatg ccttgttata tggagctccg agagttgtta    600
```

```
gaaatttaac aactacaaag gagatgccag aacttattga attaaatgag gttttagagg      660
atttaagaat ttctttggat gatttgatag atatagccat atttatggga actgactata      720
atccaggagg agttaaagga ataggattta aaagggctta tgaattggtt agaagtggtg      780
tagctaagga tgttttgaaa aagaggttg aatactacga tgagattaag aggatattta       840
aagagccaaa ggttaccgat aactattcat taagcctaaa attgccagat aaagagggaa      900
ttataaaatt cttagttgat gaaaatgact ttaattatga tagggttaaa aagcatgttg      960
ataaactcta taacttaatt gcaaacaaaa ctaagcaaaa acattagat gcatggttta      1020 aataatttat ataattttgt gggatgtcga cctgcaggca tgcaagcttg gctgttttgg     1080
cggatgagag aagatttca gcctgataca gatta                                 1115

<210> SEQ ID NO 290
<211> LENGTH: 350
<212> TYPE: DNA
<213> ORGANISM: Escherichia coli

<400> SEQUENCE: 290
agagtttgat catggctcag attgaacgct ggcggcaggc ctaacacatg caagtcgaac       60
ggtaacagga agaagcttgc ttctttgctg acgagtggcg gacgggtgag taatgtctgg      120
gaaactgcct gatggagggg gataaactact ggaaacggta gctaataccg cataacgtcg     180
caagaccaaa gaggggggacc ttcgggcctc ttgccatcgg atgtgcccag atgggattag     240
ctagtaggtg gggtaacggc tcacctaggc gacgatccct agctggtctg agaggatgac     300
cagccacact ggaactgaga cacggtccag actcctacgg gaggcagcag                350

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
agagtttgat cctggctcag                                                   20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
ctgctgcctc ccgtaggagt                                                   20

<210> SEQ ID NO 293
<211> LENGTH: 34
<212> TYPE: DNA
<213> ORGANISM: Artificial Sequence
<220> FEATURE:
<223> OTHER INFORMATION: Synthetic

<400> SEQUENCE: 293
ttttcgctgt ctcgctgaaa gcgagacagc gttt                                   34

<210> SEQ ID NO 294
<211> LENGTH: 59
<212> TYPE: DNA
```

<213> ORGANISM: Artificial Sequence
<220> FEATURE:
<223> OTHER INFORMATION: Synthetic

<400> SEQUENCE: 294
ttttcgctgt ctcgctgaaa gcgagacagc gaaagacgct cgtgaaacga gcgtctttg    59

<210> SEQ ID NO 295
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 295
atctctagca ctgctgtntt ygayggn                                       27

<210> SEQ ID NO 296
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 296
gatctctagc actgctgarg gngargcnca r                                  31

<210> SEQ ID NO 297
<211> LENGTH: 28
<212> TYPE: DNA
<213> ORGANISM: Artificial Sequence
<220> FEATURE:
<223> OTHER INFORMATION: Synthetic

<400> SEQUENCE: 297
gatctctagc actgctcarg aytaygay                                      28

<210> SEQ ID NO 298
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 298
cttaaggtag gactacytgn gcytcnccyt c                                  31

<210> SEQ ID NO 299
<211> LENGTH: 30
<212> TYPE: DNA
<213> ORGANISM: Artificial Sequence
<220> FEATURE:
<223> OTHER INFORMATION: Synthetic

<400> SEQUENCE: 299
ttaaggtagg actacytcrt aytcytgrct                                        30

<210> SEQ ID NO 300
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(28)
<223> OTHER INFORMATION: n is a, c, g, or t

<400> SEQUENCE: 300
ttaaggtagg actacytcrt aytcytgnga                                        30

<210> SEQ ID NO 301
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 301
ttaaggtagg actacrttrw artcngtncc                                        30

<210> SEQ ID NO 302
<211> LENGTH: 16
<212> TYPE: DNA
<213> ORGANISM: Artificial Sequence
<220> FEATURE:
<223> OTHER INFORMATION: Synthetic

<400> SEQUENCE: 302
gatctctagc actgct                                                       16

<210> SEQ ID NO 303
<211> LENGTH: 16
<212> TYPE: DNA
<213> ORGANISM: Artificial Sequence
<220> FEATURE:
<223> OTHER INFORMATION: Synthetic

<400> SEQUENCE: 303
cttaaggtag gactac                                                       16

<210> SEQ ID NO 304
<211> LENGTH: 27
<212> TYPE: DNA
<213> ORGANISM: Artificial Sequence
<220> FEATURE:

```
<223> OTHER INFORMATION: Synthetic

<400> SEQUENCE: 304
gccatgtcat tagttaacct agttgcc                                              27

<210> SEQ ID NO 305
<211> LENGTH: 27
<212> TYPE: DNA
<213> ORGANISM: Artificial Sequence
<220> FEATURE:
<223> OTHER INFORMATION: Synthetic

<400> SEQUENCE: 305
ggcaatggga attccagtag tgcaagc                                              27

<210> SEQ ID NO 306
<211> LENGTH: 27
<212> TYPE: DNA
<213> ORGANISM: Artificial Sequence
<220> FEATURE:
<223> OTHER INFORMATION: Synthetic

<400> SEQUENCE: 306
gccatctcgt ttgtaagtct ggttgcc                                              27

<210> SEQ ID NO 307
<211> LENGTH: 26
<212> TYPE: DNA
<213> ORGANISM: Artificial Sequence
<220> FEATURE:
<223> OTHER INFORMATION: Synthetic

<400> SEQUENCE: 307
cttacaaacg agatggcaga cgaagg                                               26

<210> SEQ ID NO 308
<211> LENGTH: 27
<212> TYPE: DNA
<213> ORGANISM: Artificial Sequence
<220> FEATURE:
<223> OTHER INFORMATION: Synthetic

<400> SEQUENCE: 308
ttgctgtgca tacttcctcg cttcagc                                              27

<210> SEQ ID NO 309
<211> LENGTH: 27
<212> TYPE: DNA
<213> ORGANISM: Artificial Sequence
<220> FEATURE:
<223> OTHER INFORMATION: Synthetic

<400> SEQUENCE: 309
ccgaggtgat agacttagaa tacaacc                                              27

<210> SEQ ID NO 310
<211> LENGTH: 27
<212> TYPE: DNA
<213> ORGANISM: Artificial Sequence
<220> FEATURE:
<223> OTHER INFORMATION: Synthetic

<400> SEQUENCE: 310
tatcgcagcg atccacttct cctctgc                                              27
```

<210> SEQ ID NO 311
<211> LENGTH: 27
<212> TYPE: DNA
<213> ORGANISM: Artificial Sequence
<220> FEATURE:
<223> OTHER INFORMATION: Synthetic

<400> SEQUENCE: 311
cttaaacggc aacctgagaa ggcttgg                                27

<210> SEQ ID NO 312
<211> LENGTH: 28
<212> TYPE: DNA
<213> ORGANISM: Artificial Sequence
<220> FEATURE:
<223> OTHER INFORMATION: Synthetic

<400> SEQUENCE: 312
ctatctcctt ctgcttgaaa acaggagg                               28

<210> SEQ ID NO 313
<211> LENGTH: 27
<212> TYPE: DNA
<213> ORGANISM: Artificial Sequence
<220> FEATURE:
<223> OTHER INFORMATION: Synthetic

<400> SEQUENCE: 313
acaagggaac agctcgtcga tatcgcg                                27

<210> SEQ ID NO 314
<211> LENGTH: 26
<212> TYPE: DNA
<213> ORGANISM: Artificial Sequence
<220> FEATURE:
<223> OTHER INFORMATION: Synthetic

<400> SEQUENCE: 314
tgctgcctcc tccttaacgg ctttcc                                 26

<210> SEQ ID NO 315
<211> LENGTH: 27
<212> TYPE: DNA
<213> ORGANISM: Artificial Sequence
<220> FEATURE:
<223> OTHER INFORMATION: Synthetic

<400> SEQUENCE: 315
ccggagctca tagagctcga caaactc                                27

<210> SEQ ID NO 316
<211> LENGTH: 26
<212> TYPE: DNA
<213> ORGANISM: Artificial Sequence
<220> FEATURE:
<223> OTHER INFORMATION: Synthetic

<400> SEQUENCE: 316
tctcgcagcc tcctccctga caaccc                                 26

<210> SEQ ID NO 317
<211> LENGTH: 27
<212> TYPE: DNA
<213> ORGANISM: Artificial Sequence
<220> FEATURE:
<223> OTHER INFORMATION: Synthetic

```
<400> SEQUENCE: 317
ctcgataaac tgctttcaaa gctgggc                                              27

<210> SEQ ID NO 318
<211> LENGTH: 27
<212> TYPE: DNA
<213> ORGANISM: Artificial Sequence
<220> FEATURE:
<223> OTHER INFORMATION: Synthetic

<400> SEQUENCE: 318
cctctttgcg tattttttgca tctcatc                                             27

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
cttaacaaag gacatcgtag agaactc                                              27

<210> SEQ ID NO 320
<211> LENGTH: 26
<212> TYPE: DNA
<213> ORGANISM: Artificial Sequence
<220> FEATURE:
<223> OTHER INFORMATION: Synthetic

<400> SEQUENCE: 320
cagtttctcc atcgcctcct ccttcc                                               26

<210> SEQ ID NO 321
<211> LENGTH: 27
<212> TYPE: DNA
<213> ORGANISM: Artificial Sequence
<220> FEATURE:
<223> OTHER INFORMATION: Synthetic

<400> SEQUENCE: 321
ttggtggaag acgcgaagag gctgttg                                              27

<210> SEQ ID NO 322
<211> LENGTH: 26
<212> TYPE: DNA
<213> ORGANISM: Artificial Sequence
<220> FEATURE:
<223> OTHER INFORMATION: Synthetic

<400> SEQUENCE: 322
catggccttc tcacgcgtct tcctcc                                               26

<210> SEQ ID NO 323
<211> LENGTH: 26
<212> TYPE: DNA
<213> ORGANISM: Artificial Sequence
<220> FEATURE:
<223> OTHER INFORMATION: Synthetic

<400> SEQUENCE: 323
ctgagctata tgggcgtacc ctgggt                                               26

<210> SEQ ID NO 324
<211> LENGTH: 26
```

```
<212> TYPE: DNA
<213> ORGANISM: Artificial Sequence
<220> FEATURE:
<223> OTHER INFORMATION: Synthetic

<400> SEQUENCE: 324
cccatggcct ccagcagctt cttagc                                          26

<210> SEQ ID NO 325
<211> LENGTH: 27
<212> TYPE: DNA
<213> ORGANISM: Artificial Sequence
<220> FEATURE:
<223> OTHER INFORMATION: Synthetic

<400> SEQUENCE: 325
aacctcgcta taacgggtaa gaggaag                                         27

<210> SEQ ID NO 326
<211> LENGTH: 27
<212> TYPE: DNA
<213> ORGANISM: Artificial Sequence
<220> FEATURE:
<223> OTHER INFORMATION: Synthetic

<400> SEQUENCE: 326
agcttgaact acaggtatac ccatagc                                         27

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
gctatgggta tacctgtagt tcaagct                                         27

<210> SEQ ID NO 328
<211> LENGTH: 26
<212> TYPE: DNA
<213> ORGANISM: Artificial Sequence
<220> FEATURE:
<223> OTHER INFORMATION: Synthetic

<400> SEQUENCE: 328
ctgcgcttcc tccctagcct cagctc                                          26

<210> SEQ ID NO 329
<211> LENGTH: 26
<212> TYPE: DNA
<213> ORGANISM: Artificial Sequence
<220> FEATURE:
<223> OTHER INFORMATION: Synthetic

<400> SEQUENCE: 329
atgggcatcc catgggtgca ggctcc                                          26

<210> SEQ ID NO 330
<211> LENGTH: 26
<212> TYPE: DNA
<213> ORGANISM: Artificial Sequence
<220> FEATURE:
<223> OTHER INFORMATION: Synthetic

<400> SEQUENCE: 330
```

```
aggttcctta caagtctcgg cgcgcc                                            26

<210> SEQ ID NO 331
<211> LENGTH: 26
<212> TYPE: DNA
<213> ORGANISM: Artificial Sequence
<220> FEATURE:
<223> OTHER INFORMATION: Synthetic

<400> SEQUENCE: 331
agctcggcat agacagggaa aagctg                                            26

<210> SEQ ID NO 332
<211> LENGTH: 26
<212> TYPE: DNA
<213> ORGANISM: Artificial Sequence
<220> FEATURE:
<223> OTHER INFORMATION: Synthetic

<400> SEQUENCE: 332
aggtttctca cgagtttcgg cgcgcc                                            26

<210> SEQ ID NO 333
<211> LENGTH: 26
<212> TYPE: DNA
<213> ORGANISM: Artificial Sequence
<220> FEATURE:
<223> OTHER INFORMATION: Synthetic

<400> SEQUENCE: 333
agcttggcat agaccgggag aaactc                                            26

<210> SEQ ID NO 334
<211> LENGTH: 31
<212> TYPE: DNA
<213> ORGANISM: Artificial Sequence
<220> FEATURE:
<223> OTHER INFORMATION: Synthetic

<400> SEQUENCE: 334
gcaaccatgg gagtagacct tgctgatttg g                                      31

<210> SEQ ID NO 335
<211> LENGTH: 32
<212> TYPE: DNA
<213> ORGANISM: Artificial Sequence
<220> FEATURE:
<223> OTHER INFORMATION: Synthetic

<400> SEQUENCE: 335
ccatgtcgac taaaaccact gatctaaacc gc                                     32

<210> SEQ ID NO 336
<211> LENGTH: 1056
<212> TYPE: DNA
<213> ORGANISM: Artificial Sequence
<220> FEATURE:
<223> OTHER INFORMATION: Synthetic

<400> SEQUENCE: 336
ataggagtag accttgctga tttggtaaaa gaaatcaaaa gagaagttca gctaagtgaa        60
ttaaaaggga agaaagtaag catagatgct tataacgcta tttaccagtt tttgactgca       120
ataagacagc cagatggtac tccactaatg gactcacaag gaagagttac tagtcatctt       180
agtggaatat tttatagaac aataagccct ttagaagaag gagtaattcc aatttatgta       240
```

```
ttcgatggaa aaccaccaga acttaaagct caagaattag aaagaagaag aaaaataaag    300
gaagaagctg agaaaaaatt ggaaaaagcc aagaagaag gagaaacaaa ggaattaaag     360
aagtattcgc aaatggcaac taggttaact aatgacatgg cagaagaaag taaaaaactt    420
ttagaggcaa tgggaattcc agtagtgcaa gctccaagtg aaggagaagc tgaggcagcg    480
tatttatgta gtcaagggta tacttgggca gcggctagcc aagattacga ttctttgctt    540
tttggtgcaa ataaattaat tagaaactta acattaactg gaagaggaa attacctaaa     600 aaagacgtat atgtagaaat taagccagaa cttatagaac ttgaagattt gcttaaaaag    660
ttcggaatta ctagagaaca actagttgat ataggaatat aatagggaac tgattatgac    720
cctgacggaa taaagggaat agggccagtt actgctctaa gaataataaa gaaatacgga    780
aatatagaaa aagctgtaga aaaggagaa ttaccgaaat acattcttga tcttaatatt     840
aatgaaatta gatctatctt tcttaatccg ccagtagtta agcctgaggg ctcgttagat    900
ctaaaagagc ctaatgagga agaaatcaag aaaatcctca tagatgagca taactttagt    960
gaggatagag taactaatgg aatagaaaga ctgattaaag ccggtaagga agctaaagga    1020
gctagtaggc agagcggttt agatcagtgg ttttag                              1056
```

<210> SEQ ID NO 337
<211> LENGTH: 351
<212> TYPE: PRT
<213> ORGANISM: Artificial Sequence
<220> FEATURE:
<223> OTHER INFORMATION: Synthetic

<400> SEQUENCE: 337

```
Ile Gly Val Asp Leu Ala Asp Leu Val Lys Glu Ile Lys Arg Glu Val
1               5                   10                  15

Gln Leu Ser Glu Leu Lys Gly Lys Lys Val Ser Ile Asp Ala Tyr Asn
            20                  25                  30

Ala Ile Tyr Gln Phe Leu Thr Ala Ile Arg Gln Pro Asp Gly Thr Pro
        35                  40                  45

Leu Met Asp Ser Gln Gly Arg Val Thr Ser His Leu Ser Gly Ile Phe
    50                  55                  60

Tyr Arg Thr Ile Ser Leu Leu Glu Glu Gly Val Ile Pro Ile Tyr Val
65                  70                  75                  80

Phe Asp Gly Lys Pro Pro Glu Leu Lys Ala Gln Glu Leu Glu Arg Arg
                85                  90                  95

Arg Lys Ile Lys Glu Glu Ala Glu Lys Lys Leu Glu Lys Ala Lys Glu
            100                 105                 110

Glu Gly Glu Thr Lys Glu Leu Lys Lys Tyr Ser Gln Met Ala Thr Arg
        115                 120                 125

Leu Thr Asn Asp Met Ala Glu Glu Ser Lys Lys Leu Leu Glu Ala Met
    130                 135                 140

Gly Ile Pro Val Val Gln Ala Pro Ser Glu Gly Glu Ala Glu Ala Ala
145                 150                 155                 160

Tyr Leu Cys Ser Gln Gly Tyr Thr Trp Ala Ala Ala Ser Gln Asp Tyr
                165                 170                 175

Asp Ser Leu Leu Phe Gly Ala Asn Lys Leu Ile Arg Asn Leu Thr Leu
            180                 185                 190

Thr Gly Lys Arg Lys Leu Pro Lys Lys Asp Val Tyr Val Glu Ile Lys
        195                 200                 205

Pro Glu Leu Ile Glu Leu Glu Asp Leu Leu Lys Lys Phe Gly Ile Thr
```

```
                210                 215                 220
Arg Glu Gln Leu Val Asp Ile Gly Ile Leu Ile Gly Thr Asp Tyr Asp
225                 230                 235                 240

Pro Asp Gly Ile Lys Gly Ile Gly Pro Val Thr Ala Leu Arg Ile Ile
                245                 250                 255

Lys Lys Tyr Gly Asn Ile Glu Lys Ala Val Glu Lys Gly Glu Leu Pro
            260                 265                 270

Lys Tyr Ile Leu Asp Leu Asn Ile Asn Glu Ile Arg Ser Ile Phe Leu
        275                 280                 285

Asn Pro Pro Val Val Lys Pro Glu Gly Ser Leu Asp Leu Lys Glu Pro
290                 295                 300

Asn Glu Glu Glu Ile Lys Lys Ile Leu Ile Asp Glu His Asn Phe Ser
305                 310                 315                 320

Glu Asp Arg Val Thr Asn Gly Ile Glu Arg Leu Ile Lys Ala Gly Lys
                325                 330                 335

Glu Ala Lys Gly Ala Ser Arg Gln Ser Gly Leu Asp Gln Trp Phe
            340                 345                 350

<210> SEQ ID NO 338
<211> LENGTH: 31
<212> TYPE: DNA
<213> ORGANISM: Artificial Sequence
<220> FEATURE:
<223> OTHER INFORMATION: Synthetic

<400> SEQUENCE: 338
cataccatgg gagtagattt atctgactta g                              31

<210> SEQ ID NO 339
<211> LENGTH: 33
<212> TYPE: DNA
<213> ORGANISM: Artificial Sequence
<220> FEATURE:
<223> OTHER INFORMATION: Synthetic

<400> SEQUENCE: 339
cttggtcgac ttaaaaccat tggtcaagtc cag                            33

<210> SEQ ID NO 340
<211> LENGTH: 1056
<212> TYPE: DNA
<213> ORGANISM: Artificial Sequence
<220> FEATURE:
<223> OTHER INFORMATION: Synthetic

<400> SEQUENCE: 340
atcggagtag atttatctga cttagttgaa gacgtaaaag ctgagataaa cttagctgag    60
ttgcgtggga aaaagtaag tattgatgca tataatgcaa tatatcaatt tttgacagct    120
atacgccaac cagacggtac accacttata gattcacaag gtaaataac aagccacctt    180 agtggaattt tttatcgaac cattaatcta atggaaaatg gtataatacc gatatatgtt    240
tttgatggaa aaccaccaga gcttaaatct gcagaattac aaagacgtaa aaaaataaaa    300
gaagaagcgg aaaagaagtt agagaaagca aagaagagg gaaaaactac agagttaaaa    360
aagtattctc aaatggcaac cagacttaca acgagatgg cagacgaagg aaaaaaattg    420
cttaaaagta tgggtattcc aatagtagaa gcaccgtctg aaggtgaagc ggaatcagca    480
tatattaacg caataggatt aagttttgct actgcaagcc aggattatga ttcactatta    540
tttggtgcga aaaatttgat aagaaactta actataactg gaaaagaaa attacctaat    600
```

```
aaagacatat acgtcgaaat aaaacctgaa agaattgaac tcgaaccact acttaaaaag    660
cttggtataa caagagaaca attaatagat atagcgattt taattggaac agattatgat    720
ccttcaggga taaaggaat aggccccaag accgcttata ggctaattaa gaaatatgga    780
agaatagaaa aaattattga agcgaatgaa attccaaaga attctattga tttcgatatt    840
aatcaaataa ggcaactatt tctaaatccg aatgtgaaaa accagaaga gaatttagac    900 ttgcaaaatc ctgaagaaca agaaattata gaaattttag taaatcaaca taatttttaat   960 gaagaaagag ttaaaagtgc attagaaaga ttaaataaag caataaaaga aactaaaggt  1020
ctctcaagac aaactggact tgaccaatgg ttttaa                              1056
```

<210> SEQ ID NO 341
<211> LENGTH: 351
<212> TYPE: PRT
<213> ORGANISM: Artificial Sequence
<220> FEATURE:
<223> OTHER INFORMATION: Synthetic

<400> SEQUENCE: 341

```
Ile Gly Val Asp Leu Ser Asp Leu Val Glu Asp Val Lys Ala Glu Ile
1               5                   10                  15

Asn Leu Ala Glu Leu Arg Gly Lys Lys Val Ser Ile Asp Ala Tyr Asn
            20                  25                  30

Ala Ile Tyr Gln Phe Leu Thr Ala Ile Arg Gln Pro Asp Gly Thr Pro
        35                  40                  45

Leu Ile Asp Ser Gln Gly Lys Ile Thr Ser His Leu Ser Gly Ile Phe
    50                  55                  60

Tyr Arg Thr Ile Asn Leu Met Glu Asn Gly Ile Ile Pro Ile Tyr Val
65                  70                  75                  80

Phe Asp Gly Lys Pro Pro Glu Leu Lys Ser Ala Glu Leu Gln Arg Arg
                85                  90                  95

Lys Lys Ile Lys Glu Glu Ala Glu Lys Lys Leu Glu Lys Ala Lys Glu
            100                 105                 110

Glu Gly Lys Thr Thr Glu Leu Lys Lys Tyr Ser Gln Met Ala Thr Arg
        115                 120                 125

Leu Thr Asn Glu Met Ala Asp Glu Gly Lys Lys Leu Leu Lys Ser Met
    130                 135                 140

Gly Ile Pro Ile Val Glu Ala Pro Ser Glu Gly Glu Ala Glu Ser Ala
145                 150                 155                 160

Tyr Ile Asn Ala Ile Gly Leu Ser Phe Ala Thr Ala Ser Gln Asp Tyr
                165                 170                 175

Asp Ser Leu Leu Phe Gly Ala Lys Asn Leu Ile Arg Asn Leu Thr Ile
            180                 185                 190

Thr Gly Lys Arg Lys Leu Pro Asn Lys Asp Ile Tyr Val Glu Ile Lys
        195                 200                 205

Pro Glu Arg Ile Glu Leu Glu Pro Leu Leu Lys Leu Gly Ile Thr
    210                 215                 220

Arg Glu Gln Leu Ile Asp Ile Ala Ile Leu Ile Gly Thr Asp Tyr Asp
225                 230                 235                 240

Pro Ser Gly Ile Lys Gly Ile Gly Pro Lys Thr Ala Tyr Arg Leu Ile
                245                 250                 255

Lys Lys Tyr Gly Arg Ile Glu Lys Ile Ile Glu Ala Asn Glu Ile Pro
            260                 265                 270

Lys Asn Ser Ile Asp Phe Asp Ile Asn Gln Ile Arg Gln Leu Phe Leu
```

```
                    275                 280                 285
Asn Pro Asn Val Lys Lys Pro Glu Glu Asn Leu Asp Leu Gln Asn Pro
        290                 295                 300

Glu Glu Gln Glu Ile Ile Glu Ile Leu Val Asn Gln His Asn Phe Asn
305                 310                 315                 320

Glu Glu Arg Val Lys Ser Ala Leu Glu Arg Leu Asn Lys Ala Ile Lys
                325                 330                 335

Glu Thr Lys Gly Leu Ser Arg Gln Thr Gly Leu Asp Gln Trp Phe
            340                 345                 350
```

<210> SEQ ID NO 342
<211> LENGTH: 27
<212> TYPE: DNA
<213> ORGANISM: Artificial Sequence
<220> FEATURE:
<223> OTHER INFORMATION: Synthetic

<400> SEQUENCE: 342
ttagccatgg gagtcaacct tagggag                                         27

<210> SEQ ID NO 343
<211> LENGTH: 30
<212> TYPE: DNA
<213> ORGANISM: Artificial Sequence
<220> FEATURE:
<223> OTHER INFORMATION: Synthetic

<400> SEQUENCE: 343
gtaagtcgac tatccgaacc acatgtcgag                                      30

<210> SEQ ID NO 344
<211> LENGTH: 1053
<212> TYPE: DNA
<213> ORGANISM: Artificial Sequence
<220> FEATURE:
<223> OTHER INFORMATION: Synthetic

<400> SEQUENCE: 344
ttgggagtca accttaggga gttgattcct cccgaggcta ggagggaggt ggagcttagg      60
gctctctcgg ggtatgttct agcgcttgac gcgtataaca tgctctacca gttcctcacc    120
gccatcaggc agcccgacgg cactcccctt ttggataggg agggcagggt tacaagccac    180
ctcagcggcc tgttctacag gaccattaac ctggtggagg agggtattaa gcccgtctac    240
gtcttcgacg ggaagcctcc tgaaatgaag agccgggagg ttgaagagag gcttaggagg    300
aaggcggagg ctgaggcgag gtataggagg gctgtcgagg cgggagaggt tgaggaggct    360
aggaagtacg ctatgatggc tgcgaggctt acgagcgaca tggtgaagga gtcgaaggag    420
ctgctggatg ctatggggat gccctgggtt caggcgcctg ccgagggtga ggctcaggca    480
gcctatatgg ctaggaaggg tgatgcatgg gcgacgggga gccaggacta cgatagcctc    540
ctgttcggct cgcctaggct tgtgagaaac ctagccataa caggtcgtag gaagctcccg    600
ggtagggatc agtatgtcga gataaagccg gagatcatag agctcgagcc tctgctcagc    660
aagctgggga taacaaggga gcagttgata gcggtgggta tcctcctcgg cacggactac    720
aaccccggcg tgtgaggggt tatgggcct aagacagccc taaggcttgt taagagcctg    780
ggagacccga tgaaggtgtt ggcttccgtc ccacgggggg aatatgaccc ggattatctt    840
agaaaggtgt acgagtactt cttgaacccc cccgtcacag acgactacaa gattgagttt    900
aggaagccgg atcaggacaa ggttagggag attcttgtag agaggcacga cttcaatccc    960

```
gagagggtgg agagggccct cgagaggctg gggaaggctt acaggagaa gctcagggc      1020 aggcagtcga ggctcgacat gtggttcgga tag                                  1053
```

<210> SEQ ID NO 345
<211> LENGTH: 350
<212> TYPE: PRT
<213> ORGANISM: Artificial Sequence
<220> FEATURE:
<223> OTHER INFORMATION: Synthetic

<400> SEQUENCE: 345

```
Leu Gly Val Asn Leu Arg Glu Leu Ile Pro Pro Glu Ala Arg Arg Glu
1               5                   10                  15

Val Glu Leu Arg Ala Leu Ser Gly Tyr Val Leu Ala Leu Asp Ala Tyr
            20                  25                  30

Asn Met Leu Tyr Gln Phe Leu Thr Ala Ile Arg Gln Pro Asp Gly Thr
        35                  40                  45

Pro Leu Leu Asp Arg Glu Gly Arg Val Thr Ser His Leu Ser Gly Leu
    50                  55                  60

Phe Tyr Arg Thr Ile Asn Leu Val Glu Glu Gly Ile Lys Pro Val Tyr
65                  70                  75                  80

Val Phe Asp Gly Lys Pro Pro Glu Met Lys Ser Arg Glu Val Glu Glu
                85                  90                  95

Arg Leu Arg Arg Lys Ala Glu Ala Glu Ala Arg Tyr Arg Arg Ala Val
            100                 105                 110

Glu Ala Gly Glu Val Glu Ala Arg Lys Tyr Ala Met Met Ala Ala
        115                 120                 125

Arg Leu Thr Ser Asp Met Val Glu Glu Ser Lys Glu Leu Leu Asp Ala
    130                 135                 140

Met Gly Met Pro Trp Val Gln Ala Pro Ala Glu Gly Glu Ala Gln Ala
145                 150                 155                 160

Ala Tyr Met Ala Arg Lys Gly Asp Ala Trp Ala Thr Gly Ser Gln Asp
                165                 170                 175

Tyr Asp Ser Leu Leu Phe Gly Ser Pro Arg Leu Val Arg Asn Leu Ala
            180                 185                 190

Ile Thr Gly Arg Arg Lys Leu Pro Gly Arg Asp Gln Tyr Val Glu Ile
        195                 200                 205

Lys Pro Glu Ile Ile Glu Leu Glu Pro Leu Leu Ser Lys Leu Gly Ile
    210                 215                 220

Thr Arg Glu Gln Leu Ile Ala Val Gly Ile Leu Leu Gly Thr Asp Tyr
225                 230                 235                 240

Asn Pro Gly Gly Val Arg Gly Tyr Gly Pro Lys Thr Ala Leu Arg Leu
                245                 250                 255

Val Lys Ser Leu Gly Asp Pro Met Lys Val Leu Ala Ser Val Pro Arg
            260                 265                 270

Gly Glu Tyr Asp Pro Asp Tyr Leu Arg Lys Val Tyr Glu Tyr Phe Leu
        275                 280                 285

Asn Pro Pro Val Thr Asp Asp Tyr Lys Ile Glu Phe Arg Lys Pro Asp
    290                 295                 300

Gln Asp Lys Val Arg Glu Ile Leu Val Glu Arg His Asp Phe Asn Pro
305                 310                 315                 320

Glu Arg Val Glu Arg Ala Leu Glu Arg Leu Gly Lys Ala Tyr Arg Glu
                325                 330                 335

Lys Leu Arg Gly Arg Gln Ser Arg Leu Asp Met Trp Phe Gly
```

<210> SEQ ID NO 346
<211> LENGTH: 28
<212> TYPE: DNA
<213> ORGANISM: Artificial Sequence
<220> FEATURE:
<223> OTHER INFORMATION: Synthetic

<400> SEQUENCE: 346
cttaccatgg gcgctgatat aggagagc                                        28

<210> SEQ ID NO 347
<211> LENGTH: 30
<212> TYPE: DNA
<213> ORGANISM: Artificial Sequence
<220> FEATURE:
<223> OTHER INFORMATION: Synthetic

<400> SEQUENCE: 347
tggagtcgac ttaaaaccac ctgtccagag                                      30

<210> SEQ ID NO 348
<211> LENGTH: 1008
<212> TYPE: DNA
<213> ORGANISM: Artificial Sequence
<220> FEATURE:
<223> OTHER INFORMATION: Synthetic

<400> SEQUENCE: 348
atgggcgctg ataggagagc tcttgaag agggaagaag ttgagataga atacttttca       60
ggaaagaaga ttgcaataga tgcctttaac acgttatacc agttcctagc gacaataaga    120
cagcctgacg gaacaccttt gatggattca aagggtagga taacatctca cctttcagga    180
attctttata gggtttcaaa tatggtggag gtcggaataa agccgatatt tgttttttgat   240 ggagaaccgc ctgagttcaa aagaaggag attgagagaa ggagaaaaat tagggaagaa    300
gctgagatca gtggaaaac agctttggat atagctgaag cgaggaagta tgcacagcaa    360
gctgtgagag ttgatgagta tattatcgaa tcttctaaga agcttttgaa tttgatggga    420
attcccatag ttcaggcacc ctcagggga gaagctcagg ccgcatacat agttagaaag     480
ggtgatgcgg attacacagg ttcgcaagat tacgattccc ttcttttcgg ctcgccaaga    540
ctggcaagga atttggccat aactggggagg agaaagttgc ccggaaagaa cgtttacacc   600
gaagttaaac ccgaggtgat agacttagaa tacaacctga aaaagcttgg aattactaga    660
gaacagctaa ttgatatagc tttacttgta ggaacagact acaacgaggg ggttgagggg    720
ataggtgtta agaaggccta caagtacgtc aaggcttatg gagacatatt caaggttctg    780
agggttctga aggttaaagt tgaggagccc atagaggaga taagaaactt cttcttaaat    840
cctccggtga cagatgatta cgagataaag tttagggagc ccaatgtcga tggaataatt    900
gagtttctat gtgaggagca cgatttcagt agggagaggg ttgaaaaagc tgtagagaag    960
cttagagcca ttaaaagcga tcagcttact ctggacaggt ggttttaa                1008

<210> SEQ ID NO 349
<211> LENGTH: 335
<212> TYPE: PRT
<213> ORGANISM: Artificial Sequence
<220> FEATURE:
<223> OTHER INFORMATION: Synthetic

<400> SEQUENCE: 349

```
Met Gly Ala Asp Ile Gly Glu Leu Leu Lys Arg Glu Val Glu Ile
1               5                   10                  15

Glu Tyr Phe Ser Gly Lys Lys Ile Ala Ile Asp Ala Phe Asn Thr Leu
            20                  25                  30

Tyr Gln Phe Leu Ala Thr Ile Arg Gln Pro Asp Gly Thr Pro Leu Met
        35                  40                  45

Asp Ser Lys Gly Arg Ile Thr Ser His Leu Ser Gly Ile Leu Tyr Arg
    50                  55                  60

Val Ser Asn Met Val Glu Val Gly Ile Lys Pro Ile Phe Val Phe Asp
65              70                  75                  80

Gly Glu Pro Pro Glu Phe Lys Lys Glu Ile Glu Arg Arg Arg Lys
                85                  90                  95

Ile Arg Glu Glu Ala Glu Ile Lys Trp Lys Thr Ala Leu Asp Ile Ala
                100                 105                 110

Glu Ala Arg Lys Tyr Ala Gln Gln Ala Val Arg Val Asp Glu Tyr Ile
            115                 120                 125

Ile Glu Ser Ser Lys Lys Leu Leu Asn Leu Met Gly Ile Pro Ile Val
    130                 135                 140

Gln Ala Pro Ser Glu Gly Glu Ala Gln Ala Ala Tyr Ile Val Arg Lys
145                 150                 155                 160

Gly Asp Ala Asp Tyr Thr Gly Ser Gln Asp Tyr Asp Ser Leu Leu Phe
                165                 170                 175

Gly Ser Pro Arg Leu Ala Arg Asn Leu Ala Ile Thr Gly Arg Arg Lys
            180                 185                 190

Leu Pro Gly Lys Asn Val Tyr Thr Glu Val Lys Pro Glu Val Ile Asp
        195                 200                 205

Leu Glu Tyr Asn Leu Lys Lys Leu Gly Ile Thr Arg Glu Gln Leu Ile
    210                 215                 220

Asp Ile Ala Leu Leu Val Gly Thr Asp Tyr Asn Glu Gly Val Glu Gly
225                 230                 235                 240

Ile Gly Val Lys Lys Ala Tyr Lys Tyr Val Lys Ala Tyr Gly Asp Ile
                245                 250                 255

Phe Lys Val Leu Arg Val Leu Lys Val Lys Val Glu Glu Pro Ile Glu
            260                 265                 270

Glu Ile Arg Asn Phe Phe Leu Asn Pro Pro Val Thr Asp Asp Tyr Glu
            275                 280                 285

Ile Lys Phe Arg Glu Pro Asn Val Asp Gly Ile Ile Glu Phe Leu Cys
        290                 295                 300

Glu Glu His Asp Phe Ser Arg Glu Arg Val Glu Lys Ala Val Glu Lys
305                 310                 315                 320

Leu Arg Ala Ile Lys Ser Asp Gln Leu Thr Leu Asp Arg Trp Phe
                325                 330                 335
```

<210> SEQ ID NO 350
<211> LENGTH: 25
<212> TYPE: DNA
<213> ORGANISM: Artificial Sequence
<220> FEATURE:
<223> OTHER INFORMATION: Synthetic

<400> SEQUENCE: 350
cattccatgg gagtgcagtt taatg    25

<210> SEQ ID NO 351
<211> LENGTH: 28

```
<212> TYPE: DNA
<213> ORGANISM: Artificial Sequence
<220> FEATURE:
<223> OTHER INFORMATION: Synthetic

<400> SEQUENCE: 351
cggagtcgac tcatctccca aaccatgc                                              28

<210> SEQ ID NO 352
<211> LENGTH: 981
<212> TYPE: DNA
<213> ORGANISM: Artificial Sequence
<220> FEATURE:
<223> OTHER INFORMATION: Synthetic

<400> SEQUENCE: 352
atgggagtgc agtttaatga tttaatccca aaaaggaaa ttccaataaa gtacttatca            60
ggaaaaactg tggctataga tgggatgaat gtcctttatc aatttttatc aagtattaga          120
ttgagagatg ggtccccttt aaggaacagg aaaggagaga taacctcaac atacaatggc         180
atattttaca aaaccatata catgctcgaa atgatataa caccggtatg ggtgtttgat           240
ggaaaaccgc caaaattgaa agagaaaacc agagaagaaa gaagaaaaat gagagaaaaa         300 gcaaagagg aattcacaaa agcaaagaa atggaaaata ttgatgagat gcaaaaatac           360
gcaaagagga tgaacttctt aacaaaggac atcgtagaga actcaaaaaa attattggat         420
ttgatggggg taccttatgt aaatgcccca gcagaagggg aaggacaagc atcatacatg         480
gcaaaaaagg gagatgtatt ctgtgttatt agtcaggact atgatgcttt gctttatggg         540
gccccaagga tagtgagaaa cttaacagca caaaggaag agttggagtt aatagagctg           600
gaaaatgttt taaatgagtt gggcatttct catgatgatt aatagacat ggcaattttg           660 ataggggactg attataatcc aaagggagtt aaaggcattg gtccaaaaaa agctctcgaa        720
atagtaaaat caaaaaacaa agaactctac ttaaaggctg ttgagaatta tgaagaaatt         780
aaaaatatat ttaaaaatcc aaagttact gatgaataca gcatcaaatt aaaaaagcca          840
gataaagaag gtattataaa gtttttggtt gaggaaaatg attttctctat ggagagagtt        900 cagccacatg ttgaaaaact ctgtaaattg attgagaaaa aaccaaaca gtaacatta            960 gatgcatggt ttgggagatg a                                                    981

<210> SEQ ID NO 353
<211> LENGTH: 326
<212> TYPE: PRT
<213> ORGANISM: Artificial Sequence
<220> FEATURE:
<223> OTHER INFORMATION: Synthetic

<400> SEQUENCE: 353
```

Met Gly Val Gln Phe Asn Asp Leu Ile Pro Lys Lys Glu Ile Pro Ile
1               5                   10                  15

Lys Tyr Leu Ser Gly Lys Thr Val Ala Ile Asp Gly Met Asn Val Leu
            20                  25                  30

Tyr Gln Phe Leu Ser Ser Ile Arg Leu Arg Asp Gly Ser Pro Leu Arg
        35                  40                  45

Asn Arg Lys Gly Glu Ile Thr Ser Thr Tyr Asn Gly Ile Phe Tyr Lys
    50                  55                  60

Thr Ile Tyr Met Leu Glu Asn Asp Ile Thr Pro Val Trp Val Phe Asp
65                  70                  75                  80

Gly Lys Pro Pro Lys Leu Lys Glu Lys Thr Arg Glu Glu Arg Arg Lys

```
                    85                  90                  95
Met Arg Glu Lys Ala Lys Glu Glu Phe Thr Lys Ala Lys Glu Met Glu
            100                 105                 110

Asn Ile Asp Glu Met Gln Lys Tyr Ala Lys Arg Met Asn Phe Leu Thr
        115                 120                 125

Lys Asp Ile Val Glu Asn Ser Lys Lys Leu Leu Asp Leu Met Gly Val
    130                 135                 140

Pro Tyr Val Asn Ala Pro Ala Glu Gly Glu Gln Ala Ser Tyr Met
145                 150                 155                 160

Ala Lys Lys Gly Asp Val Phe Cys Val Ile Ser Gln Asp Tyr Asp Ala
            165                 170                 175

Leu Leu Tyr Gly Ala Pro Arg Ile Val Arg Asn Leu Thr Ala Thr Lys
            180                 185                 190

Glu Glu Leu Glu Leu Ile Glu Leu Glu Asn Val Leu Asn Glu Leu Gly
            195                 200                 205

Ile Ser His Asp Asp Leu Ile Asp Met Ala Ile Leu Ile Gly Thr Asp
    210                 215                 220

Tyr Asn Pro Lys Gly Val Lys Gly Ile Gly Pro Lys Lys Ala Leu Glu
225                 230                 235                 240

Ile Val Lys Ser Lys Asn Lys Glu Leu Tyr Leu Lys Ala Val Glu Asn
            245                 250                 255

Tyr Glu Glu Ile Lys Asn Ile Phe Lys Asn Pro Lys Val Thr Asp Glu
            260                 265                 270

Tyr Ser Ile Lys Leu Lys Lys Pro Asp Lys Glu Gly Ile Ile Lys Phe
            275                 280                 285

Leu Val Glu Glu Asn Asp Phe Ser Met Glu Arg Val Gln Pro His Val
            290                 295                 300

Glu Lys Leu Cys Lys Leu Ile Glu Lys Thr Lys Gln Val Thr Leu
305                 310                 315                 320

Asp Ala Trp Phe Gly Arg
            325

<210> SEQ ID NO 354
<211> LENGTH: 27
<212> TYPE: DNA
<213> ORGANISM: Artificial Sequence
<220> FEATURE:
<223> OTHER INFORMATION: Synthetic

<400> SEQUENCE: 354
gataccatgg gtgttcctat cggtgac                                    27

<210> SEQ ID NO 355
<211> LENGTH: 33
<212> TYPE: DNA
<213> ORGANISM: Artificial Sequence
<220> FEATURE:
<223> OTHER INFORMATION: Synthetic

<400> SEQUENCE: 355
cttggtcgac ttagggtttc ttttttaacga acc                            33

<210> SEQ ID NO 356
<211> LENGTH: 1032
<212> TYPE: DNA
<213> ORGANISM: Artificial Sequence
<220> FEATURE:
<223> OTHER INFORMATION: Synthetic
```

<400> SEQUENCE: 356

```
atgggtgttc ctatcggtga cctcgttccg aggaaggaga tagatcttga aaatctgtat      60
ggaaagaaga tagcgataga tgccctaaac gccatctatc agttttatc aacgataaga      120
cagagggatg gaacaccact tatggactct aagggtagga taacctctca tttaagtggg     180
ctcttttata gaacgataaa tctaatggaa gccggtatta agccggccta cgtctttgat     240
ggaaagcctc cggaattcaa aaggaaggag ctcgaaaaaa ggaggaagc tagagaagag      300
gcagaactaa atggaaaga agctctagcc aagggaaacc tggaggaagc taggaaatac     360
gctcaaaggg caactaaggt taatgaaatg ctaatcgaag atgcaaagaa gcttttgcaa     420
ctaatgggaa taccaataat tcaggctcca agtgaaggag aagcccaagc ggcatacatg     480
gcaagtaaag gggatgtcta cgcgtcagcg agtcaagatt atgattcact actctttggt     540
gctccaaggt tgattaggaa tctgacaatt acgggaaaaa gaagatgcc tgggaaagat      600
gtttacgttg aaataaagcc agagttagta gttctagatg aggtactaaa agagcttaag     660
ataacaagag aaaagcttat agaacttgca attctggttg ggactgacta taatcctggg     720
ggcgtaaagg gataggacc taagaaggcc cttgagattg taagatattc aagggatccc     780
ctagcaaagt tccaaagaca gagcgatgtg gatctttacg ctattaagga attcttcctt     840
aaccctcctg tcactaatga atactcgctt agttggaagg agcctgatga ggaaggaata     900
ttaaaattcc tctgtgatga gcataatttt agcgaagaaa gggtaaaaaa tgggatagaa     960
agactaaaaa aggcgataaa agctggaaga caatcaacgc ttgagagttg gttcgttaaa    1020
aagaaaccct aa                                                         1032
```

<210> SEQ ID NO 357
<211> LENGTH: 343
<212> TYPE: PRT
<213> ORGANISM: Artificial Sequence
<220> FEATURE:
<223> OTHER INFORMATION: Synthetic

<400> SEQUENCE: 357

```
Met Gly Val Pro Ile Gly Asp Leu Val Pro Arg Lys Glu Ile Asp Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Arg Asp Gly Thr Pro Leu Met
        35                  40                  45

Asp Ser Lys Gly Arg Ile Thr Ser His Leu Ser Gly Leu Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
```

```
                    165                 170                 175
Leu Leu Phe Gly Ala Pro Arg Leu Ile Arg Asn Leu Thr Ile Thr Gly
            180                 185                 190
Lys Arg Lys Met Pro Gly Lys Asp Val Tyr Val Glu Ile Lys Pro Glu
        195                 200                 205
Leu Val Val Leu Asp Glu Val Leu Lys Glu Leu Lys Ile Thr Arg Glu
    210                 215                 220
Lys Leu Ile Glu Leu Ala Ile Leu Val Gly Thr Asp Tyr Asn Pro Gly
225                 230                 235                 240
Gly Val Lys Gly Ile Gly Pro Lys Lys Ala Leu Glu Ile Val Arg Tyr
                245                 250                 255
Ser Arg Asp Pro Leu Ala Lys Phe Gln Arg Gln Ser Asp Val Asp Leu
            260                 265                 270
Tyr Ala Ile Lys Glu Phe Phe Leu Asn Pro Pro Val Thr Asn Glu Tyr
        275                 280                 285
Ser Leu Ser Trp Lys Glu Pro Asp Glu Glu Gly Ile Leu Lys Phe Leu
    290                 295                 300
Cys Asp Glu His Asn Phe Ser Glu Glu Arg Val Lys Asn Gly Ile Glu
305                 310                 315                 320
Arg Leu Lys Lys Ala Ile Lys Ala Gly Arg Gln Ser Thr Leu Glu Ser
                325                 330                 335
Trp Phe Val Lys Lys Pro
            340
```

<210> SEQ ID NO 358
<211> LENGTH: 31
<212> TYPE: DNA
<213> ORGANISM: Artificial Sequence
<220> FEATURE:
<223> OTHER INFORMATION: Synthetic

<400> SEQUENCE: 358
taagccatgg gtgtagattt aggcgaaata g         31

<210> SEQ ID NO 359
<211> LENGTH: 35
<212> TYPE: DNA
<213> ORGANISM: Artificial Sequence
<220> FEATURE:
<223> OTHER INFORMATION: Synthetic

<400> SEQUENCE: 359
actagtcgac ttaaaaccac tgatcaagac ctgtc         35

<210> SEQ ID NO 360
<211> LENGTH: 1056
<212> TYPE: DNA
<213> ORGANISM: Artificial Sequence
<220> FEATURE:
<223> OTHER INFORMATION: Synthetic

<400> SEQUENCE: 360
ataggtgtag atttaggcga aatagttgaa gatgttaaga gagagattaa cttaaatgag     60
atgaaaggaa agaaaattag tatagatgct acaacacaa tttatcagtt tttagctgca    120
ataagacagc ctgatgggac acctttaatt gacagtaaag gcagaataac aagccattta    180
aatgggctat ttataggac tattagtata atagaaagtg gaataatccc catttttgta    240
tttgatggaa agccacctga aagaagagt gaagaaatcg aaagaaggaa aagagctaag    300

```
gaggaggcag aaaagaaatt agagaaagct aagttagagg gggagtacag agaaattaga    360
aaatatgctc aggctgctgt tagattaagc aatgaaatgg tagaggaaag taaaaaacta    420
ttagatgcta tgggtatacc tgtagttcaa gctccaggag aaggagaggc tgaggcagct    480
tatataaatt caattgatct ttcttgggct gctgcaagcc aagattatga ttccttatta    540
tttggcgcta aaagattagt cagaaacata acaatttcag gtaaaagaaa gcttccaaat    600
aaggatgttt atgtagaaat aaagcctgag ttgatagaac tagagagttt attgaaaaaa    660
ctcggcatca atagagaaca gttaatagac attgcgattc ttataggtac agattacaat    720
ccagacggcg ttaaaggaat tggtgtaaag acggcattaa gaattataaa gaatataat     780 aatatcgaga acgcaataga aaaggtgaa attcaattat ctaaaataaa ctttgatata     840
cgagagataa gaaaattatt cattacacct gaagttaaaa agcctactga acgactagaa    900
ttagcagaat gtaatgaaag ggaaataata gaacttttgg ttaaaaatca tgattttaat    960
gaagatcgtg taaataacgg aatagagaga ttaagaaagg ctataaaaga agctaagtct    1020
gttgaaaaac agacaggtct tgatcagtgg ttttaa                              1056
```

<210> SEQ ID NO 361
<211> LENGTH: 351
<212> TYPE: PRT
<213> ORGANISM: Artificial Sequence
<220> FEATURE:
<223> OTHER INFORMATION: Synthetic

<400> SEQUENCE: 361

```
Ile Gly Val Asp Leu Gly Glu Ile Val Glu Asp Val Lys Arg Glu Ile
1               5                   10                  15

Asn Leu Asn Glu Met Lys Gly Lys Lys Ile Ser Ile Asp Ala Tyr Asn
            20                  25                  30

Thr Ile Tyr Gln Phe Leu Ala Ala Ile Arg Gln Pro Asp Gly Thr Pro
        35                  40                  45

Leu Ile Asp Ser Lys Gly Arg Ile Thr Ser His Leu Asn Gly Leu Phe
    50                  55                  60

Tyr Arg Thr Ile Ser Ile Ile Glu Ser Gly Ile Pro Ile Phe Val
65                  70                  75                  80

Phe Asp Gly Lys Pro Pro Glu Lys Lys Ser Glu Glu Ile Glu Arg Arg
                85                  90                  95

Lys Arg Ala Lys Glu Glu Ala Glu Lys Lys Leu Glu Lys Ala Lys Leu
            100                 105                 110

Glu Gly Glu Tyr Arg Glu Ile Arg Lys Tyr Ala Gln Ala Ala Val Arg
        115                 120                 125

Leu Ser Asn Glu Met Val Glu Glu Ser Lys Lys Leu Leu Asp Ala Met
    130                 135                 140

Gly Ile Pro Val Val Gln Ala Pro Gly Glu Gly Glu Ala Glu Ala Ala
145                 150                 155                 160

Tyr Ile Asn Ser Ile Asp Leu Ser Trp Ala Ala Ala Ser Gln Asp Tyr
                165                 170                 175

Asp Ser Leu Leu Phe Gly Ala Lys Arg Leu Val Arg Asn Ile Thr Ile
            180                 185                 190

Ser Gly Lys Arg Lys Leu Pro Asn Lys Asp Val Tyr Val Glu Ile Lys
        195                 200                 205

Pro Glu Leu Ile Glu Leu Glu Ser Leu Leu Lys Lys Leu Gly Ile Asn
    210                 215                 220

Arg Glu Gln Leu Ile Asp Ile Ala Ile Leu Ile Gly Thr Asp Tyr Asn
```

```
                225                 230                 235                 240
Pro Asp Gly Val Lys Gly Ile Gly Val Lys Thr Ala Leu Arg Ile Ile
                245                 250                 255

Lys Lys Tyr Asn Asn Ile Glu Asn Ala Ile Glu Lys Gly Glu Ile Gln
            260                 265                 270

Leu Ser Lys Ile Asn Phe Asp Ile Arg Glu Ile Arg Lys Leu Phe Ile
        275                 280                 285

Thr Pro Glu Val Lys Lys Pro Thr Glu Arg Leu Glu Leu Ala Glu Cys
    290                 295                 300

Asn Glu Arg Glu Ile Ile Glu Leu Leu Val Lys Asn His Asp Phe Asn
305                 310                 315                 320

Glu Asp Arg Val Asn Asn Gly Ile Glu Arg Leu Lys Lys Ala Ile Lys
                325                 330                 335

Glu Ala Lys Ser Val Glu Lys Gln Thr Gly Leu Asp Gln Trp Phe
            340                 345                 350

<210> SEQ ID NO 362
<211> LENGTH: 28
<212> TYPE: DNA
<213> ORGANISM: Artificial Sequence
<220> FEATURE:
<223> OTHER INFORMATION: Synthetic

<400> SEQUENCE: 362
ctagccatgg gagttcagat aggtgagc                                           28

<210> SEQ ID NO 363
<211> LENGTH: 30
<212> TYPE: DNA
<213> ORGANISM: Artificial Sequence
<220> FEATURE:
<223> OTHER INFORMATION: Synthetic

<400> SEQUENCE: 363
tggagtcgac taccgtgtga accagctttc                                         30

<210> SEQ ID NO 364
<211> LENGTH: 1023
<212> TYPE: DNA
<213> ORGANISM: Artificial Sequence
<220> FEATURE:
<223> OTHER INFORMATION: Synthetic

<400> SEQUENCE: 364
atgggagttc agataggtga gcttgtgcca aggaaggaga tcgaacttga agctctctac        60
gggaagaagg ttgcgatcga tgccttcaac gccatgtacc agttcctctc aacgataaga      120
cagcgcgatg gaactcctct aatggactcg aagggcagga taacctccca cctcagcggc      180
ttctttacag gacgatcaa cctcatggag gccggaataa agcccgccta cgtcttcgac       240
ggaaagccgc cggagttcaa gaagaaggag atagagaaaa ggagagaggc aagggaagaa      300
gccgaggaga gtggtacga ggcccttgaa aagggtgact ggaggaagc gaagaagtac        360 gcgatgaggg caacccgcgt taacgagcaa ctcataaacg atgccaaaaa gcttctcgaa      420
ctgatgggga ttccagtcgt gcaggcgccg agcgaaggtg aagctcaggc cgcatacatg      480
gccgccaaag gaaggtcta cgcctccgcc agtcaggact acgattcgct cctcttcagc      540
gcgccgagac ttgtaaggaa cctcacgata acgggaagga gaaagctccc cggaaagaac      600
gtctacgtcg aagtgaagcc cgaactcatc gttctggatg aggttctcaa ggagctcggc      660
```

```
atagacaggg aaaagcttat agagctggcg attctggttg gaaccgacta caaccccggc    720
gggataaagg gtatcgggcc caagaaggcc ctgatgatag tcaagagaac caaagacccg    780
ctcaagaaat accagaagga gagcgacgtt gacctctacg ctataaagga gttctttctc    840
aacccgcctg ttaccgacga ctacgagctg agatggcgcg aacccgacga ggagggatt     900 ctgaagttcc tctgcgacga gcacgacttc agcgaagagc gcgttaaaac cggccttgaa    960
agactgaaga aggcggtaaa gagcggaaaa cagagaacac ttgaaagctg gttcacacgg   1020
tag                                                                 1023
```

<210> SEQ ID NO 365
<211> LENGTH: 340
<212> TYPE: PRT
<213> ORGANISM: Artificial Sequence
<220> FEATURE:
<223> OTHER INFORMATION: Synthetic

<400> SEQUENCE: 365

```
Met Gly Val Gln Ile Gly Glu Leu Val Pro Arg Lys Glu Ile Glu Leu
1               5                   10                  15

Glu Ala Leu Tyr Gly Lys Lys Val Ala Ile Asp Ala Phe Asn Ala Met
            20                  25                  30

Tyr Gln Phe Leu Ser Thr Ile Arg Gln Arg Asp Gly Thr Pro Leu Met
        35                  40                  45

Asp Ser Lys Gly Arg Ile Thr Ser His Leu Ser Gly Phe Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Lys Lys Glu Ile Glu Lys Arg Arg Glu
                85                  90                  95

Ala Arg Glu Glu Ala Glu Glu Lys Trp Tyr Glu Ala Leu Glu Lys Gly
            100                 105                 110

Asp Leu Glu Glu Ala Lys Lys Tyr Ala Met Arg Ala Thr Arg Val Asn
        115                 120                 125

Glu Gln Leu Ile Asn Asp Ala Lys Lys Leu Leu Leu Met Gly Ile
    130                 135                 140

Pro Val Val Gln Ala Pro Ser Glu Gly Glu Ala Gln Ala Ala Tyr Met
145                 150                 155                 160

Ala Ala Lys Gly Lys Val Tyr Ala Ser Ala Ser Gln Asp Tyr Asp Ser
                165                 170                 175

Leu Leu Phe Ser Ala Pro Arg Leu Val Arg Asn Leu Thr Ile Thr Gly
            180                 185                 190

Arg Arg Lys Leu Pro Gly Lys Asn Val Tyr Val Glu Val Lys Pro Glu
        195                 200                 205

Leu Ile Val Leu Asp Glu Val Leu Lys Glu Leu Gly Ile Asp Arg Glu
    210                 215                 220

Lys Leu Ile Glu Leu Ala Ile Leu Val Gly Thr Asp Tyr Asn Pro Gly
225                 230                 235                 240

Gly Ile Lys Gly Ile Gly Pro Lys Lys Ala Leu Met Ile Val Lys Arg
                245                 250                 255

Thr Lys Asp Pro Leu Lys Lys Tyr Gln Lys Glu Ser Asp Val Asp Leu
            260                 265                 270

Tyr Ala Ile Lys Glu Phe Phe Leu Asn Pro Pro Val Thr Asp Asp Tyr
        275                 280                 285

Glu Leu Arg Trp Arg Glu Pro Asp Glu Glu Gly Ile Leu Lys Phe Leu
```

```
            290                 295                 300
Cys Asp Glu His Asp Phe Ser Glu Glu Arg Val Lys Thr Gly Leu Glu
305                 310                 315                 320

Arg Leu Lys Lys Ala Val Lys Ser Gly Lys Gln Arg Thr Leu Glu Ser
                325                 330                 335

Trp Phe Thr Arg
            340

<210> SEQ ID NO 366
<211> LENGTH: 32
<212> TYPE: DNA
<213> ORGANISM: Artificial Sequence
<220> FEATURE:
<223> OTHER INFORMATION: Synthetic

<400> SEQUENCE: 366
taacgaattc ggtgcagaca taggcgaact ac                                    32

<210> SEQ ID NO 367
<211> LENGTH: 33
<212> TYPE: DNA
<213> ORGANISM: Artificial Sequence
<220> FEATURE:
<223> OTHER INFORMATION: Synthetic

<400> SEQUENCE: 367
cggtgtcgac tcaggaaaac cacctctcaa gcg                                   33

<210> SEQ ID NO 368
<211> LENGTH: 37
<212> TYPE: DNA
<213> ORGANISM: Artificial Sequence
<220> FEATURE:
<223> OTHER INFORMATION: Synthetic

<400> SEQUENCE: 368
cacaggaaac agaccatggg tgcagacata ggcgaac                               37

<210> SEQ ID NO 369
<211> LENGTH: 1017
<212> TYPE: DNA
<213> ORGANISM: Artificial Sequence
<220> FEATURE:
<223> OTHER INFORMATION: Synthetic

<400> SEQUENCE: 369
atgggtgcag acataggcga actactcgag agagaagaag ttgaacttga gtacttctcc      60
gggagaaaaa tagctattga tgcttttaac actctttacc agttcatatc tatcataagg     120
caacctgacg gcactccttt gaaggattct cagggtagaa tgacctcaca cctctccggc     180
atcctgtacc gcgtgtcaaa catgatcgag gttggaatga cccattttt cgttttcgat     240 ggtgagcctc ctgttttcaa gcagaaggag atagaggaac gaaaggaaag aagagctgaa     300
gcagaggaga agtggatcgc tgcgatagag agaggagaga gtacgcaaa gaagtacgct     360 caggcagcgg cgagggttga tgaatacatc gtcgagtcgt caaagaagct gcttgagtat     420 atggagttc catgggttca ggcgccgagt gaggagagg cacaggctgc atacatggca     480
gcgaagggcg atgtagattt tactggctcg caggattacg actcgcttct cttcggcagc     540
ccaaagcttg caagaaatct cgcgattact ggaagagga agctgcccgg aaagaatgtt     600
tacgttgagg tcaaaccaga gataatagac ttaaacggca acctgagaag gcttggaata     660
```

-continued

```
acaagggaac agctcgtcga tatcgcgttg ctcgtgggaa cggactacaa cgaaggagtg    720
aagggcgttg gggtcaagaa ggcctacaag tacataaaaa cctacggaga tgttttcaaa    780
gctctcaagg ccttaaaggt agagcaggag aacatagagg agataagaaa cttcttcctg    840
aacccgcctg ttacgaacaa ctacagcctc cacttcggaa agccagacga tgagaagatt    900
atcgagttcc tgtgtgaaga gcacgacttt agcaaggata gggtagagaa ggccgttgag    960
aagctgaaag caggaatgca agcctcgcaa tcaacgcttg agaggtggtt ttcctga      1017
```

<210> SEQ ID NO 370
<211> LENGTH: 338
<212> TYPE: PRT
<213> ORGANISM: Artificial Sequence
<220> FEATURE:
<223> OTHER INFORMATION: Synthetic

<400> SEQUENCE: 370

```
Met Gly Ala Asp Ile Gly Glu Leu Leu Glu Arg Glu Val Glu Leu
1               5                   10                  15

Glu Tyr Phe Ser Gly Arg Lys Ile Ala Ile Asp Ala Phe Asn Thr Leu
            20                  25                  30

Tyr Gln Phe Ile Ser Ile Ile Arg Gln Pro Asp Gly Thr Pro Leu Lys
        35                  40                  45

Asp Ser Gln Gly Arg Met Thr Ser His Leu Ser Gly Ile Leu Tyr Arg
    50                  55                  60

Val Ser Asn Met Ile Glu Val Gly Met Arg Pro Ile Phe Val Phe Asp
65                  70                  75                  80

Gly Glu Pro Pro Val Phe Lys Gln Lys Glu Ile Glu Glu Arg Lys Glu
                85                  90                  95

Arg Arg Ala Glu Ala Glu Lys Trp Ile Ala Ala Ile Glu Arg Gly
            100                 105                 110

Glu Lys Tyr Ala Lys Lys Tyr Ala Gln Ala Ala Ala Arg Val Asp Glu
        115                 120                 125

Tyr Ile Val Glu Ser Ser Lys Lys Leu Leu Glu Tyr Met Gly Val Pro
    130                 135                 140

Trp Val Gln Ala Pro Ser Glu Gly Glu Ala Gln Ala Ala Tyr Met Ala
145                 150                 155                 160

Ala Lys Gly Asp Val Asp Phe Thr Gly Ser Gln Asp Tyr Asp Ser Leu
                165                 170                 175

Leu Phe Gly Ser Pro Lys Leu Ala Arg Asn Leu Ala Ile Thr Gly Lys
            180                 185                 190

Arg Lys Leu Pro Gly Lys Asn Val Tyr Val Glu Val Lys Pro Glu Ile
        195                 200                 205

Ile Asp Leu Asn Gly Asn Leu Arg Arg Leu Gly Ile Thr Arg Glu Gln
    210                 215                 220

Leu Val Asp Ile Ala Leu Leu Val Gly Thr Asp Tyr Asn Glu Gly Val
225                 230                 235                 240

Lys Gly Val Gly Val Lys Lys Ala Tyr Lys Tyr Ile Lys Thr Tyr Gly
                245                 250                 255

Asp Val Phe Lys Ala Leu Lys Ala Leu Lys Val Glu Gln Glu Asn Ile
            260                 265                 270

Glu Glu Ile Arg Asn Phe Phe Leu Asn Pro Pro Val Thr Asn Asn Tyr
        275                 280                 285

Ser Leu His Phe Gly Lys Pro Asp Asp Glu Lys Ile Ile Glu Phe Leu
    290                 295                 300
```

```
Cys Glu Glu His Asp Phe Ser Lys Asp Arg Val Glu Lys Ala Val Glu
305                 310                 315                 320

Lys Leu Lys Ala Gly Met Gln Ala Ser Gln Ser Thr Leu Glu Arg Trp
                325                 330                 335

Phe Ser

<210> SEQ ID NO 371
<211> LENGTH: 36
<212> TYPE: DNA
<213> ORGANISM: Artificial Sequence
<220> FEATURE:
<223> OTHER INFORMATION: Synthetic

<400> SEQUENCE: 371
ctaagaattc ggagtagact taaaagacat tatacc                              36

<210> SEQ ID NO 372
<211> LENGTH: 29
<212> TYPE: DNA
<213> ORGANISM: Artificial Sequence
<220> FEATURE:
<223> OTHER INFORMATION: Synthetic

<400> SEQUENCE: 372
agttgtcgac tacttcggct tactgaacc                                      29

<210> SEQ ID NO 373
<211> LENGTH: 34
<212> TYPE: DNA
<213> ORGANISM: Artificial Sequence
<220> FEATURE:
<223> OTHER INFORMATION: Synthetic

<400> SEQUENCE: 373
caggaaacag accatgggag tagacttaaa agac                                34

<210> SEQ ID NO 374
<211> LENGTH: 1062
<212> TYPE: DNA
<213> ORGANISM: Artificial Sequence
<220> FEATURE:
<223> OTHER INFORMATION: Synthetic

<400> SEQUENCE: 374
atgggagtag acttaaaaga cattatacca ggcgaagcta aaacggttat cgaggatctc    60
aggatcctac atggcaagat tatagtgata gatggctata cgcattata ccagttccta   120 gctgcaatca gacaaccgga tgggaccct ctaatggata caacgggag gatcacgagt    180 catttaagcg gtttattcta tagaaccata atatcgttg aggcagggat aaaaccagtc    240
tacgtgtttg atggtaaacc ccctgaattg aaggcgaggg agatagagag gaggaaagcc    300
gttaaggagg aggcagcaaa gaagtacgag gaagccgttc aatccggaga cctcgagctc    360
gcgaggagat acgcaatgat gtcggccaag ctgacagagg aaatggtgag ggatgctaaa    420
tcattactag acgcaatggg tattccatgg gttcaagcac cagcgagggg cgaggctcag    480
gcagcctata ttgttaagaa gggggatgcc tatgcatccg cctcacagga ttacgatagc    540
ttgctattcg gctcccctaa gctcgttaga aacctgacca taagcggtag aagaaagcta    600
ccgagaaaaa acgagtatgt tgaagtaaag ccggagctca gagctcga caaactcctt    660 gttcagctag gtataaccct tgagaacctc atcgatatag gtatactcct ggggacagat    720
tacaatccag acgcttcga aggcataggc cccaagaagg ctcttcaact agttaaggca    780
```

-continued

```
tacgggggaa tcgagaagat accgaaaccc attttgaagt cgccgataga agtagatgtt    840
atagcaataa agaaatactt ccttcaacca caggtaacag acaactacag gattgaatgg    900
catacccccg atcccgatgc agtgaaaaga atattggtgg atgaacatga tttcagtata    960
gatagagtta gcacagcgct tgagagatac gtgaaggcct ttaaagaaaa tatacgggga   1020
gaacagaaag gtctctctaa atggttcagt aagccgaagt ag                      1062
```

<210> SEQ ID NO 375
<211> LENGTH: 353
<212> TYPE: PRT
<213> ORGANISM: Artificial Sequence
<220> FEATURE:
<223> OTHER INFORMATION: Synthetic

<400> SEQUENCE: 375

| Met | Gly | Val | Asp | Leu | Lys | Asp | Ile | Ile | Pro | Gly | Glu | Ala | Lys | Thr | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Glu | Asp | Leu | Arg | Ile | Leu | His | Gly | Lys | Ile | Ile | Val | Ile | Asp | Gly |
|     |     |     | 20  |     |     |     |     | 25  |     |     |     |     | 30  |     |     |

| Tyr | Asn | Ala | Leu | Tyr | Gln | Phe | Leu | Ala | Ala | Ile | Arg | Gln | Pro | Asp | Gly |
|     |     |     | 35  |     |     |     |     | 40  |     |     |     |     | 45  |     |     |

| Thr | Pro | Leu | Met | Asp | Asn | Asn | Gly | Arg | Ile | Thr | Ser | His | Leu | Ser | Gly |
|     | 50  |     |     |     |     | 55  |     |     |     |     | 60  |     |     |     |     |

| Leu | Phe | Tyr | Arg | Thr | Ile | Asn | Ile | Val | Glu | Ala | Gly | Ile | Lys | Pro | Val |
| 65  |     |     |     |     | 70  |     |     |     |     | 75  |     |     |     |     | 80  |

| Tyr | Val | Phe | Asp | Gly | Lys | Pro | Pro | Glu | Leu | Lys | Ala | Arg | Glu | Ile | Glu |
|     |     |     |     | 85  |     |     |     |     | 90  |     |     |     |     | 95  |     |

| Arg | Arg | Lys | Ala | Val | Lys | Glu | Glu | Ala | Ala | Lys | Lys | Tyr | Glu | Glu | Ala |
|     |     |     |     | 100 |     |     |     |     | 105 |     |     |     |     | 110 |     |

| Val | Gln | Ser | Gly | Asp | Leu | Glu | Leu | Ala | Arg | Arg | Tyr | Ala | Met | Met | Ser |
|     |     |     | 115 |     |     |     |     | 120 |     |     |     |     | 125 |     |     |

| Ala | Lys | Leu | Thr | Glu | Glu | Met | Val | Arg | Asp | Ala | Lys | Ser | Leu | Leu | Asp |
|     | 130 |     |     |     |     | 135 |     |     |     |     | 140 |     |     |     |     |

| Ala | Met | Gly | Ile | Pro | Trp | Val | Gln | Ala | Pro | Ala | Glu | Gly | Glu | Ala | Gln |
| 145 |     |     |     |     | 150 |     |     |     |     | 155 |     |     |     |     | 160 |

| Ala | Ala | Tyr | Ile | Val | Lys | Lys | Gly | Asp | Ala | Tyr | Ala | Ser | Ala | Ser | Gln |
|     |     |     |     | 165 |     |     |     |     | 170 |     |     |     |     | 175 |     |

| Asp | Tyr | Asp | Ser | Leu | Leu | Phe | Gly | Ser | Pro | Lys | Leu | Val | Arg | Asn | Leu |
|     |     |     | 180 |     |     |     |     | 185 |     |     |     |     | 190 |     |     |

| Thr | Ile | Ser | Gly | Arg | Arg | Lys | Leu | Pro | Arg | Lys | Asn | Glu | Tyr | Val | Glu |
|     |     | 195 |     |     |     |     | 200 |     |     |     |     | 205 |     |     |     |

| Val | Lys | Pro | Glu | Leu | Ile | Glu | Leu | Asp | Lys | Leu | Leu | Val | Gln | Leu | Gly |
|     | 210 |     |     |     |     | 215 |     |     |     |     | 220 |     |     |     |     |

| Ile | Thr | Leu | Glu | Asn | Leu | Ile | Asp | Ile | Gly | Ile | Leu | Leu | Gly | Thr | Asp |
| 225 |     |     |     |     | 230 |     |     |     |     | 235 |     |     |     |     | 240 |

| Tyr | Asn | Pro | Asp | Gly | Phe | Glu | Gly | Ile | Gly | Pro | Lys | Lys | Ala | Leu | Gln |
|     |     |     |     | 245 |     |     |     |     | 250 |     |     |     |     | 255 |     |

| Leu | Val | Lys | Ala | Tyr | Gly | Gly | Ile | Glu | Lys | Ile | Pro | Lys | Pro | Ile | Leu |
|     |     |     |     | 260 |     |     |     |     | 265 |     |     |     |     | 270 |     |

| Lys | Ser | Pro | Ile | Glu | Val | Asp | Val | Ile | Ala | Ile | Lys | Lys | Tyr | Phe | Leu |
|     |     |     | 275 |     |     |     |     | 280 |     |     |     |     | 285 |     |     |

| Gln | Pro | Gln | Val | Thr | Asp | Asn | Tyr | Arg | Ile | Glu | Trp | His | Thr | Pro | Asp |
|     | 290 |     |     |     |     | 295 |     |     |     |     | 300 |     |     |     |     |

| Pro | Asp | Ala | Val | Lys | Arg | Ile | Leu | Val | Asp | Glu | His | Asp | Phe | Ser | Ile |

```
305                 310                 315                 320
Asp Arg Val Ser Thr Ala Leu Glu Arg Tyr Val Lys Ala Phe Lys Glu
                325                 330                 335

Asn Ile Arg Gly Glu Gln Lys Gly Leu Ser Lys Trp Phe Ser Lys Pro
            340                 345                 350

Lys

<210> SEQ ID NO 376
<211> LENGTH: 31
<212> TYPE: DNA
<213> ORGANISM: Artificial Sequence
<220> FEATURE:
<223> OTHER INFORMATION: Synthetic

<400> SEQUENCE: 376
cgttgaattc ggagttactg agttgggtaa g                                  31

<210> SEQ ID NO 377
<211> LENGTH: 34
<212> TYPE: DNA
<213> ORGANISM: Artificial Sequence
<220> FEATURE:
<223> OTHER INFORMATION: Synthetic

<400> SEQUENCE: 377
tactgtcgac agaaaaagga gtcgagagag gaag                               34

<210> SEQ ID NO 378
<211> LENGTH: 1041
<212> TYPE: DNA
<213> ORGANISM: Artificial Sequence
<220> FEATURE:
<223> OTHER INFORMATION: Synthetic

<400> SEQUENCE: 378
gtgggagtta ctgagttggg taagcttatt ggcaaagagg tccgccgcga ggttaaactg     60
gaaagtctct cgggcaagtg tattgcccct gacgcgtaca acgccttgta ccaattcctt    120
gcgtctatta gacagccaga tgggacgcct ctaatggaca gagctgggag gattactagt    180
catctctcgg gtttgttcta ccgtactatc aacctccttg aggccggcat taggcctgtt    240
tatgtttttg atgggaagcc tcccgaattt aaactggctg aaattgaaga aaggaggaag    300
acgcgtgaga aggccatgga agaggtgttg agggccatta aggaggggag gagggaagac    360
gtggctaaat acgccaaaag ggctgttttt attaccagcg aaatggtgga cgaggccaag    420
aggctgctga gctatatggg cgtaccctgg gtccaagctc aagcgagggg ggaggcgcaa    480
gcggcttata tggctagaaa aggacactgc tgggccgtgg aagccagga ttacgattcg    540 ctgttatttg atcccccaa gttagtcaga atctagcgg tatcccctaa gcgtaaaatt    600
ggagaagagg taatagagct cacgccggaa attattgagc tagacgccgt cctcagggct    660
ttgaggctaa agaacagaga gcaactaata gacttggcta ttttactcgg cacagattac    720
aacccagacg gcgttcccgg agtgggcccc cagaaggcgt taaaactaat atgggaattt    780
ggatcgcttg aaaaactatt agaaactgta ttaaggcggg cgtatttccc cattgacccc    840
ctggagataa agaagttctt cctcaatccc ccagtcactg atcaatacgc cactgaggtg    900
agagacccag acgaggcggc cctcaaggac tttcttatac gcgaacacga cttcagcgag    960
gagagggtgt ctaaggcact tgagaggctg agaaaagccc gggggaagtt aaaaacttcc   1020
tctctcgact ccttttttcta a                                           1041
```

<210> SEQ ID NO 379
<211> LENGTH: 346
<212> TYPE: PRT
<213> ORGANISM: Artificial Sequence
<220> FEATURE:
<223> OTHER INFORMATION: Synthetic

<400> SEQUENCE: 379

```
Val Gly Val Thr Glu Leu Gly Lys Leu Ile Gly Lys Glu Val Arg Arg
1               5                   10                  15

Glu Val Lys Leu Glu Ser Leu Ser Gly Lys Cys Ile Ala Leu Asp Ala
            20                  25                  30

Tyr Asn Ala Leu Tyr Gln Phe Leu Ala Ser Ile Arg Gln Pro Asp Gly
        35                  40                  45

Thr Pro Leu Met Asp Arg Ala Gly Arg Ile Thr Ser His Leu Ser Gly
    50                  55                  60

Leu Phe Tyr Arg Thr Ile Asn Leu Leu Glu Ala Gly Ile Arg Pro Val
65                  70                  75                  80

Tyr Val Phe Asp Gly Lys Pro Pro Glu Phe Lys Leu Ala Glu Ile Glu
                85                  90                  95

Glu Arg Arg Lys Thr Arg Glu Lys Ala Met Glu Glu Val Leu Arg Ala
            100                 105                 110

Ile Lys Glu Gly Arg Arg Glu Asp Val Ala Lys Tyr Ala Lys Arg Ala
        115                 120                 125

Val Phe Ile Thr Ser Glu Met Val Asp Glu Ala Lys Arg Leu Leu Ser
    130                 135                 140

Tyr Met Gly Val Pro Trp Val Gln Ala Pro Ser Glu Gly Glu Ala Gln
145                 150                 155                 160

Ala Ala Tyr Met Ala Arg Lys Gly His Cys Trp Ala Val Gly Ser Gln
                165                 170                 175

Asp Tyr Asp Ser Leu Leu Phe Gly Ser Pro Lys Leu Val Arg Asn Leu
            180                 185                 190

Ala Val Ser Pro Lys Arg Lys Ile Gly Glu Glu Val Ile Glu Leu Thr
        195                 200                 205

Pro Glu Ile Ile Glu Leu Asp Ala Val Leu Arg Ala Leu Arg Leu Lys
    210                 215                 220

Asn Arg Glu Gln Leu Ile Asp Leu Ala Ile Leu Leu Gly Thr Asp Tyr
225                 230                 235                 240

Asn Pro Asp Gly Val Pro Gly Val Gly Pro Gln Lys Ala Leu Lys Leu
                245                 250                 255

Ile Trp Glu Phe Gly Ser Leu Glu Lys Leu Leu Glu Thr Val Leu Lys
            260                 265                 270

Gly Ala Tyr Phe Pro Ile Asp Pro Leu Glu Ile Lys Lys Phe Phe Leu
        275                 280                 285

Asn Pro Pro Val Thr Asp Gln Tyr Ala Thr Glu Val Arg Asp Pro Asp
    290                 295                 300

Glu Ala Ala Leu Lys Asp Phe Leu Ile Arg Glu His Asp Phe Ser Glu
305                 310                 315                 320

Glu Arg Val Ser Lys Ala Leu Glu Arg Leu Lys Ala Arg Gly Lys
                325                 330                 335

Leu Lys Thr Ser Ser Leu Asp Ser Phe Phe
            340                 345
```

<210> SEQ ID NO 380

```
<211> LENGTH: 31
<212> TYPE: DNA
<213> ORGANISM: Artificial Sequence
<220> FEATURE:
<223> OTHER INFORMATION: Synthetic

<400> SEQUENCE: 380
tcatgaattc ggagtccaga ttggtgagct t                              31

<210> SEQ ID NO 381
<211> LENGTH: 32
<212> TYPE: DNA
<213> ORGANISM: Artificial Sequence
<220> FEATURE:
<223> OTHER INFORMATION: Synthetic

<400> SEQUENCE: 381
gattgtcgac tcactttta aaccagctgt cc                              32

<210> SEQ ID NO 382
<211> LENGTH: 39
<212> TYPE: DNA
<213> ORGANISM: Artificial Sequence
<220> FEATURE:
<223> OTHER INFORMATION: Synthetic

<400> SEQUENCE: 382
aagctcacca atctggactc ccatggtctg tttcctgtg                      39

<210> SEQ ID NO 383
<211> LENGTH: 1023
<212> TYPE: DNA
<213> ORGANISM: Artificial Sequence
<220> FEATURE:
<223> OTHER INFORMATION: Synthetic

<400> SEQUENCE: 383
atgggagtcc agattggtga gcttttacca agaaaagagc ttgagcttga aaatttaaat    60
gggagaaaag ttgcgataga tgcatttaac gctatttacc agtttctctc aacaataaga   120
caacgagatg ggactccttt aatggattcc aagggaagaa taacgtccca tctttcaggg   180
cttttttaca ggactataaa cctaatgaa gcgggaataa agcctgcgta tgtattcgat    240
gggaagcctc cagagttcaa gaaaaagag cttgaaaaa gagctgaggc tagggaggaa    300
gcgcaggaaa atgggagga gccctagca aggggagact tagaagaggc gaagaaatat    360
gcacagcggg cgagcaaagt aaatgagatg cttatcgagg atgctaagaa gcttttggag   420
cttatgggca tcccatgggt gcaggctcct agcgaaggtg aagcgcaggc agcttatatg   480
gcatctaaag ggcacgtttg ggcctcggcg agccaggact acgactcgct cctcttcgga   540
acaccaaggc tagtgagaaa cctcaccata actggaaaga gaaagcttcc tgggaaggat   600
atttacgtag aagttaaacc ggagctcata gttcttgaag gtgtgttaaa ggagcttaag   660
ataacgaggg agaagttggt agagcttgca attctcgtgg gaacggacta caatcctgga   720
ggcataaaag ggattggacc aaaaaaggcc cttgaaatag tcaaatactc caaagatcct   780
ctggcaaagt accaaaaaat gagcgatgtt gatctctatg caataaagga gttcttccta   840
aacccgccga caacagacga atacaagctc gaatggaaaa tgcccgatga agaaggaata   900
ctgaagtttc tctgtgatga gcacgattc agtgaagaaa gagttaaaaa cggcttagaa   960
aggcttaaaa aagcggttaa ggcaggaaga cagtttacgc tggacagctg gtttaaaaag  1020
tga                                                               1023
```

<210> SEQ ID NO 384
<211> LENGTH: 340
<212> TYPE: PRT
<213> ORGANISM: Artificial Sequence
<220> FEATURE:
<223> OTHER INFORMATION: Synthetic

<400> SEQUENCE: 384

```
Met Gly Val Gln Ile Gly Glu Leu Leu Pro Arg Lys Glu Leu Glu Leu
1               5                   10                  15
Glu Asn Leu Asn Gly Arg Lys Val Ala Ile Asp Ala Phe Asn Ala Ile
            20                  25                  30
Tyr Gln Phe Leu Ser Thr Ile Arg Gln Arg Asp Gly Thr Pro Leu Met
        35                  40                  45
Asp Ser Lys Gly Arg Ile Thr Ser His Leu Ser Gly Leu Phe Tyr Arg
    50                  55                  60
Thr Ile Asn Leu Met Glu Ala Gly Ile Lys Pro Ala Tyr Val Phe Asp
65                  70                  75                  80
Gly Lys Pro Pro Glu Phe Lys Lys Lys Glu Leu Glu Lys Arg Ala Glu
                85                  90                  95
Ala Arg Glu Glu Ala Gln Glu Lys Trp Glu Glu Ala Leu Ala Arg Gly
            100                 105                 110
Asp Leu Glu Glu Ala Lys Lys Tyr Ala Gln Arg Ala Ser Lys Val Asn
        115                 120                 125
Glu Met Leu Ile Glu Asp Ala Lys Lys Leu Leu Glu Leu Met Gly Ile
    130                 135                 140
Pro Trp Val Gln Ala Pro Ser Glu Gly Glu Ala Gln Ala Ala Tyr Met
145                 150                 155                 160
Ala Ser Lys Gly His Val Trp Ala Ser Ala Ser Gln Asp Tyr Asp Ser
                165                 170                 175
Leu Leu Phe Gly Thr Pro Arg Leu Val Arg Asn Leu Thr Ile Thr Gly
            180                 185                 190
Lys Arg Lys Leu Pro Gly Lys Asp Ile Tyr Val Glu Val Lys Pro Glu
        195                 200                 205
Leu Ile Val Leu Glu Glu Val Leu Lys Glu Leu Lys Ile Thr Arg Glu
    210                 215                 220
Lys Leu Val Glu Leu Ala Ile Leu Val Gly Thr Asp Tyr Asn Pro Gly
225                 230                 235                 240
Gly Ile Lys Gly Ile Gly Pro Lys Lys Ala Leu Glu Ile Val Lys Tyr
                245                 250                 255
Ser Lys Asp Pro Leu Ala Lys Tyr Gln Lys Met Ser Asp Val Asp Leu
            260                 265                 270
Tyr Ala Ile Lys Glu Phe Phe Leu Asn Pro Pro Thr Thr Asp Glu Tyr
        275                 280                 285
Lys Leu Glu Trp Lys Met Pro Asp Glu Glu Gly Ile Leu Lys Phe Leu
    290                 295                 300
Cys Asp Glu His Asp Phe Ser Glu Glu Arg Val Lys Asn Gly Leu Glu
305                 310                 315                 320
Arg Leu Lys Lys Ala Val Lys Ala Gly Arg Gln Phe Thr Leu Asp Ser
                325                 330                 335
Trp Phe Lys Lys
            340
```

<210> SEQ ID NO 385

```
<211> LENGTH: 31
<212> TYPE: DNA
<213> ORGANISM: Artificial Sequence
<220> FEATURE:
<223> OTHER INFORMATION: Synthetic

<400> SEQUENCE: 385
cttggaattc ggcgtcgacc taagggaact c                            31

<210> SEQ ID NO 386
<211> LENGTH: 34
<212> TYPE: DNA
<213> ORGANISM: Artificial Sequence
<220> FEATURE:
<223> OTHER INFORMATION: Synthetic

<400> SEQUENCE: 386
aggtctgcag ttaaccctgc ttaccgggct tagc                         34

<210> SEQ ID NO 387
<211> LENGTH: 31
<212> TYPE: DNA
<213> ORGANISM: Artificial Sequence
<220> FEATURE:
<223> OTHER INFORMATION: Synthetic

<400> SEQUENCE: 387
caggaaacag accatgggcg tcgacctaag g                            31

<210> SEQ ID NO 388
<211> LENGTH: 1071
<212> TYPE: DNA
<213> ORGANISM: Artificial Sequence
<220> FEATURE:
<223> OTHER INFORMATION: Synthetic

<400> SEQUENCE: 388
atgggcgtcg acctaaggga actcatccca gacgacgcca agatcattat agaggatctg    60
aggaccctac ggggcagggt tatcgcgata cacggctata cgcgctcta ccagttccta    120 gccgccatca ggcagcccga cgggacgccc ctaatggatg gaagcggcag gatcaccagc   180
cacctcagcg ggctcttcta caggacgata acattgtgg aggcagggat taaacccgta   240
tacgtcttcg atggtaaacc ccccgagttg aaggcgaagg agatagagag gagaagggtt   300 gtcaggagg aggctgcgag aaagtatgag gaggcagtgc aagccggcga cttagagtca    360
gctagaaggt atgcgatgat gtcggctagg ctcaccgatg aaatggtgag ggatgcaaaa   420
gccctgctcg acgccatggg gataccgtgg gttcaagccc cggctgaggg cgaggcgcag   480
gcagcgtaca tggctaggaa gggcgacgcc tacgcctctg catcccagga ctacgatagc   540
ctcctcttcg ggtcgccccg cctagtgagg aatctcacta taagtggccg taggaagctc   600
ccgagaagag aggagtatgt cgaggtgaag cccgaggtaa tagagctcga taaactgctt   660
tcaaagctgg gcgtaaccta tgagaacctg gtggacatag gcatcctcct ggggacggat   720
tacaacccag acggcttcga gggcattgga cccaagaagg cgcttcaatt agtgaaggtc   780
tacgggagcg ttgagaagat accgaagccc ctcttgaaat cccctgttga agtagatgtc   840
gcagcgataa aaagtactt cctgcaaccc caggtgacag acaactatag gcttgaatgg   900
cgtaacccgg atcccgaggc tgtgaaacgc atacttgtcg gcgaacacga tttcagcgct   960
gagagagtca acgcagccct cgacaggtat cttaaagcct tcaggagaa cataaggggc   1020 gaacagaagg ggctgtcgaa gtggttcgct aagcccggta agcagggtta a           1071
```

<210> SEQ ID NO 389
<211> LENGTH: 356
<212> TYPE: PRT
<213> ORGANISM: Artificial Sequence
<220> FEATURE:
<223> OTHER INFORMATION: Synthetic

<400> SEQUENCE: 389

```
Met Gly Val Asp Leu Arg Glu Leu Ile Pro Asp Asp Ala Lys Ile Ile
 1               5                  10                  15
Ile Glu Asp Leu Arg Thr Leu Arg Gly Arg Val Ile Ala Ile Asp Gly
                20                  25                  30
Tyr Asn Ala Leu Tyr Gln Phe Leu Ala Ala Ile Arg Gln Pro Asp Gly
            35                  40                  45
Thr Pro Leu Met Asp Gly Ser Gly Arg Ile Thr Ser His Leu Ser Gly
        50                  55                  60
Leu Phe Tyr Arg Thr Ile Asn Ile Val Glu Ala Gly Ile Lys Pro Val
65                  70                  75                  80
Tyr Val Phe Asp Gly Lys Pro Pro Glu Leu Lys Ala Lys Glu Ile Glu
                85                  90                  95
Arg Arg Arg Val Val Arg Glu Glu Ala Ala Arg Lys Tyr Glu Glu Ala
                100                 105                 110
Val Gln Ala Gly Asp Leu Glu Ser Ala Arg Arg Tyr Ala Met Met Ser
            115                 120                 125
Ala Arg Leu Thr Asp Glu Met Val Arg Asp Ala Lys Ala Leu Leu Asp
        130                 135                 140
Ala Met Gly Ile Pro Trp Val Gln Ala Pro Ala Glu Gly Glu Ala Gln
145                 150                 155                 160
Ala Ala Tyr Met Ala Arg Lys Gly Asp Ala Tyr Ala Ser Ala Ser Gln
                165                 170                 175
Asp Tyr Asp Ser Leu Leu Phe Gly Ser Pro Arg Leu Val Arg Asn Leu
            180                 185                 190
Thr Ile Ser Gly Arg Arg Lys Leu Pro Arg Arg Glu Glu Tyr Val Glu
        195                 200                 205
Val Lys Pro Glu Val Ile Glu Leu Asp Lys Leu Leu Ser Lys Leu Gly
    210                 215                 220
Val Thr Tyr Glu Asn Leu Val Asp Ile Gly Ile Leu Leu Gly Thr Asp
225                 230                 235                 240
Tyr Asn Pro Asp Gly Phe Glu Gly Ile Gly Pro Lys Lys Ala Leu Gln
                245                 250                 255
Leu Val Lys Val Tyr Gly Ser Val Glu Lys Ile Pro Lys Pro Leu Leu
            260                 265                 270
Lys Ser Pro Val Glu Val Asp Val Ala Ala Ile Lys Lys Tyr Phe Leu
        275                 280                 285
Gln Pro Gln Val Thr Asp Asn Tyr Arg Leu Glu Trp Arg Asn Pro Asp
    290                 295                 300
Pro Glu Ala Val Lys Arg Ile Leu Val Gly Glu His Asp Phe Ser Ala
305                 310                 315                 320
Glu Arg Val Asn Ala Ala Leu Asp Arg Tyr Leu Lys Ala Phe Arg Glu
                325                 330                 335
Asn Ile Arg Gly Glu Gln Lys Gly Leu Ser Lys Trp Phe Ala Lys Pro
            340                 345                 350
Gly Lys Gln Gly
        355
```

<210> SEQ ID NO 390
<211> LENGTH: 28
<212> TYPE: DNA
<213> ORGANISM: Artificial Sequence
<220> FEATURE:
<223> OTHER INFORMATION: Synthetic

<400> SEQUENCE: 390
tagcgaattc ggcgtcaacc tccgcgag                                          28

<210> SEQ ID NO 391
<211> LENGTH: 28
<212> TYPE: DNA
<213> ORGANISM: Artificial Sequence
<220> FEATURE:
<223> OTHER INFORMATION: Synthetic

<400> SEQUENCE: 391
cattctgcag ctagcggcgc agccacgc                                          28

<210> SEQ ID NO 392
<211> LENGTH: 31
<212> TYPE: DNA
<213> ORGANISM: Artificial Sequence
<220> FEATURE:
<223> OTHER INFORMATION: Synthetic

<400> SEQUENCE: 392
caggaaacag accatgggcg tcaacctccg c                                      31

<210> SEQ ID NO 393
<211> LENGTH: 1053
<212> TYPE: DNA
<213> ORGANISM: Artificial Sequence
<220> FEATURE:
<223> OTHER INFORMATION: Synthetic

<400> SEQUENCE: 393
gtgggcgtca acctccgcga gatcataccc aaggaggctg taacggaaat agagctcgac        60
tcgctgcgct acaaggttgt agccatagac gcctacaacg cgctctacca gttcctcacc       120
gcgataaggc agccgacgg cacgccgctc atggactcgc gtggcaggt caccagccat        180 ctcagcggcc tcttctaccg caccataaac ctggccgagc acggggtaaa ggtggtctac       240
gtcttcgacg ggaagccgcc ggagatgaag tatctcgaga tagagaggag gaagcgtgtc       300
aaggcggagg ctgtgcggaa gtacgaggag gcagtgaaga ggggcgacca ggaggcggcg       360
aggcgctacg cccaggcagc ggcgagactc accgacgaga tggtggagga cgctaagaag       420
ctgctggagg ccatggggat accctacgtg caggcgccgg cggaggggga ggcgcaggcc       480
gcctacatgg cccggaaggg cgacgcctgg gccgcggcga gccaggacta cgactccctg       540
ctcttcgggg ccccgaggct tgcccggaac ctcgctataa cgggtaagag gaagctgccc       600
aggaagaacg tctacgtaga ggttaagccg gagctggtgg agctcgagaa gctgctcaag       660
gcactgggca ttaccaggga gcagttgata gccctaggca tactcatagg caccgactac       720 aacccgacg cgtccgggg gatcgggccc aagacggcgc tgaagatggt gcagacccac        780
cgggaccccg tgaagctcct ccaggggctc ccgcgccacg agttcccggt cgacccactg       840
aagatctacg agtacttcct gaaccccccca gtgaccagcg actataagct cgagtggagg       900
gagcccgacg agaagagggt cctcgagata ctcgtggagg agcacgactt caacccggag       960
cgtgttaaga acgccctgga gaggctgcgg agggcgtacc gcgagcactt ccagggccgc    1020
cagatgggtc tggatgcgtg gctgcgccgc tag                                1053

<210> SEQ ID NO 394
<211> LENGTH: 350
<212> TYPE: PRT
<213> ORGANISM: Artificial Sequence
<220> FEATURE:
<223> OTHER INFORMATION: Synthetic

<400> SEQUENCE: 394

Val Gly Val Asn Leu Arg Glu Ile Ile Pro Lys Glu Ala Val Thr Glu
1               5                   10                  15

Ile Glu Leu Asp Ser Leu Arg Tyr Lys Val Ala Ile Asp Ala Tyr
            20                  25                  30

Asn Ala Leu Tyr Gln Phe Leu Thr Ala Ile Arg Gln Pro Asp Gly Thr
        35                  40                  45

Pro Leu Met Asp Ser Arg Gly Arg Val Thr Ser His Leu Ser Gly Leu
    50                  55                  60

Phe Tyr Arg Thr Ile Asn Leu Ala Glu His Gly Val Lys Val Val Tyr
65                  70                  75                  80

Val Phe Asp Gly Lys Pro Pro Glu Met Lys Tyr Leu Glu Ile Glu Arg
                85                  90                  95

Arg Lys Arg Val Lys Ala Glu Ala Val Arg Lys Tyr Glu Glu Ala Val
            100                 105                 110

Lys Arg Gly Asp Gln Glu Ala Ala Arg Arg Tyr Ala Gln Ala Ala Ala
        115                 120                 125

Arg Leu Thr Asp Glu Met Val Glu Asp Ala Lys Lys Leu Leu Glu Ala
    130                 135                 140

Met Gly Ile Pro Tyr Val Gln Ala Pro Ala Glu Gly Glu Ala Gln Ala
145                 150                 155                 160

Ala Tyr Met Ala Arg Lys Gly Asp Ala Trp Ala Ala Ser Gln Asp
                165                 170                 175

Tyr Asp Ser Leu Leu Phe Gly Ala Pro Arg Leu Ala Arg Asn Leu Ala
            180                 185                 190

Ile Thr Gly Lys Arg Lys Leu Pro Arg Lys Asn Val Tyr Val Glu Val
        195                 200                 205

Lys Pro Glu Leu Val Glu Leu Glu Lys Leu Leu Lys Ala Leu Gly Ile
    210                 215                 220

Thr Arg Glu Gln Leu Ile Ala Leu Gly Ile Leu Ile Gly Thr Asp Tyr
225                 230                 235                 240

Asn Pro Asp Gly Val Arg Gly Ile Gly Pro Lys Thr Ala Leu Lys Met
                245                 250                 255

Val Gln Thr His Arg Asp Pro Val Lys Leu Leu Gln Gly Leu Pro Arg
            260                 265                 270

His Glu Phe Pro Val Asp Pro Leu Lys Ile Tyr Glu Tyr Phe Leu Asn
        275                 280                 285

Pro Pro Val Thr Ser Asp Tyr Lys Leu Glu Trp Arg Glu Pro Asp Glu
    290                 295                 300

Lys Arg Val Leu Glu Ile Leu Val Glu His Asp Phe Asn Pro Glu
305                 310                 315                 320

Arg Val Lys Asn Ala Leu Glu Arg Leu Arg Arg Ala Tyr Arg Glu His
                325                 330                 335

Phe Gln Gly Arg Gln Met Gly Leu Asp Ala Trp Leu Arg Arg
            340                 345                 350

<210> SEQ ID NO 395
<211> LENGTH: 28
<212> TYPE: DNA
<213> ORGANISM: Artificial Sequence
<220> FEATURE:
<223> OTHER INFORMATION: Synthetic

<400> SEQUENCE: 395
cataccatgg gactagctga actccgag    28

<210> SEQ ID NO 396
<211> LENGTH: 30
<212> TYPE: DNA
<213> ORGANISM: Artificial Sequence
<220> FEATURE:
<223> OTHER INFORMATION: Synthetic

<400> SEQUENCE: 396
tggatctaga tcagaagaac gcgtccaggg    30

<210> SEQ ID NO 397
<211> LENGTH: 985
<212> TYPE: DNA
<213> ORGANISM: Artificial Sequence
<220> FEATURE:
<223> OTHER INFORMATION: Synthetic

<400> SEQUENCE: 397
ttgggactag ctgaactccg agaactgatc gaacccgaag agacggacct gagagccctc    60
gccggtcggg agatcgctat cgacgcgttc aacgccctgt atcaattcct gaccacgatc   120
atgaaggacg gacgacctct catggactcg aggggcagga ttaccagcca cttaaatggc   180
ctcctgtata ggaccgtgaa cttggtcgaa gagggtatca agccggtata cgtgttcgat   240
ggtgagcccc cggacctgaa gcgtgaaacg ctggagcgtc gacgggaacg gaaggaggag   300
gcgatggaga aactgaggcg ggccaaaacg aaggaggagc gggagaagta cgcccgacaa   360
gtcgccagac tcgacgagtc gttggtgaa gacgcgaaga ggctgttgga tctcatgggc   420
atcccgtggg tacaggcccc ctcggaagga gaggcgcagt gcgcgtatat ggcgaggtgc   480
ggggacgtat gggcgacagg cagccaagac tacgactcgc tgcttttcgg cagccccagg   540
ttggttcgca acatcacgat agtcggaaag cggaagcatc cacacaccgg cgagatcata   600
gaggtcaagc ccgagatcat gaggttggag gacgtgctcg accagctggg attggaatcg   660
agggagcagc tggtggacct agcgatcctt ttgggcacgg actacaaccc ggatggagta   720
cccgggattg gtccgaagcg cgcgctgcag ttgatcagga agtacgggtc gctagacgag   780
cttaaggaca ccgacatctg gcctaagatc gagcggcacc tgccggtgga accggagaag   840
ctcaaaaggc tctttctcga gccggaagtt acgacgact accagctaga ctgggacgaa   900
cccgaccaaa agggactggt cgagttcctg gttgaggagc gtgatttctt ccaggatcga   960
gtccgccgcg ccgtcgagcg tctga   985

<210> SEQ ID NO 398
<211> LENGTH: 328
<212> TYPE: PRT
<213> ORGANISM: Artificial Sequence
<220> FEATURE:
<223> OTHER INFORMATION: Synthetic

<400> SEQUENCE: 398

-continued

```
Leu Gly Leu Ala Glu Leu Arg Glu Leu Ile Glu Pro Glu Glu Thr Asp
 1               5                  10                 15

Leu Arg Ala Leu Ala Gly Arg Glu Ile Ala Ile Asp Ala Phe Asn Ala
             20                  25                  30

Leu Tyr Gln Phe Leu Thr Thr Ile Met Lys Asp Gly Arg Pro Leu Met
         35                  40                  45

Asp Ser Arg Gly Arg Ile Thr Ser His Leu Asn Gly Leu Leu Tyr Arg
     50                  55                  60

Thr Val Asn Leu Val Glu Glu Gly Ile Lys Pro Val Tyr Val Phe Asp
 65              70                  75                  80

Gly Glu Pro Pro Asp Leu Lys Arg Glu Thr Leu Glu Arg Arg Arg Glu
                 85                  90                  95

Arg Lys Glu Glu Ala Met Glu Lys Leu Arg Arg Ala Lys Thr Lys Glu
             100                 105                 110

Glu Arg Glu Lys Tyr Ala Arg Gln Val Ala Arg Leu Asp Glu Ser Leu
         115                 120                 125

Val Glu Asp Ala Lys Arg Leu Leu Asp Leu Met Gly Ile Pro Trp Val
130                 135                 140

Gln Ala Pro Ser Glu Gly Glu Ala Gln Cys Ala Tyr Met Ala Arg Cys
145                 150                 155                 160

Gly Asp Val Trp Ala Thr Gly Ser Gln Asp Tyr Asp Ser Leu Leu Phe
                 165                 170                 175

Gly Ser Pro Arg Leu Val Arg Asn Ile Thr Ile Val Gly Lys Arg Lys
             180                 185                 190

His Pro His Thr Gly Glu Ile Ile Glu Val Lys Pro Glu Ile Met Arg
         195                 200                 205

Leu Glu Asp Val Leu Asp Gln Leu Gly Leu Glu Ser Arg Glu Gln Leu
210                 215                 220

Val Asp Leu Ala Ile Leu Leu Gly Thr Asp Tyr Asn Pro Asp Gly Val
225                 230                 235                 240

Pro Gly Ile Gly Pro Lys Arg Ala Leu Gln Leu Ile Arg Lys Tyr Gly
                 245                 250                 255

Ser Leu Asp Glu Leu Lys Asp Thr Asp Ile Trp Pro Lys Ile Glu Arg
             260                 265                 270

His Leu Pro Val Glu Pro Glu Lys Leu Lys Arg Leu Phe Leu Glu Pro
         275                 280                 285

Glu Val Thr Asp Asp Tyr Gln Leu Asp Trp Asp Glu Pro Asp Gln Lys
290                 295                 300

Gly Leu Val Glu Phe Leu Val Glu Glu Arg Asp Phe Phe Gln Asp Arg
305                 310                 315                 320

Val Arg Arg Ala Val Glu Arg Leu
                 325
```

<210> SEQ ID NO 399
<211> LENGTH: 28
<212> TYPE: DNA
<213> ORGANISM: Artificial Sequence
<220> FEATURE:
<223> OTHER INFORMATION: Synthetic

<400> SEQUENCE: 399
cgatccatgg gagttcagat cggtgagc                                    28

<210> SEQ ID NO 400
<211> LENGTH: 31
<212> TYPE: DNA

```
<213> ORGANISM: Artificial Sequence
<220> FEATURE:
<223> OTHER INFORMATION: Synthetic

<400> SEQUENCE: 400
caggctgcag tcaccttccg aaccagctct c                                    31

<210> SEQ ID NO 401
<211> LENGTH: 1023
<212> TYPE: DNA
<213> ORGANISM: Thermococcus zilligii

<400> SEQUENCE: 401
atgggagttc agatcggtga gctcgtgccg aggaaggaga tagggctgga aaaccttcat     60
gggaaaaaag ttgcagttga tgccttcaac gccatgtacc agtttctctc gacgataagg    120
cagcctgatg ggactccttt aatggactcg aagggcagga taacctctca tctcagcggc    180
ttcttctata ggacaataaa cctgatggag gccggaataa aacccgccta cgtcttcgac    240
gggaagccac cggagttcaa gaagaaggag atagagaaga ggagggaggc aagggaagag    300
gcagaagaga gtggcagga ggcccttgag aagggcgacc tggaggaggc gaagaagtac    360
gcgatgaggg caacccgcgt taacgaggag ctcataagcg atgccaaaaa gcttcttgag    420
ctaatgggca ttccggttgt ccaggcaccg agcgagggag aggctcaggc ggcctacatg    480
gccgcaaagg gcaaggttta cgcctcagcg agccaggatt atgactcact cctcttcagc    540
gcgccgaaac tcgtgagaaa cctcacgata acgggaagaa ggaagctgcc ggggaaggat    600
gtctacgttg aagtgaagcc cgagctgatc gtcctggaag aggttctcaa ggagcttggc    660
atagaccggg agaaactcat agagctggcg attcttgtgg ggacggacta caaccccggg    720
gggataaagg gcatcgggcc caagaaggcc cttatgatag tcaagagaat caatgacccg    780
ctcaggaagt acagcaatga gagtgaggtc gacctctacg cgataaagga gttctttctc    840
aatccccccg ttacagatga ctacgagctg agatggcgcg agcccgatga agatgggatt    900
ctaaggtttc tctgtgagga gcacgacttc agcgaggaga gggttaaggg tggccttgaa    960
aggctgagga aagcggtgga gagtggaaag cagagaacgc ttgagagctg gttcggaagg   1020
tga                                                                 1023

<210> SEQ ID NO 402
<211> LENGTH: 340
<212> TYPE: PRT
<213> ORGANISM: Thermococcus zilligii

<400> SEQUENCE: 402

Met Gly Val Gln Ile Gly Glu Leu Val Pro Arg Lys Glu Ile Gly Leu
1               5                   10                  15

Glu Asn Leu His Gly Lys Lys Val Ala Val Asp Ala Phe Asn Ala Met
            20                  25                  30

Tyr Gln Phe Leu Ser Thr Ile Arg Gln Pro Asp Gly Thr Pro Leu Met
        35                  40                  45

Asp Ser Lys Gly Arg Ile Thr Ser His Leu Ser Gly Phe Phe Tyr Arg
    50                  55                  60

Thr Ile Asn Leu Met Glu Ala Gly Ile Lys Pro Ala Tyr Val Phe Asp
65                  70                  75                  80

Gly Lys Pro Pro Glu Phe Lys Lys Lys Glu Ile Glu Lys Arg Arg Glu
                85                  90                  95

Ala Arg Glu Glu Ala Glu Glu Lys Trp Gln Glu Ala Leu Glu Lys Gly
```

```
                100             105             110
Asp Leu Glu Glu Ala Lys Lys Tyr Ala Met Arg Ala Thr Arg Val Asn
        115                 120                 125

Glu Glu Leu Ile Ser Asp Ala Lys Lys Leu Leu Glu Leu Met Gly Ile
    130                 135                 140

Pro Val Val Gln Ala Pro Ser Glu Gly Glu Ala Gln Ala Ala Tyr Met
145                 150                 155                 160

Ala Ala Lys Gly Lys Val Tyr Ala Ser Ala Ser Gln Asp Tyr Asp Ser
                165                 170                 175

Leu Leu Phe Ser Ala Pro Lys Leu Val Arg Asn Leu Thr Ile Thr Gly
            180                 185                 190

Arg Arg Lys Leu Pro Gly Lys Asp Val Tyr Val Glu Val Lys Pro Glu
        195                 200                 205

Leu Ile Val Leu Glu Glu Val Leu Lys Glu Leu Gly Ile Asp Arg Glu
    210                 215                 220

Lys Leu Ile Glu Leu Ala Ile Leu Val Gly Thr Asp Tyr Asn Pro Gly
225                 230                 235                 240

Gly Ile Lys Gly Ile Gly Pro Lys Lys Ala Leu Met Ile Val Lys Arg
                245                 250                 255

Ile Asn Asp Pro Leu Arg Lys Tyr Ser Asn Glu Ser Glu Val Asp Leu
            260                 265                 270

Tyr Ala Ile Lys Glu Phe Phe Leu Asn Pro Pro Val Thr Asp Asp Tyr
        275                 280                 285

Glu Leu Arg Trp Arg Glu Pro Asp Glu Asp Gly Ile Leu Arg Phe Leu
    290                 295                 300

Cys Glu Glu His Asp Phe Ser Glu Glu Arg Val Lys Gly Gly Leu Glu
305                 310                 315                 320

Arg Leu Arg Lys Ala Val Glu Ser Gly Lys Gln Arg Thr Leu Glu Ser
                325                 330                 335

Trp Phe Gly Arg
        340

<210> SEQ ID NO 403
<211> LENGTH: 16
<212> TYPE: DNA
<213> ORGANISM: Artificial Sequence
<220> FEATURE:
<223> OTHER INFORMATION: Synthetic

<400> SEQUENCE: 403
ttttcaactg ccgtga                                                       16

<210> SEQ ID NO 404
<211> LENGTH: 36
<212> TYPE: DNA
<213> ORGANISM: Artificial Sequence
<220> FEATURE:
<223> OTHER INFORMATION: Synthetic

<400> SEQUENCE: 404
tcacggcagt tggtgcgcct cggaacgagg cgcaca                                 36
```

```
<210> SEQ ID NO 405
<211> LENGTH: 45
<212> TYPE: DNA
<213> ORGANISM: Artificial Sequence
<220> FEATURE:
<223> OTHER INFORMATION: Synthetic

<400> SEQUENCE: 405
ttttcaactg cttagagaat ctaagcagtt ggtgcgcctc gttaa              45

<210> SEQ ID NO 406
<211> LENGTH: 21
<212> TYPE: DNA
<213> ORGANISM: Artificial Sequence
<220> FEATURE:
<223> OTHER INFORMATION: Synthetic

<400> SEQUENCE: 406
aacgaggcgc acatttttt t                                          21

<210> SEQ ID NO 407
<211> LENGTH: 30
<212> TYPE: DNA
<213> ORGANISM: Artificial Sequence
<220> FEATURE:
<223> OTHER INFORMATION: Synthetic

<400> SEQUENCE: 407
ccgaagcacg cacaaagcgg tgtgtcacga                                30

<210> SEQ ID NO 408
<211> LENGTH: 25
<212> TYPE: DNA
<213> ORGANISM: Artificial Sequence
<220> FEATURE:
<223> OTHER INFORMATION: Synthetic

<400> SEQUENCE: 408
gcgccgaggc cgttctctag cgtga                                     25

<210> SEQ ID NO 409
<211> LENGTH: 46
<212> TYPE: DNA
<213> ORGANISM: Artificial Sequence
<220> FEATURE:
<223> OTHER INFORMATION: Synthetic

<400> SEQUENCE: 409
gcgccgaggc tctctgccgg ttttccggca gagacctcgg cgcact             46

<210> SEQ ID NO 410
<211> LENGTH: 55
<212> TYPE: DNA
<213> ORGANISM: Artificial Sequence
<220> FEATURE:
<223> OTHER INFORMATION: Synthetic

<400> SEQUENCE: 410
gtatacagcg tcacgctaga gaacggcgtg acccaccgct tgtgcgtgc ttcgg    55
```

REACTIONS ON A SOLID SURFACE

The present invention is a continuation-in-part of U.S. application Ser. No. 09/350,309, filed Jul. 9, 1999, now U.S. Pat. No. 6,348,314 which is a divisional application of U.S. Pat. No. 5,985,557, application Ser. No. 08/756,386, filed Nov. 26, 1996; is also a continuation-in-part of U.S. application Ser. No. 09/381,212, filed Feb. 8, 2000 now U.S. Pat. No. 6,872,816 which is a national entry of PCT Appli. No. U.S. 98/05809 filed Mar. 24, 1998, which claims priority to application Ser. No. 08/823,516, now U.S. Pat. No. 5,994,069, and application Ser. No. 08/759,038, now U.S. Pat. No. 6,090,543, which is a continuation-in-part of application Ser. No. 08/756,386, now U.S. Pat. No. 5,985,557, which is a continuation-in-part of application Ser. No. 08/682,853, now U.S. Pat. No. 6,001,567, which is a continuation-in-part of application Ser. No. 08/599,491, now U.S. Pat. No. 5,846,717, and PCT Appln. No. U.S. 97/01072; all of which are hereby incorporated by reference in their entireties.

The present invention was made, in part, using government funds under the National Cancer Institute Grant No. 1R43CA81890-01. The government may have certain rights in the invention.

FIELD OF THE INVENTION

The present invention relates to compositions and methods for the detection and characterization of nucleic acid sequences and variations in nucleic acid sequences. The present invention relates to methods for forming a nucleic acid cleavage structure on a solid support and cleaving the nucleic acid cleavage structure in a site-specific manner. For example, in some embodiments, the 5' nuclease activity of a variety of enzymes is used to cleave the target-dependent cleavage structure, thereby indicating the presence of specific nucleic acid sequences or specific variations thereof.

BACKGROUND OF THE INVENTION

Methods for the detection and characterization of specific nucleic acid sequences and sequence variations have been used to detect the presence of viral or bacterial nucleic acid sequences indicative of an infection, to detect the presence of variants or alleles of genes associated with disease and cancers. These methods also find application in the identification of sources of nucleic acids, as for forensic analysis or for paternity determinations.

Various methods are known to the art that may be used to detect and characterize specific nucleic acid sequences and sequence variants. Nonetheless, with the completion of the nucleic acid sequencing of the human genome, as well as the genomes of numerous pathogenic organisms, the demand for fast, reliable, cost-effective and user-friendly tests for the detection of specific nucleic acid sequences continues to grow. Importantly, these tests must be able to create a detectable signal from samples that contain very few copies of the sequence of interest. The following discussion examines two levels of nucleic acid detection assays currently in use: I. Signal Amplification Technology for detection of rare sequences; and II. Direct Detection Technology for quantitative detection of sequences.

I. Signal Amplification Technology Methods for Amplification

The "Polymerase Chain Reaction" (PCR) comprises the first generation of methods for nucleic acid amplification. However, several other methods have been developed that employ the same basis of specificity, but create signal by different amplification mechanisms. These methods include the "Ligase Chain Reaction" (LCR), "Self-Sustained Synthetic Reaction" (3SR/NASBA), and "Qβ-Replicase" (Qβ).

Polymerase Chain Reaction (PCR)

The polymerase chain reaction (PCR), as described in U.S. Pat. Nos. 4,683,195, 4,683,202, and 4,965,188 to Mullis and Mullis et al. (the disclosures of which are hereby incorporated by reference), describe a method for increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves introducing a molar excess of two oligonucleotide primers that are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR)

The ligase chain reaction (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. Segev, PCT Public. No. WO9001069 A1 (1990). However, because the four oligonucleotides used in this assay can pair to form two short ligatable fragments, there is the potential for the generation of target-independent background signal. The use of LCR for mutant screening is limited to the examination of specific nucleic acid positions.

Self-Sustained Synthetic Reaction (3SR/NASBA)

The self-sustained sequence replication reaction (3SR) (Guatelli et al., Proc. Natl. Acad. Sci., 87:1874-1878 [1990], with an erratum at Proc. Natl. Acad. Sci., 87:7797 [1990]) is a transcription-based in vitro amplification system (Kwok et al., Proc. Natl. Acad. Sci., 86:1173-1177 [1989]) that can exponentially amplify RNA sequences at a uniform temperature. The amplified RNA can then be utilized for mutation detection (Fahy et al., PCR Meth. Appl., 1:25-33 [1991]). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

Q-Beta (Qβ) Replicase

In this method, a probe that recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37° C.). This prevents the use of high temperature as a means of achieving specificity as in the LCR, the ligation event can be used to detect a mutation at the junction site, but not elsewhere.

Table 1 below, lists some of the features desirable for systems useful in sensitive nucleic acid diagnostics, and summarizes the abilities of each of the major amplification methods (See also, Landgren, Trends in Genetics 9:199 [1993]).

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55° C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

TABLE 1

| Feature | Method | | | | |
|---|---|---|---|---|---|
| | PCR | LCR | PCR & LCR | 3SR NASBA | Qβ |
| Amplifies Target | + | + | + | + | |
| Recognition of Independent Sequences Required | + | + | + | + | + |
| Performed at High Temp. | + | + | | | |
| Operates at Fixed Temp. | | | | + | + |
| Exponential Amplification | + | + | + | + | + |
| Generic Signal Generation | | | | | + |
| Easily Automatable | | | | | |

The basis of the amplification procedure in the PCR and LCR is the fact that the products of one cycle become usable templates in all subsequent cycles, consequently doubling the population with each cycle. The final yield of any such doubling system can be expressed as: $(1+X)^n=y$, where "X" is the mean efficiency (percent copied in each cycle), "n" is the number of cycles, and "y" is the overall efficiency, or yield of the reaction (Mullis, PCR Methods Applic., 1:1 [1991]). If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220,513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al, Nucl. Acids Res., 18:999 [1990]).)

A similar 3'-mismatch strategy is used with greater effect to prevent ligation in the LCR (Barany, PCR Meth. Applic., 1:5 [1991]). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

II. Direct Detection Technology

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats. Two examples are the "Cycling Probe Reaction" (CPR), and "Branched DNA" (bDNA).

The cycling probe reaction (CPR) (Duck et al, BioTech., 9:142 [1990]), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may be carried through sample preparation.

Branched DNA (bDNA), described by Urdea et al., Gene 61:253-264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

While both of these methods have the advantages of direct detection discussed above, neither the CPR or bDNA methods can make use of the specificity allowed by the requirement of independent recognition by two or more probe (oligonucleotide) sequences, as is common in the signal amplification methods described in Section I. above. The requirement that two oligonucleotides must hybridize to a target nucleic acid in order for a detectable signal to be generated confers an extra measure of stringency on any detection assay. Requiring two oligonucleotides to bind to a target nucleic acid reduces the chance that false "positive" results will be produced due to the non-specific binding of a probe to the target. The further requirement that the two oligonucleotides must bind in a specific orientation relative to the target, as is required in PCR, where oligonucleotides must be oppositely but appropriately oriented such that the DNA polymerase can bridge the gap between the two oligonucleotides in both directions, further enhances specificity of the detection reaction. However, it is well known to those in the art that even though PCR utilizes two oligonucleotide probes (termed primers) "non-specific" amplification (i.e., amplification of sequences not directed by the two primers used) is a common artifact. This is in part because the DNA polymerase used in PCR can accommodate very large distances, measured in nucleotides, between the oligonucleotides and thus there is a large window in which non-specific binding of an oligonucleotide can lead to exponential amplification of inappropriate product. The LCR, in contrast, cannot proceed unless the oligonucleotides used are bound to the target adjacent to each other and so the full benefit of the dual oligonucleotide hybridization is realized.

An ideal direct detection method would combine the advantages of the direct detection assays (e.g., easy quantification and minimal risk of carry-over contamination) with the specificity provided by a dual oligonucleotide hybridization assay.

SUMMARY OF THE INVENTION

The present invention relates to compositions and methods for the detection and characterization of nucleic acid sequences and variations in nucleic acid sequences. The present invention relates to methods for forming a nucleic acid cleavage structure on a solid support and cleaving the nucleic acid cleavage structure in a site-specific manner. For example, in some embodiments, he 5' nuclease activity of a variety of enzymes is used to cleave the target-dependent cleavage structure, thereby indicating the presence of specific nucleic acid sequences or specific variations thereof.

The present invention provides structure-specific cleavage agents (e.g., nucleases) from a variety of sources, including mesophilic, psychrophilic, thermophilic, and hyperthermophilic organisms. The preferred structure-specific nucleases are thermostable. Thermostable structure-specific nucleases are contemplated as particularly useful in that they operate at temperatures where nucleic acid hybridization is extremely specific, allowing for allele-specific detection (including single-base mismatches). In one embodiment, the thermostable structure-specific nucleases are thermostable 5' nucleases comprising altered polymerases derived from the native polymerases of *Thermus* species, including, but not limited to *Thermus aquaticus*, *Thermus flavus*, and *Thermus thermophilus*. However, the invention is not limited to the use of thermostable 5' nucleases. Thermostable structure-specific nucleases from the FEN-1, RAD2 and XPG class of nucleases are also preferred.

The present invention provides a method for detecting a target sequence (e.g., a mutation, polymorphism, etc), comprising providing a sample suspected of containing the target sequence; oligonucleotides capable of forming an invasive cleavage structure in the presence of the target sequence; and an agent for detecting the presence of an invasive cleavage structure; and exposing the sample to the oligonucleotides and the agent. In some embodiments, the method further comprises the step of detecting a complex comprising the agent and the invasive cleavage structure (directly or indirectly). In some embodiments, the agent comprises a cleavage agent. In some preferred embodiments, the exposing of the sample to the oligonucleotides and the agent comprises exposing the sample to the oligonucleotides and the agent under conditions wherein an invasive cleavage structure is formed between the target sequence and the oligonucleotides if the target sequence is present in the sample, wherein the invasive cleavage structure is cleaved by the cleavage agent to form a cleavage product. In some embodiments, the method further comprises the step of detecting the cleavage product. In some embodiments, the target sequence comprises a first region and a second region, the second region downstream of and contiguous to the first region, and wherein the oligonucleotides comprise first and second oligonucleotides, wherein at least a portion of the first oligonucleotide is completely complementary to the first portion of the target sequence and wherein the second oligonucleotide comprises a 3' portion and a 5' portion, wherein the 5' portion is completely complementary to the second portion of said target nucleic acid.

The present invention also provides a kit for detecting such target sequences, said kit comprising oligonucleotides capable of forming an invasive cleavage structure in the presence of the target sequence. In some embodiments, the kit further comprises an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some preferred embodiments, the target sequence comprises human cytomegalovirus viral DNA; sequence containing polymorphisms in the human apolipoprotein E gene (ApoE); sequence containing mutations in the human hemochromatosis (HH) gene; sequence containing mutations in human MTHFR; sequence containing prothrombin 20210GA polymorphism; sequence containing HR-2 mutation in human factor V gene; sequence containing single nucleotide polymorphisms in human TNF-α gene, and sequence containing the Leiden mutation in human factor V gene. In some preferred embodiments, kits comprise oligonucleotides for detecting two or more target sequences. For example, information on two or more mutations may provide medically relevant information such that kits allowing detection of the plurality of mutations would be desired (e.g., Factor V and HR-2 detection). In some preferred embodiments kits are probed containing a probe oligonucleotide comprising a sequence of SEQ ID NOs: 197, 198, 199, 200, 208, 209, 211, 212, 217, 218, 223, 224, 229, 232, 236, 237, 241, 242, or 244. In still other embodiments, kits provide oligonucleotide sets, the sets including one or more of the oligonucleotides: SEQ ID NOs:195, 197, and 198 for ApoE detection; 196, 199, and 200 for ApoE detection; 202, 208, and 209 for HH detection; 203, 211, and 212 for HH detection; 216, 217, and 218 for MTHFR detection; 222, 223, and 224 for prothrombin polymorphism detection; 228, 229, 231, and 232 for HR-2 detection; 235, 236, and 237 for TNF-α detection; 240, 241, and 242 for Factor V detection; and 243, 244, 246, and 247 for MRSA detection.

The present invention also provides methods for detecting the presence of a target nucleic acid molecule by detecting non-target cleavage products comprising providing: a cleavage agent; a source of target nucleic acid, the target nucleic acid comprising a first region and a second region, the second region downstream of and contiguous to the first region; a first oligonucleotide, wherein at least a portion of the first oligonucleotide is completely complementary to the first portion of the target nucleic acid; and a second oligonucleotide comprising a 3' portion and a 5' portion, wherein the 5' portion is completely complementary to the second portion of the target nucleic acid; mixing the cleavage agent, the target nucleic acid, the first oligonucleotide and the second oligonucleotide to create a reaction mixture under reaction conditions such that at least the portion of the first oligonucleotide is annealed to the first region of said target nucleic acid and wherein at least the 5' portion of the second oligonucleotide is annealed to the second region of the target nucleic acid so as to create a cleavage structure, and wherein cleavage of the cleavage structure occurs to generate non-target cleavage product; and detecting the cleavage of the cleavage structure.

The detection of the cleavage of the cleavage structure can be carried out in any manner. In some embodiments, the detection of the cleavage of the cleavage structure comprises detecting the non-target cleavage product. In yet other embodiments, the detection of the cleavage of the cleavage structure comprises detection of fluorescence, mass, or fluorescence energy transfer. Other detection methods include, but are not limited to detection of radioactivity, luminescence, phosphorescence, fluorescence polarization, and charge. In some embodiments, detection is carried out by a method comprising providing the non-target cleavage product; a composition comprising two single-stranded nucleic acids annealed so as to define a single-stranded portion of a protein binding region; and a protein; and exposing the non-target cleavage product to the single-stranded portion of the protein binding region under conditions such that the protein binds to the protein binding region. In some embodiments, the protein comprises a nucleic acid producing protein, wherein the nucleic acid producing protein binds to the protein binding region and produces nucleic acid. In some embodiments, the protein binding region is a template-dependent RNA polymerase binding region (e.g., a T7 RNA polymerase binding region). In other embodiments, the detection is carried out by a method comprising providing the non-target cleavage product; a single continuous strand of nucleic acid comprising a sequence defining a single strand of an RNA polymerase binding region; a template-dependent DNA polymerase; and a template-dependent RNA polymerase; exposing the non-target cleavage product to the RNA polymerase binding region under conditions such that the non-target cleavage product binds to a portion of the single strand of the RNA polymerase binding region to produce a bound non-target cleavage product; exposing the bound non-target cleavage product to the template-dependent DNA polymerase under conditions such that a double-stranded RNA polymerase binding region is produced; and exposing the double-stranded RNA polymerase binding region to the template-dependent RNA polymerase under conditions such that RNA transcripts are produced. In some embodiments, the method further comprises the step of detecting the RNA transcripts. In some embodiments, the template-dependent RNA polymerase is T7 RNA polymerase.

The present invention is not limited by the nature of the 3' portion of the second oligonucleotide. In some preferred embodiments, the 3' portion of the second oligonucleotide comprises a 3' terminal nucleotide not complementary to the target nucleic acid. In some embodiments, the 3' portion of the second oligonucleotide consists of a single nucleotide not complementary to the target nucleic acid.

Any of the components of the method may be attached to a solid support. For example, in some embodiments, the first oligonucleotide is attached to a solid support. In other embodiments, the second oligonucleotide is attached to a solid support.

The cleavage agent can be any agent that is capable of cleaving invasive cleavage structures. In some preferred embodiments, the cleavage agent comprises a structure-specific nuclease. In particularly preferred embodiments, the structure-specific nuclease comprises a thermostable structure-specific nuclease (e.g., a thermostable 5' nuclease). Thermostable structure-specific nucleases include, but are not limited to, those having an amino acid sequence homologous to a portion of the amino acid sequence of a thermostable DNA polymerase derived from a thermophilic organism (e.g., *Thermus aquaticus, Thermus flavus*, and *Thermus thermophilus*). In other embodiments, the thermostable structure-specific nucleases is from the FEN-1, RAD2 or XPG class of nucleases, a chimerical structures containing one or more portions of any of the above cleavage agents.

The method is not limited by the nature of the target nucleic acid. In some embodiments, the target nucleic acid is single stranded or double stranded DNA or RNA. In some embodiments, double stranded nucleic acid is rendered single stranded (e.g., by heat) prior to formation of the cleavage structure. In some embodiment, the source of target nucleic acid comprises a sample containing genomic DNA. Sample include, but are not limited to, blood, saliva, cerebral spinal fluid, pleural fluid, milk, lymph, sputum and semen.

In some embodiments, the reaction conditions for the method comprise providing a source of divalent cations. In some preferred embodiments, the divalent cation is selected from the group comprising $Mn^{2+}$ and $Mg^{2+}$ ions. In some embodiments, the reaction conditions for the method comprise providing the first and the second oligonucleotides in concentration excess compared to the target nucleic acid.

In some embodiments, the method further comprises providing a third oligonucleotide complementary to a third portion of said target nucleic acid upstream of the first portion of the target nucleic acid, wherein the third oligonucleotide is mixed with the reaction mixture.

The present invention also provides a method for detecting the presence of a target nucleic acid molecule by detecting non-target cleavage products comprising providing: a cleavage agent; a source of target nucleic acid, the target nucleic acid comprising a first region and a second region, the second region downstream of and contiguous to the first region; a plurality of first oligonucleotides, wherein at least a portion of the first oligonucleotides is completely complementary to the first portion of the target nucleic acid; a second oligonucleotide comprising a 3' portion and a 5' portion, wherein said 5' portion is completely complementary to the second portion of the target nucleic acid; mixing the cleavage agent, the target nucleic acid, the plurality of first oligonucleotides and second oligonucleotide to create a reaction mixture under reaction conditions such that at least the portion of a first oligonucleotide is annealed to the first region of the target nucleic acid and wherein at least the 5' portion of the second oligonucleotide is annealed to the second region of the target nucleic acid so as to create a cleavage structure, and wherein cleavage of the cleavage structure occurs to generate non-target cleavage product, wherein the conditions permit multiple cleavage structures to form and be cleaved from the target nucleic acid; and detecting the cleavage of said cleavage structures. In some embodiments, the conditions comprise isothermal conditions that permit the plurality of first oligonucleotides to dissociate from the target nucleic acid. While the present invention is limited by the number of cleavage structure formed on a particular target nucleic acid, in some preferred embodiments, two or more (3, 4, 5, . . . , 10, . . . , 10000, . . . ) of the plurality of first oligonucleotides form cleavage structures with a particular target nucleic acid, wherein the cleavage structures are cleaved to produce the non-target cleavage products.

The present invention also provide methods where a cleavage product from the above methods is used in a further invasive cleavage reaction. For example, the present invention provides a method comprising providing a cleavage agent; a first target nucleic acid, the first target nucleic acid comprising a first region and a second region, the second region downstream of and contiguous to the first region; a first oligonucleotide, wherein at least a portion of the first oligonucleotide is completely complementary to the first portion of the first target nucleic acid; a second oligonucleotide comprising a 3' portion and a 5' portion, wherein the 5' portion is completely complementary to the second portion of the first target nucleic acid; a second target nucleic acid, said second target nucleic acid comprising a first region and a second region, the second region downstream of and contiguous to the first region; and a third oligonucleotide, wherein at least a portion of the third oligonucleotide is completely complementary to the first portion of the second target nucleic acid; generating a first cleavage structure wherein at least said portion of the first oligonucleotide is annealed to the first region of the first target nucleic acid and wherein at least the 5' portion of the second oligonucleotide is annealed to the second region of the first target nucleic acid and wherein cleavage of the first cleavage structure occurs via the cleavage agent thereby cleaving the first oligonucleotide to generate a fourth oligonucleotide, said fourth oligonucleotide comprising a 3' portion and a 5' portion, wherein the 5' portion is completely complementary to the second portion of the second target nucleic acid; generating a second cleavage structure under conditions wherein at least said portion of the third oligonucleotide is annealed to the first region of the second target nucleic acid and wherein at least the 5' portion of the fourth oligonucleotide is annealed to the second region of the second target nucleic acid and wherein cleavage of the second cleavage structure occurs to generate a cleavage fragment; and detecting the cleavage of the second cleavage structure. In some preferred embodiments, the 3' portion of the fourth oligonucleotide comprises a 3' terminal nucleotide not complementary to the second target nucleic acid. In some embodiments, the 3' portion of the third oligonucleotide is covalently linked to the second target nucleic acid. In some embodiments, the second target nucleic acid further comprises a 5' region, wherein the 5' region of the second target nucleic acid is the third oligonucleotide. The present invention further provides kits comprising: a cleavage agent; a first oligonucleotide comprising a 5' portion complementary to a first region of a target nucleic acid; and a second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid. In some embodiments, the kit further comprises a solid support. For example, in some embodiments, the first and/or second oligonucleotide is attached to said solid support. In some embodiments, the kit further comprises a buffer solution. In some preferred embodiments, the buffer solution comprises a source of divalent cations (e.g., $Mn^{2+}$ and/or $Mg^{2+}$ ions). In some specific embodiments, the kit further comprises a third oligonucleotide complementary to a third portion of the target nucleic acid upstream of the first portion of the first target nucleic acid. In yet other embodiments, the kit further comprises a target nucleic acid. In some embodiments, the kit further comprises a second target nucleic acid. In yet other embodiments, the kit further comprises a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the kit further comprises an ARRESTOR molecule (e.g., ARRESTOR oligonucleotide).

The present invention further provides a composition comprising a cleavage structure, the cleavage structure comprising: a) a target nucleic acid, the target nucleic acid having a first region, a second region, a third region and a fourth region, wherein the first region is located adjacent to and downstream from the second region, the second region is located adjacent to and downstream from the third region and the third region is located adjacent to and downstream from the fourth region; b) a first oligonucleotide complementary to the fourth region of the target nucleic acid; c) a second oligonucleotide having a 5' portion and a 3' portion wherein the 5' portion of the second oligonucleotide contains a sequence complementary to the second region of the target nucleic acid and wherein the 3' portion of the second oligonucleotide contains a sequence complementary to the third region of the target nucleic acid; and d) a third oligonucleotide having a 5' portion and a 3' portion wherein the 5' portion of the third oligonucleotide contains a sequence complementary to the first region of the target nucleic acid and wherein the 3' portion of the third oligonucleotide contains a sequence complementary to the second region of the target nucleic acid.

The present invention is not limited by the length of the four regions of the target nucleic acid. In one embodiment, the first region of the target nucleic acid has a length of 11 to 50 nucleotides. In another embodiment, the second region of the target nucleic acid has a length of one to three nucleotides. In another embodiment, the third region of the target nucleic acid has a length of six to nine nucleotides. In yet another embodiment, the fourth region of the target nucleic acid has a length of 6 to 50 nucleotides.

The invention is not limited by the nature or composition of the of the first, second, third and fourth oligonucleotides; these oligonucleotides may comprise DNA, RNA, PNA and combinations thereof as well as comprise modified nucleotides, universal bases, adducts, etc. Further, one or more of the first, second, third and the fourth oligonucleotides may contain a dideoxynucleotide at the 3' terminus.

In one preferred embodiment, the target nucleic acid is not completely complementary to at least one of the first, the second, the third and the fourth oligonucleotides. In a particularly preferred embodiment, the target nucleic acid is not completely complementary to the second oligonucleotide.

As noted above, the present invention contemplates the use of structure-specific nucleases in detection methods. In one embodiment, the present invention provides a method of detecting the presence of a target nucleic acid molecule by detecting non-target cleavage products comprising: a) providing: i) a cleavage means, ii) a source of target nucleic acid, the target nucleic acid having a first region, a second region, a third region and a fourth region, wherein the first region is located adjacent to and downstream from the second region, the second region is located adjacent to and downstream from the third region and the third region is located adjacent to and downstream from the fourth region; iii) a first oligonucleotide complementary to the fourth region of the target nucleic acid; iv) a second oligonucleotide having a 5' portion and a 3' portion wherein the 5' portion of the second oligonucleotide contains a sequence complementary to the second region of the target nucleic acid and wherein the 3' portion of the second oligonucleotide contains a sequence complementary to the third region of the target nucleic acid; iv) a third oligonucleotide having a 5' and a 3' portion wherein the 5' portion of the third oligonucleotide contains a sequence complementary to the first region of the target nucleic acid and wherein the 3' portion of the third oligonucleotide contains a sequence complementary to the second region of the target nucleic acid; b) mixing the cleavage means, the target nucleic acid, the first oligonucleotide, the second oligonucleotide and the third oligonucleotide to create a reaction mixture under reaction conditions such that the first oligonucleotide is annealed to the fourth region of the target nucleic acid and wherein at least the 3' portion of the second oligonucleotide is annealed to the target nucleic acid and wherein at least the 5' portion of the third oligonucleotide is annealed to the target nucleic acid so as to create a cleavage structure and wherein cleavage of the cleavage structure occurs to generate non-target cleavage products, each non-target cleavage product having a 3'-hydroxyl group; and c) detecting the non-target cleavage products.

The invention is not limited by the nature of the target nucleic acid. In one embodiment, the target nucleic acid comprises single-stranded DNA. In another embodiment, the target nucleic acid comprises double-stranded DNA and prior to step c), the reaction mixture is treated such that the double-stranded DNA is rendered substantially single-stranded. In another embodiment, the target nucleic acid comprises RNA and the first and second oligonucleotides comprise DNA.

The invention is not limited by the nature of the cleavage means. In one embodiment, the cleavage means is a structure-specific nuclease; particularly preferred structure-specific nucleases are thermostable structure-specific nucleases. In one preferred embodiment, the thermostable structure-specific nuclease is encoded by a DNA sequence selected from the group consisting of SEQ ID NOS:1-3, 9, 10, 12, 21, 30, 31, 101, 106, 110, 114, 129, 131, 132, 137, 140, 141, 142, 143, 144, 145, 147, 150, 151, 153, 155, 156, 157, 158, 161, 163, 178, 180, and 182.

In another preferred embodiment, the thermostable structure-specific nuclease is a nuclease from the FEN-1/RAD2/XPG class of nucleases. In another preferred embodiment the thermostable structure specific nuclease is a chimerical nuclease.

In an alternative preferred embodiment, the detection of the non-target cleavage products comprises electrophoretic separation of the products of the reaction followed by visualization of the separated non-target cleavage products.

In another preferred embodiment, one or more of the first, second, and third oligonucleotides contain a dideoxynucleotide at the 3' terminus. When dideoxynucleotide-containing oligonucleotides are employed, the detection of the non-target cleavage products preferably comprises: a) incubating the non-target cleavage products with a template-independent polymerase and at least one labeled nucleoside triphosphate under conditions such that at least one labeled nucleotide is added to the 3'-hydroxyl group of the non-target cleavage products to generate labeled non-target cleavage products; and b) detecting the presence of the labeled non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase are employed in the detection step, the second oligonucleotide may contain a 5' end label, the 5' end label being a different label than the label present upon the labeled nucleoside triphosphate. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

In another embodiment, detecting the non-target cleavage products comprises: a) incubating the non-target cleavage products with a template-independent polymerase and at least one nucleoside triphosphate under conditions such that at least one nucleotide is added to the 3'-hydroxyl group of the non-target cleavage products to generate tailed non-target cleavage products; and b) detecting the presence of the tailed non-target cleavage products. The invention is not limited by the nature of the template-independent polymerase employed; in one embodiment, the template-independent polymerase is selected from the group consisting of terminal deoxynucleotidyl transferase (TdT) and poly A polymerase.

When TdT or polyA polymerase are employed in the detection step, the second oligonucleotide may contain a 5' end label. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

In a preferred embodiment, the reaction conditions comprise providing a source of divalent cations; particularly preferred divalent cations are $Mn^{2+}$ and $Mg^{2+}$ ions.

The present invention further provides a method of detecting the presence of a target nucleic acid molecule by detecting non-target cleavage products comprising: a) providing: i) a cleavage means, ii) a source of target nucleic acid, the target nucleic acid having a first region, a second region and a third region, wherein the first region is located adjacent to and downstream from the second region and wherein the second region is located adjacent to and downstream from the third region; iii) a first oligonucleotide having a 5' and a 3' portion wherein the 5' portion of the first oligonucleotide contains a sequence complementary to the second-region of the target nucleic acid and wherein the 3' portion of the first oligonucleotide contains a sequence complementary to the third region of the target nucleic acid; iv) a second oligonucleotide having a length between eleven to fifteen nucleotides and further having a 5' and a 3' portion wherein the 5' portion of the second oligonucleotide contains a sequence complementary to the first region of the target nucleic acid and wherein the 3' portion of the second oligonucleotide contains a sequence complementary to the second region of the target nucleic acid; b) mixing the cleavage means, the target nucleic acid, the first oligonucleotide and the second oligonucleotide to create a reaction mixture under reaction conditions such that at least the 3' portion of the first oligonucleotide is annealed to the target nucleic acid and wherein at least the 5' portion of the second oligonucleotide is annealed to the target nucleic acid so as to create a cleavage structure and wherein cleavage of the cleavage structure occurs to generate non-target cleavage products, each non-target cleavage product having a 3'-hydroxyl group; and c) detecting the non-target cleavage products. In a preferred embodiment the cleavage means is a structure-specific nuclease, preferably a thermostable structure-specific nuclease.

The invention is not limited by the length of the various regions of the target nucleic acid. In a preferred embodiment, the second region of the target nucleic acid has a length between one to five nucleotides. In another preferred embodiment, one or more of the first and the second oligonucleotides contain a dideoxynucleotide at the 3' terminus. When dideoxynucleotide-containing oligonucleotides are employed, the detection of the non-target cleavage products preferably comprises: a) incubating the non-target cleavage products with a template-independent polymerase and at least one labeled nucleoside triphosphate under conditions such that at least one labeled nucleotide is added to the 3'-hydroxyl group of the non-target cleavage products to generate labeled non-target cleavage products; and b) detecting the presence of the labeled non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase is employed in the detection step, the second oligonucleotide may contain a 5' end label, the 5' end label being a different label than the label present upon the labeled nucleoside triphosphate. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

In another embodiment, detecting the non-target cleavage products comprises: a) incubating the non-target cleavage products with a template-independent polymerase and at least one nucleoside triphosphate under conditions such that at least one nucleotide is added to the 3'-hydroxyl group of the non-target cleavage products to generate tailed non-target cleavage products; and b) detecting the presence of the tailed non-target cleavage products. The invention is not limited by the nature of the template-independent polymerase employed; in one embodiment, the template-independent polymerase is selected from the group consisting of terminal deoxynucleotidyl transferase (TdT) and poly A polymerase. When TdT or polyA polymerase are employed in the detection step, the second oligonucleotide may contain a 5' end label. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin.

The novel detection methods of the invention may be employed for the detection of target DNAs and RNAs including, but not limited to, target DNAs and RNAs comprising wild type and mutant alleles of genes, including genes from humans or other animals that are or may be associated with disease or cancer. In addition, the methods of the invention may be used for the detection of and/or identification of strains of microorganisms, including bacteria, fungi, protozoa, ciliates and viruses (and in particular for the detection and identification of RNA viruses, such as HCV).

The present invention further provides improved enzymatic cleavage means. In one embodiment, the present invention provides a thermostable structure-specific nuclease having an amino acid sequence selected from the group consisting of SEQ ID NOS:102, 107, 130, 132, 179, 181, 183, 184, 185, 186, 187, and 188. In another embodiment, the nuclease is encoded by a DNA sequence selected from the group consisting of SEQ ID NOS:101, 106, 129 131, 178, 180, and 182.

The present invention also provides a recombinant DNA vector comprising DNA having a nucleotide sequence encoding a structure-specific nuclease, the nucleotide sequence selected from the group consisting of SEQ ID NOS:101, 106, 129 131, 137, 140, 141, 142, 143, 144, 145, 147, 150, 151, 153, 155, 156, 157, 158, 161, 163, 178, 180, and 182. In a preferred embodiment, the invention provides a host cell transformed with a recombinant DNA vector comprising DNA having a nucleotide sequence encoding a structure-specific nuclease, the nucleotide sequence selected from the group consisting of SEQ ID NOS:101, 106, 129, 131, 178, 180, and 182. The invention is not limited by the nature of the host cell employed. The art is well aware of expression vectors suitable for the expression of nucleotide sequences encoding structure-specific nucleases which can be expressed in a variety of prokaryotic and eukaryotic host cells. In a preferred embodiment, the host cell is an *Escherichia coli* cell.

The present invention provides purified FEN-1 endonucleases. In one embodiment, the present invention provides *Pyrococcus woesei* FEN-1 endonuclease. In a preferred embodiment, the purified *Pyrococcus woesei* FEN-1 endonuclease has a molecular weight of about 38.7 kilodaltons (the molecular weight may be conveniently estimated using SDS-PAGE as described in Ex. 28).

The present invention further provides an isolated oligonucleotide encoding a *Pyrococcus woesei* FEN-1 endonuclease, the oligonucleotide having a region capable of hybridizing to an oligonucleotide sequence selected from the group consisting of SEQ ID NOS:116-119. In a preferred embodiment, the oligonucleotide encoding the purified *Pyrococcus woesei* FEN-1 endonuclease is operably linked to a heterologous promoter. The present invention is not limited by the nature of the heterologous promoter employed; in a preferred embodiment, the heterologous promoter is an inducible promoter (the promoter chosen will depend upon the host cell chosen for expression as is known in the art). The invention is not limited by the nature of the inducible promoter employed. Preferred inducible promoters include the -$P_L$ promoter, the tac promoter, the trp promoter and the trc promoter.

In another preferred embodiment, the invention provides a recombinant DNA vector comprising an isolated oligonucleotide encoding a *Pyrococcus woesei* (Pwo) FEN-1 endonuclease, the oligonucleotide having a region capable of hybridizing to an oligonucleotide sequence selected from the group consisting of SEQ ID NOS:116-119. Host cells transformed with these recombinant vectors are also provided. In a preferred embodiment, the invention provides a host cell transformed with a recombinant DNA vector comprising DNA having a region capable of hybridizing to an oligonucleotide sequence selected from the group consisting of SEQ ID NOS: 116-119; these vectors may further comprise a heterologous promoter operably linked to the Pwo FEN-1-encoding polynucleotides. The invention is not limited by the nature of the host cell employed. The art is well aware of expression vectors suitable for the expression of Pwo FEN-1-encoding polynucleotides which can be expressed in a variety of prokaryotic and eukaryotic host cells. In a preferred embodiment, the host cell is an *Escherichia coli* cell.

In yet another embodiment, the invention provides an isolated oligonucleotide comprising a gene encoding a *Pyrococcus woesei* FEN-1 endonuclease having a molecular weight of about 38.7 kilodaltons. In another embodiment, the encoding a *Pyrococcus woesei* FEN-1 endonuclease is operably linked to a heterologous promoter. The present invention is not limited by the nature of the heterologous promoter employed; in a preferred embodiment, the heterologous promoter is an inducible promoter (the promoter chosen will depend upon the host cell chosen for expression as is known in the art). The invention is not limited by the nature of the inducible promoter employed. Preferred inducible promoter include the -$P_L$ promoter, the tac promoter, the trp promoter and the trc promoter.

The invention further provides recombinant DNA vectors comprising DNA having a nucleotide sequence encoding FEN-1 endonucleases. In one preferred embodiment, the present invention provides a *Pyrococcus woesei* FEN-1 endonuclease having a molecular weight of about 38.7 kilodaltons. Still further, a host cell transformed with a recombinant DNA vector comprising DNA having a nucleotide sequence encoding FEN-1 endonuclease. In a preferred embodiment, the host cell is transformed with a recombinant DNA vector comprising DNA having a nucleotide sequence encoding a *Pyrococcus woesei* FEN-1 endonuclease having a molecular weight of about 38.7 kilodaltons is provided. The invention is not limited by the nature of the host cell employed. The art is well aware of expression vectors suitable for the expression of Pwo FEN-1-encoding polynucleotides which can be expressed in a variety of prokaryotic and eukaryotic host cells. In a preferred embodiment, the host cell is an *Escherichia coli* cell.

Thus, the present invention provides multiple purified FEN-1 endonucleases, both purified native forms of the endonucleases, as well as recombinant endonucleases. In preferred embodiments, the purified FEN-1 endonucleases are obtained from archaebacterial or eubacterial organisms. In particularly preferred embodiments, the FEN-1 endonucleases are obtained from organisms selected from the group consisting of *Archaeoglobus fulgidus, Methanobacterium thermoautotrophicum, Sulfolobus solfataricus, Pyrobaculum aerophilum, Thermococcus litoralis, Archaeaglobus venefi-cus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii,* and *Aeropyrum pernix*. In a preferred embodiment, the purified FEN-1 endonucleases have molecular weights of about 39 kilodaltons (the molecular weight may be conveniently estimated using SDS-PAGE as described in Ex. 28).

The present invention further provides isolated oligonucleotides encoding *Archaeoglobus fulgidus* and *Methanobacterium thermoautotrophicum* FEN-1 endonucleases, the oligonucleotides each having a region capable of hybridizing to at least a portion of an oligonucleotide sequence, wherein the oligonucleotide sequence is selected from the group consisting of SEQ ID NOS:170, 171, 172, and 173. In some preferred embodiment, the oligonucleotides encoding the *Archaeoglobus fulgidus* and *Methanobacterium thermoautotrophicum* FEN-1 endonucleases are operably linked to heterologous promoters. However, it is not intended that the present invention be limited by the nature of the heterologous promoter employed. It is contemplated that the promoter chosen will depend upon the host cell chosen for expression as is known in the art. In some preferred embodiments, the heterologous promoter is an inducible promoter. The invention is not limited by the nature of the inducible promoter employed. Preferred inducible promoters include the -$P_L$ promoter, the tac promoter, the trp promoter and the trc promoter.

In another preferred embodiment, the invention provides recombinant DNA vectors comprising isolated oligonucleotides encoding *Archaeoglobus fulgidus* or *Methanobacterium thermoautotrophicum* FEN-1 endonucleases, each oligonucleotides having a region capable of hybridizing to at least a portion of an oligonucleotide sequence, wherein the oligonucleotide sequence is selected from the group consisting of SEQ ID NOS:170, 171, 172, and 173. The present invention further provides host cells transformed with these recombinant vectors. In a preferred embodiment, the invention provides a host cell transformed with a recombinant DNA vector comprising DNA having a region capable of hybridizing to at least a portion of an oligonucleotide sequence, wherein the oligonucleotide sequence is selected from the group consisting of SEQ ID NOS:170, 171, 172 and 173. In some embodiments, these vectors may further comprise a heterologous promoter operably linked to the FEN-1-encoding polynucleotides. The invention is not limited by the nature of the host cell employed. The art is well aware of expression vectors suitable for the expression of FEN-1-encoding polynucleotides which can be expressed in a variety of prokaryotic and eukaryotic host cells. In a preferred embodiment, the host cell is an *Escherichia coli* cell.

The present invention further provides chimeric structure-specific nucleases. In one embodiment, the present invention provides chimeric endonucleases comprising amino acid portions derived from the endonucleases selected from the group of FEN-1, XPG and RAD homologs. In a preferred embodiment, the chimeric endonucleases comprise amino acid portions derived from the FEN-1 endonucleases selected from the group of *Pyrococcus furiosus, Methanococcus jannaschi, Pyrococcus woesei, Archaeoglobus fulgidus, Methanobacterium thermoautotrophicum, Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii,* and *Aeropyrum pernix*. In a more preferred embodiment, the chimeric FEN-1 endonucleases have molecular weights of about 39 kilodaltons (the molecular weight may be conveniently estimated using SDS-PAGE as described in Ex. 28).

The present invention further provides isolated oligonucleotides encoding chimeric endonucleases. In one embodiment, the oligonucleotides encoding the chimeric endonucleases comprise nucleic acid sequences derived from the genes selected from the group of FEN-1, XPG and RAD homologs. In a preferred embodiment the oligonucleotides encoding the chimeric endonucleases comprise nucleic acid sequences derived from the genes encoding the FEN-1 endonucleases selected from the group of *Pyrococcus furiosus, Methanococcus jannaschi, Pyrococcus woesei, Archaeoglobus fulgidus, Methanobacterium thermoautotrophicum, Sulfolobus solfataricus, Pyrohaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii,* and *Aeropyrum pernix*. In a particularly preferred embodiment, the genes for the chimeric endonucleases are operably linked to heterologous promoters. The present invention is not limited by the nature of the heterologous promoter employed. It is contemplated that the promoter chosen will depend upon the host cell selected for expression, as is known in the art. In preferred embodiments, the heterologous promoter is an inducible promoter. The invention is not limited by the nature of the inducible promoter employed. Preferred inducible promoters include the -$P_L$ promoter, the tac promoter, the trp promoter and the trc promoter.

In another preferred embodiment, the invention provides recombinant DNA vectors comprising isolated oligonucleotides encoding the chimeric endonucleases described above. In one embodiment, the recombinant DNA vectors comprise isolated oligonucleotides encoding nucleic acid sequences derived from the genes selected from the group of FEN-1, XPG and RAD homologs. In a preferred embodiment, the recombinant DNA vectors comprise isolated oligonucleotides encoding the chimeric endonucleases comprising nucleic acid sequences derived from the genes encoding the FEN-1 endonucleases selected from the group of *Pyrococcus furiosus, Methanococcus jannaschi, Pyrococcus woesei, Archaeoglobus fulgidus, Methanobacterium thermoautotrophicum, Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii,* and *Aeropyrum pernix*. These vectors may further comprise a heterologous promoter operably linked to the chimeric nuclease-encoding polynucleotides.

Host cells transformed with these recombinant vectors are also provided. The invention is not limited by the nature of the host cell employed. The art is well aware of expression vectors suitable for the expression of FEN-1-encoding polynucleotides which can be expressed in a variety of prokaryotic and eukaryotic host cells. In a preferred embodiment, the host cell is an *Escherichia coli* cell.

The present invention further provides mixtures comprising a first structure-specific nuclease, wherein the first nuclease consists of a purified FEN-1 endonuclease and a second structure-specific nuclease. In preferred embodiments, the second structure-specific nuclease of the mixture is selected from the group comprising *Pyrococcus woesei* FEN-1 endonuclease, *Pyrococcus furiosus* FEN-1, *Methanococcus jannaschii* FEN-1 endonuclease, *Methanobacterium thermoautotrophicum* FEN-1 endonuclease, *Archaeoglobus fulgidus* FEN-1, *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix,* and chimerical FEN-1 endonucleases. In alternative embodiments, the purified FEN-1 endonuclease of the mixture is selected from the group consisting *Pyrococcus woesei* FEN-1 endonuclease, *Pyrococcus furiosus* FEN-1 endonuclease, *Methanococcus jannaschii* FEN-1 endonuclease, *Methanobacterium thermoautotrophicum* FEN-1 endonuclease, *Archaeoglobus fulgidus* FEN-1, *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix,* and chimerical FEN-1 endonucleases. In yet other preferred embodiments of the mixture, the second nuclease is a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase. In some preferred embodiments of the mixture, the second nuclease is selected from the group consisting of the Cleavase® BN enzyme, *Thermus aquaticus* DNA polymerase, *Thermus thermophilus* DNA polymerase, *Escherichia coli* ExoIII, *Saccharomyces cerevisiae* Rad1/Rad10 complex.

The present invention also provides methods for treating nucleic acid, comprising: a) providing a purified FEN-1 endonuclease; and a nucleic acid substrate; b) treating the nucleic acid substrate under conditions such that the substrate forms one or more cleavage structures; and c) reacting the endonuclease with the cleavage structures so that one or more cleavage products are produced. In some embodiments, the purified FEN-1 endonuclease is selected from the group consisting *Pyrococcus woesei* FEN-1 endonuclease, *Pyrococcus furiosus* FEN-1 endonuclease, *Methanococcus jannaschii* FEN-1 endonuclease, *Methanobacterium thermoautotrophicum* FEN-1 endonuclease, *Archaeoglobus fulgidus* FEN-1, *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix,* and chimerical FEN-1 endonucleases. In other embodiments, the method further comprises providing a structure-specific nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase.

In alternative embodiments of the methods, a portion of the amino acid sequence of the second nuclease is homologous to a portion of the amino acid sequence of a thermostable DNA polymerase derived from a eubacterial thermophile of the genus *Thermus*. In yet other embodiments, the thermophile is selected from the group consisting of *Thermus aquaticus, Thermus flavus* and *Thermus thermophilus*. In some alternative embodiments, the structure-specific nuclease is selected from the group consisting of the Cleavase® BN enzyme, *Thermus aquaticus* DNA polymerase, *Thermus thermophilus* DNA polymerase, *Escherichia coli* ExoIII, *Saccharomyces cerevisiae* Rad1/Rad10 complex. In some preferred embodiments, the structure-specific nuclease is the Cleavase® BN nuclease. In yet other embodiments, the nucleic acid of step (a) is substantially single-stranded. In further embodiments, the nucleic acid is selected from the group consisting of RNA and DNA. In yet further embodiments, the nucleic acid of step (a) is double stranded.

In other embodiments of the methods, the treating of step (b) comprises: rendering the double-stranded nucleic acid substantially single-stranded; and exposing the single-stranded nucleic acid to conditions such that the single-stranded nucleic acid has secondary structure. In some preferred embodiments, the double stranded nucleic acid is rendered substantially single-stranded by the use of increased temperature. In alternative preferred embodiments, the method further comprises the step of detecting the one or more cleavage products.

The present invention also provides methods for treating nucleic acid, comprising: a) providing: a first structure-specific nuclease consisting of a purified FEN-1 endonuclease in a solution containing manganese; and a nucleic acid substrate; b) treating the nucleic acid substrate with increased temperature such that the substrate is substantially single-stranded; c) reducing the temperature under conditions such that the single-stranded substrate forms one or more cleavage structures; d) reacting the cleavage means with the cleavage structures so that one or more cleavage products are produced; and e) detecting the one or more cleavage products. In some embodiments of the methods, the purified FEN-1 endonuclease is selected from the group consisting *Pyrococcus woesei* FEN-1 endonuclease, *Pyrococcus furiosus* FEN-1 endonuclease, *Methanococcus jannaschii* FEN-1 endonuclease, *Methanobacterium thermoautotrophicum* FEN-1 endonuclease, *Archaeoglobus fulgidus* FEN-1, *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix*, and chimerical FEN-1 endonucleases. In alternative embodiments, the methods further comprise providing a second structure-specific nuclease. In some preferred embodiments, the second nuclease is selected from the group consisting of the Cleavase® BN enzyme, *Thermus aquaticus* DNA polymerase, *Thermus thermophilus* DNA polymerase, *Escherichia coli* ExoIII, and the *Saccharomyces cerevisiae* Rad1/Rad10 complex. In yet other preferred embodiments, the second nuclease is a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase. In yet other embodiments, the nucleic acid is selected from the group consisting of RNA and DNA. In further embodiments, the nucleic acid of step (a) is double stranded.

The present invention also provides nucleic acid treatment kits, comprising: a) a composition comprising at least one purified FEN-1 endonuclease; and b) a solution containing manganese. In some embodiments of the kits, the purified FEN-1 endonuclease is selected from the group consisting *Pyrococcus woesei* FEN-1 endonuclease, *Pyrococcus furiosus* FEN-1 endonuclease, *Methanococcus jannaschii* FEN-1 endonuclease, *Methanobacterium thermoautotrophicum* FEN-1 endonuclease, *Archaeoglobus fulgidus* FEN-1, *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii, Aeropyrum pernix*, and chimerical FEN-1 endonucleases. In other embodiments, the kits further comprise at least one second structure-specific nuclease. In some preferred embodiments, the second nuclease is a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase. In yet other embodiments of the kits, the portion of the amino acid sequence of the second nuclease is homologous to a portion of the amino acid sequence of a thermostable DNA polymerase derived from a eubacterial thermophile of the genus *Thermus*. In further embodiments, the thermophile is selected from the group consisting of *Thermus aquaticus, Thermus flavus* and *Thermus thermophilus*. In yet other preferred embodiments, the kits further comprise reagents for detecting the cleavage products.

The present invention further provides any of the compositions, mixtures, methods, and kits described herein, used in conjunction with endonucleases comprising *Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii*, and *Aeropyrum pernix* endonucleases. These include compositions comprising purified FEN-1 endonucleases from the organisms (including specific endonucleases described by sequences provided herein, as well as, variants and homologues), kits comprising these compositions, composition comprising chimerical endonucleases comprising at least a portion of the endonucleases from these organisms, kits comprising such compositions, compositions comprising nucleic acids encoding the endonucleases from these organisms (including vectors and host cells), kits comprising such compositions, antibodies generated to the endonucleases, mixtures comprising endonucleases from these organisms, methods of using the endonuclease in cleavage assays (e.g., invasive cleavage assays, CFLP, etc.), and kits containing components useful for such methods. Examples describing the generation, structure, use, and characterization of these endonucleases are provided herein.

The present invention also provides methods for improving the methods and enzymes disclosed herein. For example, the present invention provides methods of improving enzymes for any intended purpose (e.g., use in cleavage reactions, amplification reactions, binding reactions, or any other use) comprising the step of providing an enzyme disclosed herein and modifying the enzyme (e.g., altering the amino acid sequence, adding or subtracting sequence, adding post-translational modifications, adding any other component whether biological or not, or any other modification). Likewise, the present invention provides methods for improving the methods disclosed herein comprising, conducting the method steps with one or more changes (e.g., change in a composition provided in the method, change in the order of the steps, or addition or subtraction of steps).

The improved performance in a detection assay may arise from any one of, or a combination of several improved features. For example, in one embodiment, the enzyme of the present invention may have an improved rate of cleavage (kcat) on a specific targeted structure, such that a larger amount of a cleavage product may be produced in a given time span. In another embodiment, the enzyme of the present invention may have a reduced activity or rate in the cleavage of inappropriate or non-specific structures. For example, in certain embodiments of the present invention, one aspect of improvement is that the differential between the detectable amount of cleavage of a specific structure and the detectable amount of cleavage of any alternative structures is increased. As such, it is within the scope of the present invention to provide an enzyme having a reduced rate of cleavage of a specific target structure compared to the rate of the native enzyme, and having a further reduced rate of cleavage of any alternative structures, such that the differential between the detectable amount of cleavage of the specific structure and the detectable amount of cleavage of any alternative structures is increased. However, the present invention is not limited to enzymes that have an improved differential.

The present invention contemplates structure-specific nucleases from a variety of sources, including, but not limited to, mesophilic, psychrophilic, thermophilic, and hyperthermophilic organisms. The preferred structure-specific nucleases are thermostable. Thermostable structure-specific nucleases are contemplated as particularly useful in that they allow the INVADER assay (See e.g., U.S. Pat. Nos. 5,846, 717, 5,985,557, 5,994,069, and 6,001,567 and PCT Publications WO 97/27214 and WO 98/42873, incorporated herein by reference in their entireties) to be operated near the melting temperature ($T_m$) of the downstream probe oligonucleotide, so that cleaved and uncleaved probes may cycle on and off the target during the course of the reaction. In one embodiment, the thermostable structure-specific enzymes are thermostable 5' nucleases that are selected from the group comprising altered polymerases derived from the native polymerases of *Thermus* species, including, but not limited to, *Thermus aquaticus, Thermus flavus, Thermus thermophilus, Thermus filiformis*, and *Thermus scotoductus*. However, the invention is not limited to the use of thermostable 5' nucleases. For example, certain embodiments of the present invention utilize short oligonucleotide probes that may cycle on and off of the target at low temperatures, allowing the use of non-thermostable enzymes.

In some preferred embodiments, the present invention provides a composition comprising an enzyme, wherein the enzyme comprises a heterologous functional domain, wherein the heterologous functional domain provides altered (e.g., improved) functionality in a nucleic acid cleavage assay. The present invention is not limited by the nature of the nucleic acid cleavage assay. For example, nucleic acid cleavage assays include any assay in which a nucleic acid is cleaved, directly or indirectly, in the presence of the enzyme. In certain preferred embodiments, the nucleic acid cleavage assay is an invasive cleavage assay. In particularly preferred embodiments, the cleavage assay utilizes a cleavage structure having at least one RNA component. In another particularly preferred embodiment, the cleavage assay utilizes a cleavage structure having at least one RNA component, wherein a DNA member of the cleavage structure is cleaved.

The present invention is not limited by the nature of the altered functionality provided by the heterologous functional domain. Illustrative examples of alterations include, but are not limited to, enzymes where the heterologous functional domain comprises an amino acid sequence (e.g., one or more amino acids) that provides an improved nuclease activity, an improved substrate binding activity and/or improved background specificity in a nucleic acid cleavage assay.

The present invention is not limited by the nature of the heterologous functional domain. For example, in some embodiments, the heterologous functional domain comprises two or more amino acids from a polymerase domain of a polymerase (e.g., introduced into the enzyme by insertion of a chimerical functional domain or created by mutation). In certain preferred embodiment, at least one of the two or more amino acids is from a palm or thumb region of the polymerase domain. The present invention is not limited by the identity of the polymerase from which the two or more amino acids are selected. In certain preferred embodiments, the polymerase comprises *Thermus thermophilus* polymerase. In particularly preferred embodiments, the two or more amino acids are from amino acids 300-650 of SEQ ID NO:267.

The novel enzymes of the invention may be employed for the detection of target DNAs and RNAs including, but not limited to, target DNAs and RNAs comprising wild type and mutant alleles of genes, including, but not limited to, genes from humans, other animal, or plants that are or may be associated with disease or other conditions. In addition, the enzymes of the invention may be used for the detection of and/or identification of strains of microorganisms, including bacteria, fungi, protozoa, ciliates and viruses (and in particular for the detection and identification of viruses having RNA genomes, such as the Hepatitis C and Human Immunodeficiency viruses). For example, the present invention provides methods for cleaving a nucleic acid comprising providing: an enzyme of the present invention and a substrate nucleic acid; and exposing the substrate nucleic acid to the enzyme (e.g., to produce a cleavage product that may be detected).

The present invention also provides a system comprising oligonucleotides capable of hybridizing to a target nucleic acid to form an invasive cleavage structure and a solid support, wherein one or more of said oligonucleotides is attached to said solid support. In some embodiments, the method further comprises use of an agent for detecting the presence of said invasive cleavage structure (e.g., a cleavage agent such as those described herein). The present invention is not limited by the nature of the reaction components attached to the solid support. For example, in some embodiments, a probe oligonucleotide is attached to the solid support. In other embodiments, an INVADER oligonucleotide is attached to the solid support. In yet other embodiments, both the probe and the INVADER oligonucleotides are attached to the solid support. In still further embodiments, other reactions components such as target nucleic acids, cleavage agents, stacker oligonucleotides, FRET cassettes, secondary reaction components, and the like are attached to the solid support.

In some embodiments, oligonucleotides or other components are attached to solid supports through a spacer molecule. While the present invention is not limited by the nature of the spacer molecule, in some embodiments, spacer molecules include, but are not limited to, carbon chains, polynucleotides, biotin, and polyglycols.

The present invention is also not limited by the nature of the solid support. In some preferred embodiments, solid supports comprise glass, latex, or hydrogel solid supports. In other preferred embodiments, the solid supports comprise a bead, mutli-well plate, column, or microarray. In still further preferred embodiments, the solid supports are coated with a material (e.g., gold, streptavidin, etc.).

The present invention also provides methods using such systems. For example, the present invention provides a method for characterizing a nucleic acid comprising providing: 1) a sample suspected of containing a target nucleic acid; 2) oligonucleotides capable of hybridizing to said target nucleic acid to form an invasive cleavage structure; 3) a solid support, wherein one or more of said oligonucleotides is attached to said solid support; and 4) an agent capable of detecting the presence of an invasive cleavage structure; and exposing the sample to the oligonucleotides and the agent. In some embodiments, the exposing step comprises exposing the sample to the oligonucleotides and the agent under conditions wherein an invasive cleavage structure is formed between a target nucleic acid and the oligonucleotides if the target nucleic acid is present in the sample. In some embodiments, the method further comprises the step of detecting the invasive cleavage structure.

The present invention also provides compositions and methods employing a solid support, wherein a single oligonucleotide is capable of sequentially forming multiple cleavage structures with multiple other oligonucleotides (e.g., probe oligonucleotides). For example, the present invention provides a method for cleaving multiple oligonucleotides comprising providing: 1) a plurality of first oligonucleotides attached to a solid support; 2) a second oligonucleotide attached to said solid support; and 3) a cleavage agent; and exposing the solid support to the cleavage agent under conditions such that: 1) a first cleavage structure is formed, the first cleavage structure comprising one of the first oligonucleotides and the second oligonucleotide; 2) the cleavage agent cleaves the first oligonucleotide in the first cleavage structure to produce a first cleavage fragment; 3) after cleavage of the first oligonucleotide, a second cleavage structure is formed, the second cleavage structure comprising a second of the first oligonucleotides and the second oligonucleotide; and 4) the cleavage agent cleaves the first oligonucleotide in the second cleavage structure to produce a second cleavage fragment. In some embodiments, the reaction conditions comprise exposing a target nucleic acid (or a sample suspected of containing a target nucleic acid) to the solid support. In some embodiments, the method further comprises detecting the presence of the first or the second cleavage fragments.

The present invention also provides a composition comprising a solid support; said solid support attached to a plurality of first oligonucleotides and a second oligonucleotide, wherein the second oligonucleotide is capable of forming an invasive cleavage structure with each of the plurality of first oligonucleotides in the presence of a target nucleic acid. In some embodiments, the plurality of first oligonucleotides comprises three or more (e.g., 3, 4, 5, 6, ..., 10, ...) first oligonucleotides. In some embodiments, any other reaction component (e.g., cleavage agent, target nucleic acid, etc.) may be attached to the solid support.

Definitions

To facilitate an understanding of the present invention, a number of terms and phrases are defined below:

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

"High stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42 C when a probe of about 500 nucleotides in length is employed.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "LTR" as used herein refers to the long terminal repeat found at each end of a provirus (i.e., the integrated form of a retrovirus). The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "label" as used herein refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases that cleave nucleic acid molecules without regard to secondary structure (i.e., no formation of a duplexed structure is required).

The term "folded cleavage structure" as used herein, refers to a region of a single-stranded nucleic acid substrate containing secondary structure, the region being cleavable by an enzymatic cleavage means. The cleavage structure is a substrate for specific cleavage by the cleavage means in contrast to a nucleic acid molecule that is a substrate for non-specific cleavage by agents such as phosphodiesterases which cleave nucleic acid molecules without regard to secondary structure (i.e., no folding of the substrate is required).

As used herein, the term "folded target" refers to a nucleic acid strand that contains at least one region of secondary structure (i.e., at least one double stranded region and at least one single-stranded region within a single strand of the nucleic acid). A folded target may comprise regions of tertiary structure in addition to regions of secondary structure.

The term "cleavage means" or "cleavage agent" as used herein refers to any means that is capable of cleaving a cleavage structure, including but not limited to enzymes. The cleavage means may include native DNAPs having 5' nuclease activity (e.g., Taq DNA polymerase, E. coli DNA polymerase I) and, more specifically, modified DNAPs having 5' nuclease but lacking synthetic activity. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means is not restricted to enzymes having solely 5' nuclease activity. The cleavage means may include nuclease activity provided from a variety of sources including the Cleavase enzymes, the FEN-1 endonucleases (including RAD2 and XPG proteins), Taq DNA polymerase and E. coli DNA polymerase I.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

As used herein, the term "signal probe" refers to a probe oligonucleotide containing a detectable moiety. The present invention is not limited by the nature of the detectable moiety.

As used herein, the terms "quencher" and "quencher moiety" refer to a molecule or material that suppresses or diminishes the detectable signal from a detectable moiety when the quencher is in the physical vicinity of the detectable moiety. For example, in some embodiments, quenchers are molecules that suppress the amount of detectable fluorescent signal from an oligonucleotide containing a fluorescent label when the quencher is physically near the fluorescent label.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide-whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism which is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "charge-balanced" oligonucleotide refers to an oligonucleotide (the input oligonucleotide in a reaction) that has been modified such that the modified oligonucleotide bears a charge, such that when the modified oligonucleotide is either cleaved (i.e., shortened) or elongated, a resulting product bears a charge different from the input oligonucleotide (the "charge-unbalanced" oligonucleotide) thereby permitting separation of the input and reacted oligonucleotides on the basis of charge. The term "charge-balanced" does not imply that the modified or balanced oligonucleotide has a net neutral charge (although this can be the case). Charge-balancing refers to the design and modification of an oligonucleotide such that a specific reaction product generated from this input oligonucleotide can be separated on the basis of charge from the input oligonucleotide.

For example, in an INVADER oligonucleotide-directed cleavage assay in which the probe oligonucleotide bears the sequence: 5' TTCTTTTCACCAGCGAGACGGG 3' (i.e., SEQ ID NO:61 without the modified bases) and cleavage of the probe occurs between the second and third residues, one possible charge-balanced version of this oligonucleotide would be: 5' Cy3-AminoT-Amino-TCTTTTCACCAGC-GAGAC GGG 3'. This modified oligonucleotide bears a net negative charge. After cleavage, the following oligonucleotides are generated: 5' Cy3-AminoT-Amino-T 3' and 5' CTTTTCACCAGCGAGACGGG 3' (residues 3-22 of SEQ ID NO:61). 5' Cy3-AminoT-Amino-T 3' bears a detectable moiety (the positively-charged Cy3 dye) and two amino-modified bases. The amino-modified bases and the Cy3 dye contribute positive charges in excess of the negative charges contributed by the phosphate groups and thus the 5' Cy3-AminoT-Amino-T 3'oligonucleotide has a net positive charge. The other, longer cleavage fragment, like the input probe, bears a net negative charge. Because the 5' Cy3-AminoT-Amino-T 3'fragment is separable on the basis of charge from the input probe (the charge-balanced oligonucleotide), it is referred to as a charge-unbalanced oligonucleotide. The longer cleavage product cannot be separated on the basis of charge from the input oligonucleotide as both oligonucleotides bear a net negative charge; thus, the longer cleavage product is not a charge-unbalanced oligonucleotide.

The term "net neutral charge" when used in reference to an oligonucleotide, including modified oligonucleotides, indicates that the sum of the charges present (i.e., R—NH3+ groups on thymidines, the N3 nitrogen of cytosine, presence or absence or phosphate groups, etc.) under the desired reaction or separation conditions is essentially zero. An oligonucleotide having a net neutral charge would not migrate in an electrical field.

The term "net positive charge" when used in reference to an oligonucleotide, including modified oligonucleotides, indicates that the sum of the charges present (i.e., R—NH3+ groups on thymidines, the N3 nitrogen of cytosine, presence or absence or phosphate groups, etc.) under the desired reaction conditions is +1 or greater. An oligonucleotide having a net positive charge would migrate toward the negative electrode in an electrical field.

The term "net negative charge" when used in reference to an oligonucleotide, including modified oligonucleotides, indicates that the sum of the charges present (i.e., R—NH3+ groups on thymidines, the N3 nitrogen of cytosine, presence or absence or phosphate groups, etc.) under the desired reaction conditions is −1 or lower. An oligonucleotide having a net negative charge would migrate toward the positive electrode in an electrical field.

The term "polymerization means" or "polymerization agent" refers to any agent capable of facilitating the addition of nucleoside triphosphates to an oligonucleotide. Preferred polymerization means comprise DNA and RNA polymerases.

The term "ligation means" or "ligation agent" refers to any agent capable of facilitating the ligation (i.e., the formation of a phosphodiester bond between a 3'-OH and a 5' P located at the termini of two strands of nucleic acid). Preferred ligation means comprise DNA ligases and RNA ligases.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

The term "adduct" is used herein in its broadest sense to indicate any compound or element that can be added to an oligonucleotide. An adduct may be charged (positively or negatively) or may be charge-neutral. An adduct may be added to the oligonucleotide via covalent or non-covalent linkages. Examples of adducts include, but are not limited to, indodicarbocyanine dye amidites, amino-substituted nucleotides, ethidium bromide, ethidium homodimer, (1,3-propanediamino)propidium, (diethylenetriamino)propidium, thiazole orange, (N—N'-tetramethyl-1,3-propanediamino) propyl thiazole orange, (N—N'-tetramethyl-1,2-ethanediamino)propyl thiazole orange, thiazole orange-thiazole orange homodimer (TOTO), thiazole orange-thiazole blue heterodimer (TOTAB), thiazole orange-ethidium heterodimer 1 (TOED1), thiazole orange-ethidium heterodimer 2 (TOED2) and fluorescein-ethidium heterodimer (FED), psoralens, biotin, streptavidin, avidin, etc.

Where a first oligonucleotide is complementary to a region of a target nucleic acid and a second oligonucleotide has complementary to the same region (or a portion of this region) a "region of overlap" exists along the target nucleic acid. The degree of overlap will vary depending upon the nature of the complementarity (see, e.g., region "X" in FIGS. 29 and 67 and the accompanying discussions).

As used herein, the term "purified" or "to purify" refers to the removal of contaminants from a sample. For example, recombinant Cleavase nucleases are expressed in bacterial host cells and the nucleases are purified by the removal of host cell proteins; the percent of these recombinant nucleases is thereby increased in the sample.

The term "recombinant DNA molecule" as used herein refers to a DNA molecule that comprises of segments of DNA joined together by means of molecular biological techniques.

The term "recombinant protein" or "recombinant polypeptide" as used herein refers to a protein molecule that is expressed from a recombinant DNA molecule.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n−1).

The term "nucleic acid sequence" as used herein refers to an oligonucleotide, nucleotide or polynucleotide, and fragments or portions thereof, and to DNA or RNA of genomic or synthetic origin that may be single or double stranded, and represent the sense or antisense strand. Similarly, "amino acid sequence" as used herein refers to peptide or protein sequence.

The term "peptide nucleic acid" ("PNA") as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen, et al. Anticancer Drug Des. 8:53 63 [1993]).

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

An isolated oligonucleotide (or polynucleotide) encoding a *Pyrococcus woesei* (Pwo) FEN-1 endonuclease having a region capable of hybridizing to SEQ ID NO:116 is an oligonucleotide containing sequences encoding at least the amino-terminal portion of Pwo FEN-1 endonuclease. An isolated oligonucleotide (or polynucleotide) encoding a Pwo FEN-1 endonuclease having a region capable of hybridizing to SEQ ID NO:117 is an oligonucleotide containing sequences encoding at least the carboxy-terminal portion of Pwo FEN-1 endonuclease. An isolated oligonucleotide (or polynucleotide) encoding a Pwo FEN-1 endonuclease having a region capable of hybridizing to SEQ ID NOS:118 and 119 is an oligonucleotide containing sequences encoding at least portions of Pwo FEN-1 endonuclease protein located internal to either the amino or carboxy-termini of the Pwo FEN-1 endonuclease protein.

As used herein, the term "fusion protein" refers to a chimeric protein containing the protein of interest (e.g., Cleavase BN/thrombin nuclease and portions or fragments thereof) joined to an exogenous protein fragment (the fusion partner which consists of a non Cleavase BN/thrombin nuclease protein). The fusion partner may enhance solubility of recombinant chimeric protein (e.g., the Cleavase BN/thrombin nuclease) as expressed in a host cell, may provide an affinity tag (e.g., a his-tag) to allow purification of the recombinant fusion protein from the host cell or culture supernatant, or both. If desired, the fusion protein may be removed from the protein of interest (e.g., Cleavase BN/thrombin nuclease or fragments thereof) by a variety of enzymatic or chemical means known to the art.

As used herein, the terms "chimeric protein" and "chimerical protein" refer to a single protein molecule that comprises amino acid sequences portions derived from two or more parent proteins. These parent molecules may be from similar proteins from genetically distinct origins, different proteins from a single organism, or different proteins from different organisms. By way of example but not by way of limitation, a chimeric structure-specific nuclease of the present invention may contain a mixture of amino acid sequences that have been derived from FEN-1 genes from two or more of the organisms having such genes, combined to form a non-naturally occurring nuclease. The term "chimerical" as used herein is not intended to convey any particular proportion of contribution from the naturally occurring genes, nor limit the manner in which the portions are combined. Any chimeric structure-specific nuclease constructs having cleavage activity as determined by the testing methods described herein are improved cleavage agents within the scope of the present invention.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "duplex dependent protein binding" refers to the binding of proteins to nucleic acid that is dependent on the nucleic acid being in a duplex, or helical form.

The term "duplex dependent protein binding sites or regions" as used herein refers to discrete regions or sequences within a nucleic acid that are bound with particular affinity by specific duplex-dependent nucleic acid binding proteins. This is in contrast to the generalized duplex-dependent binding of proteins that are not site-specific, such as the histone proteins that bind chromatin with little reference to specific sequences or sites.

The term "protein binding region" as used herein refers to a nucleic acid region identified by a sequence or structure as binding to a particular protein or class of proteins. It is within the scope of this definition to include those regions that contain sufficient genetic information to allow identifications of the region by comparison to known sequences, but which might not have the requisite structure for actual binding (e.g., a single strand of a duplex-depending nucleic acid binding protein site). As used herein "protein binding region" excludes restriction endonuclease binding regions.

The term "complete double stranded protein binding region" as used herein refers to the minimum region of continuous duplex required to allow binding or other activity of a duplex-dependent protein. This definition is intended to encompass the observation that some duplex dependent nucleic acid binding proteins can interact with full activity with regions of duplex that may be shorter than a canonical protein binding region as observed in one or the other of the two single strands. In other words, one or more nucleotides in the region may be allowed to remain unpaired without suppressing binding. As used here in, the term "complete double stranded binding region" refers to the minimum sequence that will accommodate the binding function. Because some such regions can tolerate non-duplex sequences in multiple places, although not necessarily simultaneously, a single protein binding region might have several shorter sub-regions that, when duplexed, will be fully competent for protein binding.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

The term "template-dependent RNA polymerase" refers to a nucleic acid polymerase that creates new RNA strands through the copying of a template strand as described above and which does not synthesize RNA in the absence of a template. This is in contrast to the activity of the template-independent nucleic acid polymerases that synthesize or extend nucleic acids without reference to a template, such as terminal deoxynucleotidyl transferase, or Poly A polymerase.

The term "ARRESTOR molecule" refers to an agent added to or included in an invasive cleavage reaction in order to stop one or more reaction components from participating in a subsequent action or reaction. This may be done by sequestering or inactivating some reaction component (e.g., by binding or base-pairing a nucleic acid component, or by binding to a protein component). The term "ARRESTOR oligonucleotide" refers to an oligonucleotide included in an invasive cleavage reaction in order to stop or arrest one or more aspects of any reaction (e.g., the first reaction and/or any subsequent reactions or actions; it is not intended that the ARRESTOR oligonucleotide be limited to any particular reaction or reaction step). This may be done by sequestering some reaction component (e.g., base-pairing to another nucleic acid, or binding to a protein component). However, it is not intended that the term be so limited as to just situations in which a reaction component is sequestered.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contain a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "functional domain" refers to a region, or a part of a region, of a protein (e.g., an enzyme) that provides one or more functional characteristic of the protein. For example, a functional domain of an enzyme may provide, directly or indirectly, one or more activities of the enzyme including, but not limited to, substrate binding capability and catalytic activity. A functional domain may be characterized through mutation of one or more amino acids within the functional domain, wherein mutation of the amino acid(s) alters the associated functionality (as measured empirically in an assay) thereby indicating the presence of a functional domain.

As used herein, the term "heterologous functional domain" refers to a protein functional domain that is not in its natural environment. For example, a heterologous functional domain includes a functional domain from one enzyme introduced into another enzyme. A heterologous functional domain also includes a functional domain native to an protein that has been altered in some way (e.g., mutated, added in multiple copies, etc.). A heterologous functional domain may comprise a plurality of contiguous amino acids or may include two or more distal amino acids are amino acids fragments (e.g., two or more amino acids or fragments with intervening, non-heterologous, sequence). Heterologous functional domains are distinguished from endogenous functional domains in that the heterologous amino acid(s) are joined to amino acid sequences that are not found naturally associated with the amino acid sequence in nature or are associated with a portion of a protein not found in nature.

As used herein, the term "altered functionality in a nucleic acid cleavage assay" refers to a characteristic of an enzyme that has been altered in some manner to differ from its natural state (e.g., to differ from how it is found in nature). Alterations include, but are not limited to, addition of a heterologous functional domain (e.g., through mutation or through creation of chimerical proteins). In some embodiments, the altered characteristic of the enzyme may be one that improves the performance of the enzyme in a nucleic acid cleavage assay. Types of improvement include, but are not limited to, improved nuclease activity (e.g., improved rate of reaction), improved substrate binding (e.g., increased or decreased binding of certain nucleic acid species [e.g., RNA or DNA] that produces a desired outcome [e.g., greater specificity, improved substrate turnover, etc.]), and improved background specificity (e.g., less undesired product is produced). The present invention is not limited by the nucleic cleavage assay used to test improved functionality. However, in some preferred embodiments of the present invention, an invasive cleavage assay is used as the nucleic acid cleavage assay. In certain particularly preferred embodiments, an invasive cleavage assay utilizing an RNA target is used as the nucleic acid cleavage assay.

As used herein, the terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminal and C-terminal ends of the polypeptide, respectively.

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as nucleic acid molecules and proteins attached to solid supports. A biological material is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linker group." Such spacer molecules are molecules that have a first portion that attaches to the biological material and a second portion that attaches to the solid support. Thus, when attached to the solid support, the spacer molecule separates the solid support and the biological materials, but is attached to both.

As used herein, the term "bead" refers to a small solid support that is capable of moving about in a solution (i.e., it has dimensions smaller than those of the enclosure in which it resides). In some preferred embodiments, beads are completely or partially spherical or cylindrical. However, beads are not limited to any particular three-dimensional shape.

As used herein, the term "microarray" refers to a solid support with a plurality of molecules (e.g., nucleotides)

bound to its surface. Microarrays, for example, are described generally in Schena, "Microarray Biochip Technology," Eaton Publishing, Natick, Mass., 2000. Additionally, the term "patterned microarrays" refers to microarray substrates with a plurality of molecules non-randomly bound to its surface.

DESCRIPTION OF THE DRAWINGS

FIG. 1 is a comparison of the nucleotide structure of the DNAP genes isolated from *Thermus aquaticus* (SEQ ID NO:1), *Thermus flavus* (SEQ ID NO:2) and *Thermus thermophilus* (SEQ ID NO:3); the consensus sequence (SEQ ID NO:7) is shown at the top of each row.

FIG. 2 is a comparison of the amino acid sequence of the DNAP isolated from *Thermus aquaticus* (SEQ ID NO:4), *Thermus flavus* (SEQ ID NO:5), and *Thermus thermophilus* (SEQ ID NO:6); the consensus sequence (SEQ ID NO:8) is shown at the top of each row.

FIG. 4A depicts the wild-type *Thermus flavus* polymerase gene.

FIG. 4B depicts a synthesis-deficient *Thermus flavus* polymerase gene.

FIGS. 9A-B are an autoradiogram displaying timed cleavage reactions, with and without primer.

FIG. 42 is the image generated by a fluorescence imager showing the products of INVADER oligonucleotide-directed cleavage assays run using a HCV RNA target and demonstrate the stability of RNA targets under INVADER oligonucleotide-directed cleavage assay conditions.

FIG. 59 provides an alignment of the amino acid sequences of several FEN-1 nucleases including the *Methanococcus jannaschii* FEN-1 protein (MJAFEN1.PRO), the *Pyrococcus furiosus* FEN-1 protein (PFUFEN1.PRO), the human FEN-1 protein (HUMFEN1.PRO), the mouse FEN-1 protein (MUSFEN1.PRO), the *Saccharomyces cerevisiae* YKL510 protein (YST510.PRO), the *Saccharomyces cerevisiae* RAD2 protein (YSTRAD2.PRO), the *Shizosaccharomyces pombe* RAD13 protein (SPORAD13.PRO), the human XPG protein (HUMXPG.PRO), the mouse XPG protein (MUSXPG.PRO), the *Xenopus laevis* XPG protein (XENXPG.PRO) and the *C. elegans* RAD2 protein (CELRAD2.PRO) (SEQ ID NOS:135-145, respectively); portions of the amino acid sequence of some of these proteins were not shown in order to maximize the alignment between proteins (specifically, amino acids 122 to 765 of the YSTRAD2 sequence were deleted; amino acids 122 to 746 of the SPORAD13 sequence were deleted; amino acids 122 to 757 of the HUMXPG sequence were deleted; amino acids 122 to 770 of the MUSXPG sequence were deleted; and amino acids 122 to 790 of the XENXPG sequence were deleted). The numbers to the left of each line of sequence refers to the amino acid residue number; dashes represent gaps introduced to maximize alignment.

FIG. 60 is a schematic showing the S-33 (SEQ ID NO:84) and 11-8-0 (SEQ ID NO:85) oligonucleotides in a folded configuration; the cleavage site is indicated by the arrowhead.

FIG. 73 shows the structure of 3-nitropyrrole and 5-nitroindole.

FIGS. 78A-C show the sequence of the S-60 hairpin (SEQ ID NO:29) (A), and the P-15 oligonucleotide (SEQ ID NO:30) (shown annealed to the S-60 hairpin in B) and the image generated by a fluorescence imager showing the products produced by cleavage of the S-60 hairpin in the presence of various INVADER oligonucleotides.

FIG. 98 shows the nucleotide sequence of the PR1 probe (SEQ ID NO:119), the IT3 INVADER-Target oligonucleotide (SEQ ID NO:118), the IT3-8, IT3-6, IT3-4, IT3-3 and IT3-0 oligonucleotides (SEQ ID NOS:147-151, respectively).

FIG. 99 displays the sequence of oligonucleotide 89-15-1 (SEQ ID NO:152), oligonucleotide 81-69-5 (SEQ ID NO:156), oligonucleotide 81-69-4 (SEQ ID NO:155), oligonucleotide 81-69-3 (SEQ ID NO:154), oligonucleotide 81-69-2 (SEQ ID NO:153) and a portion of M13mp18 (SEQ ID NO:163).

FIG. 103 shows the sequence of oligonucleotide 89-76 (SEQ ID NO:161), oligonucleotide 89-44 (SEQ ID NO:160) and nucleotides 3057-3110 of the HCMV genome (SEQ ID NO:162).

FIG. 105 is a schematic which illustrates one embodiment of the present invention, where the cut probe from an initial invasive cleavage reaction is employed as the INVADER oligonucleotide in a second invasive cleavage reaction, and where an ARRESTOR oligonucleotide prevents participation of remaining uncut first probe in the cleavage of the second probe.

FIG. 107 shows three images generated by a fluorescence imager showing that two different lengths of 2' O-methyl, 3' terminal amine-modified ARRESTOR oligonucleotide both reduce non-specific background cleavage of the secondary probe when included in the second step of a reaction where the cut probe from an initial invasive cleavage reaction is employed as an integrated INVADER-target complex in a second invasive cleavage reaction.

Figure 110A:
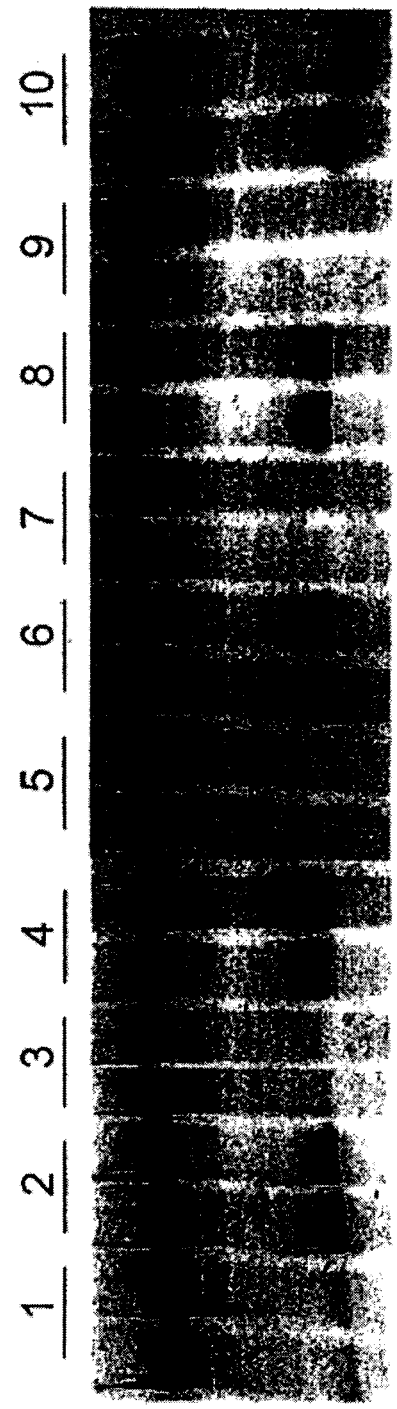
FIG. 110A shows two images generated by a fluorescence imager comparing the effects on nonspecific and specific cleavage signal of including an ARRESTOR oligonucleotides of different lengths in the second step of a reaction where the cut probe from an initial invasive cleavage reaction is employed as the INVADER oligonucleotide in a second invasive cleavage reaction.
Figure 110B:
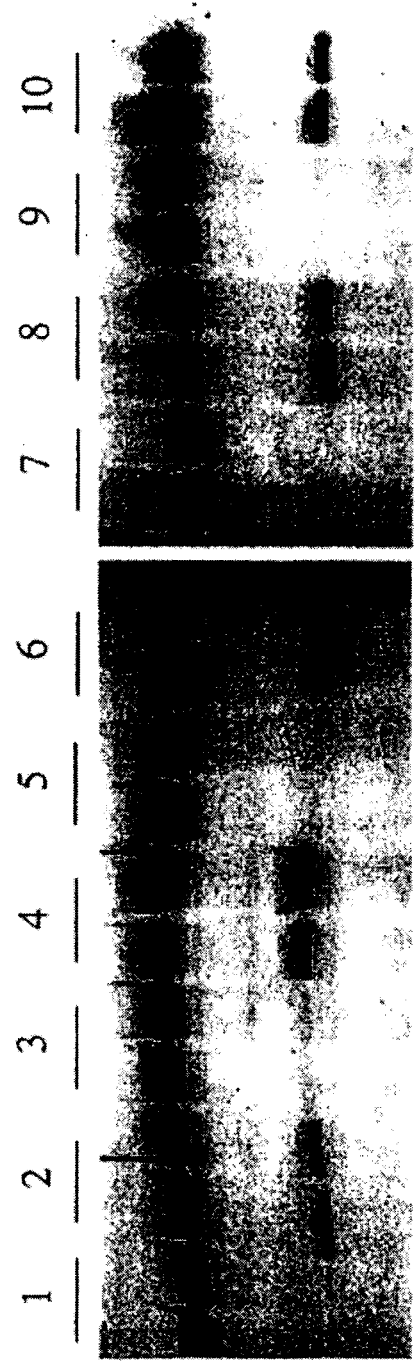

FIG. 110B shows two images generated by a fluorescence imager comparing the effects on nonspecific and specific cleavage signal of including an ARRESTOR oligonucleotides of different lengths in the second step of a reaction where the cut probe from an initial invasive cleavage reaction is employed as the INVADER oligonucleotide in a second invasive cleavage reaction, and in which a longer variant of the secondary probe used in the reactions in FIG. 110A is tested.

FIG. 110C shows a schematic diagram of a primary probe (SEQ ID NO: 175) aligned with several ARRESTOR oligonucleotides of different lengths. The region of the primary probe that is complementary to the HBV target sequence is underlined. The ARRESTOR oligonucleotides are aligned with the probe by complementarity probe (SEQ ID NOS:179-182).

Figure 111:
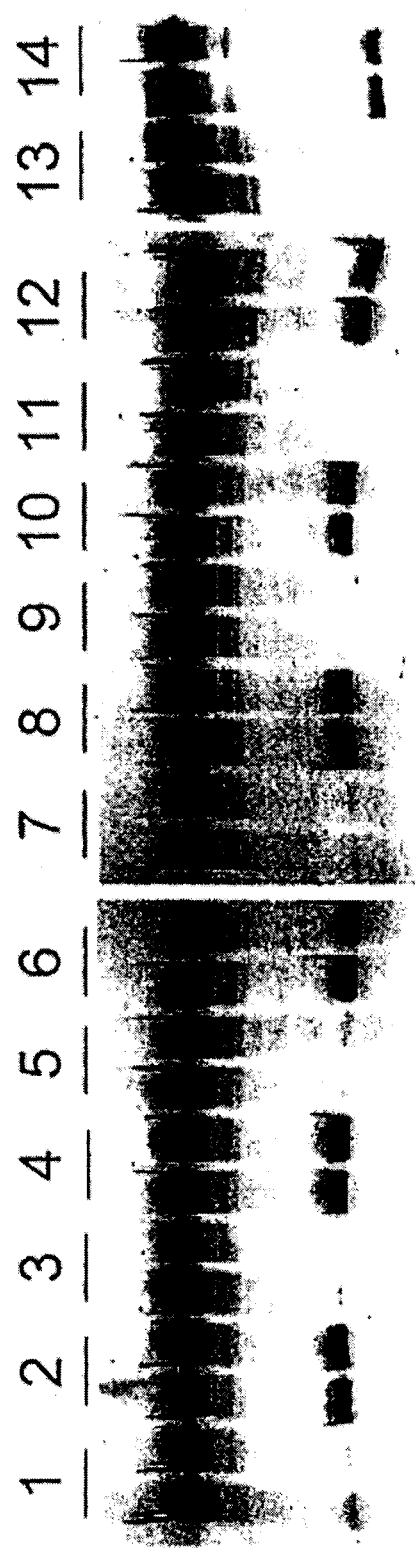

FIG. 111 shows two images generated by a fluorescence imager comparing the effects on nonspecific and specific cleavage signal of including ARRESTOR oligonucleotides of different lengths in the second step of a reaction where the cut probe from an initial invasive cleavage reaction is employed as the INVADER oligonucleotide in a second invasive cleavage reaction, using secondary probes of two different lengths.

Figure 112:
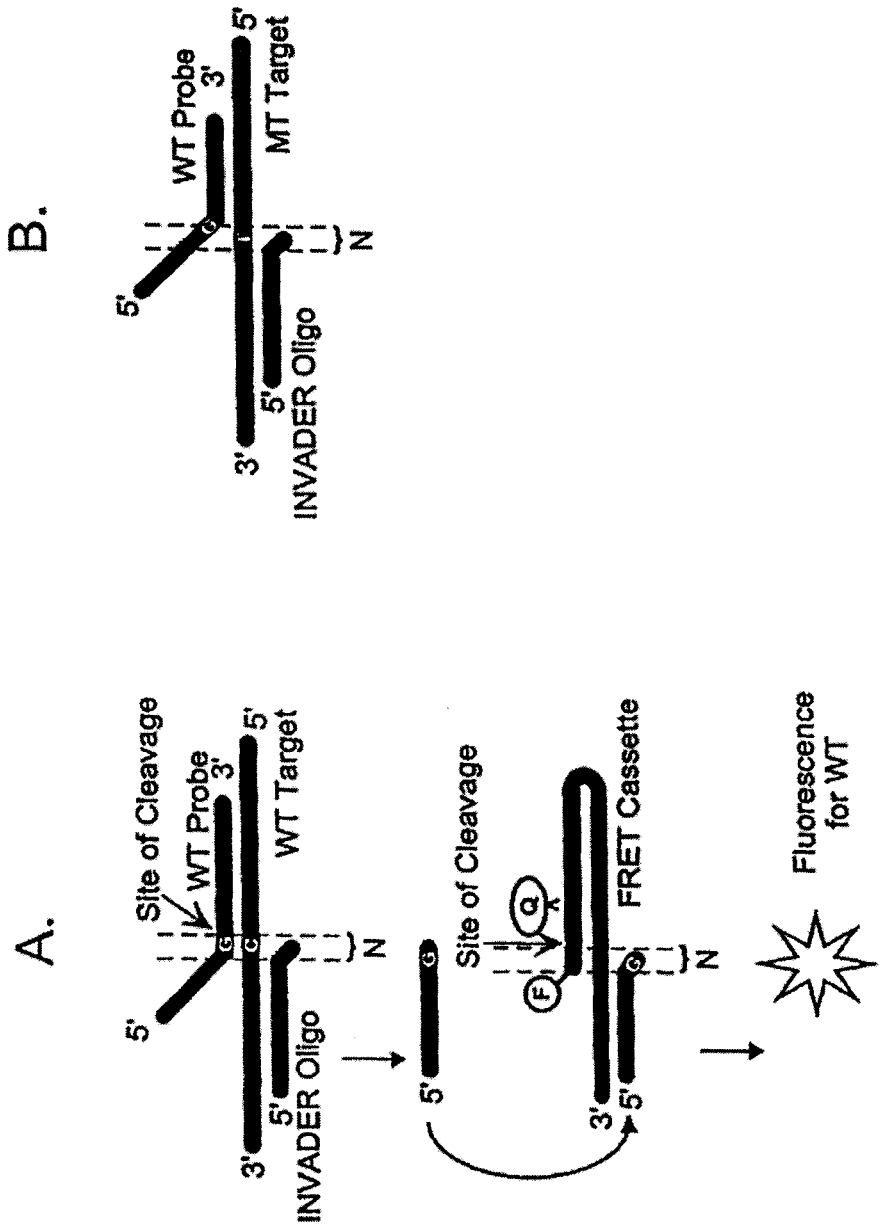

FIG. 112A provides a schematic diagram that illustrates one embodiment of the present invention wherein the cut probe from an initial invasive cleavage reaction is employed as the INVADER oligonucleotide in a second invasive cleavage reaction using a FRET cassette. The region indicated as "N" is the overlap required for cleavage in this embodiment. 112B diagrams how a mismatch between the probe and the target strand at position "N" disrupts the overlap, thereby suppressing cleavage of the probe.

Figure 113A:
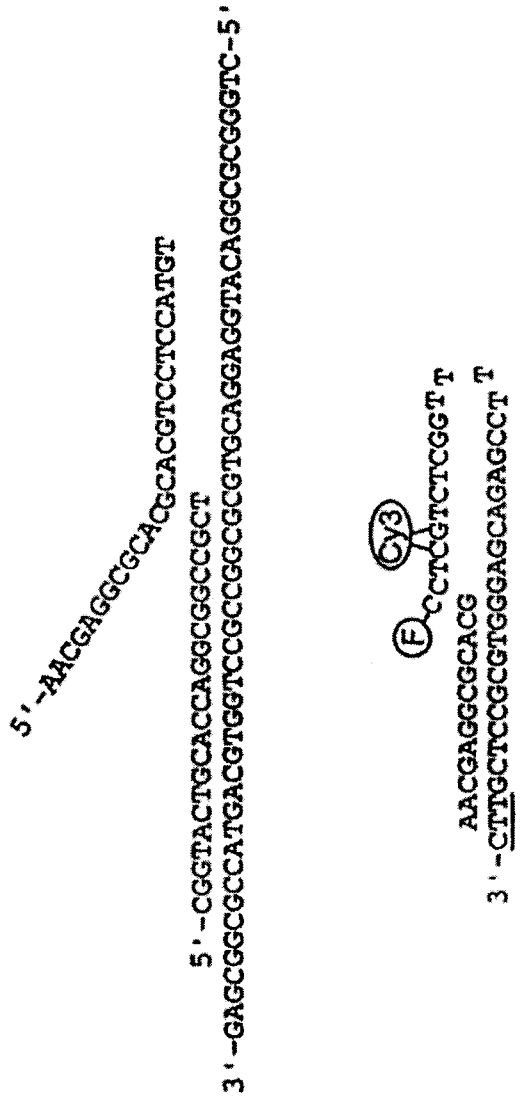

FIG. 113A shows a schematic diagram of an INVADER oligonucleotide (SEQ ID NO:195), probe oligonucleotide (SEQ ID NO:197) and FRET cassette (SEQ ID NO:201) for the detection of the Apo E 112 arg allele (SEQ ID NO:191). The flap released from the probe (SEQ ID NO:415) is shown annealed to the FRET cassette.

Figure 113B:
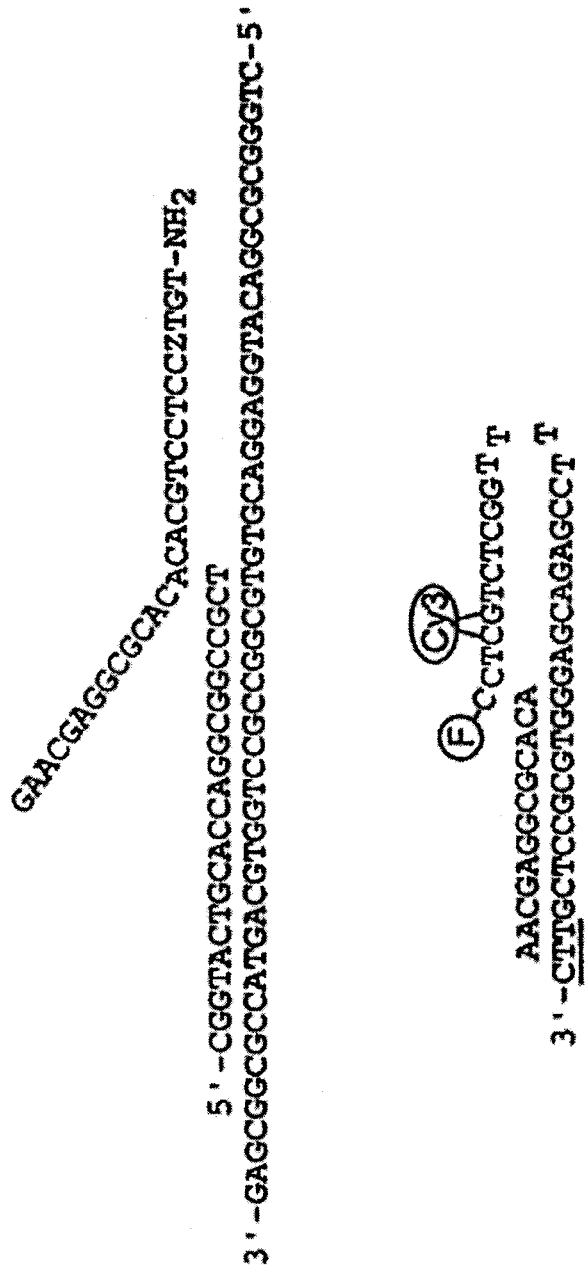

FIG. 113B shows a schematic diagram of an INVADER oligonucleotide (SEQ ID NO:195), probe oligonucleotide (SEQ ID NO:198) and FRET cassette (SEQ ID NO:201) for the detection of the Apo E 112 cys allele (SEQ ID NO:192). The flap released from the probe (SEQ ID NO:416) is shown annealed to the FRET cassette.

Figure 113C:
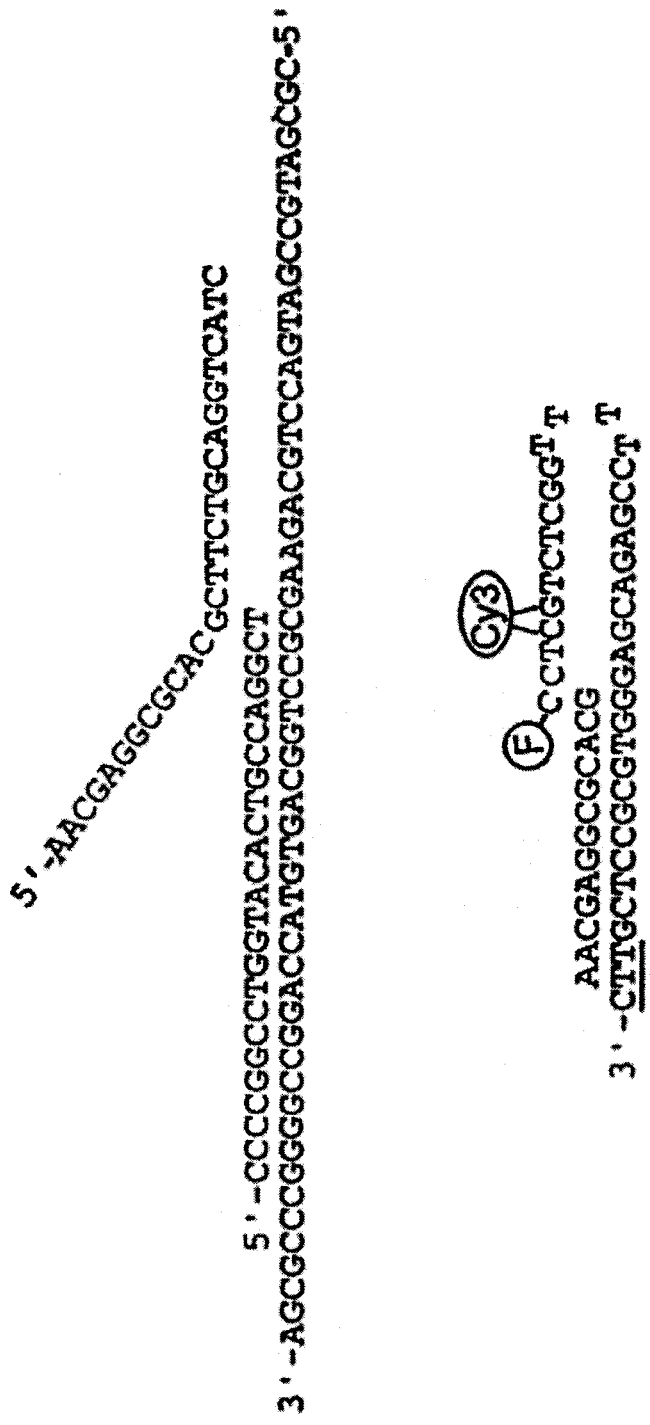

FIG. 113C shows a schematic diagram of an INVADER oligonucleotide (SEQ ID NO:196), probe oligonucleotide (SEQ ID NO:199) and FRET cassette (SEQ ID NO:201) for the detection of the Apo E 158 arg allele (SEQ ID NO:193). The flap released from the probe (SEQ ID NO:415) is shown annealed to the FRET cassette.

Figure 113D:
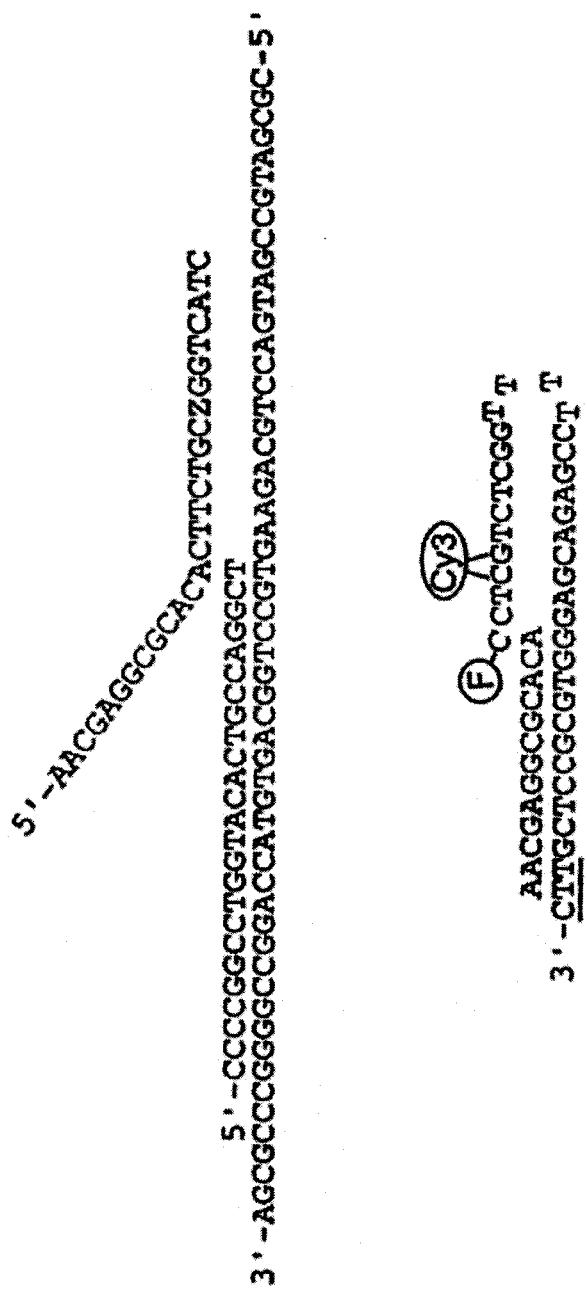

FIG. 113D shows a schematic diagram of an iNVADER oligonucleotide (SEQ ID NO:196), probe oligonucleotide (SEQ ID NO:200) and FRET cassette (SEQ ID NO:201) for the detection of the Apo E 158 cys allele (SEQ ID NO:194). The flap released from the probe (SEQ IID NO:416) is shown annealed to the FRET cassette.

Figure 114A:
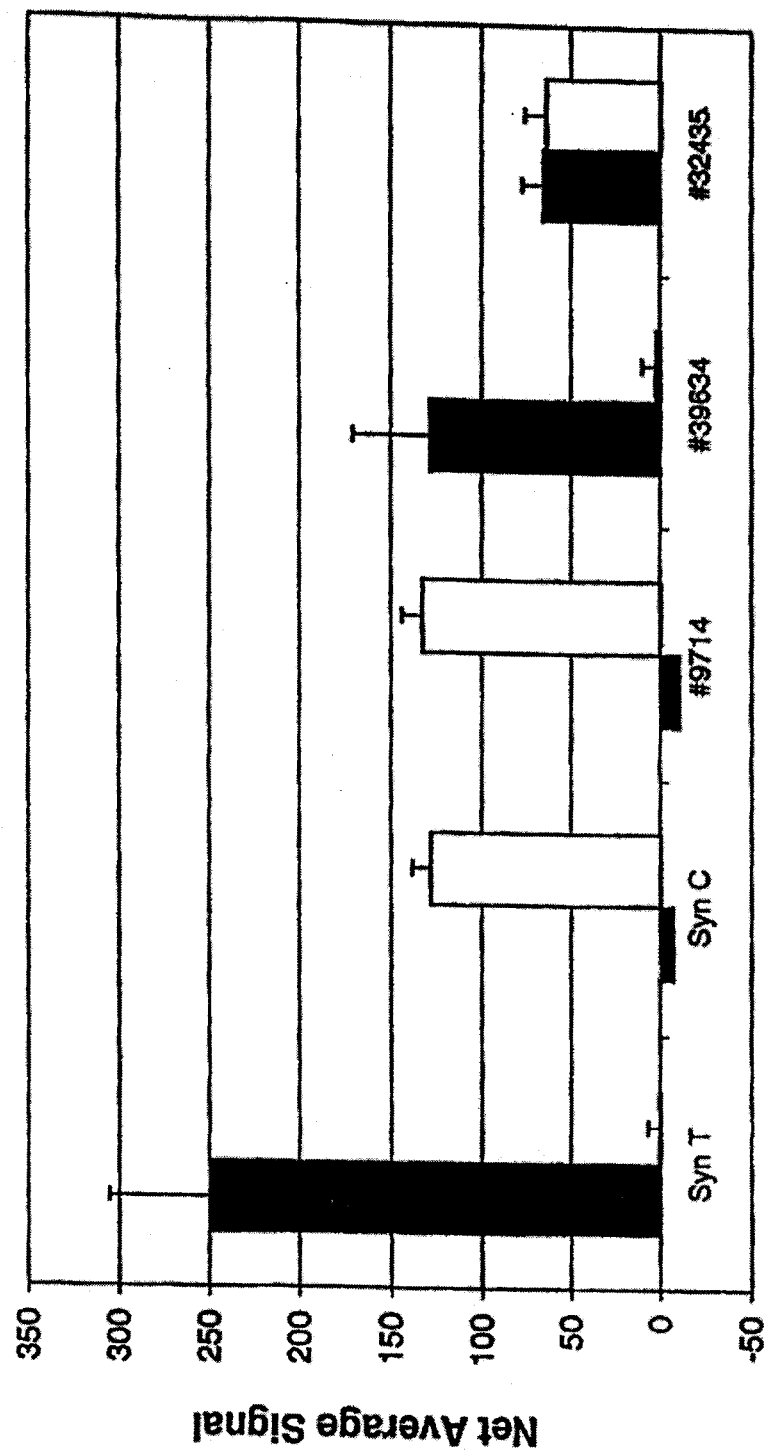

FIG. 114A provides a bar graph showing the detection of the arg and cys alleles at the Apo E 112 locus in 2 synthetic controls and 5 samples of human genomic DNA.

Figure 114B:
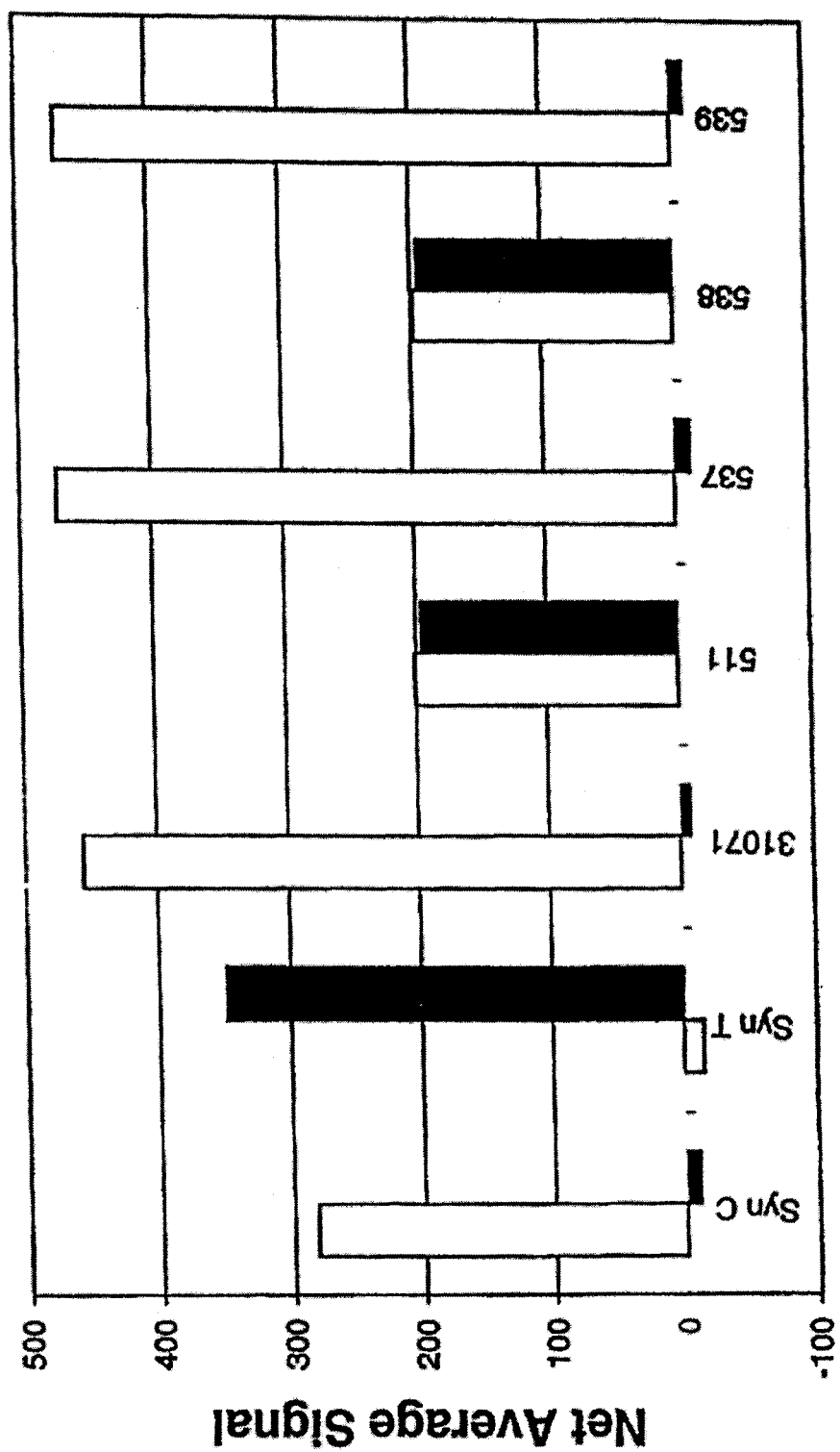

FIG. 114B provides a bar graph showing the detection of the arg and cys alleles at the Apo E 158 locus in 2 synthetic controls and 5 samples of human genomic DNA.

Figure 115A:

FIG. 115A shows a schematic diagram of an INVADER oligonucleotide (SEQ ID NO:202), probe oligonucleotide (SEQ ID NO:208) and FRET cassette (SEQ ID NO: 210) for the detection of the wild-type C282 allele of the human HFE gene (SEQ ID NO:204). The flap released from the probe (SEQ ID NO:417) is shown annealed to the FRET cassette.

Figure 115B:
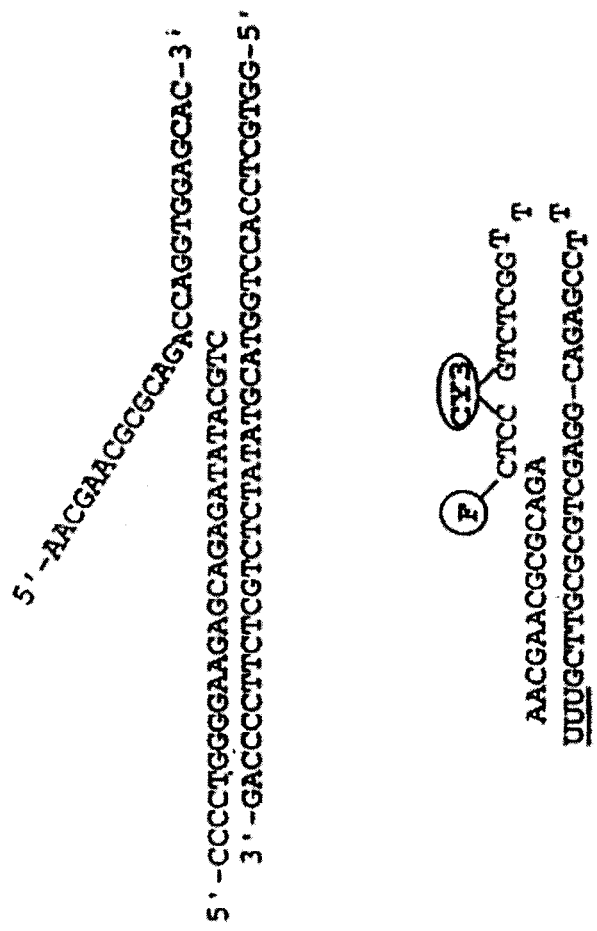

FIG. 115B shows a schematic diagram of an INVADER oligonucleotide (SEQ ID NO:202), probe oligonucleotide (SEQ ID NO:209) and FRET cassette (SEQ ID NO:210) for the detection of the C282Y mutant allele of the human HFE gene (SEQ ID NO:205). The flap released from the probe (SEQ ID NO:418) is shown annealed to the FRET cassette.

Figure 115C:
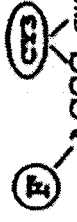

FIG. 115C shows a schematic diagram of an INVADER oligonucleotide (SEQ ID NO:203), probe oligonucleotide (SEQ ID NO:211) and FRET cassette (SEQ ID NO:213) for the detection of the wild-type H63 allele of the human HFE gene (SEQ ID NO:206). The flap released from the probe (SEQ ID NO:419) is shown annealed to the FRET cassette.

Figure 115D:
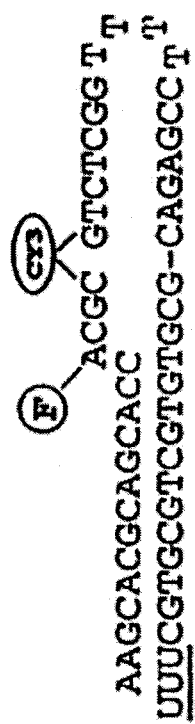

FIG. 115D shows a schematic diagram of an INVADER oligonucleotide (SEQ ID NO:203), probe oligonucleotide (SEQ ID NO:212) and FRET cassette (SEQ ID NO:213) for the detection of the H63D mutant allele of the human HFE gene (SEQ ID NO:207). The flap released from the probe (SEQ ID NO:420) is shown annealed to the FRET cassette.

Figure 116:
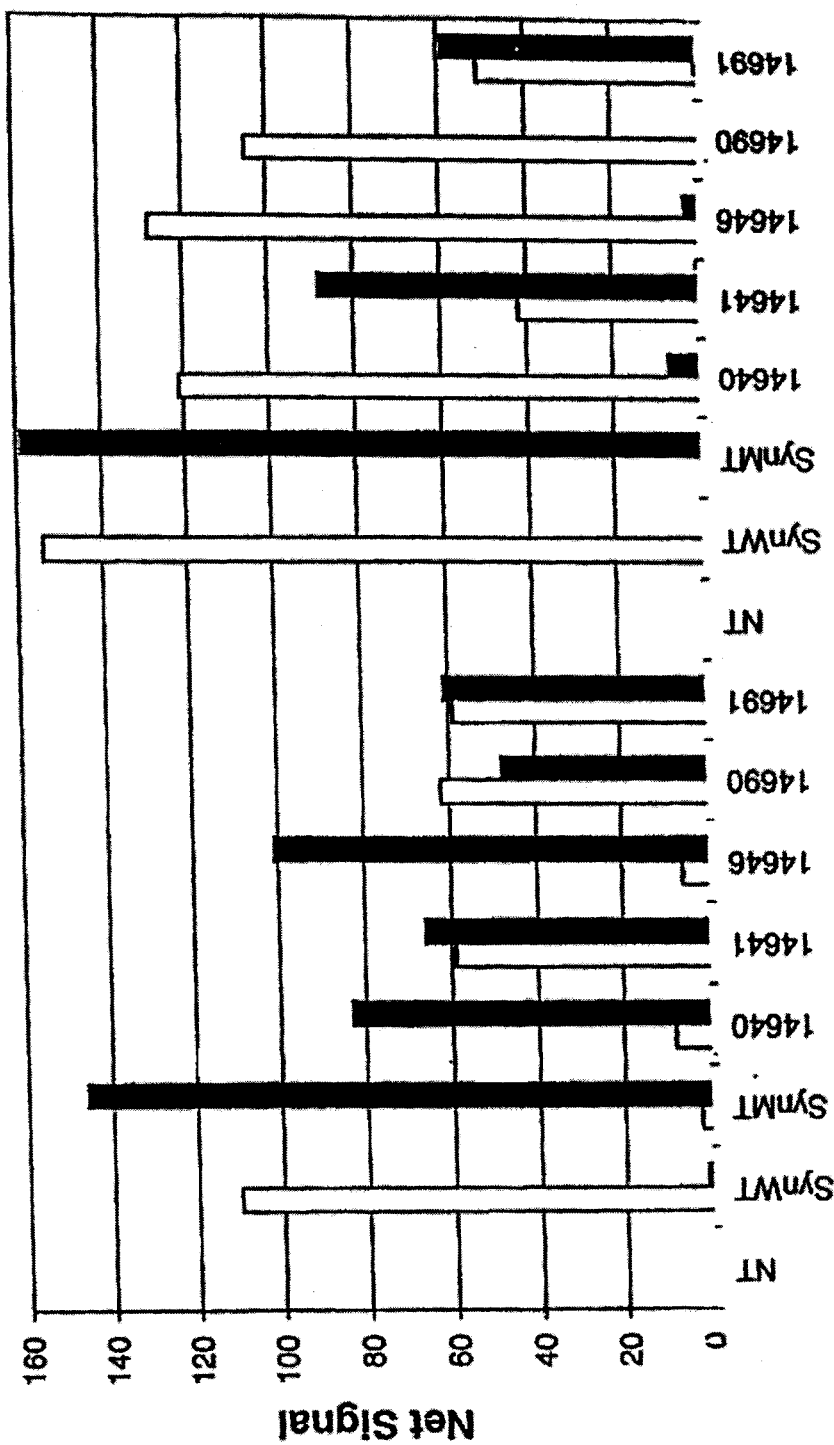

FIG. 116 provides a bar graph showing the analysis of the C282Y (first set of eight tests, left to right) and H63D (second set of eight tests, left to right) mutations in the human HFE gene, each tested in 2 synthetic controls and 5 samples of human genomic DNA.

Figure 117A:
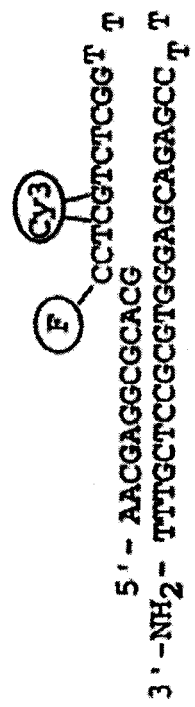

FIG. 117A shows a schematic diagram of an INVADER oligonucleotide (SEQ ID NO:216), probe oligonucleotide (SEQ ID NO:217) and FRET cassette (SEQ ID NO:225) for the detection of the wild-type allele at position 677 of the human MTHFR gene (SEQ ID NO:214). The flap released from the probe (SEQ ID NO:415) is shown annealed to the FRET cassette.

FIG. 117B shows a schematic diagram of an INVADER oligonucleotide (SEQ ID NO:216), probe oligonucleotide (SEQ ID NO:218) and FRET cassette (SEQ ID NO:225) for the detection of the mutant allele at position 677 of the human MTHFR gene (SEQ ID NO:215). The flap released from the probe (SEQ ID NO:416) is shown annealed to the FRET cassette.

Figure 118:
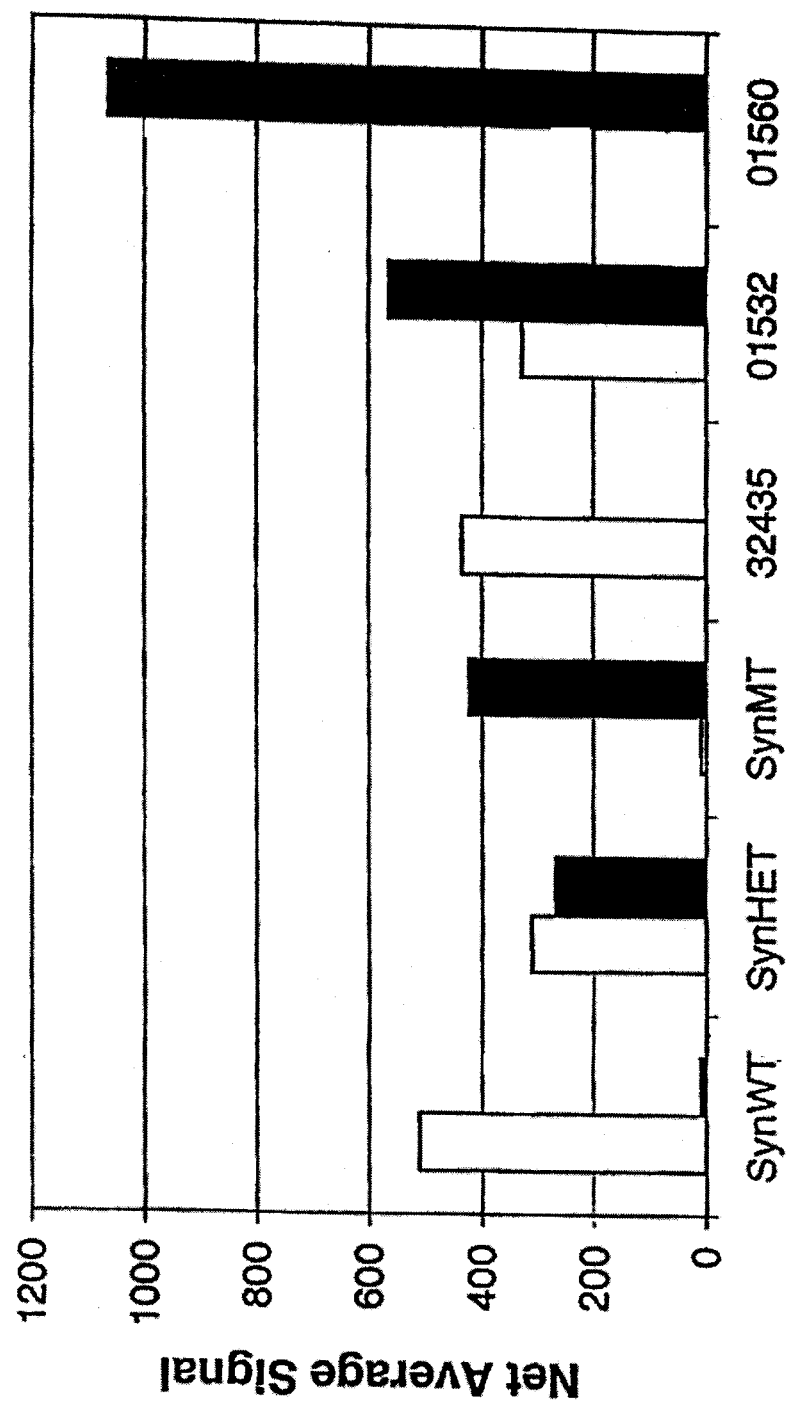

FIG. 118 provides a bar graph showing the analysis of the C677T mutation in the human MTHFR gene in 3 synthetic control samples and 3 samples of human genomic DNA.

Figure 119A:
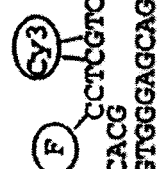

FIG. 119A shows a schematic diagram of an INVADER oligonucleotide (SEQ ID NO:222), probe oligonucleotide (SEQ ID NO:223) and FRET cassette (SEQ ID NO: 225) for the detection of the wild-type allele at position 20210 of the human prothrombin gene (SEQ ID NO:220). The flap released from the probe (SEQ ID NO:415) is shown annealed to the FRET cassette.

Figure 119B:
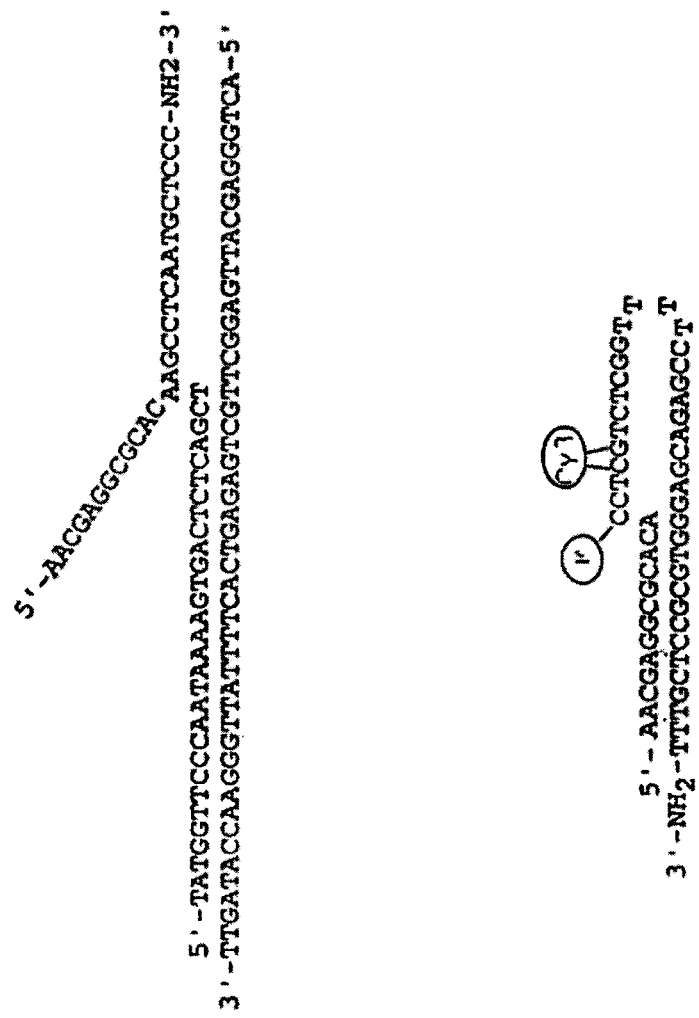

FIG. 119B shows a schematic diagram of an INVADER oligonucleotide (SEQ ID NO:222), probe oligonucleotide (SEQ ID NO:224) and FRET cassette (SEQ ID NO:225) for the detection of the mutant allele at position 20210 of the human prothrombin gene (SEQ ID NO:221). The flap released from the probe (SEQ ID NO:416) is shown annealed to the FRET cassette.

Figure 120:
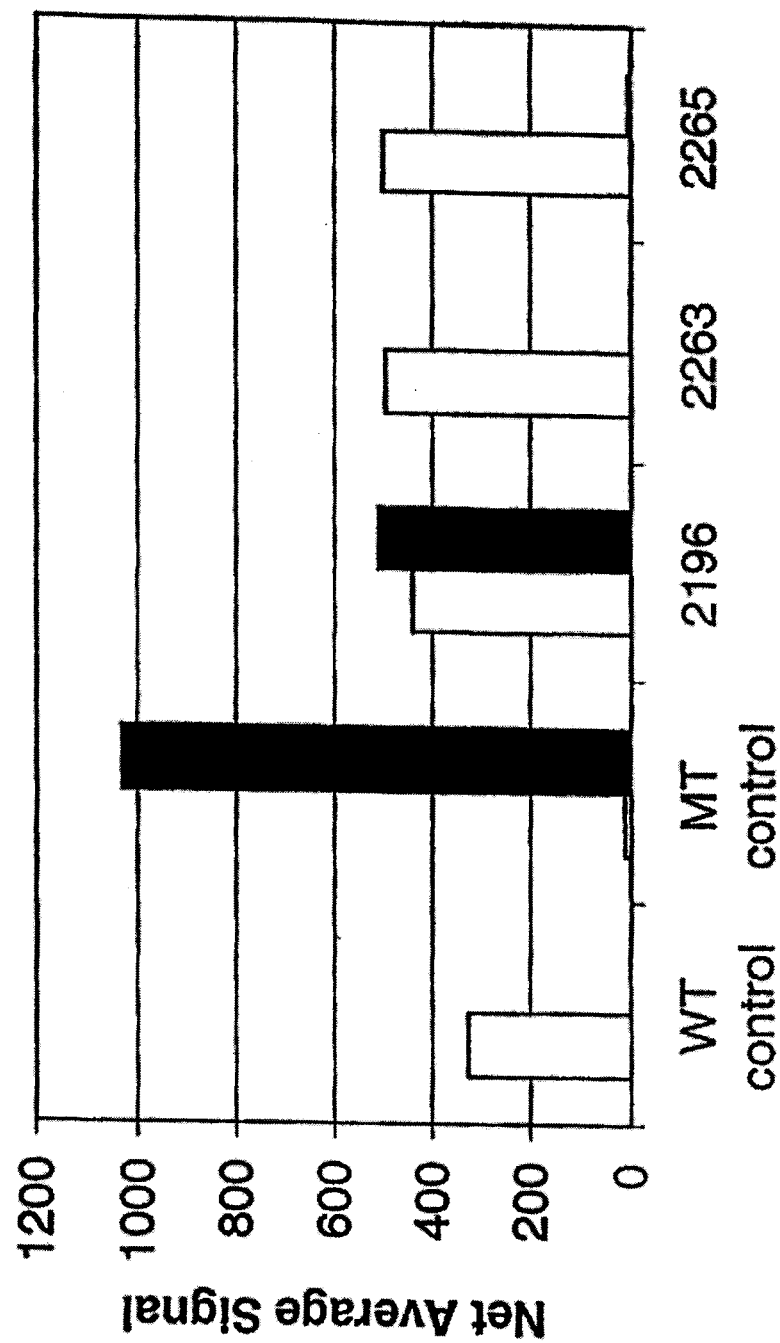

FIG. 120 provides a bar graph showing the analysis of the A20210G mutation in the human prothrombin gene in 2 synthetic control samples and 3 samples of human genomic DNA.

Figure 121A:
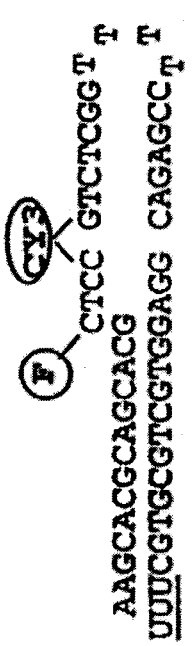

FIG. 121A shows a schematic diagram of an INVADER oligonucleotide (SEQ ID NO:228), probe oligonucleotide (SEQ ID NO:229) and FRET cassette (SEQ ID NO:230) for the detection of the R-2 mutant allele of the human factor V gene (SEQ ID NO:226). The flap released from the probe (SEQ ID NO:419) is shown annealed to the FRET cassette.

Figure 121B:

FIG. 121B shows a schematic diagram of an INVADER oligonucleotide (SEQ ID NO:231), probe oligonucleotide (SEQ ID NO:232) and FRET cassette (SEQ ID NO: 230) for the detection of the human α-actin gene (SEQ ID NO:227). The flap released from the probe (SEQ ID NO:421) is shown annealed to the FRET cassette.

Figure 122:
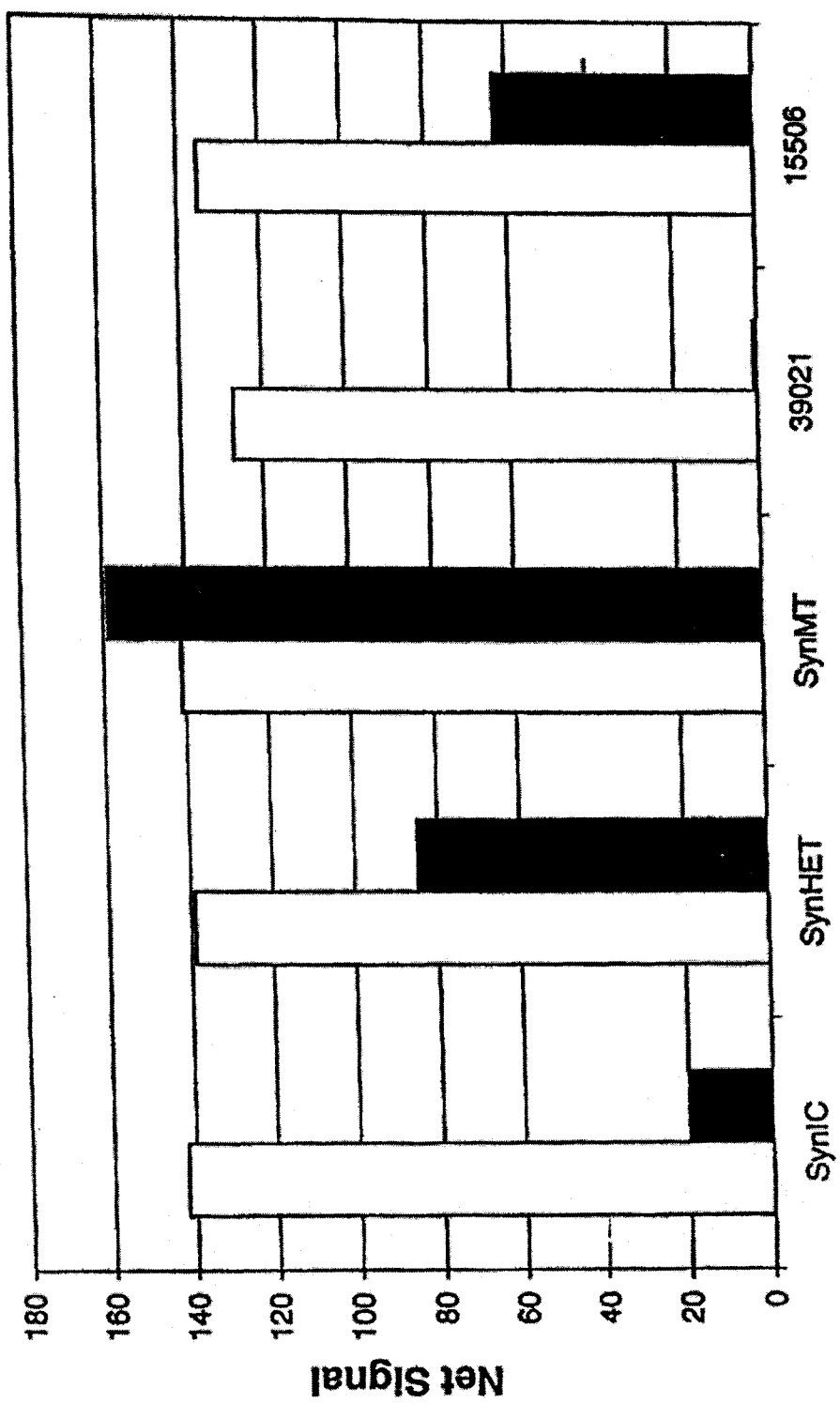

FIG. 122 provides a bar graph showing the detection of the R-2 mutant (HR-2) of the human factor V gene, compared to the detection of the internal control (IC), the α-actin gene, 3 synthetic control samples and 2 samples of human genomic DNA.

Figure 123:
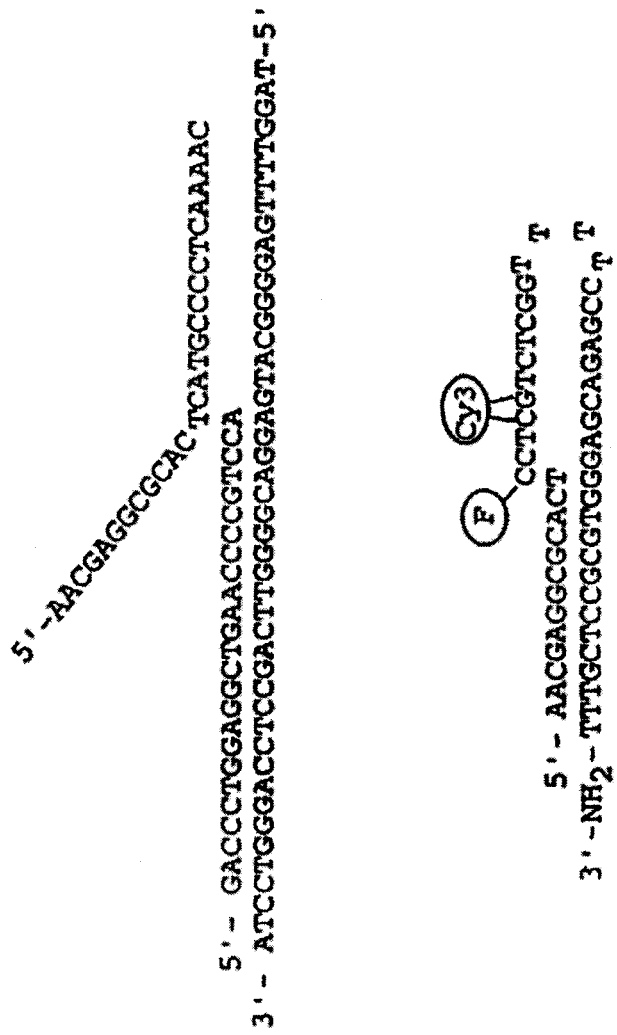

FIG. 123A shows a schematic diagram of an INVADER oligonucleotide (SEQ ID NO:235), probe oligonucleotide (SEQ ID NO:236) and FRET cassette (SEQ ID NO:225) for the detection of the wild-type allele at position -308 in the promoter of the human TNF-α gene (SEQ ID NO:233). The flap released from the probe (SEQ ID NO:422) is shown annealed to the FRET cassette.

FIG. 123B shows a schematic diagram of an INVADER oligonucleotide (SEQ ID NO:235), probe oligonucleotide (SEQ ID NO:237) and FRET cassette (SEQ ID NO:225) for the detection of the mutant allele at position -308 in the promoter of the human TNF-α gene (SEQ ID NO:234). The flap released from the probe (SEQ ID NO:423) is shown annealed to the FRET cassette.

Figure 124:
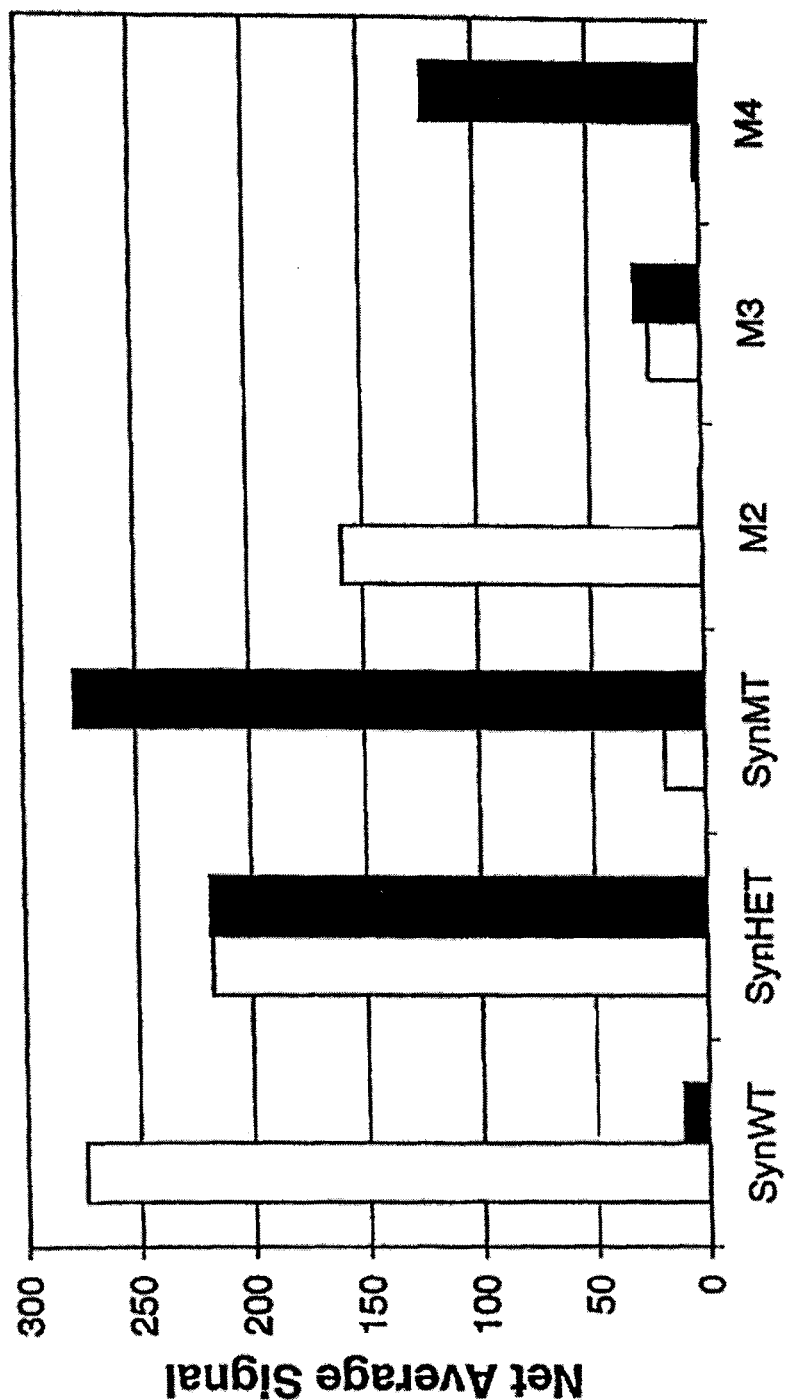

FIG. 124 provides a bar graph showing the analysis of the -308 mutation in the promoter of the human TNF-α gene in 3 synthetic control samples and 3 samples of human genomic DNA.

Figure 125A:
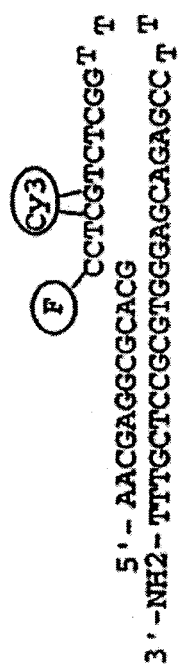

FIG. 125A shows a schematic diagram of an INVADER oligonucleotide (SEQ ID NO:240), probe oligonucleotide (SEQ ID NO:241) and FRET cassette (SEQ ID NO: 225) for the detection of the wild-type allele at codon position 506 of the human factor V gene (SEQ ID NO:238). The flap released from the probe (SEQ ID NO:415) is shown annealed to the FRET cassette.

Figure 125B:

FIG. 125B shows a schematic diagram of an INVADER oligonucleotide (SEQ ID NO:240), probe oligonucleotide (SEQ ID NO:242) and FRET cassette (SEQ ID NO:225) for the detection of the A506G mutant allele of the human factor V gene (SEQ ID NO:239). The flap released from the probe (SEQ ID NO:416) is shown annealed to the FRET cassette.

Figure 126:
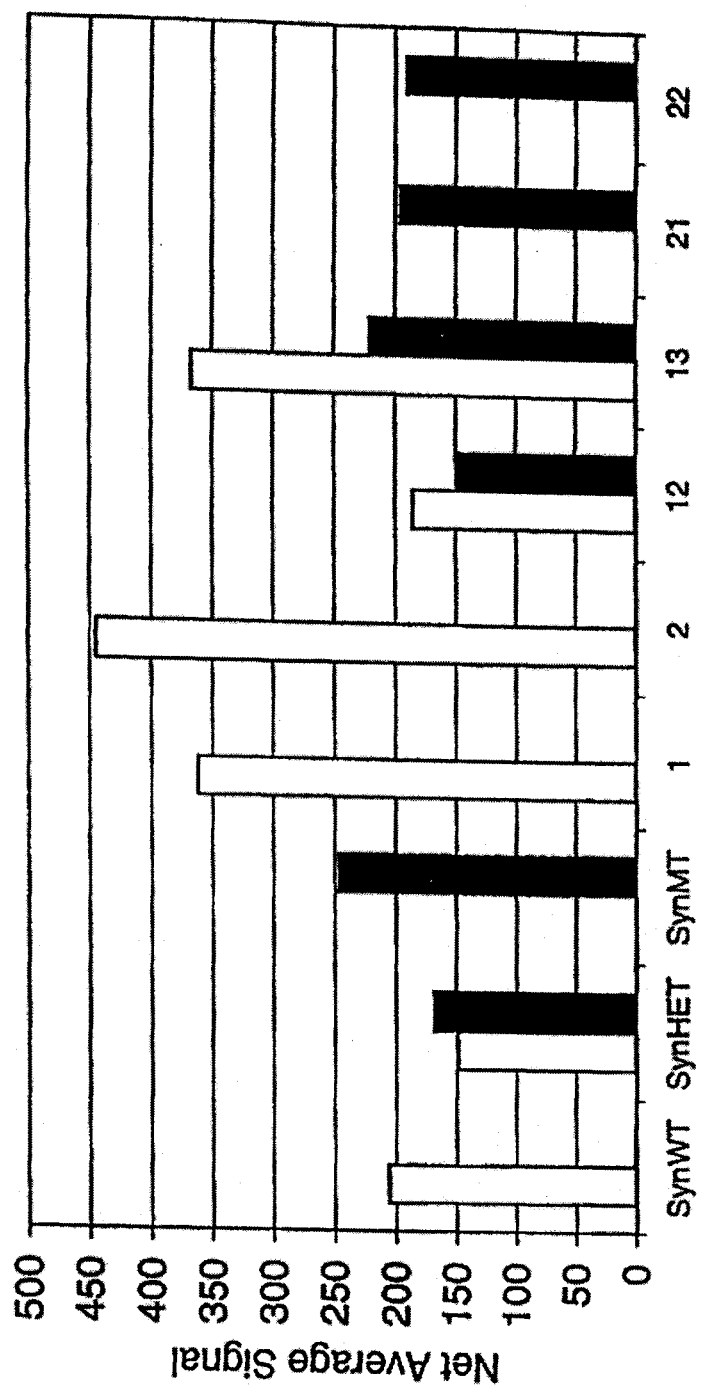

FIG. 126 provides a bar graph showing the analysis of the A506G mutation in the human factor V gene in 3 synthetic control samples and 6 samples of human genomic DNA.

Figure 127A:
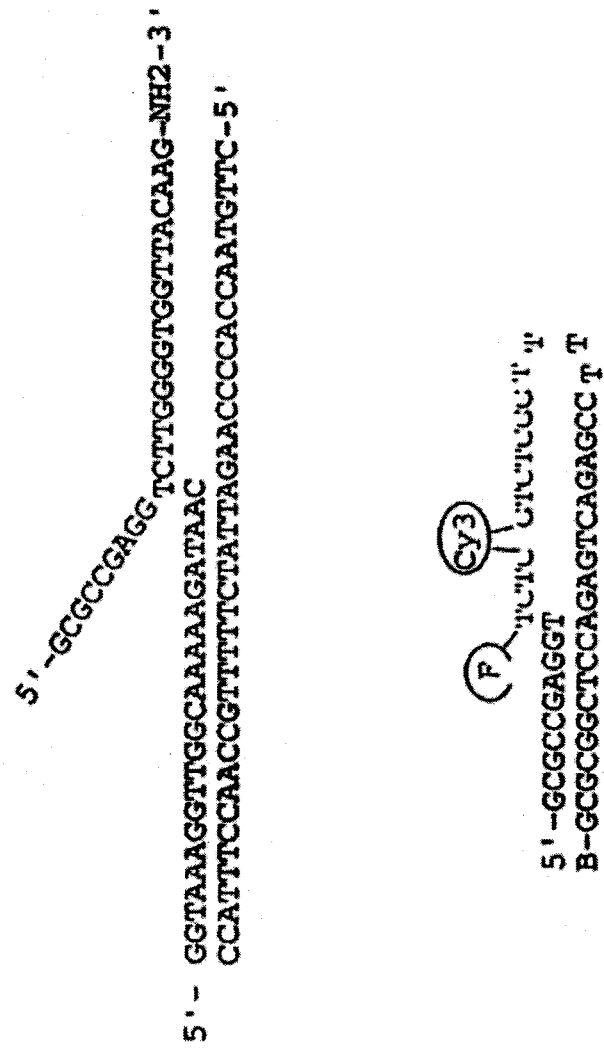

FIG. 127A shows a schematic diagram of an INVADER oligonucleotide (SEQ ID NO:243), probe oligonucleotide (SEQ ID NO:244) and FRET cassette (SEQ ID NO:245) for the detection of the mecA gene associated with methicillin resistance in S. aureus (SEQ ID NO:252). The flap released from the probe (SEQ ID NO:424) is shown annealed to the FRET cassette.

FIG. 127B shows a schematic diagram of an INVADER oligonucleotide (SEQ ID NO:246), probe oligonucleotide (SEQ ID NO:247) and FRET cassette (SEQ ID NO:245) for the detection of the nuc gene, a species-specific gene that distinguishes S. aureus from S. haemolyticus (SEQ ID NO:253). The flap released from the probe (SEQ ID NO:425) is shown annealed to the FRET cassette.

Figure 128:
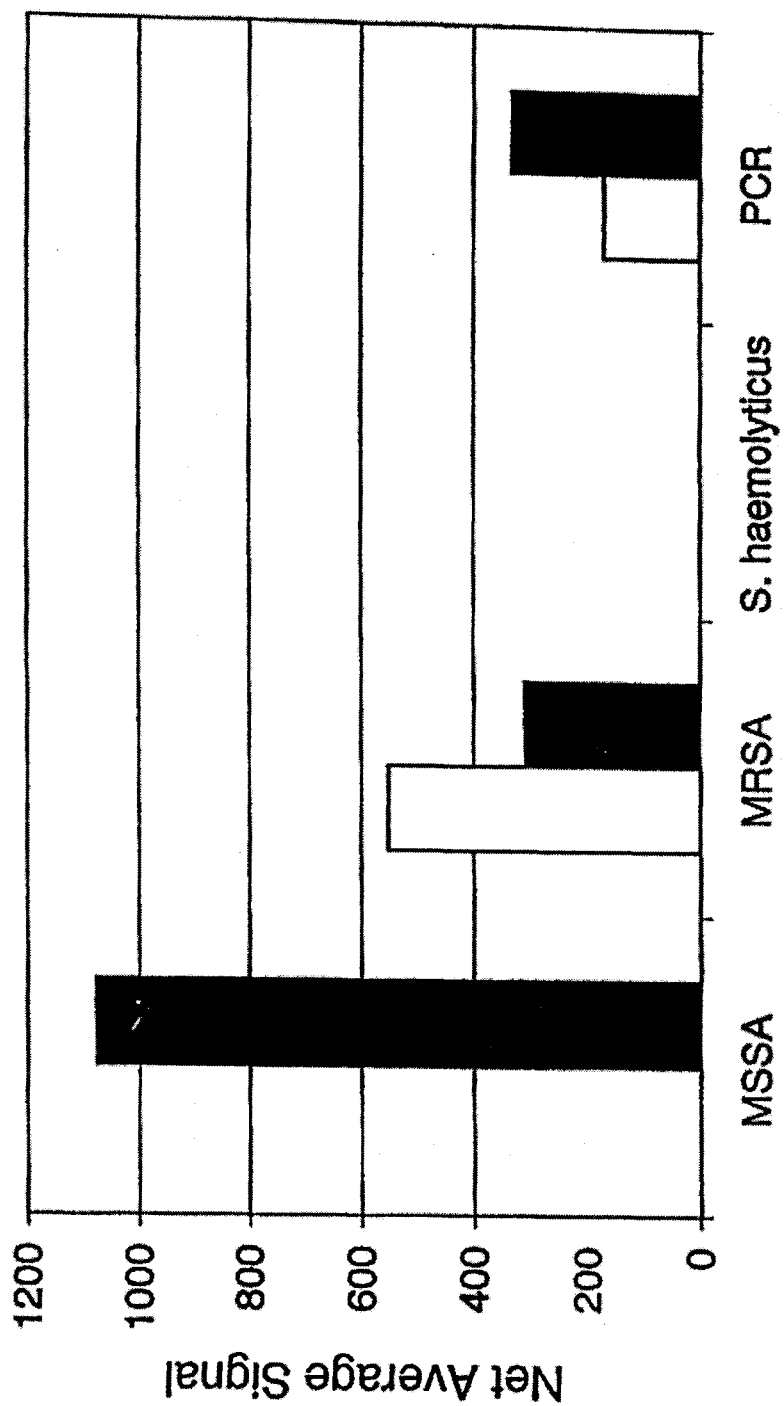

FIG. 128 provides a bar graph showing the detection of the mecA gene, compared to the detection of the S. aureus-specific nue gene in DNA from methicillin-sensitive S. aureus (MSSA), methicillin-resistant S. aureus (MRSA), S. haemolyticus, and amplified control targets for the mecA and nuc target sequences.

FIG. 129A shows the image generated by a fluorescence imager comparing the products produced by cleavage of a mixture of the oligonucleotides shown in FIG. 60 by either Pfu FEN-1 (1) or Mja FEN-1 (2).

Figure 26:
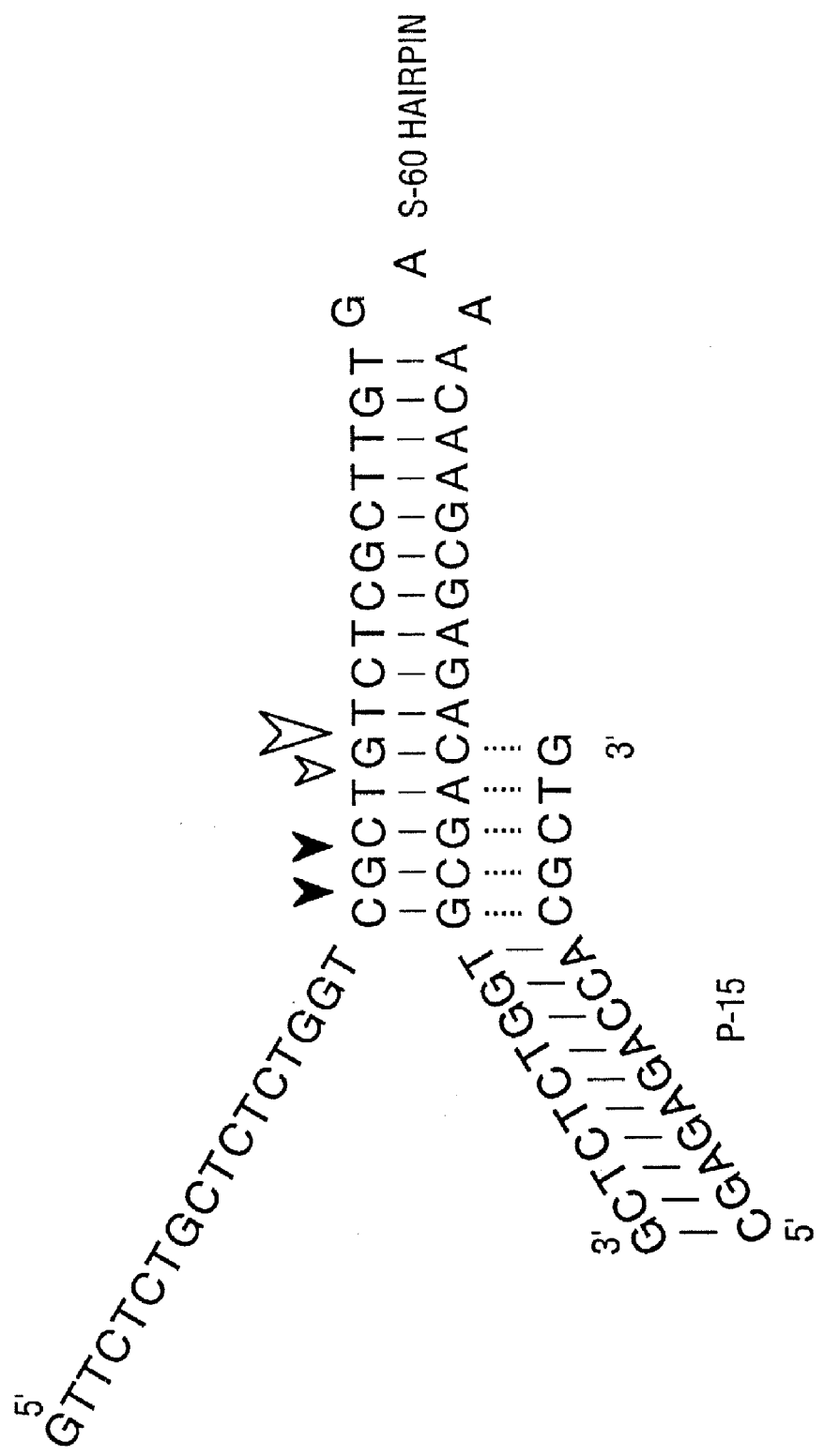
FIG. 26 provides a schematic showing the S-60 hairpin oligonucleotide (SEQ ID NO:29) with the annealed P-15 oligonucleotide (SEQ ID NO:30).

FIG. 129B shows the image generated by a fluorescence imager comparing the products produced by cleavage of the oligonucleotides shown in FIG. 26 by either Pfu FEN-1 (1) or Mja FEN-1 (2).

Figure 130:
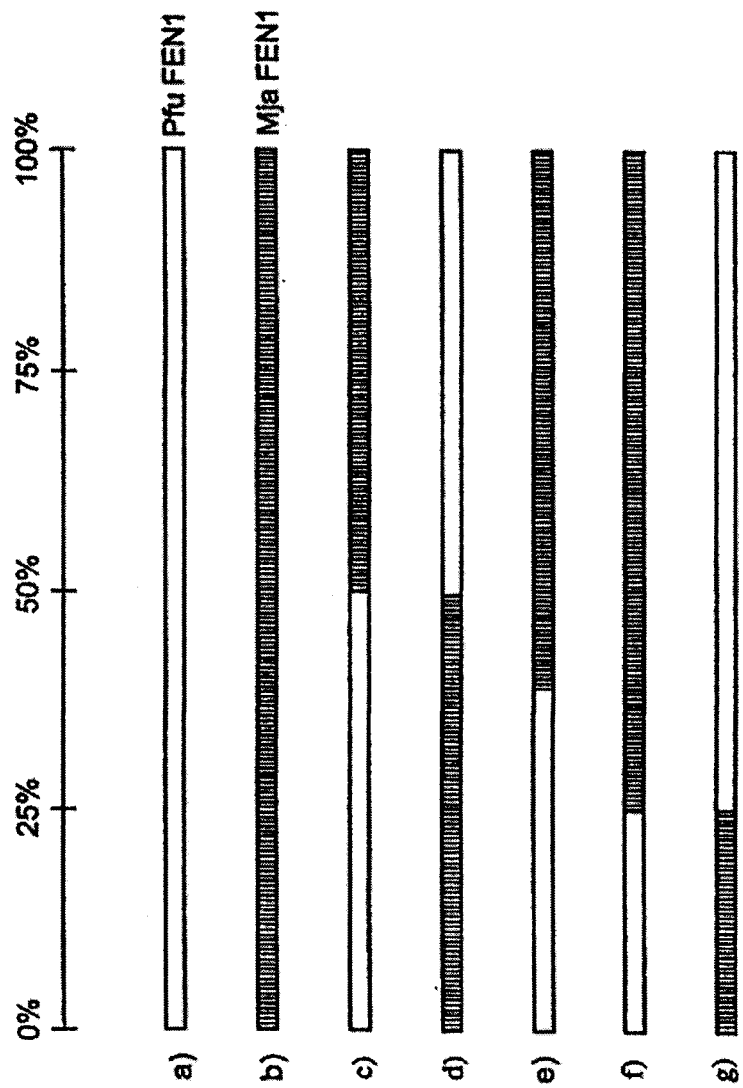

FIG. 130 shows a schematic diagram of the portions of the Pfu FEN-1 and Mja FEN-1 proteins combined to create chimeric nucleases.

FIG. 131A shows the image generated by a fluorescence imager comparing the products produced by cleavage of a mixture of the oligonucleotides shown in FIG. 60 by Pfu FEN-1 (1), Mja FEN-1 (2) or the chimeric nucleases diagrammed in FIG. 130.

FIG. 131B shows the image generated by a fluorescence imager comparing the products produced by cleavage of the oligonucleotides shown in FIG. 26 by Pfu FEN-1 (1), Mja FEN-1 (2) or the chimeric nucleases diagrammed in FIG. 130.

Figure 132:
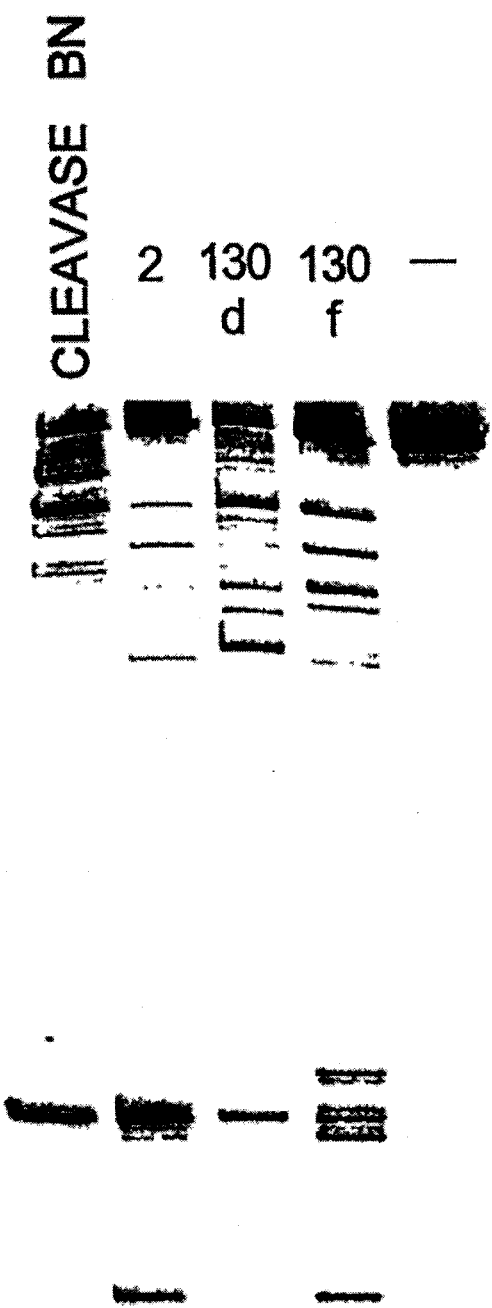
Figure 133A:
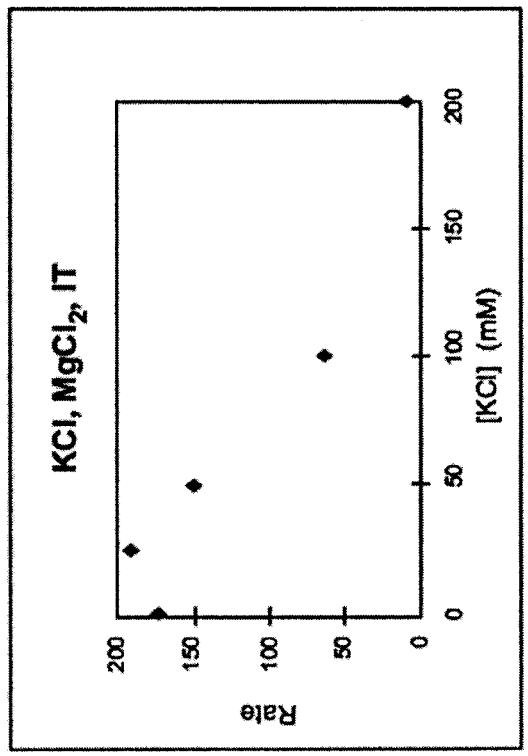
Figure 133B:
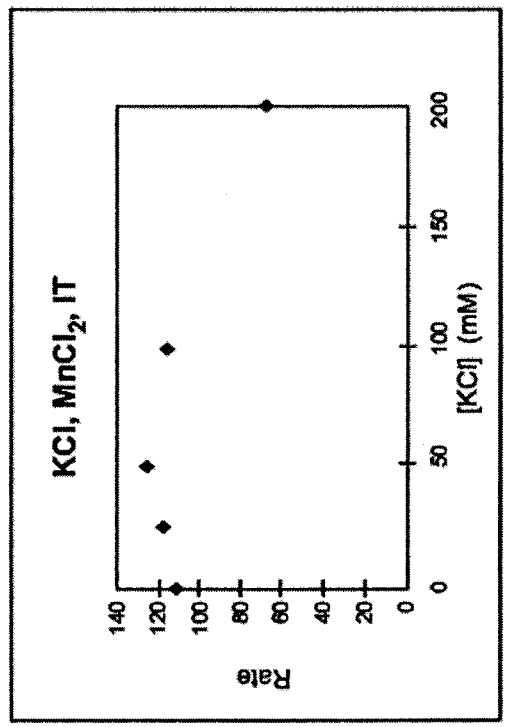
Figure 133C:
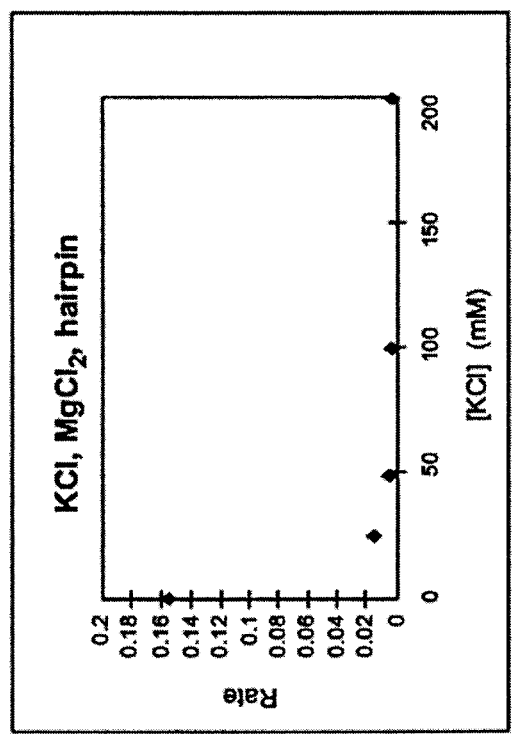
Figure 133D:
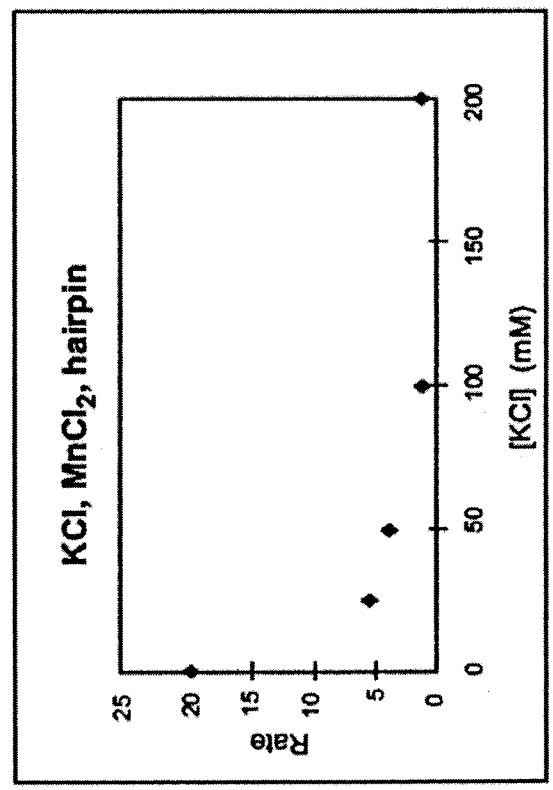
Figure 133E:
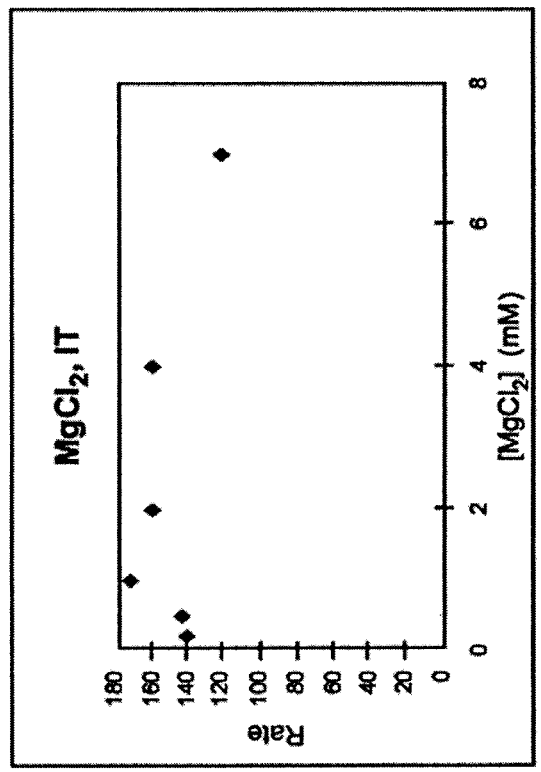
Figure 133F:
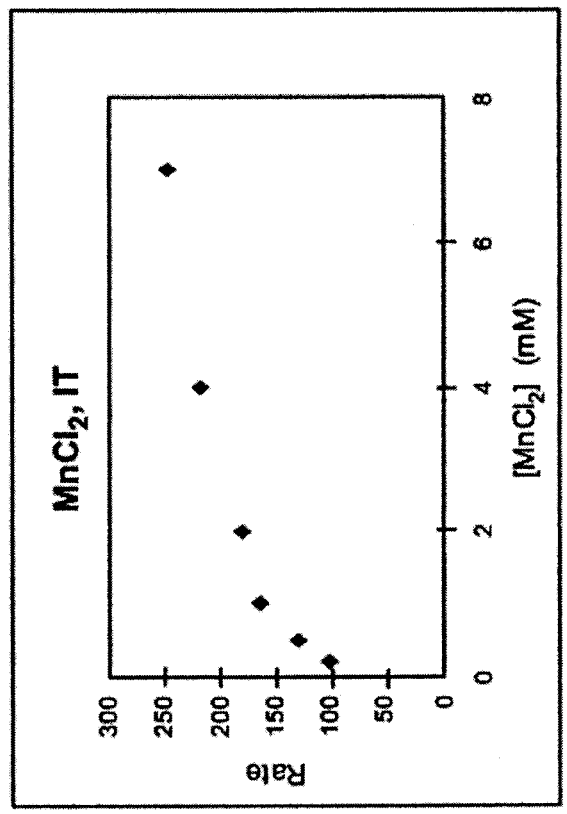
Figure 133G:
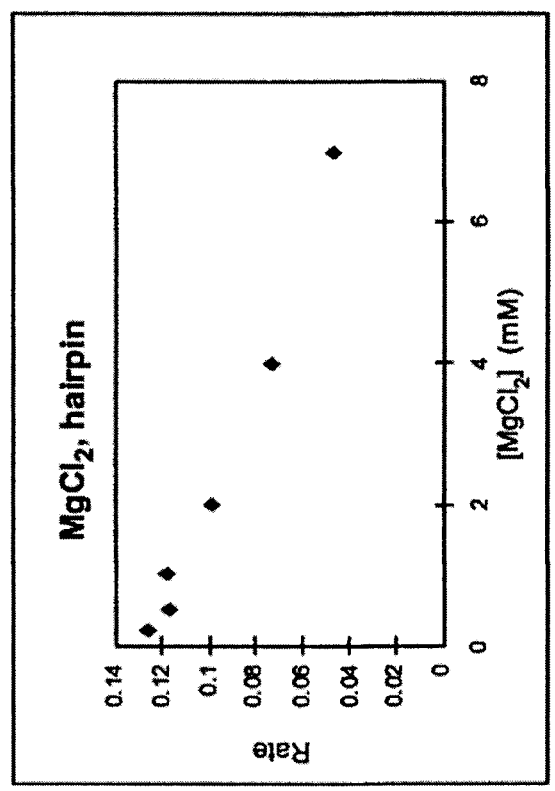
Figure 133H:
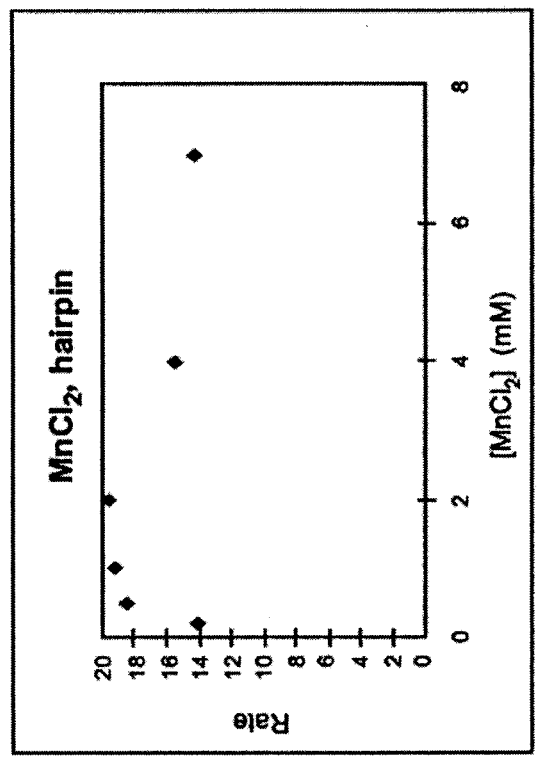
Figure 133I:
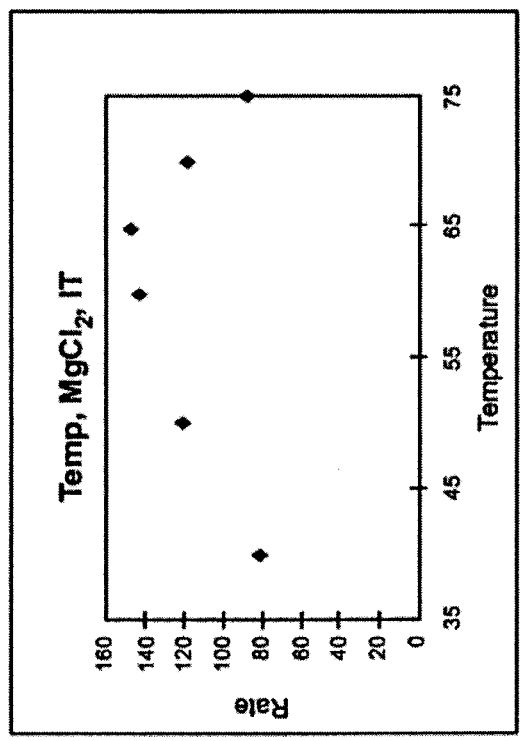
Figure 133J:
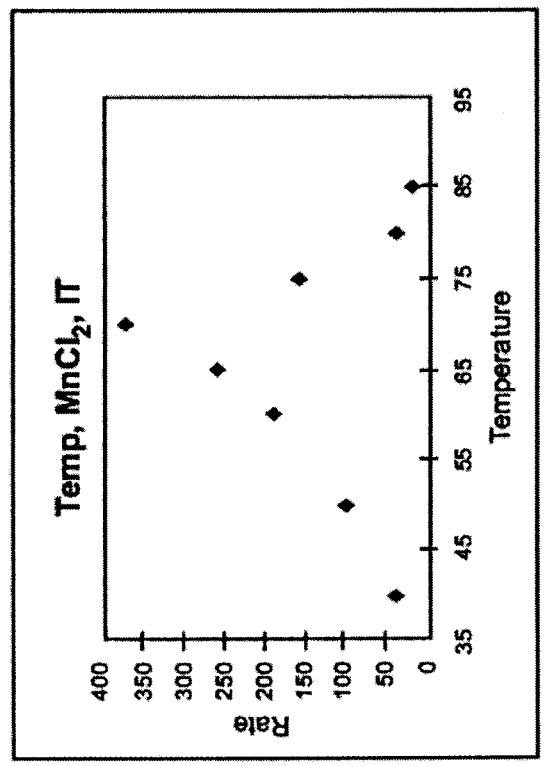

FIG. 132 shows the image generated by a fluorescence imager comparing the products produced by cleavage of folded cleavage structures by Pfu FEN-1 (1), Mja FEN-1 (2) or the chimeric nucleases diagrammed in FIG. 130.

FIG. 133A-J shows the results of various assays used to determine the activity of Cleavase BN under various conditions.

Figure 134A:
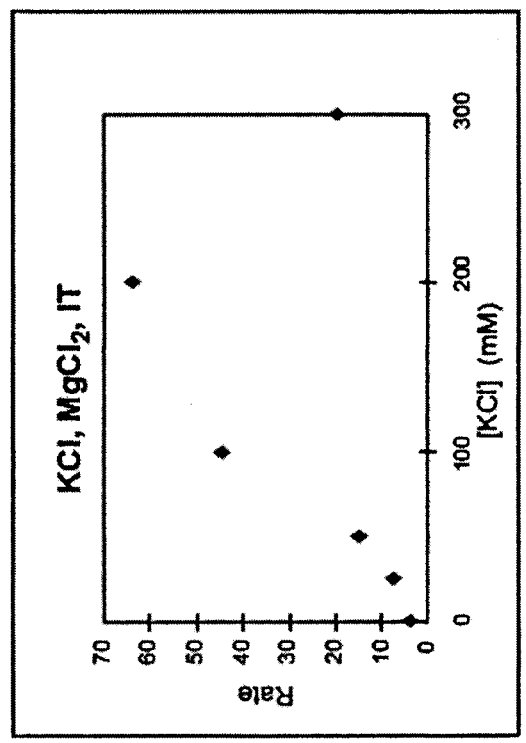
Figure 134B:
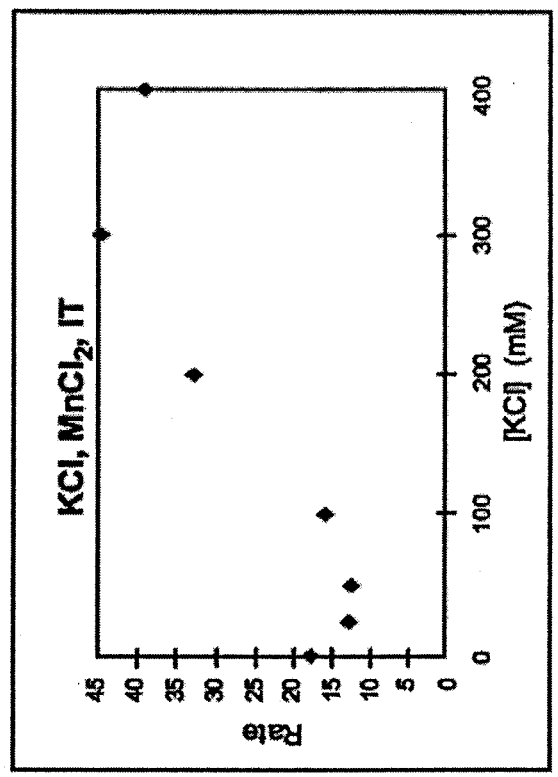
Figure 134D:
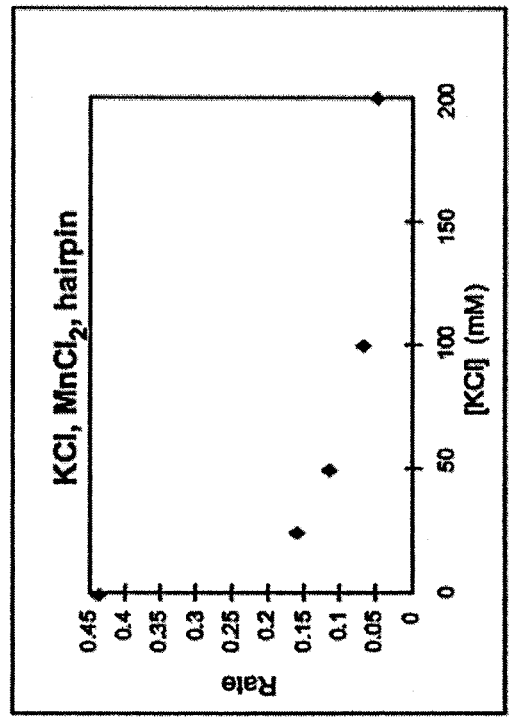
Figure 134E:
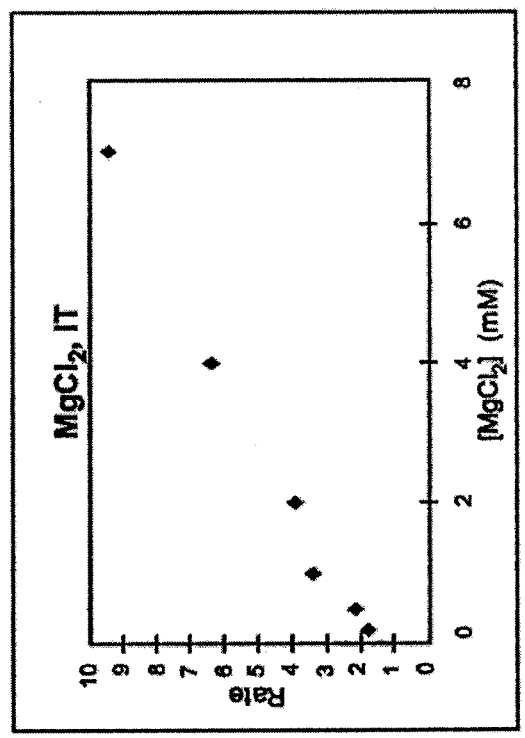
Figure 134F:
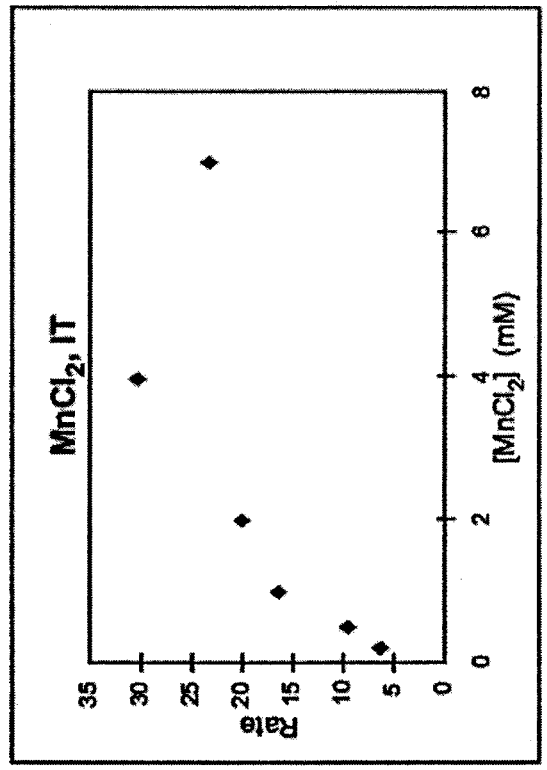
Figure 134H:
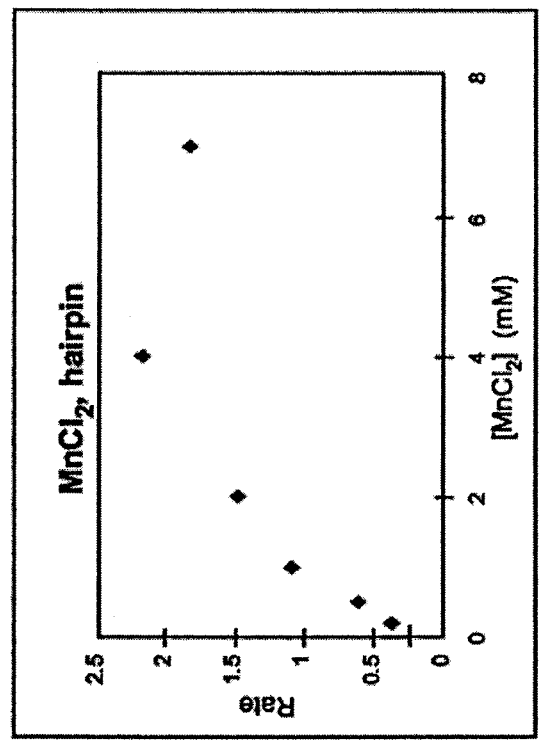
Figure 134I:
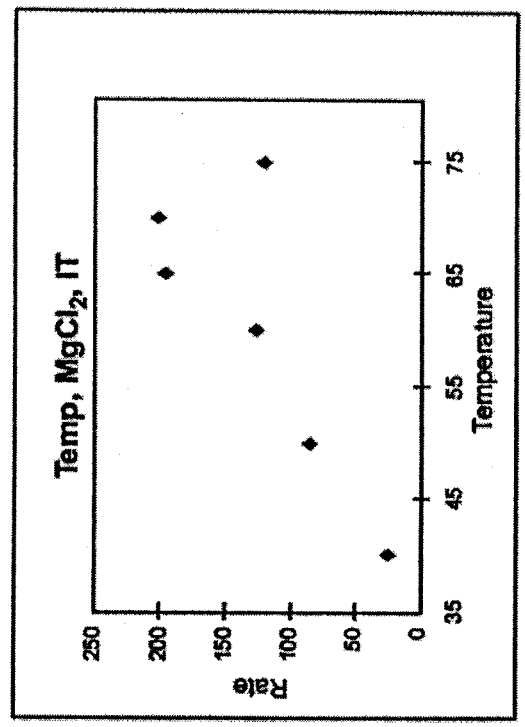
Figure 134J:
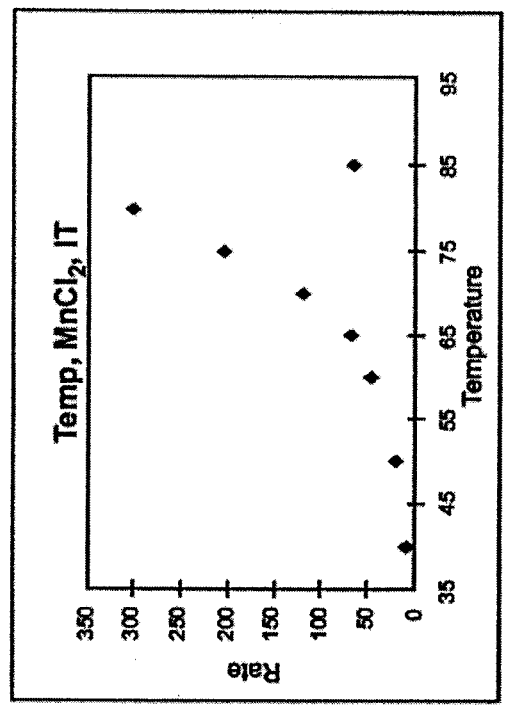

FIG. 134A-B, D-F, and H-J show the results of various assays used to determine the activity of TaqDN under various conditions.

Figure 135A:
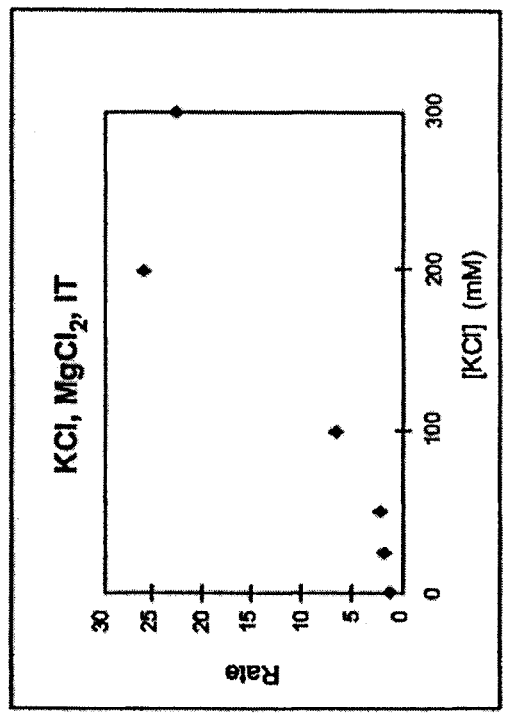
Figure 135B:
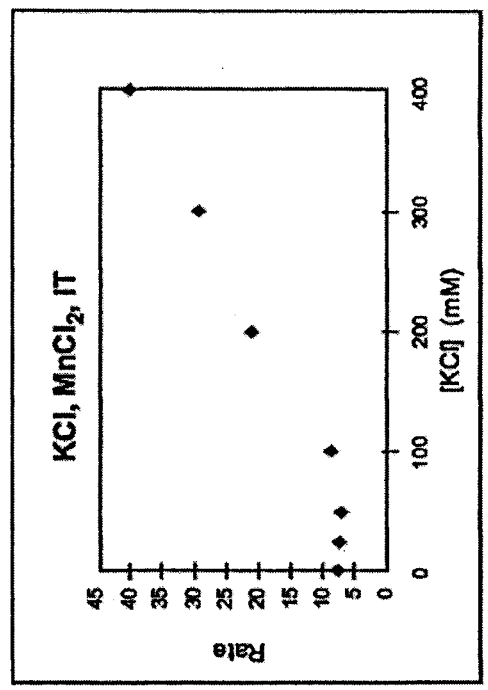
Figure 135D:
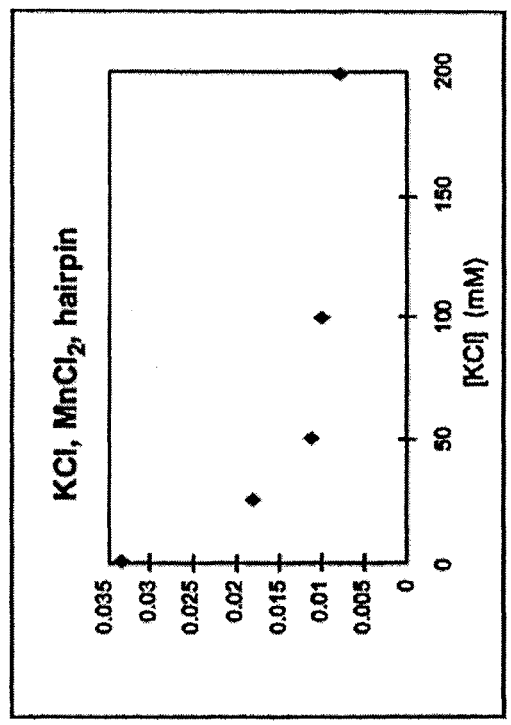
Figure 135E:
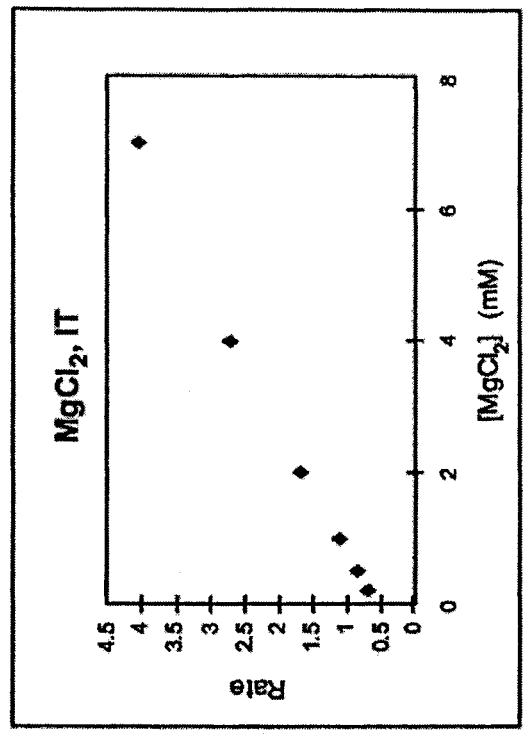
Figure 135F:
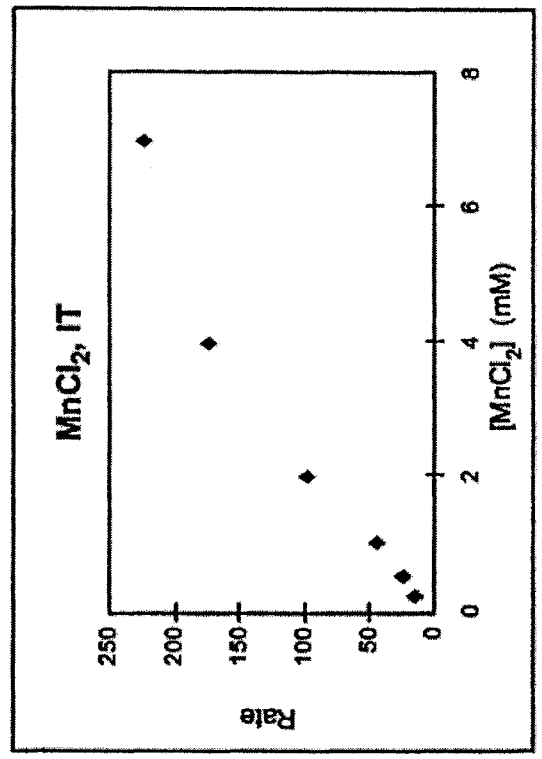
Figure 135H:
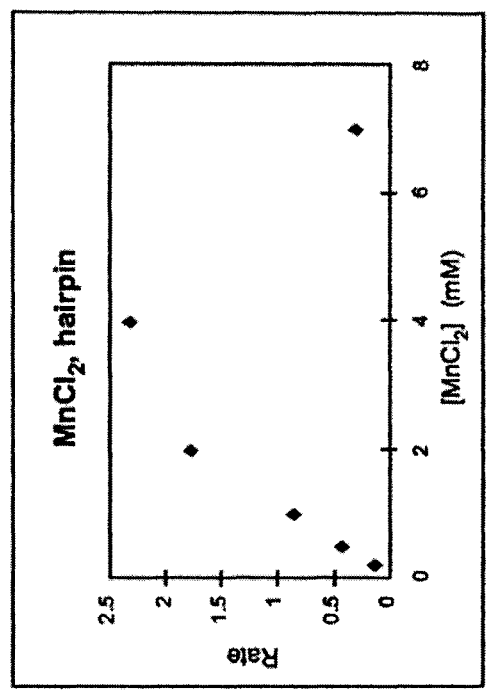
Figure 135I:
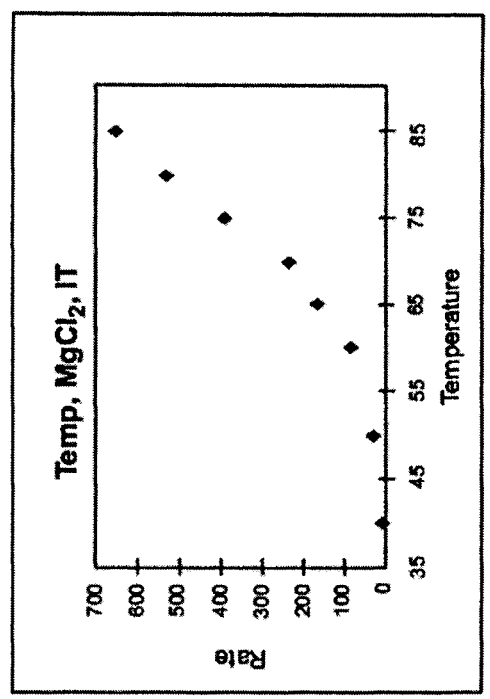
Figure 135J:
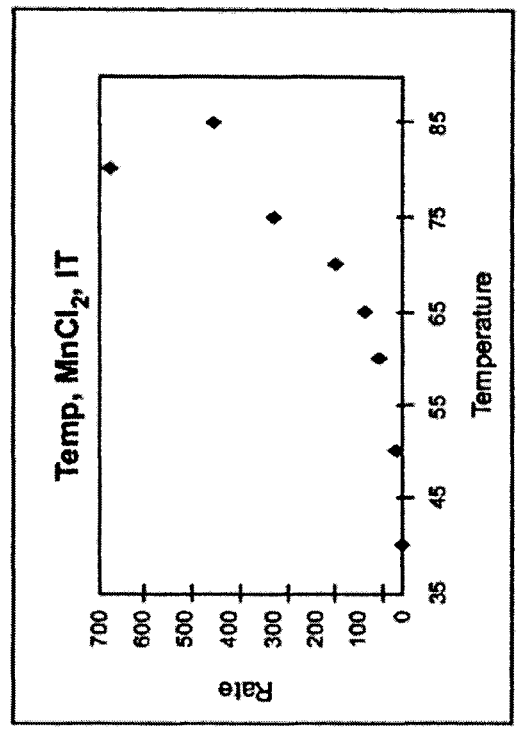

FIG. 135A-B, D-F, H-J show the results of various assays used to determine the activity of TthDN under various conditions.

Figure 136A:
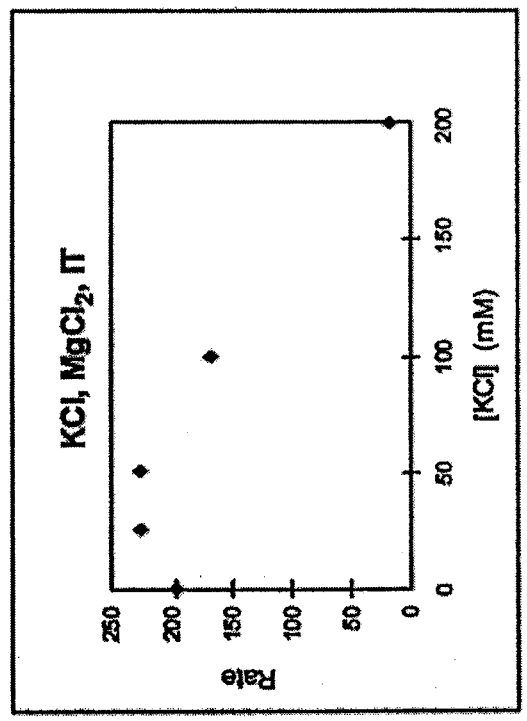
Figure 136B:
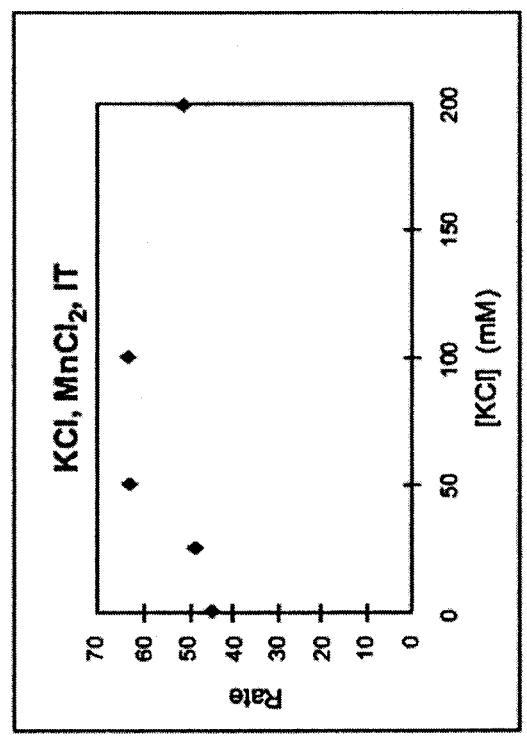
Figure 136D:
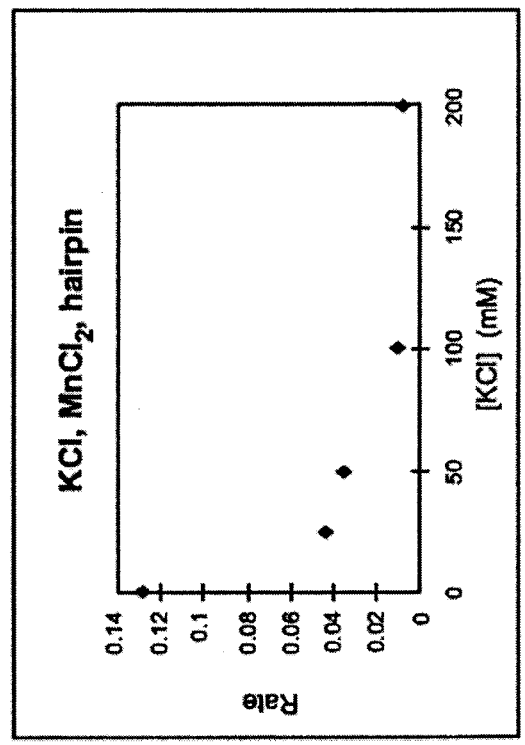
Figure 136E:
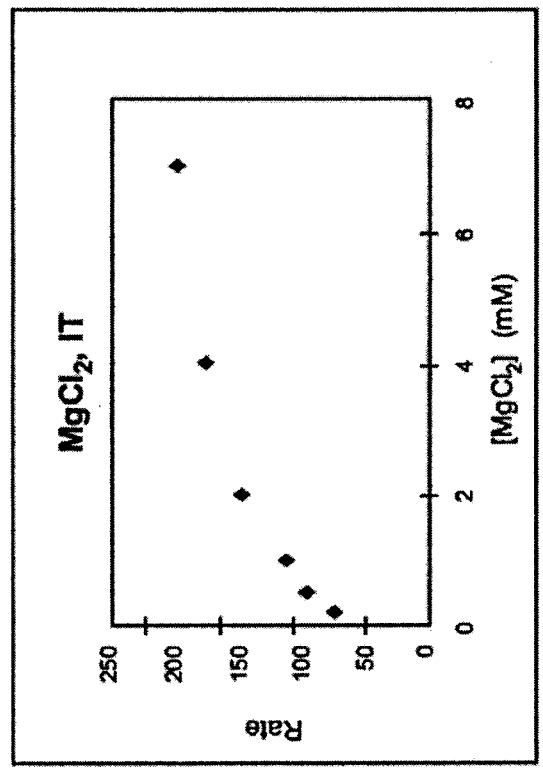
Figure 136F:
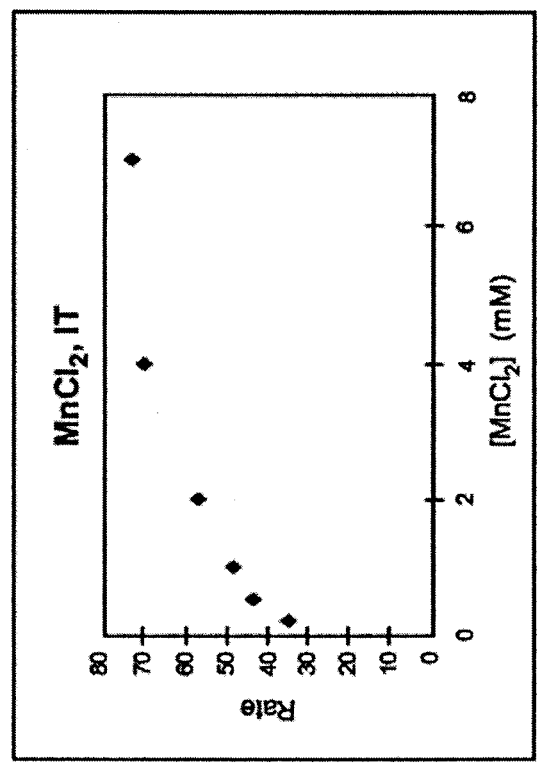
Figure 136H:
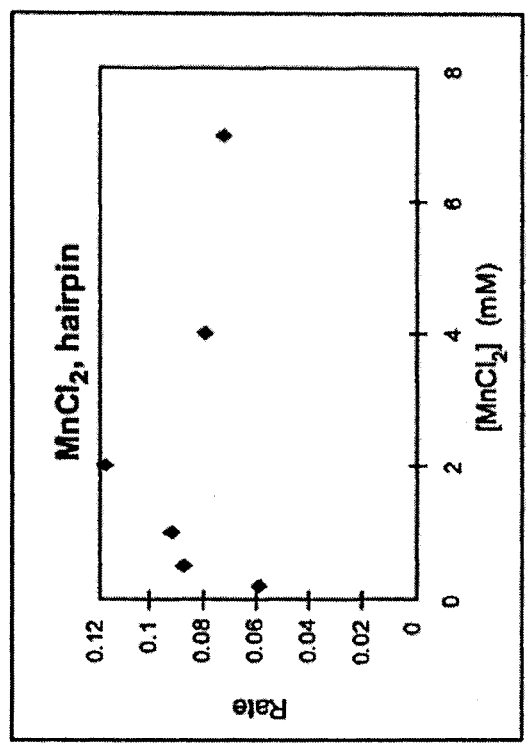
Figure 136I:
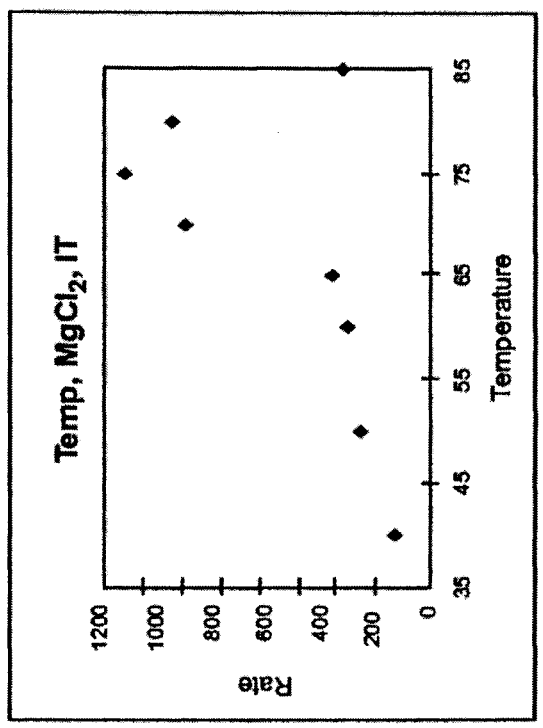
Figure 136J:
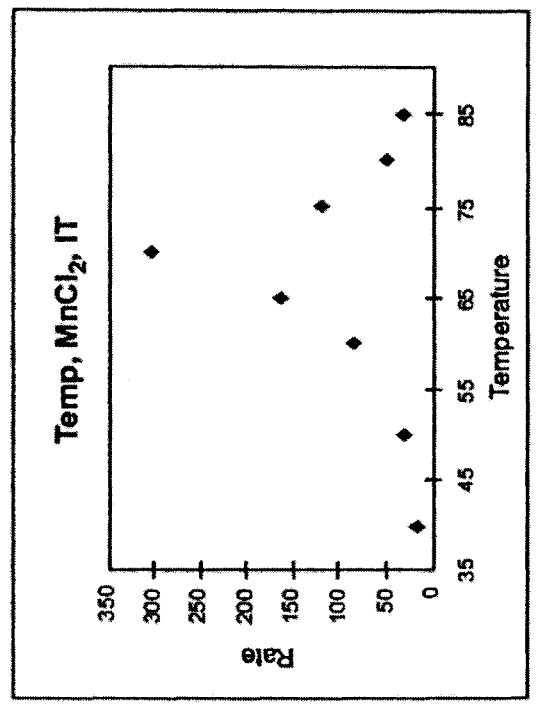
Figure 137A:
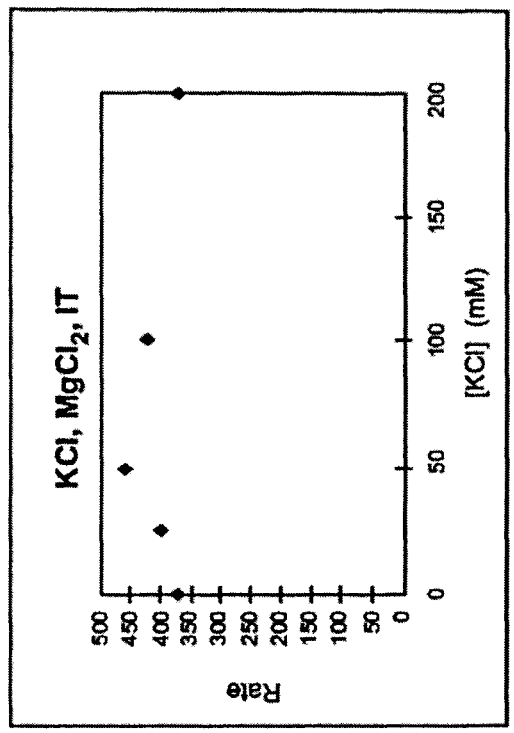
Figure 137B:
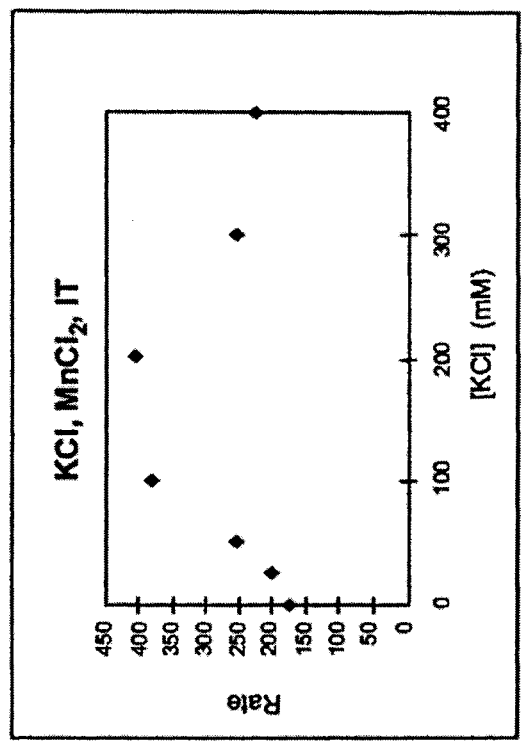
Figure 137C:
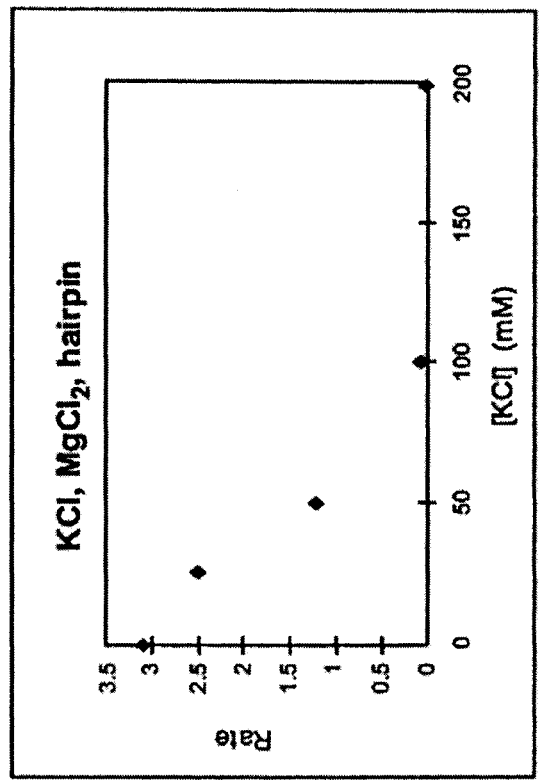
Figure 137D:
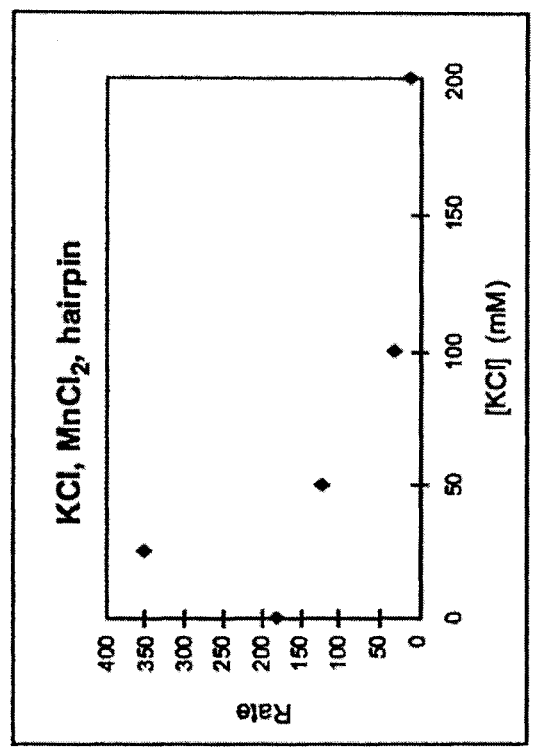
Figure 137E:
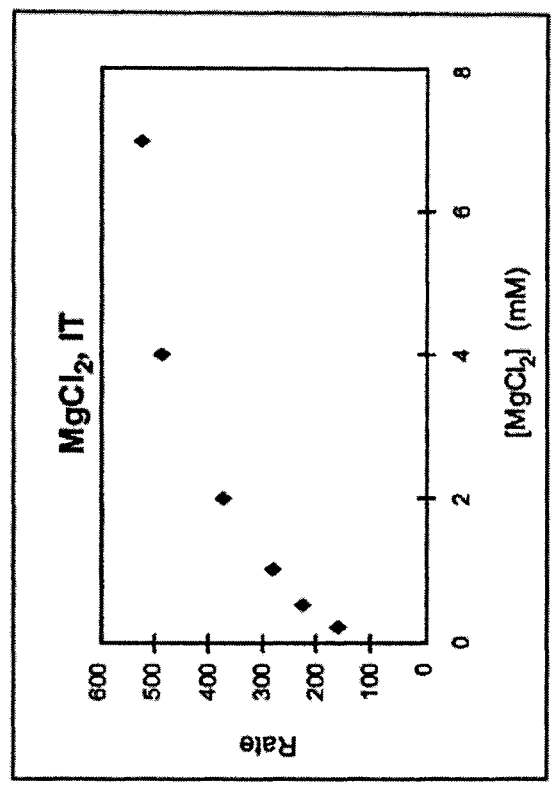
Figure 137F:
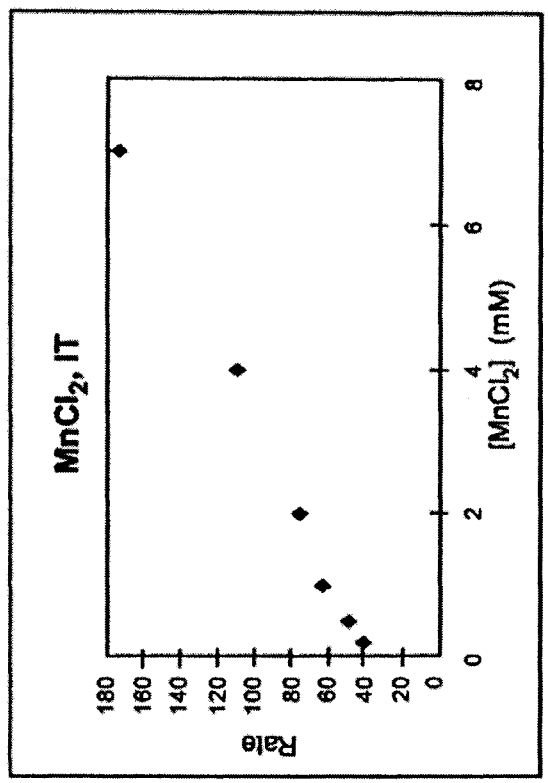
Figure 137G:
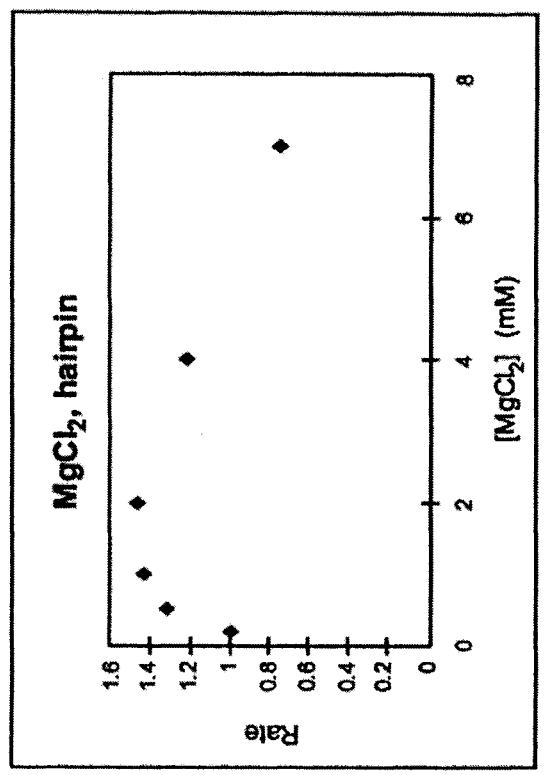
Figure 137H:
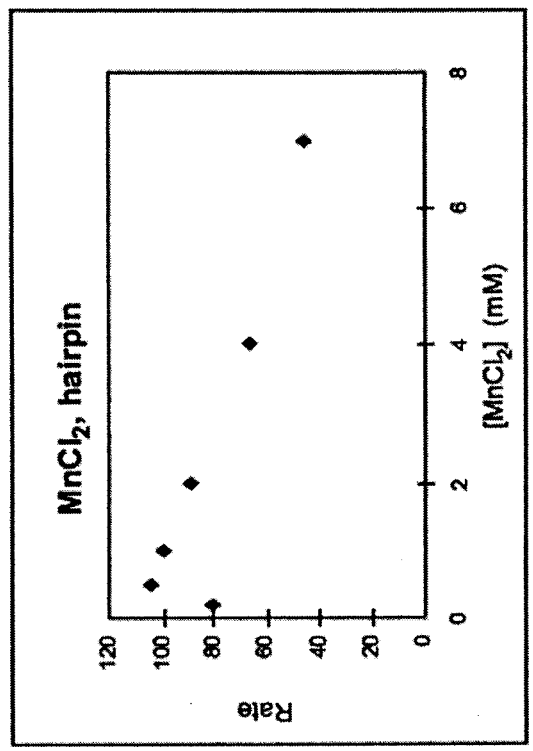
Figure 137I:
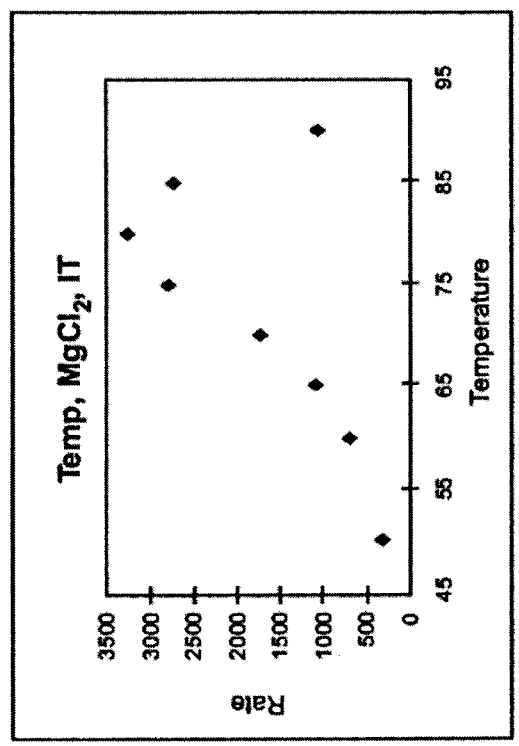
Figure 137J:
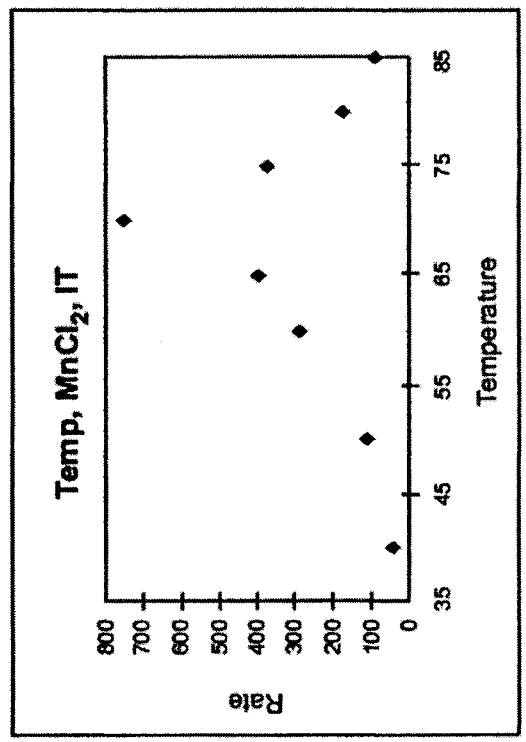

FIG. 136A-B, D-F, and H-J show the results of various assays used to determine the activity of Pfu FEN-1 under various conditions.

FIG. 137A-J show the results of various assays used to determine the activity of Mja FEN-1 under various conditions.

Figure 138A:
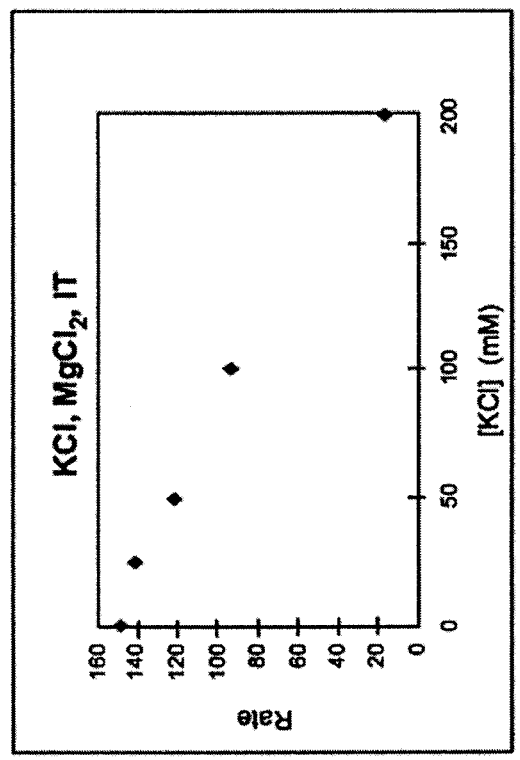
Figure 138B:
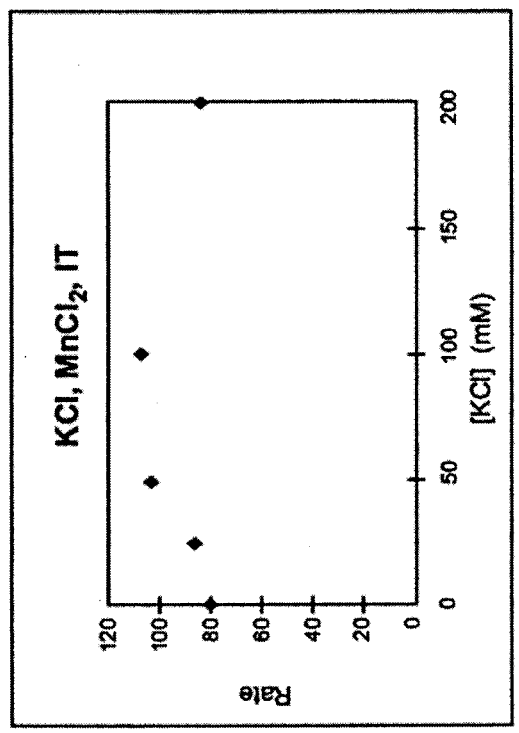
Figure 138D:
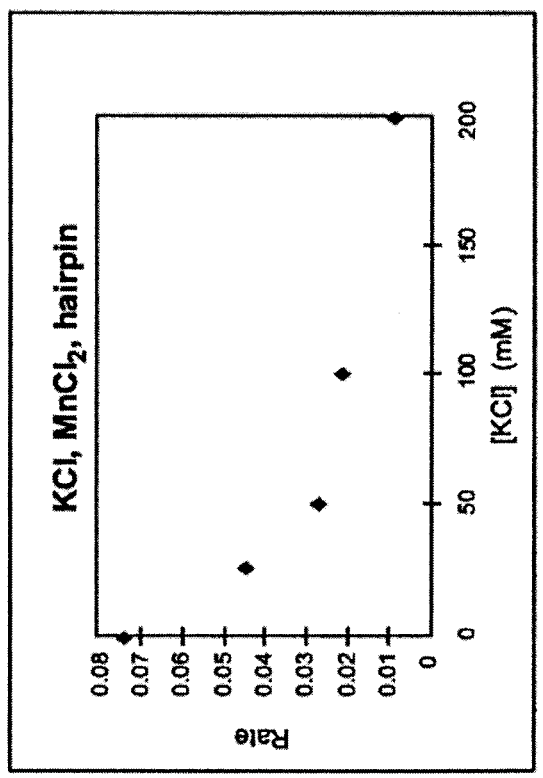
Figure 138E:
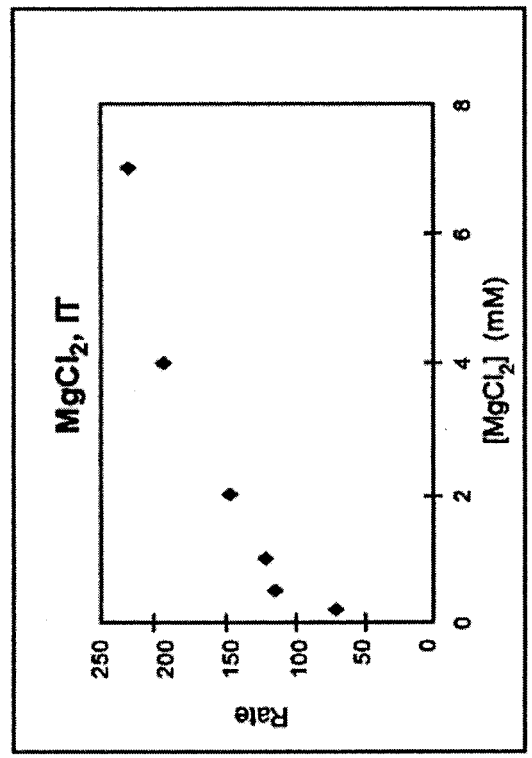
Figure 138F:
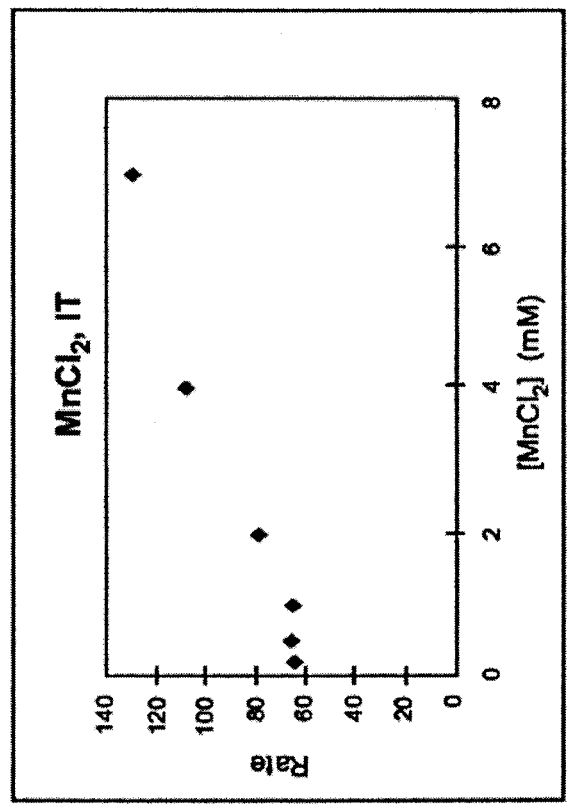
Figure 138H:
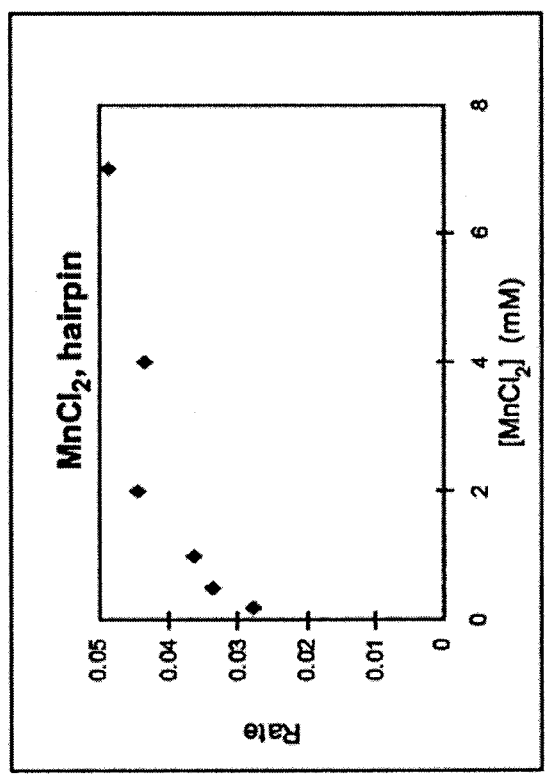
Figure 138I:
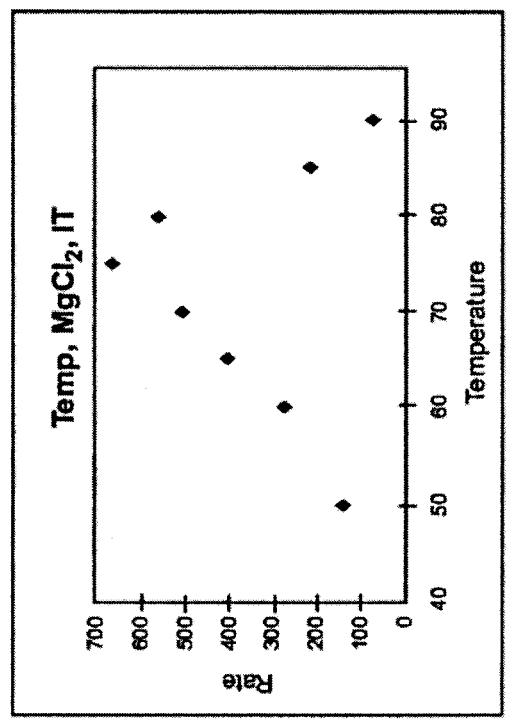
Figure 138J:
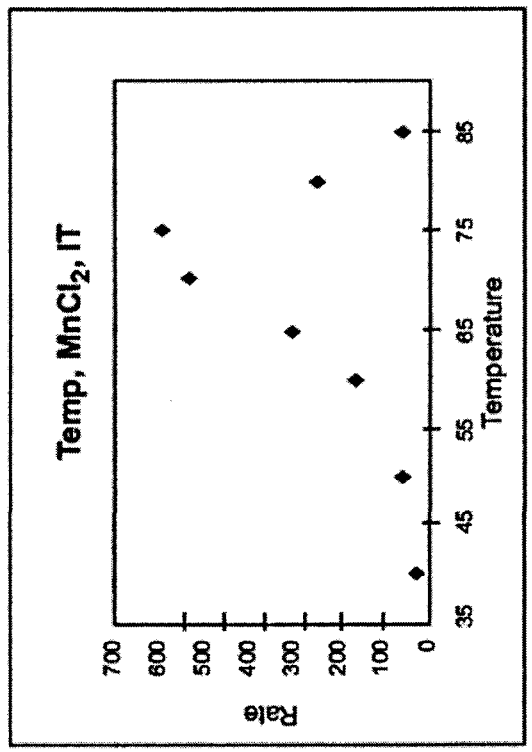
Figure 139A:
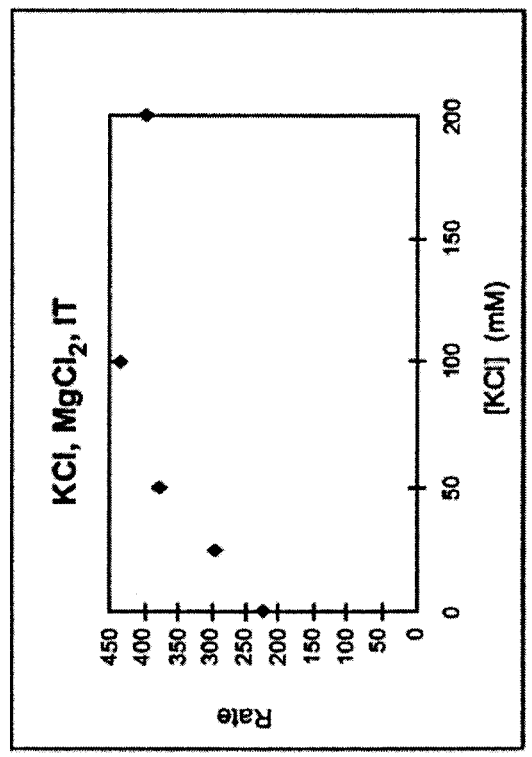
Figure 139B:
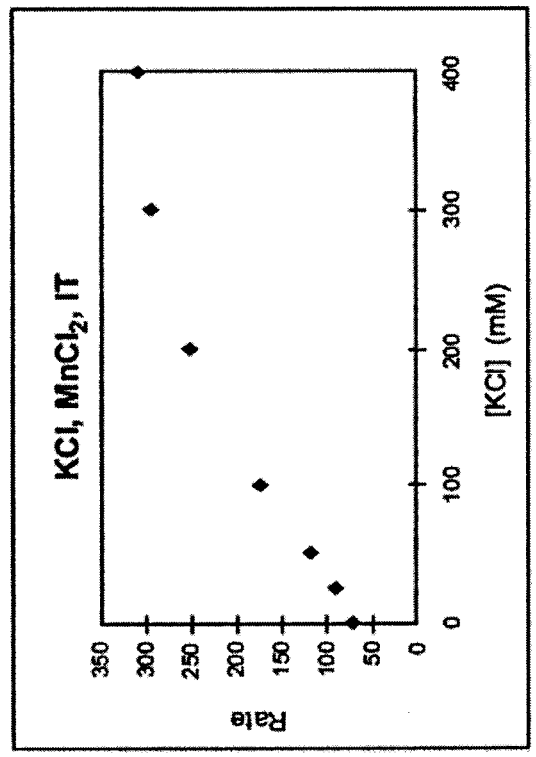
Figure 139C:
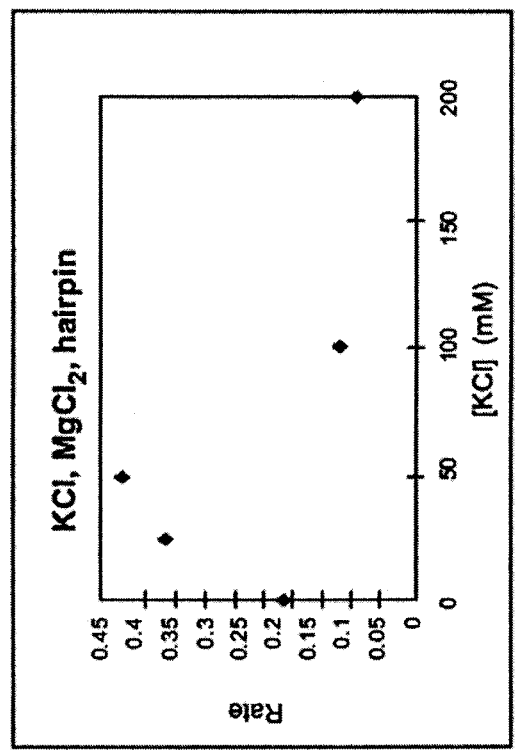
Figure 139D:
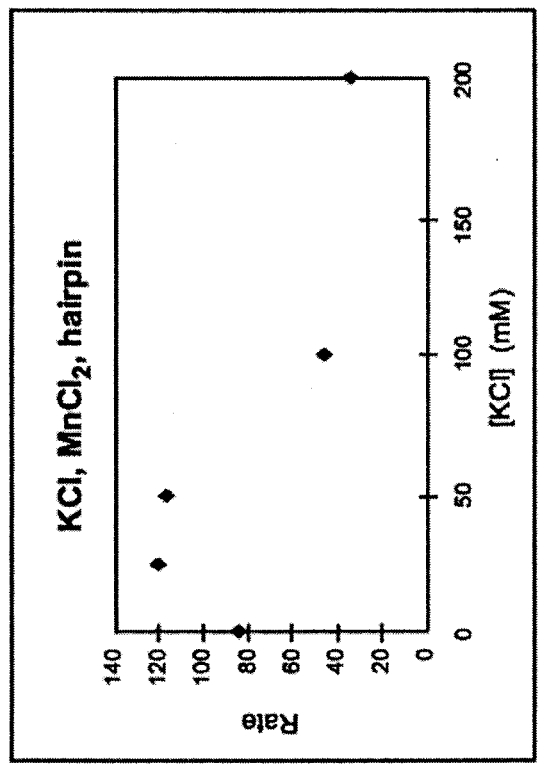
Figure 139E:
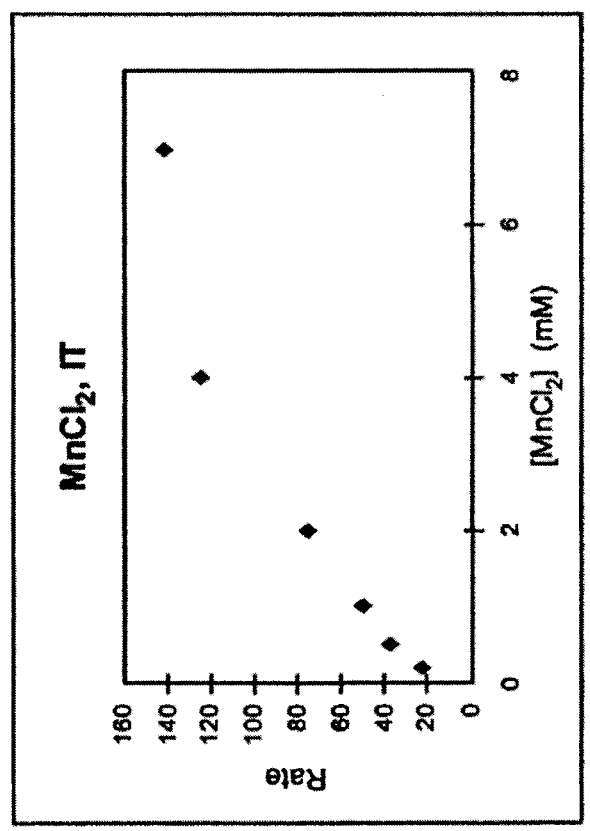
Figure 139F:
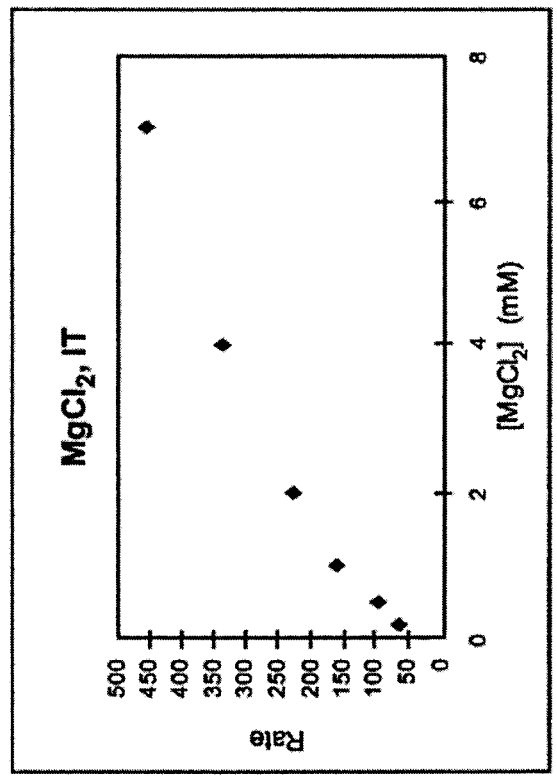
Figure 139G:
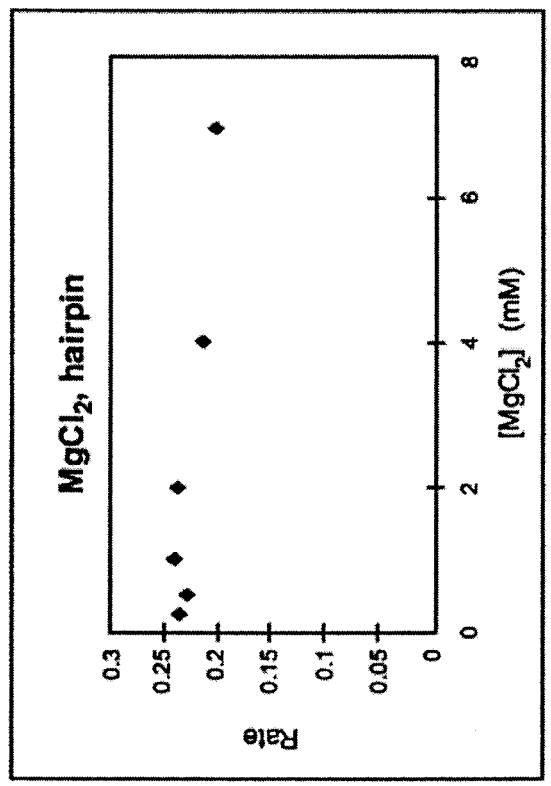
Figure 139H:
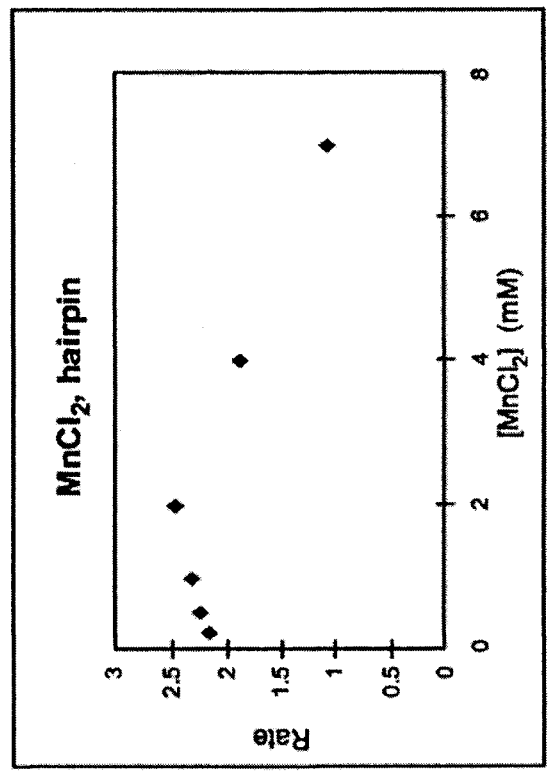
Figure 139I:
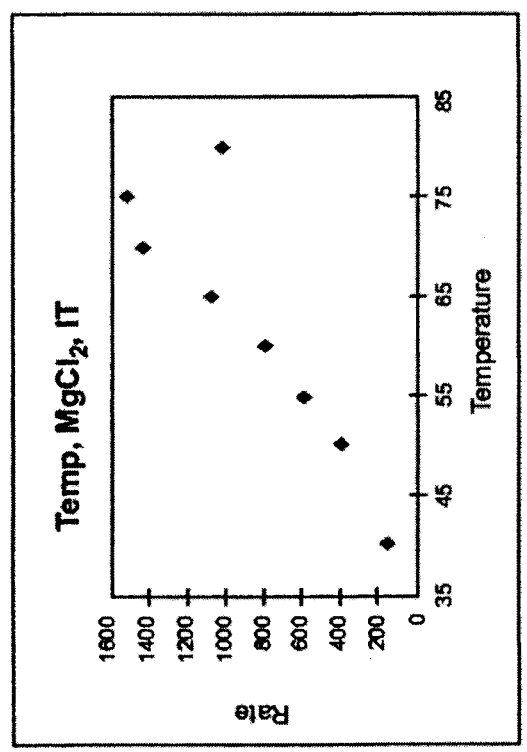
Figure 139J:
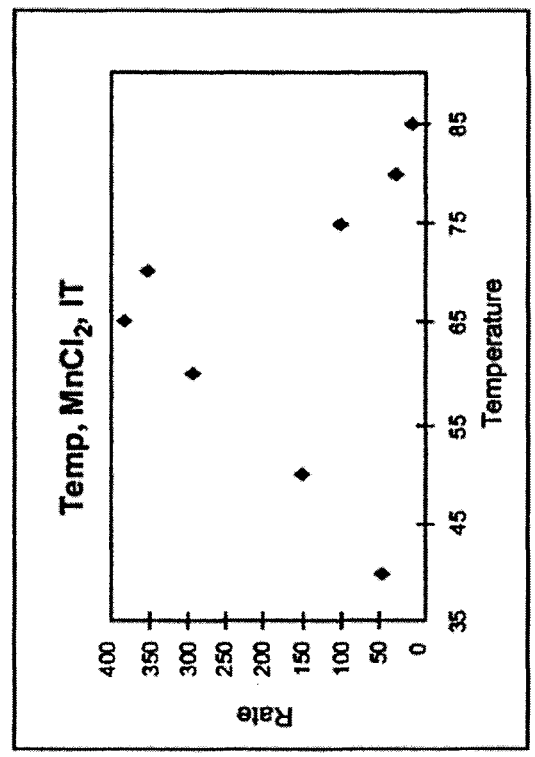

FIG. 138A-B, D-F, and H-J show the results of various assays used to determine the activity of Afu FEN-1 under various conditions.

FIG. 139A-E, and G-I show the results of various assays used to determine the activity of Mth FEN-1 under various conditions.

FIG. 140 shows the two substrates. Panel A shows the structure and sequence of the hairpin substrate (25-65-1) (SEQ ID NO:293), while Panel B shows the structure and sequence of the INVADER (IT) substrate (25-184-5)(SEQ ID NO:294).

FIG. 141A shows the structure and sequence of oligonucleotides forming an invasive cleavage structure (203-91-01, SEQ ID NO:403, and target-INVADER oligonucleotide 203-91-04, SEQ ID NO:404).

FIG. 141B shows the structure and sequence of oligonucleotides forming an X-structure substrate (203-81-02, SEQ ID NO:405 and 594-09-01, SEQ ID NO:406).

Figure 142:
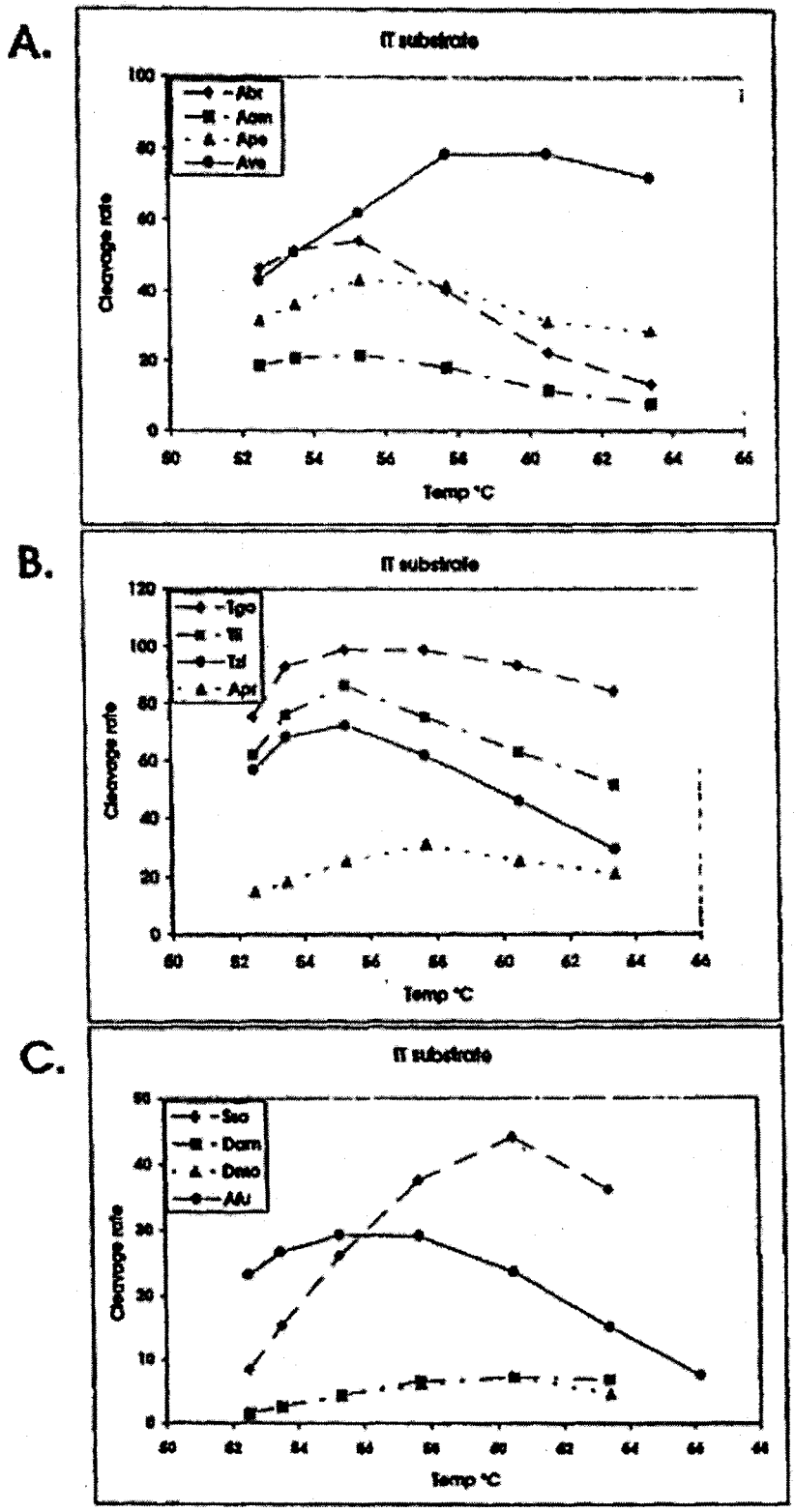

FIG. 142 shows the activities of the indicated FEN proteins on the invasive cleavage structure diagrammed in FIG. 141A.

Figure 143:
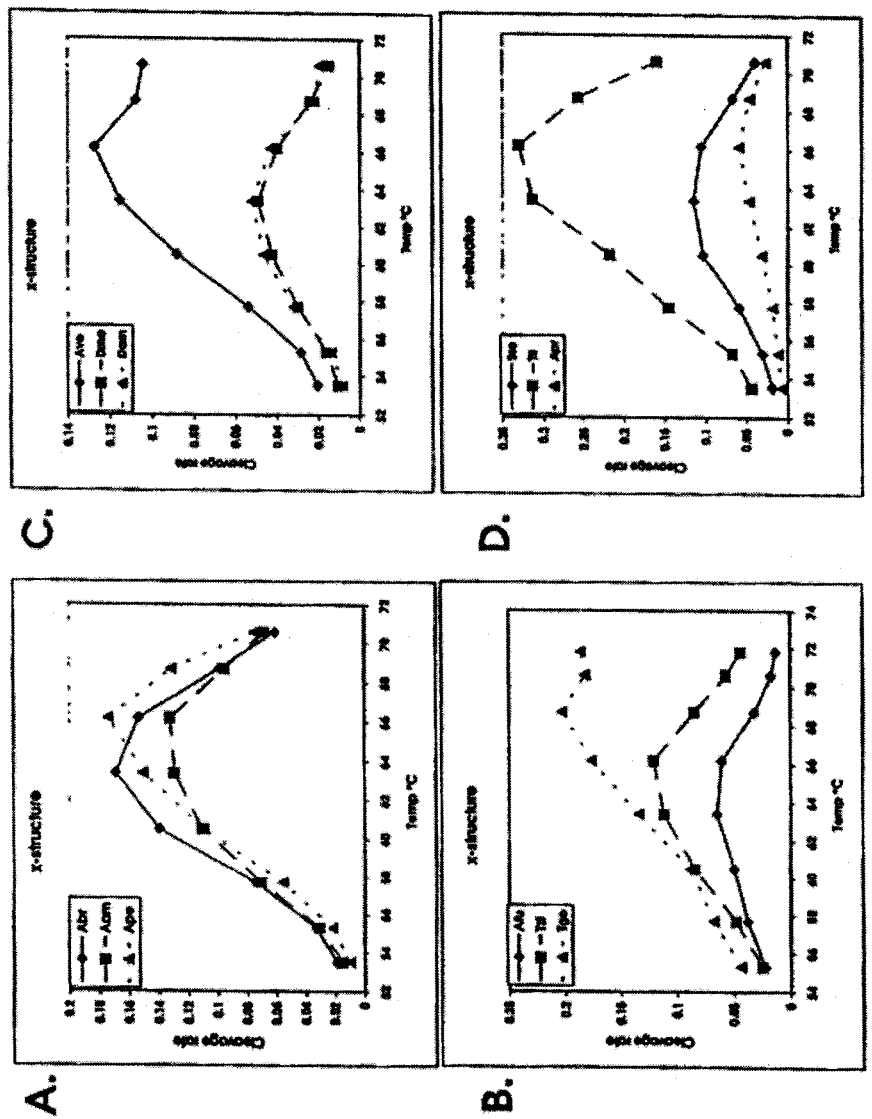

FIG. 143 shows the activities of the indicated FEN proteins on the X-structure diagrammed in FIG. 141B.

FIG. 144 shows a schematic diagram of an INVADER oligonucleotide (SEQ ID NO:407), probe oligonucleotide (SEQ ID NO:408) and FRET cassette (SEQ ID NO:409) for the detection of the polymerase gene of human cytomegalovirus (SEQ ID NO:410). The flap released from the probe (SEQ ID NO:426) is shown annealed to the FRET cassette.

Figure 145:
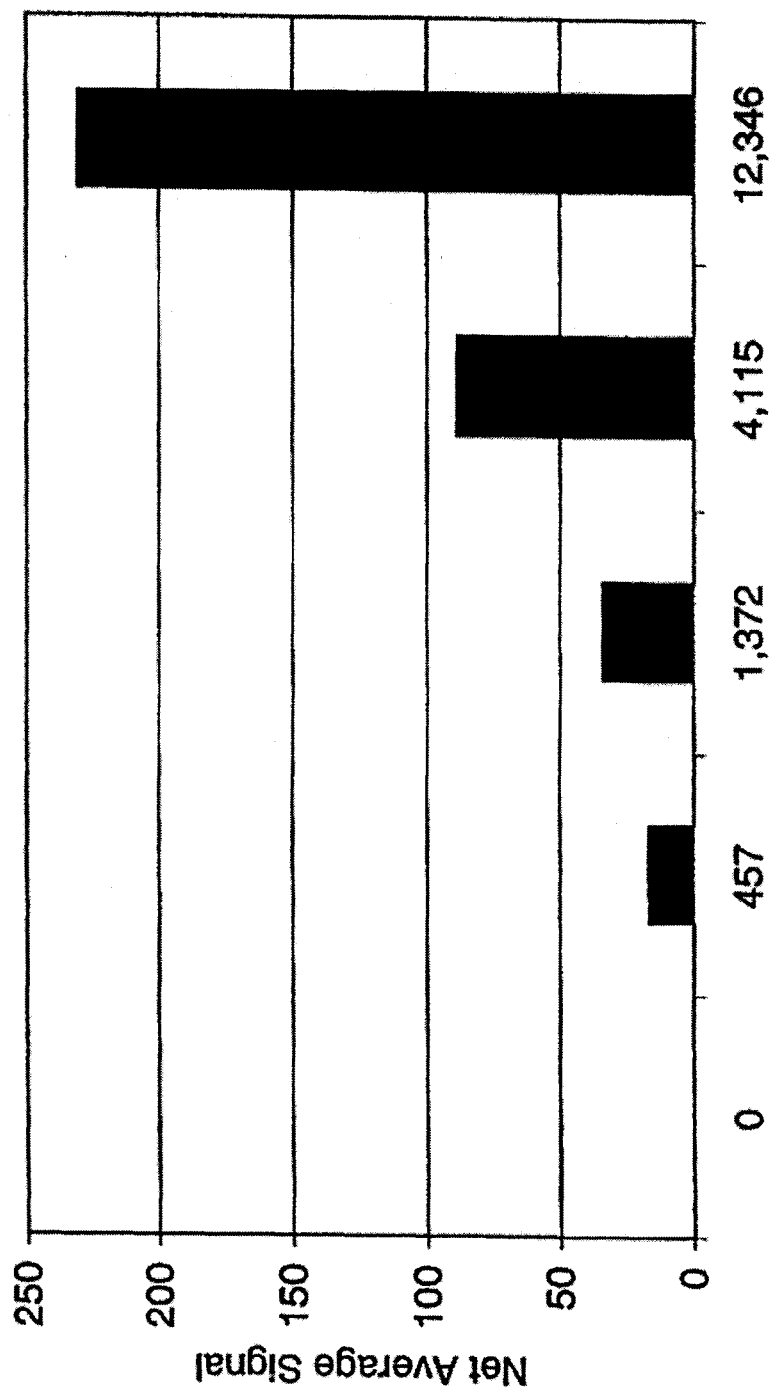

FIG. 145 provides a bar graph showing the detection of different numbers of copies of human cytomegalovirus genomic DNA.

Figure 146:
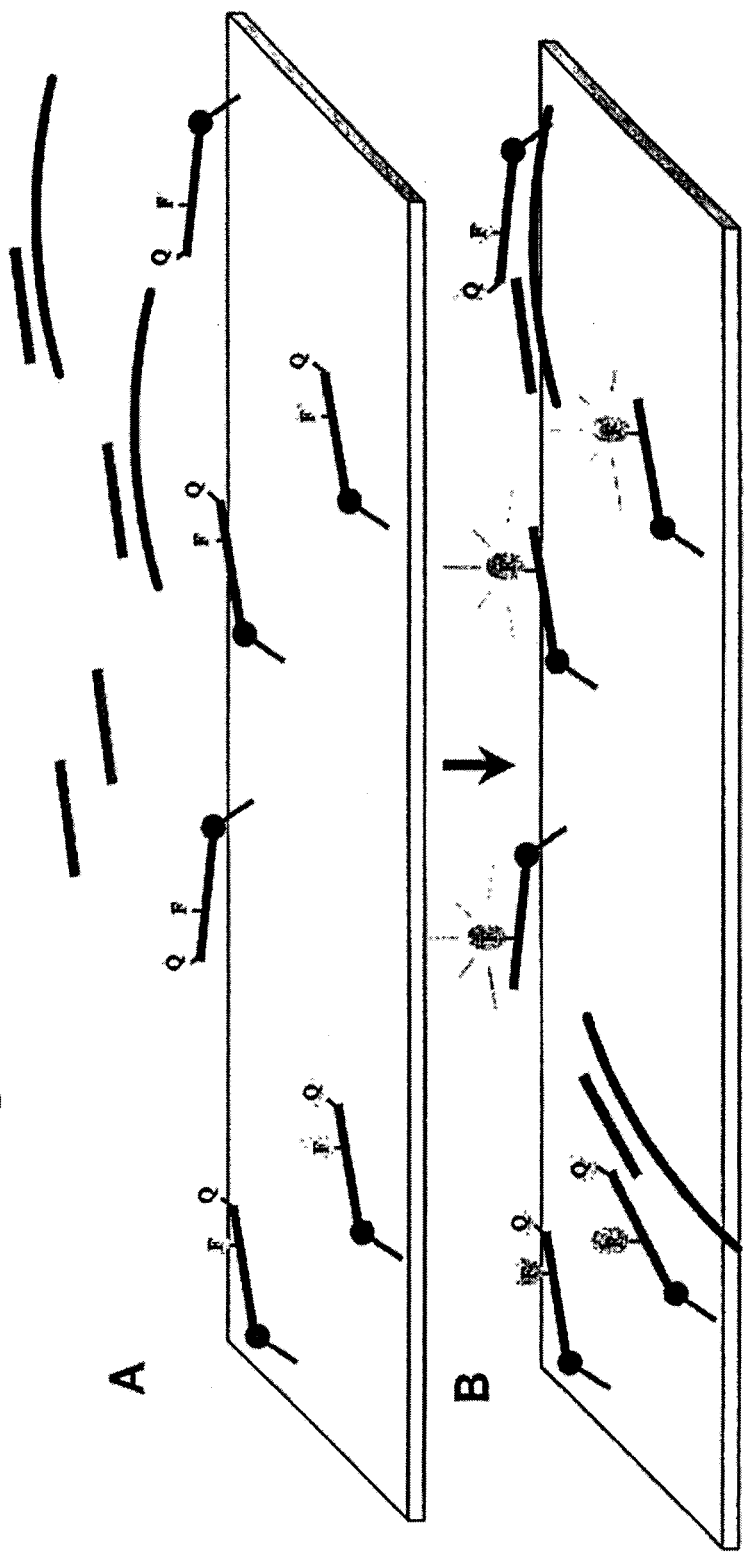

FIG. 146 shows a schematic diagram of an INVADER assay reaction performed on a surface of a solid support, wherein FRET probe oligonucleotides are bound to the surface.

Figure 147:
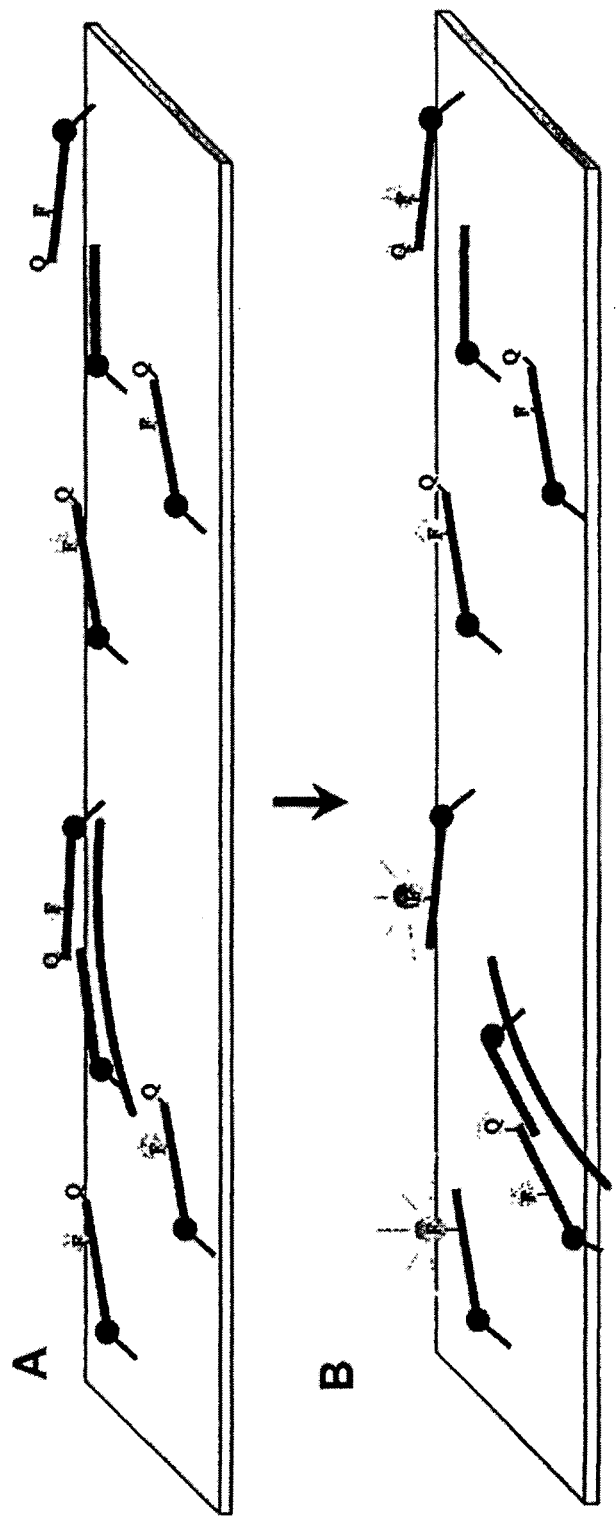

FIG. 147 shows a schematic diagram of an INVADER assay reaction performed on a surface, wherein both INVADER oligonucleotides and FRET probe oligonucleotides are bound to the surface.

Figure 148:
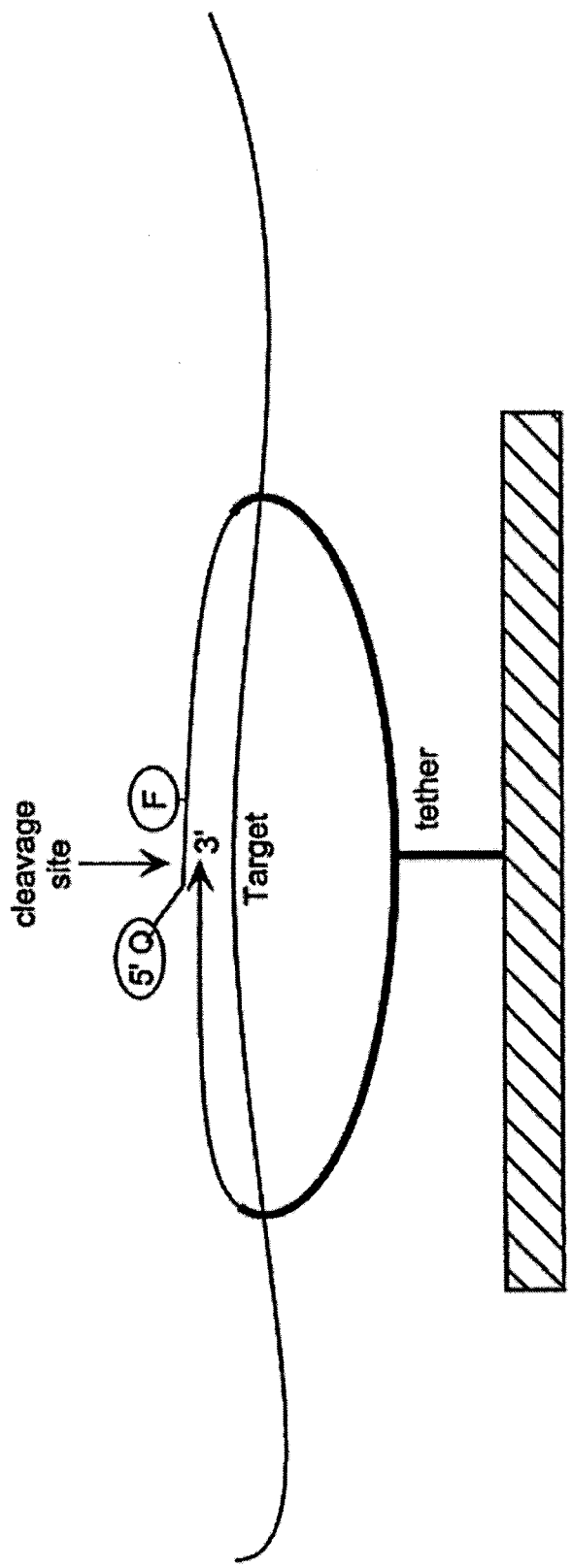

FIG. 148 shows a schematic diagram of an INVADER assay reaction performed on a surface, wherein INVADER oligonucleotides and a FRET probe oligonucleotides are provided as a single complex attached to the surface.

FIG. 149 shows a schematic diagram of an INVADER assay reaction performed on a surface, wherein FRET cassette oligonucleotides are bound to the surface.

FIG. 150A shows a schematic diagram of a DARAS column.

FIG. 150B provides a graph showing the detection of varying amounts of a target sequence in reactions performed in DARAS columns.

FIG. 151A shows schematic diagrams wherein a biotinylated FRET probe oligonucleotide (SEQ ID NO:428) attached to a surface is used with an INVADER oligonucleotide (SEQ ID NO:427) that is not attached, or wherein a biotinylated INVADER oligonucleotide (SEQ ID NO:430) attached to a surface is used wth a FRET probe (SEQ ID NO:431) that is not attached in the detection of a synthetic target nucleic acid sequence (SEQ ID NO:429).

FIG. 151B provides a graph showing the rate of fluorescence signal accumulation when either the INVADER oligonucleotide or the probe oligonucleotide is attached to a surface, or when all reaction components are provided in solution.

FIG. 152 provides a schematic diagram comparing a reverse FRET oligonucleotide configuration to a standard FRET oligonucleotide configuration.

Figure 153:

FIG. 153 provides schematic diagrams for six reverse FRET oligonucleotides, A-F (SEQ ID NOS: 433-438, respectively) for use with an INVADER oligonucleotide (SEQ ID NO:196) in the detection of a synthetic version of a human ApoE allele (SEQ ID NO:194).

Figure 154:
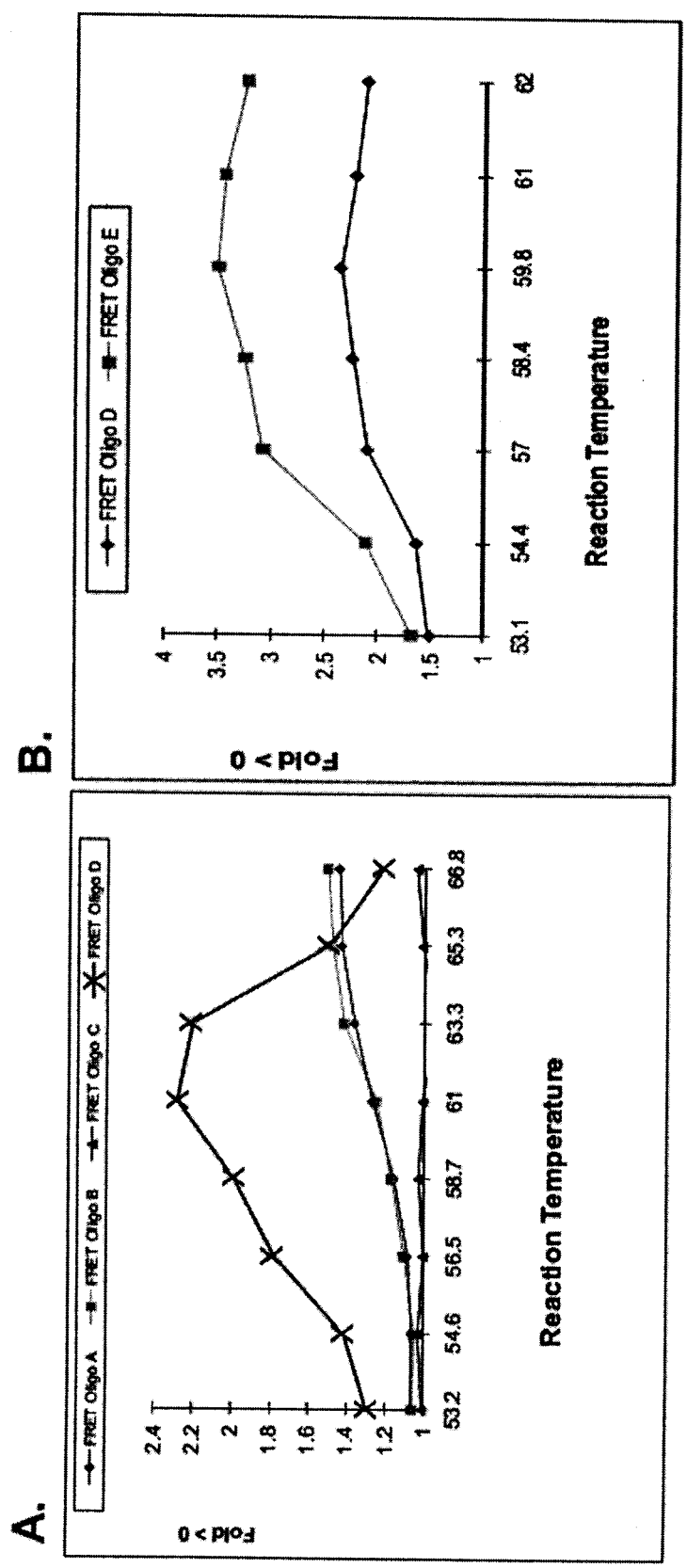

FIG. 154 provides two graphs comparing the detection of a synthetic ApoE target using five of the reverse FRET oligonucleotides depicted in FIG. 153.

FIG. 155 provides the nucleic acid and amino acid sequences, SEQ ID NOS:378-379, 360-361, 383-384, 336-337, 340-341, 344-345, 348-349, 369-370, 374-375, 388-389, 352-353, 397-398, 393-394, 356-357, 364-365, and 401-402) of a variety of FEN-1 endonucleases.

DESCRIPTION OF THE INVENTION

Introduction

The present invention relates to methods and compositions for treating nucleic acid, and in particular, methods and compositions for detection and characterization of nucleic acid sequences and sequence changes.

In preferred embodiments, the present invention relates to means for cleaving a nucleic acid cleavage structure in a site-specific manner. While the present invention provides a variety of cleavage agents, in some embodiments, the present invention relates to a cleaving enzyme having 5' nuclease activity without interfering nucleic acid synthetic ability. In other embodiments, the present invention provides novel polymerases (e.g., thermostable polymerases) possessing altered polymerase and/or nucleases activities.

For example, in some embodiments, the present invention provides 5' nucleases derived from thermostable DNA polymerases that exhibit altered DNA synthetic activity from that of native thermostable DNA polymerases. The 5' nuclease activity of the polymerase is retained while the synthetic activity is reduced or absent. Such 5' nucleases are capable of catalyzing the structure-specific cleavage of nucleic acids in the absence of interfering synthetic activity. The lack of synthetic activity during a cleavage reaction results in nucleic acid cleavage products of uniform size.

The novel properties of the nucleases of the invention form the basis of a method of detecting specific nucleic acid sequences. This method relies upon the amplification of the detection molecule rather than upon the amplification of the target sequence itself as do existing methods of detecting specific target sequences.

DNA polymerases (DNAPs), such as those isolated from *E. coli* or from thermophilic bacteria of the genus *Thermus* as well as other organisms, are enzymes that synthesize new DNA strands. Several of the known DNAPs contain associated nuclease activities in addition to the synthetic activity of the enzyme.

Some DNAPs are known to remove nucleotides from the 5' and 3' ends of DNA chains (Kornberg, DNA Replication, W.H. Freeman and Co., San Francisco, pp. 127-139 [1980]). These nuclease activities are usually referred to as 5' exonuclease and 3' exonuclease activities, respectively. For example, the 5' exonuclease activity located in the N-terminal domain of several DNAPs participates in the removal of RNA primers during lagging strand synthesis during DNA replication and the removal of damaged nucleotides during repair.

Some DNAPs, such as the *E. coli* DNA polymerase (DNAPEc1), also have a 3' exonuclease activity responsible for proof-reading during DNA synthesis (Kornberg, supra).

A DNAP isolated from *Thermus aquaticus*, termed Taq DNA polymerase (DNAPTaq), has a 5' exonuclease activity, but lacks a functional 3' exonucleolytic domain (Tindall and Kunkell, Biochem., 27:6008 [1988]). Derivatives of DNAPEc1 and DNAPTaq, respectively called the Klenow and Stoffel fragments, lack 5' exonuclease domains as a result of enzymatic or genetic manipulations (Brutlag et al., Biochem. Biophys. Res. Commun., 37:982 [1969]; Erlich et al., Science 252:1643 [1991]; Setlow and Kornberg, J. Biol. Chem., 247:232 [1972]).

The 5' exonuclease activity of DNAPTaq was reported to require concurrent synthesis (Gelfand, PCR Technology—Principles and Applications for DNA Amplification, H. A. Erlich, [Ed.], Stockton Press, New York, p. 19 [1989]). Although mononucleotides predominate among the digestion products of the 5' exonucleases of DNAPTaq and DNAPEc1, short oligonucleotides ($\leq 12$ nucleotides) can also be observed implying that these so-called 5' exonucleases can function endonucleolytically (Setlow, supra; Holland et al., Proc. Natl. Acad. Sci. USA 88:7276 [1991]).

In WO 92/06200, Gelfand et al. show that the preferred substrate of the 5' exonuclease activity of the thermostable DNA polymerases is displaced single-stranded DNA. Hydrolysis of the phosphodiester bond occurs between the displaced single-stranded DNA and the double-helical DNA with the preferred exonuclease cleavage site being a phosphodiester bond in the double helical region. Thus, the 5' exonuclease activity usually associated with DNAPs is a structure-dependent single-stranded endonuclease and is more properly referred to as a 5' nuclease. Exonucleases are enzymes that cleave nucleotide molecules from the ends of the nucleic acid molecule. Endonucleases, on the other hand, are enzymes that cleave the nucleic acid molecule at internal rather than terminal sites. The nuclease activity associated with some thermostable DNA polymerases cleaves endonucleolytically but this cleavage requires contact with the 5' end of the molecule being cleaved. Therefore, these nucleases are referred to as 5' nucleases.

When a 5' nuclease activity is associated with a eubacterial Type A DNA polymerase, it is found in the one third N-terminal region of the protein as an independent functional domain. The C-terminal two-thirds of the molecule constitute the polymerization domain that is responsible for the synthesis of DNA. Some Type A DNA polymerases also have a 3' exonuclease activity associated with the two-third C-terminal region of the molecule.

The 5' exonuclease activity and the polymerization activity of DNAPs can be separated by proteolytic cleavage or genetic manipulation of the polymerase molecule. The Klenow or large proteolytic cleavage fragment of DNAPEc1 contains the polymerase and 3' exonuclease activity but lacks the 5' nuclease activity. The Stoffel fragment of DNAPTaq (DNAPStf) lacks the 5' nuclease activity due to a genetic manipulation that deleted the N-terminal 289 amino acids of the polymerase molecule (Erlich et al., Science 252:1643 [1991]). WO 92/06200 describes a thermostable DNAP with an altered level of 5' to 3' exonuclease. U.S. Pat. No. 5,108,892 describes a *Thermus aquaticus* DNAP without a 5' to 3' exonuclease. Thermostable DNA polymerases with lessened amounts of synthetic activity are available (Third Wave Technologies, Madison, Wis.) and are described in U.S. Pat. Nos. 5,541,311, 5,614,402, 5,795,763, 5,691,142, and 5,837,450, herein incorporated by reference in their entireties. The present invention provides 5' nucleases derived from thermostable Type A DNA polymerases that retain 5' nuclease activity but have reduced or absent synthetic activity. The ability to uncouple the synthetic activity of the enzyme from the 5' nuclease activity proves that the 5' nuclease activity does not require concurrent DNA synthesis as was previously reported (Gelfand, PCR Technology, supra).

In addition to the 5'-exonuclease domains of the DNA polymerase I proteins of Eubacteria, described above, 5' nucleases have been found associated with bacteriophage, eukaryotes and archaebacteria. Overall, all of the enzymes in this family display very similar substrate specificities, despite their limited level of sequence similarity. Consequently, enzymes suitable for use in the methods of the present invention may be isolated or derived from a wide array of sources.

A mammalian enzyme with functional similarity to the 5'-exonuclease domain of *E. coli* PolI was isolated nearly 30 years ago (Lindahl, et al., Proc Natl Acad Sci USA 62(2): 597-603 [1969]). Later, additional members of this group of enzymes called flap endonucleases (FEN1) from Eukarya and Archaea were shown to possess a nearly identical structure specific activity (Harrington and Lieber. Embo J 13(5), 1235-46 [1994]; Murante et al., J Biol Chem 269(2), 1191-6 [1994]; Robins, et al., J Biol Chem 269(46), 28535-8 [1994]; Hosfield, et al., J Biol Chem 273(42), 27154-61 [1998]), despite limited sequence similarity. The substrate specificities of the FEN1 enzymes, and the eubacterial and related bacteriophage enzymes have been examined and found to be similar for all enzymes (Lyamichev, et al., Science 260(5109), 778-83 [1993], Harrington and Lieber, supra, Murante, et al., supra, Hosfield, et al, supra, Rao, et al., J Bacteriol 180(20), 5406-12 [1998], Bhagwat, et al., J. Biol Chem 272(45), 28523-30 [1997], Garforth and Sayers, Nucleic Acids Res 25(19), 3801-7 [1997]).

Using preformed substrates, many of the studies cited above determined that these nucleases leave a gap upon cleavage, leading the authors to speculate that DNA polymerase must then act to fill in that gap to generate a ligatable nick. A number of other 5' nucleases have been shown to leave a gap or overlap after cleavage of the same or similar flap substrates. It has since been determined that that all the structure-specific 5'-exonucleases leave a nick after cleavage if the substrate has an overlap between the upstream and downstream duplexes (Kaiser et al., J. Biol. Chem. 274(30): 21387-21394 [1999]). While duplexes having several bases of overlapping sequence can assume several different conformations through branch migration, it was determined that cleavage occurs in the conformation where the last nucleotide at the 3' end of the upstream strand is unpaired, with the cleavage rate being essentially the same whether the end of the upstream primer is A, C, G, or T. It was determined to be positional overlap between the 3' end of the upstream primer and downstream duplex, rather then sequence overlap, that is required for optimal cleavage. In addition to allowing these enzymes to leave a nick after cleavage, the single base of overlap causes the enzymes to cleave several orders of magnitude faster than when a substrate lacks overlap (Kaiser et al., supra).

Any of the 5' nucleases described above may find application in one or more embodiments of the methods described herein. FEN1 nucleases of particular utility in the methods of present invention include but are not limited to those of *Methanococcus jannaschii* and *Methanobacterium thermoautotrophicum*; particularly preferred FEN1 enzymes are from *Archaeoglobus fulgidus, Pyrococcus furiosus, Archaeoglobus veneficus, Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii,* and *Aeropyrum pernix.*

The detailed description of the invention is presented in the following sections:
I. Detection of Specific Nucleic Acid Sequences Using 5' Nucleases in an INVADER Directed Cleavage Assay;
II. Effect of ARRESTOR Oligonucleotides on Signal and Background in Sequential Invasive Cleavage Reactions.
III. Signal Enhancement By Incorporating The Products Of An Invasive Cleavage Reaction Into A Subsequent Invasive Cleavage Reaction;
IV. Fractionation Of Specific Nucleic Acids By Selective Charge Reversal;
V. Signal Enhancement By Tailing Of Reaction Products In The INVADER oligonucleotide-directed Cleavage Assay;
VI. Signal Enhancement By Completion Of An Activated Protein Binding Site;
VII. Generation of 5' Nucleases Derived From Thermostable DNA Polymerases;
VIII. Improved Enzymes For Use In INVADER oligonucleotide-directed Cleavage Reactions;
IX. The INVADER assay for direct detection and measurement of specific analytes;
X. Kits; and
XI. Reactions on a solid support.

I. Detection of Specific Nucleic Acid Sequences Using 5' Nucleases in an INVADER Directed Cleavage Assay 1. INVADER Assay Reaction Design The present invention provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. patent application Nos. 5,846,717, 5,985,557, 5,994,069, 6,001,567, and 6,090,543 and PCT Publications WO 97/27214 and WO 98/42873, herein incorporated by reference in their entireties.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, [The kinetics of oligonucleotide replacement. Luis P. Reynaldo, Alexander V. Vologodskii, Bruce P. Neri and Victor I. Lyamichev. J. Mol. Biol. 97:511-520 (2000)], multiple probes can hybridize to the same target, allowing multiple cleavages, and the generation of multiple cleavage products.

By the extent of its complementarity to a target nucleic acid strand, an oligonucleotide may be said to define a specific region of said target. In an invasive cleavage structure, the two oligonucleotides define and hybridize to regions of the target that are adjacent to one another (i.e., regions without any additional region of the target between them). Either or both oligonucleotides may comprise additional portions that are not complementary to the target strand. In addition to hybridizing adjacently, in order to form an invasive cleavage structure, the 3' end of the upstream oligonucleotide must comprise an additional moiety. When both oligonucleotides are hybridized to a target strand to form a structure and such a 3' moiety is present on the upstream oligonucleotide within the structure, the oligonucleotides may be said to overlap, and the structure may be described as an overlapping, or invasive cleavage structure.

In one embodiment, the 3' moiety of the invasive cleavage structure is a single nucleotide. In this embodiment the 3' moiety may be any nucleotide (i.e., it may be, but it need not be complementary to the target strand). In a preferred embodiment the 3' moiety is a single nucleotide that is not complementary to the target strand. In another embodiment, the 3' moiety is a nucleotide-like compound (i.e., a moiety having chemical features similar to a nucleotide, such as a nucleotide analog or an organic ring compound; See e.g., U.S. Pat. No. 5,985,557). In yet another embodiment the 3' moiety is one or more nucleotides that duplicate in sequence one or more nucleotides present at the 5' end of the hybridized region of the downstream oligonucleotide. In a further embodiment, the duplicated sequence of nucleotides of the 3' moiety is followed by a single nucleotide that is not further duplicative of the downstream oligonucleotide sequence, and that may be any other nucleotide. In yet another embodiment, the duplicated sequence of nucleotides of the 3' moiety is followed by a nucleotide-like compound, as described above.

The downstream oligonucleotide may have, but need not have, additional moieties attached to either end of the region that hybridizes to the target nucleic acid strand. In a preferred embodiment, the downstream oligonucleotide comprises a moiety at its 5' end (i.e., a 5' moiety). In a particularly preferred embodiment, said 5' moiety is a 5' flap or arm comprising a sequence of nucleotides that is not complementary to the target nucleic acid strand.

When an overlapping cleavage structure is formed, it can be recognized and cleaved by a nuclease that is specific for this structure (i.e., a nuclease that will cleave one or more of the nucleic acids in the overlapping structure based on recognition of this structure, rather than on recognition of a nucleotide sequence of any of the nucleic acids forming the structure). Such a nuclease may be termed a "structure-specific nuclease". In some embodiments, the structure-specific nuclease is a 5' nuclease. In a preferred embodiment, the structure-specific nuclease is the 5' nuclease of a DNA polymerase. In another preferred embodiment, the DNA polymerase having the 5' nuclease is synthesis-deficient. In another preferred embodiment, the 5' nuclease is a FEN-1 endonuclease. In a particularly preferred embodiment, the 5' nuclease is thermostable.

In some embodiments, said structure-specific nuclease preferentially cleaves the downstream oligonucleotide. In a preferred embodiment, the downstream oligonucleotide is cleaved one nucleotide into the 5' end of the region that is hybridized to the target within the overlapping structure. Cleavage of the overlapping structure at any location by a structure-specific nuclease produces one or more released portions or fragments of nucleic acid, termed "cleavage products".

In some embodiments, cleavage of an overlapping structure is performed under conditions wherein one or more of the nucleic acids in the structure can disassociate (i.e. un-hybridize, or melt) from the structure. In one embodiment, full or partial disassociation of a first cleavage structure allows the target nucleic acid to participate in the formation of one or more additional overlapping cleavage structures. In a preferred embodiment, the first cleavage structure is partially disassociated. In a particularly preferred embodiment only the oligonucleotide that is cleaved disassociates from the first cleavage structure, such that it may be replaced by another copy of the same oligonucleotide. In some embodiments, said disassociation is induced by an increase in temperature, such that one or more oligonucleotides can no longer hybridize to the target strand. In other embodiments, said disassociation occurs because cleavage of an oligonucleotide produces only cleavage products that cannot bind to the target strand under the conditions of the reaction. In a preferred embodiment, conditions are selected wherein an oligonucleotide may associate with (i.e., hybridize to) and disassociate from a target strand regardless of cleavage, and wherein the oligonucleotide may be cleaved when it is hybridized to the target as part of an overlapping cleavage structure. In a particularly preferred embodiment, conditions are selected such that the number of copies of the oligonucleotide that can be cleaved when part of an overlapping structure exceeds the number of copies of the target nucleic acid strand by a sufficient amount that when the first cleavage structure disassociates, the probability that the target strand will associate with an intact copy of the oligonucleotide is greater than the probability that that it will associate with a cleaved copy of the oligonucleotide.

In some embodiments, cleavage is performed by a structure-specific nuclease that can recognize and cleave structures that do not have an overlap. In a preferred embodiment, cleavage is performed by a structure-specific nuclease having a lower rate of cleavage of nucleic acid structures that do not comprise an overlap, compared to the rate of cleavage of structures comprising an overlap. In a particularly preferred embodiment, cleavage is performed by a structure-specific nuclease having less than 1% of the rate of cleavage of nucleic acid structures that do not comprise an overlap, compared to the rate of cleavage of structures comprising an overlap.

In some embodiments it is desirable to detect the cleavage of the overlapping cleavage structure. Detection may be by analysis of cleavage products or by analysis of one or more of the remaining uncleaved nucleic acids. For convenience, the following discussion will refer to the analysis of cleavage products, but it will be appreciated by those skilled in the art that these methods may as easily be applied to analysis of the uncleaved nucleic acids in an invasive cleavage reaction. Any method known in the art for analysis of nucleic acids, nucleic acid fragments or oligonucleotides may be applied to the detection of cleavage products.

In one embodiment, the cleavage products may be identified by chemical content, e.g., the relative amounts of each atom, each particular type of reactive group or each nucleotide base (Chargaff et al., *J. Biol. Chem.* 177:405 [1949]) they contain. In this way, a cleavage product may be distinguished from a longer nucleic acid from which it was released by cleavage, or from other nucleic acids.

In another embodiment, the cleavage products may be distinguished by a particular physical attribute, including but not limited to length, mass, charge, or charge-to-mass ratio. In yet another embodiment, the cleavage product may be distinguished by a behavior that is related to a physical attribute, including but not limited to rate of rotation in solution, rate of migration during electrophoresis, coefficient of sedimentation, time of flight in MALDI-TOF mass spectrometry, migration rate or other behavior in chromatography, melting temperature from a complementary nucleic acid, or precipitability from solution.

Detection of the cleavage products may be through release of a label. Such labels may include, but are not limited to one or more of any of dyes, radiolabels such as $^{32}P$ or $^{35}S$, binding moieties such as biotin, mass tags, such as metal ions or chemical groups, charge tags, such as polyamines or charged dyes, haptens such as digoxgenin, luminogenic, phosphorescent or fluorogenic moieties, and fluorescent dyes, either alone or in combination with moieties that can suppress or shift emission spectra, such as by fluorescence resonance energy transfer (FRET) or collisional fluorescence energy transfer.

In some embodiments, analysis of cleavage products may include physical resolution or separation, for example by electrophoresis, hybridization or by selective binding to a support, or by mass spectrometry methods such as MALDI-TOF. In other embodiments, the analysis may be performed without any physical resolution or separation, such as by detection of cleavage-induced changes in fluorescence as in FRET-based analysis, or by cleavage-induced changes in the rotation rate of a nucleic acid in solution as in fluorescence polarization analysis.

Cleavage products can be used subsequently in any reaction or read-out method that can make use of oligonucleotides. Such reactions include, but are not limited to, modification reactions, such as ligation, tailing with a template-independent nucleic acid polymerase and primer extension with a template-dependent nucleic acid polymerase. The modification of the cleavage products may be for purposes including, but not limited to, addition of one or more labels or binding moieties, alteration of mass, addition of specific sequences, or for any other purpose that would facilitate analysis of either the cleavage products or analysis of any other by-product, result or consequence of the cleavage reaction.

Analysis of the cleavage products may involve subsequent steps or reactions that do not modify the cleavage products themselves. For example, cleavage products may be used to complete a functional structure, such as a competent promoter for in vitro transcription or another protein binding site. Analysis may include the step of using the completed structure for or to perform its function. One or more cleavage products may also be used to complete an overlapping cleavage structure, thereby enabling a subsequent cleavage reaction, the products of which may be detected or used by any of the methods described herein, including the participation in further cleavage reactions.

Figure 29:
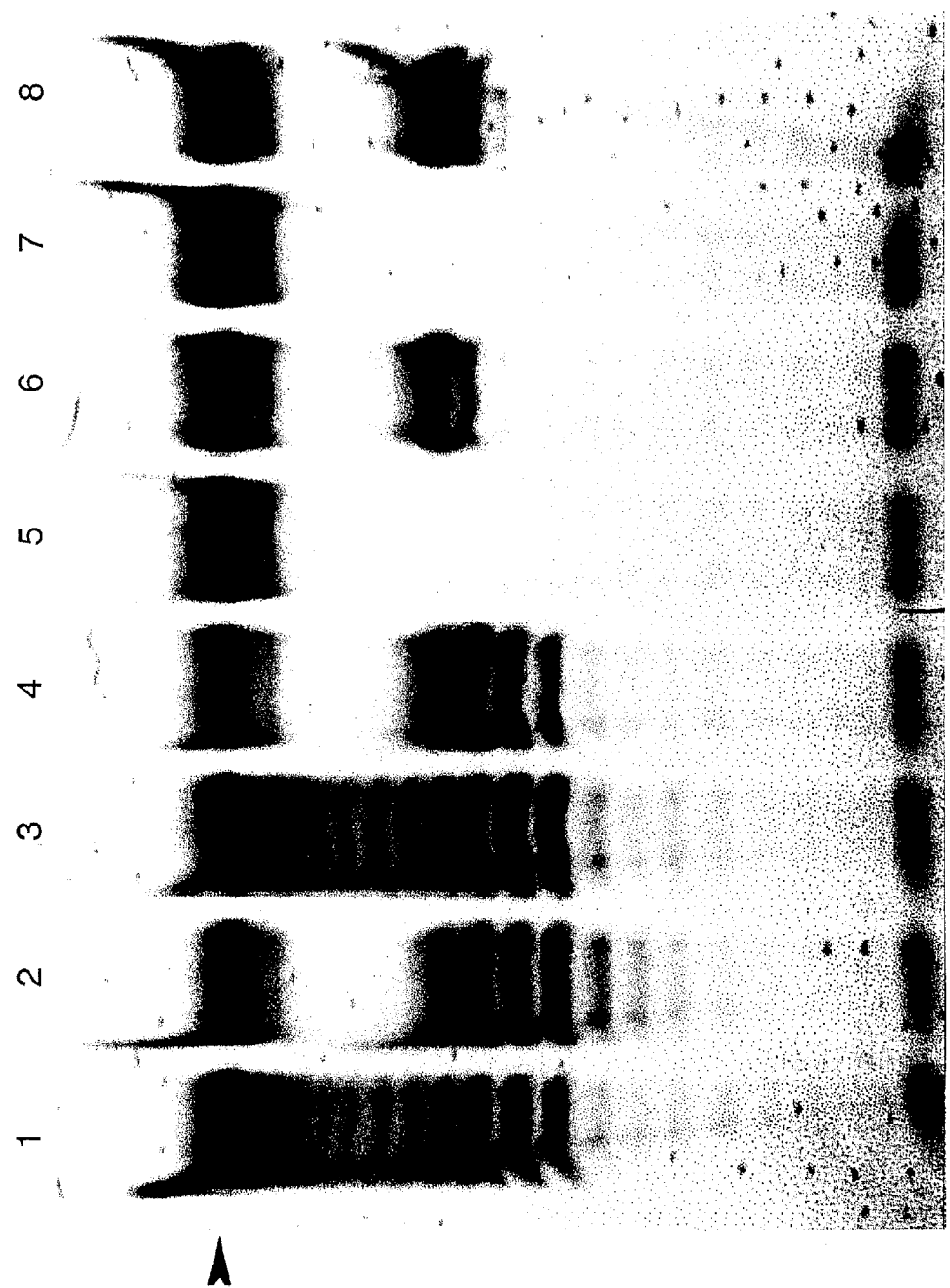
FIG. 29 is the image generated by a fluorescence imager showing that the presence of an INVADER oligonucleotide causes a shift in the site of cleavage in a probe/target duplex.

Certain preferred embodiments of the invasive cleavage reactions are provided in the following descriptions. As exemplified by the diagram in FIG. 29, the methods of the present invention employ at least a pair of oligonucleotides that interact with a target nucleic acid to form a cleavage structure for a structure-specific nuclease. In some embodiments, the cleavage structure comprises i) a target nucleic acid that may be either single-stranded or double-stranded (when a double-stranded target nucleic acid is employed, it may be rendered single stranded, e.g., by heating); ii) a first oligonucleotide, termed the "probe," that defines a first region of the target nucleic acid sequence by being the complement of that region (regions X and Z of the target as shown in FIG. 29); iii) a second oligonucleotide, termed the "INVADER," the 5' part of which defines a second region of the same target nucleic acid sequence (regions Y and X in FIG. 29), adjacent to and downstream of the first target region (regions X and Z), and the second part of which overlaps into the region defined by the first oligonucleotide (region X depicts the region of overlap). The resulting structure is diagrammed in FIG. 29.

While not limiting the invention or the instant discussion to any particular mechanism of action, the diagram in FIG. 29 represents the effect on the site of cleavage caused by this type of arrangement of a pair of oligonucleotides. The design of such a pair of oligonucleotides is described below in detail. In FIG. 29, the 3' ends of the nucleic acids (i.e., the target and the oligonucleotides) are indicated by the use of the arrowheads on the ends of the lines depicting the strands of the nucleic acids (and where space permits, these ends are also labeled "3'"). It is readily appreciated that the two oligonucleotides (the INVADER and the probe) are arranged in a parallel orientation relative to one another, while the target nucleic acid strand is arranged in an anti-parallel orientation relative to the two oligonucleotides. Further, it is clear that the INVADER oligonucleotide is located upstream of the probe oligonucleotide and that with respect to the target nucleic acid strand, region Z is upstream of region X and region X is upstream of region Y (that is, region Y is downstream of region X and region X is downstream of region Z). Regions of complementarity between the opposing strands are indicated by the short vertical lines. While not intended to indicate the precise location of the site(s) of cleavage, the area to which the site of cleavage within the probe oligonucleotide is shifted by the presence of the INVADER oligonucleotide in this embodiment is indicated by the solid vertical arrowhead. An alternative representation of the target/INVADER/probe cleavage structure is shown in FIG. 32c. Neither diagram (i.e., FIG. 29 or FIG. 32c) is intended to represent the actual mechanism of action or physical arrangement of the cleavage structure and further it is not intended that the method of the present invention be limited to any particular mechanism of action.

It can be considered that the binding of these oligonucleotides in this embodiment divides the target nucleic acid into three distinct regions: one region that has complementarity to only the probe (shown as "Z"); one region that has complementarity only to the INVADER oligonucleotide (shown as "Y"); and one region that has complementarity to both oligonucleotides (shown as "X"). As discussed above, in some preferred embodiments of the present invention, the overlap may comprise moieties other than overlapping complementary bases. Thus, in some embodiments, the region shown as "X" can represent a region where there is a physical, but not sequence, overlap between the INVADER and probe oligonucleotides, i.e., in these latter embodiments, there is not a region of the target nucleic acid between regions "Z" and "Y" that has complementarity to both oligonucleotides.

a) Oligonucleotide Design

Design of these oligonucleotides (i.e., the INVADER oligonucleotide and the probe) is accomplished using practices that are standard in the art. For example, sequences that have self complementarity, such that the resulting oligonucleotides would either fold upon themselves, or hybridize to each other at the expense of binding to the target nucleic acid, are generally avoided.

One consideration in choosing a length for these oligonucleotides is the complexity of the sample containing the target nucleic acid. For example, the human genome is approximately $3 \times 10^9$ basepairs in length. Any 10-nucleotide sequence will appear with a frequency of $1:4^{10}$, or 1:1,048,576 in a random string of nucleotides, which would be approximately 2,861 times in 3 billion basepairs. Clearly, an oligonucleotide of this length would have a poor chance of binding uniquely to a 10 nucleotide region within a target having a sequence the size of the human genome. If the target sequence were within a 3 kb plasmid, however, such an oligonucleotide might have a very reasonable chance of binding uniquely. By this same calculation it can be seen that an oligonucleotide of 16 nucleotides (i.e., a 16-mer) is the minimum length of a sequence that is mathematically likely to appear once in $3 \times 10^9$ basepairs. This level of specificity may also be provided by two or more shorter oligonucleotides if they are configured to bind in a cooperative fashion (i.e., such that they can produce the intended complex only if both or all are bound to their intended target sequences), wherein the combination of the short oligonucleotides provides the desired specificity. In one such embodiment, the cooperativity between the shorter oligonucleotides is by a coaxial stacking effect that can occur when the oligonucleotides hybridize to adjacent sites on a target nucleic acid. In another embodiment, the shorter oligonucleotides are connected to one another, either directly, or by one or more spacer regions. The short oligonucleotides thus connected may bind to distal regions of the target and may be used to bridge across regions of secondary structure in a target. Examples of such bridging oligonucleotides are described in PCT Publication WO 98/50403, herein incorporated by reference in its entirety.

A second consideration in choosing oligonucleotide length is the temperature range in which the oligonucleotides will be expected to function. A 16-mer of average base content (50% G-C bases) will have a calculated $T_m$ of about 41° C., depending on, among other things, the concentration of the oligonucleotide and its target, the salt content of the reaction and the precise order of the nucleotides. As a practical matter, longer oligonucleotides are usually chosen to enhance the specificity of hybridization. Oligonucleotides 20 to 25 nucleotides in length are often used, as they are highly likely to be specific if used in reactions conducted at temperatures which are near their $T_m$s (within about 5° C. of the $T_m$). In addition, with calculated $T_m$s in the range of 50 to 70° C., such oligonucleotides (i.e., 20 to 25-mers) are appropriately used in reactions catalyzed by thermostable enzymes, which often display optimal activity near this temperature range.

The maximum length of the oligonucleotide chosen is also based on the desired specificity. One must avoid choosing sequences that are so long that they are either at a high risk of binding stably to partial complements, or that they cannot easily be dislodged when desired (e.g., failure to disassociate from the target once cleavage has occurred or failure to disassociate at a reaction temperature suitable for the enzymes and other materials in the reaction).

The first step of design and selection of the oligonucleotides for the INVADER oligonucleotide-directed cleavage is in accordance with these sample general principles. Considered as sequence-specific probes individually, each oligonucleotide may be selected according to the guidelines listed above. That is to say, each oligonucleotide will generally be long enough to be reasonably expected to hybridize only to the intended target sequence within a complex sample, usually in the 20 to 40 nucleotide range. Alternatively, because the INVADER oligonucleotide-directed cleavage assay depends upon the concerted action of these oligonucleotides, the composite length of the 2 oligonucleotides which span/bind the X, Y, Z regions may be selected to fall within this range, with each of the individual oligonucleotides being in approximately the 13 to 17 nucleotide range. Such a design might be employed if a non-thermostable cleavage means were employed in the reaction, requiring the reactions to be conducted at a lower temperature than that used when thermostable cleavage means are employed. In some embodiments, it may be desirable to have these oligonucleotides bind multiple times within a single target nucleic acid (e.g., to bind to multiple variants or multiple similar sequences within a target). It is not intended that the method of the present invention be limited to any particular size of the probe or INVADER oligonucleotide.

The second step of designing an oligonucleotide pair for this assay is to choose the degree to which the upstream "INVADER" oligonucleotide sequence will overlap into the downstream "probe" oligonucleotide sequence, and consequently, the sizes into which the probe will be cleaved. A key feature of this assay is that the probe oligonucleotide can be made to "turn over," that is to say probe can be made to depart to allow the binding and cleavage of other copies of the probe molecule, without the requirements of thermal denaturation or displacement by polymerization. While in one embodiment of this assay probe turnover may be facilitated by an exonucleolytic digestion by the cleavage agent, it is central to the present invention that the turnover does not require this exonucleolytic activity. For example, in some embodiments, a reaction temperature and reaction conditions are selected so as to create an equilibrium wherein the probe hybridizes and disassociates from the target. In other embodiments, temperature and reaction conditions are selected so that unbound probe can initiate binding to the target strand and physically displace bound probe. In still other embodiments, temperature and reaction conditions are selected such that either or both mechanisms of probe replacement may occur in any proportion. The method of the present invention is not limited to any particular mechanism of probe replacement. By any mechanism, when the probe is bound to the target to form a cleavage structure, cleavage can occur. The continuous cycling of the probe on and off of the target allows multiple probes to bind and be cleaved for each copy of a target nucleic acid.

i) Choosing the Amount of Sequence Overlap

One way of accomplishing such turnover, where the INVADER oligonucleotide and probe oligonucleotide share a region of complementarity, can be envisioned by considering the diagram in FIG. 29. It can be seen that the $T_m$ of each oligonucleotide will be a function of the full length of that oligonucleotide: i.e., the $T_m$ of the INVADER oligonucleotide=$T_m$(Y+X), and the $T_m$ of the probe=$T_m$(X+Y) for the probe. When the probe is cleaved the X region is released, leaving the Z section. If the $T_m$ of Z is less than the reaction temperature, and the reaction temperature is less than the $T_m$(X+Z), then cleavage of the probe will lead to the departure of Z, thus allowing a new (X+Z) to hybridize. It can be seen from this example that the X region must be sufficiently long that the release of X will drop the $T_m$ of the remaining probe section below the reaction temperature: a G-C rich X section may be much shorter than an A-T rich X section and still accomplish this stability shift.

In other embodiments described herein, probe turn over is not related to a change in $T_m$ caused by cleavage of the probe, but rather is related to the association and disassociation behavior of the probe in the selected conditions, regardless of cleavage. Thus, it is not intended that the present invention be limited to the use of probes that, upon cleavage, yield products having a $T_m$s below the reaction temperature, as described above.

ii) Non-sequence Overlaps

It has been determined that the relationship between the 3' end of the upstream oligonucleotide and the desired site of cleavage on the probe should be carefully designed. It is known that the preferred site of cleavage for the types of structure-specific endonucleases employed herein is one basepair into a duplex (Lyamichev et al., supra). It was previously believed that the presence of an upstream oligonucleotide or primer allowed the cleavage site to be shifted away from this preferred site, into the single stranded region of the 5' arm (Lyamichev et al., supra and U.S. Pat. No. 5,422,253). In contrast to this previously proposed mechanism, and while not limiting the present invention to any particular mechanism, it is believed that the nucleotide immediately 5', or upstream of the cleavage site on the probe (including miniprobe and mid-range probes) should be able to basepair with the target for efficient cleavage to occur. In the case of the present invention, this would be the nucleotide in the probe sequence immediately upstream of the intended cleavage site. In addition, as described herein, it has been observed that in order to direct cleavage to that same site in the probe, the upstream oligonucleotide should have its 3' base (i.e., nt) immediately upstream of the intended cleavage site of the probe. In embodiments where the INVADER and probe oligonucleotides share a sequence overlap, this places the 3' terminal nucleotide of the upstream oligonucleotide and the base of the probe oligonucleotide 5' of the cleavage site in competition for pairing with the corresponding nucleotide of the target strand.

To examine the outcome of this competition (i.e. which base is paired during a successful cleavage event), substitutions were made in the probe and INVADER oligonucleotides such that either the probe or the INVADER oligonucleotide were mismatched with the target sequence at this position. The effects of both arrangements on the rates of cleavage were examined. When the INVADER oligonucleotide is unpaired at the 3' end, the rate of cleavage was not reduced. If this base was removed, however, the cleavage site was shifted upstream of the intended site. In contrast, if the probe oligonucleotide was not base-paired to the target just upstream of the site to which the INVADER oligonucleotide was directing cleavage, the rate of cleavage was dramatically reduced, suggesting that when a competition exists, the probe oligonucleotide was the molecule to be base-paired in this position.

It appears that the 3' end of the upstream INVADER oligonucleotide is unpaired during cleavage, and yet is important for accurate positioning of the cleavage. To examine which part(s) of the 3' terminal nucleotide are required for the positioning of cleavage, INVADER oligonucleotides were designed that terminated on this end with nucleotides that were altered in a variety of ways. Sugars examined included 2' deoxyribose with a 3' phosphate group, a dideoxyribose, 3' deoxyribose, 2' O-methyl ribose, arabinose and arabinose with a 3' phosphate. Abasic ribose, with and without 3' phosphate were tested. Synthetic "universal" bases such at 3-nitropyrrole and 5-3 nitroindole on ribose sugars were tested. Finally, a base-like aromatic ring structure, acridine, linked to the 3' end the previous nucleotide without a sugar group was tested. The results obtained support the conclusion that the aromatic ring of the base (at the 3' end of the INVADER oligonuceotide) is an important moiety for accomplishing the direction of cleavage to the desired site within the downstream probe. The 3' terminal moiety of the INVADER oligonucleotide need not be a base that is complementary to the target nucleic acid.

iii) Miniprobes and Mid-Range Probes;

As discussed above, the INVADER oligonucleotide-directed cleavage assay may be performed using INVADER and probe oligonucleotides that have a length of about 13-25 nucleotides (typically 20-25 nucleotides). It is also contemplated that the oligonucleotides may themselves be composed of shorter oligonucleotide sequences that align along a target strand but that are not covalently linked. This is to say that there is a nick in the sugar-phosphate backbone of the composite oligonucleotide, but that there is no disruption in the progression of base-paired nucleotides in the resulting duplex. When short strands of nucleic acid align contiguously along a longer strand the hybridization of each is stabilized by the hybridization of the neighboring fragments because the basepairs can stack along the helix as though the backbone was in fact uninterrupted. This cooperativity of binding can give each segment a stability of interaction in excess of what would be expected for the segment hybridizing to the longer nucleic acid alone. One application of this observation has been to assemble primers for DNA sequencing, typically about 18 nucleotides long, from sets of three hexamer oligonucleotides that are designed to hybridize in this way (Kotler et al. Proc. Natl. Acad. Sci. USA 90:4241 [1993]). The resulting doubly-nicked primer can be extended enzymatically in reactions performed at temperatures that might be expected to disrupt the hybridization of hexamers, but not of 18-mers.

The use of composite or split oligonucleotides is applied with success in the INVADER-directed cleavage assay. For example, the probe oligonucleotide may be split into two oligonucleotides that anneal in a contiguous and adjacent manner along a target oligonucleotide as diagrammed in FIG. 57. In this Figure, the downstream oligonucleotide (analogous to the probe of FIG. 25) is assembled from two smaller pieces: a short segment of 6-10 nts (termed the "miniprobe"), that is to be cleaved in the course of the detection reaction, and an oligonucleotide that hybridizes immediately downstream of the miniprobe (termed the "stacker"), that serves to stabilize the hybridization of the probe. To form the cleavage structure, an upstream oligonucleotide (the INVADER oligonucleotide) is provided to direct the cleavage activity to the desired region of the miniprobe. Assembly of the probe from non-linked pieces of nucleic acid (i.e., the miniprobe and the stacker) allows regions of sequences to be changed without requiring the re-synthesis of the entire proven sequence, thus improving the cost and flexibility of the detection system. In addition, the use of unlinked composite oligonucleotides makes the system more stringent in its requirement of perfectly matched hybridization to achieve signal generation, allowing this to be used as a sensitive means of detecting mutations or changes in the target nucleic acid sequences.

Figure 57:
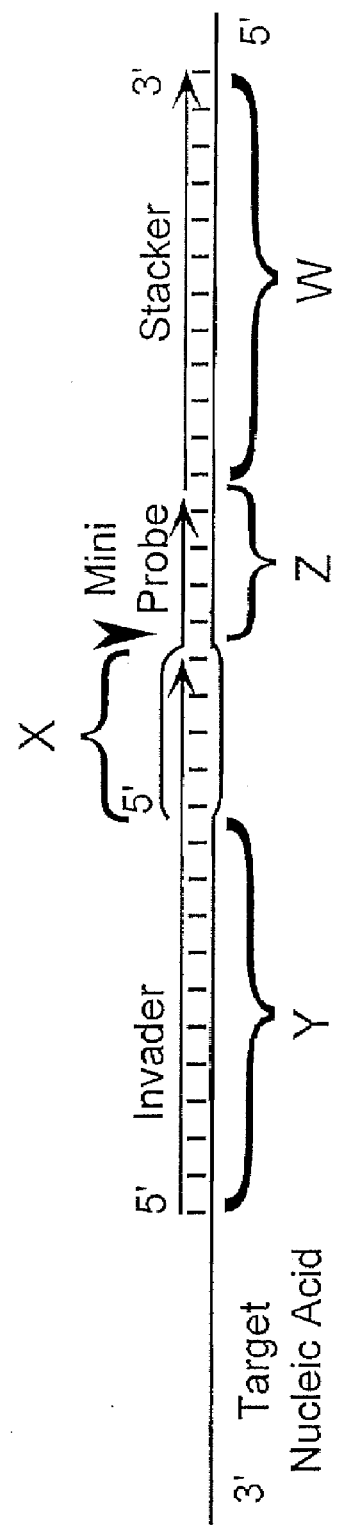
FIG. 57 provides a schematic drawing of a target nucleic acid with an INVADER oligonucleotide, a miniprobe, and a stacker oligonucleotide annealed to the target.

As illustrated in FIG. 57, in one embodiment, the methods of the present invention employ at least three oligonucleotides that interact with a target nucleic acid to form a cleavage structure for a structure-specific nuclease. More specifically, the cleavage structure comprises i) a target nucleic acid that may be either single-stranded or double-stranded (when a double-stranded target nucleic acid is employed, it may be rendered single-stranded, e.g., by heating); ii) a first oligonucleotide, termed the "stacker," that defines a first region of the target nucleic acid sequence by being the complement of that region (region W of the target as shown in FIG. 57); iii) a second oligonucleotide, termed the "miniprobe," that defines a second region of the target nucleic acid sequence by being the complement of that region (regions X and Z of the target as shown in FIG. 57); iv) a third oligonucleotide, termed the "INVADER," the 5' part of which defines a third region of the same target nucleic acid sequence (regions Y and X in FIG. 57), adjacent to and downstream of the second target region (regions X and Z), and the second or 3' part of which overlaps into the region defined by the second oligonucleotide (region X depicts the region of overlap). The resulting structure is diagrammed in FIG. 57. As described above for embodiments that do not employ a stacker, the region shown as "X" can represent a region where there is a physical, but not sequence, overlap between the INVADER and probe oligonucleotides.

While not limiting the invention or the instant discussion to any particular mechanism of action, the diagram in FIG. 57 represents the effect on the site of cleavage caused by this type of arrangement of three oligonucleotides. The design of these three oligonucleotides is described below in detail. In FIG. 57, the 3' ends of the nucleic acids (i.e., the target and the oligonucleotides) are indicated by the use of the arrowheads on the ends of the lines depicting the strands of the nucleic acids (and where space permits, these ends are also labeled "3'"). It is readily appreciated that the three oligonucleotides (the INVADER, the miniprobe and the stacker) are arranged in a parallel orientation relative to one another, while the target nucleic acid strand is arranged in an anti-parallel orientation relative to the three oligonucleotides. Further it is clear that the INVADER oligonucleotide is located upstream of the miniprobe oligonucleotide and that the miniprobe olignuceotide is located upstream of the stacker oligonucleotide and that with respect to the target nucleic acid strand, region W is upstream of region Z, region Z is upstream of upstream of region X and region X is upstream of region Y (that is region Y is downstream of region X, region X is downstream of region Z and region Z is downstream of region W). Regions of complementarity between the opposing strands are indicated by the short vertical lines. While not intended to indicate the precise location of the site(s) of cleavage, the area to which the site of cleavage within the miniprobe oligonucleotide is shifted by the presence of the INVADER oligonucleotide is indicated by the solid vertical arrowhead. FIG. 57 is not intended to represent the actual mechanism of action or physical arrangement of the cleavage structure and further it is not intended that the method of the present invention be limited to any particular mechanism of action.

It can be considered that the binding of these oligonucleotides divides the target nucleic acid into four distinct regions: one region that has complementarity to only the stacker (shown as "W"); one region that has complementarity to only the miniprobe (shown as "Z"); one region that has complementarity only to the INVADER oligonucleotide (shown as "Y"); and one region that has complementarity to both the INVADER and miniprobe oligonucleotides (shown as "X"). As discussed above, the INVADER oligonucleotide may also be employed such that a physical overlap rather than a sequence overlap with the probe is provided.

In addition to the benefits cited above, the use of a composite design for the oligonucleotides that form the cleavage structure allows more latitude in the design of the reaction conditions for performing the INVADER-directed cleavage assay. When a longer probe (e.g., 16-25 nt), as described above, is used for detection in reactions that are performed at temperatures below the $T_m$ of that probe, the cleavage of the probe may play a significant role in destabilizing the duplex of which it is a part, thus allowing turnover and reuse of the recognition site on the target nucleic acid. In contrast, reaction temperatures that are at or above the $T_m$ of the probe mean that the probe molecules are hybridizing and releasing from the target quite rapidly even without cleavage of the probe. When an upstream INVADER oligonucleotide and a cleavage means are provided the probe will be specifically cleaved, but the cleavage will not be necessary to the turnover of the probe. When a long probe (e.g., 16-25 nt) is used in this way the temperatures required to achieve this state is high, around 65 to 70° C. for a 25-mer of average base composition. Requiring the use of such elevated temperatures limits the choice of cleavage agents to those that are very thermostable, and may contribute to background in the reactions, depending of the means of detection, through thermal degradation of the probe oligonucleotides. With miniprobes, this latter mechanism of probe replacement may be accomplished at a lower temperature. Thus, shorter probes are preferred for embodiments using lower reaction temperatures.

The miniprobe of the present invention may vary in size depending on the desired application. In one embodiment, the probe may be relatively short compared to a standard probe (e.g., 16-25 nt), in the range of 6 to 10 nucleotides. When such a short probe is used, reaction conditions can be chosen that prevent hybridization of the miniprobe in the absence of the stacker oligonucleotide. In this way a short probe can be made to assume the statistical specificity and selectivity of a longer sequence. In the event of a perturbation in the cooperative binding of the miniprobe and stacker nucleic acids, as might be caused by a mismatch within the short sequence that is otherwise complementary to the target nucleic acid or at the junction between the contiguous duplexes, this cooperativity can be lost, dramatically reducing the stability of the shorter duplex (i.e., that of the miniprobe), and thus reducing the level of cleaved product in the assay of the present invention.

It is also contemplated that probes of intermediate size may be used. Such probes, in the 11 to 15 nucleotide range, may blend some of the features associated with the longer probes as originally described, these features including the ability to hybridize and be cleaved absent the help of a stacker oligonucleotide. At temperatures below the expected $T_m$ of such probes, the mechanisms of turnover may be as discussed above for probes in the 20 nt range, and be dependent on the removal of the sequence in the 'X' region for destabilization and cycling.

The mid-range probes may also be used at elevated temperatures, at or above their expected $T_m$, to allow melting rather than cleavage to promote probe turnover. In contrast to the longer probes described above, however, the temperatures required to allow the use of such a thermally driven turnover are much lower (about 40 to 60° C.), thus preserving both the cleavage means and the nucleic acids in the reaction from thermal degradation. In this way, the mid-range probes may perform in some instances like the miniprobes described above. In a further similarity to the miniprobes, the accumulation of cleavage signal from a mid-range probe may be helped under some reaction conditions by the presence of a stacker.

To summarize, a standard long probe usually does not benefit from the presence of a stacker oligonucleotide downstream (the exception being cases where such an oligonucleotide may also disrupt structures in the target nucleic acid that interfere with the probe binding), and it may be used in conditions requiring several nucleotides to be removed to allow the oligonucleotide to release from the target efficiently. If temperature of the reaction is used to drive exchange of the probes, standard probes may require use of a temperature at which nucleic acids and enzymes are at higher risk of thermal degradation.

The miniprobe is very short and performs optimally in the presence of a downstream stacker oligonucleotide. The miniprobes are well suited to reactions conditions that use the temperature of the reaction to drive rapid exchange of the probes on the target regardless of whether any bases have been cleaved. In reactions with sufficient amount of the cleavage means, the probes that do bind will be rapidly cleaved before they melt off.

The mid-range or midiprobe combines features of these probes and can be used in reactions like those favored by long probes, with longer regions of overlap ("X" regions) to drive probe turnover at lower temperature. In a preferred embodiment, the midrange probes are used at temperatures sufficiently high that the probes are hybridizing to the target and releasing rapidly regardless of cleavage. The mid-range probe may have enhanced performance in the presence of a stacker under some circumstances.

The distinctions between the mini-, midi-(i.e., mid-range) and long probes are not contemplated to be inflexible and based only on length. The performance of any given probe may vary with its specific sequence, the choice of solution conditions, the choice of temperature and the selected cleavage means.

It is shown in Example 17 that the assemblage of oligonucleotides that comprises the cleavage structure of the present invention is sensitive to mismatches between the probe and the target. The site of the mismatch used in Ex. 17 provides one example and is not intended to be a limitation in location of a mismatch affecting cleavage. It is also contemplated that a mismatch between the INVADER oligonucleotide and the target may be used to distinguish related target sequences. In the 3-oligonucleotide system, comprising an INVADER, a probe and a stacker oligonucleotide, it is contemplated that mismatches may be located within any of the regions of duplex formed between these oligonucleotides and the target sequence. In a preferred embodiment, a mismatch to be detected is located in the probe. In a particularly preferred embodiment, the mismatch is in the probe, at the base-pair immediately upstream (i.e., 5') of the site that is cleaved when the probe is not mismatched to the target.

In another preferred embodiment, a mismatch to be detected is located within the region 'Z' defined by the hybridization of a miniprobe. In a particularly preferred embodiment, the mismatch is in the miniprobe, at the base-pair immediately upstream (i.e., 5') of the site that is cleaved when the miniprobe is not mismatched to the target.

b) Design of the Reaction Conditions

Target nucleic acids that may be analyzed using the methods of the present invention that employ a 5' nuclease or other appropriate cleavage agents include of both RNA and DNA. Such nucleic acids may be obtained using standard molecular biological techniques. For example, nucleic acids (RNA or DNA) may be isolated from a tissue sample (e.g., a biopsy specimen), tissue culture cells, samples containing bacteria and/or viruses (including cultures of bacteria and/or viruses), etc. The target nucleic acid may also be transcribed in vitro from a DNA template or may be chemically synthesized or amplified in by polymerase chain reaction. Furthermore, nucleic acids may be isolated from an organism, either as genomic material or as a plasmid or similar extrachromosomal DNA, or they may be a fragment of such material generated by treatment with a restriction endonuclease or other cleavage agent, or a shearing force, or it may be synthetic.

Assembly of the target, probe, and INVADER oligonucleotide nucleic acids into the cleavage reaction of the present invention uses principles commonly used in the design of oligonucleotide-based enzymatic assays, such as dideoxynucleotide sequencing and polymerase chain reaction (PCR). As is done in these assays, the oligonucleotides are provided in sufficient excess that the rate of hybridization to the target nucleic acid is very rapid. These assays are commonly performed with 50 fmoles to 2 pmoles of each oligonucleotide per microliter of reaction mixture, although they are not necessarily limited to this range In the Examples described herein, amounts of oligonucleotides ranging from 250 fmoles to 5 pmoles per microliter of reaction volume were used. These values were chosen for the purpose of ease in demonstration and are not intended to limit the performance of the present invention to these concentrations. Other (e.g., lower) oligonucleotide concentrations commonly used in other molecular biological reactions are also contemplated.

It is desirable that an INVADER oligonucleotide be immediately available to direct the cleavage of each probe oligonucleotide that hybridizes to a target nucleic acid. In some embodiments described herein, the INVADER oligonucleotide is provided in excess over the probe oligonucleotide. While this is an effective means of making the INVADER oligonucleotide immediately available in such embodiments it is not intended that the practice of the present invention be limited to conditions wherein the INVADER oligonucleotide is in excess over the probe, or to any particular ratio of INVADER-to-probe (e.g., in some preferred embodiments described herein, the probe is provided in excess over the INVADER oligonucleotide). Another means of assuring the presence of an INVADER oligonucleotide whenever a probe binds to a target nucleic acid is to design the INVADER oligonucleotide to hybridize more stably to the target, i.e., to have a higher $T_m$ than the probe. This can be accomplished by any of the means of increasing nucleic acid duplex stability discussed herein (e.g., by increasing the amount of complementarity to the target nucleic acid).

Buffer conditions should be chosen that will be compatible with both the oligonucleotide/target hybridization and with the activity of the cleavage agent. The optimal buffer conditions for nucleic acid modification enzymes, and particularly DNA modification enzymes, generally included enough mono- and di-valent salts to allow association of nucleic acid strands by base-pairing. If the method of the present invention is performed using an enzymatic cleavage agent other than those specifically described here, the reactions may generally be performed in any such buffer reported to be optimal for the nuclease function of the cleavage agent. In general, to test the utility of any cleavage agent in this method, test reactions are performed wherein the cleavage agent of interest is tested in the MOPS/$MnCl_2$/KCl buffer or Mg-containing buffers described herein and in whatever buffer has been reported to be suitable for use with that agent, in a manufacturer's data sheet, a journal article, or in personal communication.

The products of the INVADER oligonucleotide-directed cleavage reaction are fragments generated by structure-specific cleavage of the input oligonucleotides. The resulting cleaved and/or uncleaved oligonucleotides may be analyzed and resolved by a number of methods including, but not limited to, electrophoresis (on a variety of supports including acrylamide or agarose gels, paper, etc.), chromatography, fluorescence polarization, mass spectrometry and chip hybridization. In some Examples the invention is illustrated using electrophoretic separation for the analysis of the products of the cleavage reactions. However, it is noted that the resolution of the cleavage products is not limited to electrophoresis. Electrophoresis is chosen to illustrate the method of the invention because electrophoresis is widely practiced in the art and is easily accessible to the average practitioner. In other Examples, the invention is illustrated without electrophoresis or any other resolution of the cleavage products.

The probe and INVADER oligonucleotides may contain a label to aid in their detection following the cleavage reaction. The label may be a radioisotope (e.g., a $^{32}P$ or $^{35}S$-labelled nucleotide) placed at either the 5' or 3' end of the oligonucleotide or alternatively, the label may be distributed throughout the oligonucleotide (i.e., a uniformly labeled oligonucleotide). The label may be a nonisotopic detectable moiety, such as a fluorophore, that can be detected directly, or a reactive group that permits specific recognition by a secondary agent. For example, biotinylated oligonucleotides may be detected by probing with a streptavidin molecule that is coupled to an indicator (e.g., alkaline phosphatase or a fluorophore) or a hapten such as dioxigenin may be detected using a specific antibody coupled to a similar indicator. The reactive group may also be a specific configuration or sequence of nucleotides that can bind or otherwise interact with a secondary agent, such as another nucleic acid, and enzyme, or an antibody.

c) Optimization of Reaction Conditions

The INVADER oligonucleotide-directed cleavage reaction is useful to detect the presence of specific nucleic acids. In addition to the considerations listed above for the selection and design of the INVADER and probe oligonucleotides, the conditions under which the reaction is to be performed may be optimized for detection of a specific target sequence.

One objective in optimizing the INVADER oligonucleotide-directed cleavage assay is to allow specific detection of the fewest copies of a target nucleic acid. To achieve this end, it is desirable that the combined elements of the reaction interact with the maximum efficiency, so that the rate of the reaction (e.g., the number of cleavage events per minute) is maximized. Elements contributing to the overall efficiency of the reaction include the rate of hybridization, the rate of cleavage, and the efficiency of the release of the cleaved probe.

The rate of cleavage will be a function of the cleavage means chosen, and may be made optimal according to the manufacturer's instructions when using commercial preparations of enzymes or as described in the examples herein. The other elements (rate of hybridization, efficiency of release) depend upon the execution of the reaction, and optimization of these elements is discussed below.

Three elements of the cleavage reaction that significantly affect the rate of nucleic acid hybridization are the concentration of the nucleic acids, the temperature at which the cleavage reaction is performed and the concentration of salts and/or other charge-shielding ions in the reaction solution.

The concentrations at which oligonucleotide probes are used in assays of this type are well known in the art, and are discussed above. One example of a common approach to optimizing an oligonucleotide concentration is to choose a starting amount of oligonucleotide for pilot tests; 0.01 to 2 µM is a concentration range used in many oligonucleotide-based assays. When initial cleavage reactions are performed, the following questions may be asked of the data: Is the reaction performed in the absence of the target nucleic acid substantially free of the cleavage product?; Is the site of cleavage specifically positioned in accordance with the design of the INVADER oligonucleotide?; Is the specific cleavage product easily detected in the presence of the uncleaved probe (or is the amount of uncut material overwhelming the chosen visualization method)?

A negative answer to any of these questions would suggest that the probe concentration is too high, and that a set of reactions using serial dilutions of the probe should be performed until the appropriate amount is identified. Once identified for a given target nucleic acid in a give sample type (e.g., purified genomic DNA, body fluid extract, lysed bacterial extract), it should not need to be re-optimized. The sample type is important because the complexity of the material present may influence the probe concentration optimum.

Conversely, if the chosen initial probe concentration is too low, the reaction may be slow, due to inefficient hybridization. Tests with increasing quantities of the probe will identify the point at which the concentration exceeds the optimum (e.g., at which it produces an undesirable effect, such as background cleavage not dependent on the target sequence, or interference with detection of the cleaved products). Since the hybridization will be facilitated by excess of probe, it is desirable, but not required, that the reaction be performed using probe concentrations just below this point.

The concentration of INVADER oligonucleotide can be chosen based on the design considerations discussed above. In some embodiments, the INVADER oligonucleotide is in excess of the probe oligonucleotide. In a preferred embodiment, the probe oligonucleotide is in excess of the INVADER oligonucleotide.

Temperature is also an important factor in the hybridization of oligonucleotides. The range of temperature tested will depend in large part on the design of the oligonucleotides, as discussed above. Where it is desired to have a reaction be run at a particular temperature (e.g., because of an enzyme requirement, for convenience, for compatibility with assay or detection apparatuses, etc.), the oligonucleotides that function in the reaction can be designed to optimally perform at the desired reaction temperature. Each INVADER reaction includes at least two target sequence-specific oligonucleotides for the primary reaction: an upstream INVADER oligonucleotide and a downstream probe oligonucleotide. In some preferred embodiments, the INVADER oligonucleotide is designed to bind stably at the reaction temperature, while the probe is designed to freely associate and disassociate with the target strand, with cleavage occurring only when an uncut probe hybridizes adjacent to an overlapping INVADER oligonucleotide. In preferred embodiments, the probe includes a 5' flap that is not complementary to the target, and this flap is released from the probe when cleavage occurs. The released flap can be detected directly or indirectly. In some preferred embodiments, as discussed in detail below, the released flap participate as in INVADER oligonucleotide in a secondary reaction.

Optimum conditions for the INVADER assay are generally those that allow specific detection of the smallest amount of a target nucleic acid. Such conditions may be characterized as those that yield the highest target-dependent signal in a given timeframe, or for a given amount of target nucleic acid, or that allow the highest rate of probe cleavage (i.e., probes cleaved per minute). To select a probe sequence that will perform optimally at a pre-selected reaction temperature, the melting temperature ($T_m$) of its analyte specific region (ASR, the region that is complementary to the target nucleic acid) is calculated using the nearest-neighbor model and published parameters for DNA duplex formation (SantaLucia, J., *Proc Natl Acad Sci USA* 95, 1460-5 (1998), Allawi, H. T. & SantaLucia, J., Jr. *Biochemistry* 36, 10581-94 (1997). However, there are several differences between the conditions under which the published parameters were measured and the conditions under which the INVADER assay is run in preferred embodiments. The salt concentrations are often different than the solution conditions in which the nearest-neighbor parameters were obtained (1M NaCl and no divalent metals). One can compensate for this factor by varying the value provided for the salt concentration within the melting temperature calculations. In addition to the salt concentration, the presence of and concentration of the enzyme influences the optimal reaction temperature, and an additional adjustment should be made to the calculated $T_m$ to determine the optimal temperature at which to perform a reaction. By observing the optimal temperature for a number of INVADER reactions (i.e., the temperature at which the rate of signal accumulation is highest) it has been possible to further alter the value for salt concentration within these calculations to allow the algorithm for $T_m$ calculation to be modified to instead provide an optimal cleavage reaction temperature for a given probe sequence. This additional adjustment is termed a "salt correction". As used herein, the term "salt correction" refers to a variation made in the value provided for a salt concentration, for the purpose of reflecting the effect on a $T_m$ calculation for a nucleic acid duplex of a non-salt parameter or condition affecting said duplex. Variation of the values provided for the strand concentrations will also affect the outcome of these calculations. By using a value of 0.5 M NaCl [SantaLucia, J., *Proc Natl Acad Sci USA* 95, 1460-5 (1998)] and strand concentrations of about 1 µM of the probe and 1 fM target, the algorithm used for calculating probe-target melting temperature has been adapted for use in predicting optimal INVADER assay reaction temperature. For a set of about 30 probes, the average deviation between optimal assay temperatures calculated by this method and those experimentally determined was about 1.5° C.

As noted above, the concentration of the cleavage agent can affect the actual optimum temperature for a cleavage reaction. Additionally, different cleavage agents, even if used at identical concentrations, can affect reaction temperature optima differently (e.g., the difference between the calculated probe $T_m$ and the observed optimal reaction temperature may be greater for one enzyme than for another). Determination of appropriate salt corrections for reactions using different enzymes or concentrations of enzymes, or for any other variation made in reaction conditions, involves a two step process of a) measuring reaction temperature optima under the new reaction conditions, and varying the salt concentration within the $T_m$ algorithm to produce a calculated temperature matching or closely approximating the observed optima. Measurement of an optimum reaction temperature generally involves performing reactions at a range of temperatures selected such that the range allows observation of an increase in performance as an optimal temperature is approached (either by increasing or decreasing temperatures), and a decrease in performance when an optimal temperature has been passed, thereby allowing identification of the optimal temperature or temperature range [see, for example, V. I. Lyamichev, et al., Biochemistry 39, No. 31:9523-9532 (2000)].

The length of the downstream probe analyte-specific region (ASR) is defined by the temperature selected for running the reaction, e.g., 63° C. in the experiments described in Examples 54 through 60. To select a probe sequence based on a desired reaction temperature, the probe sequence is selected in the following way (as illustrated for the design of a probe for the detection of a sequence difference at a particular location). Starting from the position of the variant nucleotide on the target DNA (position N, FIG. 112); the target base that is paired to the probe nucleotide 5' of the intended cleavage site), an iterative procedure is used by which the length of the ASR is increased by one base pair until a calculated optimal reaction temperature ($T_m$ plus salt correction to compensate for enzyme and any other reaction conditions effects) matching the desired reaction temperature is reached. The non-complementary arm of the probe is preferably selected (by a similar iterative process) to allow the secondary reaction to cycle at the same reaction temperature, and the entire probe design (ASR and 5' noncomplementary arm) is screened using programs such as mfold [Zuker, M. *Science* 244, 48-52 (1989)] or *Oligo* 5.0 [Rychlik, W. & Rhoads, R. E. *Nucleic Acids Res* 17, 8543-51 (1989)] for the possible formation of dimer complexes or secondary structures that could interfere with the reaction. The same principles are also followed for INVADER oligonucleotide design. The following describes design of an INVADER assay embodiment wherein the 3' end of the INVADER oligonucleotide, at position N on the target DNA, is designed to have a nucleotide not complementary to either allele suspected of being contained in the sample to be tested. The mismatch does not adversely affect cleavage [Lyamichev, V. et al. *Nature Biotechnology* 17, 292-296 (1999)], and it can enhance probe cycling, presumably by minimizing coaxial stabilization effects between the two probes. Briefly, starting from the position N, additional residues complementary to the target DNA starting from residue N-1 are then added in the upstream direction until the stability of the INVADER-target hybrid exceeds that of the probe (and therefore the planned assay reaction temperature). In preferred embodiments, the stability of the INVADER-target hybrid exceeds that of the probe by 15-20° C.

In some embodiments, where the released cleavage fragment from a primary reaction is to be used in a secondary reaction, one should also consider the reaction conditions of the secondary reaction in designing the oligonucleotides for the primary reaction (e.g., the sequence of the released non-complementary 5' flap of the probe in the primary reaction can be designed to optimally function in a secondary reaction). For example, as described in detail below, in some embodiments, a secondary reaction is used where the released cleavage fragment from a primary reaction hybridizes to a synthetic cassette to form a secondary cleavage reaction. In some preferred embodiments, the cassette comprises a fluorescing moiety and a quenching moiety, wherein cleavage of the secondary cleavage structure separates the fluorescing moiety from the quenching moiety, resulting in a detectable signal (e.g., FRET detection). The secondary reaction can be configured a number of different ways. For example, in some embodiments, the synthetic cassette comprises two oligonucleotides: an oligonucleotide that contains the FRET moieties and a FRET/INVADER oligonucleotide bridging oligonucleotide that allows the INVADER oligonucleotide (i.e., the released flap from the primary reaction) and the FRET oligonucleotide to hybridize thereto, such that a cleavage structure is formed. In some embodiments, the synthetic cassette is provided as a single oligonucleotide, comprising a hairpin structure (i.e., the FRET oligonucleotide is connected at its 3' end to the bridging oligonucleotide by a loop). The loop may be nucleic acid, (e.g., a string of nucleotides, such as the four T residues depicted in several Figures, including 113A) or a non-nucleic acid spacer or linker. The linked molecules may together be described as a FRET cassette. In the secondary reaction using a FRET cassette the released flap from the primary reaction, which acts as an INVADER oligonucleotide, should be able to associate and disassociate with the FRET cassette freely, so that one released flap can direct the cleavage of multiple FRET cassettes. It is one aspect of the assay design that all of the probe sequences may be selected to allow the primary and secondary reactions to occur at the same optimal temperature, so that the reaction steps can run simultaneously. In an alternative embodiment, the probes may be designed to operate at different optimal temperatures, so that the reactions steps are not simultaneously at their temperature optima. As noted above, the same iterative process used to select the ASR of the probe can be used in the design of the portion of the primary probe that participates in a secondary reaction.

Another determinant of hybridization efficiency is the salt concentration of the reaction. In large part, the choice of solution conditions will depend on the requirements of the cleavage agent, and for reagents obtained commercially, the manufacturer's instructions are a resource for this information. When developing an assay utilizing any particular cleavage agent, the oligonucleotide and temperature optimizations described above should be performed in the buffer conditions best suited to that cleavage agent.

A "no enzyme" control allows the assessment of the stability of the labeled oligonucleotides under particular reaction conditions, or in the presence of the sample to be tested e.g., in assessing the sample for contaminating nucleases). In this manner, the substrate and oligonucleotides are placed in a tube containing all reaction components, except the enzyme and treated the same as the enzyme-containing reactions. Other controls may also be included. For example, a reaction with all of the components except the target nucleic acid will serve to confirm the dependence of the cleavage on the presence of the target sequence.

d) Selection of a Cleavage Agent

As demonstrated in a number of the Examples, some 5' nucleases do not require an upstream oligonucleotide to be active in a cleavage reaction. Although cleavage may be slower without the upstream oligonucleotide, it may still occur (Lyamichev et al., Science 260:778 [1993], Kaiser et al., J. Biol. Chem., 274:21387 [1999]). When a DNA strand is the template or target strand to which probe oligonucleotides are hybridized, the 5' nucleases derived from DNA polymerases and some flap endonucleases (FENs), such as that from *Methanococcus jannaschii*, can cleave quite well without an upstream oligonucleotide providing an overlap (Lyamichev et al., Science 260:778 [1993], Kaiser et al., J. Biol. Chem., 274:21387 [1999], and U.S. Pat. No. 5,843,669, herein incorporated by reference in its entirety). These nucleases may be selected for use in some embodiments of the INVADER assay, e.g., in embodiments wherein cleavage of th probe in the absence of an INVADER oligonucleotide gives a different cleavage product, which does not interfere with the intended analysis, or wherein both types of cleavage, INVADER oligonucleotide-directed and INVADER oligonucleotide-independent, are intended to occur.

In other embodiments it is preferred that cleavage of the probe be dependent on the presence of an upstream INVADER oligonucleotide, and enzyme having this requirement would be used. Other FENs, such as those from *Archeaoglobus fulgidus* (Afu) and *Pyrococcus furiosus* (Pfu), cleave an overlapped structure on a DNA target at so much greater a rate than they do a non-overlapping structure (i.e., either missing the upstream oligonucleotide or having a non-overlapping upstream oligonucleotide) that they can be viewed as having an essentially absolute requirement for the overlap (Lyamichev et al., Nat. Biotechnol., 17:292 [1999], Kaiser et al., J. Biol. Chem., 274:21387 [1999]). When an RNA target is hybridized to DNA oligonucleotide probes to form a cleavage structure, many FENs cleave the downstream DNA probe poorly, regardless of the presence of an overlap. On such an RNA-containing structure, the 5' nucleases derived from DNA polymerases have a strong requirement for the overlap, and are essentially inactive in its absence.

e) Probing for Multiple Alleles

The INVADER oligonucleotide-directed cleavage reaction is also useful in the detection and quantification of individual variants or alleles in a mixed sample population. By way of example, such a need exists in the analysis of tumor material for mutations in genes associated with cancers. Biopsy material from a tumor can have a significant complement of normal cells, so it is desirable to detect mutations even when present in fewer than 5% of the copies of the target nucleic acid in a sample. In this case, it is also desirable to measure what fraction of the population carries the mutation. Similar analyses may also be done to examine allelic variation in other gene systems, and it is not intended that the method of the present invention by limited to the analysis of tumors.

As demonstrated below, in one embodiment, reactions can be performed under conditions that prevent the cleavage of probes bearing even a single-nucleotide difference mismatch within the region of the target nucleic acid termed "Z" in FIG. 29, but that permit cleavage of a similar probe that is completely complementary to the target in this region. In a preferred embodiment, a mismatch is positioned at the nucleotide in the probe that is 5' of the site where cleavage occurs in the absence of the mismatch.

In other embodiments, the INVADER assay may be performed under conditions that have a tight requirement for an overlap (e.g., using the Afu FEN for DNA target detection or the 5' nuclease of DNA polymerase for RNA target detection, as described above), providing an alternative means of detecting single nucleotide or other sequence variations. In one embodiment, the probe is selected such that the target base suspected of varying is positioned at the 5' end of the target-complementary region of this probe. The upstream INVADER oligonucleotide is positioned to provide a single base of overlap. If the target and the probe oligonucleotide are complementary at the base in question, the overlap forms and cleavage can occur. This embodiment is diagrammed in FIG. 112. However, if the target does not complement the probe at this position, that base in the probe becomes part of a non-complementary 5' arm, no overlap between the INVADER oligonucleotide and probe oligonucleotide exists, and cleavage is suppressed.

It is also contemplated that different sequences may be detected in a single reaction. Probes specific for the different sequences may be differently labeled. For example, the probes may have different dyes or other detectable moieties, different lengths, or they may have differences in net charges of the products after cleavage. When differently labeled in one of these ways, the contribution of each specific target sequence to final product can be tallied. This has application in detecting the quantities of different versions of a gene within a mixture. Different genes in a mixture to be detected and quantified may be wild type and mutant genes (e.g., as may be found in a tumor sample, such as a biopsy). In this embodiment, one might design the probes to precisely the same site, but one to match the wild-type sequence and one to match the mutant. Quantitative detection of the products of cleavage from a reaction performed for a set amount of time will reveal the ratio of the two genes in the mixture. Such analysis may also be performed on unrelated genes in a mixture. This type of analysis is not intended to be limited to two genes. Many variants within a mixture may be similarly measured.

Alternatively, different sites on a single gene may be monitored and quantified to verify the measurement of that gene. In this embodiment, the signal from each probe would be expected to be the same.

It is also contemplated that multiple probes may be used that are not differently labeled, such that the aggregate signal is measured. This may be desirable when using many probes designed to detect a single gene to boost the signal from that gene. This configuration may also be used for detecting unrelated sequences within a mix. For example, in blood banking it is desirable to know if any one of a host of infectious agents is present in a sample of blood. Because the blood is discarded regardless of which agent is present, different signals on the probes would not be required in such an application of the present invention, and may actually be undesirable for reasons of confidentiality.

Just as described for the two-oligonucleotide system, above, the specificity of the detection reaction will be influenced by the aggregate length of the target nucleic acid sequences involved in the hybridization of the complete set of the detection oligonucleotides. For example, there may be applications in which it is desirable to detect a single region within a complex genome. In such a case the set of oligonucleotides may be chosen to require accurate recognition by hybridization of a longer segment of a target nucleic acid, often in the range of 20 to 40 nucleotides. In other instances it may be desirable to have the set of oligonucleotides interact with multiple sites within a target sample. In these cases one approach would be to use a set of oligonucleotides that recognize a smaller, and thus statistically more common, segment of target nucleic acid sequence.

In one preferred embodiment, the INVADER and stacker oligonucleotides may be designed to be maximally stable, so that they will remain bound to the target sequence for extended periods during the reaction. This may be accomplished through any one of a number of measures well known to those skilled in the art, such as adding extra hybridizing sequences to the length of the oligonucleotide (up to about 50 nts in total length), or by using residues with reduced negative charge, such as phosphorothioates or peptide-nucleic acid residues, so that the complementary strands do not repel each other to degree that natural strands do. Such modifications may also serve to make these flanking oligonucleotides resistant to contaminating nucleases, thus further ensuring their continued presence on the target strand during the course of the reaction. In addition, the INVADER and stacker oligonucleotides may be covalently attached to the target (e.g., through the use of psoralen cross-linking).

II. Effect of ARRESTOR Molecules on Signal and Background in Sequential Invasive Cleavage Reactions.

As described above, and demonstrated in Example 36, the concentration of the probe that is cleaved can be used to increase the rate of signal accumulation, with higher concentrations of probe yielding higher final signal. However, the presence of large amounts of residual uncleaved probe can present problems for subsequent use of the cleaved products for detection or for further amplification. If the subsequent step is a simple detection (e.g., by gel resolution), the excess uncut material may cause background by streaking or scattering of signal, or by overwhelming a detector (e.g., overexposing a film in the case of radioactivity, or exceeding the quantitative detection limits of a fluorescence imager). This can be overcome by partitioning the product from the uncut probe (e.g., by using the charge reversal method described in Example 22 and discussed in detail below). In more complex detection methods, the cleaved product may be intended to interact with another entity to indicate cleavage. As noted above, the cleaved product can be used in any reaction that makes use of oligonucleotides, such as hybridization, primer extension, ligation, or the direction of invasive cleavage. In each of these cases, the fate of the residual uncut probe should be considered in the design of the reaction. In a primer extension reaction, the uncut probe can hybridize to a template for extension. If cleavage is required to reveal the correct 3' end for extension, the hybridized uncut probe will not be extended. It may, however, compete with the cleaved product for the template. If the template is in excess of the combination of cleaved and uncleaved probe, then both of the latter should be able to find a copy of template for binding. If, however, the template is limiting, any competition may reduce the portion of the cleaved probe that can find successfully bind to the available template. If a vast excess of probe was used to drive the initial reaction, the remainder may also be in vast excess over the cleavage product, and thus may provide a very effective competitor, thereby reducing the amount of the final reaction (e.g., extension) product for ultimate detection.

The participation of the uncut probe material in a secondary reaction can also contribute to background in these reactions. While the presentation of a cleaved probe for a subsequent reaction may represent an ideal substrate for the enzyme to be used in the next step, some enzymes may also be able to act, albeit inefficiently, on the uncut probe as well. It was shown in Example 43 that transcription can be promoted from a nicked promoter even when one side of the nick has additional unpaired nucleotides (termed a "branched promoter" in that Example). Similarly, when the subsequent reaction is to be an invasive cleavage, the uncleaved probe may bind to the elements intended to form the second cleavage structure with the cleaved probe. Two of the possible configurations are shown schematically in FIGS. 105 and 106. The right hand structure in the second step in each Figure shows a possible configuration formed by the secondary reaction elements (e.g., secondary targets and/or probes) and the uncleaved primary probe. In each of these cases, it was found that some of the 5' nucleases described herein can catalyze some measure of cleavage of these defective structures. Even at a low level, this aberrant cleavage can be misinterpreted as positive target-specific cleavage signal.

With these negative effects of the surfeit of uncut probe considered, there is clearly a need for some method of preventing these interactions. As noted above, it is possible to partition the cleaved product from the uncut probe after the primary reaction by traditional methods. However, these methods are often time consuming, may be expensive (e.g., disposable columns, gels, etc.), and may increase the risk for sample mishandling or contamination. It is far preferable to configure the sequential reactions such that the original sample need not be removed to a new vessel for subsequent reaction.

The present invention provides a method for reducing interactions between the primary probe and other reactants. This method provides a means of specifically diverting the uncleaved probes from participation in the subsequent reactions. The diversion is accomplished by the inclusion in the next reaction step an agent designed to specifically interact with the uncleaved primary probe. While the primary probe in an invasive cleavage reaction is discussed for reasons of convenience, it is contemplated that the ARRESTOR molecules may be used at any reaction step within a chain of invasive cleavage steps, as needed or desired for the design of an assay. It is not intended that the ARRESTOR molecules of the present invention be limited to any particular step.

The method of diverting the residual uncut probes from a primary reaction makes use of agents that can be specifically designed or selected to bind to the uncleaved probe molecules with greater affinity than to the cleaved probes, thereby allowing the cleaved probe species to effectively compete for the elements of the subsequent reaction, even when the uncut probe is present in vast excess. These agents have been termed "ARRESTOR molecules," due to their function of stopping or arresting the primary probe from participation in the later reaction. In various Examples below, an oligonucleotide is provided as an ARRESTOR oligonucleotide in an invasive cleavage assay. It can be appreciated that any molecule or chemical that can discriminate between the full-length uncut probe and the cleaved probe, and that can bind or otherwise disable the uncleaved probe preferentially may be configured to act as an ARRESTOR molecules within the meaning of the present invention. For example, antibodies can be derived with such specificity, as can the "aptamers" that can be selected through multiple steps of in vitro amplification (e.g., "SELEX," U.S. Pat. Nos. 5,270,163 and 5,567,588; herein incorporated by reference) and specific rounds of capture or other selection means.

In one embodiment, the ARRESTOR molecule is an oligonucleotide. In another embodiment the ARRESTOR oligonucleotides is a composite oligonucleotide, comprising two or more short oligonucleotides that are not covalently linked, but that bind cooperatively and are stabilized by co-axial stacking. In a preferred embodiment, the oligonucleotide is modified to reduce interactions with the cleavage agents of the present invention. When an oligonucleotide is used as an ARRESTOR oligonucleotide, it is intended that it not participate in the subsequent reactive step. Consideration of the schematic diagrams in FIGS. 105 and 106, particularly the right-most Figure in step 2b of each Figure, will show that the binding of the ARRESTOR oligonucleotide to the primary probe may, either with the participation of the secondary target, or without such participation, create a bifurcated structure that is a substrate for cleavage by the 5' nucleases used in some embodiments of the methods of the present invention. Formation of such structures would lead to some level of unintended cleavage that could contribute to background, reduce specific signal or compete for the enzyme. It is preferable to provide ARRESTOR oligonucleotides that will not create such cleavage structures. One method of doing this is to add to the ARRESTOR oligonucleotides such modifications as have been found to reduce the activity of INVADER oligonucleotides, as the INVADER oligonucleotides occupy a similar position within a cleavage structure (i.e., the 3' end of the INVADER oligonucleotide positions the site of cleavage of an unpaired 5' arm). Modification of the 3' end of the INVADER oligonucleotides was examined for the effects on cleavage in Example 35; a number of the modifications tested were found to be significantly debilitating to the function of the INVADER oligonucleotide. Other modifications not described herein may be easily characterized by performing such a test using the cleavage enzyme to be used in the reaction for which the ARRESTOR oligonucleotide is intended.

In a preferred embodiment, the backbone of an ARRESTOR oligonucleotide is modified. This may be done to increase the resistance to degradation by nucleases or temperature, or to provide duplex structure that is a less favorable substrate for the enzyme to be used (e.g., A-form duplex vs. B-form duplex). In particularly preferred embodiment, the backbone modified oligonucleotide further comprises a 3' terminal modification. In a preferred embodiment, the modifications comprise 2' O-methyl substitution of the nucleic acid backbone, while in a particularly preferred embodiment, the 2' O-methyl modified oligonucleotide further comprises a 3' terminal amine group.

The purpose of the ARRESTOR oligonucleotide is to allow the minority population of cleaved probe to effectively compete with the uncleaved probe for binding whatever elements are to be used in the next step. While an ARRESTOR oligonucleotide that can discriminate between the two probe species absolutely (i.e., binding only to uncut and never to cut) may be of the greatest benefit in some embodiments, it is envisioned that in many applications, including the sequential INVADER assays described herein, the ARRESTOR oligonucleotide of the present invention may perform the intended function with only partial discrimination. When the ARRESTOR oligonucleotide has some interaction with the cleaved probe, it may prevent detection of some portion of these cleavage products, thereby reducing the absolute level of signal generated from a given amount of target material. If this same ARRESTOR oligonucleotide has the simultaneous effect of reducing the background of the reaction (i.e., from non-target specific cleavage) by a factor that is greater than the factor of reduction in the specific signal, then the significance of the signal (i.e., the ratio of signal to background), is increased, even with the lower amount of absolute signal. Any potential ARRESTOR molecule design may be tested in a simple fashion by comparing the levels of background and specific signals from reactions that lack ARRESTOR molecules to the levels of background and specific signal from similar reactions that include ARRESTOR oligonucleotides. Each of the reactions described in Examples 49-53 demonstrate the use of such comparisons, and these can easily be adapted by those skilled in the art to other ARRESTOR molecules and target embodiments. What constitutes an acceptable level of tradeoff of absolute signal for specificity will vary for different applications (e.g., target levels, read-out sensitivity, etc.), and can be determined by any individual user using the methods of the present invention.

III. Signal Enhancement by Incorporating the Products of an Invasive Cleavage Reaction into a Subsequent Invasive Cleavage Reaction As noted above, the oligonucleotide product released by the invasive cleavage can be used subsequently in any reaction or read-out method that uses oligonucleotides in the size range of a cleavage product. In addition to the reactions involving primer extension and transcription, described herein, another enzymatic reaction that makes use of oligonucleotides is the invasive cleavage reaction. The present invention provide means of using the oligonucleotide released in a primary invasive cleavage reaction as a component to complete a cleavage structure to enable a secondary invasive cleavage reaction. One possible configuration of a primary cleavage reaction supplying a component for a secondary cleavage structure is diagrammed in FIG. 96. Is not intended that the sequential use of the invasive cleavage product be limited to a single additional step. It is contemplated that many distinct invasive cleavage reactions may be performed in sequence.

The polymerase chain reaction uses a DNA replication method to create copies of a targeted segment of nucleic acid at a logarithmic rate of accumulation. This is made possible by the fact that when the strands of DNA are separated, each individual strand contains sufficient information to allow assembly of a new complementary strand. When the new strands are synthesized the number of identical molecules has doubled. Within 20 iterations of this process, the original may be copied 1 million-fold, making very rare sequences easily detectable. The mathematical power of a doubling reaction has been incorporated into a number of amplification assays, several of which are cited in Table 1.

By performing multiple, sequential invasive cleavage reactions the method of the present invention captures an exponential mathematical advantage without producing additional copies of the target analyte. In a simple invasive cleavage reaction the yield, Y, is simply the turnover rate, K, multiplied by the time of the reaction, t (i.e., $Y=(K)(t)$). If Y is used to represent the yield of a simple reaction, then the yield of a compound (i.e., a multiple, sequential reaction), assuming that each of the individual invasive cleavage steps has the same turnover rate, can be simply represented as $Y^n$, where n is the number of invasive cleavage reactions that have been performed in the series. If the yields of each step differ the ultimate yield can be represented as the product of the multiplication of the yields of each individual reaction in the series. For example, if a primary invasive cleavage reaction can produce one thousand products in 30 minutes, and each of those products can in turn participate in 1000 additional reactions, there will be $1000^2$ copies (1000×1000) of the ultimate product in a second reaction. If a third reaction is added to the series, then the theoretical yield will be $1000^3$ (1000×1000× 1000). In the methods of the present invention the exponent comes from the number of invasive cleavage reactions in the cascade. This can be contrasted to the amplification methods described above (e.g., PCR) in which Y is limited to 2 by the number of strands in duplex DNA, and the exponent n is the number of cycles performed, so that many iterations are necessary to accumulate large amounts of product.

To distinguish the exponential amplifications described above from those of the present invention, the former can be considered reciprocating reactions because the products the reaction feed back into the same reaction (e.g., event one leads to some number of events 2, and each event 2 leads back to some number of events 1). In contrast, the events of the present invention are sequential (e.g., event 1 leads to some number of events 2; each event 2 leads to some number of events 3, etc., and no event can contribute to an event earlier in the chain).

The sensitivity of the reciprocating methods is also one of the greatest weaknesses when these assays are used to determine if a target nucleic acid sequence is present or absent in a sample. Because the product of these reactions is detectable copies of the starting material, contamination of a new reaction with the products of an earlier reaction can lead to false positive results, (i.e., the apparent detection of the target nucleic acid in samples that do not actually contain any of that target analyte). Furthermore, because the concentration of the product in each positive reaction is so high, amounts of DNA sufficient to create a strong false positive signal can be communicated to new reactions very easily either by contact with contaminated instruments or by aerosol. In contrast to the reciprocating methods, the most concentrated product of the sequential reaction (i.e., the product released in the ultimate invasive cleavage event) is not capable of initiating a like reaction or cascade if carried over to a fresh test sample. This is a marked advantage over the exponential amplification methods described above because the reactions of the present invention may be performed without the costly containment arrangements (e.g., either by specialized instruments or by separate laboratory space) required by any reciprocating reaction. While the products of a penultimate event may be inadvertently transferred to produce a background of the ultimate product in the absence of the a target analyte, the contamination would need to be of much greater volume to give an equivalent risk of a false positive result.

When the term sequential is used it is not intended to limit the invention to configurations in which that one invasive cleavage reaction or assay must be completed before the initiation of a subsequent reaction for invasive cleavage of a different probe. Rather, the term refers to the order of events as would occur if only single copies of each of the oligonucleotide species were used in an assay. The primary invasive cleavage reaction refers to that which occurs first, in response to the formation of the cleavage structure on the target nucleic acid. Subsequent reactions may be referred to as secondary, tertiary and so forth, and may involve artificial "target" strands that serve only to support assembly of a cleavage structure, and which are unrelated to the nucleic acid analyte of interest. While the complete assay may, if desired, be configured with each step of invasive cleavage separated either in space (e.g., in different reaction vessels) or in time (e.g., using a shift in reaction conditions, such as temperature, enzyme identity or solution condition, to enable the later cleavage events), it is also contemplated that all of the reaction components may be mixed so that secondary reactions may be initiated as soon as product from a primary cleavage becomes available. In such a format, primary, secondary and subsequent cleavage events involving different copies of the cleavage structures may take place simultaneously.

Several levels of this sort of linear amplification can be envisioned, in which each successive round of cleavage produces an oligonucleotide that can participate in the cleavage of a different probe in subsequent rounds. The primary reaction would be specific for the analyte of interest with secondary (and tertiary, etc.) reactions being used to generate signal while still being dependent on the primary reaction for initiation.

Figure 96:
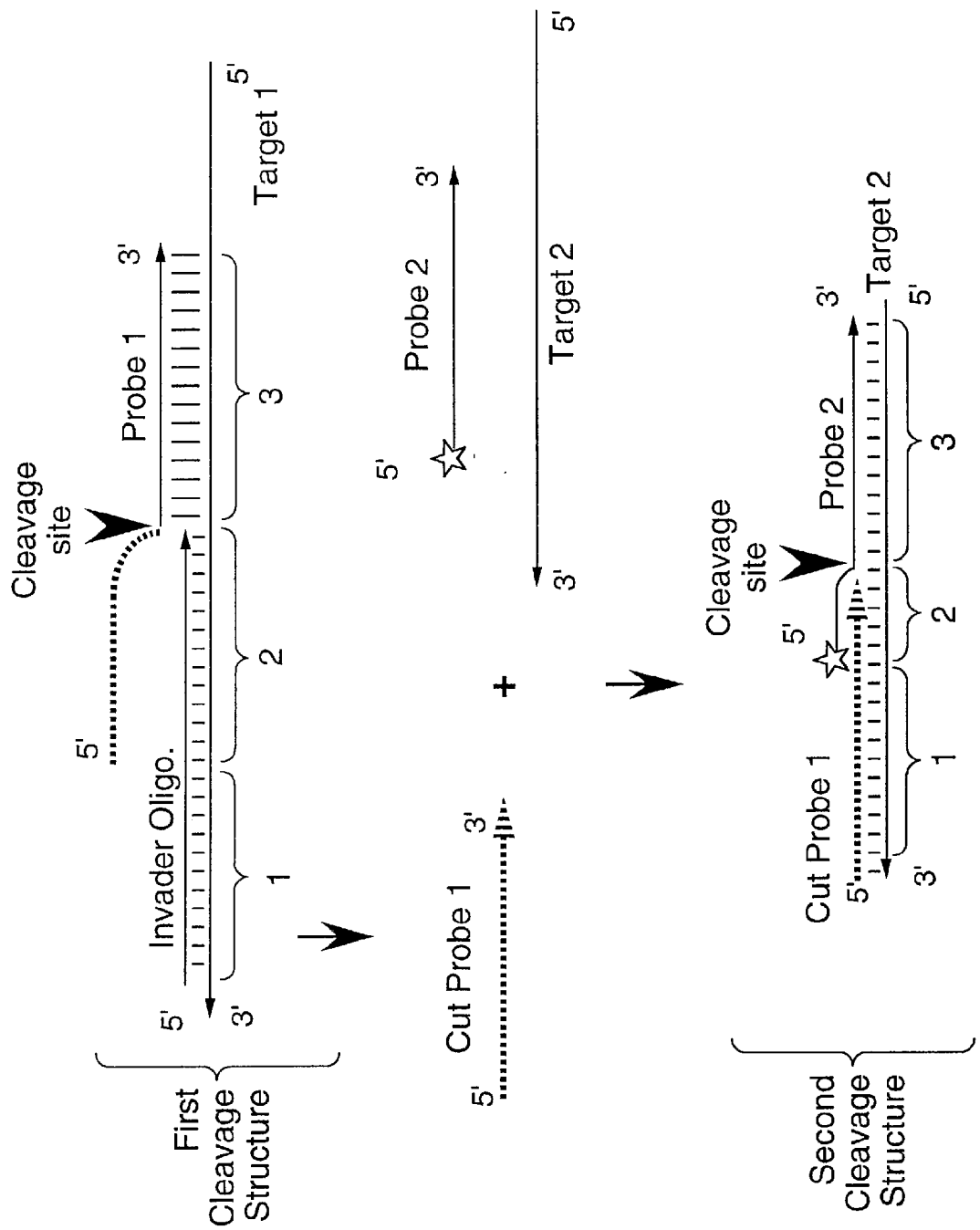
FIG. 96 is a schematic which illustrates one embodiment of the present invention where the cut probe from an initial invasive cleavage reaction is employed as the INVADER oligonucleotide in a second invasive cleavage reaction.

The released product may perform in several capacities in the subsequent reactions. One of the possible variations is shown in FIG. 96, in which the product of one invasive cleavage reaction becomes the INVADER oligonucleotide to direct the specific cleavage of another probe in a second reaction. In FIG. 96, the first invasive cleavage structure is formed by the annealing of the INVADER oligonucleotide ("Invader") and the probe oligonucleotide ("Probe 1") to the first target nucleic acid ("Target 1"). The target nucleic acid is divided into three regions based upon which portions of the INVADER and probe oligonucleotides are capable of hybridizing to the target (as discussed above and as shown in FIG. 25). Region 1 (region Y in FIG. 25) of the target has complementarity to only the INVADER oligonucleotide; region 3 (region Z in FIG. 25) of the target has complementarity to only the probe; and region 2 (region X in FIG. 25) of the target has complementarity to both the INVADER and probe oligonucleotides. It is noted that the sequential invasive cleavage reaction diagrammed in FIG. 96 employs an INVADER and a probe oligonucleotide; the sequential cleavage reaction is not limited to the use of such a first cleavage structure. The first cleavage structure in the sequential reaction may also employ an INVADER oligonucleotide, a mini probe and a stacker oligonucleotide as discussed above. Further, as discussed above, the overlap in any or all of the cleavage structures in the sequential reactions may comprise moieties other than overlapping complementary bases, such that the region shown as "X" represents a region where there is a physical rather than sequence overlap between the INVADER and probe oligonucleotides.

In FIG. 96, cleavage of Probe 1 releases the "Cut Probe 1" (indicated by the hatched line in both the cleaved and uncleaved Probe 1 in FIG. 96). The released Probe 1 is then used as the INVADER oligonucleotide in second cleavage. The second cleavage structure is formed by the annealing of the Cut Probe 1, a second probe oligonucleotide ("Probe 2") and a second target nucleic acid ("Target 2") In some embodiments, Probe 2 and the second target nucleic acid are covalently connected, preferably at their 3' and 5' ends, respectively, thus forming a hairpin stem and loop, termed herein a "cassette". The loop may be nucleic acid, (e.g., a string of nucleotides, such as the four T residues depicted in several Figures, including 113A) or a non-nucleic acid spacer or linker. Inclusion of an excess of the cassette molecule allows each Cut Probe 1 to serve as an INVADER to direct the cleavage of multiple copies of the cassette.

Probe 2 may be labeled (e.g., as indicated by the star in FIG. 96) and detection of cleavage of the second cleavage structure may be accomplished by detecting the labeled cut Probe 2; the label may a radioisotope (e.g., $^{32}P$, $^{35}S$), a fluorophore (e.g., fluorescein), a reactive group capable of detection by a secondary agent (e.g., biotin/streptavidin), a positively charged adduct which permits detection by selective charge reversal (as discussed in Section IV above), etc. Alternatively, the cut Probe 2 may used in a tailing reaction, or to complete or activate a protein binding site, or may be detected or used by any of the means for detecting or using an oligonucleotide described herein.

Figure 97:
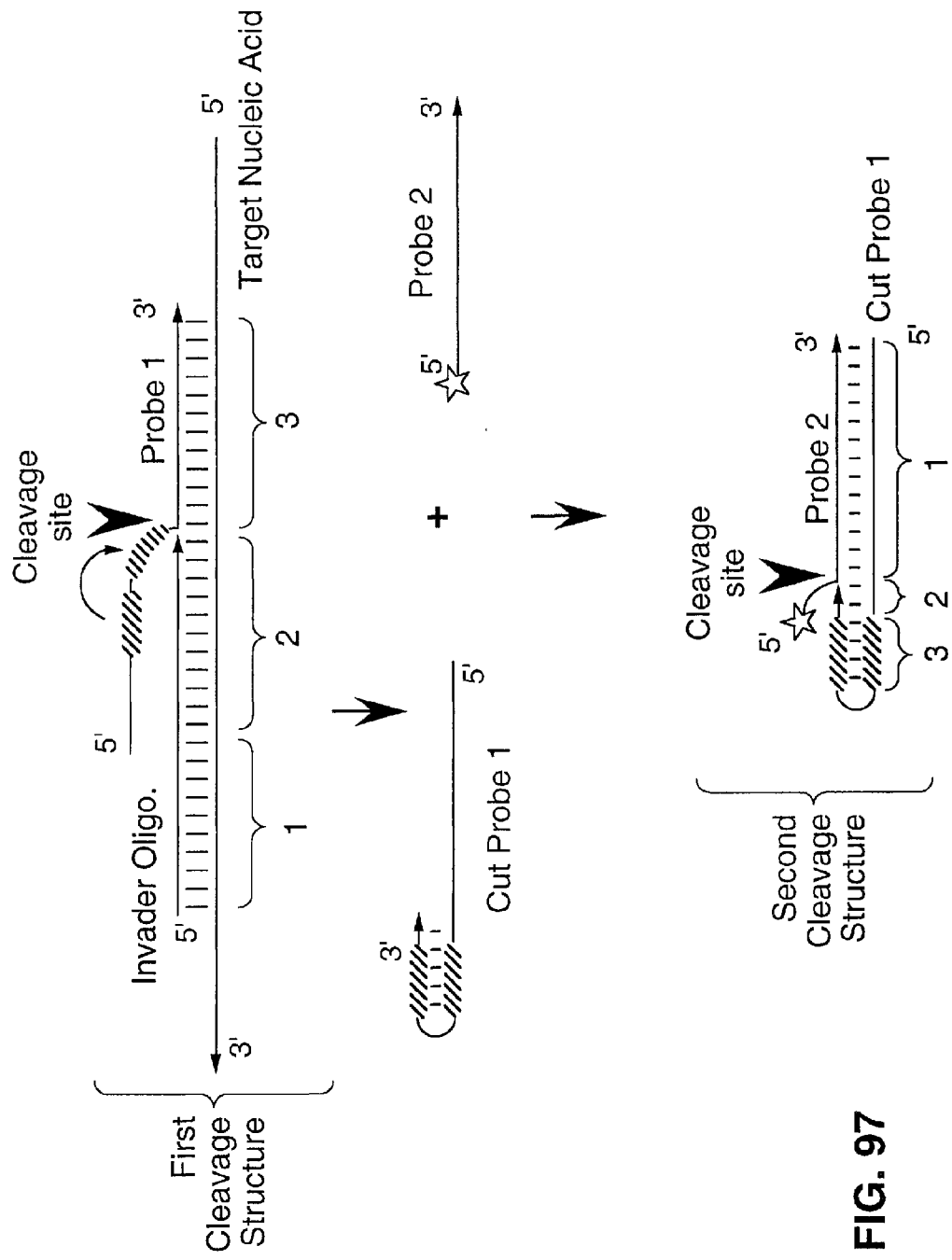
FIG. 97 is a schematic which illustrates one embodiment of the present invention where the cut probe from an initial invasive cleavage reaction is employed as an integrated INVADER-target complex in a second invasive cleavage reaction.

Another possible configuration for performing a sequential invasive cleavage reaction is diagrammed in FIG. 97. In this embodiment, probe oligonucleotides that are cleaved in the primary reaction can be designed to fold back on themselves (i.e., they contain a region of self-complementarity) to create a molecule that can serve as both the INVADER and target oligonucleotide (termed here an "IT" complex). The IT complex then enables cleavage of a different probe present in the secondary reaction. Inclusion of an excess of the secondary probe molecule ("Probe 2"), allows each IT molecule to serve as the platform for the generation of multiple copies of cleaved secondary probe. In FIG. 97, the regions of self-complementarity contained within the 5' portion of the INVADER oligonucleotide is indicated by the hatched ovals; the arrow between these two ovals indicates that these two regions can self-pair (as shown in the "Cut Probe 1"). The target nucleic acid is divided into three regions based upon which portions of the INVADER and probe oligonucleotides are capable of hybridizing to the target (as discussed above and it is noted that the target may be divided into four regions if a stacker oligonucleotide is employed). The second cleavage structure is formed by the annealing of the second probe ("Probe 2") to the fragment of Probe 1 ("Cut Probe 1") that was released by cleavage of the first cleavage structure. The Cut Probe 1 forms a hairpin or stem/loop structure near its 3' terminus by virtue of the annealing of the regions of self-complementarity contained within Cut Probe 1 (this self-annealed Cut Probe 1 forms the IT complex). The IT complex (Cut Probe 1) is divided into three regions. Region 1 of the IT complex has complementarity to the 3' portion of Probe 2; region 2 has complementarity to both the 3' end of Cut Probe 1 and to the 5' portion of Probe 2 (analogous to the region of overlap "X" shown in FIG. 25); and region 3 contains the region of self-complementarity (i.e., region 3 is complementary to the 3' portion of the Cut Probe 1). Note that with regard to the IT complex (i.e., Cut Probe 1), region 1 is located upstream of region 2 and region 2 is located upstream of region 3. As for other embodiments of invasive cleavage, the region shown as "2" can represent a region where there is a physical, but not sequence, overlap between the INVADER portion of the Cut Probe 1 and the Probe 2 oligonucleotide.

The cleavage products of the secondary invasive cleavage reaction (i.e., Cut Probe 2) can either be detected, or can in turn be designed to constitute yet another integrated INVADER-target complex to be used with a third probe molecule, again unrelated to the preceding targets.

The present invention is not limited to the configurations diagrammed in FIGS. 96 and 97. It is envisioned that the oligonucleotide product of a primary cleavage reaction may fill the role of any of the oligonucleotides described herein (e.g., it may serve as a target strand without an attached INVADER oligonucleotide-like sequence, or it may serve as a stacker oligonucleotide, as described above), to enhance the turnover rate seen in the secondary reaction by stabilizing the probe hybridization through coaxial stacking.

Secondary cleavage reactions in some preferred embodiments of the present invention include the use of FRET cassettes such as those described in Examples 54 through 62. Such molecules provide both a secondary target and a FRET labeled cleavable sequence, allowing homogeneous detection (i.e., without product separation or other manipulation after the reaction) of the sequential invasive cleavage reaction.

Other preferred embodiments use a secondary reaction system in which the FRET probe and synthetic target are provided as separate oligonucleotides.

In a preferred embodiment, each subsequent reaction is facilitated by (i.e., is dependent upon) the product of the previous cleavage, so that the presence of the ultimate product may serve as an indicator of the presence of the target analyte. However, cleavage in the second reaction need not be dependent upon the presence of the product of the primary cleavage reaction; the product of the primary cleavage reaction may merely measurably enhance the rate of the second cleavage reaction.

In summary, the INVADER assay cascade (i.e., sequential invasive cleavage reactions) of the present invention is a combination of two or more linear assays that allows the accumulation of the ultimate product at an exponential rate, but without significant risk of carryover contamination. It is an important to note that background that does not arise from sequential cleavage, such as thermal breakage of the secondary probe, generally increases linearly with time. In contrast, signal generation from a 2-step sequential reaction follows quadratic kinetics. Thus, collection of data as a time course, either by taking time points or through the use of an instrument that allows real-time detection during the INVADER assay reaction incubations, provides the attractive capability of discriminating between the true signal and any background solely on the basis of quadratic versus linear increases in signal over time. For example, when viewed graphically, the real signal will appear as a quadratic curve, while any accumulating background will be linear, and thus easy to distinguish, even if the absolute level of the background signal (e.g., fluorescence in a FRET detection format) is substantial.

The sequential invasive cleavage amplification of the present invention can be used as an intermediate boost to any of the detection methods (e.g., gel based analysis by either standard or by charge reversal), polymerase tailing, and incorporation into a protein binding region, described herein. When used is such combinations the increased production of a specific cleavage product in the invasive cleavage assay reduces the burdens of sensitivity and specificity on the read-out systems, thus facilitating their use.

In addition to enabling a variety of detection platforms, the cascade strategy is suitable for multiplex analysis of individual analytes (i.e., individual target nucleic acids) in a single reaction. The multiplex format can be categorized into two types. In one case, it is desirable to know the identity (and amount) of each of the analytes that can be present in a clinical sample, or the identity of each of the analytes as well as an internal control. To identify the presence of multiple individual analytes in a single sample, several distinct secondary amplification systems may be included. Each probe cleaved in response to the presence of a particular target sequence (or internal control) can be designed to trigger a different cascade coupled to different detectable moieties, such as different sequences to be extended by DNA polymerase or different dyes in an FRET format. The contribution of each specific target sequence to final product can thereby be tallied, allowing quantitative detection of different genes or alleles in a sample containing a mixture of genes or alleles.

In the second configuration, it is desirable to determine if any of several analytes are present in a sample, but the exact identity of each does not need to be known. For example, in blood banking it is desirable to know if any one of a host of infectious agents is present in a sample of blood. Because the blood is discarded regardless of which agent is present, different signals on the probes would not be required in such an application of the present invention, and may actually be undesirable for reasons of confidentiality. In this case, the 5' arms (i.e., the 5' portion which will be released upon cleavage) of the different analyte-specific probes would be identical and would therefore trigger the same secondary signal cascade. A similar configuration would permit multiple probes complementary to a single gene to be used to boost the signal from that gene or to ensure inclusivity when there are numerous alleles of a gene to be detected.

Figure 100:
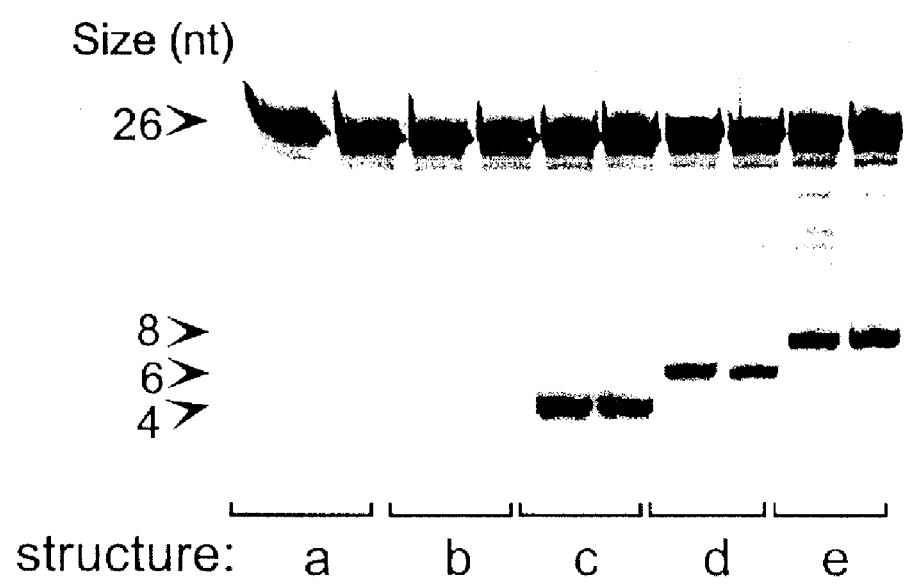
FIG. 100 shows the image generated by a fluorescence imager which shows the dependence of Pfu FEN-1 on the presence of an overlapping upstream oligonucleotide for specific cleavage of the probe.

In the primary INVADER reaction, there are two potential sources of background. The first is from INVADER-independent cleavage of probe annealed to the target, to itself, or to one of the other oligonucleotides present in the reaction. It can be seen by consideration of FIGS. 96 and 97 that the probes of the primary cleavage reactions depicted are designed to have regions of complementarity to the other oligonucleotides involved in the subsequent reactions, and, as depicted in FIG. 97, to other regions of the same molecule. The use of an enzyme that cannot efficiently cleave a structure that lacks a primer (e.g., that cannot cleave the structures diagrammed in FIG. 16A or 16D) is preferred for this reason. As shown in FIGS. 99 and 100, the enzyme Pfu FEN-1 gives no detectable cleavage in the absence of the upstream oligonucleotide or even in the presence of an upstream oligonucleotide that fails to invade the probe-target complex. This indicates that the Pfu FEN-1 endonuclease is a suitable enzyme for use in the methods of the present invention.

Other structure-specific nucleases may be suitable as a well. As discussed in the first example, some 5' nucleases can be used in conditions that significantly reduce this primer-independent cleavage. For example, it has been shown that when the 5' nuclease of DNAPTaq is used to cleave hairpins the primer-independent cleavage is markedly reduced by the inclusion of a monovalent salt in the reaction (Lyamichev, et al., [1993], supra).

Test for INVADER Oligonucleotide-Independent Cleavage

Figure 30:
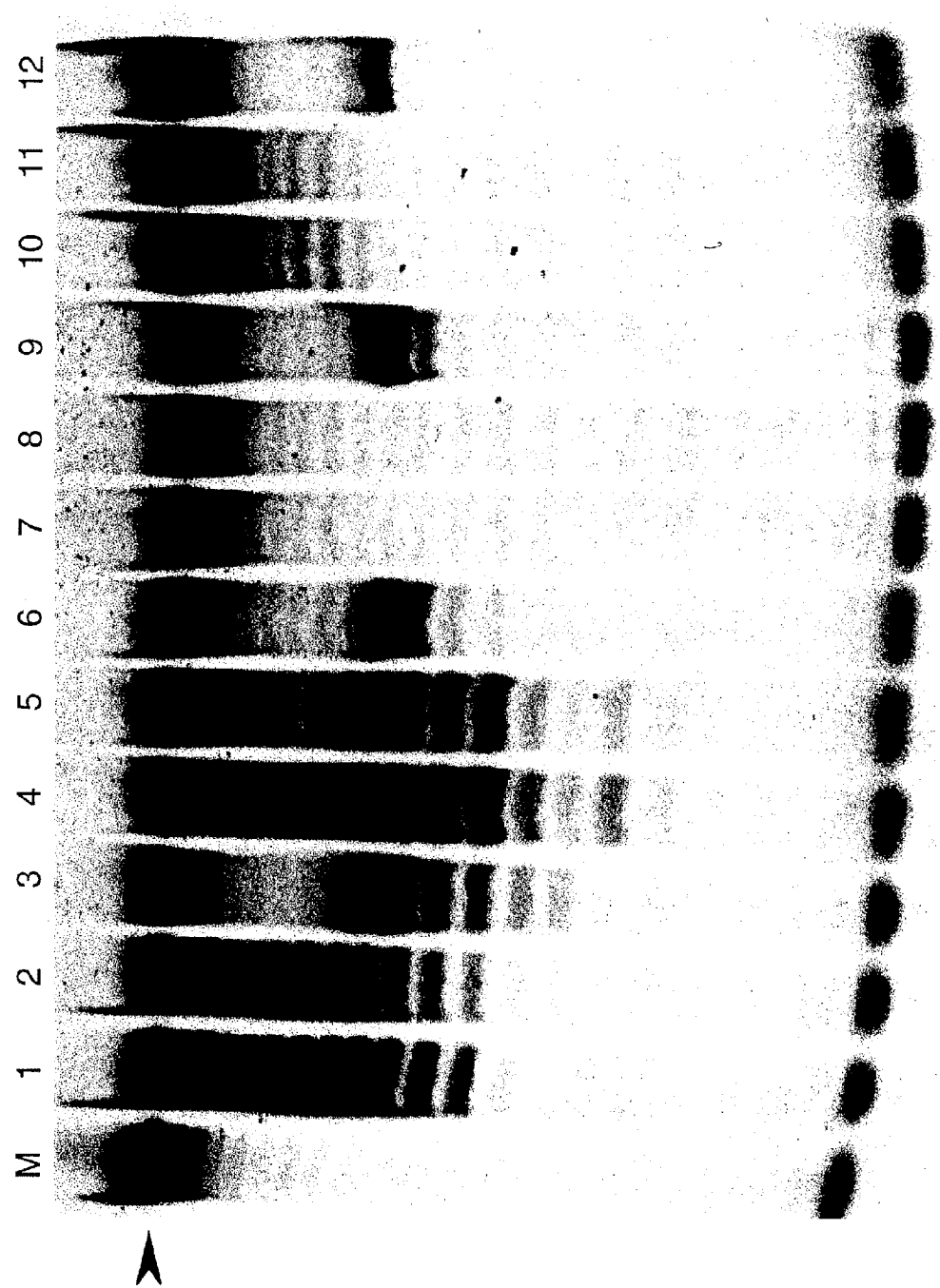
FIG. 30 is the image generated by a fluorescence imager showing the products of INVADER oligonucleotide-directed cleavage assays run using the three target-specific oligonucleotides diagrammed in FIG. 28.

A simple test can be performed for any enzyme in combination with any reaction buffer to gauge the amount of INVADER oligonucleotide-independent cleavage to be expected from that combination. A small hairpin-like test molecule that can be used with or without a primer hybridized to a 3' arm, the S-60 molecule, is depicted in FIG. 30. The S-60 and the oligonucleotide P15 are a convenient set of molecules for testing the suitability of an enzyme for application in the present invention and conditions for using these molecules are described in Example 11. Other similar hairpins may be used. A cleavage structure may be assembled from separate oligonucleotides as diagrammed in FIGS. 99a-e. Reactions using these structures to examine the activity of the Pfu FEN-1 enzyme in the presence or absence of an upstream overlapping oligonucleotide are described in Example 45 and the results are displayed in FIG. 100. To test any particular combination of enzyme and cleavage conditions, similar reactions can be assembled. Outside of the variables of reaction conditions to be tested for any particular enzyme (e.g., salt sensitivities, divalent cation requirements) the test reactions should accommodate any known limitations of the test enzyme. For example, the test reactions should be performed at a temperature that is within the operating temperature range of the candidate enzyme, if known.

Figures 99A, 99B, 99C:
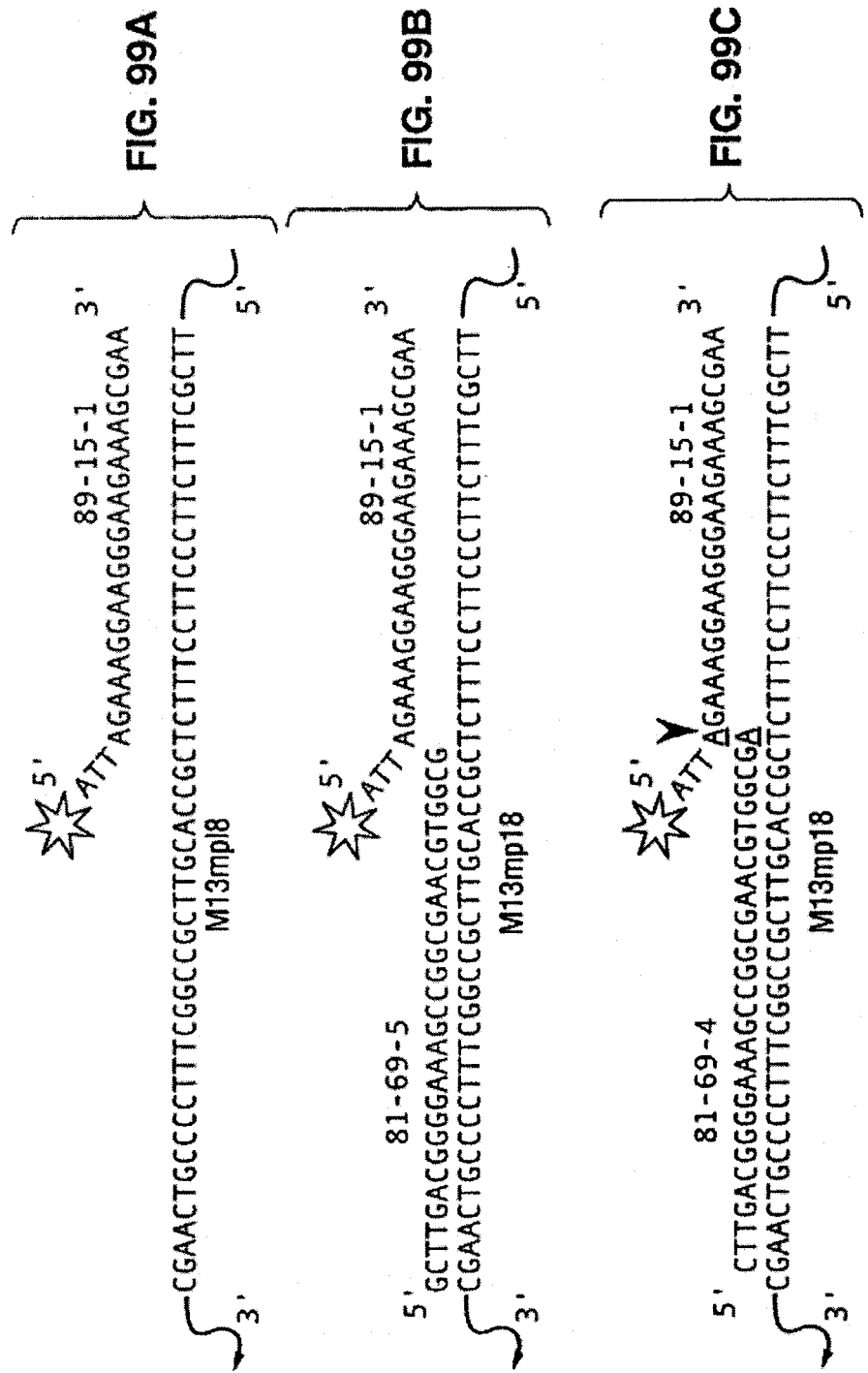
FIG. 99 depicts structures that may be employed to determine the ablity of an enzyme to cleave a probe in the presence and the absence of an upstream oligonucleotide.
Figure 100:
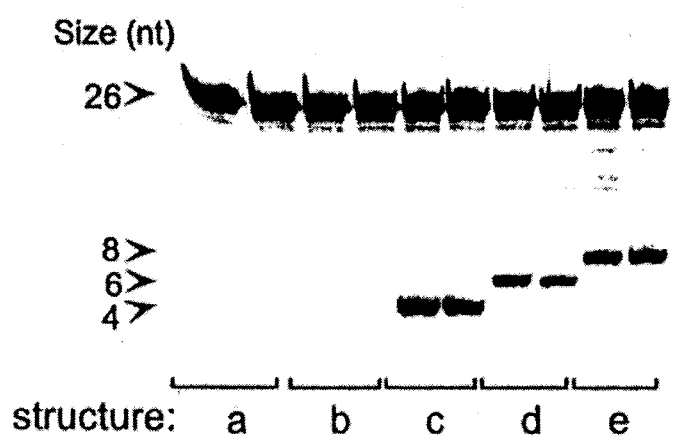
Figure 101A:
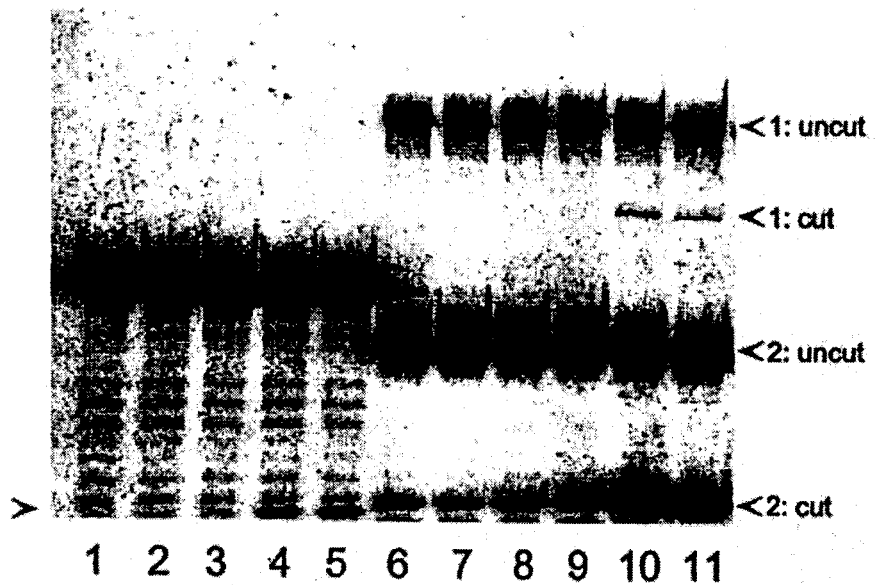
Figure 101B:
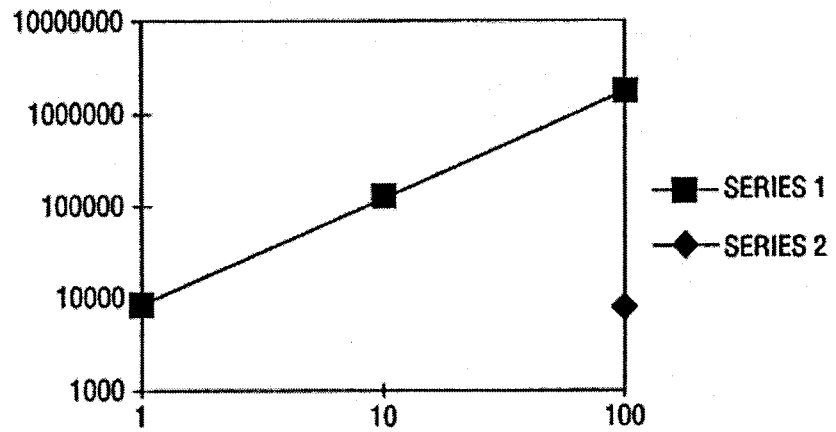

It is not necessary that multiple lengths of overlap be demonstrated for each candidate enzyme, but the activity of the enzyme in the absence of an upstream oligonucleotide (sequence or physical overlap) (as shown in FIG. 99a) and in the presence of an oligonucleotide that does not overlap (FIG. 99b) should be assessed. It is preferable that structures lacking an upstream oligonucleotide be cleaved at less than one half of the rate seen in the presence of an upstream overlapping oligonucleotide. It is more preferable that these structures be cleaved at less than about on tenth the rate of the invasive cleavage structure. It is most preferred that cleavage of these structures occur at less than one percent the rate of the invasive cleavage structure.

If the cleaved product is to serve as an upstream oligonucleotide in a subsequent cleavage reaction, as diagrammed in FIG. 96, the most rapid reaction will be achieved if the other components of the second cleavage structure (i.e., Target 2 and Probe 2 in FIG. 96) are provided in excess compared to the amount of first cleavage product, so that cleavage may proceed immediately after the upstream oligonucleotide (i.e, Cut Probe 1 in FIG. 96) is made available. To provide an abundance of the second target strand or cassette (Target 2 in FIG. 96) one may use an isolated natural nucleic acid, such as bacteriophage M13 DNA, or one may use a synthetic oligonucleotide. If a synthetic oligonucleotide is chosen as the second target sequence, the sequence employed should be examined for regions of unintended self-complementarity (similar considerations apply to short isolated natural nucleic acids such as restriction enzyme fragments or PCR products; natural nucleic acid targets whose 3' end is located $\geqq 100$ nucleotides downstream of the probe binding site on the target strand are generally long enough to obviate the design considerations discussed below). Specifically, it should be determined that the 3' end of the synthetic oligonucleotide may not hybridize to the target strand (i.e., intra-strand hybridization) upstream of the probe, triggering unintended cleavage. Simple examination of the sequence of the synthetic oligonucleotide should reveal if the 3' end has sufficient complementarity to the region of the target upstream of the probe binding site to pose a problem (i.e, it would reveal whether the synthetic oligonucleotide can form a hairpin at its 3' end which could act as an invading oligonucleotide to cause cleavage of the $2^{nd}$ probe in the absence of the hybridization of the intended INVADER oligonucleotide (i.e., the cleavage product from the first invasive cleavage reaction)). If 3 or more of the last 4 to 7 nucleotides (the 3' terminal region) of the synthetic target can basepair upstream of the probe such that there is an overlap with the probe-target duplex, or such that the duplexes formed by the synthetic target strand with its own 3' terminal region and with the probe abut without a gap and the 3' terminal region has an additional 1 or 2 nucleotides unpaired at the extreme 3' end of the synthetic target, then the sequence of the synthetic target oligonucleotide should be modified. The sequence may be changed to disrupt the interaction of the 3' terminal region or to increase the distance between the probe binding site and the regions to which the 3' terminus is binding. Alternatively, the 3' end may be modified to reduce its ability to direct cleavage (e.g., by adding a 3' phosphate during synthesis) (see Ex. 35, Table 3) or by adding several additional nucleotides that will not basepair in a self-complementary manner (i.e., they will not participate in the formation of a hairpin structure).

When the product of a first invasive cleavage reaction is designed to form a target that can fold on itself to direct cleavage of a second probe, the IT complex as diagrammed in FIG. 97, the design of the sequence used to form the stem/loop of the IT complex should be considered. To be factored into the design of such a probe are 1) the length of the region of self-complementarity, 2) the type of overlap (i.e., what 3' moiety) and, if an overlap in sequence is selected, the length of the region of overlap (region "X" in FIG. 25) and 3) the stability of the hairpin or stem/loop structure as predicted by both Watson-Crick base pairing and by the presence or absence of a particularly stable loop sequence (e.g., a tetraloop [Tinoco et al., supra], or a triloop [Hirao et al., supra]). It is desirable that this sequence have nucleotides that can base pair (intrastrand), so that the second round of invasive cleavage may occur, but that the structure not be so strong that its presence will prevent the cleavage of the probe in the primary reaction (i.e., Probe 1 in FIG. 96). As shown herein, the presence of a secondary structure in the 5' arm of a cleavage structure cleaved by a structure-specific nuclease may inhibit cleavage by some structure-specific nucleases (Ex. 1).

The length of the region of self-complementarity within Probe 1 determines the length of the region of the duplex upstream of Probe 2 in the second cleavage structure (see FIG. 97). Different enzymes have different length requirements for this duplex to effect invasive cleavage efficiently. For example, the Pfu FEN-1 and Mja FEN-1 enzymes have been tested for the effect of this duplex length using the set of target/INVADER oligonucleotide molecules depicted in FIG. 98 (i.e., SEQ ID NOS:118, 119, 147-151). The invasive cleavage reactions were performed as described in Example 38, using 1 pM IT3 (SEQ ID NO:118), 2 µM probe PR1 (SEQ ID NO:119) for 5 min, and the rates of cleavage are shown in Table 2.

TABLE 2

| Length of Duplex | Pfu FEN-1 Turnover, per min. | Mja FEN-1 Turnover, per min. |
| --- | --- | --- |
| 0 | 0 | 0 |
| 3 | 1 | 29 |
| 4 | 10 | 57 |
| 6 | 44 | 51 |
| 8 | 45 | 46 |

The data shown in Table 2 demonstrate that the Pfu FEN-1 enzyme can be used with stems of 3 or 4 bases, but that the rate of cleavage is maximized when the stem is greater than 4 basepairs in length. Table 2 shows that the Mja FEN-1 enzyme can cleave efficiently using shorter stems; however, as this enzyme can also cleave a probe in the absence of an upstream oligonucleotide, Mja FEN-1 is not preferred for use in the sequential invasive cleavage methods of the present invention.

A similar test can be performed using any candidate enzyme to determine how much self-complementarity may be designed into the Probe 1. The use of a shorter stem means that the overall probe may be shorter. This is beneficial because shorter probes are less costly to synthesize, and because shorter probes will have fewer sequences that might form unintended intrastrand structures. In assessing the activity of a candidate enzyme on the structures such as those shown in FIG. 98 it is not required that the stem length chosen allow the maximum rate of cleavage to occur. For example, in considering the case of Pfu FEN-1, the advantages of using a 4 basepair stem (e.g., cost or sequence limitations), with a cleavage rate of 10 cleavages per minute, may outweigh the rate advantage of using a longer 6 basepair stem (44 cleavages/min.), in the context of a particular experiment. It is within the scope of the present invention that some elements chosen for use in the assay be sub-optimal for performance of that particular element, if the use of a sub-optimal design benefits the objectives of that particular experiment as a whole.

In designing oligonucleotides to be employed as a probe that, once cleaved, forms a stem-loop structure as diagrammed in FIG. 97 (i.e., Probe 1 in FIG. 97), it has been found that the stability of the loop is not a factor in the efficiency of cleavage of either Probe 1 or Probe 2. Loops tested have included stable triloops, loops of 3 and 4 nucleotides that were not predicted to be particularly stable (i.e., the stability is determined by the duplex sequence and not by additional stabilizing interactions within the loop), and large loops of up to about 25 nucleotides.

IV. Fractionation of Specific Nucleic Acids by Selective Charge Reversal

Some nucleic acid-based detection assays involve the elongation and/or shortening of oligonucleotide probes. For example, as described herein, the primer-directed, primer-independent, and INVADER-directed cleavage assays, as well as the "nibbling" assay all involve the cleavage (i.e., shortening) of oligonucleotides as a means for detecting the presence of a target nucleic sequence. Examples of other detection assays that involve the shortening of an oligonucleotide probe include the "TaqMan" or nick-translation PCR assay described in U.S. Pat. No. 5,210,015 to Gelfand et al. (the disclosure of which is herein incorporated by reference), the assays described in U.S. Pat. Nos. 4,775,619 and 5,118,605 to Urdea (the disclosures of which are herein incorporated by reference), the catalytic hybridization amplification assay described in U.S. Pat. No. 5,403,711 to Walder and Walder (the disclosure of which is herein incorporated by reference), and the cycling probe assay described in U.S. Pat. Nos. 4,876,187 and 5,011,769 to Duck et al. (the disclosures of which are herein incorporated by reference). Examples of detection assays that involve the elongation of an oligonucleotide probe (or primer) include the polymerase chain reaction (PCR) described in U.S. Pat. Nos. 4,683,195 and 4,683,202 to Mullis and Mullis et al. (the disclosures of which are herein incorporated by reference) and the ligase chain reaction (LCR) described in U.S. Pat. Nos. 5,427,930 and 5,494,810 to Birkenmeyer et al. and Barany et al. (the disclosures of which are herein incorporated by reference). The above examples are intended to be illustrative of nucleic acid-based detection assays that involve the elongation and/or shortening of oligonucleotide probes and do not provide an exhaustive list.

Typically, nucleic acid-based detection assays that involve the elongation and/or shortening of oligonucleotide probes require post-reaction analysis to detect the products of the reaction. It is common that the specific reaction product(s) must be separated from the other reaction components, including the input or unreacted oligonucleotide probe. One detection technique involves the electrophoretic separation of the reacted and unreacted oligonucleotide probe. When the assay involves the cleavage or shortening of the probe, the unreacted product will be longer than the reacted or cleaved product. When the assay involves the elongation of the probe (or primer), the reaction products will be greater in length than the input. Gel-based electrophoresis of a sample containing nucleic acid molecules of different lengths separates these fragments primarily on the basis of size. This is due to the fact that in solutions having a neutral or alkaline pH, nucleic acids having widely different sizes (i.e., molecular weights) possess very similar charge-to-mass ratios and do not separate (Andrews, Electrophoresis, 2nd Edition, Oxford University Press (1986), pp. 153-154]. The gel matrix acts as a molecular sieve and allows nucleic acids to be separated on the basis of size and shape (e.g., linear, relaxed circular or covalently closed supercoiled circles).

Unmodified nucleic acids have a net negative charge due to the presence of negatively charged phosphate groups contained within the sugar-phosphate backbone of the nucleic acid. Typically, the sample is applied to gel near the negative pole and the nucleic acid fragments migrate into the gel toward the positive pole with the smallest fragments moving fastest through the gel.

The present invention provides a novel means for fractionating nucleic acid fragments on the basis of charge. This novel separation technique is related to the observation that positively charged adducts can affect the electrophoretic behavior of small oligonucleotides because the charge of the adduct is significant relative to charge of the whole complex. In addition to the use of positively charged adducts (e.g., Cy3 and Cy5 fluorescent dyes, the positively charged heterodimeric DNA-binding dyes shown in FIG. 66, etc.), the oligonucleotide may contain amino acids (particularly useful amino acids are the charged amino acids: lysine, arginine, asparate, glutamate), modified bases, such as amino-modified bases, and/or a phosphonate backbone (at all or a subset of the positions). In other embodiments, as discussed further below, a neutral dye or detection moiety (e.g., biotin, streptavidin, etc.) may be employed in place of a positively charged adduct, in conjunction with the use of amino-modified bases and/or a complete or partial phosphonate backbone.

This observed effect is of particular utility in assays based on the cleavage of DNA molecules. Using the assays described herein as an example, when an oligonucleotide is shortened through the action of a CLEAVASE enzyme or other cleavage agent, the positive charge can be made to not only significantly reduce the net negative charge, but to actually override it, effectively "flipping" the net charge of the labeled entity. This reversal of charge allows the products of target-specific cleavage to be partitioned from uncleaved probe by extremely simple means. For example, the products of cleavage can be made to migrate towards a negative electrode placed at any point in a reaction vessel, for focused detection without gel-based electrophoresis; Example 24 provides examples of devices suitable for focused detection without gel-based electrophoresis. When a slab gel is used, sample wells can be positioned in the center of the gel, so that the cleaved and uncleaved probes can be observed to migrate in opposite directions. Alternatively, a traditional vertical gel can be used, but with the electrodes reversed relative to usual DNA gels (i.e., the positive electrode at the top and the negative electrode at the bottom) so that the cleaved molecules enter the gel, while the uncleaved disperse into the upper reservoir of electrophoresis buffer.

An important benefit of this type of readout is the absolute nature of the partition of products from substrates (i.e., the separation is virtually 100%). This means that an abundance of uncleaved probe can be supplied to drive the hybridization step of the probe-based assay, yet the unconsumed (i.e., unreacted) probe can, in essence, be subtracted from the result to reduce background by virtue of the fact that the unreacted probe will not migrate to the same pole as the specific reaction product.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which lack a 3' phosphate, and the products of thermal degradation, which generally retain a 3' phosphate (and thus two additional negative charges). Examples 22 and 23 demonstrate the ability to separate positively charged reaction products from a net negatively charged substrate oligonucleotide. As discussed in these examples, oligonucleotides may be transformed from net negative to net positively charged compounds. In Example 23, the positively charged dye, Cy3 was incorporated at the 5' end of a 22-mer (SEQ ID NO:50) which also contained two amino-substituted residues at the 5' end of the oligonucleotide; this oligonucleotide probe carries a net negative charge. After cleavage, which occurred 2 nucleotides into the probe, the following labeled oligonucleotide was released: 5'-Cy3-AminoT-AminoT-3' (in addition to unlabeled fragment comprising the remaining 20 nucleotides of SEQ ID NO:50). This short fragment bears a net positive charge while the remainder of the cleaved oligonucleotide and the unreacted or input oligonucleotide bear net negative charges.

Figure 45:
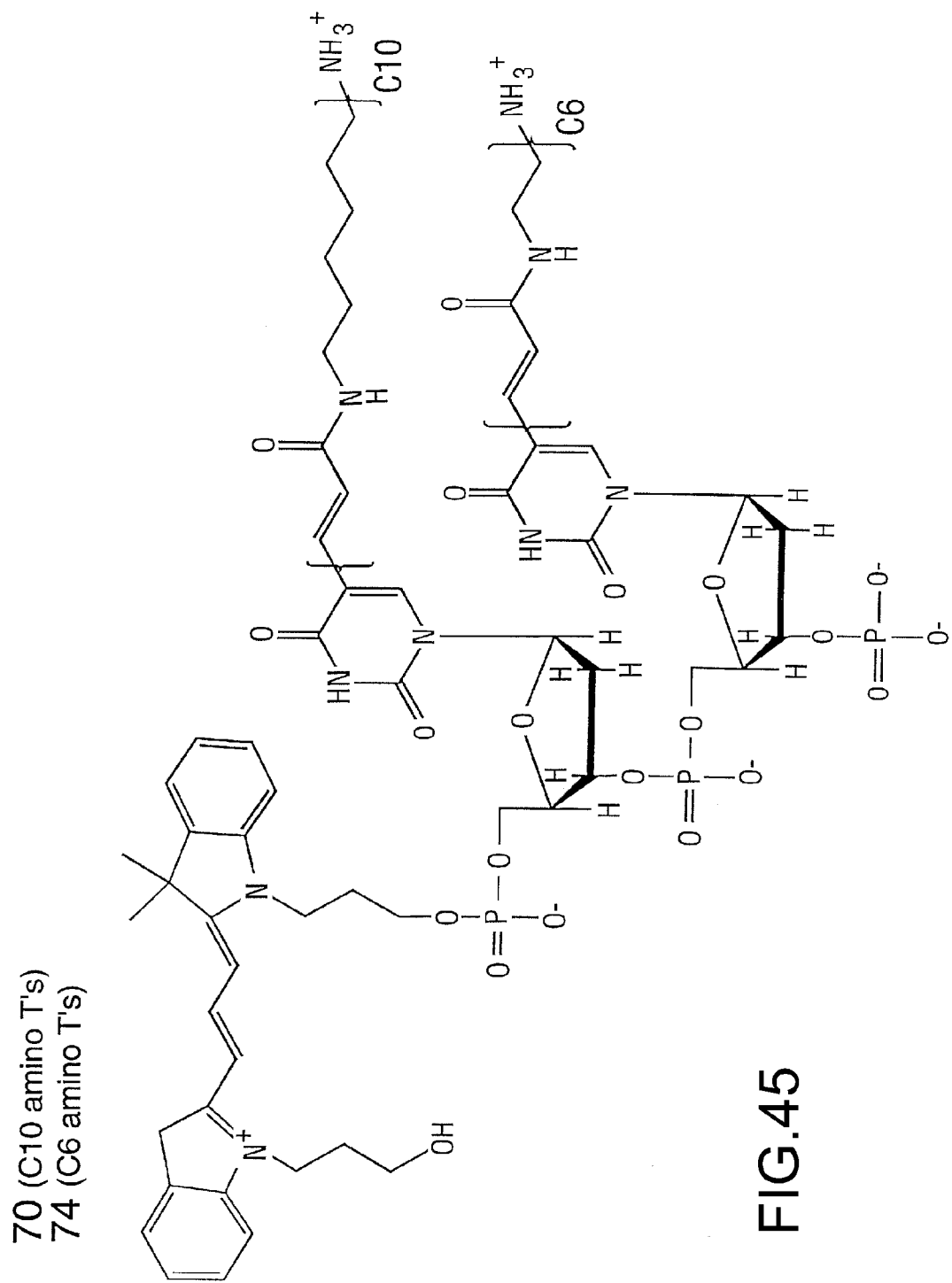
FIG. 45 depicts the structure of amino-modified oligonucleotides 70 and 74.
Figure 46:
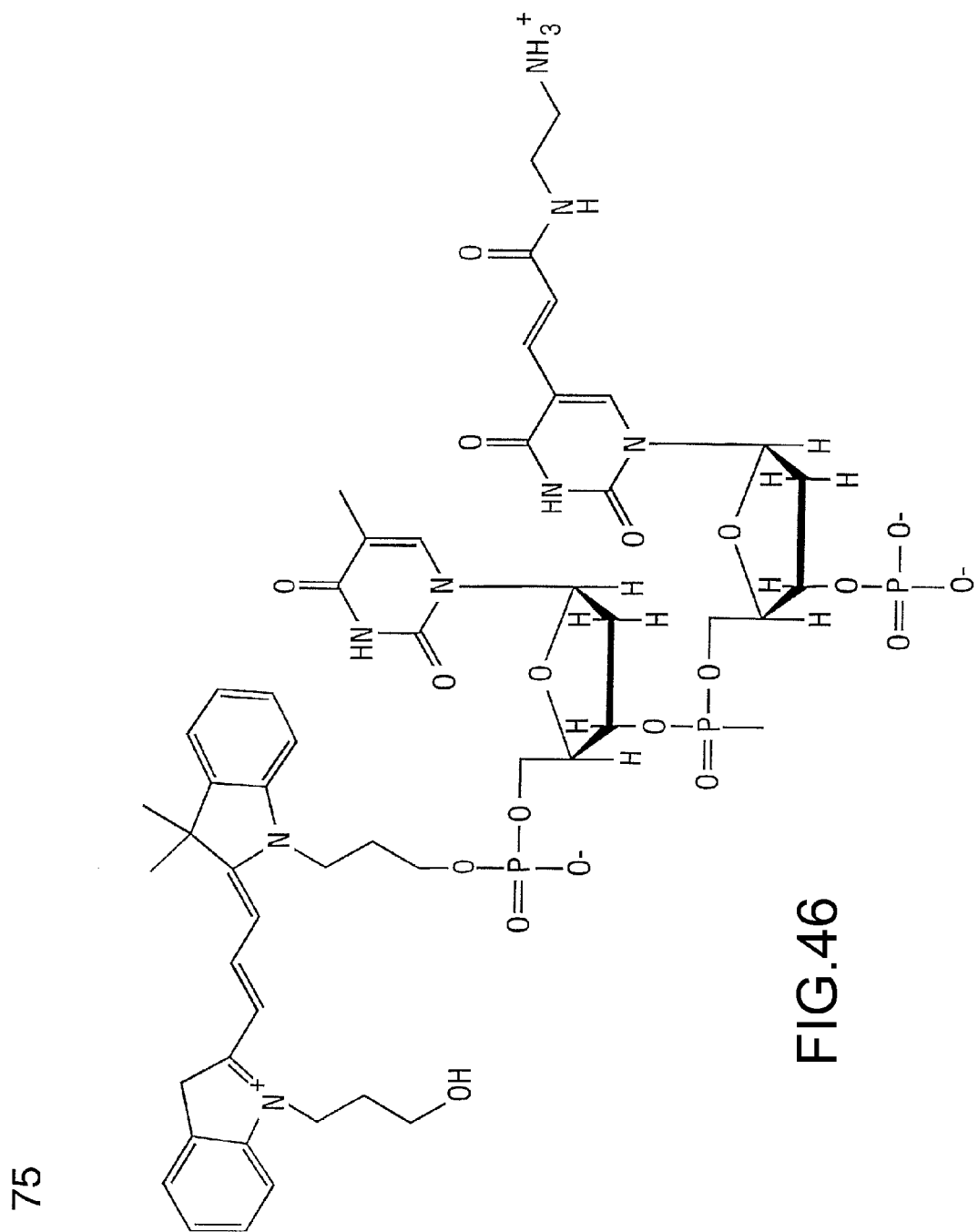
FIG. 46 depicts the structure of amino-modified oligonucleotide 75

The present invention contemplates embodiments wherein the specific reaction product produced by any cleavage of any oligonucleotide can be designed to carry a net positive charge while the unreacted probe is charge neutral or carries a net negative charge. The present invention also contemplates embodiments where the released product may be designed to carry a net negative charge while the input nucleic acid carries a net positive charge. Depending on the length of the released product to be detected, positively charged dyes may be incorporated at the one end of the probe and modified bases may be placed along the oligonucleotide such that upon cleavage, the released fragment containing the positively charged dye carries a net positive charge. Amino-modified bases may be used to balance the charge of the released fragment in cases where the presence of the positively charged adduct (e.g., dye) alone is not sufficient to impart a net positive charge on the released fragment. In addition, the phosphate backbone may be replaced with a phosphonate backbone at a level sufficient to impart a net positive charge (this is particularly useful when the sequence of the oligonucleotide is not amenable to the use of amino-substituted bases); FIGS. 45 and 46 show the structure of short oligonucleotides containing a phosphonate group on the second T residue). An oligonucleotide containing a fully phosphonate-substituted backbone would be charge neutral (absent the presence of modified charged residues bearing a charge or the presence of a charged adduct) due to the absence of the negatively charged phosphate groups. Phosphonate-containing nucleotides (e.g., methylphosphonate-containing nucleotides are readily available and can be incorporated at any position of an oligonucleotide during synthesis using techniques which are well known in the art.

In essence, the invention contemplates the use of charge-based separation to permit the separation of specific reaction products from the input oligonucleotides in nucleic acid-based detection assays. The foundation of this novel separation technique is the design and use of oligonucleotide probes (typically termed "primers" in the case of PCR) which are "charge balanced" so that upon either cleavage or elongation of the probe it becomes "charge unbalanced," and the specific reaction products may be separated from the input reactants on the basis of the net charge.

In the context of assays that involve the elongation of an oligonucleotide probe (i.e., a primer), such as is the case in PCR, the input primers are designed to carry a net positive charge. Elongation of the short oligonucleotide primer during polymerization will generate PCR products that now carry a net negative charge. The specific reaction products may then easily be separated and concentrated away from the input primers using the charge-based separation technique described herein (the electrodes will be reversed relative to the description in Example 23 as the product to be separated and concentrated after a PCR will carry a negative charge).

V. Signal Enhancement by Tailing of Reaction Products in the INVADER Oligonucleotide-Directed Cleavage Assay It has been determined that when oligonucleotide probes are used in cleavage detection assays at elevated temperature, some fraction of the truncated probes will have been shortened by nonspecific thermal degradation, and that such breakage products can make the analysis of the target-specific cleavage data more difficult. The thermal degradation that creates a background ladder of bands when the probes of the present invention are treated at high temperature for more than a few minutes occurs as a two step process. In the first step the N-glycosyl bond breaks, leaving an abasic site in the DNA strand. At the abasic site the DNA chain is weakened and undergoes spontaneous cleavage through a beta-elimination process. It has been determined that purine bases are about 20 times more prone to breakage than pyrimidine bases (Lindahl, Nature 362:709 [1993]). This suggests that one way of reducing background in methods using oligonucleotides at elevated temperatures is to select target sequences that allow the use of pyrimidine-rich probes. It is preferable, where possible, to use oligonucleotides that are entirely composed of pyrimidine residues. If only one or a few purines are used, the background breakage will appear primarily at the corresponding sites, and these bands (due to thermal breakdown) may be mistaken for the intended cleavage products if care is not taken in the data analysis (i.e., proper controls must be run).

Background cleavage due to thermal breakdown of probe oligonucleotides can, when not resolved from specific cleavage products, reduce the accuracy of quantitation of target nucleic acids based on the amount of accumulated product in a set timeframe. One means of distinguishing the specific from the nonspecific products is disclosed above, and is based on partitioning the products of these reactions by differences in the net charges carried by the different molecular species in the reaction. As was noted in that discussion, the thermal breakage products usually retain 3' phosphates after breakage, while the enzyme-cleaved products do not. The two negative charges on the phosphate facilitate charge-based partition of the products.

The absence of a 3' phosphate on the desired subset of the probe fragments may be used to advantage in enzymatic assays as well. Nucleic acid polymerases, both non-templated (e.g., terminal deoxynucleotidyl transferase, polyA polymerase) and template-dependent (e.g., Pol 1-type DNA polymerases), require an available 3' hydroxyl by which to attach further nucleotides. This enzymatic selection of 3' end structure may be used as an effective means of partitioning specific from non-specific products.

In addition to the benefits of the partitioning described above, the addition of nucleotides to the end of the specific product of an INVADER oligonucleotide-specific cleavage offers an opportunity to either add label to the products, to add capturable tails to facilitate solid-support based readout systems, or to do both of these things at the same time. Some possible embodiments of this concept are illustrated in FIG. 56.

Figure 56:
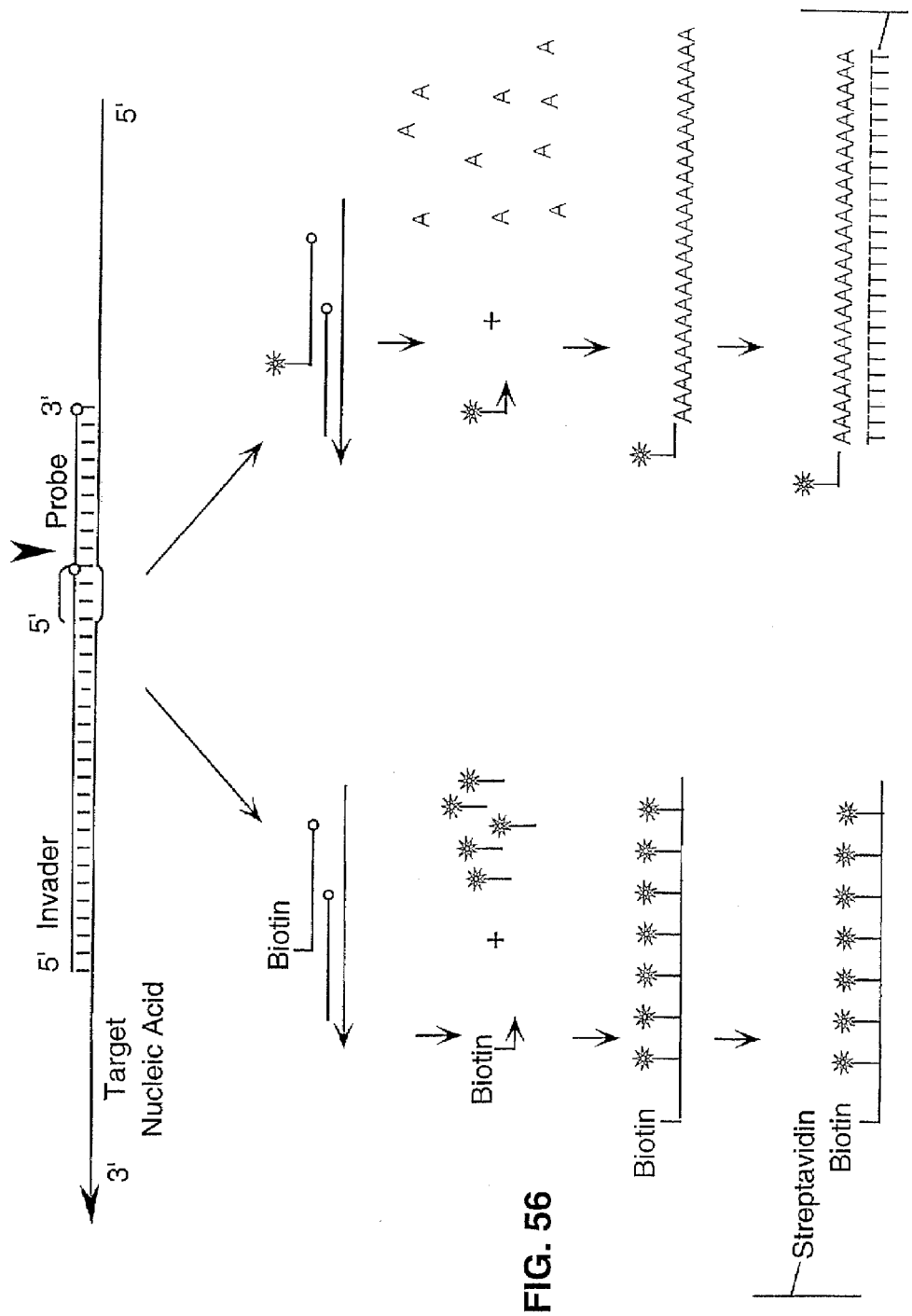
FIG. 56 is a schematic showing alternative methods for the tailing and detection of specific cleavage products in the context of the INVADER oligonucleotide-directed cleavage assay.

In FIG. 56, an INVADER cleavage structure comprising an INVADER oligonucleotide containing a blocked or non-extendible 3' end (e.g., a 3' dideoxynucleotide) and a probe oligonucleotide containing a blocked or non-extendable 3' end (the open circle at the 3' end of the oligonucleotides represents a non-extendible nucleotide) and a target nucleic acid is shown; the probe oligonucleotide may contain a 5' end label such as a biotin or a fluorescein (indicated by the stars) label (cleavage structures which employ a 5' biotin-labeled probe or a 5' fluorescein-labeled probe are shown below the large diagram of the cleavage structure to the left and the right, respectively). Following cleavage of the probe (the site of cleavage is indicated by the large arrowhead), the cleaved biotin-labeled probe is extended using a template-independent polymerase (e.g., TdT) and fluoresceinated nucleotide triphosphates. The fluorescein tailed cleaved probe molecule is then captured by binding via its 5' biotin label to streptavidin and the fluorescence is then measured. Alternatively, following, cleavage of a 5'-fluoresceinated probe, the cleaved probe is extended using a template-independent polymerase (e.g., TdT) and dATP. The polyadenylated (A-tailed) cleaved probe molecule is then captured by binding via the polyA tail to oligo dT attached to a solid support.

The examples described in FIG. 56 are based on the use of TdT to tail the specific products of INVADER-directed cleavage. The description of the use of this particular enzyme is presented by way of example and is not intended as a limitation (indeed, when probe oligonucleotides comprising RNA are employed, cleaved RNA probes may be extended using polyA polymerase). It is contemplated that an assay of this type can be configured to use a template-dependent polymerase, as described above. While this would require the presence of a suitable copy template distinct from the target nucleic acid, on which the truncated oligonucleotide could prime synthesis, it can be envisaged that a probe that before cleavage would be unextendible, due to either mismatch or modification of the 3' end, could be activated as a primer when cleaved by an INVADER oligonucleotide-directed cleavage. A template directed tailing reaction also has the advantage of allowing greater selection and control of the nucleotides incorporated.

The use of nontemplated tailing does not require the presence of any additional nucleic acids in the detection reaction, avoiding one step of assay development and troubleshooting. In addition, the use of non-templated synthesis eliminated the step of hybridization, potentially speeding up the assay. Furthermore, the TdT enzyme is fast, able to add at least >700 nucleotides to substrate oligonucleotides in a 15 minute reaction.

As mentioned above, the tails added can be used in a number of ways. It can be used as a straight-forward way of adding labeled moieties to the cleavage product to increase signal from each cleavage event. Such a reaction is depicted in the left side of FIG. 66. The labeled moieties may be anything that can, when attached to a nucleotide, be added by the tailing enzyme, such as dye molecules, haptens such as digoxigenin, or other binding groups such as biotin.

In a preferred embodiment the assay includes a means of specifically capturing or partitioning the tailed INVADER oligonucleotide-directed cleavage products in the mixture. It can be seen that target nucleic acids in the mixture may be tailed during the reaction. If a label is added, it is desirable to partition the tailed INVADER oligonucleotide-directed cleavage products from these other labeled molecules to avoid background in the results. This is easily done if only the cleavage product is capable of being captured. For example, consider a cleavage assay of the present invention in which the probe used has a biotin on the 5' end and is blocked from extension on the 3' end, and in which a dye is added during tailing. Consider further that the products are to be captured onto a support via the biotin moiety, and the captured dye measured to assess the presence of the target nucleic acid. When the label is added by tailing, only the specifically cleaved probes will be labeled. The residual uncut probes can still bind in the final capture step, but they will not contribute to the signal. In the same reaction, nicks and cuts in the target nucleic acid may be tailed by the enzyme, and thus become dye labeled. In the final capture these labeled targets will not bind to the support and thus, although labeled, they will not contribute to the signal. If the final specific product is considered to consist of two portions, the probe-derived portion and the tail portion, it can be seen from this discussion that it is particularly preferred that, when the probe-derived portion is used for specific capture, whether by hybridization, biotin/ streptavidin, or other method, that the label be associated with the tail portion. Conversely, if a label is attached to the probe-derived portion, then the tail portion may be made suitable for capture, as depicted on the right side of FIG. 66. Tails may be captured in a number of ways, including hybridization, biotin incorporation with streptavidin capture, or by virtue if the fact that the longer molecules bind more predictably and efficiently to a number of nucleic acid minding matrices, such as nitrocellulose, nylon, or glass, in membrane, paper, resin, or other form. While not required for this assay, this separation of functions allows effective exclusion from signal of both unreacted probe and tailed target nucleic acid.

In addition to the supports described above, the tailed products may be captured onto any support that contains a suitable capture moiety. For example, biotinylated products are generally captured with avidin-treated surfaces. These avidin surfaces may be in microtitre plate wells, on beads, on dipsticks, to name just a few of the possibilities. Such surfaces can also be modified to contain specific oligonucleotides, allowing capture of product by hybridization. Capture surfaces as described herein are generally known to those skilled in the art and include nitrocellulose dipsticks (e.g., GENECOMB, BioRad, Hercules, Calif.).

VI. Signal Enhancement by Completion of an Activated Protein Binding Site

In addition to the DNA polymerase tailing reaction described above, the present invention also contemplates the use of the products of the invasive cleavage reaction to form activated protein binding sites, such as RNA polymerase promoter duplexes, thereby allowing the interaction of the completed site to be used as an indicator of the presence of the nucleic acid that is the target of the invasive cleavage reaction. By way of example, when an RNA polymerase promoter duplex is activated by being made complete (i.e., double-stranded over that portion of the promoter region required for polymerase binding) through the hybridization of the oligonucleotide product of the invasive cleavage reaction, the synthesis of RNA can be used as such an indicator.

It is not intended that the transcription reaction of the present invention be limited to the use of any particular RNA polymerase or RNA polymerase promoter region. Promoter sequences are well characterized for several bacteriophage, including bacteriophage SP6, T7 and T3. In addition, promoter sequences have been well characterized for a number of both eukaryotic and prokaryotic RNA polymerases. In a preferred embodiment, the promoter used enables transcription from one of the bacteriophage RNA polymerases. In a particularly preferred embodiment, the promoter used enables transcription by T7 RNA polymerase. Means of performing transcription in vitro are well known in the art and commercial kits are available for performing transcription with eukaryotic, prokaryotic or bacteriophage RNA polymerases (e.g., from Promega Corp., Madison, Wis.).

The protein binding regions of the present invention are not limited to the bacteriophage RNA polymerase promoters described above. Other promoter sequences that are contemplated are those of prokaryotes and eukaryotes. For example, many strains of bacteria and fungi are used for the expression of heterologous proteins. The minimal promoters required for transcription by the RNA polymerases of organisms such as yeast and other fungi, eubacteria, nematodes, and cultured mammalian cells are well described in the literature and in the catalogs of commercial suppliers of DNA vectors for the expression of foreign proteins in these organisms.

The binding sites for other types of nucleic acid (e.g., DNA) binding proteins are contemplated for use in the present invention. For example, proteins involved in the regulation of genes exert their effects by binding to the DNA in the vicinity of the promoter from which the RNA from that gene is transcribed. The lac operator of E. coli is one example of a particularly well characterized and commonly used gene regulation system in which the lac repressor protein binds to specific sequences that overlap, and thus block, the promoter for the genes under the repressor's control (Jacob and Monod, Cold Spring Harbor Symposium on Quantitative Biol. XXVI: 193-211 [1961]). Many similar systems have been described in bacteria, including the trp and AraC regulatory systems. Given the large amount of information available about bacterial promoters, the steps described below for the design of suitable partial promoters for the bacteriophage RNA polymerases can be readily adapted to the design of detection systems based on these other promoters.

As noted above, many of the bacterial promoters are under the control of a repressor or other regulatory protein. It is considered to be within the scope of the present invention to include the creation of composite binding sites for these regulatory proteins through the provision of a nucleic acid fragment (e.g., a non-target cleavage product generated in an invasive cleavage reaction). The binding of the regulatory protein to the completed protein binding region (e.g., the composite binding region) can be assessed by any one of a number of means, including slowed electrophoretic migration of either the protein or the DNA fragment, or by a conformational change in the protein or DNA upon binding. In addition, transcription from a downstream promoter can be monitored for up- or down-regulation as a result of the binding of the regulatory protein to the completed protein binding region.

In addition to the bacterial systems described above, many genes in eukaryotic systems have also been found to be under the control of specific proteins that bind to specific regions of duplex DNA. Examples include, but are not limited to, the OCT-1, OCT-2 and AP-4 proteins in mammals and the GAL4 and GCN4 proteins in yeast. Such regulatory proteins usually have a structural motif associated with duplex nucleic acid binding, such as a helix-turn-helix, a zinc finger or a leucine zipper [for review, see, *Molecular and Cellular Biology*, Wolfe (Ed.), Wadsworth Publishing Co., Belmont, Calif., pp. 694-715 [1993]).

For simplicity the test reaction described here will refer to T7 RNA polymerase, and its promoter. This is not intended to limit the invention to the use of this RNA polymerase, and those skilled in the art of molecular biology would be able to readily adapt this described test to the examination of any of the DNA binding proteins, RNA polymerases and their binding or promoter sites discussed above.

Figure 88A:
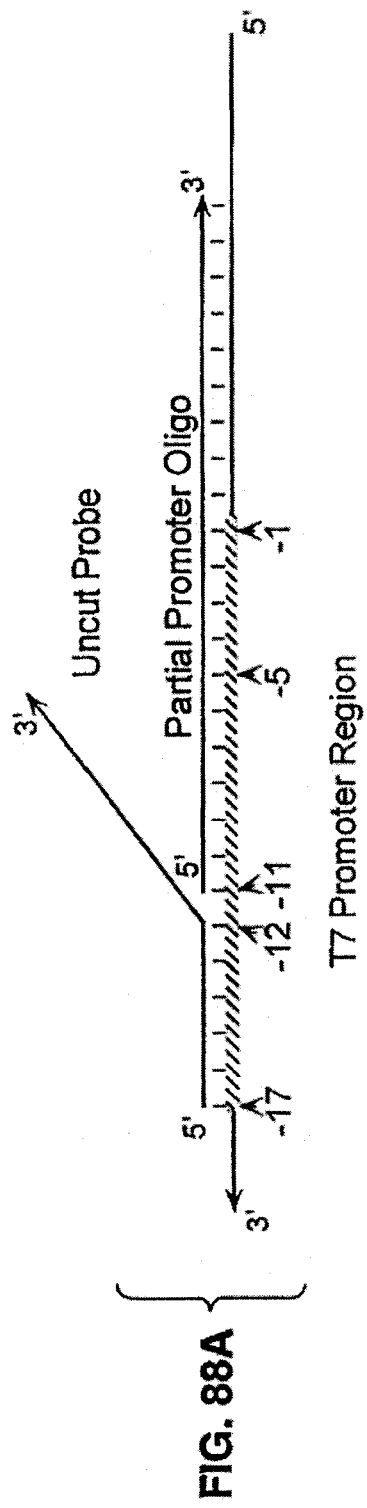
FIG. 88 provides a schematic illustrating that an uncut probe combined with a partial promoter oligonucleotide does not permit transcription while a cut probe combined with a partial promoter oligonucleotide generates a complete (but nicked) promoter which supports transcription.
Figure 88B:
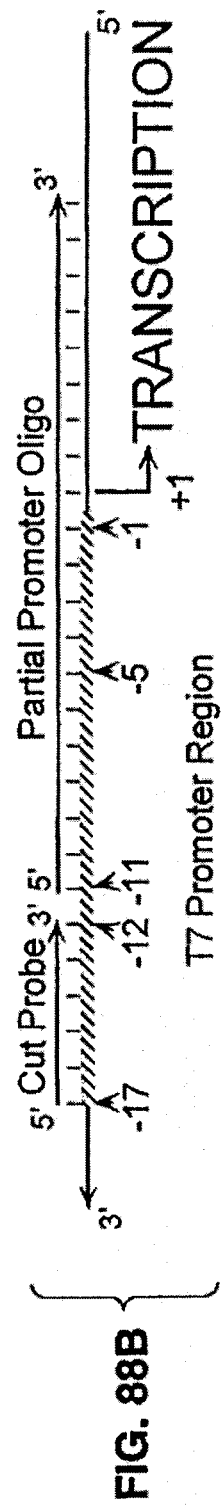
Figure 89:
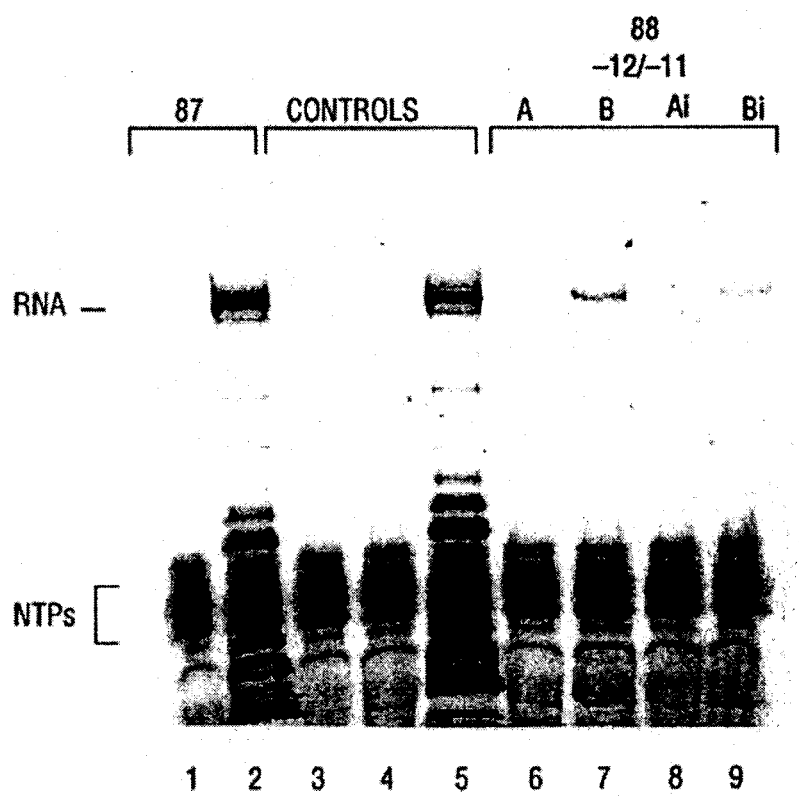
Figure 91:
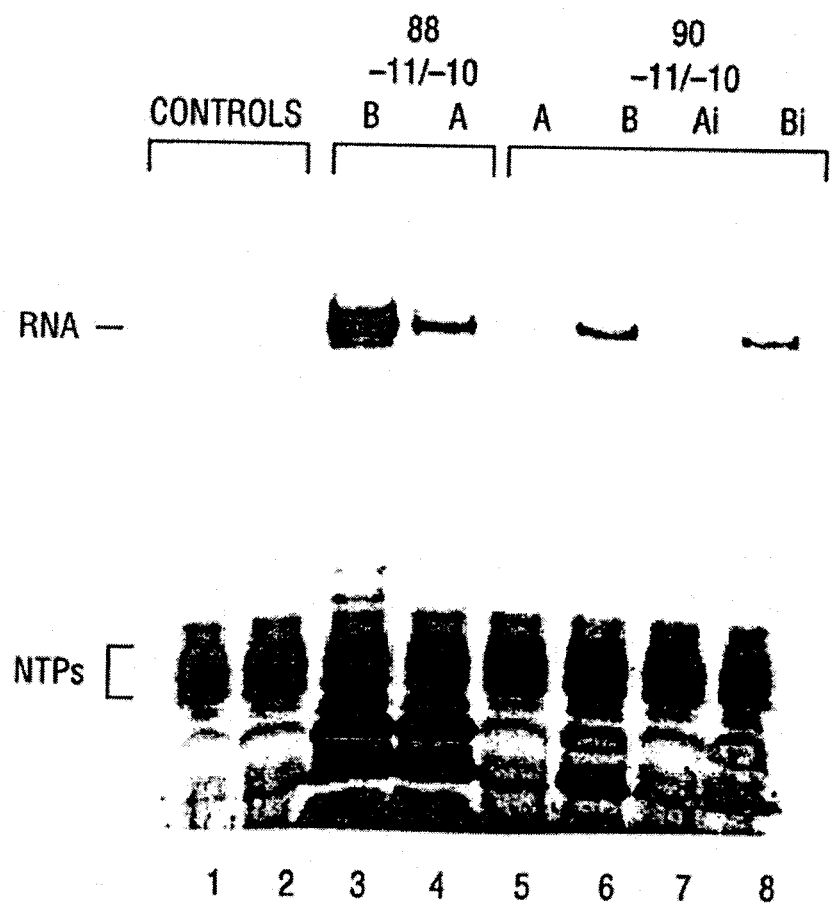
Figure 92:
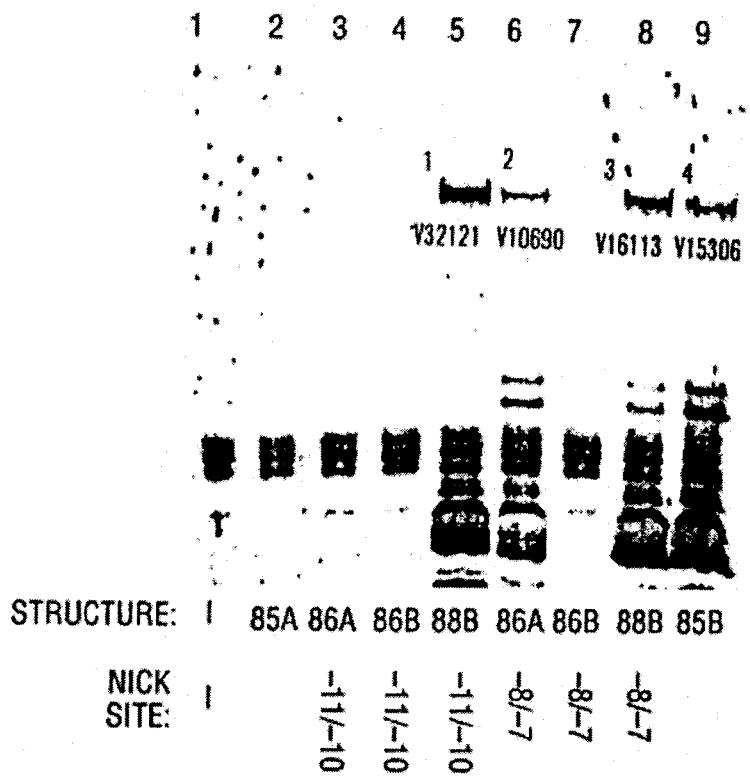

It is known in the art that active T7 promoters can be formed by the hybridization of two oligonucleotides, each comprising either the top or bottom strand of the promoter sequence, such that a complete un-nicked duplex promoter is formed (Milligan et al., Nucl. Acids Res., 15:21, 8783-8798 (1987)]. The present invention shows that one way of making the initiation of transcription dependent on the products of an invasive cleavage reaction is to design the probe for the cleavage reaction such that a portion of an RNA polymerase promoter is released as product. The remaining DNA piece or pieces required to assemble a promoter duplex may either be provided as elements in the reaction mixture, or they may be produced by other invasive cleavage events. If the oligonucleotide pieces are designed to comprise appropriate regions of complementarity they may base pair to form a complete promoter duplex composed of three or more nucleic acid fragments, as depicted in FIG. 88B. A promoter assembled in this way will have nicks in the backbone of one or both strands. In one embodiment, these nicks may be covalently closed through the use of a DNA ligase enzyme. In a preferred embodiment, the nicks are positioned such that transcription can proceed without ligation. In selecting the site of a nick created by the assembly of the partial promoter fragment, at least one nick should be within the recognized promoter region for the RNA polymerase to be used. When a bacteriophage promoter is used, a nick should be between nucleotides −17 and −1, measured from the site of transcription initiation at +1. In a preferred embodiment, a nick will be between nucleotides −13 and −8. In a particularly preferred embodiment, a nick will be between nucleotides −12 and −10 on the non-template strand of the bacteriophage promoter.

When nicks are to be left unrepaired (i.e., not covalently closed with a DNA ligase) it is important to assess the effect of the nick location on the level of transcription from the assembled promoter. A simple test is to combine the oligonucleotides that comprise the separate portions of the promoter with an oligonucleotide that comprises one entire strand of the promoter to be assembled, thereby forming a duplex promoter with a nick in one strand. If the nick is in the top, or non-template strand of the promoter, then the oligonucleotide that comprises the complete promoter is made to include additional non-promoter sequence on its 5' end to serve as a template to be copied in the transcription. This arrangement is depicted in FIG. 88B. Alternatively, if the nick is to be in the bottom, or template strand of the promoter, then the partial promoter oligonucleotide that covers the +1 position, the transcription start site, will include the additional template sequence. This arrangement is depicted in FIGS. 95A-D (this Figure shows several different embodiments in which a cut probe or non-target cleavage product is used to form a composite promoter which contains one or more nicks on the template strand). In either case, the separate oligonucleotides are combined to form the complete promoter, and the assembly is used in a transcription reaction to create RNA.

To measure the effect of the nick, a substantially identical promoter fragment is created by hybridization of two oligonucleotides that each comprise one strand of the full-length promoter to create an un-nicked version of the same promoter. These two molecular assemblies are tested in parallel transcription reactions and the amount of the expected RNA that is produced in each reaction is measured for both size and yield. A preferred method of assessing the size of the RNA is by electrophoresis with subsequent visualization. If a labeled nucleotide (e.g., $^{32}$P-GTP, or fluorescein-UTP) is used in the transcription, the RNA can be detected and quantitated by autoradiography, fluorescence imaging or by transfer to support membrane with subsequent detection (e.g., by antibody or hybridization probing). Alternatively, if unlabeled RNA is produced the amounts may be determined by other methods known in the art, such as by spectrophotometry or by electrophoresis with subsequent staining and comparison to known standards.

If the size of the RNA is as predicted by the template sequence, or if it matches that produced from the control promoter, it can be presumed to have initiated transcription at the same site in the complex, and to have produced essentially the same RNA product. If the product is much shorter then transcription is either initiating at an internal site or is terminating prematurely (Schenborn and Mierendorf, Nucl. Acids Res., 13:17, 6223 [1985]; and Milligan et al., supra.). While this does not indicate that the assembly tested is completely unsuitable for the assay, the partial transcripts will reduce the gross amount of RNA created, perhaps compromising the signal from the assay, and such products would require further characterization (e.g., finger printing or sequencing) to identify the nucleotide content of the product. It is preferred that the size of the RNA produced matches that of the RNA produced in the control reaction.

The yield of the reaction is also examined. It is not necessary that the level of transcription matches that of the control reaction. In some instances (see Ex. 41, below) the nicked promoter may have an enhanced rate of transcription, while in other arrangements transcription may be reduced (relative to the rate from the un-nicked promoter assembly). It is only required that the amount of product be within the detection limits of the method to be used with the test promoter.

It is reported that transcription from a bacteriophage promoter can produce 200 to 1000 copies of each transcription template (template plus active promoter) in a reaction. These levels of transcription are not required by the present invention. Reactions in which one RNA is produced for each template are also contemplated.

The test described above will allow a promoter with a nick in any position to be assessed for utility in this assay. It is an objective of this invention to provide one or more of the oligonucleotides that comprise a partial promoter region through invasive cleavage event(s). In this embodiment, the partial promoter sequences are attached to the probe oligonucleotide in the invasive cleavage assay, and are released by cleavage at specific site, as directed by the INVADER oligonucleotide. It is also intended that transcription be very poor or nonexistent in the absence of the correctly cleaved probe. To assess the success of any oligonucleotide design at meeting these objectives, several transcription reaction tests can be performed.

Figure 85A:
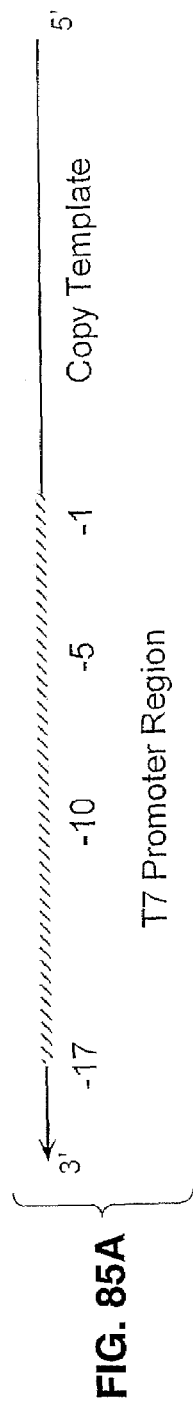
FIGS. 85A-C provide schematics showing particular embodiments of the present invention wherein a T7 promoter region and copy template annealed with either no oligonucleotide (A), a complete promoter oligonucleotide (B) or a complete promoter oligonucleotide with a 3' tail (C); one strand of the T7 promoter region is indicated by the hatched line.
Figure 85B:
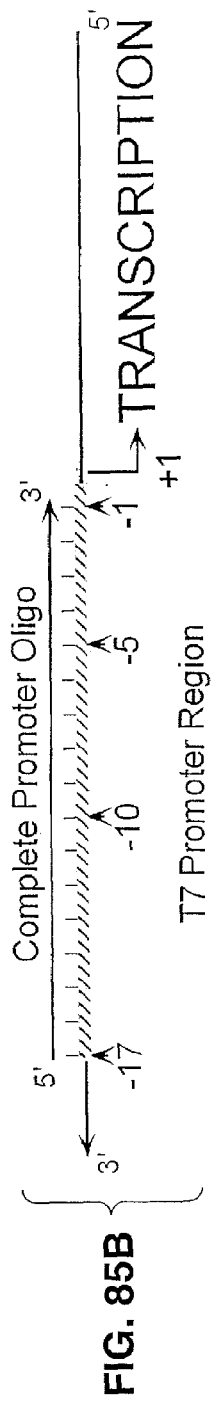
Figure 86A:
FIGS. 86A-D provide schematics showing particular embodiments of the present invention wherein a T7 promoter region and copy template annealed with either a cut probe (A), a partial promoter oligonucleotide (B), an uncut oligonucleotide (C) or both an uncut probe and a partial promoter oligonucleotide (D).

For a promoter assembly that will have a nick on the non-template strand, several partial assemblies that should be tested are shown in FIGS. 86A-D. By way of example, but not by way of limitation, this Figure depicts the tests for a nicked promoter in which the upstream, or 5' portion of the non-template strand is to be provided by the invasive cleavage assay. This fragment is seen in FIG. 86A labeled as "cut probe". Transcription reactions incubated in the presence of the duplex shown in FIG. 86A will test the ability of the upstream partial promoter to allow initiation of transcription when hybridized to a bottom strand, termed a "copy template." Similarly, a reaction performed in the presence of the duplex depicted in FIG. 86B will test the ability of the partial promoter fragment nearest the initiation site (the +1 site, as indicated in FIG. 85B) to support transcription of the copy template. It is an important feature of the present invention that neither of these partial promoter duplexes be able to support transcription at the same level as would by seen in transcription from an intact promoter as depicted in FIG. 85B. It is preferred that neither of these partial promoters be sufficient to initiate detectable transcription in the time course of an average transcription reaction (i.e., within about an hour of incubation).

Figure 86B:
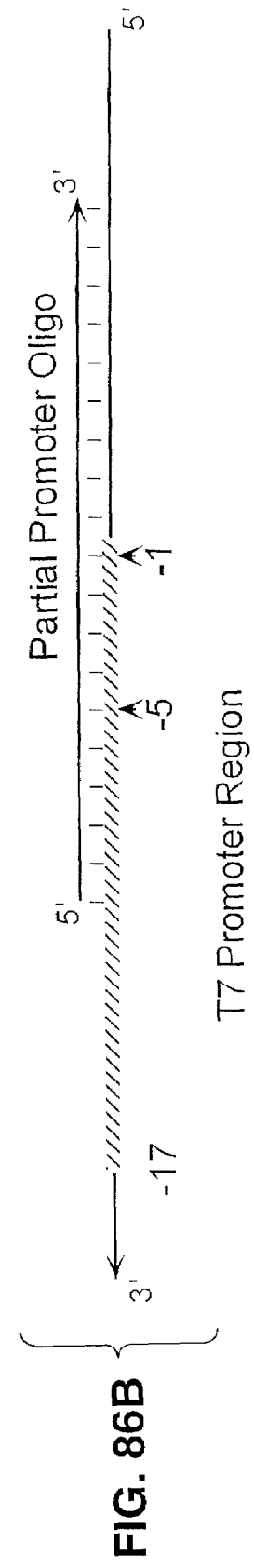
Figure 86C:
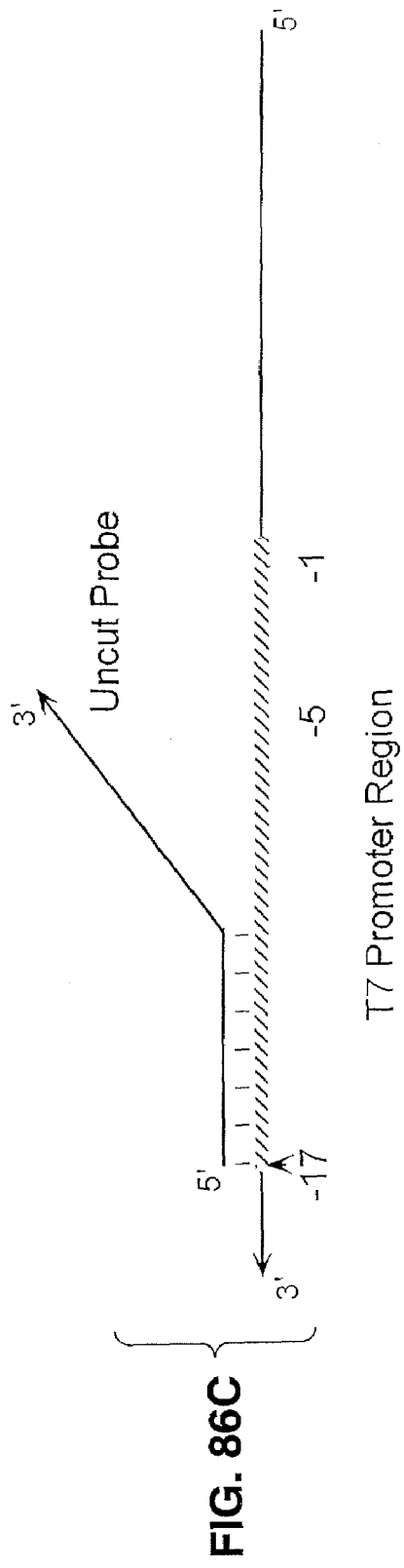
Figure 86D:
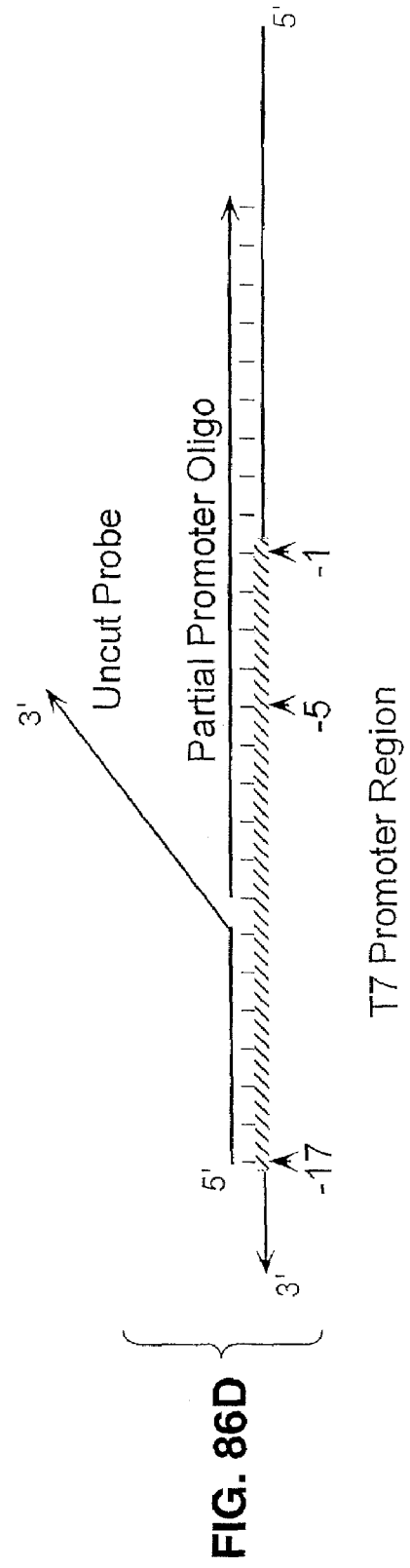

FIGS. 86C and 86D depict two other duplex arrangements designed to test the effect of uncut probe within the transcription reaction. FIG. 86C depicts the duplex formed between only the uncut probe and the copy template, while FIG. 86D includes the other portion of the promoter. The 3' region of the probe is not complementary to the promoter sequence and therefore produces an unpaired branch in the middle of the promoter. It is an important feature of the present invention that neither of these branched promoter duplexes be able to support transcription at the same level as would by seen in transcription from an intact promoter as depicted in FIG. 85B. It is preferred that neither of these branched promoters be sufficient to initiate detectable transcription in the time course of an average transcription reaction (i.e., within about an hour of incubation).

Figure 90A:
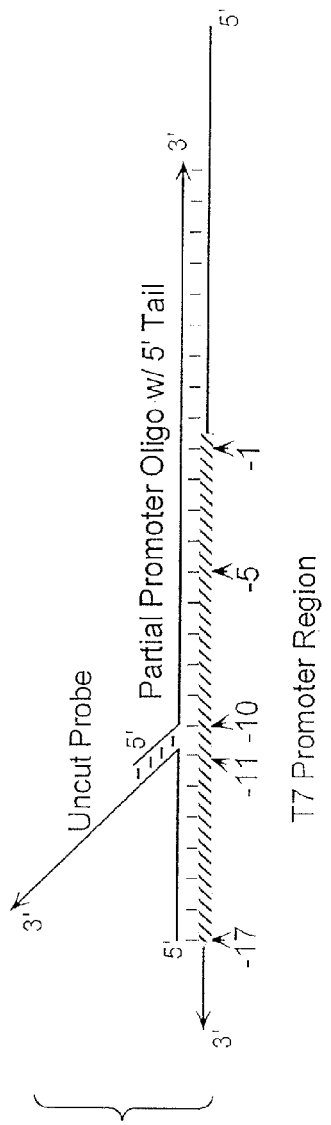
FIGS. 90A-C provide schematics showing particular embodiments of the present invention which illustrate that the use of a partial promoter oligonucleotide with a paired 5' tail can be used to block transcription from a composite promoter formed by the annealing of an uncut probe.
Figure 90B:
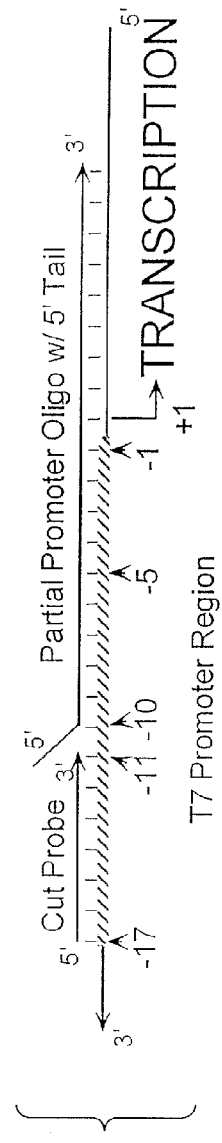
Figure 90C:
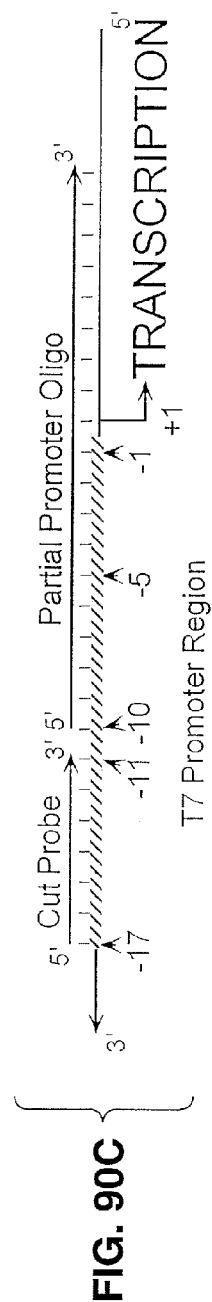

In one embodiment of the transcription system of the present invention, the initiation of transcription from the copy template in the absence of a complete promoter, or in the presence of a branched promoter, is prevented by the judicious placement of the nick or nicks in the composite promoter. For example, as shown in the examples below, placement of a nick between the −12 and −11 nucleotides of the non-template strand of the bacteriophage T7 promoter allows transcription to take place only when the probe has been successfully cut, as in an invasive cleavage reaction. However, in some instances where the invasive cleavage reaction is to provide the upstream portion of the non-template strand of the promoter (e.g., as depicted in FIG. 88B) it may be necessary or desirable to place the nick on that strand in a particular position for reasons other than providing an optimal composite promoter (i.e., one that is inactive in the absence of any one of the promoter pieces). It may be necessary or desirable to place the nick in such a way that the creation of a branched complete promoter (FIG. 86D) has an undesirable level of transcription, reducing dependence of RNA production on the success of the invasive cleavage step. It is shown in the examples below that transcription from such a branched promoter can be suppressed by a modification of the downstream non-template promoter piece, shown as the "Partial Promoter Oligonucleotide" in FIGS. 86, 88, 90 and 95D. As depicted in FIG. 90, the partial promoter oligonucleotide can be provided with a 5' "tail" of nucleotides that are not complementary to the template strand of the promoter, but that are complementary to the 3' portion of the probe oligonucleotide that would be removed in the invasive cleavage reaction. When uncut probe hybridizes to the copy template with the bound 5' tailed partial promoter oligonucleotide, the 5' tail can basepair to the 3' region of the probe, forming a three-way junction as depicted in FIG. 90A. This can effectively shut off transcription, as shown below. When a cut probe hybridizes, as shown in FIG. 90B, a promoter with a small branch is formed, and it is shown herein that such a branched promoter can initiate transcription. Furthermore, if care is taken in selecting the sequence of the 5' tail (i.e., if the first unpaired base is the same nucleotide at the 3' nucleotide of the cut probe, so that they compete for hybridization to the same template strand base), the resulting branched structure may also be cleaved by one of the structure specific nucleases of the present invention, creating the un-branched promoter depicted in FIG. 90C, in some instances enhancing transcription over that seen with the FIG. 90B promoter.

The promoter duplex that is intended to be created, in this embodiment, by the successful execution of the INVADER directed cleavage assay will include both the "cut probe" and the partial promoter oligonucleotide depicted in FIGS. 86A and B, aligned on a single copy template nucleic acid. The testing of the efficiency of transcription of such a nicked promoter segment in comparison to the intact promoter is described above. All of the oligonucleotides described for these test molecules may be created using standard synthesis chemistries.

Figure 94:
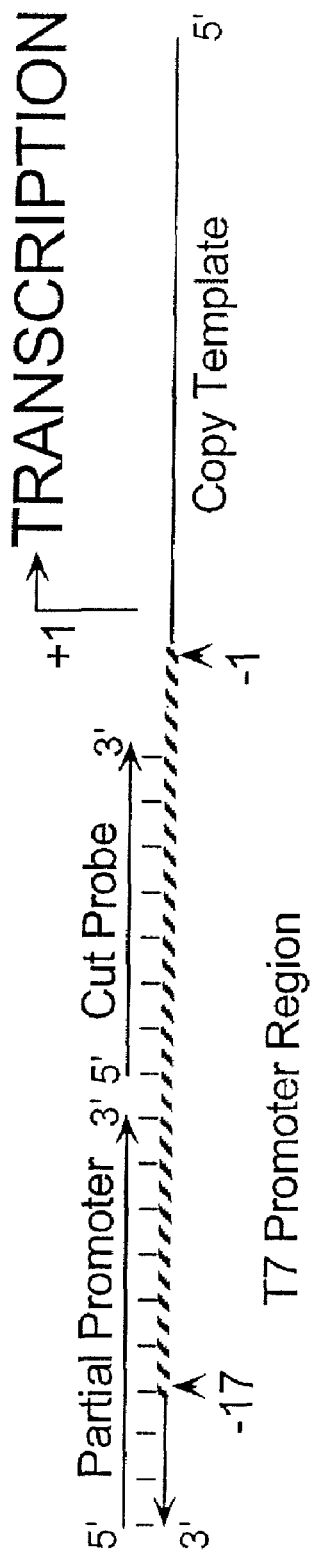
FIG. 94 is a schematic which illustrates one embodiment of the present invention where a composite T7 promoter region is created by the binding of the cut probe oligonucleotide downstream of the partial promoter oligo.

The set of test molecules depicted in FIG. 86 is designed to assess the transcription capabilities of the variety of structures that may be present in reactions in which the 5' portion of the non-template strand of the promoter is to be supplied by the INVADER directed cleavage. It is also envisioned that a different portion of partial promoter may be supplied by the invasive cleavage reaction (e.g., the downstream segment of the non-template strand of the promoter), as is shown in FIG. 94. Portions of the template strand of the promoter may also be provided by the cut probe, as shown in FIGS. 95A-D. An analogous set of test molecules, including "cut" and uncut versions of the probe to be used in the invasive cleavage assay may be created to test any alternative design, whether the nick is to be located on the template or non template strand of the promoter.

The transcription-based visualization methods of the present invention may also be used in a multiplex fashion. Reactions can be constructed such that the presence of one particular target leads to transcription from one type of promoter, while the presence of a different target sequence (e.g., a mutant or variant) or another target suspected of being present, may lead to transcription from a different (i.e., a second) type of promoter. In such an embodiment, the identity of the promoter from which transcription was initiated could be deduced from the type or size of the RNA produced.

By way of example, but not by way of limitation, the bacteriophage promoters can be compared with such an application in view. The promoters for the phage T7, T3 and SP6 are quite similar, each being about 15 to 20 basepairs long, and sharing about 45% identity between −17 and −1 nucleotides, relative to the start of transcription. Despite these similarities, the RNA polymerases from these phage are highly specific for their cognate promoters, such that the other promoters may be present in a reaction, but will not be transcribed (Chamberlin and Ryan, Enzymes XV: 87-108 [1982]). Because these promoters are similar in size and in the way in which they are recognized by their polymerases (Li et al., Biochem. 35:3722 [1996]) similar nicked versions of the promoters may be designed for use in the methods of the present invention by analogy to the examples described herein which employ the T7 promoter. Because of the high degree of specificity of the RNA polymerases, these nicked promoters may be used together to detect multiple targets in a single reaction. There are many instances in which it would be highly desirable to detect multiple nucleic acid targets in a single sample, including cases in which multiple infectious agents may be present, or in which variants of a single type of target may need to be identified. Alternatively, it is often desirable to use a combination of probes to detect both a target sequence and an internal control sequence, to gauge the effects of sample contaminants on the output of the assay. The use of multiple promoters allows the reaction to be assessed for both the efficiency of the invasive cleavage and the robustness of the transcription.

As stated above, the phage promoters were described in detail as an example of suitable protein binding regions (e.g., which can be used to generate a composite promoter) for use in the methods of the present invention. The invention is not limited to the use of phage RNA polymerase promoter regions, in particular, and RNA polymerase promoter regions, in general. Suitably specific, well characterized promoters are also found in both prokaryotic and eukaryotic systems.

The RNA that is produced in a manner that is dependent of the successful detection of the target nucleic acid in the invasive cleavage reaction may be detected in any of several ways. If a labeled nucleotide is incorporated into the RNA during transcription, the RNA may be detected directly after fractionation (e.g., by electrophoresis or chromatography). The labeled RNA may also be captured onto a solid support, such as a microtitre plate, a bead or a dipstick (e.g., by hybridization, antibody capture, or through an affinity interaction such as that between biotin and avidin). Capture may facilitate the measuring of incorporated label, or it may be an intermediate step before probe hybridization or similar detection means. If the maximum amount of label is desired to be incorporated into each transcript, it is preferred that the copy template be very long, around 3 to 10 kilobases, so that each RNA molecule will carry many labels. Alternatively, it may be desired that a single site or a limited number of sites within the transcript be specifically labeled. In this case, it may be desirable to have a short copy template with only one or a few residues that would allow incorporation of the labeled nucleotide.

The copy template may also be selected to produce RNAs that perform specified functions. In a simple case, if an duplex-dependent intercalating fluorophore is to be used to detect the RNA product, it may be desirable to transcribe an RNA that is known to form duplexed secondary structures, such as a ribosomal RNA or a tRNA. In another embodiment, the RNA may be designed to interact specifically, or with particular affinity, with a different substance. It has been shown that a process of alternating steps of selection (e.g., by binding to a target substance) and in vitro amplification (e.g., by PCR) can be used to identify nucleic acid ligands with novel and useful properties (Tuerk and Gold, Science 249: 505 [1990]). This system has been used to identify RNAs, termed ligands or aptamers, that bind tightly and specifically to proteins and to other types of molecules, such as antibiotics (Wang et al, Biochem. 35:12338 [1996]) and hormones. RNAs can even be selected to bind to other RNAs through non-Watson-Crick interactions (Schmidt et al., Ann. N.Y. Acad. Sci. 782:526 [1996]). A ligand RNA may be used to either inactivate or enhance the activity of a molecule to which it binds. Any RNA segment identified through such a process may also be produced by the methods of the present invention, so that the observation of the activity of the RNA ligand may be used as a specific sign of the presence of the target material in the invasive cleavage reaction. The ligand binding to its specific partner may also be used as another way of capturing a readout signal to a solid support.

The product RNA might also be designed to have a catalytic function (e.g., to act as a ribozyme), allowing cleavage another molecule to be indicative of the success of the primary invasive cleavage reaction (Uhlenbeck, Nature 328:596 [1987]). In yet another embodiment, the RNA may be made to encode a peptide sequence. When coupled to an in vitro translation system (e.g., the S-30 system derived from E. coli [Lesley, Methods Mol. Biol., 37:265 (1985)], or a rabbit reticulocyte lysate system [Dasso and Jackson, Nucleic Acids Res. 17:3129 (1989)], available from Promega), the production of the appropriate protein may be detected. In a preferred embodiment, the proteins produced include those that allow either calorimetric or luminescent detection, such as beta-galactosidase (lac-Z) or luciferase, respectively.

The above discussion focused on the use of the present transcription visualization methods in the context of the INVADER-directed cleavage assay (i.e., the non-target cleavage products produced in the INVADER assay were used to complete and activate a protein binding region, such as a promoter region). However, the transcription visualization methods are not limited to this context. Any assay that produces an oligonucleotide product having relatively discrete ends can be used in conjunction with the present transcription visualization methods. For example, the homogenous assay described in U.S. Pat. No. 5,210,015, particularly when conducted under conditions where polymerization cannot occur, produces short oligonucleotide fragments as the result of cleavage of a probe. If this assay is conducted under conditions where polymerization occurs, the site of cleavage of the probe may be focused through the use of nucleotide analogs that have uncleavable linkages at particular positions within the probe. These short oligonucleotides can be employed in a manner analogous to the cut probe or non-target cleavage products produced in the invasive cleavage reactions of the present invention. Additional assays that generate suitable oligonucleotide products are known to the art. For example, the non-target cleavage products produced in assays such as the "Cycling Probe Reaction" (Duck et al., BioTech., 9:142 [1990] and U.S. Pat. Nos. 4,876,187 and 5,011,769, herein incorporated by reference), in which shorter oligonucleotides are released from longer oligonucleotides after hybridization to a target sequence would be suitable, as would short restriction fragments released in assays where a probe is designed to be cleaved when successfully hybridized to an appropriate restriction recognition sequence (U.S. Pat. No. 4,683,194, herein incorporated by reference).

Figure 95A:
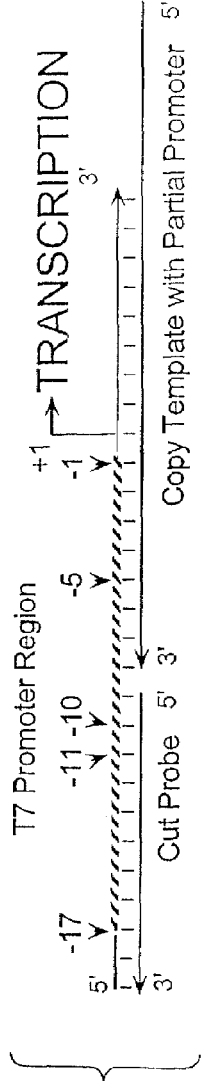
FIGS. 95A-D provide schematics showing particular embodiments of the present invention which show various ways in which a composite promoter can be formed wherein the nick is located in the template (or bottom) strand.
Figure 95B:
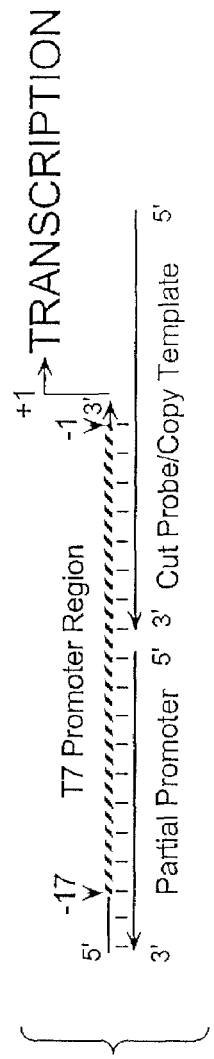
Figure 95C:
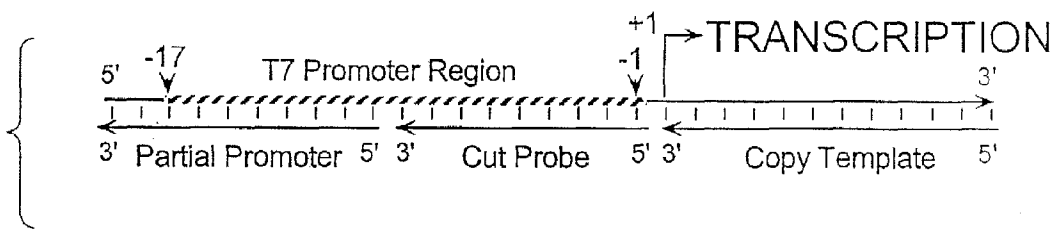
Figure 95D:
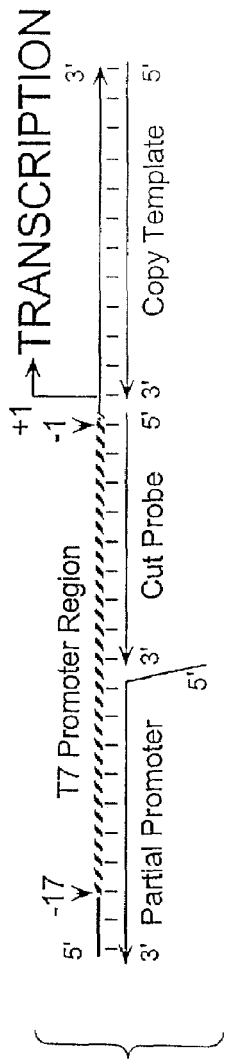

Assays that generate short oligonucleotides having "ragged" (i.e., not discrete) 3' ends can also be employed with success in the transcription reactions of the present invention when the oligonucleotide provided by this non-transcription reaction are used to provide a portion of the promoter region located downstream of the other oligonucleotide(s) that are required to complete the promoter region (that is a 3' tail or unpaired extension can be tolerated when the oligonucleotide is being used as the "Cut Probe" is in FIGS. 94 and 95A).

VII. Generation of 5' Nucleases Derived from Thermostable DNA Polymerases

The 5' nucleases of the invention form the basis of a novel detection assay for the identification of specific nucleic acid sequences. FIG. 1A provides a schematic of one embodiment of the detection method of the present invention. The target sequence is recognized by two distinct oligonucleotides in the triggering or trigger reaction. In a preferred embodiment, one of these oligonucleotides is provided on a solid support. The other can be provided free in solution. In FIG. 1A the free oligonucleotide is indicated as a "primer" and the other oligonucleotide is shown attached to a bead designated as type 1. The target nucleic acid aligns the two oligonucleotides for specific cleavage of the 5' arm (of the oligonucleotide on bead 1) by the 5' nucleases of the present invention (not shown in FIG. 1A). The site of cleavage (indicated by a large solid arrowhead) is controlled by the position of the 3' end of the "primer" relative to the downstream fork of the oligonucleotide on bead 1.

Successful cleavage releases a single copy of what is referred to as the alpha signal oligonucleotide. This oligonucleotide may contain a detectable moiety (e.g., fluorescein) . On the other hand, it may be unlabeled.

In one embodiment of the detection method, two more oligonucleotides are provided on solid supports. The oligonucleotide shown in FIG. 1A on bead 2 has a region that is complementary to the alpha signal oligonucleotide (indicated as alpha prime) allowing for hybridization. This structure can be cleaved by the 5' nucleases of the present invention to release the beta signal oligonucleotide. The beta signal oligonucleotide can then hybridize to type 3 beads having an oligonucleotide with a complementary region (indicated as beta prime). Again, this structure can be cleaved by the 5' nucleases of the present invention to release a new alpha oligonucleotide.

Up to this point, the amplification has been linear. To increase the power of the method, it is desired that the alpha signal oligonucleotide hybridized to bead type 2 be liberated after release of the beta oligonucleotide so that it may go on to hybridize with other oligonucleotides on type 2 beads. Similarly, after release of an alpha oligonucleotide from type 3 beads, it is desired that the beta oligonucleotide be liberated.

With the liberation of signal oligonucleotides by such techniques, each cleavage results in a doubling of the number of signal oligonucleotides. In this manner, detectable signal can quickly be achieved.

FIG. 1B provides a schematic of a second embodiment of the detection method of the present invention. Again, the target sequence is recognized by two distinct oligonucleotides in the triggering or trigger reaction and the target nucleic acid aligns the two oligonucleotides for specific cleavage of the 5' arm by the DNAPs of the present invention (not shown in FIG. 1B). In this specific example, the first oligonucleotide is completely complementary to a portion of the target sequence. The second oligonucleotide is partially complementary to the target sequence; the 3' end of the second oligonucleotide is fully complementary to the target sequence while the 5' end is non-complementary and forms a single-stranded arm. The non-complementary end of the second oligonucleotide may be a generic sequence that can be used with a set of standard hairpin structures (described below). The detection of different target sequences would require unique portions of two oligonucleotides: the entire first oligonucleotide and the 3' end of the second oligonucleotide. The 5' arm of the second oligonucleotide can be invariant or generic in sequence.

The second part of the detection method allows the annealing of the fragment of the second oligonucleotide liberated by the cleavage of the first cleavage structure formed in the triggering reaction (called the third or trigger oligonucleotide) to a first hairpin structure. This first hairpin structure has a single-stranded 5' arm and a single-stranded 3' arm. The third oligonucleotide triggers the cleavage of this first hairpin structure by annealing to the 3' arm of the hairpin thereby forming a substrate for cleavage by the 5' nuclease of the present invention. The cleavage of this first hairpin structure generates two reaction products: 1) the cleaved 5' arm of the hairpin called the fourth oligonucleotide, and 2) the cleaved hairpin structure that now lacks the 5' arm and is smaller in size than the uncleaved hairpin. This cleaved first hairpin may be used as a detection molecule to indicate that cleavage directed by the trigger or third oligonucleotide occurred. Thus, this indicates that the first two oligonucleotides found and annealed to the target sequence thereby indicating the presence of the target sequence in the sample.

The detection products may be amplified by having the fourth oligonucleotide anneal to a second hairpin structure. This hairpin structure has a 5' single-stranded arm and a 3' single-stranded arm. The fourth oligonucleotide generated by cleavage of the first hairpin structure anneals to the 3' arm of the second hairpin structure thereby creating a third cleavage structure recognized by the 5' nuclease. The cleavage of this second hairpin structure also generates two reaction products: 1) the cleaved 5' arm of the hairpin called the fifth oligonucleotide, and 2) the cleaved second hairpin structure which now lacks the 5' arm and is smaller in size than the uncleaved hairpin. In one embodiment, the fifth oligonucleotide is similar or identical in sequence to the third nucleotide. The cleaved second hairpin may be viewed as a detection molecule that amplifies the signal generated by the cleavage of the first hairpin structure. Simultaneously with the annealing of the forth oligonucleotide, the third oligonucleotide is dissociated from the cleaved first hairpin molecule so that it is free to anneal to a new copy of the first hairpin structure. The disassociation of the oligonucleotides from the hairpin structures may be accomplished by heating or other means suitable to disrupt base-pairing interactions. As described above, conditions may be selected that allow the association and disassociation of hybridized oligonucleotides without temperature cycling.

If fifth oligonucleotide is similar or identical in sequence to the third oligonucleotide, further amplification of the detection signal is achieved by annealing the fifth oligonucleotide to another molecule of the first hairpin structure. Cleavage is then performed and the oligonucleotide that is liberated then is annealed to another molecule of the second hairpin structure. Successive rounds of annealing and cleavage of the first and second hairpin structures, provided in excess, are performed to generate a sufficient amount of cleaved hairpin products to be detected.

As discussed above for other embodiments of detection using structure-specific nuclease cleavage, any method known in the art for analysis of nucleic acids, nucleic acid fragments or oligonucleotides may be applied to the detection of these cleavage products.

The hairpin structures may be attached to a solid support, such as an agarose, styrene or magnetic bead, via the 3' end of the hairpin. A spacer molecule may be placed between the 3' end of the hairpin and the bead, if so desired. The advantage of attaching the hairpin structures to a solid support is that this prevents the hybridization of the two hairpin structures to one another over regions which are complementary. If the hairpin structures anneal to one another, this would reduce the amount of hairpins available for hybridization to the primers released during the cleavage reactions. If the hairpin structures are attached to a solid support, then additional methods of detection of the products of the cleavage reaction may be employed. These methods include, but are not limited to, the measurement of the released single-stranded 5' arm when the 5' arm contains a label at the 5' terminus. This label may be radioactive, fluorescent, biotinylated, etc. If the hairpin structure is not cleaved, the 5' label will remain attached to the solid support. If cleavage occurs, the 5' label will be released from the solid support.

The 3' end of the hairpin molecule may be blocked through the use of dideoxynucleotides. A 3' terminus containing a dideoxynucleotide is unavailable to participate in reactions with certain DNA modifying enzymes, such as terminal transferase. Cleavage of the hairpin having a 3' terminal dideoxynucleotide generates a new, unblocked 3' terminus at the site of cleavage. This new 3' end has a free hydroxyl group that can interact with terminal transferase thus providing another means of detecting the cleavage products.

The hairpin structures are designed so that their self-complementary regions are very short (generally in the range of 3-8 base pairs). Thus, the hairpin structures are not stable at the high temperatures at which this reaction is performed (generally in the range of 50-75° C.) unless the hairpin is stabilized by the presence of the annealed oligonucleotide on the 3' arm of the hairpin. This instability prevents the polymerase from cleaving the hairpin structure in the absence of an associated primer thereby preventing false positive results due to non-oligonucleotide directed cleavage.

VIII. Improved Enzymes for Use in INVADER Oligonucleotide-Directed Cleavage Reactions A cleavage structure is defined herein as a structure that is formed by the interaction of a probe oligonucleotide and a target nucleic acid to form a duplex, the resulting structure being cleavable by a cleavage agent, including but not limited to an enzyme. The cleavage structure is further defined as a substrate for specific cleavage by the cleavage means in contrast to a nucleic acid molecule that is a substrate for nonspecific cleavage by agents such as phosphodiesterases. Examples of some possible cleavage structures are shown in FIG. 15. In considering improvements to enzymatic cleavage agents, one may consider the action of said enzymes on any of these structures, and on any other structures that fall within the definition of a cleavage structure. The cleavage sites indicated on the structures in FIG. 15 are presented by way of example. Specific cleavage at any site within such a structure is contemplated.

Improvements in an enzyme may be an increased or decreased rate of cleavage of one or more types of structures. Improvements may also result in more or fewer sites of cleavage on one or more of said cleavage structures. In developing a library of new structure-specific nucleases for use in nucleic acid cleavage assays, improvements may have many different embodiments, each related to the specific substrate structure used in a particular assay.

As an example, one embodiment of the INVADER oligonucleotide-directed cleavage assay of the present invention may be considered. In the INVADER oligonucleotide-directed cleavage assay, the accumulation of cleaved material is influenced by several features of the enzyme behavior. Not surprisingly, the turnover rate, or the number of structures that can be cleaved by a single enzyme molecule in a set amount of time, is very important in determining the amount of material processed during the course of an assay reaction. If an enzyme takes a long time to recognize a substrate (e.g., if it is presented with a less-than-optimal structure), or if it takes a long time to execute cleavage, the rate of product accumulation is lower than if these steps proceeded quickly. If these steps are quick, yet the enzyme "holds on" to the cleaved structure, and does not immediately proceed to another uncut structure, the rate will be negatively affected.

Enzyme turnover is not the only way in which enzyme behavior can negatively affect the rate of accumulation of product. When the means used to visualize or measure product is specific for a precisely defined product, products that deviate from that definition may escape detection, and thus the rate of product accumulation may appear to be lower than it is. For example, if one had a sensitive detector for trinucleotides that could not see di- or tetranucleotides, or any sized oligonucleotide other that 3 residues, in the INVADER-directed cleavage assay of the present invention any errant cleavage would reduce the detectable signal proportionally. It can be seen from the cleavage data presented here that, while there is usually one site within a probe that is favored for cleavage, there are often products that arise from cleavage one or more nucleotides away from the primary cleavage site. These are products that are target-dependent, and are thus not non-specific background. Nevertheless, if a subsequent visualization system can detect only the primary product, these represent a loss of signal. One example of such a selective visualization system is the charge reversal readout presented herein, in which the balance of positive and negative charges determines the behavior of the products. In such a system the presence of an extra nucleotide or the absence of an expected nucleotide can excluded a legitimate cleavage product from ultimate detection by leaving that product with the wrong balance of charge. It can be easily seen that any assay that can sensitively distinguish the nucleotide content of an oligonucleotide, such as standard stringent hybridization, suffers in sensitivity when some fraction of the legitimate product is not eligible for successful detection by that assay.

These discussions suggest two highly desirable traits in any enzyme to be used in the method of the present invention. First, the more rapidly the enzyme executes an entire cleavage reaction, including recognition, cleavage and release, the more signal it may potentially created in the INVADER oligonucleotide-directed cleavage assay. Second, the more successful an enzyme is at focusing on a single cleavage site within a structure, the more of the cleavage product can be successfully detected in a selective read-out.

The rationale cited above for making improvements in enzymes to be used in the INVADER oligonucleotide-directed cleavage assay are meant to serve as an example of one direction in which improvements might be sought, but not as a limit on either the nature or the applications of improved enzyme activities. As another direction of activity change that would be appropriately considered improvement, the DNAP-associated 5' nucleases may be used as an example. In creating some of the polymerase-deficient 5' nucleases described herein it was found that the those that were created by deletion of substantial portions of the polymerase domain, as depicted in FIG. 4, assumed activities that were weak or absent in the parent proteins. These activities included the ability to cleave the non-forked structure shown in FIG. 15D, a greatly enhanced ability to exonucleolytically remove nucleotides from the 5' ends of duplexed strands, and a nascent ability to cleave circular molecules without benefit of a free 5' end.

In addition to the 5' nucleases derived from DNA polymerases, the present invention also contemplates the use of structure-specific nucleases that are not derived from DNA polymerases. For example, a class of eukaryotic and archaebacterial endonucleases have been identified which have a similar substrate specificity to 5' nucleases of PolI-type DNA polymerases. These are the FEN1 (Flap EndoNuclease), RAD2, and XPG (Xeroderma Pigmentosa-complementation group G) proteins. These proteins are involved in DNA repair, and have been shown to favor the cleavage of structures that resemble a 5' arm that has been displaced by an extending primer during polymerization, similar to the model depicted in FIG. 15B. Similar DNA repair enzymes have been isolated from single cell and higher eukaryotes and from archaea, and there are related DNA repair proteins in eubacteria. Similar 5' nucleases have also been associated with bacteriophage such as T5 and T7.

Figure 58:
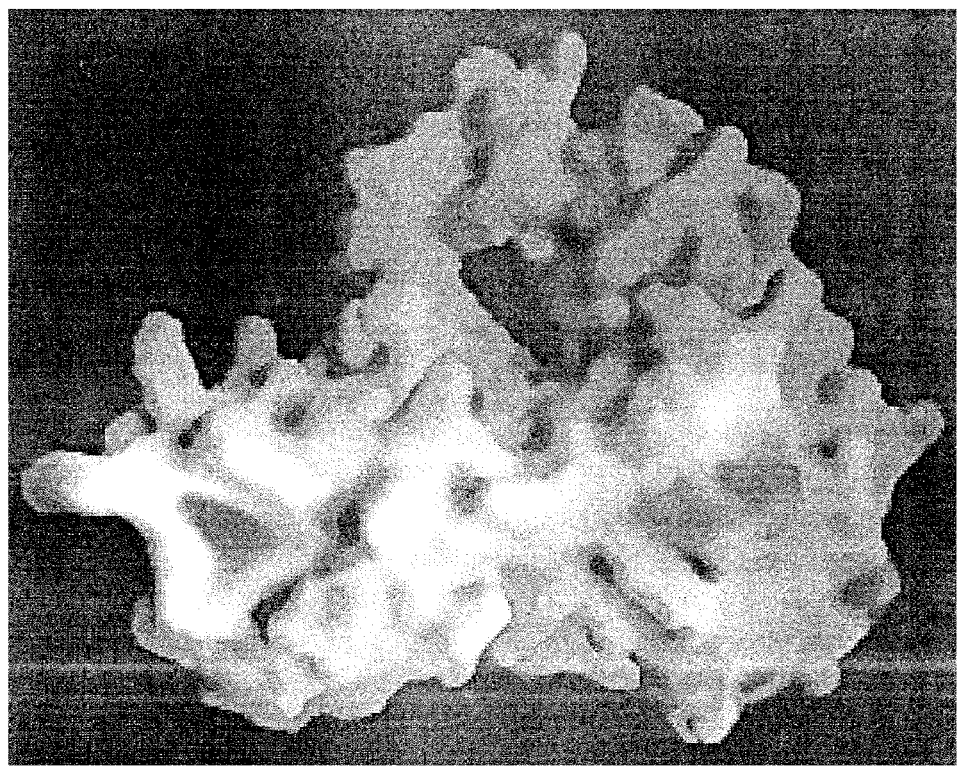
FIG. 58 provides a space-filling model of the 3-dimensional structure of the T5 5'-exonuclease.

Recently, the 3-dimensional structures of DNAPTaq and T5 phage 5'-exonuclease (FIG. 58) were determined by X-ray diffraction (Kim et al., Nature 376:612 [1995]; and Ceska et al., Nature 382:90 [1995]). The two enzymes have very similar 3-dimensional structures despite limited amino acid sequence similarity. The most striking feature of the T5 5'-exonuclease structure is the existence of a triangular hole formed by the active site of the protein and two alpha helices (FIG. 58). This same region of DNAPTaq is disordered in the crystal structure, indicating that this region is flexible, and thus is not shown in the published 3-dimensional structure. However, the 5' nuclease domain of DNAPTaq is likely to have the same structure, based its overall 3-dimensional similarity to T5 5'-exonuclease, and that the amino acids in the disordered region of the DNAPTaq protein are those associated with alpha helix formation. The existence of such a hole or groove in the 5' nuclease domain of DNAPTaq was predicted based on its substrate specificity (Lyamichev et al., supra).

It has been suggested that the 5' arm of a cleavage structure must thread through the helical arch described above to position said structure correctly for cleavage (Ceska et al., supra). One of the modifications of 5' nucleases described herein opened up the helical arch portion of the protein to allow improved cleavage of structures that cut poorly or not at all (e.g., structures on circular DNA targets that would preclude such threading of a 5' arm). The gene construct that was chosen as a model to test this approach was the one called CLEAVASE BN, which was derived from DNAPTaq but does not contain the polymerase domain (Ex. 2). It comprises the entire 5' nuclease domain of DNAP Taq, and thus should be very close in structure to the T5 5' exonuclease. This 5' nuclease was chosen to demonstrate the principle of such a physical modification on proteins of this type. The arch-opening modification of the present invention is not intended to be limited to the 5' nuclease domains of DNA polymerases, and is contemplated for use on any structure-specific nuclease that includes such an aperture as a limitation on cleavage activity. The present invention contemplates the insertion of a thrombin cleavage site into the helical arch of DNAPs derived from the genus *Thermus* as well as 5' nucleases derived from DNAPs derived from the genus *Thermus*. The specific example shown herein using the CLEAVASE BN/thrombin nuclease merely illustrates the concept of opening the helical arch located within a nuclease domain. As the amino acid sequence of DNAPs derived from the genus *Thermus* are highly conserved, the teachings of the present invention enable the insertion of a thrombin site into the helical arch present in these DNAPs and 5' nucleases derived from these DNAPs.

The opening of the helical arch was accomplished by insertion of a protease site in the arch. This allowed post-translational digestion of the expressed protein with the appropriate protease to open the arch at its apex. Proteases of this type recognize short stretches of specific amino acid sequence. Such proteases include thrombin and factor Xa. Cleavage of a protein with such a protease depends on both the presence of that site in the amino acid sequence of the protein and the accessibility of that site on the folded intact protein. Even with a crystal structure it can be difficult to predict the susceptibility of any particular region of a protein to protease cleavage. Absent a crystal structure it must be determined empirically.

In selecting a protease for a site-specific cleavage of a protein that has been modified to contain a protease cleavage site, a first step is to test the unmodified protein for cleavage at alternative sites. For example, DNAPTaq and CLEAVASE BN nuclease were both incubated under protease cleavage conditions with factor Xa and thrombin proteases. Both nuclease proteins were cut with factor Xa within the 5' nuclease domain, but neither nuclease was digested with large amounts of thrombin. Thus, thrombin was chosen for initial tests on opening the arch of the CLEAVASE BN enzyme.

In the protease/CLEAVASE modifications described herein the factor Xa protease cleaved strongly in an unacceptable position in the unmodified nuclease protein, in a region likely to compromise the activity of the end product. Other unmodified nucleases contemplated herein may not be sensitive to the factor Xa, but may be sensitive to thrombin or other such proteases. Alternatively, they may be sensitive to these or other such proteases at sites that are immaterial to the function of the nuclease sought to be modified. In approaching any protein for modification by addition of a protease cleavage site, the unmodified protein should be tested with the proteases under consideration to determine which proteases give acceptable levels of cleavage in other regions.

Working with the cloned segment of DNAPTaq from which the CLEAVASE BN protein is expressed, nucleotides encoding a thrombin cleavage site were introduced in-frame near the sequence encoding amino acid 90 of the nuclease gene. This position was determined to be at or near the apex of the helical arch by reference to both the 3-dimensional structure of DNAPTaq, and the structure of T5 5' exonuclease. The encoded amino acid sequence, LVPRGS, was inserted into the apex of the helical arch by site-directed mutagenesis of the nuclease gene. The proline (P) in the thrombin cleavage site was positioned to replace a proline normally in this position in CLEAVASE BN because proline is an alpha helix-breaking amino acid, and may be important for the 3-dimensional structure of this arch. This construct was expressed, purified and then digested with thrombin. The digested enzyme was tested for its ability to cleave a target nucleic acid, bacteriophage M13 genomic DNA, that does not provide free 5' ends to facilitate cleavage by the threading model.

While the helical arch in this nuclease was opened by protease cleavage, it is contemplated that a number of other techniques could be used to achieve the same end. For example, the nucleotide sequence could be rearranged such that, upon expression, the resulting protein would be configured so that the top of the helical arch (amino acid 90) would be at the amino terminus of the protein, the natural carboxyl and amino termini of the protein sequence would be joined, and the new carboxyl terminus would lie at natural amino acid 89. This approach has the benefit that no foreign sequences are introduced and the enzyme is a single amino acid chain, and thus may be more stable that the cleaved 5' nuclease. In the crystal structure of DNAPTaq, the amino and carboxyl termini of the 5'-exonuclease domain lie in close proximity to each other, which suggests that the ends may be directly joined without the use of a flexible linker peptide sequence as is sometimes necessary. Such a rearrangement of the gene, with subsequent cloning and expression could be accomplished by standard PCR recombination and cloning techniques known to those skilled in the art.

The present invention also contemplates the use of nucleases isolated from organisms that grow under a variety of conditions. The genes for the FEN-1/XPG class of enzymes are found in organisms ranging from bacteriophage to humans to the extreme thermophiles of Kingdom Archaea. For assays in which high temperature is to be used, it is contemplated that enzymes isolated from extreme thermophiles may exhibit the thermostability required of such an assay. For assays in which it might be desirable to have peak enzyme activity at moderate temperature or in which it might be desirable to destroy the enzyme with elevated temperature, those enzymes from organisms that favor moderate temperatures for growth may be of particular value.

An alignment of a collection of FEN-1 proteins sequenced by others is shown in FIGS. 59A-E (SEQ ID NOS:135-145). It can be seen from this alignment that there are some regions of conservation in this class of proteins, suggesting that they are related in function, and possibly in structure. Regions of similarity at the amino acid sequence level can be used to design primers for in vitro amplification (PCR) by a process of back translating the amino acid sequence to the possible nucleic acid sequences, then choosing primers with the fewest possible variations within the sequences. These can be used in low stringency PCR to search for related DNA sequences. This approach permits the amplification of DNA encoding a FEN-1 nuclease without advance knowledge of the actual DNA sequence.

It can also be seen from this alignment that there are regions in the sequences that are not completely conserved. The degree of difference observed suggests that the proteins may have subtle or distinct differences in substrate specificity. In other words, they may have different levels of cleavage activity on the cleavage structures of the present invention.

When a particular structure is cleaved at a higher rate than the others, this is referred to a preferred substrate, while a structure that is cleaved slowly is considered a less preferred substrate. The designation of preferred or less preferred substrates in this context is not intended to be a limitation of the present invention. It is contemplated that some embodiments the present invention will make use of the interactions of an enzyme with a less preferred substrate. Candidate enzymes are tested for suitability in the cleavage assays of the present invention using the assays described below.

1. Structure Specific Nuclease Assay

Testing candidate nucleases for structure-specific activities in these assays is done in much the same way as described for testing modified DNA polymerases in Example 2, but with the use of a different library of model structures. In addition to assessing the enzyme performance in primer-independent and primer-directed cleavage, a set of synthetic hairpins are used to examine the length of duplex downstream of the cleavage site preferred by the enzyme.

The FEN-1 and XPG 5' nucleases used in the present invention should be tested for activity in the assays in which they are intended to be used, including but not limited to the INVADER-directed cleavage detection assay of the present invention and the CFLP method of characterizing nucleic acids (the CFLP method is described in U.S. Pat. Nos. 5,843,654, 5,843,669, 5,719,028, and 5,888,780 and PCT Publication WO 96/15267; the disclosures of which are incorporated herein by reference). The INVADER assay uses a mode of cleavage that has been termed "primer directed" of "primer dependent" to reflect the influence of the an oligonucleotide hybridized to the target nucleic acid upstream of the cleavage site. In contrast, the CFLP reaction is based on the cleavage of folded structure, or hairpins, within the target nucleic acid, in the absence of any hybridized oligonucleotide. The tests described herein are not intended to be limited to the analysis of nucleases with any particular site of cleavage or mode of recognition of substrate structures. It is contemplated that enzymes may be described as 3' nucleases, utilizing the 3' end as a reference point to recognize structures, or may have a yet a different mode of recognition. Further, the use of the term 5' nucleases is not intended to limit consideration to enzymes that cleave the cleavage structures at any particular site. It refers to a general class of enzymes that require some reference or access to a 5' end to effect cleavage of a structure.

A set of model cleavage structures has been created to allow the cleavage ability of unknown enzymes on such structures to be assessed. Each of the model structures is constructed of one or more synthetic oligonucleotides made by standard DNA synthesis chemistry. Examples of such synthetic model substrate structures are shown in FIGS. 26 and 60. These are intended only to represent the general folded configuration desirable is such test structures. While a sequence that would assume such a structure is indicated in the Figures, there are numerous other sequence arrangements of nucleotides that would be expected to fold in such ways. The essential features to be designed into a set of oligonucleotides to perform the tests described herein are the presence or absence of a sufficiently long 3' arm to allow hybridization of an additional nucleic acid to test cleavage in a "primer-directed" mode, and the length of the duplex region. In the set depicted in FIG. 60, the duplex lengths of the S-33 and the 11-8-0 structures are 12 and 8 basepairs, respectively. This difference in length in the test molecules facilitates detection of discrimination by the candidate nuclease between longer and shorter duplexes. Additions to this series expanding the range of duplex molecules presented to the enzymes, both shorter and longer, may be used. The use of a stabilizing DNA tetraloop (Antao et al, Nucl. Acids Res., 19:5901 [1991]) or triloop (Hiraro et al., Nuc. Acids Res., 22:576 [1994]) at the closed end of the duplex helps ensure formation of the expected structure by the oligonucleotide.

The model substrate for testing primer directed cleavage, the "S-60 hairpin" (SEQ ID NO:40) is described in Example 11. In the absence of a primer this hairpin is usually cleaved to release 5' arm fragments of 18 and 19 nucleotides length. An oligonucleotide, termed P-14 (5'-CGAGAGAC-CACGCT-3'; SEQ ID NO:108), that extends to the base of the duplex when hybridized to the 3' arm of the S-60 hairpin gives cleavage products of the same size, but at a higher rate of cleavage.

To test invasive cleavage a different primer is used, termed P-15 (5'-CGAGAGACCACGCTG-3'; SEQ ID NO:30). In a successful invasive cleavage the presence of this primer shifts the site of cleavage of S-60 into the duplex region, usually releasing products of 21 and 22 nucleotides length.

The S-60 hairpin may also be used to test the effects of modifications of the cleavage structure on either primer-directed or invasive cleavage. Such modifications include, but are not limited to, use of mismatches or base analogs in the hairpin duplex at one, a few or all positions, similar disruptions or modifications in the duplex between the primer and the 3' arm of the S-60, chemical or other modifications to one or both ends of the primer sequence, or attachment of moieties to, or other modifications of the 5' arm of the structure. In all of the analyses using the S-60 or a similar hairpin described herein, activity with and without a primer may be compared using the same hairpin structure.

The assembly of these test reactions, including appropriate amounts of hairpin, primer and candidate nuclease is described in Example 2. As cited therein, the presence of cleavage products is indicated by the presence of molecules which migrate at a lower molecular weight than does the uncleaved test structure. When the reversal of charge of a label is used the products will carry a different net charge than the uncleaved material. Any of these cleavage products indicate that the candidate nuclease has the desired structure-specific nuclease activity. By "desired structure-specific nuclease activity" it is meant only that the candidate nuclease cleaves one or more test molecules. It is not necessary that the candidate nuclease cleave at any particular rate or site of cleavage to be considered successful cleavage.

2. Enzyme Chimeras and Variants

The present invention further provides chimerical structure-specific nucleases. Chimerical structure-specific nucleases comprise one or more portions of any of the enzymes described herein in combination with another sequence. In preferred embodiments, the chimerical structure-specific nucleases comprise a functional domain (e.g., a region of the enzyme containing an arch region or sequence physically associated therewith) from a 5'-nuclease in combination with domains from other enzymes (e.g., from other 5'-nucleases). In some preferred embodiments, a given functional domain comprises sequence from two or more enzymes. For example, the amino acid sequence of a functional domain of a first structure-specific nuclease may be altered at one or more amino acid positions to convert the functional domain, or a portion thereof, to the sequence of a second structure-specific nuclease, thereby imparting characteristics of the second nuclease on the first. Such characteristics include, but are not limited to catalytic activity, specificity, and stability (e.g., thermostability).

In one embodiment, the present invention provides chimerical enzymes comprising amino acid portions derived from the enzymes selected from the group of DNA polymerases and FEN-1, XPG and RAD endonucleases. In a preferred embodiment, the chimerical enzymes comprise amino acid portions derived from the FEN-1 endonucleases selected from the group of *Pyrococcus furiosus, Methanococcus jannaschi, Pyrococcus woesei, Archaeoglobus fulgidus, Methanobacterium thermoautotrophicum, Sulfolobus solfataricus, Pyrobaculum aerophilum, Thermococcus litoralis, Archaeaglobus veneficus, Archaeaglobus profundus, Acidianus brierlyi, Acidianus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus horikoshii,* and *Aeropyrum pernix.*

Some embodiments of the present invention provide mutant or variant forms of enzymes described herein. It is possible to modify the structure of a peptide having an activity of the enzymes described herein for such purposes as enhancing cleavage rate, substrate specificity, stability, and the like. For example, a modified peptide can be produced in which the amino acid sequence has been altered, such as by amino acid substitution, deletion, or addition. For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of enzymes described herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), Biochemistry, 2nd ed, WH Freeman and Co. [1981]). Whether a change in the amino acid sequence of a peptide results in a functional homolog can be readily determined by assessing the ability of the variant peptide to produce a response in a fashion similar to the wild-type protein using the assays described herein. Peptides in which more than one replacement has taken place can readily be tested in the same manner.

It is contemplated that the nucleic acids encoding the enzymes can be utilized as starting nucleic acids for directed evolution. These techniques can be utilized to develop enzyme variants having desirable properties. In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung et al., Technique, 1:11-15 [1989]; Eckert and Kunkel, PCR Methods Appl., 1:17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity (e.g., ability to cleave a cleavage structure such as those described in Example 66). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324-25 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in different clones becoming mixed and accumulating in some of the resulting sequences. Multiple cycles of selection and shuffling have led to the functional enhancement of a number of enzymes (Stemmer, Nature, 370:398-91 [1994]; Stemmer, Proc. Natl. Acad. Sci. USA, 91, 10747-51 [1994]; Crameri et al., Nat. Biotech., 14:315-19 [1996]; Zhang et al., Proc. Natl. Acad. Sci. USA, 94:4504-09 [1997]; and Crameri et al., Nat. Biotech., 15:436-38 [1997]).

IX. The INVADER Assay for Direct Detection and Measurement of Specific Analytes.

The following description provides illustrative examples of target sequence detection through the use of the compositions and methods of the present invention. These example include the detection of human cytomegalovirus viral DNA, single nucleotide polymorphisms in the human apolipoprotein E gene, mutations in the human hemochromatosis gene, mutations in the human MTHFR, prothrombin 20210GA polymorphism, the HR-2 mutation in the human Factor V gene, single nucleotide polymorphisms in the human TNF-α Gene, and Leiden mutation in the human Factor V gene. Included in these descriptions are novel nucleic acid compositions for use in the detection of such sequence. Examples 54-61 below provide details on the design and execution of these illustrative embodiments.

A. Detection of Human *Cytomegalovirus* Viral DNA By Invasive Cleavage

Human cytomegalovirus (HCMV) causes, or is associated with, a wide variety of diseases in humans (Table 3). More than 90% of bone marrow or kidney transplant recipients (immunocompromised hosts) develop HCMV infections, most of which are due to reactivation of latent virus by immunosuppressive drugs, as well as transmission of virus by latently infected donor tissue or blood (Ackerman et al., Transplant. Proc., 20(S1): 468 [1988]; and Peterson et al., Medicine 59:283 [1980]).

TABLE 3

Diseases Caused By Human Cytomegalovirus cytomegalic inclusion
heterophil-negative disease in neonates
mononucleosis
interstitial pneumonia
pneumonitis
retinitis
hepatitis
pancreatitis
meningoencephalitis
gastrointestinal disease
disseminated infection There are instances in which rapid, sensitive, and specific diagnosis of HCMV disease is imperative. In recent years, the number of patients undergoing organ and tissue transplantations has increased markedly. HCMV is the most frequent cause of death in immunocompromised transplant recipients, thereby confirming the need for rapid and reliable laboratory diagnosis. Lymphocytes, monocytes, and possibly arterial endothelial or smooth muscle cells, are sites of HCMV latency. Therefore, prevention of HCMV infections in immunocompromised individuals (e.g., transplant recipients) includes use of HCMV-negative blood products and organs. Additionally, HCMV can be spread transplacentally, and to newborns by contact with infected cervical secretions during birth. Thus, a rapid, sensitive, and specific assay for detecting HCMV in body fluids or secretions may be desirable as a means to monitor infection, and consequently, determine the necessity of cesarean section.

Diagnosis of HCMV infection may be performed by conventional cell culture using human fibroblasts; shell vial centrifugation culture utilizing monoclonal antibodies and immunofluorescent staining techniques; serological methods; the HCMV antigenemia assay which employs a monoclonal antibody to detect HCMV antigen in peripheral blood leukocytes (PBLs); or by nucleic acid hybridization assays. These various methods have their advantages and limitations. Conventional cell culture is sensitive but slow, as cytopathic effect (CPE) may take 30 or more days to develop. Shell vial centrifugation is more rapid but still requires 24-48 hours for initial results. Both culture methods are affected by antiviral therapy. In immunocompromised patients, the ability to mount IgG and/or IgM antibody responses to HCMV infection are impaired, and serological methods are thus not reliable in this setting. Alternatively, IgM antibodies may be persistent for months after infection is resolved, and thus their presence may not be indicative of active infection. The HCMV antigenemia assay is labor intensive and is not applicable to specimens other than PBLs.

Recent advances in molecular biology have spurred the use of DNA probes in attempts to provide a more rapid, sensitive and specific assay for detecting HCMV in clinical specimens. For example, radiolabeled DNA probes have been used to hybridize to tissue cultures infected with or by HCMV, or in clinical samples suspected of containing HCMV ("hybridization assays"). However, probing of tissue cultures requires at least 18-24 hours for growth to amplify the antigen (HCMV) to be detected, if present, and additional time for development of autoradiographic detection systems. Using hybridization assays for assaying clinical specimens for HCMV may lack sensitivity, depending upon the titer of virus and the clinical sample assayed. Detection of HCMV in clinical samples has been reported using the polymerase chain reaction (PCR) to enzymatically amplify HCMV DNA. Methods using PCR compare favorably with virus isolation, in situ hybridization assays, and Southern blotting; See, e.g., Bamborschke et al., J. Neurol., 239:205 [1992]; Drouet et al., J. Virol. Meth., 45:259 [1993]; Einsele et al., Blood 77:1104-1110 [1991]; Einsele et al., Lancet 338:1170 [1991]; Lee et al., Aust. NZ J. Med., 22:249 [1992]; Miller et al., J. Clin. Microbiol., 32:5 [1994]; Rowley et al., Transplant. 51:1028 [1991]; Spector et al. J. Clin. Microbiol., 30:2359 [1992]; and Stanier et al., Mol. Cell. Probes 8:51 [1992]). Others, comparing the HCMV antigenemia assay with PCR methods, have found PCR methods as efficient or slightly more efficient in the detection of HCMV (van Dorp et al. (1992) Transplant. 54:661; Gerna et al. (1991) J. Infect. Dis. 164:488; Vleiger et al. (1992) Bone Marrow Transplant. 9:247; Zipeto et al. (1992) J. Clin. Microbiol. 30:527]. In addition, PCR methods have exhibited great sensitivity when specimens other than PBLs are assayed (Natori et al., Kansenshogaku Zasshi 67:1011 [1993]; Peterson et al., Medicine 59:283 [1980]; Prosch et al., J. Med. Virol., 38:246 [1992]; Ratnamohan et al., J. Med. Virol. 38:252 [1992]). However, because of the dangers of false positive reactions, these PCR-based procedures require rigid controls to prevent contamination and carry over (Ehrlich et al., in *PCR-Based Diagnostics in Infectious Diseases*, Ehrlich and Greenberg (eds), Blackwell Scientific Publications, [1994], pp. 3-18). Therefore, there exists a need for a rapid, sensitive, and specific assay for HCMV that has a reduced risk of false positive result due to contamination by reaction product carried over from other samples.

As shown herein, the INVADER-directed cleavage assay is rapid, sensitive and specific. Because the accumulated products do not contribute to the further accumulation of signal, reaction products carried over from one standard (i.e., non-sequential) INVADER-directed cleavage assay to another cannot promote false positive results. The use of multiple sequential INVADER-directed cleavage assays will further boost the sensitivity of HCMV detection without sacrifice of these advantages.

B. Detection of Single Nucleotide Polymorphisms in the Human Apolipoprotein E Gene Apolipoprotein E (ApoE) performs various functions as a protein constituent of plasma lipoproteins, including its role in cholesterol metabolism. It was first identified as a constituent of liver-synthesized very low density lipoproteins which function in the transport of triglycerides from the liver to peripheral tissues. There are three major isoforms of ApoE, referred to as ApoE2, ApoE3 and ApoE4 which are products of three alleles at a single gene locus. Three homozygous phenotypes (Apo-E2/2, E3/3, and E4/4) and three heterozygous phenotypes (ApoE3/2, E4/3 and E4/2) arise from the expression of any two of the three alleles. The most common phenotype is ApoE3/3 and the most common allele is E3. See Mahley, R. W., Science 240:622-630 (1988).

The amino acid sequences of the three types differ only slightly. ApoE4 differs from ApoE3 in that in ApoE4 arginine is substituted for the normally occurring cysteine at amino acid residue 112. The most common form of ApoE2 differs from ApoE3 at residue 158, where cysteine is substituted for the normally occurring arginine. See Mahley, Science, supra.

The frequency of the apoE4 allele has been shown to be markedly increased in sporadic Alzheimer's Disease (AD) (Poirier, J. et al., 1993, Apolipoprotein E phenotype and Alzheimer's Disease, Lancet, 342:697-699; Noguchi, S. et al., 1993, Lancet (letter), 342:737) and late onset familial Alzheimer's disease (AD) (Corder, E. H. et al., 1993, Science, 261:921-923; Payami, H. et al., 1993, Lancet (letter), 342: 738). This gene dosage effect was observed in both sporadic and familial cases (i.e., as age of onset increases, E4 allele copy number decreases). Women, who are generally at a greater risk of developing Alzheimer's disease, show increased E4 allele frequency when compared to age matched men.

C. Detection of Mutations in the Human Hemochromatosis Gene

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses.

HH is inherited as a recessive trait; heterozygotes are asymptomatic and only homozygotes are affected by the disease. It is estimated that approximately 10% of individuals of Western European descent carry an HH gene mutation and that there are about one million homozygotes in the United States. Although ultimately HH produces debilitating symptoms, the majority of homozygotes have not been diagnosed. Indeed, it has been estimated that no more than 10,000 people in the United States have been diagnosed with this condition. The symptoms are often confused with those of other conditions, and the severe effects of the disease often do not appear immediately. It would be desirable to provide a method to identify persons who are ultimately destined to become symptomatic in order to intervene in time to prevent excessive tissue damage. One reason for the lack of early diagnosis is the inadequacy of presently available diagnostic methods to ascertain which individuals are at risk.

Although blood iron parameters can be used as a screening tool, a confirmed diagnosis often employs HLA typing, which is tedious, nonspecific, and expensive and/or liver biopsy which is undesirably invasive and costly. Accordingly, others have attempted to develop inexpensive and noninvasive diagnostics both for detection of homozygotes having existing disease, in that presymptomatic detection would guide intervention to prevent organ damage, and for identification of carriers. The need for such diagnostics is documented for example, in Finch, C. A. West J Med (1990) 153:323-325; McCusick, V. et al. Mendelian Inheritance in Man 11th ed., Johns Hopkins University Press (Baltimore, 1994) pp. 1882-1887; Report of the Joint World Health Organization/HH Foundation/French HH Association Meeting, 1993.

D. Detection of Mutations in the Human MTHFR

Folic acid derivatives are coenzymes for several critical single-carbon transfer reactions, including reactions in the biosynthesis of purines, thymidylate and methionine. Methylenetetrahydrofolate reductase (MTHFR; EC 1.5.1.20) catalyzes the NADPH-linked reduction of 5,10-methylenetetrahydrofolate to 5-methyltetrahydrofolate, a co-substrate for methylation of homocysteine to methionine. The porcine liver enzyme, a flavoprotein, has been purified to homogeneity; it is a homodimer of 77-kDa subunits. Partial proteolysis of the porcine peptide has revealed two spatially distinct domains: an N-terminal domain of 40 kDa and a C-terminal domain of 37 kDa. The latter domain contains the binding site for the allosteric regulator S-adenosylmethionine.

Hereditary deficiency of MTHFR, an autosomal recessive disorder, is the most common inborn error of folic acid metabolism. A block in the production of methyltetrahydrofolate leads to elevated homocysteine with low to normal levels of methionine. Patients with severe deficiencies of MTHFR (0-20% activity in fibroblasts) can have variable phenotypes. Developmental delay, mental retardation, motor and gait abnormalities, peripheral neuropathy, seizures and psychiatric disturbances have been reported in this group, although at least one patient with severe MTHFR deficiency was asymptomatic. Pathologic changes in the severe form include the vascular changes that have been found in other conditions with elevated homocysteine, as well as reduced neurotransmitter and methionine levels in the CNS. A milder deficiency of MTHFR (35-50% activity) has been described in patients with coronary artery disease. Genetic heterogeneity is likely, considering the diverse clinical features, the variable levels of enzyme activity, and the differential heat inactivation profiles of the reductase in patients' cells. Methods to detect the MTHFR mutation include: AS-PCR (Hessner, et al Br J Haematol 106, 237-9 (1999)) and PCR-RFLP (Nature Genetics, Frosst et al. 1995:10; 111-113).

E. Detection of Prothrombin 20210GA Polymorphism and the Factor V Leiden Polymorphism The coagulation cascade is a complex series of zymogen activations, inactivations and feed back loops involving numerous enzymes and their cofactors. The entire cascade, from tissue injury or venous trauma to clotting has been well described (refs). The cascade culminates in the conversion of prothrombin (Factor II) to thrombin. This is catalyzed by the activated form of factor X, factor Xa and its cofactor, activated factor V, factor Va. Thrombin then converts fibrinogen to fibrin and promotes fibrin cross-linking and clot formation by activating factor XIII. In addition to the above stated functions, thrombin a serine protease, can also activate factor V in a positive feed-back loop. Factor Va is a pro-coagulant cofactor in the clotting cascade, and when clot formation is sufficient, is inactivated by activated protein C (APC).

Venous thrombosis is the obstruction of the circulation by clots that have been formed in the veins or have been released from a thrombus formed elsewhere. The most frequent sites of clot formation are the deep veins of the legs, but it also may occur in veins in the brain, retina, liver and mesentery. Factors other than heritable defects that can play a role in the development of thrombosis include recent surgery, malignant disorders, pregnancy and labor and long term immobilization.

Studies of hereditary thrombophilia, defined as an increased tendency towards venous thrombotic disease in relatively young adults, have provided insights into the genetic factors that regulate thrombosis. In 1993, Dahlback et al. (Proc Natl Acad Sci USA 1993; 90:1004-1008) described an insensitivity to APC, a critical anti-coagulant in the clotting cascade, in three unrelated families with hereditary thrombophilia. The anticoagulant property of APC resides in its capacity to inactivate the activated cofactors Va and VIIIa by limited proteolysis (ref 3). This inactivation of cofactors Va and VIIIa results in reduction of the rate of formation of thrombin, the end product of the cascade. This observation was confirmed by other investigators (ref) and the term "APC resistance" was coined to describe this particular phenotype in thrombophilic patients. In a subsequent study of 20 families with thrombophilia and APC resistance, an autosomal dominant pattern of inheritance was observed (17). Bertina et al (Nature, 1994, May 5; 369 (6475): 64-7) then demonstrated that the phenotype of APC resistance is associated with heterozygosity or homozygosity for a single point mutation at nucleotide 1691 in exon 10 of the factor V gene. This single base change, a guanine to adenine substitution, yields a mutant factor V molecule wherein the arginine at position 506 is replaced with glutamine. This form of the factor V molecule, characterized at Leiden University, (Bertenia et al) is known as the FV Q506 or FV Leiden mutation, and is inactivated less efficiently by APC than the wild type protein. It has been postulated that the prolonged circulation of activated factor V promotes a hypercoagulable state and increases the risk of thrombosis. Subsequent analysis of various patient groups exhibiting symptoms of venous thrombosis indicate that the factor V Leiden mutation is the single most common heritable factor contributing to an increased risk of venous thrombosis.

In 1996, studies by Poort et al. (Blood. 1996:88; 3698-703) revealed the second most common heritable factor contributing to increase thrombotic risk. In studying the sequence of the prothrombin gene in selected patients with a documented familial history of venous thrombophilia, the Poort group identified a single point mutation in the 3' untranslated region. This G to A transition at position 20210 is strongly correlated with elevated plasma prothrombin levels, and was also shown to be associated with an almost threefold increased risk of venous thrombosis (abstract, Howard).

The first reported case of a thrombophilia pateint genetically homozygous for the G to A polymorphism in the 3' untranslated region was by Howard, et al (*Blood Coagulation Fibrinolysis* 1997 July; 8(5): 316-9). The patient, a healthy young Mexican male presented with a myocardial infarction, venous thrombosis and embolism. The patient was found to be homozygous for the prothrombin mutation and heterozygous for the Factor V Leiden mutation, supporting the double-hit theory for thrombophilia in young patients.

Studies by Hessner et al. show that the prothrombin 20210GA genotype was nearly 5 times as prevalent in the symptomoatic FVL carriers than in a random Caucasian control group (*British Journal of Haematology,* 1999, 106), and that allele frequencies for the prothrombin and Factor V mutants vary among different ethnic backgrounds (*Thromb Haemostat* 1999; 81:733-8). The above discussion confirms that early detection of the factor V Leiden mutation and the factor II prothrombin mutation are paramount in hereditary thrombotic risk assessment. The nature of these two mutations, that is, a single base change in the nucleic acid sequence, make them amenable to a variety of nucleic acid detection methods known to the art, though the demand for faster, more reliable, cost-effective and user-friendly tests for the detection of specific nucleic acid sequences continues to grow. The most common methods to test for these mutations include PCR/RFLP, AS-PCR and functional, coagulation assay.

F. Detection of the HR-2 Mutation in the Human Factor V Gene

The R-2 polymorphism is located in exon 13 of the factor V gene, and is the result of an A to G transition at base 4070, replacing the wild-type amino acid histine with the mutant argenine in the mature protein. The R-2 polymorphism is one of a set of mutations termed collectively HR-2. The HR-2 haplotype is defined by 6 nucleotide base substitutions in exons 13 and 16 of the factor V gene. The haplotype is associated with an increased functional resistance to activated protein C both in normal subjects and in thrombophilic patients. When present as a compound heterozygote in conjunction with the factor V Leiden mutation, clinical symptoms are comparable to those seen in patients homozygous for the factor V Leiden mutation, and include increased risk of deep vein thrombosis.

G. Detection of Single Nucleotide Polymorphisms in the Human TNF-αGene

The human cytokine tumor necrosis factor alpha (TNF-alpha) has been shown to be a major factor in graft rejection; the more TNF-alpha present in the system, the greater the rejection response to transplanted tissue. Mutations in TNF-alpha have also been correlated with cerebral malaria (Nature 1994; 371:508-510), fulminas purpura (J Infect Dis. 1996; 174:878-880), and mucocutaneous leishmaniaisis (J Exp Med. 1995; 182:1259-1264). The mutation detected in this example is located in the promoter region of the TNF-alpha gene at position minus 308. The wild-type guanine (G) is replaced with a mutant adenine (A). This result of this promoter mutation is the enhancement of transcription of TNF-alpha by 6-7 fold. Methods to detect mutations in TNF-alpha include sequencing, denaturing gradient gel electorphoresis, PCR methods, and methods involving both PCR and post-PCR hybridization with specific oligos.

H. Detection of Methicillin Resistant *Staphylococcus aureus*

*Staphylococcus aureus* is recognized as one of the major causes of infections in humans occurring in both in the hospital and in the community at large. One of the most serious concerns in treating any bacterial infection is the increasing resistance to antibiotics. The growing incidence of methicillin-resistant *S. aureus* (MRSA) infections worldwide has underscored the importance of both early detection of the infective agent, and defining a resistance profile such that proper treatment can be given. The primary mechanism for resistance to methicillin involves the production of a protein called PBP2a, encoded by the mecA gene. The mecA gene not specific to *Staphalococcus aureus*, but is of extraspecies origin. The mecA gene is however, indicative of methicillin resistance and is used as a marker for the detection of resistant bacteria. So, to identify methicillin resistant *S. aureus* via nucleic acid techniques, both the mecA gene and at least one species specific gene must be targeted. A particular species specific gene, the nuclease or nuc gene is used in the following example. Methods used to detect MRSA include time consuming and laborious culturing and coagulation assays and growth assays on antibiotic media. Molecular approaches include a Cycling Probe™ assay, the Velogene™ Kit from Alexon-Trend (Ramsey, Minn. cat # 818-48), anti-body test which bind the PBP2a protein, bDNA Assay (Chiron, Emeryville, Calif.), all of which tests only for the presence of the mecA gene and are not *Staph. aureus* specific.

X. Kits

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). The kit may include any and all components necessary or desired for the enzymes or assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

Additionally, in some embodiments, the present invention provides methods of delivering kits or reagents to customers for use in the methods of the present invention. The methods of the present invention are not limited to a particular group of customers. Indeed, the methods of the present invention find use in the providing of kits or reagents to customers in many sectors of the biological and medical community, including, but not limited to customers in academic research labs, customers in the biotechnology and medical industries, and customers in governmental labs. The methods of the present invention provide for all aspects of providing the kits or reagents to the customers, including, but not limited to, marketing, sales, delivery, and technical support.

In some embodiments of the present invention, quality control (QC) and/or quality assurance (QA) experiments are conducted prior to delivery of the kits or reagents to customers. Such QC and QA techniques typically involve testing the reagents in experiments similar to the intended commercial uses (e.g., using assays similar to those described herein). Testing may include experiments to determine shelf life of products and their ability to withstand a wide range of solution and/or reaction conditions (e.g., temperature, pH, light, etc.).

In some embodiments of the present invention, the compositions and/or methods of the present invention are disclosed and/or demonstrated to customers prior to sale (e.g., through printed or web-based advertising, demonstrations, etc.) indicating the use or functionality of the present invention or components of the present invention. However, in some embodiments, customers are not informed of the presence or use of one or more components in the product being sold. In such embodiments, sales are developed, for example, through the improved and/or desired function of the product (e.g., kit) rather than through knowledge of why or how it works (i.e., the user need not know the components of kits or reaction mixtures). Thus, the present invention contemplates making kits, reagents, or assays available to users, whether or not the user has knowledge of the components or workings of the system.

Accordingly, in some embodiments, sales and marketing efforts present information about the novel and/or improved properties of the methods and compositions of the present invention. In other embodiments, such mechanistic information is withheld from marketing materials. In some embodiments, customers are surveyed to obtain information about the type of assay components or delivery systems that most suits their needs. Such information is useful in the design of the components of the kit and the design of marketing efforts.

XI. Reaction on a Solid Support

A. Existing Technology

The majority of methods for scoring known SNPs/mutations fall into two broad categories: (1) hybridization methods, i.e. those that detect mutations based on the effects that a mismatch causes on the thermodynamics of oligonucleotide hybridization (i.e. melting temperature, or $T_m$); and (2) enzymatic methods that amplify, cleave, or extend nucleic acids based on either their sequence, their structure, or both.

1. Hybridization-Based Methods

One area of extremely active technology development is an array-based approach to DNA sequencing, or sequencing by hybridization (SBH). These methods employ a solid phase probing system (Smith et al., J Comput Biol Summer; 5:255 [1998]). This allows for facilitated sample handling and oligonucleotide purification; decreased losses during sample handling; reduction of interference between oligonucleotides and, perhaps most importantly, unique identifying information through "addressing" of oligonucleotides. Second, the ability to attach thousands of oligonucleotides (or target molecules) gives these methods the potential to interrogate vast numbers of loci in parallel.

SBH is based on the well-established principle of allele specific oligonucleotide hybridization (ASO). Instead of using chemistry to fractionate DNA based on its sequence, SBH relies on elucidating sequence by virtue of complementarity of a test sequence, i.e. a target molecule, to an array of oligonucleotides of known sequence. There are two principal formats being developed at present. In Format 1, the DNA target is affixed to a solid support in multiple, repeating arrays of microspots (~6 mm$^2$; Drmanac et al., Nature Biotechnology, 16:54 [1998]). These arrays are compartmentalized, either physically (e.g. with a metal grid) or chemically (e.g. with hydrophobic substances). Each compartment becomes a hybridization chamber to which distinct sets of oligonucleotides are added. This approach was pioneered by Hyseq (Sunnyvale, Calif.), which claims the ability to analyze multiple targets per array as a key advantage of this design.

Format 2 relies on an inverse approach. Multiple oligonucleotides are bound to the solid support—typically the oligonucleotides are synthesized directly on the surface by combinatorial masking—and the DNA target, which must be a small, amplified locus, is simultaneously interrogated by the entire array. Affymetrix (Santa Clara, Calif.) has led the field in developing high resolution photolithographic processes for creating increasingly complex arrays. As many as 400,000 oligonucleotides have been synthesized on 1.6 cm$^2$ chip surfaces, though published studies have emphasized arrays comprising 96,000 (Hacia et al., Nature Genetics 14:441 [1996]) to 135,000 (Chee et al., Science, 274:610 [1996]) elements. The application of electric fields to each hybridization position is a variation of this approach, developed by Nanogen (San Diego, Calif.), that dramatically reduces the time required for hybridization from 1-2 hours to a matter of seconds (Sosonowski et al., PNAS, 94:1119 [1997]).

The use of such arrays for SNP discovery requires as many as 8-16 oligonucleotides per nucleotide interrogated, hence the complex arrays comprising hundreds of thousands of elements. However, their use for SNP scoring is potentially much less complicated. Two oligonucleotides, one in which the central position is designed to be complementary to the SNP, and another complementary to the wild type sequence, are sufficient to indicate the presence or absence of a given polymorphism. Nonetheless, SBH applications suffer from significant limitations that preclude their immediate adoption as a broad-based solution to SNP genotyping. Most notably, they are only appropriate for those applications in which fewer than 100 samples are processed per day in a given laboratory. Furthermore, reliance on PCR (or other target amplification procedures) to generate ample copies of target molecules for analysis severely limits throughput and increases cost. SBH is also hampered by the very nature of allele specific hybridization. Namely, the efficiency of hybridization and the thermal stability of hybrids formed between the target and a short oligonucleotide depend strongly on the particular sequences involved. So too, the degree of destabilization of the target molecule mismatched with an oligonucleotide at a single position depends on the sequence of the bases flanking the mismatch. Thus, it is impossible to design a single set of hybridization conditions that would function optimally for a large number of oligonucleotide elements (Pastinen et al., Genome Research, 7:606 [1997]). There have been reports of the use of small molecule additives that may minimize sequence dependent hybridization differences; however, at present little information on these innovations is available.

2. Multiplexed Allele-Specific Diagnostic Assay (MASDA)

MASDA is a forward dot blot procedure in which hundreds of target samples are spotted onto a membrane and then hybridized with a multiplexed solution of pooled, labeled probes (Shuber et al., Human Molecular Genetics, 6:337 [1997]). The labeled probes are then eluted from the filter and identified by conventional sequencing or chemical cleavage methods. The chief advantage of this method is its suitability for analyzing large numbers of target sequences (>500) with large numbers of probes (>100) in a single hybridization assay, though each target-probe hybrid must be analyzed individually. MASDA is extremely cumbersome, not amenable to automation, and dependent on target amplification to obtain sufficient amounts of hybrid for analysis.

3. Enzymatic Approaches i. Minisequencing

One method designed to circumvent the inherent limitations of allele specific hybridization is minisequencing. This technique, designed to detect SNPs/point mutations, uses a DNA polymerase to extend an oligonucleotide primer immediately adjacent to the polymorphism on an amplified target molecule (Pastinen et al., Genome Research, 7:606 [1997]). A single labeled nucleotide and the remaining three unlabeled dNTPs are then added. DNA polymerization is allowed to occur for only a few seconds, such that the primer is extended by only a small number of bases. When a test molecule is compared to a reference, all positions, except that of the SNP, are identical. By relying on enzymatic activity rather than on the thermodynamics of hybrid formation to detect point mutations, this assay is able to achieve at least an order of magnitude greater degree of discrimination between mutant and wild type samples. Pastinen et al have recently demonstrated that this technique can be carried out in a chip format (Pastinen et al., Genome Research, 7:606 [1997]). Despite the potential of this approach to overcome some of the shortcomings of ASO-based SNP scoring, minisequencing is limited to examination of amplified targets, limiting its potential throughput.

ii. Taq Man and Other PCR-Based Assays

Methods that rely on enzymatic or chemical agents to detect the presence of a mismatch can be considered to be structure, rather than sequence, specific. These methods include Allele-specific PCR, PCR-Ligase Detection Reaction (PCR-LDR), PCR-TaqMan (PE Biosystems, Foster City, Calif.), and Bridge Amplification Technology (Mosaic Technologies, Boston, Mass.). Allele-specific PCR makes use of PCR primers designed to amplify one allele but not another. The most common approach is to position the polymorphic base at the 3' terminus of a primer (Kwok et al., Nuc. Acid. Res., 18:999 [1990]). Although such 3' terminal mismatches do not significantly destabilize the primer, they are less efficiently extended by DNA polymerases. This discrimination, however, is considered to be very "leaky", meaning that many such mismatches are extended to some degree. PCR-LDR is an elegant means of evaluating PCR products that has been successfully applied to detection of drug resistance mutations in HIV (Landegren et al., Science, 241:1077 [1988]). In this approach, the ability to discriminate single base changes relies on the requirements of DNA ligase for fully annealed 3' ends of the upstream fragments being ligated to downstream primers (Landegren et al., Science, 241:1077 [1988]). However, in a best case, this method achieves only about 10% discrimination of mutant from wild type virus when multiple variants are present in a single sample. TaqMan is based on exonucleolytic degradation of a labeled probe hybridized to a PCR product (Livak et al., PCR Methods and Applications, 4:357 [1995]). The presence of a mismatch impairs hybridization, resulting in a reduction of signal generated from the mismatched probe and making the technique of questionable value for mixed samples, particularly when one allele is present as a small fraction of the total population. Because it is dependent on target amplification, the TaqMan procedure is typically carried out in sealed chambers in a dedicated, semi-automated fluorescence detection instrument.

Bridge Amplification Technology (Mosiac Technologies, Waltham, Mass.) is another method utilizing PCR for highly multiplexed detection. The basis of this approach is that the two PCR primers are affixed adjacent to one another on a solid surface. Double stranded target DNA is denatured and allowed to anneal to the primers. During the first annealing, each target strand hybridizes to a bound primer. During the extension, complementary strands are synthesized and are covalently attached to the surface via a primer. During the second annealing step, the 3' end of each newly synthesized single strand anneals with an adjacent primer, which is then extended to create a covalently attached, double-stranded product. By relying on primers bound to the surface, this technique avoids many of the shortcomings of PCR amplification that have precluded its widespread use for clinical applications. The most important of these is that this method does not promote carry-over contamination, which is the single greatest obstacle to the use of PCR in clinical settings. This method is suitable for high level multiplexing and parallel analysis of hundreds or thousands of loci from a single sample; however, it has yet to be applied to single base discrimination. Moreover, any SNP analysis based on this approach will by necessity rely on the allelic discrimination inherent in the PCR reaction. As described above, such methods are leaky and not likely to allow precise detection of a rare allele present as less than ~10% of a mixed population (Shafer et al., J. clinical Microbiology, 34:1849 [1996]).

B. INVADER Assay-Based SNP Genotyping Chip

The existing SNP genotyping technologies fall short in key areas. Notably, most existing methods rely on investigating small loci (usually no more than a few hundred base pairs) generated by target amplification procedures, usually PCR. Furthermore, target amplification methods are notoriously low throughput, costly, and cumbersome to execute.

An ideal method for SNP genotyping would be capable of massively parallel analysis of multiple sites (Wang et al., Science, 280:1077 [1998]), be suitable for the analysis of genomic DNA extracted from patient samples, i.e. without intervening target amplification steps (Pastinen et al., Genome Research, 7:606 [1997]), be able to detect a rare allele in a mixed population of nucleic acid molecules, provide a high degree of discrimination between wild type and polymorphic sequences (Pastinen et al., Genome Research, 7:606 [1997]), be readily adapted to include additional SNPs as they are discovered (Wang et al., Science, 280:1077 [1998]; Collins et al., Science, 278:1580 [1997]), be able to include an internal control or reference sample (Wang et al., Science, 280:1077 [1998]), and be inexpensive, simple to execute and automatable. As the discovery of SNPs accelerates due to the rapid progress of the Human Genome Project, it is clear that there will be an acute need for high throughput methods that meet all of these criteria.

Accordingly, in some embodiments, the present invention provides a solid phase INVADER assay system suitable for the analysis of multiple polymorphisms from a single genomic sample. In some embodiments, the target molecule is provided in solution and one or more of the oligonucleotides used in the INVADER assay reaction is immobilized.

However, in other embodiments, any or all of the nucleic acids, including the target, is immobilized. Additionally, in yet other embodiments, the cleavage mean (e.g., enzyme) and one or more of the nucleic acids are immobilized.

C. Formats for INVADER Assay on a Solid Support

The present invention is not limited to a particular configuration of the INVADER assay. Any number of suitable configurations of the component oligonucleotides may be utilized. For example, in some embodiments of the present invention, the probe oligonucleotide is bound to a solid support and the INVADER oligonucleotide and genomic DNA (or RNA) target are provided in solution. In other embodiments of the present invention, the INVADER oligonucleotide is bound to the support and the probe and target are in solution. In yet other embodiments, both the probe and INVADER oligonucleotides are bound to the solid support. In further embodiments, the target nucleic acid is bound directly or indirectly (e.g., through hybridization to a bound oligonucleotide that is not part of a cleavage structure) to a solid support, and either or both of the probe and INVADER oligonucleotides are provided either in solution, or bound to a support. In still further embodiments, a primary INVADER assay reaction is carried out in solution and one or more components of a secondary reaction are bound to a solid support. In yet other embodiments, all of the components necessary for an INVADER assay reaction, including cleavage agents, are bound to a solid support.

The present invention is not limited to the configurations described herein. Indeed, one skilled in the art recognizes that any number of additional configurations may be utilized. Any configuration that supports a detectable invasive cleavage reaction may be utilized. Additional configurations are identified using any suitable method, including, but not limited to, those disclosed herein.

1. Probe Oligonucleotide Bound

In some embodiments, the probe oligonucleotide is bound to a solid support. In some embodiments, the probe is a labeled Signal Probe oligonucleotide. See FIG. 146 for an overview of the INVADER assay reaction when a FRET signal probe oligonucleotide is bound to a solid support. The signal probe is cleaved to release a signal molecule indicative of the presence of a given target molecule. In some embodiments, the signal molecule is a fluorescence donor in an energy transfer reaction (e.g., FRET), whose emission increases in response to separation from a quenching fluorescence acceptor. In other embodiments, the signal molecule is a fluorescent moiety that is detected only upon its release into solution. It yet other embodiments, the signal molecule is a fluorescently labeled small molecule that is separated from the full length Signal Probe by carrying a distinct charge.

In some embodiments, a system is designed in which no separation steps are required to visualize the signal generated by the reaction. In some embodiments, this is accomplished in the FRET system in which the fluorescence donor remains affixed to the solid support following cleavage of the signal probe (e.g., the reverse FRET oligonucleotides described in FIG. 152). This design has several complexities that stem from the nature of the FRET reaction. The quenching in the FRET signal molecule is only 97-99% efficient (i.e. not all of the energy emitted by the donor will be absorbed by the quencher). To detect the fluorescence of the unquenched donor above the background of the uncleaved probes, it is necessary to cleave 1-3% of the probe molecules. Assuming that in a 100 μm×100 μm area, there are ~$10^8$ probes bound, then ~$10^6$ should be cleaved to generate a signal detectable above the inherent background generated by those probes. Probe cycling in an INVADER assay reaction on a single target molecule can generate approximately 1000-2000 cleaved probe molecules per hour (assuming a turnover rate of 15-30 events/target/min). Roughly 1000 target molecules are required to generate this level of cleaved Signal Probes. Assuming a reaction volume of 1 nL, the necessary target concentration becomes 1 pM, well within the range of the maximum that can be manipulated (e.g., 0.5-2.5 pM). At less than maximal probe densities, it would nonetheless be necessary to deliver at least 10-20 target molecules (i.e. a 10-20 fM solution) to each reaction area to ensure a statistical likelihood that each will contain target. The same target concentration considerations apply to other, non-FRET alternatives, for example, release of a single fluorescent group into solution, with or without a quenching fluorophore and release of a positively charged signal molecule even though <1% cleavage would be detectable with these other methods. Accordingly, in some embodiments, dilute solutions are used in conjunction with longer reaction times (e.g. a 100 fM solution could be applied and the reactions run for 10-24 hours).

2. INVADER Oligonucleotide Bound

In some embodiment of the present invention, the INVADER oligonucleotide is bound to the solid support and the probe oligonucleotide is free in solution. In this emobodiment, there are no restrictions on the length of the INVADER oligonucleotide-target duplex, since the INVADER oligonucleotide does not need to cycle on and off the target, as does the signal probe. Thus, in some embodiments where the INVADER oligonucleotide is bound to a solid support, the INVADER oligonucleotide is used as a "capture" oligonucleotide to concentrate target molecules from solution onto the solid phase through continuous application of sample to the solid support. For example, by applying 1 ml of a 1 mg/ml target solution, it is possible to bind $10^6$-$10^8$ target molecules in a 100 μM×100 μM area. Moreover, because the INVADER oligonucleotide-target interaction is designed to be stable, in some embodiments, the support is washed to remove unbound target and unwanted sample impurities prior to applying the signal probes, enzyme, etc., to ensure even lower background levels. In other embodiments, a capture oligonucleotide complementary to a distinct region in the proximity of the locus being investigated is utilized.

Several possibilities exist for separation of cleaved from uncleaved signal probes reactions where INVADER oligonucleotides are bound the solid support and signal probe olignucleotides are free in solution. In preferred embodiments, a labeling strategy is utilized that makes it possible to chemically differentiate cleaved from uncleaved probe since both full length and cleaved probes are in solution. For example, in some embodiments (e.g., FRET signal probe), full length probe is quenched but the cleavage product generates fluorescent signal. In other embodiment (e.g, CRE), the full length probe is negatively charged but the cleaved probe is positively charged.

However, in some preferred embodiments, CRE separation is utilized. First, the cleaved signal probes generated by the CRE approach are actively captured on a negatively charged electrode. This capture results in partitioning from uncleaved molecules as well as concentration of the labeled, cleaved probes by as much as an order of magnitude. Second, the use of an electric field to capture the cleaved probe eliminates the need to micromachine tiny wells to prevent diffusion of the cleaved probes.

3. Both Probe and INVADER Oligonucleotide Bound

In some embodiments of the present invention, both a probe and an INVADER oligonucleotide are bound to a solid support. See FIG. 147 for an overview of INVADER assay reactions when both a probe and an INVADER oligonucleotide are bound to a solid support. In preferred embodiments, probe and INVADER oligonucleotides are placed in close proximity on the same solid support such that a target nucleic acid may bind both the probe and INVADER oligonucleotides. In some embodiments, the oligonucleotides are attached via spacer molecules in order to improve their accessibility and decrease interactions between oligonucleotides.

In some preferred embodiments, a single INVADER oligonucleotide is configured to allow it to contact and initiate multiple cleavage reactions. For example, in some embodiments, one INVADER oligonucleotide is surrounded on a solid support by multiple Signal Probe oligonucleotides (See e.g., FIG. 147). A target nucleic acid binds to an INVADER and a probe oligonucleotide. The Signal Probe is cleaved (generating signal) and released, leaving the target bound to the INVADER oligonucleotide. This target:INVADER oligonucleotide complex is then able to contact another Signal Probe and promote another cleavage event. In this manner, the signal generated from one target and one INVADER oligonucleotide is amplified.

In other embodiments, the probe and INVADER oligoucleotides are combined in one molecule. An example of such a molecule is shown in FIG. 148. The connection between the probe and INVADER portions of the single molecule may be nucleic acid, or may be a non-nucleic acid linker (e.g., a carbon linker, a peptide chain).

4. Secondary Reaction Bound

In some embodiments, a primary INVADER assay reaction is performed in solution and a secondary reaction is performed on a solid support. Cleaved probes from the primary INVADER assay reaction are contacted with a solid support containing one or more components of a cleavage structure, including but not limited to a secondary target nucleic acid, a secondary probe or a secondary INVADER oligonucleotide. In a preferred embodiment, the component is a one-piece secondary oligonucleotide, or cassette, comprising both a secondary target portion and a secondary probe portion. In a particularly preferred embodiment, the cassette is labeled to allow detection of cleavage of the cassette by a FRET mechanism (See FIG. 149 for an Example of an INVADER reaction utilizing a one piece a secondary oligonucleotide on a solid support). The secondary signal oligonucleotide may be labeled using any suitable method including, but not limited to, those disclosed herein. It will be appreciated that any of the embodiments described above for configuring an INVADER assay reaction on a support may be used in configuring a secondary or subsequent INVADER assay reaction on a support.

5. Target Bound

In some embodiments of the present invention, the target nucleic acid (e.g, genomic DNA) is bound to the solid support. In some embodiments, the INVADER and Probe oligonucleotides are free in solution. In other embodiments, both the target nucleic acid, the INVADER oligonucleotide, and the Probe (e.g, Signal Probe) oligonucleotides are bound. In yet other embodiments, a secondary oligonucleotide (e.g, a FRET oligonucleotide) is included in the reaction. In some embodiments, the FRET oligonucleotide is free in solution. In other embodiments, the FRET oligonucleotide is bound to the solid support.

6. Enzyme Bound

In some embodiments, the cleavage means (e.g., enzyme) is bound to a solid support. In some embodiments, the target nucleic acid, probe oligonucleotide, and INVADER oligonucleotide are provided in solution. In other embodiments, one or more of the nucleic acids is bound to the solid support.

Any suitable method may be used for the attachment of a cleavage enzyme to a solid support, including, but not limited to, covalent attachment to a support (See e.g., Chemukhin and Klenova, Anal. Biochem., 280:178 [2000]), biotinylation of the enzyme and attachment via avidin (See e.g., Suter et al., Immunol. Lett. 13:313 [1986]), and attachment via antibodies (See e.g., Bilkova et al., J. Chromatogr. A, 852:141 [1999]).

D. Spacers

In some embodiments of the present invention, oligonucleotides are attached to a solid support via a spacer or linker molecule. The present invention is not limited to any one mechanism. Indeed, an understanding of the mechanism is not necessary to practice the present invention. Nonetheless, it is contemplated that spacer molecules enhance INVADER assay reactions by improving the accessibility of oligonucleotides and decreasing interactions between oligonucleotides. The use of linkers, which can be incorporated during oligonucleotide synthesis, has been shown to increase hybridization efficiency relative to capture oligonucleotides that contain no linkers (Guo et al., Nucleic Acids Res., 22:5456 [1994]; Maskos and Southern, Nucleic Acids Res., 20:1679 [1992]; Shchepinov et al., Nucleic Acids Research 25:1155 [1997]).

Spacer molecules may be comprised of any suitable material. Preferred materials are those that are stable under reaction conditions utilized and non-reactive with the components of the INVADER assay. Suitable materials include, but are not limited to, carbon chains (e.g., including but not limited to $C_{18}$), poly nucleotides (e.g., including, but not limited to, polyI, polyT, polyG, polyC, and polyA), and polyglycols (e.g., hexaethylene glycol).

Spacer molecules may be of any length. Accordingly in some embodiments, multiple spacer molecules are attached end to end to achieve the desired length spacer. For example, in some embodiments, multiple $C_{18}$ or hexaethylene glycol spacers (e.g., including, but not limited to, 5, 10, or 20 spacer molecules) are combined. The optimum spacer length is dependent on the particular application and solid support used. To determine the appropriate length, different lengths are selected (e.g, 5, 10, or 20 $C_{18}$ or hexaethylene glycol spacers molecules) and reactions are performed as described herein to determine which spacer gives the most efficient reaction.

E. Solid Supports

The present invention is not limited to any one solid support. In some embodiments, reactions are performed on microtiter plates (e.g., polystyrene plates containing either containing 96 or 384 wells). For example, in some embodiments, streptavidin (SA) coated 96-well or 384-well microtiter plates (Boehringer Mannheim Biochemicals, Indianapolis, Ind.) are used as solid supports. In such embodiments, signal can be measured using standard fluorescent, chemiluminescent or colorimetric microtiter plate readers.

In some embodiments, INVADER assay reactions are carried out on particles or beads. The particles can be made of any suitable material, including, but not limited to, latex. In some embodiments, columns containing a particle matrix suitable for attachment of oligonucleotides are used. In a some embodiments, reactions are performed in minicolumns (e.g. DARAS, Tepnel, Cheshire, England). The columns contain microbeads to which oligonucleotides are covalently bound and subsequently used as capture probes or in enzymatic reactions. The use of minicolumns allows approximation of the bound oligonucleotide concentrations that will be attainable in a miniaturized chip format. Oligonucleotide binding is limited by the capacity of the support (i.e. ~$10^{12}$/ cm²). Thus, bound oligonucleotide concentration can only be increased by increasing the surface area to volume ratio of the reaction vessel. For example, one well of a 96-well microtiter plate, with a surface area of ~1 cm² and a volume of 400 µl has a maximal bound oligonucleotide concentration of ~25 nM. On the other hand, a 100 µm×100 µm×100 µM volume in a microchip has a surface area of $10^4$ µm² and a volume of 1 nL, resulting in a bound oligonucleotide concentration of 0.2 µM. Similar increased surface area: volume ratios can be obtained by using microbeads. Given a binding capacity of $\geq 10^{14}$ oligonucleotides in a 30 µl volume, these beads allow bound oligonucleotide concentrations of 0.2-10 µM, i.e. comparable to those anticipated for microchips.

In some embodiments, INVADER reaction are carried out on a HydroGel (Packard Instrument Company, Meriden, Conn.) support. HydroGel is porous 3D hydrophilic polymer matrix. The matrix consists of a film of polyacrylamide polymerized onto a microscope slide. A coupling moiety is co-polymerized into the matrix that permits the immobilization of aminated oligonucleotide molecules by reductive amination. Covalent attachment by amine groups permits the immobilization of nucleic acid probes at specific attachment points (usually their ends), and the hydrogel provides a 3D matrix approximating a bulk solution phase, avoiding a solid/solution phase interface.

In other embodiments, INVADER reactions are conducted on a solid support using a BEADARRAY (Illumina, San Diego, Calif.) technology. The technology combines fiber optic bundles and beads that self-assemble into an array. Each fiber optic bundle contains thousands to millions of individual fibers depending on the diameter of the bundle. Sensors are affixed to each beads in a given batch. The particular molecules on a bead define that bead's function as a sensor. To form an array, fiber optic bundles are dipped into pools of coated beads. The coated beads are drawn into the wells, one bead per well, on the end of each fiber in the bundle. The present invention is not limited to the solid supports described above. Indeed, a variety of other solid supports are contemplated including, but not limited to, glass microscope slides, glass wafers, gold, silicon, microchips, and other plastic, metal, ceramic, or biological surfaces.

F. Surface Coating and Attachment Chemistries

In some embodiments of the present invention, solid supports are coated with a material to aid in the attachment of oligonucleotides. The present invention is not limited to any one surface coating. Indeed, a variety of coatings are contemplated including, but not limited to, those described below.

In some embodiments, solid support INVADER assay reactions are carried out on solid supports coated with gold. The gold can be attached to any suitable solid support including, but not limited to, microparticles, microbeads, microscope slides, and microtiter plates. In some embodiments, the gold is functionalized with thiol-reactive maleimide moieties that can be reacted with thiol modified DNA (See e.g., Frutos et al., Nuc. Acid. Res., 25:4748 [1997]; Frey and Corn, Analytical Chem, 68:3187 [1996]; Jordan et al., Analytical Chem, 694939 [1997]; and U.S. Pat. No. 5,472,881; herein incorporated by reference).

In other embodiments, solid support INVADER assay reactions are carried out on supports coated with silicon. The silicon can be attached to any suitable support, including, but not limited to, those described above and in the illustrative examples provided below.

Additionally, in some embodiments, solid supports are coated with a molecule (e.g., a protein) to aid in the attachment of nucleic acids. The present invention is not limited to any particular surface coating. Any suitable material may be utilized including, but not limited to, proteins such as streptavidin. Thus, in some embodiments, oligonucleotides are attached to solid supports via terminal biotin or $NH_2$-mediated linkages included during oligonucleotide synthesis. INVADER oligonucleotides are attached to the support at their 5' ends and Signal Probes are attached at their 3' ends. In some embodiment, oligonucleotides are attached via a linker proximal to the attachment point. In a preferred embodiment, attachment is via a 40 atom linker with a low negative charge density as described in (Shchepinov et al., Nucleic Acids Research 25:1155 [1997]).

In other embodiments, oligonucleotides are attached to solid support via antigen:antibody interaction. For Example, in some embodiments, an antigen (e.g., protein A or Protein G) is attached to a solid support and IgG is attached to oligonucleotides. In other embodiments, IgG is attached to a solid support and an antigen (e.g., Protein A or Protein G) is attached to oligonucleotides.

G. Addressing of Oligonucleotides

In some embodiments, oligonucleotides are targeted to specific sites on the solid support. Any number of techniques for the addressing of oligonucleotides may be utilized. For example, in some embodiments, solid support surfaces are electrically polarized at one given site in order to attract a particular DNA molecule (e.g, Nanogen, Calif.). In other embodiments, a pin tool may be used to load the array mechanically (Shalon, Genome Methods, 6:639 [1996]. In other embodiments, ink jet technology is used to print oligonucleotides onto an active surface (e.g., O'Donnelly-Maloney et al., Genetic Analysis: Biomolecular Engineering, 13:151 [1996]).

In some preferred embodiments utilizing gold surfaces, the gold surfaces are further modified to create addressable DNA arrays by photopatterning self-assembled monolayers to form hydrophilic and hydrophobic regions. Alkanethiol chemistry is utilized to create self-assembled monolayers (Nuzzo et al., JACS, 105:4481 [1983]). DNA is placed on the hydrophilic regions by using an automated robotic device (e.g., a pin-loading tool).

H. Detection

In some embodiments of the present invention, products of an INVADER assay reaction are detected using any suitable method. For example, in some embodiments, a signal probe is utilized for the detection of cleavage products. In some embodiments, the signal probe comprises a fluorescent moiety and a quenching moiety (e.g., a FRET signal probe) Cleavage result in the separation of the quenching group from the fluorescent group, thus generating signal. In other embodiments, cleavage is detected using charge-based separation (e.g, the uncleaved and cleaved signal probes have different charges).

However, the present invention is not limited to any particular detection method. Indeed, a variety of additional methods are contemplated, including, but not limited to, scanning probe microscopy, atomic force microscopy, confocal microscopy, scanning tunneling microscopy, angle-dependent x-ray photoelectron spectroscopy, and Auger electron spectroscopy. For example, in some embodiments, thiol-modified oligonucleotides are attached to gold surfaces (See e.g., U.S. Pat. No. 5,472,881; herein incorporated by reference) and detection of cleavage is accomplished using scanning tunneling microscopy or atomic force microscopy. These techniques make it possible to visualize individual atoms in a DNA molecule. For example, in some embodiments, cleaved probe molecules are distinguished from uncleaved probe molecules on the basis of size. Instruments for the microscopy techniques disclosed herein are available commercially (e.g., Thermomicroscopes, Sunnyvale, Calif.).

In other embodiments, signal probe cleavage may be characterized by ellipsometry. For example, in some embodiments, signal probes are labeled with a biotin or other hapten allowing attachement of an enzyme such as peroxidase. Attachment of a peroxidase to a surface allows deposition of an insoluble thin film that can be detected and quantitated using an instrument such as a fixed polarizer ellipsometer (See e.g., Ostroff et al., Cleinical Chem., 45:1659 [1999]), which can sensitively detect perturbations in the layer such as those created by cleavage of a labeled probe. One skilled in the relevant art recognizes that any number of additional suitable methods may be utilized to detect products of an INVADER assay reaction.

I. Activity Assays

In some embodiments, the parameters of solid-phase INVADER system are optimized using a model system. Initial characterization of INVADER assay performance may be done using short double-stranded PCR products or synthetic oligonucleotide as substrates. In some embodiments, the hybridization reaction time and temperature may be optimized. In other embodiments, sheared genomic DNA may be added to investigate interference with the specific reaction from any competing sequences present.

In some embodiments, it may be useful to compare the performance of variously configured INVADER assay reactions in the presence of a solid support. Different reaction supports may differently affect the rate of cleavage observed in an INVADER assay reaction, e.g., due to differences in the interactions between the support and one or more reactions components. For example, significant differences in the cleavage rate may indicate impaired access of the enzyme to the cleavage sites bound to the support, or may indicate some other inhibition of the enzyme. In some embodiments, a support may be pre-washed before exposure to the reaction components, as one way of determining if the support has inhibiting factors that may be removed by washing. In other embodiments, the support may be pre-treated with carriers, (e.g., agents that are chemically similar to reaction components but which are not intended to participate in the INVADER assay reaction), for the purpose or neutralizing or occupying support factors that might otherwise interact with reaction components. For example, supports may be pre-treated with a protein such as BSA or a nucleic acid such as yeast tRNA, both commonly used carriers, to reduce unintended interactions between the support and its associated factors and the protein or nucleic acid components of the INVADER assay reaction, respectively. In some embodiments, carriers are added directly to the reaction mixture, instead of, or in addition to their use in pretreatment of a support. Carriers may be used alone, as described above, or they may be combined (e.g., protein and nucleic acid carriers may be combined in a single pretreatment of a support). Use of carriers in the treatment of supports and in the optimization of reactions is not limited to those cited above. Many carriers for protein and nucleic acid-based reactions are known in the art.

EXAMPLES

The following examples serve to illustrate certain preferred embodiments and aspects of the present invention and are not to be construed as limiting the scope thereof.

In the disclosure which follows, the following abbreviations apply: Afu (*Archaeoglobus fulgidus*); Mth (*Methanobacterium thermoautotrophicum*); Mja (*Methanococcus jannaschii*); Pfu (*Pyrococcus furiosus*); Pwo (*Pyrococcus woesei*); Taq (*Thermus aquaticus*); Taq DNAP, DNAPTaq, and Taq PolI (*T. aquaticus* DNA polymerase I); DNAPStf (the Stoffel fragment of DNAPTaq); DNAPEc1 (*E. coli* DNA polymerase I); Tth (*Thermus thermophilus*); Ex. (Example); Fig. (Figure); ° C. (degrees Centigrade); g (gravitational field); hr (hour); min (minute); olio (oligonucleotide); rxn (reaction); vol (volume); w/v (weight to volume); v/v (volume to volume); BSA (bovine serum albumin); CTAB (cetyl-trimethylammonium bromide); HPLC (high pressure liquid chromatography); DNA (deoxyribonucleic acid); p (plasmid); µl (microliters); ml (milliliters); µg (micrograms); mg (milligrams); M (molar); mM (milliMolar); µM (microMolar); pmoles (picomoles); amoles (attomoles); zmoles (zeptomoles); nm (nanometers); kdal (kilodaltons); OD (optical density); EDTA (ethylene diamine tetra-acetic acid); FITC (fluorescein isothiocyanate); SDS (sodium dodecyl sulfate); $NaPO_4$ (sodium phosphate); NP-40 (Nonidet P-40); Tris (tris (hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); ATCC (American Type Culture Collection, Rockville, Md.); Coriell (Coriell Cell Repositories, Camden, N.J.); DSMZ (Deutsche Sammlung von Mikroorganismen und Zellculturen, Braunschweig, Germany); Ambion (Ambion, Inc., Austin, Tex.); Boehringer (Boehringer Mannheim Biochemical, Indianapolis, Ind.); MJ Research (MJ Research, Watertown, Mass.; Sigma (Sigma Chemical Company, St. Louis, Mo.); Dynal (Dynal A. S., Oslo, Norway); Gull (Gull Laboratories, Salt Lake City, Utah); Epicentre (Epicentre Technologies, Madison, Wis.); Lampire (Biological Labs., Inc., Coopersberg, Pa.); MJ Research (MJ Research, Watertown, Mass.); National Biosciences (National Biosciences, Plymouth, Minn.); NEB (New England Biolabs, Beverly, Mass.); Novagen (Novagen, Inc., Madison, Wis.); Promega (Promega, Corp., Madison, Wis.); Stratagene (Stratagene Cloning Systems, La Jolla, Calif.); Clonetech (Clonetech, Palo Alto, Calif.) Pharmacia (Pharmacia, Piscataway, N.J.); Milton Roy (Milton Roy, Rochester, N.Y.); Amersham (Amersham International, Chicago, Ill.); and USB (U.S. Biochemical, Cleveland, Ohio). Glen Research (Glen Research, Sterling, Va.); Coriell (Coriell Cell Repositories, Camden, N.J.); Gentra (Gentra, Minneapolis, Minn.); Third Wave Technologies (Third Wave Technologies, Madison, Wis.); PerSeptive Biosystems (PerSeptive Biosystems, Framington, Mass.); Microsoft (Microsoft, Redmond, Wash.); Qiagen (Qiagen, Valencia, Calif.); Molecular Probes (Molecular Probes, Eugene, Oreg.); VWR (VWR Scientific,); Advanced Biotechnologies (Advanced Biotechnologies, INC., Columbia, Md.); and Perkin Elmer (also known as PE Biosytems and Applied Biosystems, Foster City, Calif.).

Example 1

Characteristics of Native Thermostable DNA Polymerases

A. 5' Nuclease Activity of DNAPTaq

Figure 5:
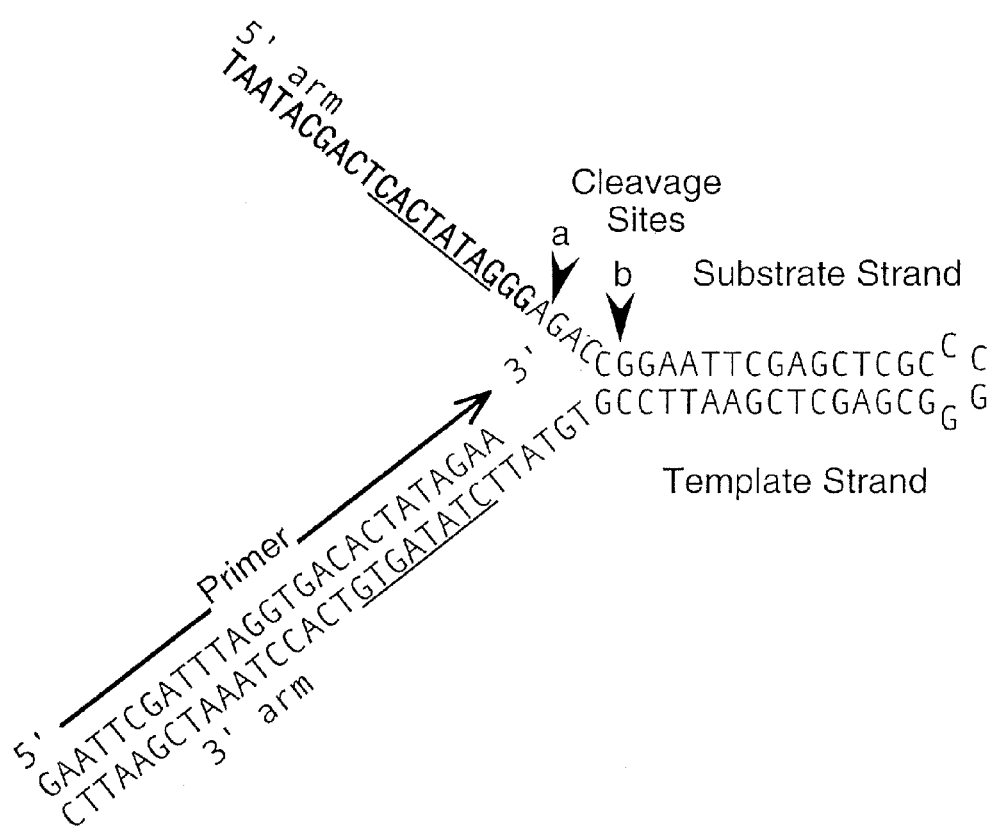
FIG. 5 depicts a structure which cannot be amplified using DNAPTaq; this Figure shows SEQ ID NO:17 (primer) and SEQ ID NO:15 (hairpin).

During the polymerase chain reaction (PCR) (Saiki et al., Science 239:487 [1988]; Mullis and Faloona, Meth. Enzymol., 155:335 [1987]), DNAPTaq is able to amplify many, but not all, DNA sequences. One sequence that cannot be amplified using DNAPTaq is shown in FIG. 5 (Hairpin structure is SEQ ID NO:15, FIG. 5 also shows a primer: SEQ ID NO:17)

This DNA sequence has the distinguishing characteristic of being able to fold on itself to form a hairpin with two single-stranded arms, which correspond to the primers used in PCR.

To test whether this failure to amplify is due to the 5' nuclease activity of the enzyme, the abilities of DNAPTaq and DNAPStf to amplify this DNA sequence during 30 cycles of PCR were compared. Synthetic oligonucleotides were obtained from The Biotechnology Center at the University of Wisconsin-Madison. The DNAPTaq and DNAPStf were from Perkin Elmer (i.e., AMPLITAQ DNA polymerase and the Stoffel fragment of AMPLITAQ DNA polymerase). The substrate DNA comprised the hairpin structure shown in FIG. 6 cloned in a double-stranded form into pUC19. The primers used in the amplification are listed as SEQ ID NOS:16-17. Primer SEQ ID NO:17 is shown annealed to the 3' arm of the hairpin structure in FIG. 5. Primer SEQ ID NO:16 is shown as the first 20 nucleotides in bold on the 5' arm of the hairpin in FIG. 5.

Polymerase chain reactions comprised 1 ng of supercoiled plasmid target DNA, 5 pmoles of each primer, 40 μM each dNTP, and 2.5 units of DNAPTaq or DNAPStf, in a 50 μl solution of 10 mM Tris•Cl pH 8.3. The DNAPTaq reactions included 50 mM KCl and 1.5 mM $MgCl_2$. The temperature profile was 95° C. for 30 sec., 55° C. for 1 min. and 72° C. for 1 min., through 30 cycles. Ten percent of each reaction was analyzed by gel electrophoresis through 6% polyacrylamide (cross-linked 29:1) in a buffer of 45 mM Tris•Borate, pH 8.3, 1.4 mM EDTA.

Figure 6:
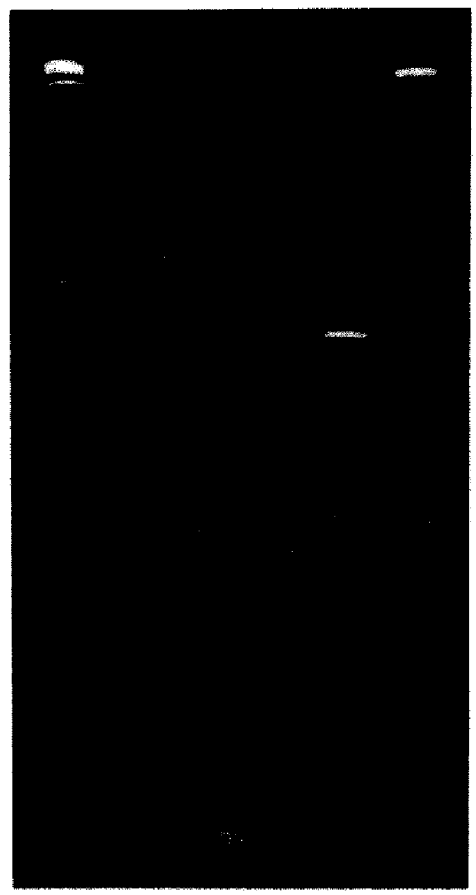
FIG. 6 is a ethidium bromide-stained gel demonstrating attempts to amplify a bifurcated duplex using either DNAPTaq or DNAPStf (i.e., the Stoffel fragment of DNAPTaq).

The results are shown in FIG. 6. The expected product was made by DNAPStf (indicated simply as "S") but not by DNAPTaq (indicated as "T"). It was concluded that the 5' nuclease activity of DNAPTaq is responsible for the lack of amplification of this DNA sequence.

Figure 7:
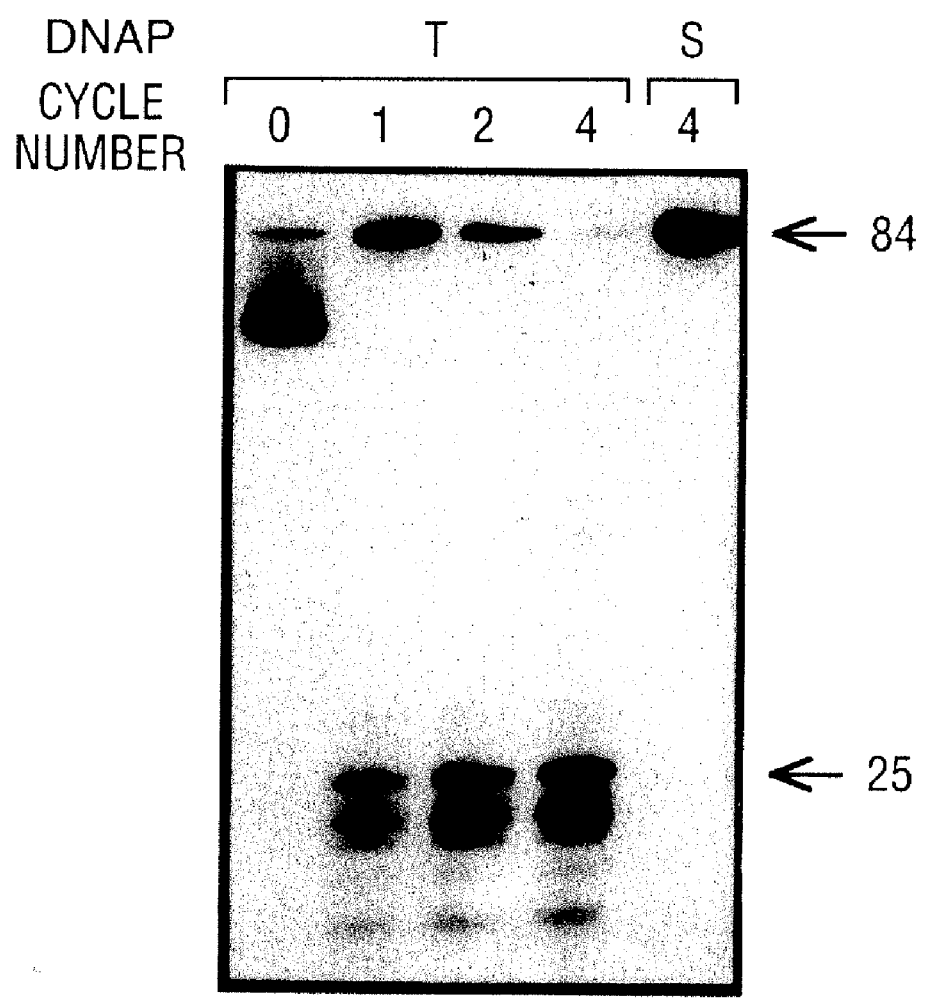
FIG. 7 is an autoradiogram of a gel analyzing the cleavage of a bifurcated duplex by DNAPTaq and lack of cleavage by DNAPStf.

To test whether the 5' unpaired nucleotides in the substrate region of this structured DNA are removed by DNAPTaq, the fate of the end-labeled 5' arm during four cycles of PCR was compared using the same two polymerases (FIG. 7). The hairpin templates, such as the one described in FIG. 5, were made using DNAPStf and a $^{32}P$-5'-end-labeled primer. The 5'-end of the DNA was released as a few large fragments by DNAPTaq but not by DNAPStf. The sizes of these fragments (based on their mobilities) show that they contain most or all of the unpaired 5' arm of the DNA. Thus, cleavage occurs at or near the base of the bifurcated duplex. These released fragments terminate with 3' OH groups, as evidenced by direct sequence analysis, and the abilities of the fragments to be extended by terminal deoxynucleotidyl transferase.

Figures 8A, 8B:
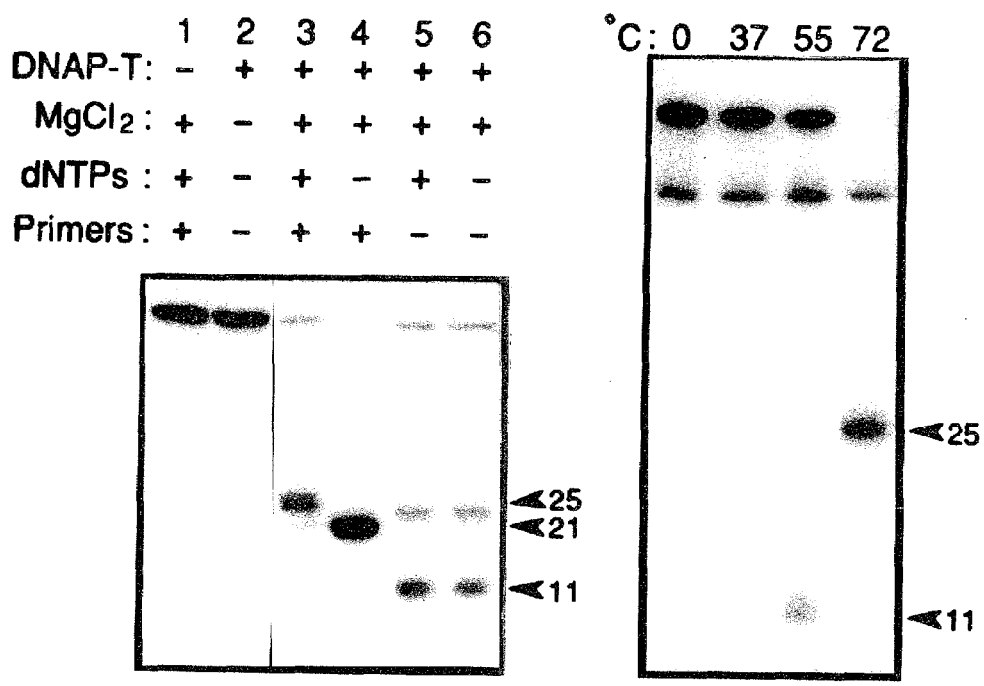
FIGS. 8A-B are a set of autoradiograms of gels analyzing cleavage or lack of cleavage upon addition of different reaction components and change of incubation temperature during attempts to cleave a bifurcated duplex with DNAPTaq.
Figure 8A:
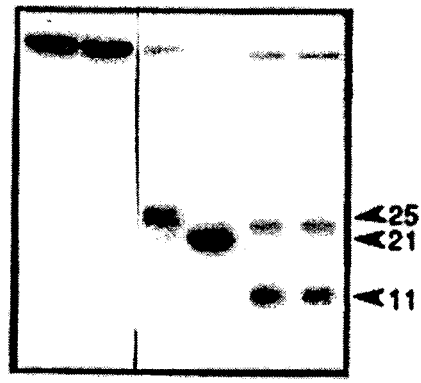
Figure 8B:
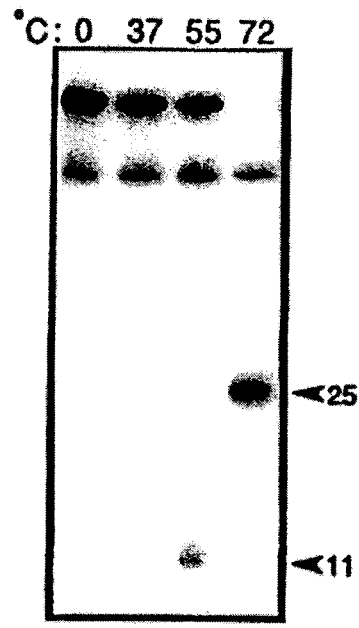
Figure 11A:
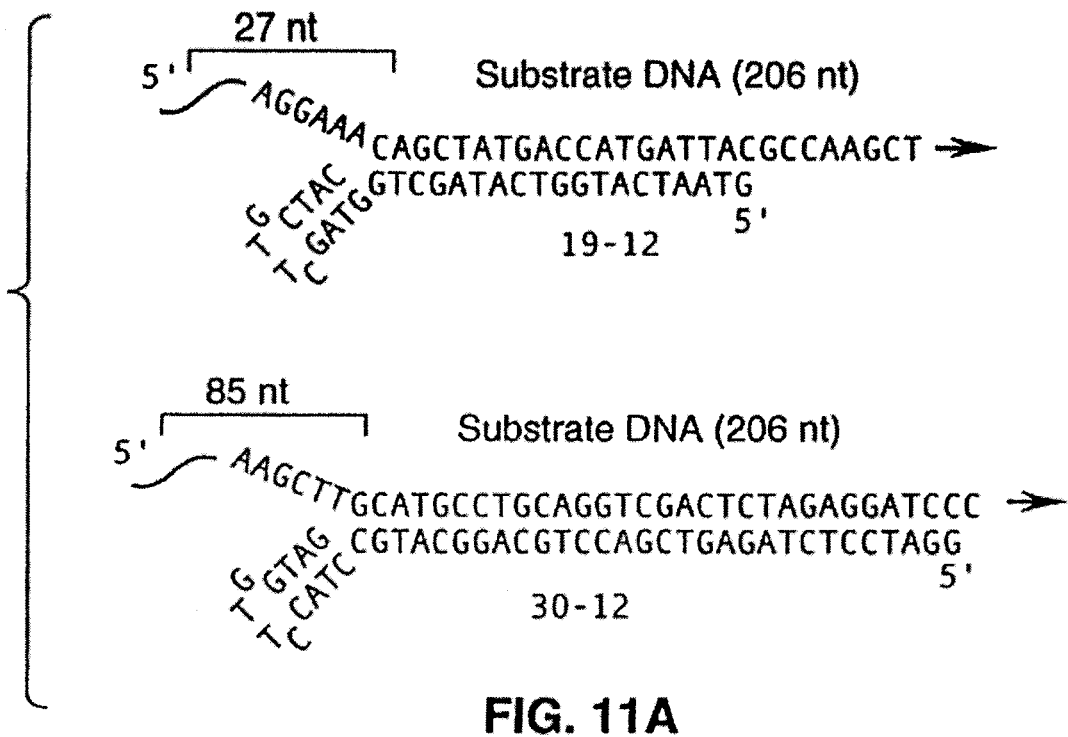
Figure 12A:
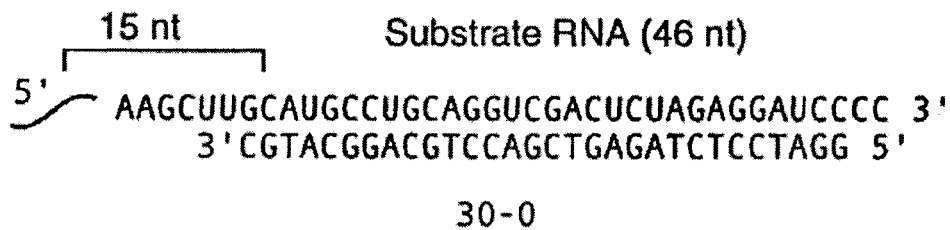
Figure 11B:
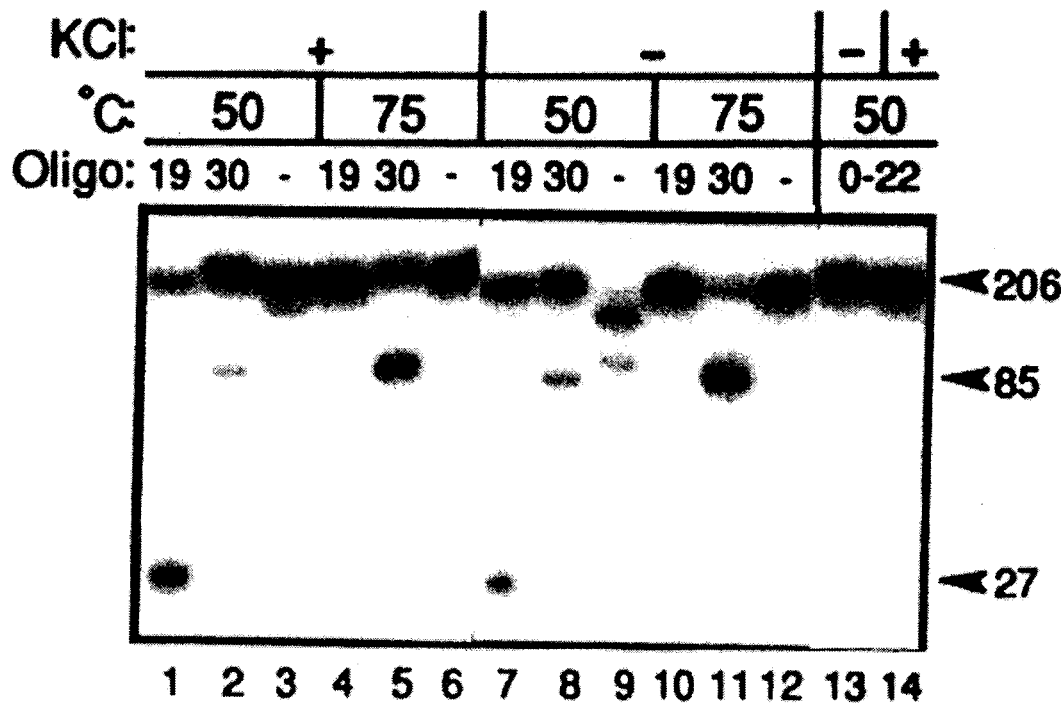
Figure 12B:
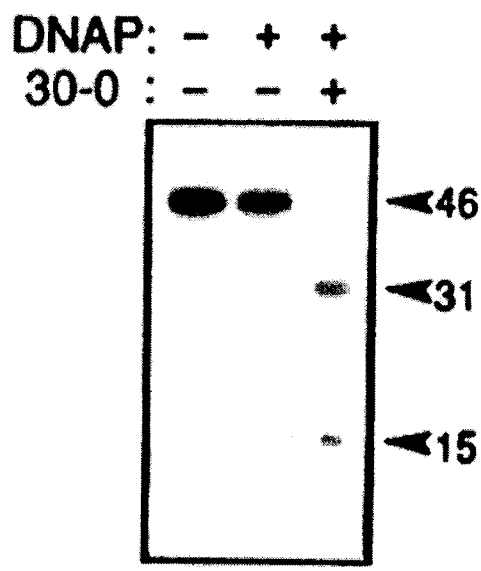
Figure 13:
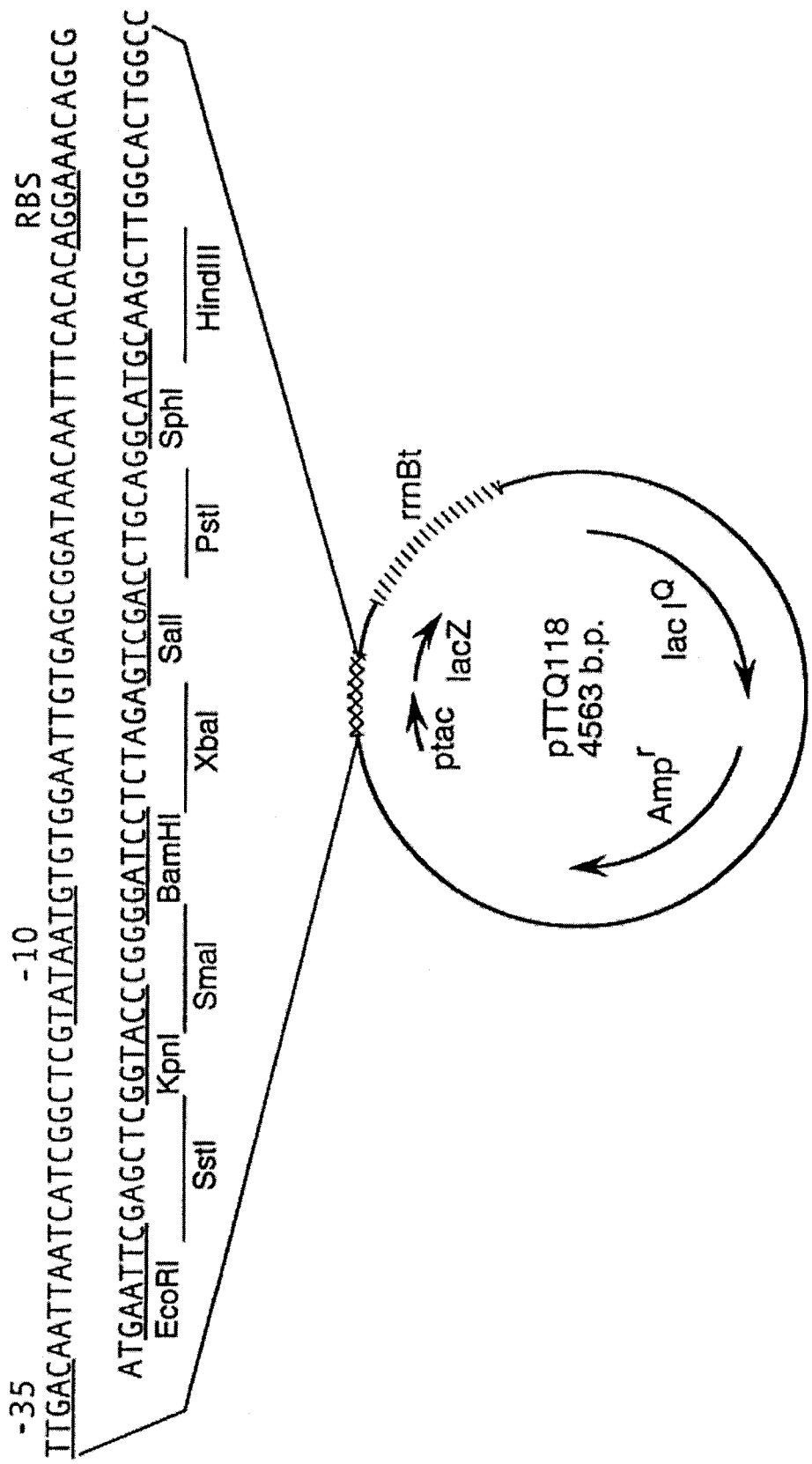
Figure 14:
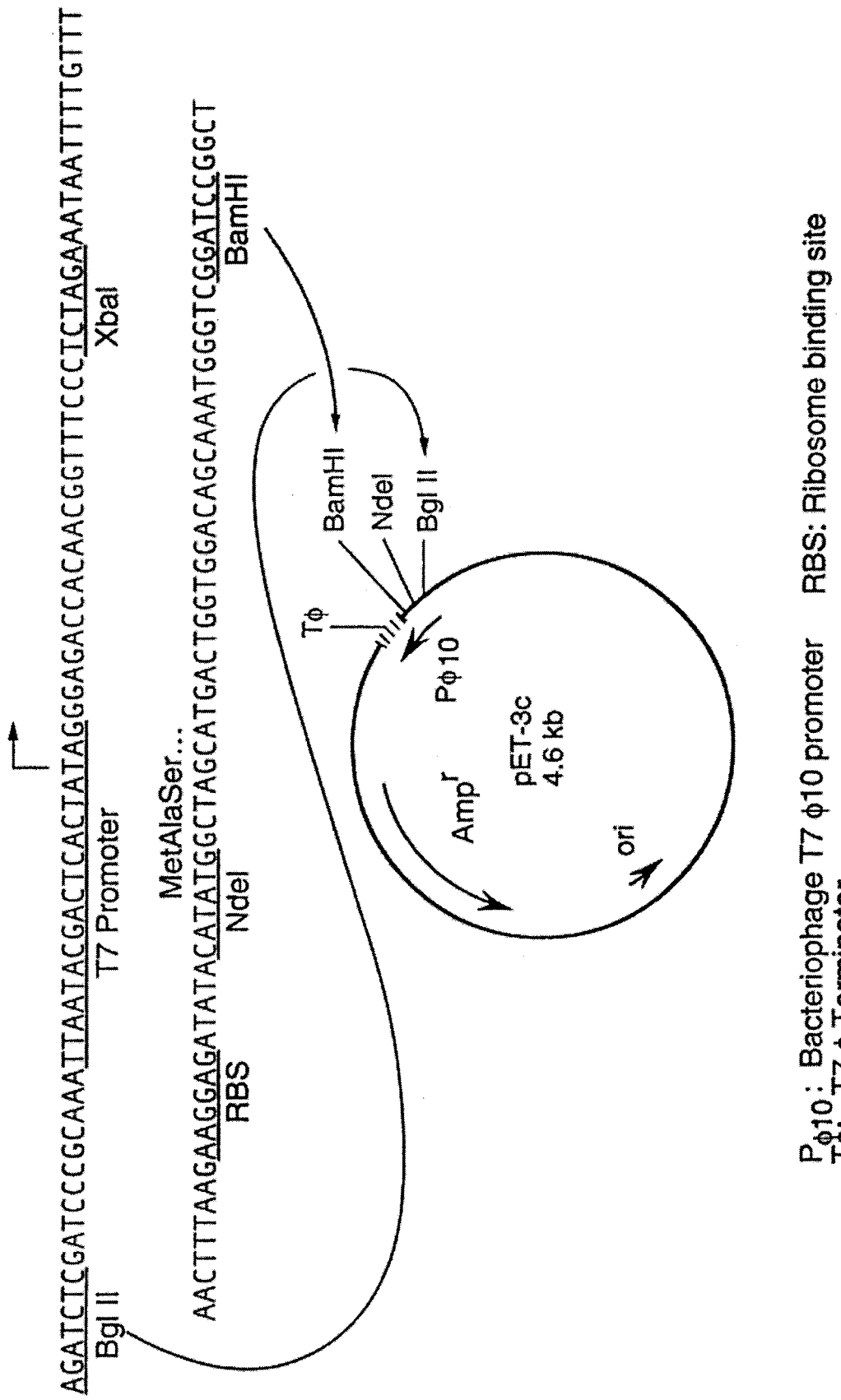
Figure 15A:
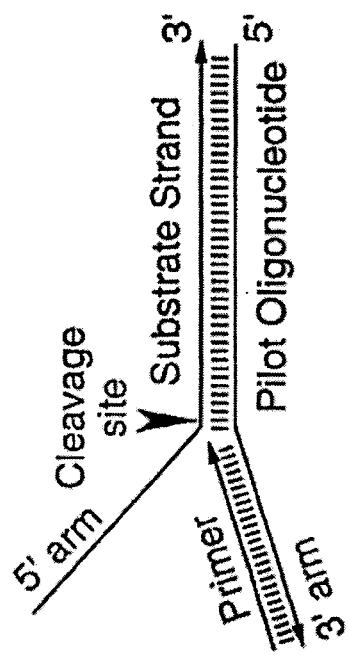
Figure 15B:
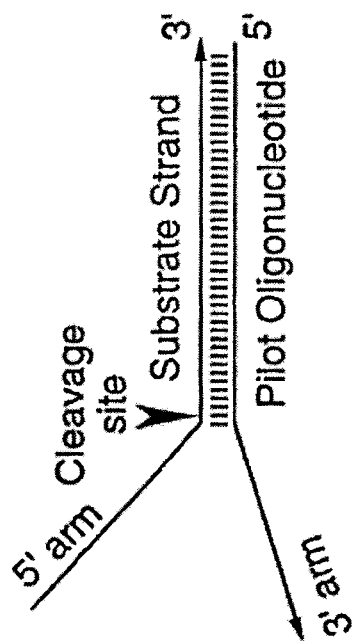
Figure 15C:
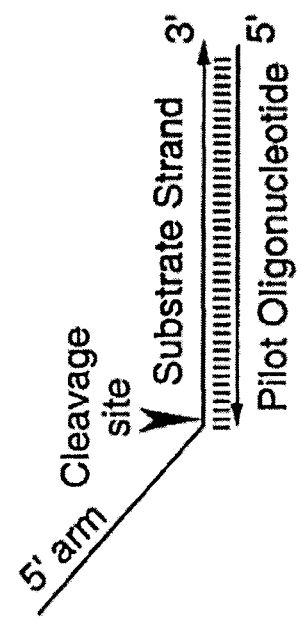
Figure 15D:
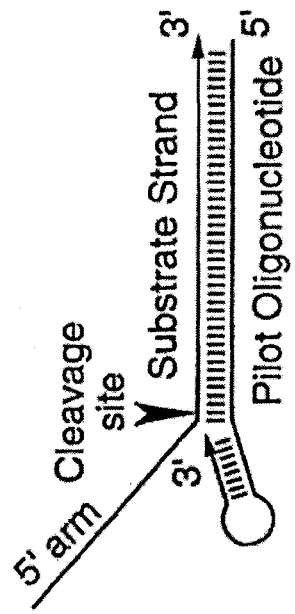
Figure 15E:
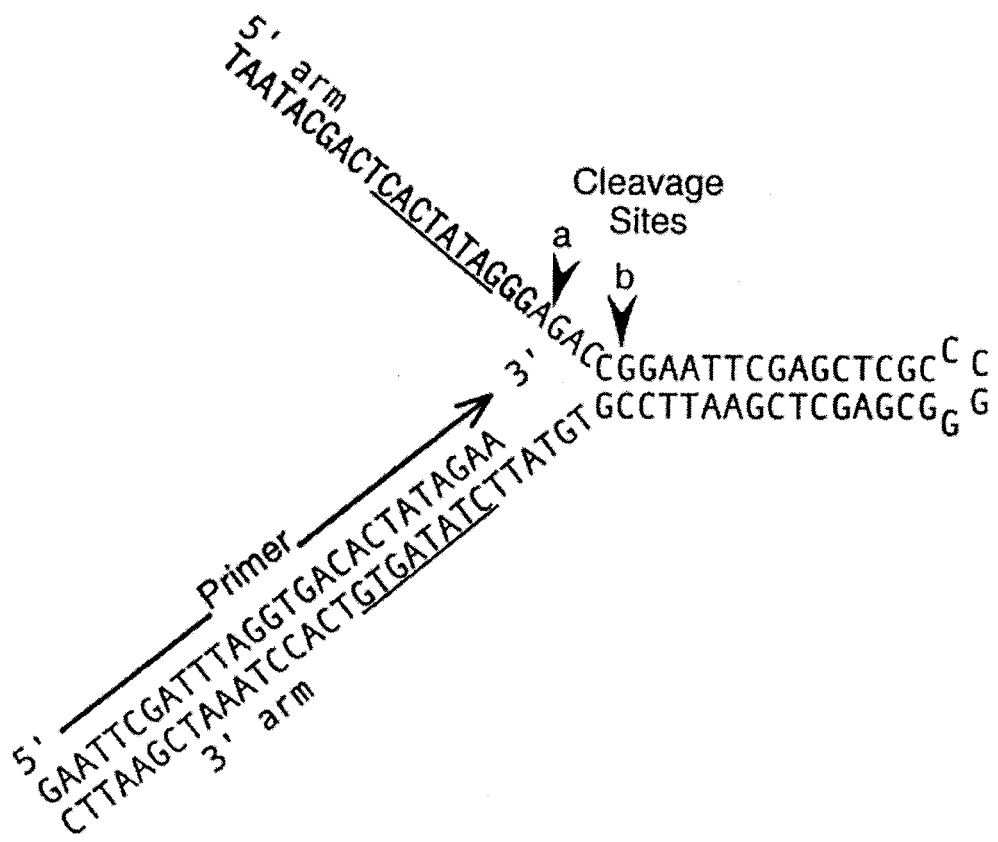
Figure 16:
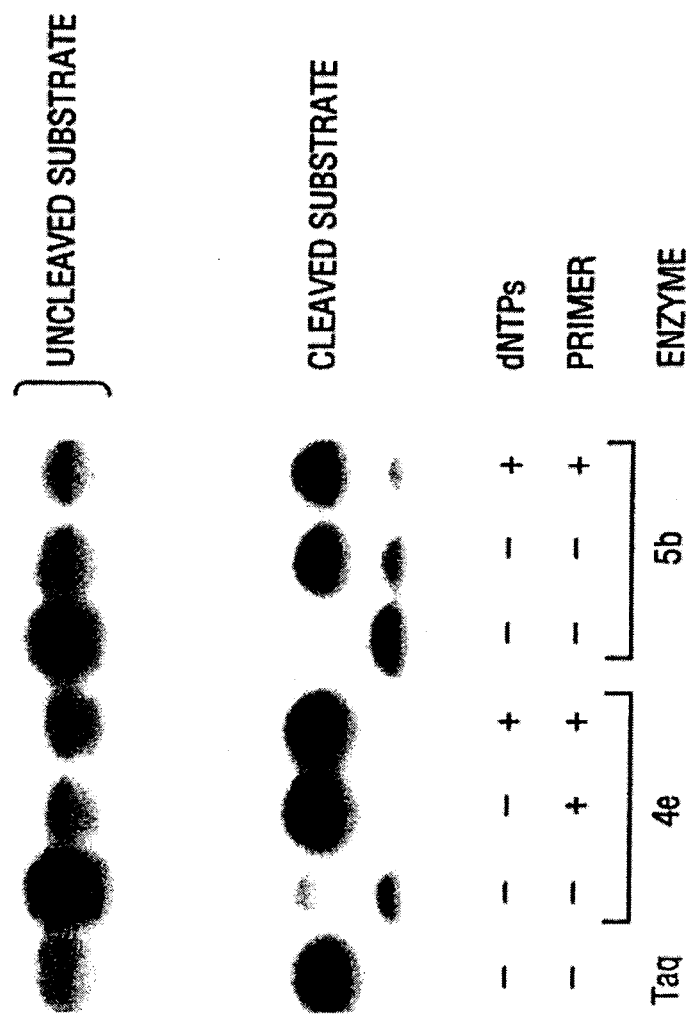

FIGS. 8-10 show the results of experiments designed to characterize the cleavage reaction catalyzed by DNAPTaq. Unless otherwise specified, the cleavage reactions comprised 0.01 pmoles of heat-denatured, end-labeled hairpin DNA (with the unlabeled complementary strand also present), 1 pmole primer (complementary to the 3' arm) and 0.5 units of DNAPTaq (estimated to be 0.026 pmoles) in a total volume of 10 μl of 10 mM Tris-Cl, ph 8.5, 50 mM KCl and 1.5 mM $MgCl_2$. As indicated, some reactions had different concentrations of KCl, and the precise times and temperatures used in each experiment are indicated in the individual Figures. The reactions that included a primer used the one shown in FIG. 5 (SEQ ID NO:17). In some instances, the primer was extended to the junction site by providing polymerase and selected nucleotides.

Reactions were initiated at the final reaction temperature by the addition of either the $MgCl_2$ or enzyme. Reactions were stopped at their incubation temperatures by the addition of 8 μl of 95% formamide with 20 mM EDTA and 0.05% marker dyes. The $T_m$ calculations listed were made using the Oligo™ primer analysis software from National Biosciences, Inc. These were determined using 0.25 μM as the DNA concentration, at either 15 or 65 mM total salt (the 1.5 mM $MgCl_2$ in all reactions was given the value of 15 mM salt for these calculations).

FIG. 8 is an autoradiogram containing the results of a set of experiments and conditions on the cleavage site. FIG. 8A is a determination of reaction components that enable cleavage. Incubation of 5'-end-labeled hairpin DNA was for 30 minutes at 55° C., with the indicated components. The products were resolved by denaturing polyacrylamide gel electrophoresis and the lengths of the products, in nucleotides, are indicated. FIG. 8B describes the effect of temperature on the site of cleavage in the absence of added primer. Reactions were incubated in the absence of KCl for 10 minutes at the indicated temperatures. The lengths of the products, in nucleotides, are indicated.

Surprisingly, cleavage by DNAPTaq requires neither a primer nor dNTPs (See FIG. 8A). Thus, the 5' nuclease activity can be uncoupled from polymerization. Nuclease activity requires magnesium ions, though manganese ions can be substituted, albeit with potential changes in specificity and activity. Neither zinc nor calcium ions support the cleavage reaction. The reaction occurs over a broad temperature range, from 25° C. to 85° C., with the rate of cleavage increasing at higher temperatures.

Still referring to FIG. 8, the primer is not elongated in the absence of added dNTPs. However, the primer influences both the site and the rate of cleavage of the hairpin. The change in the site of cleavage (FIG. 8A) apparently results from disruption of a short duplex formed between the arms of the DNA substrate. In the absence of primer, the sequences indicated by underlining in FIG. 5 could pair, forming an extended duplex. Cleavage at the end of the extended duplex would release the 11 nucleotide fragment seen on the FIG. 8A lanes with no added primer. Addition of excess primer (FIG. 8A, lanes 3 and 4) or incubation at an elevated temperature (FIG. 8B) disrupts the short extension of the duplex and results in a longer 5' arm and, hence, longer cleavage products.

The location of the 3' end of the primer can influence the precise site of cleavage. Electrophoretic analysis revealed that in the absence of primer (FIG. 8B), cleavage occurs at the end of the substrate duplex (either the extended or shortened form, depending on the temperature) between the first and second base pairs. When the primer extends up to the base of the duplex, cleavage also occurs one nucleotide into the duplex. However, when a gap of four or six nucleotides exists between the 3' end of the primer and the substrate duplex, the cleavage site is shifted four to six nucleotides in the 5' direction.

FIG. 9 describes the kinetics of cleavage in the presence (FIG. 9A) or absence (FIG. 9B) of a primer oligonucleotide. The reactions were run at 55° C. with either 50 mM KCl (FIG. 9A) or 20 mM KCl (FIG. 9B). The reaction products were resolved by denaturing polyacrylamide gel electrophoresis and the lengths of the products, in nucleotides, are indicated. "M", indicating a marker, is a 5' end-labeled 19-nt oligonucleotide. Under these salt conditions, FIGS. 9A and 9B indicate that the reaction appears to be about twenty times faster in the presence of primer than in the absence of primer. This effect on the efficiency may be attributable to proper alignment and stabilization of the enzyme on the substrate.

The relative influence of primer on cleavage rates becomes much greater when both reactions are run in 50 mM KCl. In the presence of primer, the rate of cleavage increases with KCl concentration, up to about 50 mM. However, inhibition of this reaction in the presence of primer is apparent at 100 mM and is complete at 150 mM KCl. In contrast, in the absence of primer the rate is enhanced by concentration of KCl up to 20 mM, but it is reduced at concentrations above 30 mM. At 50 mM KCl, the reaction is almost completely inhibited. The inhibition of cleavage by KCl in the absence of primer is affected by temperature, being more pronounced at lower temperatures.

Recognition of the 5' end of the arm to be cut appears to be an important feature of substrate recognition. Substrates that lack a free 5' end, such as circular M13 DNA, cannot be cleaved under any conditions tested. Even with substrates having defined 5' arms, the rate of cleavage by DNAPTaq is influenced by the length of the arm. In the presence of primer and 50 mM KCl, cleavage of a 5' extension that is 27 nucleotides long is essentially complete within 2 minutes at 55° C. In contrast, cleavages of molecules with 5' arms of 84 and 188 nucleotides are only about 90% and 40% complete after 20 minutes. Incubation at higher temperatures reduces the inhibitory effects of long extensions indicating that secondary structure in the 5' arm or a heat-labile structure in the enzyme may inhibit the reaction. A mixing experiment, run under conditions of substrate excess, shows that the molecules with long arms do not preferentially tie up the available enzyme in non-productive complexes. These results may indicate that the 5' nuclease domain gains access to the cleavage site at the end of the bifurcated duplex by moving down the 5' arm from one end to the other. Longer 5' arms would be expected to have more adventitious secondary structures (particularly when KCl concentrations are high), which would be likely to impede this movement.

Cleavage does not appear to be inhibited by long 3' arms of either the substrate strand target molecule or pilot nucleic acid, at least up to 2 kilobases. At the other extreme, 3' arms of the pilot nucleic acid as short as one nucleotide can support cleavage in a primer-independent reaction, albeit inefficiently. Fully paired oligonucleotides do not elicit cleavage of DNA templates during primer extension.

The ability of DNAPTaq to cleave molecules even when the complementary strand contains only one unpaired 3' nucleotide may be useful in optimizing allele-specific PCR. PCR primers that have unpaired 3' ends could act as pilot oligonucleotides to direct selective cleavage of unwanted templates during preincubation of potential template-primer complexes with DNAPTaq in the absence of nucleoside triphosphates.

B. 5' Nuclease Activities of Other DNAPs

To determine whether other 5' nucleases in other DNAPs would be suitable for the present invention, an array of enzymes, several of which were reported in the literature to be free of apparent 5' nuclease activity, were examined. The ability of these other enzymes to cleave nucleic acids in a structure-specific manner was tested using the hairpin substrate shown in FIG. 5 under conditions reported to be optimal for synthesis by each enzyme.

DNAPEc1 and DNAP Klenow were obtained from Promega; the DNAP of *Pyrococcus furious* ("Pfu", Bargseid et al., Strategies 4:34 [1991]) was from Stratagene; the DNAP of *Thermococcus litoralis* ("Tli", Vent™(exo-), Perler et al., Proc. Natl. Acad. Sci. USA 89:5577 [1992] was from New England Biolabs; the DNAP of *Thermus flavus* ("Tfl", Kaledin et al., Biokhimiya 46:1576 [1981] was from Epicentre Technologies; and the DNAP of *Thermus thermophilus* ("Tth", Carballeira et al., Biotechn., 9:276 [1990]; Myers et al., Biochem., 30:7661 (1991)] was from U.S. Biochemicals.

0.5 units of each DNA polymerase was assayed in a 20 μl reaction, using either the buffers supplied by the manufacturers for the primer-dependent reactions, or 10 mM Tris•Cl, pH 8.5, 1.5 mM MgCl$_2$, and 20 mM KCl. Reaction mixtures were at held 72° C. before the addition of enzyme.

Figures 10A, 10B:
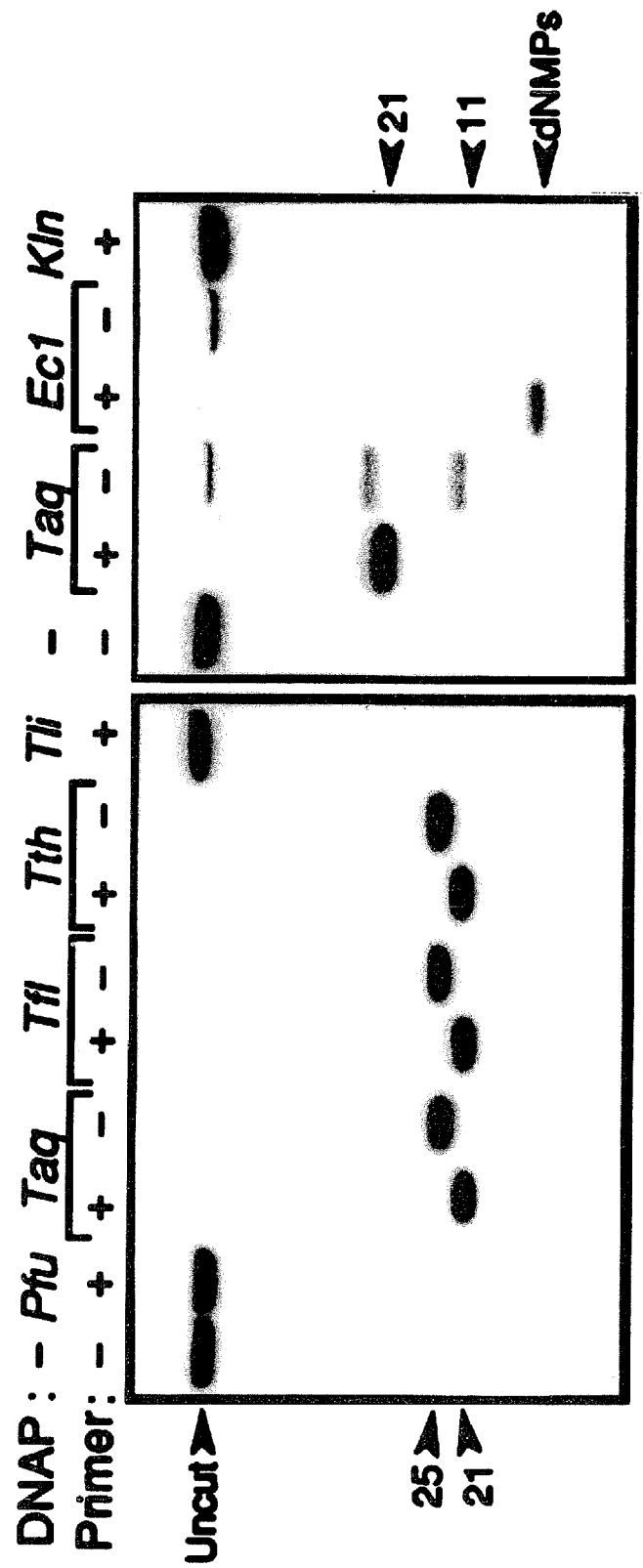
FIGS. 10A-B are a set of autoradiograms of gels demonstrating attempts to cleave a bifurcated duplex (with and without primer) with various DNAPs.

FIG. 10 is an autoradiogram recording the results of these tests. FIG. 10A demonstrates reactions of endonucleases of DNAPs of several thermophilic bacteria. The reactions were incubated at 55° C. for 10 minutes in the presence of primer or at 72° C. for 30 minutes in the absence of primer, and the products were resolved by denaturing polyacrylamide gel electrophoresis. The lengths of the products, in nucleotides, are indicated. FIG. 10B demonstrates endonucleolytic cleavage by the 5' nuclease of DNAPEc1. The DNAPEc1 and DNAP Klenow reactions were incubated for 5 minutes at 37° C. Note the light band of cleavage products of 25 and 11 nucleotides in the DNAPEc1 lanes (made in the presence and absence of primer, respectively). FIG. 8A also demonstrates DNAPTaq reactions in the presence (+) or absence (−) of primer. These reactions were run in 50 mM and 20 mM KCl, respectively, and were incubated at 55° C. for 10 minutes.

Referring to FIG. 10A, DNAPs from the eubacteria *Thermus thermophilus* and *Thermus flavus* cleave the substrate at the same place as DNAPTaq, both in the presence and absence of primer. In contrast, DNAPs from the archaebacteria *Pyrococcus furiosus* and *Thermococcus litoralis* are unable to cleave the substrates endonucleolytically. The DNAPs from *Pyrococcus furious* and *Thermococcus litoralis* share little sequence homology with eubacterial enzymes (Ito et al., Nucl. Acids Res. 19:4045 (1991); Mathur et al., Nucl. Acids. Res. 19:6952 (1991); see also Perler et al.). Referring to FIG. 10B, DNAPEc1 also cleaves the substrate, but the resulting cleavage products are difficult to detect unless the 3' exonuclease is inhibited. The amino acid sequences of the 5' nuclease domains of DNAPEc1 and DNAPTaq are about 38% homologous (Gelfand, supra).

The 5' nuclease domain of DNAPTaq also shares about 19% homology with the 5' exonuclease encoded by gene 6 of bacteriophage T7 (Dunn et al, J. Mol. Biol., 166:477 [1983]). This nuclease, which is not covalently attached to a DNAP polymerization domain, is also able to cleave DNA endonucleolytically, at a site similar or identical to the site that is cut by the 5' nucleases described above, in the absence of added primers.

C. Transcleavage

Figure 11A:
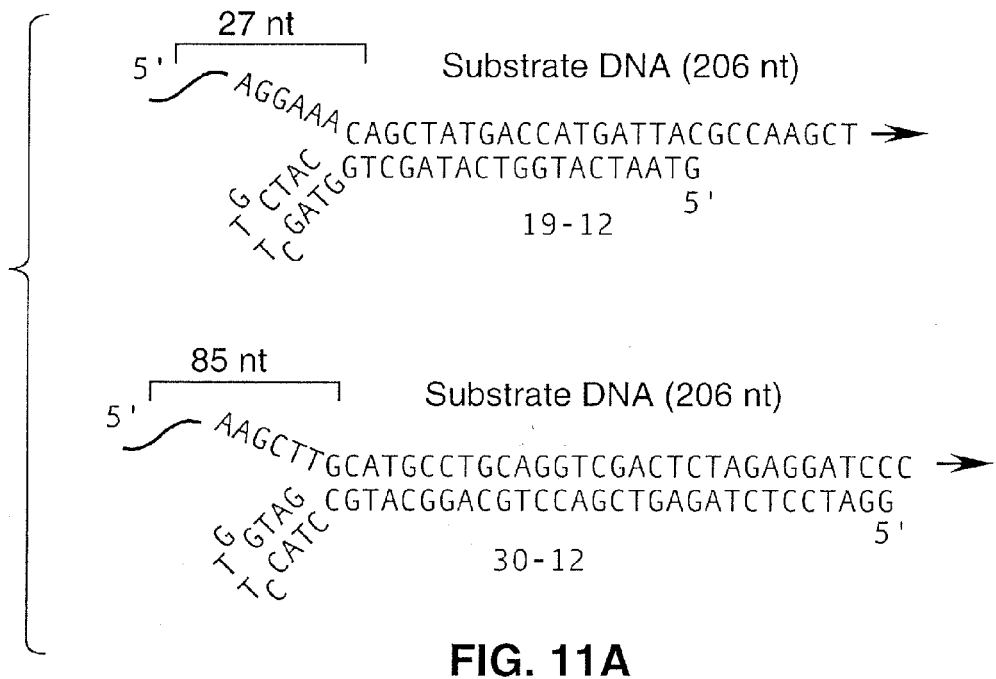
FIG. 11A shows the substrate and oligonucleotides (19-12 [SEQ ID NO:18] and 30-12 [SEQ ID NO:19]) used to test the specific cleavage of substrate DNAs targeted by pilot oligonucleotides (SEQ ID NO:27).

The ability of a 5' nuclease to be directed to cleave efficiently at any specific sequence was demonstrated in the following experiment. A partially complementary oligonucleotide termed a "pilot oligonucleotide" was hybridized to sequences at the desired point of cleavage. The non-complementary part of the pilot oligonucleotide provided a structure analogous to the 3' arm of the template (see FIG. 5), whereas the 5' region of the substrate strand became the 5' arm. A primer was provided by designing the 3' region of the pilot so that it would fold on itself creating a short hairpin with a stabilizing tetra-loop (Antao et al, Nucl. Acids Res. 19:5901 [1991]). Two pilot oligonucleotides are shown in FIG. 11A. Oligonucleotides 19-12 (SEQ ID NO:18), 30-12 (SEQ ID NO:19) and 30-0 (SEQ ID NO:20) are 31, 42 or 30 nucleotides long, respectively. However, oligonucleotides 19-12 (SEQ ID NO:18) and 34-19 (SEQ ID NO:19) have only 19 and 30 nucleotides, respectively, that are complementary to different sequences in the substrate strand. The pilot oligonucleotides are calculated to melt off their complements at about 50° C. (19-12) and about 75° C. (30-12). Both pilots have 12 nucleotides at their 3' ends, which act as 3' arms with base-paired primers attached.

To demonstrate that cleavage could be directed by a pilot oligonucleotide, a single-stranded target DNA with DNAPTaq was incubated in the presence of two potential pilot oligonucleotides. The transcleavage reactions, where the target and pilot nucleic acids are not covalently linked, includes 0.01 pmoles of single end-labeled substrate DNA, 1 unit of DNAPTaq and 5 pmoles of pilot oligonucleotide in a volume of 20 µl of the same buffers. These components were combined during a one minute incubation at 95° C., to denature the PCR-generated double-stranded substrate DNA, and the temperatures of the reactions were then reduced to their final incubation temperatures. Oligonucleotides 30-12 and 19-12 can hybridize to regions of the substrate DNAs that are 85 and 27 nucleotides from the 5' end of the targeted strand.

Figure 19:
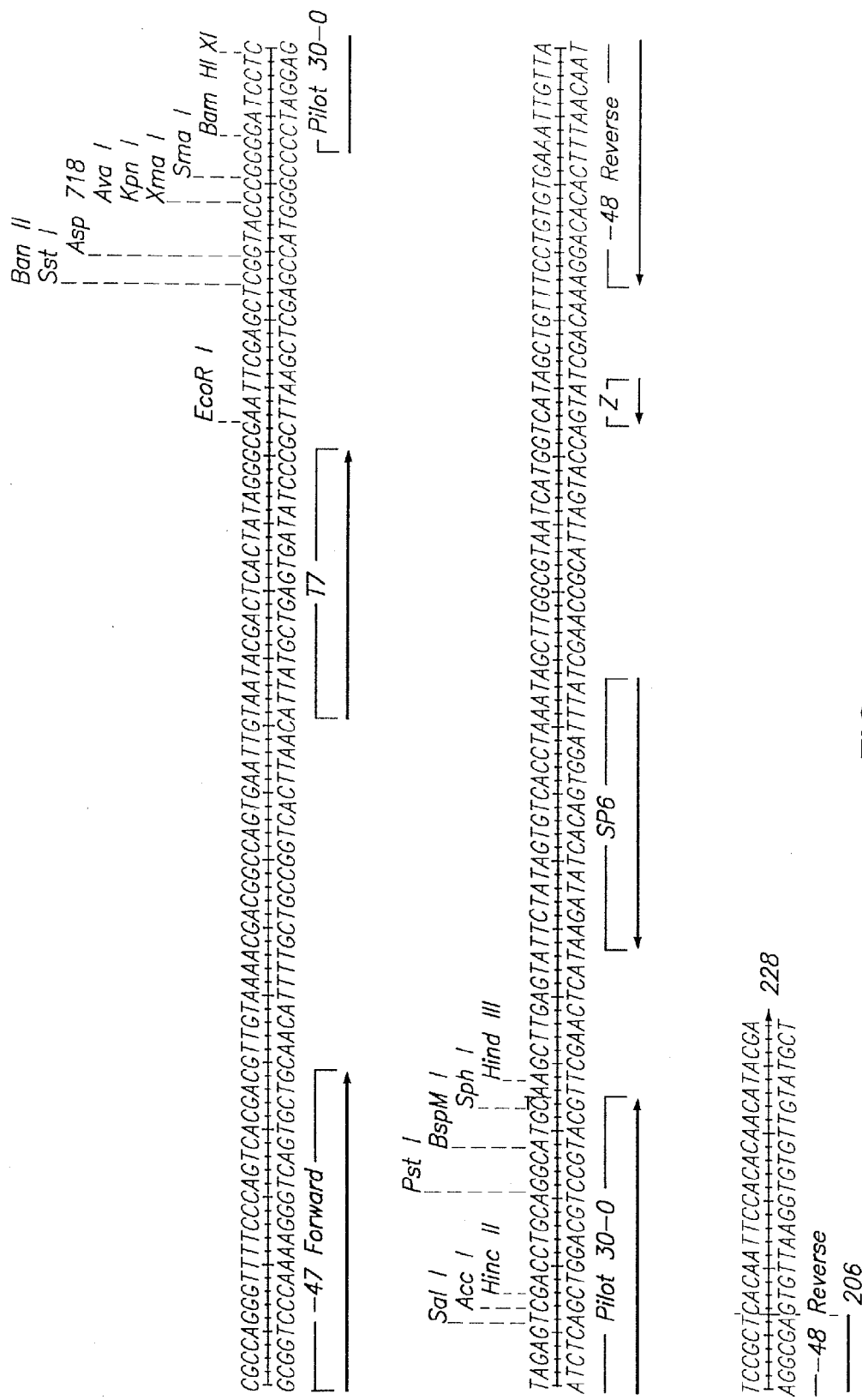
FIG. 19 provides the complete 206-mer duplex sequence (SEQ ID NO:27) employed as a substrate for the 5' nucleases of the present invention FIGS. 20A and B show the cleavage of linear nucleic acid substrates (based on the 206-mer of FIG. 21) by wild type DNAPs and 5' nucleases isolated from *Thermus aquaticus* and *Thermus flavus*.

FIG. 19 shows the complete 206-mer sequence (SEQ ID NO:27). The 206-mer was generated by PCR. The M13/pUC 24-mer reverse sequencing (−48) primer and the M13/pUC sequencing (−47) primer from NEB (catalogue nos. 1233 and 1224 respectively) were used (50 pmoles each) with the pGEM3z(f+) plasmid vector (Promega) as template (10 ng) containing the target sequences. The conditions for PCR were as follows: 50 µM of each dNTP and 2.5 units of Taq DNA polymerase in 100 µl of 20 mM Tris-Cl, pH 8.3, 1.5 mM $MgCl_2$, 50 mM KCl with 0.05% Tween-20 and 0.05% NP-40. Reactions were cycled 35 times through 95° C. for 45 seconds, 63° C. for 45 seconds, then 72° C. for 75 seconds. After cycling, reactions were finished off with an incubation at 72° C. for 5 minutes. The resulting fragment was purified by electrophoresis through a 6% polyacrylamide gel (29:1 cross link) in a buffer of 45 mM Tris-Borate, pH 8.3, 1.4 mM EDTA, visualized by ethidium bromide staining or autoradiography, excised from the gel, eluted by passive diffusion, and concentrated by ethanol precipitation.

Figure 11B:
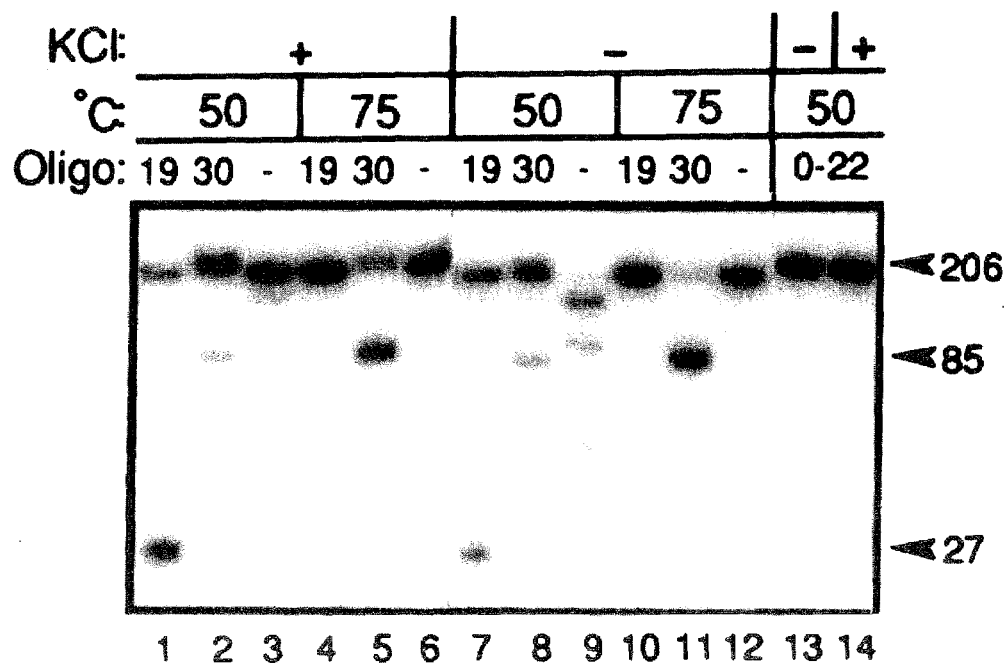
FIG. 11B shows an autoradiogram of a gel showing the results of cleavage reactions using the substrates and oligonucleotides shown FIG. 12A.

Cleavage of the substrate DNA occurred in the presence of the pilot oligonucleotide 19-12 at 50° C. (FIG. 11B, lanes 1 and 7) but not at 75° C. (lanes 4 and 10). In the presence of oligonucleotide 30-12 cleavage was observed at both temperatures. Cleavage did not occur in the absence of added oligonucleotides (lanes 3, 6 and 12) or at about 80° C. even though at 50° C. adventitious structures in the substrate allowed primer-independent cleavage in the absence of KCl (FIG. 11B, lane 9). A non-specific oligonucleotide with no complementarity to the substrate DNA did not direct cleavage at 50° C., either in the absence or presence of 50 mM KCl (lanes 13 and 14). Thus, the specificity of the cleavage reactions can be controlled by the extent of complementarity to the substrate and by the conditions of incubation.

D. Cleavage of RNA

Figure 12A:
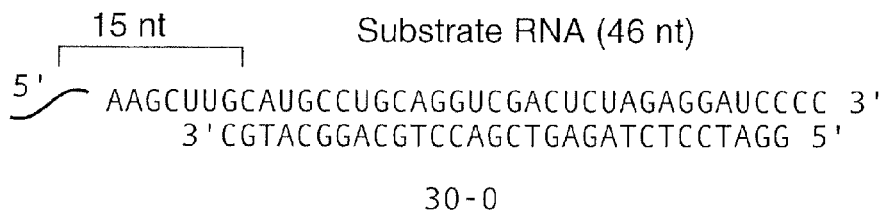
FIG. 12A shows the substrate and ohigonucleotide (30-0 [SEQ ID NO:20]) used to test the specific cleavage of a substrate RNA targeted by a pilot oligonucleotide (SEQ ID NO:411).

A shortened RNA version of the sequence used in the transcleavage experiments discussed above was tested for its ability to serve as a substrate in the reaction. The RNA is cleaved at the expected place, in a reaction that is dependent upon the presence of the pilot oligonucleotide. The RNA substrate, made by T7 RNA polymerase in the presence of ($\alpha$-$^{32}$P)UTP, corresponds to a truncated version of the DNA substrate used in FIG. 11B. Reaction conditions were similar to those in used for the DNA substrates described above, with 50 mM KCl; incubation was for 40 minutes at 55° C. The pilot oligonucleotide used is termed 30-0 (SEQ ID NO:20) and is shown in FIG. 12A.

Figure 12B:
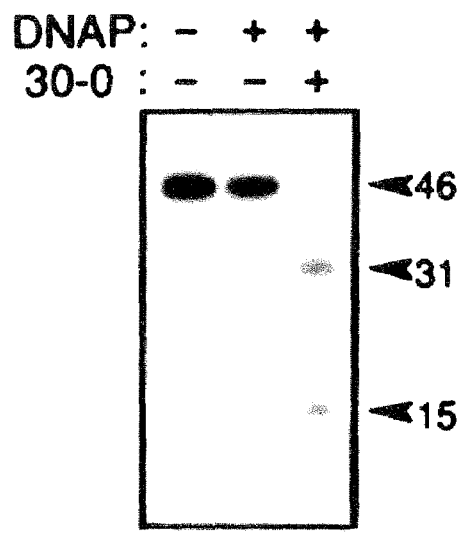

The results of the cleavage reaction is shown in FIG. 13B. The reaction was run either in the presence or absence of DNAPTaq or pilot oligonucleotide as indicated in FIG. 12B.

Strikingly, in the case of RNA cleavage, a 3' arm is not required for the pilot oligonucleotide. It is very unlikely that this cleavage is due to previously described RNaseH, which would be expected to cut the RNA in several places along the 30 base-pair long RNA-DNA duplex. The 5' nuclease of DNAPTaq is a structure-specific RNaseH that cleaves the RNA at a single site near the 5' end of the heteroduplexed region.

It is surprising that an oligonucleotide lacking a 3' arm is able to act as a pilot in directing efficient cleavage of an RNA target because such oligonucleotides are unable to direct efficient cleavage of DNA targets using native DNAPs. However, some 5' nucleases of the present invention (for example, clones E, F and G of FIG. 4) can cleave DNA in the absence of a 3' arm. In other words, a non-extendable cleavage structure is not required for specific cleavage with some 5' nucleases of the present invention derived from thermostable DNA polymerases.

Tests were then conducted to determine whether cleavage of an RNA template by DNAPTaq in the presence of a fully complementary primer could help explain why DNAPTaq is unable to extend a DNA oligonucleotide on an RNA template, in a reaction resembling that of reverse transcriptase. Another thermophilic DNAP, DNAPTth, is able to use RNA as a template, but only in the presence of Mn++, so it was predicted that this enzyme would not cleave RNA in the presence of this cation. Accordingly, an RNA molecule was incubated with an appropriate pilot oligonucleotide in the presence of DNAPTaq or DNAPTth, in buffer containing either Mg++ or Mn++. As expected, both enzymes cleaved the RNA in the presence of Mg++. However, DNAPTaq, but not DNAPTth, degraded the RNA in the presence of Mn++. It was concluded that the 5' nuclease activities of many DNAPs may contribute to their inability to use RNA as templates.

Example 2

Generation of 5' Nucleases from Thermostable DNA Polymerases

Thermostable DNA polymerases were generated which have reduced synthetic activity, an activity that is an undesirable side-reaction during DNA cleavage in the detection assay of the invention, yet have maintained thermostable nuclease activity. The result is a thermostable polymerase which cleaves nucleic acids DNA with extreme specificity.

Type A DNA polymerases from eubacteria of the genus *Thermus* share extensive protein sequence identity (90% in the polymerization domain, using the Lipman-Pearson method in the DNA analysis software from DNAStar, WI) and behave similarly in both polymerization and nuclease assays. Therefore, the genes for the DNA polymerase of *Thermus aquaticus* (DNAPTaq) and *Thermus flavus* (DNAPTfl) are used as representatives of this class. Polymerase genes from other eubacterial organisms, such as *Thermus thermophilus, Thermus* sp., *Thermotoga maritima, Thermosipho africanus* and *Bacillus stearothermophilus* are equally suitable. The DNA polymerases from these thermophilic organisms are capable of surviving and performing at elevated temperatures, and can thus be used in reactions in which temperature is used as a selection against non-specific hybridization of nucleic acid strands.

The restriction sites used for deletion mutagenesis, described below, were chosen for convenience. Different sites situated with similar convenience are available in the *Thermus thermophilus* gene and can be used to make similar constructs with other Type A polymerase genes from related organisms.

A. Creation of 5' Nuclease Constructs

1. Modified DNAPTaq Genes

The first step was to place a modified gene for the Taq DNA polymerase on a plasmid under control of an inducible promoter. The modified Taq polymerase gene was isolated as follows: The Taq DNA polymerase gene was amplified by polymerase chain reaction from genomic DNA from *Thermus aquaticus*, strain YT-1 (Lawyer et al., supra), using as primers the oligonucleotides esdcribed in SEQ ID NOS:13-14. The resulting fragment of DNA has a recognition sequence for the restriction endonuclease EcoRI at the 5' end of the coding sequence and a BglII sequence at the 3' end. Cleavage with BglII leaves a 5' overhang or "sticky end" that is compatible with the end generated by BamHI. The PCR-amplified DNA was digested with EcoRI and BamHI. The 2512 bp fragment containing the coding region for the polymerase gene was gel purified and then ligated into a plasmid which contains an inducible promoter.

Figure 13:
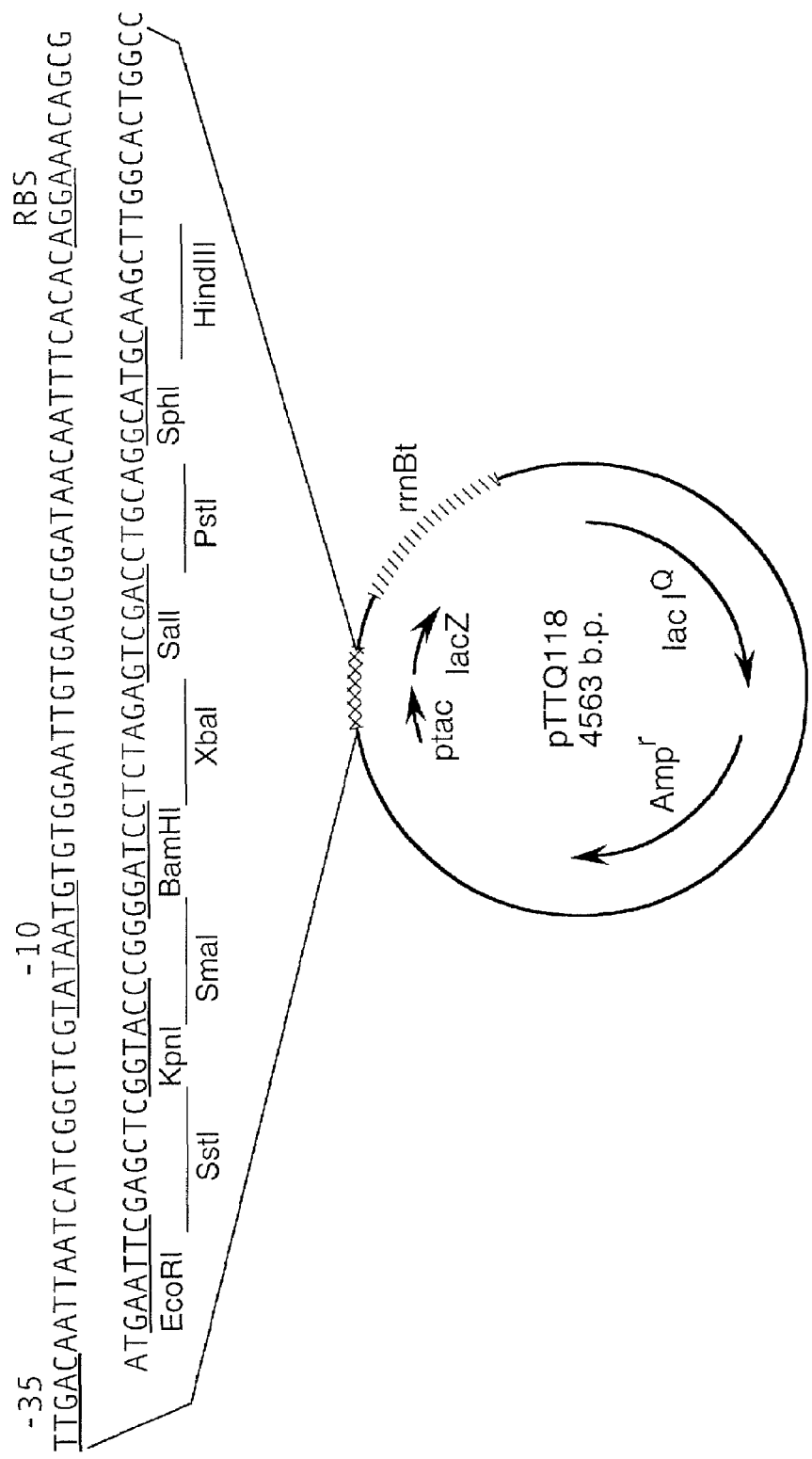
FIG. 13 is a diagram of vector pTTQ18 (SEQ ID NO:412).

In one embodiment of the invention, the pTTQ18 vector, which contains the hybrid trp-lac (tac) promoter, was used (Stark, Gene 5:255 [1987]) and shown in FIG. 13.

The tac promoter is under the control of the *E. coli* lac repressor. Repression allows the synthesis of the gene product to be suppressed until the desired level of bacterial growth has been achieved, at which point repression is removed by addition of a specific inducer, isopropyl-β-D-thiogalactopyranoside (IPTG). Such a system allows the expression of foreign proteins that may slow or prevent growth of transformants.

Bacterial promoters, such as tac, may not be adequately suppressed when they are present on a multiple copy plasmid. If a highly toxic protein is placed under control of such a promoter, the small amount of expression leaking through can be harmful to the bacteria. In another embodiment of the invention, another option for repressing synthesis of a cloned gene product was used. The non-bacterial promoter, from bacteriophage T7, found in the plasmid vector series pET-3 was used to express the cloned mutant Taq polymerase genes (FIG. 15; Studier and Moffatt, J. Mol. Biol., 189:113 [1986]). This promoter initiates transcription only by T7 RNA polymerase. In a suitable strain, such as BL21 (DE3)pLYS, the gene for this RNA polymerase is carried on the bacterial genome under control of the lac operator. This arrangement has the advantage that expression of the multiple copy gene (on the plasmid) is completely dependent on the expression of T7 RNA polymerase, which is easily suppressed because it is present in a single copy.

For ligation into the pTTQ18 vector (FIG. 13), the PCR product DNA containing the Taq polymerase coding region (mutTaq, clone 4B, SEQ ID NO:21) was digested with EcoRI and BglII and this fragment was ligated under standard "sticky end" conditions (Sambrook et al. *Molecular Cloning*, Cold Spring Harbor Laboratory Press, Cold Spring Harbor, pp. 1.63-1.69 [1989]) into the EcoRI and BamHI sites of the plasmid vector pTTQ18. Expression of this construct yields a translational fusion product in which the first two residues of the native protein (Met-Arg) are replaced by three from the vector (Met-Asn-Ser), but the remainder of the natural protein would not change. The construct was transformed into the JM109 strain of *E. coli* and the transformants were plated under incompletely repressing conditions that do not permit growth of bacteria expressing the native protein. These plating conditions allow the isolation of genes containing pre-existing mutations, such as those that result from the infidelity of Taq polymerase during the amplification process.

Using this amplification/selection protocol, a clone (depicted in FIG. 3B) containing a mutated Taq polymerase gene (mutTaq, clone 3B) was isolated. The mutant was first detected by its phenotype, in which temperature-stable 5' nuclease activity in a crude cell extract was normal, but polymerization activity was almost absent (approximately less than 1% of wild type Taq polymerase activity).

DNA sequence analysis of the recombinant gene showed that it had changes in the polymerase domain resulting in two amino acid substitutions: an A to G change at nucleotide position 1394 causes a Glu to Gly change at amino acid position 465 (numbered according to the natural nucleic and amino acid sequences, SEQ ID NOS:1 and 4) and another A to G change at nucleotide position 2260 causes a Gln to Arg change at amino acid position 754. Because the Gln to Gly mutation is at a nonconserved position and because the Glu to Arg mutation alters an amino acid that is conserved in virtually all of the known Type A polymerases, this latter mutation is most likely the one responsible for curtailing the synthesis activity of this protein. The nucleotide sequence for the FIG. 3B construct is given in SEQ ID NO:21. The enzyme encoded by this sequence is referred to as Cleavase® A/G.

Figures 3A, 3B, 3C, 3D, 3E, 3F, 3G:
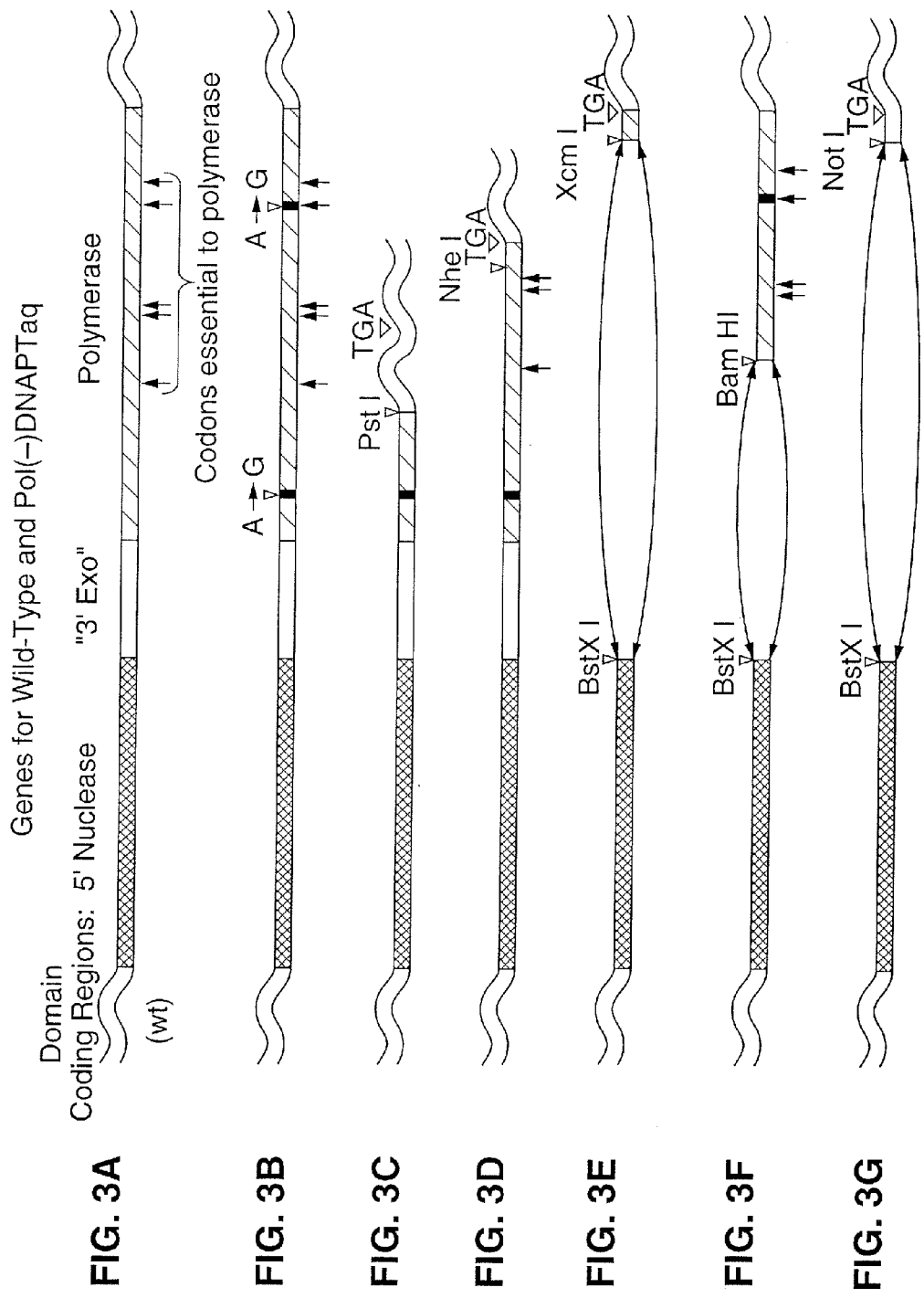
FIGS. 3A-G are a set of diagrams of wild-type and synthesis-deficient DNAPTaq genes.

Subsequent derivatives of DNAPTaq constructs were made from the mutTaq gene, thus, they all bear these amino acid substitutions in addition to their other alterations, unless these particular regions were deleted. These mutated sites are indicated by black boxes at these locations in the diagrams in FIG. 3. In FIG. 3, the designation "3' Exo" is used to indicate the location of the 3' exonuclease activity associated with Type A polymerases which is not present in DNAPTaq. All constructs except the genes shown in FIGS. 3E, F and G were made in the pTTQ18 vector.

Figure 14:
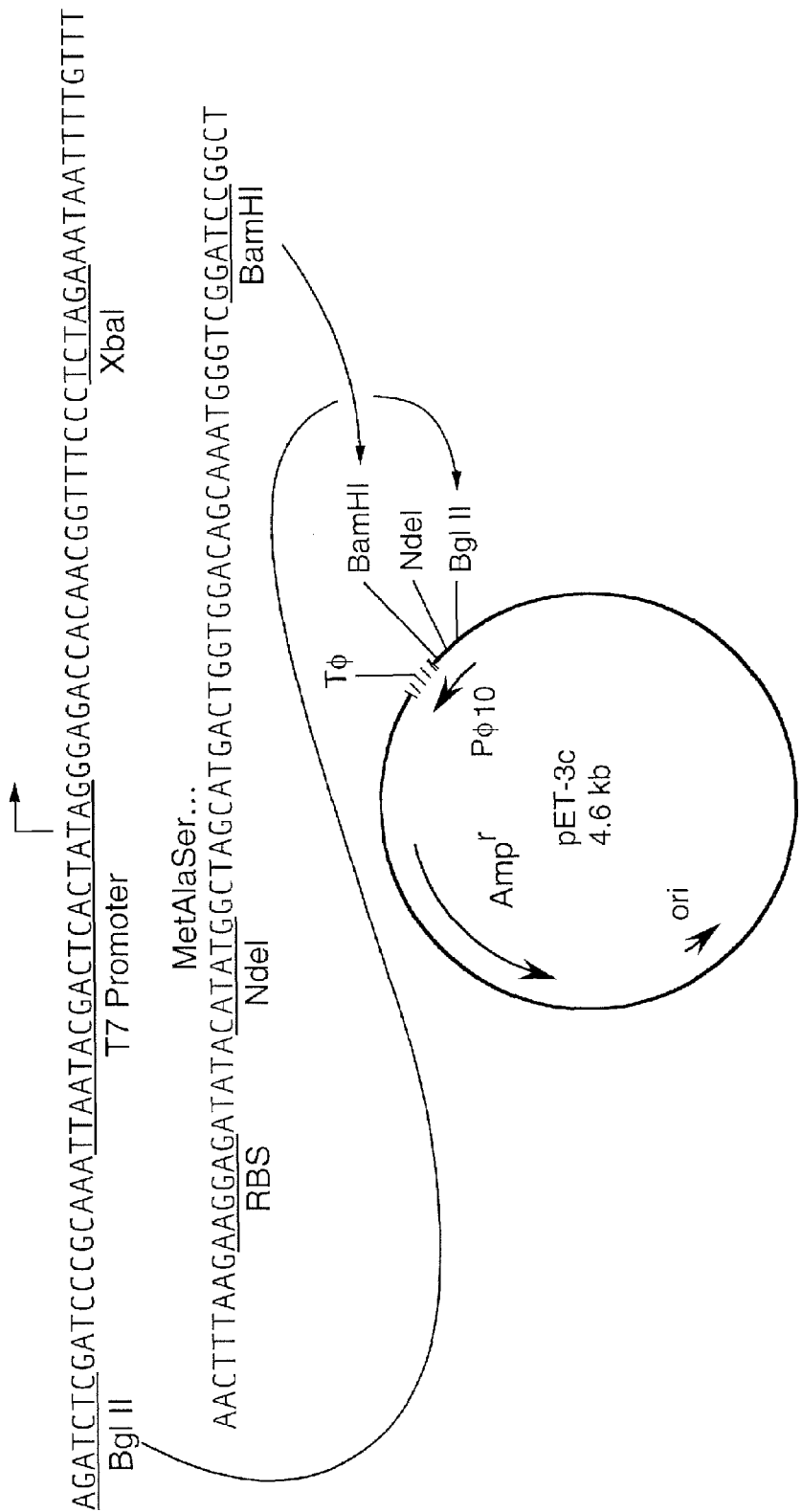
FIG. 14 is a diagram of vector pET-3c (SEQ ID NO:413).

The cloning vector used for the genes in FIGS. 3E and F was from the commercially available pET-3 series, described above. Though this vector series has only a BamHI site for cloning downstream of the T7 promoter, the series contains variants that allow cloning into any of the three reading frames. For cloning of the PCR product described above, the variant called pET-3c was used (FIG. 14). The vector was digested with BamHI, dephosphorylated with calf intestinal phosphatase, and the sticky ends were filled in using the Klenow fragment of DNAPEc1 and dNTPs. The gene for the mutant Taq DNAP shown in FIG. 3B (mutTaq, clone 3B) was released from pTTQ18 by digestion with EcoRI and SalI, and the "sticky ends" were filled in as was done with the vector. The fragment was ligated to the vector under standard blunt-end conditions (Sambrook et al., Molecular Cloning, supra), the construct was transformed into the BL21(DE3)pLYS strain of *E. coli*, and isolates were screened to identify those that were ligated with the gene in the proper orientation relative to the promoter. This construction yields another translational fusion product, in which the first two amino acids of DNAPTaq (Met-Arg) are replaced by 13 from the vector plus two from the PCR primer (Met-Ala-Ser-Met-Thr-Gly-Gly-Gln-Gln-Met-Gly-Arg-Ile-Asn-Ser) (SEQ ID NO:24).

In these experiments, the goal was to generate enzymes that lacked the ability to synthesize DNA, but retained the ability to cleave nucleic acids with a 5' nuclease activity. The act of primed, templated synthesis of DNA is actually a coordinated series of events, so it is possible to disable DNA synthesis by disrupting one event while not affecting the others. These steps include, but are not limited to, primer recognition and binding, dNTP binding and catalysis of the inter-nucleotide phosphodiester bond. Some of the amino acids in the polymerization domain of DNAPEcI have been linked to these functions, but the precise mechanisms are as yet poorly defined.

One way of destroying the polymerizing ability of a DNA polymerase is to delete all or part of the gene segment that encodes that domain for the protein, or to otherwise render the gene incapable of making a complete polymerization domain. Individual mutant enzymes may differ from each other in stability and solubility both inside and outside cells.

For instance, in contrast to the 5' nuclease domain of DNAPEcI, which can be released in an active form from the polymerization domain by gentle proteolysis (Setlow and Kornberg, J. Biol. Chem., 247:232 [1972]), the *Thermus* nuclease domain, when treated similarly, becomes less soluble and the cleavage activity is often lost.

Using the mutant gene shown in FIG. 3B as starting material, several deletion constructs were created. All cloning technologies were standard (Sambrook et al., supra) and are summarized briefly, as follows:

FIG. 3C: The mutTaq construct was digested with PstI, which cuts once within the polymerase coding region, as indicated, and cuts immediately downstream of the gene in the multiple cloning site of the vector. After release of the fragment between these two sites, the vector was re-ligated, creating an 894-nucleotide deletion, and bringing into frame a stop codon 40 nucleotides downstream of the junction. The nucleotide sequence of this 5' nuclease (clone 4C) is given in SEQ ID NO:9.

FIG. 3D: The mutTaq construct was digested with NheI, which cuts once in the gene at position 2047. The resulting four-nucleotide 5' overhanging ends were filled in, as described above, and the blunt ends were re-ligated. The resulting four-nucleotide insertion changes the reading frame and causes termination of translation ten amino acids downstream of the mutation. The nucleotide sequence of this 5' nuclease (clone 3D) is given in SEQ ID NO:10.

FIG. 3E: The entire mutTaq gene was cut from pTTQ18 using EcoRI and SalI and cloned into pET-3c, as described above. This clone was digested with BstXI and XcmI, at unique sites that are situated as shown in FIG. 3E. The DNA was treated with the Klenow fragment of DNAPEc1 and dNTPs, which resulted in the 3' overhangs of both sites being trimmed to blunt ends. These blunt ends were ligated together, resulting in an out-of-frame deletion of 1540 nucleotides. An in-frame termination codon occurs 18 triplets past the junction site. The nucleotide sequence of this 5' nuclease (clone 3E) is given in SEQ ID NO:11, with the appropriate leader sequence given in SEQ ID NO:25. It is also referred to as Cleavase® BX.

FIG. 3F: The entire mutTaq gene was cut from pTTQ18 using EcoRI and SalI and cloned into pET-3c, as described above. This clone was digested with BstXI and BamHI, at unique sites that are situated as shown in the diagram. The DNA was treated with the Klenow fragment of DNAPEc1 and dNTPs, which resulted in the 3' overhang of the BstXI site being trimmed to a blunt end, while the 5' overhang of the BamHI site was filled in to make a blunt end. These ends were ligated together, resulting in an in-frame deletion of 903 nucleotides. The nucleotide sequence of the 5' nuclease (clone 3F) is given in SEQ ID NO:12. It is also referred to as Cleavase® BB.

FIG. 3G: This polymerase is a variant of that shown in FIG. 4E. It was cloned in the plasmid vector pET-21 (Novagen). The non-bacterial promoter from bacteriophage T7, found in this vector, initiates transcription only by T7 RNA polymerase. See Studier and Moffatt, supra. In a suitable strain, such as (DES)pLYS, the gene for this RNA polymerase is carried on the bacterial genome under control of the lac operator. This arrangement has the advantage that expression of the multiple copy gene (on the plasmid) is completely dependent on the expression of T7 RNA polymerase, which is easily suppressed because it is present in a single copy. Because the expression of these mutant genes is under this tightly controlled promoter, potential problems of toxicity of the expressed proteins to the host cells are less of a concern.

The pET-21 vector also features a "His*Tag", a stretch of six consecutive histidine residues that are added on the carboxy terminus of the expressed proteins. The resulting proteins can then be purified in a single step by metal chelation chromatography, using a commercially available (Novagen) column resin with immobilized $Ni^{++}$ ions. The 2.5 ml columns are reusable, and can bind up to 20 mg of the target protein under native or denaturing (guanidine*HCl or urea) conditions.

*E. coli* (DES)pLYS cells are transformed with the constructs described above using standard transformation techniques, and used to inoculate a standard growth medium (e.g., Luria-Bertani broth). Production of T7 RNA polymerase is induced during log phase growth by addition of IPTG and incubated for a further 12 to 17 hours. Aliquots of culture are removed both before and after induction and the proteins are examined by SDS-PAGE. Staining with Coomassie Blue allows visualization of the foreign proteins if they account for about 3-5% of the cellular protein and do not co-migrate with any of the major protein bands. Proteins that co-migrate with major host protein must be expressed as more than 10% of the total protein to be seen at this stage of analysis.

Some mutant proteins are sequestered by the cells into inclusion bodies. These are granules that form in the cytoplasm when bacteria are made to express high levels of a foreign protein, and they can be purified from a crude lysate, and analyzed by SDS-PAGE to determine their protein content. If the cloned protein is found in the inclusion bodies, it must be released to assay the cleavage and polymerase activities. Different methods of solubilization may be appropriate for different proteins, and a variety of methods are known (See e.g., Builder & Ogez, U.S. Pat. No. 4,511,502 (1985); Olson, U.S. Pat. No. 4,518,526 (1985); Olson & Pai, U.S. Pat. No. 4,511,503 (1985); and Jones et al., U.S. Pat. No. 4,512,922 (1985), all of which are hereby incorporated by reference).

The solubilized protein is then purified on the $Ni^{++}$ column as described above, following the manufacturers instructions (Novagen). The washed proteins are eluted from the column by a combination of imidazole competitor (1 M) and high salt (0.5 M NaCl), and dialyzed to exchange the buffer and to allow denature proteins to refold. Typical recoveries result in approximately 20 µg of specific protein per ml of starting culture. The DNAP mutant is referred to as the CLEAVASE BN nuclease and the sequence is given in SEQ ID NO:26 (the amino acid sequence of the CLEAVASE BN nuclease is obtained by translating the DNA sequence of SEQ ID NO:26).

2. Modified DNAPTfl Gene

The DNA polymerase gene of *Thermus flavus* was isolated from the "*T. flavus*" AT-62 strain obtained from the American Type Tissue Collection (ATCC 33923). This strain has a different restriction map then does the *T. flavus* strain used to generate the sequence published by Akhmetzjanov and Vakhitov, supra. The published sequence is listed as SEQ ID NO:2. No sequence data has been published for the DNA polymerase gene from the AT-62 strain of *T. flavus*.

Genomic DNA from *T. flavus* was amplified using the same primers used to amplify the *T. aquaticus* DNA polymerase gene (SEQ ID NOS:13-14). The approximately 2500 base pair PCR fragment was digested with EcoRI and BamHI. The over-hanging ends were made blunt with the Klenow fragment of DNAPEc1 and dNTPs. The resulting approximately 1800 base pair fragment containing the coding region for the N-terminus was ligated into pET-3c, as described above. This construct, clone 4B, is depicted in FIG. 4B. The wild type *T. flavus* DNA polymerase gene is depicted in FIG. 4A. The 4B clone has the same leader amino acids as do the DNAPTaq clones 4E and F which were cloned into pET-3c; it is not known precisely where translation termination occurs, but the vector has a strong transcription termination signal immediately downstream of the cloning site.

B. Growth and Induction of Transformed Cells

Bacterial cells were transformed with the constructs described above using standard transformation techniques and used to inoculate 2 mls of a standard growth medium (e.g., Luria-Bertani broth). The resulting cultures were incubated as appropriate for the particular strain used, and induced if required for a particular expression system. For all of the constructs depicted in FIGS. 3 and 4, the cultures were grown to an optical density (at 600 nm wavelength) of 0.5 OD.

To induce expression of the cloned genes, the cultures were brought to a final concentration of 0.4 mM IPTG and the incubations were continued for 12 to 17 hours. Then, 50 µl aliquots of each culture were removed both before and after induction and were combined with 20 µl of a standard gel loading buffer for sodium dodecyl sulfate-polyacrylamide gel electrophoresis (SDS-PAGE). Subsequent staining with Coomassie Blue (Sambrook et al., supra) allows visualization of the foreign proteins if they account for about 3-5% of the cellular protein and do not co-migrate with any of the major $E.$ $coli$ protein bands. Proteins that do co-migrate with a major host protein must be expressed as more than 10% of the total protein to be seen at this stage of analysis.

C. Heat Lysis and Fractionation

Expressed thermostable proteins (i.e., the 5' nucleases), were isolated by heating crude bacterial cell extracts to cause denaturation and precipitation of the less stable $E.$ $coli$ proteins. The precipitated $E.$ $coli$ proteins were then, along with other cell debris, removed by centrifugation. Then, 1.7 mls of the culture were pelleted by microcentrifugation at 12,000 to 14,000 rpm for 30 to 60 seconds. After removal of the supernatant, the cells were resuspended in 400 µl of buffer A (50 mM Tris-HCl, pH 7.9, 50 mM dextrose, 1 mM EDTA), re-centrifuged, then resuspended in 80 µl of buffer A with 4 mg/ml lysozyme. The cells were incubated at room temperature for 15 minutes, then combined with 80 µl of buffer B (10 mM Tris-HCl, pH 7.9, 50 mM KCl, 1 mM EDTA, 1 mM PMSF, 0.5% Tween-20, 0.5% Nonidet-P40).

This mixture was incubated at 75° C. for 1 hour to denature and precipitate the host proteins. This cell extract was centrifuged at 14,000 rpm for 15 minutes at 4° C., and the supernatant was transferred to a fresh tube. An aliquot of 0.5 to 1 µl of this supernatant was used directly in each test reaction, and the protein content of the extract was determined by subjecting 7 µl to electrophoretic analysis, as above. The native recombinant Taq DNA polymerase (Engelke, Anal. Biochem., 191:396 [1990]), and the double point mutation protein shown in FIG. 3B are both soluble and active at this point.

The foreign protein may not be detected after the heat treatments due to sequestration of the foreign protein by the cells into inclusion bodies. These are granules that form in the cytoplasm when bacteria are made to express high levels of a foreign protein, and they can be purified from a crude lysate, and analyzed SDS PAGE to determine their protein content. Many methods have been described in the literature, and one approach is described below.

D. Isolation and Solubilization of Inclusion Bodies

A small culture was grown and induced as described above. A 1.7 ml aliquot was pelleted by brief centrifugation, and the bacterial cells were resuspended in 100 µl of Lysis buffer (50 mM Tris-HCl, pH 8.0, 1 mM EDTA, 100 mM NaCl). Then, 2.5 µl of 20 mM PMSF were added for a final concentration of 0.5 mM, and lysozyme was added to a concentration of 1.0 mg/ml. The cells were incubated at room temperature for 20 minutes, deoxycholic acid was added to 1 mg/ml (1 µl of 100 mg/ml solution), and the mixture was further incubated at 37° C. for about 15 minutes or until viscous. DNAse I was added to 10 µg/ml and the mixture was incubated at room temperature for about 30 minutes or until it was no longer viscous.

From this mixture the inclusion bodies were collected by centrifugation at 14,000 rpm for 15 minutes at 4° C., and the supernatant was discarded. The pellet was resuspended in 100 µl of lysis buffer with 10 mM EDTA (pH 8.0) and 0.5% Triton X-100. After 5 minutes at room temperature, the inclusion bodies were pelleted as before, and the supernatant was saved for later analysis. The inclusion bodies were resuspended in 50 µl of distilled water, and 5 µl was combined with SDS gel loading buffer (which dissolves the inclusion bodies) and analyzed electrophoretically, along with an aliquot of the supernatant.

If the cloned protein is found in the inclusion bodies, it may be released to assay the cleavage and polymerase activities and the method of solubilization must be compatible with the particular activity. Different methods of solubilization may be appropriate for different proteins, and a variety of methods are discussed in Molecular Cloning (Sambrook et al, supra). The following is an adaptation used for several of the isolates used in the development of the present invention.

Twenty µl of the inclusion body-water suspension were pelleted by centrifugation at 14,000 rpm for 4 minutes at room temperature, and the supernatant was discarded. To further wash the inclusion bodies, the pellet was resuspended in 20 µl of lysis buffer with 2M urea, and incubated at room temperature for one hour. The washed inclusion bodies were then resuspended in 2 µl of lysis buffer with 8 M urea; the solution clarified visibly as the inclusion bodies dissolved. Undissolved debris was removed by centrifugation at 14,000 rpm for 4 minutes at room temperature, and the extract supernatant was transferred to a fresh tube.

To reduce the urea concentration, the extract was diluted into $KH_2PO_4$. A fresh tube was prepared containing 180 µl of 50 mM $KH_2PO_4$, pH 9.5, 1 mM EDTA and 50 mM NaCl. A 2 µl aliquot of the extract was added and vortexed briefly to mix. This step was repeated until all of the extract had been added for a total of 10 additions. The mixture was allowed to sit at room temperature for 15 minutes, during which time some precipitate often forms. Precipitates were removed by centrifugation at 14,000 rpm, for 15 minutes at room temperature, and the supernatant was transferred to a fresh tube. To the 200 µl of protein in the $KH_2PO_4$ solution, 140-200 µl of saturated $(NH_4)_2SO_4$ were added, so that the resulting mixture was about 41% to 50% saturated $(NH_4)_2SO_4$. The mixture was chilled on ice for 30 minutes to allow the protein to precipitate, and the protein was then collected by centrifugation at 14,000 rpm, for 4 minutes at room temperature. The supernatant was discarded, and the pellet was dissolved in 20 µl Buffer C (20 mM HEPES, pH 7.9, 1 mM EDTA, 0.5% PMSF, 25 mM KCl and 0.5% each of Tween-20 and Nonidet P 40). The protein solution was centrifuged again for 4 minutes to pellet insoluble materials, and the supernatant was removed to a fresh tube. The protein contents of extracts prepared in this manner were visualized by resolving 1-4 µl by SDS-PAGE; 0.5 to 1 µl of extract was tested in the cleavage and polymerization assays as described.

E. Protein Analysis for Presence of Nuclease and Synthetic Activity

The 5' nucleases described above and shown in FIGS. 3 and 4 were analyzed by the following methods.

1. Structure Specific Nuclease Assay

A candidate modified polymerase is tested for 5' nuclease activity by examining its ability to catalyze structure-specific cleavages. By the term "cleavage structure" as used herein, is meant a nucleic acid structure which is a substrate for cleavage by the 5' nuclease activity of a DNAP.

The polymerase is exposed to test complexes that have the structures shown in FIG. 15. Testing for 5' nuclease activity involves three reactions: 1) a primer-directed cleavage (FIG. 15B) is performed because it is relatively insensitive to variations in the salt concentration of the reaction and can, therefore, be performed in whatever solute conditions the modified enzyme requires for activity; this is generally the same conditions preferred by unmodified polymerases; 2) a similar primer-directed cleavage is performed in a buffer which permits primer-independent cleavage (i.e., a low salt buffer), to demonstrate that the enzyme is viable under these conditions; and 3) a primer-independent cleavage (FIG. 15A) is performed in the same low salt buffer.

The bifurcated duplex is formed between a substrate strand and a template strand as shown in FIG. 15. By the term "substrate strand" as used herein, is meant that strand of nucleic acid in which the cleavage mediated by the 5' nuclease activity occurs. The substrate strand is always depicted as the top strand in the bifurcated complex which serves as a substrate for 5' nuclease cleavage (FIG. 15). By the term "template strand" as used herein, is meant the strand of nucleic acid which is at least partially complementary to the substrate strand and which anneals to the substrate strand to form the cleavage structure. The template strand is always depicted as the bottom strand of the bifurcated cleavage structure (FIG. 15). If a primer (a short oligonucleotide of 19 to 30 nucleotides in length) is added to the complex, as when primer-dependent cleavage is to be tested, it is designed to anneal to the 3' arm of the template strand (FIG. 15B). Such a primer would be extended along the template strand if the polymerase used in the reaction has synthetic activity.

Figure 15B:
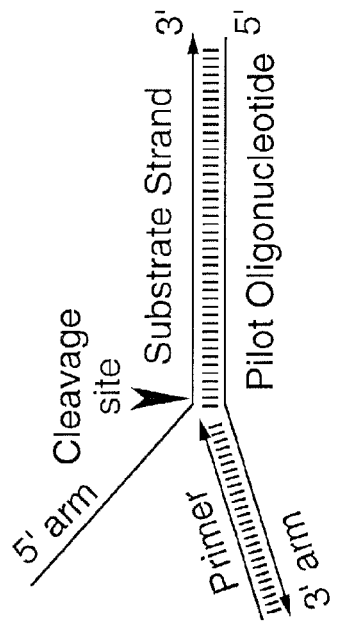
FIGS. 15A-E depicts a set of molecules which are suitable substrates for cleavage by the 5' nuclease activity of DNAPs (SEQ ID NOS:15 and 17 are depicted in FIG. 15E).
Figure 15D:
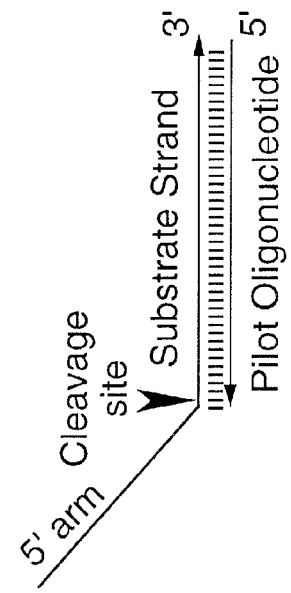
Figure 15A:
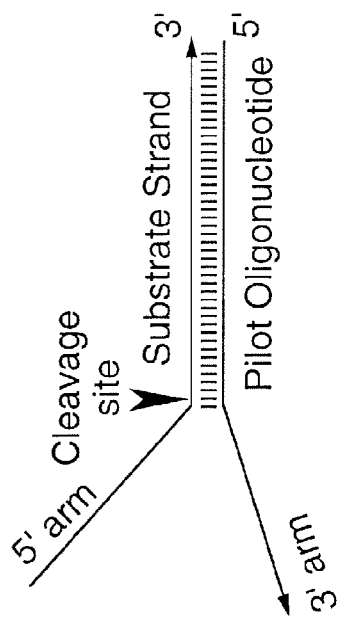
Figure 15C:
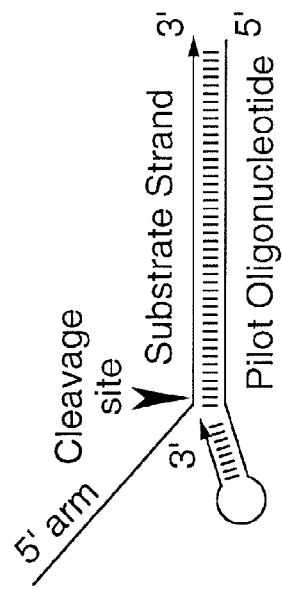
Figure 15E:
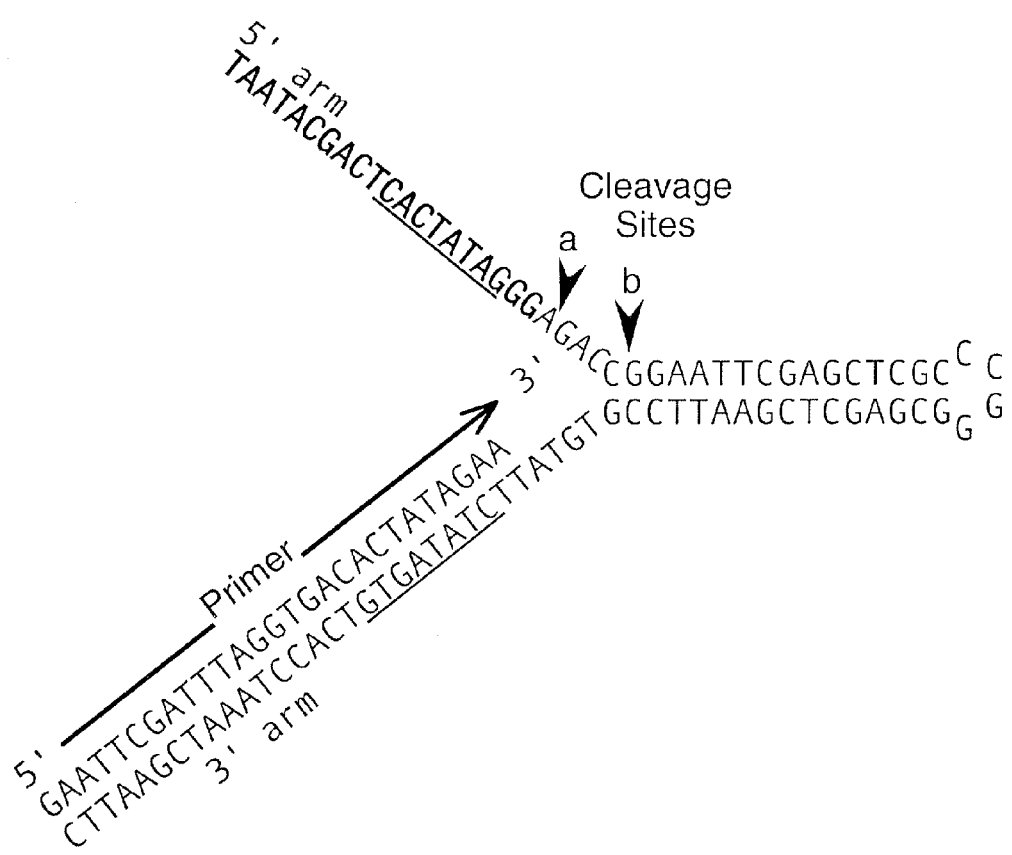

The cleavage structure may be made as a single hairpin molecule, with the 3' end of the target and the 5' end of the pilot joined as a loop as shown in FIG. 15E. A primer oligonucleotide complementary to the 3' arm is also required for these tests so that the enzyme's sensitivity to the presence of a primer may be tested.

Nucleic acids to be used to form test cleavage structures can be chemically synthesized, or can be generated by standard recombinant DNA techniques. By the latter method, the hairpin portion of the molecule can be created by inserting into a cloning vector duplicate copies of a short DNA segment, adjacent to each other but in opposing orientation. The double-stranded fragment encompassing this inverted repeat, and including enough flanking sequence to give short (about 20 nucleotides) unpaired 5' and 3' arms, can then be released from the vector by restriction enzyme digestion, or by PCR performed with an enzyme lacking a 5' exonuclease (e.g., the Stoffel fragment of AMPLITAQ DNA polymerase, Vent™ DNA polymerase).

The test DNA can be labeled on either end, or internally, with either a radioisotope, or with a non-isotopic tag. Whether the hairpin DNA is a synthetic single strand or a cloned double strand, the DNA is heated prior to use to melt all duplexes. When cooled on ice, the structure depicted in FIG. 16E is formed, and is stable for sufficient time to perform these assays.

To test for primer-directed cleavage (Reaction 1), a detectable quantity of the test molecule (typically 1-100 fmol of $^{32}$P-labeled hairpin molecule) and a 10 to 100-fold molar excess of primer are placed in a buffer known to be compatible with the test enzyme. For Reaction 2, where primer-directed cleavage is performed under condition which allow primer-independent cleavage, the same quantities of molecules are placed in a solution that is the same as the buffer used in Reaction 1 regarding pH, enzyme stabilizers (e.g., bovine serum albumin, nonionic detergents, gelatin) and reducing agents (e.g., dithiothreitol, 2-mercaptoethanol) but that replaces any monovalent cation salt with 20 mM KCl; 20 mM KCl is the demonstrated optimum for primer-independent cleavage. Buffers for enzymes, such as DNAPEc1, that usually operate in the absence of salt are not supplemented to achieve this concentration. To test for primer-independent cleavage (Reaction 3) the same quantity of the test molecule, but no primer, are combined under the same buffer conditions used for Reaction 2.

All three test reactions are then exposed to enough of the enzyme that the molar ratio of enzyme to test complex is approximately 1:1. The reactions are incubated at a range of temperatures up to, but not exceeding, the temperature allowed by either the enzyme stability or the complex stability, whichever is lower, up to 80° C. for enzymes from thermophiles, for a time sufficient to allow cleavage (10 to 60 minutes). The products of Reactions 1, 2 and 3 are resolved by denaturing polyacrylamide gel electrophoresis, and visualized by autoradiography or by a comparable method appropriate to the labeling system used. Additional labeling systems include chemiluminescence detection, silver or other stains, blotting and probing and the like. The presence of cleavage products is indicated by the presence of molecules which migrate at a lower molecular weight than does the uncleaved test structure. These cleavage products indicate that the candidate polymerase has structure-specific 5' nuclease activity.

To determine whether a modified DNA polymerase has substantially the same 5' nuclease activity as that of the native DNA polymerase, the results of the above-described tests are compared with the results obtained from these tests performed with the native DNA polymerase. By "substantially the same 5' nuclease activity" it is meant that the modified polymerase and the native polymerase will both cleave test molecules in the same manner. It is not necessary that the modified polymerase cleave at the same rate as the native DNA polymerase.

Some enzymes or enzyme preparations may have other associated or contaminating activities that may be functional under the cleavage conditions described above and that may interfere with 5' nuclease detection. Reaction conditions can be modified in consideration of these other activities, to avoid destruction of the substrate, or other masking of the 5' nuclease cleavage and its products. For example, the DNA polymerase I of *E. coli* (PolI), in addition to its polymerase and 5' nuclease activities, has a 3' exonuclease that can degrade DNA in a 3' to 5' direction. Consequently, when the molecule in FIG. 15E is exposed to this polymerase under the conditions described above, the 3' exonuclease quickly removes the unpaired 3' arm, destroying the bifurcated structure required of a substrate for the 5' exonuclease cleavage and no cleavage is detected. The true ability of PolI to cleave the structure can be revealed if the 3' exonuclease is inhibited by a change of conditions (e.g., pH), mutation, or by addition of a competitor for the activity. Addition of 500 pmoles of a single-stranded competitor oligonucleotide, unrelated to the FIG. 15E structure, to the cleavage reaction with PolI effectively inhibits the digestion of the 3' arm of the FIG. 15E structure without interfering with the 5' exonuclease release of the 5' arm. The concentration of the competitor is not critical, but should be high enough to occupy the 3' exonuclease for the duration of the reaction.

Similar destruction of the test molecule may be caused by contaminants in the candidate polymerase preparation. Several sets of the structure specific nuclease reactions may be performed to determine the purity of the candidate nuclease and to find the window between under and over exposure of the test molecule to the polymerase preparation being investigated.

The above described modified polymerases were tested for 5' nuclease activity as follows: Reaction 1 was performed in a buffer of 10 mM Tris-Cl, pH 8.5 at 20° C., 1.5 mM $MgCl_2$ and 50 mM KCl and in Reaction 2 the KCl concentration was reduced to 20 mM. In Reactions 1 and 2, 10 fmoles of the test substrate molecule shown in FIG. 15E were combined with 1 pmole of the indicated primer and 0.5 to 1.0 µl of extract containing the modified polymerase prepared as described above). This mixture was then incubated for 10 minutes at 55° C. For all of the mutant polymerases tested these conditions were sufficient to give complete cleavage. When the molecule shown in FIG. 15E was labeled at the 5' end, the released 5' fragment, 25 nucleotides long, was conveniently resolved on a 20% polyacrylamide gel (19:1 cross-linked) with 7 M urea in a buffer containing 45 mM Tris-borate pH 8.3, 1.4 mM EDTA. Clones 3C-F and 4B exhibited structure-specific cleavage comparable to that of the unmodified DNA polymerase. Additionally, clones 3E, 3F and 3G have the added ability to cleave DNA in the absence of a 3' arm as discussed above. Representative cleavage reactions are shown in FIG. 16.

Figure 16:
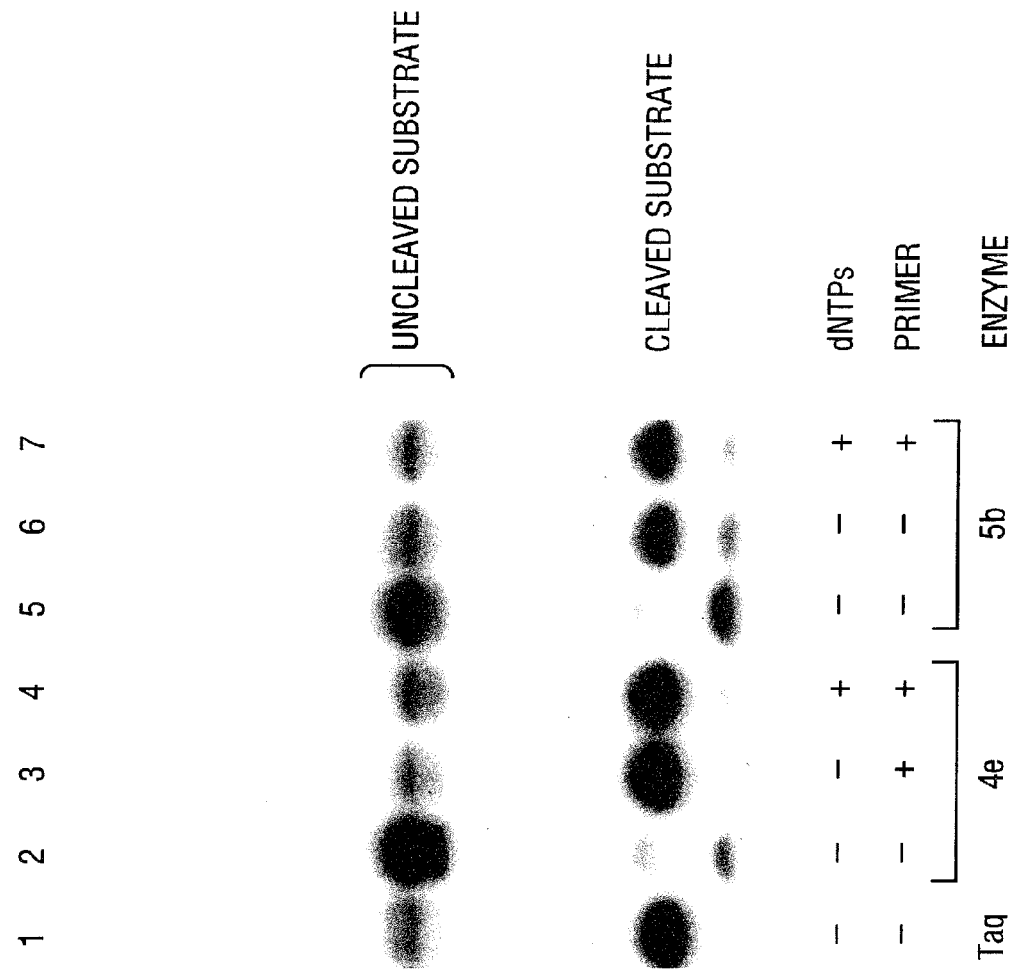
FIG. 16 is an autoradiogram of a gel showing the results of a cleavage reaction run with synthesis-deficient DNAPs.

For the reactions shown in FIG. 16, the mutant polymerase clones 3E (Taq mutant) and 4B (Tfl mutant) were examined for their ability to cleave the hairpin substrate molecule shown in FIG. 15E. The substrate molecule was labeled at the 5' terminus with $^{32}$P. Ten fmoles of heat-denatured, end-labeled substrate DNA and 0.5 units of DNAPTaq (lane 1) or 0.5 µl of 3E or 4B extract (FIG. 16, lanes 2-7, extract was prepared as described above) were mixed together in a buffer containing 10 mM Tris-Cl, pH 8.5, 50 mM KCl and 1.5 mM $MgCl_2$. The final reaction volume was 10 µl. Reactions shown in lanes 4 and 7 contain in addition 50 µM of each dNTP. Reactions shown in lanes 3, 4, 6 and 7 contain 0.2 µM of the primer oligonucleotide (complementary to the 3' arm of the substrate and shown in FIG. 15E). Reactions were incubated at 55° C. for 4 minutes. Reactions were stopped by the addition of 8 µl of 95% formamide containing 20 mM EDTA and 0.05% marker dyes per 10 µl reaction volume. Samples were then applied to 12% denaturing acrylamide gels. Following electrophoresis, the gels were autoradiographed. FIG. 16 shows that clones 3E and 4B exhibit cleavage activity similar to that of the native DNAPTaq. Note that some cleavage occurs in these reactions in the absence of the primer. When long hairpin structure, such as the one used here (FIG. 15E), are used in cleavage reactions performed in buffers containing 50 mM KCl a low level of primer-independent cleavage is seen. Higher concentrations of KCl suppress, but do not eliminate, this primer-independent cleavage under these conditions.

2. Assay for Synthetic Activity

The ability of the modified enzyme or proteolytic fragments is assayed by adding the modified enzyme to an assay system in which a primer is annealed to a template and DNA synthesis is catalyzed by the added enzyme. Many standard laboratory techniques employ such an assay. For example, nick translation and enzymatic sequencing involve extension of a primer along a DNA template by a polymerase molecule.

In a preferred assay for determining the synthetic activity of a modified enzyme an oligonucleotide primer is annealed to a single-stranded DNA template (e.g., bacteriophage M13 DNA), and the primer/template duplex is incubated in the presence of the modified polymerase in question, deoxynucleoside triphosphates (dNTPs) and the buffer and salts known to be appropriate for the unmodified or native enzyme. Detection of either primer extension (by denaturing gel electrophoresis) or dNTP incorporation (by acid precipitation or chromatography) is indicative of an active polymerase. A label, either isotopic or non-isotopic, is preferably included on either the primer or as a dNTP to facilitate detection of polymerization products. Synthetic activity is quantified as the amount of free nucleotide incorporated into the growing DNA chain and is expressed as amount incorporated per unit of time under specific reaction conditions.

Figure 17:
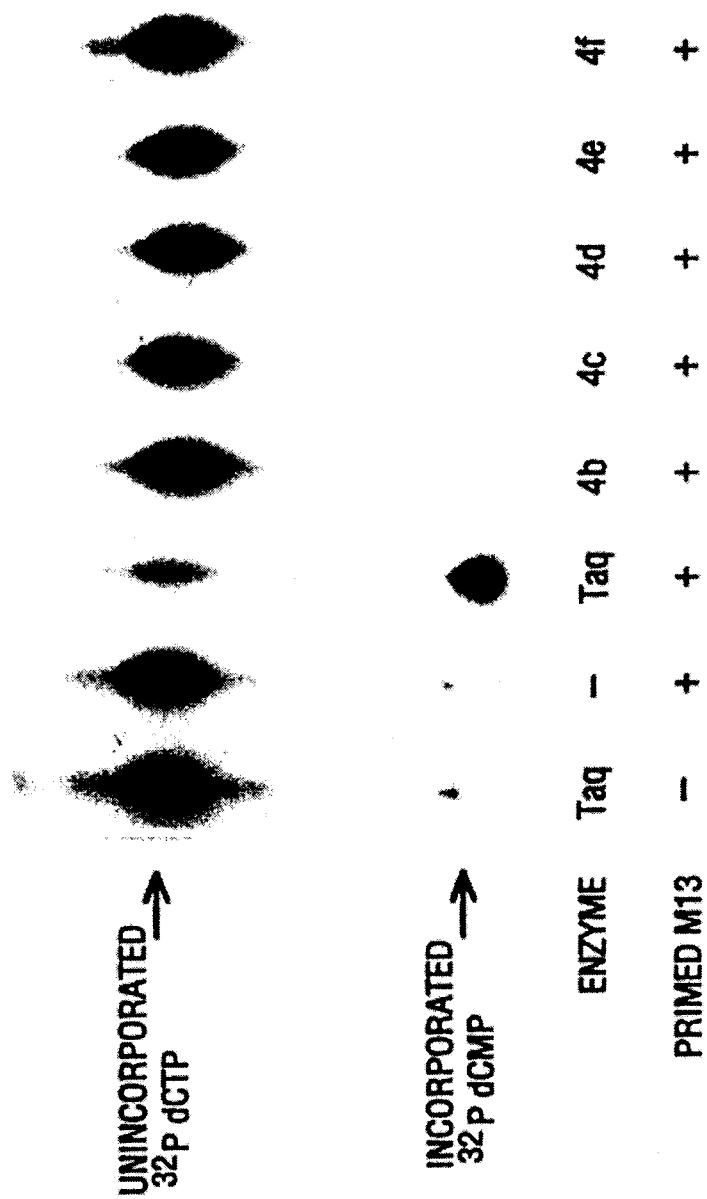
FIG. 17 is an autoradiogram of a PEI chromatogram resolving the products of an assay for synthetic activity in synthesis-deficient DNAPTaq clones.
Figure 18A:
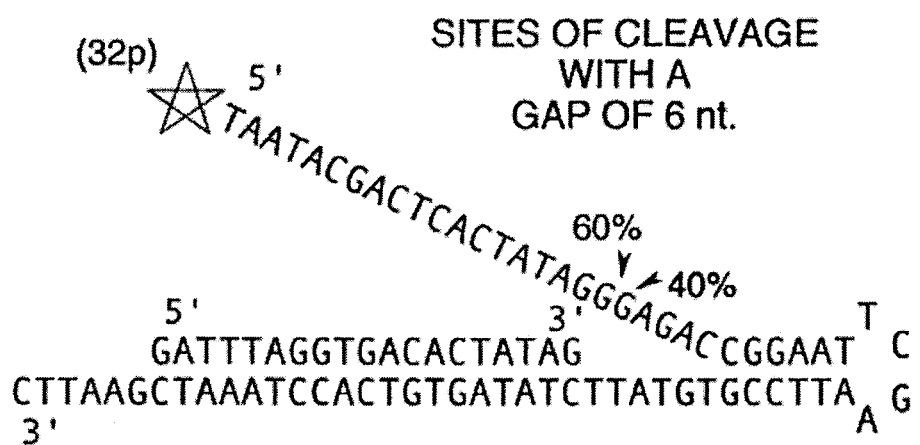
Figure 18:
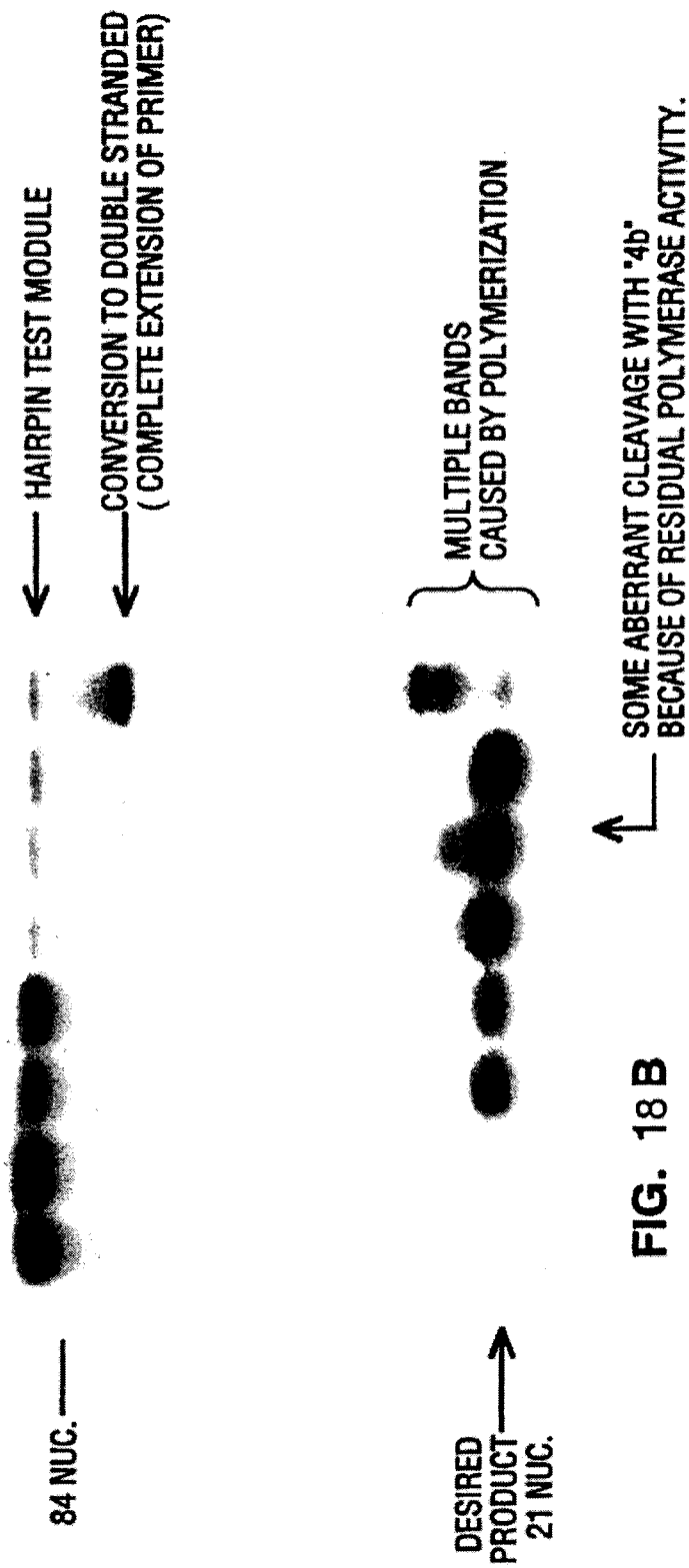
Figure 19:
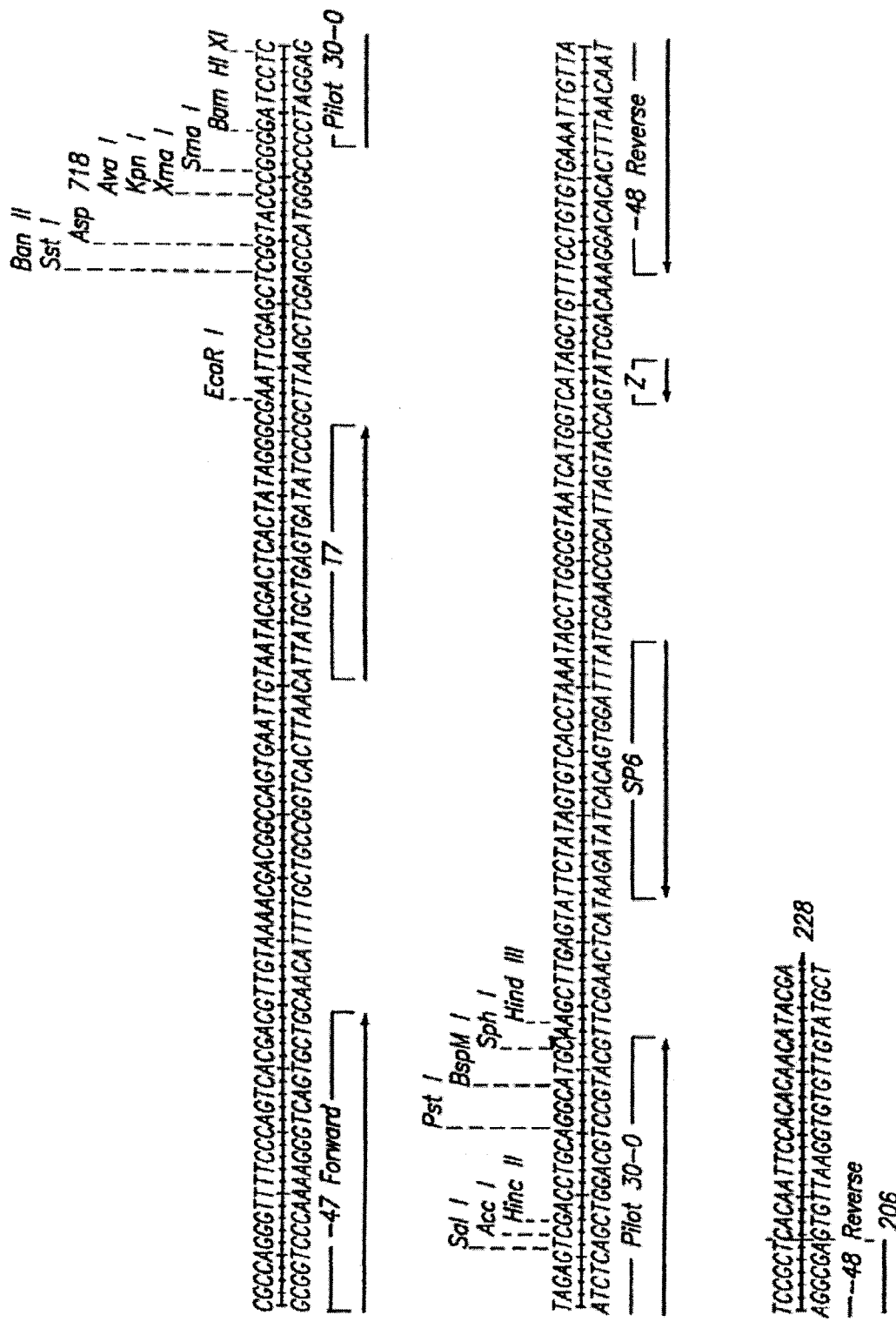
Figure 20A:
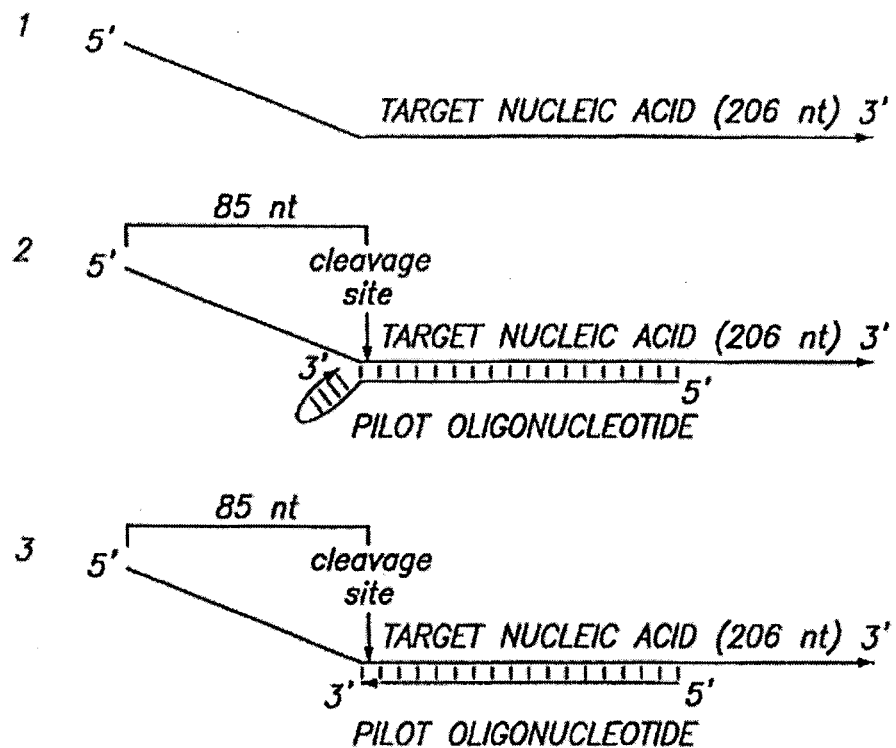
Figure 23:
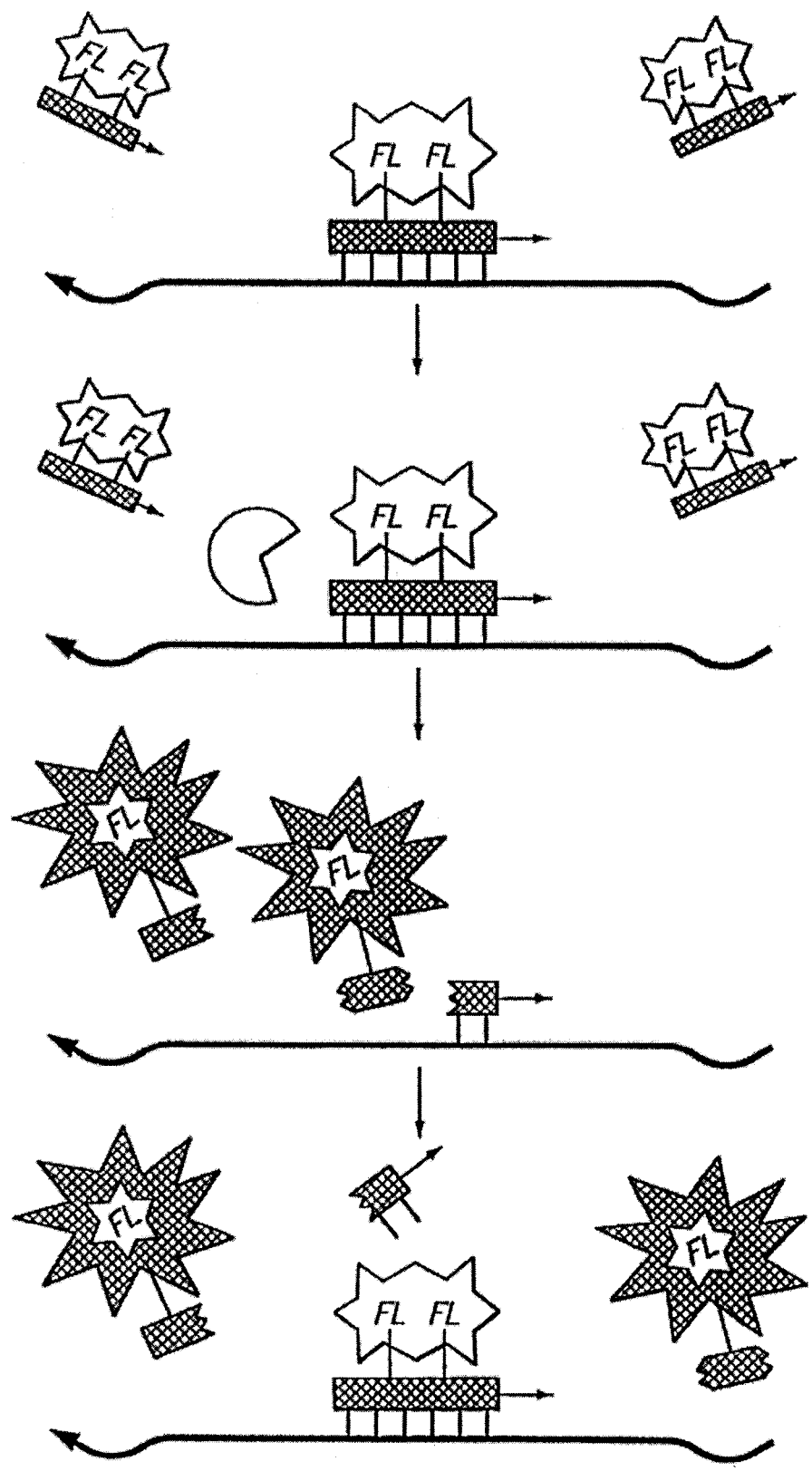
Figure 24A:
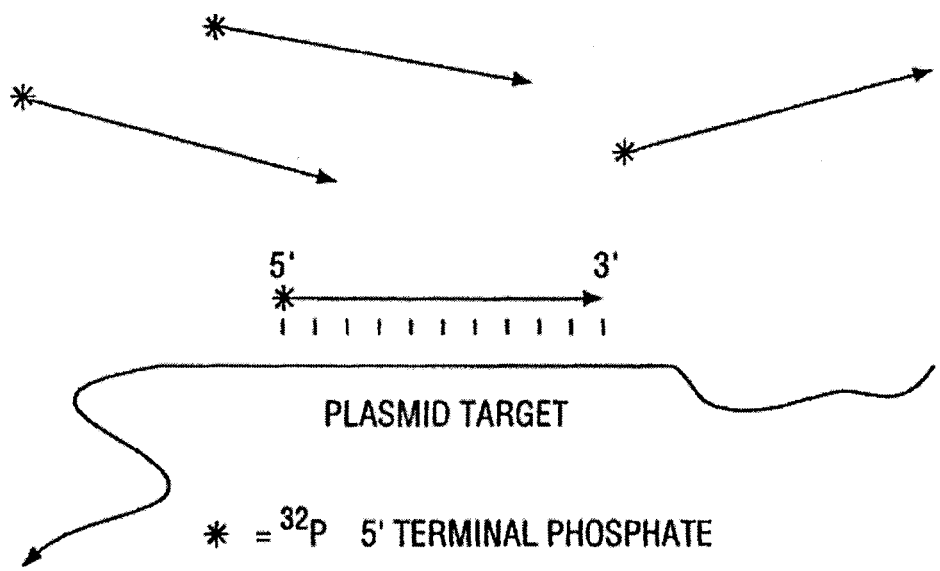
Figure 24B:
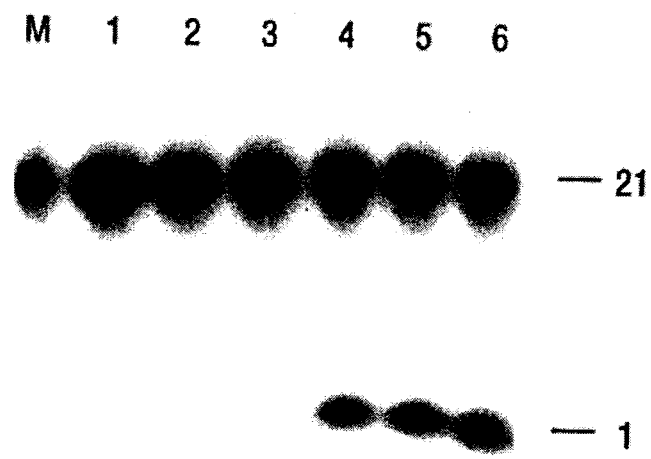
Figure 25:
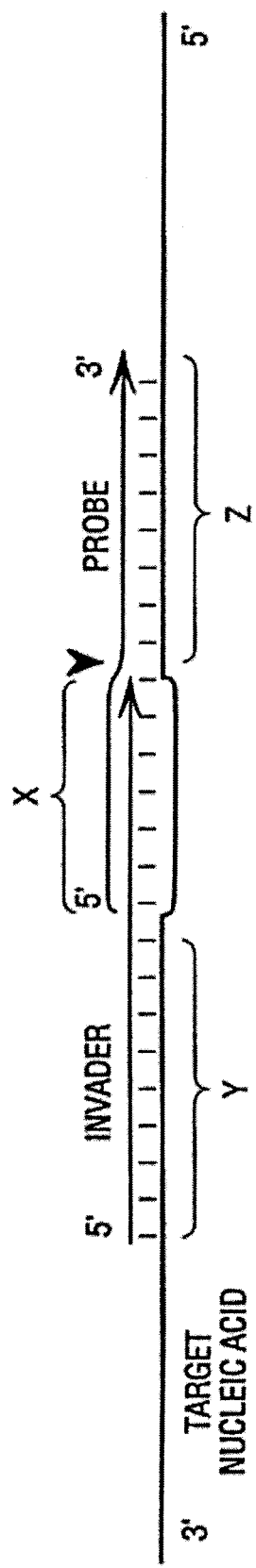
Figure 27:
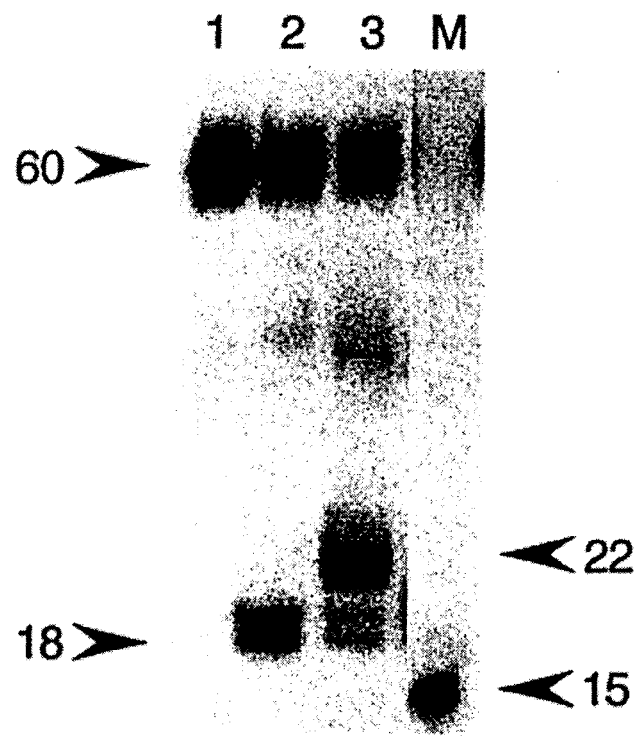

Representative results of an assay for synthetic activity is shown in FIG. 17. The synthetic activity of the mutant DNAPTaq clones 3B-F was tested as follows: A master mixture of the following buffer was made: 1.2×PCR buffer (1×PCR buffer contains 50 mM KCl, 1.5 mM $MgCl_2$, 10 mM Tris-Cl, pH 8.5 and 0.05% each Tween 20 and Nonidet P40), 50 µM each of dGTP, dATP and dTTP, 5 µM dCTP and 0.125 µM α-$^{32}$P-dCTP at 600 Ci/mmol. Before adjusting this mixture to its final volume, it was divided into two equal aliquots. One received distilled water up to a volume of 50 µl to give the concentrations above. The other received 5 µg of single-stranded M13mp18 DNA (approximately 2.5 pmol or 0.05 µM final concentration) and 250 pmol of M13 sequencing primer (5 µM final concentration) and distilled water to a final volume of 50 µl. Each cocktail was warmed to 75° C. for 5 minutes and then cooled to room temperature. This allowed the primers to anneal to the DNA in the DNA-containing mixtures.

For each assay, 4 µl of the cocktail with the DNA was combined with 1 µl of the mutant polymerase, prepared as described, or 1 unit of DNAPTaq (Perkin Elmer) in 1 µl of $dH_2O$. A "no DNA" control was done in the presence of the DNAPTaq (FIG. 17, lane 1), and a "no enzyme" control was done using water in place of the enzyme (lane 2). Each reaction was mixed, then incubated at room temperature (approx. 22° C.) for 5 minutes, then at 55° C. for 2 minutes, then at 72° C. for 2 minutes. This step incubation was done to detect polymerization in any mutants that might have optimal temperatures lower than 72° C. After the final incubation, the tubes were spun briefly to collect any condensation and were placed on ice. One µl of each reaction was spotted at an origin 1.5 cm from the bottom edge of a polyethyleneimine (PEI) cellulose thin layer chromatography plate and allowed to dry. The chromatography plate was run in 0.75 M $NaH_2PO_4$, pH 3.5, until the buffer front had run approximately 9 cm from the origin. The plate was dried, wrapped in plastic wrap, marked with luminescent ink, and exposed to X-ray film. Incorporation was detected as counts that stuck where originally spotted, while the unincorporated nucleotides were carried by the salt solution from the origin.

Comparison of the locations of the counts with the two control lanes confirmed the lack of polymerization activity in the mutant preparations. Among the modified DNAPTaq clones, only clone 3B retains any residual synthetic activity as shown in FIG. 17.

Example 3

5' Nucleases Derived from Thermostable DNA Polymerases can Cleave Short Hairpin Structures with Specificity

Figure 18A:
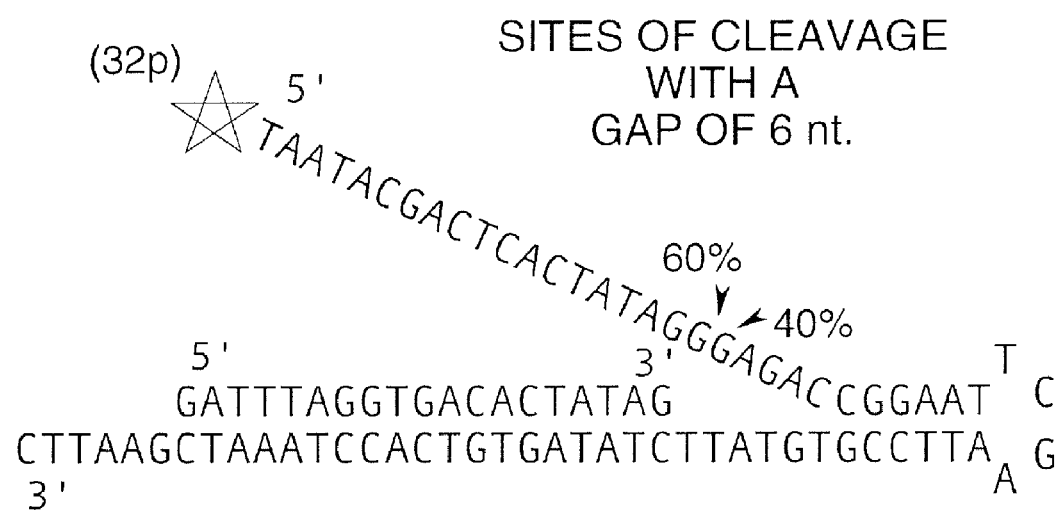
FIG. 18A depicts the substrate molecule (SEQ ID NOS: 414 and 22) used to test the ability of synthesis-deficient DNAPs to cleave short hairpin structures.
Figure 18:
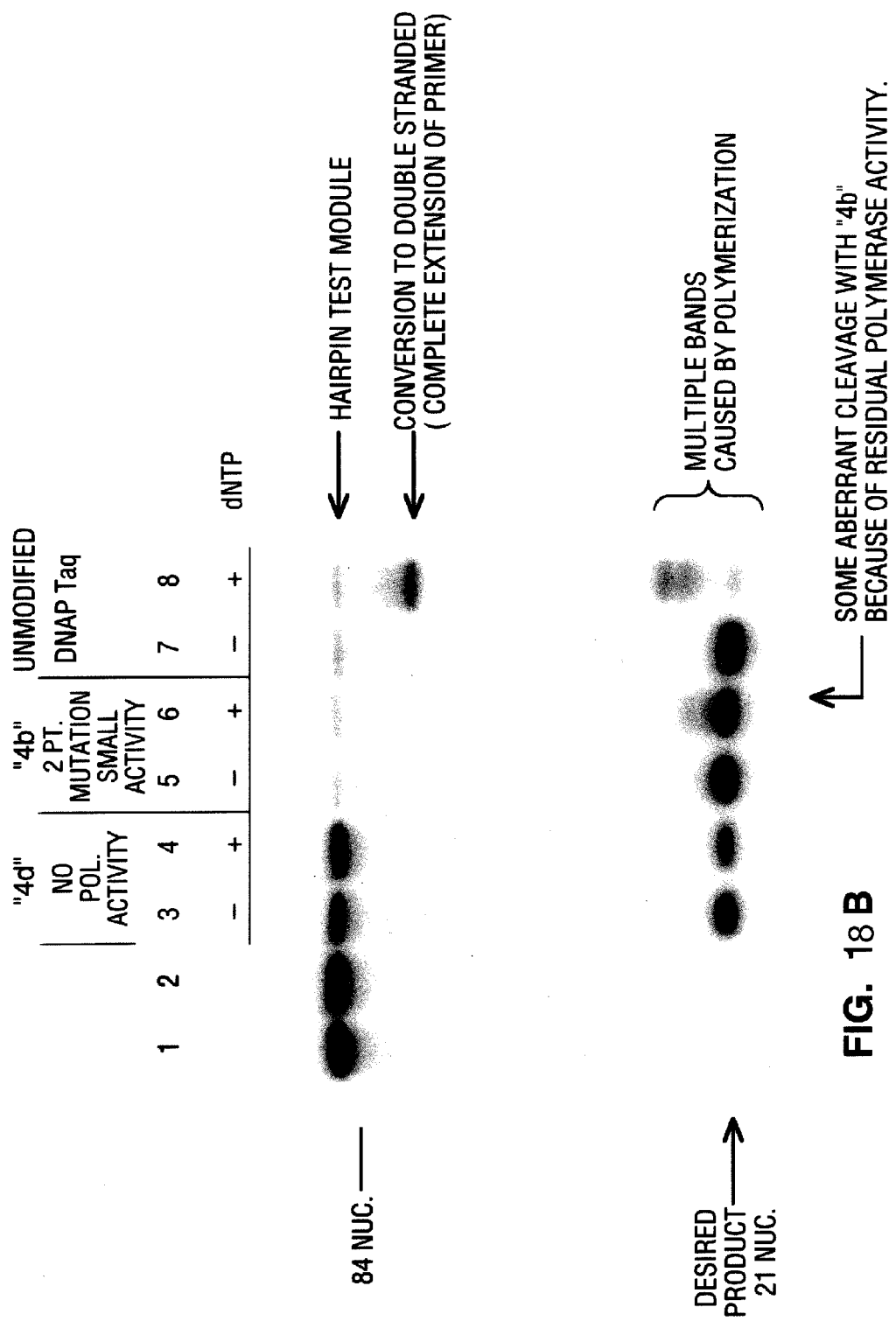
FIG. 18B shows an autoradiogram of a gel resolving the products of a cleavage reaction run using the substrate shown in FIG. 19A.

The ability of the 5' nucleases to cleave hairpin structures to generate a cleaved hairpin structure suitable as a detection molecule was examined. The structure and sequence of the hairpin test molecule is shown in FIG. 18A (SEQ ID NO:15). The oligonucleotide (labeled "primer" in FIG. 18A, SEQ ID NO:22) is shown annealed to its complementary sequence on the 3' arm of the hairpin test molecule. The hairpin test molecule was single-end labeled with $^{32}$P using a labeled T7 promoter primer in a polymerase chain reaction. The label is present on the 5' arm of the hairpin test molecule and is represented by the star in FIG. 18A.

The cleavage reaction was performed by adding 10 fmoles of heat-denatured, end-labeled hairpin test molecule, 0.2 µM of the primer oligonucleotide (complementary to the 3' arm of the hairpin), 50 µM of each dNTP and 0.5 units of DNAPTaq (Perkin Elmer) or 0.5 µl of extract containing a 5' nuclease (prepared as described above) in a total volume of 10 µl in a buffer containing 10 mM Tris-Cl, pH 8.5, 50 mM KCl and 1.5 mM MgCl$_2$. Reactions shown in lanes 3, 5 and 7 were run in the absence of dNTPs.

Reactions were incubated at 55° C. for 4 minutes. Reactions were stopped at 55° C. by the addition of 8 µl of 95% formamide with 20 mM EDTA and 0.05% marker dyes per 10 µl reaction volume. Samples were not heated before loading onto denaturing polyacrylamide gels (10% polyacrylamide, 19:1 crosslinking, 7 M urea, 89 mM Tris-borate, pH 8.3, 2.8 mM EDTA). The samples were not heated to allow for the resolution of single-stranded and re-duplexed uncleaved hairpin molecules.

FIG. 18B shows that altered polymerases lacking any detectable synthetic activity cleave a hairpin structure when an oligonucleotide is annealed to the single-stranded 3' arm of the hairpin to yield a single species of cleaved product (FIG. 18B, lanes 3 and 4). 5' nucleases, such as clone 3D, shown in lanes 3 and 4, produce a single cleaved product even in the presence of dNTPs. 5' nucleases that retain a residual amount of synthetic activity (less than 1% of wild type activity) produce multiple cleavage products as the polymerase can extend the oligonucleotide annealed to the 3' arm of the hairpin thereby moving the site of cleavage (clone 3B, lanes 5 and 6). Native DNATaq produces even more species of cleavage products than do mutant polymerases retaining residual synthetic activity and additionally converts the hairpin structure to a double-stranded form in the presence of dNTPs due to the high level of synthetic activity in the native polymerase (FIG. 18B, lane 8).

Example 4

Cleavage of Linear Nucleic Acid Substrates

Figure 20A:
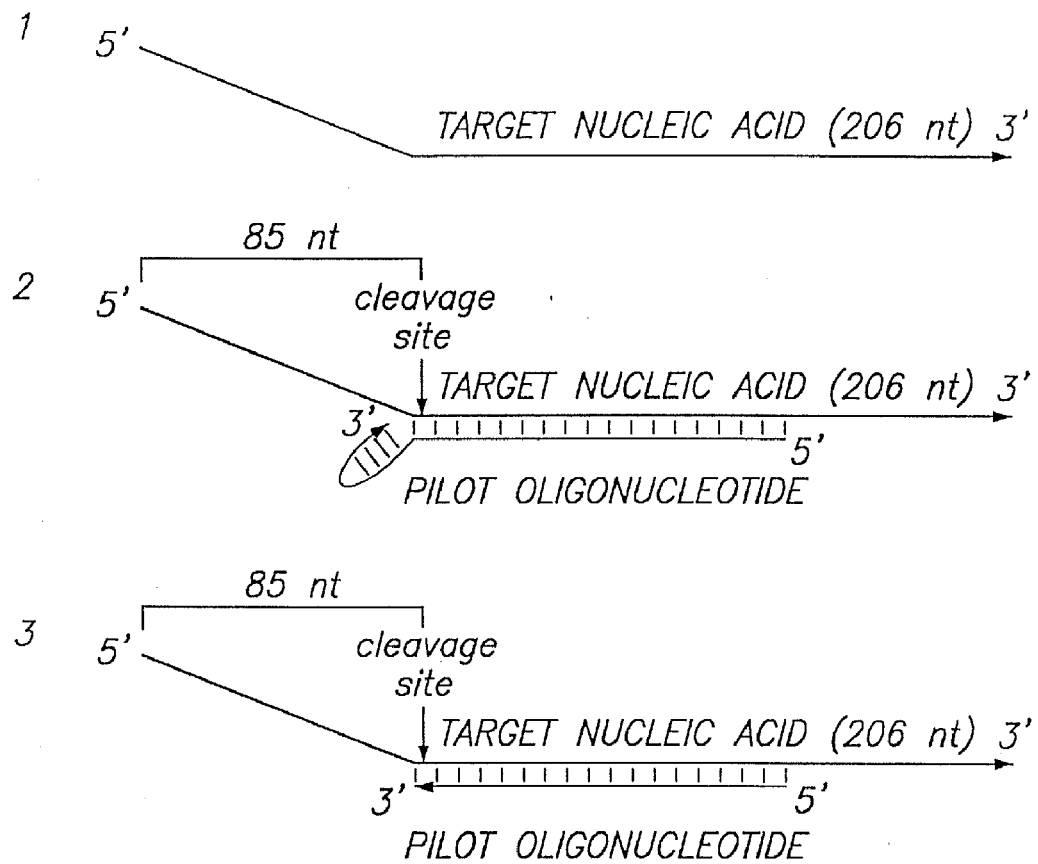

From the above, it should be clear that native (i.e., "wild type") thermostable DNA polymerases are capable of cleaving hairpin structures in a specific manner and that this discovery can be applied with success to a detection assay. In this example, the mutant DNAPs of the present invention are tested against three different cleavage structures shown in FIG. 20A. Structure 1 in FIG. 20A is simply single stranded 206-mer (the preparation and sequence information for which was discussed in Example 1C). Structures 2 and 3 are duplexes; structure 2 is the same hairpin structure as shown in FIG. 11A (bottom), while structure 3 has the hairpin portion of structure 2 removed.

The cleavage reactions comprised 0.01 pmoles of the resulting substrate DNA, and 1 pmole of pilot oligonucleotide in a total volume of 10 µl of 10 mM Tris-Cl, pH 8.3, 100 mM KCl, 1 mM MgCl$_2$. Reactions were incubated for 30 minutes at 55° C., and stopped by the addition of 8 µl of 95% formamide with 20 mM EDTA and 0.05% marker dyes. Samples were heated to 75° C. for 2 minutes immediately before electrophoresis through a 10% polyacrylamide gel (19:1 cross link), with 7M urea, in a buffer of 45 mM Tris-Borate, pH 8.3, 1.4 mM EDTA.

Figure 20B:
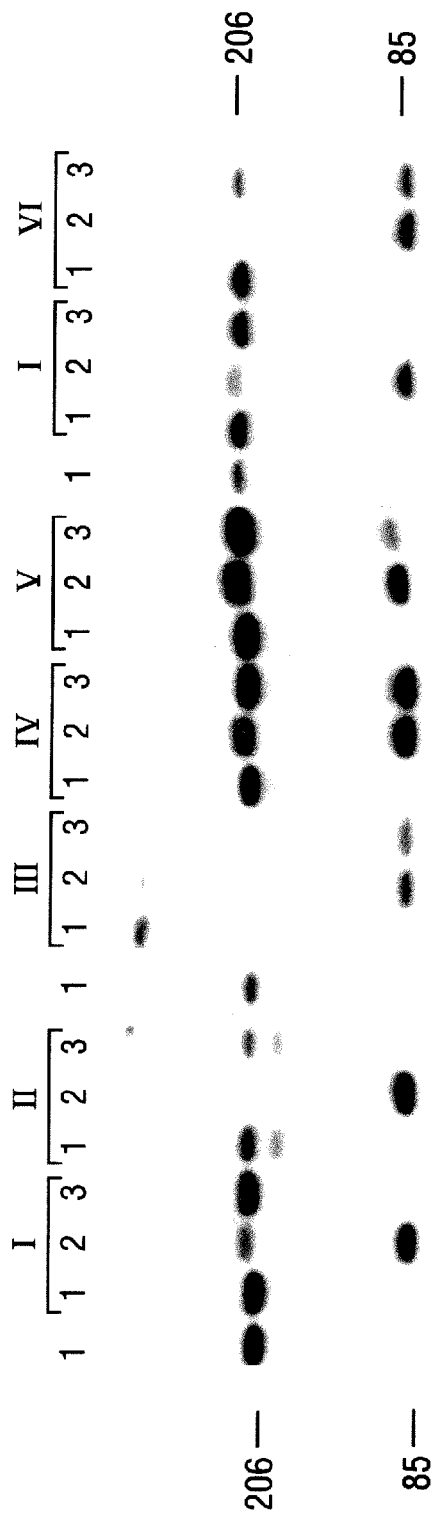

The results were visualized by autoradiography and are shown in FIG. 20B with the enzymes indicated as follows: I is native Taq DNAP; II is native Tfl DNAP; III is CLEAVASE BX shown in FIG. 3E; IV is CLEAVASE BB shown in FIG. 3F; V is the mutant shown in FIG. 4B; and VI is CLEAVASE BN shown in FIG. 3G.

Structure 2 was used to "normalize" the comparison. For example, it was found that it took 50 ng of Taq DNAP and 300 ng of CLEAVASE BN to give similar amounts of cleavage of Structure 2 in thirty (30) minutes. Under these conditions native Taq DNAP is unable to cleave Structure 3 to any significant degree. Native Tfl DNAP cleaves Structure 3 in a manner that creates multiple products.

By contrast, all of the mutants tested cleave the linear duplex of Structure 3. This finding indicates that this characteristic of the mutant DNA polymerases is consistent of thermostable polymerases across thermophilic species.

Example 5

5' Exonucleolytic Cleavage ("Nibbling") by Thermostable DNAPs

It has been found that thermostable DNAPs, including those of the present invention, have a true 5' exonuclease capable of nibbling the 5' end of a linear duplex nucleic acid structures. In this Example, the 206 base pair DNA duplex substrate is again employed (See, Example 1C). In this case, it was produced by the use of one $^{32}$P-labeled primer and one unlabeled primer in a polymerase chain reaction. The cleavage reactions comprised 0.01 pmoles of heat-denatured, end-labeled substrate DNA (with the unlabeled strand also present), 5 pmoles of pilot oligonucleotide (see pilot oligos in FIG. 11A) and 0.5 units of DNAPTaq or 0.5µ of CLEAVASE BB in the E. coli extract (see above), in a total volume of 10 µl of 10 mM TrisCl, pH 8.5, 50 mM KCl, 1.5 mM MgCl$_2$.

Figures 21A, 21B:
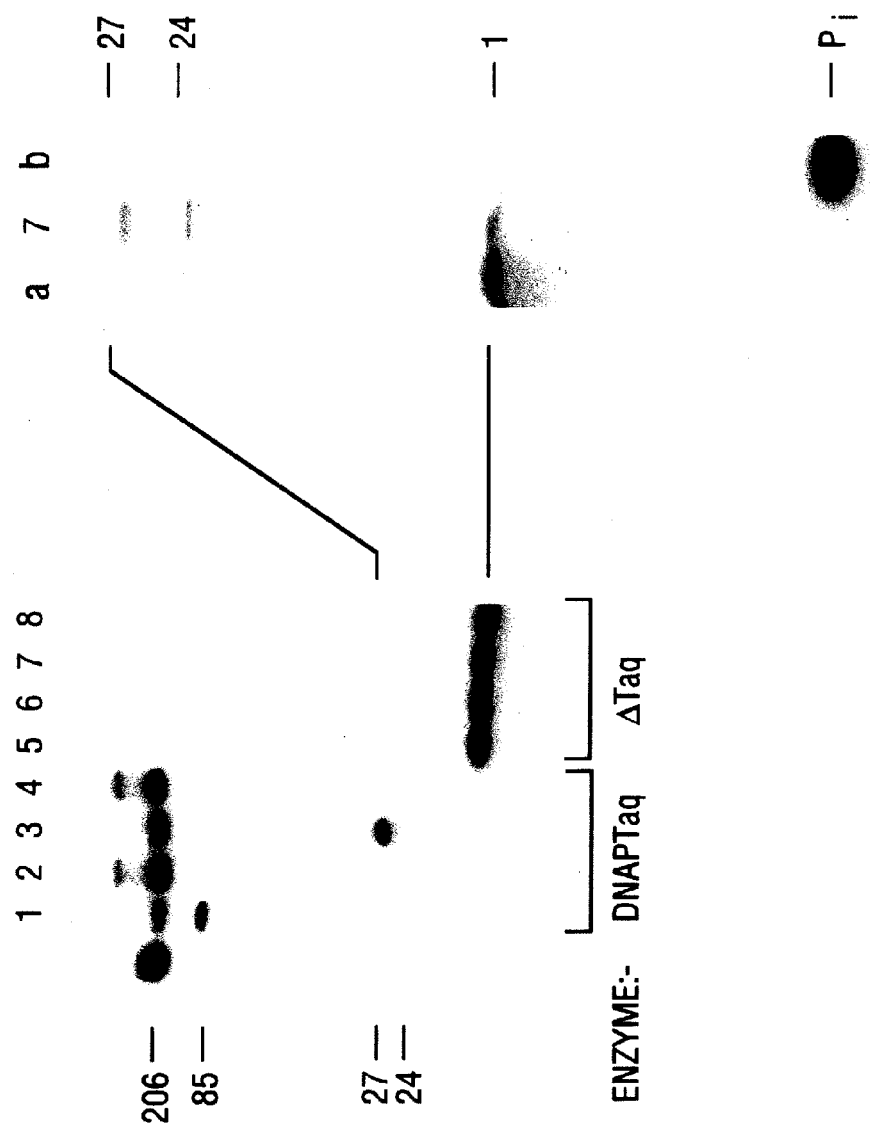
FIG. 21A shows the "nibbling" phenomenon detected with the DNAPs of the present invention.
FIG. 21B shows that the "nibbling" of FIG. 25A is 5' nucleolytic cleavage and not phosphatase cleavage.

Reactions were initiated at 65° C. by the addition of pre-warmed enzyme, then shifted to the final incubation temperature for 30 minutes. The results are shown in FIG. 21A. Samples in lanes 1-4 are the results with native Taq DNAP, while lanes 5-8 shown the results with CLEAVASE BB. The reactions for lanes 1, 2, 5, and 6 were performed at 65° C. and reactions for lanes 3, 4, 7, and 8 were performed at 50° C. and all were stopped at temperature by the addition of 8 µl of 95% formamide with 20 mM EDTA and 0.05% marker dyes. Samples were heated to 75° C. for 2 minutes immediately before electrophoresis through a 10% acrylamide gel (19:1 cross-linked), with 7 M urea, in a buffer of 45 mM TrisBorate, pH 8.3, 1.4 mM EDTA. The expected product in reactions 1, 2, 5, and 6 is 85 nucleotides long; in reactions 3 and 7, the expected product is 27 nucleotides long. Reactions 4 and 8 were performed without pilot, and should remain at 206 nucleotides. The faint band seen at 24 nucleotides is residual end-labeled primer from the PCR.

The surprising result is that CLEAVASE BB under these conditions causes all of the label to appear in a very small species, suggesting the possibility that the enzyme completely hydrolyzed the substrate. To determine the composition of the fastest-migrating band seen in lanes 5-8 (reactions performed with the deletion mutant), samples of the 206 base pair duplex were treated with either T7 gene 6 exonuclease (USB) or with calf intestine alkaline phosphatase (Promega), according to manufacturers' instructions, to produce either labeled mononucleotide (lane a of FIG. 21B) or free $^{32}$P-labeled inorganic phosphate (lane b of FIG. 21B), respectively. These products, along with the products seen in lane 7 of panel A were resolved by brief electrophoresis through a 20% acrylamide gel (19:1 cross-link), with 7 M urea, in a buffer of 45 mM TrisBorate, pH 8.3, 1.4 mM EDTA. CLEAVASE BB is thus capable of converting the substrate to mononucleotides.

Example 6

Nibbling is Duplex Dependent

The nibbling by CLEAVASE BB is duplex dependent. In this Example, internally labeled, single strands of the 206-mer were produced by 15 cycles of primer extension incorporating α-$^{32}$P labeled dCTP combined with all four unlabeled dNTPs, using an unlabeled 206-bp fragment as a template. Single and double stranded products were resolved by electrophoresis through a non-denaturing 6% polyacrylamide gel (29:1 cross-link) in a buffer of 45 mM TrisBorate, pH 8.3, 1.4 mM EDTA, visualized by autoradiography, excised from the gel, eluted by passive diffusion, and concentrated by ethanol precipitation.

The cleavage reactions comprised 0.04 pmoles of substrate DNA, and 2 µl of CLEAVASE BB (in an $E.$ $coli$ extract as described above) in a total volume of 40 µl of 10 mM TrisCl, pH 8.5, 50 mM KCl, 1.5 mM $MgCl_2$. Reactions were initiated by the addition of pre-warmed enzyme; 10 µl aliquots were removed at 5, 10, 20, and 30 minutes, and transferred to prepared tubes containing 8 µl of 95% formamide with 30 mM EDTA and 0.05% marker dyes. Samples were heated to 75° C. for 2 minutes immediately before electrophoresis through a 10% acrylamide gel (19:1 cross-linked), with 7 M urea, in a buffer of 45 mM TrisBorate, pH 8.3, 1.4 mM EDTA. Results were visualized by autoradiography as shown in FIG. 22. Clearly, the cleavage by CLEAVASE BB depends on a duplex structure; no cleavage of the single strand structure is detected whereas cleavage of the 206-mer duplex is complete.

Example 7

Nibbling can be Target Directed

Figure 23:
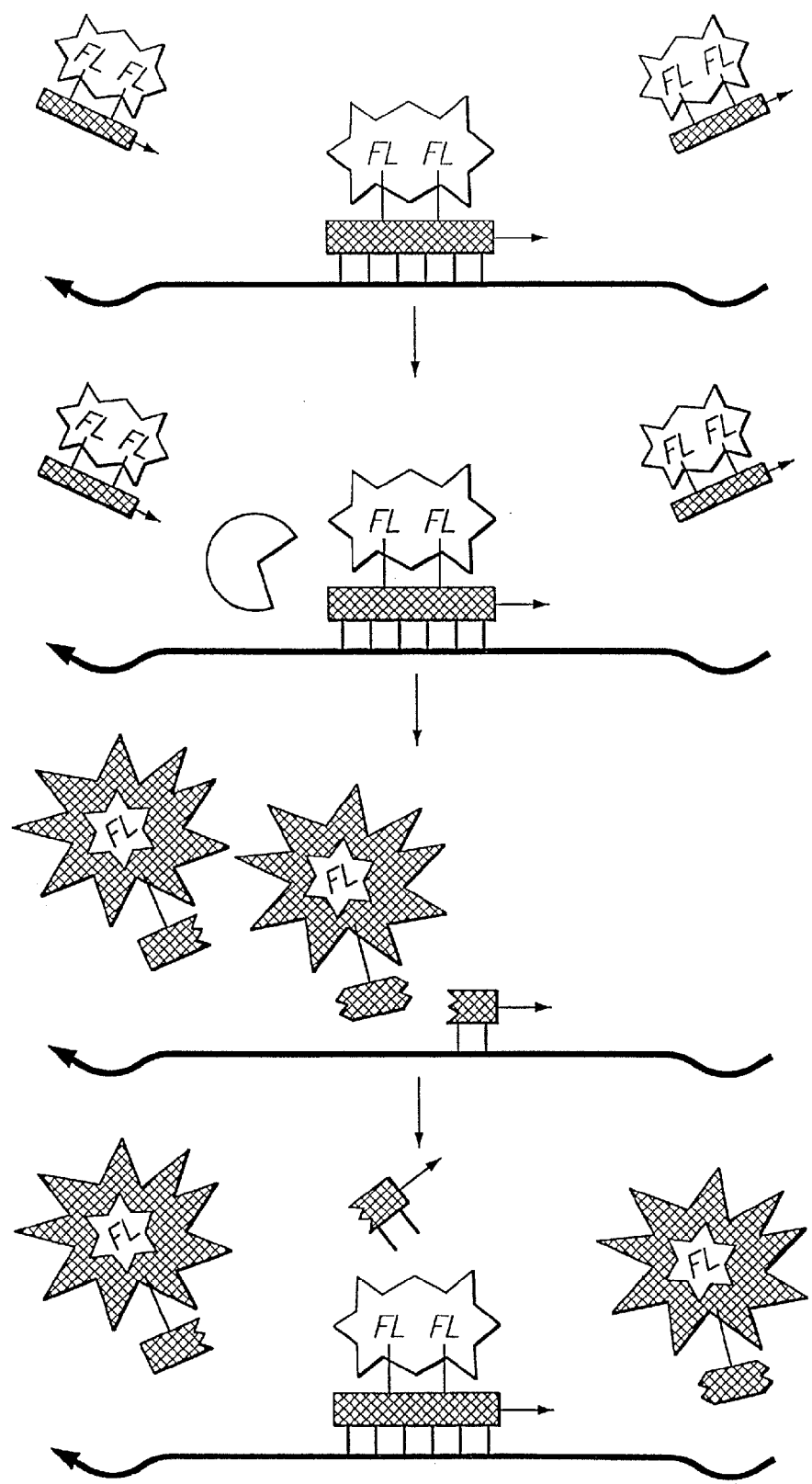
FIG. 23 is a schematic showing how "nibbling" can be employed in a detection assay.

The nibbling activity of the DNAPs of the present invention can be employed with success in a detection assay. One embodiment of such an assay is shown in FIG. 23. In this assay, a labeled oligo is employed that is specific for a target sequence. The oligo is in excess of the target so that hybridization is rapid. In this embodiment, the oligo contains two fluorescein labels whose proximity on the oligo causes their emission to be quenched. When the DNAP is permitted to nibble the oligo the labels separate and are detectable. The shortened duplex is destabilized and disassociates. Importantly, the target is now free to react with an intact labeled oligo. The reaction can continue until the desired level of detection is achieved. An analogous, although different, type of cycling assay has been described employing lambda exonuclease. See C. G. Copley and C. Boot, $BioTechniques$ 13:888 (1992).

Figure 24A:
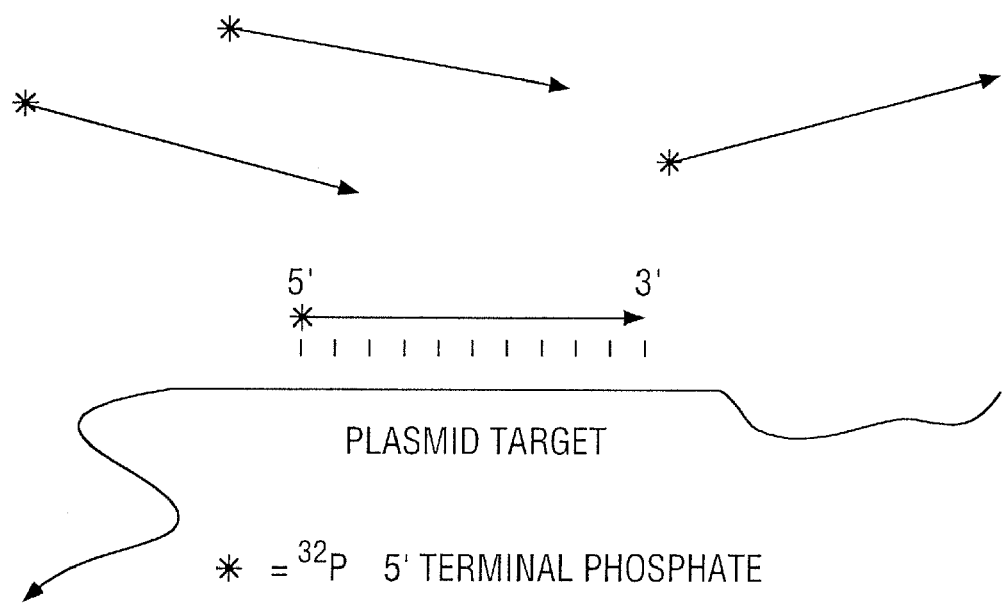
FIGS. 24A and B demonstrates that "nibbling" can be target directed.

The success of such an assay depends on specificity. In other words, the oligo must hybridize to the specific target. It is also preferred that the assay be sensitive; the oligo ideally should be able to detect small amounts of target. FIG. 24A shows a 5'-end $^{32}$P-labeled primer bound to a plasmid target sequence. In this case, the plasmid was pUC19 (commercially available) which was heat denatured by boiling two (2) minutes and then quick chilling. The primer is a 21-mer (SEQ ID NO:28). The enzyme employed was CLEAVASE BX (a dilution equivalent to 5×10$^{-3}$ µl extract) in 100 mM KCl, 10 mM Tris-Cl, pH 8.3, 2 mM $MnCl_2$. The reaction was performed at 55° C. for sixteen (16) hours with or without genomic background DNA (from chicken blood). The reaction was stopped by the addition of 8 µl of 95% formamide with 20 mM EDTA and marker dyes.

Figure 24B:
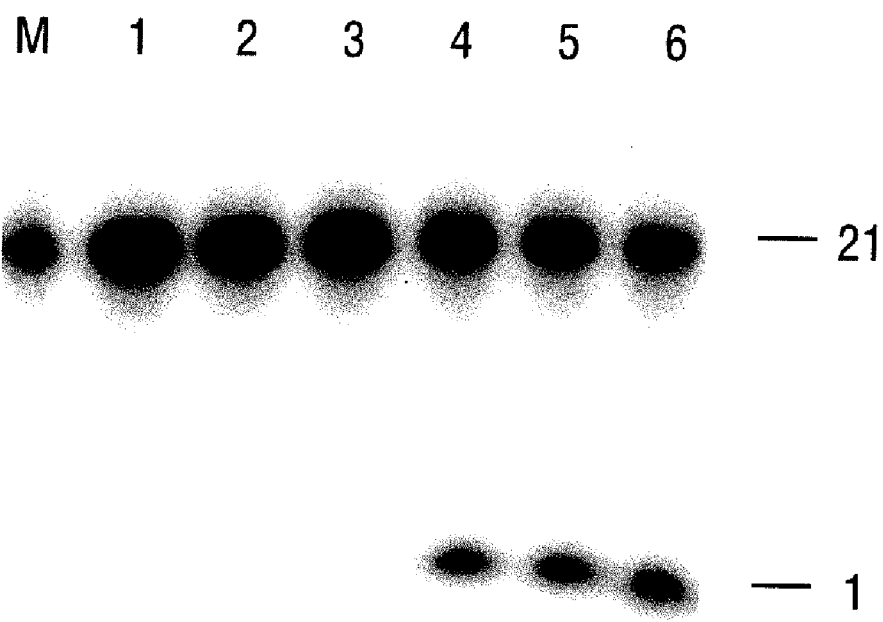

The products of the reaction were resolved by PAGE (10% polyacrylamide, 19:1 cross link, 1×TBE) as seen in FIG. 24B. Lane "M" contains the labeled 21-mer. Lanes 1-3 contain no specific target, although Lanes 2 and 3 contain 100 ng and 200 ng of genomic DNA, respectively. Lanes 4, 5 and 6 all contain specific target with either 0 ng, 100 ng, or 200 ng of genomic DNA, respectively. It is clear that conversion to mononucleotides occurs in Lanes 4, 5 and 6 regardless of the presence or amount of background DNA. Thus, the nibbling can be target directed and specific.

Example 8

Cleavase Purification

As noted above, expressed thermostable proteins (i.e., the 5' nucleases), were isolated by crude bacterial cell extracts. The precipitated $E.$ $coli$ proteins were then, along with other cell debris, removed by centrifugation. In this Example, cells expressing the BN clone were cultured and collected (500 grams). For each gram (wet weight) of $E.$ $coli,$ 3 ml of lysis buffer (50 mM Tris-HCl, pH 8.0, 1 mM EDTA, 100 µM NaCl) was added. The cells were lysed with 200 µg/ml lysozyme at room temperature for 20 minutes. Thereafter deoxycholic acid was added to make a 0.2% final concentration and the mixture was incubated 15 minutes at room temperature.

The lysate was sonicated for approximately 6-8 minutes at 0° C. The precipitate was removed by centrifugation (39,000 g for 20 minutes). Polyethyleneimine was added (0.5%) to the supernatant and the mixture was incubated on ice for 15 minutes. The mixture was centrifuged (5,000 g for 15 minutes) and the supernatant was retained. This was heated for 30 minutes at 60° C. and then centrifuged again (5,000 g for 15 minutes) and the supernatant was again retained.

The supernatant was precipitated with 35% ammonium sulfate at 4° C. for 15 minutes. The mixture was then centrifuged (5,000 g for 15 minutes) and the supernatant was removed. The precipitate was then dissolved in 0.25M KCl, 20 Tris pH 7.6, 0.2% Tween and 0.1 EDTA) and then dialyzed against Binding Buffer (8× Binding Buffer comprises: 40 mM imidazole, 4M NaCl, 160 mM Tris-HCl, pH 7.9).

The solubilized protein is then purified on the Ni$^{++}$column (Novagen). The Binding Buffer is allows to drain to the top of the column bed and load the column with the prepared extract. A flow rate of about 10 column volumes per hour is optimal for efficient purification. If the flow rate is too fast, more impurities will contaminate the eluted fraction.

The column is washed with 25 ml (10 volumes) of 1× Binding Buffer and then washed with 15 ml (6 volumes) of 1X Wash Buffer (8× Wash Buffer comprises: 480 mM imidazole, 4 M NaCl, 160 mM Tris-HCl, pH 7.9). The bound protein was eluted with 15 ml (6 volumes) of 1X Elute Buffer (4× Elute Buffer comprises: 4 mM imidazole, 2 M NaCl, 80 mM Tris-HCl, pH 7.9). Protein is then reprecipitated with 35% ammonium sulfate as above. The precipitate was then dissolved and dialyzed against: 20 mM Tris, 100 mM KCl, 1 mM EDTA). The solution was brought up to 0.1% each of Tween 20 and NP-40 and stored at 4° C.

Example 9

The Use of Various Divalent Cations in the Cleavage Reaction Influences the Nature of the Resulting Cleavage Products In comparing the 5' nucleases generated by the modification and/or deletion of the C-terminal polymerization domain of *Thermus aquaticus* DNA polymerase (DNAPTaq), as diagrammed in FIG. 3B-G, significant differences in the strength of the interactions of these proteins with the 3' end of primers located upstream of the cleavage site (as depicted in FIG. 5) were noted. In describing the cleavage of these structures by PolI-type DNA polymerases (See, Example 1, and Lyamichev et al., Science 260:778 [1993]), it was observed that in the absence of a primer, the location of the junction between the double-stranded region and the single-stranded 5' and 3' arms determined the site of cleavage, but in the presence of a primer, the location of the 3' end of the primer became the determining factor for the site of cleavage. It was postulated that this affinity for the 3' end was in accord with the synthesizing function of the DNA polymerase.

Structure 2, shown in FIG. 20A, was used to test the effects of a 3' end proximal to the cleavage site in cleavage reactions comprising several different solutions (e.g., solutions containing different salts [KCl or NaCl], different divalent cations [$Mn^{2+}$ or $Mg^{2+}$], etc.) as well as the use of different temperatures for the cleavage reaction. When the reaction conditions were such that the binding of the enzyme (e.g., a DNAP comprising a 5' nuclease, a modified DNAP or a 5' nuclease) to the 3' end (of the pilot oligonucleotide) near the cleavage site was strong, the structure shown is cleaved at the site indicated in FIG. 20A. This cleavage releases the unpaired 5' arm and leaves a nick between the remaining portion of the target nucleic acid and the folded 3' end of the pilot oligonucleotide. In contrast, when the reaction conditions are such that the binding of the DNAP (comprising a 5' nuclease) to the 3' end was weak, the initial cleavage was as described above, but after the release of the 5' arm, the remaining duplex is digested by the exonuclease function of the DNAP.

One way of weakening the binding of the DNAP to the 3' end is to remove all or part of the domain to which at least some of this function has been attributed. Some of 5' nucleases created by deletion of the polymerization domain of DNAPTaq have enhanced true exonuclease function, as demonstrated in Example 5.

The affinity of these types of enzymes (i.e., 5' nucleases associated with or derived from DNAPs) for recessed 3' ends may also be affected by the identity of the divalent cation present in the cleavage reaction. It was demonstrated by Longley et al. (Nucl. Acids Res., 18:7317 [1990]) that the use of $MnCl_2$ in a reaction with DNAPTaq enabled the polymerase to remove nucleotides from the 5' end of a primer annealed to a template, albeit inefficiently. Similarly, by examination of the cleavage products generated using Structure 2 from FIG. 20A, as described above, in a reaction containing either DNAPTaq or the CLEAVASE BB nuclease, it was observed that the substitution of $MnCl_2$ for $MgCl_2$ in the cleavage reaction resulted in the exonucleolytic "nibbling" of the duplex downstream of the initial cleavage site. While not limiting the invention to any particular mechanism, it is thought that the substitution of $MnCl_2$ for $MgCl_2$ in the cleavage reaction lessens the affinity of these enzymes for recessed 3' ends.

In all cases, the use of $MnCl_2$ enhances the 5' nuclease function, and in the case of the CLEAVASE BB nuclease, a 50- to 100-fold stimulation of the 5' nuclease function is seen. Thus, while the exonuclease activity of these enzymes was demonstrated above in the presence of $MgCl_2$, the assays described below show a comparable amount of exonuclease activity using 50 to 100-fold less enzyme when $MnCl_2$ is used in place of $MgCl_2$. When these reduced amounts of enzyme are used in a reaction mixture containing $MgCl_2$, the nibbling or exonuclease activity is much less apparent than that seen in Examples 5-7.

Similar effects are observed in the performance of the nucleic acid detection assay described in Examples 10-39 below when reactions performed in the presence of either $MgCl_2$ or $MnCl_2$ are compared. In the presence of either divalent cation, the presence of the INVADER oligonucleotide (described below) forces the site of cleavage into the probe duplex, but in the presence of $MnCl_2$ the probe duplex can be further nibbled producing a ladder of products that are visible when a 3' end label is present on the probe oligonucleotide. When the INVADER oligonucleotide is omitted from a reaction containing $Mn^{2+}$, the probe is nibbled from the 5' end. $Mg^{2+}$-based reactions display minimal nibbling of the probe oligonucleotide. In any of these cases, the digestion of the probe is dependent upon the presence of the target nucleic acid. In the examples below, the ladder produced by the enhanced nibbling activity observed in the presence of $Mn^{2+}$ is used as a positive indicator that the probe oligonucleotide has hybridized to the target sequence.

Example 10

Invasive 5' Endonucleolytic Cleavage by Thermostable 5' Nucleases in the Absence of Polymerization As described in the Examples above, 5' nucleases cleave near the junction between single-stranded and base-paired regions in a bifurcated duplex, usually about one base pair into the base-paired region. In this Example, it is shown that thermostable 5' nucleases, including those of the present invention (e.g., CLEAVASE BN nuclease, CLEAVASE A/G nuclease), have the ability to cleave a greater distance into the base paired region when provided with an upstream oligonucleotide bearing a 3' region that is homologous to a 5' region of the subject duplex, as shown in FIG. 26.

FIG. 26 shows a synthetic oligonucleotide that was designed to fold upon itself and that consists of the following sequence: 5'-GTTCTCTGCTCTCTGGTCGCTG TCTCGCTTGTGAAACAAGCGAGA-CAGCGTGGTCTCTCG-3' (SEQ ID NO:29). This oligonucleotide is referred to as the "S-60 Hairpin." The 15 base-pair hairpin formed by this oligonucleotide is further stabilized by a "tri-loop" sequence in the loop end (i.e., three nucleotides form the loop portion of the hairpin) (Hiraro et al., Nucleic Acids Res., 22(4): 576 [1994]). FIG. 26 also show the sequence of the P-15 oligonucleotide and the location of the region of complementarity shared by the P-15 and S-60 hairpin oligonucleotides. The sequence of the P-15 oligonucleotide is 5'-CGAGAGACCACGCTG-3' (SEQ ID NO:30). As discussed in detail below, the solid black arrowheads shown in FIG. 26 indicate the sites of cleavage of the S-60 hairpin in the absence of the P-15 oligonucleotide and the hollow arrow heads indicate the sites of cleavage in the presence of the P-15 oligonucleotide. The size of the arrow head indicates the relative utilization of a particular site.

Figure 27:
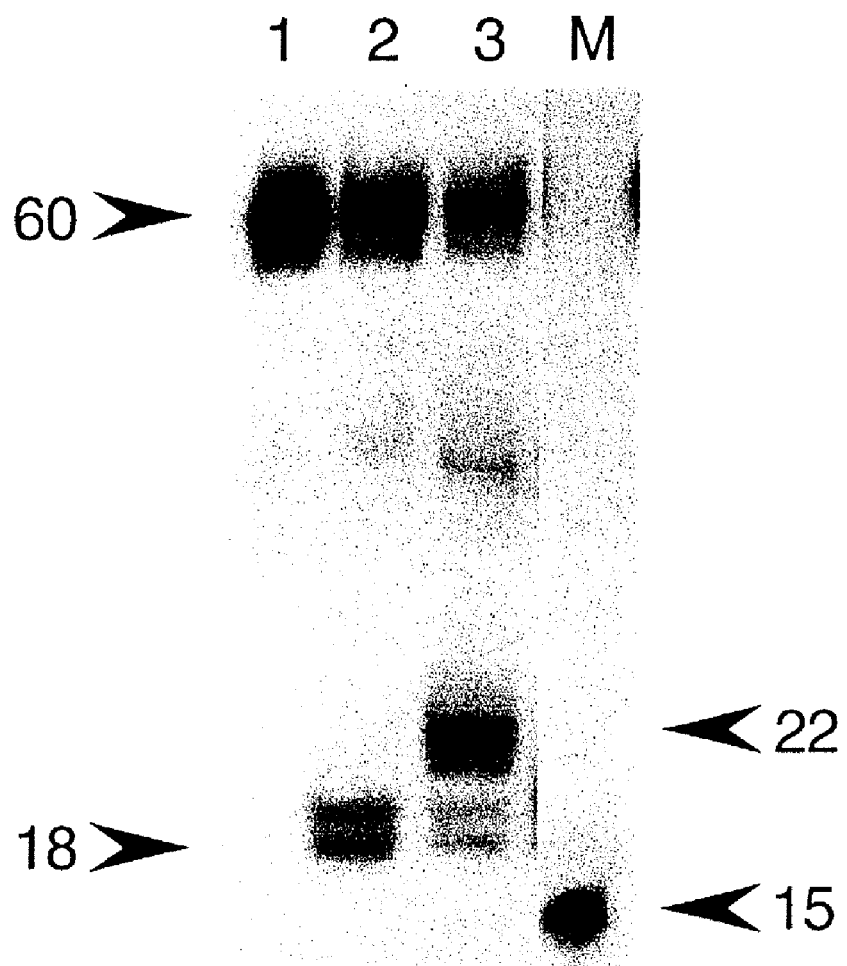
FIG. 27 is an autoradiogram of a gel showing the results of a cleavage reaction run using the S-60 hairpin in the presence or absence of the P-15 oligonucleotide.

The S-60 hairpin molecule was labeled on its 5' end with biotin for subsequent detection. The S-60 hairpin was incubated in the presence of a thermostable 5' nuclease in the presence or the absence of the P-15 oligonucleotide. The presence of the full duplex that can be formed by the S-60 hairpin is demonstrated by cleavage with the CLEAVASE BN 5' nuclease, in a primer-independent fashion (i.e., in the absence of the P-15 oligonucleotide). The release of 18 and 19-nucleotide fragments from the 5' end of the S-60 hairpin molecule showed that the cleavage occurred near the junction between the single and double stranded regions when nothing is hybridized to the 3' arm of the S-60 hairpin (FIG. 27, lane 2).

The reactions shown in FIG. 27 were conducted as follows. Twenty fmole of the 5' biotin-labeled hairpin DNA (SEQ ID NO:29) was combined with 0.1 ng of CLEAVASE BN enzyme and 1 µl of 100 mM MOPS (pH 7.5) containing 0.5% each of Tween-20 and NP-40 in a total volume of 9 µl. In the reaction shown in lane 1, the enzyme was omitted and the volume was made up by addition of distilled water (this served as the uncut or no enzyme control). The reaction shown in lane 3 of FIG. 27 also included 0.5 pmole of the P15 oligonucleotide (SEQ ID NO:30), which can hybridize to the unpaired 3' arm of the S-60 hairpin (SEQ ID NO:29), as diagrammed in FIG. 26.

The reactions were overlaid with a drop of mineral oil, heated to 95° C. for 15 seconds, then cooled to 37° C., and the reaction was started by the addition of 1 µl of 10 mM $MnCl_2$ to each tube. After 5 minutes, the reactions were stopped by the addition of 6 µl of 95% formamide containing 20 mM EDTA and 0.05% marker dyes. Samples were heated to 75° C. for 2 minutes immediately before electrophoresis through a 15% acrylamide gel (19:1 cross-linked), with 7 M urea, in a buffer of 45 mM Tris-Borate, pH 8.3, 1.4 mM EDTA.

After electrophoresis, the gel plates were separated allowing the gel to remain flat on one plate. A 0.2 mm-pore positively-charged nylon membrane (NYTRAN, Schleicher and Schuell, Keene, N.H.), pre-wetted in $H_2O$, was laid on top of the exposed gel. All air bubbles were removed. Two pieces of 3 MM filter paper (Whatman) were then placed on top of the membrane, the other glass plate was replaced, and the sandwich was clamped with binder clips. Transfer was allowed to proceed overnight. After transfer, the membrane was carefully peeled from the gel and allowed to air dry. After complete drying, the membrane was washed in 1.2× Sequenase Images Blocking Buffer (United States Biochemical) using 0.3 ml of buffer/cm² of membrane. The wash was performed for 30 minutes at room temperature. A streptavidin-alkaline phosphatase conjugate (SAAP, United States Biochemical) was added to a 1:4000 dilution directly to the blocking solution, and agitated for 15 minutes. The membrane was rinsed briefly with $H_2O$ and then washed three times for 5 minutes per wash using 0.5 ml/cm² of 1×SAAP buffer (100 mM Tris-HCl, pH 10, 50 mM NaCl) with 0.1% sodium dodecyl sulfate (SDS). The membrane was rinsed briefly with $H_2O$ between each wash. The membrane was then washed once in 1×SAAP buffer containing 1 mM $MgCl_2$ without SDS, drained thoroughly and placed in a plastic heat-sealable bag. Using a sterile pipet, 5 mls of CDP-Star™ (Tropix, Bedford, Mass.) chemiluminescent substrate for alkaline phosphatase were added to the bag and distributed over the entire membrane for 2-3 minutes. The CDP-Star™-treated membrane was exposed to XRP X-ray film (Kodak) for an initial exposure of 10 minutes.

The resulting autoradiograph is shown in FIG. 27. In FIG. 27, the lane labeled "M" contains the biotinylated P-15 oligonucleotide, which served as a marker. The sizes (in nucleotides) of the uncleaved S-60 hairpin (60 nuc; lane 1), the marker (15 nuc; lane "M") and the cleavage products generated by cleavage of the S-60 hairpin in the presence (lane 3) or absence (lane 2) of the P-15 oligonucleotide are indicated.

Because the complementary regions of the S-60 hairpin are located on the same molecule, essentially no lag time should be needed to allow hybridization (i.e., to form the duplex region of the hairpin). This hairpin structure would be expected to form long before the enzyme could locate and cleave the molecule. As expected, cleavage in the absence of the primer oligonucleotide was at or near the junction between the duplex and single-stranded regions, releasing the unpaired 5' arm (FIG. 27, lane 2). The resulting cleavage products were 18 and 19 nucleotides in length.

It was expected that stability of the S-60 hairpin with the tri-loop would prevent the P-15 oligonucleotide from promoting cleavage in the "primer-directed" manner described in Example 1 above, because the 3' end of the "primer" would remain unpaired. Surprisingly, it was found that the enzyme seemed to mediate an "invasion" by the P-15 primer into the duplex region of the S-60 hairpin, as evidenced by the shifting of the cleavage site 3 to 4 basepairs further into the duplex region, releasing the larger products (22 and 21 nuc.) observed in lane 3 of FIG. 27.

The precise sites of cleavage of the S-60 hairpin are diagrammed on the structure in FIG. 26, with the solid black arrowheads indicating the sites of cleavage in the absence of the P-15 oligonucleotide and the hollow arrow heads indicating the sites of cleavage in the presence of P-15.

These data show that the presence on the 3' arm of an oligonucleotide having some sequence homology with the first several bases of the similarly oriented strand of the downstream duplex can be a dominant factor in determining the site of cleavage by 5' nucleases. Because the oligonucleotide that shares some sequence homology with the first several bases of the similarly oriented strand of the downstream duplex appears to invade the duplex region of the hairpin, it is referred to as an "INVADER" oligonucleotide. As shown in the Examples below, an INVADER oligonucleotide appears to invade (or displace) a region of duplexed nucleic acid regardless of whether the duplex region is present on the same molecule (i.e., a hairpin) or whether the duplex is formed between two separate nucleic acid strands.

Example 11

The INVADER Oligonucleotide Shifts the Site of Cleavage in a Pre-Formed Probe/Target Duplex In Example 10, it was demonstrated that an INVADER oligonucleotide could shift the site at which a 5' nuclease cleaves a duplex region present on a hairpin molecule. In this Example, the ability of an INVADER oligonucleotide to shift the site of cleavage within a duplex region formed between two separate strands of nucleic acid molecules was examined.

A single-stranded target DNA comprising the single-stranded circular M13mp19 molecule and a labeled (fluorescein) probe oligonucleotide were mixed in the presence of the reaction buffer containing salt (KCl) and divalent cations ($Mg^{2+}$ or $Mn^{2+}$) to promote duplex formation. The probe oligonucleotide refers to a labeled oligonucleotide that is complementary to a region along the target molecule (e.g., M13mp19). A second oligonucleotide (unlabeled) was added to the reaction after the probe and target had been allowed to anneal. The second oligonucleotide binds to a region of the target that is located downstream of the region to which the probe oligonucleotide binds. This second oligonucleotide contains sequences that are complementary to a second region of the target molecule. If the second oligonucleotide contains a region that is complementary to a portion of the sequences along the target to which the probe oligonucleotide also binds, this second oligonucleotide is referred to as an INVADER oligonucleotide (see FIG. 28c).

Figure 32:
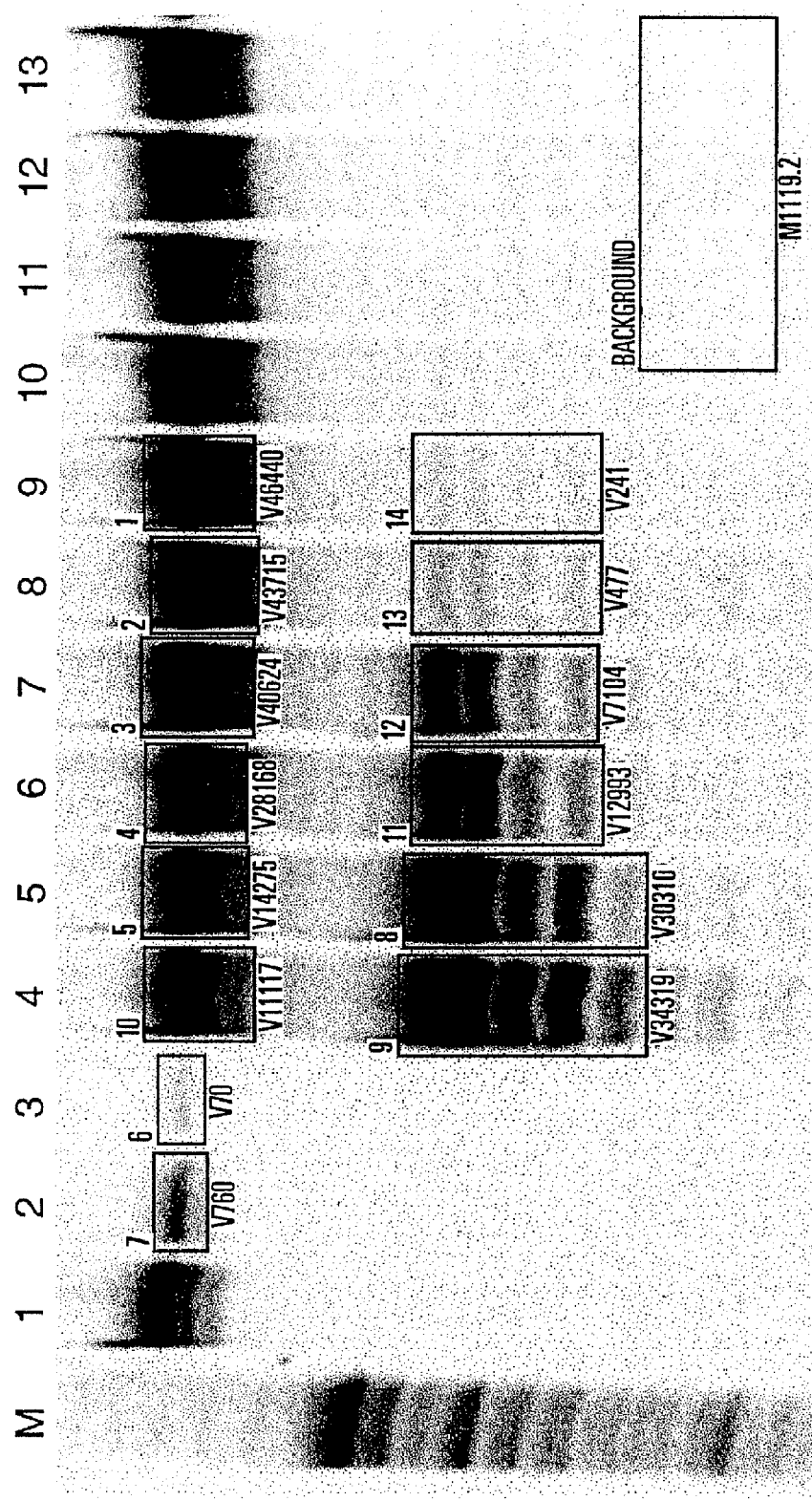
FIG. 32 is the image generated by a fluorescence imager showing the products of INVADER oligonucleotide-directed cleavage assays run in the presence of decreasing amounts of target nucleic acid.
Figure 28A:
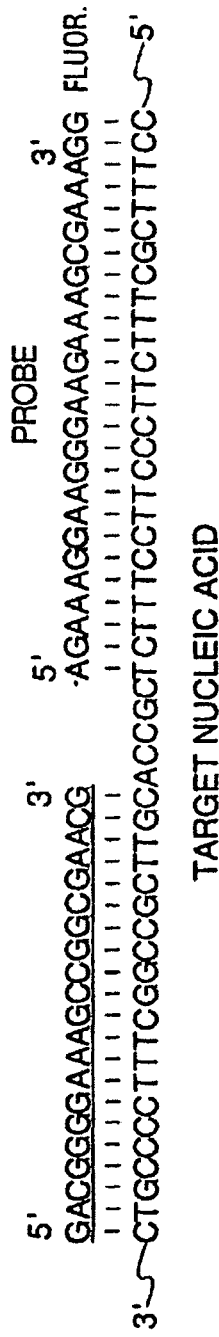
FIG. 28 provides a schematic showing three different arrangements of target-specific oligonucleotides and their hybridization to a target nucleic acid which also has a probe oligonucleotide annealed thereto (SEQ ID NOS:31-35).
Figure 28B:
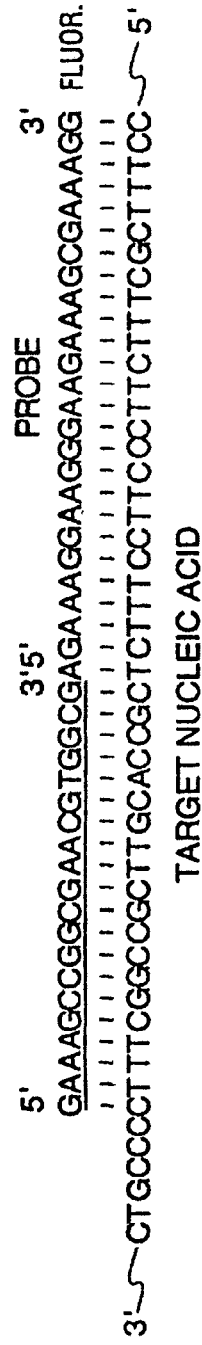
Figure 28C:
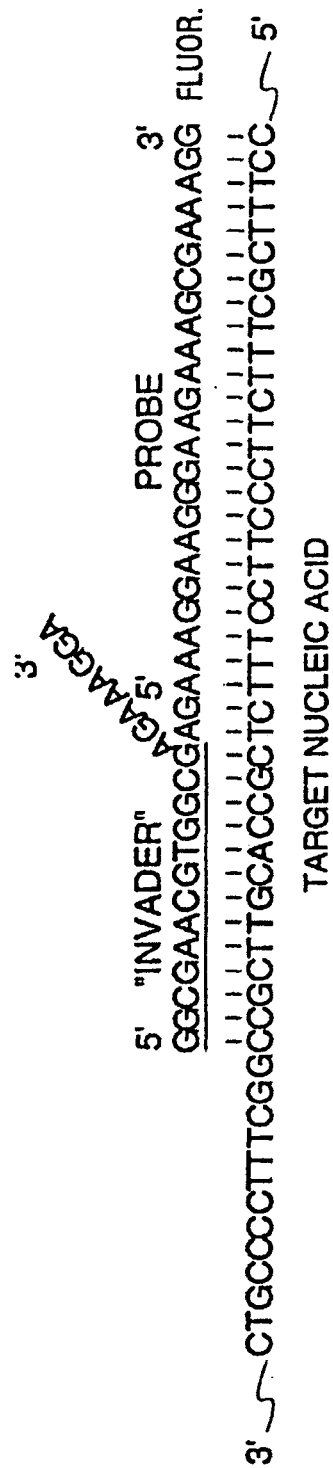
Figure 29:
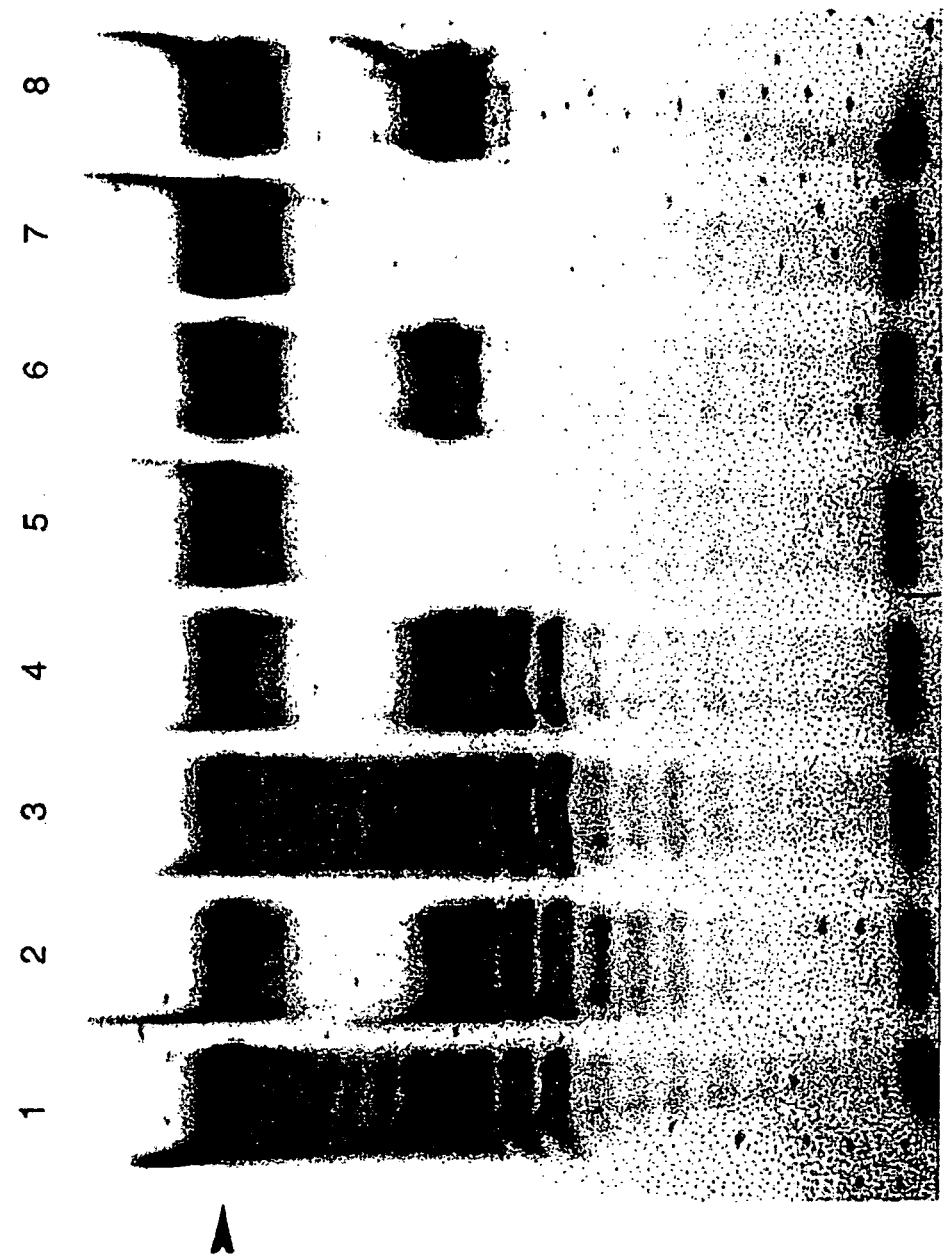
Figure 30:
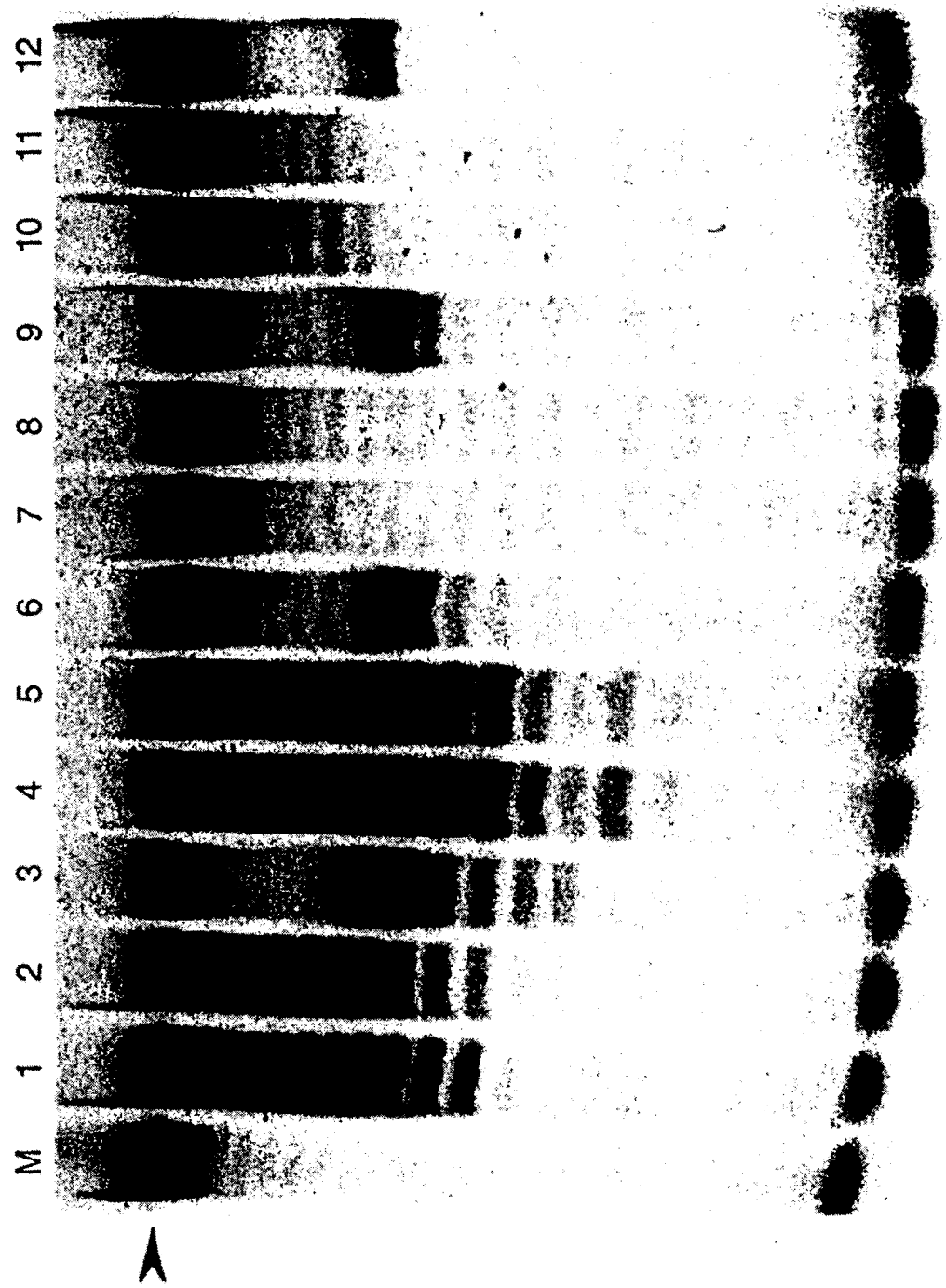
Figure 31:
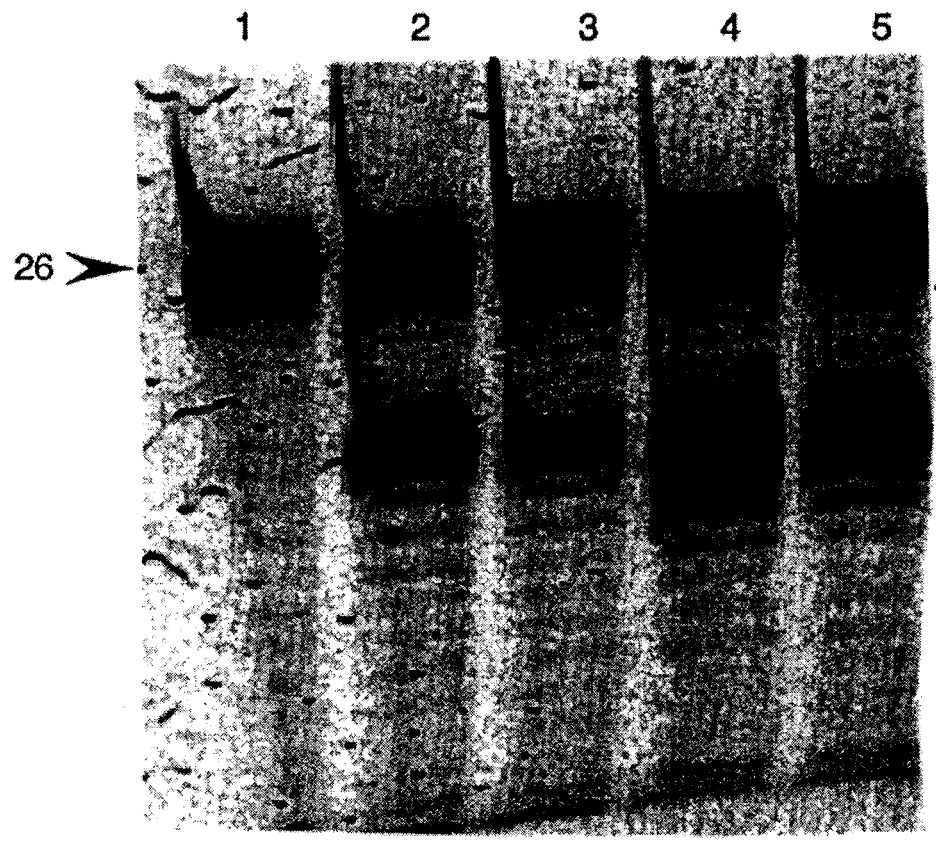
Figure 32:
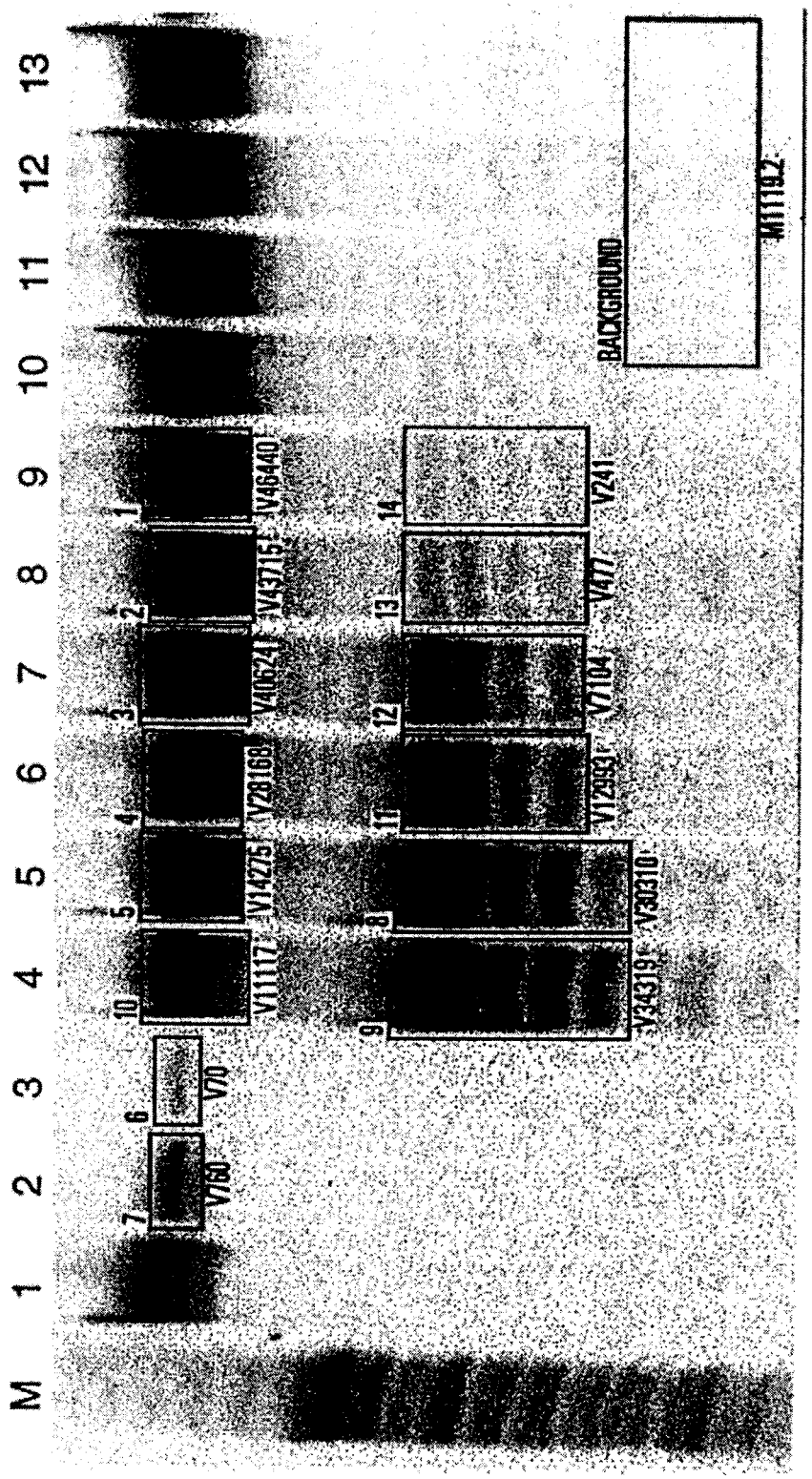
Figure 33:
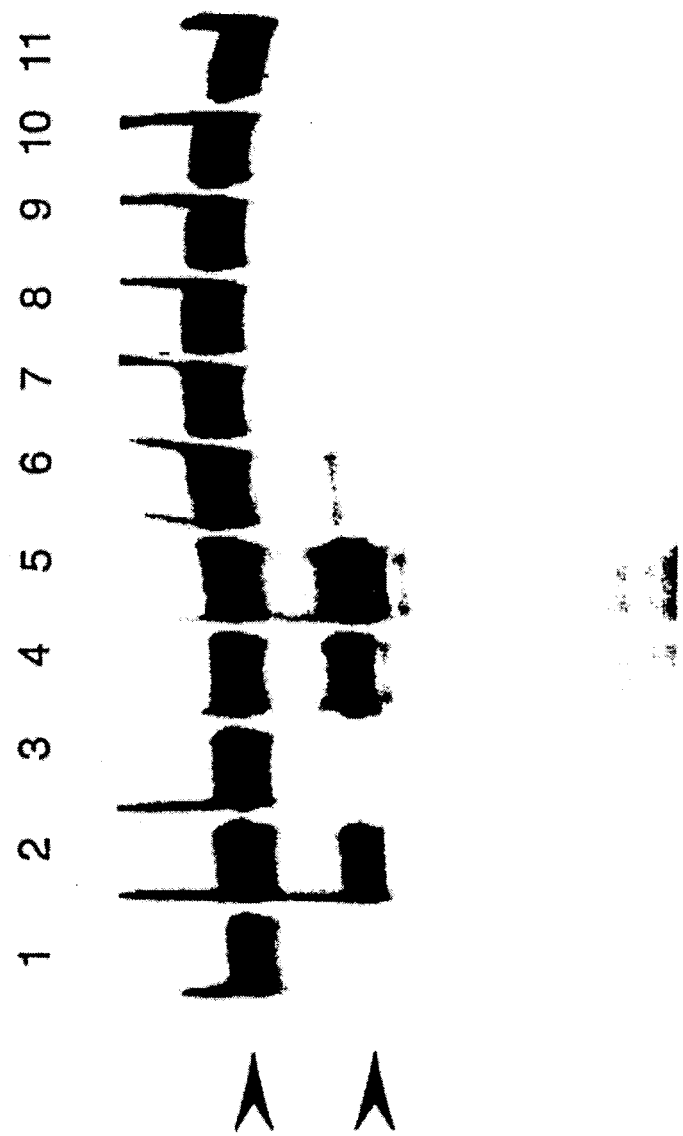
Figure 34:
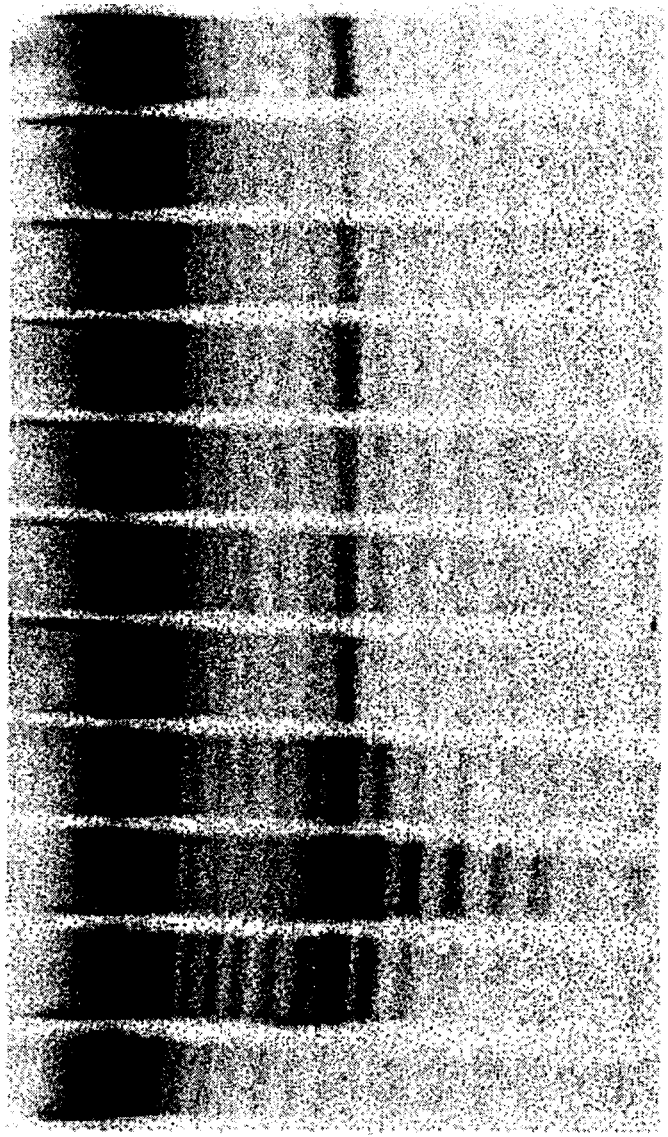
Figure 35:
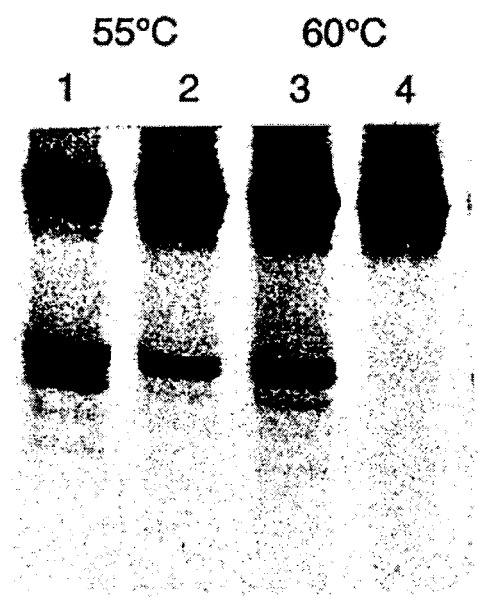
Figure 36A:
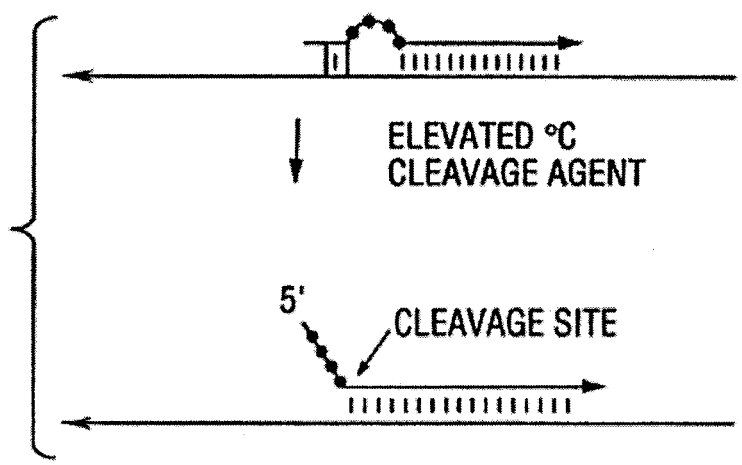
Figure 36B:
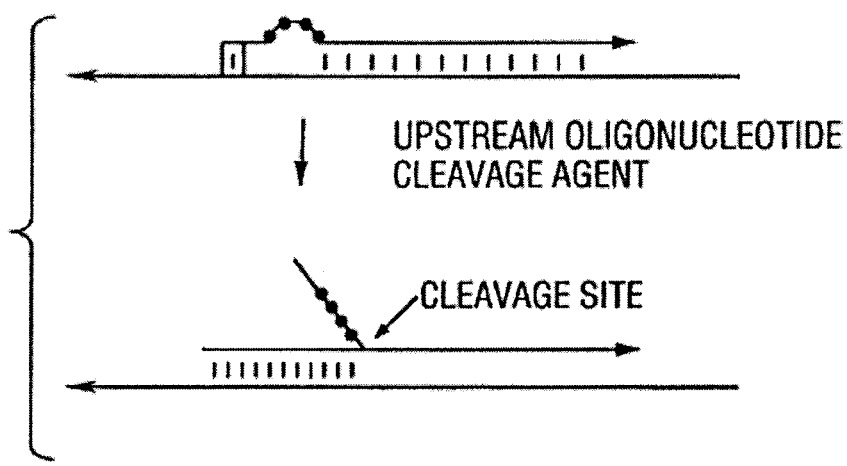
Figure 37:
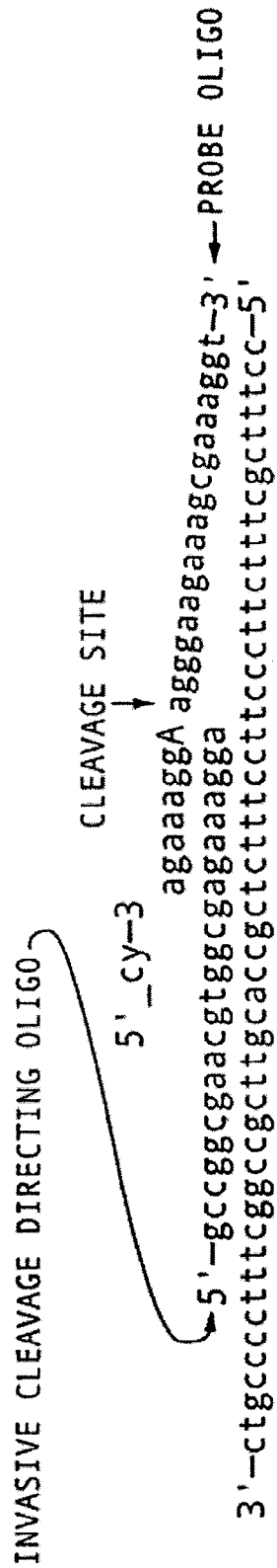
Figure 38:
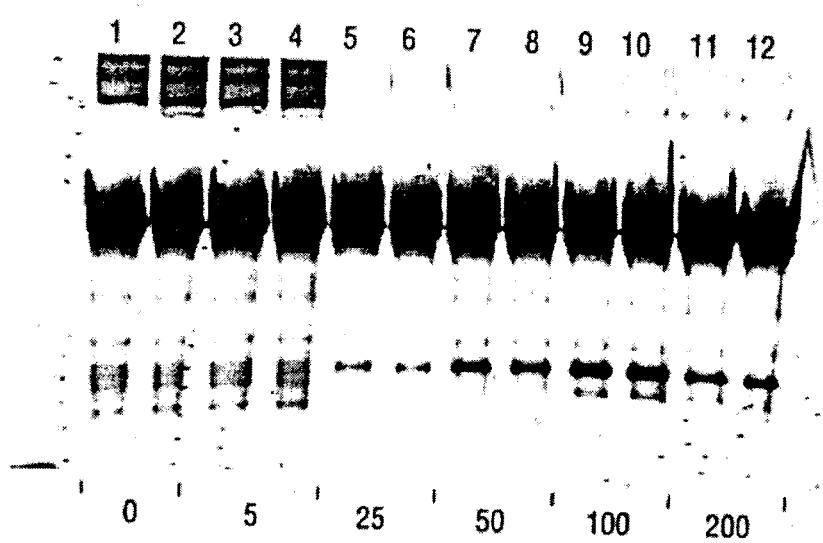
Figure 39:
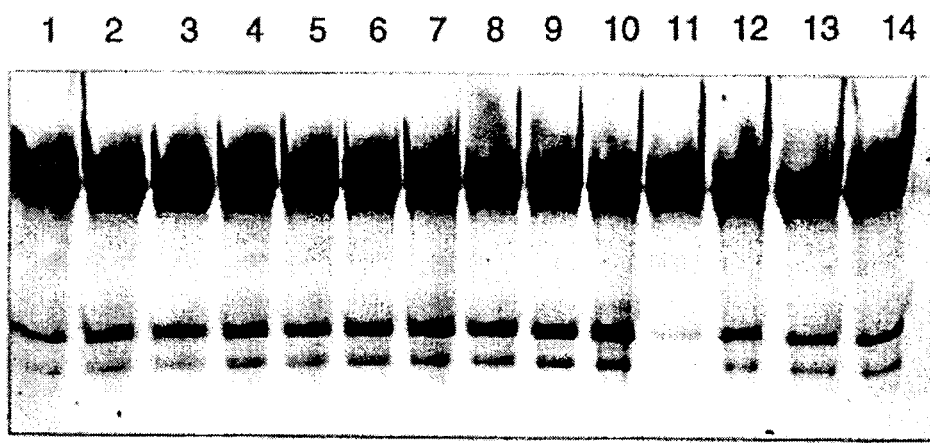
Figure 40:
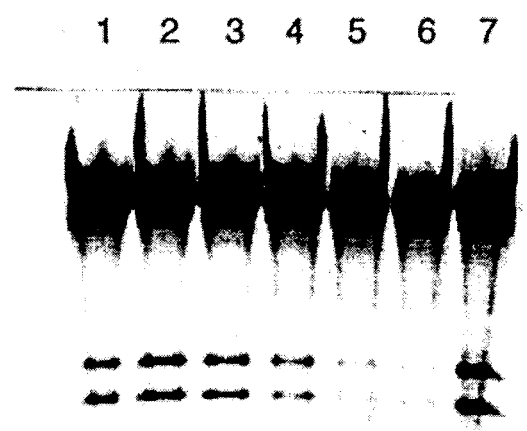
Figure 41:
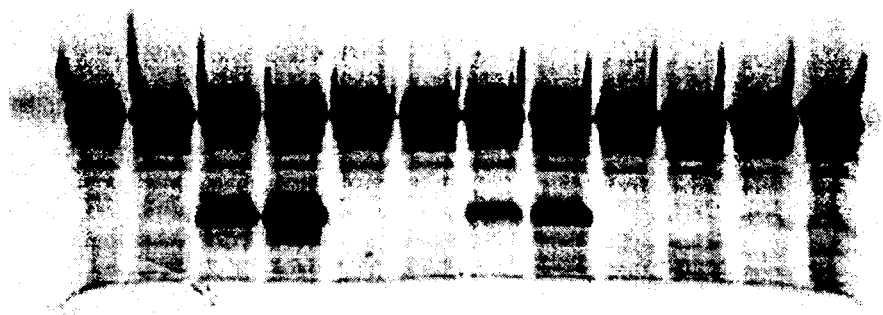
Figure 43:
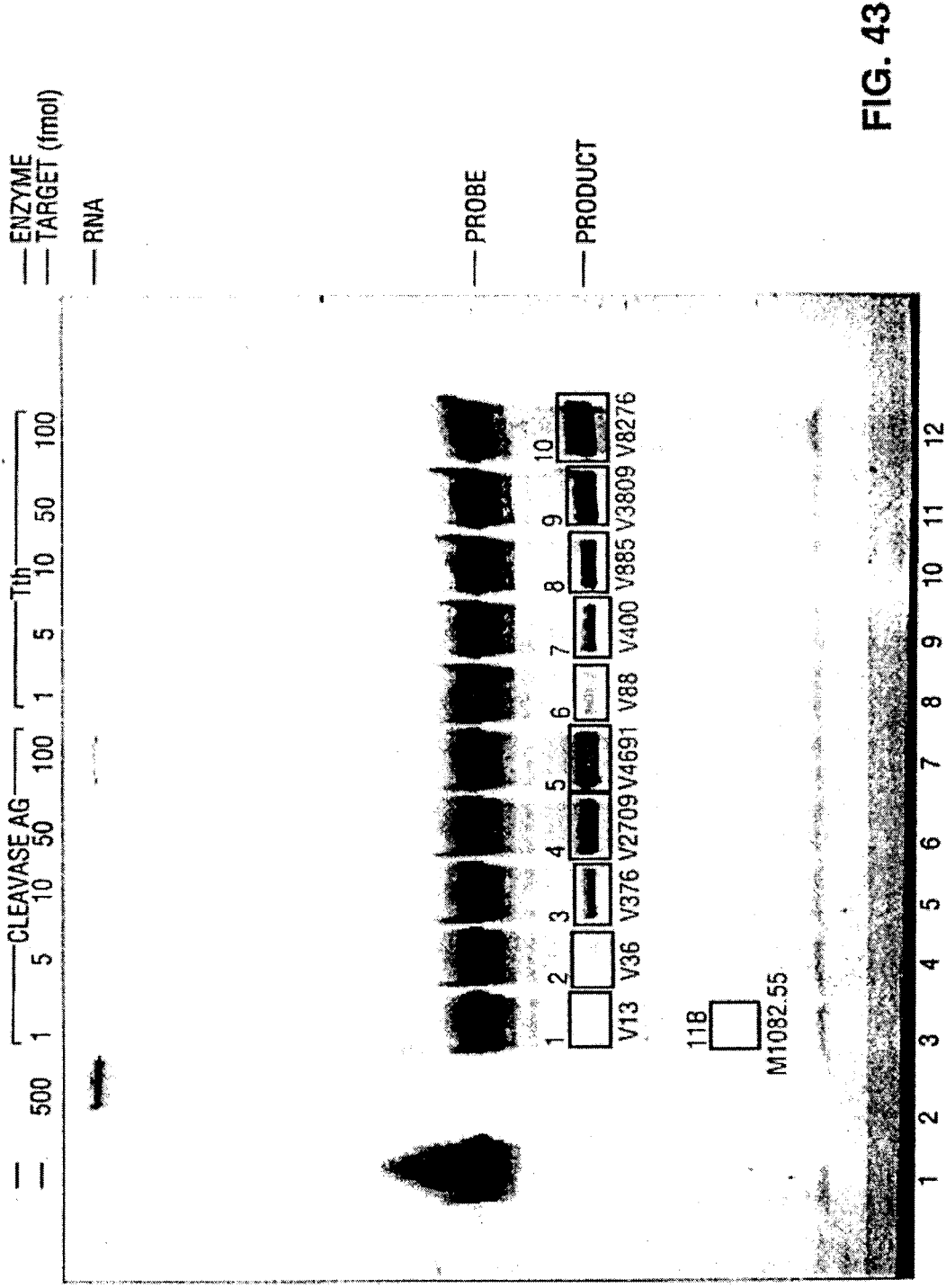

FIG. 32 depicts the annealing of two oligonucleotides to regions along the M13mp19 target molecule (bottom strand in all three structures shown). In FIG. 28 only a 52 nucleotide portion of the M13mp19 molecule is shown; this 52 nucleotide sequence is listed in SEQ ID NO:31. The probe oligonucleotide contains a fluorescein label at the 3' end; the sequence of the probe is 5'-AGAAAGGAAGGGAA-GAAAGCGAAAGG-3' (SEQ ID NO:32). In FIG. 28, sequences comprising the second oligonucleotide, including the INVADER oligonucleotide are underlined. In FIG. 28a, the second oligonucleotide, which has the sequence 5'-GACGGGGAAAGCCGGCGAACG-3' (SEQ ID NO:33), is complementary to a different and downstream region of the target molecule than is the probe oligonucleotide (labeled with fluorescein or "Fluor"); there is a gap between the second, upstream oligonucleotide and the probe for the structure shown in FIG. 28a. In FIG. 28b, the second, upstream oligonucleotide, which has the sequence 5'-GAAAGCCGGC-GAACGTGGCG-3' (SEQ ID NO:34), is complementary to a different region of the target molecule than is the probe oligonucleotide, but in this case, the second oligonucleotide and the probe oligonucleotide abut one another (that is the 3' end of the second, upstream oligonucleotide is immediately adjacent to the 5' end of the probe such that no gap exists between these two oligonucleotides). In FIG. 28c, the second, upstream oligonucleotide (5'-GGCGAACGTGGC-GAGAAAGGA-3' [SEQ ID NO:35]) and the probe oligonucleotide share a region of complementarity with the target molecule. Thus, the upstream oligonucleotide has a 3' arm that has a sequence identical to the first several bases of the downstream probe. In this situation, the upstream oligonucleotide is referred to as an "INVADER" oligonucleotide.

The effect of the presence of an INVADER oligonucleotide upon the pattern of cleavage in a probe/target duplex formed prior to the addition of the INVADER was examined. The INVADER oligonucleotide and the enzyme were added after the probe was allowed to anneal to the target and the position and extent of cleavage of the probe were examined to determine a) if the INVADER was able to shift the cleavage site to a specific internal region of the probe, and b), if the reaction could accumulate specific cleavage products over time, even in the absence of thermal cycling, polymerization, or exonuclease removal of the probe sequence.

The reactions were carried out as follows. Twenty µl each of two enzyme mixtures were prepared, containing 2 µl of CLEAVASE A/G nuclease extract (prepared as described in Example 2), with or without 50 pmole of the INVADER oligonucleotide (SEQ ID NO:35), as indicated, per 4 µl of the mixture. For each of the eight reactions shown in FIG. 29, 150 fmole of M13mp19 single-stranded DNA (available from Life Technologies, Inc.) was combined with 5 pmoles of fluorescein labeled probe (SEQ ID NO:32), to create the structure shown in FIG. 28c, but without the INVADER oligonucleotide present (the probe/target mixture). One half (4 tubes) of the probe/target mixtures were combined with 1 µl of 100 mM MOPS, pH 7.5 with 0.5% each of Tween-20 and NP-40, 0.5 µl of 1 M KCl and 0.25 µl of 80 mM $MnCl_2$, and distilled water to a volume of 6 µl. The second set of probe/target mixtures were combined with 1 µl of 100 mM MOPS, pH 7.5 with 0.5% each of Tween-20 and NP-40, 0.5 µl of 1 M KCl and 0.25 µl of 80 mM $MgCl_2$. The second set of mixtures therefore contained $MgCl_2$ in place of the $MnCl_2$ present in the first set of mixtures.

The mixtures (containing the probe/target with buffer, KCl and divalent cation) were covered with a drop of CHILLOUT evaporation barrier and were brought to 60° C. for 5 minutes to allow annealing. Four µl of the above enzyme mixtures without the INVADER oligonucleotide was added to reactions whose products are shown in lanes 1, 3, 5 and 7 of FIG. 29. Reactions whose products are shown lanes 2, 4, 6, and 8 of FIG. 29 received the same amount of enzyme mixed with the INVADER oligonucleotide (SEQ ID NO:35). Reactions 1, 2, 5 and 6 were incubated for 5 minutes at 60° C. and reactions 3, 4, 7 and 8 were incubated for 15 minutes at 60° C.

All reactions were stopped by the addition of 8 µl of 95% formamide with 20 mM EDTA and 0.05% marker dyes. Samples were heated to 90° C. for 1 minute immediately before electrophoresis through a 20% acrylamide gel (19:1 cross-linked), containing 7 M urea, in a buffer of 45 mM Tris-Borate, pH 8.3, 1.4 mM EDTA. Following electrophoresis, the reaction products and were visualized by the use of an Hitachi FMBIO fluorescence imager, the output of which is seen in FIG. 29. The very low molecular weight fluorescent material seen in all lanes at or near the salt front in FIG. 29 and other fluoro-imager Figures is observed when fluorescently-labeled oligonucleotides are electrophoresed and imaged on a fluoro-imager. This material is not a product of the cleavage reaction.

The use of $MnCl_2$ in these reactions (lanes 1-4) stimulates the true exonuclease or "nibbling" activity of the CLEAVASE enzyme, as described in Example 6, as is clearly seen in lanes 1 and 3 of FIG. 29. This nibbling of the probe oligonucleotide (SEQ ID NO:32) in the absence of INVADER oligonucleotide (SEQ ID NO:35) confirms that the probe oligonucleotide is forming a duplex with the target sequence. The ladder-like products produced by this nibbling reaction may be difficult to differentiate from degradation of the probe by nucleases that might be present in a clinical specimen. In contrast, introduction of the INVADER oligonucleotide (SEQ ID NO:35) caused a distinctive shift in the cleavage of the probe, pushing the site of cleavage 6 to 7 bases into the probe, confirming the annealing of both oligonucleotides. In presence of $MnCl_2$, the exonuclease "nibbling" may occur after the INVADER-directed cleavage event, until the residual duplex is destabilized and falls apart.

In a magnesium based cleavage reaction (lanes 5-8), the nibbling or true exonuclease function of the CLEAVASE A/G is enzyme suppressed (but the endonucleolytic function of the enzyme is essentially unaltered), so the probe oligonucleotide is not degraded in the absence of the INVADER (FIG. 29, lanes 5 and 7). When the INVADER is added, it is clear that the INVADER oligonucleotide can promote a shift in the site of the endonucleolytic cleavage of the annealed probe. Comparison of the products of the 5 and 15 minute reactions with INVADER (lanes 6 and 8 in FIG. 29) shows that additional probe hybridizes to the target and is cleaved. The calculated melting temperature ($T_m$) of the portion of probe that is not invaded (i.e., nucleotides 9-26 of SEQ ID NO:32) is 56° C., so the observed turnover (as evidenced by the accumulation of cleavage products with increasing reaction time) suggests that the full length of the probe molecule, with a calculated $T_m$ of 76° C., is must be involved in the subsequent probe annealing events in this 60° C. reaction.

Example 12

The Overlap of the 3' INVADER Oligonucleotide Sequence with the 5' Region of the Probe Causes a Shift in the Site of Cleavage In Example 11, the ability of an INVADER oligonucleotide to cause a shift in the site of cleavage of a probe annealed to a target molecule was demonstrated. In this Example, experiments were conducted to examine whether the presence of an oligonucleotide upstream from the probe was sufficient to cause a shift in the cleavage site(s) along the probe or whether the presence of nucleotides on the 3' end of the INVADER oligonucleotide that have the same sequence as the first several nucleotides at the 5' end of the probe oligonucleotide were required to promote the shift in cleavage.

To examine this point, the products of cleavage obtained from three different arrangements of target-specific oligonucleotides are compared. A diagram of these oligonucleotides and the way in which they hybridize to a test nucleic acid, M13mp19, is shown in FIG. 28. In FIG. 28*a*, the 3' end of the upstream oligonucleotide (SEQ ID NO:33) is located upstream of the 5' end of the downstream "probe" oligonucleotide (SEQ ID NO:32) such that a region of the M13 target that is not paired to either oligonucleotide is present. In FIG. 28*b*, the sequence of the upstream oligonucleotide (SEQ ID NO:34) is immediately upstream of the probe (SEQ ID NO:32), having neither a gap nor an overlap between the sequences. FIG. 28*c* diagrams the arrangement of the substrates used in the assay of the present invention, showing that the upstream "INVADER" oligonucleotide (SEQ ID NO:35) has the same sequence on a portion of its 3' region as that present in the 5' region of the downstream probe (SEQ ID NO:32). That is to say, these regions will compete to hybridize to the same segment of the M13 target nucleic acid.

In these experiments, four enzyme mixtures were prepared as follows (planning 5 µl per digest): Mixture 1 contained 2.25 µl of CLEAVASE A/G nuclease extract (prepared as described in Example 2) per 5 µl of mixture, in 20 mM MOPS, pH 7.5 with 0.1% each of Tween 20 and NP-40, 4 mM $MnCl_2$ and 100 mM KCl. Mixture 2 contained 11.25 units of Taq DNA polymerase (Promega) per 5 µl of mixture in 20 mM MOPS, pH 7.5 with 0.1% each of Tween 20 and NP-40, 4 mM $MnCl_2$ and 100 mM KCl. Mixture 3 contained 2.25 µl of CLEAVASE A/G nuclease extract per 5 µl of mixture in 20 mM Tris-HCl, pH 8.5, 4 mM $MgCl_2$ and 100 mM KCl. Mixture 4 contained 11.25 units of Taq DNA polymerase per 5 µl of mixture in 20 mM Tris-HCl, pH 8.5, 4 mM $MgCl_2$ and 100 mM KCl.

For each reaction, 50 fmole of M13mp19 single-stranded DNA (the target nucleic acid) was combined with 5 pmole of the probe oligonucleotide (SEQ ID NO:32 which contained a fluorescein label at the 3' end) and 50 pmole of one of the three upstream oligonucleotides diagrammed in FIG. 28 (i.e., one of SEQ ID NOS:33-35), in a total volume of 5 µl of distilled water. The reactions were overlaid with a drop of ChillOut™ evaporation barrier and warmed to 62° C. The cleavage reactions were started by the addition of 5 µl of an enzyme mixture to each tube, and the reactions were incubated at 62° C. for 30 min. The reactions shown in lanes 1-3 of FIG. 30 received Mixture 1; reactions 4-6 received Mixture 2; reactions 7-9 received Mixture 3 and reactions 10-12 received Mixture 4.

After 30 minutes at 62° C., the reactions were stopped by the addition of 8 µl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA.

Following electrophoresis, the products of the reactions were visualized by the use of an Hitachi FMBIO fluorescence imager, the output of which is seen in FIG. 30. The reaction products shown in lanes 1, 4, 7 and 10 of FIG. 30 were from reactions that contained SEQ ID NO:33 as the upstream oligonucleotide (see FIG. 28*a*). The reaction products shown in lanes 2, 5, 8 and 11 of FIG. 30 were from reactions that contained SEQ ID NO:34 as the upstream oligonucleotide (see FIG. 28*b*). The reaction products shown in lanes 3, 6, 9 and 12 of FIG. 30 were from reactions that contained SEQ ID NO:35, the INVADER oligonucleotide, as the upstream oligonucleotide (see FIG. 28*c*).

Examination of the $Mn^{2+}$ based reactions using either CLEAVASE A/G nuclease or DNAPTaq as the cleavage agent (lanes 1 through 3 and 4 through 6, respectively) shows that both enzymes have active exonuclease function in these buffer conditions. The use of a 3' label on the probe oligonucleotide allows the products of the nibbling activity to remain labeled, and therefore visible in this assay. The ladders seen in lanes 1, 2, 4 and 5 confirm that the probe hybridize to the target DNA as intended. These lanes also show that the location of the non-invasive oligonucleotides have little effect on the products generated. The uniform ladder created by these digests would be difficult to distinguish from a ladder causes by a contaminating nuclease, as one might find in a clinical specimen. In contrast, the products displayed in lanes 3 and 6, where an INVADER oligonucleotide was provided to direct the cleavage, show a very distinctive shift, so that the primary cleavage product is smaller than those seen in the non-invasive cleavage. This product is then subject to further nibbling in these conditions, as indicated by the shorter products in these lanes. These INVADER-directed cleavage products would be easily distinguished from a background of non-specific degradation of the probe oligonucleotide.

When $Mg^{2+}$ is used as the divalent cation the results are even more distinctive. In lanes 7, 8, 10 and 11 of FIG. 30, where the upstream oligonucleotides were not invasive, minimal nibbling is observed. The products in the DNAPTaq reactions show some accumulation of probe that has been shortened on the 5' end by one or two nucleotides consistent with previous examination of the action of this enzyme on nicked substrates (Longley et al., supra). When the upstream oligonucleotide is invasive, however, the appearance of the distinctively shifted probe band is seen. These data clearly indicated that it is the invasive 3' portion of the upstream oligonucleotide that is responsible for fixing the site of cleavage of the downstream probe.

Thus, the above results demonstrate that it is the presence of the free or initially non-annealed nucleotides at the 3' end of the INVADER oligonucleotide that mediate the shift in the cleavage site, not just the presence of an oligonucleotide annealed upstream of the probe. Nucleic acid detection assays that employ the use of an INVADER oligonucleotide are termed "INVADER-directed cleavage" assays.

Example 13

INVADER-Directed Cleavage Recognizes Single and Double Stranded Target Molecules in a Background of Non-Target DNA Molecules For a nucleic acid detection method to be broadly useful, it must be able to detect a specific target in a sample that may contain large amounts of other DNA, (e.g., bacterial or human chromosomal DNA). The ability of the INVADER directed cleavage assay to recognize and cleave either single- or double-stranded target molecules in the presence of large amounts of non-target DNA was examined. In these experiments a model target nucleic acid, M13, in either single or double stranded form (single-stranded M13mp18 is available from Life Technologies, Inc and double-stranded M13mp19 is available from NEB), was combined with human genomic DNA (Novagen) and then utilized in INVADER-directed cleavage reactions. Before the start of the cleavage reaction, the DNAs were heated to 95° C. for 15 minutes to completely denature the samples, as is standard practice in assays, such as polymerase chain reaction or enzymatic DNA sequencing, which involve solution hybridization of oligonucleotides to double-stranded target molecules.

Figure 31:
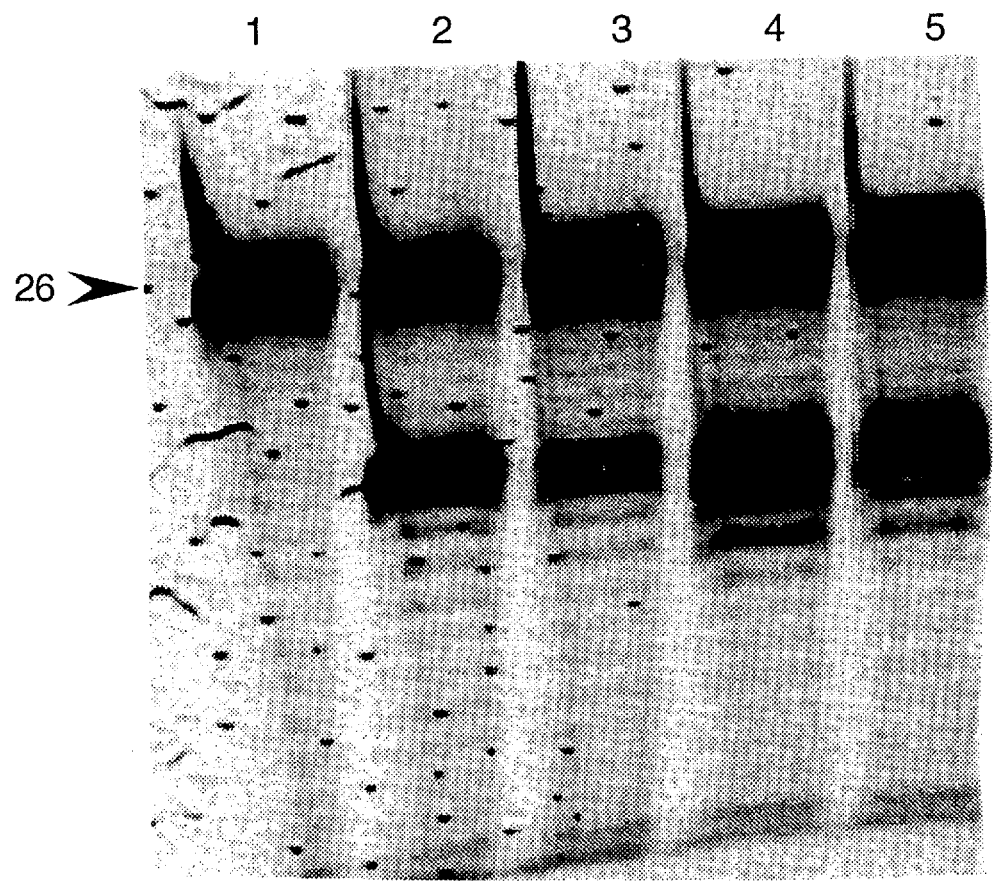
FIG. 31 is the image generated by a fluorescence imager showing the products of INVADER oligonucleotide-directed cleavage assays run in the presence or absence of non-target nucleic acid molecules.

For each of the reactions shown in lanes 2-5 of FIG. 31, the target DNA (25 fmole of the ss DNA or 1 pmole of the ds DNA) was combined with 50 pmole of the INVADER oligonucleotide (SEQ ID NO:35); for the reaction shown in lane 1 the target DNA was omitted. Reactions 1, 3 and 5 also contained 470 ng of human genomic DNA. These mixtures were brought to a volume of 10 µl with distilled water, overlaid with a drop of ChillOut™ evaporation barrier, and brought to 95° C. for 15 minutes. After this incubation period, and still at 95° C., each tube received 10 µl of a mixture comprising 2.25 µl of CLEAVASE A/G nuclease extract (prepared as described in Example 2) and 5 pmole of the probe oligonucleotide (SEQ ID NO:32), in 20 mM MOPS, pH 7.5 with 0.1% each of Tween 20 and NP-40, 4 mM $MnCl_2$ and 100 mM KCl. The reactions were brought to 62° C. for 15 minutes and stopped by the addition of 12 µl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA. The products of the reactions were visualized by the use of an Hitachi FMBIO fluorescence imager. The results are displayed in FIG. 31.

In FIG. 31, lane 1 contains the products of the reaction containing the probe (SEQ ID NO:32), the INVADER oligonucleotide (SEQ ID NO:35) and human genomic DNA. Examination of lane 1 shows that the probe and INVADER oligonucleotides are specific for the target sequence, and that the presence of genomic DNA does not cause any significant background cleavage.

In FIG. 31, lanes 2 and 3 contain reaction products from reactions containing the single-stranded target DNA (M13mp18), the probe (SEQ ID NO:32) and the INVADER oligonucleotide (SEQ ID NO:35) in the absence or presence of human genomic DNA, respectively. Examination of lanes 2 and 3 demonstrate that the INVADER detection assay may be used to detect the presence of a specific sequence on a single-stranded target molecule in the presence or absence of a large excess of competitor DNA (human genomic DNA).

In FIG. 31, lanes 4 and 5 contain reaction products from reactions containing the double-stranded target DNA (M13mp19), the probe (SEQ ID NO:32) and the INVADER oligonucleotide (SEQ ID NO:35) in the absence or presence of human genomic DNA, respectively. Examination of lanes 4 and 5 show that double stranded target molecules are eminently suitable for INVADER-directed detection reactions. The success of this reaction using a short duplexed molecule, M13mp19, as the target in a background of a large excess of genomic DNA is especially noteworthy as it would be anticipated that the shorter and less complex M13 DNA strands would be expected to find their complementary strand more easily than would the strands of the more complex human genomic DNA. If the M13 DNA reannealed before the probe and/or INVADER oligonucleotides could bind to the target sequences along the M13 DNA, the cleavage reaction would be prevented. In addition, because the denatured genomic DNA would potentially contain regions complementary to the probe and/or INVADER oligonucleotides it was possible that the presence of the genomic DNA would inhibit the reaction by binding these oligonucleotides thereby preventing their hybridization to the M13 target. The above results demonstrate that these theoretical concerns are not a problem under the reaction conditions employed above.

In addition to demonstrating that the INVADER detection assay may be used to detect sequences present in a double-stranded target, these data also show that the presence of a large amount of non-target DNA (470 ng/20 µl reaction) does not lessen the specificity of the cleavage. While this amount of DNA does show some impact on the rate of product accumulation, probably by binding a portion of the enzyme, the nature of the target sequence, whether single- or double-stranded nucleic acid, does not limit the application of this assay.

Example 14

Signal Accumulation in the INVADER-Directed Cleavage Assay as a Function of Target Concentration To investigate whether the INVADER-directed cleavage assay could be used to indicate the amount of target nucleic acid in a sample, the following experiment was performed. Cleavage reactions were assembled that contained an INVADER oligonucleotide (SEQ ID NO:35), a labeled probe (SEQ ID NO:32) and a target nucleic acid, M13mp19. A series of reactions, which contained smaller and smaller amounts of the M13 target DNA, was employed in order to examine whether the cleavage products would accumulate in a manner that reflected the amount of target DNA present in the reaction.

The reactions were conducted as follows. A master mix containing enzyme and buffer was assembled. Each 5 µl of the master mixture contained 25 ng of CLEAVASE BN nuclease in 20 mM MOPS (pH 7.5) with 0.1% each of Tween 20 and NP-40, 4 mM $MnCl_2$ and 100 mM KCl. For each of the cleavage reactions shown in lanes 4-13 of FIG. 32, a DNA mixture was generated that contained 5 pmoles of the fluorescein-labeled probe oligonucleotide (SEQ ID NO:32), 50 pmoles of the INVADER oligonucleotide (SEQ ID NO:35) and 100, 50, 10, 5, 1, 0.5, 0.1, 0.05, 0.01 or 0.005 fmoles of single-stranded M13mp19, respectively, for every 5 µl of the DNA mixture. The DNA solutions were covered with a drop of CHILLOUT evaporation barrier and brought to 61° C. The cleavage reactions were started by the addition of 5 µl of the enzyme mixture to each of tubes (final reaction volume was 10 µl). After 30 minutes at 61° C., the reactions were terminated by the addition of 8 µl of 95% formamide with 20 mM EDTA and 0.05% marker dyes. Samples were heated to 90° C. for 1 minute immediately before electrophoresis through a 20% denaturing acrylamide gel (19:1 cross-linked) with 7 M urea, in a buffer containing 45 mM Tris-Borate (pH 8.3), 1.4 mM EDTA. To provide reference (i.e., standards), 1.0, 0.1 and 0.01 pmole aliquots of fluorescein-labeled probe oligonucleotide (SEQ ID NO:32) were diluted with the above formamide solution to a final volume of 18 µl. These reference markers were loaded into lanes 1-3, respectively of the gel.

The products of the cleavage reactions (as well as the reference standards) were visualized following electrophoresis by the use of a Hitachi FMBIO fluorescence imager. The results are displayed in FIG. 32.

In FIG. 32, boxes appear around fluorescein-containing nucleic acid (i.e., the cleaved and uncleaved probe molecules) and the amount of fluorescein contained within each box is indicated under the box. The background fluorescence of the gel (see box labeled "background") was subtracted by the fluoro-imager to generate each value displayed under a box containing cleaved or uncleaved probe products (the boxes are numbered 1-14 at top left with a V followed by a number below the box). The lane marked "M" contains fluoresceinated oligonucleotides, which served as markers.

The results shown in FIG. 32, demonstrate that the accumulation of cleaved probe molecules in a fixed-length incubation period reflects the amount of target DNA present in the reaction. The results also demonstrate that the cleaved probe products accumulate in excess of the copy number of the target. This is clearly demonstrated by comparing the results shown in lane 3, in which 10 fmole (0.01 pmole) of uncut probe are displayed with the results shown in 5, where the products that accumulated in response to the presence of 10 fmole of target DNA are displayed. These results show that the reaction can cleave hundreds of probe oligonucleotide molecules for each target molecule present, dramatically amplifying the target-specific signal generated in the INVADER-directed cleavage reaction.

Example 15

Effect of Saliva Extract on the INVADER-Directed Cleavage Assay

For a nucleic acid detection method to be useful in a medical (i.e., a diagnostic) setting, it must not be inhibited by materials and contaminants likely to be found in a typical clinical specimen. To test the susceptibility of the INVADER-directed cleavage assay to various materials, including but not limited to nucleic acids, glycoproteins and carbohydrates, likely to be found in a clinical sample, a sample of human saliva was prepared in a manner consistent with practices in the clinical laboratory and the resulting saliva extract was added to the INVADER-directed cleavage assay. The effect of the saliva extract upon the inhibition of cleavage and upon the specificity of the cleavage reaction was examined.

One and one-half milliliters of human saliva were collected and extracted once with an equal volume of a mixture containing phenol:chloroform:isoamyl alcohol (25:24:1). The resulting mixture was centrifuged in a microcentrifuge to separate the aqueous and organic phases. The upper, aqueous phase was transferred to a fresh tube. One-tenth volumes of 3 M NaOAc were added and the contents of the tube were mixed. Two volumes of 100% ethyl alcohol were added to the mixture and the sample was mixed and incubated at room temperature for 15 minutes to allow a precipitate to form. The sample was centrifuged in a microcentrifuge at 13,000 rpm for 5 minutes and the supernatant was removed and discarded. A milky pellet was easily visible. The pellet was rinsed once with 70% ethanol, dried under vacuum and dissolved in 200 µl of 10 mM Tris-HCl, pH 8.0, 0.1 mM EDTA (this constitutes the saliva extract). Each µl of the saliva extract was equivalent to 7.5 µl of saliva. Analysis of the saliva extract by scanning ultraviolet spectrophotometry showed a peak absorbance at about 260 nm and indicated the presence of approximately 45 ng of total nucleic acid per µl of extract.

The effect of the presence of saliva extract upon the following enzymes was examined: CLEAVASE BN nuclease, CLEAVASE A/G nuclease and three different lots of DNAPTaq: AmpliTaq® (Perkin Elmer; a recombinant form of DNAPTaq), AmpliTaq® LD (Perkin-Elmer; a recombinant DNAPTaq preparation containing very low levels of DNA) and Taq DNA polymerase (Fischer). For each enzyme tested, an enzyme/probe mixture was made comprising the chosen amount of enzyme with 5 pmole of the probe oligonucleotide (SEQ ID NO:32) in 10 µl of 20 mM MOPS (pH 7.5) containing 0.1% each of Tween 20 and NP-40, 4 mM $MnCl_2$, 100 mM KCl and 100 µg/ml BSA. The following amounts of enzyme were used: 25 ng of CLEAVASE BN prepared as described in Example 8; 2 µl of CLEAVASE A/G nuclease extract prepared as described in Example 2; 2.25 µl (11.25 polymerase units) the following DNA polymerases: AmpliTaq® DNA polymerase (Perkin Elmer); AmpliTaq® DNA polymerase LD (low DNA; from Perkin Elmer); Taq DNA polymerase (Fisher Scientific).

Figure 33:
FIG. 33 is the image generated by a fluorescence imager showing the products of INVADER oligonucleotide-directed cleavage assays run in the presence or absence of saliva extract using various thermostable 5' nucleases or DNA polymerases.

For each of the reactions shown in FIG. 33, except for that shown in lane 1, the target DNA (50 fmoles of single-stranded M13mp19 DNA) was combined with 50 pmole of the INVADER oligonucleotide (SEQ ID NO:35) and 5 pmole of the probe oligonucleotide (SEQ ID NO:32); target DNA was omitted in reaction 1 (lane 1). Reactions 1, 3, 5, 7, 9 and 11 included 1.5 µl of saliva extract. These mixtures were brought to a volume of 5 µl with distilled water, overlaid with a drop of CHILLOUT evaporation barrier and brought to 95° C. for 10 minutes. The cleavage reactions were then started by the addition of 5 µl of the desired enzyme/probe mixture; reactions 1, 4 and 5 received CLEAVASE A/G nuclease. Reactions 2 and 3 received CLEAVASE BN; reactions 6 and 7 received AmpliTaq®; reactions 8 and 9 received AmpliTaq® LD; and reactions 10 and 11 received Taq DNA Polymerase from Fisher Scientific.

The reactions were incubated at 63° C. for 30 minutes and were stopped by the addition of 6 µl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA. The products of the reactions were visualized by the use of an Hitachi FMBIO fluorescence imager, and the results are displayed in FIG. 33.

A pairwise comparison of the lanes shown in FIG. 33 without and with the saliva extract, treated with each of the enzymes, shows that the saliva extract has different effects on each of the enzymes. While the CLEAVASE BN nuclease and the AmpliTaq® are significantly inhibited from cleaving in these conditions, the CLEAVASE A/G nuclease and AmpliTaq® LD display little difference in the yield of cleaved probe. The preparation of Taq DNA polymerase from Fisher Scientific shows an intermediate response, with a partial reduction in the yield of cleaved product. From the standpoint of polymerization, the three DNAPTaq variants should be equivalent; these should be the same protein with the same amount of synthetic activity. It is possible that the differences observed could be due to variations in the amount of nuclease activity present in each preparation caused by different handling during purification, or by different purification protocols. In any case, quality control assays designed to assess polymerization activity in commercial DNAP preparations would be unlikely to reveal variation in the amount of nuclease activity present. If preparations of DNAPTaq were screened for full 5' nuclease activity (i.e., if the 5' nuclease activity was specifically quantitated), it is likely that the preparations would display sensitivities (to saliva extract)

Example 16

Comparison of Additional 5' Nucleases in the INVADER-Directed Cleavage Assay A number of eubacterial Type A DNA polymerases (i.e., PolI type DNA polymerases) have been shown to function as structure specific endonucleases (See, Example 1, and Lyamichev et al., supra). In this Example, it was demonstrated that the enzymes of this class can also be made to catalyze the INVADER-directed cleavage of the present invention, albeit not as efficiently as the CLEAVASE enzymes.

Figure 34:
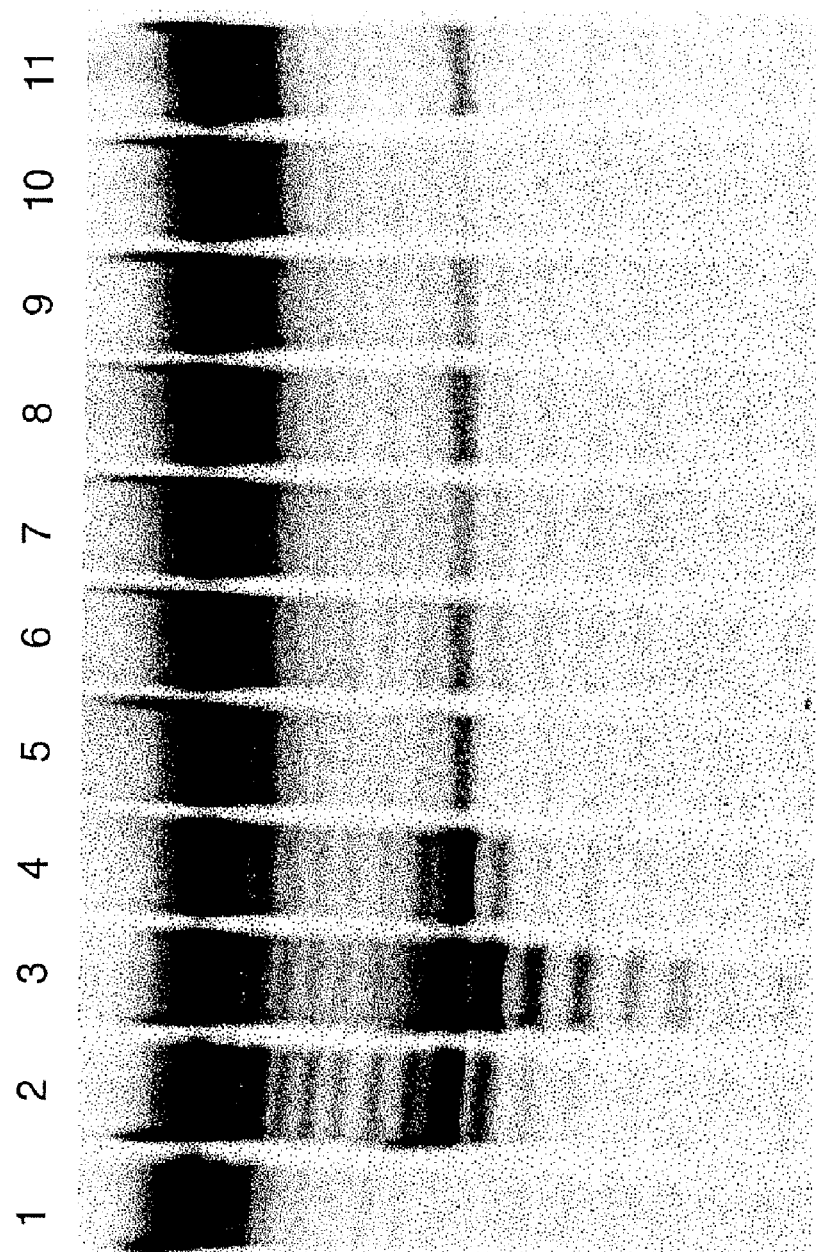
FIG. 34 is the image generated by a fluorescence imager showing the products of INVADER oligonucleotide-directed cleavage assays run using various 5' nucleases.

CLEAVASE BN nuclease and CLEAVASE A/G nuclease were tested along side three different thermostable DNA polymerases: *Thermus aquaticus* DNA polymerase (Promega), *Thermus thermophilus* and *Thermus flavus* DNA polymerases (Epicentre). The enzyme mixtures used in the reactions shown in lanes 1-11 of FIG. 34 contained the following, each in a volume of 5 μl: Lane 1:20 mM MOPS (pH 7.5) with 0.1% each of Tween 20 and NP-40, 4 mM $MnCl_2$, 100 mM KCl; Lane 2:25 ng of CLEAVASE BN nuclease in the same solution described for lane 1; Lane 3:2.25 μl of CLEAVASE A/G nuclease extract (prepared as described in Example 2), in the same solution described for lane 1; Lane 4:2.25 μl of CLEAVASE A/G nuclease extract in 20 mM Tris-Cl, (pH 8.5), 4 mM $MgCl_2$ and 100 mM KCl; Lane 5:11.25 polymerase units of Taq DNA polymerase in the same buffer described for lane 4; Lane 6:11.25 polymerase units of Tth DNA polymerase in the same buffer described for lane 1; Lane 7:11.25 polymerase units of Tth DNA polymerase in a 2× concentration of the buffer supplied by the manufacturer, supplemented with 4 mM $MnCl_2$; Lane 8:11.25 polymerase units of Tth DNA polymerase in a 2× concentration of the buffer supplied by the manufacturer, supplemented with 4 mM $MgCl_2$; Lane 9:2.25 polymerase units of Tfl DNA polymerase in the same buffer described for lane 1; Lane 10:2.25 polymerase units of Tfl polymerase in a 2× concentration of the buffer supplied by the manufacturer, supplemented with 4 mM $MnCl_2$; Lane 11:2.25 polymerase units of Tfl DNA polymerase in a 2× concentration of the buffer supplied by the manufacturer, supplemented with 4 mM $MgCl_2$.

Sufficient target DNA, probe and INVADER for all 11 reactions was combined into a master mix. This mix contained 550 fmoles of single-stranded M13mp19 target DNA, 550 pmoles of the INVADER oligonucleotide (SEQ ID NO:35) and 55 pmoles of the probe oligonucleotide (SEQ ID NO:32), each as depicted in FIG. 28c, in 55 μl of distilled water. Five μl of the DNA mixture was dispensed into each of 11 labeled tubes and overlaid with a drop of CHILLOUT evaporation barrier. The reactions were brought to 63° C. and cleavage was started by the addition of 5 μl of the appropriate enzyme mixture. The reaction mixtures were then incubated at 63° C. temperature for 15 minutes. The reactions were stopped by the addition of 8 μl of 95% formamide with 20 mM EDTA and 0.05% marker dyes. Samples were heated to 90° C. for 1 minute immediately before electrophoresis through a 20% acrylamide gel (19:1 cross-linked), with 7 M urea, in a buffer of 45 mM Tris-Borate (pH 8.3), 1.4 mM EDTA. Following electrophoresis, the products of the reactions were visualized by the use of an Hitachi FMBIO fluorescence imager, and the results are displayed in FIG. 34. Examination of the results shown in FIG. 34 demonstrates that all of the 5' nucleases tested have the ability to catalyze INVADER-directed cleavage in at least one of the buffer systems tested. Although not optimized here, these cleavage agents are suitable for use in the methods of the present invention.

Example 17

Figure 25:
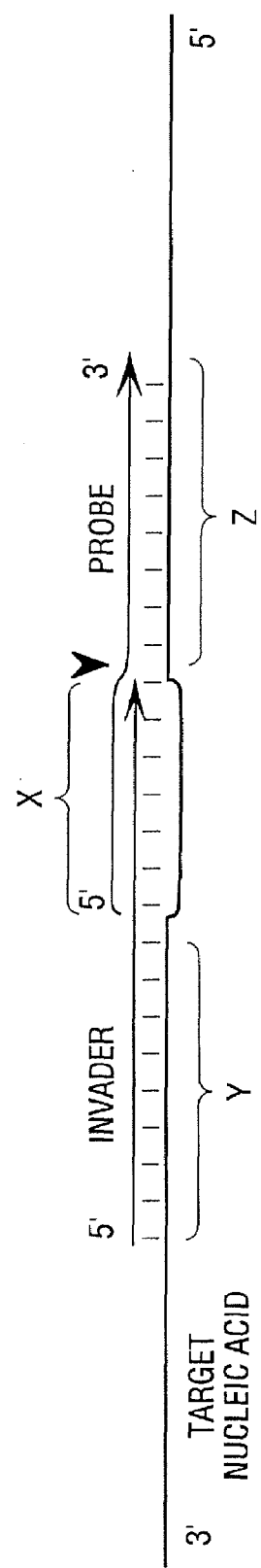
FIG. 25 provides a schematic drawing of a target nucleic acid with an INVADER oligonucleotide and a probe oligonucleotide annealed to the target.

The INVADER-Directed Cleavage Assay can Detect Single Base Differences in Target Nucleic Acid Sequences The ability of the INVADER-directed cleavage assay to detect single base mismatch mutations was examined. Two target nucleic acid sequences containing CLEAVASE enzyme-resistant phosphorothioate backbones were chemically synthesized and purified by polyacrylamide gel electrophoresis. Targets comprising phosphorothioate backbones were used to prevent exonucleolytic nibbling of the target when duplexed with an oligonucleotide. A target oligonucleotide, which provides a target sequence that is completely complementary to the INVADER oligonucleotide (SEQ ID NO:35) and the probe oligonucleotide (SEQ ID NO:32), contained the following sequence: 5'-CCTTTCGCTTTCTTC-CCTTCCTTTCTCGCCACGTTCGCCGGC-3' (SEQ ID NO:36). A second target sequence containing a single base change relative to SEQ ID NO:36 was synthesized: 5'-CCTTTCGCTCTCTTCCCTTC-CTTTCTCGCCACGTTCGCCGGC-3 (SEQ ID NO:37; the single base change relative to SEQ ID NO:36 is shown using bold and underlined type). The consequent mismatch occurs within the "Z" region of the target as represented in FIG. 25.

To discriminate between two target sequences that differ by the presence of a single mismatch), INVADER-directed cleavage reactions were conducted using two different reaction temperatures (55° C. and 60° C.). Mixtures containing 200 fmoles of either SEQ ID NO:36 or SEQ ID NO:37, 3 pmoles of fluorescein-labeled probe oligonucleotide (SEQ ID NO:32), 7.7 pmoles of INVADER oligonucleotide (SEQ ID NO:35) and 2 μl of CLEAVASE A/G nuclease extract (prepared as described in Example 2) in 9 μl of 10 mM MOPS (pH 7.4) with 50 mM KCl were assembled, covered with a drop of CHILLOUT evaporation barrier and brought to the appropriate reaction temperature. The cleavage reactions were initiated by the addition of 1 μl of 20 mM $MgCl_2$. After 30 minutes at either 55° C. or 60° C., 10 μl of 95% formamide with 20 mM EDTA and 0.05% marker dyes was added to stop the reactions. The reaction mixtures where then heated to 90° C. for one minute prior to loading 4 μl onto 20% denaturing polyacrylamide gels. The resolved reaction products were visualized using a Hitachi FMBIO fluorescence imager. The resulting image is shown in FIG. 35.

Figure 35:
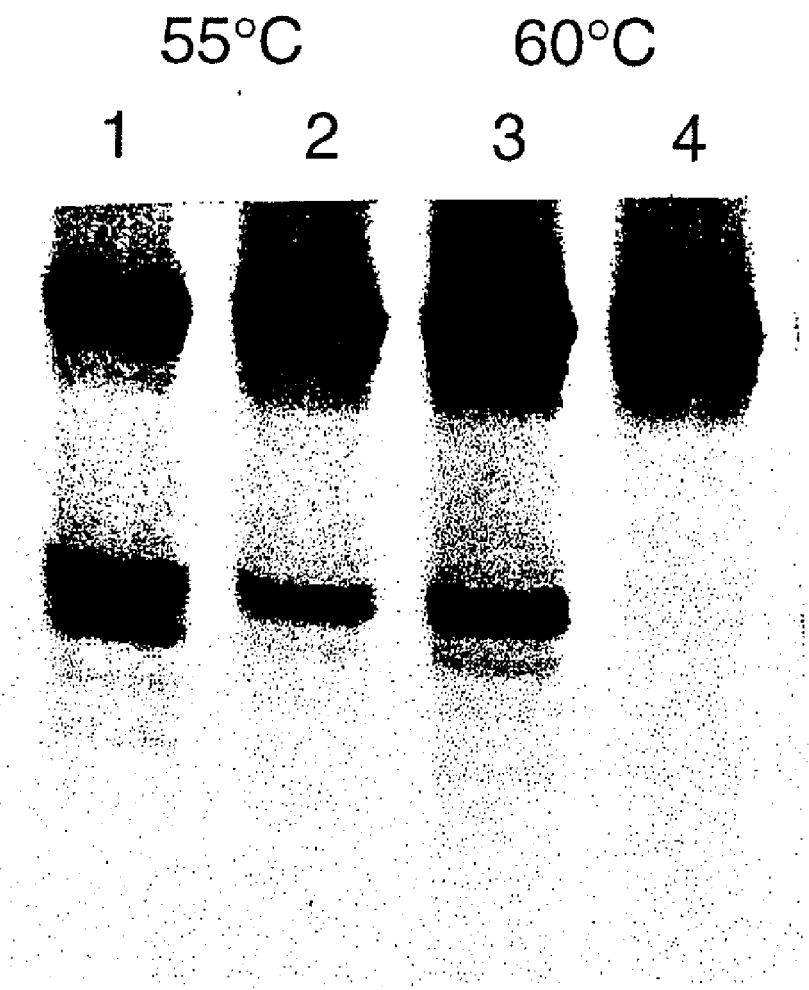
FIG. 35 is the image generated by a fluorescence imager showing the products of INVADER oligonucleotide-directed cleavage assays run using two target nucleic acids which differ by a single basepair at two different reaction temperatures.
Figure 36A:
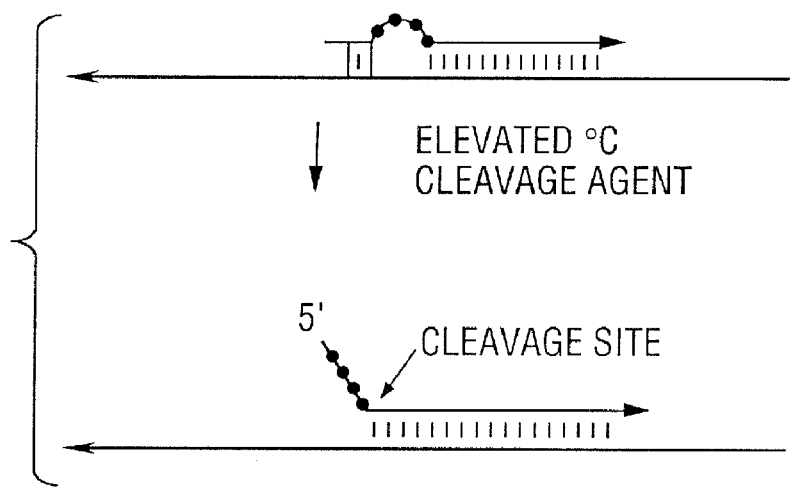
FIG. 36A provides a schematic showing the effect of elevated temperature upon the annealing and cleavage of a probe oligonucleotide along a target nucleic acid wherein the probe contains a region of noncomplementarity with the target.
Figure 36B:
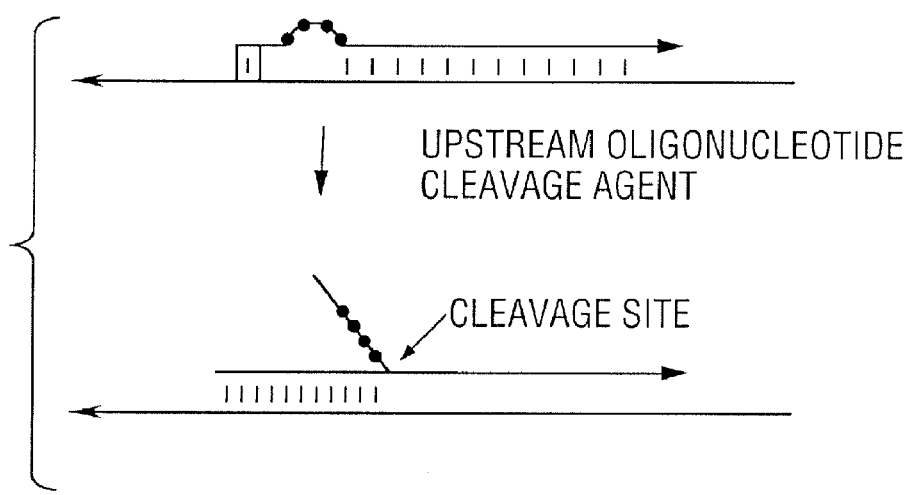
FIG. 36B provides a schematic showing the effect of adding an upstream oligonucleotide upon the annealing and cleavage of a probe oligonucleotide along a target nucleic acid wherein the probe contains a region of noncomplementarity with the target.

In FIG. 35, lanes 1 and 2 show the products from reactions conducted at 55° C.; lanes 3 and 4 show the products from reactions conducted at 60° C. Lanes 1 and 3 contained products from reactions containing SEQ ID NO:36 (perfect match to probe) as the target. Lanes 2 and 4 contained products from reactions containing SEQ ID NO:37 (single base mis-match with probe) as the target. The target that does not have a perfect hybridization match (i.e., complete complementarity) with the probe will not bind as strongly (i.e., the $T_m$ of that duplex will be lower than the $T_m$ of the same region if perfectly matched). The results presented here show that reaction conditions can be varied to either accommodate the mismatch (e.g., by lowering the temperature of the reaction) or to exclude the binding of the mismatched sequence (e.g., by raising the reaction temperature).

The results shown in FIG. 35 demonstrate that the specific cleavage event that occurs in INVADER-directed cleavage reactions can be eliminated by the presence of a single base mis-match between the probe oligonucleotide and the target sequence. Thus, reaction conditions can be chosen so as to exclude the hybridization of mismatched INVADER-directed cleavage probes thereby diminishing or even eliminating the cleavage of the probe. In an extension of this assay system, multiple cleavage probes, each possessing a separate reporter molecule (i.e., a unique label), could also be used in a single cleavage reaction, to simultaneously probe for two or more variants in the same target region. The products of such a reaction would allow not only the detection of mutations that exist within a target molecule, but would also allow a determination of the relative concentrations of each sequence (i.e., mutant and wild type or multiple different mutants) present within samples containing a mixture of target sequences. When provided in equal amounts, but in a vast excess (e.g., at least a 100-fold molar excess; typically at least 1 pmole of each probe oligonucleotide would be used when the target sequence was present at about 10 fmoles or less) over the target and used in optimized conditions. As discussed above, any differences in the relative amounts of the target variants will not affect the kinetics of hybridization, so the amounts of cleavage of each probe will reflect the relative amounts of each variant present in the reaction.

The results shown in the Example clearly demonstrate that the INVADER-directed cleavage reaction can be used to detect single base difference between target nucleic acids.

Example 18

The INVADER-Directed Cleavage Reaction is Insensitive to Large Changes in Reaction Conditions The results shown above demonstrated that the INVADER-directed cleavage reaction can be used for the detection of target nucleic acid sequences and that this assay can be used to detect single base difference between target nucleic acids. These results demonstrated that 5' nucleases (e.g., CLEAVASEBN, CLEAVASE A/G, DNAPTaq, DNAPTth, DNAPTfl) could be used in conjunction with a pair of overlapping oligonucleotides as an efficient way to recognize nucleic acid targets. In the experiments below it is demonstrated that invasive cleavage reaction is relatively insensitive to large changes in conditions thereby making the method suitable for practice in clinical laboratories.

The effects of varying the conditions of the cleavage reaction were examined for their effect(s) on the specificity of the invasive cleavage and the on the amount of signal accumulated in the course of the reaction. To compare variations in the cleavage reaction a "standard" INVADER cleavage reaction was first defined. In each instance, unless specifically stated to be otherwise, the indicated parameter of the reaction was varied, while the invariant aspects of a particular test were those of this standard reaction. The results of these tests are either shown in FIGS. 38-40, or the results described below.

a) The Standard INVADER-Directed Cleavage Reaction

The standard reaction was defined as comprising 1 fmole of M13mp18 single-stranded target DNA (NEB), 5 pmoles of the labeled probe oligonucleotide (SEQ ID NO:38), 10 pmole of the upstream INVADER oligonucleotide (SEQ ID NO:39) and 2 units of CLEAVASE A/G in 10 µl of 10 mM MOPS, pH 7.5 with 100 mM KCl, 4 mM $MnCl_2$, and 0.05% each Tween-20 and Nonidet-P40. For each reaction, the buffers, salts and enzyme were combined in a volume of 5 µl; the DNAs (target and two oligonucleotides) were combined in 5 µl of $dH_2O$ and overlaid with a drop of CHILLOUT evaporation barrier. When multiple reactions were performed with the same reaction constituents, these formulations were expanded proportionally.

Unless otherwise stated, the sample tubes with the DNA mixtures were warmed to 61° C., and the reactions were started by the addition of 5 µl of the enzyme mixture. After 20 minutes at this temperature, the reactions were stopped by the addition of 8 µl of 95% formamide with 20 mM EDTA and 0.05% marker dyes. Samples were heated to 75° C. for 2 minutes immediately before electrophoresis through a 20% acrylamide gel (19:1 cross-linked), with 7 M urea, in a buffer of 45 mM Tris-Borate, pH 8.3, 1.4 mM EDTA. The products of the reactions were visualized by the use of an Hitachi FMBIO fluorescence imager. In each case, the uncut probe material was visible as an intense black band or blob, usually in the top half of the panel, while the desired products of INVADER specific cleavage were visible as one or two narrower black bands, usually in the bottom half of the panel. Under some reaction conditions, particularly those with elevated salt concentrations, a secondary cleavage product is also visible (thus generating a doublet). Ladders of lighter grey bands generally indicate either exonuclease nibbling of the probe oligonucleotide or heat-induced, non-specific breakage of the probe.

Figure 37:
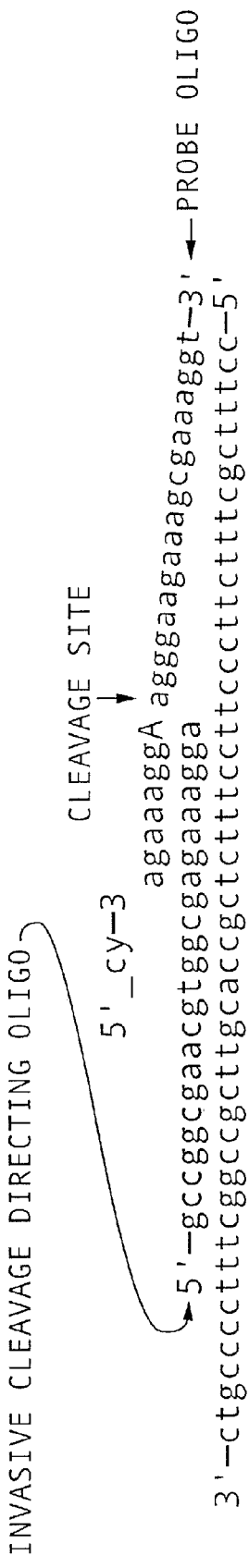
FIG. 37 provides a schematic showing an arrangement of a target-specific INVADER oligonucleotide (SEQ ID NO:39) and a target-specific probe oligonucleotide (SEQ ID NO:38) bearing a 5' Cy3 label along a target nucleic acid (SEQ ID NO:31).

FIG. 37 depicts the annealing of the probe and INVADER oligonucleotides to regions along the M13mp18 target molecule (the bottom strand). In FIG. 37 only a 52 nucleotide portion of the M13mp18 molecule is shown; this 52 nucleotide sequence is listed in SEQ ID NO:31 (this sequence is identical in both M13mp18 and M13mp19). The probe oligonucleotide (top strand) contains a Cy3 amidite label at the 5' end; the sequence of the probe is 5'-AGAAAGGAAGG-GAAGAAAGCGAAAGGT-3' (SEQ ID NO:38. The bold type indicates the presence of a modified base (2'-O—$CH_3$). Cy3 amidite (Pharmacia) is a indodicarbocyanine dye amidite that can be incorporated at any position during the synthesis of oligonucleotides; Cy3 fluoresces in the yellow region (excitation and emission maximum of 554 and 568 nm, respectively). The INVADER oligonucleotide (middle strand) has the following sequence:

5'-GCCGGCGAACGTGGCGAGAAAGGA-3'.　(SEQ ID NO:39)

b) KCl Titration

Figure 38:
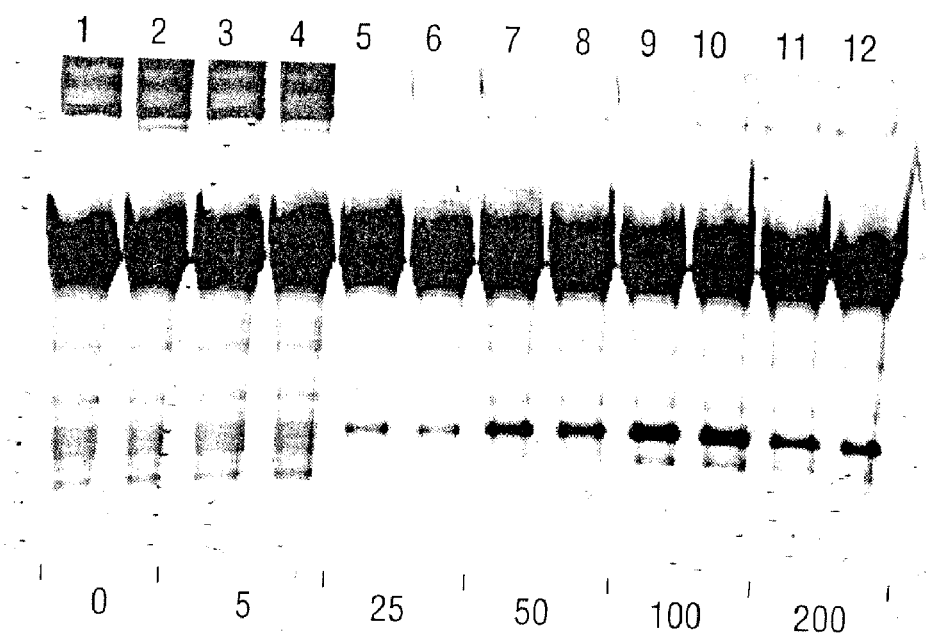
FIG. 38 is the image generated by a fluorescence imager showing the products of INVADER oligonucleotide-directed cleavage assays run in the presence of increasing concentrations of KCl.

FIG. 38 shows the results of varying the KCl concentration in combination with the use of 2 mM $MnCl_2$, in an otherwise standard reaction. The reactions were performed in duplicate for confirmation of observations; the reactions shown in lanes 1 and 2 contained no added KCl, lanes 3 and 4 contained KCl at 5 mM, lanes 5 and 6 contained 25 mM KCl, lanes 7 and 8 contained 50 mM KCl, lanes 9 and 10 contained 100 mM KCl and lanes 11 and 12 contained 200 mM KCl. These results show that the inclusion of KCl allows the generation of a specific cleavage product. While the strongest signal is observed at the 100 mM KCl concentration, the specificity of signal in the other reactions with KCl at or above 25 mM indicates that concentrations in the full range (i.e., 25-200 mM) may be chosen if it is so desirable for any particular reaction conditions.

As shown in FIG. 38, the INVADER-directed cleavage reaction requires the presence of salt (e.g., KCl) for effective cleavage to occur. In other reactions, it has been found that KCl can inhibit the activity of certain CLEAVASE enzymes when present at concentrations above about 25 mM. For example, in cleavage reactions using the S-60 oligonucleotide shown in FIG. 26, in the absence of primer, the CLEAVASE BN enzyme loses approximately 50% of its activity in 50 mM KCl. Therefore, the use of alternative salts in the INVADER-directed cleavage reaction was examined. In these experiments, the potassium ion was replaced with either $Na^+$ or $Li^+$ or the chloride ion was replaced with glutamic acid. The replacement of KCl with alternative salts is described below in Sections c-e.

c) NaCl Titration

NaCl was used in place of KCl at 75, 100, 150 or 200 mM, in combination with the use 2 mM $MnCl_2$, in an otherwise standard reaction. These results showed that NaCl can be used as a replacement for KCl in the INVADER-directed cleavage reaction, with like concentration giving like results, (i.e., the presence of NaCl, like KCl, enhances product accumulation).

d) LiCl Titration

LiCl was used in place of KCl in otherwise standard reactions. Concentrations tested were 25, 50, 75, 100, 150 and 200 mM LiCl. The results demonstrated that LiCl can be used as a suitable replacement for KCl in the INVADER-directed cleavage reaction (i.e., the presence of LiCl, like KCl, enhances product accumulation), in concentrations of about 100 mM or higher.

e) KGlu Titration

The results of using a glutamate salt of potassium (KGlu) in place of the more commonly used chloride salt (KCl) in reactions performed over a range of temperatures were examined. KGlu has been shown to be a highly effective salt source for some enzymatic reactions, showing a broader range of concentrations that permit maximum enzymatic activity (Leirmo et al., Biochem., 26:2095 [1987]). The ability of KGlu to facilitate the annealing of the probe and INVADER oligonucleotides to the target nucleic acid was compared to that of LiCl. In these experiments, the reactions were run for 15 minutes, rather than the standard 20 minutes, in standard reactions that replaced KCl 200 mM, 300 mM or 400 mM KGlu. The reactions were run at 65° C., 67° C., 69° C. or 71° C. The results showed demonstrated that KGlu was very effective as a salt in the invasive cleavage reactions, with full activity apparent even at 400 mM KGlu, though at the lowest temperature cleavage was reduced by about 30% at 300 mM KGlu, and by about 90% to 400 mM KGlu.

f) $MnCl_2$ and $MgCl_2$ Titration and Ability to Replace $MnCl_2$ with $MgCl_2$ In some instances it may be desirable to perform the invasive cleavage reaction in the presence of $Mg^{2+}$, either in addition to, or in place of $Mn^{2+}$ as the necessary divalent cation required for activity of the enzyme employed. For example, some common methods of preparing DNA from bacterial cultures or tissues use $MgCl_2$ in solutions that are used to facilitate the collection of DNA by precipitation. In addition, elevated concentrations (i.e., greater than 5 mM) of divalent cation can be used to facilitate hybridization of nucleic acids, in the same way that the monovalent salts were used above, thereby enhancing the invasive cleavage reaction. In this experiment, the tolerance of the invasive cleavage reaction was examined for 1) the substitution of $MgCl_2$ for $MnCl_2$ and for the ability to produce specific product in the presence of increasing concentrations of $MgCl_2$ and $MnCl_2$.

Figure 39:
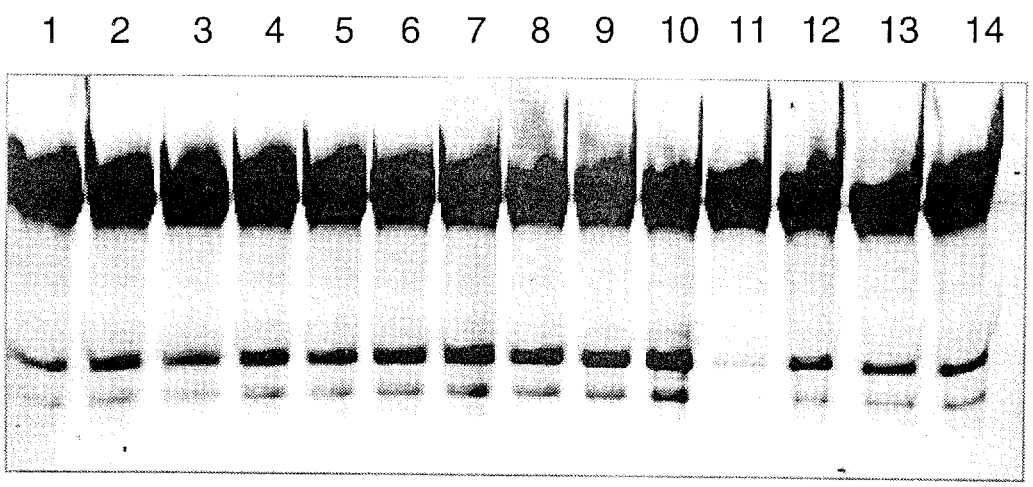
FIG. 39 is the image generated by a fluorescence imager showing the products of INVADER oligonucleotide-directed cleavage assays run in the presence of increasing concentrations of $MnCl_2$ or $MgCl_2$.

FIG. 39 shows the results of either varying the concentration of $MnCl_2$ from 2 mM to 8 mM, replacing the $MnCl_2$ with $MgCl_2$ at 2 to 4 mM, or of using these components in combination in an otherwise standard reaction. The reactions analyzed in lanes 1 and 2 contained 2 mM each $MnCl_2$ and $MgCl_2$, lanes 3 and 4 contained 2 mM $MnCl_2$ only, lanes 5 and 6 contained 3 mM $MnCl_2$, lanes 7 and 8 contained 4 mM $MnCl_2$, lanes 9 and 10 contained 8 mM $MnCl_2$. The reactions analyzed in lanes 11 and 12 contained 2 mM $MgCl_2$ and lanes 13 and 14 contained 4 mM $MgCl_2$. These results show that both $MnCl_2$ and $MgCl_2$ can be used as the necessary divalent cation to enable the cleavage activity of the CLEAVASE A/G enzyme in these reactions and that the invasive cleavage reaction can tolerate a broad range of concentrations of these components.

In addition to examining the effects of the salt environment on the rate of product accumulation in the invasive cleavage reaction, the use of reaction constituents shown to be effective in enhancing nucleic acid hybridization in either standard hybridization assays (e.g., blot hybridization) or in ligation reactions was examined. These components may act as volume excluders, increasing the effective concentration of the nucleic acids of interest and thereby enhancing hybridization, or they may act as charge-shielding agents to minimize repulsion between the highly charged backbones of the nucleic acids strands. The results of these experiments are described in Sections g and h below.

g) Effect of CTAB Addition

The polycationic detergent cetyltrietheylammonium bromide (CTAB) has been shown to dramatically enhance hybridization of nucleic acids (Pontius and Berg, Proc. Natl. Acad. Sci. USA 88:8237 [1991]). The effect of adding the detergent CTAB in concentrations from 100 mM to 1 mM to invasive cleavage reactions in which 150 mM LiCl was used in place of the KCl in otherwise standard reactions was also investigated. These results showed that 200 mM CTAB may have a very moderate enhancing effect under these reaction conditions, and the presence of CTAB in excess of about 500 µM was inhibitory to the accumulation of specific cleavage product.

h) Effect of PEG Addition

The effect of adding polyethylene glycol (PEG) at 4.8 or 12% (w/v) concentrations to otherwise standard reactions was also examined. The effects of increasing the reaction temperature of the PEG-containing reactions was examined by performing duplicate sets of PEG titration reactions at 61° C. and 65° C. The results showed that at all percentages tested, and at both temperatures tested, the inclusion of PEG substantially eliminated the production of specific cleavage product.

In addition to, the presence of 1× Denhardts in the reaction mixture was found to have no adverse effect upon the cleavage reaction (50× Denhardts contains per 500 ml: 5 g Ficoll, 5 g polyvinylpyrrolidone, 5 g BSA). Further, the presence of each component of Denhardt's was examined individually (i.e., Ficoll alone, polyvinylpyrrolidone alone, BSA alone) for the effect upon the INVADER-directed cleavage reaction; no adverse effect was observed.

i) Effect of the Addition of Stabilizing Agents

Another approach to enhancing the output of the invasive cleavage reaction is to enhance the activity of the enzyme employed, either by increasing its stability in the reaction environment or by increasing its turnover rate. Without regard to the precise mechanism by which various agents operate in the invasive cleavage reaction, a number of agents commonly used to stabilize enzymes during prolonged storage were tested for the ability to enhance the accumulation of specific cleavage product in the invasive cleavage reaction.

The effects of adding glycerol at 15% and of adding the detergents Tween-20 and Nonidet-P40 at 1.5%, alone or in combination, in otherwise standard reactions were also examined. The results demonstrated that under these conditions these adducts had little or no effect on the accumulation of specific cleavage product.

The effects of adding gelatin to reactions in which the salt identity and concentration were varied from the standard reaction were also investigated. The results demonstrated that in the absence of salt the gelatin had a moderately enhancing effect on the accumulation of specific cleavage product, but when either salt (KCl or LiCl) was added to reactions performed under these conditions, increasing amounts of gelatin reduced the product accumulation.

j) Effect of Adding Large Amounts of Non-Target Nucleic Acid

In detecting specific nucleic acid sequences within samples, it is important to determine if the presence of additional genetic material (i.e., non-target nucleic acids) will have a negative effect on the specificity of the assay. In this experiment, the effect of including large amounts of non-target nucleic acid, either DNA or RNA, on the specificity of the invasive cleavage reaction was examined. The data was examined for either an alteration in the expected site of cleavage, or for an increase in the nonspecific degradation of the probe oligonucleotide.

Figure 40:
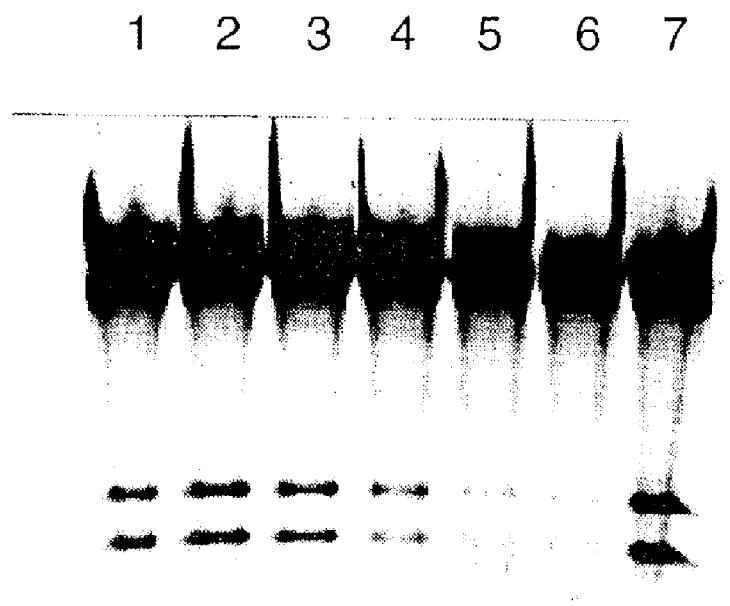
FIG. 40 is the image generated by a fluorescence imager showing the products of INVADER oligonucleotide-directed cleavage assays run in the presence of increasing amounts of genomic DNA or tRNA.

FIG. 40 shows the effects of adding non-target nucleic acid (e.g., genomic DNA or tRNA) to an invasive cleavage reaction performed at 65° C., with 150 mM LiCl in place of the KCl in the standard reaction. The reactions assayed in lanes 1 and 2 contained 235 and 470 ng of genomic DNA, respectively. The reactions analyzed in lanes 3, 4, 5 and 6 contained 100 ng, 200 ng, 500 ng and 1 µg of tRNA, respectively. Lane 7 represents a control reaction that contained no added nucleic acid beyond the amounts used in the standard reaction. The results shown in FIG. 40 demonstrate that the inclusion of non-target nucleic acid in large amounts could visibly slow the accumulation of specific cleavage product (while not limiting the invention to any particular mechanism, it is thought that the additional nucleic acid competes for binding of the enzyme with the specific reaction components). In additional experiments it was found that the effect of adding large amounts of non-target nucleic acid can be compensated for by increasing the enzyme in the reaction. The data shown in FIG. 40 also demonstrate that a key feature of the invasive cleavage reaction, the specificity of the detection, was not compromised by the presence of large amounts of non-target nucleic acid.

In addition to the data presented above, invasive cleavage reactions were run with succinate buffer at pH 5.9 in place of the MOPS buffer used in the "standard" reaction; no adverse effects were observed.

The data shown in FIGS. 38-40 and described above demonstrate that the invasive cleavage reaction can be performed using a wide variety of reaction conditions and is therefore suitable for practice in clinical laboratories.

Example 19

Detection of RNA Targets by INVADER-Directed Cleavage

In addition to the clinical need to detect specific DNA sequences for infectious and genetic diseases, there is a need for technologies that can quantitatively detect target nucleic acids that are composed of RNA. For example, a number of viral agents, such as hepatitis C virus (HCV) and human immunodeficiency virus (HIV) have RNA genomic material, the quantitative detection of which can be used as a measure of viral load in a patient sample. Such information can be of critical diagnostic or prognostic value.

Hepatitis C virus (HCV) infection is the predominant cause of post-transfusion non-A, non-B (NANB) hepatitis around the world. In addition, HCV is the major etiologic agent of hepatocellular carcinoma (HCC) and chronic liver disease world wide. The genome of HCV is a small (9.4 kb) RNA molecule. In studies of transmission of HCV by blood transfusion it has been found the presence of HCV antibody, as measured in standard immunological tests, does not always correlate with the infectivity of the sample, while the presence of HCV RNA in a blood sample strongly correlates with infectivity. Conversely, serological tests may remain negative in immunosuppressed infected individuals, while HCV RNA may be easily detected (Cuthbert, Clin. Microbiol. Rev., 7:505 [1994]).

The need for and the value of developing a probe-based assay for the detection the HCV RNA is clear. The polymerase chain reaction has been used to detect HCV in clinical samples, but the problems associated with carry-over contamination of samples has been a concern. Direct detection of the viral RNA without the need to perform either reverse transcription or amplification would allow the elimination of several of the points at which existing assays may fail.

The genome of the positive-stranded RNA hepatitis C virus comprises several regions including 5' and 3' noncoding regions (i.e., 5' and 3' untranslated regions) and a polyprotein coding region that encodes the core protein (C), two envelope glycoproteins (E1 and E2/NS1) and six nonstructural glycoproteins (NS2-NS5b). Molecular biological analysis of the HCV genome has showed that some regions of the genome are very highly conserved between isolates, while other regions are fairly rapidly changeable. The 5' noncoding region (NCR) is the most highly conserved region in the HCV. These analyses have allowed these viruses to be divided into six basic genotype groups, and then further classified into over a dozen sub-types (the nomenclature and division of HCV genotypes is evolving; see Altamirano et al., J. Infect. Dis., 171:1034 (1995) for a recent classification scheme).

In order to develop a rapid and accurate method of detecting HCV present in infected individuals, the ability of the INVADER-directed cleavage reaction to detect HCV RNA was examined. Plasmids containing DNA derived from the conserved 5'-untranslated region of six different HCV RNA isolates were used to generate templates for in vitro transcription. The HCV sequences contained within these six plasmids represent genotypes 1 (four sub-types represented; 1a, 1b, 1c, and Δ1c), 2, and 3. The nomenclature of the HCV genotypes used herein is that of Simmonds et al (as described in Altamirano et al., supra). The Δ1c subtype was used in the model detection reaction described below.

a) Generation of Plasmids Containing HCV Sequences

Six DNA fragments derived from HCV were generated by RT-PCR using RNA extracted from serum samples of blood donors; these PCR fragments were a gift of Dr. M. Altamirano (University of British Columbia, Vancouver). These PCR fragments represent HCV sequences derived from HCV genotypes 1a, 1b, 1c, Δ1c, 2c and 3a.

The RNA extraction, reverse transcription and PCR were performed using standard techniques (Altamirano et al., supra). Briefly, RNA was extracted from 100 µl of serum using guanidine isothiocyanate, sodium lauryl sarkosate and phenol-chloroform (Inchauspe et al., Hepatol., 14:595 [1991]). Reverse transcription was performed according to the manufacturer's instructions using a GeneAmp rTh reverse transcriptase RNA PCR kit (Perkin-Elmer) in the presence of an external antisense primer, HCV342. The sequence of the HCV342 primer is 5'-GGTTTTTCTTTGAGGTTTAG-3' (SEQ ID NO:40). Following termination of the RT reaction, the sense primer HCV7 (5'-GCGACACTCCACCATAGAT-3' [SEQ ID NO:41]) and magnesium were added and a first PCR was performed. Aliquots of the first PCR products were used in a second (nested) PCR in the presence of primers HCV46 (5'-CTGTCTTCACGCAGAAAGC-3' [SEQ ID NO:42]) and HCV308 [5'-GCACGGT CTACGAGACCTC-3' [SEQ ID NO:43]). The PCRs produced a 281 bp product that corresponds to a conserved 5' noncoding region (NCR) region of HCV between positions −284 and −4 of the HCV genome (Altramirano et al., supra).

The six 281 bp PCR fragments were used directly for cloning or they were subjected to an additional amplification step using a 50 μl PCR comprising approximately 100 fmoles of DNA, the HCV46 and HCV308 primers at 0.1 μM, 100 μM of all four dNTPs and 2.5 units of Taq DNA polymerase in a buffer containing 10 mM Tris-HCl, pH 8.3, 50 mM KCl, 1.5 mM MgCl$_2$ and 0.1% Tween 20. The PCRs were cycled 25 times at 96° C. for 45 sec., 55° C. for 45 sec. and 72° C. for 1 min. Two microliters of either the original DNA samples or the reamplified PCR products were used for cloning in the linear pT7Blue T-vector (Novagen) according to manufacturer's protocol. After the PCR products were ligated to the pT7Blue T-vector, the ligation reaction mixture was used to transform competent JM109 cells (Promega). Clones containing the pT7Blue T-vector with an insert were selected by the presence of colonies having a white color on LB plates containing 40 μg/ml X-Gal, 40 μg/ml IPTG and 50 μg/ml ampicillin. Four colonies for each PCR sample were picked and grown overnight in 2 ml LB media containing 50 μg/ml carbenicillin. Plasmid DNA was isolated using the following alkaline miniprep protocol. Cells from 1.5 ml of the overnight culture were collected by centrifugation for 2 min. in a microcentrifuge (14K rpm), the supernatant was discarded and the cell pellet was resuspended in 50 μl TE buffer with 10 μg/ml RNAse A (Pharmacia). One hundred microliters of a solution containing 0.2 N NaOH, 1% SDS was added and the cells were lysed for 2 min. The lysate was gently mixed with 100 μl of 1.32 M potassium acetate, pH 4.8, and the mixture was centrifuged for 4 min. in a microcentrifuge (14K rpm); the pellet comprising cell debris was discarded. Plasmid DNA was precipitated from the supernatant with 200 μl ethanol and pelleted by centrifugation a microcentrifuge (14K rpm). The DNA pellet was air dried for 15 min. and was then redissolved in 50 μl TE buffer (10 mM Tris-HCl, pH 7.8, 1 mM EDTA).

b) Reamplification of HCV Clones to Add the Phage T7 Promoter for Subsequent In Vitro Transcription To ensure that the RNA product of transcription had a discrete 3' end it was necessary to create linear transcription templates that stopped at the end of the HCV sequence. These fragments were conveniently produced using the PCR to reamplify the segment of the plasmid containing the phage promoter sequence and the HCV insert. For these studies, the clone of HCV type Δ1c was reamplified using a primer that hybridizes to the T7 promoter sequence: 5'-TAATACGACT-CACTATAGGG-3' (SEQ ID NO:44; "the T7 promoter primer") (Novagen) in combination with the 3' terminal HCV-specific primer HCV308 (SEQ ID NO:43). For these reactions, 1 μl of plasmid DNA (approximately 10 to 100 ng) was reamplified in a 200 μl PCR using the T7 and HCV308 primers as described above with the exception that 30 cycles of amplification were employed. The resulting amplicon was 354 bp in length. After amplification the PCR mixture was transferred to a fresh 1.5 ml microcentrifuge tube, the mixture was brought to a final concentration of 2 M NH$_4$OAc, and the products were precipitated by the addition of one volume of 100% isopropanol. Following a 10 min. incubation at room temperature, the precipitates were collected by centrifugation, washed once with 80% ethanol and dried under vacuum. The collected material was dissolved in 100 μl nuclease-free distilled water (Promega).

Segments of RNA were produced from this amplicon by in vitro transcription using the RiboMAX™ Large Scale RNA Production System (Promega) in accordance with the manufacturer's instructions, using 5.3 μg of the amplicon described above in a 100 μl reaction. The transcription reaction was incubated for 3.75 hours, after which the DNA template was destroyed by the addition of 5-6 μl of RQ1 RNAse-free DNAse (1 unit/μl) according to the RiboMAX™ kit instructions. The reaction was extracted twice with phenol/chloroform/isoamyl alcohol (50:48:2) and the aqueous phase was transferred to a fresh microcentrifuge tube. The RNA was then collected by the addition of 10 μl of 3M NH$_4$OAc, pH 5.2 and 110 μl of 100% isopropanol. Following a 5 min. incubation at 4° C., the precipitate was collected by centrifugation, washed once with 80% ethanol and dried under vacuum. The sequence of the resulting RNA transcript (HCV 1.1 transcript) is listed in SEQ ID NO:45.

c) Detection of the HCV1.1 Transcript in the INVADER-Directed Cleavage Assay

Detection of the HCV1.1 transcript was tested in the INVADER-directed cleavage assay using an HCV-specific probe oligonucleotide (5'-CCGGTCGTCCTGGCAAT XCC-3' [SEQ ID NO:46]); X indicates the presence of a fluorescein dye on an abasic linker) and an HCV-specific INVADER oligonucleotide (5'-GTTTATCCAAGAAAG-GAC CCGGTC-3' [SEQ ID NO:47]) that causes a 6-nucleotide invasive cleavage of the probe.

Each 10 μl of reaction mixture comprised 5 pmole of the probe oligonucleotide (SEQ ID NO:46) and 10 pmole of the INVADER oligonucleotide (SEQ ID NO:47) in a buffer of 10 mM MOPS, pH 7.5 with 50 mM KCl, 4 mM MnCl$_2$, 0.05% each Tween-20 and Nonidet-P40 and 7.8 units RNasin® ribonuclease inhibitor (Promega). The cleavage agents employed were CLEAVASE A/G (used at 5.3 ng/10 μl reaction) or DNAPTth (used at 5 polymerase units/10 μl reaction). The amount of RNA target was varied as indicated below. When RNAse treatment is indicated, the target RNAs were pre-treated with 10 μg of RNase A (Sigma) at 37° C. for 30 min. to demonstrate that the detection was specific for the RNA in the reaction and not due to the presence of any residual DNA template from the transcription reaction. RNase-treated aliquots of the HCV RNA were used directly without intervening purification.

For each reaction, the target RNAs were suspended in the reaction solutions as described above, but lacking the cleavage agent and the MnCl$_2$ for a final volume of 10 μl, with the INVADER and probe at the concentrations listed above. The reactions were warmed to 46° C. and the reactions were started by the addition of a mixture of the appropriate enzyme with MnCl$_2$. After incubation for 30 min. at 46° C., the reactions were stopped by the addition of 8 μl of 95% formamide, 10 mM EDTA and 0.02% methyl violet (methyl violet loading buffer). Samples were then resolved by electrophoresis through a 15% denaturing polyacrylamide gel (19:1 cross-linked), containing 7 M urea, in a buffer of 45 mM Tris-Borate, pH 8.3, 1.4 mM EDTA. Following electrophoresis, the labeled reaction products were visualized using the FMBIO-100 Image Analyzer (Hitachi), with the resulting imager scan shown in FIG. 41.

Figure 41:
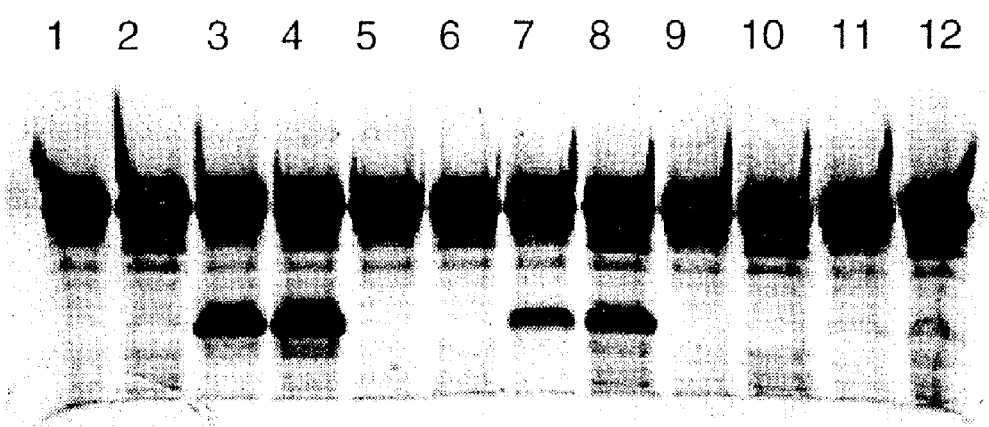
FIG. 41 is the image generated by a fluorescence imager showing the products of INVADER oligonucleotide-directed cleavage assays run use a HCV RNA target.

In FIG. 41, the samples analyzed in lanes 1-4 contained 1 pmole of the RNA target, the reactions shown in lanes 5-8 contained 100 fmoles of the RNA target and the reactions shown in lanes 9-12 contained 10 fmoles of the RNA target. All odd-numbered lanes depict reactions performed using CLEAVASE A/G enzyme and all even-numbered lanes depict reactions performed using DNAPTth. The reactions analyzed in lanes 1, 2, 5, 6, 9 and 10 contained RNA that had been pre-digested with RNase A. These data demonstrate that the invasive cleavage reaction efficiently detects RNA targets and further, the absence of any specific cleavage signal in the RNase-treated samples confirms that the specific cleavage product seen in the other lanes is dependent upon the presence of input RNA.

Example 20

The Fate of the Target RNA in the INVADER-Directed Cleavage Reaction

In this Example, the fate of the RNA target in the INVADER-directed cleavage reaction was examined. As shown above in Example 1D, when RNAs are hybridized to DNA oligonucleotides, the 5' nucleases associated with DNA polymerases can be used to cleave the RNAs; such cleavage can be suppressed when the 5' arm is long or when it is highly structured (Lyamichev et al., Science 260:778 [1993], and U.S. Pat. No. 5,422,253, the disclosure of which is herein incorporated by reference). In this experiment, the extent to which the RNA target would be cleaved by the cleavage agents when hybridized to the detection oligonucleotides (i.e., the probe and INVADER oligonucleotides) was examined using reactions similar to those described in Example 20, performed using fluorescein-labeled RNA as a target.

Transcription reactions were performed as described in Example 19 with the exception that 2% of the UTP in the reaction was replaced with fluorescein-12-UTP (Boehringer Mannheim) and 5.3 μg of the amplicon was used in a 100 μl reaction. The transcription reaction was incubated for 2.5 hours, after which the DNA template was destroyed by the addition of 5-6 μl of RQ1 RNAse-free DNAse (1 unit/μl) according to the RiboMAX™ kit instructions. The organic extraction was omitted and the RNA was collected by the addition of 10 μl of 3M NaOAc, pH 5.2 and 110 μl of 100% isopropanol. Following a 5 min. incubation at 4° C., the precipitate was collected by centrifugation, washed once with 80% ethanol and dried under vacuum. The resulting RNA was dissolved in 100 μl of nuclease-free water. Half (i.e., 50%) of the sample was purified by electrophoresis through a 8% denaturing polyacrylamide gel (19:1 cross-linked), containing 7 M urea, in a buffer of 45 mM Tris-Borate, pH 8.3, 1.4 mM EDTA. The gel slice containing the full-length material was excised and the RNA was eluted by soaking the slice overnight at 4° C. in 200 μl of 10 mM Tris-Cl, pH 8.0, 0.1 mM EDTA and 0.3 M NaOAc. The RNA was then precipitated by the addition of 2.5 volumes of 100% ethanol. After incubation at −20° C. for 30 min., the precipitates were recovered by centrifugation, washed once with 80% ethanol and dried under vacuum. The RNA was dissolved in 25 μl of nuclease-free water and then quantitated by UV absorbance at 260 nm.

Samples of the purified RNA target were incubated for 5 or 30 min. in reactions that duplicated the CLEAVASE A/G and DNAPTth INVADER reactions described in Example 20 with the exception that the reactions lacked probe and INVADER oligonucleotides. Subsequent analysis of the products showed that the RNA was very stable, with a very slight background of non-specific degradation, appearing as a gray background in the gel lane. The background was not dependent on the presence of enzyme in the reaction.

INVADER detection reactions using the purified RNA target were performed using the probe/INVADER pair described in Example 19 (SEQ ID NOS:46 and 47). Each reaction included 500 fmole of the target RNA, 5 pmoles of the fluorescein-labeled probe and 10 pmoles of the INVADER oligonucleotide in a buffer of 10 mM MOPS, pH 7.5 with 150 mM LiCl, 4 mM MnCl$_2$, 0.05% each Tween-20 and Nonidet-P40 and 39 units RNAsin® (Promega). These components were combined and warmed to 50° C. and the reactions were started by the addition of either 53 ng of CLEAVASE A/G or 5 polymerase units of DNAPTth. The final reaction volume was 10 μl. After 5 min at 50° C., 5 μl aliquots of each reaction were removed to tubes containing 4 μl of 95% formamide, 10 mM EDTA and 0.02% methyl violet. The remaining aliquot received a drop of CHILLOUT evaporation barrier and was incubated for an additional 25 min. These reactions were then stopped by the addition of 4 μl of the above formamide solution. The products of these reactions were resolved by electrophoresis through separate 20% denaturing polyacrylamide gels (19:1 cross-linked), containing 7 M urea, in a buffer of 45 mM Tris-Borate, pH 8.3, 1.4 mM EDTA. Following electrophoresis, the labeled reaction products were visualized using the FMBIO-100 Image Analyzer (Hitachi), with the resulting imager scans shown in FIGS. 42A (5 min reactions) and 42B (30 min. reactions).

Figure 53:
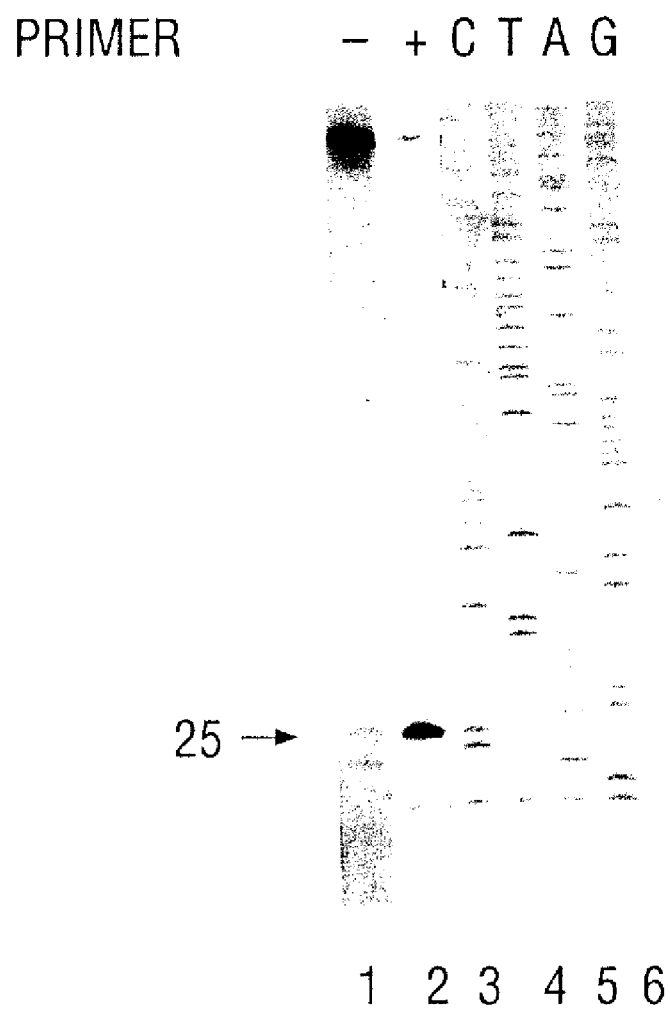
FIG. 53 shows an autoradiogram of a gel showing the results of cleavage reactions run in the presence or absence of a primer oligonucleotide; a sequencing ladder is shown as a size marker.

In FIG. 53 the target RNA is seen very near the top of each lane, while the labeled probe and its cleavage products are seen just below the middle of each panel. The FMBIO-100 Image Analyzer was used to quantitate the fluorescence signal in the probe bands. In each panel, lane 1 contains products from reactions performed in the absence of a cleavage agent, lane 2 contains products from reactions performed using CLEAVASE A/G and lane 3 contains products from reactions performed using DNAPTth.

Quantitation of the fluorescence signal in the probe bands revealed that after a 5 min. incubation, 12% or 300 fmole of the probe was cleaved by the CLEAVASE A/G and 29% or 700 fmole was cleaved by the DNAPTth. After a 30 min. incubation, CLEAVASE A/G had cleaved 32% of the probe molecules and DNAPTth had cleaved 70% of the probe molecules. (The images shown in FIGS. 42A and 42B were printed with the intensity adjusted to show the small amount of background from the RNA degradation, so the bands containing strong signals are saturated and therefore these images do not accurately reflect the differences in measured fluorescence)

The data shown in FIG. 42 clearly shows that, under invasive cleavage conditions, RNA molecules are sufficiently stable to be detected as a target and that each RNA molecule can support many rounds of probe cleavage.

Example 21

Titration of Target RNA in the INVADER-Directed Cleavage Assay

One of the primary benefits of the INVADER-directed cleavage assay as a means for detection of the presence of specific target nucleic acids is the correlation between the amount of cleavage product generated in a set amount of time and the quantity of the nucleic acid of interest present in the reaction. The benefits of quantitative detection of RNA sequences was discussed in Example 19. In this Example, the quantitative nature of the detection assay was demonstrated through the use of various amounts of target starting material.

In addition to demonstrating the correlation between the amounts of input target and output cleavage product, these data graphically show the degree to which the RNA target can be recycled in this assay.

The RNA target used in these reactions was the fluorescein-labeled material described in Example 20 (i.e., SEQ ID NO:45). Because the efficiency of incorporation of the fluorescein-12-UTP by the T7 RNA polymerase was not known, the concentration of the RNA was determined by measurement of absorbance at 260 nm, not by fluorescence intensity. Each reaction comprised 5 pmoles of the fluorescein-labeled probe (SEQ ID NO:46) and 10 pmoles of the INVADER oligonucleotide (SEQ ID NO:47) in a buffer of 10 mM MOPS, pH 7.5 with 150 mM LiCl, 4 mM $MnCl_2$, 0.05% each Tween-20 and Nonidet-P40 and 39 units of RNAsin® (Promega). The amount of target RNA was varied from 1 to 100 fmoles, as indicated below. These components were combined, overlaid with CHILLOUT evaporation barrier and warmed to 50° C.; the reactions were started by the addition of either 53 ng of CLEAVASE A/G or 5 polymerase units of DNAPTth, to a final reaction volume of 10 µl. After 30 minutes at 50° C., reactions were stopped by the addition of 8 µl of 95% formamide, 10 mM EDTA and 0.02% methyl violet. The unreacted markers in lanes 1 and 2 were diluted in the same total volume (18 µl). The samples were heated to 90° C. for 1 minute and 2.5 µl of each of these reactions were resolved by electrophoresis through a 20% denaturing polyacrylamide gel (19:1 cross link) with 7M urea in a buffer of 45 mM Tris-Borate, pH 8.3, 1.4 mM EDTA, and the labeled reaction products were visualized using the FMBIO-100 Image Analyzer (Hitachi), with the resulting imager scans shown in FIG. 43.

Figure 43:
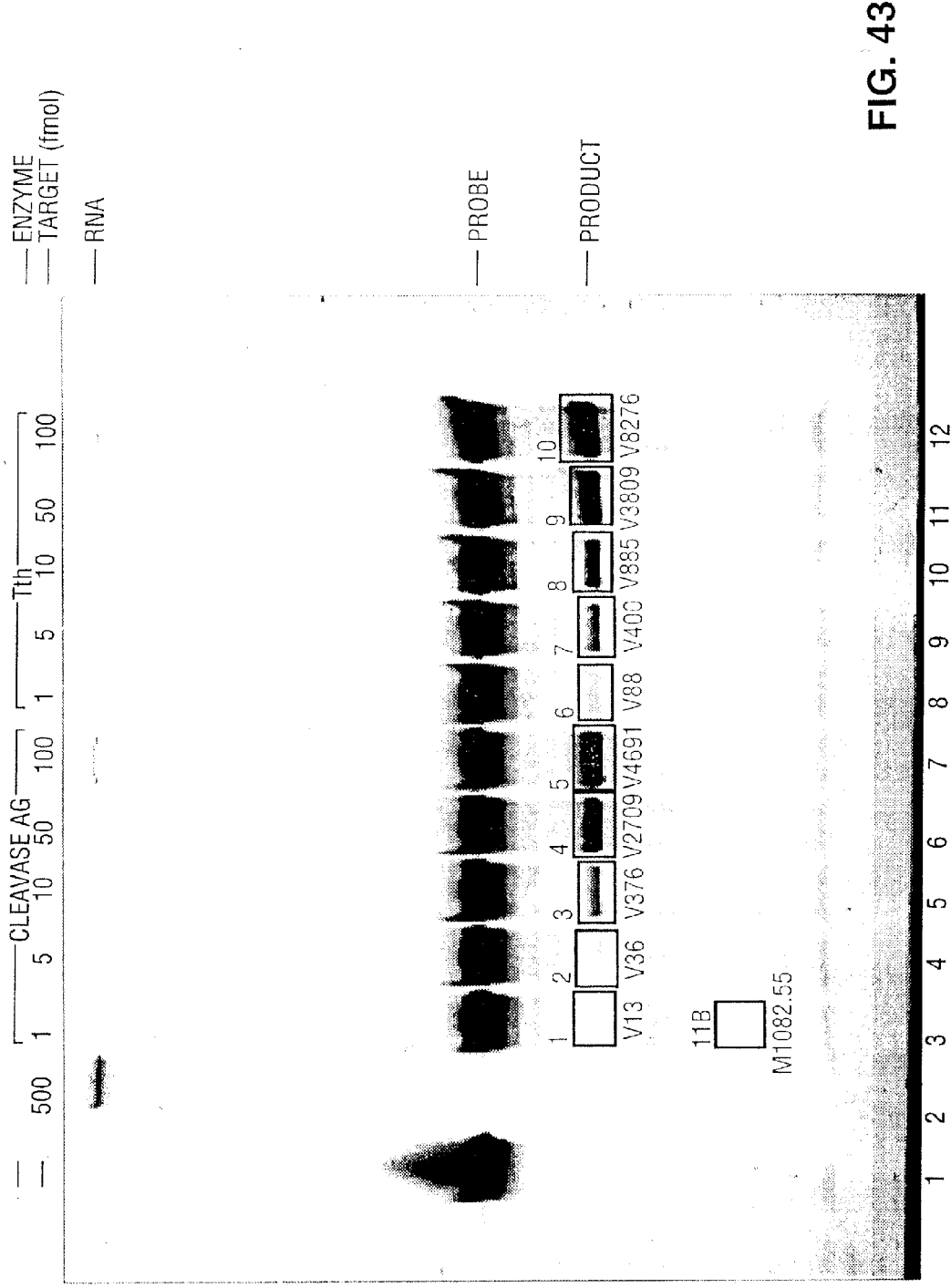
FIG. 43 is the image generated by a fluorescence imager showing the sensitivity of detection and the stability of RNA in INVADER oligonucleotide-directed cleavage assays run using a HCV RNA target.

In FIG. 43, lanes 1 and 2 show 5 pmoles of uncut probe and 500 fmoles of untreated RNA, respectively. The probe is the very dark signal near the middle of the panel, while the RNA is the thin line near the top of the panel. These RNAs were transcribed with a 2% substitution of fluorescein-12-UTP for natural UTP in the transcription reaction. The resulting transcript contains 74 U residues, which would give an average of 1.5 fluorescein labels per molecule. With one tenth the molar amount of RNA loaded in lane 2, the signal in lane 2 should be approximately one seventh (0.15×) the fluorescence intensity of the probe in lane 1. Measurements indicated that the intensity was closer to one fortieth, indicating an efficiency of label incorporation of approximately 17%. Because the RNA concentration was verified by A260 measurement this does not alter the experimental observations below, but it should be noted that the signal from the RNA and the probes does not accurately reflect the relative amounts in the reactions.

The reactions analyzed in lanes 3 through 7 contained 1, 5, 10, 50 and 100 fmoles of target, respectively, with cleavage of the probe accomplished by CLEAVASE A/G. The reactions analyzed in lanes 8 through 12 repeated the same array of target amounts, with cleavage of the probe accomplished by DNAPTth. The boxes seen surrounding the product bands show the area of the scan in which the fluorescence was measured for each reaction. The number of fluorescence units detected within each box is indicated below each box; background florescence was also measured.

It can be seen by comparing the detected fluorescence in each lane that the amount of product formed in these 30 minute reactions can be correlated to the amount of target material. The accumulation of product under these conditions is slightly enhanced when DNAPTth is used as the cleavage agent, but the correlation with the amount of target present remains. This demonstrates that the INVADER assay can be used as a means of measuring the amount of target RNA within a sample.

Comparison of the fluorescence intensity of the input RNA with that of the cleaved product shows that the INVADER-directed cleavage assay creates signal in excess of the amount of target, so that the signal visible as cleaved probe is far more intense than that representing the target RNA. This further confirms the results described in Example 20, in which it was demonstrated that each RNA molecule could be used many times.

Example 22

Detection of DNA by Charge Reversal

The detection of specific targets is achieved in the INVADER-directed cleavage assay by the cleavage of the probe oligonucleotide. In addition to the methods described in the preceding Examples, the cleaved probe may be separated from the uncleaved probe using the charge reversal technique described below. This novel separation technique is related to the observation that positively charged adducts can affect the electrophoretic behavior of small oligonucleotides because the charge of the adduct is significant relative to charge of the whole complex. Observations of aberrant mobility due to charged adducts have been reported in the literature, but in all cases found, the applications pursued by other scientists have involved making oligonucleotides larger by enzymatic extension. As the negatively charged nucleotides are added on, the positive influence of the adduct is reduced to insignificance. As a result, the effects of positively charged adducts have been dismissed and have received infinitesimal notice in the existing literature.

This observed effect is of particular utility in assays based on the cleavage of DNA molecules. When an oligonucleotide is shortened through the action of a CLEAVASE enzyme or other cleavage agent, the positive charge can be made to not only significantly reduce the net negative charge, but to actually override it, effectively "flipping" the net charge of the labeled entity. This reversal of charge allows the products of target-specific cleavage to be partitioned from uncleaved probe by extremely simple means. For example, the products of cleavage can be made to migrate towards a negative electrode placed at any point in a reaction vessel, for focused detection without gel-based electrophoresis. When a slab gel is used, sample wells can be positioned in the center of the gel, so that the cleaved and uncleaved probes can be observed to migrate in opposite directions. Alternatively, a traditional vertical gel can be used, but with the electrodes reversed relative to usual DNA gels (i.e., the positive electrode at the top and the negative electrode at the bottom) so that the cleaved molecules enter the gel, while the uncleaved disperse into the upper reservoir of electrophoresis buffer.

An additional benefit of this type of readout is that the absolute nature of the partition of products from substrates means that an abundance of uncleaved probe can be supplied to drive the hybridization step of the probe-based assay, yet the unconsumed probe can be subtracted from the result to reduce background.

Through the use of multiple positively charged adducts, synthetic molecules can be constructed with sufficient modification that the normally negatively charged strand is made nearly neutral. When so constructed, the presence or absence of a single phosphate group can mean the difference between a net negative or a net positive charge. This observation has particular utility when one objective is to discriminate between enzymatically generated fragments of DNA, which lack a 3' phosphate, and the products of thermal degradation, which retain a 3' phosphate (and thus two additional negative charges).

a) Characterization of the Products of Thermal Breakage of DNA Oligonucleotides

Thermal degradation of DNA probes results in high background that can obscure signals generated by specific enzymatic cleavage, decreasing the signal-to-noise ratio. To better understand the nature of DNA thermal degradation products, the 5' tetrachlorofluorescein (TET)-labeled oligonucleotides 78 (SEQ ID NO:48) and 79 (SEQ ID NO:49) (100 pmole each) were incubated in 50 µl 10 mM $NaCO_3$ (pH 10.6), 50 mM NaCl at 90° C. for 4 hours. To prevent evaporation of the samples, the reaction mixture was overlaid with 50 µl of CHILLOUT liquid wax. The reactions were then divided in two equal aliquots (A and B). Aliquot A was mixed with 25 µl of methyl violet loading buffer and Aliquot B was dephosphorylated by addition of 2.5 µl of 100 mM $MgCl_2$ and 1 µl of 1 unit/µl Calf Intestinal Alkaline Phosphatase (CIAP) (Promega), with incubation at 37° C. for 30 min. after which 25 µl of methyl violet loading buffer was added. One microliter of each sample was resolved by electrophoresis through a 12% polyacrylamide denaturing gel and imaged as described in Example 21; a 585 nm filter was used with the FMBIO Image Analyzer. The resulting imager scan is shown in FIG. 44.

Figure 44:
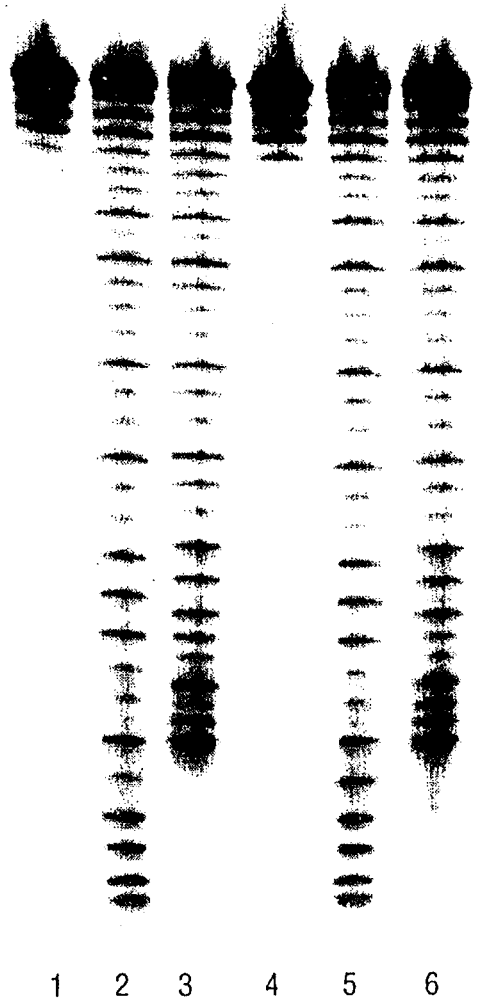
FIG. 44 is the image generated by a fluorescence imager showing thermal degradation of oligonucleotides containing or lacking a 3' phosphate group.
Figure 45:
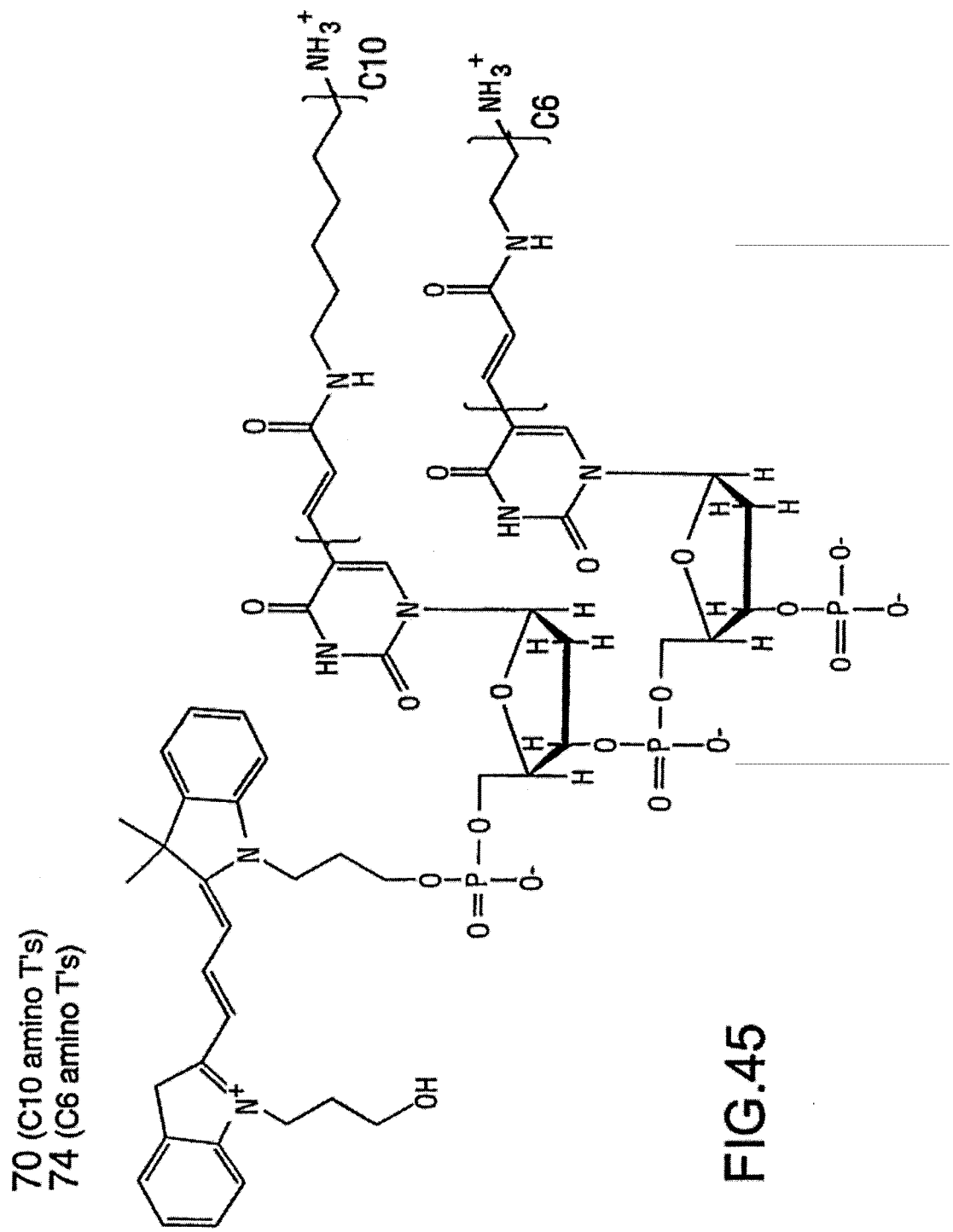
Figure 46:
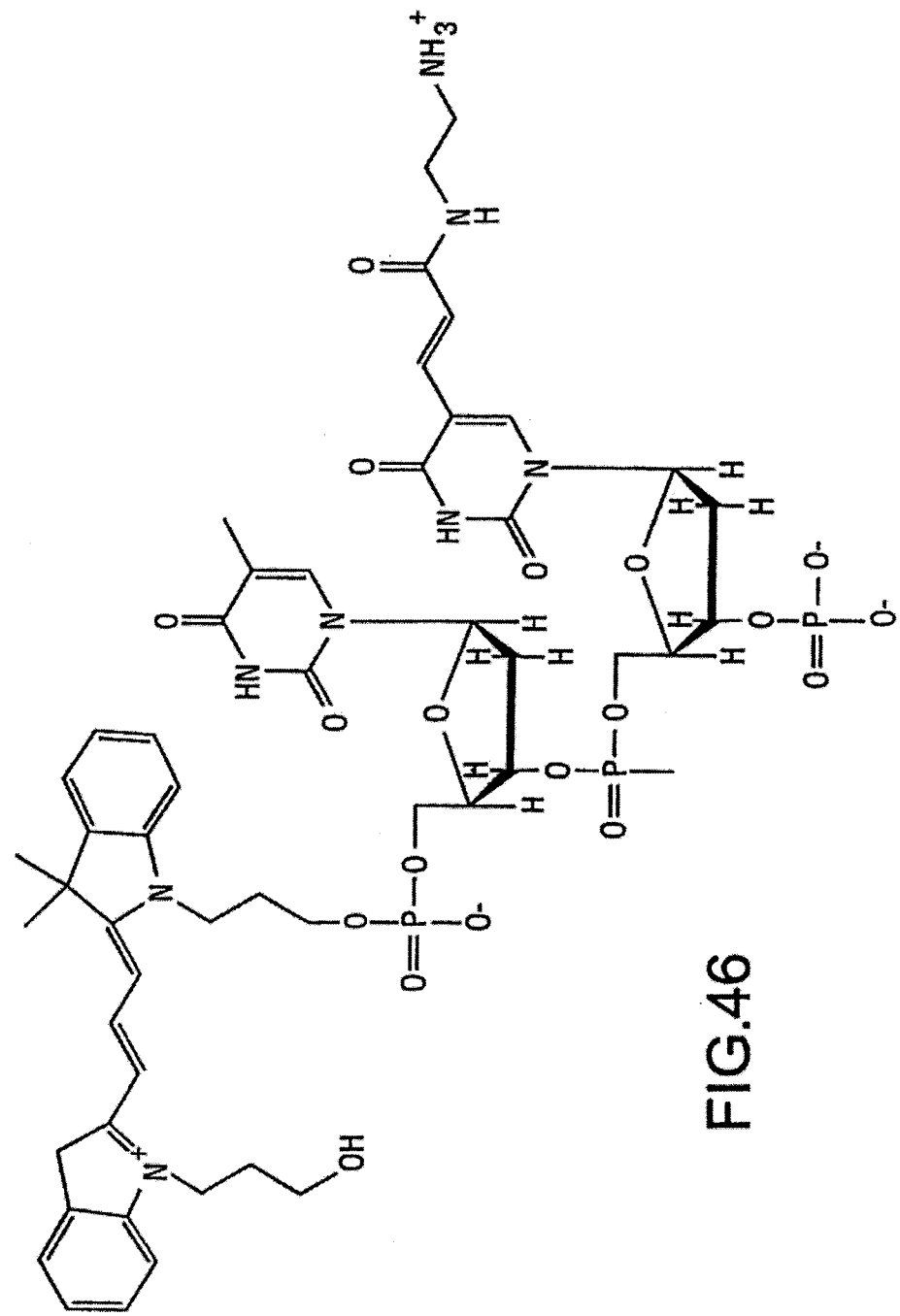
Figure 47:
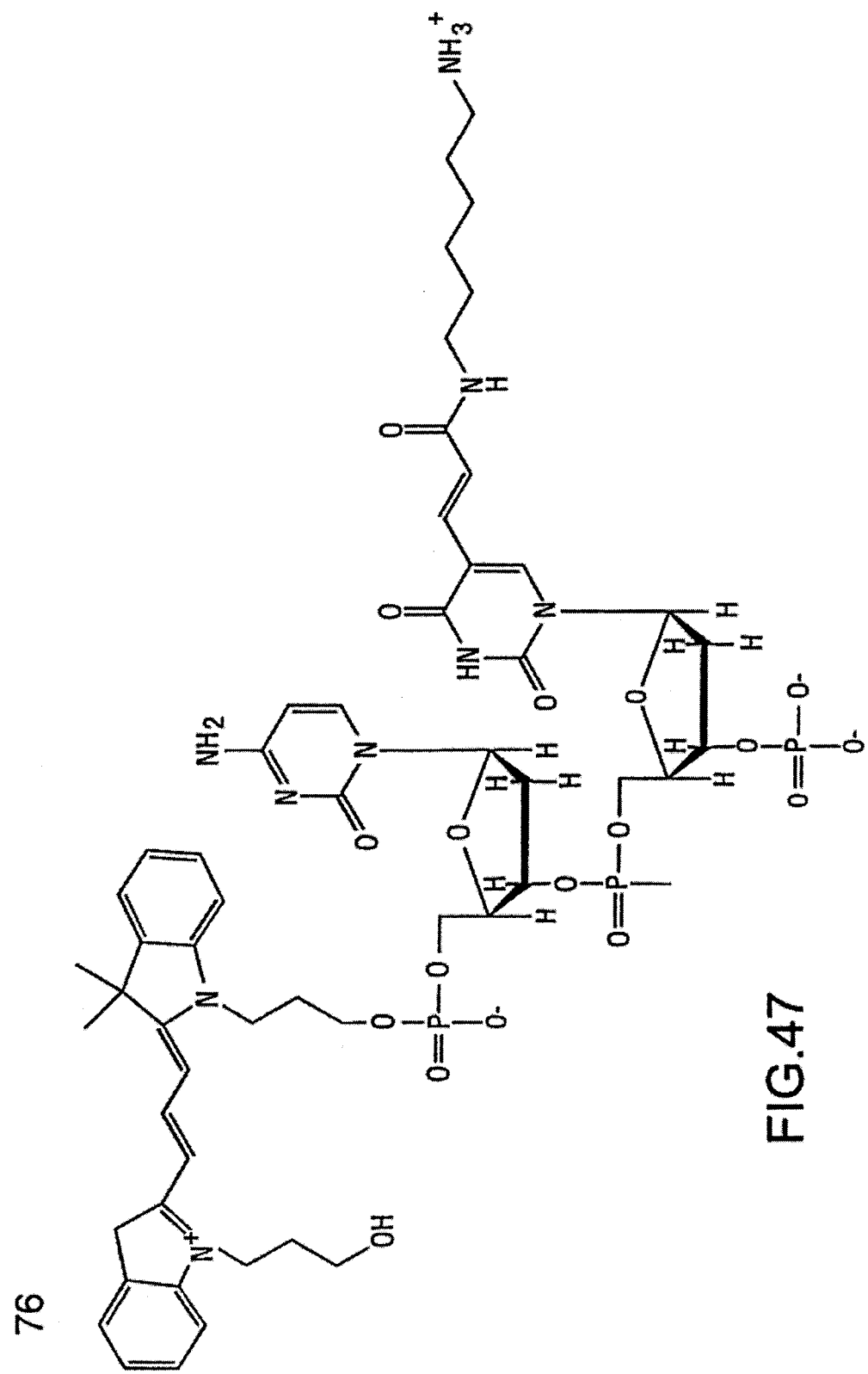
Figure 48:
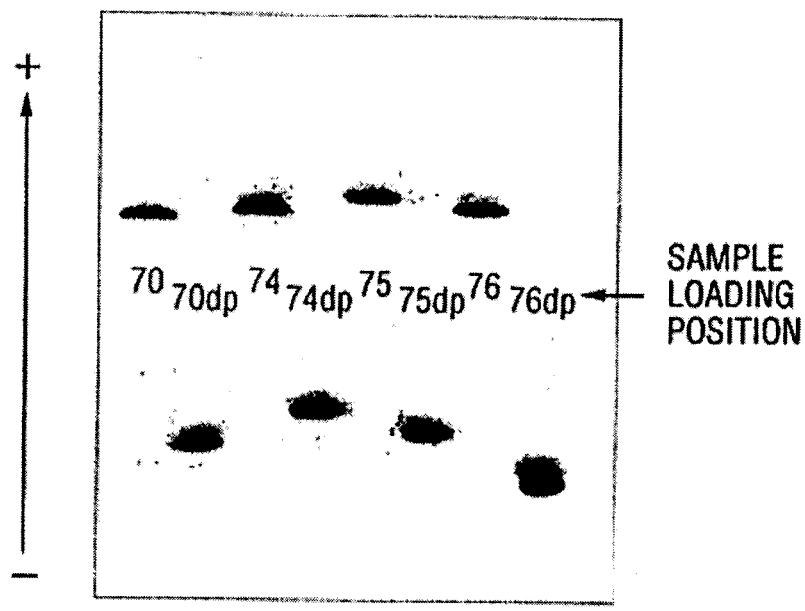
Figure 49B:
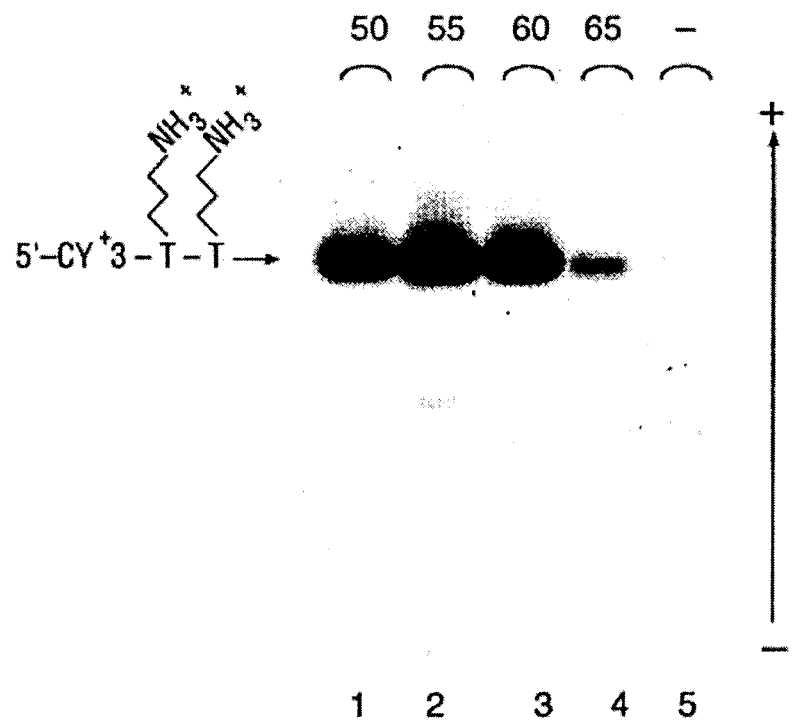
Figure 50:
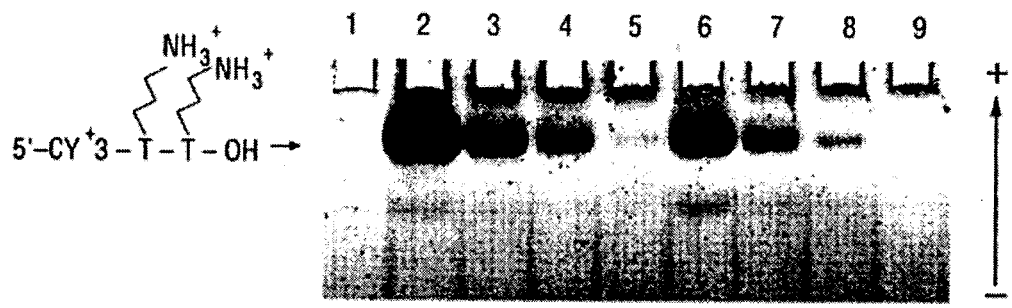
Figure 51:
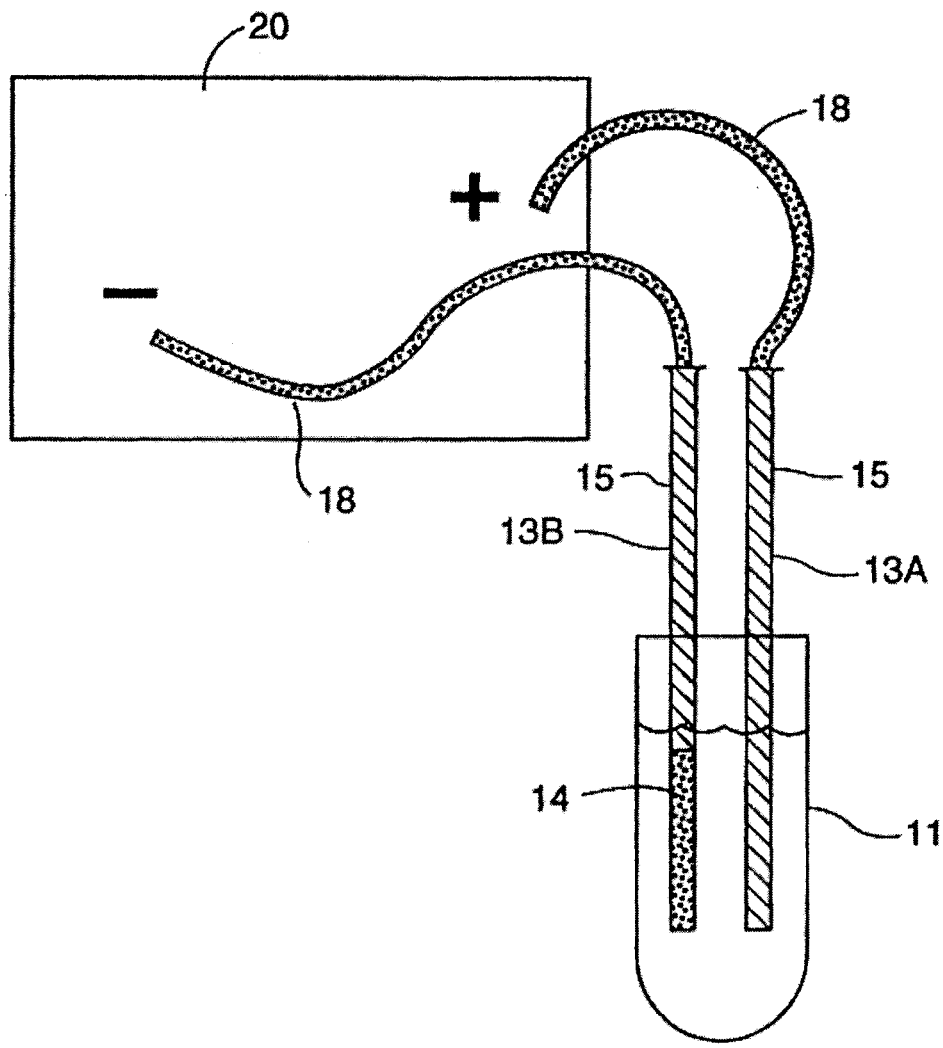
Figure 52:
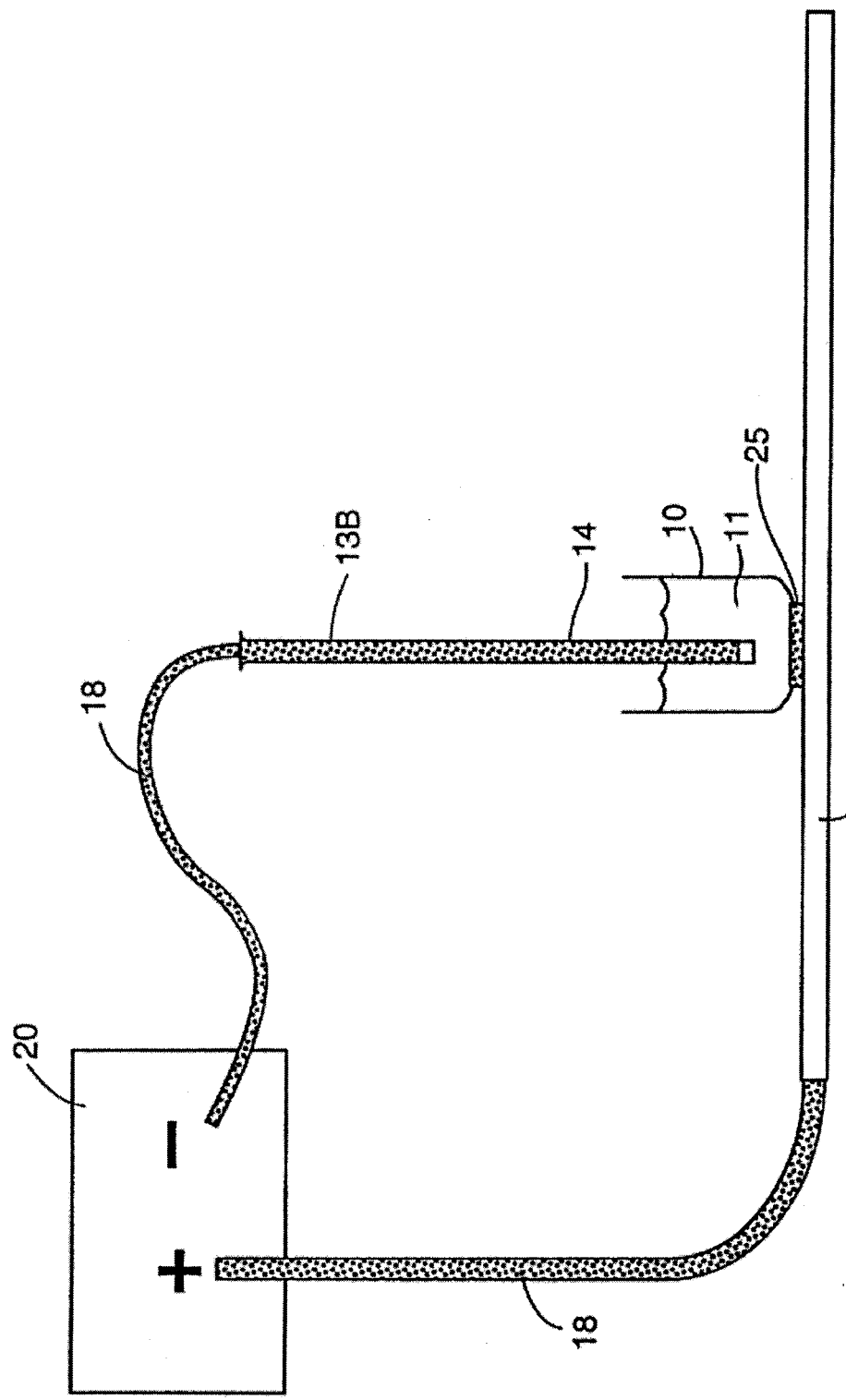
Figure 53:
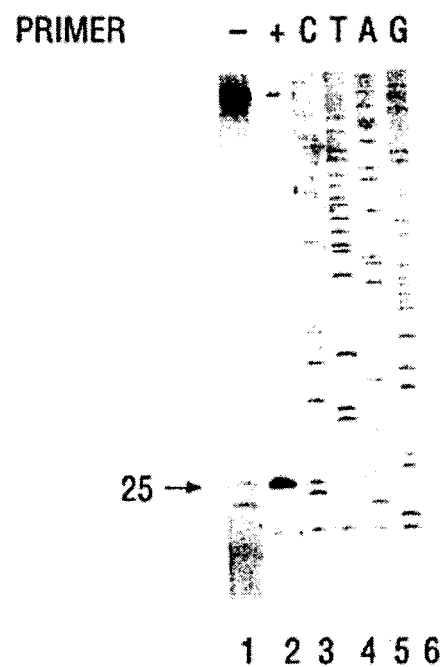
Figure 55:
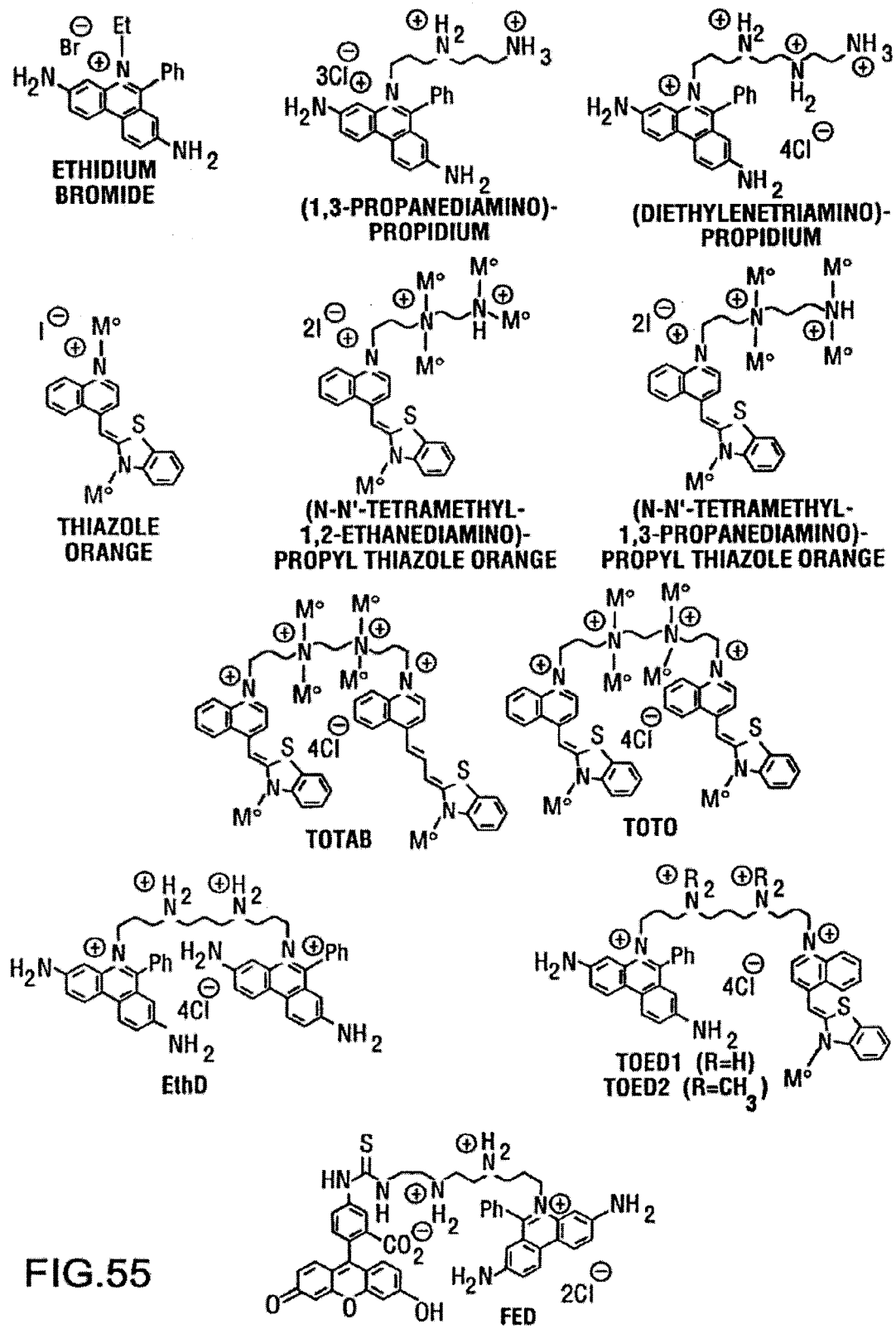
Figure 56:
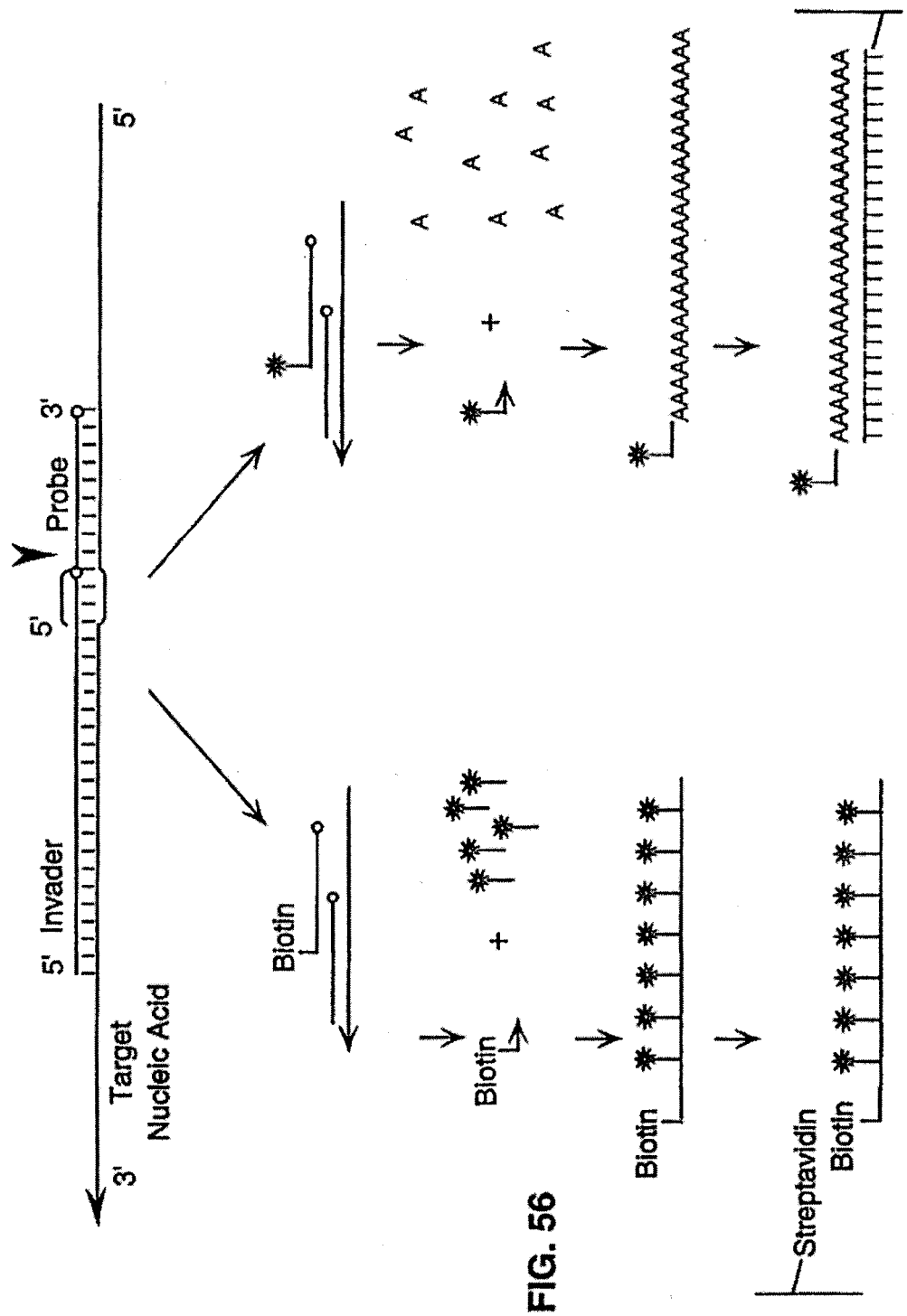
Figure 57:
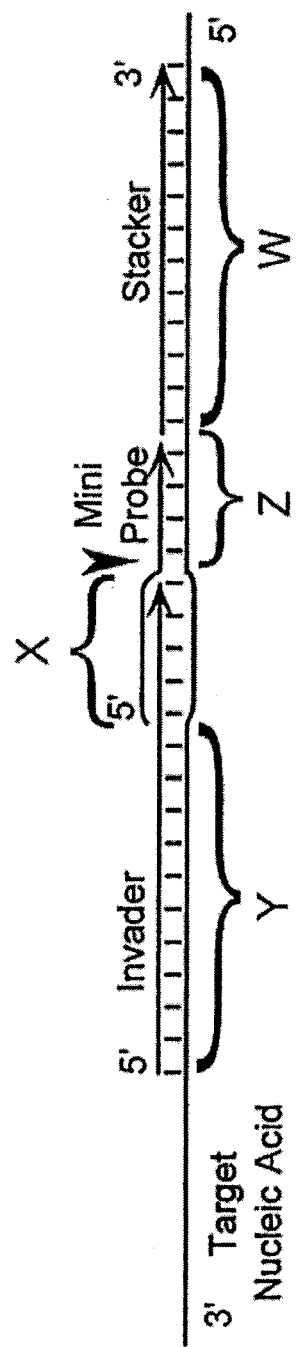
Figure 58:
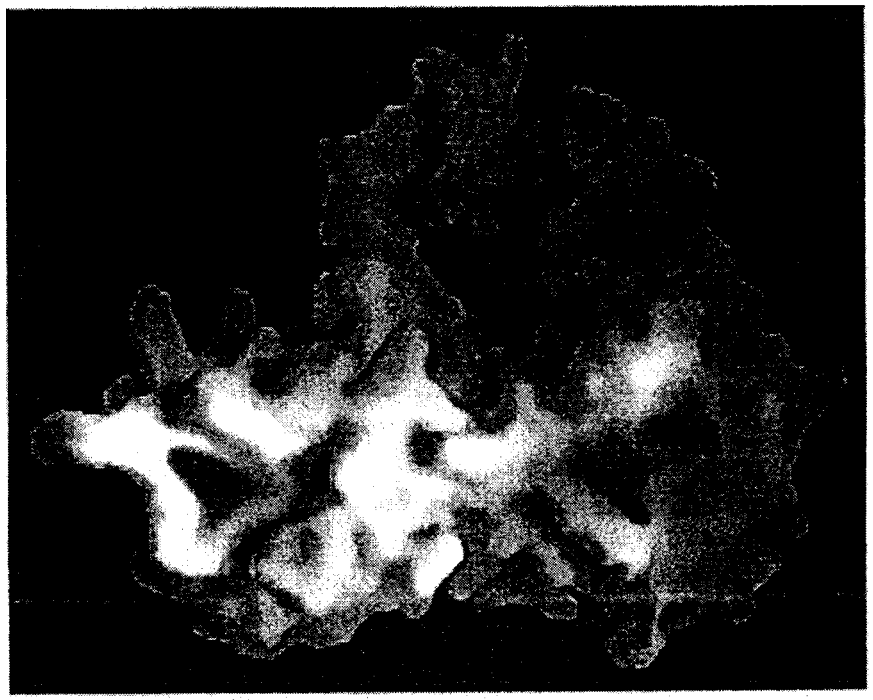
Figure 61:
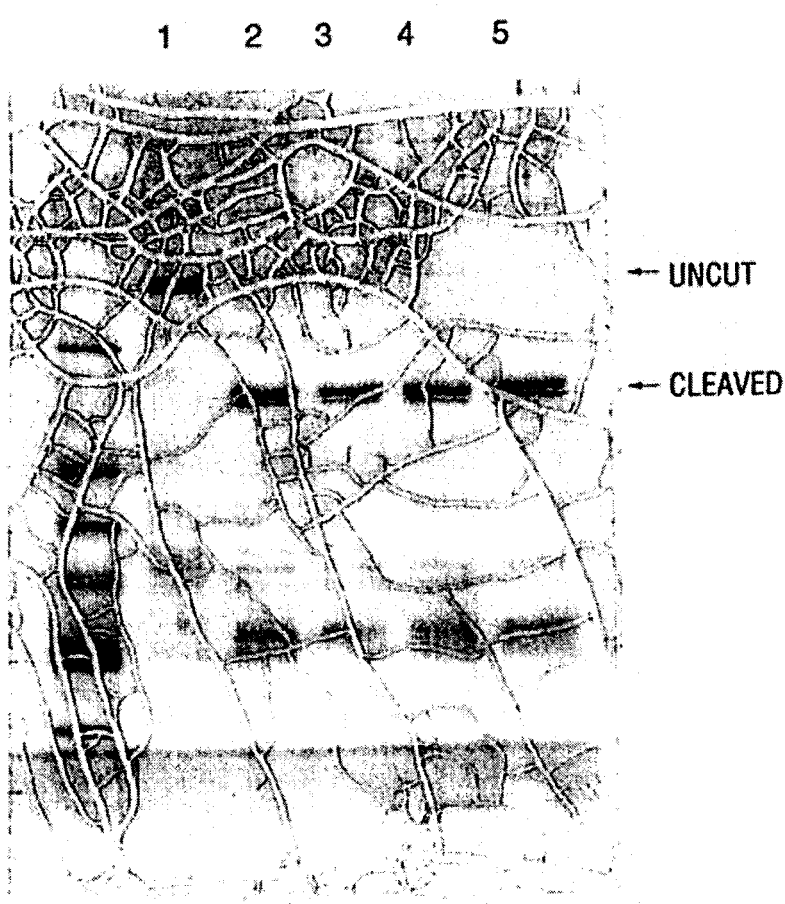
Figure 62:
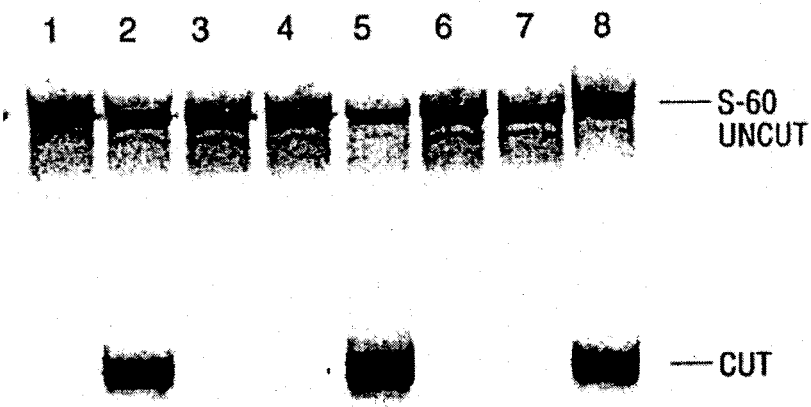
Figure 63:
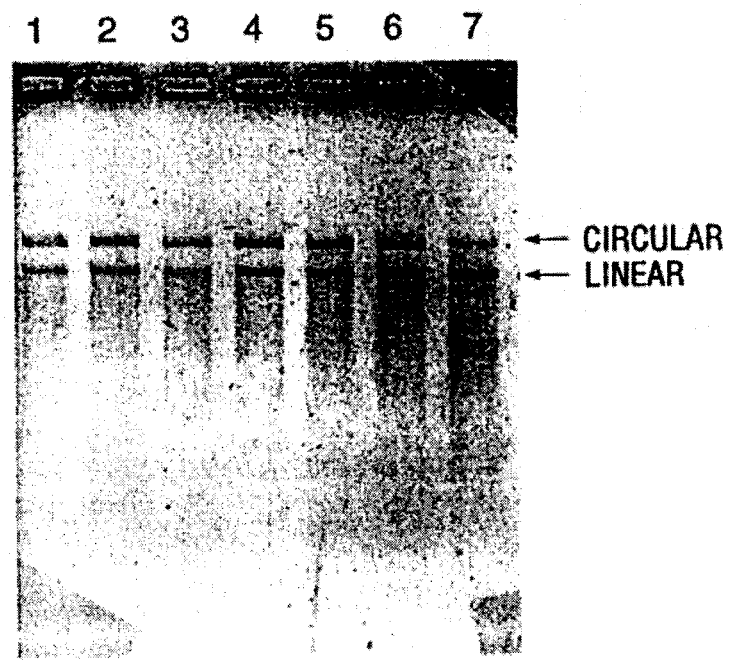
Figure 64:
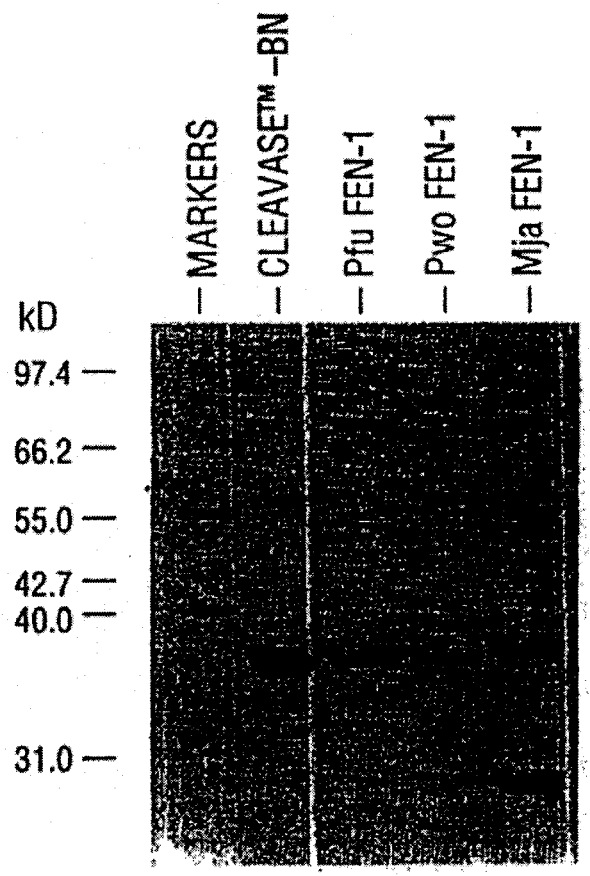
Figure 65:
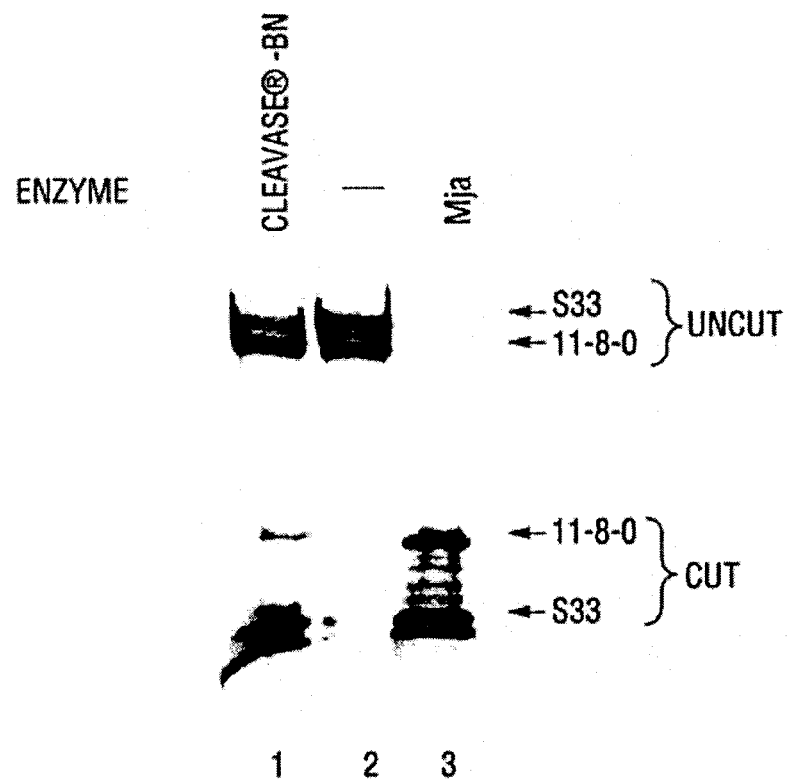
Figure 66:
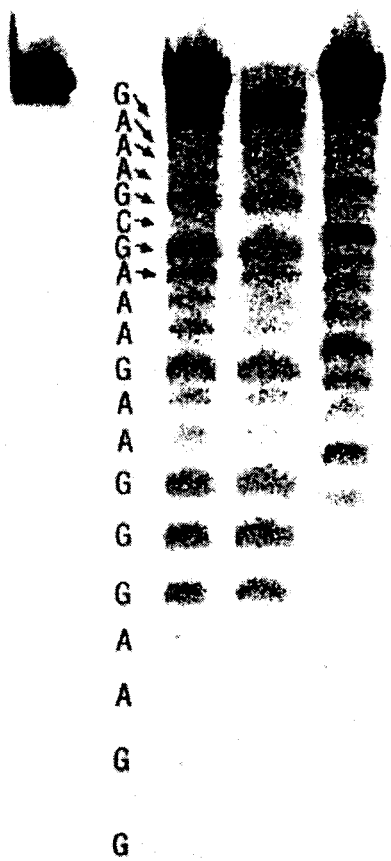
Figure 67:
Figure 68:
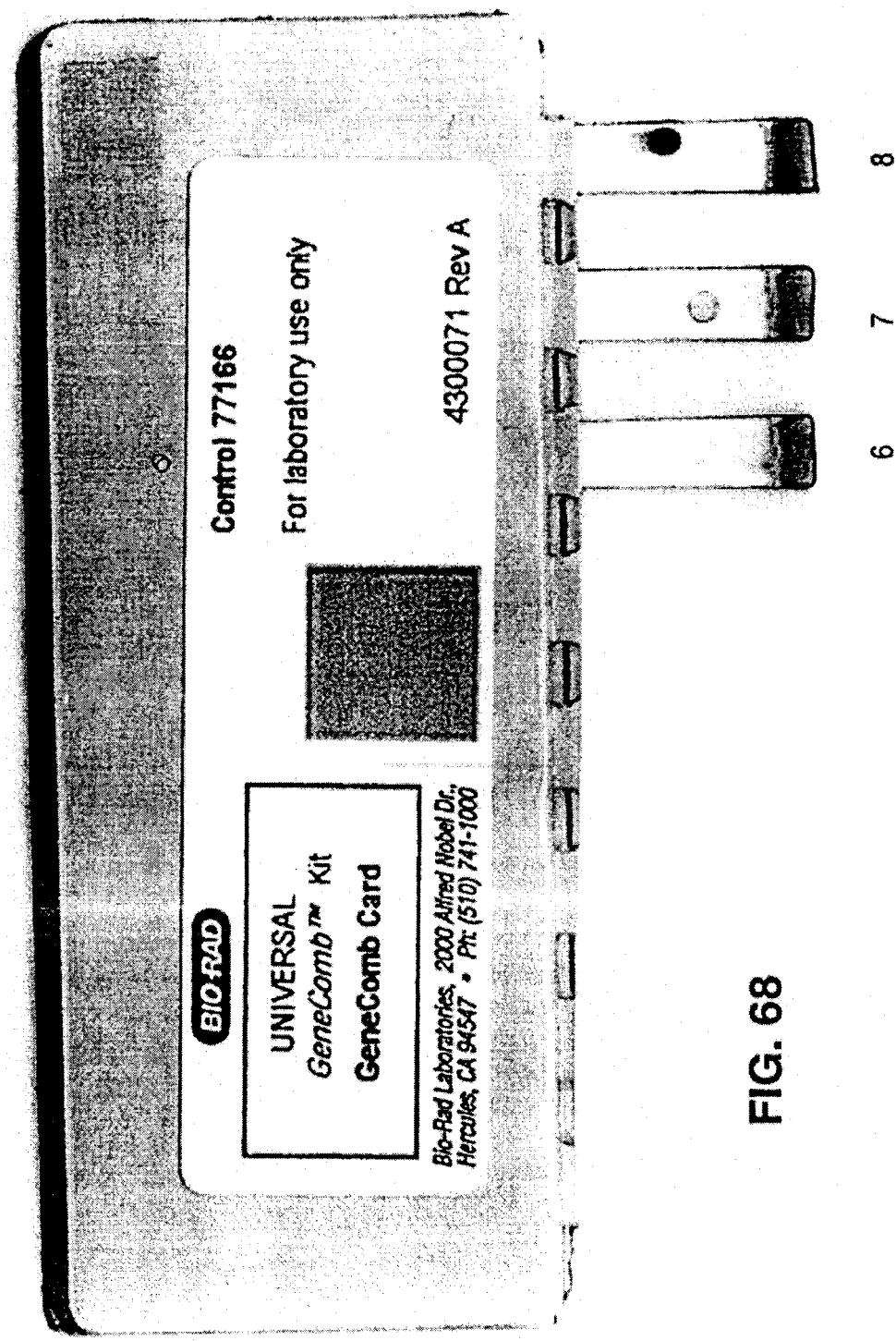
Figure 69:
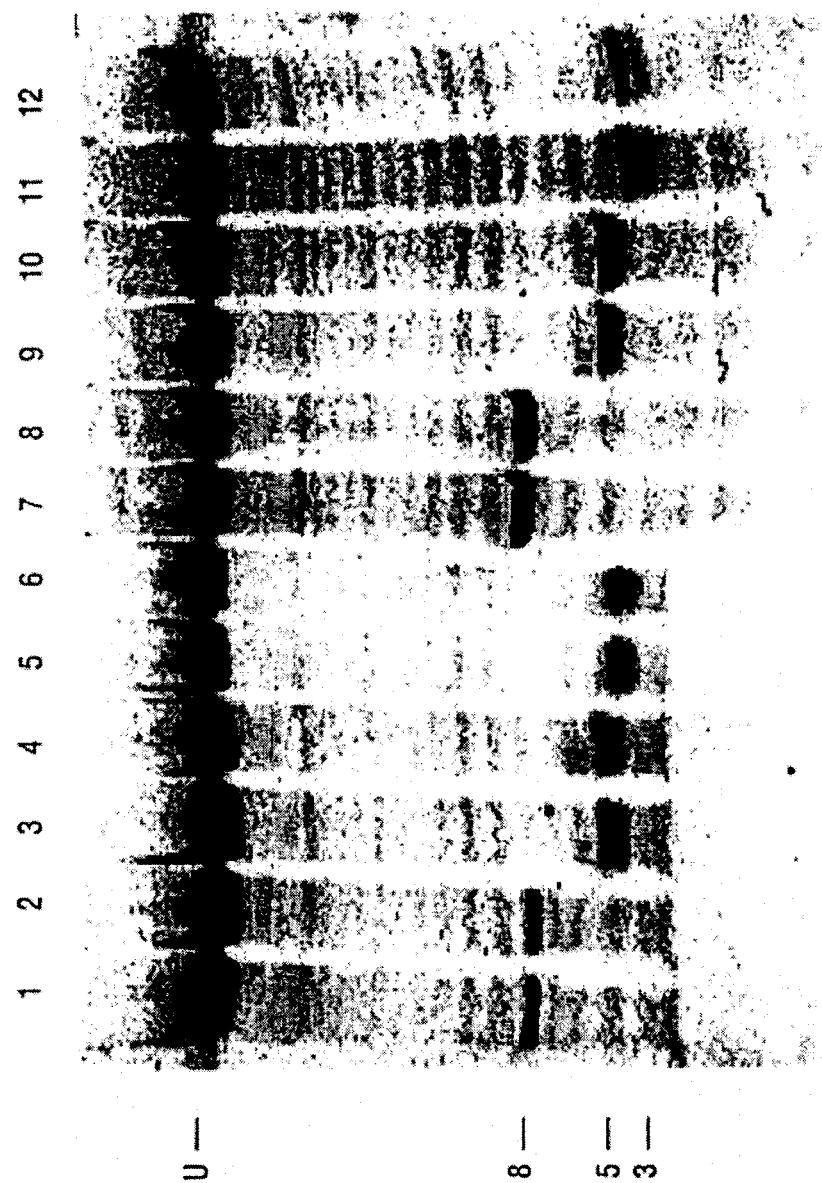
Figure 70:
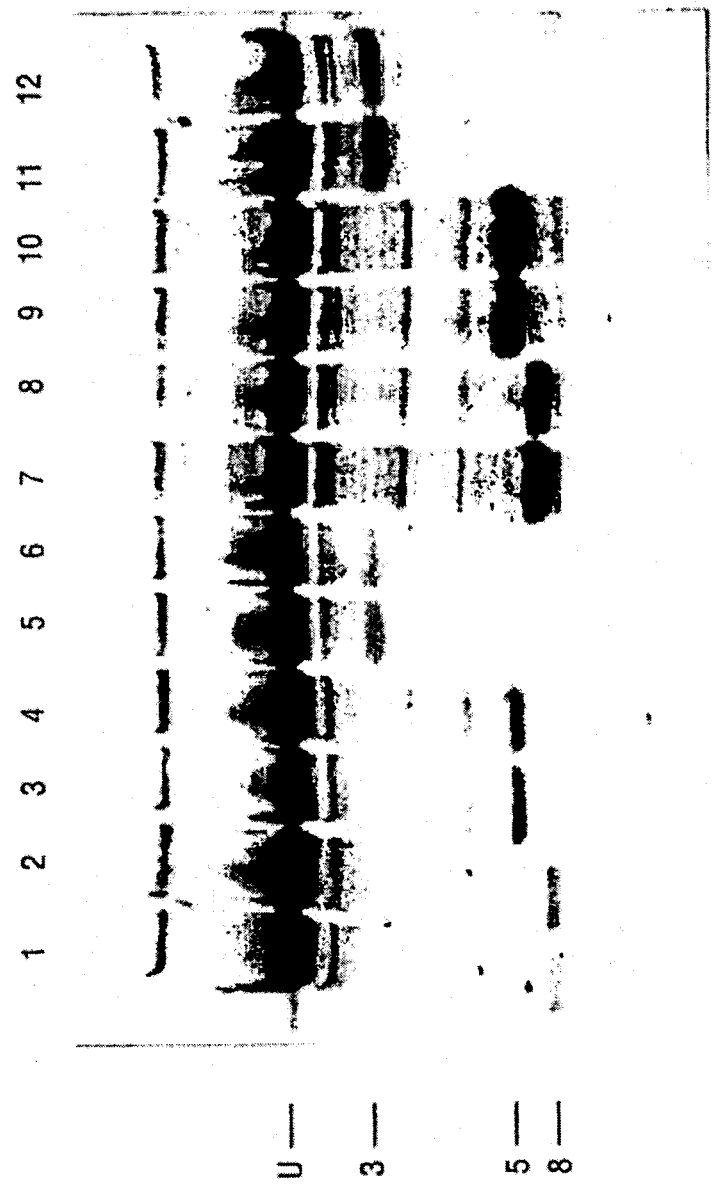
Figure 71:
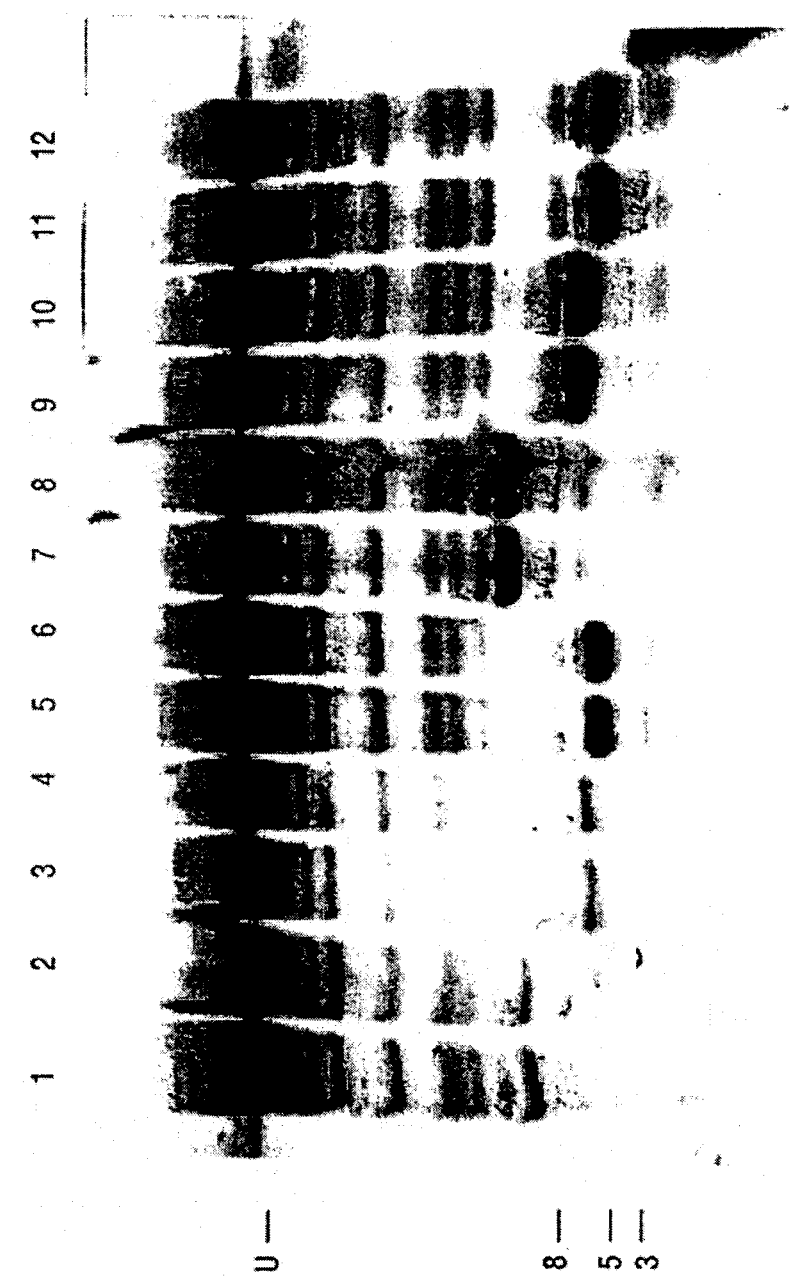
Figure 72A:
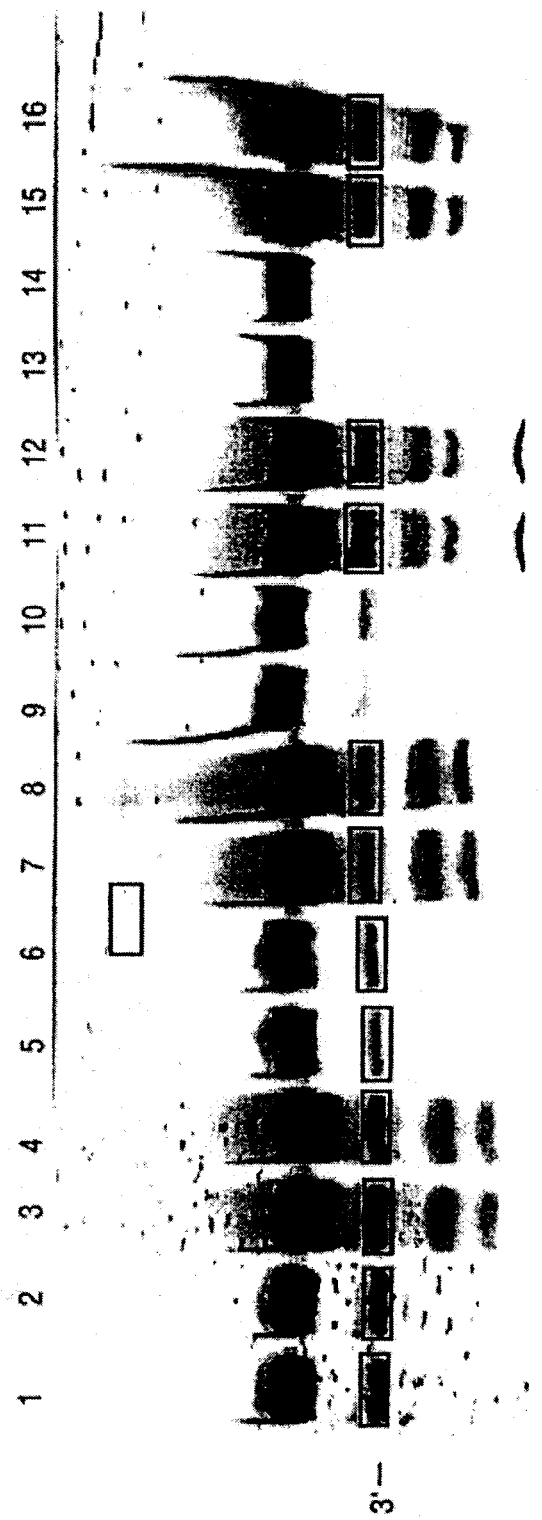
Figure 72B:
Figure 74:
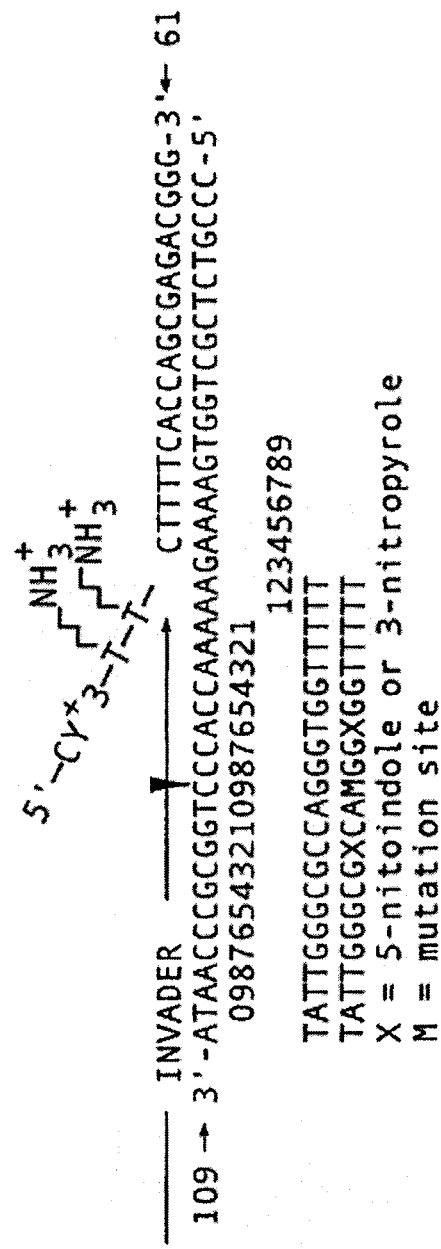
Figure 75A:
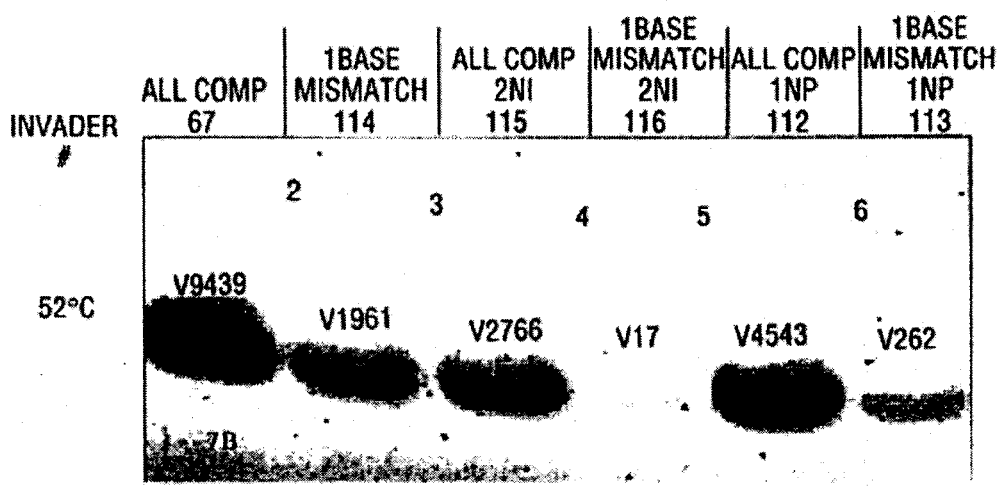
Figure 75B:
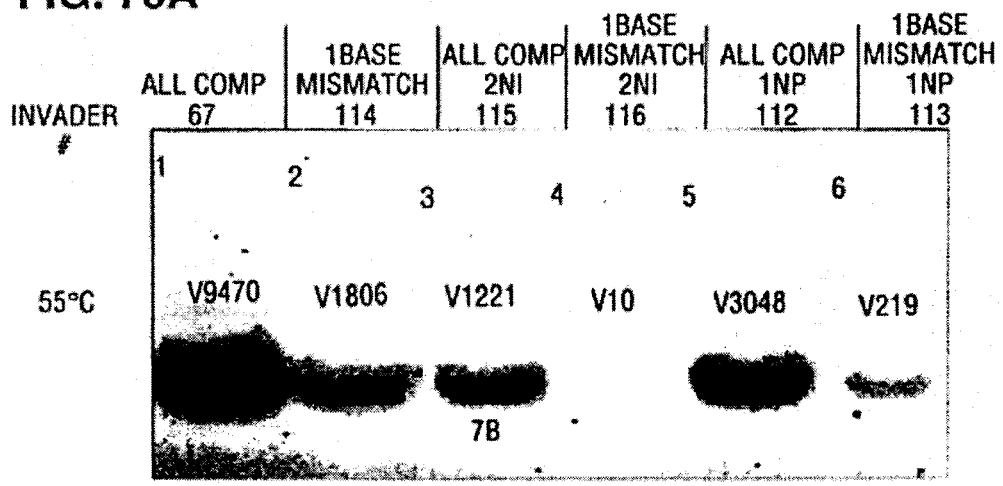
Figure 75C:
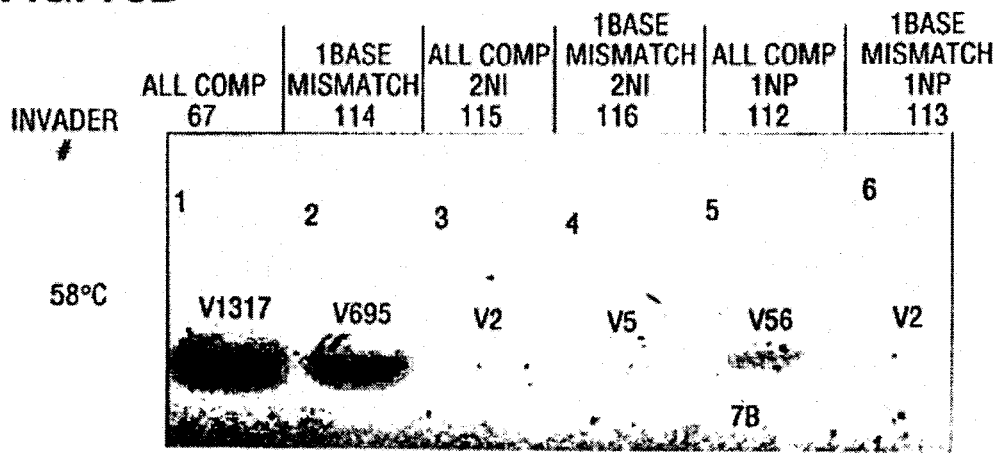
Figure 76:
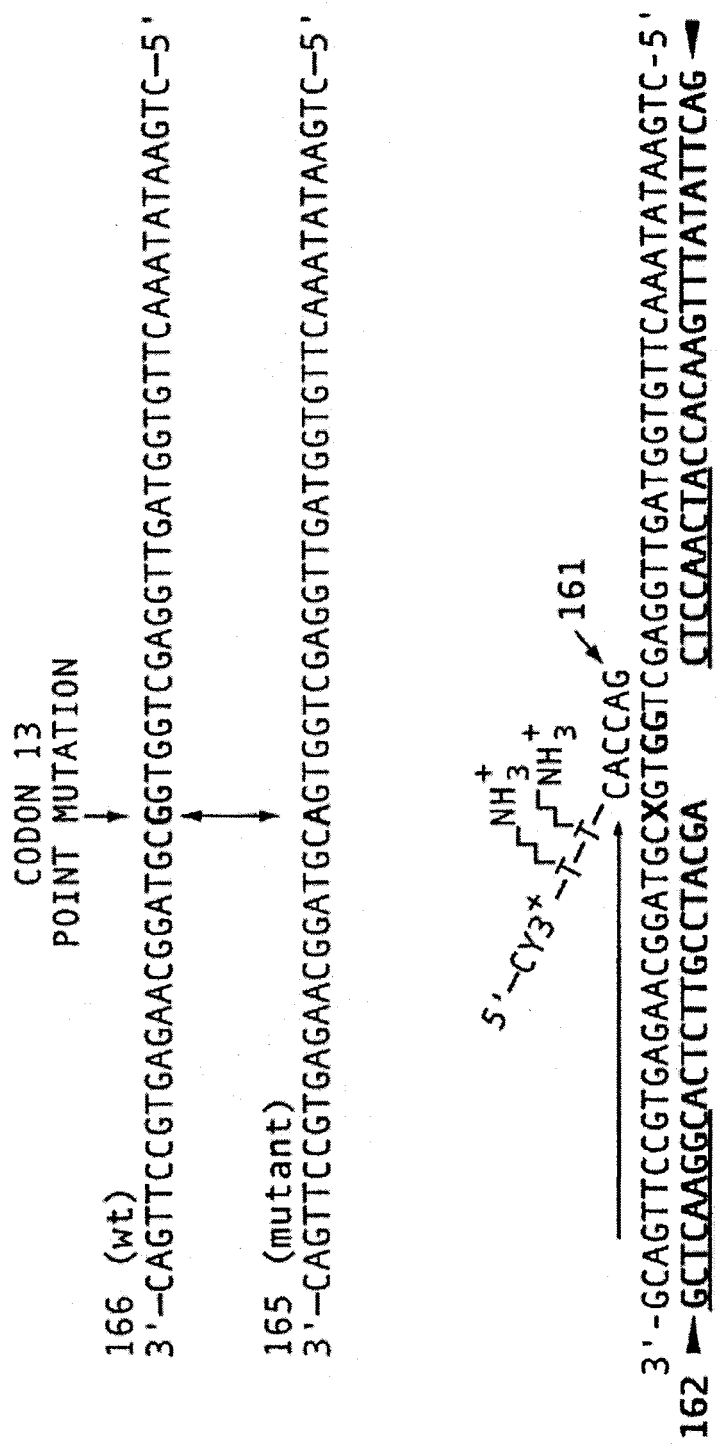
Figure 77:

In FIG. 44, lanes 1-3 contain the TET-labeled oligonucleotide 78 and lanes 4-6 contain the TET-labeled oligonucleotides 79. Lanes 1 and 4 contain products of reactions that were not heat treated. Lanes 2 and 5 contain products from reactions that were heat treated and lanes 3 and 6 contain products from reactions that were heat treated and subjected to phosphatase treatment.

As shown in FIG. 44, heat treatment causes significant breakdown of the 5'-TET-labeled DNA, generating a ladder of degradation products (FIG. 44, lanes 2, 3, 5 and 6). Band intensities correlate with purine and pyrimidine base positioning in the oligonucleotide sequences, indicating that backbone hydrolysis may occur through formation of abasic intermediate products that have faster rates for purines than for pyrimidines (Lindahl and Karlstrom, Biochem., 12:5151 [1973]).

Dephosphorylation decreases the mobility of all products generated by the thermal degradation process, with the most pronounced effect observed for the shorter products (FIG. 44, lanes 3 and 6). This demonstrates that thermally degraded products possess a 3' end terminal phosphoryl group that can be removed by dephosphorylation with CIAP. Removal of the phosphoryl group decreases the overall negative charge by 2. Therefore, shorter products that have a small number of negative charges are influenced to a greater degree upon the removal of two charges. This leads to a larger mobility shift in the shorter products than that observed for the larger species.

Figure 47:
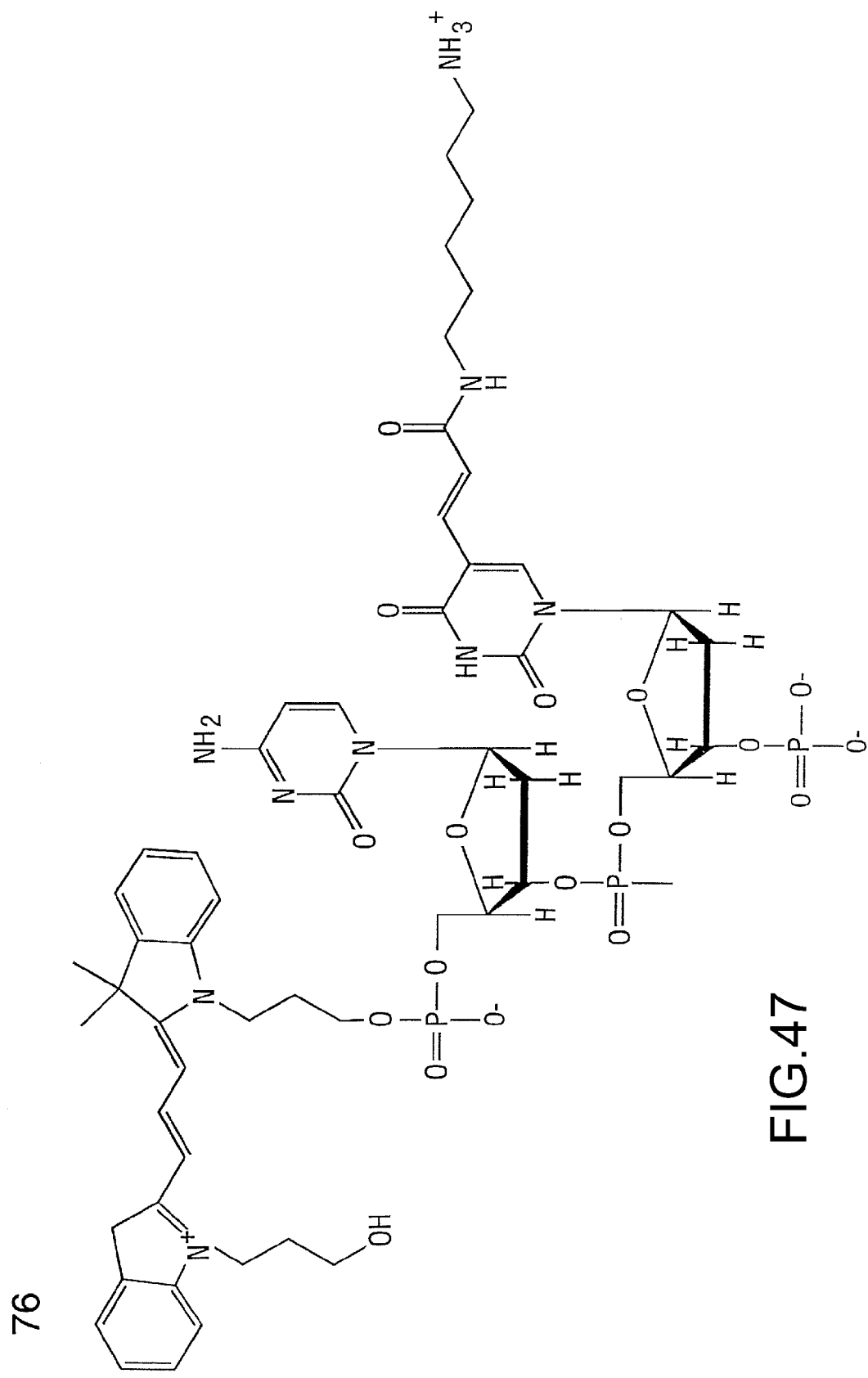
FIG. 47 depicts the structure of amino-modified oligonucleotide 76.

The fact that the majority of thermally degraded DNA products contain 3' end phosphate groups and CLEAVASE enzyme-generated products do not allowed the development of simple isolation methods for products generated in the INVADER-directed cleavage assay. The extra two charges found in thermal breakdown products do not exist in the specific cleavage products. Therefore, if one designs assays that produce specific products that contain a net positive charge of one or two, then similar thermal breakdown products will either be negative or neutral. The difference can be used to isolate specific products by reverse charge methods as shown below.

b) Dephosphorylation of Short Amino-Modified Oligonucleotides can Reverse the Net Charge of the Labeled Product To demonstrate how oligonucleotides can be transformed from net negative to net positively charged compounds, the four short amino-modified oligonucleotides labeled 70, 74, 75 and 76 and shown in FIGS. 45-47 were synthesized (FIG. 45 shows both oligonucleotides 70 and 74). All four modified oligonucleotides possess Cy-3 dyes positioned at the 5'-end, which individually are positively charged under reaction and isolation conditions described in this Example. Compounds 70 and 74 contain two amino modified thymidines that, under reaction conditions, display positively charged $R—NH_3^+$ groups attached at the C5 position through a $C_{10}$ or $C_6$ linker, respectively. Because compounds 70 and 74 are 3'-end phosphorylated, they consist of four negative charges and three positive charges. Compound 75 differs from 74 in that the internal $C_6$ amino modified thymidine phosphate in 74 is replaced by a thymidine methyl phosphonate. The phosphonate backbone is uncharged and so there are a total of three negative charges on compound 75. This gives compound 75 a net negative one charge. Compound 76 differs from 70 in that the internal amino modified thymidine is replaced by an internal cytosine phosphonate. The $pK_a$ of the N3 nitrogen of cytosine can be from 4 to 7. Thus, the net charges of this compound, can be from −1 to 0 depending on the pH of the solution. For the simplicity of analysis, each group is assigned a whole number of charges, although it is realized that, depending on the $pK_a$ of each chemical group and ambient pH, a real charge may differ from the whole number assigned. It is assumed that this difference is not significant over the range of pHs used in the enzymatic reactions studied here.

Dephosphorylation of these compounds, or the removal of the 3' end terminal phosphoryl group, results in elimination of two negative charges and generates products that have a net positive charge of one. In this experiment, the method of isoelectric focusing (IEF) was used to demonstrate a change from one negative to one positive net charge for the described substrates during dephosphorylation.

Substrates 70, 74, 75 and 76 were synthesized by standard phosphoramidite chemistries and deprotected for 24 hours at 22° C. in 14 M aqueous ammonium hydroxide solution, after which the solvent was removed in vacuo. The dried powders were resuspended in 200 µl of $H_2O$ and filtered through 0.2 µm filters. The concentration of the stock solutions was estimated by UV-absorbance at 261 nm of samples diluted 200-fold in $H_2O$ using a spectrophotometer (Spectronic Genesys 2, Milton Roy, Rochester, N.Y.).

Dephosphorylation of compounds 70 and 74, 75 and 76 was accomplished by treating 10 µl of the crude stock solutions (ranging in concentration from approximately 0.5 to 2 mM) with 2 units of CIAP in 100 µl of CIAP buffer (Promega) at 37° C. for 1 hour. The reactions were then heated to 75° C. for 15 min. in order to inactivate the CIAP. For clarity, dephosphorylated compounds are designated 'dp'. For example, after dephosphorylation, substrate 70 becomes 70dp.

To prepare samples for IEF experiments, the concentration of the stock solutions of substrate and dephosphorylated product were adjusted to a uniform absorbance of $8.5 \times 10^{-3}$ at 532 nm by dilution with water. Two microliters of each sample were analyzed by IEF using a PhastSystem electrophoresis unit (Pharmacia) and PhastGel IEF 3-9 media (Pharmacia) according to the manufacturer's protocol. Separation was performed at 15° C. with the following program: pre-run; 2,000 V, 2.5 mA, 3.5 W, 75 Vh; load; 200 V, 2.5 mA, 3.5 W, 15 Vh; run; 2,000 V; 2.5 mA; 3.5 W, 130 Vh. After separation, samples were visualized by using the FMBIO Image Analyzer (Hitachi) fitted with a 585 nm filter. The resulting imager scan is shown in FIG. 48.

Figure 48:
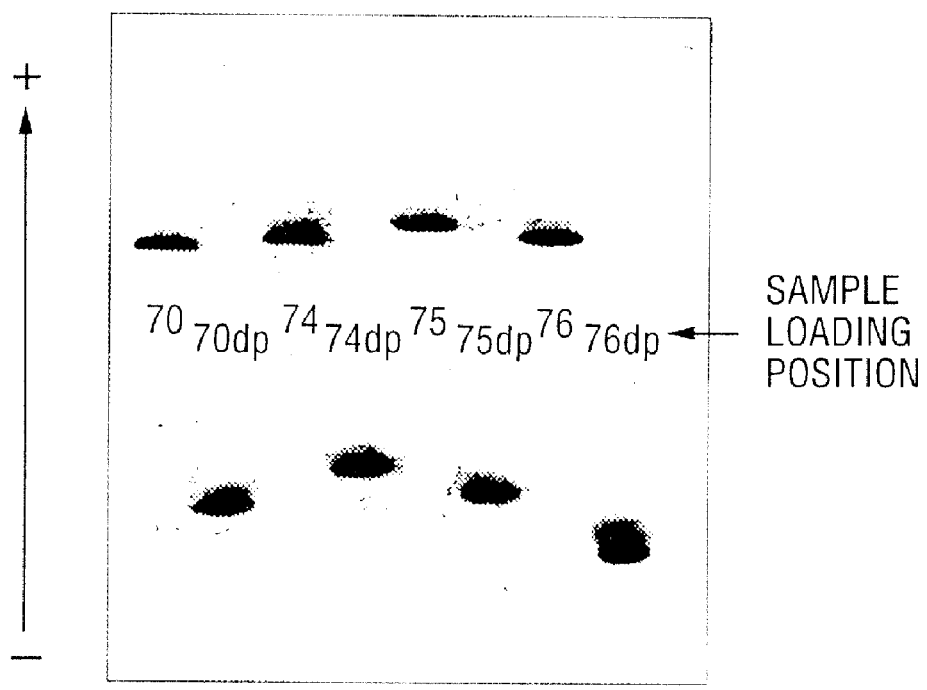
FIG. 48 is the image generated by a fluorescence imager scan of an IEF gel showing the migration of substrates 70, 70dp, 74, 74dp, 75, 75dp, 76 and 76dp.

FIG. 48 shows results of IEF separation of substrates 70, 74, 75 and 76 and their dephosphorylated products. The arrow labeled "Sample Loading Position" indicates a loading line, the '+' sign shows the position of the positive electrode and the '−' sign indicates the position of the negative electrode.

The results shown in FIG. 48 demonstrate that substrates 70, 74, 75 and 76 migrated toward the positive electrode, while the dephosphorylated products 70dp, 74dp, 75dp and 76dp migrated toward negative electrode. The observed differences in mobility direction was in accord with predicted net charge of the substrates (minus one) and the products (plus one). Small perturbations in the mobilities of the phosphorylated compounds indicate that the overall pIs vary. This was also true for the dephosphorylated compounds. The presence of the cytosine in 76dp, for instance, moved this compound further toward the negative electrode, which was indicative of a higher overall pI relative to the other dephosphorylated compounds. It is important to note that additional positive charges can be obtained by using a combination of natural amino modified bases (70dp and 74dp) along with uncharged methylphosphonate bridges (products 75dp and 76dp).

The results shown above demonstrate that the removal of a single phosphate group can flip the net charge of an oligonucleotide to cause reversal in an electric field, allowing easy separation of products, and that the precise base composition of the oligonucleotides affect absolute mobility but not the charge-flipping effect.

Example 23

Detection of Specific Cleavage Products in the INVADER-Directed Cleavage Reaction by Charge Reversal In this Example the ability to isolate products generated in the INVADER-directed cleavage assay from all other nucleic acids present in the reaction cocktail was demonstrated using charge reversal. This experiment utilized the following Cy3-labeled oligonucleotide: 5'-Cy3-AminoT-AminoT-CTTTTCACCAGCGAGACGGG-3' (SEQ ID NO:50; termed "oligo 61"). Oligo 61 was designed to release upon cleavage a net positively charged labeled product. To test whether or not a net positively charged 5'-end labeled product would be recognized by the CLEAVASE enzymes in the INVADER-directed cleavage assay format, probe oligo 61 (SEQ ID NO:50) and invading oligonucleotide 67 (SEQ ID NO:51) were chemically synthesized on a DNA synthesizer (ABI 391) using standard phosphoramidite chemistries and reagents obtained from Glen Research (Sterling, Va.).

Each assay reaction comprised 100 fmoles of M13mp18 single stranded DNA, 10 pmoles each of the probe (SEQ ID NO:50) and INVADER (SEQ ID NO:51) oligonucleotides, and 20 units of CLEAVASE A/G in a 10 µl solution of 10 mM MOPS, pH 7.4 with 100 mM KCl. Samples were overlaid with mineral oil to prevent evaporation. The samples were brought to either 50° C., 55° C., 60° C., or 65° C. and cleavage was initiated by the addition of 1 µl of 40 mM $MnCl_2$. Reactions were allowed to proceed for 25 minutes and then were terminated by the addition of 10 µl of 95% formamide containing 20 mM EDTA and 0.02% methyl violet. The negative control experiment lacked the target M13mp18 and was run at 60° C. Five microliters of each reaction were loaded into separate wells of a 20% denaturing polyacrylamide gel (crosslinked 29:1) with 8 M urea in a buffer containing 45 mM Tris-Borate (pH 8.3) and 1.4 mM EDTA. An electric field of 20 watts was applied for 30 minutes, with the electrodes oriented as indicated in FIG. 49B (i.e., in reverse orientation). The products of these reactions were visualized using the FMBIO fluorescence imager and the resulting imager scan is shown in FIG. 49B.

Figure 49A:
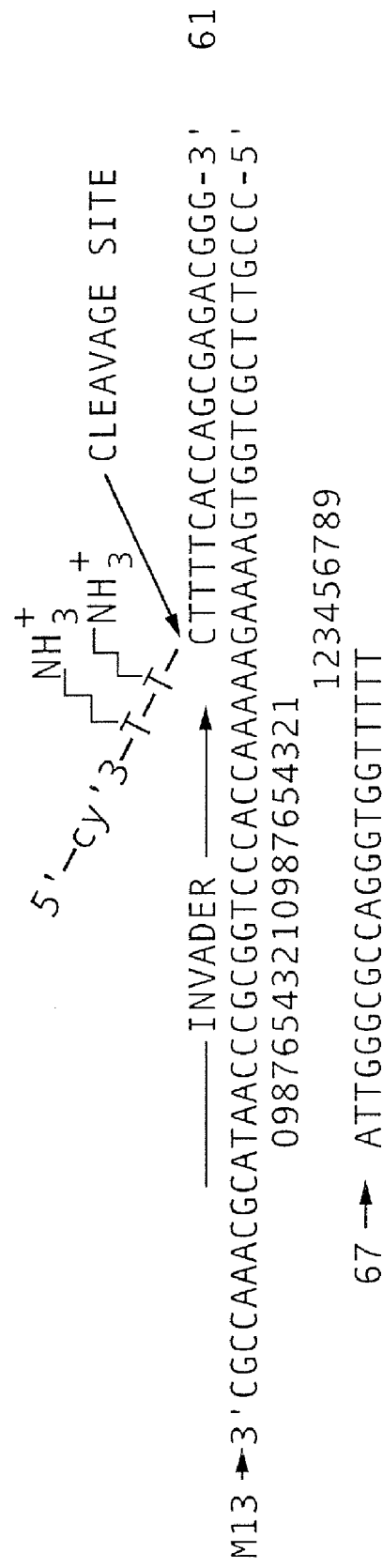
FIG. 49A provides a schematic showing an arrangement of a target-specific INVADER oligonucleotide (SEQ ID NO:50) and a target-specific probe oligonucleotide (SEQ ID NO:51) bearing a 5' Cy3 label along a target nucleic acid (SEQ ID NO:52).
Figure 49B:
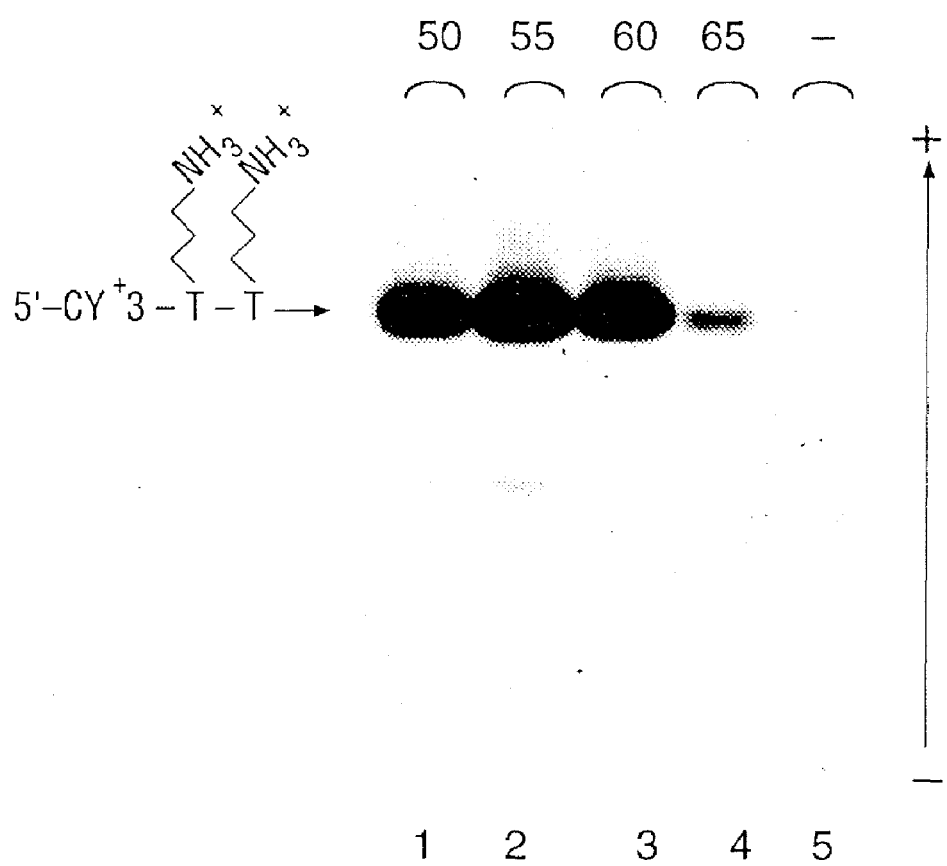
FIG. 49B is the image generated by a fluorescence imager showing the detection of specific cleavage products generated in an invasive cleavage assay using charge reversal (i.e., charge based separation of cleavage products).

FIG. 49A provides a schematic illustration showing an alignment of the INVADER (SEQ ID NO:50) and probe (SEQ ID NO:51) along the target M13mp18 DNA; only 53 bases of the M13mp18 sequence is shown (SEQ ID NO:52). The sequence of the INVADER oligonucleotide is displayed under the M13mp18 target and an arrow is used above the M13mp18 sequence to indicate the position of the INVADER relative to the probe and target. As shown in FIG. 49A, the INVADER and probe oligonucleotides share a 2 base region of overlap.

In FIG. 49B, lanes 1-6 contain reactions performed at 50° C., 55° C., 60° C., and 65° C., respectively; lane 5 contained the control reaction (lacking target). In FIG. 49B, the products of cleavage are seen as dark bands in the upper half of the panel; the faint lower band seen appears in proportion to the amount of primary product produced and, while not limiting the invention to a particular mechanism, may represent cleavage one nucleotide into the duplex. The uncleaved probe does not enter the gel and is thus not visible. The control lane showed no detectable signal over background (lane 5). As expected in an invasive cleavage reaction, the rate of accumulation of specific cleavage product was temperature-dependent. Using these particular oligonucleotides and target, the fastest rate of accumulation of product was observed at 55° C. (lane 2) and very little product observed at 65° C. (lane 4).

When incubated for extended periods at high temperature, DNA probes can break non-specifically (i.e., suffer thermal degradation) and the resulting fragments contribute an interfering background to the analysis. The products of such thermal breakdown are distributed from single-nucleotides up to the full length probe. In this experiment, the ability of charge based separation of cleavage products (i.e., charge reversal) would allow the sensitive separation of the specific products of target-dependent cleavage from probe fragments generated by thermal degradation was examined.

To test the sensitivity limit of this detection method, the target M13mp18 DNA was serially diluted ten fold over than range of 1 fmole to 1 amole. The INVADER and probe oligonucleotides were those described above (i.e., SEQ ID NOS:50 and 51). The invasive cleavage reactions were run as described above with the following modifications: the reactions were performed at 55° C., 250 mM or 100 mM KGlu was used in place of the 100 mM KCl and only 1 pmole of the INVADER oligonucleotide was added. The reactions were initiated as described above and allowed to progress for 12.5 hours. A negative control reaction that lacked added M13m18 target DNA was also run. The reactions were terminated by the addition of 10 µl of 95% formamide containing 20 mM EDTA and 0.02% methyl violet, and 5 µl of these mixtures were electrophoresed and visualized as described above. The resulting imager scan is shown in FIG. 50.

Figure 50:
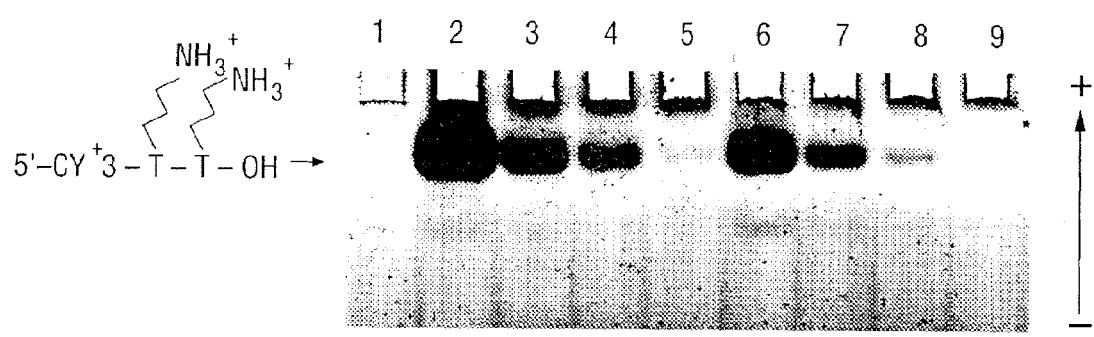
FIG. 50 is the image generated by a fluorescence imager which depicts the sensitivity of detection of specific cleavage products generated in an invasive cleavage assay using charge reversal.

In FIG. 50, lane 1 contains the negative control; lanes 2-5 contain reactions performed using 100 mM KGlu; lanes 6-9 contain reactions performed using 250 mM KGlu. The reactions resolved in lanes 2 and 6 contained 1 fmole of target DNA; those in lanes 3 and 7 contained 100 amole of target; those in lanes 4 and 8 contained 10 amole of target and those in lanes 5 and 9 contained 1 amole of target. The results shown in FIG. 50 demonstrate that the detection limit using charge reversal to detect the production of specific cleavage products in an invasive cleavage reaction is at or below 1 attomole or approximately $6.02 \times 10^5$ target molecules. No detectable signal was observed in the control lane, which indicates that non-specific hydrolysis or other breakdown products do not migrate in the same direction as enzyme-specific cleavage products. The excitation and emission maxima for Cy3 are 554 and 568, respectively, while the FMBIO Imager Analyzer excites at 532 and detects at 585. Therefore, the limit of detection of specific cleavage products can be improved by the use of more closely matched excitation source and detection filters.

Example 24

Devices and Methods for the Separation and Detection of Charged Reaction Products This Example is directed at methods and devices for isolating and concentrating specific reaction products produced by enzymatic reactions conducted in solution whereby the reactions generate charged products from either a charge neutral substrate or a substrate bearing the opposite charge borne by the specific reaction product. The methods and devices of this Example allow isolation of, for example, the products generated by the INVADER-directed cleavage assay of the present invention.

The methods and devices of this Example are based on the principle that when an electric field is applied to a solution of charged molecules, the migration of the molecules toward the electrode of the opposite charge occurs very rapidly. If a matrix or other inhibitory material is introduced between the charged molecules and the electrode of opposite charge such that this rapid migration is dramatically slowed, the first molecules to reach the matrix will be nearly stopped, thus allowing the lagging molecules to catch up. In this way a dispersed population of charged molecules in solution can be effectively concentrated into a smaller volume. By tagging the molecules with a detectable moiety (e.g., a fluorescent dye), detection is facilitated by both the concentration and the localization of the analytes. This Example illustrates two embodiments of devices contemplated by the present invention; of course, variations of these devices will be apparent to those skilled in the art and are within the spirit and scope of the present invention.

Figure 51:
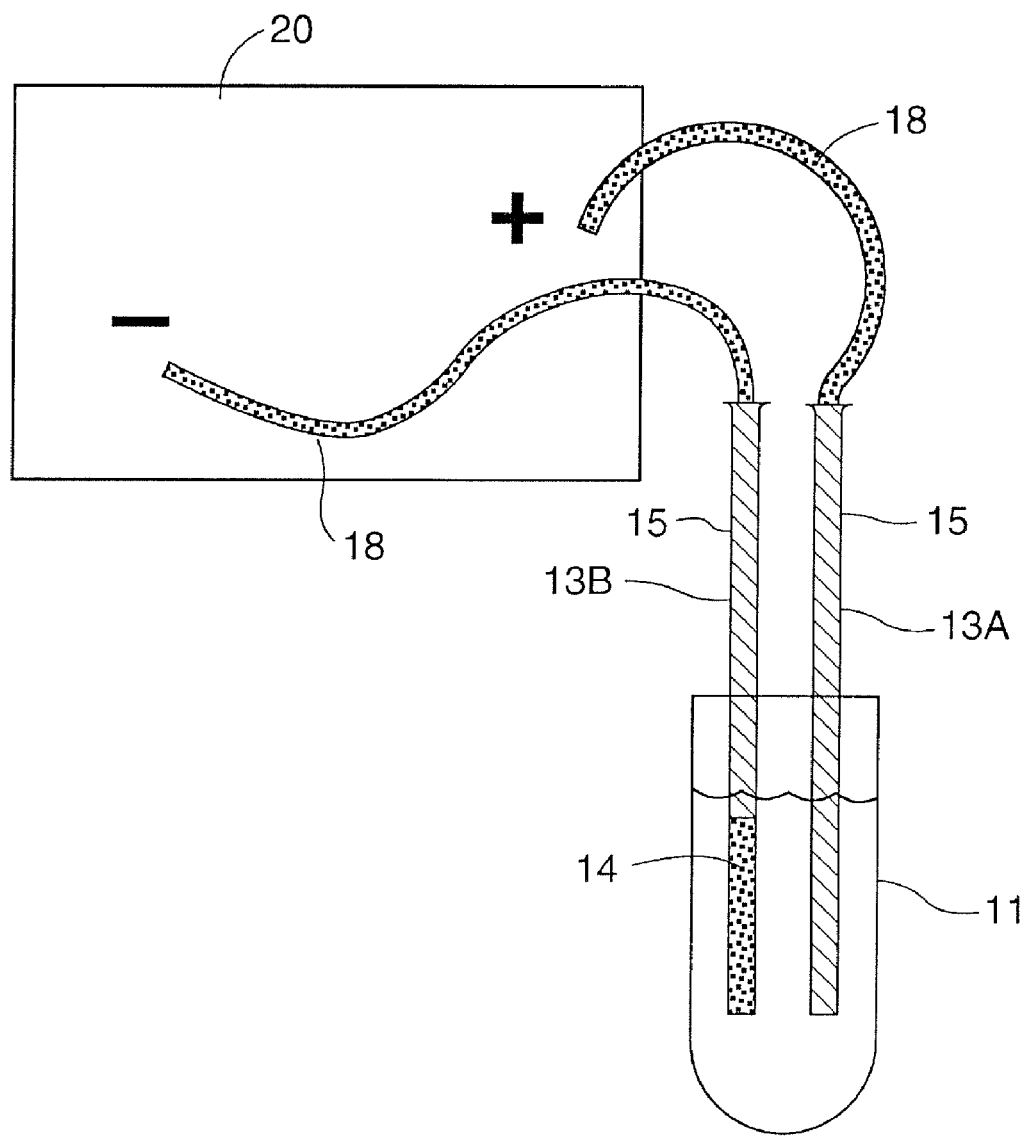
FIG. 51 depicts a first embodiment of a device for the charge-based separation of oligonucleotides.

FIG. 51 depicts one embodiment of a device for concentrating the positively-charged products generated using the methods of the present invention. As shown in FIG. 51, the device comprises a reaction tube (10) that contains the reaction solution (11). One end of each of two thin capillaries (or other tubes with a hollow core) (13A and 13B) are submerged in the reaction solution (11). The capillaries (13A and 13B) may be suspended in the reaction solution (11) such that they are not in contact with the reaction tube itself; one appropriate method of suspending the capillaries is to hold them in place with clamps (not shown). Alternatively, the capillaries may be suspended in the reaction solution (11) such that they are in contact with the reaction tube itself. Suitable capillaries include glass capillary tubes commonly available from scientific supply companies (e.g., Fisher Scientific or VWR Scientific) or from medical supply houses that carry materials for blood drawing and analysis. Though the present invention is not limited to capillaries of any particular inner diameter, tubes with inner diameters of up to about ⅛ inch (approximately 3 mm) are particularly preferred for use with the present invention; for example, Kimble No. 73811-99 tubes (VWR Scientific) have an inner diameter of 1.1 mm and are a suitable type of capillary tube. Although the capillaries of the device are commonly composed of glass, any nonconductive tubular material, either rigid or flexible, that can contain either a conductive material or a trapping material is suitable for use in the present invention. One example of a suitable flexible tube is Tygon® clear plastic tubing (Part No. R3603; inner diameter=1/16 inch; outer diameter=⅛ inch).

As illustrated in FIG. 51, capillary 13A is connected to the positive electrode of a power supply (20) (e.g., a controllable power supply available through the laboratory suppliers listed above or through electronics supply houses like Radio Shack) and capillary 13B is connected to the negative electrode of the power supply (20). Capillary 13B is filled with a trapping material (14) capable of trapping the positively-charged reaction products by allowing minimal migration of products that have entered the trapping material (14). Suitable trapping materials include, but are not limited to, high percentage (e.g., about 20%) acrylamide polymerized in a high salt buffer (0.5 M or higher sodium acetate or similar salt); such a high percentage polyacrylamide matrix dramatically slows the migration of the positively-charged reaction products. Alternatively, the trapping material may comprise a solid, negatively-charged matrix, such as negatively-charged latex beads, that can bind the incoming positively-charged products. It should be noted that any amount of trapping material (14) capable of inhibiting any concentrating the positively-charged reaction products may be used. Thus, while the capillary 13B in FIG. 51 only contains trapping material in the lower, submerged portion of the tube, the trapping material (14) can be present in the entire capillary (13B); similarly, less trapping material (14) could be present than that shown in FIG. 51 because the positively-charged reaction products generally accumulate within a very small portion of the bottom of the capillary (13B). The amount of trapping material need only be sufficient to make contact with the reaction solution (11) and have the capacity to collect the reaction products. When capillary 13B is not completely filled with the trapping material, the remaining space is filled with any conductive material (15); suitable conductive materials are discussed below.

By comparison, the capillary (13A) connected to the positive electrode of the power supply 20 may be filled with any conductive material (15; indicated by the hatched lines in FIG. 51). This may be the sample reaction buffer (e.g., 10 mM MOPS, pH 7.5 with 150 mM LiCl, 4 mM $MnCl_2$), a standard electrophoresis buffer (e.g., 45 mM Tris-Borate, pH 8.3, 1.4 mM EDTA), or the reaction solution (11) itself. The conductive material (15) is frequently a liquid, but a semi-solid material (e.g., a gel) or other suitable material might be easier to use and is within the scope of the present invention. Moreover, that trapping material used in the other capillary (i.e., capillary 13B) may also be used as the conductive material. Conversely, it should be noted that the same conductive material used in the capillary (13A) attached to the positive electrode may also be used in capillary 13B to fill the space above the region containing the trapping material (14) (see FIG. 51).

The top end of each of the capillaries (13A and 13B) is connected to the appropriate electrode of the power supply (20) by electrode wire (18) or other suitable material. Fine platinum wire (e.g., 0.1 to 0.4 mm, Aesar Johnson Matthey, Ward Hill, Mass.) is commonly used as conductive wire because it does not corrode under electrophoresis conditions. The electrode wire (18) can be attached to the capillaries (13A and 13B) by a nonconductive adhesive (not shown), such as the silicone adhesives that are commonly sold in hardware stores for sealing plumbing fixtures. If the capillaries are constructed of a flexible material, the electrode wire (18) can be secured with a small hose clamp or constricting wire (not shown) to compress the opening of the capillaries around the electrode wire. If the conducting material (15) is a gel, an electrode wire (18) can be embedded directly in the gel within the capillary.

The cleavage reaction is assembled in the reaction tube (10) and allowed to proceed therein as described in proceeding Examples (e.g., Examples 22-23). Though not limited to any particular volume of reaction solution (11), a preferred volume is less than 10 ml and more preferably less than 0.1 ml. The volume need only be sufficient to permit contact with both capillaries. After the cleavage reaction is completed, an electric field is applied to the capillaries by turning on the power source (20). As a result, the positively-charged products generated in the course of the INVADER-directed cleavage reaction that employs an oligonucleotide, which when cleaved, generates a positively charged fragment (described in Ex. 23) but when uncleaved bears a net negative charge, migrate to the negative capillary, where their migration is slowed or stopped by the trapping material (14), and the negatively-charged uncut and thermally degraded probe molecules migrate toward the positive electrode. Through the use of this or a similar device, the positively-charged products of the invasive cleavage reaction are separated from the other material (i.e., uncut and thermally degraded probe) and concentrated from a large volume. Concentration of the product in a small amount of trapping material (14) allows for simplicity of detection, with a much higher signal-to-noise ratio than possible with detection in the original reaction volume. Because the concentrated product is labeled with a detectable moiety like a fluorescent dye, a commercially-available fluorescent plate reader (not shown) can be used to ascertain the amount of product. Suitable plate readers include both top and bottom laser readers. Capillary 13B can be positioned with the reaction tube (10) at any desired position so as to accommodate use with either a top or a bottom plate reading device.

Figure 52:
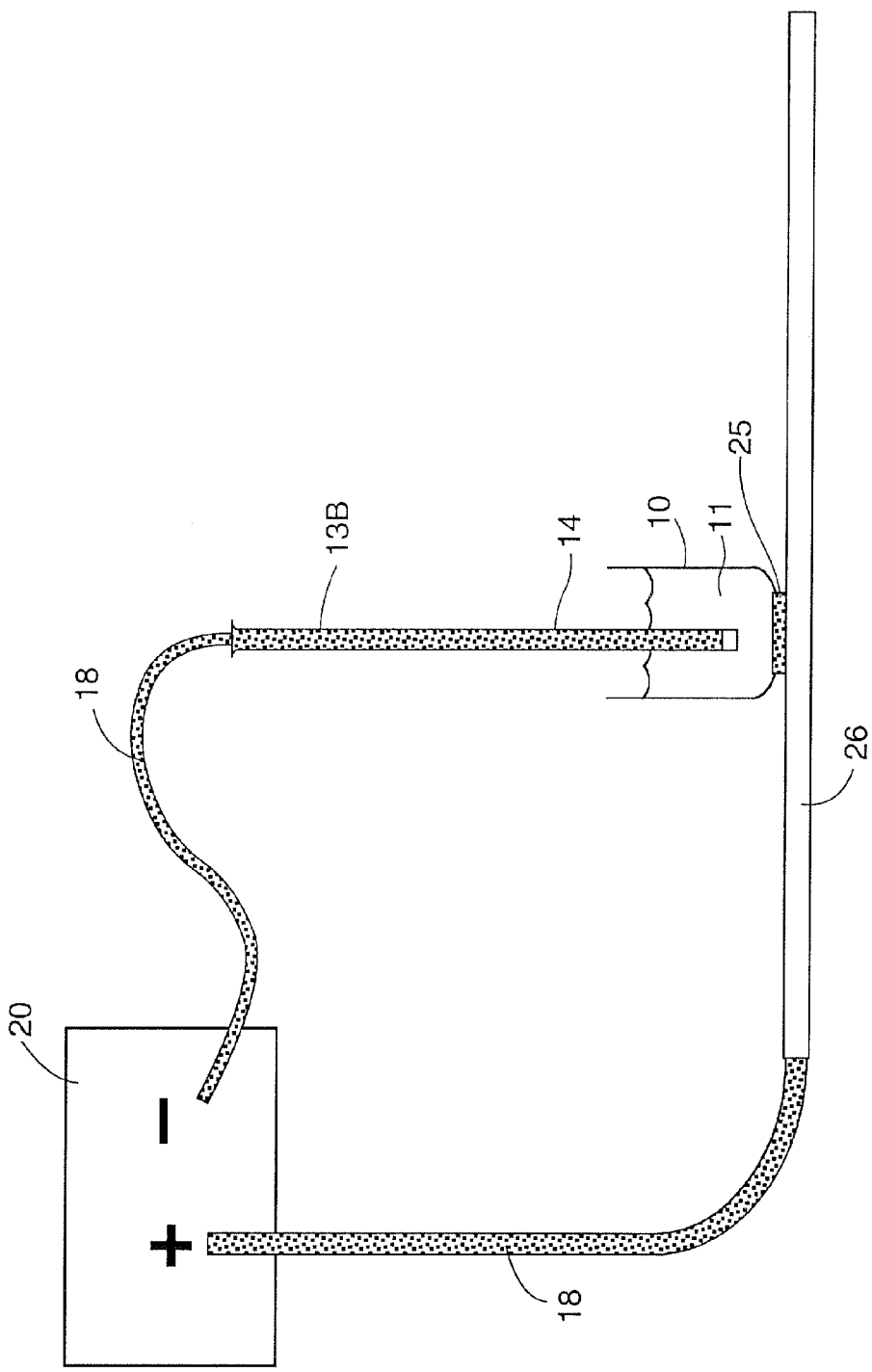
FIG. 52 depicts a second embodiment of a device for the charge-based separation of oligonucleotides.

In the alternative embodiment of the present invention depicted in FIG. 52, the procedure described above is accomplished by utilizing only a single capillary (13B). The capillary (13B) contains the trapping material (14) described above and is connected to an electrode wire (18), which in turn is attached to the negative electrode of a power supply (20). The reaction tube (10) has an electrode (25) embedded into its surface such that one surface of the electrode is exposed to the interior of the reaction tube (10) and another surface is exposed to the exterior of the reaction tube. The surface of the electrode (25) on the exterior of the reaction tube is in contact with a conductive surface (26) connected to the positive electrode of the power supply (20) through an electrode wire (18). Variations of the arrangement depicted in FIG. 52 are also contemplated by the present invention. For example, the electrode (25) may be in contact with the reaction solution (11) through the use of a small hole in the reaction tube (10); furthermore, the electrode wire (18) can be directly attached to the electrode wire (18), thereby eliminating the conductive surface (26).

As indicated in FIG. 52, the electrode (25) is embedded in the bottom of a reaction tube (10) such that one or more reaction tubes may be set on the conductive surface (26). This conductive surface could serve as a negative electrode for multiple reaction tubes; such a surface with appropriate contacts could be applied through the use of metal foils (e.g., copper or platinum, Aesar Johnson Matthey, Ward Hill, Mass.) in much the same way contacts are applied to circuit boards. Because such a surface contact would not be exposed to the reaction sample directly, less expensive metals, such as the copper could be used to make the electrical connections.

The above devices and methods are not limited to separation and concentration of positively charged oligonucleotides. As will be apparent to those skilled in the art, negatively charged reaction products may be separated from neutral or positively charged reactants using the above device and methods with the exception that capillary 13B is attached to the positive electrode of the power supply (20) and capillary 13A or alternatively, electrode 25, is attached to the negative electrode of the power supply (20).

Example 25

Primer-Directed and Primer Independent Cleavage Occur at the Same Site when the Primer Extends to the 3' Side of a Mismatched "Bubble" in the Downstream Duplex As discussed above in Example 1, the presence of a primer upstream of a bifurcated duplex can influence the site of cleavage, and the existence of a gap between the 3' end of the primer and the base of the duplex can cause a shift of the cleavage site up the unpaired 5' arm of the structure (see also Lyamichev et al., supra and U.S. Pat. No. 5,422,253). The resulting non-invasive shift of the cleavage site in response to a primer is demonstrated in FIGS. 8, 9 and 10, in which the primer used left a 4-nucleotide gap (relative to the base of the duplex). In FIGS. 8-10, all of the "primer-directed" cleavage reactions yielded a 21 nucleotide product, while the primer-independent cleavage reactions yielded a 25 nucleotide product. The site of cleavage obtained when the primer was extended to the base of the duplex, leaving no gap was examined. The results are shown in FIG. 53 (FIG. 53 is a reproduction of FIG. 2C in Lyamichev et al. These data were derived from the cleavage of the structure shown in FIG. 5, as described in Example 1. Unless otherwise specified, the cleavage reactions comprised 0.01 pmoles of heat-denatured, end-labeled hairpin DNA (with the unlabeled complementary strand also present), 1 pmole primer (complementary to the 3' arm shown in FIG. 5 and having the sequence: 5'-GAATTC-GATTTAGGTGACAC TATAGAATACA [SEQ ID NO:53]) and 0.5 units of DNAPTaq (estimated to be 0.026 pmoles) in a total volume of 10 μl of 10 mM Tris-Cl, pH 8.5, and 1.5 mM $MgCl_2$ and 50 mM KCl. The primer was omitted from the reaction shown in the first lane of FIG. 53 and included in lane 2. These reactions were incubated at 55° C. for 10 minutes. Reactions were initiated at the final reaction temperature by the addition of either the $MgCl_2$ or enzyme. Reactions were stopped at their incubation temperatures by the addition of 8 μl of 95% formamide with 20 mM EDTA and 0.05% marker dyes.

FIG. 53 is an autoradiogram that indicates the effects on the site of cleavage of a bifurcated duplex structure in the presence of a primer that extends to the base of the hairpin duplex. The size of the released cleavage product is shown to the left (i.e., 25 nucleotides). A dideoxynucleotide sequencing ladder of the cleavage substrate is shown on the right as a marker (lanes 3-6).

These data show that the presence of a primer that is adjacent to a downstream duplex (lane 2) produces cleavage at the same site as seen in reactions performed in the absence of the primer (lane 1). (See FIGS. 8A and B, 9B and 10A for additional comparisons). When the 3' terminal nucleotides of the upstream oligonucleotide can base pair to the template strand but are not homologous to the displaced strand in the region immediately upstream of the cleavage site (i.e., when the upstream oligonucleotide is opening up a "bubble" in the duplex), the site to which cleavage is apparently shifted is not wholly dependent on the presence of an upstream oligonucleotide.

As discussed above in the Background, and in Table 1, the requirement that two independent sequences be recognized in an assay provides a highly desirable level of specificity. In the invasive cleavage reactions of the present invention, the INVADER and probe oligonucleotides must hybridize to the target nucleic acid with the correct orientation and spacing to enable the production of the correct cleavage product. When the distinctive pattern of cleavage is not dependent on the successful alignment of both oligonucleotides in the detection system these advantages of independent recognition are lost.

Example 26

Invasive Cleavage and Primer-Directed Cleavage when there is Only Partial Homology in the "X" Overlap Region While not limiting the present invention to any particular mechanism, invasive cleavage occurs when the site of cleavage is shifted to a site within the duplex formed between the probe and the target nucleic acid in a manner that is dependent on the presence of an upstream oligonucleotide that shares a region of overlap with the downstream probe oligonucleotide. In some instances, the 5' region of the downstream oligonucleotide may not be completely complementary to the target nucleic acid. In these instances, cleavage of the probe may occur at an internal site within the probe even in the absence of an upstream oligonucleotide (in contrast to the base-by-base nibbling seen when a fully paired probe is used without an INVADER). Invasive cleavage is characterized by an apparent shifting of cleavage to a site within a downstream duplex that is dependent on the presence of the INVADER oligonucleotide.

A comparison between invasive cleavage and primer-directed cleavage may be illustrated by comparing the expected cleavage sites of a set of probe oligonucleotides having decreasing degrees of complementarity to the target strand in the 5' region of the probe (i.e., the region that overlaps with the INVADER). A simple test, similar to that performed on the hairpin substrate above (Ex. 25), can be performed to compare invasive cleavage with the non-invasive primer-directed cleavage described above. Such a set of test oligonucleotides is diagrammed in FIG. 54. The structures shown in FIG. 54 are grouped in pairs, labeled "a", "b", "c", and "d". Each pair has the same probe sequence annealed to the target strand (SEQ ID NO:54), but the top structure of each pair is drawn without an upstream oligonucleotide, while the bottom structure includes this oligonucleotide (SEQ ID NO:55). The sequences of the probes shown in FIGS. 54a-54d are listed in SEQ ID NOS:32, 56, 57 and 58, respectively. Probable sites of cleavage are indicated by the black arrowheads. (It is noted that the precise site of cleavage on each of these structures may vary depending on the choice of cleavage agent and other experimental variables. These particular sites are provided for illustrative purposes only.)

To conduct this test, the site of cleavage of each probe is determined both in the presence and the absence of the upstream oligonucleotide, in reaction conditions such as those described in Example 18. The products of each pair of reactions are then be compared to determine whether the fragment released from the 5' end of the probe increases in size when the upstream oligonucleotide is included in the reaction.

Figure 54A:
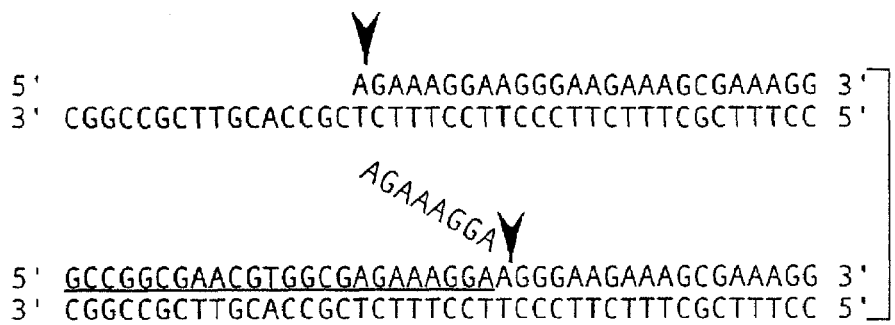
FIGS. 54A-D depict four pairs of oligonucleotides; in each pair shown, the upper arrangement of a probe annealed to a target nucleic acid lacks an upstream oligonucleotide and the lower arrangement contains an upstream oligonucleotide (SEQ ID NOS:32 and 54-58 are shown in FIGS. 54A-D).

The arrangement shown in FIG. 54a, in which the probe molecule is completely complementary to the target strand, is similar to that shown in FIG. 28. Treatment of the top structure with the 5' nuclease of a DNA polymerase would cause exonucleolytic nibbling of the probe (i.e., in the absence of the upstream oligonucleotide). In contrast, inclusion of an INVADER oligonucleotide would cause a distinctive cleavage shift similar, to those observed in FIG. 29.

Figure 54B:
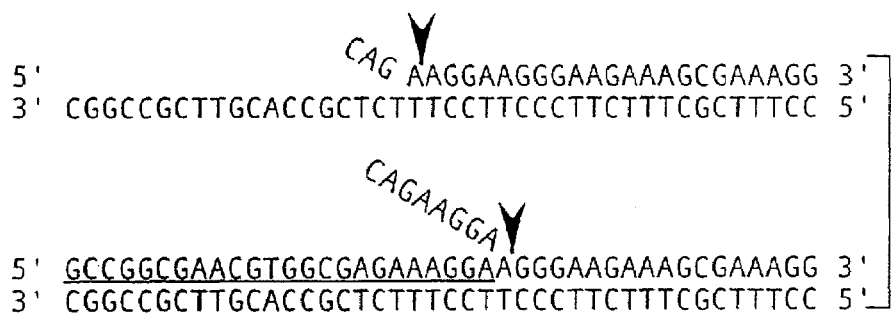
Figure 54C:

The arrangements shown in FIGS. 54b and 54c have some amount of unpaired sequence at the 5' terminus of the probe (3 and 5 bases, respectively). These small 5' arms are suitable cleavage substrate for the 5' nucleases and would be cleaved within 2 nucleotide's of the junction between the single stranded region and the duplex. In these arrangements, the 3' end of the upstream oligonucleotide shares identity with a portion of the 5' region of the probe that is complementary to the target sequence (that is the 3' end of the INVADER has to compete for binding to the target with a portion of the 5' end of the probe). Therefore, when the upstream oligonucleotide is included it is thought to mediate a shift in the site of cleavage into the downstream duplex (although the present invention is not limited to any particular mechanism of action), and this would, therefore, constitute invasive cleavage. If the extreme 5' nucleotides of the unpaired region of the probe were able to hybridize to the target strand, the cleavage site in the absence of the INVADER might change but the addition of the INVADER oligonucleotide would still shift the cleavage site to the proper position.

Figure 54D:
Figure 55:
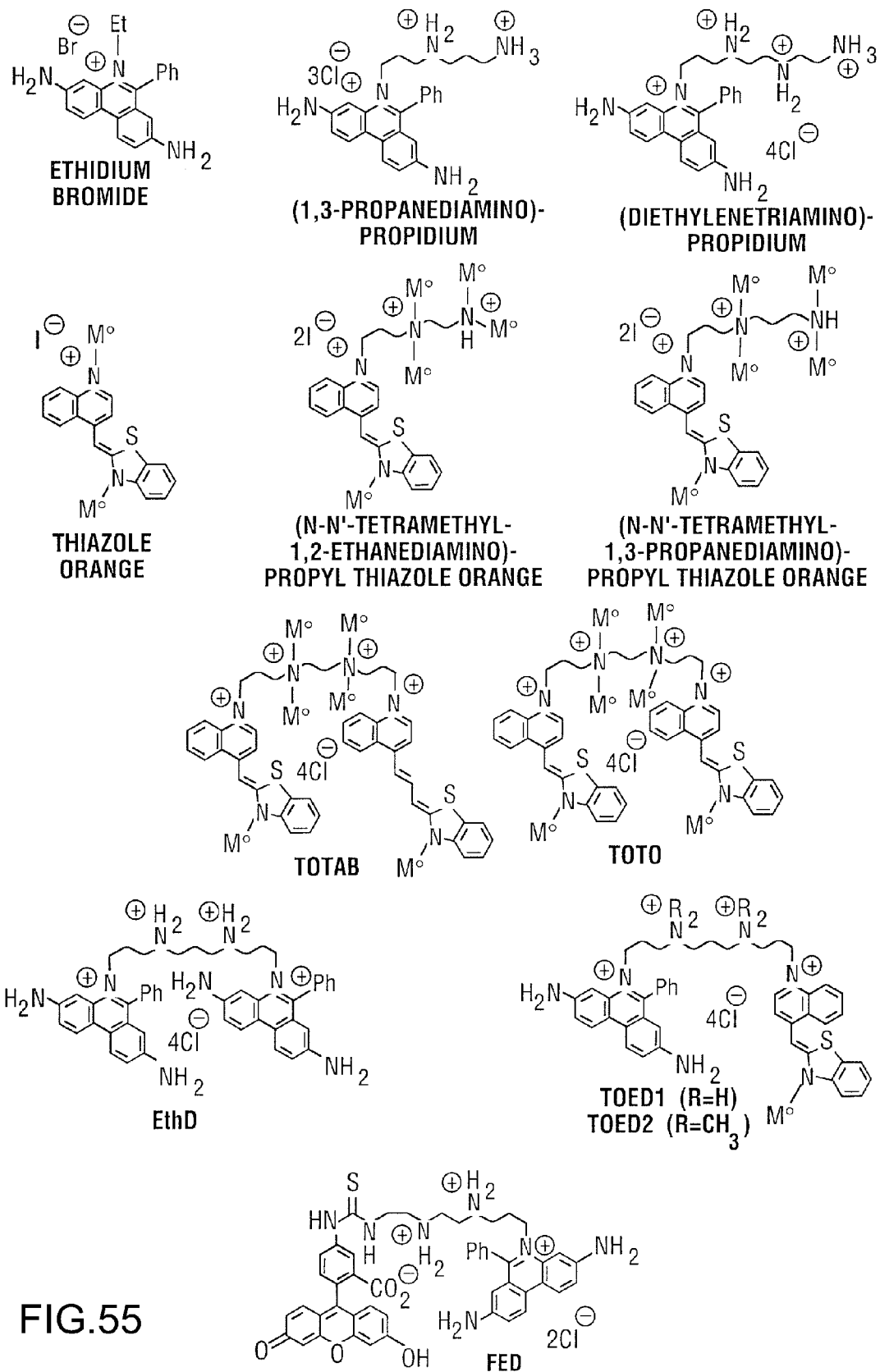
FIG. 55 shows the chemical structure of several positively charged heterodimeric DNA-binding dyes.

Finally, in the arrangement shown in FIG. 54d, the probe and upstream oligonucleotides share no significant regions of homology, and the presence of the upstream oligonucleotide would not compete for binding to the target with the probe. Cleavage of the structures shown in FIG. 54d would occur at the same site with or without the upstream oligonucleotide, and is thus would not constitute invasive cleavage.

By examining any upstream oligonucleotide/probe pair in this way, it can easily be determined whether the resulting cleavage is invasive or merely primer-directed. Such analysis is particularly useful when the probe is not fully complementary to the target nucleic acid, so that the expected result may not be obvious by simple inspection of the sequences.

Example 27

Modified CLEAVASE Enzymes

In order to develop nucleases having useful activities for the cleavage of nucleic acids the following modified nucleases were produced.

a) CLEAVASE BN/Thrombin Nuclease i) Cloning and Expression of CLEAVASE BN/thrombin Nuclease Site directed mutagenesis was used to introduce a protein sequence recognized by the protease thrombin into the region of the CLEAVASE BN nuclease that is thought to form the helical arch of the protein through which the single-stranded DNA that is cleaved must presumably pass. Mutagenesis was carried out using the Transformer™ mutagenesis kit (Clonetech, Palo Alto, Calif.) according to manufacturer's protocol using the mutagenic oligonucleotide 5'-GG-GAAAGTCCTCGCAGCCGCGCGGGAC-GAGCGTGGGGGCCCG (SEQ ID NO:59). After mutagenesis, the DNA was sequenced to verify the insertion of the thrombin cleavage site. The DNA sequence encoding the CLEAVASE BN/thrombin nuclease is provided in SEQ ID NO:60; the amino acid sequence of CLEAVASE BN/thrombin nuclease is provided in SEQ ID NO:61.

A large scale preparation of the thrombin mutant (i.e., CLEAVASE BN/thrombin) was done using *E. coli* cells over-expressing the CLEAVASE BN/thrombin nuclease as described in Example 28.

ii) Thrombin Cleavage of CLEAVASE BN/Thrombin

Six point four (6.4) mg of the purified CLEAVASE BN/thrombin nuclease was digested with 0.4 U of thrombin (Novagen) for 4 hours at 23° C. or 37° C. Complete digestion was verified by electrophoresis on a 15% SDS polyacrylamide gel followed by staining with Coomassie Brilliant Blue R. Wild-type CLEAVASE BN nuclease was also digested with thrombin as a control. The resulting gel is shown in FIG. 61.

Figure 61:
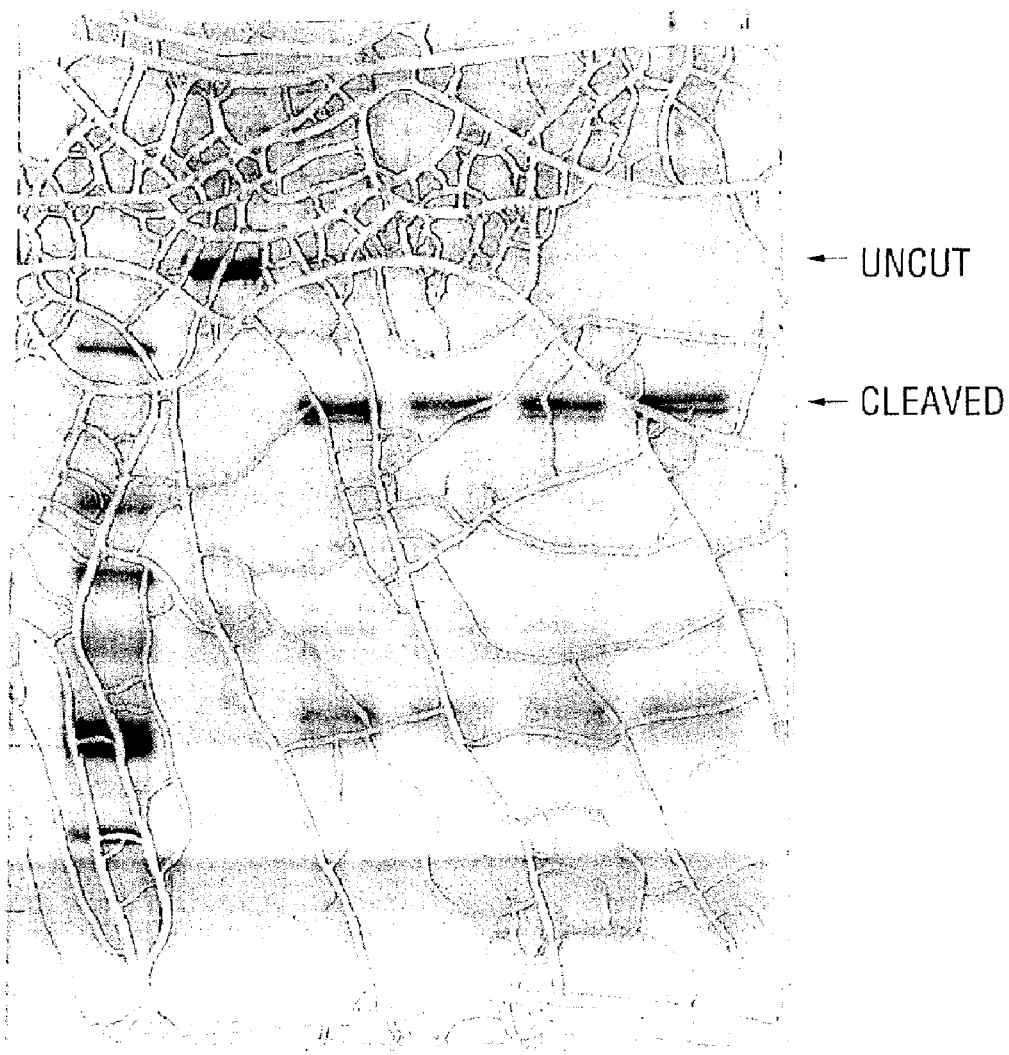
FIG. 61 shows a Coomassie stained SDS-PAGE gel showing the thrombin digestion of CLEAVASE BN/thrombin.

In FIG. 61, lane 1 contains molecular weight markers (Low-Range Protein Molecular Weight Markers; Promega), lane 2 contains undigested CLEAVASE BN/throbin nuclease, lanes 3 and 4 contain CLEAVASE BN/thrombin nuclease digested with thrombin at 23° C. for 2 and 4 hours, respectively, and lanes 5 and 6 contain CLEAVASE BN/thrombin nuclease digested with thrombin at 37° C. for 2 and 4 hours, respectively. These results show that the CLEAVASE BN/thrombin nuclease has an apparent molecular weight of 36.5 kilodaltons and demonstrate that CLEAVASE BN/thrombin nuclease is efficiently cleaved by thrombin. In addition, the thrombin cleavage products have approximate molecular weights of 27 kilodaltons and 9 kilodaltons, the size expected based upon the position of the inserted thrombin site in the CLEAVASE BN/thrombin nuclease.

To determine the level of hairpin cleavage activity in digested and undigested CLEAVASE BN/thrombin nuclease, dilutions were made and used to cleave a test hairpin containing a 5' fluoroscein label. Varying amounts of digested and undigested CLEAVASE BN/thrombin nuclease were incubated with 5 μM oligonucleotide S-60 hairpin (SEQ ID NO:29; see FIG. 26) in 10 mM MOPS (pH 7.5), 0.05% Tween-20, 0.05% NP-40, and 1 mM $MnCl_2$ for 5 minutes at 60° C. The digested mixture was electrophoresed on a 20% acrylamide gel and visualized on a Hitachi FMBIO 100 fluoroimager. The resulting image is shown in FIG. 62.

Figure 62:
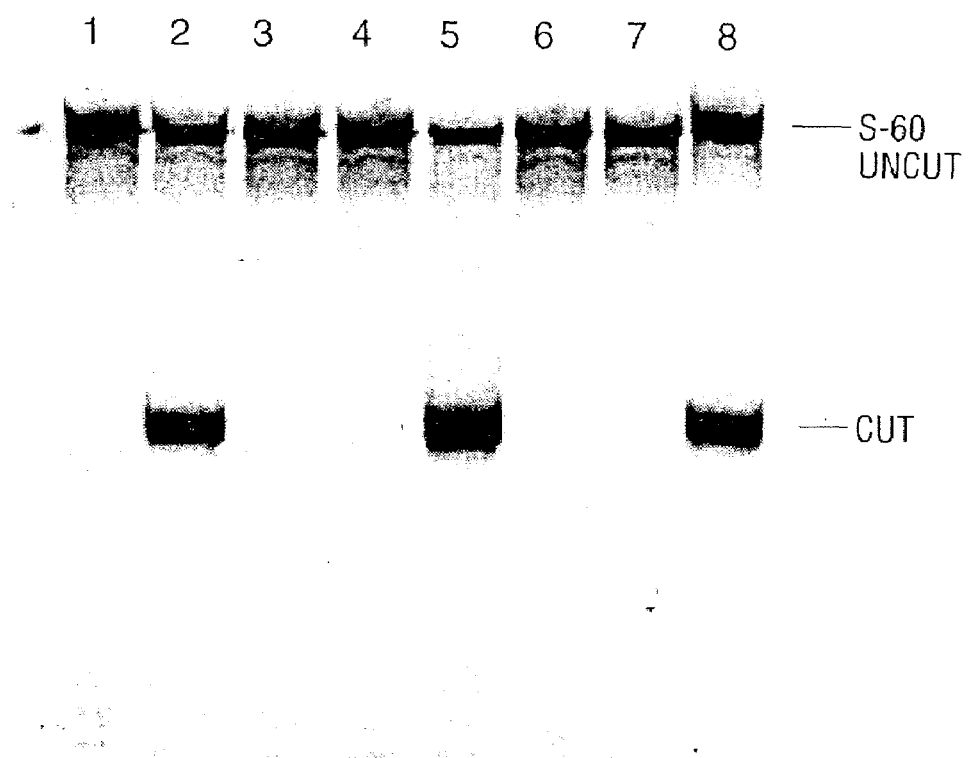
FIG. 62 is the image generated by a fluorescence imager showing the products produced by the cleavage of the S-60 hairpin using CLEAVASE BN/thrombin (before and after thrombin digestion).

In FIG. 62, lane 1 contains the no enzyme control, lane 2 contains reaction products produced using 0.01 ng of CLEAVASE BN nuclease, lanes 3, 4, and 5 contain reaction products produced using 0.01 ng, 0.04 ng, and 4 ng of undigested CLEAVASE BN/thrombin nuclease, respectively, and lanes 6, 7, and 8 contain reaction products produced using 0.01 ng, 0.04 ng, and 4 ng of thrombin-digested CLEAVASE BN/thrombin nuclease, respectively. The results shown in FIG. 62 demonstrated that the insertion of the thrombin cleavage site reduced cleavage activity about 200-fold (relative to the activity of CLEAVASE BN nuclease), but that digestion with thrombin did not reduce the activity significantly.

M13 single-stranded DNA was used as a substrate for cleavage by CLEAVASE BN nuclease and digested and undigested CLEAVASE BN/thrombin nuclease. Seventy nanograms of single-stranded M13 DNA (NEB) was incubated in 10 mM MOPS, pH 7.5, 0.05% Tween-20, 0.05% NP-40, 1 mM $MgCl_2$ or 1 mM $MnCl_2$, with 8 ng of CLEAVASE BN nuclease, undigested CLEAVASE BN/thrombin nuclease, or digested CLEAVASE BN/thrombin nuclease for 10 minutes at 50° C. Reaction mixtures were electrophoresed on a 0.8% agarose gel and then stained with a solution containing 0.5 μg/ml ethidium bromide (EtBr) to visualize DNA bands. A negative image of the EtBr-stained gel is shown in FIG. 63.

Figure 63:
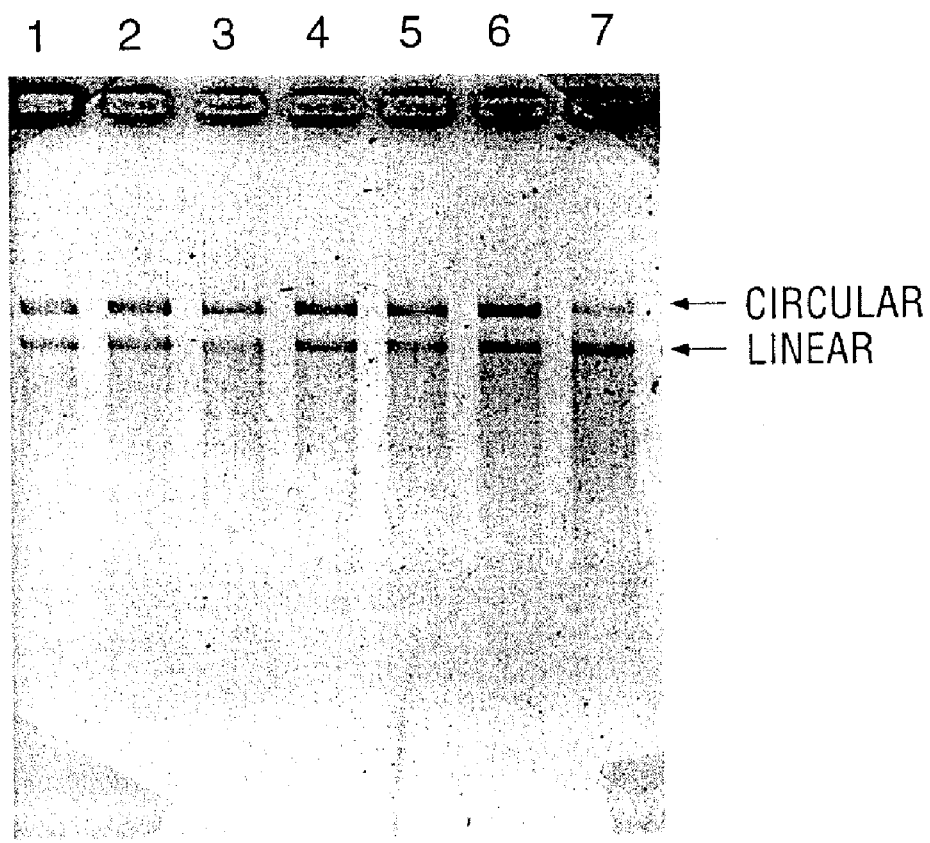
FIG. 63 is the image generated by a fluorescence imager showing the products produced by the cleavage of circular M13 DNA using CLEAVASE BN/thrombin.

In FIG. 63, lane 1 contains the no enzyme control, lane 2 contains reaction products produced using CLEAVASE BN nuclease and 1 mM $MgCl_2$, lane 3 contains reaction products produced using CLEAVASE BN nuclease and 1 mM $MnCl_2$, lane 4 contains reaction products produced using undigested CLEAVASE BN/thrombin nuclease and 1 mM $MgCl_2$, lane 5 contains reaction products produced using undigested CLEAVASE BN/thrombin nuclease and 1 mM $MnCl_2$, lane 6 contains reaction products produced using thrombin-digested CLEAVASE BN/thrombin nuclease and 1 mM $MgCl_2$, and lane 7 contains reaction products produced using thrombin-digested CLEAVASE BN/thrombin nuclease and 1 mM $MnCl_2$. The results shown in FIG. 63 demonstrated that the CLEAVASE BN/thrombin nuclease had an enhanced ability to cleave circular DNA (and thus a reduced requirement for the presence of a free 5' end) as compared to the CLEAVASE BN nuclease.

It can be seen from these data that the helical arch of these proteins can be opened without destroying the enzyme or its ability to specifically recognize cleavage structures. The CLEAVASE BN/thrombin mutant has an increased ability to cleave without reference to a 5' end, as discussed above. The ability to cleave such structures will allow the cleavage of long molecules, such as genomic DNA that, while often not circular, may present many desirable cleavage sites that are at a far removed from any available 5' end. Cleavage structures may be made at such sites either by folding of the strands (i.e., CFLP® cleavage) or by the introduction of structure-forming oligonucleotides (U.S. Pat. No. 5,422,253). 5' ends of nucleic acids can also be made unavailable because of binding of a substance too large to thread through the helical arch. Such binding moieties may include proteins such as streptavidin or antibodies, or solid supports such as beads or the walls of a reaction vessel. A cleavage enzyme with an opening in the loop of the helical arch will be able to cleave DNAs that are configured in this way, extending the number of ways in which reactions using such enzymes can be formatted.

b) CLEAVASE DN Nuclease i) Construction and Expression of CLEAVASE DN Nuclease

A polymerization deficient mutant of Taq DNA polymerase, termed CLEAVASE DN nuclease, was constructed. CLEAVASE DN nuclease contains an asparagine residue in place of the wild-type aspartic acid residue at position 785 (D785N).

DNA encoding the CLEAVASE DN nuclease was constructed from the gene encoding for CLEAVASE A/G (mutTaq, Ex. 2) in two rounds of site-directed mutagenesis. First, the G at position 1397 and the G at position 2264 of the CLEAVASE A/G gene (SEQ ID NO:21) were changed to A at each position to recreate a wild-type DNAPTaq gene. As a second round of mutagenesis, the wild type DNAPTaq gene was converted to the CLEAVASE DN gene by changing the G at position 2356 to A. These manipulations were performed as follows.

DNA encoding the CLEAVASE A/G nuclease was recloned from pTTQ18 plasmid (Ex. 2) into the pTrc99A plasmid (Pharmacia) in a two step procedure. First, the pTrc99A vector was modified by removing the G at position 270 of the pTrc99A map, creating the pTrc99G cloning vector. To this end, pTrc99A plasmid DNA was cut with NcoI and the recessive 3' ends were filled-in using the Klenow fragment of *E. coli* polymerase I in the presence of all four dNTPs at 37° C. for 15 min. After inactivation of the Klenow fragment by incubation at 65° C. for 10 min, the plasmid DNA was cut with EcoRI, the ends were again filled-in using the Klenow fragment in the presence of all four dNTPs at 37° C. for 15 min. The Klenow fragment was then inactivated by incubation at 65° C. for 10 min. The plasmid DNA was ethanol precipitated, recircularized by ligation, and used to transform *E. coli* JM109 cells (Promega). Plasmid DNA was isolated from single colonies and deletion of the G at position 270 of the pTrc99A map was confirmed by DNA sequencing.

As a second step, DNA encoding the CLEAVASE A/G nuclease was removed from the pTTQ18 plasmid using EcoRI and SalI and the DNA fragment carrying the CLEAVASE A/G nuclease gene was separated on a 1% agarose gel and isolated with Geneclean II Kit (Bio 101, Vista, Calif.). The purified fragment was ligated into the pTrc99G vector, which had been cut with EcoRI and SalI. The ligation mixture was used to transform competent *E. coli* JM109 cells (Promega). Plasmid DNA was isolated from single colonies and insertion of the CLEAVASE A/G nuclease gene was confirmed by restriction analysis using EcoRI and SalI.

Plasmid DNA pTrcAG carrying the CLEAVASE A/G nuclease gene cloned into the pTrc99A vector was purified from 200 ml of JM109 overnight culture using QIAGEN Plasmid Maxi kit (QIAGEN, Chatsworth, Calif.) according to manufacturer's protocol. pTrcAG plasmid DNA was mutagenized using two mutagenic primers, E465 (SEQ ID NO:62) (Integrated DNA Technologies, Iowa) and R754Q (SEQ ID NO:63) (Integrated DNA Technologies), and the selection primer Trans Oligo AlwNI/SpeI (Clontech, Palo Alto, Calif., catalog #6488-1) according to Transformer™ Site-Directed Mutagenesis Kit protocol (Clontech) to produce a restored wild-type DNAPTaq gene (pTrcWT).

pTrcWT plasmid DNA carrying the wild-type DNAPTaq gene cloned into the pTrc99A vector was purified from 200 ml of JM109 overnight culture using QIAGEN Plasmid Maxi kit (QIAGEN, Chatsworth, Calif.) according to manufacturer's protocol. pTrcWT was then mutagenized using the mutagenic primer D785N (SEQ ID NO:64) (Integrated DNA Technologies) and the selection primer Switch Oligo SpeI/AlwNI (Clontech, catalog #6373-1) according to Transformer™ Site-Directed Mutagenesis Kit protocol (Clontech) to create a plasmid containing DNA encoding the CLEAVASE DN nuclease. The DNA sequence encoding the CLEAVASE DN nuclease is provided in SEQ ID NO:65; the amino acid sequence of CLEAVASE DN nuclease is provided in SEQ ID NO:66.

A large scale preparation of the CLEAVASE DN nuclease was done using *E. coli* cells overexpressing the CLEAVASE DN nuclease as described in Example 28.

c) CLEAVASE DA Nuclease and CLEAVASE DV Nuclease

Two polymerization deficient mutants of Taq DNA polymerase, termed CLEAVASE DA nuclease and CLEAVASE DV nuclease, were constructed. The CLEAVASE DA nuclease contains a alanine residue in place of the wild-type aspartic acid residue at position 610 (D785A). The CLEAVASE DV nuclease contains a valine residue in place of the wild-type aspartic acid residue at position 610 (D610V).

i) Construction and Expression of the CLEAVASE DA and CLEAVASE DV Nucleases

To construct vectors encoding the CLEAVASE DA and DV nucleases, the CLEAVASE A/G nuclease gene contained within pTrcAG was mutagenized with two mutagenic primers, R754Q (SEQ ID NO:63) and D610AV (SEQ ID NO:67) and the selection primer Trans Oligo AlwNI/SpeI (Clontech, catalog #6488-1) according to the Transformer™ Site-Directed Mutagenesis Kit protocol (Clontech,) to create a plasmid containing DNA encoding the CLEAVASE DA nuclease or CLEAVASE DV nuclease. The D610AV oligonucleotide was synthesized to have a purine, A or G, at position 10 from the 5' end of the oligonucleotide. Following mutagenesis, plasmid DNA was isolated from single colonies and the type of mutation present, DA or DV, was determined by DNA sequencing. The DNA sequence encoding the CLEAVASE DA nuclease is provided in SEQ ID NO:68; the amino acid sequence of CLEAVASE DA nuclease is provided in SEQ ID NO:69. The DNA sequence encoding the CLEAVASE DV nuclease is provided in SEQ ID NO:70; the amino acid sequence of CLEAVASE DV nuclease is provided in SEQ ID NO:71.

d) CLEAVASE Tth DN Nuclease i) Construction and Expression of CLEAVASE TthDN Nuclease The DNA polymerase enzyme from the bacterial species *Thermus thermophilus* (Tth) was produced by cloning the gene for this protein into an expression vector and overproducing it in *E. coli* cells. Genomic DNA was prepared from 1 vial of dried *Thermus thermophilus* strain HB-8 from ATCC (ATCC #27634) as described in Ex. 28a. The DNA polymerase gene was amplified by PCR as described in Ex. 27b using the following primers: 5'-CACGAATTCCGAGGC-GATGCTTCCGCTC-3' (SEQ ID NO:254) and 5'-TC-GACGTCGACTAACCCTTGGCGGAAAGCC-3' (SEQ ID NO:255), as described in Ex. 28a.

The resulting PCR product was digested with EcoRI and SalI restriction endonucleases and inserted into EcoRI/SalI digested plasmid vector pTrc99g (described in Example 27b) by ligation, as described in Example 27b, to create the plasmid pTrcTth-1. This Tth polymerase construct is missing a single nucleotide which was inadvertently omitted from the 5' oligonucleotide, resulting in the polymerase gene being out of frame. This mistake was corrected by mutagenesis of pTrcTth-1 as described in Example 27b using the following oligonucleotide: 5'-GCATCGCCTCGGAATTCATGGTC-3' (SEQ ID NO:256), to create the plasmid pTrcTth-2. The Tth DN construct was created by mutating the sequence encoding an aspartic acid at position 787 to a sequence encoding asparagine. Mutagenesis of pTrcTth-2 with the following oligonucleotide: 5'-CAGGAGGAGCTCGTTGTGGACCTGGA-3' (SEQ ID NO:257) as described in Example 27b, to create the plasmid pTrcTth-DN. The resulting polymerase-deficient nuclease, Cleavase® TthDN was expressed and purified as described in Ex. 28.

Large scale preparations of the CLEAVASE DA and CLEAVASE DV nucleases was done using *E. coli* cells overexpressing the CLEAVASE DA nuclease or the CLEAVASE DV nuclease as described in Example 28.

Example 28

Cloning and Expression of Thermostable FEN-1 Endonucleases

Sequences encoding thermostable FEN-1 proteins derived from several Archaebacterial species were cloned and overexpressed in *E. coli*. This Example involved a) cloning and expression of a FEN-1 endonuclease from *Methanococcus jannaschii*; b) cloning and expression of a FEN-1 endonuclease from *Pyrococcus furiosus*; c) cloning and expression of a FEN-1 endonuclease from *Pyrococcus woesei*; d) cloning and expression of a FEN-1 endonuclease from *Archaeoglobus fulgidus*; e) large scale preparation of recombinant thermostable FEN-1 proteins; and f) activity assays using FEN-1 endonucleases.

a) Cloning and Expression of a FEN-1 Endonuclease from *Methanococcus jannaschii*

DNA encoding the FEN-1 endonuclease from *Methanococcus jannaschii* (*M. jannaschii*) was isolated from *M jannaschii* cells and inserted into a plasmid under the transcriptional control of an inducible promoter as follows. Genomic DNA was prepared from 1 vial of live *M jannaschii* bacteria (DSMZ, Deutsche Sammlung von Mikroorganismen und Zellkulturen, Braunschweig, Germany #2661) with the DNA XTRAX kit (Gull Laboratories, Salt Lake City, Utah) according to the manufacturer's protocol. The final DNA pellet was resuspended in 100 µl of TE (10 mM Tris HCl, pH 8.0, 1 mM EDTA). One microliter of the DNA solution was employed in a PCR using the Advantage™ cDNA PCR kit (Clonetech); the PCR was conducted according to manufacturer's recommendations. The 5'-end primer (SEQ ID NO:72) is complementary to the 5' end of the Mja FEN-1 open reading frame with a one base substitution to create an NcoI restriction site (a fragment of the *M. jannaschii* genome that contains the gene encoding *M. jannaschii* (Mja) FEN-1 is available from GenBank as accession # U67585). The 3'-end primer (SEQ ID NO:73) is complementary to a sequence about 15 base pairs downstream from the 3' end of the Mja FEN-1 open reading frame with 2 base substitutions to create a SalI restriction enzyme site. The sequences of the 5'-end and 3'-end primers are: 5'-GGGATACCA TGGGAGTGCAGTTTGG-3' (SEQ ID NO:72) and 5'-GGTAAATTTTTCTCGTCGA CATCCCAC-3' (SEQ ID NO:73), respectively. The PCR reaction resulted in the amplification (i.e., production) of a single major band about 1 kilobase in length. The open reading frame (ORF) encoding the Mja FEN-1 endonuclease is provided in SEQ ID NO:74; the amino acid sequence encoded by this ORF is provided in SEQ ID NO:75.

Following the PCR amplification, the entire reaction was electrophoresed on a 1.0% agarose gel and the major band was excised from the gel and purified using the Geneclean II kit (Bio101, Vista, Calif.) according to manufacturer's instructions. Approximately 1 µg of the gel-purified Mja FEN-1 PCR product was digested with NcoI and SalI. After digestion, the DNA was purified using the Geneclean II kit according to manufacturer's instructions. One microgram of the pTrc99a vector (Pharmacia) was digested with NcoI and SalI in preparation for ligation with the digested PCR product. One hundred nanograms of digested pTrc99a vector and 250 ng of digested Mja FEN-1 PCR product were combined and ligated to create pTrc99-MJFEN1. pTrc99-MJFEN1 was used to transform competent *E. coli* JM109 cells (Promega) using standard techniques.

b) Cloning and Expression of a FEN-1 Endonuclease from *Pyrococcus furiosus*

DNA encoding the *Pyrococcus furiosus* (*P. furiosus*) FEN-1 endonuclease was obtained by PCR amplification using a plasmid containing DNA encoding the *P. furiosus* (Pfu) FEN-1 endonuclease (obtained from Dr. Frank Robb, Center of Marine Biotechnology, Baltimore, Md.). DNA sequences encoding a portion of the Pfu FEN-1 endonuclease can be obtained from GenBank as accession Nos. AA113505 and W36094. The amplified Pfu FEN-1 gene was inserted into the pTrc99a expression vector (Pharmacia) to place the Pfu FEN-1 gene under the transcriptional control of the inducible trc promoter. The PCR amplification was conducted as follows. One hundred microliter reactions contained 50 mM Tris HCl, pH 9.0, 20 mM $(NH_4)_2SO_4$, 2 mM $MgCl_2$, 50 µM dNTPs, 50 pmole each primer, 1 U Tfl polymerase (Epicentre Technologies, Madison, Wis.) and 1 ng of FEN-1 gene-containing plasmid DNA. The 5'-end primer (SEQ ID NO:76) is complementary to the 5' end of the Pfu FEN-1 open reading frame but with two substitutions to create an NcoI site and the 3'-end primer (SEQ ID NO:77) is complementary to a region located about 30 base pairs downstream of the FEN-1 open reading frame with two substitutions to create a PstI site. The sequences of the 5'-end and 3'-end primers are: 5'-GAGGTGATACCATG GGTGTCC-3' (SEQ ID NO:76) and 5'-GAAACTCTGCAGCGCGTCAG-3' (SEQ ID NO:77), respectively. The PCR reaction resulted in the amplification of a single major band about 1 kilobase in length. The open reading frame (ORF) encoding the Pfu FEN-1 endonuclease is provided in SEQ ID NO:78; the amino acid sequence encoded by this ORF is provided in SEQ ID NO:79.

Following the PCR amplification, the entire reaction was electrophoresed on a 1.0% agarose gel and the major band was excised from the gel and purified using the Geneclean II kit (Bio101) according to manufacturer's instructions. Approximately 1 µg of gel purified Pfu FEN-1 PCR product was digested with NcoI and PstI. After digestion, the DNA was purified using the Geneclean II kit according to manufacturer's instructions. One microgram of the pTrc99a vector was digested with NcoI and PstI prior to ligation with the digested PCR product. One hundred nanograms of digested pTrc99a and 250 ng of digested Pfu FEN-1 PCR product were combined and ligated to create pTrc99-PFFEN1. pTrc99-PFFEN1 was used to transform competent *E. coli* JM109 cells (Promega) using standard techniques.

c) Cloning and Expression of a FEN-1 Endonuclease from *Pyrococcus woesei*

For the cloning of DNA encoding the *Pyrococcus woesei* (Pwo) FEN-1 endonuclease, DNA was prepared from lyophilized *P. woesei* bacteria (DSMZ # 3773) as described (Zwickl et al., J. Bact., 172:4329 [1990]) with several changes. Briefly, one vial of *P. woesei* bacteria was rehydrated and resuspended in 0.5 ml of LB (Luria broth). The cells were centrifuged at 14,000×g for 1 min and the cell pellet was resuspended in 0.45 ml of TE. Fifty microliters of 10% SDS was added and the mixture was incubated at RT for 5 min. The cell lysate was then extracted three time with 1:1 phenol:chloroform and three times with chloroform. Five hundred microliters of isopropanol was added to the extracted lysate and the DNA was pelleted by centrifugation at 14,000×g for 10 min. The DNA pellet was washed in 0.5 ml of 70% ethanol and the DNA was pelleted again by centrifugation at 14,000×g for 5 min. The DNA pellet was dried and resuspended in 100 µl of TE and used for PCR reactions without further purification.

To generate a *P. woesei* FEN-1 gene fragment for cloning into an expression vector, low stringency PCR was attempted with primers complementary to the ends of the *P. furiosus* FEN-1 gene open reading frame. The sequences of the 5'-end and 3'-end primers are 5'-GATACCATGGGTGTCCCAAT-TGGTG-3' (SEQ ID NO:80) and 5'-TCGACGTCGACT-TATCTCTTGAACCAACTTTCAAGGG-3' (SEQ ID NO:81), respectively. The high level of sequence similarity of protein homologs (i.e., proteins other than FEN-1 proteins) from *P. furiosus* and *P. woesei* suggested that there was a high probability that the *P. woesei* FEN-1 gene could be amplified using primers containing sequences complementary to the *P. furiosus* FEN-1 gene. However, this approach was unsuccessful under several different PCR conditions.

The DNA sequence of FEN-1 genes from *P. furiosus* and *M. jannaschii* were aligned and blocks of sequence identity between the two genes were identified. These blocks were used to design internal primers (i.e., complementary to sequences located internal to the 5' and 3' ends of the ORF) for the FEN-1 gene that are complementary to the *P. furiosus*

FEN-1 gene in those conserved regions. The sequences of the 5'- and 3'-internal primers are 5'-AGCGAGGGAGAGGC-CCAAGC-3' (SEQ ID NO:82) and 5'-GCCTATGCCCTT-TATTCCTCC-3' (SEQ ID NO:83), respectively. A PCR employing these internal primers was conducted using the Advantage™ PCR kit and resulted in production of a major band of ~300 bp.

Since the PCR with the internal primers was successful, reactions were attempted that contained mixtures of the internal (SEQ ID NOS:82 and 83) and external (SEQ ID NOS:80 and 81) primers. A reaction containing the 5'-end external primer (SEQ ID NO:80) and 3'-end internal primer (SEQ ID NO:83) resulted in the production of a 600 bp band and a reaction containing the 5'-end internal primer (SEQ ID NO:82) and 3'-end external primer (SEQ ID NO:81) resulted in the production of a 750 bp band. These overlapping DNA fragments were gel-purified and combined with the external primers (SEQ ID NOS:80 and 81) in a PCR reaction. This reaction generated a 1 kb DNA fragment containing the entire Pwo FEN-1 gene open reading frame. The resulting PCR product was gel-purified, digested, and ligated exactly as described above for the Mja FEN-1 gene PCR product. The resulting plasmid was termed pTrc99-PWFEN1. pTrc99-PWFEN1 was used to transform competent E. coli JM109 cells (Promega) using standard techniques.

d) Cloning and Expression of a FEN-1 Endonuclease from Archaeoglobus fulgidus

The preliminary Archaeoglobus fulgidus (Afu) chromosome sequence of 2.2 million bases was downloaded from the TIGR (The Institute for Genomic Research) world wide web site, and imported into a software program (MacDNAsis), used to analyze and manipulate DNA and protein sequences. The unannotated sequence was translated into all 6 of the possible reading frames, each comprising approximately 726, 000 amino acids. Each frame was searched individually for the presence of the amino acid sequence "VFDG" (valine, phenylalanine, aspartic acid, glycine), a sequence that is conserved in the FEN-1 family. The amino acid sequence was found in an open reading frame that contained other amino acid sequences conserved in the FEN-1 genes and that was approximately the same size as the other FEN-1 genes. The ORF DNA sequence is shown in SEQ ID NO:164, while the ORF protein sequence is shown in SEQ ID NO:165. Based on the position of this amino acid sequence within the reading frame, the DNA sequence encoding a putative FEN-1 gene was identified.

The sequence information was used to design oligonucleotide primers that were used for PCR amplification of the FEN-1-like sequence from A. fulgidus genomic DNA. Genomic DNA was prepared from A. fulgidus as described in Ex. 29a for M. janaschii, except that one vial (approximately 5 ml of culture) of live A. fulgidus bacteria from DSMZ (DSMZ #4304) was used. One microliter of the genomic DNA was used for PCR reaction as described in Ex. 29a. The 5' end primer is complementary to the 5' end of the Afu FEN-1 gene except it has a 1 base pair substitution to create an NcoI site. The 3' end primer is complentary to the 3' end of the Afu FEN-1 gene downstream from the FEN-1 ORF except it contains a 2 base substitution to create a SalI site. The sequences of the 5' and 3' end primers are 5'-CCGTCAA-CATTTACCATGGGTGCGGA-3' (SEQ ID NO: 166) and 5'-CCGCCACCTCGTAGTCGACATCCTTTTCGTG (SEQ ID NO:167), respectively.

Cloning of the resulting fragment was as described for the PfuFEN1 gene, above, to create the plasmid pTrc99-AFFEN1. The pTrcAfuHis plasmid was constructed by modifying pTrc99-AFFEN1, by adding a histidine tail to facilitate purification. To add this histidine tail, standard PCR primer-directed mutagenesis methods were used to insert the coding sequence for six histidine residues between the last amino acid codon of the pTrc99-AFFEN1 coding region and the stop codon. The resulting plasmid was termed pTrcAfuHis. The protein was then expressed as described in Example 28f), and purified by binding to a Ni++ affinity column, as described in Example 8.

e) Cloning and Expression of a FEN-1 Endonuclease from Methanobacterium thermoautotrophicum A tentative listing of all open reading frames of the Methanobacterium thermoautotrophicum (Mth) genome on the Genome Therapeutics world wide web page was searched for amino acid sequences conserved in the FEN-1 genes. The amino acid sequence "VFDG" (valine, phenylalanine, aspartic acid, glycine) was found in an open reading frame that also contained other conserved FEN-1 sequences. SEQ ID NO:260 provides the Mth FEN-1 ORF DNA sequence as indicated by Genome Therapeutics, while SEQ ID NO:261 provides the Mth FEN-1 ORF protein sequence as indicated by Genome Therapeutics. However, this open reading frame was 259 amino acids in length, as compared to the other archael FEN-1 genes, which are approximately 325 amino acids long. To determine the cause of this discrepancy, the DNA sequence for Mth FEN-1 was obtained in an identical manner as described above for Afu FEN-1.

Upon examination of the sequence, it was apparent that the open reading frame could be extended to 328 amino acids by deletion of a single base at about position 750 of the open reading frame. The additional amino sequence added by deleting one base is 39% identical to the same region of the P. furiosus FEN-1 gene. The DNA sequence of the putative Mth FEN-1 gene was used to design oligonucleotide primers complementary to the 5' and 3' ends of the gene. The 5' oligonucleotide is complementary to the 5' end of the Mth FEN-1 gene except that it contains 2 substitutions which create an NcoI site. The 3' oligonucleotide is complementary to the 3' end of the gene about 100 base pairs downstream of where it is believed that the true open reading frame ends. This region contains a natural PstI site. The sequences of the 5' and 3' oligonucleotides are 5'-GGGTGTTCCCATGG-GAGTTAAACTCAGG-3' (SEQ ID NO:262) and 5'-CT-GAATTCTGCAGAAAAAGGGG-3' (SEQ ID NO:263), respectively.

Genomic DNA was prepared from 1 vial of frozen M. thermoautotrophicum bacteria from ATCC (ATCC # 29096) as described in Ex. 28a. PCR, cloning, expression, and purification of Mth FEN-1 was done as described in Examples 28a and 28f, except PstI was used instead of SalI. The resulting plasmid was termed pTrc99-MTFEN1. Sequencing of the cloned Mth FEN-1 gene revealed the presence of additional "T" nucleotide when compared to the genome sequence published on the world wide web. This "T" residue at position 775 of the FEN-1 open reading frame causes a frame shift, creating the larger open reading frame that originally thought, based on comparison to the FEN genes from other organisms. SEQ ID NO:264 provides the sequence of the Mth ORF DNA sequence of the present invention, while SEQ ID NO:265 provides the sequence of the Mth FEN-1 protein sequence of the present invention.

f) Large Scale Preparation of Recombinant Thermostable FEN-1 Proteins

The Mja, Pwo and Pfu FEN-1 proteins were purified by the following technique, which is derived from a Taq DNA polymerase preparation protocol (Engelke et al., Anal. Biochem., 191:396 [1990]) as follows. E. coli cells (strain JM109) containing either pTrc99-PFFEN1, pTrc99-PWFEN1, or pTrc99-MJFEN1 were inoculated into 3 ml of LB (Luria Broth) containing 100 µg/ml ampicillin and grown for 16 hrs at 37° C. The entire overnight culture was inoculated into 200 ml or 350 ml of LB containing 100 µg/ml ampicillin and grown at 37° C. with vigorous shaking to an $A_{600}$ of 0.8. IPTG (1 M stock solution) was added to a final concentration of 1 mM and growth was continued for 16 hrs at 37° C.

The induced cells were pelleted and the cell pellet was weighed. An equal volume of 2×DG buffer (100 mM Tris-HCl, pH 7.6, 0.1 mM EDTA) was added and the pellet was resuspended by agitation. Fifty mg/ml lysozyme (Sigma, St. Louis, Mo.) was added to 1 mg/ml final concentration and the cells were incubated at room temperature for 15 min. Deoxycholic acid (10% solution) was added dropwise to a final concentration of 0.2% while vortexing. One volume of $H_2O$ and 1 volume of 2×DG buffer was added and the resulting mixture was sonicated for 2 minutes on ice to reduce the viscosity of the mixture. After sonication, 3 M $(NH_4)_2SO_4$ was added to a final concentration of 0.2 M and the lysate was centrifuged at 14000×g for 20 min at 4° C. The supernatant was removed and incubated at 70° C. for 60 min at which time 10% polyethylimine (PEI) was added to 0.25%. After incubation on ice for 30 min., the mixture was centrifuged at 14,000×g for 20 min at 4° C. At this point, the supernatant was removed and the FEN-1 proteins was precipitated by the addition of $(NH_4)_2SO_4$ as follows.

For the Pwo and the Pfu FEN-1 preparations, the FEN-1 protein was precipitated by the addition of 2 volumes of 3 M $(NH_4)_2SO_4$. The mixture was incubated overnight at room temperature for 16 hrs and the protein was centrifuged at 14,000×g for 20 min at 4° C. The protein pellet was resuspended in 0.5 ml of Q buffer (50 mM Tris-HCl, pH 8.0, 0.1 mM EDTA, 0.1% Tween 20). For the Mja FEN-1 preparation, solid $(NH_4)_2SO_4$ was added to a final concentration of 3 M (~75% saturated), the mixture was incubated on ice for 30 min, and the protein was spun down and resuspended as described above.

Figure 64:
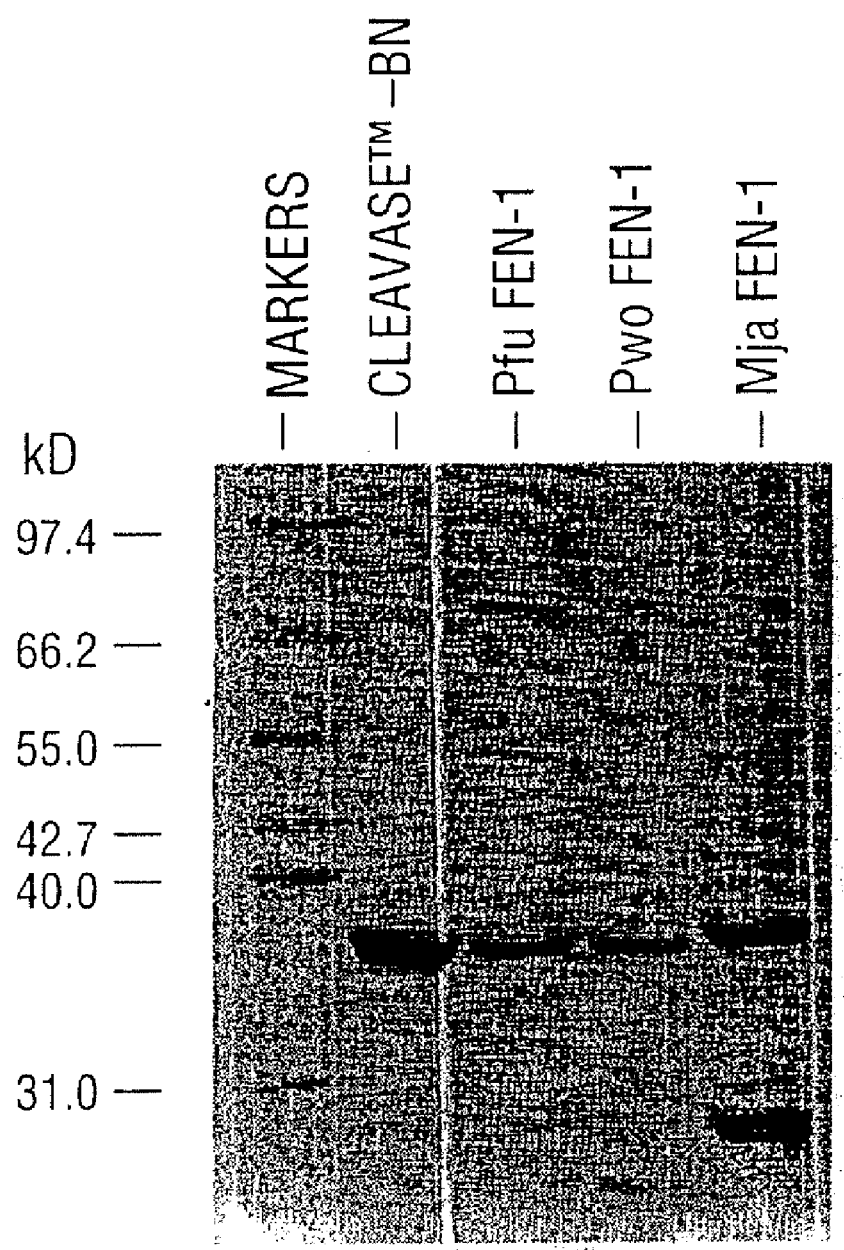
FIG. 64 is an SDS-PAGE gel showing the migration of purified CLEAVASE BN nuclease, Pfu FEN-1, Pwo FEN-1 and Mja FEN-1.

The resuspended protein preparations were quantitated by determination of the $A_{279}$ and aliquots containing 2-4 µg of total protein were electrophoresed on a 10% SDS polyacrylamide gel (29:1 acrylamide: bis-acrylamide) in standard Laemmli buffer [Laemmli, Nature 277:680 [1970]) and stained with Coomassie Brilliant Blue R; the results are shown in FIG. 64.

In FIG. 64, lane 1 contains molecular weight markers (Mid-Range Protein Molecular Weight Markers; Promega); the size of the marker proteins is indicated to the left of the gel. Lane 2 contains purified CLEAVASE BN nuclease; lanes 3-5 contain extracts prepared from E. coli expressing the Pfu, Pwo and Mja FEN-1 nucleases, respectively. The calculated (i.e., using a translation of the DNA sequence encoding the nuclease) molecular weight of the Pfu FEN-1 nuclease is 38,714 daltons and the calculated molecular weight for the Mja FEN-1 nuclease is 37,503 Daltons. The Pwo and Pfu FEN-1 proteins co-migrated on the SDS-PAGE gel and therefore, the molecular weight of the Pwo FEN-1 nuclease was estimated to be 38.7 kDa.

g) Activity Assays Using FEN-1 Endonucleases
i) Mixed Hairpin Assay

The CLEAVASE BN nuclease has an approximately 60-fold greater affinity for a 12 base pair stem-loop structure than an 8 base pair stem-loop DNA structure. As a test for activity differences between the CLEAVASE BN nuclease and the FEN-1 nucleases, a mixture of oligonucleotides having either a 8 or a 12 bp stem-loop (see FIG. 60, which depicts the S-33 and 11-8-0 oligonucleotides) was incubated with an extract prepared from E. coli cells overexpressing the Mja FEN-1 nuclease (prepared as described above). Reactions contained 0.05 µM of oligonucleotides S-33 (SEQ ID NO:84) and 11-8-0 (SEQ ID NO:85) (both oligonucleotides contained 5'-fluorescein labels), 10 mM MOPS, pH 7.5, 0.05% Tween-20, 0.05% NP-40, 1 mM $MnCl_2$. Reactions were heated to 90° C. for 10 seconds, cooled to 55° C., then 1 µl of crude extract (Mja FEN-1) or purified enzyme (CLEAVASE BN nuclease) was added and the mixtures were incubated at 55° C. for 10 minutes; a no enzyme control was also run. The reactions were stopped by the addition of formamide/EDTA, the samples were electrophoresed on a denaturing 20% acrylamide gel and visualized on a Hitachi FMBIO 100 fluoroimager. The resulting image is shown in FIG. 65.

Figure 65:
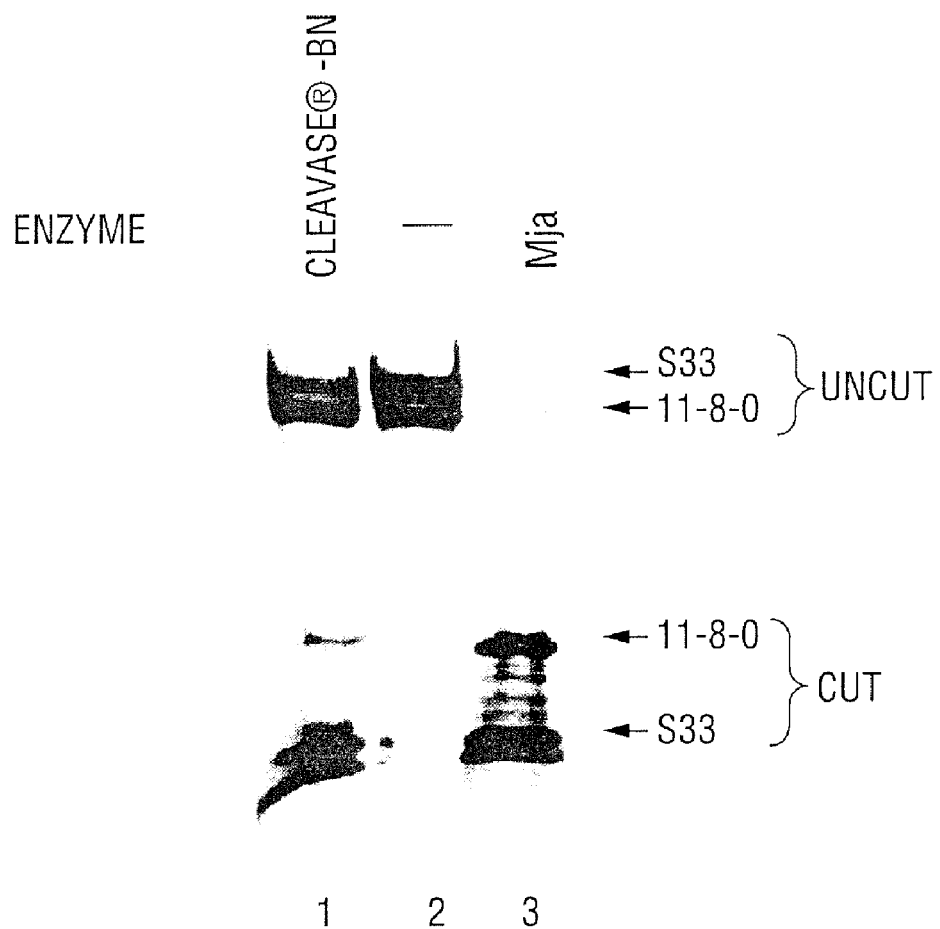
FIG. 65 is the image generated by a fluorescence imager showing the products produced by the cleavage of the S-33 and 11-8-0 oligonucleotides by CLEAVASE BN and the Mja FEN-1 nucleases.

In FIG. 65, lane 1 contains the reaction products generated by the CLEAVASE BN nuclease, lane 2 contains the reaction products from the no enzyme control reaction and lane 3 contains the reaction products generated by the Mja FEN-1 nuclease. The data shown in FIG. 76 demonstrates that the CLEAVASE BN nuclease strongly prefers the S33 structure (12 bp stem-loop) while the Mja FEN-1 nuclease cleaves structures having either an 8 or a 12 bp stem-loop with approximately the same efficiency. This shows that the Mja FEN-1 nuclease has a different substrate specificity than the CLEAVASE BN nuclease, a useful feature for INVADER assays or CFLP® analysis as discussed in the Description of the Invention.

Example 29

Terminal Deoxynucleotidyl Transferase Selectively Extends the Products of INVADER-Directed Cleavage The majority of thermal degradation products of DNA probes will have a phosphate at the 3'-end. To investigate if the template-independent DNA polymerase, terminal deoxynucleotide transferase (TdT) can tail or polymerize the aforementioned 3'-end phosphates (i.e., add nucleotide triphosphates to the 3' end) the following experiment was performed.

To create a sample containing a large percentage of thermal degradation products, the 5' fluorescein-labeled oligonucleotide 34-078-01 (SEQ ID NO:86) (200 pmole) was incubated in 100 µl 10 mM $NaCO_3$ (pH 10.6), 50 mM NaCl at 95° C. for 13 hours. To prevent evaporation, the reaction mixture was overlaid with 60 µl ChillOut™ 14 liquid wax. The reaction mixture was then divided into two equal aliquots (A and B). Aliquot A was mixed with one-tenth volume 3M NaOAc followed by three volumes ethanol and stored at −20° C. Aliquot B was dephosphorylated by the addition of 0.5 µl of 1M $MgCl_2$ and 1 µl of 1 unit/µl Calf Intestine Alkaline Phosphatase (CIAP) (Promega), with incubation at 37° C. for 30 minutes. An equal volume of phenol:chloroform:isomayl alcohol (24:24:1) was added to the sample followed by vortexing for one minute and then centrifugation 5 minutes at maximum speed in a microcentrifuge to separate the phases. The aqueous phase was removed to a new tube to which one-tenth volume 3M NaOAc, and three volumes ethanol was added followed by storage at −20° C. for 30 minutes. Both aliquots (A and B) were then centrifuged for 10 minutes at maximum speed in a microcentrifuge to pellet the DNA. The pellets were then washed two times each with 80% ethanol and then desiccated to dryness. The dried pellets were then dissolved in 70 µl dd$H_2O$ each.

The TdT reactions were conducted as follows. Six mixes were assembled, all mixes contained 10 mM Tris OAc (pH 7.5), 10 mM MgOAc, 50 mM KCl, and 2 mM dATP. Mixes 1 and 2 contained one pmole of untreated 34-078-01 (SEQ ID NO:86), mixes 3 and 4 contained 2 μl of aliquot A (above), mixes 5 and 6 contained 2 μl of aliquot B (above). To each 9 μl of mixes 1, 3 and 5, 1 μl ddH$_2$O was added, to each 9 μl of mixes 2, 4, and 6, 1 μl of 20 units/μl TdT (Promega) was added. The mixes were incubated at 37° C. for 1 hour and then the reaction was terminated by the addition of 5 μl 95% formamide with 10 mM EDTA and 0.05% marker dyes. Five microliters of each mixture was resolved by electrophoresis through a 20% denaturing acrylamide gel (19:1 cross-linked) with 7 M urea, in a buffer containing 45 mM Tris-Borate (pH 8.3), 1.4 mM EDTA, and imaged using with the FMBIO Image Analyzer with a 505 nm filter. The resulting imager scan is shown in FIG. 66.

Figure 66:
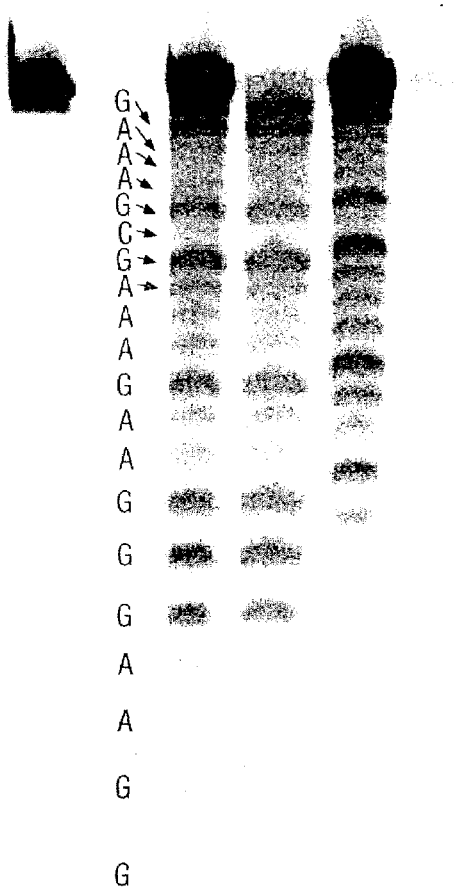
FIG. 66 is the image generated by a fluorescence imager showing the products produced by the incubation of an oligonucleotide either having or lacking a 3'-OH group with TdT (SEQ ID NO:432).

In FIG. 66, lanes 1, 3 and 5 contain untreated 34-078-01 (SEQ ID NO:86), heat-degraded 34-078-01, and heat-degraded, dephosphorylated, 34-078-01, respectively incubated in the absence of TdT. Lanes 2, 4 and 6 contain, untreated 34-078-01, heat-degraded 34-078-01, and heat-degraded, dephosphorylated, 34-078-01, respectively incubated in the presence of TdT.

As shown in FIG. 66, lane 4, TdT was unable to extend thermal degradation products that contain a 3'-end phosphate group, and selectively extends molecules that have a 3'-end hydroxyl group.

Example 30

Specific TdT Tailing of the Products of INVADER-Directed Cleavage with Subsequent Capture and Detection on Nitrocellulose Supports When TdT is used to extend the specific products of cleavage, one means of detecting the tailed products is to selectively capture the extension products on a solid support before visualization. This Example demonstrates that the cleavage products can be selectively tailed by the use of TdT and deoxynucleotide triphosphates, and that the tailed products can be visualized by capture using a complementary oligonucleotide bound to a nitrocellulose support.

To extend the cleavage product produced in an INVADER-directed cleavage reaction, the following experiment was performed. Three reaction mixtures were assembled, each in a buffer of 10 mM MES (pH 6.5), 0.5% Tween-20, 0.5% NP-40. The first mixture contained 5 fmols of target DNA-M13mp18, 10 pmols of probe oligo 32-161-2 (SEQ ID NO:87; this probe oligonucleotide contains 3' ddC and a Cy3 amidite group near the 3' end), and 5 pmols of INVADER oligonucleotide 32 161-1 (SEQ ID NO:88; this oligo contains a 3' ddC). The second mixture contained the probe and INVADER oligonucleotides without target DNA. The third mixture was the same as the first mixture, and contained the same probe sequence, but with a 5' fluorescein label (oligo 32-161-4 [SEQ ID NO:89; this oligo contains a 3' ddC, 5' fluorescein label, and a Cy3 dye group near the 3' end]), so that the INVADER-directed cleavage products could be detected before and after cleavage by fluorescence imaging. The probe only control sample contained 10 pmols of oligo 32-161-2 (SEQ ID NO:87). Each 3 μl of enzyme mix contained 5 ng of CLEAVASE DN nuclease in 7.5 mM MgCl$_2$. The TdT mixture (per each 4 μl) contained: 10 U of TdT (Promega), 1 mM CoCl$_2$, 50 mM KCl, and 100 μM of dTTP. The INVADER cleavage reaction mixtures described above were assembled in thin wall tubes, and the reactions were initiated by the addition of 3 μl of CLEAVASE DN enzyme mix. The reactions were incubated at 65° C. for 20 min. After cooling to 37° C., 4 μl of the TdT mix was added and the samples were incubated for 4 min at 37° C., Biotin-16-dUTP was then added to 100 μM and the samples were incubated for 50 min at 37° C. The reactions were terminated by the addition of 1 μl of 0.5 M EDTA.

To test the efficiency of tailing the products were run on an acrylamide gel. Four microliters of each reaction mixture was mixed with 2.6 μl of 95% formamide, 10 mM EDTA and 0.05% methyl violet and heated to 90° C. for 1 min, and 3 μl were loaded on a 20% denaturing acrylamide gel (19:1 cross-linked) with 7 M urea, in buffer containing 45 mM Tris-Borate (pH 8.3), 1.4 mM EDTA. A marker (ΦX174-HinfI [fluorescein labeled]) also was loaded. After electrophoresis, the gel was analyzed using a FMBIO-100 Image Analyzer (Hitachi) equipped with a 505 nm filter. The resulting scan is shown in FIG. 67.

Figure 67:
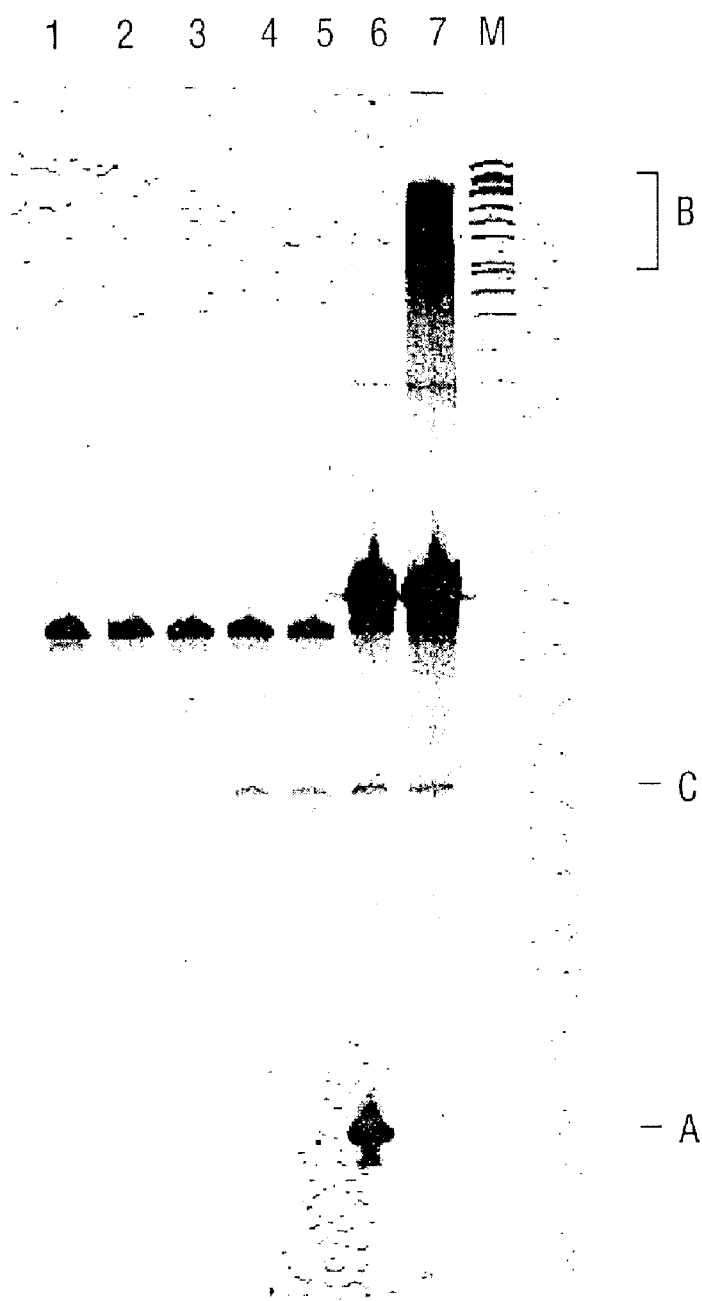
FIG. 67 is the image generated by a fluorescence imager showing the products produced the incubation of cleavage products with TdT.

In FIG. 67, lane 1 contained the probe 32-161-2 only, without any treatment. Lanes 2 and 3 contained the products of reactions run without target DNA, without or with subsequent TdT tailing, respectively. Lanes 4 and 5 contained the products of reactions run with target DNA, probe oligo 32-161-2 (SEQ ID NO:87) and INVADER oligo 32-161-1 (SEQ ID NO:88), without or with subsequent TdT tailing, respectively. Lanes 6 and 7 show the products of reactions containing target DNA, probe oligo 32-161-4 (SEQ ID NO:89) and INVADER oligo 32-161-1 (SEQ ID NO:88), without or with subsequent TdT tailing, respectively. Lane M contains the marker ΦX174-HinfI.

The reaction products in lanes 4 and 5 are the same as those seen in lanes 6 and 7, except that the absence of a 5' fluorescein on the probe prevents detection of the relased 5' product (indicated as "A" near the bottom of the gel) or the TdT extended 5' product (indicated as "B", near the top of the gel). The Cy3-labeled 3' portion of the cleaved probe is visible in all of these reactions (indicated as "C", just below the center of the gel).

Figure 68:
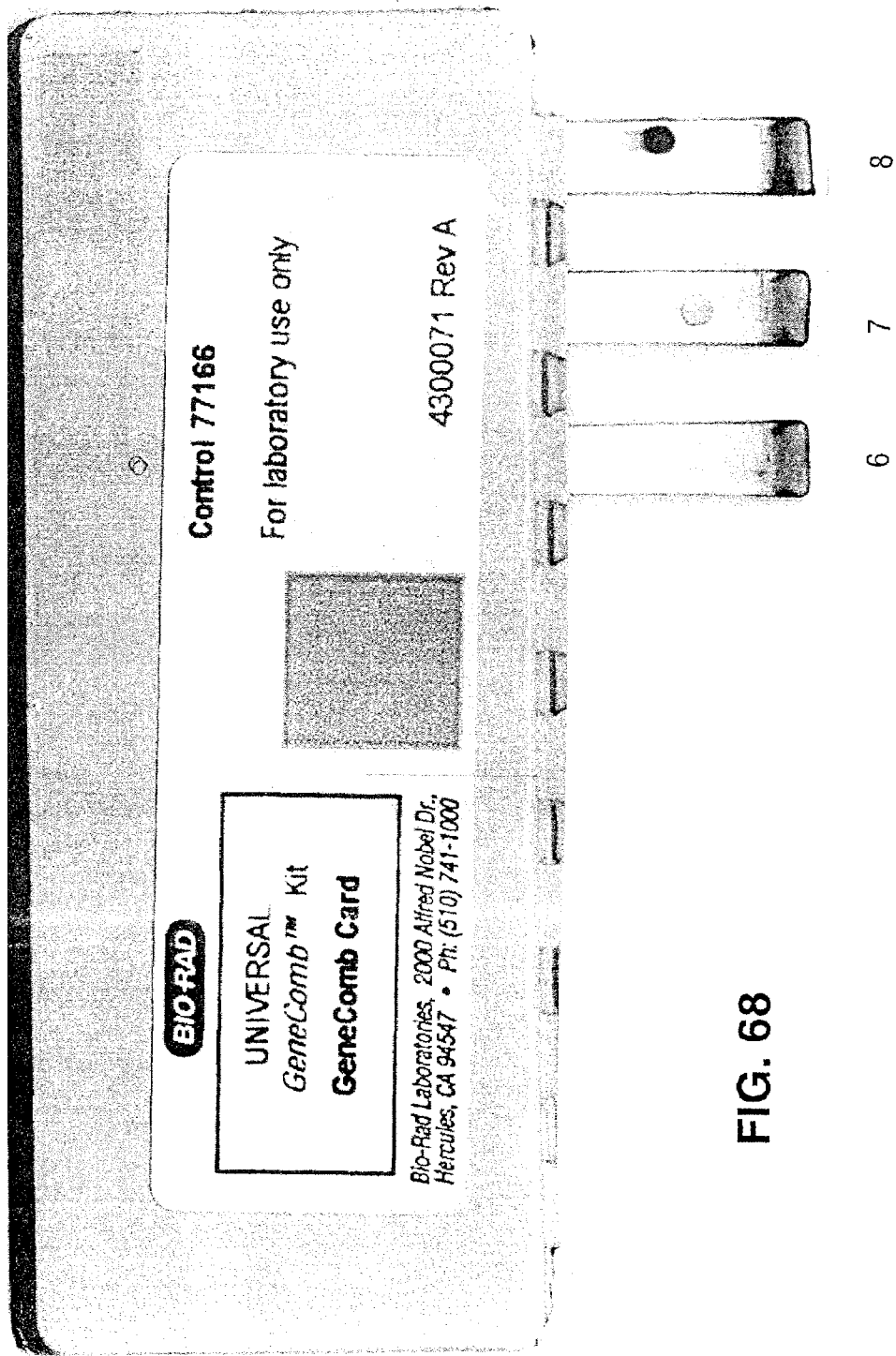
FIG. 68 is a photograph of a Universal GeneComb™ card showing the capture and detection of cleavage products on a nitrocellulose support.

To demonstrate detection of target-dependent INVADER-directed cleavage products on a solid support, the reactions from lanes 3 and 5 were tested on the Universal GENECOMB (Bio-Rad), which is a standard nitrocellulose matrix on a rigid nylon backing styled in a comb format, as depicted in FIG. 68. Following the manufacturer's protocol, with one modification: 10 μl of the INVADER-directed cleavage reactions were used instead the recommended 10% of a PCR. To capture the cleavage products, 2.5 pmols of the capture oligo 59-28-1 (SEQ ID NO:90) were spotted on each tooth. The capture and visualization steps were conducted according to the manufacturer's directions. The results are shown in FIG. 68.

In FIG. 68, teeth numbered 6 and 7 show the capture results of reactions performed without and with target DNA present. Tooth 8 shows the kit positive control.

The darkness of the spot seen on tooth 7, when compared to tooth 6, clearly indicates that products of INVADER-directed cleavage assays may be specifically detected on solid supports. While the Universal GENECOMB was used to demonstrate solid support capture in this instance, other support capture methods known to those skilled in the art would be equally suitable. For example, beads or the surfaces of reaction vessels may easily be coated with capture oligonucleotides so that they can then be used in this step. Alternatively, similar solid supports may easily be coated with streptavidin or antibodies for the capture of biotin- or hapten-tagged products of the cleavage/tailing reaction. In any of these embodiments, the products may be appropriately visualized by detecting the resulting fluorescence, chemiluminescence, calorimetric changes, radioactive emissions, optical density change or any other distinguishable feature of the product.

Example 31

Comparison of the Effects of Invasion Length and 5' Label of the Probe on INVADER-Directed Cleavage by the CLEAVASE A/G and Pfu FEN-1 Nucleases To investigate the effect of the length of invasion as well as the effect of the type of dye on ability of Pfu FEN-1 and the CLEAVASE A/G nuclease to cleave 5' arms, the following experiment was performed. Three probes of similar sequences labeled with either fluorescein, TET, or Cy3, were assembled in reactions with three INVADER oligonucleotides that created overlapping target hybridization regions of eight, five, and three bases along the target nucleic acid, M13mp18.

The reactions were conducted as follows. All conditions were performed in duplicate. Enzyme mixes for Pfu FEN-1 and the CLEAVASE A/G nuclease were assembled. Each 2 µl of the Pfu FEN-1 mix contained 100 ng of Pfu FEN-1 (prepared as described in Ex. 28) and 7.5 mM $MgCl_2$. Each 2 µl of the CLEAVASE A/G mix contained 5.3 ng of the CLEAVASE A/G nuclease and 4.0 mM $MnCl_2$. Six master mixes containing buffer, M13mp18, and INVADER oligonucleotides were assembled. Each 7 µl of mixes 1-3 contained 1 fmol M13mp18, 10 pmoles INVADER oligonucleotide (34-078-4 [SEQ ID NO:39], 24-181-2 [SEQ ID NO:91], or 24-181-1 [SEQ ID NO:92], in 10 mM MOPS (pH 7.5), 150 mM LiCl. Each 7 µl of mixes 4-6 contained 1 fmol of M13mp18, 10 pmoles of INVADER oligonucleotide [34-078-4 (SEQ ID NO:39), 24-181-2 (SEQ ID NO:91), or 24-181-1 (SEQ ID NO:92)] in 10 mM Tris (pH 8.0). Mixtures 1-6 were then divided into three mixtures each, to which was added either the fluorescein-labeled probe (oligo 34-078-01; SEQ ID NO:86), the Cy3-labeled probe (oligo 43-20; SEQ ID NO:93) or the TET-labeled probe (oligo 90; SEQ ID NO:32 containing a 5' TET label). Each 7 µl of all mixtures contained 10 pmoles of corresponding probe. The DNA solutions described above were covered with 10 µl of CHILLOUT evaporation barrier and brought to 68° C.

Figure 69:
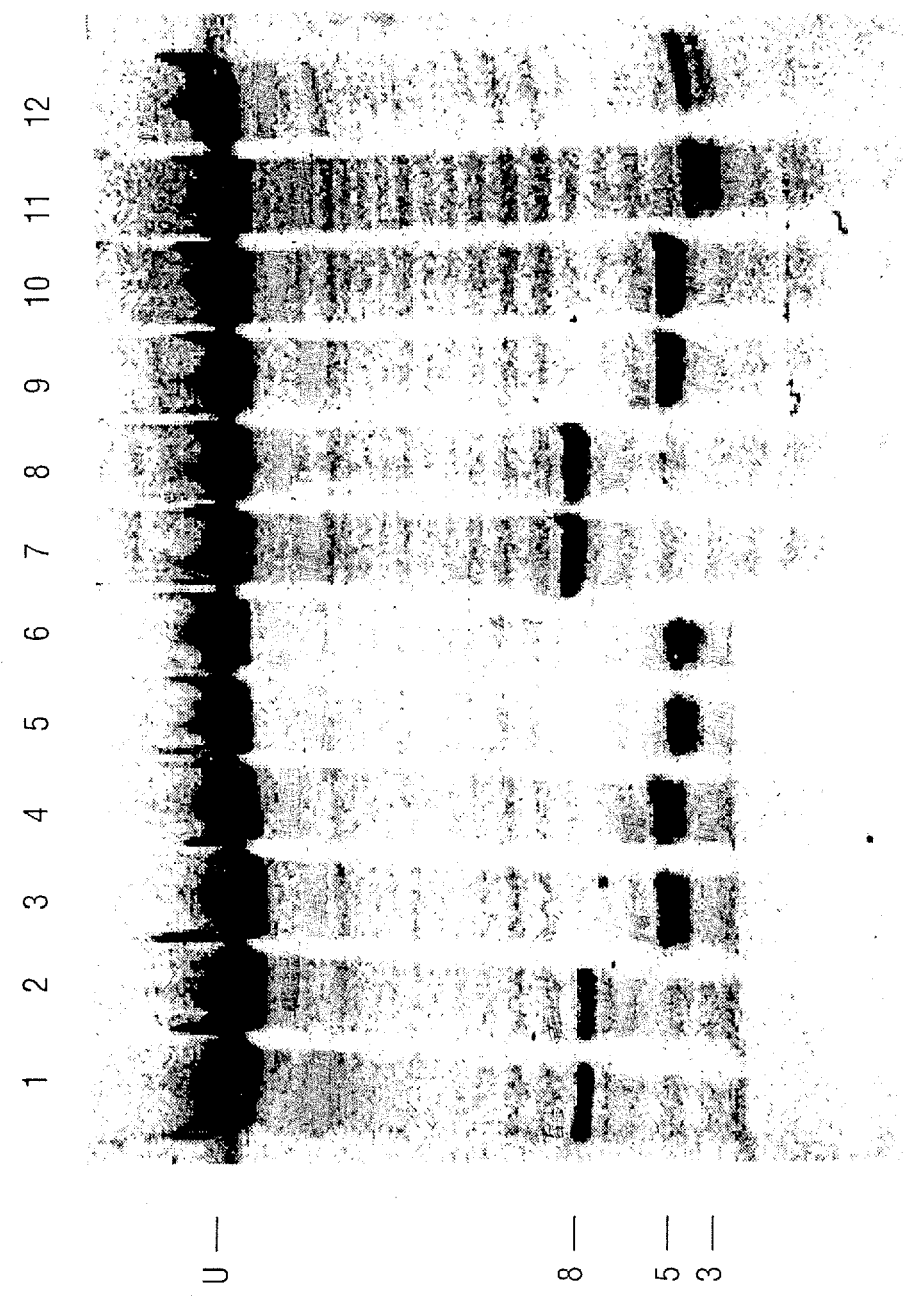
FIG. 69 is the image generated by a fluorescence imager showing the products produced using the CLEAVASE A/G and Pfu FEN-1 nucleases and a fluorescein-labeled probe.
Figure 70:
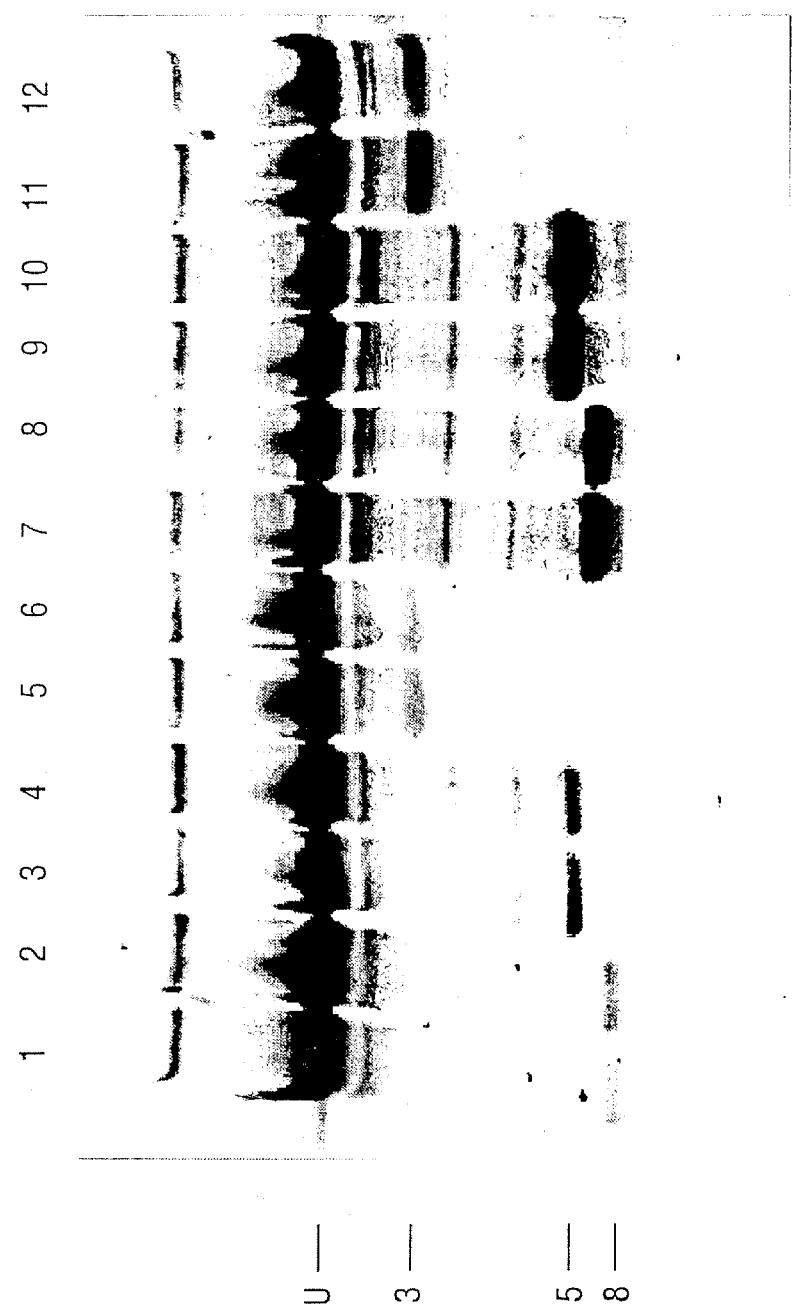
FIG. 70 is the image generated by a fluorescence imager showing the products produced using the CLEAVASE A/G and Pfu FEN-1 nucleases and a Cy3-labeled probe.
Figure 71:
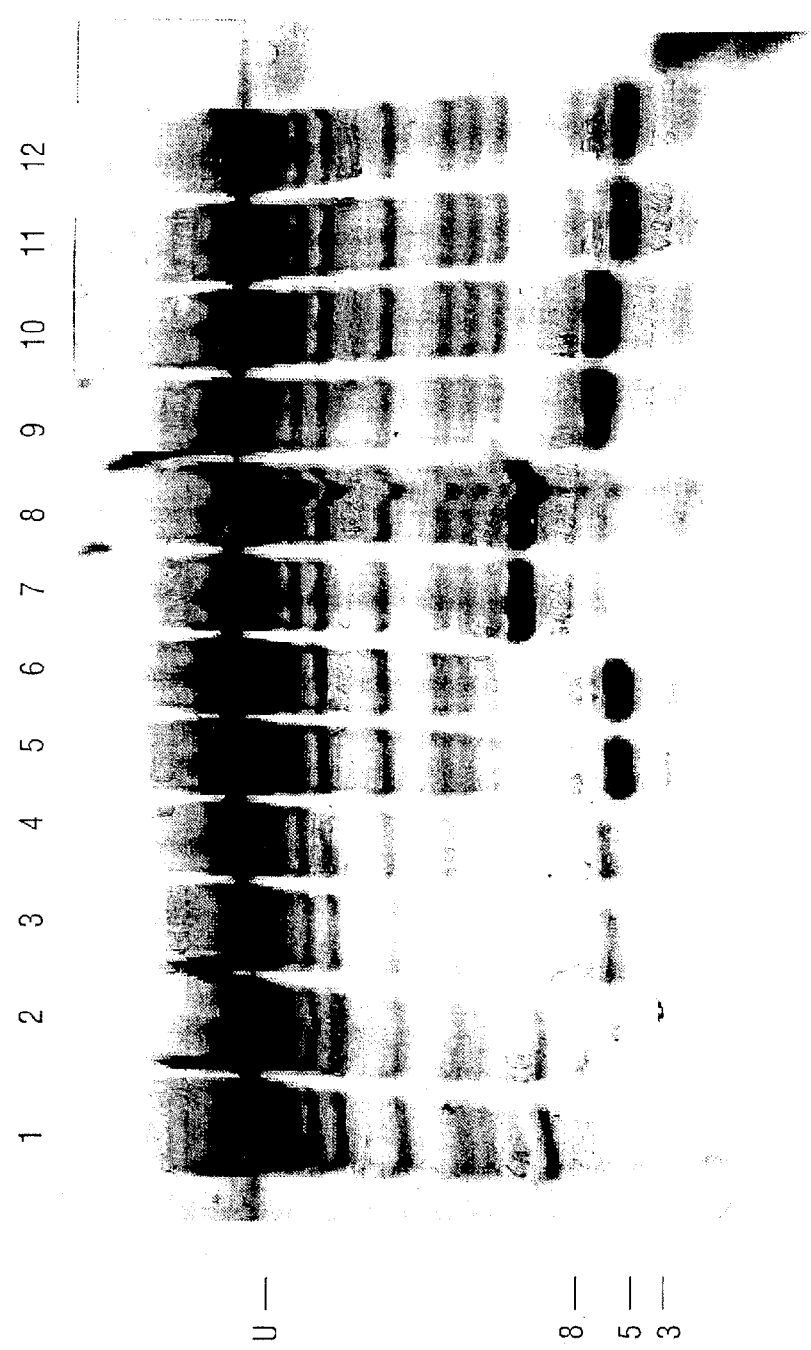
FIG. 71 is the image generated by a fluorescence imager showing the products produced using the CLEAVASE A/G and Pfu FEN-1 nucleases and a TET-labeled probe.

The reactions made from mixes 1-3 were started with 2 µl of the CLEAVASE A/G nuclease mix, and the reactions made from mixes 4-6 were started with 2 µl of the Pfu FEN-1 mix. After 30 minutes at 68° C., the reactions were terminated by the addition of 8 µl of 95% formamide with 10 mM EDTA and 0.05% marker dyes. Samples were heated to 90° C. for 1 minute immediately before electrophoresis through a 20% denaturing acrylamide gel (19:1 cross-linked) with 7 M urea, in a buffer containing 45 mM Tris-Borate (pH 8.3), 1.4 mM EDTA. The products of the cleavage reactions were visualized following electrophoresis by the use of a Hitachi FMBIO fluorescence imager. Results from the fluorescein-labeled probe are shown in FIG. 69, results from the Cy3-labeled probe in FIG. 70, and results from the TET-labeled probe in FIG. 71. In each of these Figures, the products of cleavage by CLEAVASE A/G are shown in lanes 1-6 and the products of cleavage by PfuFEN-1 are shown in lanes 7-12. In each in case the uncut material appears as a very dark band near the top of the gel, indicated by a "U" on the left. The products of cleavage directed by INVADER oligonucleotides with 8, 5 or 3 bases of overlap (i.e., the "X" region was 8, 5, or 3 nt long) are shown in the first, second and third pair of lanes in each set, respectively and the released labeled 5' ends from these reactions are indicated by the numbers 8, 5, and 3 on the left. Note that in the cleavage reactions shown in FIG. 70 the presence of the positively charged Cy3 dye causes the shorter products to migrate more slowly than the larger products. These products do not contain any additional positive charges (e.g., amino modifications as used in Example 23), and thus still carry a net negative charge, and migrate towards the positive electrode in a standard electrophoresis run.

It can be seen from these data that the CLEAVASE A/G and Pfu FEN-1 structure-specific nucleases respond differently to both dye identity and to the size of the piece to be cleaved from the probe. The Pfu FEN-1 nuclease showed much less variability in response to dye identity than did the CLEAVASE A/G nuclease, showing that any dye wold be suitable for use with this enzyme. In contrast, the amount of cleavage catalyzed by the CLEAVASE A/G nuclease varied substantially with dye identity. Use of the fluorescein dye gave results very close to those seen with the Pfu FEN-1 nuclease, while the use of either Cy3 or TET gave dramatically reduced signal when compared to the Pfu FEN-1 reactions. The one exception to this was in the cleavage of the 3 nt product carrying a TET dye (lanes 5 and 6, FIG. 71), in which the CLEAVASE A/G nuclease gave cleavage at the same rate as the Pfu FEN-1 nuclease. These data indicate that, while CLEAVASE A/G may be used to cleave probes labeled with these other dyes, the Pfu FEN-1 nuclease is a preferred nuclease for cleavage of Cy3- and TET-labeled probes.

Example 32

Examination of the Effects of a 5' Positive Charge on the Rate of Invasive Cleavage Using the Cleavase A/G or Pfu FEN-1 Nucleases To investigate whether the positive charges on 5' end of probe oligonucleotides containing a positively charged adduct(s) (i.e., charge reversal technology or CRT probes as described in Ex. 23 and 24 have an effect on the ability of the CLEAVASE A/G or Pfu FEN-1 nucleases to cleave the 5' arm of the probe, the following experiment was performed.

Two probe oligonucleotides having the following sequences were utilized in INVADER reactions: Probe 34-180-1: (N-Cy3)$T_{NH2}T_{NH2}$CCAGAGCCTAATTTGCCAGT(N-fluorescein)A, where N represents a spacer containing either the Cy3 or fluorescein group (SEQ ID NO:94) and Probe 34-180-2:5'-(N-TET)TTCCAGAGCCTAATTTGCCAGT-(N-fluorescein)A, where N represents a spacer containing either the TET or fluorescein group (SEQ ID NO:95). Probe 34-180-1 has amino-modifiers on the two 5' end T residues and a Cy3 label on the 5' end, creating extra positive charges on the 5' end. Probe 34-180-2 has a TET label on the 5' end, with no extra positive charges. The fluorescein label on the 3' end of probe 34-180-1 enables the visualization of the 3' cleaved products and uncleaved probes together on an acrylamide gel run in the standard direction (i.e., with the DNA migrating toward the positive electrode). The 5' cleaved product of probe 34-180-1 has a net positive charge and will not migrate in the same direction as the uncleaved probe, and is thus visualized by resolution on a gel run in the opposite direction (i.e.; with this DNA migrating toward the negative electrode).

The cleavage reactions were conducted as follows. All conditions were performed in duplicate. Enzyme mixes for the Pfu FEN-1 and CLEAVASE A/G nucleases were assembled. Each 2 µl of the Pfu FEN-1 mix contained 100 ng of Pfu FEN-1 (prepared as described in Ex. 28) and 7.5 mM $MgCl_2$. Each 2 µl of the CLEAVASE A/G nuclease mix contained 26.5 ng of CLEAVASE A/G nuclease and 4.0 mM $MnCl_2$. Four master mixes containing buffer, M13mp18, and INVADER oligonucleotides were assembled. Each 7 µl of mix 1 contained 5 fmol M13mp18, 10 pmoles INVADER oligonucleotide 123 (SEQ ID NO:96) in 10 mM HEPES (pH 7.2). Each 7 μl of mix 2 contained 1 fmol M13mp18, 10 pmoles INVADER oligonucleotide 123 in 10 mM HEPES (pH 7.2). Each 7 μl of mix 3 contained 5 fmol M13mp18, 10 pmoles INVADER oligonucleotide 123 in 10 mM HEPES (pH 7.2), 250 mM KGlu. Each 7 μl of mix 4 contained 1 fmol M13mp18, 10 pmoles INVADER oligonucleotide 123 in 10 mM HEPES (pH 7.2), 250 mM KGlu. For every 7 μl of each mix, 10 pmoles of either probe 34-180-1 (SEQ ID NO:94) or probe 34-180-2 (SEQ ID NO:95) was added. The DNA solutions described above were covered with 10 μl of CHILLOUT evaporation barrier and brought to 65° C. The reactions made from mixes 1-2 were started by the addition of 2 μl of the Pfu FEN-1 mix, and the reactions made from mixes 3-4 were started by the addition of 2 μl of the CLEAVASE A/G nuclease mix. After 30 minutes at 65° C., the reactions were terminated by the addition of 8 μl of 95% formamide containing 10 mM EDTA. Samples were heated to 90° C. for 1 minute immediately before electrophoresis through a 20% denaturing acrylamide gel (19:1 cross-linked) with 7 M urea, in a buffer containing 45 mM Tris-Borate (pH 8.3), 1.4 mM EDTA and a 20% native acrylamide gel (29:1 cross-linked) in a buffer containing 45 mM Tris-Borate (pH 8.3), 1.4 mM EDTA.

Figure 72A:
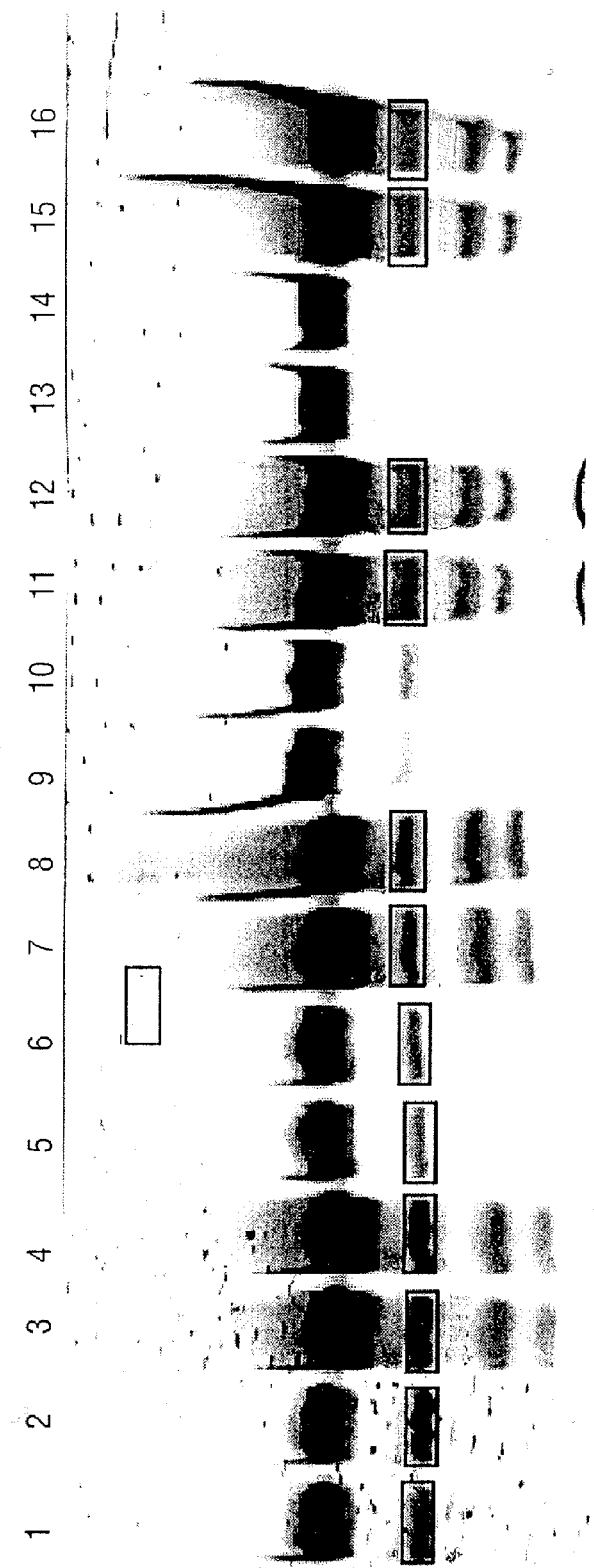
FIGS. 72A and 72B are images generated by a fluorescence imager showing the products produced using the CLEAVASE A/G and Pfu FEN-1 nucleases and probes having or lacking a 5' positive charge; the gel shown in FIG. 83A was run in the standard direction and the gel shown in FIG. 84B was run in the reverse direction.
Figure 72B:
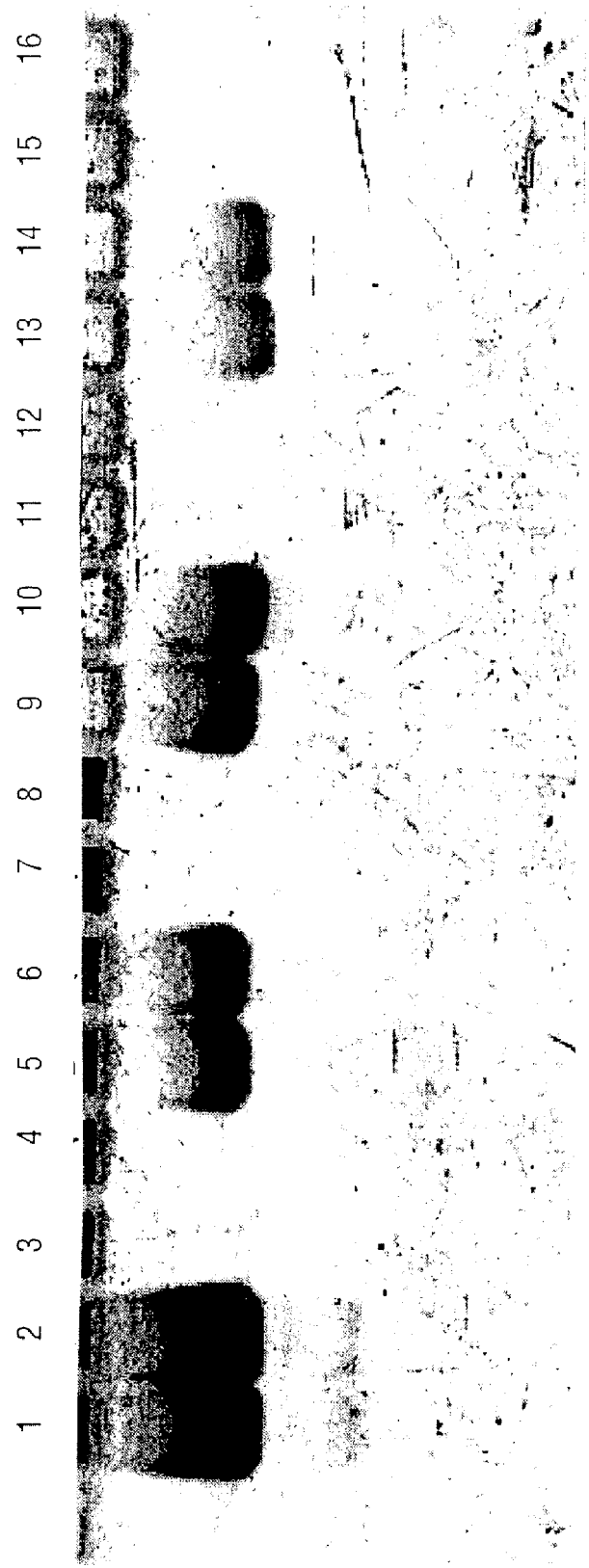

The products of the cleavage reactions were visualized following electrophoresis by the use of a Hitachi FMBIO fluorescence imager. The resulting images are shown in FIG. 72. FIG. 72A shows the denaturing gel, which was run in the standard electrophoresis direction, and FIG. 72B shows the native gel, which was run in the reverse direction. The reaction products produced by Pfu FEN-1 and CLEAVASE A/G nucleases are shown in lanes 1-8 and 9-16, respectively. The products from the 5 fmol M13mp18 and 1 fmol M13mp18 reactions are shown in lanes 1-4, 9-12 (5 fmol) and 5-8, 13-16 (1 fmol). Probe 34-180-1 is in lanes 1-2, 5-6, 9-10, 13-14 and probe 34-180-2 is in lanes 3-4, 7-8, 11-12, 15-16.

The fluorescein-labeled 3' end fragments from all cleavage reactions are shown in FIG. 72A, indicated by a "3'" mark at the left. The 3 nt 5' TET-labeled products are not visible in this Figure, while the 5' Cy3-labeled products are shown in FIG. 72B.

The 3' end bands in FIG. 72A can be used to compare the rates of cleavage by the different enzymes in the presence of the different 5' end labels. It can be seen from this band that regardless of the amount of target nucleic acid present, both the Pfu FEN-1 and the CLEAVASE A/G nucleases show more product from the 5' TET-labeled probe. With the Pfu FEN-1 nuclease this preference is modest, with only an approximately 25 to 40% increase in signal. In the case of the CLEAVASE A/G nuclease, however, there is a strong preference for the 5' TET label. Therefore, although when the charge reversal method is used to resolve the products, a substantial amount of product is observed from the CLEAVASE A/G nuclease-catalyzed reactions, the Pfu FEN-1 nuclease is a preferred enzyme for cleavage of Cy3-labeled probes.

Example 33

The Use of Universal Bases in the Detection of Mismatches by INVADER Directed Cleavage The term "degenerate base" refers to a base on a nucleotide that does not hydrogen bond in a standard "Watson-Crick" fashion to a specific base complement (i.e., A to T and G to C). For example, the inosine base can be made to pair via one or two hydrogen bonds to all of the natural bases (the "wobble" effect) and thus is called degenerate. Alternatively, a degenerate base may not pair at all; this type of base has been referred to as a "universal" base because it can be placed opposite any nucleotide in a duplex and, while it cannot contribute stability by base-pairing, it does not actively destabilize by crowding the opposite base. Duplexes using these universal bases are stabilized by stacking interactions only. Two examples of universal bases, 3-nitropyrrole and 5-nitroindole, are shown in FIG. 73. In hybridization, placement of a 3-nitropyrrole three bases from a mismatch position enhances the differential recognition of one base mismatches. The enhanced discrimination seems to come from the destabilizing effect of the unnatural base (i.e., an altered $T_m$ in close proximity to the mismatch). To test this same principle as a way of sensitively detecting mismatches using the INVADER-directed cleavage assay, INVADER oligonucleotides were designed using the universal bases shown in FIG. 73, in the presence or absence of a natural mismatch. In these experiments, the use of single nitropyrrole bases or pairs of nitroindole bases that flank the site of the mismatch were examined.

Figure 74:
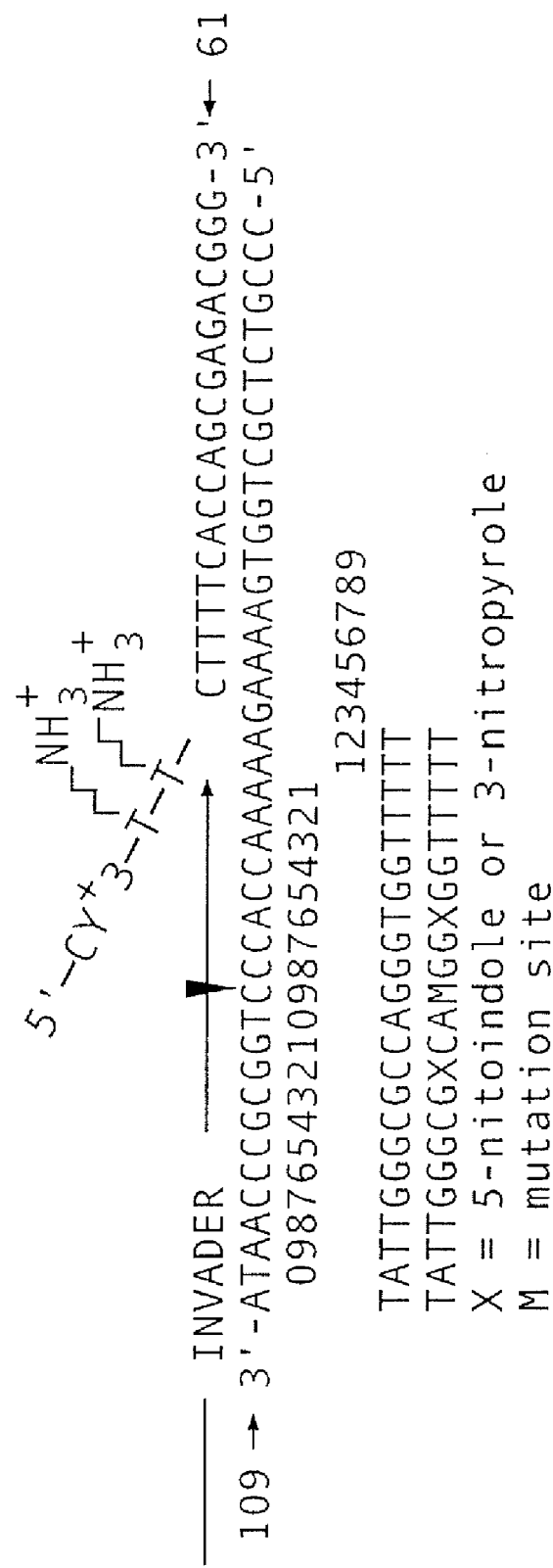
FIG. 74 shows the sequence of oligonucleotides 109, 61 and 67 (SEQ ID NOS:97, 50 and 51) annealed into a cleavage structure as well as the sequence of oligonucleotide 67 (SEQ ID NO:51) and a composite of SEQ ID NOS:98, 99, 101 and 102.

The target, probe and INVADER oligonucleotides used in these assays are shown in FIG. 74. A 43 nucleotide oligonucleotide (oligo 109; SEQ ID NO:97) was used as the target. The probe oligonucleotide (oligo 61; SEQ ID NO:50) releases a net positively charged labeled product upon cleavage. In FIG. 74, the INVADER oligonucleotide is shown schematically above the target oligonucleotide as an arrow; the large arrowhead indicates the location of the mismatch between the INVADER oligos and the target. Under the target oligonucleotide, the completely complementary, all natural (i.e., no universal bases) INVADER oligo (oligo 67; SEQ ID NO:51) and a composite of INVADER oligos containing universal bases ("X") on either side of the mismatch ("M") are shown. The following INVADER oligos were employed: oligo 114 (SEQ ID NO:98), which contains a single nt mismatch; oligo 115 (SEQ ID NO:99), which contains two 5-nitroindole bases and no mismatch; oligo 116 (SEQ ID NO:100), which contains two 5-nitroindole bases and a single nt mismatch; oligo 112 (SEQ ID NO:101), which contains one 3-nitropyrrole base and no mismatch; oligo 113 (SEQ ID NO:102), which contains one 5-nitropyrrole base and a single nt mismatch; and oligo 67 (SEQ ID NO:51), which is completely complementary to the target.

Figure 75A:
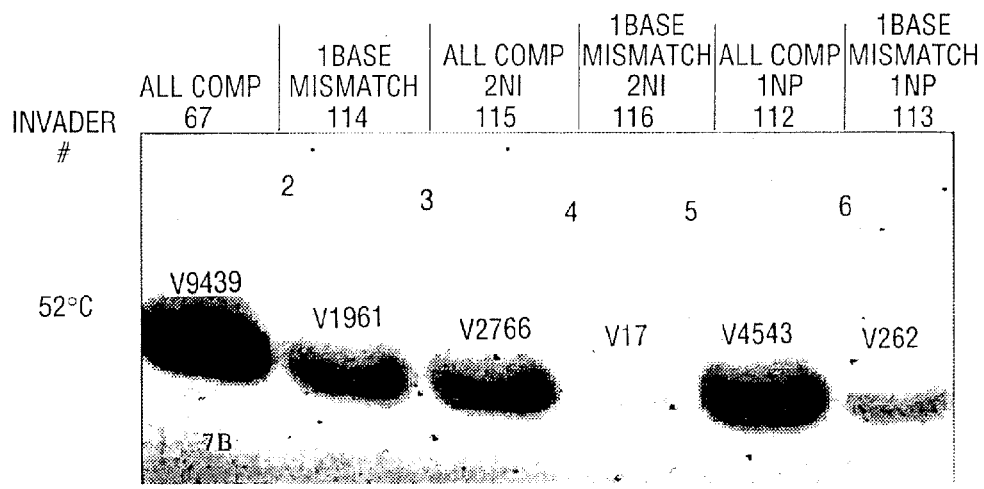
FIG. 75A-C show images generated by a fluorescence imager showing the products produced in an INVADER oligonucleotide-directed cleavage assay performed at various temperatures using a miniprobe which is either completely complementary to the target or contains a single mismatch with the target.
Figure 75B:
Figure 75C:
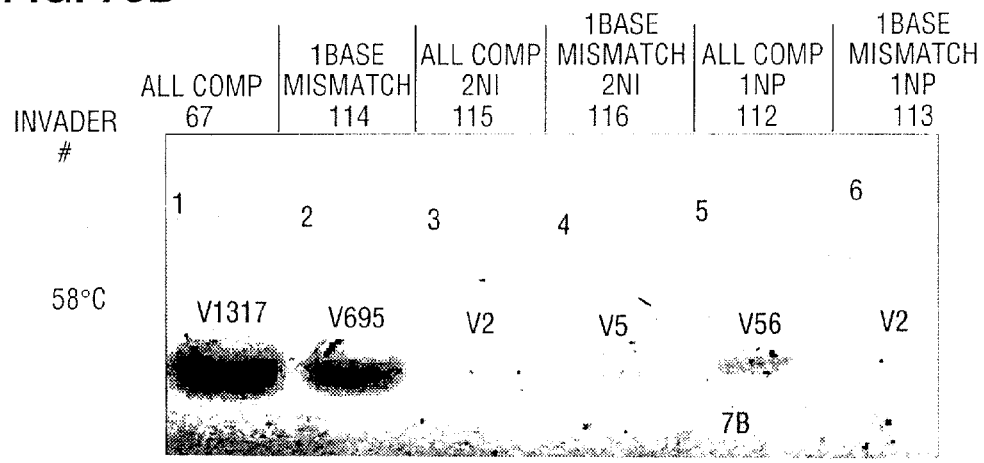

The INVADER-directed cleavage reactions were carried out in 10 μl of 10 mM MOPS (pH 7.2), 100 mM KCl, containing 1 μM of the appropriate invading oligonucleotide (oligos 67, 112-116), 10 nM synthetic target 109, 1 μM Cy-3 labeled probe 61 and 2 units of CLEAVASE DV (prepared as described in Ex. 27). The reactions were overlayed with Chill-Out® liquid wax, brought to the appropriate reaction temperature, 52° C., 55° C., or 58° C. and initiated with the addition of 1 μl of 40 mM $MnCl_2$. Reactions were allowed to proceed for 1 hour and were stopped by the addition of 10 μl formamide. One fourth of the total volume of each reaction was loaded onto 20% non-denaturing polyacrylamide gels, which were electrophoresed in the reverse direction. The products were visualized using an Hitachi FMBIO-100 fluorescent scanner using a 585 nm filter. The resulting images are shown in FIGS. 75A-C. In each panel, lanes 1-6 contain reactions products from reactions using INVADER oligo 67, 114, 115, 116, 112 and 113, respectively. Reactions run at 52° C., 55° C. and 58° C. are shown in Panels A, B and C, respectively.

These data show that two flanking 5-nitroindoles display a significantly greater differentiation then does the one 3-nitropyrrole system, or the all natural base hybridization, and this increased sensitivity is not temperature dependent. This demonstrates that the use of universal bases is a useful means of sensitively detecting single base mismatches between the target nucleic acid and the complex of detection oligonucleotides of the present invention.

Example 34

Detection of Point Mutations in the Human Ras Oncogene Using a Miniprobe

Figure 76:
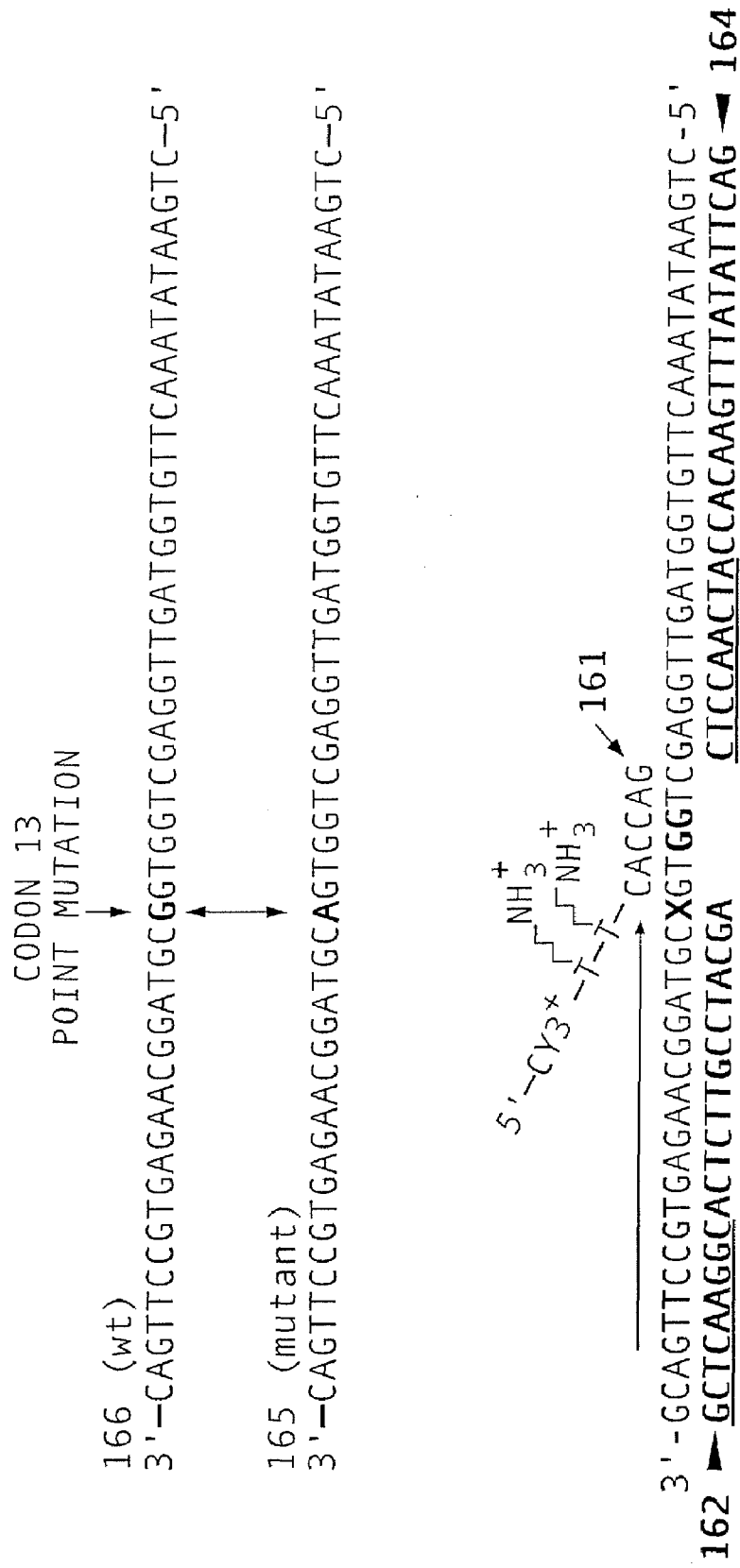
FIG. 76 shows the sequence of oligonucleotides 166 (SEQ ID NO:103), 165 (SEQ ID NO:104), 161 (SEQ ID NO:106), 162 (SEQ ID NO:105) and 164 (SEQ ID NO:107) as well as a cleavage structure.

It is demonstrated herein that very short probes can be used for sensitive detection of target nucleic acid sequences (Ex. 37). In this Example, it is demonstrated that the short probes work very poorly when mismatched to the target, and thus can be used to distinguish a given nucleic acid sequence from a close relative with only a single base difference. To test this system synthetic human ras oncogene target sequences were created that varied from each other at one position. Oligonucleotide 166 (SEQ ID NO:103) provided the wild-type ras target sequence. Oligonucleotide 165 (SEQ ID NO:104) provided the mutant ras target sequence. The sequence of these oligonucleotides are shown in FIG. 76, and the site of the sequence variation in the site corresponding to codon 13 of the ras gene is indicated. The INVADER oligonucleotide (oligo 162) has the sequence: 5'-$G_S C_S T_S C_S A_S A_S G_S G_S C_S$-ACTCTTGCCTACGA-3' (SEQ ID NO:105), where the "S" indicates thiol linkages (i.e., these are 2'-deoxynucleotide-5'-O-(1-thiomonophates)). The miniprobe (oligo 161) has the sequence: 5'-(N-Cy3) $T_{NH2} T_{NH2}$CACCAG-3' (SEQ ID NO:106) and is designed to detect the mutant ras target sequence (i.e., it is completely complementary to oligo 165). The stacker oligonucleotide (oligo 164) has the sequence: 5'-$C_S T_S C_S C_S A_S A_S C_S T_S A_S$CCACAAGTTTATATTCAG-3' (SEQ ID NO:107). A schematic showing the assembly of these oligonucleotides into a cleavage structure is depicted in FIG. 76.

Each cleavage reaction contained 100 nM of both the invading (oligo 162) and stacking (oligo 164) oligonucleotides, 10 µM Cy3-labeled probe (oligo 161) and 100 pM of either oligo 165 or oligo 166 (target DNA) in 10 µl of 10 mM HEPES (pH 7.2), 250 mM KGlu, 4 mM $MnCl_2$. The DNA mixtures were overlaid with mineral oil, heated to 90° C. for 15 sec then brought to a reaction temperature of 47°, 50°, 53° or 56° C. Reactions were initiated by the addition of 1 µl of 100 ng/µl Pfu FEN-1. Reactions were allowed to proceed for 3 hours and stopped by the addition of 10 µl formamide. One fourth of the total volume od each reaction was loaded onto a 20% non-denaturing polyacrylamide gel, which was electrophoresed in the reverse direction. The gel was scanned using an Hitachi FMBIO-100 fluorescent scanner fitted with a 585 nm filter, and the resulting image is shown in FIG. 77.

Figure 77:
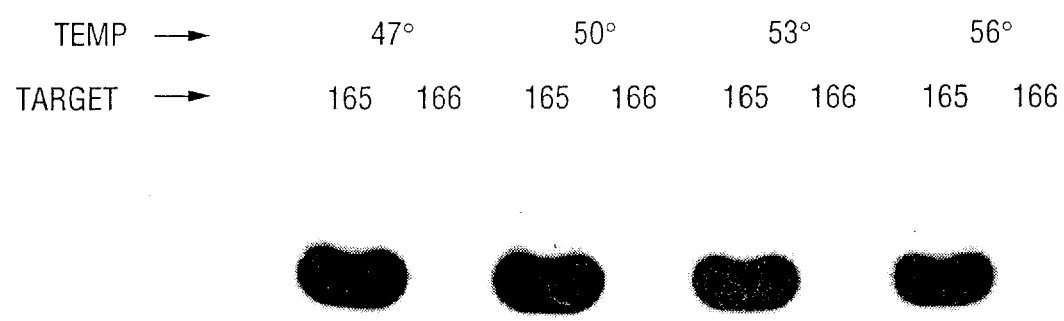
FIG. 77 shows the image generated by a fluorescence imager showing the products produced in an INVADER oligonucleotide-directed cleavage assay performed using ras gene sequences as the target.

In FIG. 77, for each reaction temperature tested, the products from reactions containing either the mutant ras target sequence (oligo 165) or the wild-type (oligo 166) are shown.

These data demonstrate that the miniprobe can be used to sensitively discriminate between sequences that differ by a single nucleotide. The miniprobe was cleaved to produce a strong signal in the presence of the mutant target sequence, but little or no miniprobe was cleaved in the presence of the wild-type target sequence. Furthermore, the discrimination between closely related targets is effective over a temperature range of at least 10° C., which is a much broader range of temperature than can usually be tolerated when the selection is based on hybridization alone (e.g., hybridization with ASOs). This suggests that the enzyme may be a factor in the discrimination, with the perfectly matched miniprobe being the preferred substrate when compared to the mismatched miniprobe. Thus, this system provides sensitive and specific detection of target nucleic acid sequences.

Example 35

Effects of 3' End Identity on Site of Cleavage of a Model Oligonucleotide Structure As described in the Examples above, structure-specific nucleases cleave near the junction between single-stranded and base-paired regions in a bifurcated duplex, usually about one base pair into the base-paired region. It was shown in Example 10 that thermostable 5' nucleases, including those of the present invention (e.g., CLEAVASE BN nuclease, CLEAVASE A/G nuclease), have the ability to cleave a greater distance into the base paired region when provided with an upstream oligonucleotide bearing a 3' region that is homologous to a 5' region of the subject duplex, as shown in FIG. 26. It has also been determined that the 3' terminal nucleotide of the INVADER oligonucleotide may be unpaired to the target nucleic acid, and still shift cleavage the same distance into the down stream duplex as when paired. It is shown in this Example that it is the base component of the nucleotide, not the sugar or phosphate, that is necessary to shift cleavage.

FIGS. 78A and B shows a synthetic oligonucleotide that was designed to fold upon itself, and that consists of the following sequence: 5'-GTTCTCTGCTCTCTGGTCGCT-GTCTCGCTTGTGAAACAAGCGAGA-CAGCGTGGTCTCTCG-3' (SEQ ID NO:29). This oligonucleotide is referred to as the "S-60 Hairpin." The 15 basepair hairpin formed by this oligonucleotide is further stabilized by a "tri-loop" sequence in the loop end (i.e., three nucleotides form the loop portion of the hairpin) (Hiraro et al., Nucleic Acids Res., 22(4): 576 [1994]). FIG. 78B shows the sequence of the P-15 oligonucleotide (SEQ ID NO:30) and the location of the region of complementarity shared by the P-15 and S-60 hairpin oligonucleotides. In addition to the P-15 oligonucleotide shown, cleavage was also tested in the presence of the P-14 oligonucleotide (SEQ ID NO:108) (P-14 is one base shorter on the 3' end as compared to P-15), the P-14 with an abasic sugar (P-14d; SEQ ID NO:109) and the P14 with an abasic sugar with a 3' phosphate (P-14dp; SEQ ID NO:110). A P-15 oligo with a 3' phosphate, P-15p (SEQ ID NO:111) was also examined. The black arrows shown in FIG. 78 indicate the sites of cleavage of the S-60 hairpin in the absence (top structure; A) or presence (bottom structure; B) of the P-15 oligonucleotide.

The S-60 hairpin molecule was labeled on its 5' end with fluorescein for subsequent detection. The S-60 hairpin was incubated in the presence of a thermostable 5' nuclease in the presence or the absence of the P-15 oligonucleotide. The presence of the full duplex that can be formed by the S-60 hairpin is demonstrated by cleavage with the CLEAVASE BN 5' nuclease, in a primer-independent fashion (i.e., in the absence of the P-15 oligonucleotide). The release of 18 and 19-nucleotide fragments from the 5' end of the S-60 hairpin molecule showed that the cleavage occurred near the junction between the single and double stranded regions when nothing is hybridized to the 3' arm of the S-60 hairpin (FIG. 27, lane 2).

Figure 78C:
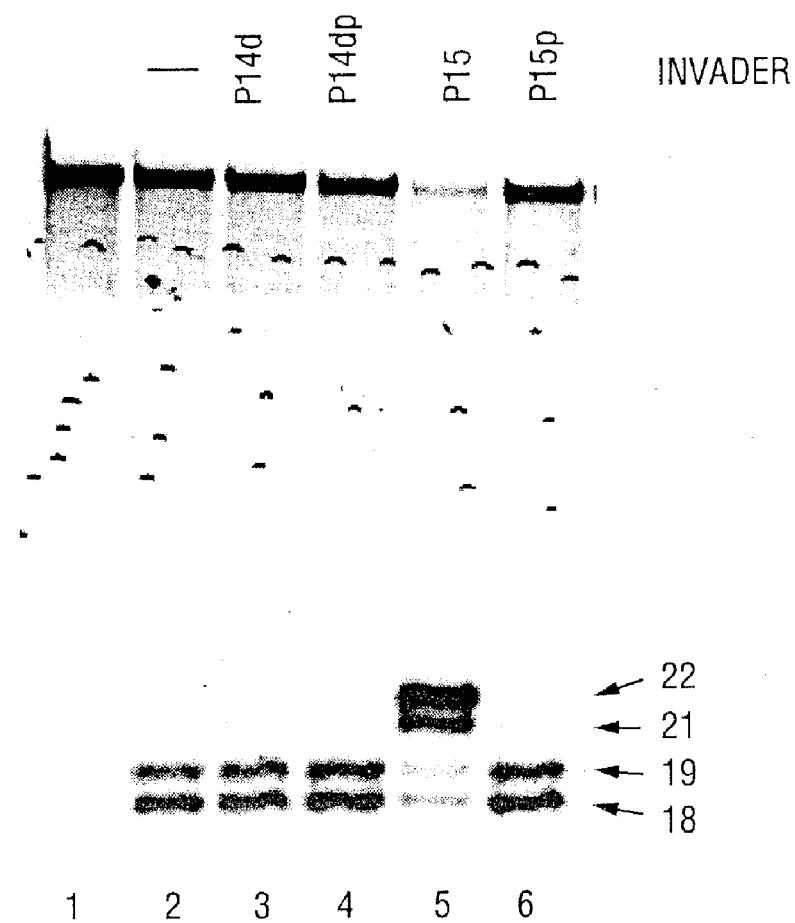
Figure 78C:
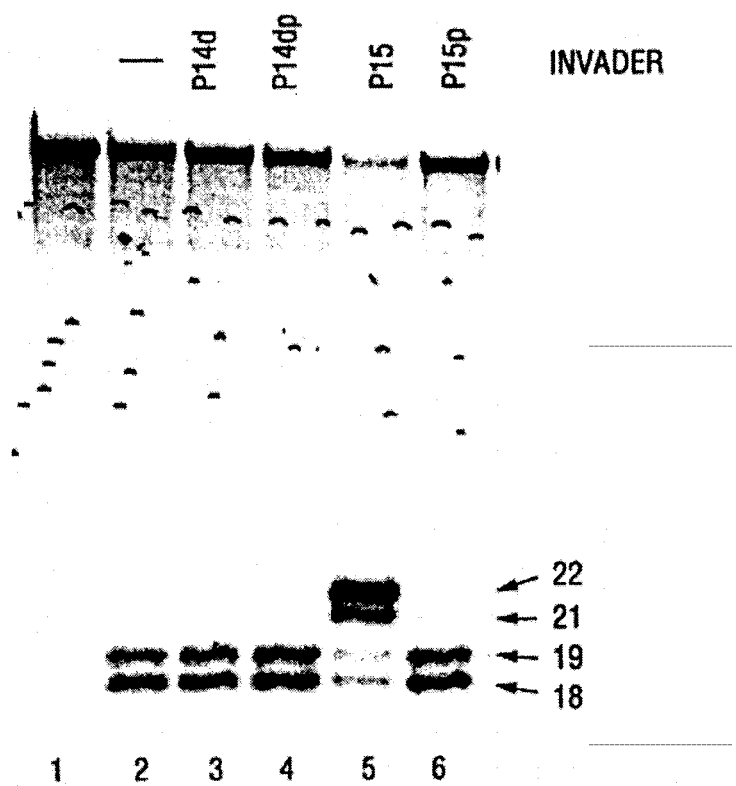
Figure 80:
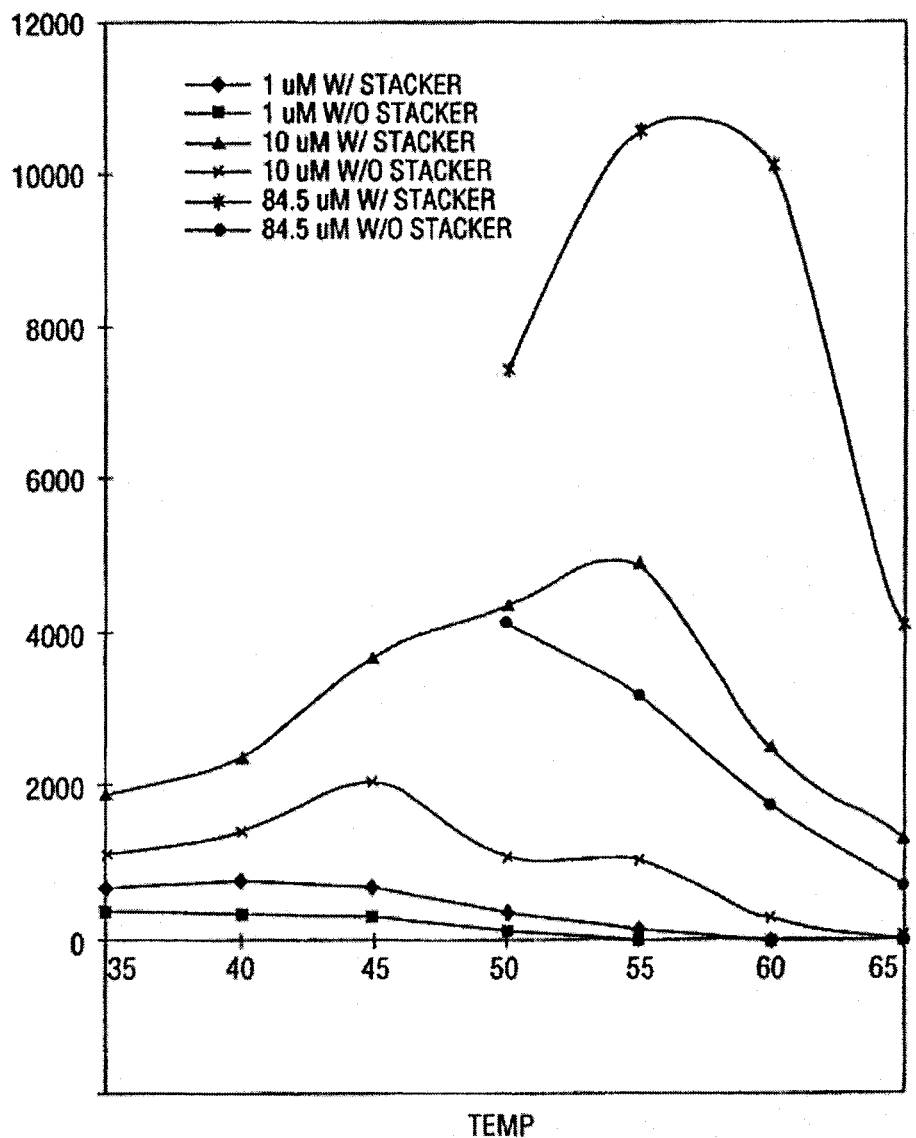

The reactions shown in FIG. 78C were conducted in 10 µl IX CFLP buffer with 1 mM $MnCl_2$ and 50 mM K-Glutamate, in the presence of 0.02 µM S-60, 0.5 µM INVADER oligonucleotide and 0.01 ng per µl CLEAVASE BN nuclease.

Reactions were incubated at 40° C. for 5 minutes and stopped by the addition of 8 μl of stop buffer (95% formamide, 20 mM EDTA, 0.02% methyl violet). Samples were heated to 75° C. for 2 min immediately before electrophoresis through a 15% acrylamide gel (19:1 cross-linked), with 7 M urea, in a buffer of 45 mM Tris-Borate, pH 8.3, 1.4 mM EDTA. Gels were then analyzed with a FMBIO-100 Image Analyzer (Hitachi) equipped with 505 nm filter. The resulting image is shown in FIG. 78C.

In FIG. 78C lane 1 contains products from the no enzyme control; lane 2 contains products from a reaction run in the absence of an INVADER oligo; lanes 3-6 contain products from reactions run the presence of the P-14d, P-14dp, P-15 and P-15p INVADER oligos, respectively.

From the data shown in FIG. 78C, it can be seen that the use of the P-15 INVADER oligonucleotide produces a shift in the cleavage site, while the P14 INVADER oligonucleotide with either a ribose (P14d) or a phosphorylated ribose (P14dp) did not This indicates that the 15th residue of the INVADER oligonucleotide must have the base group attached to promote the shift in cleavage. Interestingly, the addition of phosphate to the 3' end of the P15 oligonucleotide apparently reversed the shifting of cleavage site. The cleavage in this lane may in fact be cleavage in the absence of an INVADER oligonucleotide as is seen in lane 2. In experiments with 5' dye-labeled INVADER oligonucleotides with 3' phosphate groups these oligonucleotides have been severely retarded in gel migration, suggesting that either the enzyme or another constituent of the reaction (e.g., BSA) is able to bind the 3' phosphate irrespective of the rest of the cleavage structure. If the INVADER oligonucleotides are indeed being sequestered away from the cleavage structure, the resulting cleavage of the S-60 hairpin would occur in a "primer-independent' fashion, and would thus not be shifted.

In addition to the study cited above, the effects of other substituents on the 3' ends of the INVADER oligonucleotides were investigated in the presence of several different enzymes, and in the presence of either Mn++ or Mg++. The effects of these 3' end modifications on the generation of cleaved product are summarized in the following table. All of modifications were made during standard oligonucleotide synthesis by the use of controlled pore glass (CPG) synthesis columns with the listed chemical moiety provided on the support as the synthesis starting residue. All of these CPG materials were obtained from Glen Research Corp. (Sterling, Va.).

Figure 79:
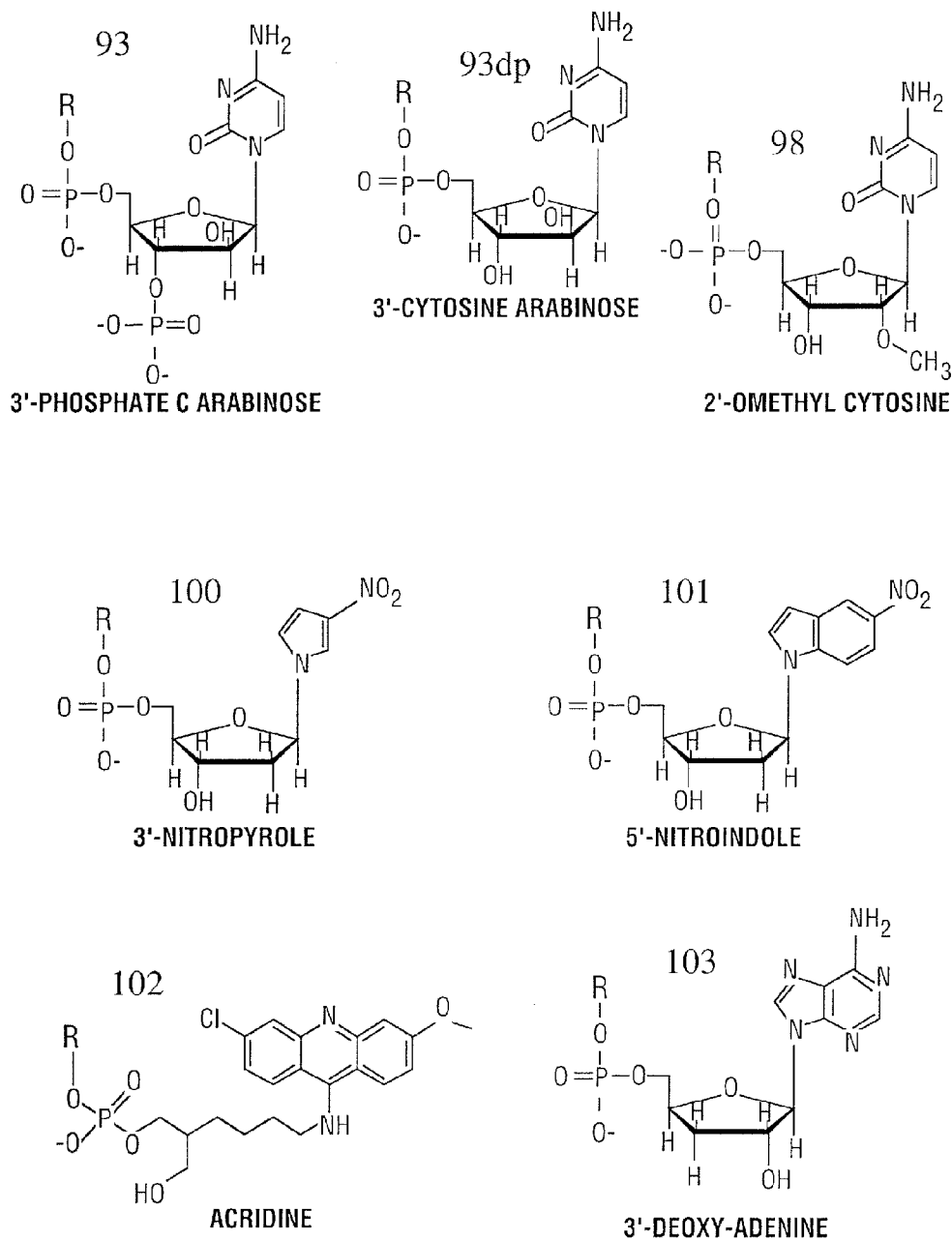
FIG. 79 shows the structure of various 3' end substituents.

FIG. 79 provides the structures for the 3' end substituents used in these experiments.

TABLE 4

Modification Studies At 3' End Of INVADER Oligo

| 3'-End Modification | Extension By Terminal Transferase | Effect on INVADER Rxn. (As INVADER) Enzyme:Condition - Effect |
|---|---|---|
| 3' phosphate Glen part # 20-2900-42 | no | A:5 - inhibits reaction, no detectable activity |
| 3' acridine Glen part # 20-2973-42 | yes, poorly | A:5 - decrease in activity, <10% B:5 - decrease in activity, <10% B:4 - decrease in activity, <10% C:1 - decrease in activity, <10% C:2 - decrease in activity, ~20% C:4 - decrease in activity, ~50% C:3 - decrease in activity, <5% |
| 3' carboxylate Glen part # 20-4090-42 | no | A:1 - decrease in activity, ~50% activity shift in cleavage site C:3 - reduces rate, <10% activity |
| 3' nitropyrole Glen part # 20-2143-42 | yes | A:5 - increase in activity, ~2X |
| 3' nitroindole Glen part # 20-2144-42 | yes | A:5 - decrease in activity, ~33% activity |
| 3' arabinose Glen part # 10-4010-90 | yes | A:5 - decrease in activity, ~50% activity |
| 3'dideoxyUTP-flourescein | no | A:5 - decrease in activity, ~40% activity |
| 3'-3' linkage Glen part # 20-0002-01 | no | A:1 - equivalent cleavage activity shift in cleavage site C:3 - decrease in activity, ~25% activity |
| 3' glyceryl | yes, very poorly | C:3 - decrease in activity, ~30% |
| 3' phosphate Glen part # 20-2900-42 Glen part # 20-2902-42 | no | A:5 - inhibits reaction, no detectable activity activity loss of specificity of cleavage (2 sites) |
| 3' amino modifier C7 Glen part # 20-2957-42 | yes | C:3 - decrease in activity, ~30% activity loss of specificity, multiple sites |
| 3'deoxy, 2'OH Glen part # 20-2104-42 | yes, very poorly | A:5 - decrease in activity, <20% activity B:5 - decrease in activity, <20% activity B:3 - decrease in activity, <20% activity C:1 - equivalent activity C:2 - equivalent activity C:4 - ? increase in activity C:3 - decrease in activity, ~40% activity |

Enzymes:
  A) CLEAVASE DV nuclease
  B) CLEAVASE BN nuclease
  C) Pfu FEN-1

Condition:
  1) 4 mM $MnCl_2$, 150 mM LiCl
  2) 4 mM $MnCl_2$, 50 mM KCl
  3) 7.5 mM $MgCl_2$, no monovalent
  4) 4 mM $MgCl_2$, 50 mM KCl
  5) 10 mM MgOAc, 50 mM KCl It can be seen from these data that many different modifications can be used on the 3' end of the INVADER oligonucleotide without detriment. In various embodiments of the present invention, such 3' end modifications may be used to block, facilitate, or otherwise alter the hybridization characteristics of the INVADER oligonucleotide, (e.g., to increase discrimination against mismatches, or to increase tolerance of mismatches, or to tighten the association between the INVADER oligonucleotide and the target nucleic acid). Some substituents may be used to alter the behavior of the enzyme in recognizing and cleaving within the assembled complex.

Altered 3' ends may also be used to prevent extension of the INVADER oligonucleotide by either template-dependent or template-independent nucleic acid polymerases. The use of otherwise unmodified dideoxynucleotides (i.e., without attached dyes or other moieties) are a particularly preferred means of blocking extension of INVADER oligonucleotides, because they do not decrease cleavage activity, and they are absolutely unextendable.

Example 36

Effect of Probe Concentration, Temperature and a Stacker Oligonucleotide on the Cleavage of Miniprobes by INVADER-Directed Cleavage The stacker oligonucleotides employed to form cleavage structures may serve two purposes in the detection of a nucleic acid target using a miniprobe. The stacker oligonucleotide may help stabilize the interaction of the miniprobe with the target nucleic acid, leading to greater accumulation of cleaved probe. In addition, the presence of this oligo in the complex elongates the duplex downstream of the cleavage site, which may enhance the cleavage activity of some of the enzymes of the present invention. An example of different preferences for the length of this duplex by different structure-specific nucleases is seen in the comparison of the CLEAVASE BN nuclease and the Mja FEN-1 nuclease cleavage of 8 bp and 12 bp duplex regions in FIG. 65. Increased affinity of the enzyme for the cleavage structure also results in increased accumulation of cleaved probe during reactions done for a set amount of time.

The amount of miniprobe binding to the target is also affected by the concentration of the miniprobe in the reaction mixture. Even when a miniprobe is only marginally likely to hybridize (e.g., when the reaction is performed at temperatures in excess of the expected melting temperature of the probe/target duplex), the amount of probe on the target at any given time can be increased by using high concentrations of the miniprobe.

The need for a stacker oligonucleotide to enhance cleavage of the miniprobe was examined at both low and high probe concentrations. The reactions were carried out in 10 μl of 10 mM HEPES (pH 7.2), 250 mM KGlu, 4 mM $MnCl_2$, containing 100 nM of both the invading (oligo 135; SEQ ID NO:112) and stacking oligonucleotides (oligo 147; SEQ ID NO:113) and 100 pM ssM13 DNA. The reactions were overlayed with mineral oil, heated to 90° C. for 15 sec then brought to the reaction temperature. Reactions were performed at 35°, 40°, 45°, 50°, 55°, 60°, and 65° C. The cleavage reactions were initiated by the addition of 1 μl of 100 ng/μl Pfu FEN-1 and 1 μl of varying concentrations of Cy-3 labeled 142 miniprobe oligonucleotide (SEQ ID NO:114). Reactions were allowed to proceed for 1 hour and stopped by the addition of 10 μl formaldehyde. One fourth of the total volume of each reaction was loaded onto 20% non-denaturing polyacrylamide gels, which were electrophoresed in the reverse direction. Gels were visualized using an Hitachi FMBIO-100 fluorescent scanner using a 585 nm filter. The fluorescence in each product band was measured and the graph shown in FIG. 80 was created using a Microsoft Excel spreadsheet.

Figure 80:
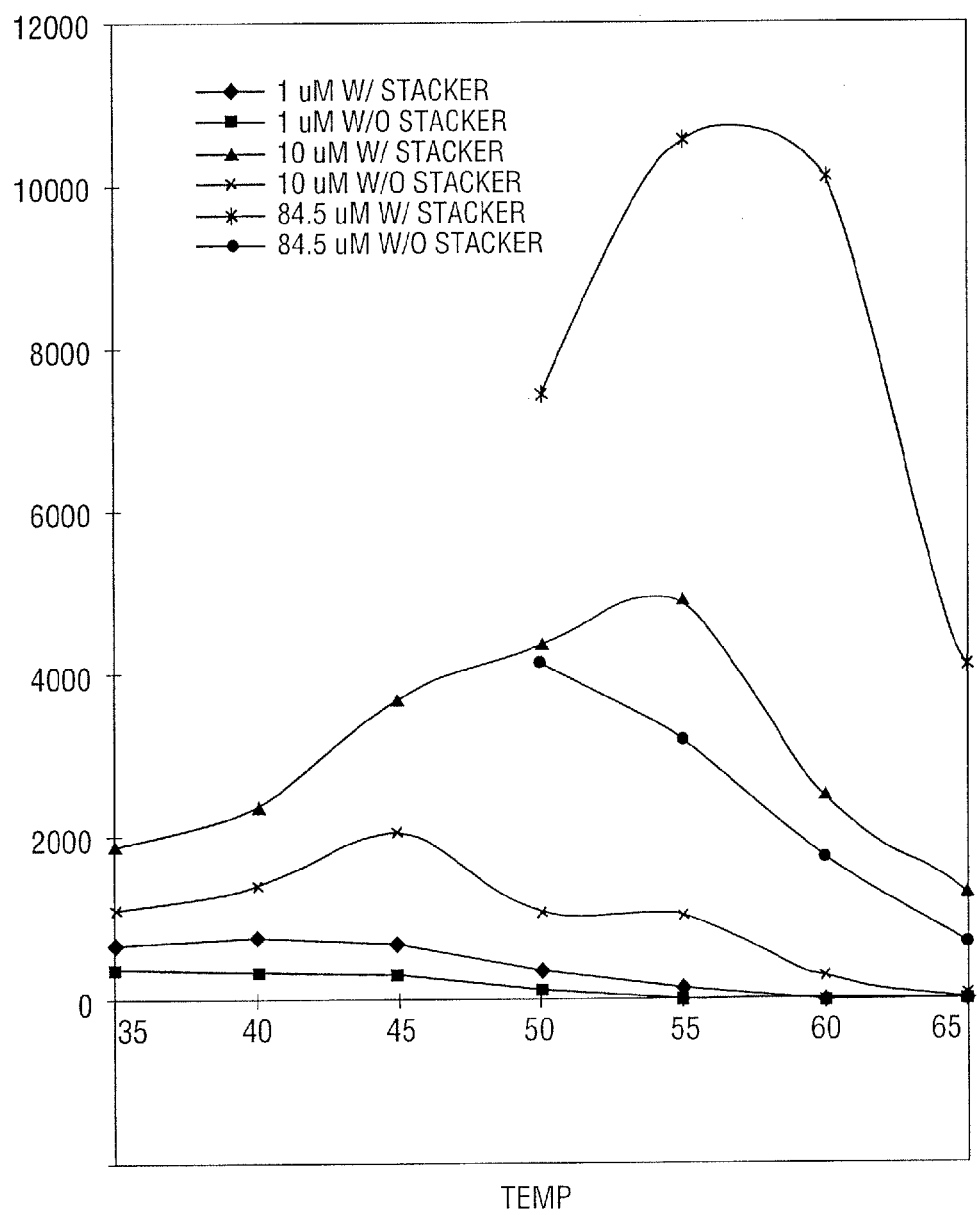
FIG. 80 is a composite graph showing the effect of probe concentration, temperature and a stacker oligonucleotide on the cleavage of miniprobes.

The data summarized in FIG. 80 showed that the concentration of the miniprobe had a significant effect on the final measure of product, showing dramatic increases as the concentration was raised. Increases in the concentration of the miniprobe also shifted the optimum reaction temperature upward. It is known in the art that the concentration of the complementary strands in a hybridization will affect the apparent $T_m$ of the duplex formed between them. More significantly to the methods and compositions of the present invention is the fact that the presence of the stacker oligonucleotide has a profound influence on the cleavage rate of the miniprobe at all probe concentrations. At each of the probe concentrations the presence of the stacker as much as doubled the signal from the cleavage product. This demonstrated the utility of using the stacker oligonucleotide in combination with the miniprobes described herein.

Example 37

The Presence of a Mismatch in the INVADER Oligonucleotide Decreases the Cleavage Activity of the CLEAVASE A/G Nuclease In any nucleic acid detection assay it is of additional benefit if the assay can be made to sensitively detect minor differences between related nucleic acids. In the following experiment, model cleavage substrates were used that were identical except for the presence or absence of a mismatch near the 3' end of the INVADER oligonucleotide when hybridized to the model target nucleic acid. The effect of a mismatch in this region on the accumulation of cleaved probe was then assessed.

Figure 81:
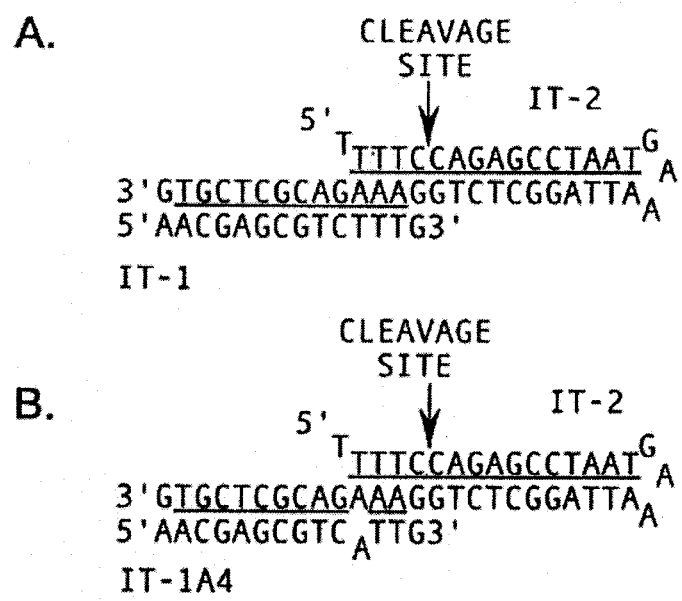
FIG. 81 shows the sequence of the IT-2 oligonucleotide (SEQ ID NO:115; shown in a folded configuration) as well as the sequence of the IT-1 (SEQ ID NO:116) and IT-A (SEQ ID NO:117) oligonucleotides.
Figure 82:
Figure 83:
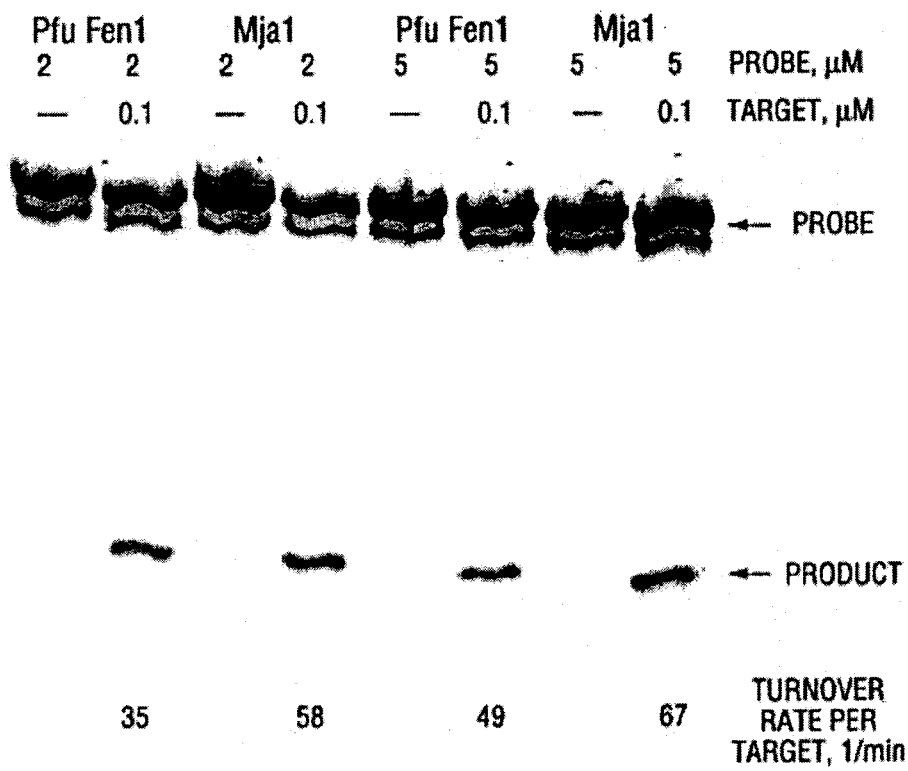
Figure 84:
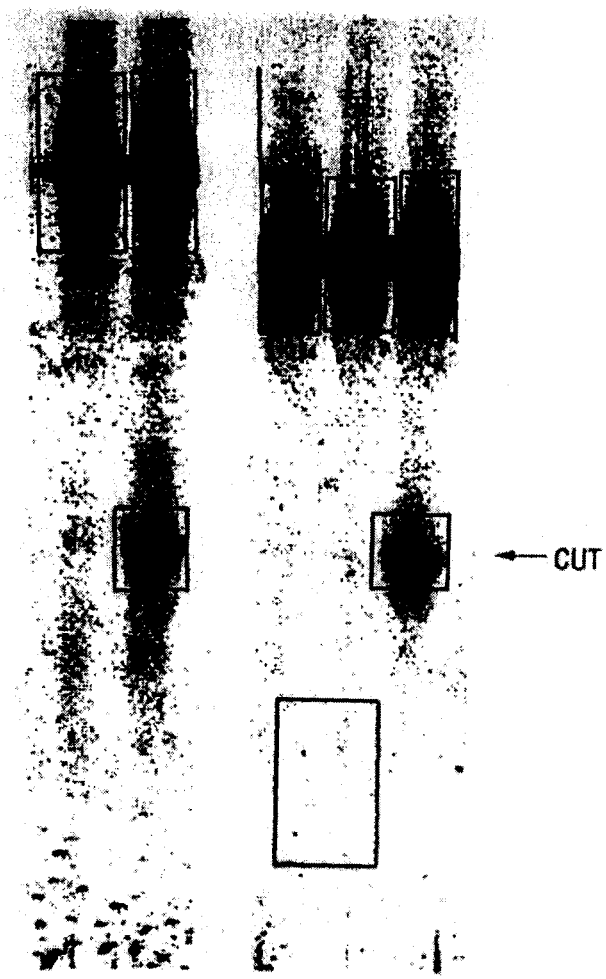
Figure 85A:
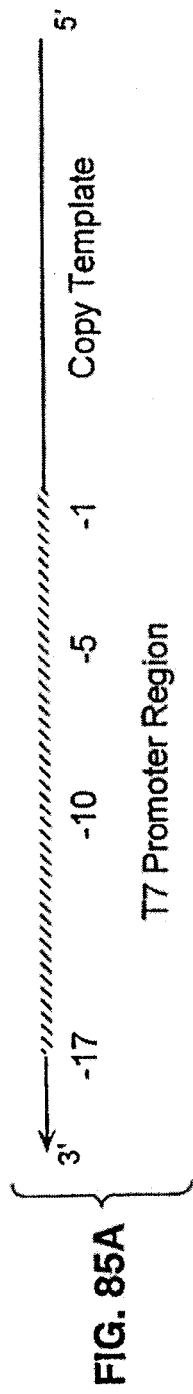
Figure 85B:
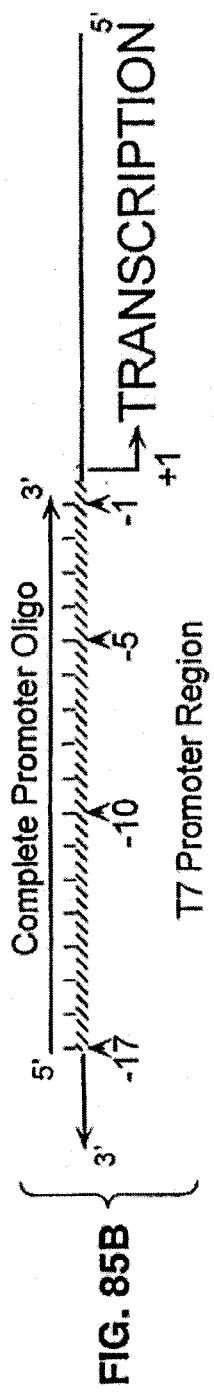
Figure 85C:
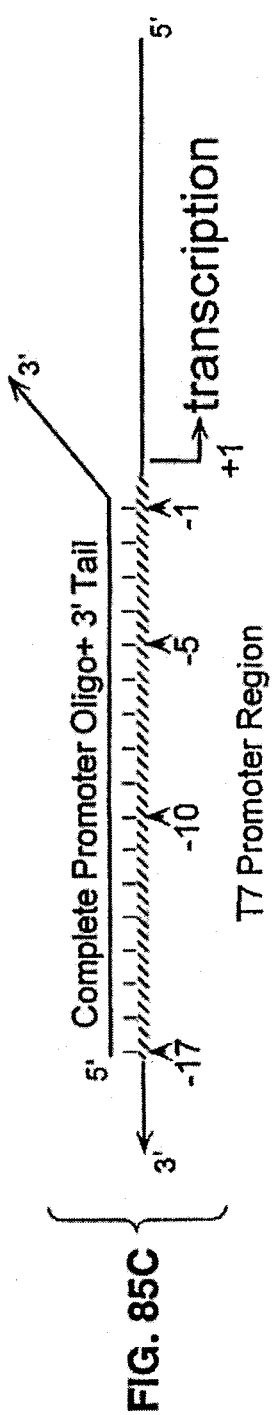
Figure 87:
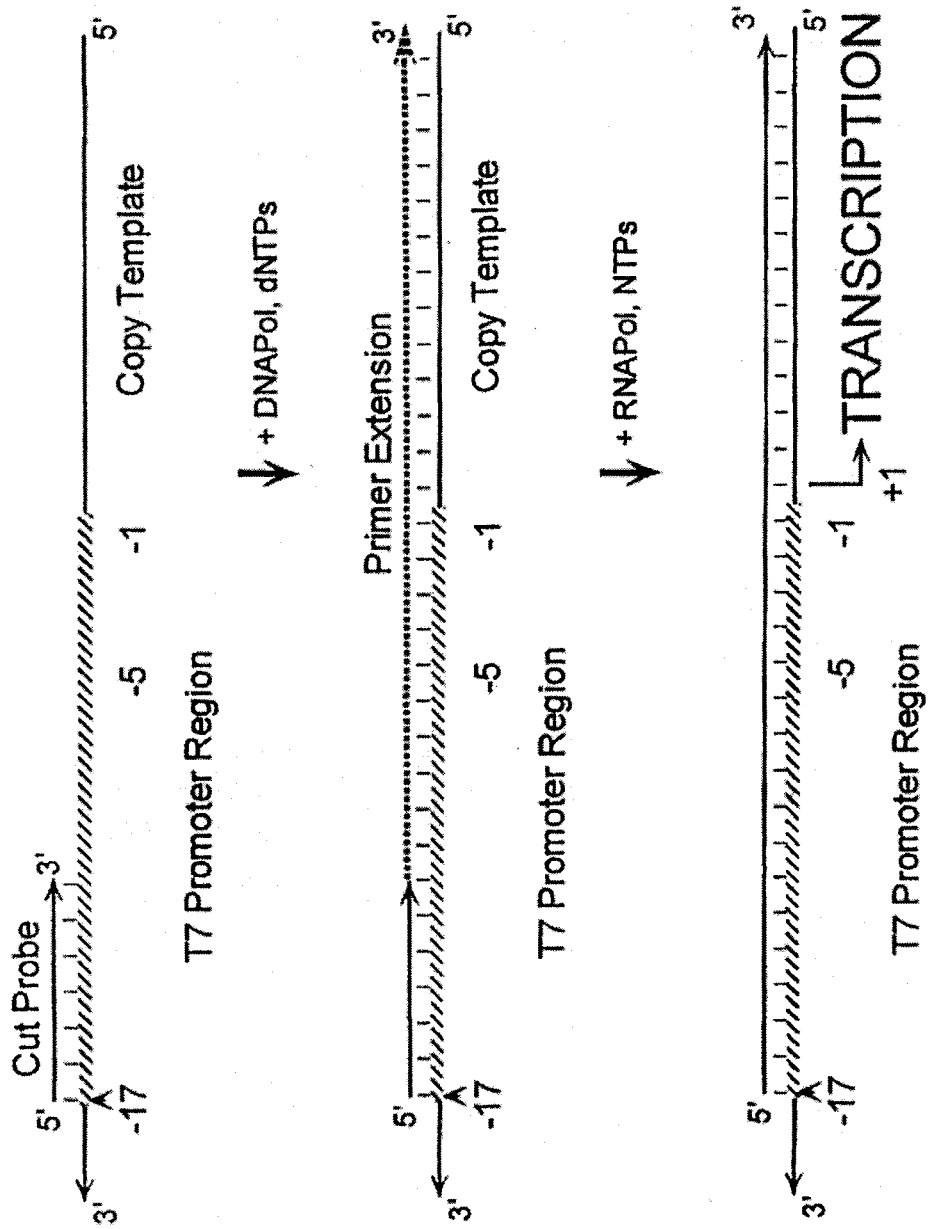

To demonstrate the effect of the presence of a mismatch in the INVADER oligonucleotide on the ability of the CLEAVASE A/G nuclease to cleave the probe oligonucleotide in an INVADER assay the following experiment was conducted. Cleavage of the test oligonucleotide IT-2 (SEQ ID NO:115) in the presence of INVADER oligonucleotides IT-1 (SEQ ID NO:116) and IT-1A4 (SEQ ID NO:117). Oligonucleotide IT-1 is fully complementary to the 3' arm of IT-2, whereas oligonucleotide IT-1A4 has a T->A substitution at position 4 from the 3' end that results in an A/A mismatch in the INVADER-target duplex. Both the matched and mismatched INVADER oligonucleotides would be expected to hybridize at the temperature at which the following reaction was performed. FIG. 81 provides a schematic showing IT-1 annealed to the folded IT-2 structure and showing IT-1A4 annealed to the folded IT-2 structure.

The reactions were conducted as follows. Test oligonucleotide IT-2 (0.1 μM), labeled at the 5' end with fluorescein (Integrated DNA Technologies), was incubated with 0.26 ng/μl CLEAVASE AG in 10 μl of CFLP® buffer with 4 mM $MgCl_2$, in the presence of 1 μM IT-1 or IT-1A4 at 40° C. for 10 min; a no enzyme control was also run. Samples were overlaid with 15 μl Chill-Out® liquid wax to prevent evaporation. Reactions were stopped by addition of 4 μl stop buffer (95% formamide, 20 mM EDTA, 0.02% methyl violet). The cleavage products were separated on a 20% denaturing polyacrylamide gel and analyzed with the FMBIO-100 Image Analyzer (Hitachi) equipped with 505 nm filter. The resulting image is shown in FIG. 82.

Figure 82:
FIG. 82 shows the image generated by a fluorescence imager showing the products produced by cleavage of the oligonucleotides shown in FIG. 92 by CLEAVASE A/G nuclease.

In FIG. 82, lane 1 contains reaction products from the no enzyme control and shows the migration of the uncut IT-2 oligo; lanes 2-4 contain products from reactions containing no INVADER oligo, the IT-1 INVADER oligo and the IT-1A4 INVADER oligo, respectively.

These data show that cleavage is markedly reduced by the presence of the mismatch, even under conditions in which the mismatch would not be expected to disrupt hybridization. This demonstrates that the INVADER oligonucleotide binding region is one of the regions within the complex in which can be used for mismatch detection, as revealed by a drop in the cleavage rate.

Example 38

Comparison of the Activity of the Pfu FEN-1 and Mja EN-1 Nucleases in the INVADER Reaction To compare the activity of the Pfu FEN-1 and the Mja FEN-1 nucleases in INVADER reaction the following experiment was performed. A test oligonucleotide IT3 (SEQ ID NO:118) that forms an INVADER-Target hairpin structure and probe oligonucleotide PR1 (SEQ ID NO:119) labeled at the 5' end with fluorescein (Integrated DNA Technologies) were employed in INVADER assays using either the Pfu FEN-1 or the Mja FEN-1 nucleases.

Figure 83:
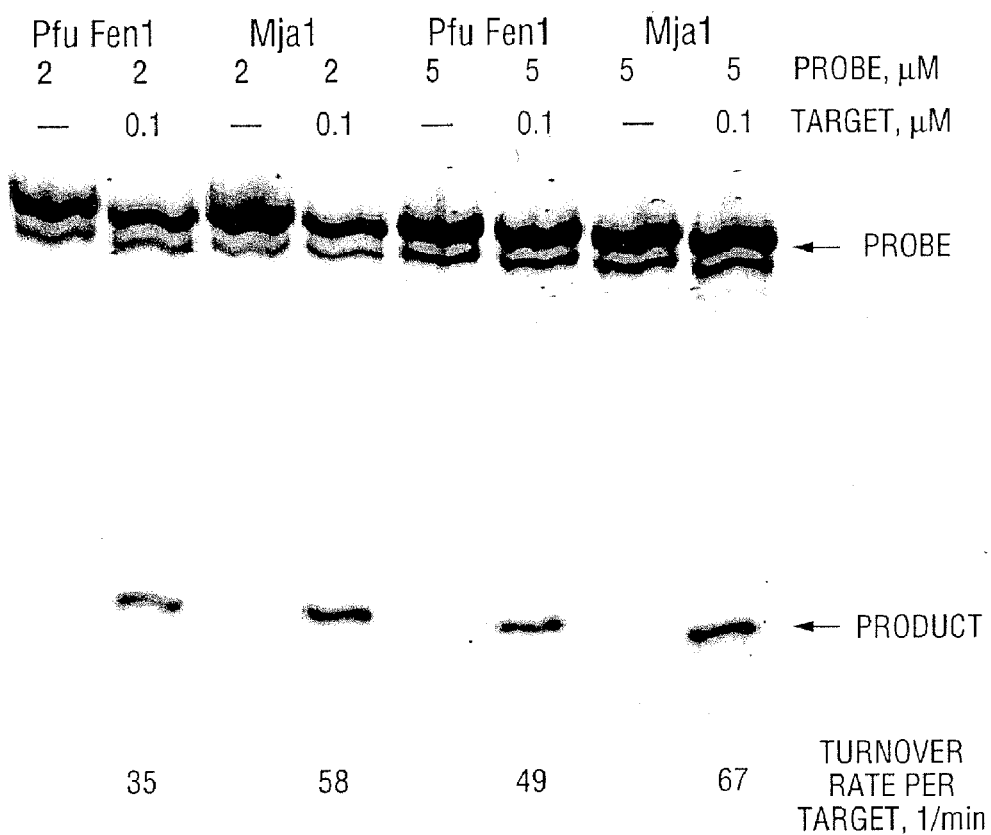
FIG. 83 shows the image generated by a fluorescence imager which provides a comparison of the rates of cleavage by the Pfu FEN-1 and Mja FEN-1 nucleases.

The assays were conducted as follows. Pfu FEN-1 (13 ng/µl) and Mja FEN-1 (10 ng/µl) (prepared as described in Ex. 28) were incubated with the IT3 (0.1 nM) and PR1 (2 and 5 µM) oligonucleotides in 10 µL CFLP® buffer, 4 mM $MgCl_2$, 20 mg/ml tRNA at 55° C. for 41 min. Samples were overlaid with 15 µl Chill-Out® evaporation barrier to prevent evaporation. Reactions were stopped by addition of 70 µl stop buffer (95% formamide, 20 mM EDTA, 0.02% methyl violet). Reaction products (1 µl) were separated on a 20% denaturing polyacrylamide gel, visualized using a fluroimager and the bands corresponding to the probe and the product were quantitiated. The resulting image is shown in FIG. 83. In FIG. 83, the turnover rate per target per minute is shown below the image for each nuclease at each concentration of probe and target tested.

It was demonstrated in Example 32 that the use of the Pfu FEN-1 structure-specific nuclease in the INVADER-directed cleavage reaction resulted in a faster rate of product accumulation than did the use of the CLEAVASE A/G. The data presented here demonstrates that the use of Mja FEN-1 nuclease with the fluorescein labeled probe further increases the amount of product generated by an average of about 50%, demonstrating that, in addition to the Pfu FEN-1 nuclease, the Mja FEN-1 nuclease is a preferred structure-specific nuclease for the detection of nucleic acid targets by the method of the present invention.

Example 39

Detection of RNA Target Nucleic Acids Using Miniprobe and Stacker Oligonucleotides In addition to the detection of the M13 DNA target material described above, a miniprobe/stacker system was designed to detect the HCV-derived RNA sequences described in Example 19. A probe of intermediate length, either a long mid-range or a short standard probe, was also tested. The miniprobe used (oligo 42-168-1) has the sequence: 5'-TET-CCGGTCGTCCTGG-3' (SEQ ID NO:120), the stacker oligonucleotide used (oligo 32-085) with this miniprobe has the sequence: 5'-CAATTCCGGTGTACTACCGGTTCC-3' (SEQ ID NO:121). The slightly longer probe, used without a stacker (oligo 42-088), has the sequence: 5'-TET-CCG-GTCGTCCTGGCAA-3' (SEQ ID NO:122). The INVADER oligonucleotide used with both probes has the sequence: 5'-GTTTATCCAAGAAAGGACCCGGTC-3' (SEQ ID NO:47). The reactions included 50 fmole of target RNA, 10 pmole of the INVADER oligonucleotide and 5 pmole of the miniprobe oligonucleotide in 10 µl of buffer containing 10 mM MES, pH 6.5 with 150 mM LiCl, 4 mM $MnCl_2$, 0.05% each Tween-20 and NP-40, and 39 units of RNAsin (Promega). When used, 10 pmoles of the stacker oligonucleotide was added. These components were combined, overlaid with CHILLOUT evaporation barrier, and warmed to 50° C.; the reactions were started by the addition of 5 polymerase units of DNAPTth, to a final reaction volume of 10 µl. After 30 minutes at 50° C., reactions were stopped by the addition of 8 µl of 95% formamide, 10 mM EDTA and 0.02% methyl violet. The samples were heated to 90° C. for 1 minute and 2.5 µl of each of these reactions were resolved by electrophoresis through a 20% denaturing polyacrylamide (19:1 cross link) with 7M urea in a buffer of 45 mM Tris-Borate, pH 8.3, 1.4 mM EDTA, and the labeled reaction products were visualized using the FMBIO-100 Image Analyzer (Hitachi). The resulting image is shown in FIG. 84.

Figure 84:
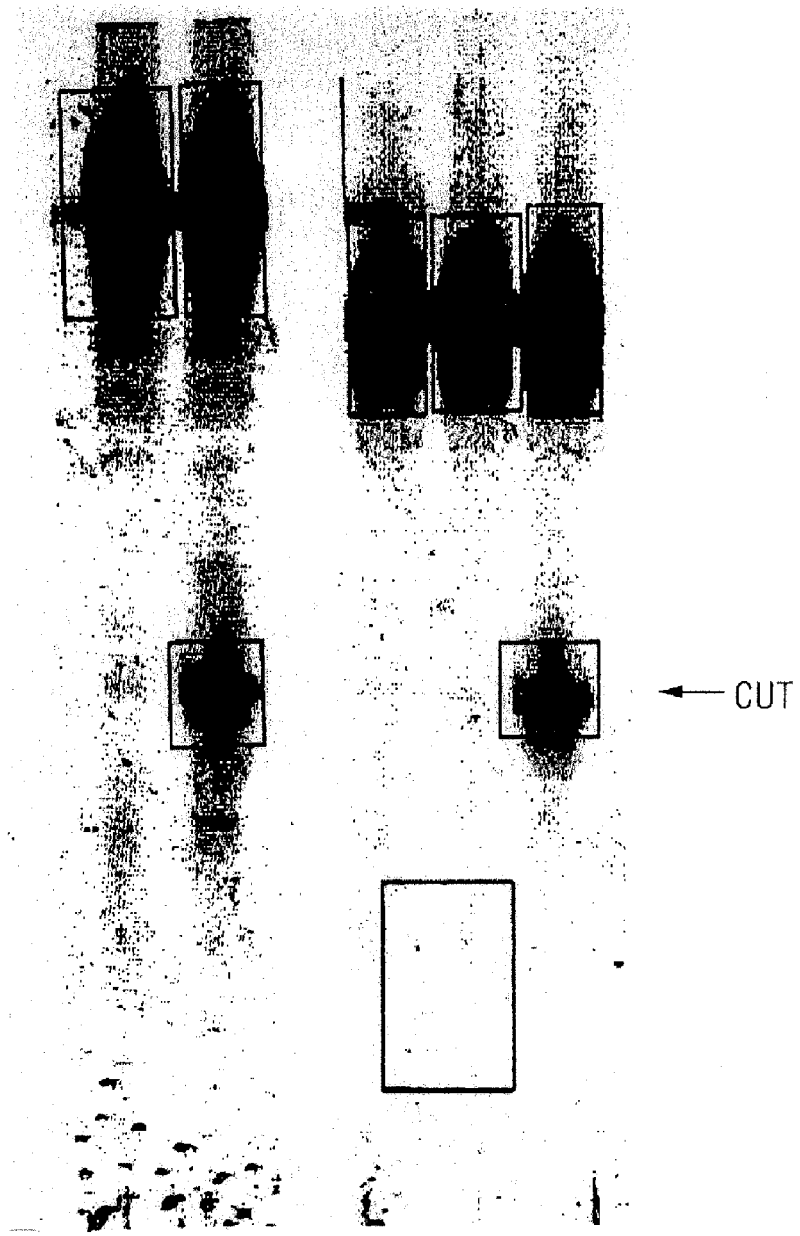
FIG. 84 shows the image generated by a fluorescence imager which depicts the detection of RNA targets using a miniprobe and stacker oligonucleotides.

In FIG. 84, lanes 1 and 2 show the products of reactions containing the HCV INVADER oligonucleotide and the longer probe (oligo 42-088), without and with the target RNA present, respectively. Lanes 3, 4, and 5 show the products of reactions containing the INVADER oligonucleotide and the shorter probe (oligo 42-168-1). Lane 3 is a control reaction without target RNA present, while lanes 4 and 5 have the target, but are without or with the stacker oligonucleotide, respectively.

Under these conditions the slightly longer (16 nt) probe oligonucleotide was cleaved quite easily without the help of a stacker oligonucleotide. In contrast, the shorter probe (13 nt) required the presence of the stacker oligonucleotide to produce detectable levels of cleavage. These data show that the miniprobe system of target detection by INVADER-directed cleavage is equally applicable to the detection of RNA and DNA targets. In addition, the comparison of the cleavage performance of longer and shorter probes in the absence of a stacker oligonucleotide give one example of the distinction between the performance of the miniprobe/stacker system and the performance of the mid-range and long probes in the detection of nucleic acid targets.

Example 40

Figure 85C:
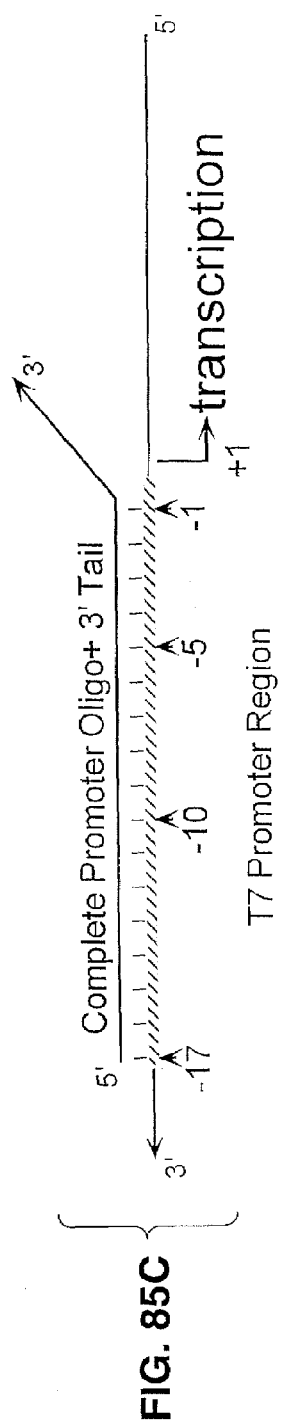
Figure 93D:
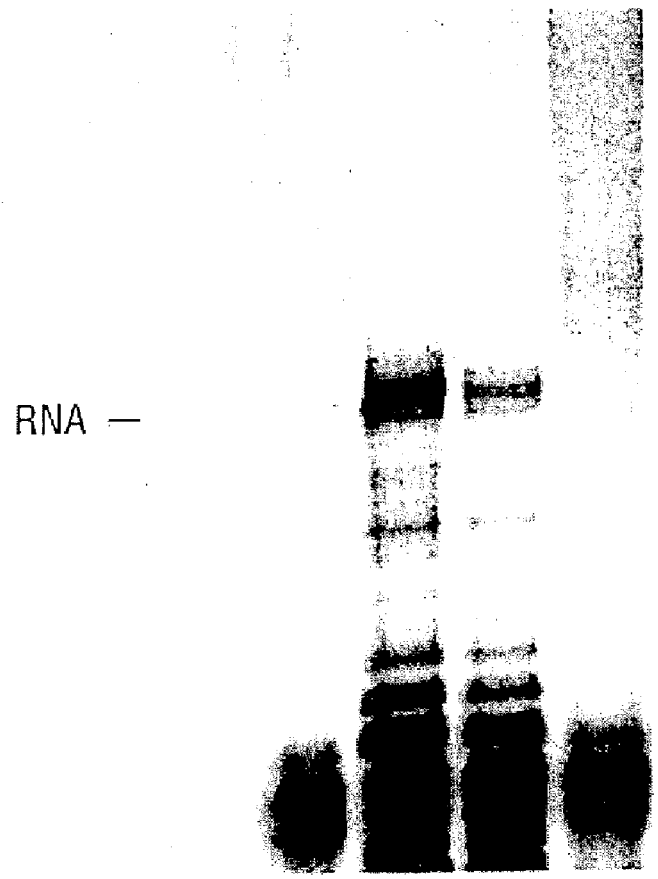
FIG. 93 shows the image generated by a fluorescence imager which shows that the presence of an unpaired 3' tail on a full-length promoter oligonucleotide decreases but does not abolish transcription. Beneath the image are schematics showing the nucleic acids tested in reactions 1-4; these schematics show SEQ ID NOS:123-125.
Figure 93D:
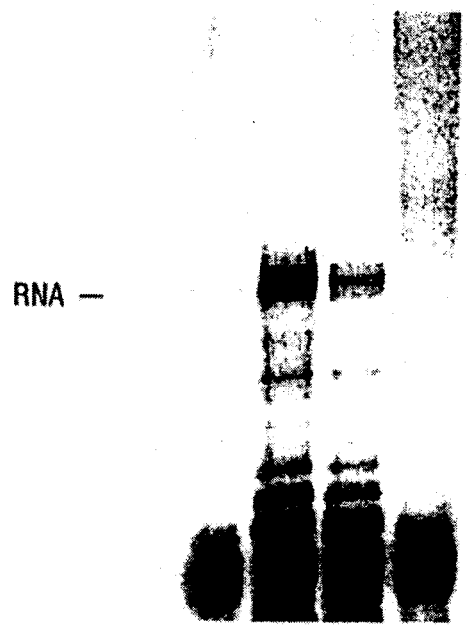
Figure 94:
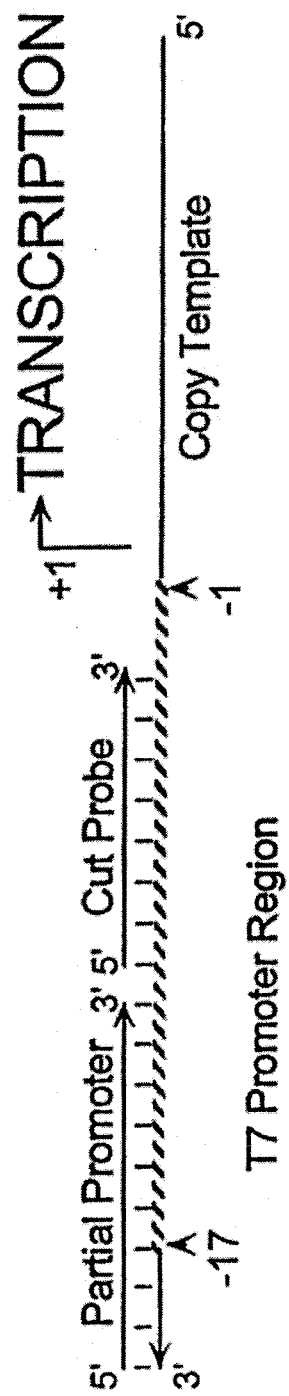
Figure 95A:
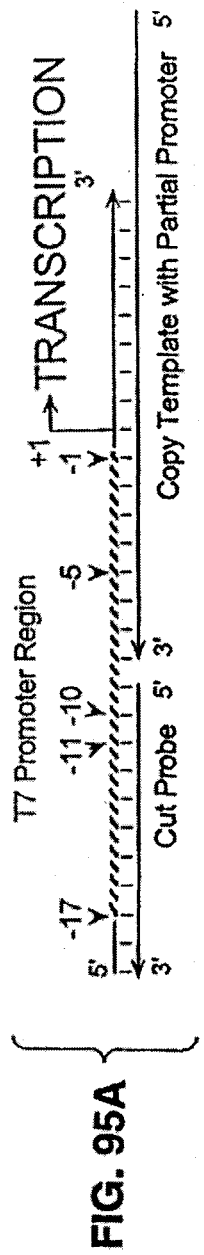
Figure 95B:
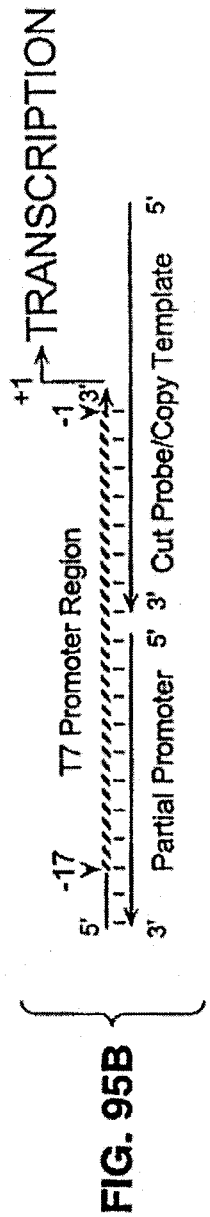
Figure 95C:
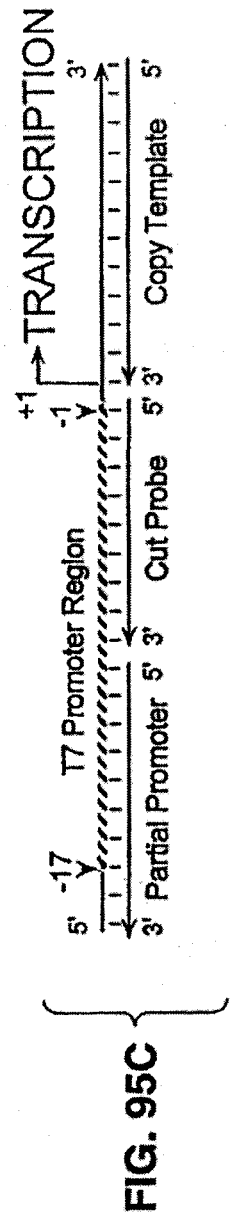
Figure 95D:
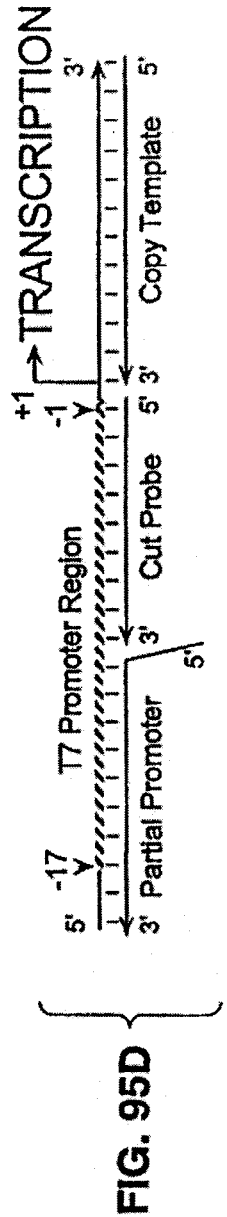
Figure 96:
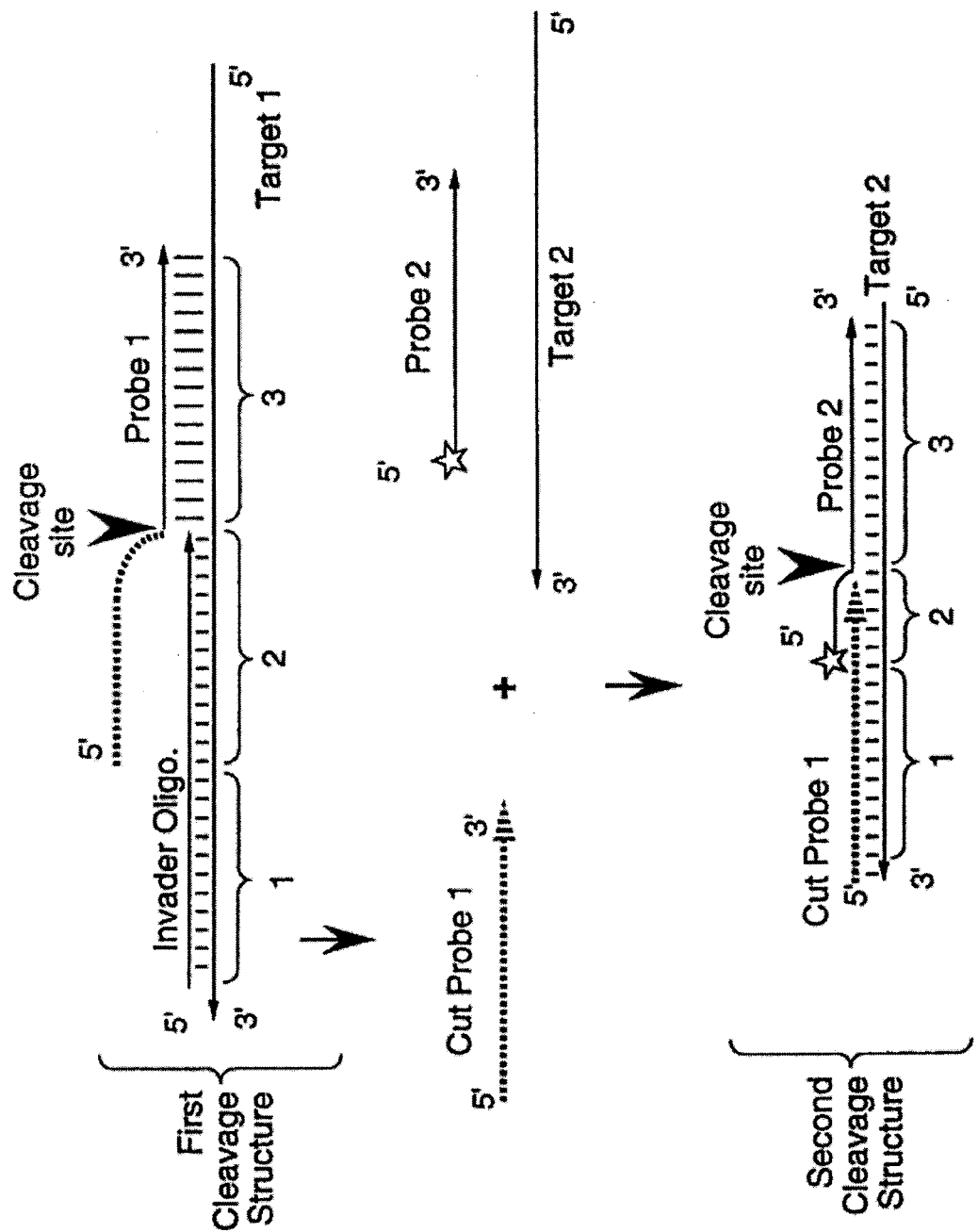
Figure 97:
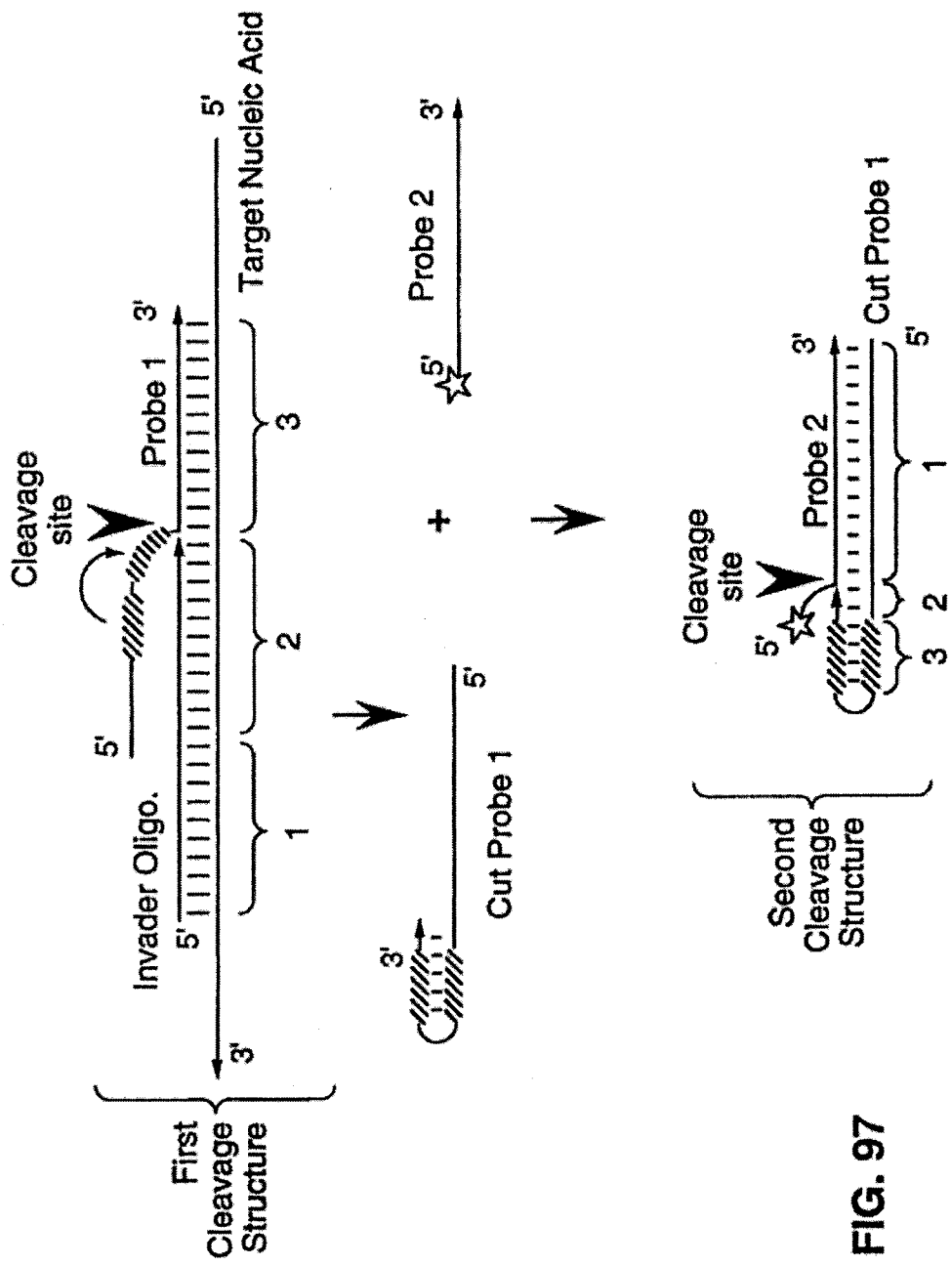

Effect of an Unpaired 3' Tail on Transcription from a Complete (Un-Nicked) Promoter In designing the method of transcription-based visualization of the products of INVADER-directed cleavage, it was first necessary to assess the effect of a 3' tail on the efficiency of transcription from a full length promoter. The duplexes tested in this Example are shown at the bottom of FIG. 93, and are shown schematically in FIGS. 85A-C.

Transcription reactions were performed using the MEGAshortscript™ system from Ambion, Inc. (Austin, Tex.), in accordance with the manufacturer's instructions with the exception that a fluorescein labeled ribonucleotide was added. Each DNA sample was assembled in 4 µl of RNAse-free $dH_2O$. Reactions 1-3 each contained 10 pmole of the copy template oligo 150 (SEQ ID NO:123); reaction 2 contained 10 pmole of the promoter oligo 151 (SEQ ID NO:124); sample 3 contained 10 pmole of the 3' tailed promoter oligo 073-065 (SEQ ID NO:125); sample 4 had no added DNA. To each sample, 6 µl of a solution containing 1 µl of 10× Transcription Buffer, 7.5 mM each rNTP, 0.125 mM fluorescein-12-UTP (Boehringer) and 1 µl T7 MEGAshortscript™ Enzyme Mix was added. The samples were then incubated at 37° C. for 1 hour. One microliter of RNase-free DNase 1 (2 U/µl) was added to each sample and the samples were incubated an additional 15 minutes at 37° C. The reactions were then stopped by the addition of 10 µl of a solution of 95% formamide, 5 mM $Na_2EDTA$, with loading dyes. All samples were heated to 95° C. for 2 minutes and 4 µl of each sample were resolved by electrophoresis through a 20% denaturing acrylamide gel (19:1 cross-linked) with 7M urea, in a buffer containing 45 mM Tris-Borate (pH 8.3), 1.4 mM EDTA. The gel was analyzed with a FMBIO II fluorescence image analyzer, and the resulting image is shown in FIG. 93. The RNA produced by successful transcription appears near the middle of the panel, as indicated ("RNA").

Examination of the products of transcription shown in lanes 2 and 3 show that the presence of the 3' tail on the full-length promoter has an adverse affect on the efficiency of transcription, but does not shut it off completely. Because the objective of the transcription-based visualization assays of the present invention is to discriminate between uncleaved probe and the shorter products of the invasive cleavage assay (cut probe), these data indicate that production of a full-length promoter in the cleavage reaction would be difficult to resolve from the background created by transcription from promoters containing the uncleaved probe if no other oligonucleotides were included in the assay. Means of suppressing transcription from such a branched promoter are discussed in the Description of the Invention and discussed below in Ex. 43.

Example 41

Examination of the Influence of the Position of the Nick on the Efficiency of Transcription from Partial and Complete Composite Bacteriophage T7 Promoters In the Description of the Invention, the procedure for testing prospective promoter pieces for suitability in an invasive cleavage-linked assay is described. One aspect of the test is to examine the effect a chosen nick site has on the efficiency of transcription from the final composite promoter. In addition, the individual pieces of nicked promoter are tested for transcription activity in the presence of the full-length un-nicked strand. In this experiment, a comparison on these points is made between a composite promoter having a nick in the non-template strand between nucleotides −11 and −10 relative to the initiation site (+1), and a promoter having a nick on the same strand, but positioned between nucleotides −8 and −7. The Figure numbers for the schematic representations of the contents of each reaction are indicated below each lane (e.g., 85A=FIG. 85A). The site where the nick would be in a fully assembled composite promoter using the reaction oligonucleotides is also indicated below each lane ("−11/−10" and "−8/−7").

Transcription reactions were performed using the MEGAshortscript™ system, in accordance with the manufacturer's instructions, but with the exception that a fluorescein labeled ribonucleotide was added. Each DNA sample was assembled in 4 μl of RNAse-free dH$_2$O. Reaction 1 had no added DNA. Reactions 2-9 each contained 10 pmole of 10 the copy template oligo 150 (SEQ ID NO:123). Reactions 3 and 4 contained 10 pmole of the −11 "cut" probe (oligo 073-061-01; SEQ ID NO:127) or 20 pmole of the −10 partial promoter oligo 073-061-02 (SEQ ID NO:130), respectively, and reaction 5 contained both. Reactions 6 and 7 contained either the 10 pmole of the −8 "cut" probe (oligo 073-062-01; SEQ ID NO:126) or 20 pmoles of the −7 partial promoter oligo 073-062-02 (SEQ ID NO:129), respectively, and reaction 8 contained them both. Reaction 9 contained 10 pmole of the intact promoter oligo 151 (SEQ ID NO:124).

Figure 92:
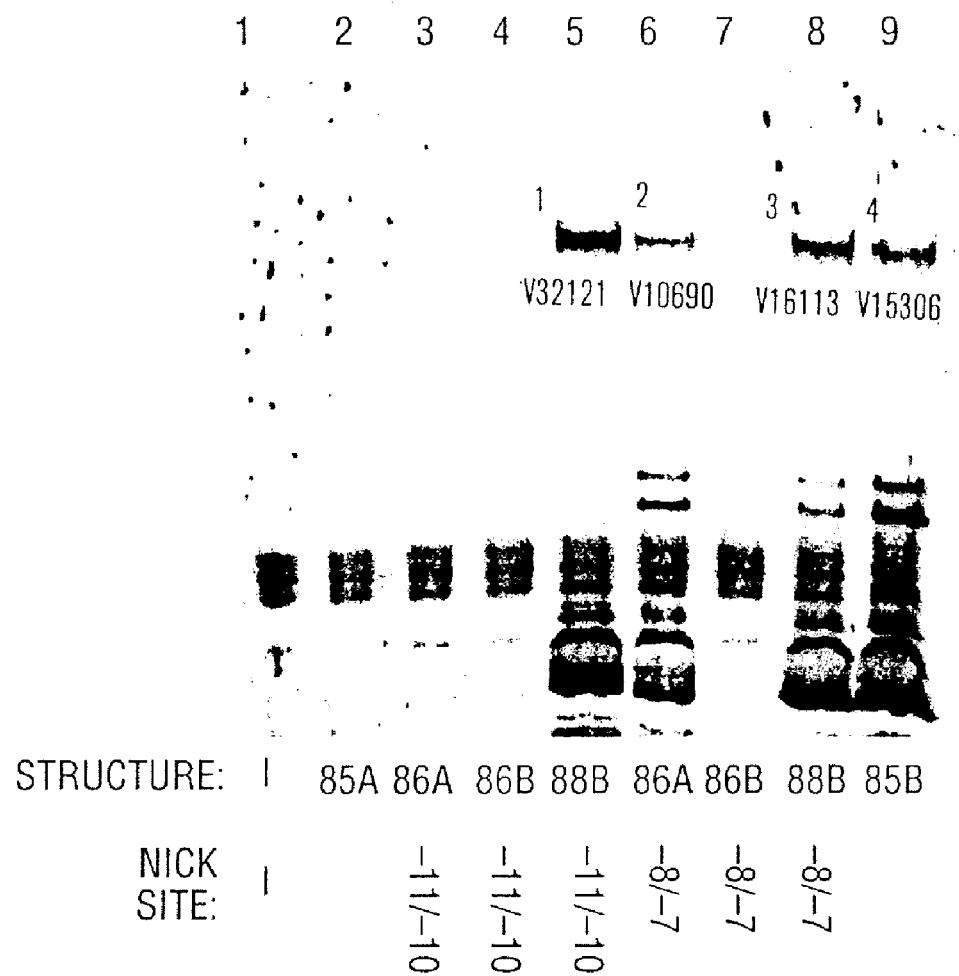
FIG. 92 shows the image generated by a fluorescence imager which shows that the location of the nick site in a nicked composite T7 promoter can effect the efficiency of transcription.

The transcription reactions were initiated, incubated, terminated and the reaction products were resolved and imaged as described in Ex. 40. The resulting image is shown in FIG. 92. The reaction numbers correspond to the lane numbers above the image. The RNA created by successful transcription appears in the upper third of the image. Comparison to the positive control reaction (rxn. 9) shows that the full-length RNA produced by each of the composite promoters is the same size as that produced in the control reaction, indicated that transcription initiated at the same site in each reaction.

In FIG. 92, lanes 3, 4, and 5 compare transcription from the two species of partially assembled promoters (see schematics in FIGS. 86A and B) and the fully assembled composite promoter (FIG. 88B) having a nick between nucleotides −11 and −10 relative to the start of transcription. It can be seen from these data that neither partial promoter (lanes 3 and 4) is able to support transcription of the copy template, but that the composite promoter (lane 5) with this nick site is strongly transcribed. Surprisingly, comparison to the control reaction (lane 9) shows that the presence of a nick at this site (−11/−10) actually enhances transcription. While not limiting the present invention to any particular mechanism, it is believed that the enhancement of transcription is a result of both suppressing the formation of the shorter abortive transcripts and by allowing greater accumulation of the full length product. This result is highly reproducible.

In FIG. 92, lanes 6, 7, and 8 compare transcription a similar set of partial and complete promoters in which the nick is shifted 3 residues closer to the transcription start site. Examination of lane 6 shows that the presence of 3 extra bases on the −8 "cut" probe (compared to the −11 "cut" probe in lane 3) allow this partial promoter to initiate transcription. This indicates that the −8/−7 site would be a poor choice for use in this embodiment of the present invention.

This experiment demonstrates the process for determining the suitable placement of a nick within a promoter assembly to achieve the desired result. Similar tests can easily be designed for testing other nicks within the bacteriophage T7 promoter tested in this Example, or for testing suitable nick placement in any desired phage, prokaryotic or eukaryotic promoter.

Example 42

Detection of the Products of INVADERr-Directed Cleavage Through Transcription from a Composite Promoter The Examples described above indicate that a small oligonucleotide can be used to complete assembly of a composite T7 promoter, thereby enabling transcription from that promoter. Earlier Examples demonstrate that the invasive cleavage reaction can be used release specific small oligonucleotide products from longer probe oligonucleotides. In this Example, it is demonstrated that these two observations can be combined, and that the products of the invasive cleavage reaction can be used to complete a promoter and enable subsequent transcription. The schematic representations of the composite promoters tested in this Example are shown in FIG. 88.

Two invasive cleavage reactions were set up, one without (rxn. 1) and one with (rxn. 2) input target DNA. The reactions (1 and 2) comprised 10 mM MOPS (pH 7.5), 0.05% Tween-20, 0.05% NP-40 and 20 pmoles probe oligo 073-067-01 (SEQ ID NO:132) and 10 pmoles INVADER oligo 073-073-02 (SEQ ID NO:134) in a volume of 14 μl. Reaction 2 also included 100 fmoles M13mp18 ssDNA. The samples were placed at 60° C. and 6 μl of a solution containing 20 ng of Mja FEN-1 and 40 mM Mg$_2$Cl were added to each sample to start the reactions. The samples were incubated at 60° C. for 30 minutes and stopped by the addition of 3 μl of 2.5M NaOAc, 83 mM Na$_2$EDTA (pH 8.0). Each sample was transferred to a 1.5 ml microcentrifuge tube and then the DNAs were precipitated by the addition of 60 μl of chilled 100% ethanol, and were stored at −20° C. for 20 minutes. The pellets were collected by microcentrifugation, washed once with 80% ethanol to remove excess salt, then dried under vacuum. The product of this invasive cleavage reaction is a 12 nt oligonucleotide having the sequence: 5'-CGAAATTAATAC-3' (SEQ ID NO:128), termed the −12 cut probe (same sequence as oligo 073-073-03).

For transcription, the dried samples were each dissolved in 4 µl of a solution containing 1 pmole copy template oligo 150 and 2 pmoles −11 partial promoter oligo 073-073-012 (SEQ ID NO:131). Control samples 3 and 4 each contained 1 pmole of the copy template oligo 150; sample 3 also contained 1 pmole probe oligo 073-067-01 (SEQ ID NO:132) and 2 pmoles −11 partial promoter oligo 073-073-012 (see structure 88A); sample 4 contained 1 pmole −12 "cut" probe oligo 073-073-03 (SEQ ID NO:128) and 2 pmoles −11 partial promoter oligo 073-073-012 (see structure 88B). These are the structures that would be expected to exist in the transcription reactions from the two invasive cleavage reactions described above.

The transcription reactions were initiated, incubated, terminated and the products were resolved and imaged as described in Ex. 40. The resulting image is shown in the right half of FIG. 89 (lanes 6-9). Samples 3 and 4 appear in lanes 6 and 7, respectively, and the reactions 1 and 2 from the invasive cleavage reaction products (indicated by the use of the lower case "i"), appear in lanes 8 and 9, respectively. The number of the Fig. showing the schematic representation of the expected promoter structure in each reaction is indicated above each lane, and the placement of the nick is also indicated. The uppercase letters indicate which structure in the particular Figure to examine for each reaction. The lowercase "i" above lanes 8 and 9 indicate that these transcriptions were derived from actual invasive cleavage reactions. These products are compared to the RNA produced in the control reaction in lane 5, the procedure for which is described in Ex. 44. The RNA created by successful transcription appears in the upper third of the panel (indicated by "RNA").

The reaction shown in lane 6 shows no transcription. This demonstrates that a nick between nucleotides −12 and −11 in the on-template strand of the T7 promoter eliminates transcription if the promoter is assembled from uncut probe such as the 3' end of the probe forms a branch within the promoter sequence. This is in contrast to the results seen with the −11/−10 nick examined below. Further, the transcript apparent in lane 7 shows that an unbranched promoter with a nick at the same site (−12/−11) produces the correct RNA, with few abortive initiation products (see lanes 2 and 5 of FIG. 89, described in Ex. 44). The reactions in lanes 8 and 9 demonstrate that the same effect is observed when the invasive cleavage reaction is the sole source of the upstream piece (−12 cut probe) of the T7 promoter. It is worthy of note that the promoter that is transcribed in lane 8 is made complete by the presence of 1 pmole of a synthetic "cut" probe oligo, without any uncut probe in the mixture, while the promoter that is transcribed in lane 9 is completed by the product of an invasive cleavage reaction that had only 100 fmole of target DNA in it. This reaction also included the residual uncut probe (up to approx. 10 pmoles), which may compete for binding at the same site. Nonetheless, the transcriptions from the invasive cleavage reaction products are only slightly reduced in efficiency, and are just as free of background as is the "no target" sample (lane 8). This Example clearly demonstrates that the cleavage products from the invasive cleavage reaction can be used in combination with a partial promoter oligo to promote the production of RNA, without background transcription generated by the presence of the uncut probe. This RNA product is clearly dependent on the presence of the target material in the invasive cleavage reaction.

Example 43

Shutting Down Transcription from a "Leaky" Branched T7 Composite Promoter Through the Use of a Downstream Partial Promoter Oligonucleotide Having a 5' Tail The previous Example demonstrated that placement of a nick in the non-template strand of a bacteriophage T7 promoter between the −12 and −11 nucleotides, relative to the transcription start site, prevents transcription of the branched promoter while allowing transcription when the composite promoter is assembled using the cut probe. When the nick is placed in other locations in the T7 promoter, transcription may be initiated from either promoter, although it is usually less efficient from the branched promoter. This Example demonstrates that the addition of a 5' tail that can base pair to the uncut probe (FIG. 90A) to the downstream partial promoter piece effectively blocks transcription from that promoter, but does not prevent transcription when a cut probe completes the promoter (FIG. 90B).

Two invasive cleavage reactions were set up, one without (rxn. 7) and one with (rxn. 8) input target DNA. The reactions (7 and 8) comprised 10 mM MOPS (pH 7.5), 0.05% Tween-20, 0.05% NP-40 and 20 pmoles probe oligo 073-067-01 (SEQ ID NO:132) and 10 pmoles INVADER oligo 073-067-02 (SEQ ID NO:133) in a volume of 14 µl. Reaction 8 also included 100 fmoles M13mp18 ssDNA. The samples were placed at 60° C. and 6 µl of a solution containing 20 ng of Mja FEN-1 and 40 mM Mg$_2$Cl were added to each sample to start the reactions. The samples were incubated at 60° C. for 30 minutes and then stopped by the addition of 3 µl of 2.5M NaOAc, 83 mM Na$_2$EDTA (pH.8.0). Each sample was transferred to a 1.5 ml microcentrifuge tube and the DNAs were precipitated, washed and dried as described in Ex. 42. The product of this invasive cleavage reaction is 13 nt oligonucleotide sequence, 5'-CGAAATTAATACG-3' (SEQ ID NO:127), termed the −11 cut probe (same sequence as oligo 073-061-01 which is referred to as the −11 "cut" probe to indicate it was not generated in an invasive cleavage reaction).

In the transcription reactions, all of the DNAs were dissolved in 4 µl of RNase-free dH$_2$O. Sample 1 had no added DNA, samples 2-8 contained 1 pmole of the copy template oligo 150 (SEQ ID NO:123). In addition, sample 3 contained 1 pmole of −11 "cut" probe oligo 073-061-01 (SEQ ID NO:127) and 2 pmoles of −10 partial promoter oligo 073-061-02 (SEQ ID NO:130), sample 4 contained 1 pmole of probe oligo 073-067-01 and 2 pmoles of −10 partial promoter oligo 073-061-02. Control sample 5 contained 1 pmole of probe oligo 073-067-01 and 2 pmoles of partial promoter w/5' tail oligo 073-074 (5'-TACTGACTCACTATAGGGTCTTC-TATGGAG GTC-3' (SEQ ID NO:146) (see structure in FIG. 90A) and sample 6 contained 1 pmole of −11 "cut" probe oligo 073-061-01 and 2 pmoles of partial promoter w/5' tail oligo 073-074 (see structure in FIG. 90B). These are the structures (i.e., 90A and 90B) that would be expected to exist in the transcription reactions from the two invasive cleavage reactions described above.

The dried samples 7 and 8 from the invasive cleavage (above) were each dissolved in 4 µl of dH$_2$O containing 1 pmole copy template oligo 150 and 2 pmoles partial promoter w/5' tail oligo 073-074. The transcription reactions were initiated, incubated, terminated and the reaction products were resolved and imaged as described in Ex. 40. The resulting image is shown in FIG. 91.

Figure 91:
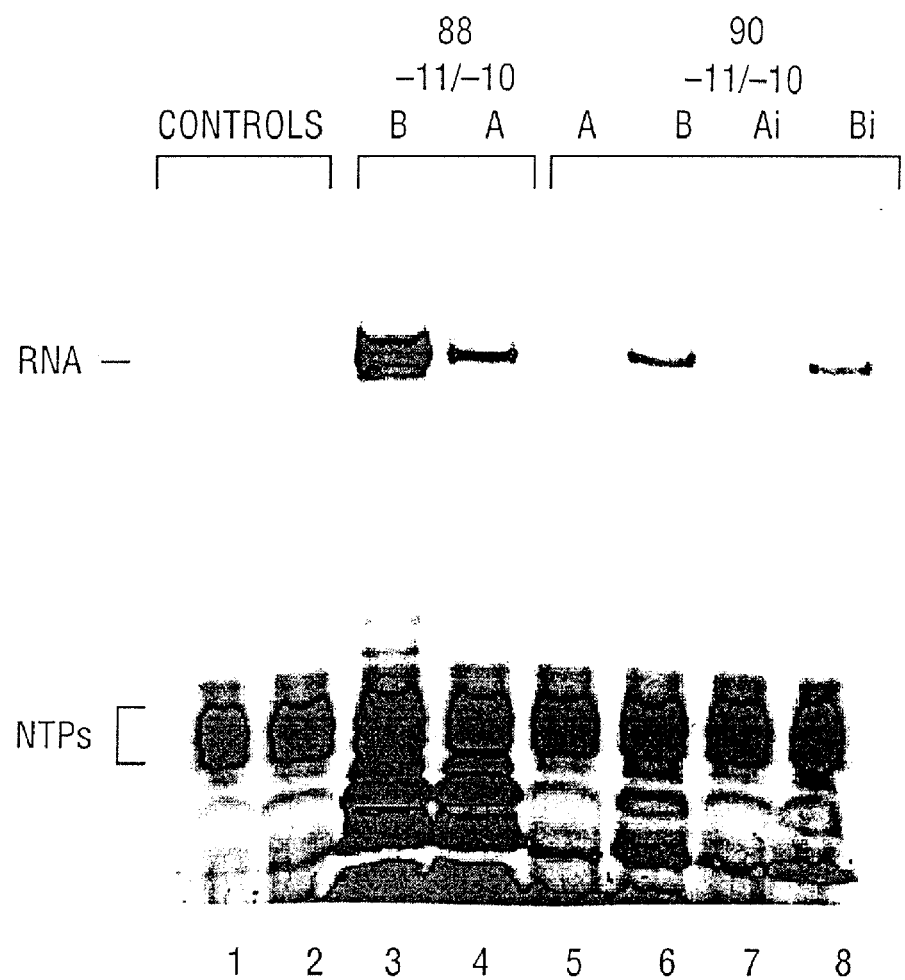
FIG. 91 shows the image generated by a fluorescence imager which shows that transcription from a "leaky" branched T7 composite promoter can be shut down by the use of a downstream partial promoter oligonucleotide having a paired 5' tail.

In FIG. 91 the lane numbers correspond to the sample numbers; the number of the Figure showing the schematic representation of the expected promoter structure in each reaction is indicated above each lane ("88" and "90"), and the placement of the nick is also indicated ("−11/−10"). The upper-case letters indicate which structure in the particular Figure to examine for each reaction. The lower case "i" above lanes 7 and 8 indicates that these transcriptions were derived from actual invasive cleavage reactions. The RNA created by successful transcription appears in the upper third of the panel, as indicated ("RNA").

The control reactions in lanes 1 and 2, having either no DNA or having the only the copy template, produced no RNA as expected. The product in lane 4 demonstrates that the branched T7 promoter with a nick in the non-template strand between nucleotides −11 and −10 can support transcription, albeit not as efficiently as the un-branched promoter with the nick at the same site (lane 3). Examination of lane 5 shows that the use of a partial promoter oligonucleotide with a short 5' tail that can basepair to the uncut probe as depicted in FIG. 90A, effectively suppresses this transcription but allows transcription when the probe does not have a 3' tail (lane 6; schematic FIG. 90B). The reactions in lanes 7 and 8 demonstrate that the same effect as observed when the invasive cleavage reaction is the sole source of the upstream piece (−11 cut probe, SEQ ID NO:127) of the T7 promoter. It is worthy of note that the promoter that is transcribed in sample 6 is made complete by the presence of 1 pmole of a synthetic "cut probe", without any uncut probe in the mixture, while the promoter that is transcribed in sample 8 is completed by the product of an invasive cleavage reaction that had only 100 fmole of target DNA in it. This reaction also included the residual uncut probe (up to approximately 19 pmoles), which may compete for binding at the same site. Nonetheless, the transcriptions from the invasive cleavage reaction products are just as strong and just as free of background in the "no target" samples.

This Example clearly demonstrates that the cleavage products from the invasive cleavage reaction can be used in combination with a partial promoter oligonucleotide having a 5' tail to promote the production of RNA, without background transcription generated by the uncut probe. This RNA product is clearly dependent on the presence of the target material in the invasive cleavage reaction.

Example 44

Creation of a Complete Bacteriophage T7 Promoter by DNA Polymerase-Mediated Extension of a Cut Probe Comprising a Partial T7 Promoter As demonstrated in the Examples above, transcription cannot occur from the T7 promoter unless a complete promoter region is present. In the above Examples, a complete promoter containing a nick in one strand was created by annealing a cut probe generated from an invasive cleavage reaction to a copy template that was annealed to a partial promoter oligo. An alternative means of creating a complete promoter in a manner dependent upon detection of a target sequence in an invasive cleavage reaction is to anneal the cut probe to a copy template devoid of a partial promoter oligo. The 3'-OH present at the end of the annealed cut probe is then extended by a DNA polymerase to create a complete and un-nicked promoter that is transcription-competent.

Figure 87:
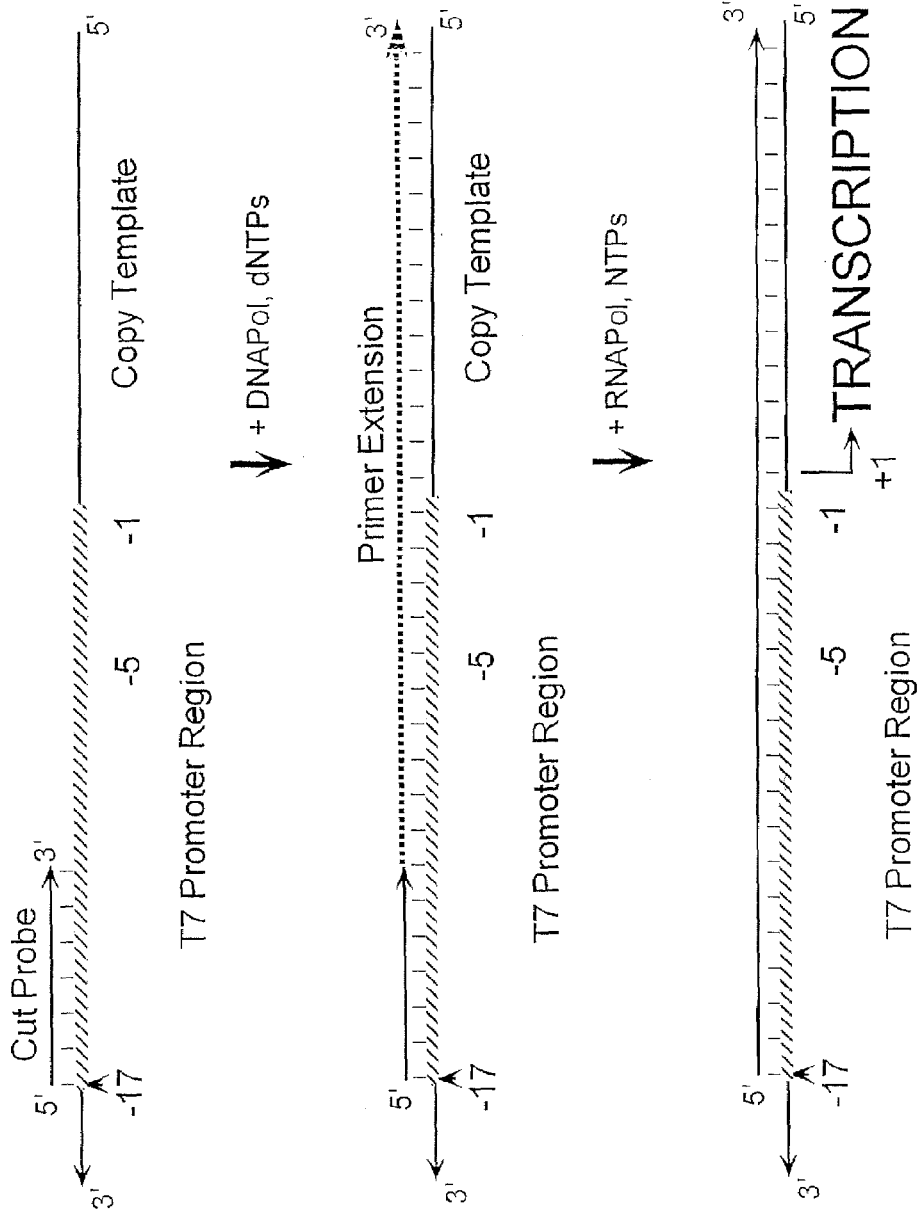
FIG. 87 provides a schematic illustrating one embodiment of the present invention wherein a template-dependent DNA polymerase is used to extend a cut probe to complete a T7 promoter region and thereby allow transcription.

In this Example, the promoter was made complete through the use of primer extension, rather that by the co-hybridization of another oligonucleotide. The reaction steps are diagrammed schematically in FIG. 87. Two invasive cleavage reactions were set up, one without (rxn. 1) and one with (rxn. 2) input target DNA. The reactions (1 and 2) comprised 10 mM MOPS (pH 7.5), 0.05% Tween-20, 0.05% NP-40 and 20 pmoles probe oligo 073-067-01 (SEQ ID NO:132) and 10 pmoles INVADER oligo 073-073-02 (SEQ ID NO:134) in a volume of 14 µl. Reaction 2 also included 100 fmoles M13mp18 ssDNA. The samples were placed at 60° C. and 6 µl of a solution containing 20 ng of Mja FEN-1 and 40 mM $Mg_2Cl$ were added to each sample to start the reactions. The samples were incubated at 60° C. for 30 minutes and stopped by the addition of 3 µl of 2.5M NaOAc, 83 mM $Na_2$EDTA (pH 8.0). Each sample was transferred to a 1.5 ml microcentrifuge tube and then the DNAs were precipitated, washed and dried as described in Ex. 42. The product of this invasive cleavage reaction is the 12 nt oligonucleotide sequence: 5'-CGAAAT-TAATAC-3' (SEQ ID NO:128), termed the −12 cut probe (same sequence as oligo 073-073-03 which is referred to as the −12 "cut" probe to indicate it was not generated in an invasive cleavage reaction).

To allow extension of these products using a template-dependent DNA polymerase, a 20 µl solution containing 20 mM Tris-HCl (pH 8.5), 1.5 mM $Mg_2Cl$, 50 mM KCl, 0.05% Tween-20, 0.05% NP-40, 25 µM each dNTP, 0.25 units Taq DNA polymerase (Boehringer) and 2 µM copy template oligo 150 (SEQ ID NO:123) was added to each of the dried cleavage samples. The samples were incubated at 30° C. for 1 hr. The primer extension reactions were stopped by the addition of 3 µl of 2.5M NaOAc with 83 mM $Na_2$EDTA (pH 8.0)/sample. Each sample was transferred to a 1.5 ml microcentrifuge tube and the DNAs were precipitated, washed and dried as described in Ex. 42.

Samples 1 and 2 were then dissolved in 4 µl RNase-free $dH_2O$. Samples 3, 4 and 5 are control reactions: sample 3 was 4 µl of RNase-free $dH_2O$ without added DNA, sample 4 contained 1 pmole of the copy template oligo 150 (SEQ ID NO:123) in 4 µl of RNase-free $dH_2O$, and sample 5 contained 1 pmole of the same copy template and 1 pmole of the complete promoter oligo 151 (SEQ ID NO:124) in RNase-free $dH_2O$.

Transcription reactions were performed using the MEGAshortscript™ system, in accordance with the manufacturer's instructions, but with the addition of a fluorescein labeled ribonucleotide. To each sample, 6 µl of a solution containing 1 µl of 10× Transcription Buffer, 7.5 mM each rNTP, 0.125 mM fluorescein-12-UTP (Boehringer) and 1 µl T7 MEGAshortscript™ Enzyme Mix was added. The samples were incubated at 37° C. for 1 hour. One µl of RNase-free DNase 1 (2 U/µl) was added to each sample and they were incubated an additional 15 minutes at 37° C. The reactions were stopped by the addition of 10 µl of a solution of 95% formamide, 5 mM NaEDTA, with loading dyes. All samples were heated to 95° C. for 2 minutes and four µl of each sample were resolved by electrophoresis through a 20% denaturing acrylamide gel (19:1 cross-linked) with 7 M urea, in a buffer containing 45 mM Tris-Borate (pH 8.3), 1.4 mM EDTA. The results were imaged using the Molecular Dynamics Fluoroimager 595, with excitation at 488 nm and, emission detected at 530 nm.

Figure 89:
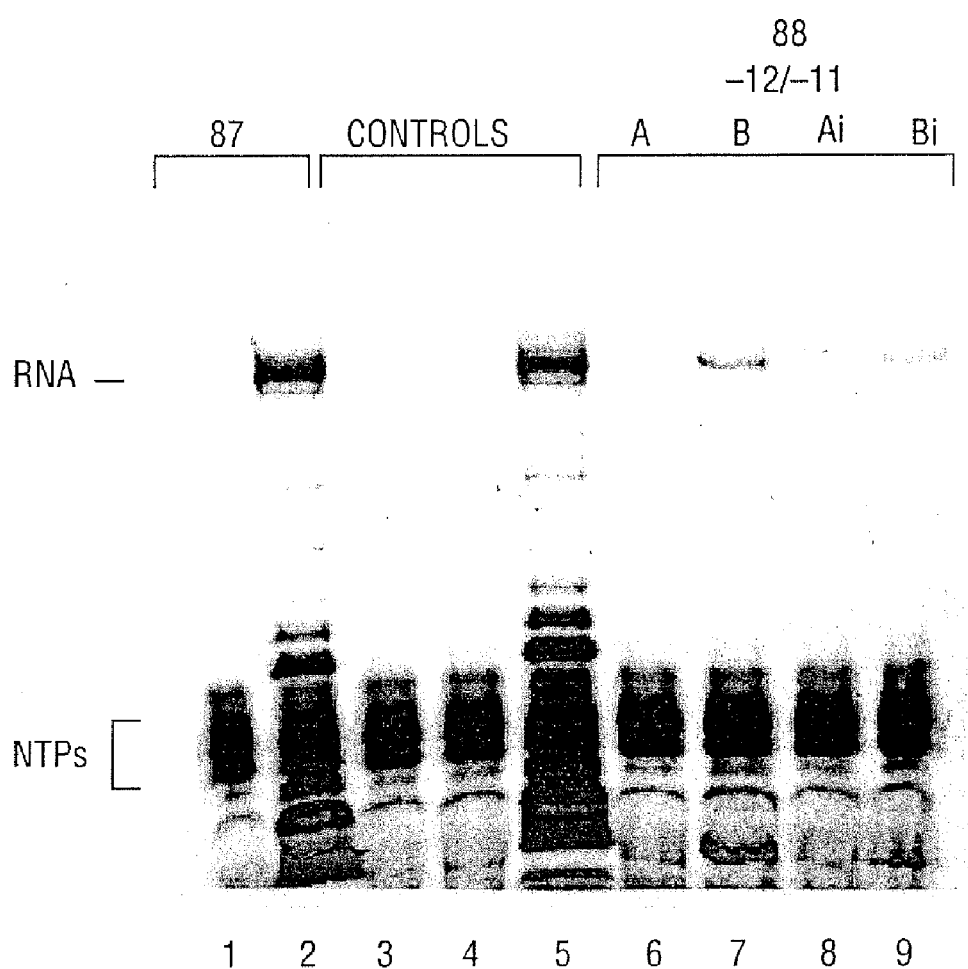
FIG. 89 shows the image generated by a fluorescence imager which shows that primer extension can be used to complete a partial promoter formed by a cut probe (lanes 1-5) and that annealing a cut probe generated in an invasive cleavage assay can complete a partial T7 promoter to permit transcription (lanes 6-9).

The resulting image is shown in lanes 1 through 5 of FIG. 89; the lane numbers correspond to the sample numbers. The Figure numbers corresponding to the schematic representations of the promoters transcribed in each reaction as indicated above the lanes. The RNA product from successful transcription appears in the upper third of the panel, as indicated ("RNA"). Unincorporated labeled nucleotide appears as a dense signal near the bottom ("NTPs"). Short transcription products caused by aborted initiation events (Milligan and Uhlenbeck, Methods Enzymol., 180:51 [1989]) appear as bands just above the free nucleotide in the lanes showing active transcription (i.e., lanes 2 and 5).

It can clearly be seen from the data in lanes 1 and 2 that the transcription is dependent on the presence of the target material in the invasive cleavage reaction. It is shown elsewhere (see lane 3, FIG. 92) that the product of the cleavage reaction is not in itself sufficient to allow transcription from the copy template. Thus, the action of the DNA polymerase in extending the hybridized cut probe across the promoter is a necessary step in enabling the transcription in this embodiment. These data clearly demonstrate that both template-dependent extension by DNA polymerase, and extension followed by transcription are suitable methods of visualizing the products of the invasive cleavage assay. As discussed in the Description of the Invention, the products of thermal breakdown that possess 3' terminal phosphates would not be extended, and would thus be precluded from contributing to background transcription.

Example 45

Test for the Dependence of an Enzyme on the Presence of an Upstream Oligonucleotide When choosing a structure-specific nuclease for use in a sequential invasive cleavage reaction it is preferable that the enzyme have little ability to cleave a probe 1) in the absence of an upstream oligonucleotide, and 2) in the absence of overlap between the upstream oligonucleotide and the downstream labeled probe oligonucleotide. FIGS. 99a-e depicts the several structures that can be used to examine the activity of an enzyme that is confronted with each of these types of structures. The structure a (FIG. 99a) shows the alignment of a probe oligonucleotide with a target site on bacteriophage M13 DNA (M13 sequences shown in FIG. 99 are provided in SEQ ID NO:163) in the absence of an upstream oligonucleotide. Structure b (FIG. 99b) is provided with an upstream oligonucleotide that does not contain a region of overlap with the labeled probe (the label is indicated by the star). In structures c, d and e (FIGS. 99c-e) the upstream oligonucleotides have overlaps of 1, 3 or 5 nucleotides, respectively, with the downstream probe oligonucleotide and each of these structures represents a suitable invasive cleavage structure. The enzyme Pfu FEN-1 was tested for activity on each of these structures and all reactions were performed in duplicate.

Each reaction comprised 1 µM 5' TET labeled probe oligonucleotide 89-15-1 (SEQ ID NO:152), 50 nM upstream oligonucleotide (either oligo 81-69-2 [SEQ ID NO:153], oligo 81-69-3 [SEQ ID NO:154], oligo 81-69-4 [SEQ ID NO:155], oligo 81-69-5 [SEQ ID NO:156], or no upstream oligonucleotide), 1 fmol M13 target DNA, 10 mg/ml tRNA and 10 ng of Pfu FEN-1 in 10 µl of 10 mM MOPS (pH 7.5), 7.5 mM $MgCl_2$ with 0.05% each of Tween 20 and Nonidet P-40.

All of the components except the enzyme and the $MgCl_2$ were assembled in a final volume of 8 µl and were overlaid with 10 µl of Chill-Out™ liquid wax. The samples were heated to the reaction temperature of 69° C. The reactions were started by the addition of the Pfu FEN-1 and $MgCl_2$, in a 2 µl volume. After incubation at 69° C. for 30 minutes, the reactions were stopped with 10 µl of 95% formamide, 10 mM EDTA, 0.02% methyl violet. Samples were heated to 90° C. for 1 min immediately before electrophoresis through a 20% denaturing acrylamide gel (19:1 cross-linked), with 7 M urea, in a buffer of 45 mM Tris-Borate, pH 8.3, 1.4 mM EDTA.

Gels were then analyzed with a FMBIO-100 Hitachi FMBIO fluorescence imager. The resulting image is displayed in FIG. 100.

In FIG. 100, lanes labeled "a" contain the products generated from reactions conducted without an upstream oligonucleotide (structure a), lanes labeled "b" contain an upstream oligonucleotide that does not invade the probe/target duplex (structure b). Lanes labeled "c", "d" and "e" contain the products generated from reactions conducted using an upstream oligonucleotide that invades the probe/target duplex by 1, 3 or 5 bases, respectively. The size (in nucleotides) of the uncleaved probe and the cleavage products is indicated to the left of the image in FIG. 100.

As shown in FIG. 100, cleavage of the probe was not detectable when structures a and b were utilized. In contrast, cleavage products were generated when invasive cleavage structures were utilized (structures c-e). These data show that the Pfu FEN-1 enzyme requires an overlapping upstream oligonucleotide for specific cleavage of the probe.

Any enzyme may be examined for its suitability for use in a sequential invasive cleavage reaction by examining the ability of the test enzyme to cleave structures a-e (it is understood by those in the art that the specific oligonucleotide sequences shown in FIGS. 99a-e need not be employed in the test reactions; these structures are merely illustrative of suitable test structures). Desirable enzymes display little or no cleavage of structures a and b and display specific cleavage of structures c-e (i.e., they generate cleavage products of the size expected from the degree of overlap between the two oligonucleotides employed to form the invasive cleavage structure).

Example 46

Use of the Products of a First Invasive Cleavage Reaction to Enable a Second Invasive Cleavage Reaction with a Net Gain in Sensitivity As discussed in the Description of The Invention above, the detection sensitivity of the invasive cleavage reaction can be increased by the performing a second round of invasive cleavage using the products of the first reaction to complete the cleavage structure in the second reaction (shown schematically in FIG. 96). In this Example, the use of a probe that, when cleaved in a first invasive cleavage reaction, forms an integrated INVADER oligo and target molecule for use in a second invasive cleavage reaction, is illustrated (shown schematically in FIG. 97).

A first probe was designed to contain some internal complementarity so that when cleaved in a first invasive cleavage reaction the product ("Cut Probe 1") could form a target strand comprising an integral INVADER oligonucleotide, as depicted in FIG. 97. A second probe was provided in the reaction that would be cleaved at the intended site when hybridized to the newly formed target/INVADER (FIG. 97). To demonstrate the gain in signal due to the performance of sequential invasive cleavages, a standard invasive cleavage assay, as described above, was performed in parallel.

All reactions were performed in duplicate. Each standard (i.e., non-sequential) invasive cleavage reaction comprised 1 µM 5' fluorescein-labeled probe oligo 073-182 (5' Fl-AGAAAGGAAGGGAAGAAAGCGAA-3'; SEQ ID NO:157), 10 nM upstream oligo 81-69-4 (5'-CTTGACGGG-GAAAGCCGGCGAACGTGGCGA-3'; SEQ ID NO:155), 10 to 100 attomoles of M13 target DNA, 10 mg/ml tRNA and 10 ng of Pfu FEN-1 in 10 µl of 10 mM MOPS (pH 7.5), 8 mM $MgCl_2$ with 0.05% each of Tween 20 and Nonidet P-40. All of the components except the enzyme and the $MgCl_2$ were assembled in a volume of 7 µl and were overlaid with 10 µl of Chill-Out™ liquid wax. The samples were heated to the reaction temperature of 62° C. The reactions were started by the addition of the Pfu FEN-1 and MgCl$_2$, in a 2 µl volume. After incubation at 62° C. for 30 minutes, the reactions were stopped with 10 µl of 95% formamide, 10 mM EDTA, 0.02% methyl violet.

Each sequential invasive cleavage reaction comprised 1 µM 5' fluorescein-labeled oligonucleotide 073-191 (the first probe or "Probe 1", 5' Fl-TGGAGGTCAAAACATCG ATAAGTCGAAGAAAGGAAGGGAAGAAAT-3'; SEQ ID NO:158), 10 nM upstream oligonucleotide 81-69-4 (5'-CT-TGACGGGGAAA GCCGGCGAACGTGGCGA-3'; SEQ ID NO:155), 1 µM of 5' fluorescein labeled oligonucleotide 106-32 (the second probe or "Probe 2", 5' Fl-TGTTTTGACCT CCA-3'; SEQ ID NO:159), 1 to 100 amol of M13 target DNA, 10 mg/ml tRNA and 10 ng of Pfu FEN-1 in 10 µl of 10 mM MOPS (pH 7.5), 8 mM MgCl$_2$ with 0.05% each of Tween 20 and Nonidet P-40. All of the components except the enzyme and the MgCl$_2$ were assembled in a volume of 8 µl and were overlaid with 10 µl of Chill-Out™ liquid wax. The samples were heated to the reaction temperature of 62° C. (this temperature is the optimum temperature for annealing of Probe 1 to the first target). The reactions were started by the addition of Pfu FEN-1 and MgCl$_2$, in a 2 µl volume. After incubation at 62° C. for 15 minutes, the temperature was lowered to 58° C. (this temperature is the optimum temperature for annealing of Probe 2 to the second target) and the samples were incubated for another 15 min. Reactions were stopped by the addition of 10 µl of 95% formamide, 20 mM EDTA, 0.02% methyl violet.

Samples from both the standard and the sequential invasive cleavage reactions were heated to 90° C. for 1 min immediately before electrophoresis through a 20% denaturing acrylamide gel (19:1 cross-linked), with 7 M urea, in a buffer of 45 mM Tris-Borate, pH 8.3, 1.4 mM EDTA. The gel was then analyzed with a Molecular Dynamics FluorImager 595. The resulting image is displayed in FIG. 101*a*. A graph showing measure of fluorescence intensity for each of the product bands is shown in FIG. 101*b*.

Figure 101A:
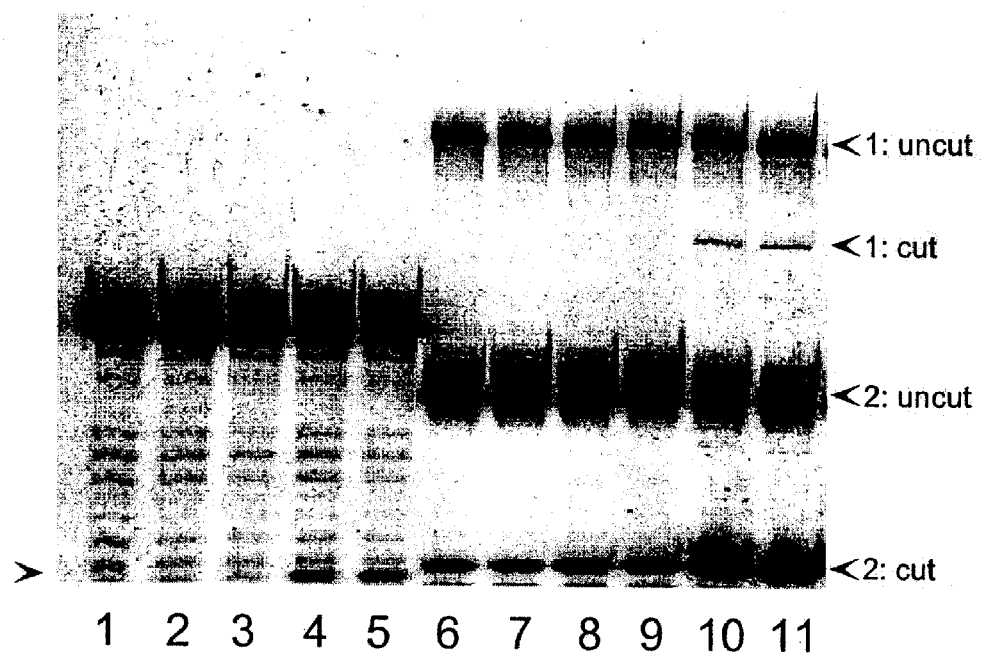
FIG. 101*a* shows the image generated by a fluorescence imager which compares the amount of product generated in a standard (i.e., a non-sequential invasive cleavage reaction) and a sequential invasive cleavage reaction.

In FIG. 101*a*, lanes 1-5 contain the products generated in standard invasive cleavage reactions that contained either no target (lane 1), 10 amol of target (lanes 2 and 3) or with 100 amol of target (lanes 4 and 5). The uncleaved probe is seen as a dark band in each lane about half way down the panel and the cleavage products appear as a smaller black band near the bottom of the panel, the position of the cleavage product is indicated by an arrow head to the left of FIG. 101*a*. The gray ladder of bands seen in lanes 1-5 is due to the thermal degradation of the probe as discussed above and is not related to the presence or absence of the target DNA. The remaining lanes display products generated in sequential invasive cleavage reactions that contained 1 amol of target (lanes 6 and 7), 10 amol of target (lanes 8 and 9) and 100 amol of target (lanes 10 and 11). The uncleaved first probe (Probe 1; labeled "1 uncut") is seen near the top of the panel, while the cleaved first probe is indicated as "1: cut". Similarly, the uncleaved and cleaved second probe are indicated as "2: uncut" and 2: cut," respectively.

Figure 101B:
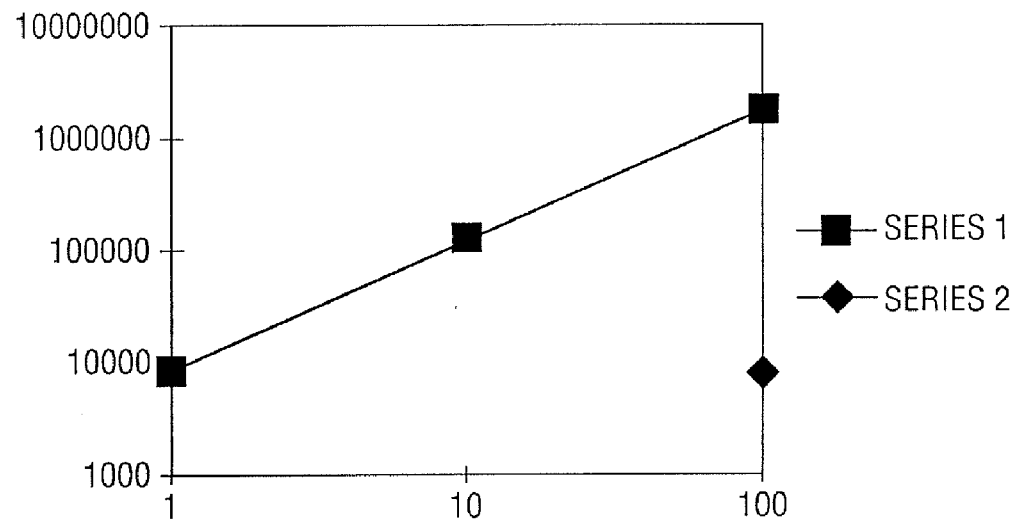
FIG. 101*b* is a graph comparing the amount of product generated in a standard or basic (i.e., a non-sequential invasive cleavage reaction) and a sequential invasive cleavage reaction ("invader sqrd") (y axis=fluorescence units; x axis=attomoles of target).

The graph shown in FIG. 101*b* compares the amount of product generated from the standard reaction ("Series 1") to the amount of product generated from the second step of the sequential reaction ("Series 2"). The level of background fluorescence measured from a reaction that lacked target DNA was subtracted from each measurement. It can be seen from the table located below the graph that the signal from the standard invasive cleavage assay that contained 100 attomoles of target DNA was nearly identical to the signal from the sequential invasive cleavage assay in which 1 attomole of target was present, indicating that the inclusion of a second cleavage structure increases the sensitivity of the assay 100 to 200-fold. This boost in signal allows easy detection of target nucleic acids at the sub attomole level using the sequential invasive cleavage assay, while the standard assay, when performed using this enzyme for only 30 minutes, does not generate detectable product in the presence of 10 attomoles of target.

When the amount of target was decreased by 10 or 100 fold in the sequential invasive cleavage assay, the intensity of the signal was decreased by the same proportion. This indicates that the quantitative capability of the invasive cleavage assay is retained even when reactions are performed in series, thus providing a nucleic acid detection method that is both sensitive and quantitative.

While in this Example, the two probes used had different optimal hybridization temperatures (i.e., the temperature empiracally determined to give the greatest turnover rate in the given reaction conditions), the probes may also be selected (i.e., designed) to have the same optimal hybridization temperature so that a temperature shift during incubation is not necessary.

Example 47

The Products of a Completed Sequential Invasive Cleavage Reaction Cannot Cross Contaminate Subsequent Similar Reactions As discussed in the Description of the Invention, the serial nature of the multiple invasive cleavage events that occur in the sequential invasive cleavage reaction, in contrast to the reciprocating nature of the polymerase chain reaction and similar doubling assays, means that the sequential invasive cleavage reaction is not subject to contamination by the products of like reactions because the products of the first cleavage reaction do not participate in the generation of new signal in the second cleavage reaction. If a large amount of a completed reaction were to be added to a newly assembled reaction, the background that would be produced would come from the amount of target that was also carried in, combined with the amount of already-cleaved probe that was carried in. In this Example, it is demonstrated that a very large portion of a primary reaction must be introduced into the secondary reaction to create significant signal.

A first or primary sequential invasive cleavage reaction was performed as described above using 100 amol of target DNA. A second set of 5 reactions were assembled as described in Ex. 46 with the exception that portions of the first reaction were introduced and no additional target DNA was included. These secondary reactions were initiated and incubated as described above, and included 0, 0.01, 0.1, 1, or 10% of the first reaction material. A control reaction including 100 amol of target was included in the second set also. The reactions were stopped, resolved by electrophoresis and visualized as described above, and the resulting image is displayed in FIG. 102. The primary probe, uncut second probe and the cut 2nd probe are indicated on the left as "1: cut", 2: uncut" and 2: cut", respectively.

Figure 102:
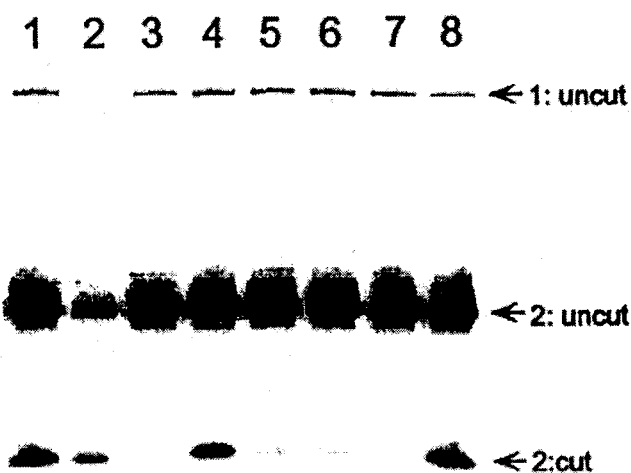
FIG. 102 shows the image generated by a fluorescence imager which shows that the products of a completed sequential invasive cleavage reaction cannot cross contaminant a subsequent similar reaction.

In FIG. 102, lane 1 shows the results of the first reaction with the accumulated product at the bottom of the panel, and lane 2 show a 1:10 dilution of the same reaction, to demonstrate the level of signal that could be expected from that level of contamination, without further amplification. Lanes 3 through 7 show the results of the secondary cleavage reactions that contained 0, 10, 1, 0.1 or 0.01% of the first reaction material added as contaminant, respectively and lane 8 shows a control reaction that had 100 amol of target DNA added to verify the activity of the system in the secondary reaction. The signal level in lane 4 is as would be expected when 10% of the pre-cleaved material is transferred (as in lane 2) and 10% of the transferred target material from the lane 1 reaction is allowed to further amplify. At all levels of further dilution the signal is not readily distinguished from background. These data demonstrate that while a large-scale transfer from one reaction to another may be detectable, cross contamination by the minute quantities that would be expected from aerosol or from equipment contamination would not be easily mistaken for a false positive result. These data also demonstrate that when the products of one reaction are deliberately carried over into a fresh sample, these products do not participate in the new reaction, and thus do not affect the level of target-dependent signal that may be generated in that reaction.

Example 48

Detection of Human *Cytomegalovirus* Viral DNA by Invasive Cleavage

Figure 103:
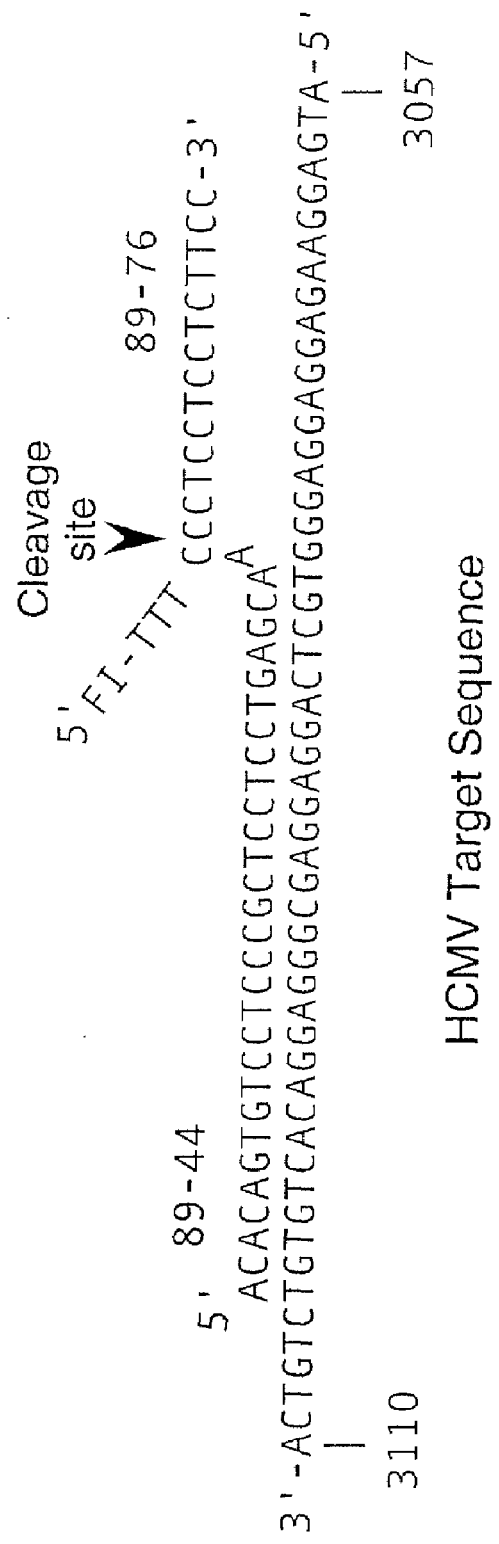
FIG. 103 shows the sequence of the oligonucleotide employed in an invasive cleavage reaction for the detection of HCMV viral DNA.

The previous Example demonstrates the ability of the invasive cleavage reaction to detect minute quantities of viral DNA in the presence of human genomic DNA. In this Example, the probe and INVADER oligonucleotides were designed to target the 3104-3061 region of the major immediate early gene of human cytomegalovirus (HCMV) as shown in FIG. 103. In FIG. 103, the INVADER oligo (89-44; SEQ ID NO:160) and the fluorescein (Fl)-labeled probe oligo (89-76; SEQ ID NO:161) are shown annealed along a region of the HCMV genome corresponding to nucleotides 3057-3110 of the viral DNA (SEQ ID NO:162). The probe used in this Example is a poly-pyrimidine probe and as shown herein the use of a poly-pyrimidine probe reduces background signal generated by the thermal breakage of probe oligos.

The genomic viral DNA was purchased from Advanced Biotechnologies, Incorporated (Columbia, Md.). The DNA was estimated (but not certified) by personnel at Advanced Biotechnologies to be at a concentration of 170 amol ($1\times10^8$ copies) per microliter. The reactions were performed in quadruplicate. Each reaction comprised 1µM 5' fluorescein labeled probe oligonucleotide 89-76 (SEQ ID NO:161), 100 nM INVADER oligonucleotide 89-44 (SEQ ID NO:160), 1 ng/ml human genomic DNA, and one of five concentrations of target HCMV DNA in the amounts indicated above each lane in FIG. 104, and 10 ng of Pfu FEN-1 in 10 µl of 10 mM MOPS (pH 7.5), 6 mM $MgCl_2$ with 0.05% each of Tween 20 and Nonidet P-40. All of the components except the labeled probe, enzyme and $MgCl_2$ were assembled in a final volume of 7 µl and were overlaid with 10 µl of Chill-Out™ liquid wax. The samples were heated to 95° C. for 5 min, then reduced to 62° C. The reactions were started by the addition of probe, Pfu FEN-1 and $MgCl_2$, in a 3 µl volume. After incubation at 62° C. for 60 minutes, the reactions were stopped with 10 µl of 95% formamide, 10 mM EDTA, 0.02% methyl violet. Samples were heated to 90° C. for 1 min immediately before electrophoresis through a 20% acrylamide gel (19:1 cross-linked), with 7 M urea, in a buffer of 45 mM Tris-Borate, pH 8.3, 1.4 mM EDTA. Gels were then analyzed with a Molecular Dynamics FluorImager 595.

Figure 104:
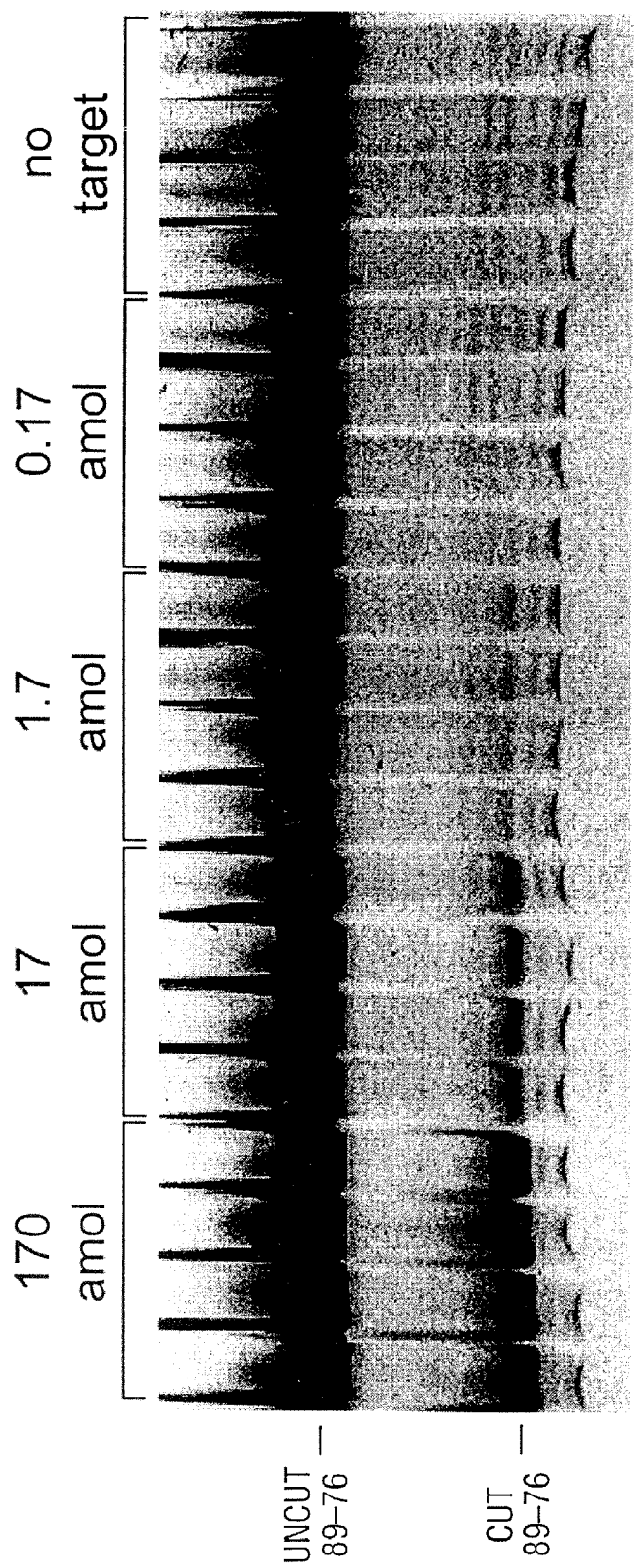
FIG. 104 shows the image generated by a fluorescence imager which shows the sensitive detection of HCMV viral DNA in samples containing human genomic DNA using an invasive cleavage reaction.
Figure 5:
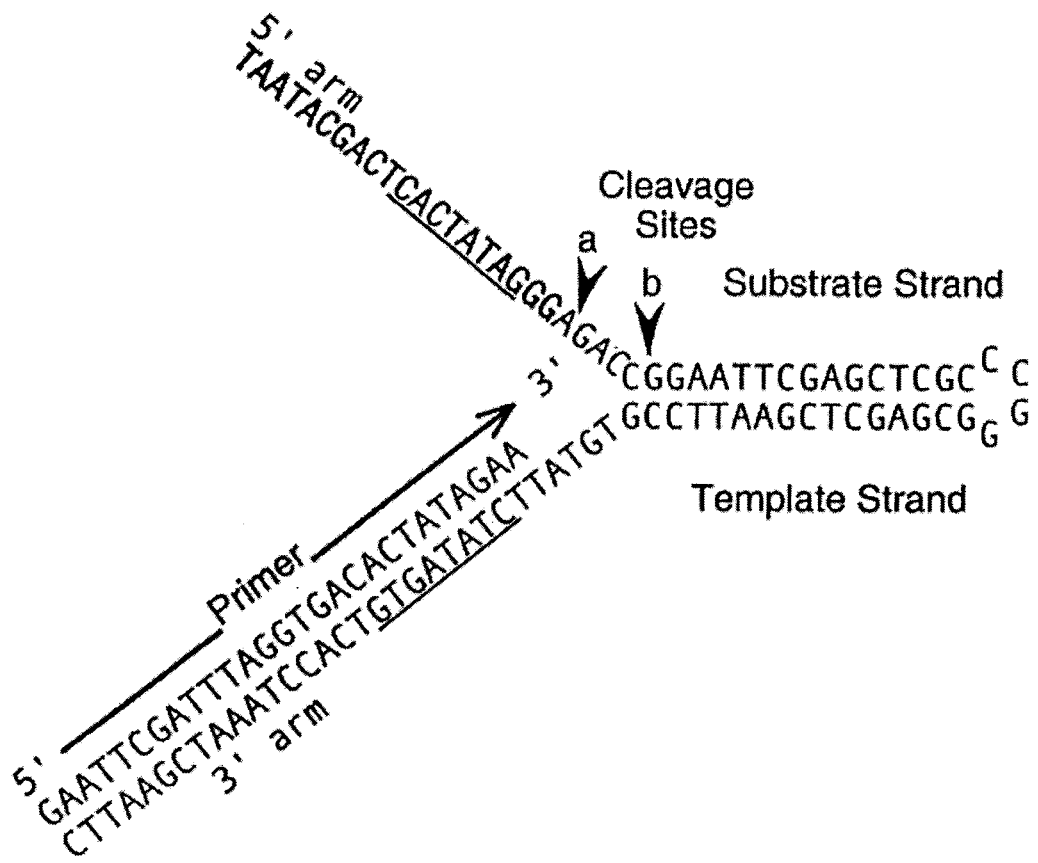
Figure 6:
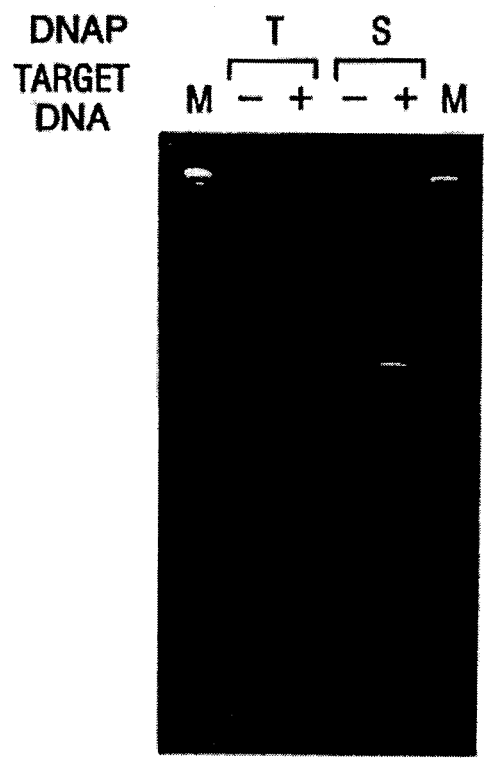
Figure 7:
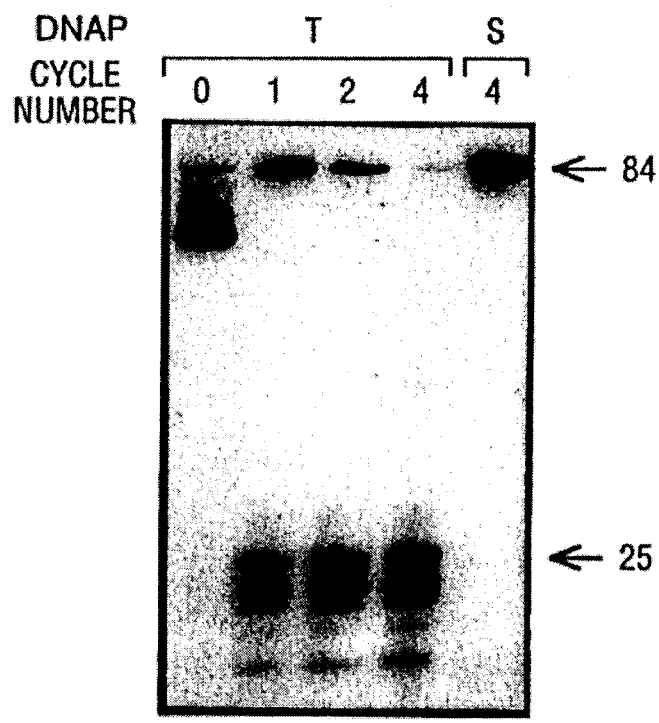

The resulting image is displayed in FIG. 104. The replicate reactions were run in groups of four lanes with the target HCMV DNA content of the reactions indicated above each set of lanes (0-170 amol). The uncleaved probe is seen in the upper third of the panel ("Uncut 89-76") while the cleavage products are seen in the lower two-thirds of the panel ("Cut 89-76"). It can be seen that the intensity of the accumulated cleavage product is proportional to the amount of the target DNA in the reaction. Furthermore, it can be clearly seen in reactions that did not contain target DNA ("no target") that the probe is not cleaved, even in a background of human genomic DNA. While 10 ng of human genomic DNA was included in each of the reactions shown in FIG. 104, inclusion of genomic DNA up to 200 ng has slight impact on the amount of product accumulated. The data did not suggest that 200 ng per 10 µl of reaction mixture represented the maximum amount of genomic DNA that could be tolerated without a significant reduction in signal accumulation. For reference, this amount of DNA exceeds what might be found in 0.2 ml of urine (a commonly tested amount for HCMV in neonates) and is equivalent to the amount that would be found in about 5 µl of whole blood.

These results demonstrate that the standard (i.e., non-sequential) invasive cleavage reaction is a sensitive, specific and reproducible means of detecting viral DNA. It can also be seen from these data that the use of a poly-pyrimidine probe reduces the background from thermal breakage of the probe, as discussed in Example 22. Detection of 1.7 amol of target is roughly equivalent to detection of $10^6$ copies of the virus. This is equivalent to the number of viral genomes that might be found in 0.2 mls of urine from a congenitally infected neonate ($10^2$ to $10^6$ genome equivalents per 0.2 mls; Stagno et al., J. Infect. Dis., 132:568 [1975]). Use of the sequential invasive cleavage assay would permit detection of even fewer viral DNA molecules, facilitating detection in blood ($10^1$ to $10^5$ viral particles per ml; Pector et al., J. Clin. Microbiol., 30:2359 [1992]), which carries a much larger amount of heterologous DNA.

From the above it is clear that the invention provides reagents and methods to permit the detection and characterization of nucleic acid sequences and variations in nucleic acid sequences. The INVADER-directed cleavage reaction and the sequential INVADER-directed cleavage reaction of the present invention provide ideal direct detection methods that combine the advantages of the direct detection assays (e.g., easy quantification and minimal risk of carry-over contamination) with the specificity provided by a dual or tri oligonucleotide hybridization assay.

As indicated in the Description of the Invention, the use of sequential invasive cleavage reactions can present the problem of residual uncut first, or primary, probe interacting with the secondary target, and either competing with the cut probe for binding, or creating background through low level cleavage of the resulting structure. This is shown diagramatically in FIGS. 105 and 106. In FIG. 105, the reaction depicted makes use of the cleavage product from the first cleavage structure to form an INVADER oligonucleotide for a second cleavage reaction. The structure formed between the secondary target, the secondary probe and the uncut primary probe is depicted in FIG. 105, as the right hand structure shown in step 2a. This structure is recognized and cleaved by the 5' nucleases, albeit very inefficiently (i.e., at less than about 1% in most reaction conditions). Nonetheless, the resulting product is indistinguishable from the specific product, and thus may lead to a false positive result. The same effect can occur when the cleaved primary probe creates and integrated INVADER/target (IT) molecule, as described in Example 46; the formation of the undesirable complex is depicted schematically in FIG. 106, as the right hand structure shown in step 2a.

The improvements provided by the inclusion of ARRESTOR oligonucleotides of various compositions in each of these types of sequential INVADER assays are demonstrated in the following Examples. These ARRESTOR oligonucleotides are configured to bind the residual uncut probe from the first cleavage reaction in the series, thereby increasing the efficacy of and reducing the non-specific background in the subsequent reaction(s).

Example 49

Figure 106:
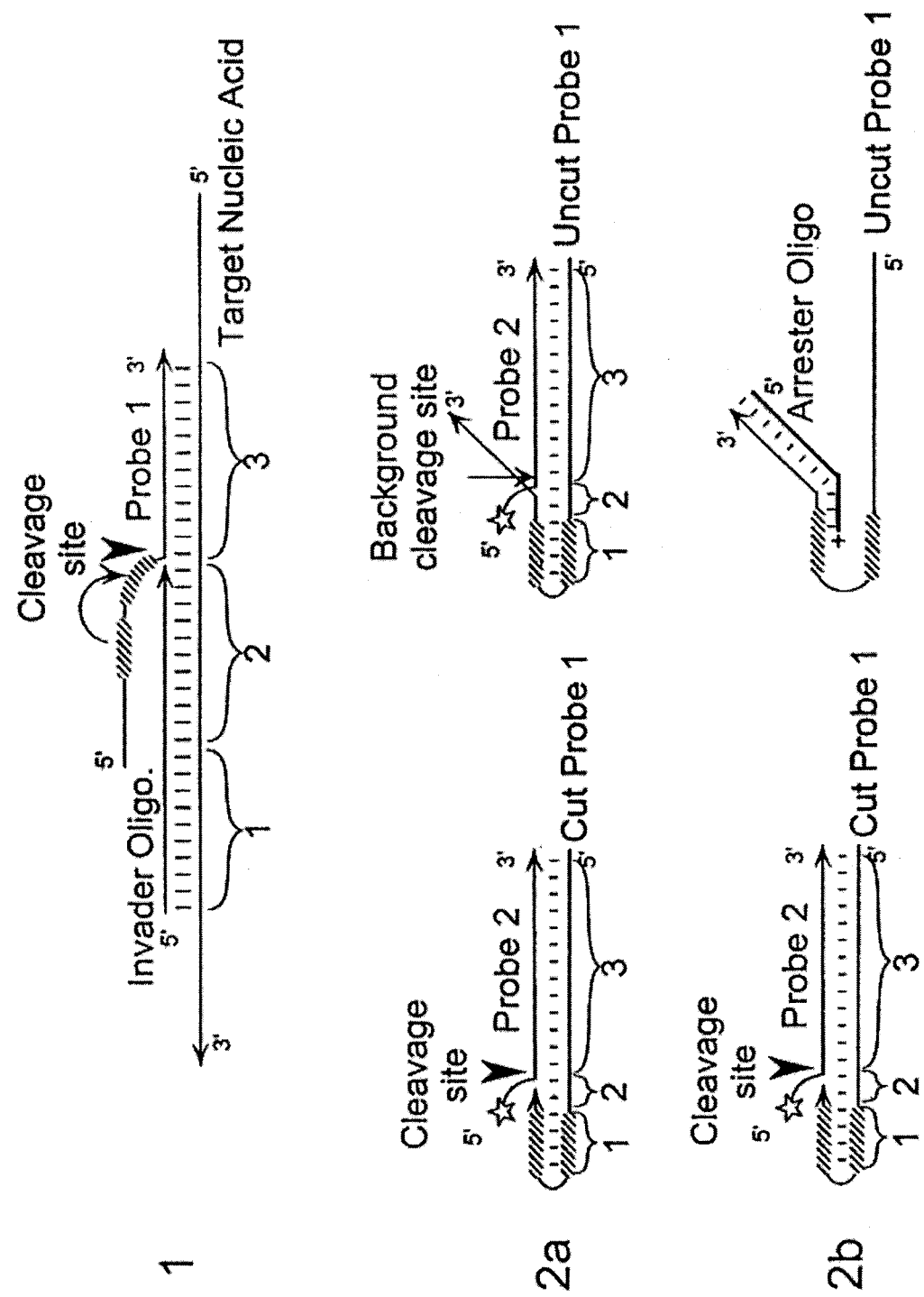
FIG. 106 is a schematic which illustrates one embodiment of the present invention, where the cut probe from an initial invasive cleavage reaction is employed as an integrated INVADER-target complex in a second invasive cleavage reaction, and where an ARRESTOR oligonucleotide prevents participation of remaining uncut first probe in the cleavage of the second probe.

"ARRESTOR" Oligonucleotides Improve Sensitivity of Multiple Sequential Invasive Cleavage Assays In this Example, the effect of including an ARRESTOR oligonucleotide on the generation of signal using the IT probe system depicted in FIGS. 97 and 106 is demonstrated. The ARRESTOR oligonucleotide hybridizes to the primary probe, mainly in the portion that recognizes the target nucleic acid during the first cleavage reaction. In addition to examining the effects of adding an ARRESTOR oligonucleotide, the effects of using ARRESTOR oligonucleotides that extended in complementarity different distances into the region of the primary probe that composes the secondary IT structure were also investigated. These effects were compared in reactions that included the target DNA over a range of concentrations, or that lacked target DNA, in order to demonstrate the level of nonspecific (i.e., not related to target nucleic acid) background in each set of reaction conditions.

The target DNA for these reactions was a fragment that comprised the full length of the hepatitis B genome from strain of serotype adw. This material was created using the polymerase chain reaction from plasmid pAM6 (ATCC #45020D). The PCRs were conducted using a vector-based forward primer, oligo # 156-022-001 (5'-ggcgaccacacccgtc-ctgt-3'; SEQ ID NO:168) and a reverse primer, oligo #156-022-02 (5'-ccacgatgcgtccggcgtag-3'; SEQ ID NO:169) to amplify the full length of the HBV insert, an amplicon of about 3.2 kb. The cycling conditions included a denaturation of the plasmid at 95° C. for 5 minutes, followed by 30 cycles of 95° C., 30 seconds; 60° C., 40 seconds; and 72° C., 4 minutes. This was followed by a final extension at 72° C. for 10 minutes. The resulting amplicon, termed pAM6#2, was adjusted to 2 M NH$_4$OAc, and collected by precipitation wiht isopropanol. After drying in vacuo, DNA was dissolved in 10 mM Tris pH 0.0, 0.1 mM EDTA. The concentration was determined by OD$_{200}$ measurement, and by INVADER assay with comparison to a standard of known concentration.

The INVADER reactions were conducted as follows. Five master mixes, termed "A," "B," "C," "D," and "E," were assembled; all mixes contained 12.5 mM MOPS, pH 7.5, 500 fmoles primary INVADER oligo #218-55-05 (SEQ ID NO:171), 10 ng human genomic DNA (Novagen) and 30 ng AfuFEN1 enzyme, for every 8 μl of mix. Mix A contained no added HBV genomic amplicon DNA; mix B contained 600 molecules of HBV genomic amplicon DNA pAM6 #2; mix C contained 6,000 molecules pAM6 #2; mix D contained 60,000 molecules pAM6 #2; and mix E contained 600,000 molecules pAM6 #2. The mixes were aliquotted to the reaction tubes, 8 μl/tube: mix A to tubes 1, 2, 11, 12, 21 and 22; mix B to tubes 3, 4, 13, 14, 23 and 24; mix C to tubes 5, 6, 15, 16, 25 and 26; mix D to tubes 7, 8, 17, 18, 27 and 28; and mix E to tubes 9, 10, 19, 20, 29 and 30. The samples were incubated at 95° C. for 4 minutes to denature the HBV genomic amplicon DNA. The reactions were then cooled to 67° C., and 2 μl of a mix containing 37.5 mM MgCl$_2$ and 2.5 pmoles 218-95-06 (SEQ ID NO:183) for every 2 μl, was added to each sample. The samples were incubated at 67° C. for 60 minutes. Three secondary reaction master mixes were prepared, all mixes contained 10 pmoles of secondary probe oligonucleotide #228-48-04 (SEQ ID NO:173) for every 2 μl of mix. Mix 2A contained no additional oligonucleotide, mix 2B contained 5 pmoles "ARRESTOR" oligo # 218-95-03 (SEQ ID NO:184) and mix 2C contained 5 pmoles of "ARRESTOR" oligo # 218-95-01 (SEQ ID NO:174). After the 60 minute incubation at 67° C. (the primary reaction described above), 2 μl of the secondary reaction mix was added to each sample: Mix 2A was added to samples #1-10; Mix 2B was added to samples #11-20; and Mix 2C was added to samples #21-30. The temperature was adjusted to 52° C. and the samples were incubated for 30 minutes at 52° C. The reactions were then stopped by the addition of 10 μl of a solution of 95% formamide, 5 mM EDTA and 0.02% crystal violet. All samples were heated to 95° C. for 2 minutes, and 4 μl of each sample were resolved by electrophoresis through 20% denaturing acrylamide gel (19:1 cross-linked) with 7 M urea, in a buffer containing 45 mM Tris-Borate (pH8.3) and 1.4 mM EDTA. The results were imaged using the Molecular Dynamics Fluoroimager 595, excitation 488, emission 530. The resulting images are shown in FIG. 107.

In FIG. 107, Panel A shows the results of the target titration when no ARRESTOR oligonucleotide was included in the secondary reaction; Panel B shows the results of the same target titration using an ARRESTOR oligonucleotide that extended 2 nt into the non-target complementary region of the primary probe; and Panel C shows the results of the same target titration using an ARRESTOR oligonucleotide that extended 4 nt into the non-target complementary region of the primary probe. The product of the secondary cleavage reaction is seen as a band near the bottom of each panel. The first two lanes of each panel (i.e., 1 and 2, 11 and 12, 21 and 22) lacked target DNA, and the signal the co-migrates with the product band represents the nonspecific background under each set of conditions.

It can be seen by visual inspection of these panels that the background signal is both reduced, and made more predictable, by the inclusion of either species of ARRESTOR oligonucleotides. In addition to reducing the background in the no-target control lanes, the background reduction in the reactions that had the more dilute amounts of target included is reduced, leading to a signal that is a more accurate reflection of the target contained within the reaction, thus improving the quantitative range of the multiple, sequential invasive cleavage reaction.

To quantify the impact of including the ARRESTOR oligonucleotide in the secondary cleavage reaction under these conditions, the average product band signal from the reactions having the largest amount of target (i.e., averages of the signals from lanes 9 and 10, lanes 19 and 20, and lanes 29 and 30), were compared to the averaged signal from the no-target contol lanes for each panel, determine the "fold over background," the factor of signal amplification over background, under each set of conditions. For the reactions without the ARRESTOR oligonucleotide, Panel A, the fold over background was 5.3; for Panel B, the fold over background was 12.7; and for Panel C, the fold over background was 13.4, indicating that in this system inclusion of any ARRESTOR oligonucleotide at least doubled the specificity of the signal over the ARRESTOR oligonucleotide-less reactions, and that the ARRESTOR oligonucleotide that extended slightly farther into the non-target complementary region may be slightly more effective, at least in this embodiment of the system. This clearly shows the benefits of using an ARRES- TOR oligonucleotide to enhance the specificity of these reactions, an advantage that is of particular benefit at low levels of target nucleic acid.

Example 50

"ARRESTOR" Oligonucleotides Allow use of Higher Concentrations of Primary Probe without Increasing Background Signal It was demonstrated in Example 36, that increasing the concentration of the probe in the invasive cleavage reaction could dramatically increase the amount of signal generated for a given amount of target DNA. While not intending to limit the explanation to any specific mechanism, this is believed to be caused by the fact that increased concentration of probe increases the rate at which the cleaved probe is supplanted by an uncleaved copy, thereby increasing the apparent turnover rate of the cleavage reaction. Unfortunately, this effect could not heretofore be applied in the primary cleavage reaction of a multiple sequential INVADER assay because the residual uncleaved primary probe can hybridize to the secondary target, in competition with the cleaved molecules, thereby reducing the efficacy of the secondary reaction. Elevated concentrations of primary probe exacerbate this problem. Further, the resulting complexes, as described above, can be cleaved at a low level, contributing to background. Therefore, increasing the primary probe can have the double negative effect of both slowing the secondary reaction and increasing the level of this form of non target-specific background. The use of an ARRESTOR oligonucleotide to sequester or neutralize the residual primary probe allows this concentration-enhancing effect to be applied to these sequential reactions.

To demonstrate this effect, two sets of reactions were conducted. In the first set of reactions, the reactions were conducted using a range of primary probe concentrations, but no ARRESTOR oligonucleotide was supplied in the secondary reaction. In the second set of reactions, the same probe concentrations were used, but an ARRESTOR oligonucleotide was added for the secondary reactions.

Figure 108A:
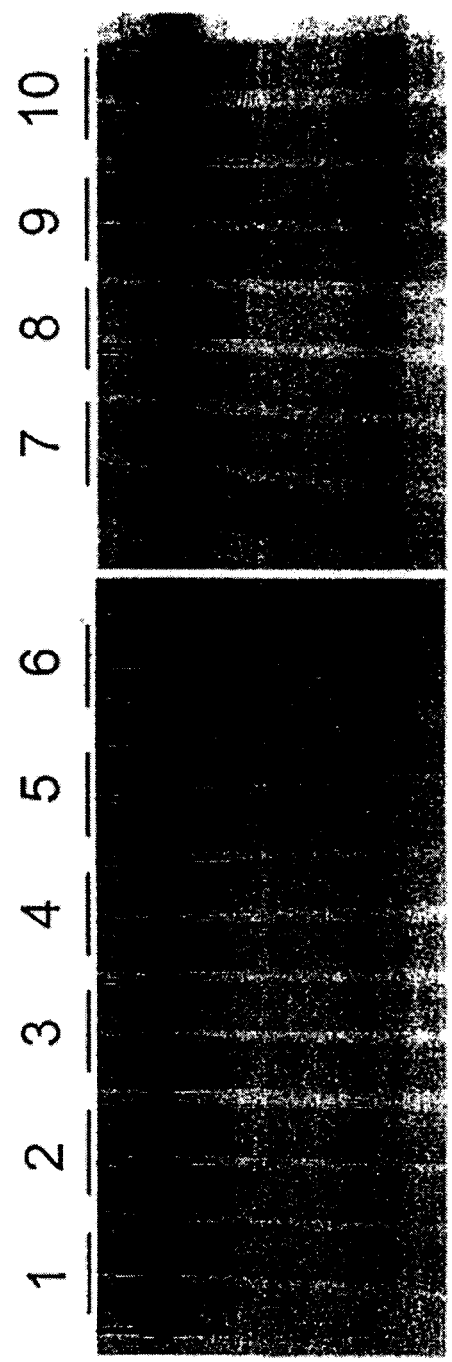
FIG. 108A shows two images generated by a fluorescence imager showing the effects on nonspecific and specific cleavage signal of increasing concentrations of primary probe in the first step of a reaction where the cut probe from an initial invasive cleavage reaction is employed as the INVADER oligonucleotide in a second invasive cleavage reaction.
Figure 108B:
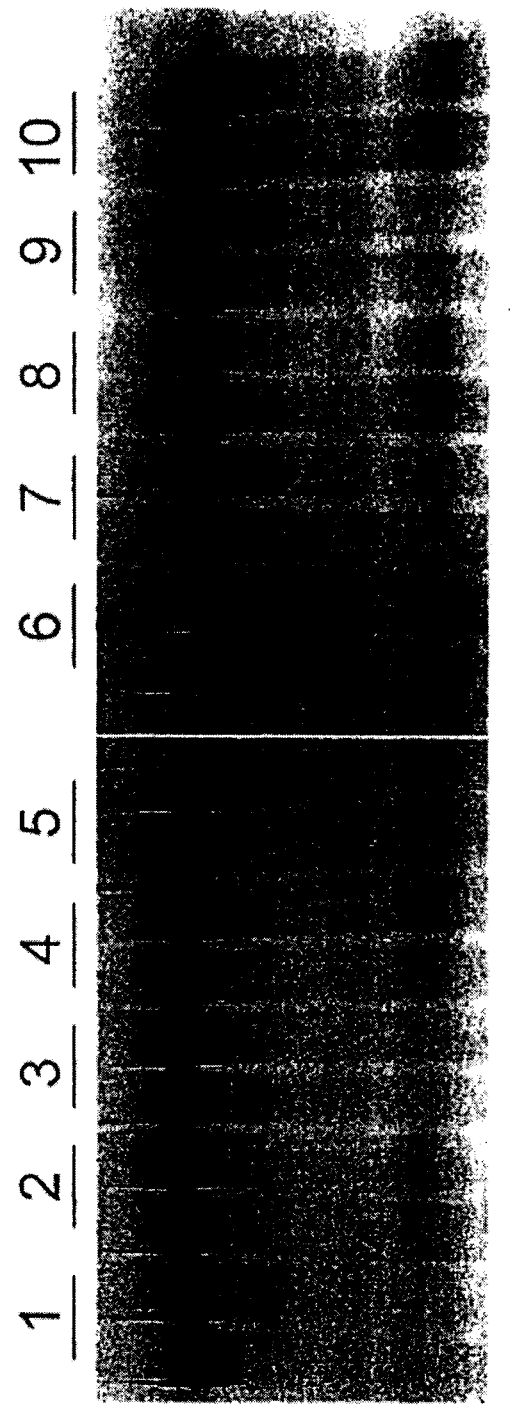
FIG. 108B shows two images generated by a fluorescence imager showing the effects on nonspecific and specific cleavage signal of increasing concentrations of primary probe in the first step of a reaction, and inclusion of a 2' O-methyl, 3' terminal amine-modified ARRESTOR oligonucleotide in the second step of a reaction where the cut probe from an initial invasive cleavage reaction is employed as the INVADER oligonucleotide in a second invasive cleavage reaction.

All reactions were performed in duplicate. Primary INVADER reactions were done in a final volume of 10 μl and contained: 10 mM MOPS, pH 7.5, 7.5 mM MgCl$_2$, 500 fm of primary INVADER (218-55-05; SEQ ID NO:171); 30 ng of AfuFEN1 enzyme and 10 ng of human genomic DNA. 100 zeptomoles of HBV pAM6 #2 amplicon was included in all even numbered reactions (by reference to FIGS. 108A and B). Reactions included 10 pmoles, 20 pmoles, 50 pmoles, 100 pmoles or 150 pmoles of primary probe (218-55-02; SEQ ID NO:170). MOPS, target and INVADER oligonucleotides were combined to a final volume of 7 μl. Samples were heat denatured at 95° C. for 5 minutes, then cooled to 67° C. During the 5 minute denaturation, MgCl$_2$, probe and enzyme were combined. The primary INVADER reactions were initiated by the addition of 3 μl of MgCl$_2$, probe and enzyme mix, to the final concentrations indicated above. Reactions were incubated for 30 minutes at 67° C. The reactions were then cooled to 52° C., and each primary INVADER reaction received the following secondary reaction components in a total volume of 4 μl: 2.5 pmoles secondary target (oligo number 218-95-04; SEQ ID NO:172); 10 pmoles secondary probe (oligo number 228-48-04; SEQ ID NO:173). The reactions that included the ARRESTOR oligonucleotide had either 40 pmoles, 80 pmoles, 200 pmoles, 400 pmoles or 600 pmoles of ARRESTOR oligonucleotide (oligo number 218-95-01; SEQ ID NO:174), added at a 4-fold molar excess over the primary probe amount for each reaction, with this mix. Reactions were then incubated at 52° C. for 30 minutes. The reactions were stopped by the addition of 10 μl of a solution of 95% formamide, 10 mM EDTA and 0.02% crystal violet. All samples were heated to 95° C. for 1 minute, and 4 μl of each sample were resolved by electrophoresis through 20% denaturing acrylamide gel (19:1 cross-linked) with 7 M urea, in a buffer containing 45 mM Tris-Borate (pH8.3) and 1.4 mM EDTA. The results were imaged using the Molecular Dynamics Fluoroimager 595, excitation 488, emission 530. The resulting images for the reactions either without or with an ARRESTOR oligonucleotide are shown in FIGS. 108A and 108B, respectively. The products of cleavage of the secondary probe are seen as a band near the bottom of each panel.

In FIG. 108A, lane sets 1 and 2 show results with 10 pmoles of primary probe; 3 and 4 had 20 pmoles; 5 and 6 had 50 pmoles; 7 and 8 had 100 pmoles; and 9 and 10 ha 150 pmoles. It can be seen by visual examination, that the increases in the amount of primary probe have the combined effect of slightly increasing the background in the no-target lanes (odd numbers) while reducing the specific signal in the presence of target (even numbered lanes), and therefore the reducing the specificity of the reaction if viewed as the measure of "fold over background," demonstrating that the approach of increasing signal by increasing probe cannot be applied in these sequential reactions.

In FIG. 108B, lane sets 1 and 2 show results with 10 pmoles of primary probe; while 3 and 4 had 20 pmoles; 5 and 6 had 50 pmoles; 7 and 8 had 100 pmoles; and 9 a 10 had 150 pmoles. In addition, each reaction included 4-fold molar excess of the ARRESTOR oligonucleotide added before the secondary cleavage reaction. It can be seen by visual examination that the background in the no-target lanes (odd numbers) is lower in all cases, while the specific signal in the presence of target (even numbered lanes) increases with increased amounts of primary probe, leading to a greater "fold over background" sensitivity at this target level.

Figure 108C:
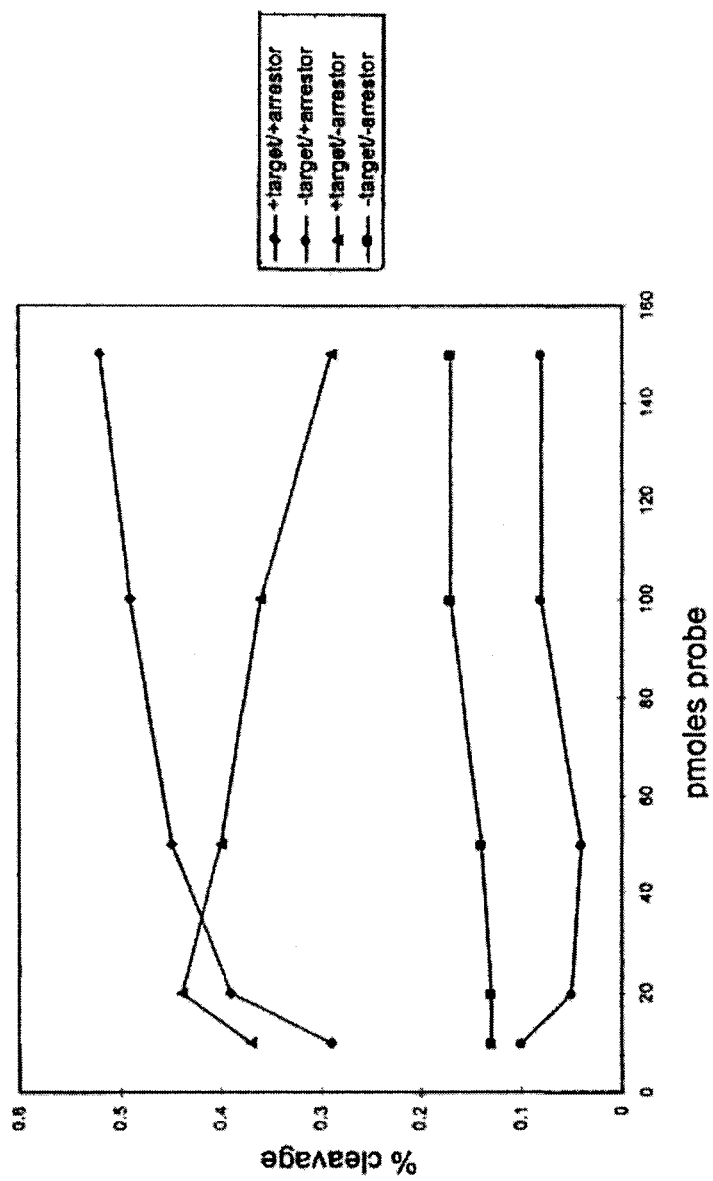
FIG. 108C shows a graph generated using the spreadsheet Microsoft Excel software, comparing the effects on nonspecific and specific cleavage signal of increasing concentrations of primary probe in the first step of a reaction, in the presence or absence of a 2' O-methyl, 3' terminal amine-modified ARRESTOR oligonucleotide in the second step of a reaction where the cut probe from an initial invasive cleavage reaction is employed as the INVADER oligonucleotide in a second invasive cleavage reaction.

To quantitatively compare these effects, the fluorescence signal from the products of both non-specific and specific cleavage were measured. The results are depicted graphically in FIG. 108C, graphed as a measure of the percentage of the secondary probe cleaved during the reaction, compared to the amount of primary probe used. Examination of the plots from the no-target reactions confirms that the background in the absence of the ARRESTOR oligonucleotide is, in general, roughly two-fold higher, and that both increase slightly with the increasing probe amounts. The specific signals however, diverge between the two sets of reaction more dramatically. While the signal in the no-ARRESTOR oligonucleotide reactions decreases steadily as primary probe was increased, the signal in the ARRESTOR oligonucleotide reactions continued to increase. At the highest primary probe concentrations tested, the no-ARRESTOR oligonucleotide reactions had specific signal that was only 1.7 fold over background, while the ARRESTOR oligonucleotide reactions detected the 100 zmoles (60,000 copies) of target with a signal 6.5 fold over background, thus demonstrating the improvement in the sequential invasive cleavage reaction when an ARRESTOR oligonucleotide is included.

Example 51

Modified Backbones Improve Performance of ARRESTOR Oligonucleotides All Natural "ARRESTOR" Oligo with No 3'-Amine The reactions described in the previous two Examples used ARRESTOR oligonucleotides that were constructed using 2' O-methyl ribose backbone, and that included a positively charged amine group on the 3' terminal nucleotide. The modifications were made specifically to reduce enzyme interaction with the primary probe/ARRESTOR oligonucleotide complex. During the development of the present invention, it was determined that the 2' O-methy modified oligonucleotides are somewhat resistant to cleavage by the 5' nucleases, just as they are slowly degraded by nucleases when used in antisense applications (See e.g., Kawasaki et al., J. Med. Chem., 36:831 [1993]).

Further, as demonstrated in Example 35, the presence of an amino group on the 3' end of an oligonucleotide reduces its ability to direct invasive cleavage. To reduce the possibility that the ARRESTOR oligonucleotide would form a cleavage structure in this way, an amino group was included in the design of the experiments described in this and other Examples.

Initial designs of the ARRESTOR oligonucleotides (sometimes referred to as "blockers") did not include these modifications, and these molecules were found to provide no benefit in reducing background cleavage in the sequential invasive cleavage assay and, in fact, sometimes contributed to background by inducing cleavage at an unanticipated site, presumably by providing some element to an alternative cleavage structure. The effects of natural and modified ARRESTOR oligonucleotide on the background noise in these reactions are examined in this Example.

The efficacy of an "all-natural ARRESTOR oligonucleotide (i.e., an ARRESTOR oligonucleotide that did not contain any base analogs or modifications) was examined by comparison to an identical reactions that lacked ARRESTOR oligonucleotide. All reactions were performed in duplicate, and were conducted as follows. Two master mixes were assembled, each containing 12.5 mM MOPS, pH 7.5, 500 fmoles primary INVADER oligonucleotide #218-55-05 (SEQ ID NO:171), 10 ng human genomic DNA (Novagen) and 30 ng AfuFEN1 enzyme for every 8 µl of mix. Mix A contained no added HBV genomic amplicon DNA, mix B contained 600,000 molecules of HBV genomic amplicon DNA, pAM6 #2. The mixes were distributed to the reaction tubes, in aliquots of 8 µl/tube as follows: mix A to tubes 1, 2, 5 and 6; and mix B to tubes 3, 4, 7 and 8. The samples were incubated at 95° C. for 4 minutes to denature the HBV genomic amplicon DNA. The reactions were then cooled to 67° C. and 2 ul of a mix containing 37.5 mM $MgCl_2$ and 10 pmoles 218-55-02B (SEQ ID NO:185) for every 2 µl, was added to each sample. The samples were then incubated at 67° C. for 30 minutes. Two secondary reaction master mixes were prepared, each containing 10 pmoles of secondary probe oligo #228-48-04N (SEQ ID NO:178) and 2.5 pmoles of secondary target oligonucleotide #218-95-04 (SEQ ID NO:172) for every 3 µl of mix. Mix 2A contained no additional oligonucleotide, while mix 2B contained 50 pmoles of the natural "ARRESTOR" oligonucleotide #241-62-02 (SEQ ID NO:186). After the initial 30 minute incubation at 67° C., the temperature was adjusted to 52° C., and 3 µl of a secondary reaction mix was added to each sample, as follows: Mix 2A was added to samples #1-4; and Mix 2B was added to samples #5-8. The samples were then incubated for 30 minutes at 52° C. The reactions were then stopped by the addition of 10 µl of a solution of 95% formamide, 10 mM EDTA and 0.02% crystal violet.

All of the samples were heated to 95° C. for 2 minutes, and 4 µl of each sample were resolved by electrophoresis through a 20% denaturing acrylamide gel (19:1 crosslinked) with 7 M urea, in a buffer containing 45 mM Tris-Borate (pH8.3) and 1.4 mM EDTA. The results were imaged using the Molecular Dynamics Fluoroimager 595, excitation 488, emission 530. The resulting image is shown in FIG. 109A.

To compare the effects of the various modifications made to the ARRESTOR oligonucleotides, reactions were performed using ARRESTOR oligonucleotides having all natural bases, but including a 3' terminal amine; ARRESTOR oligonucleotide having the 3' portion composed of 2' O-methyl nucleotides, plus the 3' terminal amine; and ARRESTOR oligonucleotide composed entirely of 2' O-methyl nucleotides, plus the 3' terminal amine. These were compared to reactions performed without an ARRESTOR oligonucleotide. The reactions were conducted as follows. Two master mixes were assembled, all mixes contained 14.3 mM MOPS, pH 7.5, 500 fmoles primary INVADER oligo #218-55-05 (SEQ ID NO:171) and 10 ng human genomic DNA (Novagen) for every 7 µl of mix. Mix A contained no added HBV genomic amplicon DNA, mix B contained 600,000 molecules of HBV genomic amplicon DNA, pAM6 #2. The mixes were distributed to the reaction tubes, at 7 µl/tube: mix A to tubes 1, 2, 5, 6, 9, 10, 13 and 14; and mix B to tubes 3, 4, 7, 8, 11, 12, 15 and 16. The samples were warmed to 95° C. for 4 minutes to denature the HBV DNA. The reactions were then cooled to 67° C. and 3 µl of a mix containing 25 mM $MgCl_2$, 25 pmoles 218-55-02B (SEQ ID NO:185) and 30 ng AfuFEN1 enzyme per 3 µl, were added to each sample. The samples were then incubated at 67° C. for 30 minutes. Four secondary reaction master mixes were prepared; all mixes contained 10 pmoles of secondary probe oligonucleotide #228-48-04B (SEQ ID NO:190) and 2.5 pmoles of secondary target oligonucleotide #218-95-04 (SEQ ID NO:172) for every 3 µl of mix. Mix 2A contained no additional oligonucleotide, while mix 2B contained 100 pmoles of the natural+amine ARRESTOR oligonucleotide # 241-62-01 (SEQ ID NO:187), mix 2C contained 100 pmoles of partially O-methyl+amine oligonucleotide # 241-62-03 (SEQ ID NO:188) and mix 2D contained 100 pmoles of all O-methyl+amine oligonucleotide # 241-64-01 (SEQ ID NO:189). After the initial 30 minute incubation at 67° C., the temperature was adjusted to 52° C. and 3 µl of a secondary reaction mix was added to each sample, as follows: mix 2A was added to samples #1-4; mix 2B was added to samples #5-8; mix 2C was added to samples #9-12; and mix 2D was added to samples #13-16. The samples were incubated for 30 minutes at 52° C., then stopped by the addition of 10 µl of a solution of 95% formamide, 10 mM NaEDTA, and 0.2% crystal violet.

All samples were heated to 95° C. for 2 minutes, and 4 µl of each sample were resolved by electrophoresis through a 20% denaturing acrylamide gel (19:1 cross-linked) with 7 M urea, in a buffer containing 45 mM Tris-Borate (pH8.3) and 1.4 mM EDTA. The results were imaged using the Molecular Dynamics Fluoroimager 595, excitation 488, emission 530. The resulting image is shown in FIG. 109B.

Figure 109A:
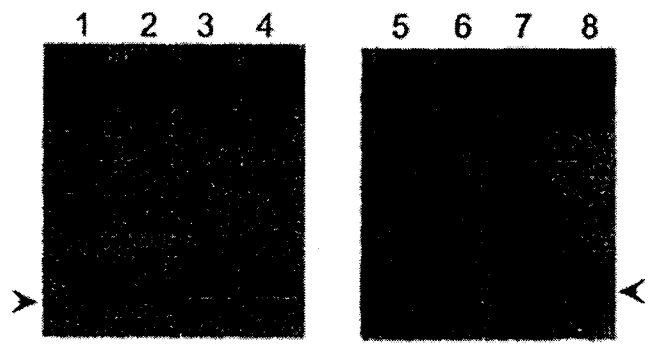
FIG. 109A shows two images generated by a fluorescence imager showing the effects on nonspecific and specific cleavage signal of including an unmodified ARRESTOR oligonucleotide in the second step of a reaction where the cut probe from an initial invasive cleavage reaction is employed as the INVADER oligonucleotide in a second invasive cleavage reaction.

In FIG. 109A, the left hand panel shows the reactions that lacked an ARRESTOR oligonucleotide, while the right hand panel shows the data from reactions that included the all natural ARRESTOR oligonucleotide. The first two lanes of each panel are from no-target controls, the second set of lanes contained target. The products of cleavage are visible in the bottom one/fourth of each panel. The position at which the specific reaction products should run is indicated by arrows on left and right.

It can be seen by examination of these data, that the reactions run in the absence of ARRESTOR oligonucleotide show reproducible quality between the replicates, and show significant cleavage only when target is present. In contrast, the addition of another unmodified oligonucleotide into the reactions causes great variation between the replicate lanes (e.g., lanes 5 and 6 were provided with the same reactants, but produced markedly different results). The introduction of the all natural ARRESTOR oligonucleotide produced, rather than reduced, background in these no-target lanes, and increased cleavage at other sites (i.e., the bands other that those indicated by the arrows flanking the panels). For these reasons the modifications that are described above, the effects of which are shown on FIG. 109B, were incorporated.

Figure 109B:
FIG. 109B shows two images generated by a fluorescence imager showing the effects on nonspecific and specific cleavage signal of including a 3' terminal amine modified ARRESTOR, a partially 2' O-methyl substituted, 3' terminal amine modified ARRESTOR oligonucleotide, or an entirely 2' O-methyl, 3' terminal amine modified ARRESTOR oligonucleotide in the second step of a reaction where the cut probe from an initial invasive cleavage reaction is employed as the INVADER oligonucleotide in a second invasive cleavage reaction.

The first 4 lanes of FIG. 109B show the products of duplicate reactions without an ARRESTOR oligonucleotide, plus or minus the HBV target (lanes 1, 2, and lanes 3, 4, respectively); The next 4 lanes, 5, 6 and 7, 8 used a natural ARRESTOR oligonucleotide having a 3' terminal amine; lanes 9, 10 and 11, 12 used the ARRESTOR oligonucleotide with a 3' portion composed of 2' O-methyl nucleotides, and having a 3' terminal amine; lanes 13, 14 and 15, 16 used the ARRESTOR oligonucleotide composed entirely of 2' O-methyl nucleotides and having a 3' terminal amine. The products of cleavage of the secondary probe are visible in the lower one third of each panel.

Visual inspection of these data shows that the addition of the 3' terminal amine to the natural ARRESTOR oligonucleotide suppresses the aberrant cleavage seen in FIG. 109A, but this ARRESTOR oligonucleotide does not improve the performance of the reaction, as compared to the no-ARRESTOR oligonucleotide controls. In contrast, the use of the 2' O-methyl nucleotides in the body of the ARRESTOR oligonucleotide does reduce background, whether partially or completely substituted. To quantify the relative effects of these modifications, the fluorescence from each of the co-migrating product bands was measured, the signals from the duplicate lanes were averaged and the "fold over background" was calculated for each reaction containing target nucleic acid.

When ARRESTOR oligonucleotide was omitted, the target specific signal (lanes 3, 4) was 27-fold over the no target background; the natural ARRESTOR oligonucleotide+amine gave a signal of 17-fold over background; the partial 2' O-methyl+amine gave a signal of 47-fold over background; and the completely 2' O-methyl+amine gave a signal of 33 fold over background.

These Figures show that both modifications can have a beneficial effect on the specificity of the multiple, sequential invasive cleavage assay. They also show that the use of the 2' O-methyl substituted backbone, either partial or entire, markedly improves the specificity of these reactions. It is intended that in various embodiments of the present inventon, that any number of modifications that make either the ARRESTOR oligonucleotide or the complex it forms with the primary target resistant to nucleases will provide similar enhancement.

Example 52

Effect of ARRESTOR Oligonucleotide Length on Signal Enhancement in Multiple Sequential Invasive Cleavage Assays As noted in the Description of the Invention, the optimal length for an ARRESTOR oligonucleotide depends upon the design of the other nucleic acid elements of the INVADER reaction, particularly on the design of the primary probe. In this Example, the effects of varying the length of the ARRESTOR oligonucleotide were explored in systems using two different secondary probes. A schematic diagram showing these ARRESTOR oligonucleotides aligned as they would hybridize to the primary probe oligonucleotide is provided in FIG. 11C. In this Figure, the region of the primary probe that recognizes the target nucleic acid is shown underlined; the non-underlined portion, plus the first underlined base is the portion that is released by the first cleavage, and goes on to participate in the second or subsequent cleavage structure.

All reactions were performed in duplicate. The INVADER reactions were done in a final volume of 10 µl final volume containing 10 mM MOPS, pH 7.5, mM $MgCl_2$, 500 fmoles of primary INVADER 241-95-01, (SEQ ID NO:176), 25 pmoles of primary probe 241-95-02 (SEQ ID NO:175), 30 ng of AfuFEN1 enzyme, and 10 ng of human genomic DNA, and if included, 1 amoles of HBV amplicon pAM 6 #2. MOPS, target DNA, and INVADER oligonucleotides were combined to a final volume of 7 µl. Samples were heat denatured at 95° C. for 5 minutes, then cooled to 67° C. During the 5 minute denaturation, $MgCl_2$, probe and enzyme were combined. The primary INVADER reactions were initiated by the addition of 3 µl of $MgCl_2$, probe and enzyme mix, to the final concentrations indicated above. Reactions were incubated for 30 minutes at 67° C. The reaction were then cooled to 52° C., and each primary INVADER reaction received the following secondary reaction components in a total volume of 3 µl: 2.5 pmoles secondary target 241-95-07 (SEQ ID NO:177), 10 pmoles of either secondary probe 228-48-04 (SEQ ID NO:173), or 228-48-04N (SEQ ID NO:178) and 100 pmoles of an ARRESTOR oligonucleotide, either 241-95-03 (SEQ ID NO:179), 241-95-04 (SEQ ID NO:180), 241-95-05 (SEQ ID NO:181) or 241-95-06 (SEQ ID NO:182). The ARRESTOR oligonucleotide were omitted from some reactions as controls for ARRESTOR oligonucleotide effects.

The reactions were incubated at 52° C. for 34 minutes, and were then stopped by the addition of 10 µl of 95% formamide, 10 mM EDTA, and 0.02% crystal violet. All samples were heated to 95° C. for 1 minute, and 4 µl of each sample were resolved by electrophoresis through 20% denaturing acrylamide gel (19:1 cross-linked) with 7 M urea, in a buffer containing 45 mM Tris-Borate (pH8.3) and 1.4 mM EDTA. The results were imaged using the Molecular Dynamics Fluorimager 595, excitation 488, emission 530. The resulting images for the reactions with the shorter and longer secondary probes are shown in FIGS. 110A and 110B, respectively.

In each Figure, the products of cleavage are visible as bands in the bottom half of each lane. The first 4 lanes of each Figure show the products of duplicate reactions without an ARRESTOR oligonucleotide, plus or minus the HBV target (lanes sets 1 and 2 respectively); in the next 4 lanes, sets 3 and 4 used the shortest ARRESTOR 241-95-03 (SEQ ID NO:179); lanes 5 and 6 used 241-95-04 (SEQ ID NO:180); lanes 7 and 8 used 241-95-05 (SEQ ID NO:181); and lanes 9 and 10 used 241-95-06 (SEQ ID NO:182).

The principal background of concern is the band that appears in the "no target" control lanes (odd numbers; this band co-migrates with the target-specific signal near the bottom of each gel panel). Visual inspection shows that the shortest ARRESTOR oligonucleotide was the least effective at suppressing this background, and that the efficacy was increased when the ARRESTOR oligonucleotide extended further into the portion that participates in the subsequent cleavage reaction. Even with this difference in effect, it can be seen from these data that there is much latitude in the design of the ARRESTOR oligonucleotide. The choice of lengths will be influenced by the temperature at which the reaction making use of the ARRESTOR oligonucleotide is performed, the lengths of the duplexes formed between the primary probe and the target, the primary probe and the secondary target, and the relative concentrations of the different nucleic acid species in the reactions.

Example 53

Effect of ARRESTOR Oligonucleotide Concentration on Signal Enhancement in Multiple Sequential Invasive Cleavage Assays In examining the effects of including ARRESTOR oligonucleotides in these cleavage reactions, it was of interest to determine if the concentration of the ARRESTOR oligonucleotide in excess of the primary probe concentration would have an effect on yields of either non-specific or specific signal, and if the length of the ARRESTOR oligonucleotide would be a factor. These two variable were investigated in the following Example.

All reactions were performed in duplicate. The primary INVADER reactions were done in a final volume of 10 µl and contained 10 mM MOPS, pH 7.5; 7.5 mM $MgCl_2$, 500 fmoles of primary INVADER 241-95-01 (SEQ ID NO:176), 25 pmoles of primary probe 241-95-02 (SEQ ID NO:175), 30 ng of AfuFEN1 enzyme, and 10 ng of human genomic DNA. Where included, the target DNA was 1 amole of HBV amplicon pAM 6 #2, as described above. MOPS, target and INVADER were combined to a final volume of 7 µl. The samples were heat denatured at 95° C. for 5 minutes, then cooled to 67° C. During the 5 minute denaturation, $MgCl_2$, probe and enzyme were combined. The primary INVADER reactions were initiated by the addition of 3 µl of $MgCl_2$, probe and enzyme mix. The reactions were incubated for 30 minutes at 67° C. The reactions were then cooled to 52° C. and each primary INVADER reaction received the following secondary reaction components: 2.5 pmoles secondary target 241-95-07 (SEQ ID NO:177), 10 pmoles secondary probe 228-48-04 (SEQ ID NO:173); and, if included, 50, 100 or 200 pmoles of either ARRESTOR oligonucleotide 241-95-03 (SEQ ID NO:179) or 241-95-05 (SEQ ID NO:181), in a total volume of 3 µl. Reactions were then incubated at 52° C. for 35 minutes. Reactions were stopped by the addition of 10 µl of 95% formamide, 10 mM EDTA, and 0.02% crystal violet. All of the samples were heated to 95° C. for 1 minute, and 4 µl of each sample were resolved by electrophoresis through 20% denaturing acrylamide gel (19:1 cross-linked) with 7 M urea, in a buffer containing 45 mM Tris-Borate (pH8.3), and 1.4 mM EDTA. The results were imaged using the Molecular Dynamics Fluoroimager 595, excitation 488, emission 530. The resulting images are shown as a composite image in FIG. 111.

Each of the duplicate reactions were loaded on the gel in adjacent lanes and are labeled with a single lane number. All odd numbered lanes were no-target controls. Lanes 1 and 2 had no ARRESTOR oligonucleotide added; lanes 3-8 show results from reactions containing the shorter ARRESTOR oligonucleotide, 241-95-03 (SEQ ID NO:179); lanes 9-14 show results from reactions containing the longer ARRESTOR oligonucleotide, 241-95-05 (SEQ ID NO:181). The products of cleavage from the secondary reaction are visible in the bottom one third of each panel. Visual inspection of these data (i.e., comparison of the specific products to the background bands) shows that both ARRESTOR oligonucleotides have some beneficial effect at all concentration.

To quantify the relative effects of ARRESTOR oligonucleotide length and concentration, the fluorescence from each of the co-migrating product bands was measured, the signals from the duplicate lanes were averaged and the "fold over background" (signal+target/signal−target) was calculated for each reaction containing target nucleic acid. The reaction lacking an ARRESTOR oligonucleotide yielded a signal approximately 27-fold over background. Inclusion of the shorter ARRESTOR oligonucleotide at 50, 100 or 200 pmoles produced products at 42, 51 and 60-fold over background, respectively. This shows that while the short arrestr at the lowest concentration seems to be less effective than the longer ARRESTOR oligonucleotides (See, previous Example) this can be compensated for by increasing the concentration of ARRESTOR oligonucleotide, and thereby the ARRESTOR oligonucleotide:primary probe ratio.

In contrast, inclusion of the longer ARRESTOR oligonucleotide at 50, 100 or 200 pmoles produced products at 60, 32 and 24 fold over background, respectively. At the lowest concentration, the efficacy of this longer ARRESTOR oligonucleotide relative to the shorter ARRESTOR oligonucleotide is consistent with the previous Example. Increasing the concentration, however, decreased the yield of specific product, suggesting a competition effect with some element of the secondary cleavage reaction.

These data show that the ARRESTOR oligonucleotides can be used to advantage in a number of specific reaction designs. The choice of concentration will be influenced by the temperature at which the reaction making use of the ARRESTOR oligonucleotide is performed, the lengths of the duplexes formed between the primary probe and the target, the primary probe and the secondary target, and between the primary probe and the ARRESTOR oligonucleotide.

Selection of oligonucleotides for target nucleic acids other than the HBV shown here, (e.g., oligonucleotide composition and length), and the optimization of cleavage reaction conditions in accord with the models provided here follow routine methods and common practice well known to those skilled in the methods of molecular biology.

Example 45 demonstrated that some enzymes require an overlap between an upstream INVADER oligonucleotide and a downstream probe oligonucleotide to create a cleavage structure (FIG. 100). It has also been determined that the 3' terminal nucleotide of the INVADER oligonucleotide need not be complementary to the target strand, even if it is the only overlapping base in the INVADER oligonucleotide (e.g., as with the HCMV probes shown in FIG. 103). The requirement for an overlap can serve as a convenient basis for detecting single base polymorphisms (SNPs) or mutations in a nucleic acid sample.

For detection of single base variations, at least two oligonucleotides (e.g., a probe and an INVADER oligonucleotide) hybridize in tandem to the target nucleic acid to form the overlapping structure recognized by the CLEAVASE enzyme to be used in the reaction. An unpaired "flap" is included on the 5' end of the probe. The enzyme recognizes the overlap and cleaves off the unpaired flap, releasing it as a target-specific product. Enzymes that have a strong preference for an overlapping structure, i.e., that cleave the overlapping structure at a much greater rate than they cleave a non-overlapping structure include the FEN-1 enzymes from *Archaeoglobus fulgidus* and *Pyrococcus furiosus* and such enzymes are particularly preferred in the detection of mutations and SNPs. In the secondary reaction, the released flap serves as an INVADER oligonucleotide to create another overlapping cleavage structure (e.g., as shown in FIG. 96). In the following examples, the released flap creates this overlapping structure in conjunction with a FRET cassette, a single oligonucleotide having a region of self-complementarity to form a hairpin (FIG. 112A) When the FRET cassette is cleaved to release its 5' nucleotide, the fluorescent dye (F) and the quencher (Q) on the cassette are separated and a detectable fluorescence signal is produced. If the probe and the target sequence do not match perfectly at the cleavage site (e.g., as in FIG. 112B), the overlapped structure does not form, cleavage is suppressed, and no fluorescence will be produced.

The reactions may be performed under conditions in which the probes and FRET cassettes turn over continuously without temperature cycling or cleavage. When an uncut probe hybridizes to the target next to an overlapping INVADER oligonucleotide, the probe can be cleaved to produce a target-specific product, which in turn enables the cleavage of many FRET cassettes.

The following eight examples demonstrate the design and application of the sequential INVADER assay with FRET cassette detection to analysis of SNPs and mutations in a variety of nucleic acid samples.

Example 54

Detection of Single Nucleotide Polymorphisms in the Human Apolipoprotein E Gene

This Example describes an assay for the detection of SNPs in the human Apolipoprotein E gene. Probe and INVADER oligonucleotides were designed to target single nucleotide polymorphisms (SNPs) at two positions in the human apolipoprotein E (apoE) gene. Three different alleles exist for the apoE gene, epsilon 2, epsilon 3, and epsilon 4, which code for 3 different isoforms of the apoE protein, termed E2, E3 and E4. The different isoforms vary in at amino acid positions 112 or 158 (see Table A), and each variation is caused by a single base change in the corresponding codon.

TABLE A

| | 112 | | 158 | |
|---|---|---|---|---|
| ISOFORM | codon | amino acid | codon | amino acid |
| E2 | TGC | cys | TGC | cys |
| E3 | TGC | cys | CGC | arg |
| E4 | CGC | arg | CGC | arg |

INVADER and probe oligonucleotides were designed using the algorithm described above (detailed description of the invention), with the probe set selected to operate at 63° C. As shown in FIGS. 113A-D, one INVADER oligonucleotide and two unlabelled, probe oligonucleotides, one for each variant at a given locus, were designed for each codon. For codon 112, the probes were designed to detect either the C nucleotide (to code for arginine; SEQ ID NO:197) or a T nucleotide (to code for cysteine; SEQ ID NO:198). For codon 158, the probes were designed to detect either a C nucleotide (to code for arginine; SEQ ID NO:199) or a T nucleotide (to code for cysteine; SEQ ID NO:200). A FRET cassette to be used with all of the probe sets was also synthesized (SEQ ID NO:201, FIG. 113). In this Example and in the following Examples, all oligonucleotides were synthesized using standard phosphoramidite chemistries. Primary probe oligonucleotides were unlabeled. The FRET cassettes were labeled by the incorporation of Cy3 phosphoramidite and fluorescein phosphoramidite (Glen Research). While designed for 5' terminal use, the Cy3 phosphoramidite has an additional monomethoxy trityl (MMT) group on the dye that can be removed to allow further synthetic chain extension, resulting in an internal label with the dye bridging a gap in the sugar-phosphate backbone of the oligonucleotide (as diagrammed in the panels of FIG. 113). While a nucleotide may be omitted at this position to accommodate the dye, we have determined it is not necessary, and no nucleotides were omitted from the FRET cassettes used in these examples. Amine or phosphate modifications, where indicated, were used on the 3' ends of the primary probes and the FRET cassettes to prevent their use as invasive oligonucleotides. 2'-O-methyl bases in the secondary target oligonucleotides are indicated by underlining and were also used to minimize enzyme recognition of 3' ends. In addition, reactions having synthetic target DNAs were used as positive controls to verify the activity of the reaction components. The control targets are illustrated in FIGS. 113A-D. The 112 arg, 112 cys, 158 arg, and 158 cys control oligonucleotides are SEQ ID NOS:191-194, respectively.

Genomic DNA sample AG09714 was purchased from Coriell. This sample was quantitated via Pico Green and diluted with Tris with 0.1 mM EDTA to a concentration of approximately 100 ng/µl. This sample (9714 in FIG. 114A) was used to test for the 112 mutation. Samples 39634, 32435 and 31071 were purchased as whole blood from Lampire Biological Labs., Inc. Samples 511, 537, 538 and 539 were whole blood samples donated by the Blood Center of Southeast Wisconsin (Milwaukee, Wis.). Genomic DNA was prepared via the PUREGENE Blood Kit (Gentra) according to the manufacturer's instructions. Samples 39634 and 32435 were used to test for the 112 mutation, and sample 31071, 511, 537, 538 and 539 were used to test for the 158 mutation. One µl of genomic DNA was used per reaction, with 9 µl of water, for a final volume of 10 µl. Although determination of the full genotype for any one sample generally requires analysis of both loci, the samples listed above were selected to show representative signals from, and thus the functioning of, each probe set. Complete genotyping requires each sample to be tested with both probe sets.

The experiment comprised testing each genomic DNA for the indicated alleles, along with reactions having no target DNA to allow measurement of any background signal not attributable to the presence of a target sequence. Reactions testing the 112 locus were done in quadruplicate, reactions testing the 158 locus were done in triplicate.

Reaction components were prepared as batch mixes for dispensing to the individual test reactions. Batches of INVADER mix for each allele were prepared, comprising for each planned reaction: 4 µl of 16% PEG 8000/50 mM MOPS pH 7.5 and 1 µl of 1 µM INVADER oligonucleotide (either the 112 or the 158). Batches of CLEAVASE enzyme/Mg$^{2+}$/probe mix for each allele were prepared, comprising for each planned reaction: 2 µl of 75 mM MgCl$_2$, 1 µl of 10 µM FRET cassette, 1 µl 10 µM probe oligonucleotide (any one of the 112 or the 158 T or C probe oligonucleotides), and 1 µl of 200 ng/µl Afu FEN-1 enzyme.

For each reaction, 5 µl of INVADER reaction mix were aliquoted into each well of a 96-well Low Profile Polypropylene Microplate (MJ Research,). Ten μl of each control DNA or genomic sample (approximately 100 ng-190 ng) were added and mixed by pipetting up and down. The no-target controls received 1 μg of yeast tRNA instead of target DNA. The reactions comprising the synthetic targets as positive controls included either 150 or 100 zeptomoles (zmoles) of the 112 or 158 synthetic targets, respectively, and 1 μg of yeast tRNA. Each reaction was overlaid with 20 μl of clear CHILLOUT liquid wax, and incubated at 95° C. for 5 minutes. The reaction temperature was then lowered to 63° C., 51 μl of the appropriate CLEAVASE enzyme/$Mg^{2+}$/Probe reaction mix was added to each reaction and mixed by pipetting up and down 3-5 times, and the reactions were further incubated for 4 hours at 63° C., and were read directly on a CYTOFLUOR Series 4000 Fluorescence Multi-well Plate Reader, (PerSeptive Biosystems), using the following settings: Excitation (wavelength/bandwidth): 485/20 nm; Emission (wavelength/bandwidth): 530/25 nm; Gain: 37. The net averaged fluorescence signal was calculated by subtracting the averaged no-target signal (background) from the corresponding averaged target DNA reaction signal and the data were plotted using Excel spreadsheet software (Microsoft).

Results for the ApoE 112 and ApoE 158 loci are shown graphically in FIGS. 114A and 114B, respectively, with target DNAs indicated on the horizontal axis and the fluorescence units indicated on the vertical axis. The white bars represent the net averaged signal from the "C" probe, while the dark bars represent the net averaged signal from the "T" probe. The reactions having synthetic targets are indicated as Syn C and Syn T for the C and T controls, respectively. At both loci, the samples that are homozygous for either the C or T allele are easily identified by having a strong signal from only one probe or the other, while the heterozygous samples, are easily identified by having strong signals from both the C and T probes.

Example 55

Detection of Mutations in the Human Hemochromatosis (HFE) Gene

The human hemochromatosis (HFE gene) gene is located in the MHC region of chromosome 6, and was initially named HLA-H. It was later renamed the HFE gene, in accordance with the WHO Nomenclature Committee for Factors of the HLA System. Two different, single-base variations in the HFE gene are responsible for the vast majority of the cases of hereditary hemochromatosis, or iron overload disease. The most common variant, termed C282Y, is caused by a change from the wild type (WT) adenine (A) to the mutant (MT) guanine (G) at codon 282 that causes an amino acid change from a cysteine to a tyrosine residue. The second variation commonly detected in individuals suffering from iron overload disorder is termed H63D, and is caused by a WT cytosine (C) to a MT guanine (G) change at codon 63 that causes an amino acid change from a histidine to an aspartic acid residue in the expressed protein.

INVADER and probe oligonucleotide sets were designed as described above to detect both the WT and MT alleles for both the C282Y and H63D sites and are shown in FIGS. 115A-D. Detection of the C282 polymorphism used one INVADER oligonucleotide (SEQ ID NO:202), one probe specific for each variant of the allele (WT and MT, SEQ ID NOS:208 and 209, respectively) and a first FRET cassette (SEQ ID NO:210). Oligonucleotides for the H63 locus included an INVADER oligonucleotide (SEQ ID NO:203), one probe specific for each variant of the allele (WT and MT, SEQ ID NOS:211 and 212, respectively), and a second FRET cassette (SEQ ID NO:213). In addition, reactions having synthetic target DNAs were used as positive controls to verify the activity of the reaction components. The control targets are illustrated in FIGS. 115A-D. The C282 WT, C282 MT, H63 WT and H63 MT control oligonucleotides are SEQ ID NOS: 204-207, respectively. Human genomic DNA samples 14640, 14641, 14646, 14690, and 14691 were purchased from Coriell Cell Repositories (Catalog #s NA14640, NA14641, NA1446, NA14690, and NA14691).

Reactions were performed and analyzed as described in Example 54. The reactions comprising the synthetic targets as positive controls included 100 zmoles of the synthetic target and 1 μg of yeast tRNA.

Results are shown graphically in FIG. 116, with target DNAs indicated on the horizontal axis and the fluorescence units indicated on the vertical axis. The white bars represent the net signal from the wild-type probe, while the dark bars represent the net signal from the mutant probe. The left half of the graph indicates samples tested for the C282Y polymorphism, while the right half of the graph indicates samples tested for the H63D polymorphism. No target controls are indicated as "NT" and the synthetic targets are indicated as SynWT and SynMT for wild-type and mutant controls, respectively. At both loci, the samples that are homozygous for either WT or MT are easily identified by having a strong signal from only one probe or the other, while the heterozygous samples, are easily identified by having strong signals from both the WT and MT probes.

Example 56

Detection of Mutations in the Human MTHFR

Human 5,10-methylene-tetrahydrofolate reductase (MTHFR) is a major enzyme in the folate-dependent regulation of methionine and homocysteine concentrations. The wild-type protein plays a critical role in the conversion of homocysteine to methionine. A particular variation in the MTHFR protein, termed C677T and caused by a C to T transition in the MTHFR gene, has been correlated with myriad diseases and defects, including cardiovascular and neurological disorders. This Example describes an assay for the detection of the WT and MT alleles for the MTHFR 677 SNP.

INVADER and probe oligonucleotide sets were designed as described above to detect both the WT and MT allele for the MTHFR 677 site (INVADER, WT probe, MT probe, and FRET cassette are SEQ ID NOS:216, 217, 218 and 225, respectively). Positive control targets were synthesized for the WT and MT alleles at the 677 site (SEQ ID NOS:214 and 215, respectively); oligonucleotides are shown in FIGS. 117A and 117B.

Human genomic DNA samples 01532 and 01560 were purchased from Coriell. These samples had been characterized by "PCR" at Coriell for the MTHFR genotype. They were also characterized in house by PCR/RFLP analysis for genotype confirmation. Human genomic sample 32435 was purchased as whole blood from Lampire Biological Labs., Inc. (Coopersberg, Pa.), and genomic DNA was prepared via the Gentra PUREGENE Blood Kit (Minneapolis, Minn.) according to the manufacturer's instructions. Samples were quantitated via PicoGreen (Molecular Probes, Eugene Oreg.) and diluted with TE to a concentration of approximately 10 ng/μl. 100 ng (10 μl) of each sample was used in each reaction.

Triplicate reactions were performed and analyzed as described in Example 54, except the INVADER mixes contained 1 µl of 0.5 µM INVADER oligonucleotide for each reaction. The reactions comprising the synthetic targets as positive controls included 50 zmoles of the synthetic target and 1 µg of yeast tRNA. Reactions simulating a heterozygous sample included 50 zmoles of each control target.

Results are shown graphically in FIG. 118, with target DNAs indicated on the horizontal axis and the fluorescence units indicated on the vertical axis. The white bars represent the net averaged signal from the wild-type probe, while the dark bars represent the net averaged signal from the mutant probe. The synthetic targets are indicated as SynWT and SynMT for wild-type and mutant controls, respectively and SynHET for a mixture of the two to simulate a heterozygous sample. At both loci, the samples that are homozygous for either WT or MT are easily identified by having a strong signal from only one probe or the other, while the heterozygous samples are easily identified by having strong signals from both the WT and MT probes.

Example 57

Detection of Mutations in the Human Prothrombin (Factor II) Gene

The prothrombin A20210G mutation has been determined to be a risk factor for thromboembolism. The mutation occurs in the 3' untranslated region of the prothrombin gene, replacing the WT adenine (A) at position 20210 with the MT guanine (G). This Example describes an assay for the detection of the WT and MT alleles of the prothrombin A20210G mutation.

INVADER and probe oligonucleotide sets were designed as described above to detect both the WT and MT alleles at the prothrombin 20210 site (INVADER, WT probe, MT probe and FRET cassette are SEQ ID NOS: 222-225, respectively). Positive control targets were synthesized for the WT and MT alleles at the 20210 site (SEQ ID NOS:220 and 221, respectively); oligonucleotides are shown in FIGS. 119A and 119B.

Three patient samples of human genomic DNA were donated by the Blood Center of Southeast Wisconsin, identified as 2196, 2263 and 2265. These samples were purified at the Blood Center via QIAGEN BioRobot 9600 (QIAGEN # 900200), quantitated by Pico Green (Molecular Probes) and were found to be at a concentration of 30-50 ng/µl.

Duplicate reactions were performed and analyzed as described in Example 54, except the INVADER mixes contained 1 µl of 0.5 µM INVADER oligonucleotide for each reaction, and the mix was diluted with 1 volume of dH$_2$O (i.e., 5 µl per reaction) so that the INVADER mix was dispensed 10 µl aliquots, while the DNA was dispensed in 5 µl aliquots, adding 150-250 ng of genomic DNA per reaction. Each no target control reaction received 1 µg of yeast tRNA, and the reactions comprising the synthetic targets as positive controls included 300 zmoles of WT control or 50 zmoles of MT control and 1 µg of yeast tRNA.

Results are shown graphically in FIG. 120, with target DNAs indicated on the horizontal axis and the fluorescence units indicated on the vertical axis. The white bars represent the net averaged signal from the wild-type probe, while the dark bars represent the net averaged signal from the mutant probe. Synthetic targets are indicated as SynWT and SynMT for wild-type and mutant controls, respectively. Samples that are homozygous for the WT are easily identified by having a strong signal from only the WT probe, while the heterozygous sample is easily identified by having strong signals from both the WT and MT probes.

Example 58

Detection of the HR-2 Mutation in the Human Factor V Gene

This Example describes an assay for the deteciton of the R-2 polymorphism in the human factor V gene. The R-2 polymorphism in the human factor V gene is located in exon 13 of the factor V gene, and is the result of an A to G transition at base 4070, replacing the wild-type amino acid histidine with the mutant arginine in the mature protein. The R-2 polymorphism is one of a set of mutations termed collectively HR-2. The HR-2 haplotype is defined by 6 nucleotide base substitutions in exons 13 and 16 of the factor V gene, and is associated with an increased functional resistance to activated protein C both in normal subjects and in thrombophilic patients. When present as a compound heterozygote in conjunction with the Leiden mutation (see Example 60, below), clinical symptoms are comparable to those seen in patients homozygous for the Leiden mutation.

Within about a 600-base pair region surrounding the R2 allele, four sub-regions of DNA, each encompassing the sequence of the WT INVADER probe set, (approximately 22 bases in length), contain sequence similar to that immediately surrounding the R2 allele. These repeated sequences can be detected by an INVADER and probe oligonucleotide set designed for the wild-type R-2 sequence. Because of the repeated sequence, reactions with this INVADER/probe set yield very high signal, even with genomic samples containing R-2 mutants, thus greatly increasing the risk of misinterpreting the data. In the example of an R-2 heterozygote, the signal generated by the R-2 mutant would be extremely low compared to the wild-type signal. It is thus possible that one might err and interpret the data as wild-type, not as heterozygous. The same would hold true even for a homozygous mutant R-2 sample. Therefore, instead of having an INVADER/probe set to detect the WT R-2 allele, an INVADER/probe set was developed to detect sequences in the single copy α-actin gene, thus providing an internal reaction control, as well as an internal signal intensity control. Since the α-actin gene is single copy, the signal levels generated in the detection of this sequence will be comparable to that generated in the detection of the R-2 mutant allele, and the probability of incorrect data interpretation due to WT signal overwhelming that generated by the MT is no longer an issue.

In the previous examples, each sample was assayed in two different reactions, one reaction tested for the presence of wild-type sequence and one reaction tested for the presence of mutant sequence. In this example, each sample is tested with both the α-actin internal control and the MT R-2 INVADER/probe sets. INVADER and probe oligonucleotide sets were designed as described above to detect both the MT R-2 and α-actin control sequence (MT R-2 INVADER and probe, and the FRET cassette are SEQ ID NOS:228, 229 and 230, respectively; α-actin INVADER and probe are SEQ ID NOS: 231 and 232, respectively). Positive control targets were synthesized for the Mutant R-2 allele and the α-actin gene (SEQ ID NOS:226 and 227, respectively); oligonucleotides are shown in FIGS. 121A and B.

Human genomic DNA sample 39021 was obtained from Sigma (Catalog # D6537) and uncharacterized human genomic sample 15506 was obtained from Coriell (Catalog # NA15506, Camden, N.J. 08103) Samples were diluted to 10 ng/μl with Tris-EDTA, pH 8.0. Ten μl (100 ng) was used per reaction. No target controls received 1 μg of yeast tRNA instead of human genomic DNA. Reactions were performed and analyzed as described in Example 54, except the INVADER mixes contained 0.5 μl each of 2 μM R-2 INVADER oligonucleotide and 2.0 μM α-actin INVADER oligonucleotide. The probe master mixes contained 1 μl of either the 10 μM R-2 probe or 1 μl of 10 μM α-actin probe, 2 μl of 75 mM $MgCl_2$, 1 μl of 10 μM FRET cassette and 1 μl 200 ng/μl Afu FEN-1 enzyme per reaction. The reactions comprising the synthetic targets as positive controls included 100 zmoles of the synthetic target and 1 μg of yeast tRNA. The SynHET and SynMT reactions contained mixtures of synthetic targets at 2:1 and 1:1 of the α-actin:R-2 mutant targets, respectively.

Reactions were read directly on a CYTOFLUOR Multi-well Plate Reader Series 4000 (PerSeptive Biosystems) using the following parameters: Excitation wavelength/bandwidth 485 nm/20 nm, Emission wavelength/bandwidth 530 mm/25 nm, gain 36.

Results are shown graphically in FIG. 122, with target DNAs indicated on the horizontal axis and the fluorescence units indicated on the vertical axis. The white bars represent the net signal from the internal control probe, while the dark bars represent the net signal from the R-2 mutant probe. Synthetic targets are indicated as SynIC and SynMT for internal control and mutant R-2 controls, respectively and SynHET for a mixture of the two to simulate a sample that is heterozygous at the R-2 allele. The sample that does not have the MT R-2 allele is easily identified by having a strong signal from only the IC probe, while that which is heterozygous at the R-2 allele is identified by having signals from both the IC and the MT R-2 probes, but at a ratio near 2:1. A sample homozygous for the mutation at the R-2 allele (not shown) would show nearly equal signal from each probe, as shown with the SynMT control.

Example 59

Detection of Single Nucleotide Polymorphisms in the Human TNF-α Gene

The human cytokine tumor necrosis factor α (TNF-α) gene has been shown to be a major factor in graft rejection; the more TNF-α present in the system, the greater the rejection response to transplanted tissue. The mutation detected in this example is located in the promoter region of the TNF-α gene at position −308 (minus 308). The WT guanine (G) is replaced with a MT adenine (A). This result of this promoter mutation is the enhancement of transcription of TNF-α by 6 to 7 fold. This Example describes an assay for the detection of the −308 mutation in the promoter of the human TNF-α gene.

INVADER and probe oligonucleotide sets were designed as described above to detect both the WT and MT alleles at the −308 site (INVADER, WT probe, and MT probe are SEQ ID NOS:235, 236 and 237, respectively; FRET cassette is SEQ ID NO:225). Positive control targets were synthesized for the WT and MT alleles at the −308 site (SEQ ID NOS:233 and 234, respectively); oligonucleotides are shown in FIGS. 123A and 123B.

Purified human genomic DNA samples (M2, M3 and M4) were donated by the Mayo Clinic (Rochester Minn.).

Triplicate reactions were performed as described in Example 54, except they were stopped after the four hour incubation at 63° C. by the addition 100 μl of 100 mM EDTA. Reactions comprising the synthetic targets as positive controls included 100 zmoles of the synthetic target and 1 μg of yeast tRNA. No target controls received 1 μg of yeast tRNA instead of human genomic DNA. 100 μl of each stopped reaction was transferred to a Nunc 96 well Maxisorb plate (VWR Scientific) and read on a CYTOFLUOR Multi-well Plate Reader Series 4000 (PerSeptive Biosystems) using the following parameters: Excitation wavelength/bandwidth 485 nm/20 nm, Emission wavelength/bandwidth 530 nm/25 nm; gain 65.

Results are shown graphically in FIG. 124, with target DNAs indicated on the horizontal axis and the fluorescence units indicated on the vertical axis. The white bars represent the net averaged signal from the wild-type probe, while the dark bars represent the net averaged signal from the mutant probe. The synthetic targets are indicated as SynWT and SynMT for wild-type and mutant controls, respectively and SynHET for a mixture of the two to simulate a heterozygous sample. The samples that are homozygous for either WT or MT are easily identified by having a strong signal from only one probe or the other, while the heterozygous sample is easily identified by having signals from both the WT and MT probes.

Example 60

Detection of the Factor V Leiden Mutation

The "Leiden" mutation in blood coagulation factor V results from a cytosine "C" to a thymidine "T" base change in exon 1 of the factor V gene. The mutant protein has glutamine at amino acid position 506, instead of the wild-type arginine. This substitution prevents activated protein C from cleaving and inactivating factor V. The active form of the protein therefore remains abundant in the blood stream and continues to promote coagulation. This Example describes an assay for the detection of the Leiden mutation of the human factor V gene.

INVADER and probe oligonucleotide sets were designed as described above to detect both the WT and MT alleles at the 506 site (INVADER, WT probe, and MT probe are SEQ ID NOS:240, 241 and 242, respectively; the FRET cassette is SEQ ID NO:225). Positive control targets were synthesized for the WT and MT alleles at the 506 site (SEQ ID NOS:238 and 239, respectively); oligonucleotides are shown in FIGS. 125A and 125B.

Whole blood samples were obtained from the Midwest Hemostasis Center (Muncie, Ind.). Samples were characterized for the Factor V Leiden genotype by the Midwest Hemostasis Center via methods involving PCR. Buffy coats were isolated as previously described, and genomic DNA was purified using the QIAamp 96 DNA Blood Kit (Qiagen, Valencia) according to the manufacturer's instructions, except that the samples were eluted in 200 μl of elution buffer. The purified DNA samples were quantitated by Pico Green (Molecular Probes) and were then diluted with TE to a concentration of 15-60 ng per μl. Single reactions were performed as described in Example 54. The no-target control reaction received 1 μg of yeast tRNA instead of DNA, and the reactions comprising the synthetic targets as positive controls included 200 zmoles of the synthetic target and 1 μg of yeast tRNA.

After the 4 hour incubation at 63° C., reactions were read directly on a CYTOFLUOR Multi-well Plate Reader Series 4000 (PerSeptive Biosystems) using the following parameters: Excitation wavelength/bandwidth 485 nm/20 nm, Emission wavelength/bandwidth 530 nm/25 nm, gain 65.

Results are shown graphically in FIG. 126, with target DNAs indicated on the horizontal axis and the fluorescence units indicated on the vertical axis. The white bars represent the net averaged signal from the wild-type probe, while the dark bars represent the net averaged signal from the mutant probe. The synthetic targets are indicated as SynWT and SynMT for wild-type and mutant controls, respectively and SynHET for a mixture of the two to simulate a heterozygous sample. The samples that are homozygous for either WT or MT are easily identified by having a strong signal from only one probe or the other, while the heterozygous samples are easily identified by having signals from both the WT and MT probes.

Example 61

Detection of Methicillin-Resistant *Staphalococcus aureus*

*Staphylococcus aureus* is recognized as one of the major causes of infections in humans occurring both in the hospital and in the community at large. One of the most serious concerns in treating any bacterial infection is the increasing resistance to antibiotics. The growing incidence of methicillin-resistant *S. aureus* (MRSA) infections worldwide has underscored the importance of both early detection of the infective agent, and defining a resistance profile such that proper treatment can be given. The primary mechanism for resistance to methicillin involves the production of a protein called PBP2a, encoded by the mecA gene. The mecA gene is not native to *Staphalococcus aureus*, but is of extra-species origin. The mecA gene is, however, indicative of methicillin resistance and is used as a marker for the detection of resistant bacteria. To identify methicillin resistant *S. aureus* via nucleic acid techniques, both the mecA gene and at least one species specific gene must be targeted. A particular species-specific gene, the nuclease or nuc gene is used in the following example. This Example describes an assay for the detection of MRSA.

INVADER and probe oligonucleotide sets were designed as described above to detect both the mecA gene and the nuc gene (meA INVADER and probe, are SEQ ID NOS:243 and 244, respectively; nuc INVADER and probe are SEQ ID NOS:246 and 247, respectively; the FRET cassette for both INVADER/probe sets is SEQ ID NO:245); oligonucleotides are shown in FIGS. 127A and 127B. The mecA and nuc target sequences shown are SEQ ID NOS:252 and 253, respectively. Samples of methicillin-resistant *Staphalococcus aureus* were purchased from American Type Culture Collection (ATCC, Catalog # 33591). Samples of methicillin sensitive *Staphalococcus aureus* (MSSA) were obtained from Gene Trak, Inc. (GT#2431), and samples of *Staphalococcus haemolyticus* were obtained from ATCC (ATCC#29970). The bacterial samples were streaked onto standard blood agar plates and grown at 37° C. for 14-18 hours. DNA samples from MRSA, MSSA, and *S. haemolyticus* were prepared as follows. A single colony was suspended in 50 µl of 10 mM TRIS pH 7.5 in a 1.5 ml microfuge tube. The sample was incubated at 65° C. for 5 minutes, and then micro-waved on the highest setting for 4 minutes. Ten µl of this preparation was used in each reaction.

Positive controls were created by polymerase chain reaction. A 533 base-pair DNA fragment of the mecA sequence and a 467 base pair DNA fragment of the nuc gene sequence were amplified and isolated as follows. PCR primer sequences used for mecA gene amplification were 5'-AAA ATC GAT GGT AAA GGT TGG C-3" (SEQ ID NO:248) and 5'-AGT TCT GCA GTA CCG GAT TTG C-3' (SEQ ID NO:249). PCR primer sequences used for nuc gene amplification were 5'-TCGCTACTAGTTGCTTAGTG-3' (SEQ ID NO:250) and 5'-GTAAACATAAGCAACTTTAG-3' (SEQ ID NO:251). MRSA and MSSA target DNA was isolated as described above. PCR reactions were done using the AMPLITAQ DNA Polymerase Kit with GENEAMP (PE Corporation Catalog # $N_8O_8$-0152). Separate reactions were done for the mecA and nuc sequences, and were performed in a 100 µl final volume containing the following components: 10 µl of 10×PCR buffer, 2.5 µl of 10 µM upstream primer and downstream primer, 2 µl of 10 mM dNTP mix, 1.0 µl AMPLITAQ DNA polymerase, 2 µl (10-50 ng) of bacterial DNA (the MRSA or the MSSA), and 80 µl of water for a final volume of 100 µl. Reactions were covered with approximately 50 µl of CHILLOUT liquid wax (MJ Research) and cycled as follows: the mecA reactions were denatured at 97° C. for 3 minutes. Reactions were then cycled at 97° C. for 1 minute, 52° C. for 30 seconds, 72° C. for 1 minute. This was repeated 5 t After the final 72° C. 1 minute incubation, reactions were again heated to 94° C. for 30 seconds, 52° C. for 30 seconds and 72° C. for 1 minute, for 30 cycles. mecA reactions were then incubated at 72° C. for 7 minutes, then held at 4° C. until purification.

The nuc amplification reactions were denatured at 97° C. for 3 minutes. Reactions were then cycled at 97° C. for 1 minute, 48° C. for 30 seconds, 72° C. for 1 minute. This was repeated for 5 cycles. After the final 72° C., 1 minute incubation, reactions were heated to 94° C. for 30 seconds, 48° C. for 30 seconds and 72° C. for 1 minute. This was repeated for 30 cycles. Reactions were then incubated at 72° C. for 7 minutes, and finally cooled to 4° C. and held until purification.

After amplification, reactions were run on a 1% agarose gel in 1% TBE buffer with 50-2000 base-pair markers (Novagen, Cat# 69278-3); bands were visualized via ethidium bromide staining followed by ultraviolet illumination. The appropriately sized bands were excised from the gel and purified by the QIAquick Gel Extraction Kit (QiagenCat# 28704) according to the manufacturer's protocol. Each column was eluted twice with 50 µl of elution buffer. The concentration of the purified PCR synthetic target DNA was determined by $OD_{260}$, and diluted to a stock concentration of 50 fmoles per microliter. Positive controls were used at a concentration of 10 amole per reaction with a 10 µl addition. Control reactions with no target were also performed, using human genomic DNA at 10 ng/µl in place of a bacterial sample. All samples were added in a volume of 10 µl.

INVADER reactions were performed in MJ 96 well Low Profile Polypropylene Microplates (MJ Research MLL-9601) in duplicate in a final volume of 15 µl. An INVADER reaction master mix was prepared and contained (per reaction) 1.5 µl water, 2.5 µl 100 mM MOPS, 5 µl of 20% PEG (8000 MW), 0.5 µl of 1 µM nuc INVADER oligonucleotide and 0.5 µl of mecA INVADER oligonucleotide. Five µl of the INVADER master mix were added to each sample and control well. 10 µl of the target bacterial DNA samples, prepared as described above, or 10 µl (10 amoles) of positive control target, or 10 µl (10 ng of human genomic DNA) of the no target control sample were added to each well. Samples were overlaid with 15 µl clear Chill-out wax (MJ Research,) and incubated at 95° C. for 5 minutes in an MJ Research Thermocycler with Hot Bonnet. Two different probe master mixes were prepared, one containing the mecA probe oligonucleotide, one containing the nuc probe oligonucleotide. The probe master mixes contained (per reaction) 2 µl of 93.75 mM $MgCl_2$, 1 µl of 10 µM FRET oligonucleotide, 1 µl of either 10 µM mecA probe oligonucleotide or 10 µM nuc probe oligonucleotide, 1 µl of 100 ng/µl Afu FEN-1 enzyme (Third Wave Technologies, Cat # 96004D). The temperature was cooled to 64° C. and 5 µl of the appropriate probe master mix (such that each control or sample reaction is tested with both the mecA and the nuc probe) was added below the Chill-out wax layer to each well and mixed by pipetting up and down 5 times. The plate was covered with MICROSEAL 'A' Film (MJ Research,) and incubated at 64° C. for 30 minutes. After the 30 minute incubation, reactions were cooled to room temperature, placed on a Perkin Elmer MICROAMP base (cat# N801-0531) and read on a CYTOFLUOR Multi-well Plate Reader Series 4000 (PerSeptive Biosystems) using the following parameters: Excitation wavelength/bandwidth 485 nm/20 nm, Emission wavelength/bandwidth 530 nm/25 μm, gain 40, 30 reads per well, temperature 25° C.

Results are shown graphically in FIG. 128, with target DNAs indicated on the horizontal axis and the fluorescence units indicated on the vertical axis. The white bars represent the net averaged signal from the mecA probe, while the dark bars represent the net averaged signal from the nuc probe.

Example 62

Construction of Chimerical Structure Specific Nucleases

FIG. 59 provides an alignment of the amino acid sequences of several structure-specific nucleases including several each of the FEN-1, XPG and RAD type nucleases. The numbers to the left of each line of sequence refers to the amino acid residue number; portions of the amino acid sequence of some of these proteins were not shown in order to maximize the alignment between proteins. Dashes represent gaps introduced to maximize alignment. From this alignment, it can be seen that the proteins can be roughly divided into blocks of conservation, which may also represent functional regions of the proteins. While not intended as a limitation on the chimeric nucleases of the present invention, these blocks of conservation may be used to select junction sites for the creation of such chimeric proteins.

The *Methanococcus jannaschii* FEN-1 protein (MJAFEN1.PRO), the *Pyrococcus furiosus* FEN-1 protein (PFUFEN1.PRO) are shown in the alignment in FIG. 59. These two natural genes were used to demonstrate the creation of chimeric nucleases having different activities than either of the parent nucleases. As known to those of skill in the art, appropriately sited restriction cleavage and ligation would also be a suitable means of creating the nucleases of the present invention. The activities of the parent nucleases on two types of cleavage structures, namely folded structures (See e.g., FIG. 60), and invasive structures (See e.g., FIG. 26) are demonstrated in the data shown in FIGS. 129A and 129B, respectively. These test molecules were digested as described in Ex. 29g. Lanes marked with "1" show cleavage by Pfu FEN-1, while lanes marked with "2" indicate cleavage by Maj FEN-1.

In this example, PCR was used to construct complete coding sequences for the chimeric proteins. This is a small subset of the possible combinations. It would also be within common practice in the art to design primers to allow the combination of any fragment of a gene for a nuclease with one or more other nuclease gene fragments, to create further examples of the chimeric nucleases of the present invention. The present invention provides methods, including an activity test, so that the activity of any such chimeric nuclease not explicitly described herein may be determined and characterized. Thus, it is intended that the present invention encompass any chimeric nuclease meeting the requirements of chimeric nucleases, as determined by methods such as the test methods described herein.

To make chimeric nucleases from the *M. jannaschii* and *P. furiosus* 5' nuclease genes, homologous parts were PCR amplified using sets of external and internal primers as shown in FIG. 130. In the next step, 5' portions from one gene and a 3' portions from the other gene were joined in pairs by recombinant PCR, such that each combination created a different full size chimerical gene. The resulting coding regions were cloned into the pTrc99A vector and expressed to produce chimerical nucleases. The specific details of construction of each of the chimeric genes shown in FIG. 130 are described below.

a) Construction of Chimerical 5' Nuclease with *M. Jannaschii* N-Terminal Portion and *P. furiosus* C-Terminal Portion with a Junction Point at Codon 84 (FIG. 130g).

A fragment of the pTrc99A vector carrying the *M. jannaschii* 5' nuclease gene was PCR amplified with TrcFwd (SEQ ID NO:266) and 025-141-02 (SEQ ID NO:267) primers (5 pmole each) in a 50 μl reaction using the ADVANTAGE cDNA PCR kit (Clonetech), for 30 cycles (92° C., 30 s; 55° C., 1 min; 72° C. 1 min) to make an N-terminus-encoding gene fragment (SEQ ID NO:268). The TrcRev (SEQ ID NO:269) and 025-141-01 (SEQ ID NO:270) primers were used to amplify a fragment of the pTrc99A vector carrying the *P. furiosus* gene to produce a C-terminus encoding gene fragment (SEQ ID NO:271). The PCR products were cleaned with the High Pure PCR Product Purification kit (Boehringer Mannheim, Germany) as described in the manufacturer's protocol and eluted in 100 μl water.

The 025-141-02 (SEQ ID NO:267) primer and the 025-141-01 (SEQ ID NO:270) primer are complementary to each other, so that the PCR fragments created above had the corresponding regions of complementarity on one end. When these fragments are combined in an amplification reaction, the region of complementarity allows the parts to hybridize to each other, to be filled in with the DNA polymerase, and then to be amplified using the outer primer pair, TrcFwd (SEQ ID NO:266) and TrcRev (SEQ ID NO:269) in this case, to form one fragment (SEQ ID NO:272). Five pmole of each outer primer was then placed in 50 μl PCR reaction using the ADVANTAGE cDNA PCR kit (Clonetech) as described above. The full length PCR product (SEQ ID NO:272) including the chimerical coding region (positions 45-1067 of SEQ ID NO:272) was separated in 1% agarose gel by standard procedures and isolated using the Geneclean II Kit (Bio 101, Vista, Calif.). The isolated fragment was then cut with NcoI and PstI restriction enzymes and cloned in pTrc99A vector.

b) Construction of Chimerical 5' Nuclease with *P. furiosus* N-Terminal Portion and *M. jannaschii* C-Terminal Portion with a Junction Point at Codon 84 (FIG. 130f).

A fragment of the pTrc99A vector carrying the *P. furiosus* 5' nuclease gene was PCR amplified with TrcFwd (SEQ ID NO:266) and 025-141-02 (SEQ ID NO:267) primers (5 pmole each) as described above to make an N-terminus-encoding gene fragment (SEQ ID NO:273). The TrcRev (SEQ ID NO:269) and 025-141-01 (SEQ ID NO:270) primers were used to amplify a fragment of the pTrc99A vector carrying the *M. jannaschii* gene to produce a C-terminus encoding gene fragment (SEQ ID NO:274). The fragments were purified and combined in a PCR, as described above to form one fragment (SEQ ID NO:275), containing the entire chimerical gene (positions 45-1025 of SEQ ID NO:275). This chimerical gene was cut with NcoI and PstI, and cloned into pTrc99A vector as described in a) above.

c) Construction of Chimerical 5' Nuclease with *P. furiosus* N-Terminal Portiono and *M. jannaschii* C-Terminal Portion with a Junction Point at Codon 114 (FIG. 130*e*).

A fragment of the pTrcPfuHis plasmid was PCR amplified with TrcFwd (SEQ ID NO:266) and 025-164-04 (SEQ ID NO:277) primers (5 pmole each), as described above to make an N-terminus-encoding gene fragment (SEQ ID NO:276). The pTrcPfuHis plasmid was constructed by modifying pTrc99-PFFFEN1 (described in Ex. 28), by adding a histidine tail to facilitate purification. To add this histidine tail, standard primer directed mutagenesis methods were used to insert the coding sequence for six histidine residues between the last amino acid codon of the pTrc99-PFFFEN1 coding region and the stop codon. The resulting plasmid was termed pTrcPfu-His.

The 159-006-01 (SEQ ID NO:279) and 025-164-07 (SEQ ID NO:280) primers were used as described in section a) above, to amplify a fragment of the pTrcMjaHis plasmid to produce a C-terminus encoding gene fragment (SEQ ID NO:278). The pTrcMjaHis plasmid was constructed by modifying pTrc99-MJFEN1 (described in Ex. 28), by adding a histidine tail to facilitate purification. To add this histidine tail, standard PCR mutagenesis methods were used to insert the coding sequence for six histidine residues between the last amino acid codon of the pTrc99-MJFEN1 coding region and the stop codon. The resulting plasmid was termed pTrcMja-His. The fragments were purified, and combined by PCR amplification with TrcFwd (SEQ ID NO:266) and 159-006-01 (SEQ ID NO:279) primers in one fragment (SEQ ID NO:281) containing the chimerical gene (positions 45-1043). This chimerical gene was cut with NcoI and PstI, and cloned into pTrc99A vector as described in a), above.

d) Construction of Chimerical 5' Nuclease with *M. jannaschii* N-Terminal Portion and *P. furiosus* C-Terminal Portion with a Junction Point at Codon 148 (FIG. 130*d*).

A fragment of the pTrc99A vector carrying the *M. jannaschii* 5' nuclease gene was PCR amplified with TrcFwd (SEQ ID NO:266) and 025-119-05 (SEQ ID NO:283) primers, as described above, to make an N-terminus-encoding gene fragment (SEQ ID NO:282). The TrcRev (SEQ ID NO:269) and 025-119-04 (SEQ ID NO:285) primers were used to amplify a fragment of the pTrc99A vector carrying the *P. furiosus* gene to produce a C-terminus encoding gene fragment (SEQ ID NO:284). The fragments were purified as described above and combined by PCR amplification with the TrcFwd (SEQ ID NO:266) and TrcRev (SEQ ID NO:269) primers into one fragment (SEQ ID NO:286) containing the chimerical gene (positions 45-1067). This chimerical gene was cut with NcoI and PstI, and cloned into pTrc99A vector as described in a), above.

e) Construction of Chimerical 5' Nuclease with *P. furiosus* N-Terminal Portion and *M. jannaschii* C-Terminal Portion Art with a Junction Point at Codon 148 (FIG. 130*c*).

A fragment of the pTrcPfuHis plasmid was PCR amplified with TrcFwd (SEQ ID NO:266) and 025-119-05 (SEQ ID NO:283) primers as described above to make an N-terminus-encoding gene fragment (SEQ ID NO:287). The TrcRev (SEQ ID NO:269) and 025-119-04 (SEQ ID NO:285) primers were used to amplify a fragment of the pTrcMjaHis plasmid to produce a C-terminus encoding gene fragment (SEQ ID NO:288). The fragments were purified as described above and combined by PCR amplification with TrcFwd (SEQ ID NO:266) and TrcRev (SEQ ID NO:269) primers in one fragment (SEQ ID NO:289) containing the chimerical gene (positions 45-1025). This chimerical gene was cut with NcoI and PstI, and cloned into pTrc99A vector as described in a), above.

f) Expression and Purification of Chimeras.

All of the chimerical enzymes described above except *P. furiosus-M. jannaschii* construct containing a junction point at the codon 114 (i.e., Example 62c) were purified as described for Taq DN. The *P. furiosus-M. jannaschii* codon 114 chimera with His-tag was purified as described for the 5' nuclease domain BN of Taq PolI.

g) Activity Characterization of Natural and Chimerical Structure-Specific Nuclease.

All of the chimerical enzymes produced as described above were characterized. In one assay, the enzymes were tested using a mixture of long and short hairpin substrates in the assay system described in Example 28g.

In these tests, reactions were done using 50 ng of each enzyme for 2 min., at 50° C. The results of the analysis are shown in FIG. 131A. In this Figure, the lanes marked "1" and "2" in FIG. 131A, indicate reactions with the Pfu and Maj parent enzymes, respectively. The remaining uncut hairpin molecules are visible as two bands at the top of each lane. Each chimeric enzyme tested is represented by reference in FIG. 130. For example, the lane marked "130f" shows the cleavage of these test molecules by the chimerical 5' nuclease with the *P. furiosus* N-terminus and the *M. jannaschii* C-terminus joined at codon 84. The various products of cleavage are seen in the lower portion of each lane. These data show that the chimerical nucleases may display cleavage activities (i.e., substrate specificities) like either parent (e.g., 130c and parent Pfu FEN-1 show little cleavage in this test) or distinct from either parent (i.e., different product profiles).

Similarly, the chimerical enzymes were examined for invasive cleavage activity using the S-60 structure and the P15 oligonucleotide depicted in FIG. 26, as described in Ex. 11. The results are shown in FIG. 131B. The uncleaved labeled P15 oligonucleotide appears in the upper portion of each lane, while the labeled product of cleavage appears in the lower portion.

These results indicate that chimerical enzymes are different in activity and specificity from the original (i.e., wild-type) *M. jannaschii* and *P. furiosus* 5' nucleases.

Example 63

Comparison of Digestion of Folded Cleavage Structures with Chimeric Nucleases

CFLP analysis was applied to a PCR amplified segment derived from *E coli* 16S rRNA genes. Although bacterial 16S rRNA genes vary throughout the phylogenetic tree, these genes contain segments that are conserved at the species, genus or kingdom level. These features have been exploited to generate primers containing consensus sequences which flank regions of variability. In prokaryotes, the ribosomal RNA genes are present in 2 to 10 copies, with an average of 7 copies in *Escherichia* strains. Any PCR amplification produces a mixed population of these genes and is in essence a "multiplex" PCR from that strain. CFLP analysis represents a composite pattern from the slightly varied rRNA genes within that organism, such that no one particular rRNA sequence is directly responsible for the entire "bar code." As a representative example of an amplicon as described below from the *E. coli* 16s rrsE gene is provided (SEQ ID NO:290). Despite the variable nature of these genes, amplification by PCR can be performed between conserved regions of the rRNA genes, so prior knowledge of the entire collection of rRNA sequences for any microbe of interest is not required (See e.g., Brow et al., *J. Clin. Microbiol.*, 34:3129 [1996]).

In this Example, the 1638 (5'-AGAGTTTGATCCTGGCT-CAG-3')(SEQ ID NO:291)/TET-1659 (5'-CTGCTGCCTC-CCGTAGGAGT-3')(SEQ ID NO:292) primer pair was used to amplify an approximately 350 bp fragment of rrsE from genomic DNA derived from *E. coli* 0157: H7 (ATCC #43895). The PCR reactions contained 10 mM Tris-HCl (pH 8.3 at 25° C.), 50 mM KCl, 1.5 mM MgCl2, 0.001% w/v gelatin, 60 µM each of dGTP, dATP, dTTP, and dCTP, 1 µM of each primer, 25 ng of genomic DNA, and 2.5 units AmpliTaq DNA polymerase, LD in a volume of 100 µl. Control reactions that contained no input bacterial genomic DNA were also run to examine the amount of 16S rRNA product produced due to contaminants in the DNA polymerase preparations. The reactions were subjected to 30 cycles of 95° C. for 30 sec; 60° C. for 1 min; 72° C. for 30 sec; after the last cycle the tubes were cooled to 4° C.

After thermal cycling, the PCR mixtures were treated with *E. coli* exonuclease I (ExoI, Amersham) to remove single-stranded partial amplicons and primers. One unit of ExoI was added directly to each PCR mixture, and the samples were incubated at 37° C. for 20 minutes. Then, the nuclease was inactivated by heating to 70° C. for 15 min. The reaction mixtures were brought to 2 M NH4OAc, and the DNAs were precipitated by the addition of 1 volume of 100% ethanol.

Cleavage reactions comprising 1 µl of TET-labeled PCR products (approximately 100 fmoles) in a total volume of 10 µl containing 1×CFLP buffer (10 mM MOPS, pH 7.5; 0.5% each Tween 20 and NP-40) and 0.2 mM MnCl$_2$, were then conducted. All components except the enzyme were assembled in a volume of 9 µl. The reactions were heated to 95° C. for 15 sec., cooled to 55° C., and the cleavage reactions were started by the addition of 50 ng of enzyme. After 2 minutes at 55° C., the reactions were stopped by the addition of 6 µl of a solution containing 95% formamide, 10 mM EDTA and 0.02% methyl violet.

Reaction mixtures were heated at 85° C. for 2 min, and were then resolved by electrophoresis through a 10% denaturing polyacrylamide gel (19:1 cross link) with 7M urea in a buffer of 45 mM Tris-Borate, pH 8.3, 1.4 mM EDTA, and were visualized using the FMBIO-100 Image Analyzer (Hitachi). The resulting scanned image is shown in FIG. 132. In this Figure, the enzymes used in each digest are indicated at the top of each lane. CLEAVASE BN is described in Ex. 2. Lane 2 shows the results of digestion with the Mja FEN-1 parent nuclease, while digests with the chimerical nucleases are indicated by reference to the diagrams in FIG. 130. These data show that the use of each of these nucleases under identical reaction conditions (i.e., conditions in which the DNA assumes similar folded structures) can produce distinct pattern differences, indicating differences in the specificities of the enzymes. Thus, each enzyme can provide additional information about the folded structure assumed by a nucleic acid of interest, thereby allowing more accurate comparisons of molecules for identification, genotyping, and/or mutation detection.

These data show that the activities of these enzymes may vary substantially in similar reaction situations. The performance of an optimization panel for an unknown enzyme can help in selection of the optimal enzyme and conditions for a given application. For example, in the invasive cleavage reactions it is often desirable to choose a combination of nuclease and conditions that perform invasive cleavage, but that do not exhibit activity in the absence of the invader oligonucleotide (i.e., do not cut a hairpin type substrate). The optimization panel allows selection of conditions that do not favor hairpin cleavage, such as the use of the Pfu FEN-1 enzyme in a MgCl$_2$-containing solution. Conversely, hairpin cleavage is desirable for CFLP-type cleavage, so it is contemplated that reaction conditions be screened accordingly for strength in this activity.

Example 64

Characterization of Performance of Structure-Specific Nucleases

Two substrates were used to determine the optimal conditions for seven enzymes, Afu, Pfu, Mth and Mja FEN-1s, CLEAVASE BN, Taq DN and Tth DN. As shown in FIG. 140 Panel A, Substrate 25-65-1 (5'-Fluorescein-TTTTCGCT-GTCTCGCTGAAAGCGAGACAGCGTTT-3'; SEQ ID NO:293) is a stem-loop structure with a 5' arm labeled at its 5' end with fluorescein. As shown in FIG. 140 Panel B, substrate 25-184-5 (INVADER-like "IT" test substrate") (5'-Fluorescein-TTTTCGCTGTCTCGCTGAAAGCGAGA-CAGCGAAAGACGCTCGTGAAACGAGC GTCTTTG-3'; SEQ ID NO:294) is a substrate with an upstream primer adjacent to the 5' fluoroscein labled arm; this mimics an INVADER oligonucleotide and target ("IT"). Standard reactions contained 2 µM labeled substrate, 10 mM MOPS, pH7.5, 0.05% TWEEN 20, 0.05% NP-40, 20 µg/ml tRNA (Sigma # R-5636) and 2 mM MgCl2 or 2 mM MnCl2. Ten µl reactions were heated to 90° C. for 15 seconds in the absence of enzyme and divalent cation, after which the reactions were cooled to room temperature and enzyme was added. Reactions were heated to 50° C. for 20 seconds and divalent cation was then added to start the reaction. The incubation time varied from 1 minute to 1 hour depending on the particular enzyme/substrate combination. Reaction times were adjusted so that less than 25% of the substrate was cleaved during the incubation. Reactions were stopped with the addition of 10 µl of 95% formamide, 20 mM EDTA, methyl violet. One µl of each reaction was electrophoresed on a 20% denaturing acrylamide gel and then scanned on an FMBIO 100 scanner (Hitachi).

Divalent cation titrations varied MgCl$_2$ or MnCl$_2$ from 0.25 mM to 7 mM under otherwise standard conditions. Salt titrations varied KCl from 0 mM to 200 mM or 400 mM for salt tolerant enzymes under otherwise standard conditions. For temperature titrations, reactions with CLEAVASE BN and the FEN-1 enzymes contained 50 mM KCl and 4 mM MgCl$_2$ or MnCl$_2$. Temperature titrations with Taq DN and Tth DN contained 200 mM KCl and 4 mM MgCl$_2$ or MnCl$_2$. Temperature was varied from 40° C. to 85° C. in 5 or 10 degree increments depending on the particular enzyme used.

The results are shown in FIGS. 133-139. FIG. 133 shows the results for CLEAVASE BN, while FIG. 134 shows the results for Taq DN, FIG. 135 shows the results for Tth DN, FIG. 136 shows the results for Pfu FEN-, FIG. 137 shows the results for Mja FEN-, FIG. 138 shows the results for Afu FEN-1, and FIG. 139 shows the results for Mth FEN-1. In each of the Panels within these Figures, the activity of the enzyme is defined as cleavages per molecule of enzyme per minute. Panels marked "IT" refer to cleavage of the 25-184-5 structure (SEQ ID NO:294; FIG. 140B), which mimics an INVADER oligo/target DNA structure, while Panels marked with "hairpin" refer to cleavage of the 25-65-1 structure (SEQ ID NO:293; FIG. 140A), which indicates activity on folded cleavage structures.

In each of these Figures, Panel A shows the results from reactions containing 2 mM MgCl$_2$ and the IT substrate as described in the text, with KCl varied as indicated; Panel B shows the results from reactions containing 2 mM MnCl$_2$ and the IT substrate as described in the text, with KCl varied as indicated; Panel C shows the results from reactions containing 2 mM MgCl$_2$ and the hairpin substrate as described in the text, with KCl varied as indicated; Panel D shows the results from reactions containing 2 mM MnCl$_2$ and the hairpin substrate as described in the text, with KCl varied as indicated; Panel E shows the results from reactions containing the IT substrate as described in the text, with MgCl$_2$ varied as indicated; Panel F shows the results from reactions containing the IT substrate as described in the text, with MnCl$_2$ varied as indicated; Panel G shows the results from reactions containing the hairpin substrate as described in the text, with MgCl$_2$ varied as indicated; Panel H shows the results from reactions containing the hairpin substrate as described in the text, with MnCl$_2$ varied as indicated; Panel I shows the results from reactions containing the IT substrate, 4 mM MgCl$_2$, and 50 mM KCl (Afu FEN-1, Pfu FEN-1, Mja FEN-1, Mth FEN-1, and CLEAVASE FN) or 200 mM KCl (Taq DN and Tth DN) as described in the text, with the temperature varied as indicated; and Panel J shows the results from reactions containing the IT substrate, 4 mM MnCl2, and 50 mM KCl (Afu FEN-1, Pfu FEN-1, Mja FEN-1, Mth FEN-1, and CLEAVASE BN) or 200 mM KCl (Taq DN and Tth DN) as described in the text, with the temperature varied as indicated. It is noted that some of these Figures (e.g., 134, 135, 136, and 138) do not show each of the above-named panels A-J.

From the above it is clear that the invention provides reagents and methods to permit the detection and characterization of nucleic acid sequences and variations in nucleic acid sequences. The INVADER-directed cleavage reaction of the present invention provides an ideal direct detection method that combines the advantages of the direct detection assays (e.g., easy quantification and minimal risk of carryover contamination) with the specificity provided by a dual or tri oligonucleotide hybridization assay.

Example 65

Cloning and Expression of Unknown FEN1 Nucleases

A common method for cloning new members of a gene family is to run PCR reactions using degenerate oligonucleotides complementary to conserved amino acid sequences in that family, and then to clone and sequence the gene-specific PCR fragments. This sequence information can then be used to design sense and anti-sense gene-specific primers which can be used in PCR walking reactions (Nucleic Acids Res. 1995a. 23(6) 1087-1088) to obtain the remainder of the gene sequence. The sequences obtained from the sense and anti-sense PCR walks can then be combined to generate the DNA sequence for the entire open reading frame (ORF) of the gene of interest. Once the entire ORF is know, primers specific to both the 5' and the 3' end of the gene can be designed, and PCR reactions can be performed on genomic DNA to amplify the gene in its entirety. This organism-specific, amplified fragment can then be cloned into an expression vector, and via methods know in the art, and detailed below, the protein of interest can be expressed and purified.

The following examples utilize this series of steps in the cloning and expression of 14 novel FEN-1 nucleases. The steps and reagents (such as cloning vectors, expression vectors, PCR kits or PCR walking kits, etc) are intended to be examples and not limitations to the current invention; those skilled in the art would know that different cloning vectors, expression vectors, PCR kits or PCR walking kits, etc. may be substituted for those exemplified.

The following example is divided into 2 main sections:
A. degenerate PCR and PCR walking to obtain the sequence of 14 novel FEN-1 nucleases
B. cloning and expression of 16 FEN-1 nucleases A. Degenerate PCR and PCR Walking to Obtain the Sequence of 14 Novel FEN-1 Nucleases The protein sequences of the FEN1 genes from *Pyrococcus furiosus* (SEQ ID NO:79) *Methanococcus jannaschii* (SEQ ID NO:75), *Methanobacterium thermoautotrophicum* (SEQ ID NO:265), and *Archaeoglobus fulgidus* (SEQ ID NO:165) were aligned and blocks of conserved amino acids were identified. The conserved sequence blocks VFDG (valine, phenylalanine, aspartic acid, glycine), EGEAQ (glutamic acid, glycine, glutamic acid, alanine, glutamine), SQDYD (serine, glutamine, aspartic acid, tyrosine, aspartic acid), and GTDYN/GTDFN (glycine, threonine, aspartic acid, tyrosine or phenylalanine, asparagine) were chosen as sequences that would likely be present in all Archaeal FEN1 genes. Degenerate oligonucleotides were designed for each of these conserved sequence blocks. In addition to the FEN1 gene specific portion of the oligonucleotides a 15 nucleotide tail was added to the 5' end of the oligonucleotides to enable nested PCR. A different tail sequence was used depending on whether the degenerate oligonucleotide targets the sense or antisense strand of the FEN1 gene.

Forward and/or reverse versions of the oligonucleotides were made and target the sense and antisense strands of the FEN1 gene respectively. The oligonucleotides are VFDG-Fwd (SEQ ID NO:295), EGEAQ-Fwd (SEQ ID NO:296) QDYD-Fwd (SEQ ID NO:297), EGEAQ-Rev (SEQ ID NO:298), SQDYD-Rev1 (SEQ ID NO:299), SQDYD-Rev2 (SEQ ID NO:300), and GTDYN-Rev (SEQ ID NO:301). Two oligonucleotides were made for the SQDYD-Rev sequence because serine is encoded by 6 different codons. For use in PCR, the SQDYD-Rev1 and SQDYD-Rev2 oligonucleotides were mixed in a ratio of 1:2. For the QDYD-Fwd oligonucleotide, the requirement for mixing was avoided by targeting only the last four amino acids of the conserved SQDYD sequence. The GTDYN-Rev oligonucleotide also recognizes the sequence GTDFN since the codons for tyrosine and phenylalanine share 2 of 3 nucleotides.

First, genomic DNA was prepared from 1 vial of the live bacterial strain as described below. All bacterial strains were obtained from the DSMZ (Deutsche Sammlung von Mikroorganismen und Zellkulturen, *Acidianus ambivalens*—DSM # 3772). When the cells were lyophilized, they were resuspended in 200 µl of TNE (10 mM Tris HCL, pH 8.0, 1 mM EDTA, 100 mM NaCl). When the cells were in liquid suspension, they were spun down at 20,000×G for 2 minutes and the cell pellets were resuspended in 200 µl of TNE. 20 µl of 20% SDS (sodium dodecylsulfate) and 2 µl of 1 mg/ml proteinase K were added and the suspension was incubated at 65° C. for 30 minutes. The lysed cell suspension was extracted in sequential order with buffered phenol, 1:1 phenol: chloroform, and chloroform. The nucleic acid was precipitated by the addition of on equal volume of cold 100% ethanol. The nucleic acid was pelleted by spinning at 20,000×G for 5 minutes. The nucleic acid pellet was washed with 70% ethanol, air dried and resuspended in 50 µl of TE (10 mM Tris HCL, pH 8.0, 1 mM EDTA). The final DNA pellet was re-suspended in 50 µl of TE (10 mM Tris HCl, pH 8.0, 1 mM EDTA).

Both reactions of the nested PCR were done using the Advantage cDNA PCR kit (Clontech) according to manufacturer's instructions using a final concentration of 1 µM for all oligonucleotides. The first reaction is done in a 20 µl volume with one of the 6 possible combinations of forward and reverse degenerate oligonucleotides, and includes either 1 µl of the genomic DNA preparation described above, or in the case of Tgo and Tzi, 1 µl (4 ng/µl stock and 6 ng/µl stock, respectively) of DNA purchased from ATCC (ATCC#s 700654D and 700529D, respectively). The cycling conditions were 20 cycles of 95° C. for 15 seconds, 50° C. or 55° C. for 15 seconds, and 68° C. for 30 seconds. The second reactions utilize primers that have the same sequence as the 5' tail sequence of the degenerate oligonucleotides described above. The two primers are 203-01-01 (SEQ ID NO:302) and 203-01-02 (SEQ ID NO:303). The second reaction is carried out exactly as described for the first reaction, except 30 cycles are done instead of 20 and the reaction volume is 25 µl. Following the second PCR, 5 µl of the reaction were loaded on a 2% or 4% agarose gel and the DNA was visualized by ethidium bromide staining. The expected product sizes based on the previously identified FEN1 sequences for all primer pairs are as follows: VFDG-Fwd and EGEAQ-Rev; 275 base pairs, VFDG-Fwd and SQDYD-Rev; 325 base pairs, VFDG Fwd and GTDYN-Rev; 510 base pairs, EGEAQ-Fwd and SQDYD-Rev; 100 base pairs, EGEAQ-Fwd and GTDYN-Rev; 290 base pairs, QDYD-Fwd and GTDYN-Rev; 230 base pairs. The primer pair, VFDG-Fwd and EGEAQ-Rev was able to generate a correctly sized DNA product for all samples attempted. The primer pair, VFDG-Fwd and GTDYN-Rev was able to generate a correctly sized DNA product for most of the DNA samples attempted.

When a DNA product of the expected size was made by the degenerate PCR, that DNA fragment was isolated and cloned into pGEM-T Easy (Promega) using the pGEM-T Easy ligation kit according to the manufacturer's instructions. The DNA sequence was determined and the sequence was used to generate sense and antisense genome walking oligonucleotides for cloning the remainder of the FEN1 genes. The oligonucleotides were designed according to the parameters of the GenomeWalker kit (Clontech) which was used prepare the various genomic DNA samples for the genome walking PCR reactions.

Since many of the organisms of interest cannot be easily cultured in a standard laboratory setting (due to requirements of very specialized temperature, pressure and medium conditions), quantities of genomic DNA were limiting. Therefore, the DNA was randomly amplified using a random 12-mer oligonucleotide. One hundred-µl PCR reactions were set up with the Advantage cDNA PCR kit (Clontech) and contained 10 µl of genomic DNA and 15 µM random 12-mer oligonucleotide. 50 cycles were carried out with the following parameters: 95° C. for 30 seconds, 50° C. for 30 seconds, 68° C. for 5 minutes. After the PCR reactions were complete, amplified DNA was purified with the High Pure PCR Product Purification kit (Boehringer Mannheim). The purified DNA was eluted into a total of 200 µl of 10 mM Tris HCL, pH 8.5.

The genome walking protocol consists of 3 steps. First, a genomic DNA sample is cut with 5 different blunt-end restriction enzymes in 5 separate reactions. Second, the cut DNA is ligated to an adapter that serves as a tag sequence and also is designed to prevent background amplification. Third, the ligated DNA is amplified with a gene-specific primer and a primer with the same sequence as a portion of the adapter sequence.

50 µl restriction digests contained 30 µl of randomly amplified genomic DNA and one of the following enzymes: DraI, EcoRV, PvuII, ScaI or StuI. After 4 hours at 37° C., the cut DNA was purified with either GENECLEANII (Bio 101) or QIAEX II (Qiagen) according to manufacturer's instructions.

DNA was eluted into 10 µl of 10 mM TrisHCl, pH 8.5 in either case. 5.6 µl of this cut DNA was used in 10 µl ligation reactions containing 6 µM GenomeWalker adapter. Reactions were carried out at room temperature overnight followed by heating at 70° C. for 10 minutes to inactivate the T4 DNA ligase. The ligation reactions were then diluted with 70 µl of TE (10 mM TrisHCl, pH 8.0, 1 mM EDTA).

One µl of the diluted ligation mix was used in 25 µl PCR reactions with 0.2 µM gene-specific primer and 0.2 µM primer AP-1 (Clontech) which has the same sequence as the 5' portion of the GenomeWalker adapter. Ten reactions were done for each DNA sample. Five antisense walk PCR reactions (for the 5 different restriction enzymes used to cut the genomic sample) were done using the sense gene-specific primer and five sense walk PCR reactions were done using the antisense gene-specific primer for each DNA sample. The cycling parameters were as recommended by the Universal Genome Walking kit (Clontech) and were as follows: 7 cycles of 94° C. for 25 seconds and 72° C. for 3 minutes, 32 cycles of 94° C. for 25 seconds and 67° C. for 3 minutes, followed by 67° C. for 7 minutes. The source of DNA for the genome walking PCR reactions was, in most cases, genomic DNA which had been randomly amplified with a random 12-mer oligonucleotide, as described above. The exceptions were for *Sulfolobus solfataricus* (Sso), *Thermococcus gorgonarius* (Tgo), and *Thermococcus zilligii* (Tzi). Because we were able to grow, Sso, there was a large quantity of Sso genomic DNA, and the DNA was used directly. A 500 ml culture of *Sulfolobus solfataricus* (ATCC # 35091) was grown in DSM medium 182 at 75° C. for 48 hours. After growth, the cells were spun down for 10 minutes at 20,000×G at 4° C. The cell pellet was resuspended in 10 ml of TE (10 mM Tris HCL, 1 mM EDTA) and frozen in 1 ml aliquots at −70° C. DNA was prepared by the method described above using 1 ml aliquots, but all volumes were increased 10-fold. As noted above, the Tgo and Tzi genomic DNAs were purchased from ATCC.

After the PCR reactions were completed, 5 µl of each reaction was run on a 1% agarose gel and the DNA was visualized by ethidium bromide staining. The presence of a major product was used as an indication of a successful reaction. When a major product was made, it was gel purified with GENECLEAN II (Bio101) or QIAEX II (Qiagen) and ligated into pGEM-T Easy (Promega) according to manufacturer's instructions. The plasmids were sequenced with primers flanking the insert and the sequence obtained was compared to the sequence of the fragment generated by PCR with degenerate oligonucleotides from the same species. The sequences obtained for the degenerate PCR and the sense and antisense walks were combined to generate the DNA sequence for the entire FEN1 open reading frame. Specific information regarding genome walking and cloning for each of the 14 novel FEN-1 nucleases is detailed below.

1. *Acidianus ambivalens* (Aam)

The *Acidianus ambivalens* (Aam) genome walks were done as follows. The antisense primer was Aam 39AS (SEQ ID NO:304) and the sense primer was Aam 44S (SEQ ID NO:305). The antisense PCR walk on ScaI digested Aam genomic sample generated a 1 kilobase DNA product which was cloned into pGEM-T Easy (Promega) following manufacturer's instructions and sequenced. The sense PCR walk on DraI digested Aam genomic sample generated a 600 base pair fragment which was cloned into pGEM-T Easy (Promega) following manufacturer's instructions and sequenced.

2. The *Acidianus brierlyi* (Abr)

The *Acidianus brierlyi* (Abr) genome walks were done as follows. The antisense primer was Abr 39AS (SEQ ID NO:306) and the sense primer was Abr 40S (SEQ ID NO:307). The antisense PCR walk on EcoRV digested Abr genomic sample generated a 1.5 kilobase DNA product which was cloned into pGEM-T Easy (Promega) following manufacturer's instructions and sequenced. The sense PCR walk on DraI digested Abr genomic sample generated a 600 base pair fragment which was cloned into pGEM-T Easy (Promega) following manufacturer's instructions and sequenced.

3. *Archaeoglobus profundus* (Apr)

The *Archaeoglobus profundus* (Apr) genome walks were done as follows. The antisense primer was Apr 35AS (SEQ ID NO:308) and the sense primer was Abr 63S (SEQ ID NO:309). The antisense PCR walk on DraI digested Apr genomic sample generated a 1.8 kilobase DNA product which was cloned into pGEM-T Easy (Promega) following manufacturer's instructions and sequenced. The antisense PCR walk on PvuII digested Apr genomic sample generated a 2 kilobase DNA product which was cloned into pGEM-T Easy (Promega) following manufacturer's instructions and sequenced. The sense PCR walk on DraI digested Apr genomic sample generated a 1 kilobase fragment which was cloned into pGEM-T Easy (Promega) following manufacturer's instructions and sequenced.

4. *Archaeoglobus veneficus* (Ave)

The *Archaeoglobus veneficus* (Ave) genome walks were done as follows. The primary antisense primer was Ave 34AS (SEQ ID NO:310) and the primary sense primer was Ave 65S (SEQ ID NO:311). For Ave, the primary genome walk PCR reactions generated a strong product for only the sense walk on the DraI cut Ave DNA sample. Therefore, nested PCR reactions were done using the nested primer AP-2 and either the nested antisense primer Ave 32AS (SEQ ID NO:312) or the nested sense primer Ave 67S (SEQ ID NO:313). 25 µl nested reactions were done as descibed above for the primary PCR walk reactions. The primary reactions were diluted 1:50 in H$_2$O and 0.5 µl of those dilutions were added to the nested PCR reactions. The cycling parameters for the nested PCR reactions were as recommeded by the Universal Genome Walking kit (Clontech) and are as follows: 5 cycles of 94° C. for 25 seconds and 72° C. for 3 minutes, 20 cycles of 94° C. for 25 seconds and 67° C. for 3 minutes, followed by 7 minutes at 67° C. The nested antisense PCR reaction on StuI cut Ave genomic sample generated a 1 kilobase DNA product which was cloned into pGEM-T Easy (Promega) following manufacturer's instructions and sequenced. The nested sense PCR reaction on EcoRV cut Ave genomic sample generated a 1.1 kilobase product which was cloned into pGEM-T Easy (Promega) following manufacturer's instructions and sequenced.

5. *Desulfurococcus amylolyticus* (Dam)

The *Desulfurococcus amylolyticus* (Dam) genome walks were done as follows. The antisense primer was Dam 31AS (SEQ ID NO:314) and the sense primer was Dam 65S (SEQ ID NO:315). The antisense PCR walk on StuI digested Dam genomic sample generated a 1 kilobase DNA product which was cloned into pGEM-T Easy (Promega) following manufacturer's instructions and sequenced. The sense PCR walk on PvuII digested Dam genomic sample generated a 800 base pair DNA product which was cloned into pGEM-T Easy (Promega) following manufacturer's instructions and sequenced. The sense PCR walk on StuI digested Dam genomic sample generated a 400 base pair fragment which was cloned into pGEM-T Easy (Promega) following manufacturer's instructions and sequenced.

6. *Desulfurococcus mobilis* (Dmo)

The *Desulfurococcus mobilis* (Dmo) genome walks were done as follows. The antisense primer was Dmo 31AS (SEQ ID NO:316) and the sense primer was Dmo 66S (SEQ ID NO:317). The antisense PCR walk on EcoRV digested Dmo genomic sample generated a 450 base pair DNA product which was cloned into pGEM-T Easy (Promega) following manufacturer's instructions and sequenced. The sense PCR walk on PvuII digested Dmo genomic sample generated a 1 kilobase fragment which was cloned into pGEM-T Easy (Promega) following manufacturer's instructions and sequenced.

7. *Methanococcus igneus* (Mig)

The *Methanococcus igneus* (Mig) genome walks were done as follows. The antisense primer was Mig 36AS (SEQ ID NO:318) and the sense primer was Mig 39S (SEQ ID NO:319). The antisense PCR walk on DraI digested Mig genomic sample generated a 900 base pair DNA product which was cloned into pGEM-T Easy (Promega) following manufacturer's instructions and sequenced. The sense PCR walk on EcoRV digested Mig genomic sample generated a 2.5 kilobase fragment which was cloned into pGEM-T Easy (Promega) following manufacturer's instructions and sequenced.

8. *Methanopyrus kandleri* (Mka)

The *Methanopyrus kandleri* (Mka) genome walks were done as follows. The antisense primer was Mka 31AS (SEQ ID NO:320) and the sense primer was Mka 41S (SEQ ID NO:321). The antisense PCR walk on EcoRV digested Mka genomic sample generated a 500 base pair DNA product which was cloned into pGEM-T Easy (Promega) following manufacturer's instructions and sequenced. The sense PCR walk on EcoRV digested Mka genomic sample generated a 1.6 kilobase fragment which was cloned into pGEM-T Easy (Promega) following manufacturer's instructions and sequenced.

9. *Pyrobaculum aerophilum* (Pae)

The *Pyrobaculum aerophilum* (Pae) genome walks were done as follows. The antisense primer was Pae 28AS (SEQ ID NO:322) and the sense primer was Pae 45S (SEQ ID NO:323). The antisense PCR walk on EcoRV digested Pae genomic sample generated a 400 base pair DNA product which was cloned into pGEM-T Easy (Promega) following manufacturer's instructions and sequenced. The sense PCR walk on PvuII digested Pae genomic sample generated a 700 base pair fragment which was cloned into pGEM-T Easy (Promega) following manufacturer's instructions and sequenced.

10. *Pyrodictium brockii* (Pbr)

The *Pyrodictium brockii* (Pbr) genome walks were done as follows. The antisense primer was Pbr 42AS (SEQ ID NO:324) and the sense primer was Pbr 56S (SEQ ID NO:325). The antisense PCR walk on EcoRV digested Pbr genomic sample generated a 650 base pair DNA product which was cloned into pGEM-T Easy (Promega) following manufacturer's instructions and sequenced. The sense PCR walk on PvuII digested Pbr genomic sample generated a 800 base pair fragment which was cloned into pGEM-T Easy (Promega) following manufacturer's instructions and sequenced.

11. *Sulfolobus solfataricus* (Sso)

The *Sulfolobus solfataricus* (Sso) genome walks were done as follows. The antisense primer was Sso 27AS (SEQ ID NO:326) and the sense primer was Sso 27S (SEQ ID NO:327). The antisense PCR walk on PvuII digested Sso genomic DNA generated a 1 kilobase DNA product which was cloned into pGEM-T Easy (Promega) following manufacturer's instructions and sequenced. The sense PCR walk on DraI digested Sso genomic DNA generated a 750 base pair fragment which was cloned into pGEM-T Easy (Promega) following manufacturer's instructions and sequenced.

12. *Thermococcus gorgonarius* (Tgo)

The *Thermococcus gorgonarius* (Tgo) genome walks were done as follows. The antisense primer was Tgo 55AS (SEQ ID NO:330) and the sense primer was Tgo 67S (SEQ ID NO:331). The antisense PCR walk on DraI digested Tgo genomic sample generated a 1 kilobase DNA product which was cloned into pGEM-T Easy (Promega) following manufacturer's instructions and sequenced. The sense PCR walk on StuI digested Tgo genomic sample generated a 850 base pair fragment which was cloned into pGEM-T Easy (Promega) following manufacturer's instructions and sequenced.

13. *Thermococcus litoralis* (Tli)

The *Thermococcus litoralis* (Tli) genome walks were done as follows. The antisense primer was Tli 28AS (SEQ ID NO:328) and the sense primer was Tli 48S (SEQ ID NO:329). The antisense PCR walk on EcoRV digested Tli genomic sample generated a 1 kilobase DNA product which was cloned into pGEM-T Easy (Promega) following manufacturer's instructions and sequenced. The sense PCR walk on EcoRV digested Tli genomic sample generated a 1.9 kilobase fragment which was cloned into pGEM-T Easy (Promega) following manufacturer's instructions and sequenced.

14. *Thermococcus zilligii* (Tzi)

The *Thermococcus zilligii* (Tzi) genome walks were done as follows. The antisense primer was Tzi 55AS (SEQ ID NO:332) and the sense primer was Tzi 67S (SEQ ID NO:333). The antisense PCR walk on DraI digested Tzi genomic sample generated a 1 kilobase DNA product which was cloned into pGEM-T Easy (Promega) following manufacturer's instructions and sequenced. The sense PCR walk on StuI digested Tzi genomic sample generated a 850 base pair fragment which was cloned into pGEM-T Easy (Promega) following manufacturer's instructions and sequenced.

B. Cloning of 16 FEN-1 Nucleases

The previous section detailed the cloning and sequencing of novel FEN-1 nucleases. This section will describe the cloning of these novel FEN-1's into an expression vector, as well as the cloning of two additional, previously known FEN-1's, *Aeropyrnum pernix* (Ape) and *Pyrococcus horikoshii* (Pho). The process comprises either 4 or 5 steps, and is broadly outlined below.

The first step involves the design of 5' and 3' gene specific PCR primers. Since the complete sequence of all 16 FEN-1 genes has been determined, specific primers were designed to target and amplify the entire FEN-1 gene of interest. For each FEN1 endonuclease to be cloned, the 5'-end primer and the 3-end primer are mostly complementary to the 5' end and the 3' end of the FEN1 open reading frame. The first few nucleotides of the primer constitute a spacer and sequences necessary to introduce a restriction endonuclease site to facilitate cloning. The choice of restriction endonuclease sequence to incorporate into the primer is dependent on the sequence of the FEN-1 enzyme. Ideally, unique restriction sites are created at the 5' and 3' ends of the PCR product (they are not the same as any restriction sites that may be internal to the FEN-1 sequence). Also, the sites incorporated into the primers correspond to restriction enzyme sites that are commonly found on expression vectors used in the art. Examples of such enzymes are EcoRI, SalI, NcoI, XbaI and PstI.

Second, PCR reactions were performed using the primers designed above and genomic DNA from the organism of interest. Third, the PCR products were gel purified and then cut with restriction endonucleases corresponding to the sites incorporated in the PCR primers. The cut PCR products were then purified away from the smaller digest fragments and, fourth, these cut products were cloned into an expression vector. In some cases, this was the final step of the cloning process, prior to transformation and protein expression/purification. In some cases a fifth step was needed. In some cases, a mutagenesis step had to be performed to remove any nucleotides that were incorporated into the ORF as a result of primer sequences required for cloning.

Finally, a bacterial host (e.g., *E. coli* JM109) was transformed with the expression vector containing the cloned FEN-1, and protein expression and purification were done as detailed in Experimental Example 28f. Four of the isolated FEN gene constructs (Pae FEN-1, Pbr FEN-1, Mig FEN-1 and Mka FEN-1) produced little or no detectable protein in the host that was transformed.

The following section details the PCR, restriction digests, cloning, mutagenesis reactions (if required) and transformation for each FEN-1 nuclease. The description is sub-divided in order to group the FEN-1 nucleases according to the restriction endonucleases used in cloning. The sub-divisions are as follows:

I. FEN-1 endonucleases cloned with restriction endonucleases NcoI/SalI
II. FEN-1 endonucleases cloned with restriction endonucleases EcoRI/SalI
III. FEN-1 endonucleases cloned with other restriction endonucleases I. Cloning Of FEN-1 Endonucleases Using the Restriction Endonucleases NcoI and SalI.

In this example, DNA encoding the FEN-1 endonuclease from *Acidianus ambivalens* (Aam), *Acidianus brierlyi* (Abr), *Aeropyrum pernix* (Ape), *Archaeaglobus profundus* (Apr), *Methanococcus igneus* (Mig), *Pyrococcus horikoshii* (Pho), *Sulfolobus solfataricus* (S so), *Thermococcus gorgonarius* (Tgo), were isolated and inserted into a plasmid under the transcriptional control of an inducible promoter as follows.

1. Cloning of *Acidianus ambivalens* FEN-1 (Aam)

One microliter of the genomic DNA solution described above (in section 65A) was employed in a PCR using the ADVANTAGE cDNA PCR kit (Clonetech); the PCR was conducted according to manufacturer's recommendations. For each FEN1 endonuclease to be cloned, the 5'-end primer is mostly complementary to the 5' end of the FEN1 open reading frame. The first 6 nucleotides of the primer constitute a spacer and 2 bases of an NcoI site to facilitate cloning. An 'A' at postion 3 of the Aam ORF sequence (SEQ ID NO: 336) was mutated to a 'G' in the 5' primer to create an ATP start codon. Likewise, the 3'-end primer is mostly complementary to the 3' end of the FEN-1 open reading frame. The first 10 nucleotides constitute a spacer and SalI site to facilitate cloning. The PCR primers used for Aam are: Aam5'-5' GCAAC-CATGGGAGTAGACCTTGCTGATTTGG (SEQ ID NO:334) and Aam 3'-5' CCATGTCGACTAAAAC CACT-GATCTAAACCGC (SEQ ID NO:335). The PCR reaction for each FEN1 resulted in the amplification (i.e. production) of a single major band about 1 kilobase in length. The open reading frame (ORF) encoding the Aam FEN-1 endonuclease is provided in SEQ ID NO:336; the amino acid sequence encoded by the Aam ORF is provided in SEQ ID NO:337.

Following the PCR amplification, the entire reaction was electrophoresed on a 1.0% agarose gel and the major band was excised from the gel and purified using the GENECLEAN II kit (Bio 101, Vista Calif.) according to manufacturer's instructions. Approximately 1 µg of the gel-purified FEN-1 PCR product was digested with NcoI and SalI. After digestion, the DNA was purified using the Geneclean II kit according to manufacturer's instructions. One microgram of the pTrc99a vector (Pharmacia) was digested with NcoI and SalI in preparation for ligation with the digested PCR product. One hundred nanograms of digested pTrc99a vector and 250 ng of digested FEN-1 PCR product were combined and ligated to create pTrc99-(enzyme TLA)FEN1. pTrc99-(enzyme TLA) FEN-1 was used to transform competent *E. coli* JM 109 cells (Promega) using standard techniques.

2. Cloning of a FEN-1 Endonuclease from *Acidianus brierlyi*

Cloning of the FEN-1 from *Acidianus brierlyi* (Abr) was performed as described above, except the DSM# is 1651 and the PCR primers used are Abr 5'-5' CATACCATGGGAGTA-GATTTATCTGACTTAG (SEQ ID NO:338) and Abr 3'-5' CTTGGTCGACTTAAAACCATTGGTCAAGTCCAG (SEQ ID NO:339). A 'C' at postion 3 of the Abr ORF sequence (SEQ ID NO: 338) was mutated to a 'G' in the 5' primer to create an ATP start codon. The open reading frame (ORF) encoding the Abr FEN-1 endonuclease is provided in SEQ ID NO:340; the amino acid sequence encoded by this ORF is provided in SEQ ID NO:341.

3. Cloning of a FEN-1 Endonuclease from *Aeropyrum pernix*

Cloning of the FEN-1 from *Aeropyrum pernix* (Ape) was performed as described above, except the sequence of this enzyme was obtained from GENBANK (accession #H72765), the DSM# is 11879, and the PCR primers used are Ape 5'-5' TTAGCCATGGGAGTCAACCTTAGGGAG (SEQ ID NO:342) and Ape 3'-5' GTAAGTCGACTATC-CGAACCACATGTCGAG (SEQ ID NO:343). An 'T' at postion 1 of the Ape ORF sequence (SEQ ID NO: 344) was mutated to an 'A' in the 5' primer to create an ATP start codon. The open reading frame (ORF) encoding the Ape FEN-1 endonuclease is provided in SEQ ID NO:344; the amino acid sequence encoded by this ORF is provided in SEQ ID NO:345.

4. Cloning of a FEN-1 Endonuclease from *Archaeaglobus profundus*

Cloning and expression of the FEN-1 from *Archaeaglobus profundus* (Apr) was performed as described above, except the DSM# is 5631 and the PCR primers used are Apr 5'-5' CTTACCATGGGCGCTGATATAGGAGAGC (SEQ ID NO:346) and Apr 3'-5' TGGAGTCGACTTAAAACCACCT-GTCCAGAG (SEQ ID NO:347). The open reading frame (ORF) encoding the Apr FEN-1 endonuclease is provided in SEQ ID NO:348; the amino acid sequence encoded by this ORF is provided in SEQ ID NO:349.

5. Cloning of a FEN-1 Endonuclease from *Methanococcus igneus*

Cloning and expression of the FEN-1 from *Methanococcus igneus* (Mig) was performed as described above except the DSM # is 5666 and the PCR primers used are Mig 5'-5' CATTCCATGGGAGTGCAGTTTAATG (SEQ ID NO:350) and Mig 3'-5' CGGAGTCGACTCATCTCCCAAACCATGC (SEQ ID NO:351). The open reading frame (ORF) encoding the Mig FEN-1 endonuclease is provided in SEQ ID NO:352; the amino acid sequence encoded by this ORF is provided in SEQ ID NO:353.

6. Cloning of a FEN-1 Endonuclease from *Pyrococcus horikoshii*

Cloning and expression of the FEN-1 from Pho *Pyrococcus horikoshii* (Pho) was performed as described above except the sequence of this enzyme was obtained from GEN-BANK (accession #A71015), the DSM # is 12428, and the PCR primers used are

```
                                                    (SEQ ID NO:354)
    Pho 5'-5' GATACCATGGGTGTTCCTATCGGTGAC (SEQ ID NO:355)
    Pho 3'-5' CTTGGTCGACTTAGGGTTTCTTTTTAACGAACC.
```

The open reading frame (ORF) encoding the Pho FEN-1 endonuclease is provided in SEQ ID NO:356; the amino acid sequence encoded by this ORF is provided in SEQ ID NO:357.

7. Cloning of a FEN-1 Endonuclease from *Sulfolobus solfataricus*

Cloning and expression of *Sulfolobus solfataricus* (Sso) FEN-1 was performed as described above except the bacterial stocks were obtained from the American Type Culture Collection (Manassas, Va.) ATCC # is 5091, and the PCR primers used are Sso 5'-5' TAAGCCATGGGTGTAGATTTAGGC-GAAATAG (SEQ ID NO:358) Sso 3'-5' ACTAGTCGACT-TAAAACCACTGATCAAGACCTGTC (SEQ ID NO:359). An 'A' at postion 3 of the Sso ORF sequence (SEQ ID NO: 360) was mutated to a 'G' in the 5' primer to create an ATP start codon. The open reading frame (ORF) encoding the Sso FEN-1 endonuclease is provided in SEQ ID NO:360; the amino acid sequence encoded by this ORF is provided in SEQ ID NO:361.

8. Cloning of a FEN-1 Endonuclease from *Thermococcus gorgonarius*

Cloning and expression of *Thermococcus gorgonarius* (Tgo) was performed as above except the ATCC # is 700653D, and the PCR primers used are Tgo 5'-5' CTAGC-CATGGGAGTTCAGATAGGTGAGC (SEQ ID NO:362) and Tgo 3'-5' TGGAGTCGACTACCGTGTGAAC-CAGCTTTC (SEQ ID NO:363). The open reading frame (ORF) encoding the Tgo FEN-1 endonuclease is provided in SEQ ID NO:364; the amino acid sequence encoded by this ORF is provided in SEQ ID NO:365.

II. Cloning of FEN-1 Endonucleases with EcoRI/SalI

The FEN-1's in this group were cloned as described above, except the restriction endonucleases used for the cloning step are EcoRI and SalI. This is due to the presence of an internal NcoI site in these FEN-1 sequences. EcoRI is a good choice since it is common in the art of cloning, is found in many expression vectors, and the following FEN-1's contain no internal EcoRI sites. Interestingly, cloning these PCR fragments into the pTRC99a vector yields an ORF containing two amino acids not present in the native sequence. To correct this and obtain a native ORF, mutagenesis reactions were performed with the Transformer™ Site-Directed Mutagenesis Kit (Palo Alto Calif., cat # K1600-1) according to the manufacturer's instructions, using the mutagenic oligonucleotide specified for each FEN-1 endonuclease. After the mutagenesis reaction, selection was achieved by cutting the products with EcoRI. Since the mutant constructs have no EcoRI site, they will not be cut. Any constructs that were not properly mutagenized would still contain and EcoRI restriction site and would be cut during the digest reaction. Bacterial cells were then transformed and grown on selective medium (ampicillin) according to the Transformer™ Site-Directed Mutagenesis Kit instructions. Mutangenic plasmid was isolated according to the manufacturer's instructions, the resultant DNA was again cut with EcoRI, and the products of this reaction were used to transform competent E. coli JM 109 cells (Promega) using standard techniques.

9. Cloning of a FEN-1 Endonuclease from Archaeaglobus veneficus

The cloning of a FEN-1 from Archaeaglobus veneficus (Ave) was performed as described above except the DSM # 11195, the PCR primers used are Ave 5'-5' TAACGAATTCG-GTGCAGACATAGGCGAACTAC (SEQ ID NO:366) and Ave 3'-5' CGGTGTCGACTCAGGAAAACCACCTC-CAAGCG (SEQ ID NO:367), and the mutagenic oligonulceotide used was Ave ΔR1-5' CACAGGAAACAGAC-CATGGGTGCAGACATAGGCGAAC (SEQ ID NO:368). The open reading frame (ORF) encoding the Ave FEN-1 endonuclease is provided in SEQ ID NO:369; the amino acid sequence encoded by this ORF is provided in SEQ ID NO:370.

10. Cloning of a FEN-1 Endonuclease from Desulfurococcus amylolyticus

The cloning of a FEN-1 from Desulfurococcus amylolyticus (Dam) was performed as described above except the DSM #3822, the PCR primers used are Dam 5'-5' CTAA-GAATTCGGAGTAGACTTAAAAGACATTATACC (SEQ ID NO:371) and Dam 3'-5' AGTTGTCGACTACTTCGGCT-TACTGAACC (SEQ ID NO:372), and the mutagenic oligonucleotide used was Dam ΔR1-5' CAGGAAACAGAC-CATGGGAGTAGACTTAAAAGAC (SEQ ID NO:373). The open reading frame (ORF) encoding the Dam FEN-1 endonuclease is provided in SEQ ID NO:374; the amino acid sequence encoded by this ORF is provided in SEQ ID NO:375.

11. Cloning of a FEN-1 Endonuclease from Pyrobaculum aerophilum

The cloning of a FEN-1 from Pyrobaculum aerophilum (Pae) was performed as described above except the DSM #7523, the PCR primers used were Cloned using EcoR I and SalI Pae 5'-5' CGTTGAATTCGGAGTTACTGAGTTGGG-TAAG (SEQ ID NO:376) and Pae 3'-5' TACTGTCGACA-GAAAAAGGAGTCGAGAGAGGAAG (SEQ ID NO:377). A 'G' at postion 1 of the Pae ORF sequence (SEQ ID NO: 378) was mutated to an 'A' in the 5' primer to create an ATP start codon. The mutagenesis reaction for this enzyme has not yet been done. There are two, non-native amino acids at the 5' end of this protein. The open reading frame (ORF) encoding the Pae FEN-1 endonuclease is provided in SEQ ID NO378; the amino acid sequence encoded by this ORF is provided in SEQ ID NO:379.

12. Cloning of a FEN-1 Endonuclease from Thermococcus litoralis

The cloning of a FEN-1 from Thermococcus litoralis (Tli) was performed as described above except the DSM# is 5473, the PCR primers used were Tli 5'-5' TCATGAATTCG-GAGTCCAGATTGGTGAGCTT (SEQ ID NO:380) and Tli 3'-5' GATTGTCGACTCACTTTTTAAACCAGCTGTCC (SEQ ID NO:381), and the mutagenic primer was Tli ΔR1-5' AAGCTCACCAATCTGGACTCCCATG-GTCTGTTTCCTGTG (SEQ ID NO:382). The open reading frame (ORF) encoding the Tli FEN-1 endonuclease is provided in SEQ ID NO:383; the amino acid sequence encoded by this ORF is provided in SEQ ID NO:384.

13. Cloning of a FEN-1 Endonuclease from Desulfurococcus mobilis

The cloning of a FEN-1 from Desulfurococcus mobilis (Dmo) was performed as described above except the DSM # 2161, the PCR primers used were Dmo 5'-5' CTTGGAAT-TCGGCGTCGACCTAAGGGAACTC (SEQ ID NO:385) and Dmo 3'-5' AGGTCTGCAGTTAACCCTGCTTAC-CGGGCTTAGC (SEQ ID NO:386), and the mutagenic primer used was Dmo ΔR1-5' CAGGAAACAGAC-CATGGGCGTCGACCTAAGG (SEQ ID NO:387). The open reading frame (ORF) encoding the Dmo FEN-1 endonuclease is provided in SEQ ID NO:388; the amino acid sequence encoded by this ORF is provided in SEQ ID NO:389.

14. Cloning of a FEN-1 Endonuclease from Pyrodictium brockii

The cloning of a FEN-1 from Pyrodictium brockii (Pbr) was performed as described above, except the DSM # 2708, the PCR primers used were Pbr 5'-5' TAGCGAATTCG-GCGTCAACCTCCGCGAG (SEQ ID NO:390) and Pbr 3'-5' CATTCTGCAGCTAGCGGCGCAGCCACGC (SEQ ID NO:391), and the mutagenic primer was Pbr ΔR1-5' CAG-GAAACAGACCATGGGCGTCAACCTCCGC (SEQ ID NO:392). A 'G' at postion 1 of the Pbr ORF sequence (SEQ ID NO: 393) was mutated to an 'A' in the 5' primer to create an ATP start codon. The open reading frame (ORF) encoding the Pbr FEN-1 endonuclease is provided in SEQ ID NO:393; the amino acid sequence encoded by this ORF is provided in SEQ ID NO:394.

III. Cloning of FEN-1 Endonucleases with Other Enzymes

The following FEN-1 endonucleases were cloned using restriction endonucleases other than those already described. These particular FEN-1 sequences contain either internal EcoRI sites or internal SalI sites and therefore require different restriction enzymes in the cloning step. None of the PCR primers used in this section yield cloned products containing an ORF with aberrant (non-natural) nucleotides, therefore there is no need for an additional mutagenesis step. All reactions described in this section were performed as in section I, with any exceptions noted below.

15. Cloning of a FEN-1 Endonuclease from Methanopyrus kandleri

The cloning of a FEN-1 from Methanopyrus kandleri (Mka) was performed as described above, except the DSM # 6324 and the PCR primers used were Mka 5'-5' CATAC-CATGGGACTAGCTGAACTCCGAG (SEQ ID NO:395) and Mka 3'-5' TGGATCTAGATCAGAAGAACGCGTC-CAGGG (SEQ ID NO:396). A 'T' at postion 1 of the Mka ORF sequence (SEQ ID NO: 397) was mutated to an 'A' in the 5' primer to create an ATP start codon. The restriction enzymes used in the cloning reaction were NcoI and XbaI. The open reading frame (ORF) encoding the Mka FEN-1 endonuclease is provided in SEQ ID NO:397; the amino acid sequence encoded by this ORF is provided in SEQ ID NO:398.

16. Cloning of a FEN-1 Endonuclease from Thermococcus zilligii

The cloning of a FEN-1 from Thermococcus zilligii (Tzi) was performed as described above, except genomic DNA obtained was obtained from the American Type Culture Collection (ATCC # 700529D) and the PCR primers used were Tzi 5'-5' CGATCCATGGGAGTTCAGATCGGTGAGC (SEQ ID NO:399) and Tzi 3'-5' CAGGCTGCAGTCACCT-TCCGAACCAGCTCTC (SEQ ID NO:400). The restriction enzyme used in the cloning reaction were NcoI and PstI. The open reading frame (ORF) encoding the Tzi FEN-1 endonuclease is provided in SEQ ID NO:401; the amino acid sequence encoded by this ORF is provided in SEQ ID NO:402.

Example 66

Activity Assay for Cloned FEN1 Nucleases

The INVADER assay test was done using a combination target and upstream (INVADER) oligonucleotide and a large molar excess of labeled probe oligonucleotide (as diagrammed FIG. 141A). Ten μl reactions contained 10 mM MOPS (pH 7.5), 0.05% NP-40, 0.05% Tween 20, 20 ng/μl tRNA (Sigma), 4 mM MgCl2, 100 ng enzyme, 2 μM labeled probe 203-91-01 (5'-(Tet)TTTTCAACTGCCGTGA; SEQ ID NO:403) and 0.2 nM target-Invader 203-91-04 (5'-TCACGGCAGTTGGTGCGCCTCGGAAC-GAGGCGCACA; SEQ ID NO:404),. Reactions were set up by adding all components to individual wells of a 96-well plate in an ice water bath. The reactions were started by placing the 96-well plate on a prewarmed gradient thermal cycler (Eppendorf Mastercycler) and incubated at the set temperature for 20 minutes. The 96-well plate was then put back in the ice water bath to stop the reactions and 10 μl of stop mix (95% formamide, 20 mM EDTA, 0.05% methyl violet) was added. 1 μl of each reaction was loaded onto a denaturing 20% acrylamide gel. After electrophoresis, the gels were visualized using an FMBIO fluoroimager (Hitachi) and quantitated with FMBIO Analysis software. Results are shown graphically in FIG. 142.

Cleavage of an 'X-structure' as diagrammed in FIG. 141B can provide one source of background signal in the sequential invasive cleavage reactions of the present invention, thus it is desireable to determine the level of activity that enzymes have in cleaving such a structure. Ten-μl reactions on the X-structure substrate contained 10 mM MOPS (pH 7.5), 0.05% NP-40, 0.05% Tween 20, 20 ng/μl tRNA (Sigma), 4 mM MgCl2, 100 ng enzyme, and 2 μM labeled 203-81-02 (5'-(Tet) TTTTCAACTGCTTAGAGAATCTAAG-CAGTTGGTGCGCCTCGTTAA-NH2; SEQ ID NO:405) and 2 μM target 594-09-01 (5'-AACGAGGCGCA-CATTTTTTTT; SEQ ID NO:406). Reactions were done as described above except incubation at the reaction temperature was carried out for 60 minutes. Samples were electrophoresed and analzyed as descibed above. Results are shown graphically in FIG. 143.

Together these test allow characterization of the cleavage activities of FEN enzymes and other 5' nucleases, and of any new enzyme suspected of being able to cleave an invasive cleavage structure.

Example 67

Detection of the Human Cytomegalovirus pol Gene

Example 48 demonstrated the use of the invasive cleavage assay to detect human cytomegalovirus sequences in a background of human genomic DNA. In this example, another embodiment of the multiple invasive cleavage reaction will be demonstrated for the detection of human cytomegalovirus sequence. Example 48 utilized an INVADER and a labeled, primary probe oligonucleotide targeting the region 3104-3061 of hCMV. In this example bases 2302-2248 of the hCMV genome were targeted. As in previous examples, a FRET cassette was used to generate signal in the presence of the target DNA.

INVADER and probe oligonucleotides were designed as described above to detect the polymerase gene of HCMV (SEQ ID NO:407 and 408, respectively); the FRET cassette is SEQ ID NO:409. Oligonucleotides are diagrammed in FIG. 144. The HCMV target sequence detected by this probe set is SEQ ID NO:410.

Genomic viral DNA was purchased from Advanced Biotechnologies, Inc. (Columbia Md.). The DNA was estimated (but not certified) by personnel at Advanced Biotechnologies to be at a concentration of 170 amol ($1 \times 10^8$ copies) per microliter. The viral stock was diluted in 10 ng/μl human genomic DNA to final concentrations of 45.7, 137.2, 411.5 and 1234.6 viral copies per microliter. Reactions were performed in MJ 96 well MULTIPLATE (MJ Research MLP-9601) plates, in triplicate in a final volume of μl. Each reaction comprised 12 mM MOPS (pH 7.5), 12 mM $MgC_2$, 0.5 pmol INVADER oligonucleotide, 10 pmol unlabeled, primary probe, 5 pmol One-Piece FRET cassette, 0, 457, 1372, 4115 or 12346 copies of CMV Viral DNA, 100 ng human genomic DNA and 60 ng AveFEN1, and water to a final volume of 2 μl. The MOPS, INVADER oligonucleotide, water, CMV viral DNA and human genomic DNA were combined, overlaid with CHILL-OUT liquid wax, and denatured for 5 minutes at 95° C. Reactions were then cooled to 20° C. and $MgCl_2$, unlabeled primary probe, FRET cassette, and AveFEN1 enzyme were added below the Chill-out layer. The reaction were mixed by pipetting up and down 5-10 times, with care being taken to remain clear of the CHILLOUT layer. Reactions were then incubated for 4 hours at 65° C., and plates were read directly on a Cytoflour plate reader using the following settings: Excitation=485/20, Emission=530/25, Gain=40 at 10 reads/well.

Results are shown graphically in FIG. 145, with number of copies of the target DNA indicated on the horizontal axis and the fluorescence units indicated on the vertical axis. These results indicate sensitive detection of HCMV using the sequential invasive cleavage FRET format.

Selection of oligonucleotides for target nucleic acids other than the analytes shown here, (e.g., oligonucleotide composition and length), and the optimization of cleavage reaction conditions in accord with the models provided here follow routine methods and common practice well known to those skilled in the methods of molecular biology.

Example 68

Automated INVADER Assay Reactions Performed in DARAS Minicolumns

This Example describes the ability of the DARAS minicolumns to support the INVADER assay reaction (FIG. 150A). INVADER assay reaction mixes were prepared in a final volume of 30 μl containing: 10 mM MOPS, 7.5 mM $MgCl_2$, 10 pmoles INVADER oligonucleotide, 30 pmoles probe, 100 ng AfuFEN 1 enzyme, and 3500 bp target fragments amplified by PCR from Hepatitis B Virus. 100, 10,000 or 1,000,000 genome equivalents of target were added to the reactions as indicated. Twenty five μl of the reaction mixes were aspirated into the DARAS columns. The columns were incubated at 95° C. for 5 minutes to denature the DNA and then held at 67° C. for 2 hours with mixing for the INVADER assay reaction. Following the INVADER assay reaction, 15 μl of an extension mix containing: 1× buffer (10 mM MOPS, 10 mM $MgSO_4$), 2.5 U KlenTaq, and 2 μm biotin-dUTP were aspirated into the columns. The cleaved probe was designed to act as a primer on the extension template captured to the particles in the columns (100 pmoles, assuming 100% attachment). The extension reaction was performed at 57° C. for 10 minutes. The columns were washed and the extended product detected with a SA phosphatase conjugate and a colorimetric readout with an on-line photometric detector. The background (i.e. no target) counts are superimposed on the 100 genome equivalent counts, indicating that, in this experiment 100 molecules were not detected above background. However, both the $10^4$ and $10^6$ genome counts are well above background (FIG. 150B).

INVADER assay reaction products were also detected by a DNA polymerase extension to incorporate biotin labeled dUTP and then detected by calorimetric detection following exclusion from the column. The results are shown in FIG. 150B and indicate that this solid phase reaction is linear with respect to time. This experiment shows that the columns support the enzymatic modification of bound oligonucleotides and do not interfere with the INVADER assay reaction.

Example 69

Comparison Solid Support INVADER Assay Reaction Formats

Figure 151:
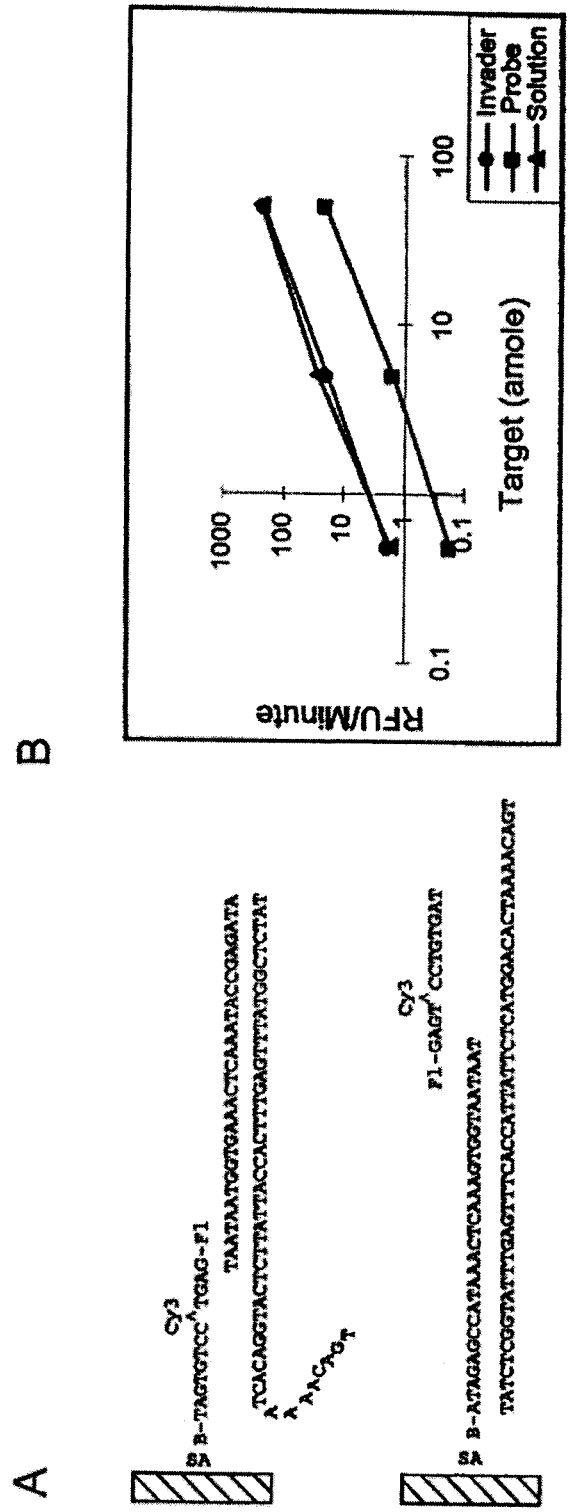

This Example describes experiments in which either the Signal Probe or the INVADER oligonucleotide were bound via a terminal biotin moiety to one well of a 96-well microtiter plate coated with a SA monolayer (FIG. 151). In the first format, the signal probe is attached to the support surface at its 3' end, while in the second format, the INVADER oligonucleotide is attached to the support at its 5' end (FIG. 151A).

INVADER reactions were conducted in a final volume of 50 µl containing: 10 mM MOPS, 7.5 mM $MgCl_2$, 100 ng AfuFEN 1 enzyme, 25 pmoles of probe (attached or in solution), 5 pmoles INVADER oligonucleotide (attached or in solution), and synthetic target from 0.5 to 100 amole. The reactions were initiated by adding all reaction components at once. The reactions were incubated at 45° C. in a Cytofluor instrument and read every minute at the following settings: gain was 700; excitation wavelength was 485 µm with a 20 µm band width, and the emission wavelength was 530 nm with a 25 nm band width.

In each case, saturating amounts of the biotinylated oligonucleotide were added to the microtiter plate wells, which were then washed. For the Signal Probe oligonucleotide bound experiments, free INVADER oligonucleotides were added, for INVADER oligonucleotide bound experiments, free FRET Signal Probes were added along with the other reaction components and variable concentrations of a 50-mer synthetic oligonucleotide target. As a comparison, standard solution phase reactions were performed at each of the target concentrations. The reactions were started by the addition of the CLEAVASE enzyme and the release of the fluorescein moiety was monitored by end point fluorometric analysis. The results are plotted in FIG. 151B and indicate that experiments in which the INVADER oligonucleotide was bound to the solid support exhibit reaction rates and maximal signal levels comparable to those of the solution phase reaction while experiments in which the Signal Probe was bound exhibit a 10-fold slower reaction rate.

The results shown in FIG. 151B indicate that configurations in which an INVADER oligonucleotide is bound to a solid support and configurations in which a Signal Probe is bound to a solid support all demonstrate cleavage.

Example 70

INVADER Assays with Reverse FRET Oligonucleotide

Experiments in Example 69) demonstrated that the solid-phase INVADER assay would operate successfully. But in the solid-phase format, the probe oligonucleotide must be anchored to the support by its 3' end. To develop a model system in which the signal from a FRET oligonucleotide would not be released into solution, but rather remain attached to a support at an addressable location, reverse FRET oligonucleotides were designed. In the reverse FRET oligonucleotide, the signal dye is attached 3' of the cleavage site, so that after the CLEAVASE enzyme cuts the FRET oligonucleotide, the quenching moiety is released into solution, and the signal dye remains attached to the FRET oligonucleotide, and thus to the support. FIG. 152 provides a schematic showing the differences between the standard and the reverse FRET oligonucleotides.

A. Design Considerations for Reverse FRET Oligonucleotides

Two major considerations influenced the design of the reverse FRET oligonucleotides. The optimal spacing of the best signal/quenching dye pair so that the uncleaved reverse FRET oligonucleotide would have satisfactory quenching, but would still allow maximal enzymatic cleavage during the assay was determined. Dabcyl, which absorbs light over a broad range (Vet et al., PNAS USA, 96:6394 [1999]) was used as a quenching dye. Both fluorescein and the cyanine dye, cy-3, can be used as signal dyes with the dabcyl quencher. Fluorescein is available in multiple forms, offering flexibility in designing how the dye is attached to the FRET oligonucleotides. FIG. 153 shows the structures of six FRET oligonucleotide designs in which the dye pairs and/or the spacing of the fluorescence signal and quenching dyes were varied (fluorescein and dabcyl, respectively). FIG. 153 also shows the synthetic nucleotide target and the INVADER oligonucleotide used in these experiments.

FRET oligonucleotides labeled with fluorescein at the 5' end and with dabcyl connected by a dT linker three nucleotides downstream function well in INVADER assays. FRET oligonucleotide B (FIG. 153) maintained the spacing, but reversed the orientation of the dyes. FRET oligonucleotide A, which has the dabcyl group attached to a base that is located one base 5' of the cleavage site. FRET oligonucleotide A was used to determine if the CLEAVASE enzyme would accept this FRET oligonucleotide design more readily than a design that had the dabcyl attached directly to the released base, as in FRET oligonucleotide B. FRET oligonucleotide C was designed to test the effect of attaching a fluorescein to a spacer (fluorescein Sp) rather than directly to a base (fluorescein dT, as in FRET oligonucleotide B). FRET oligonucleotide D, which has fluorescein attached to a spacer at position 5, was designed to test the effect of the position of the signal dye in relation to the cleavage site.

B. Methods

The synthetic target used in these experiments duplicates a region of the ApoE gene that contains a mutation in codon 158, which is believed to play a role in genetic susceptibility to Alzheimer's disease. All reverse FRET oligonucleotides tested were designed to detect the Cys allele of codon 158. In one series of experiments testing FRET oligonucleotides A, B, C, and D (see FIG. 153), mixtures containing 1.25 µl MOPS (200 mM, pH 7.5), 5 µl PEG 8000 (16%), 1 µl INVADER oligonucleotide (5 µM), +/−1 µl synthetic target (1 nM) and H₂O to 20 µl were prepared (in each case, the volumes given correspond to the amounts used for a single assay). Twenty-µl aliquots were transferred to the appropriate wells of a low profile microtiter plate. After transfer, these components were overlaid with 25 µl clear Chill-Out 14 (MJ Research, Watertown, Mass.). The reaction plate was placed in an Eppendorf Mastercycler gradient thermal cycler programmed to incubate at 60° C., +/−an 8-degree gradient. Next, 5 µl of a mixture containing 1.25 µl MgCl₂ (150 mM), 1 µl AfuFEN 1 enzyme (200 ng), 1 µl FRET oligonucleotide (10 µM), and 1.75 µl H₂O was added to each well with mixing to initiate the assay. The final reaction volume was 25 µl with final concentrations of 0.2 µM INVADER oligonucleotide, 0.4 µM FRET oligonucleotide, 0.04 nM synthetic target oligonucleotide, and 200 ng Cleavase VIII enzyme in a buffer containing 10 mM MOPS (pH 7.5), 3.2% PEG 8000 and 7.5 mM MgCl₂. The microtiter plate was incubated for 1 hour and results were read directly on a CytoFluor Series 4000 Fluorescence Multi-Well Plate Reader (PerSeptive Biosystems, Framingham, Mass.) using the following settings: Excitation: 485/20 nm (Wavelength/Bandwidth); Emission: 530/25 nm (Wavelength/Bandwidth); Gain: 40; Reads/well: 10; Set-Temp: 25° C.

In a second series of experiments testing FRET oligonucleotides D and E the same protocol was followed. The same components were used as in the first series of experiments, except that H₂O was added to only 15 µl in the first step, giving a final reaction volume of 20 µl. In addition, 100 ng AfuFEN 1 enzyme was used and no PEG 8000 was added. Due to the volume change, the final concentrations of the oligonucleotides were 0.25 µM INVADER oligonucleotide, 0.5 µM FRET oligonucleotide and 0.05 nM synthetic target. The concentrations of the MOPS buffer (10 mM) and MgCl₂ (7.5 mM) were unchanged. Finally, the microtiter plate was incubated in a gradient thermal cycler that was programmed to incubate at 58° C., +/−a 5-degree gradient and the reactions were allowed to incubate for 2 h before results were read as above.

C. Results

FRET oligonucleotide F, the dabcyl-cy-3 pair, showed the highest background and lowest quenching efficiency (90%) of the dye pairs examined without any compensating effects in the reaction turnover rate.

FIGS. 154A and 154B show the results obtained with the five different fluorescein-dabcyl FRET oligonucleotides as a function of temperature. The results are presented as the "fold," which is the ratio of the measured fluorescence intensity at the assay endpoint (e.g., 60 or 120 min.) to the fluorescein intensity at the beginning (which is identical to the fluorescence measured in the control experiment with no target DNA). This manner of presenting the data takes into account both the quenching efficiency of the quenching dye (background fluorescence) and the cleaving efficiency of the enzyme (signal fluorescence). Cleavage of the FRET oligonucleotide leads to an enhanced fluorescent signal. The degree of quenching for all fluorescein/dabcyl combinations tested was approximately 98%. Quenching showed no strong dependence upon the spacing between the signal and quenching dyes.

Results of this experiment indicated that the fluorescein-dT/5'-dabcyl combination used for FRET oligonucleotide E is a particularly favorable configuration for this embodiment.

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for cleaving multiple oligonucleotides comprising:
   a) providing:
      i. a plurality of first oligonucleotides attached to a single solid support;
      ii. a second oligonucleotide attached to the same solid support as said plurality of first oligonucleotides;
      iii. a target nucleic acid, wherein said target nucleic acid comprises a first region and a second region, said second region downstream of and contiguous to said first region, wherein at least a portion of each of said first oligonucleotides is completely complementary to said first region of said target nucleic acid, and wherein said second oligonucleotide comprises a 3' portion and a 5' portion, wherein said 5' portion is completely complementary to said second region of said target nucleic acid; and
      iv. a cleavage agent comprising a FEN-1 endonuclease from an archaebacterial species;
   and
   b) exposing said solid support to said cleavage agent under conditions such that:
      i. a first invasive cleavage structure is formed, said first invasive cleavage structure comprising a first one of said plurality of first oligonucleotides, said second oligonucleotide, and said target nucleic acid;
      ii. said cleavage agent cleaves said first one of said plurality of first oligonucleotides in said first invasive cleavage structure to produce a first cleavage fragment;
      iii. after cleavage of said first one of said plurality of first oligonucleotides, a second invasive cleavage structure is formed, said second invasive cleavage structure comprising a second one of said plurality of first oligonucleotides and the same second oligonucleotide as was used in said first invasive cleavage structure;
      iv. said cleavage agent cleaves said first oligonucleotide in said second cleavage structure to produce a second cleavage fragment.

2. The method of claim 1, further comprising the step of c) detecting the presence of said first or said second cleavage fragments.

3. The method of claim 1, wherein said second oligonucleotide is attached to said solid support through a spacer molecule.

4. The method of claim 3, wherein said spacer molecule is selected to allow said second oligonucleotide to form a cleavage structure with three or more of said plurality of first oligonucleotides.

5. The method of claim 4, wherein said spacer molecule is selected to allow said second oligonucleotide to form a cleavage structure with ten or more of said plurality of first oligonucleotides.

6. The method of claim 3, wherein said spacer molecule is selected from the group consisting of a carbon chain, a polynucleotide, biotin, and a polyglycol.

7. The method of claim 1, wherein said solid support comprises a glass solid support.

8. The method of claim 1, wherein said solid support comprises a latex solid support.

9. The method of claim 1, wherein said solid support comprises a hydrogel solid support.

10. The method of claim 1, wherein said solid support comprises a bead.

11. The method of claim 1, wherein said solid support comprises a multi-well plate.

12. The method of claim 1, wherein said solid support comprises a column.

13. The method of claim 1, wherein said solid support comprises a microarray.

14. The method of claim 1, wherein said solid support is coated with a material selected from the group consisting of gold and streptavidin.

* * * * *

UNITED STATES PATENT AND TRADEMARK OFFICE
CERTIFICATE OF CORRECTION

| | |
|---|---|
| PATENT NO. | : 7,432,048 B2 |
| APPLICATION NO. | : 09/732622 |
| DATED | : October 7, 2008 |
| INVENTOR(S) | : Neri et al. |

It is certified that error appears in the above-identified patent and that said Letters Patent is hereby corrected as shown below:

Delete drawing sheets 1-127 and substitute therefor the drawings sheets 1 of 261 consisting of figures 1-155 as shown on the attached pages.

Signed and Sealed this
Seventeenth Day of July, 2012

David J. Kappos
*Director of the United States Patent and Trademark Office*

(12) United States Patent
Neri et al.

(10) Patent No.: US 7,432,048 B2
(45) Date of Patent: ***Oct. 7, 2008

(54) REACTIONS ON A SOLID SURFACE

(75) Inventors: Bruce P. Neri, Madison, WI (US); Jeff G. Hall, Madison, WI (US); Victor Lyamichev, Madison, WI (US); Lloyd M. Smith, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/732,622

(22) Filed: Dec. 8, 2000

(65) Prior Publication Data

US 2005/0164177 A1    Jul. 28, 2005

Related U.S. Application Data

(60) Continuation-in-part of application No. 09/350,309, filed on Jul. 9, 1999, now Pat. No. 6,348,314, which is a division of application No. 08/756,386, filed on Nov. 26, 1996, now Pat. No. 5,985,557, and a continuation-in-part of application No. 09/381,212, filed as application No. PCT/US98/05809 on Mar. 24, 1998, now Pat. No. 6,872,816.

(51) Int. Cl.
*C12Q 1/68* (2006.01)

(52) U.S. Cl. .................... 435/6; 435/91.1; 435/91.2

(58) Field of Classification Search .................. None
See application file for complete search history.

(56) References Cited

U.S. PATENT DOCUMENTS

| | | | |
|---|---|---|---|
| 5,011,769 A | 4/1991 | Duck et al. | 435/6 |
| 5,118,605 A | 6/1992 | Urdea | 435/6 |
| 5,210,015 A | 5/1993 | Gelfand et al. | 435/6 |
| 5,403,711 A | 4/1995 | Walder et al. | 435/6 |
| 5,422,253 A | 6/1995 | Dahlberg et al. | 435/91.53 |
| 5,424,186 A | 6/1995 | Fodor et al. | 435/6 |
| 5,472,881 A | 12/1995 | Beebe et al. | 436/94 |
| 5,516,663 A | 5/1996 | Backman et al. | 435/91.2 |
| 5,541,311 A * | 7/1996 | Dahlberg et al. | 536/23.7 |
| 5,609,907 A * | 3/1997 | Natan | 427/2.12 |
| 5,614,402 A | 3/1997 | Dahlberg et al. | 435/199 |
| 5,691,142 A | 11/1997 | Dahlberg et al. | 435/6 |
| 5,719,028 A | 2/1998 | Dahlberg et al. | 435/6 |
| 5,744,305 A | 4/1998 | Fodor et al. | 435/6 |
| 5,795,763 A | 8/1998 | Dahlberg et al. | 435/194 |
| 5,807,682 A | 9/1998 | Grossman et al. | 435/6 |
| 5,830,664 A | 11/1998 | Rosemeyer et al. | 435/6 |
| 5,837,450 A | 11/1998 | Dahlberg et al. | 435/6 |
| 5,843,654 A | 12/1998 | Heisler et al. | 435/6 |
| 5,843,669 A | 12/1998 | Kaiser et al. | 435/6 |
| 5,846,717 A | 12/1998 | Brow et al. | 435/6 |
| 5,874,283 A * | 2/1999 | Harrington et al. | 435/252.3 |
| 5,882,867 A | 3/1999 | Ullman et al. | 435/6 |
| 5,888,780 A | 3/1999 | Dahlberg et al. | 435/91.53 |
| 5,985,557 A | 11/1999 | Prudent et al. | 435/6 |
| 5,994,069 A | 11/1999 | Hall et al. | 435/6 |
| 6,001,567 A | 12/1999 | Brow et al. | 435/6 |
| 6,060,288 A * | 5/2000 | Adams et al. | 435/91.2 |
| 6,090,543 A | 7/2000 | Prudent et al. | 435/6 |
| 6,090,606 A | 7/2000 | Kaiser et al. | 435/6 |
| 6,280,950 B1 * | 8/2001 | Lipshutz et al. | 435/6 |
| 6,348,314 B1 | 2/2002 | Prudent et al. | 435/6 |
| 6,372,424 B1 | 4/2002 | Brow et al. | 435/5 |
| 6,372,813 B1 * | 4/2002 | Johnson et al. | 522/114 |
| 6,375,903 B1 | 4/2002 | Cerrina et al. | 422/131 |
| 6,458,535 B1 | 10/2002 | Hall et al. | 435/6 |
| 6,500,622 B2 | 12/2002 | Bruchez, Jr. et al. | 435/6 |
| 6,692,917 B2 | 2/2004 | Neri et al. | 435/6 |
| 6,872,816 B1 | 3/2005 | Hall et al. | 536/24.3 |
| 6,875,572 B2 | 4/2005 | Prudent et al. | 435/6 |
| 2002/0187486 A1 | 12/2002 | Hall et al. | 435/6 |
| 2002/0197623 A1 | 12/2002 | Prudent et al. | 435/6 |
| 2003/0096245 A1 | 5/2003 | Prudent et al. | 435/6 |

FOREIGN PATENT DOCUMENTS

| | | |
|---|---|---|
| WO | 94/29482 | 12/1994 |
| WO | 95/11995 | 5/1995 |
| WO | 97/27214 | 7/1997 |
| WO | 99/42813 | 8/1999 |
| WO | 02/04597 | 1/2002 |

OTHER PUBLICATIONS

Ryan et al. Molecular Diagnosis vol. 4:135-144. 1999.*
Shen et al. TIBS. 1998.*
Drmanac et al., Accurate sequencing by hybridization for DNA diagnostics and individual genomics. Nature Biotechnology, 16:54 (1998].
Chee et al., Science, 274:610 [1996].
Sosnowski et al., PNAS, 94:1119 [1997].
Pastinen et al., Genome Research, 7:606 [1997].
Shuber et al., Human Molecular Genetics, 6:337 [1997].
Kwok et al., Nuc. Acid. Res., 18:999 [1990].
Landegren et al., Science, 241:1077 [1988].
Livak et al., PCR Methods and Applications, 4:357 [1995].
Shafer et al., J. clinical Microbiology, 34:1849 [1996].
Wang et al., Science, 280:1077 [1998].
Collins et al., Science, 278:1580 [1997].
Chernukhin and Klenova, Anal. Biochem., 280:178 [2000].
Bilkova et al., J. Chromatogr. A, 852:141 [1999].
Guo et al., Nucleic Acids Res., 22:5456 [1994].
Maskos and Southern, Nucleic Acids Res., 20:1679 [1992].
Frutos et al., Nuc. Acid. Res., 25:4748 [1997].
Frey and Corn, Analytical Chem. 68-3187 (1996).

(Continued)

*Primary Examiner* — Gary Benzion
*Assistant Examiner* — Heather G. Calamita
(74) *Attorney, Agent, or Firm* — Casimir Jones, S.C.

(57) ABSTRACT

The present invention relates to compositions and methods for the detection and characterization of nucleic acid sequences and variations in nucleic acid sequences. The present invention relates to methods for forming a nucleic acid cleavage structure on a solid support and cleaving the nucleic acid cleavage structure in a site-specific manner. For example, in some embodiments, a 5' nuclease activity from any of a variety of enzymes is used to cleave the target-dependent cleavage structure, thereby indicating the presence of specific nucleic acid sequences or specific variations thereof.

14 Claims, 262 Drawing Sheets

OTHER PUBLICATIONS

Jordan et al., Analytical Chem. 694939 [1997].

Shchepinov et al., Nucleic Acids Research 25: 1155 [1997].

Ostroff et al., Cleinical Chem., 45:1659 [1999].

Bambara et al., "Enzymes and Reactions at the Eukaryotic DNA Replication Fork," *J. Biol. Chem.* 272:4647-4650 (1997.

Harrington et al., "DNA Structural Elements Required for FEN-1 Binding," *J. Biol. Chem.* 270:4503-4508 (1995).

Harrington et al., "The characterization of a mammalian DNA structure-specific endonuclease," *EMBO Journ.* 13:1235-1246 (1994).

Harrington and Lieber, "Functional domains within FEN-1 and RAD2 define a family of structure-specific endonucleases: implications for nucleotide excision repair," *Genes and Develop.* 8:1344-1355 (1994).

Lyamichev et al."Structure-Specific Endonucleolytic Cleavage of Nucleic Acids by Eubacterial DNA Polymerases," *Science* 260:778-783 (1993).

Murante et al., "Calf 5' to 3' Exo/Endonuclease Must Slide from a 5' End of the Substrate to Perform Structure-specific Cleavage," *J. Biol. Chem.* 270:30377-30383 (1995).

Murante et al., "The Calf 5'- to 3'-Exonuclease Is Also an Endonuclease with Both Activities Dependent on Primers Annealed Upstream of the Point of Cleavage," *J. Biol. Chem.* 269:1191-1196 (1994).

Hessner et al., Genotyping of Factor V G1691A (Leiden) without the Use of PCR by Invasive Cleavage of Oligonucleotide Probes, *Clinical Chemistry* 46:1051-1056 (2000).

Lyamichev et al., Experimental and Theoretical Analysis of the Invasive Signal Amplification Reaction, *Biochemistry* 39:9523-9532 (2000).

Neri et al., Transferring Automation for Large-scale Development and Production of Invader™ SNP Assays, *Progress in Biomedical Optics* 1:117-125 (2000).

Newlin et al., The Invader Assay: An Alternative To PCR-Based Testing For The Detection Of Point Mutations Associated With Venous Thrombosis, *Clinical Hemostasis Review*, 14:10-12 (2000).

Hall et al., Sensitive detection of DNA polymorphisms by the serial invasive signal amplification reaction, PNAS 97:8272-8277 (2000).

Ledford et al., A Multi-Site Study for Detection of the Factor V (Leiden) Mutation from Genomic DNA Using Homogeneous Invader Microtiter Plate Fluorescence Resonance Energy Transfer (FRET) Assay, *J. Molecular Diagnostics* 2:97-104 (2000).

Ma et al., RNA Template-dependent 5' Nuclease Activity of *Thermus aquaticus* and *Thermus thermophilus* DNA Polymerases, *J. Biol. Chem.*, 275:24693-24700 (2000).

Fors et al., Large-scale SNP scoring from unamplified genomic DNA, *Pharmacogenomics* 1(2):219-229 (2000).

Agarwal et al., Comparison Study For Identifying Promoter Allelic Polymorphism in Interleukin 10 and Tumor Necrosis Factor á Genes, *Diagn Mol Pathol* 9(3):158-164 (2000).

Cooksey et al., Evaluation of the Invader Assay, a Linear Signal Amplification Method, for Identification of Mutation Associated with Resistance to Rifampin and Isoniazid in *Mycobacterium tuberculosis, Antimicrobial Agents and Chemotherapy*, 44:1296-1301 (2000).

Mein et al., Evaluation of Single Nucleotide Polymorphism Typing with Invader or PCR Amplicons and Its Automation, *Genome Research* 10:330-343 (2000).

Lieder, Excitement Builds in Molecular Biology, *Advance for Administrators of the Laboratory*50-52 (1999).

Lieder, Invader Technology Provices Alternative to PCR, *Advance for Administrators of the Laboratory*, 70-71 (2000).

Treble et al., Invader ? technology for SNP detection, *Gene & Medicine* 4:68-72 (2000).

Kwiatkowski et al., Clinical, Genetic, and Pharmacogenetic Applications of the Invader Assay, *Molecular Diagnosis*, 4:353-364 (1999).

Check, Labs home in on mutant alleles, *College of American Pathologists Today*, 1-5 Sep. 1999.

Griffin et al., Direct genetic analysis by matrix-assisted laser desorption/ionization mass spectrometry, *PNAS* 96:6301-6306 (1999).

Ryan et al., Non-PCR-Dependent Detection of the Factor V Leiden Mutation From Genomic DNA Using a Homogeneous Invader Microtiter Plate Assay, *Molecular Diagnosis*, :135-144 (1999).

Kaiser et al., A Comparison of Eubacterial and Archaeal Structure-specific 5'-Exonucleases, *J. Biol. Chem.*, 274:21387-21394 (1999).

Lyamichev et al., Polymorphism indentification and quantitative detection of genomic DNA by invasive cleavage of oligonucleotide probes, *Nature Biotech.* 17:292-296-(1999).

Harrington, The Characterization of the Fen-1 Family of Structure-Specific Endonucleases: Implications for DNA Replication, Recombination, And Repair, Dissertation submitted to the Program in Cancer Biology and the Committee on Graduate Studies of Stanford University (1994).

DeFrancesco, The Next New Wave in Genome Analysis, *The Scientist*, 12(21):1-3 (1998).

Order and Opinion on Motion for Summary Judgment, *Third Wave Technologies, Inc. v. Eragen Biosciences, James Prudent, and David Marshall*, 02-C-507-C, United States District Court for the Western District of Wisconsin.

Order and Opinion, *Third Wave Technologies, Inc. v. Stratagene Corp.*, 04-C-680-C 02-C-507-C, United States District Court for the Western District of Wisconsin, Aug. 4, 2005.

Lieber, The FEN-1 family of structure-specific nucleases in eukaryotic DNA replication, recombination and repair, BioEssays 19:223-240 (1997).

Order and Opinion on Post-Trial Motions, *Third Wave Technologies, Inc. v. Stratagene Corp.*, 04-C-680-C 02-C-507-C, United States District Court for the Western District of Wisconsin, Dec. 16, 2005.

* cited by examiner

FIG. 1A

```
MAJORITY  CGAGGCGGACGACGTXCTGGCCACCCTGGCCAAGAAGGCGGAAAAGGAGGGGTACGAGGTGCCGCATCCTC

DNAPTAQ   .........................C..........................C................  417
DNAPTFL   T...........G.................CG......................................  414
DNAPTTH   ............T.C...............................................C.......  420

MAJORITY  ACCGCCGACCGCGACCTCTACCAGCTCCTTTCCGACCGCATCGCCGTCCTCCACCCCGAGGGTACCTCA

DNAPTAQ   ........AAA...T.....................................................CA  487
DNAPTFL   ..T................................G.G........A.................G.....  484
DNAPTTH   ..................................A..G.C.........CC....................  490

MAJORITY  TCACCCCGGCGTGGCTTTGGGAGAAGTACGGCCTGAGGCCGGAGCAGTGGGTGGACTACCGGGCCCTGGC

DNAPTAQ   .............C........A.........CC..........C.C........CC..............A..  557
DNAPTFL   ...............AC.............C.C................................C......  554
DNAPTTH   ...............A.........................C..................T......C.T  560

MAJORITY  GGGGACCCCTCCGACAACCTCCCCGGGTCAAGGGCATCGGGGAGAAGACCGCCCXGAAGCTCCTCXAG

DNAPTAQ   C....GAG..............T.....................G.GAG....T..GG..  627
DNAPTFL   ......G.T..A.................G.....................A..G.....A..CGC  624
DNAPTTH   .....A.............................................TC........A..  630

MAJORITY  GAGTGGGGAGCCTGGAAAACCTCTCAAGAACCTGGACCGGGTGAAGCCCGC..CXTCCGGGAGAAGA

DNAPTAQ   ........................GC......................C..........A.......  694
DNAPTFL   .............A.........................T.C.C...A.........T.G.........C  691
DNAPTTH   ..........A..............................A....A.AAAA.G.............  700
```

FIG. 1B

```
MAJORITY  TCCAGGCCCACATGGAXGACCTGAXGCTCTCCTGGGAGCTXTCCCAGGTGCGCACCGACCTGCCCCTGGA  764

DNAPTAQ   ...T..............C.T....A...............C..GG..A..................  761
DNAPTFL   .......GGG......G.C...GCC..T...C.A...T........A..T.................  761
DNAPTTH   ..A.............C.G..............T......C.......G...........C......  770

MAJORITY  GGTGGACTTCGCCAAGXGGCGGGAGCCCGACCGGGAGGGGCTTAGGGCCTTTCTGGAGAGGCTGGAGTTT  834

DNAPTAQ   .....................AA......................A......T..............  831
DNAPTFL   .......GG.G.C.C..CACA.....A...T.......T.GC....T.....C.T............  831
DNAPTTH   ......C....C..G..................................C................C  840

MAJORITY  GGCAGCCTCCTCCACGAGTTCGGCCTCCTGGAAGCCCCTGAGGGGCCCCAAGGCCCCTGGAGGAGGCCCCTGGCCCCGC  904

DNAPTAQ   .................T..AA...............G.G....GGCA...................  901
DNAPTFL   ..A.....................................C....GCCC..................  901
DNAPTTH   ............................................................C....  910

MAJORITY  CGGAAGGGGCCTTCGTGGGCCTTTGTCCTTCCCGCCCGAGCCCATGTGGGCCGAGCTTCTGGCCCTGGC  974

DNAPTAQ   ..........................G................T......................  971
DNAPTFL   .............T..TT.......TC.T...T.....................G....AAA.....  971
DNAPTTH   ...................................C..C............................  980

MAJORITY  CGCCGCCAGGGAGGGCCGGGTCCACCGGGCACCAGACCCCTTTAXGGGCCTXAGGGACCTXAAGGAGGTG  1044

DNAPTAQ   .......G...............T..........C.C..G..T.A..AA.C....C.......G...C  1041
DNAPTFL   T.GG..GT......G..CC..T.........A......C..G..............G...T..G...C  1041
DNAPTTH   ...TG......C........G...............GGC..G..A.A.........C..........C  1050
```

FIG. 1C

```
MAJORITY  CGGGGXCTCCTCGCCAAGGACCTGGCCGTTTTGGCCCTGAGGGAGGGCCTXGACCTCXTGCCCGGGACG   1114
DNAPTAQ   .....G..T........A......AG...C.................A.......T.G......CC.....   1111
DNAPTFL   .....AA..........G......................C.................T.C..A.A....   1120
DNAPTTH   .....C..................................TC................G.A....G....   1120

MAJORITY  ACCCCATGCTCCTCGCTTCCTGGACCCCTCCAACACCACCCCGAGGGGTGGCCCGGCGCTACGG   1184
DNAPTAQ   ...................T............T.......................T.....   1181
DNAPTFL   .................G..........T............................G....   1190
DNAPTTH   .........................................................G....   1190

MAJORITY  GGGGAGTGGACGGAGGAXGCGGGGGAGCGGCCCTCCTXTCCGAGAGGCTCTTCCXGAACCTXXXGGAG   1254
DNAPTAQ   C...........................GC...T......................GCC....GTG..G..   1260
DNAPTFL   ............T......A.........GG...C.C....A..C.............A..C..AAA....   1260
DNAPTTH   ............C..C.CCC.C.............C..G..........CAT.G.......CCTTA....   1260

MAJORITY  CGCCTTGAGGGGGGAGGAGAGGCTCCTTTGGCTTTACCAGGAGGTGGAGAAGCCCCTTTCCCGGGTCCIGG   1324
DNAPTAQ   A.G..................A....A.A..AC.C..G.......G...........G......GCT....   1321
DNAPTFL   .......................................................................GT....   1330
DNAPTTH   ..........C......................A.........C..........A......C........   1330

MAJORITY  CCCACATGGAGGCCACGGGGGTXCGGCTGGACGTGGCCTACCTTCCAGGCCCTXTCCCTGGAGGTGGCGGA   1394
DNAPTAQ   ......GG.....................T.G.....T.AG....T.G......C............C..   1391
DNAPTFL   .........................................................C........A..C.....   1400
DNAPTTH   ............................A..................T..................C..T.....   1400
```

FIG. 1D

```
MAJORITY GGAGATCCGCCGCCTCGAGGAGGAGGTCTTCCGCCTGGCCGGCCACCCTTCAACCTCAACTCCCGGGAC    1464
DNAPTAQ  .......GC...........CC...........................................    1461
DNAPTFL  ...G.G....AG..G......................T....G......................    1470
DNAPTTH  ..................................................................

MAJORITY CAGCTGGAAAGGGTGCTCTTTGACGAGCTXGGGCTTCCCGCCATCGGCAAGACGGAGAAGACXGGCAAGC    1534
DNAPTAQ  ..............C..................A...........................C...    1531
DNAPTFL  ..............GC...................G..C.G.T...........G..G..A....    1540
DNAPTTH  ............................TA..........T.G.G..........C.A.......

MAJORITY GCTCCACCAGCGCCGCCGTGCTGGAGGCCCTXCGXGAGGCCCACCCCATCGTGGAGAAGATCCTGCAGTA    1604
DNAPTAQ  ............................C.....................C.C...........    1601
DNAPTFL  .................T..............G..A...CCGC................C...    1610
DNAPTTH  .................G..............A..G............................

MAJORITY CCGGGAGCTCACCAAGCTCAAGAACACCTACATXGACCCCCTGCCXGXCCTCGTCCACCCAGGACGGGC    1674
DNAPTAQ  .....................G..............T.....G.A...A................    1671
DNAPTFL  ..........................G..............A....C.C..G.....A..C....    1680
DNAPTTH  ....................................G.G........AAG.........G.....

MAJORITY CGCCTCCACACCCGCTTCAACCAGACGGCCACGGGCCAGGCTTAGTAGCTCCGACCCCAACCTGC    1744
DNAPTAQ  .........................................A..........T.......C..    1741
DNAPTFL  ..G......................................TCC....................    1750
DNAPTTH  ..........................................................G.....
```

FIG. 1E

FIG. 1F

```
MAJORITY  AGCTTCCCCAAGGTGCGGGCCTGGATTGAGAAGACCCTGGAGAGGGCAGGAGGCGGGGGTACGTGGAGA   2164

DNAPTAQ   ....A.................................C..CC.......T..........         2161
DNAPTFL   ......................GG..........A.A...........G..A........A.      2170
DNAPTTH   ..........................................C..................

MAJORITY  CCCTCTTCGGCGCCGGCGCTACGTGCCCGACCTCAACGCCCTGGGTGAAGAGCGTGCGGGAGGCGGGA   2234

DNAPTAQ   ..............................C........A.....AG.G..........C.       2231
DNAPTFL   .............................T.........................C..          2240
DNAPTTH   .............AA.AA...................................CA.....C.

MAJORITY  GCGCATGGCCTTCAACATGCCGTCCAGGGCACCGCCGACCTCATGAAGCTGGCCATGGTGAAGCTC    2304

DNAPTAQ   ................................................T..............      2301
DNAPTFL   ..........................G.....................................CG...T   2310
DNAPTTH   ...........................................................C.

MAJORITY  TTCCCCGGCTXCAGGAAATGGGGCCAGGATGCTCCTXCAGGTCCACGACGAGCTGGTCCTCGAGGCCC   2374

DNAPTAQ   ......A....GG..........C.........................T..............      2371
DNAPTFL   ...........T.....C........G........TT.G....G..............            2380
DNAPTTH   ...........C..C.G..G.............CC...........CC......G.

MAJORITY  CCAAGAGAGCGGGGAGXGGTGCCGCGTTTGGCCAAGGAGGTCATGGAGGGGTCTATCCCCTGGCCGT   2444

DNAPTAQ   A.........A.........CC......CGGC.................G..............      2441
DNAPTFL   ...G..C....AG....A................................GG.....CAG...      2450
DNAPTTH   ..C..C......C.......A.......G..................C..........AA..C.

FIG. 1G
```

```
MAJORITY  GCCCCTGGAGGTGGAGGTGGGGATGGGGAGGACTGGCTCTCCGCCAAGGAGTAG

DNAPTAQ   ..........................A...............GA     2499
DNAPTFL   ................CC............................   2496
DNAPTTH   ..................................T.......GT...  2505
```

FIG. 1H

```
MAJORITY  MXAMLPLFEPKGRVLLVDGHHLAYRTFFALKGLTTSRGEPVQAVYGFAKSLLKALKEDG·DAVXVVFDAK

TAQ PRO   .RG...........................H........................................I.....  69
TFL PRO   .  ............................ .......................................V.V....  68
TTH PRO   .E...................................................................YK..F....  70

MAJORITY  APSFRHEAYEAYKAGRAPTPEDFPROLALIKELVDLLGLXRLEVPGYEADDVLATLAKKAEKEGYEVRIL

TAQ PRO   ............GG........................A...............S..............  139
TFL PRO   ......................................V....F..........................  138
TTH PRO   ........................................FT...........R................  140

MAJORITY  TADRDLYQLLSDRIAVLHPEGYLITPAWLNEKYGLRPEQWVDYRALXGDPSDNLPGVKGIGEKTAXKLLX

TAQ PRO   ...K................H...................D.A....T.E............R...E  209
TFL PRO   .......E..I.........Y................A.......I...........QR.IR  208
TTH PRO   ......V..V........H...E.............F..V...................L...K  210

MAJORITY  EWGSLENLLKNLDRVKP·XXREKIXAHMEDLXLSXXLSXVRTDLPLEVDFAXRREPDREGLRAFLERLEF

TAQ PRO   .........A.......AI....L....D.K..WD.AK............K.......R........  278
TFL PRO   .........FQH.Q....SL...LQ.G..A.A.RK..Q.H..........GR..T.NL.........  277
TTH PRO   .............ENV....K..L...R..LE..R...............L.QG.............  280

MAJORITY  GSLLHEFGLLEXPKALEEEAPWPPPEGAFVGFVLSRPEPMWAELLALAAARXGRVHRAXDPLXGLRDLKEV

TAQ PRO   .........S......................K.....D...............PE.YKA......A  348
TFL PRO   .........G..A............L..SF............................Q...R....G.  347
TTH PRO   .........A.AP...................K.......C.D........A..A..K........  350
```

FIG. 2A

```
                                                                            418
MAJORITY  RGLLAKDLAVLALREGLDLXPGDDPMLLAYLLDPSNTTPEGVARRYGGEWTEDAGERALLSERLFXNLXX

TAQ PRO   ......S.................G.P.....................E.............A..WG   418
TFL PRO   ..I..............F.E.............................A............QT.KE   417
TTH PRO   .........S........V..........................AH..................HR..LK  420

488
MAJORITY  RLEGEERLLWLYXEVEKPLSRVLAHMEATGVRLDVAYLQALSLEVAEEIRRLEEEVFRLAGHPFNLNSRD

TAQ PRO   ......R...R..A............R.................R..A...A...............   488
TFL PRO   .K....E..........................EA.V.Q..............................   487
TTH PRO   .......K.....H...............L.......................................  490

558
MAJORITY  QLERVLFDELGLPAIGKTEKTGKRSTSAAVLEALREAHPIVEKILQYRELTKLKNTYIDPLPXLVHPRTG

TAQ PRO   .........................................S.........D.I..............   558
TFL PRO   ............DR...............................A....K..................  557
TTH PRO   ..R..L..Q.............................H..........V.......S...........  560

628
MAJORITY  RLHTRFNQTATATGRLSSSDPNLQNIPVRTPLGQRIRRAFVAEEGWXLVALDYSQIELRVLAHLSGDENL

TAQ PRO   .........................................I.....L....................  628
TFL PRO   .................................................V..V...............  627
TTH PRO   ..................................................A..A..............  630

698
MAJORITY  IRVFQEGRDIHTQTASWMFGVPPEAVDPLMRRAAKTINFGVLYGMSAHRLSQELAIPYEEAVAFIERYFQ

TAQ PRO   ...........E...........R.........................Q...................  698
TFL PRO   ..............S.G..............................G.S...................  697
TTH PRO   ..K..................V...............................................  700
```

FIG. 2B

```
MAJORITY  SFPKVRAWIEKTLEEGRRRGYVETLFGRRRYVPDLNARVKSVREAAERMAFNMPVQGTAADLMKLAMVKL

TAQ PRO   ......Y.........G..................E.......................             768
TFL PRO   ................................................................R.       767
TTH PRO   ..............K.................................................         770

MAJORITY  FPRLXEMGARMLLQVHDELVLEAPKXRAEXVAALAKEVMEGVYPLAVPLEVEVGXGEDWLSAKEX

TAQ PRO   ....E...........E...A..R...........I..........                           833
TFL PRO   ...Q.L..........D...R..........W.Q..L.........                           831
TTH PRO   ...R.......L....QA..E.......A..KA..M..........G                          835
```

FIG. 2C

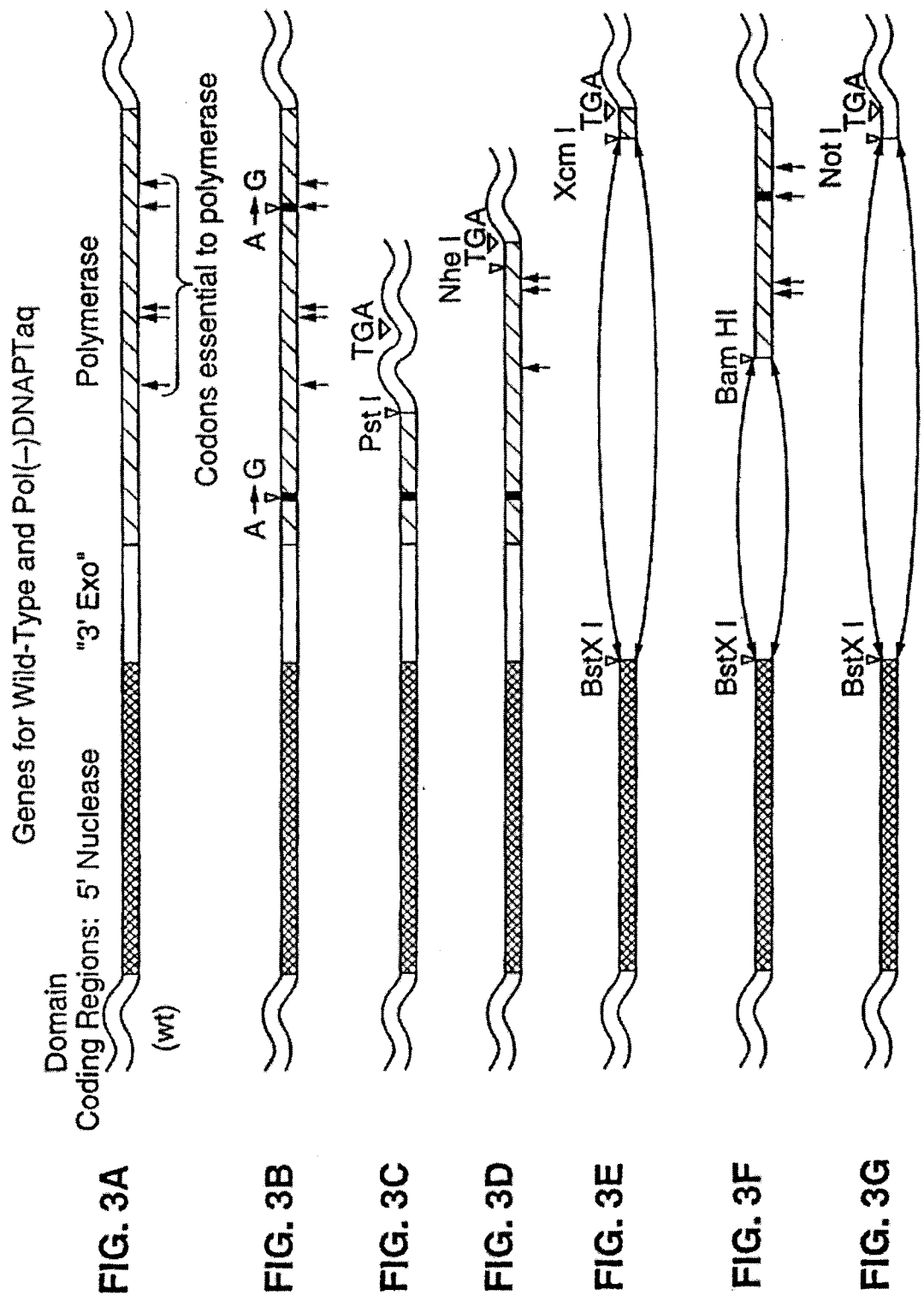

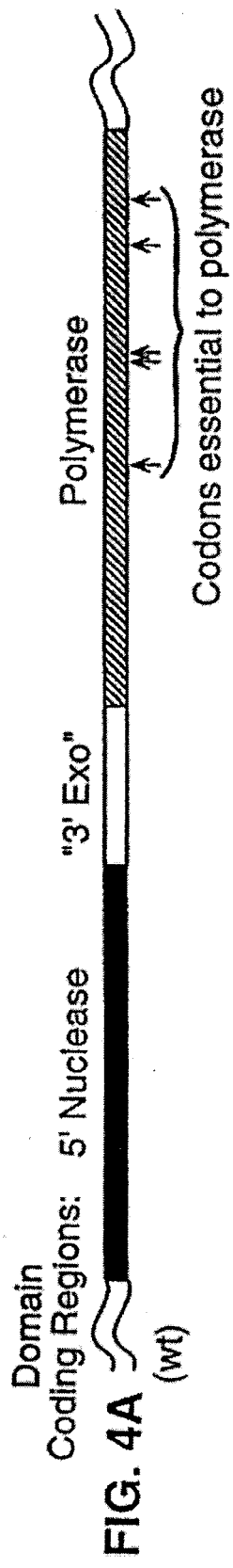
FIG. 4A
FIG. 4B

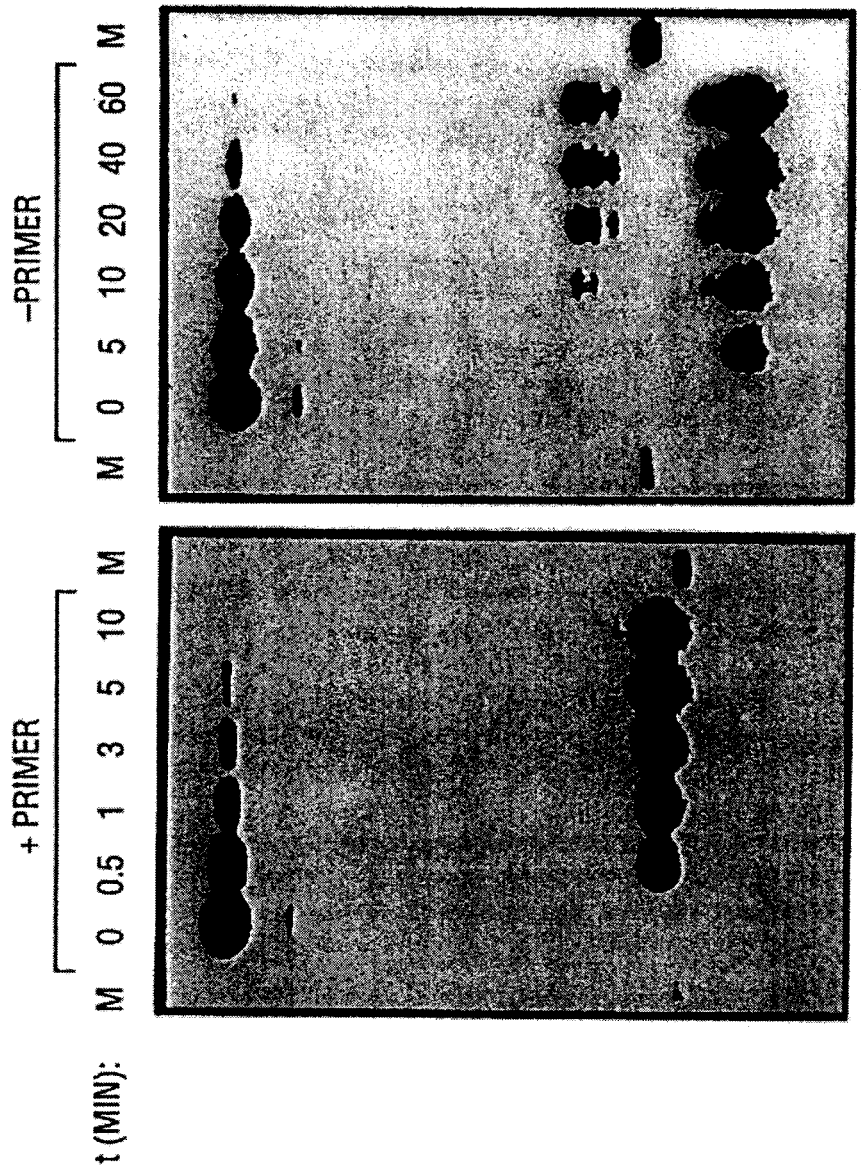

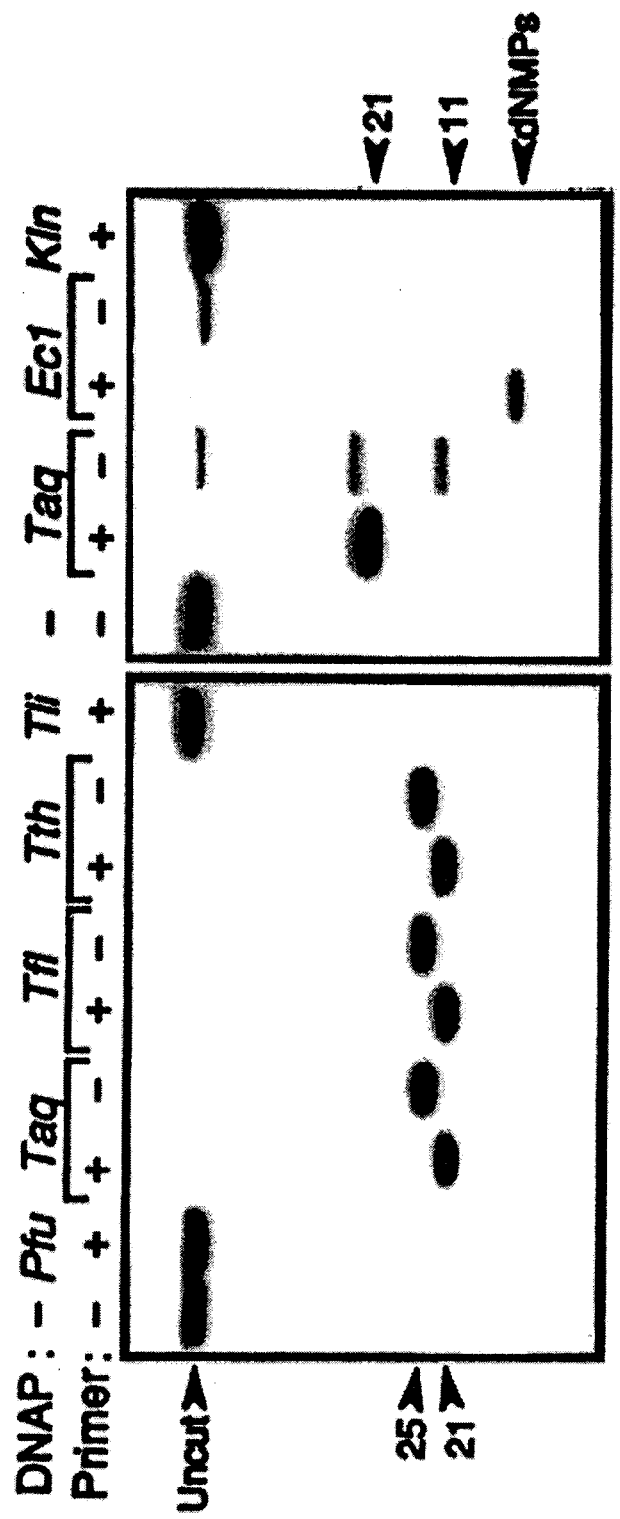

FIG.20B

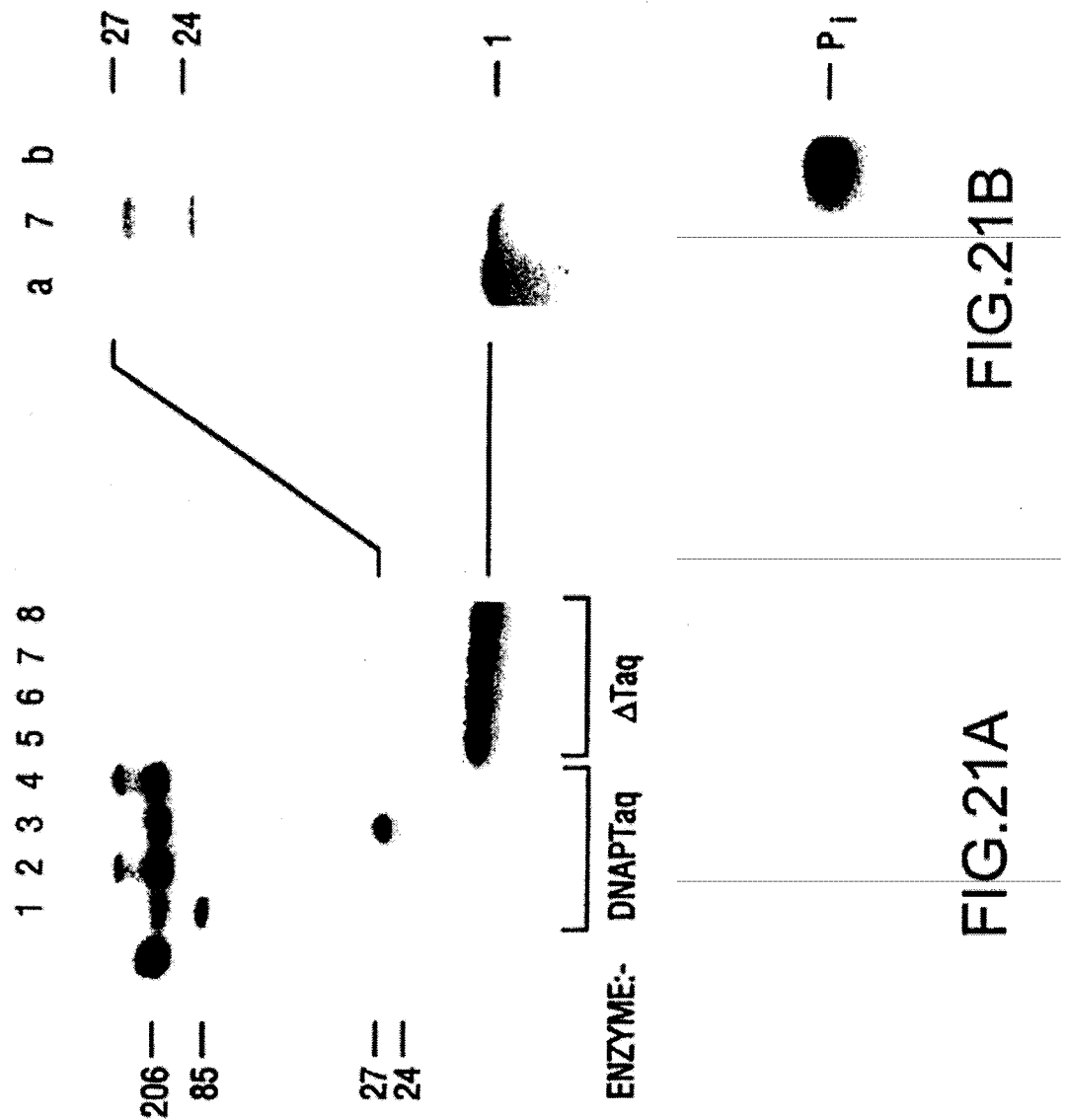

Figures 22A, 22B:
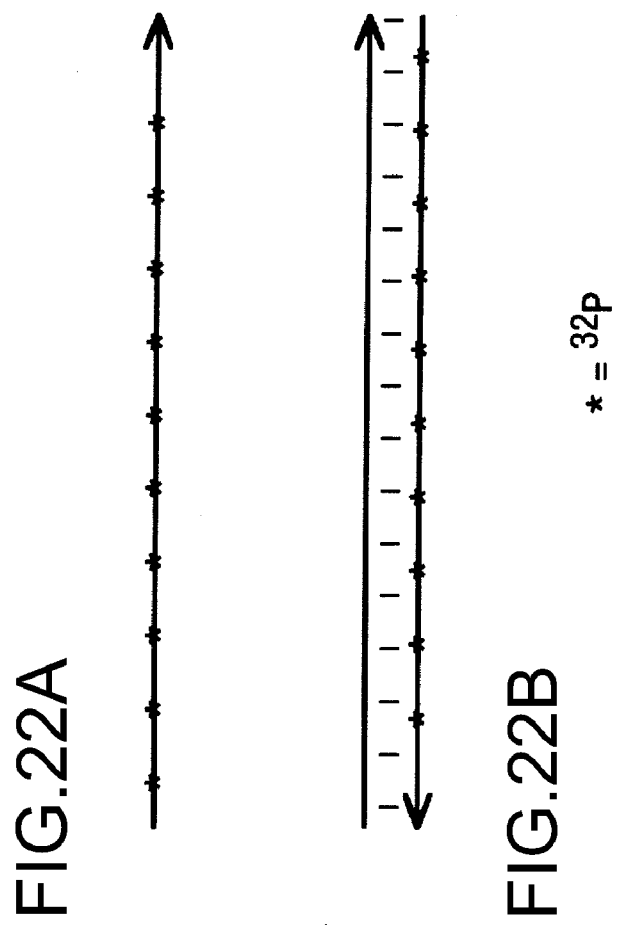
FIG. 22 demonstrates that the "nibbling" phenomenon is duplex dependent.

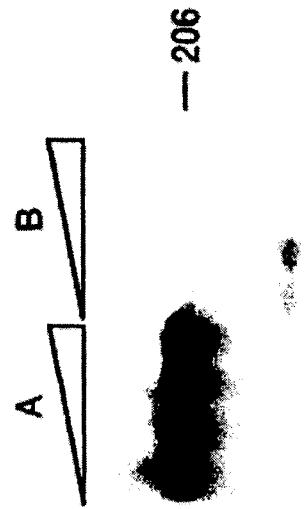
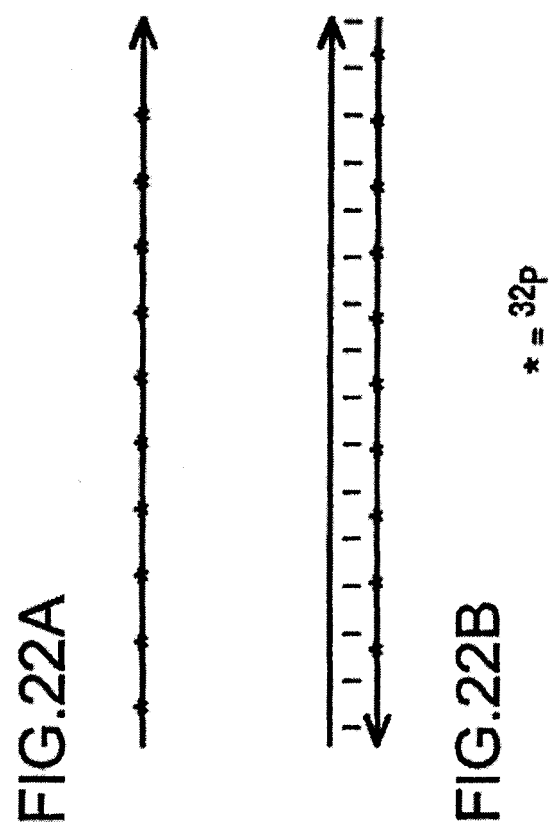
FIG.22A
FIG.22B
* = ³²P

FIG. 26

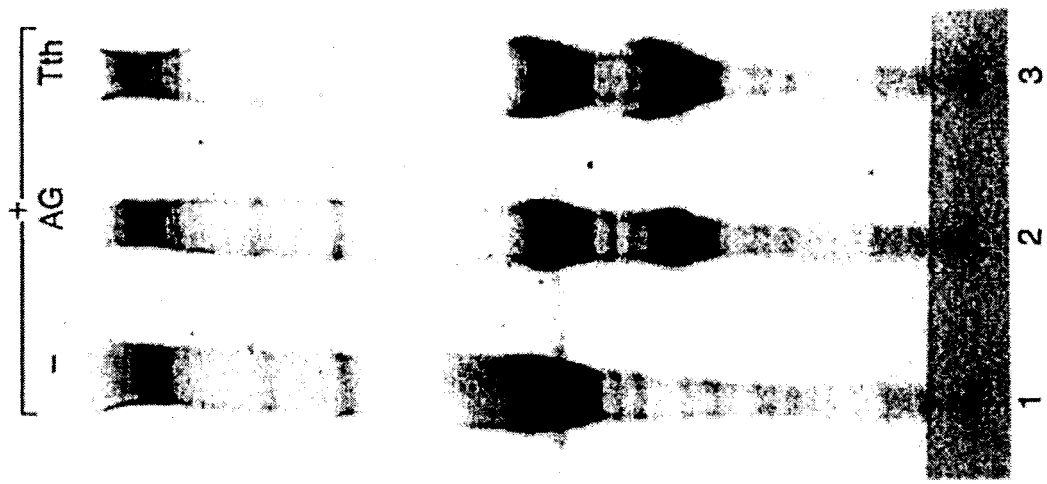
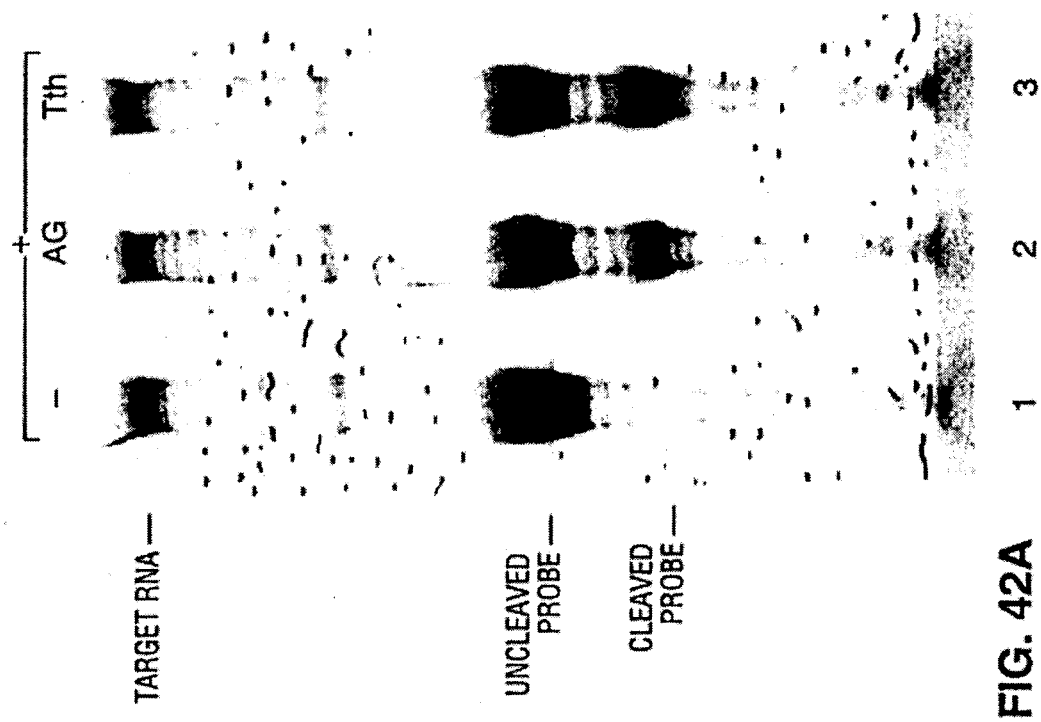
FIG. 42B
FIG. 42A

```
                                    6
                                    1
                  +      +
                NH₃    NH₃
                 \    /
                  T--T--CLEAVAGE SITE
                 /          ↓
        5'-Cy'3-T         CTTTTCACCAGCGAGACGGG-3'
                         ↑
              ─────INVADER─────
              CGGCCAAACGCGATAACCCGCGGGTCCCACCAAAAAGAAAAAGTGGTCGCTCTGCCC-5'
              0987654321098765432 1
                                  123456789
       M13→3'
              67→ATTGGGCGCCAGGGTGGTTTT
```

FIG. 49A

```
                        v
5'            AGAAAGGAAGGGAAGAAAGCGAAAGG 3'
3' CGGCCGCTTGCACCGCTCTTTCCTTCCCTTCTTTCGCTTTCC 5'

AGAAAGGA v
5' GCCGGCGAACGTGGCGAGAAAGGAAGGGAAGAAAGCGAAAGG 3'
3' CGGCCGCTTGCACCGCTCTTTCCTTCCCTTCTTTCGCTTTCC 5'
```
FIG. 54A

```
              v
5'       CAG AAGGAAGGGAAGAAAGCGAAAGG 3'
3' CGGCCGCTTGCACCGCTCTTTCCTTCCCTTCTTTCGCTTTCC 5'

CAGAAGGA v
5' GCCGGCGAACGTGGCGAGAAAGGAAGGGAAGAAAGCGAAAGG 3'
3' CGGCCGCTTGCACCGCTCTTTCCTTCCCTTCTTTCGCTTTCC 5'
```
FIG. 54B

```
              v
5'     CAGGG GGAAGGGAAGAAAGCGAAAGG 3'
3' CGGCCGCTTGCACCGCTCTTTCCTTCCCTTCTTTCGCTTTCC 5'

CAGGGGGA v
5' GCCGGCGAACGTGGCGAGAAAGGAAGGGAAGAAAGCGAAAGG 3'
3' CGGCCGCTTGCACCGCTCTTTCCTTCCCTTCTTTCGCTTTCC 5'
```
FIG. 54C

```
                v
5'    CAGGGTAC AGGGAAGAAAGCGAAAGG 3'
3' CGGCCGCTTGCACCGCTCTTTCCTTCCCTTCTTTCGCTTTCC 5'

CAGGGTAC v
5' GCCGGCGAACGTGGCGAGAAAGGAAGGGAAGAAAGCGAAAGG 3'
3' CGGCCGCTTGCACCGCTCTTTCCTTCCCTTCTTTCGCTTTCC 5'
```
FIG. 54D

```
  1 MGVQ-----FGDFIPK--NIISFEDLKGKKVAIDGMNALYQFLTSIRLRDGSPLRNRKGEITSAYNGVFY  MJAFEN1.PRO
  1 MGVP-----IGEIIPR--KEIELENLYGKKIAIDALNAIYQFLSTIRQKDGTPLMDSKGRITSHLSGLFY  PFUFEN1.PRO
  1 MGIQGLAKLIADVAPSAIRENDIKSYFGRKVAIDASMSIYQFLIAVRQ-GGDVLQNEEGETTSHLMGMFY  HUMFEN1.PRO
  1 MGIHGLAKLIADVAPSAIRENDIKSYFGRKVAIDASMSIYQFLIAVRQ-GGDVLQNEEGETTS-LMGMFY  MUSFEN1.PRO
  1 MGIKGLNAIISEHVPSAIRKSDIKSFFGRKVAIDASMSLYQFLIAVRQQDGGQLTNEAGETTSHLMGMFY  YST510.PRO
  1 MGVHSFWDIAG----PTARPVRLESLEDKRMAVDASIWIYQFLKAVRDQEGNAVKN-----SHITGFFR  YSTRAD2.PRO
  1 MGVSGLWNILE-----PVKRPVKLETLVNKRLAIDASIWIYQFLKAVRDKEGNQLKS-----SHVVGFFR  SPORAD13.PRO
  1 MGVQGLWKLLE-----CSGROVSPEALEGKILAVDISIWLNQALKGVRDRHGNSIEN-----PHLLTLFH  HUMXPG.PRO
  1 MGVQGLWKLLE-----CSGHRVSPEALEGKVLAVDISIWLNQALKGVRDSHGNVIEN-----AHLLTLFH  MUSXPG.PRO
  1 MGVQGLWKLLE-----CSGRPINPGTLEGKILAVDISIWLNQAVKGARDRQGNAIQN-----AHLLTLFH  XENXPG.PRO
  1 MTINGIWEWANHVV---RKVPNETMRDKTLSIDGHIWLYESLKGCEAHHQQT------PNSYLVTFFT  CELRAD2.PRO

64 KTIHLLENDITPIWVFDGEPPKLKEKTRKVRREMKEKAELKMKEAIKK----EDFEEAAKYAKRVSYLTP  MJAFEN1.PRO
 64 RTINLMEAGIKPVYVFDGEPPEFKKKELEKRREAREEAEEKWREALEK----GEIEEARKYAQRATRVNE  PFUFEN1.PRO
 70 RTIRMENGIKPVYYVFDGKPPQLKSGELAKRSERRAEAEKQLQQAQAA----GAEOEVEKFTKRLVKVTK  HUMFEN1.PRO
 69 RTIRM-ENGIKPVYVFDGKPPQLKSGELAKRSERRAEAEKQLQQAQEA----GMEEEVEKFTKRLVKVTK  MUSFEN1.PRO
 71 RTLRMIDNGIKPCYVFDGKPPDLKSHELTKRSSRRVETEKKLA---EA----TTELEKMKQERRLVKVSK  YST510.PRO
 61 RICKLLYFGIRPVFVFDGGVPVLKRETIRQRKERRQGKRESAKSTARKLLALQLQNGSNDNKRDSDEVTM  YSTRAD2.PRO
 61 RICKLLFFGIKPVFVFDGGAPSLKRQTIQKRQARRLDREENATVTANKLLALQMRHQAMLLKRQAIKTER IAATVTG  SPORAD13.PRO
 61 RLCKLLFFGIKPIFVFDGDAPLLKKQTLVKRRQRKDLASSDSRKTTEKLLKTFLKRQAIKTERIAATVTG  HUMXPG.PRO
 61 RLCKLLFFGIKPIFVFDGDAPLLKKQTLVKRRQRQKDSASIDSRKTTEKLLKTFLKRQALKTDRIAASVTG  MUSXPG.PRO
 61 RLCKLLFFRIRPIFVFDGEAPLLKRQTLAKRRQRTDKASNDARKTNEKLLRTFLKRQAIKAERIAATVTG  XENXPG.PRO
 60 RIQRLLELKIIPIVVFDNINASSSAHESKDQNEFVPRKRRSFGDSPFTNLV---------  CELRAD2.PRO
```

FIG. 59A

```
                150         160         170         180         190         200         210
130 KMVENCKYLLSLMGIPYVEAPSEGEAQASYMAKKGDVWAVVSQDYDALLYGAPRVVRNLTTTKEM----        MJAFEN1.PRO
130 MLIEDAKKLLELMGIPIVQAPSEGEAQAAYMAAKGSVYASASQDYDSLLFGAPRLVRNLTITGKRKLPGK        PFUFEN1.PRO
136 QHNDECKHLLSLMGIPYLDAPSEAEASCAALVKAGKVYAAATEDMDCLTFGSPVLMRHLTASEAKKLPIQ        HUMFEN1.PRO
134 QHNDECKHLLSLMGIPYLDAPSEAEASCAALAKAGKVYAAATEDMDCLTFGSPVLMRHLTASEAKKLPIQ        MUSFEN1.PRO
134 EHNEEAQKLLGLMGIPYIIAPTEAEAQCAELLQNLVDGIITDDSDVFLFGGTKIYKNMFHEKNY---VE        YST5IO.PRO
131 DMIKEVQELLSRFGIPYITAPMEAEAQCAELLQNLVDGIITDDSDVFLFGGTRVYRNMFNQNKF----VE        YSTRAD2.PRO
131 VMIKECQELLRLFGLPYIVAPOEAEAQCSKLLELKLVDGIVTDDSDVFLFGGTRVYRNMFNQNKF----VE        SPORAD13.PRO
131 QMFLESQELLRLFGIPYIQAPMEAEAEQCAILDLTDQTSGTITDDSDIWLFGARHVYRNFFNKNKF---VE        HUMXPG.PRO
131 QMFLESQELLRLFGVPYIQAPMEAEAEQCAVLDLSDQTSGTITDDSDIWLFGARHVYKNFFNKNKF---VE        MUSXPG.PRO
131 QMCLESQELLQLFGIPYIVAPMEAEAEQCAILDLTDQTSGTITDDSDIWLFGARHVYKNFFSQNKH----VE       XENXPG.PRO
111 DHVYKTNALLTELGIKVIIAPGDGEAQCARLEQLGVTSGCITTDFDYFLFGGKNLYRFDFTAGT-----          CELRAD2.PRO 220         230         240         250         260         270         280
195 ------PELIELNEVLEDLRISLDDLIDIAIFMGTDYNPGGV--K--GIGFKRAYELVRSGVAK--DV         MJAFEN1.PRO
200 NVYVE-IKPELILEEVLKELKLTREKLIELAILVGTDYNPGGI--K--GIGLKKALEIVRHSKDPLAKF         PFUFEN1.PRO
206 EFHLSRILQELQELGLNQEQFVDLCILLGSDYCESIRGIGPKRAVDLIQK--HKSIEEIVRRLDPN----KY     HUMFEN1.PRO
204 EFHLSRVLQELQELGLNQEQFVDLCILLGSDYCESIRGIGAKRAVDLIQK--HKSIEEIVRRLDPS----KY     MUSFEN1.PRO
204 EIDTELVLRGLDLTIEQFVDLCIMLGCDYCESIRGVGPVTALKLIKT--HGSIEKIVEFIESGESNNTKW       YST5IO.PRO
198 FYDAESILKLLGLDRKNMIELAQLLGSDYTNGLKGMGPVSSIEVIAEF---GNLKNFKDWYNNGOFDKRK       YSTRAD2.PRO
198 LYLMDDMKREFNVNQMDLIKLAHLLGSDYTMGLSRVGPVLALEILHEFPGDTGLFEFKKWFQRLSTGHAS       SPORAD13.PRO
198 YYQYVDFHNQLGLDRNKLINLAYLLGSDYTEGIPTVGCVTAMEILNEFPGHGLEPLLKFSEWWHEAQKNP       HUMXPG.PRO
119 YYQYVDFYSQLGLDRNKLINLAYLLGSDYTEGIPTVGCVTAMEILNEFPGRGLDPLLKFSEWWHEAQNNK       MUSXPG.PRO
198 YYQYADIHNOLGLDRSKLINLAYLLGSDYTEGIPTVGYSAMEILNEFPGQGLEPLVKFKEWWSEAQKDK        XENXPG.PRO
175 ------------------SSTACLHDIMHLSLGRMFM-----                                   CELRAD2.PRO
```

FIG. 59B

```
                                      290              300              310              320              330              340              350
251 LKKEVEYYDEIKRIFKEPKV-------------------------------TD--NYSLSLKLPDKEGIIKFLVDENDFNYD  MJAFEN1.PRO
265 QKQSDVDLYAIKEFFLNPPV-------------------------------TD--NYNLVWRDPDEEGILKFLCDEHDFSEE  PFUFEN1.PRO
269 PVPENWLHKEAHQLFLEPEV-------------------------------LDPESVELKWSEPNEEELIKFMCGEKQFSEE  HUMFEN1.PRO
267 PVPENWLHKEAQQLFLEPEV-------------------------------VDPESVELKWSEPNEEELVKFMCGEKQFSEE  MUSFEN1.PRO
272 KIPEDWPYKQARMLFLDPEV-------------------------------IDGNEINLKWSPPKEKELIEYLCDDKKFSEE  YST510.PRO
265 QETENKFEKDLRKKLVNNEIILDDDFPSVMVYDAYMRPEVDHDTTPFVWGVPDLDMLRSFMKTQLGWPHE  YSTRAD2.PRO
268 KNDVNTPVKKRINKLVGK-IILPSEFPNPLVDEAYLHPAVDDSKQSFQWGIPDLDELRQFLMATVGHSKQ  SPORAD13.PRO
268 KIRPNPHDTKVKKKL--RTLQLTPGFPNPAVAEAYLKPVVDDSKGSFLWGKPDLDKIREFCQRYFGWNRT  HUMXPG.PRO
268 KVAENPYDTKVKKKL--RKLQLTPGFPNPAVADAYLRPVVDDSRGSFLWGKPDVDKIREFCORYFGWNRM  MUSXPG.PRO
268 KMRPNPNDTKVKKKL--RLLDLQQSFPNPAVASAYLKPVVDESKSAFSWGRPDLEQIREFCESRFGWYRL  XENXPG.PRO
194 ------EKKVSRPHLISTAILLGCDYFORGVQNIGIVSVFD-ILGEFGDDGNEEIDPHVILDRFASYVRE  CELRAD2.PRO 360              370              380              390              400              410              420
300 RVKKHVDKLYNLIA--------------------------------------------------------  MJAFEN1.PRO
314 RVKNGLERLKKAI---------------------------------------------------------  PFUFEN1.PRO
320 RIRSGVKRLSKSRQGS-TQGRLDDFFKVT-----------------------------------------  HUMFEN1.PRO
318 RIRSGVKRLSKSRQGS-TQGRLDDFFKVT-----------------------------------------  MUSFEN1.PRO
323 RVKSGISRLKKGLKSG-IQGRLDGFFQVV-----------------------------------------  YST510.PRO
335 KSDEILIPLIRDVNKRKK-----------------------------------------------KGKQ  YSTRAD2.PRO
337 RTNEVLLPVIQDMHKKOF-----------------------------------------------VGTQ  SPORAD13.PRO
336 KTDESLFPVLKQLDAQQTQLRIDSFFRLAQQEKEDAKRIKSQRLNRAVTCMLRKEKEAAASEIEAVSVAM  HUMXPG.PRO
336 KTDESLYPVLKHLNAHQTQLRIDSFFRLAQQEKQDAKLIKSHRLSRAVTCMLRKEREEKAPELTKVTEAM  MUSXPG.PRO
336 KTDEVLLPVLKQLNAQQTQLRIDSFFRLEQHEAAG--LKSQRLRRAVTCMKRKERDVEAEEVEAAVAVM  XENXPG.PRO
257 EIPARSEDTQRKLRLRRKKYNFPVGFPNCDAVHNAITMYLRPPVSSEIPKIIPR----AANFQQVAEIM  CELRAD2.PRO
```

FIG. 59C

FIG. 59D

| | 430 | 440 | 450 | 460 | 470 | 480 | 490 | |
|---|---|---|---|---|---|---|---|---|
| 314 | ---- | ---- | ---- | ---- | ---- | ---- | ---- | MJAFEN1.PRO |
| 327 | ---- | ---- | ---- | ---- | ---- | ---- | ---- | PFUFEN1.PRO |
| 348 | ---- | ---- | ---- | ---- | ---- | ---- | GSLS | HUMFEN1.PRO |
| 346 | ---- | ---- | ---- | ---- | ---- | ---- | GSLS | MUSFEN1.PRO |
| 351 | ---- | ---- | ---- | ---- | ---- | ---- | -PK-T | YST510.PRO |
| 357 | KRINEFF | ---- | ---- | ---- | ---- | ---- | ---- | YSTRAD2.PRO |
| 359 | SNLTQFFEGGNTNVYAPRVAYHFSKRLENALSSFKNQISNQSPMSEEIQADADAFGESKGSDELQSRIL | SPORAD13.PRO |
| 406 | EKEFELLDKAKRKTQKRGITNTLEESSSLKRKRLSDSKRKNTCGGFLGETCLSESSDGSSSEHAESSSLM | HUMXPG.PRO |
| 406 | EKEFELLDDAKGKTOKRELPYK------KETSVPKRRRPSGNGGFLGDPYCSESPQESSCEDGEGSSVM | MUSXPG.PRO |
| 403 | ERECTNQRKGQKTNTKS------QGTKRRKPTECSQEDQPGGGFIGIELKTLSSKAYSSD------ | XENXPG.PRO |
| 322 | MKECGWPATRTQKELALSIRRKVHLTTTVAQTRIPDFFAATKSKNFTPIVEPCESLEDYISANN----T | CELRAD2.PRO |

| | 500 | 510 | 520 | 530 | 540 | 550 | 560 | |
|---|---|---|---|---|---|---|---|---|
| 314 | ---- | ---- | ---- | ---- | ---- | --NKTKQKTL | MJAFEN1.PRO |
| 327 | ---- | ---- | ---- | ---- | ---- | --KSGKQSTL | PFUFEN1.PRO |
| 352 | SAKRKEPEPKGST | ---- | ---- | ---- | ---- | --KKKAKTGAAG | HUMFEN1.PRO |
| 350 | SAKRKEPEPKGPA | ---- | ---- | ---- | ---- | --KKKAKTGGAG | MUSFEN1.PRO |
| 354 | KEQLAAAKRAQE | ---- | ---- | ---- | ---- | --NKKLNKNKNK | YST510.PRO |
| 364 | ---- | ---- | --PREYISGDKKLNTSKRISTATGKL | ---- | --KK | YSTRAD2.PRO |
| 429 | RRKKMMASKNSSDSDSDEDNFLASLTPKTNSSSISIENLPRKTKLSTSLL | ---- | --KKP | SPORAD13.PRO |
| 476 | NVQRRTAAKEPKTSASDSONSVKEAPVKNGGATTSSSSDSDDDGGKEKMVLVTARSVFGKKRRKLRRARG | HUMXPG.PRO |
| 469 | SARQRSAAESSKIGCSDVPDLVRDSPHGRQGCVSTSSSDSEDGEDKAKTVLVTARPVFGKKRRKLKSMK- | MUSXPG.PRO |
| 458 | ---GSSSDAEDLPSGLIDKQSQSGIVGROKASNKVESSSSSDDEDRTVMVTAKPVFQGKKTKSKTMKE | XENXPG.PRO |
| 387 | WMRKRKRSESPQILQHHAKRQVPDRK---- | ---- | --RSVKIRAFKPYPTDVI | CELRAD2.PRO |

| | | |
|---|---|---|
| 322 | DAWFKZ | MJAFEN1.PRO |
| 335 | ESWFKR | PFUFEN1.PRO |
| 375 | KFKRGK | HUMFEN1.PRO |
| 373 | KFRRGK | MUSFEN1.PRO |
| 377 | VTKGRR | YST510.PRO |
| 390 | ---RKM | YSTRAD2.PRO |
| 483 | SKRRRK | SPORAD13.PRO |
| 546 | RKRKTZ | HUMXPG.PRO |
| 538 | RRKKKT | MUSXPG.PRO |
| 523 | TVKRK | XENXPG.PRO |
| 429 | ELGDSD | CELRAD2.PRO |

FIG. 59E

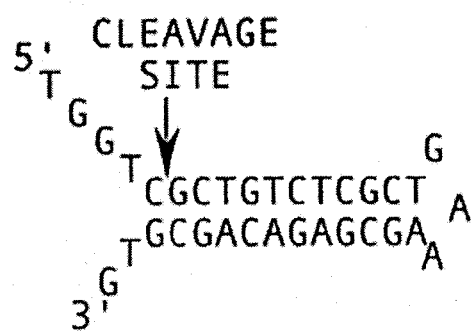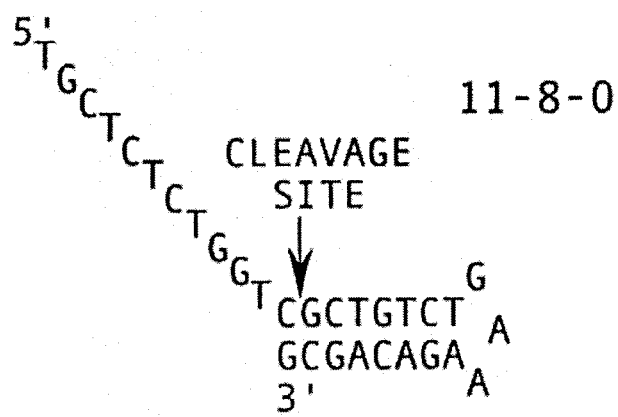
FIG. 60

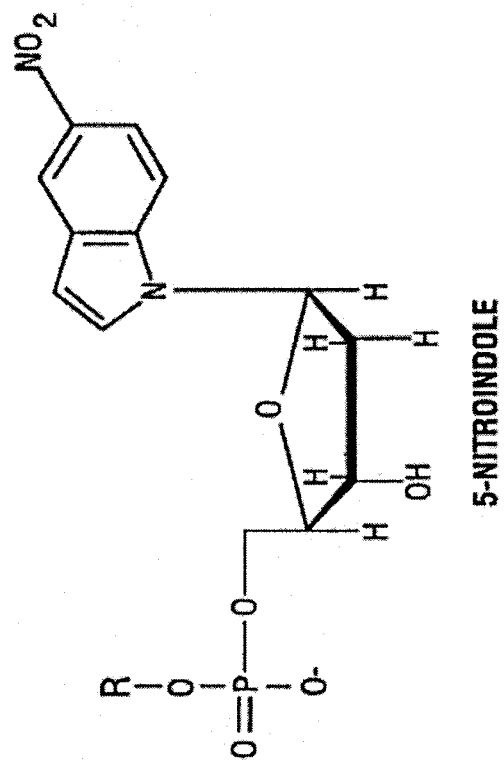
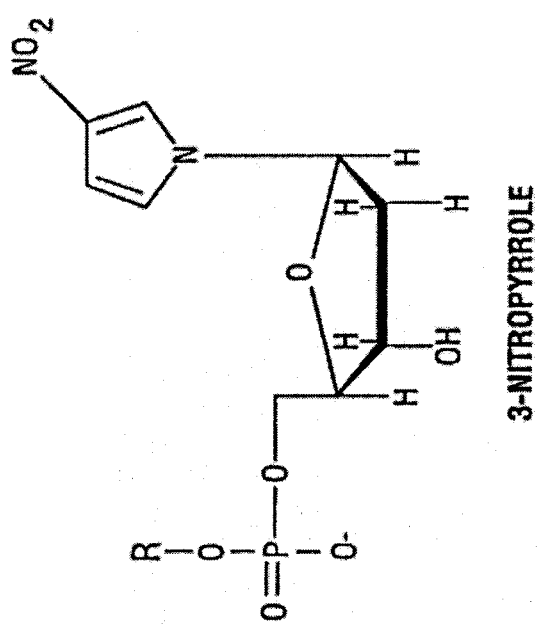
FIG. 73

F1

5' GTTCTCTGCTCTCTGGT
                    1819
                    ↓↓
                    CGCTGTCTCGCTTGT G
                                    A
                    GCGACAGAGCGAACA A
                                    A
3'GCTCTCTGGT

FIG. 78A

F1

5'GTTCTCTGCTCTCTGGTCGCT
                       2122
                       ↓↓
                       GTCTCGCTTGT G
                                   A
3'GCTCTCTGGTGCGACAGAGCGAACA A
                            A
5'CGAGAGACCACGCT
         P15    G

FIG. 78B

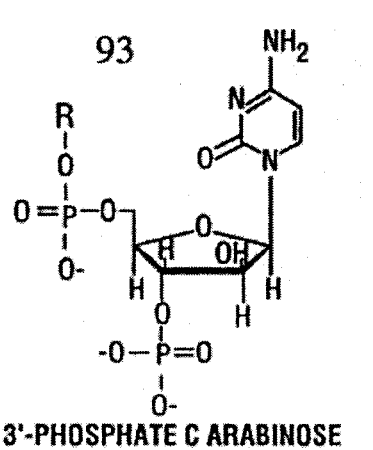
3'-PHOSPHATE C ARABINOSE
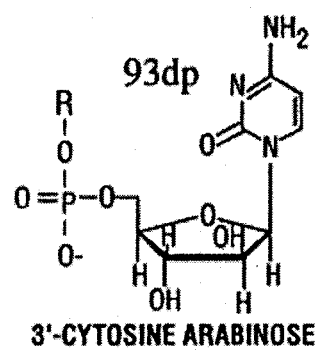
3'-CYTOSINE ARABINOSE
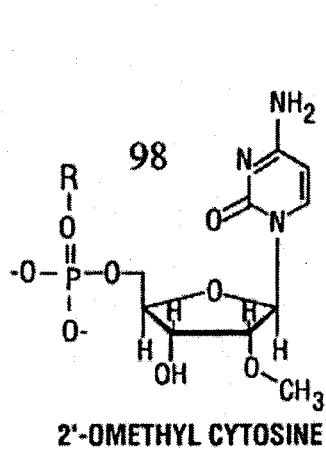
2'-OMETHYL CYTOSINE
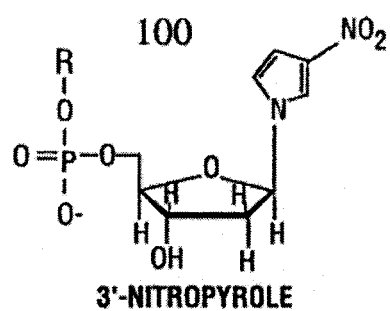
3'-NITROPYROLE
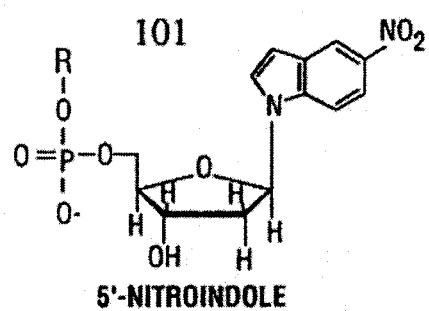
5'-NITROINDOLE
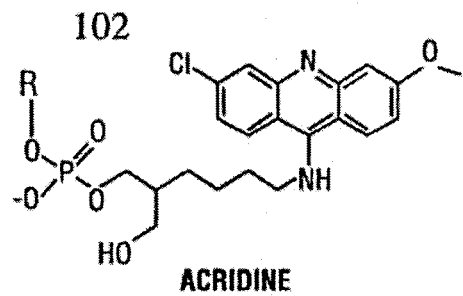
ACRIDINE
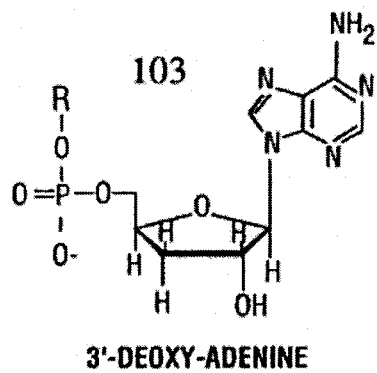
3'-DEOXY-ADENINE
FIG. 79

CONCENTRATION OF PROBE W/ AND W/O STACKER vs TEMP

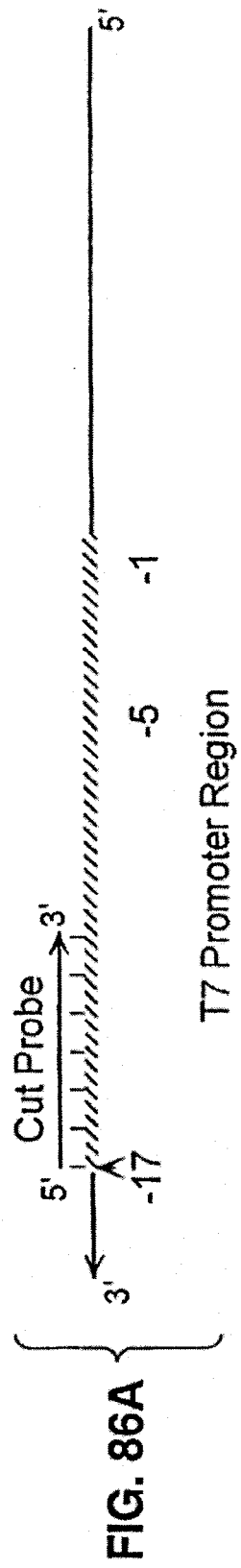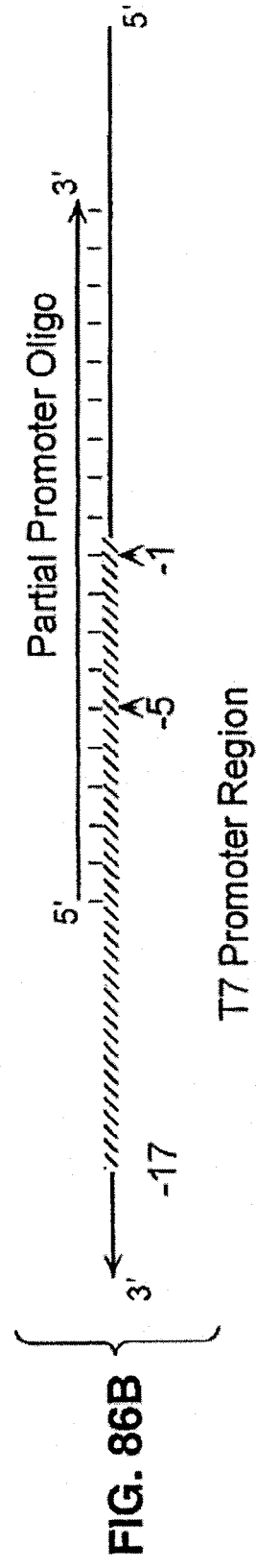
FIG. 86A
FIG. 86B

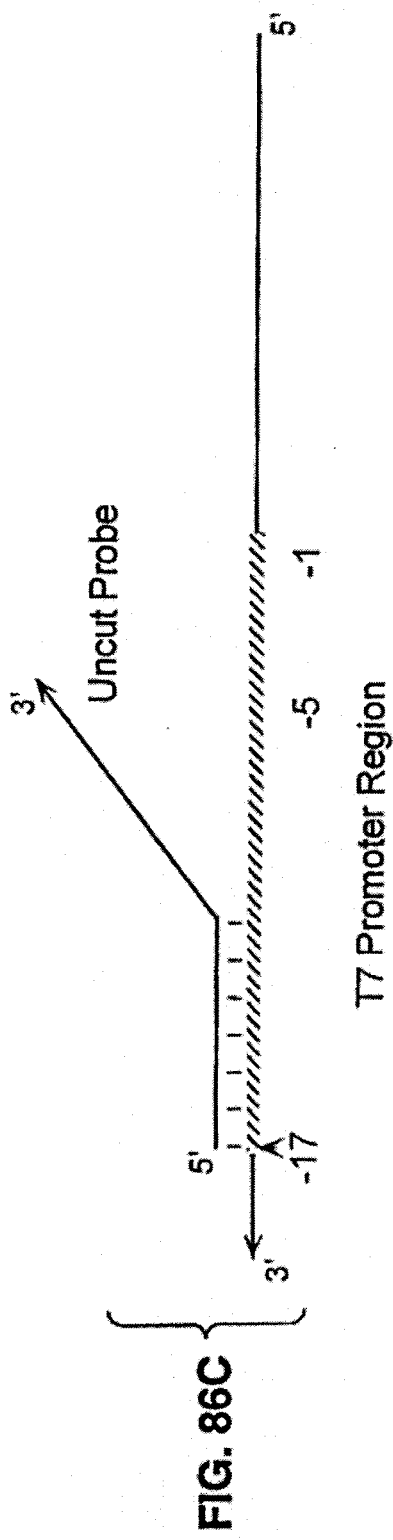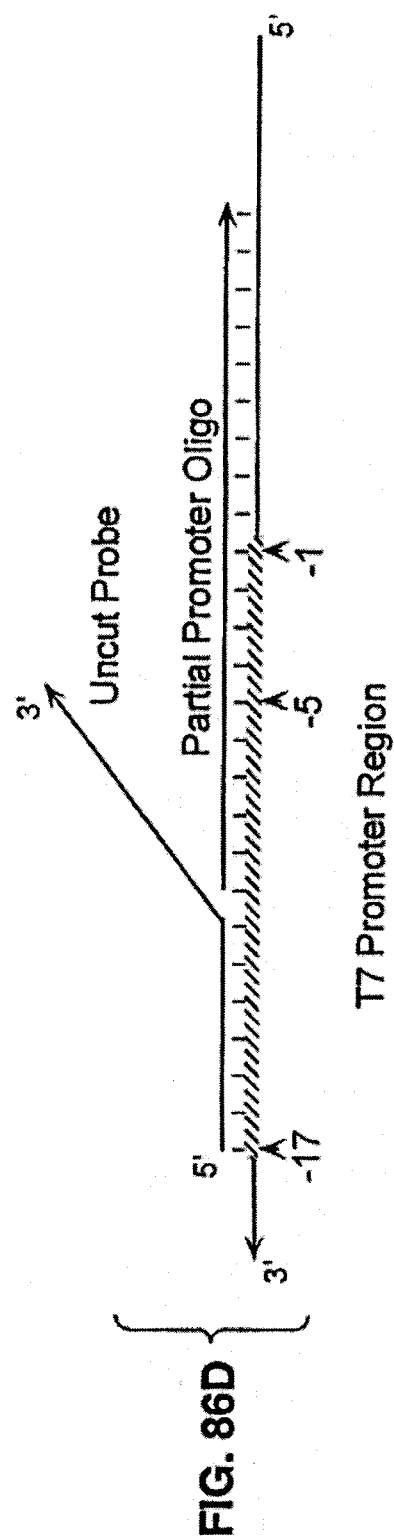

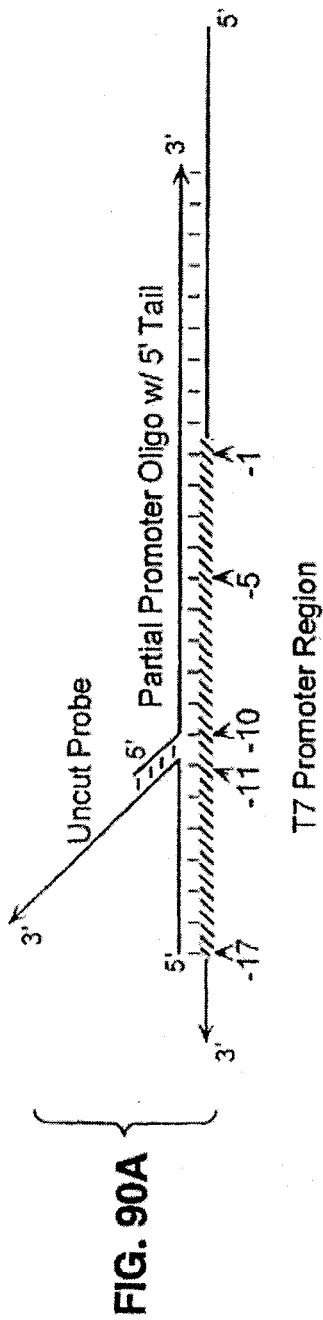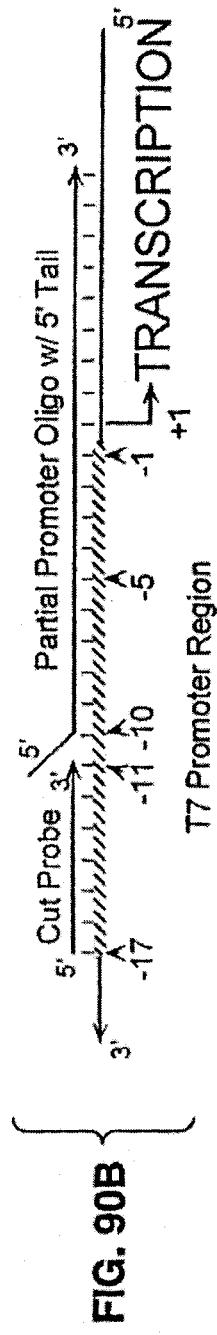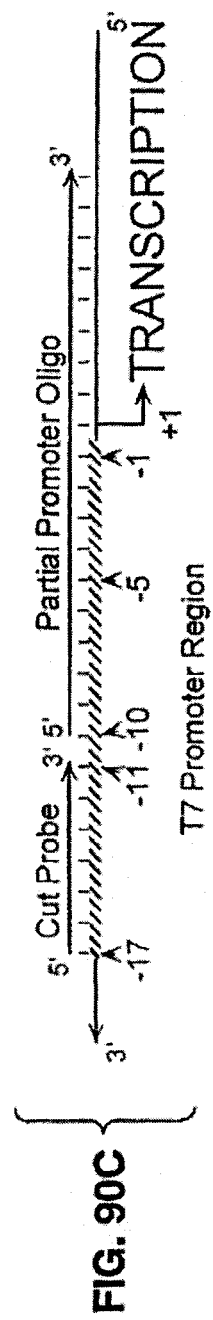

FIG. 93A

FIG. 93B

FIG. 93C 1  3'-gctttaattatgctgagtgatatcccagaagatacttccagttttgt-5'
   |—-23—-20—-15—-10—-5—-1|
   | T7 promoter region |

2  5'-cgaaattaatacgactcactata-3'
   3'-gctttaattatgctgagtgatatcccagaagatacttccagttttgt-5'
   |—-23—-20—-15—-10—-5—-1|
   | T7 promoter region |

3  #073-065
   5'-cgaaattaatacgactcactataccagaa-3'
   3'-gctttaattatgctgagtgatatcccagaagatacttccagttttgt-5'
   |—-23—-20—-15—-10—-5—-1|
   | T7 promoter region |

4  NO DNA

PR1 probe          Cleavage site
                         ▼
           5'FITTTTCCAGAGCCTAAT G3'

IT3 Invader-Target

ₐ ᴬACGAGCGTCTTT G3'
          GTGCTCGCAGAAGGTCTCGGATTAATTTTTTTTT5'

IT3-8 Invader-Target

ₐ ᴬAGCGTCTT G3'
          ɢTCGCAGAAGGTCTCGGATTAATTTTTTTTT5'

IT3-6 Invader-Target

ₐ ᴬCGTCTT G3'
          ɢGCAGAAGGTCTCGGATTAATTTTTTTTT5'

IT3-4 Invader-Target

ₐ ᴬTCTT G3'
          ɢAGAAGGTCTCGGATTAATTTTTTTTT5'

IT3-3 Invader-Target

ₐ ᴬCTT G3'
          ɢGAAGGTCTCGGATTAATTTTTTTTT5'

IT3-0 Invader-Target

3'GAAGGTCTCGGATTAATTTTTTTTT5'

FIG. 98

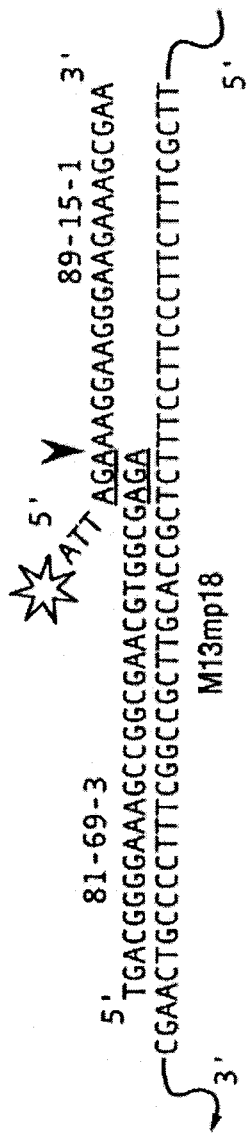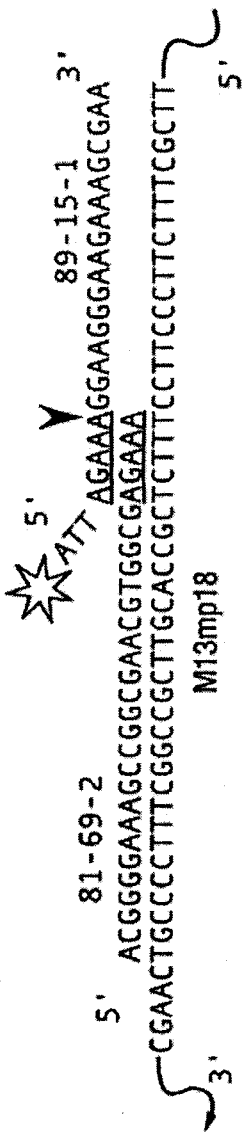

```
                              Cleavage
                                site
                          89-76
                    5'Fl-TTT↘ CCCTCCTCCTCTTCC-3'
                          A
    5' ACACAGTGTCCTCCCGCTCCTCCTGAGCA
       89-44
    3'-ACTGTCTGTGTCACAGGAGGGCGAGGAGGACTCGTGGGAGGAGGAGAAGGAGTA-5'
       |                                                    |
       3110                                                 3057
                    HCMV Target Sequence
```

FIG. 103

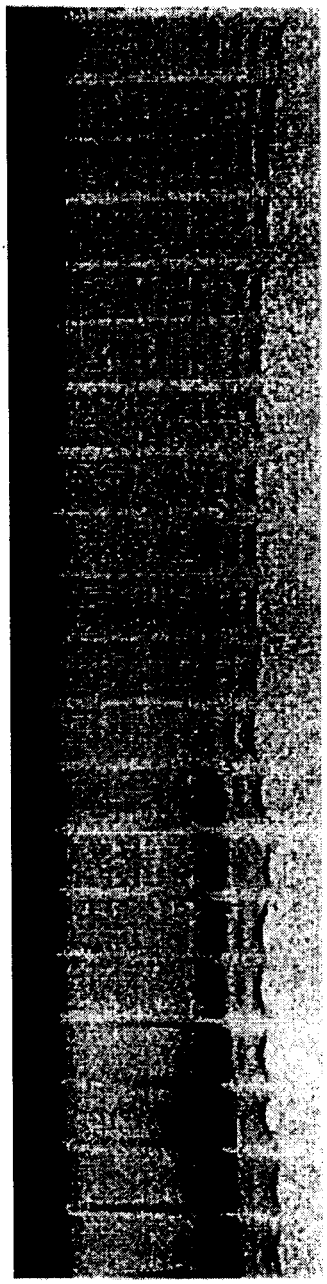
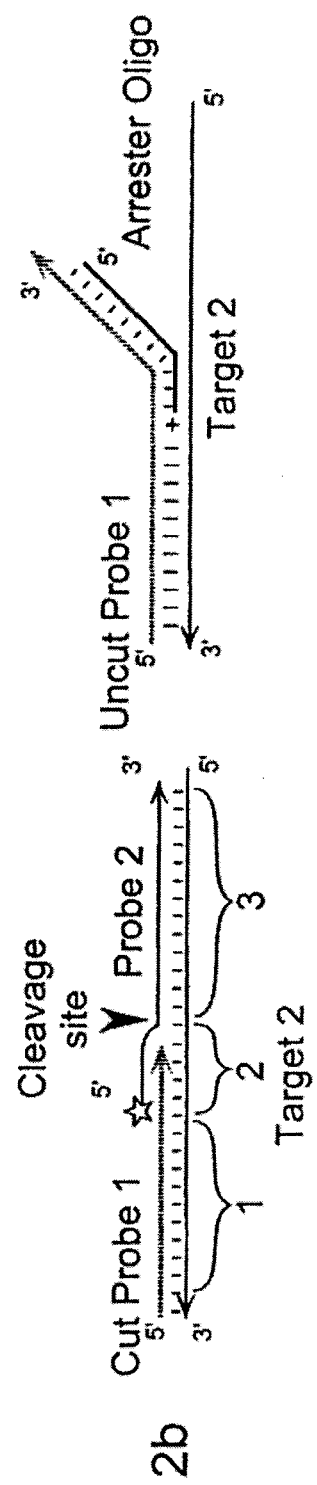
FIG. 104

FIGURE 107
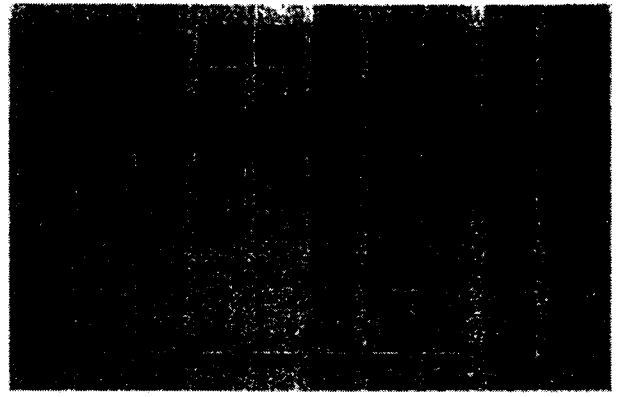
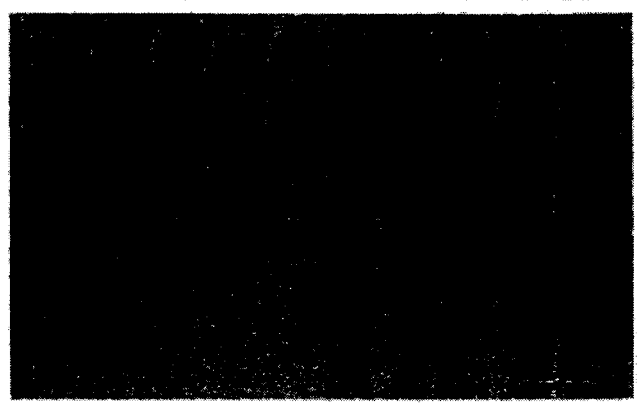
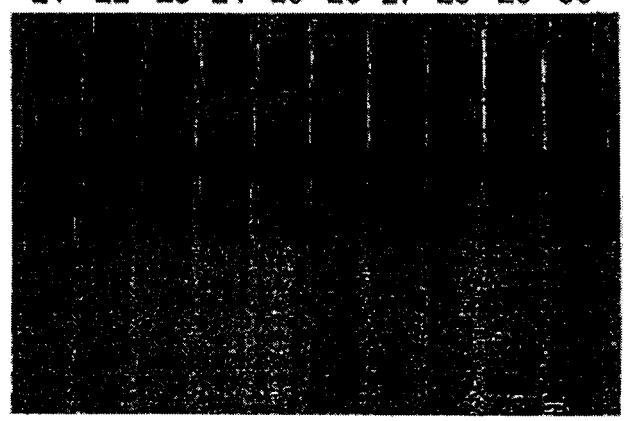

FIGURE 110C

Primary Probe 241-95-02
5' AACGAGGGCGCACCCAAGGCACAGC-NH3+ 3'

3' NH3+GGGTGGGTTCCGTGTCG 5' 241-95-03
3'NH3+TGGGGTGGGTTCCGTGTCG 5' 241-95-04
3'NH3+TGCGGGTGGGTTCCGTGTCG 5' 241-95-05
3'NH3+TGCGCGGGTGGGTTCCGTGTCG 5' 241-95-06

Arrestors

FIGURE 117B

5'-CAAAGAAAAGCTGCGTGATGATGAAATCGC
           CACTCCCGCAGACACC-3'
3'-GGAGTTTCTTTTCGACGCACTACTACTTTAGCTGAGGGCGTCTGTGGAAG-5'

5'-AACGAGGCGCA
3'-NH$_2$-TTTGCTCCGCGTGGGAGCAGAGCC T T
                              (Cy3) T
                         (F)

FIGURE 127B

5'-CGCGCCGAGG ACACCTTTTTAGGTGCTTTGT-NH2-3'

5'-CACTTGCTTCAGGACCATATTTCTCTC
GTGAACGAAGTCCTGGTATAAAGAGAGATGTGAAAAATCCCACGAAACA-5'

5'-CGCGCCGAGGA TCTC GTCTCG T T
B-GCGCGGCTCCAGAGTCAGAGCC T T (with Cy3 and P labels)

FIGURE 129
A  B 
 

FIGURE 131A

FIGURE 131B

FIGURE 140

Hairpin Substrate

A.

```
5'Fl-TTT T V
         CGCTGTCTCGCT G
                       A
  3'TTT GCGACAGAGCGA A
          25-65-1
```

B.

Invader (IT) substrate

```
            5'Fl-TTT  V
                    G T
  A ACGAGCGTCTTT G   CGCTGTCTCGCT G
 A                                  A
  G TGCTCGCAGAAA — GCGACAGAGCGA A
                25-184-5
```

FIGURE 141

Invader (IT) substrate

A.
```
         5'TET-TTT    203-91-01
                  T Y
       A CGAGGCGCAC A  CAACTGCCGTGA
      A                
       G GCTCCGCGTG — GTTGACGGCACT
              203-91-04
```

B.
```
              5'TET-TTT     203-81-02
                       T Y
                         CAACTGCTTAGA G
       NH2-AATTGCTCCGCGTGGTTGACGAATCT   A
         5'-AACGAGGCGCAC A              A
              594-09-01     A TTTTTTTTT-3'
```

FIGURE 144

5' GCGCCGAGG CCGTTCTCTAGCGTGA-PO4 3'

5' CCGAAGCACGCACAAAGCGGTGTCACGA
3' GGCTTCGTGCGTGTTTCGCCACCAGTGCGGAAGATCGCACTGCGACATATG 5'

5' GCGCCGAGGC ⓓ TCTCTGCCGG T T
3'-BIOTIN-TCACGGGCTCCAGAGACGGCCT T

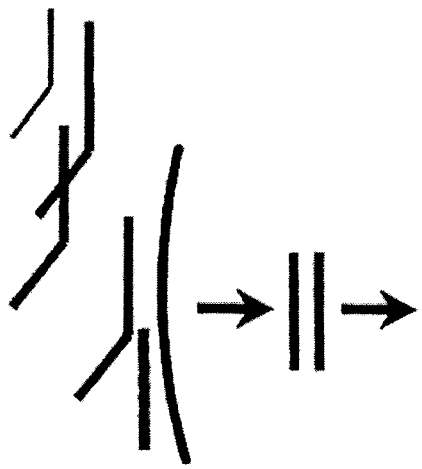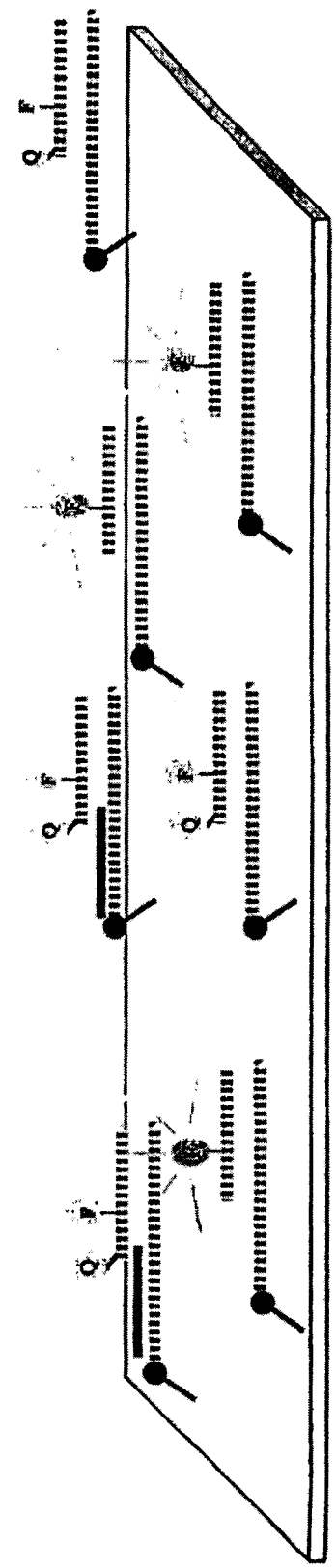
Figure 149

FIGURE 150
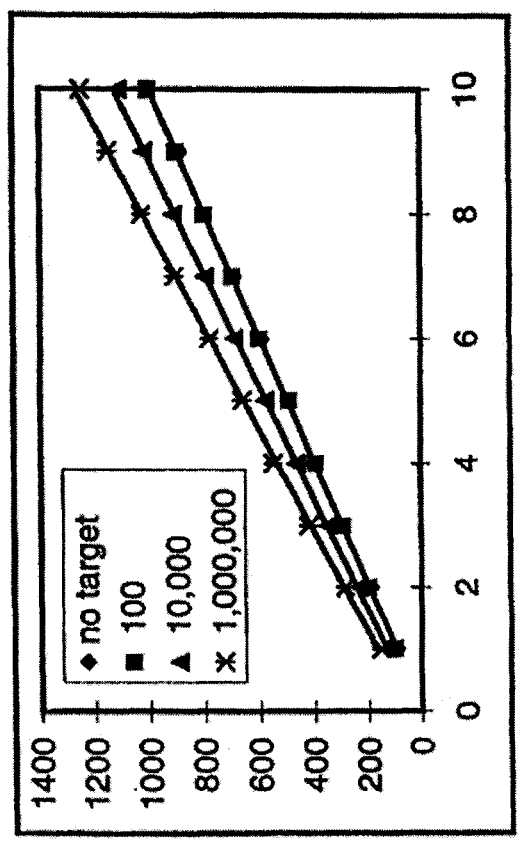
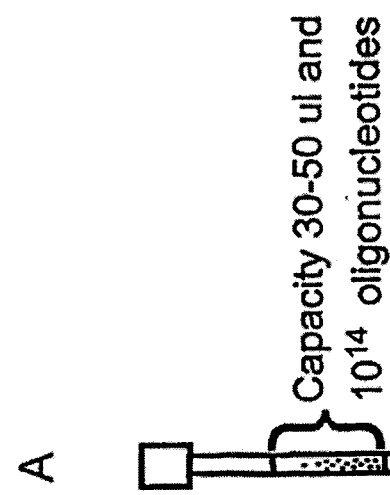

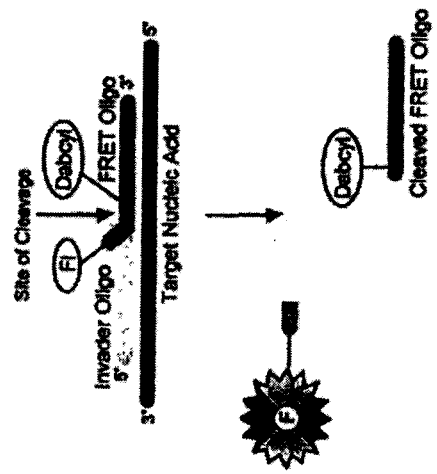
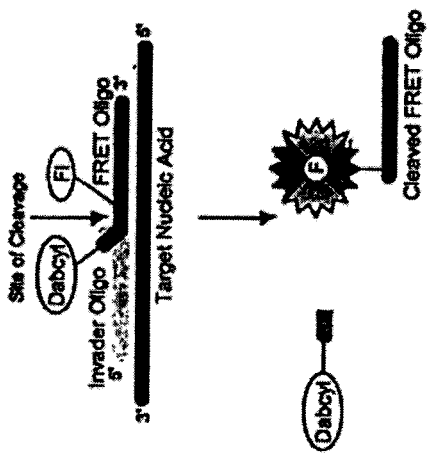
Figure 152

FIGURE 155

Pae FEN1 ORF DNA sequence

```
GTGGGAGTTACTGAGTTGGGTAAGCTTATTGGCAAGAGGTCCGCCGCGAGGTTAAACTGGAAAGT
CTCTCGGGCAAGTGTATTGCCCTTGACGCGTACAACGCCTTGTACCAATTCCTTGCGTCTATTAGA
CAGCCAGATGGGACGCCTCTAATGGACAGAGCTGGGAGGATTACTAGTCATCTCTCGGGTTTGTTC
TACCGTACTATCAACCTCCTTGAGGCCGGCATTAGGCCTGTTTATGTTTTTGATGGGAAGCCTCCC
GAATTTAAACTGGCTGAAATTGAAGAAAGGAGGAAGACGCGTGAGAAGGCCATGGAAGAGGTGTTG
AGGGCCATTAAGGAGGGGAGGAGGGAAGACGTGGCTAAATACGCCAAAAGGGCTGTTTTTATTACC
AGCGAAATGGTGGACGAGGCCAAGAGGCTGCTGAGCTATATGGGCGTACCCTGGGTCCAAGCTCCA
AGCGAGGGGGAGGCGCAAGCGGCTTATATGGCTAGAAAAGGACACTGCTGGGCCGTGGGAAGCCAG
GATTACGATTCGCTGTTATTTGGATCCCCCAAGTTAGTCAGAAATCTAGCGGTATCCCCTAAGCGT
AAAATTGGAGAAGAGGTAATAGAGCTCACGCCGGAAATTATTGAGCTAGACGCCGTCCTCAGGGCT
TTGAGGCTAAAGAACAGAGAGCAACTAATAGACTTGGCTATTTTACTCGGCACAGATTACAACCCA
GACGGCGTTCCCGGAGTGGGCCCCCAGAAGGCGTTAAAACTAATATGGGAATTTGGATCGCTTGAA
AAACTATTAGAAACTGTATTAAAGGGGCGTATTTCCCCATTGACCCCCTGGAGATAAAGAAGTTC
TTCCTCAATCCCCCAGTCACTGATCAATACGCCACTGAGGTGAGAGACCCAGACGAGGCGGCCCTC
AAGGACTTTCTTATACGCGAACACGACTTCAGCGAGGAGAGGGTGTCTAAGGCACTTGAGAGGCTG
AGAAAAGCCCGGGGGAAGTTAAAAACTTCCTCTCTCGACTCCTTTTTCTAA
```

Pae FEN1 protein sequence

```
VGVTELGKLIGKEVRREVKLESLSGKCIALDAYNALYQFLASIRQPDGTPLMDRAGRITSHLSGLF
YRTINLLEAGIRPVYVFDGKPPEFKLAEIEERRKTREKAMEEVLRAIKEGRREDVAKYAKRAVFIT
SEMVDEAKRLLSYMGVPWVQAPSEGEAQAAYMARKGHCWAVGSQDYDSLLFGSPKLVRNLAVSPKR
KIGEEVIELTPEIIELDAVLRALRLKNREQLIDLAILLGTDYNPDGVPGVGPQKALKLIWEFGSLE
KLLETVLKGAYFPIDPLEIKKFFLNPPVTDQYATEVRDPDEAALKDFLIREHDFSEERVSKALERL
RKARGKLKTSSLDSFF
```

Sso FEN1 ORF DNA sequence

```
ATAGGTGTAGATTTAGGCGAAATAGTTGAAGATGTTAAGAGAGAGATTAACTTAAATGAGATGAAA
GGAAAGAAAATTAGTATAGATGCTTACAACACAATTTATCAGTTTTTAGCTGCAATAAGACAGCCT
GATGGGACACCTTTAATTGACAGTAAAGGCAGAATAACAAGCCATTTAAATGGGCTATTTTATAGG
ACTATTAGTATAATAGAAAGTGGAATAATCCCCATTTTTGTATTTGATGGAAAGCCACCTGAAAAG
AAGAGTGAAGAAATCGAAAGAAGGAAAAGAGCTAAGGAGGAGGCAGAAAAGAAATTAGAGAAAGCT
AAGTTAGAGGGGGAGTACAGAGAAATTAGAAAATATGCTCAGGCTGCTGTTAGATTAAGCAATGAA
ATGGTAGAGGAAAGTAAAAAACTATTAGATGCTATGGGTATACCTGTAGTTCAAGCTCCAGGAGAA
GGAGAGGCTGAGGCAGCTTATATAAATTCAATTGATCTTTCTTGGGCTGCTGCAAGCCAAGATTAT
GATTCCTTATTATTTGGCGCTAAAAGATTAGTCAGAAACATAACAATTTCAGGTAAAAGAAAGCTT
CCAAATAAGGATGTTTATGTAGAAATAAAGCCTGAGTTGATAGAACTAGAGAGTTTATTGAAAAAA
CTCGGCATCAATAGAGAACAGTTAATAGACATTGCGATTCTTATAGGTACAGATTACAATCCAGAC
GGCGTTAAAGGAATTGGTGTAAAGACGGCATTAAGAATTATAAAGAAATATAATAATATCGAGAAC
GCAATAGAAAAGGTGAAATTCAATTATCTAAAATAAACTTTGATATACGAGAGATAAGAAAATTA
```

FIGURE 155 (continued)

TTCATTACACCTGAAGTTAAAAAGCCTACTGAACGACTAGAATTAGCAGAATGTAATGAAAGGGAA
ATAATAGAACTTTTGGTTAAAAATCATGATTTTAATGAAGATCGTGTAAATAACGGAATAGAGAGA
TTAAAGAAGGCTATAAAAGAAGCTAAGTCTGTTGAAAAACAGACAGGTCTTGATCAGTGGTTTTAA

Sso FEN1 protein sequence

IGVDLGEIVEDVKREINLNEMKGKKISIDAYNTIYQFLAAIRQPDGTPLIDSKGRITSHLNGLFYR
TISIIESGIIPIFVFDGKPPEKKSEEIERRKRAKEEAEKKLEKAKLEGEYREIRKYAQAAVRLSNE
MVEESKKLLDAMGIPVVQAPGEGEAEAAYINSIDLSWAAASQDYDSLLFGAKRLVRNITISGKRKL
PNKDVYVEIKPELIELESLLKKLGINREQLIDIAILIGTDYNPDGVKGIGVKTALRIIKKYNNIEN
AIEKGEIQLSKINFDIREIRKLFITPEVKKPTERLELAECNEREIIELLVKNHDFNEDRVNNGIER
LKKAIKEAKSVEKQTGLDQWF

Tli FEN1 ORF DNA sequence

ATGGGAGTCCAGATTGGTGAGCTTTTACCAAGAAAAGAGCTTGAGCTTGAAAATTTAAATGGGAGA
AAAGTTGCGATAGATGCATTTAACGCTATTTACCAGTTTCTCTCAACAATAAGACAACGAGATGGG
ACTCCTTTAATGGATTCCAAGGGAAGAATAACGTCCCATCTTTCAGGGCTTTTTTACAGGACTATA
AACCTAATGGAAGCGGGAATAAAGCCTGCGTATGTATTCGATGGGAAGCCTCCAGAGTTCAAGAAA
AAAGAGCTTGAAAAAGAGCTGAGGCTAGGGAGGAAGCGCAGGAAAAATGGGAGGAAGCCCTAGCA
AGGGGAGACTTAGAAGAGGCGAAGAAATATGCACAGCGGGCGAGCAAAGTAAATGAGATGCTTATC
GAGGATGCTAAGAAGCTTTTGGAGCTTATGGGCATCCCATGGGTGCAGGCTCCTAGCGAAGGTGAA
GCGCAGGCAGCTTATATGGCATCTAAAGGGCACGTTTGGGCCTCGGCGAGCCAGGACTACGACTCG
CTCCTCTTCGGAACACCAAGGCTAGTGAGAAACCTCACCATAACTGGAAAGAGAAAGCTTCCTGGG
AAGGATATTTACGTAGAAGTTAAACCGGAGCTCATAGTTCTTGAAGAGGTGTTAAAGGAGCTTAAG
ATAACGAGGGAGAAGTTGGTAGAGCTTGCAATTCTCGTGGGAACGGACTACAATCCTGGAGGCATA
AAAGGGATTGGACCAAAAAAGGCCCTTGAAATAGTCAAATACTCCAAAGATCCTCTGGCAAAGTAC
CAAAAAATGAGCGATGTTGATCTCTATGCAATAAAGGAGTTCTTCCTAAACCCGCCGACAACAGAC
GAATACAAGCTCGAATGGAAAATGCCCGATGAAGAAGGAATACTGAAGTTTCTCTGTGATGAGCAC
GATTTCAGTGAAGAAAGAGTTAAAAACGGCTTAGAAAGGCTTAAAAAAGCGGTTAAGGCAGGAAGA
CAGTTTACGCTGGACAGCTGGTTTAAAAAGTGA

Tli FEN1 protein sequence

MGVQIGELLPRKELELENLNGRKVAIDAFNAIYQFLSTIRQRDGTPLMDSKGRITSHLSGLFYRTI
NLMEAGIKPAYVFDGKPPEFKKKELEKRAEAREEAQEKWEEALARGDLEEAKKYAQRASKVNEMLI
EDAKKLLELMGIPVVQAPSEGEAQAAYMASKGHVWASASQDYDSLLFGTPRLVRNLTITGKRKLPG
KDIYVEVKPELIVLEEVLKELKITREKLVELAILVGTDYNPGGIKGIGPKKALEIVKYSKDPLAKY
QKMSDVDLYAIKEFFLNPPTTDEYKLEWKMPDEEGILKFLCDEHDFSEERVKNGLERLKKAVKAGR
QFTLDSWFKK

Aam FEN1 ORF DNA sequence

FIGURE 155 (continued)

```
ATAGGAGTAGACCTTGCTGATTTGGTAAAAGAAATCAAAAGAGAAGTTCAGCTAAGTGAATTAAAA
GGGAAGAAAGTAAGCATAGATGCTTATAACGCTATTTACCAGTTTTTGACTGCAATAAGACAGCCA
GATGGTACTCCACTAATGGACTCACAAGGAAGAGTTACTAGTCATCTTAGTGGAATATTTTATAGA
ACAATAAGCCTTTTAGAAGAAGGAGTAATTCCAATTTATGTATTCGATGGAAAACCACCAGAACTT
AAAGCTCAAGAATTAGAAAGAAGAAGAAAAATAAAGGAAGAAGCTGAGAAAAAATTGGAAAAAGCC
AAAGAAGAAGGAGAAACAAAGGAATTAAAGAAGTATTCGCAAATGGCAACTAGGTTAACTAATGAC
ATGGCAGAAGAAAGTAAAAAACTTTTAGAGGCAATGGGAATTCCAGTAGTGCAAGCTCCAAGTGAA
GGAGAAGCTGAGGCAGCGTATTTATGTAGTCAAGGGTATACTTGGGCAGCGGCTAGCCAAGATTAC
GATTCTTTGCTTTTTGGTGCAAATAAATTAATTAGAAACTTAACATTAACTGGAAAGAGGAAATTA
CCTAAAAAAGACGTATATGTAGAAATTAAGCCAGAACTTATAGAACTTGAAGATTTGCTTAAAAAG
TTCGGAATTACTAGAGAACAACTAGTTGATATAGGAATATTAATAGGAACTGATTATGACCCTGAC
GGAATAAAGGGAATAGGGCCAGTTACTGCTCTAAGAATAATAAAGAAATACGGAAATATAGAAAAA
GCTGTAGAAAAAGGAGAATTACCGAAATACATTCTTGATCTTAATATTAATGAAATTAGATCTATC
TTTCTTAATCCGCCAGTAGTTAAGCCTGAGGGCTCGTTAGATCTAAAAGAGCCTAATGAGGAAGAA
ATCAAGAAAATCCTCATAGATGAGCATAACTTTAGTGAGGATAGAGTAACTAATGGAATAGAAAGA
CTGATTAAAGCCGGTAAGGAAGCTAAAGGAGCTAGTAGGCAGAGCGGTTTAGATCAGTGGTTTTAG
```

Aam FEN1 protein sequence

```
IGVDLADLVKEIKREVQLSELKGKKVSIDAYNAIYQFLTAIRQPDGTPLMDSQGRVTSHLSGIFYR
TISLLEEGVIPIYVFDGKPPELKAQELERRRKIKEEAEKKLEKAKEEGETKELKKYSQMATRLTND
MAEESKKLLEAMGIPVVQAPSEGEAEAAYLCSQGYTWAAASQDYDSLLFGANKLIRNLTLTGKRKL
PKKDVYVEIKPELIELEDLLKKFGITREQLVDIGILIGTDYDPDGIKGIPVTALRIIKKYGNIEK
AVEKGELPKYILDLNINEIRSIFLNPPVVKPEGSLDLKEPNEEEIKKILIDEHNFSEDRVTNGIER
LIKAGKEAKGASRQSGLDQWF
```

Abr FEN1 ORF DNA sequence

```
ATCGGAGTAGATTTATCTGACTTAGTTGAAGACGTAAAAGCTGAGATAAACTTAGCTGAGTTGCGT
GGGAAAAAAGTAAGTATTGATGCATATAATGCAATATATCAATTTTTGACAGCTATACGCCAACCA
GACGGTACACCACTTATAGATTCACAAGGTAAAATAACAAGCCACCTTAGTGGAATTTTTTATCGA
ACCATTAATCTAATGGAAAATGGTATAATACCGATATATGTTTTTGATGGAAAACCACCAGAGCTT
AAATCTGCAGAATTACAAAGACGTAAAAAATAAAGAAGAAGCGGAAAAGAAGTTAGAGAAAGCA
AAAGAAGAGGGAAAAACTACAGAGTTAAAAAAGTATTCTCAAATGGCAACCAGACTTACAAACGAG
ATGGCAGACGAAGGAAAAAAATTGCTTAAAAGTATGGGTATTCCAATAGTAGAAGCACCGTCTGAA
GGTGAAGCGGAATCAGCATATATTAACGCAATAGGATTAAGTTTTGCTACTGCAAGCCAGGATTAT
GATTCACTATTATTTGGTGCGAAAAATTTGATAAGAAACTTAACTATAACTGGAAAAAGAAATTA
CCTAATAAAGACATATACGTCGAAATAAAACCTGAAAGAATTGAACTCGAACCACTACTTAAAAAG
CTTGGTATAACAAGAGAACAATTAATAGATATAGCGATTTTAATTGGAACAGATTATGATCCTTCA
GGGATAAAAGGAATAGGCCCCAAGACCGCTTATAGGCTAATTAAGAAATATGGAAGAATAGAAAAA
ATTATTGAAGCGAATGAAATTCCAAAGAATTCTATTGATTTCGATATTAATCAAATAAGGCAACTA
TTTCTAAATCCGAATGTGAAAAAACCAGAAGAGAATTTAGACTTGCAAAATCCTGAAGAACAAGAA
```

FIGURE 155 (continued)

ATTATAGAAATTTTAGTAAATCAACATAATTTTAATGAAGAAAGAGTTAAAAGTGCATTAGAAAGA
TTAAATAAAGCAATAAAAGAAACTAAAGGTCTCTCAAGACAAACTGGACTTGACCAATGGTTTTAA

Abr FEN1 protein sequence

IGVDLSDLVEDVKAEINLAELRGKKVSIDAYNAIYQFLTAIRQPDGTPLIDSQGKITSHLSGIFYR
TINLMENGIIPIYVFDGKPPELKSAELQRRKKIKEEAEKKLEKAKEEGKTTELKKYSQMATRLTNE
MADEGKKLLKSMGIPIVEAPSEGEAESAYINAIGLSFATASQDYDSLLFGAKNLIRNLTITGKRKL
PNKDIYVEIKPERIELEPLLKKLGITREQLIDIAILIGTDYDPSGIKGIGPKTAYRLIKKYGRIEK
IIEANEIPKNSIDFDINQIRQLFLNPNVKKPEENLDLQNPEEQEIIEILVNQHNFNEERVKSALER
LNKAIKETKGLSRQTGLDQWF

Ape FEN1 ORF DNA sequence

TTGGGAGTCAACCTTAGGGAGTTGATTCCTCCCGAGGCTAGGAGGGAGGTGGAGCTTAGGGCTCTC
TCGGGGTATGTTCTAGCGCTTGACGCGTATAACATGCTCTACCAGTTCCTCACCGCCATCAGGCAG
CCCGACGGCACTCCCCTTTTGGATAGGGAGGGCAGGGTTACAAGCCACCTCAGCGGCCTGTTCTAC
AGGACCATTAACCTGGTGGAGGAGGGTATTAAGCCCGTCTACGTCTTCGACGGGAAGCCTCCTGAA
ATGAAGAGCCGGGAGGTTGAAGAGAGGCTTAGGAGGAAGGCGGAGGCTGAGGCGAGGTATAGGAGG
GCTGTCGAGGCGGGAGAGGTTGAGGAGGCTAGGAAGTACGCTATGATGGCTGCGAGGCTTACGAGC
GACATGGTGGAGGAGTCGAAGGAGCTGCTGGATGCTATGGGGATGCCCTGGGTTCAGGCGCCTGCC
GAGGGTGAGGCTCAGGCAGCCTATATGGCTAGGAAGGGTGATGCATGGGCGACGGGGAGCCAGGAC
TACGATAGCCTCCTGTTCGGCTCGCCTAGGCTTGTGAGAAACCTAGCCATAACAGGTCGTAGGAAG
CTCCCGGGTAGGGATCAGTATGTCGAGATAAAGCCGGAGATCATAGAGCTCGAGCCTCTGCTCAGC
AAGCTGGGGATAACAAGGGAGCAGTTGATAGCGGTGGGTATCCTCCTCGGCACGGACTACAACCCC
GGCGGTGTGAGGGGTTATGGGCCTAAGACAGCCCTAAGGCTTGTTAAGAGCCTGGGAGACCCGATG
AAGGTGTTGGCTTCCGTCCCACGGGGGGAATATGACCCGGATTATCTTAGAAAGGTGTACGAGTAC
TTCTTGAACCCCCCCGTCACAGACGACTACAAGATTGAGTTTAGGAAGCCGGATCAGGACAAGGTT
AGGGAGATTCTTGTAGAGAGGCACGACTTCAATCCCGAGAGGGTGGAGAGGGCCCTCGAGAGGCTG
GGGAAGGCTTACAGGGAGAAGCTCAGGGGCAGGCAGTCGAGGCTCGACATGTGGTTCGGATAG

Ape FEN1 protein sequence

LGVNLRELIPPEARREVELRALSGYVLALDAYNMLYQFLTAIRQPDGTPLLDREGRVTSHLSGLFY
RTINLVEEGIKPVYVFDGKPPEMKSREVEERLRRKAEAEARYRRAVEAGEVEEARKYAMMAARLTS
DMVEESKELLDAMGMPWVQAPAEGEAQAAYMARKGDAWATGSQDYDSLLFGSPRLVRNLAITGRRK
LPGRDQYVEIKPEIIELEPLLSKLGITREQLIAVGILLGTDYNPGGVRGYGPKTALRLVKSLGDPM
KVLASVPRGEYDPDYLRKVYEYFLNPPVTDDYKIEFRKPDQDKVREILVERHDFNPERVERALERL
GKAYREKLRGRQSRLDMWFG

Apr FEN1 ORF DNA sequence

FIGURE 155 (continued)

```
ATGGGCGCTGATATAGGAGAGCTCTTGAAGAGGGAAGAAGTTGAGATAGAATACTTTTCAGGAAAG
AAGATTGCAATAGATGCCTTTAACACGTTATACCAGTTCCTAGCGACAATAAGACAGCCTGACGGA
ACACCTTTGATGGATTCAAAGGGTAGGATAACATCTCACCTTTCAGGAATTCTTTATAGGGTTTCA
AATATGGTGGAGGTCGGAATAAAGCCGATATTTGTTTTTGATGGAGAACCGCCTGAGTTCAAAAAG
AAGGAGATTGAGAGAAGGAGAAAAATTAGGGAAGAAGCTGAGATCAAGTGGAAAACAGCTTTGGAT
ATAGCTGAAGCGAGGAAGTATGCACAGCAAGCTGTGAGAGTTGATGAGTATATTATCGAATCTTCT
AAGAAGCTTTTGAATTTGATGGGAATTCCCATAGTTCAGGCACCCTCAGAGGGAGAAGCTCAGGCC
GCATACATAGTTAGAAAGGGTGATGCGGATTACACAGGTTCGCAAGATTACGATTCCCTTCTTTTC
GGCTCGCCAAGACTGGCAAGGAATTTGGCCATAACTGGGAGGAGAAAGTTGCCCGGAAAGAACGTT
TACACCGAAGTTAAACCCGAGGTGATAGACTTAGAATACAACCTGAAAAAGCTTGGAATTACTAGA
GAACAGCTAATTGATATAGCTTTACTTGTAGGAACAGACTACAACGAGGGGGTTGAGGGGATAGGT
GTTAAGAAGGCCTACAAGTACGTCAAGGCTTATGGAGACATATTCAAGGTTCTGAGGGTTCTGAAG
GTTAAAGTTGAGGAGCCCATAGAGGAGATAAGAAACTTCTTCTTAAATCCTCCGGTGACAGATGAT
TACGAGATAAAGTTTAGGGAGCCCAATGTCGATGGAATAATTGAGTTTCTATGTGAGGAGCACGAT
TTCAGTAGGGAGAGGGTTGAAAAAGCTGTAGAGAAGCTTAGAGCCATTAAAAGCGATCAGCTTACT
CTGGACAGGTGGTTTTAA
```

Apr FEN1 protein sequence

```
MGADIGELLKREEVEIEYFSGKKIAIDAFNTLYQFLATIRQPDGTPLMDSKGRITSHLSGILYRVS
NMVEVGIKPIFVFDGEPPEFKKKEIERRRKIREEAEIKWKTALDIAEARKYAQQAVRVDEYIIESS
KKLLNLMGIPIVQAPSEGEAQAAYIVRKGDADYTGSQDYDSLLFGSPRLARNLAITGRRKLPGKNV
YTEVKPEVIDLEYNLKKLGITREQLIDIALLVGTDYNEGVEGIGVKKAYKYVKAYGDIFKVLRVLK
VKVEEPIEEIRNFFLNPPVTDDYEIKFREPNVDGIIEFLCEEHDFSRERVEKAVEKLRAIKSDQLT
LDRWF
```

Ave FEN1 ORF DNA sequence

```
ATGGGTGCAGACATAGGCGAACTACTCGAGAGAGAAGAAGTTGAACTTGAGTACTTCTCCGGGAGA
AAAATAGCTATTGATGCTTTTAACACTCTTTACCAGTTCATATCTATCATAAGGCAACCTGACGGC
ACTCCTTTGAAGGATTCTCAGGGTAGAATGACCTCACACCTCTCCGGCATCCTGTACCGCGTGTCA
AACATGATCGAGGTTGGAATGAGACCCATTTTCGTTTTCGATGGTGAGCCTCCTGTTTTCAAGCAG
AAGGAGATAGAGGAACGAAAGGAAGAAGAGCTGAAGCAGAGGAGAAGTGGATCGCTGCGATAGAG
AGAGGAGAGAAGTACGCAAAGAAGTACGCTCAGGCAGCGGCGAGGGTTGATGAATACATCGTCGAG
TCGTCAAAGAAGCTGCTTAGTATATGGGAGTTCCATGGGTTCAGGCGCCGAGTGAGGGAGAGGCA
CAGGCTGCATACATGGCAGCGAAGGGCGATGTAGATTTTACTGGCTCGCAGGATTACGACTCGCTT
CTCTTCGGCAGCCCAAAGCTTGCAAGAAATCTCGCGATTACTGGAAAGAGGAAGCTGCCCGGAAAG
AATGTTTACGTTGAGGTCAAACCAGAGATAATAGACTTAAACGGCAACCTGAGAAGGCTTGGAATA
ACAAGGGAACAGCTCGTCGATATCGCGTTGCTCGTGGGAACGGACTACAACGAAGGAGTGAAGGGC
GTTGGGGTCAAGAAGGCCTACAAGTACATAAAAACCTACGGAGATGTTTCAAAGCTCTCAAGGCC
TTAAAGGTAGAGCAGGAGAACATAGAGGAGATAAGAAACTTCTTCCTGAACCCGCCTGTTACGAAC
AACTACAGCCTCCACTTCGGAAAGCCAGACGATGAGAAGATTATCGAGTTCCTGTGTGAAGAGCAC
```

FIGURE 155 (continued)

GACTTTAGCAAGGATAGGGTAGAGAAGGCCGTTGAGAAGCTGAAAGCAGGAATGCAAGCCTCGCAA
TCAACGCTTGAGAGGTGGTTTTCCTGA

Ave FEN1 protein sequence

MGADIGELLEREEVELEYFSGRKIAIDAFNTLYQFISIIRQPDGTPLKDSQGRMTSHLSGILYRVS
NMIEVGMRPIFVFDGEPPVFKQKEIEERKERRAEAEEKWIAAIERGEKYAKKYAQAAARVDEYIVE
SSKKLLEYMGVPWVQAPSEGEAQAAYMAAKGDVDFTGSQDYDSLLFGSPKLARNLAITGKRKLPGK
NVYVEVKPEIIDLNGNLRRLGITREQLVDIALLVGTDYNEGVKGVGVKKAYKYIKTYGDVFKALKA
LKVEQENIEEIRNFFLNPPVTNNYSLHFGKPDDEKIIEFLCEEHDFSKDRVEKAVEKLKAGMQASQ
STLERWFS

Dam FEN1 ORF DNA sequence

ATGGGAGTAGACTTAAAAGACATTATACCAGGCGAAGCTAAAACGGTTATCGAGGATCTCAGGATC
CTACATGGCAAGATTATAGTGATAGATGGCTATAACGCATTATACCAGTTCCTAGCTGCAATCAGA
CAACCGGATGGGACCCCTCTAATGGATAACAACGGGAGGATCACGAGTCATTTAAGCGGTTTATTC
TATAGAACCATAAATATCGTTGAGGCAGGGATAAAACCAGTCTACGTGTTTGATGGTAAACCCCCT
GAATTGAAGGCGAGGGAGATAGAGAGGAGGAAAGCCGTTAAGGAGGAGGCAGCAAAGAAGTACGAG
GAAGCCGTTCAATCCGGAGACCTCGAGCTCGCGAGGAGATACGCAATGATGTCGGCCAAGCTGACA
GAGGAAATGGTGAGGGATGCTAAATCATTACTAGACGCAATGGGTATTCCATGGGTTCAAGCACCA
GCGGAGGGCGAGGCTCAGGCAGCCTATATTGTTAAGAAGGGGGATGCCTATGCATCCGCCTCACAG
GATTACGATAGCTTGCTATTCGGCTCCCCTAAGCTCGTTAGAAACCTGACCATAAGCGGTAGAAGA
AAGCTACCGAGAAAAAACGAGTATGTTGAAGTAAAGCCGGAGCTCATAGAGCTCGACAAACTCCTT
GTTCAGCTAGGTATAACCCTTGAGAACCTCATCGATATAGGTATACTCCTGGGGACAGATTACAAT
CCAGACGGCTTCGAAGGCATAGGCCCCAAGAAGGCTCTTCAACTAGTTAAGGCATACGGGGGAATC
GAGAAGATACCGAAACCCATTTTGAAGTCGCCGATAGAAGTAGATGTTATAGCAATAAAGAAATAC
TTCCTTCAACCACAGGTAACAGACAACTACAGGATTGAATGGCATACCCCCGATCCCGATGCAGTG
AAAAGAATATTGGTGGATGAACATGATTTCAGTATAGATAGAGTTAGCACAGCGCTTGAGAGATAC
GTGAAGGCCTTTAAAGAAAATATACGGGGAGAACAGAAAGGTCTCTCTAAATGGTTCAGTAAGCCG
AAGTAG

Dam FEN1 protein sequence

MGVDLKDIIPGEAKTVIEDLRILHGKIIVIDGYNALYQFLAAIRQPDGTPLMDNNGRITSHLSGLF
YRTINIVEAGIKPVYVFDGKPPELKAREIERRKAVKEEAAKKYEEAVQSGDLELARRYAMMSAKLT
EEMVRDAKSLLDAMGIPWVQAPAEGEAQAAYIVKKGDAYASASQDYDSLLFGSPKLVRNLTISGRR
KLPRKNEYVEVKPELIELDKLLVQLGITLENLIDIGILLGTDYNPDGFEGIGPKKALQLVKAYGGI
EKIPKPILKSPIEVDVIAIKKYFLQPQVTDNYRIEWHTPDPDAVKRILVDEHDFSIDRVSTALERY
VKAFKENIRGEQKGLSKWFSKPK

Dmo FEN1 ORF DNA sequence

FIGURE 155 (continued)

ATGGGCGTCGACCTAAGGGAACTCATCCCAGACGACGCCAAGATCATTATAGAGGATCTGAGGACC
CTACGGGGCAGGGTTATCGCGATAGACGGCTATAACGCGCTCTACCAGTTCCTAGCCGCCATCAGG
CAGCCCGACGGGACGCCCCTAATGGATGGAAGCGGCAGGATCACCAGCCACCTCAGCGGGCTCTTC
TACAGGACGATAAACATTGTGGAGGCAGGGATTAAACCCGTATACGTCTTCGATGGTAAACCCCCC
GAGTTGAAGGCGAAGGAGATAGAGAGGAGAAGGGTTGTCAGGGAGGAGCTGCGAGAAAGTATGAG
GAGGCAGTGCAAGCCGGCGACTTAGAGTCAGCTAGAAGGTATGCGATGATGTCGGCTAGGCTCACC
GATGAAATGGTGAGGGATGCAAAAGCCCTGCTCGACGCCATGGGGATACCGTGGGTTCAAGCCCCG
GCTGAGGGCGAGGCGCAGGCAGCGTACATGGCTAGGAAGGGCGACGCCTACGCCTCTGCATCCCAG
GACTACGATAGCCTCCTCTTCGGGTCGCCCCGCCTAGTGAGGAATCTCACTATAAGTGGCCGTAGG
AAGCTCCCGAGAAGAGAGGAGTATGTCGAGGTGAAGCCCGAGGTAATAGAGCTCGATAAACTGCTT
TCAAAGCTGGGCGTAACCTATGAGAACCTGGTGGACATAGGCATCCTCCTGGGGACGGATTACAAC
CCAGACGGCTTCGAGGGCATTGGACCCAAGAAGGCGCTTCAATTAGTGAAGGTCTACGGGAGCGTT
GAGAAGATACCGAAGCCCCTCTTGAAATCCCCTGTTGAAGTAGATGTCGCAGCGATAAAAAAGTAC
TTCCTGCAACCCCAGGTGACAGACAACTATAGGCTTGAATGGCGTAACCCGGATCCCGAGGCTGTG
AAACGCATACTTGTCGGCGAACACGATTTCAGCGCTGAGAGAGTCAACGCAGCCCTCGACAGGTAT
CTTAAAGCCTTCAGGGAGAACATAAGGGGCGAACAGAAGGGGCTGTCGAAGTGGTTCGCTAAGCCC
GGTAAGCAGGGTTAA

Dmo FEN1 protein sequence

MGVDLRELIPDDAKIIEDLRTLRGRVIAIDGYNALYQFLAAIRQPDGTPLMDGSGRITSHLSGLF
YRTINIVEAGIKPVYVFDGKPPELKAKEIERRRVVREEAARKYEEAVQAGDLESARRYAMMSARLT
DEMVRDAKALLDAMGIPWVQAPAEGEAQAAYMARKGDAYASASQDYDSLLFGSPRLVRNLTISGRR
KLPRREEYVEVKPEVIELDKLLSKLGVTYENLVDIGILLGTDYNPDGFEGIGPKKALQLVKVYGSV
EKIPKPLLKSPVEVDVAAIKKYFLQPQVTDNYRLEWRNPDPEAVKRILVGEHDFSAERVNAALDRY
LKAFRENIRGEQKGLSKWFAKPGKQG

Mig FEN1 ORF DNA sequence

ATGGGAGTGCAGTTTAATGATTTAATCCCAAAAAAGGAAATTCCAATAAAGTACTTATCAGGAAAA
ACTGTGGCTATAGATGGGATGAATGTCCTTTATCAATTTTTATCAAGTATTAGATTGAGAGATGGG
TCCCCTTTAAGGAACAGGAAAGGAGAGATAACCTCAACATACAATGGCATATTTTACAAAACCATA
TACATGCTCGAAAATGATATAACACCGGTATGGGTGTTTGATGGAAAACCGCCAAAATTGAAAGAG
AAAACCAGAGAAGAAAGAAGAAAAATGAGAGAAAAAGCAAAAGAGGAATTCACAAAAGCAAAGAA
ATGGAAAATATTGATGAGATGCAAAATACGCAAAGAGGATGAACTTCTTAACAAAGGACATCGTA
GAGAACTCAAAAAAATTATTGGATTTGATGGGGGTACCTTATGTAAATGCCCCAGCAGAAGGGGAA
GGACAAGCATCATACATGGCAAAAAAGGGAGATGTATTCTGTGTTATTAGTCAGGACTATGATGCT
TTGCTTTATGGGCCCCAAGGATAGTGAGAAACTTAACAGCAACAAAGGAAGAGTTGGAGTTAATA
GAGCTGGAAAATGTTTTAAATGAGTTGGGCATTTCTCATGATGATTTAATAGACATGGCAATTTTG
ATAGGGACTGATTATAATCCAAAGGGAGTTAAAGGCATTGGTCCAAAAAAAGCTCTCGAAATAGTA
AAATCAAAAAACAAAGAACTCTACTTAAAGGCTGTTGAGAATTATGAAGAAATTAAAAATATATTT
AAAAATCCAAAAGTTACTGATGAATACAGCATCAAATTAAAAAAGCCAGATAAAGAAGGTATTATA

FIGURE 155 (continued)

AAGTTTTTGGTTGAGGAAAATGATTTCTCTATGGAGAGAGTTCAGCCACATGTTGAAAAACTCTGT
AAATTGATTGAGAAAAAAACCAAACAAGTAACATTAGATGCATGGTTTGGGAGATGA

Mig FEN1 protein sequence

MGVQFNDLIPKKEIPIKYLSGKTVAIDGMNVLYQFLSSIRLRDGSPLRNRKGEITSTYNGIFYKTI
YMLENDITPVWVFDGKPPKLKEKTREERRKMREKAKEEFTKAKEMENIDEMQKYAKRMNFLTKDIV
ENSKKLLDLMGVPYVNAPAEGEGQASYMAKKGDVFCVISQDYDALLYGAPRIVRNLTATKEELELI
ELENVLNELGISHDDLIDMAILIGTDYNPKGVKGIGPKKALEIVKSKNKELYLKAVENYEEIKNIF
KNPKVTDEYSIKLKKPDKEGIIKFLVEENDFSMERVQPHVEKLCKLIEKKTKQVTLDAWFGR

Mka FEN1 ORF DNA sequence

TTGGGACTAGCTGAACTCCGAGAACTGATCGAACCCGAAGAGACGGACCTGAGAGCCCTCGCCGGT
CGGGAGATCGCTATCGACGCGTTCAACGCCCTGTATCAATTCCTGACCACGATCATGAAGGACGGA
CGACCTCTCATGGACTCGAGGGGCAGGATTACCAGCCACTTAAATGGCCTCCTGTATAGGACCGTG
AACTTGGTCGAAGAGGGTATCAAGCCGGTATACGTGTTCGATGGTGAGCCCCGGACCTGAAGCGT
GAAACGCTGGAGCGTCGACGGGAACGGAAGGAGGAGGCGATGGAGAAACTGAGGCGGGCCAAAACG
AAGGAGGAGCGGGAGAAGTACGCCCGACAAGTCGCCAGACTCGACGAGTCGTTGGTGGAAGACGCG
AAGAGGCTGTTGGATCTCATGGGCATCCCGTGGGTACAGGCCCCCTCGGAAGGAGAGGCGCAGTGC
GCGTATATGGCGAGGTGCGGGGACGTATGGGCGACAGGCAGCCAAGACTACGACTCGCTGCTTTTC
GGCAGCCCCAGGTTGGTTCGCAACATCACGATAGTCGGAAAGCGGAAGCATCCACACACCGGCGAG
ATCATAGAGGTCAAGCCCGAGATCATGAGGTTGGAGGACGTGCTCGACCAGCTGGGATTGGAATCG
AGGGAGCAGCTGGTGGACCTAGCGATCCTTTTGGGCACGGACTACAACCCGGATGGAGTACCCGGG
ATTGGTCCGAAGCGCGCGCTGCAGTTGATCAGGAAGTACGGGTCGCTAGACGAGCTTAAGGACACC
GACATCTGGCCTAAGATCGAGCGGCACCTGCCGGTGGAACCGGAGAAGCTCAAAAGGCTCTTTCTC
GAGCCGGAAGTTACGGACGACTACCAGCTAGACTGGGACGAACCCGACCAAAAGGGACTGGTCGAG
TTCCTGGTTGAGGAGCGTGATTTCTTCCAGGATCGAGTCCGCCGCGCCGTCGAGCGTCTGA

Mka FEN1 protein sequence

LGLAELRELIEPEETDLRALAGREIAIDAFNALYQFLTTIMKDGRPLMDSRGRITSHLNGLLYRTV
NLVEEGIKPVYVFDGEPPDLKRETLERRRERKEEAMEKLRRAKTKEEREKYARQVARLDESLVEDA
KRLLDLMGIPWVQAPSEGEAQCAYMARCGDVWATGSQDYDSLLFGSPRLVRNITIVGKRKHPHTGE
IIEVKPEIMRLEDVLDQLGLESREQLVDLAILLGTDYNPDGVPGIGPKRAIQLIRKYGSLDELKDT
DIWPKIERHLPVEPEKLKRLFLEPEVTDDYQLDWDEPDQKGLVEFLVEERDFFQDRVRRAVERL

Pbr FEN1 ORF DNA sequence

GTGGGCGTCAACCTCCGCGAGATCATACCCAAGGAGGCTGTAACGGAAATAGAGCTCGACTCGCTG
CGCTACAAGGTTGTAGCCATAGACGCCTACAACGCGCTCTACCAGTTCCTCACCGCGATAAGGCAG
CCGGACGGCACGCCGCTCATGGACTCGCGTGGCAGGGTCACCAGCCATCTCAGCGGCCTCTTCTAC
CGCACCATAAACCTGGCCGAGCACGGGGTAAAGGTGGTCTACGTCTTCGACGGGAAGCCGCCGGAG

FIGURE 155 (continued)

ATGAAGTATCTCGAGATAGAGAGGAGGAAGCGTGTCAAGGCGGAGGCTGTGCGGAAGTACGAGGAG
GCAGTGAAGAGGGGCGACCAGGAGGCGGCGAGGCGCTACGCCCAGGCAGCGGCGAGACTCACCGAC
GAGATGGTGGAGGACGCTAAGAAGCTGCTGGAGGCCATGGGGATACCCTACGTGCAGGCGCCGGCG
GAGGGGGAGGCGCAGGCCGCCTACATGGCCCGGAAGGGCGACGCCTGGGCCGCGGCGAGCCAGGAC
TACGACTCCCTGCTCTTCGGGGCCCCGAGGCTTGCCCGGAACCTCGCTATAACGGGTAAGAGGAAG
CTGCCCAGGAAGAACGTCTACGTAGAGGTTAAGCCGGAGCTGGTGGAGCTCGAGAAGCTGCTCAAG
GCACTGGGCATTACCAGGGAGCAGTTGATAGCCCTAGGCATACTCATAGGCACCGACTACAACCCG
GACGGCGTCCGGGGGATCGGCCCAAGACGGCGCTGAAGATGGTGCAGACCCACCGGGACCCCGTG
AAGCTCCTCCAGGGGCTCCCGCGCCACGAGTTCCCGGTCGACCCACTGAAGATCTACGAGTACTTC
CTGAACCCCCCAGTGACCAGCGACTATAAGCTCGAGTGGAGGGAGCCCGACGAGAAGAGGGTCCTC
GAGATACTCGTGGAGGAGCACGACTTCAACCCGGAGCGTGTTAAGAACGCCCTGGAGAGGCTGCGG
AGGGCGTACCGCGAGCACTTCCAGGGCCGCCAGATGGGTCTGGATGCGTGGCTGCGCCGCTAG

Pbr FEN1 protein sequence

VGVNLREIIPKEAVTEIELDSLRYKVVAIDAYNALYQFLTAIRQPDGTPLMDSRGRVTSHLSGLFY
RTINLAEHGVKVVYVFDGKPPEMKYLEIERRKRVKAEAVRKYEEAVKRGDQEAARRYAQAAARLTD
EMVEDAKKLLEAMGIPYVQAPAEGEAQAAYMARKGDAWAAASQDYDSLLFGAPRLARNLAITGKRK
LPRKNVYVEVKPELVELEKLLKALGITREQLIALGILIGTDYNPDGVRGIGPKTALKMVQTHRDPV
KLLQGLPRHEFPVDPLKIYEYFLNPPVTSDYKLEWREPDEKRVLEILVEEHDFNPERVKNALERLR
RAYREHFQGRQMGLDAWLRR

Pho FEN1 ORF DNA sequence

ATGGGTGTTCCTATCGGTGACCTCGTTCCGAGGAAGGAGATAGATCTTGAAAATCTGTATGGAAAG
AAGATAGCGATAGATGCCCTAAACGCCATCTATCAGTTTTTATCAACGATAAGACAGAGGGATGGA
ACACCACTTATGGACTCTAAGGGTAGGATAACCTCTCATTTAAGTGGGCTCTTTTATAGAACGATA
AATCTAATGGAAGCCGGTATTAAGCCGGCCTACGTCTTTGATGGAAAGCCTCCGGAATTCAAAAGG
AAGGAGCTCGAAAAAGGAGGGAAGCTAGAGAAGAGGCAGAACTAAAATGGAAAGAAGCTCTAGCC
AAGGGAAACCTGGAGGAAGCTAGGAAATACGCTCAAAGGGCAACTAAGGTTAATGAAATGCTAATC
GAAGATGCAAAGAAGCTTTTGCAACTAATGGGAATACCAATAATTCAGGCTCCAAGTGAAGGAGAA
GCCCAAGCGGCATACATGGCAAGTAAAGGGGATGTCTACGCGTCAGCGAGTCAAGATTATGATTCA
CTACTCTTTGGTGCTCCAAGGTTGATTAGGAATCTGACAATTACGGGAAAAAGAAAGATGCCTGGG
AAAGATGTTTACGTTGAAATAAAGCCAGAGTTAGTAGTTCTAGATGAGGTACTAAAAGAGCTTAAG
ATAACAAGAGAAAAGCTTATAGAACTTGCAATTCTGGTTGGGACTGACTATAATCCTGGGGCGTA
AAGGGGATAGGACCTAAGAAGGCCCTTGAGATTGTAAGATATTCAAGGGATCCCCTAGCAAAGTTC
CAAAGACAGAGCGATGTGGATCTTTACGCTATTAAGGAATTCTTCCTTAACCCTCCTGTCACTAAT
GAATACTCGCTTAGTTGGAAGGAGCCTGATGAGGAAGGAATATTAAAATTCCTCTGTGATGAGCAT
AATTTTAGCGAAGAAAGGGTAAAAAATGGGATAGAAAGACTAAAAAAGGCGATAAAAGCTGGAAGA
CAATCAACGCTTGAGAGTTGGTTCGTTAAAAAGAAACCCTAA

Pho FEN1 protein sequence

FIGURE 155 (continued)

MGVPIGDLVPRKEIDLENLYGKKIAIDALNAIYQFLSTIRQRDGTPLMDSKGRITSHLSGLFYRTI
NLMEAGIKPAYVFDGKPPEFKRKELEKRREAREEAELKWKEALAKGNLEEARKYAQRATKVNEMLI
EDAKKLLQLMGIPIIQAPSEGEAQAAYMASKGDVYASASQDYDSLLFGAPRLIRNLTITGKRKMPG
KDVYVEIKPELVVLDEVLKELKITREKLIELAILVGTDYNPGGVKGIGPKKALEIVRYSRDPLAKF
QRQSDVDLYAIKEFFLNPPVTNEYSLSWKEPDEEGILKFLCDEHNFSEERVKNGIERLKKAIKAGR
QSTLESWFVKKKP

Tgo FEN1 ORF DNA sequence

ATGGGAGTTCAGATAGGTGAGCTTGTGCCAAGGAAGGAGATCGAACTTGAAGCTCTCTACGGGAAG
AAGGTTGCGATCGATGCCTTCAACGCCATGTACCAGTTCCTCTCAACGATAAGACAGCGCGATGGA
ACTCCTCTAATGGACTCGAAGGGCAGGATAACCTCCCACCTCAGCGGCTTCTTTTACAGGACGATC
AACCTCATGGAGGCCGGAATAAAGCCCGCCTACGTCTTCGACGGAAAGCCGCCGGAGTTCAAGAAG
AAGGAGATAGAGAAAGGAGAGAGGCAAGGGAAGAAGCCGAGGAGAAGTGGTACGAGGCCCTTGAA
AAGGGTGACTTGGAGGAAGCGAAGAAGTACGCGATGAGGGCAACCCGCGTTAACGAGCAACTCATA
AACGATGCCAAAAAGCTTCTCGAACTGATGGGGATTCCAGTCGTGCAGGCGCCGAGCGAAGGTGAA
GCTCAGGCCGCATACATGGCCGCCAAAGGAAAGGTCTACGCCTCCGCCAGTCAGGACTACGATTCG
CTCCTCTTCAGCGCGCCGAGACTTGTAAGGAACCTCACGATAACGGGAAGGAGAAAGCTCCCCGGA
AAGAACGTCTACGTCGAAGTGAAGCCCGAACTCATCGTTCTGGATGAGGTTCTCAAGGAGCTCGGC
ATAGACAGGGAAAAGCTTATAGAGCTGGCGATTCTGGTTGGAACCGACTACAACCCCGGCGGGATA
AAGGGTATCGGGCCCAAGAAGGCCCTGATGATAGTCAAGAGAACCAAAGACCCGCTCAAGAAATAC
CAGAAGGAGAGCGACGTTGACCTCTACGCTATAAAGGAGTTCTTTCTCAACCCGCCTGTTACCGAC
GACTACGAGCTGAGATGGCGCGAACCCGACGAGGAGGGGATTCTGAAGTTCCTCTGCGACGAGCAC
GACTTCAGCGAAGAGCGCGTTAAAACCGGCCTTGAAAGACTGAAGAAGGCGGTAAAGAGCGGAAAA
CAGAGAACACTTGAAAGCTGGTTCACACGGTAG

Tgo FEN1 protein sequence

MGVQIGELVPRKEIELEALYGKKVAIDAFNAMYQFLSTIRQRDGTPLMDSKGRITSHLSGFFYRTI
NLMEAGIKPAYVFDGKPPEFKKKEIEKRREAREEAEEKWYEALEKGDLEEAKKYAMRATRVNEQLI
NDAKKLLELMGIPVVQAPSEGEAQAAYMAAKGKVYASASQDYDSLLFSAPRLVRNLTITGRRKLPG
KNVYVEVKPELIVLDEVLKELGIDREKLIELAILVGTDYNPGGIKGIGPKKALMIVKRTKDPLKKY
QKESDVDLYAIKEFFINPPVTDDYELRWREPDEEGILKFLCDEHDFSEERVKTGLERLKKAVKSGK
QRTLESWFTR

Tzi FEN1 ORF DNA sequence

ATGGGAGTTCAGATCGGTGAGCTCGTGCCGAGGAAGGAGATAGGGCTGGAAAACCTTCATGGGAAA
AAAGTTGCAGTTGATGCCTTCAACGCCATGTACCAGTTTCTCTCGACGATAAGGCAGCCTGATGGG
ACTCCTTTAATGGACTCGAAGGGCAGGATAACCTCTCATCTCAGCGGCTTCTTCTATAGGACAATA
AACCTGATGGAGGCCGGAATAAAACCCGCCTACGTCTTCGACGGGAAGCCACCGGAGTTCAAGAAG
AAGGAGATAGAGAAGAGGAGGGAGGCAAGGGAAGAGGCAGAAGAGAAGTGGCAGGAGGCCCTTGAG
AAGGGCGACCTGGAGGAGGCGAAGAAGTACGCGATGAGGGCAACCCGCGTTAACGAGGAGCTCATA

FIGURE 155 (continued)

```
AGCGATGCCAAAAAGCTTCTTGAGCTAATGGGCATTCCGGTTGTCCAGGCACCGAGCGAGGGAGAG
GCTCAGGCGGCCTACATGGCCGCAAAGGGCAAGGTTTACGCCTCAGCGAGCCAGGATTATGACTCA
CTCCTCTTCAGCGCGCCGAAACTCGTGAGAAACCTCACGATAACGGGAAGAAGGAAGCTGCCGGGG
AAGGATGTCTACGTTGAAGTGAAGCCCGAGCTGATCGTCCTGGAAGAGGTTCTCAAGGAGCTTGGC
ATAGACCGGGAGAAACTCATAGAGCTGGCGATTCTTGTGGGGACGGACTACAACCCCGGGGGGATA
AAGGGCATCGGGCCCAAGAAGGCCCTTATGATAGTCAAGAGAATCAATGACCCGCTCAGGAAGTAC
AGCAATGAGAGTGAGGTCGACCTCTACGCGATAAAGGAGTTCTTTCTCAATCCCCCCGTTACAGAT
GACTACGAGCTGAGATGGCGCGAGCCCGATGAAGATGGGATTCTAAGGTTTCTCTGTGAGGAGCAC
GACTTCAGCGAGGAGAGGGTTAAGGGTGGCCTTGAAAGGCTGAGGAAAGCGGTGGAGAGTGGAAAG
CAGAGAACGCTTGAGAGCTGGTTCGGAAGGTGA
```

Tzi FEN1 protein sequence

```
MGVQIGELVPRKEIGLENLHGKKVAVDAFNAMYQFLSTIRQPDGTPLMDSKGRITSHLSGFFYRTI
NLMEAGIKPAYVFDGKPPEFKKKEIEKRREAREEAEEKWQEALEKGDLEEAKKYAMRATRVNEELI
SDAKKLLELMGIPVVQAPSEGEAQAAYMAAKGKVYASASQDYDSLLFSAPKLVRNLTITGRRKLPG
KDVYVEVKPELIVLEEVLKELGIDREKLIELAILVGTDYNPGGIKGIGPKKALMIVKRINDPLRKY
SNESEVDLYAIKEFFLNPPVTDDYELRWREPDEDGILRFLCEEHDFSEERVKGGLERLRKAVESGK
QRTLESWFGR
```